United States Patent
Horan et al.

(10) Patent No.: US 12,275,742 B2
(45) Date of Patent: Apr. 15, 2025

(54) HETEROAROMATIC MACROCYCLIC ETHER CHEMOTHERAPEUTIC AGENTS

(71) Applicant: Nuvalent, Inc., Cambridge, MA (US)

(72) Inventors: Joshua Courtney Horan, Cambridge, MA (US); Xinxing Tang, Pudong (CN); Scot Richard Mente, Cambridge, MA (US); Henry Efrem Pelish, Cambridge, MA (US); Matthew D. Shair, Cambridge, MA (US); Anupong Tangpeerachaikul, Cambridge, MA (US)

(73) Assignee: Nuvalent, Inc., Cambridge, MA (US)

( * ) Notice: Subject to any disclaimer, the term of this patent is extended or adjusted under 35 U.S.C. 154(b) by 0 days.

(21) Appl. No.: 17/834,127

(22) Filed: Jun. 7, 2022

(65) Prior Publication Data

US 2023/0076627 A1 Mar. 9, 2023

Related U.S. Application Data

(60) Division of application No. 17/524,169, filed on Nov. 11, 2021, now Pat. No. 11,667,649, which is a continuation of application No. PCT/US2021/030940, filed on May 5, 2021.

(60) Provisional application No. 63/125,747, filed on Dec. 15, 2020, provisional application No. 63/060,331, filed on Aug. 3, 2020.

(30) Foreign Application Priority Data

May 5, 2020 (WO) ................ PCT/CN2020/088589

(51) Int. Cl.
C07D 491/22 (2006.01)
(52) U.S. Cl.
CPC ................ *C07D 491/22* (2013.01)
(58) Field of Classification Search
None
See application file for complete search history.

(56) References Cited

U.S. PATENT DOCUMENTS

| | | | |
|---|---|---|---|
| 4,172,896 A | 10/1979 | Uno et al. |
| 5,358,970 A | 10/1994 | Ruff et al. |
| 5,427,798 A | 6/1995 | Ludwig et al. |
| 5,541,231 A | 7/1996 | Ruff et al. |
| 5,569,655 A | 10/1996 | Dority, Jr. et al. |
| 5,731,000 A | 3/1998 | Ruff et al. |
| 5,763,493 A | 6/1998 | Ruff et al. |
| 5,849,735 A | 12/1998 | Albright et al. |
| 6,110,973 A | 8/2000 | Young |
| 6,583,124 B2 | 6/2003 | Asgharian |
| 6,660,867 B2 | 12/2003 | Shimizu et al. |
| 7,312,225 B2 | 12/2007 | Luecking et al. |
| 7,338,973 B2 | 3/2008 | Sui et al. |
| 7,445,211 B1 | 11/2008 | Walton |
| 7,514,466 B2 | 4/2009 | Wilk et al. |
| 7,641,703 B2 | 1/2010 | Guerin et al. |
| 7,696,239 B2 | 4/2010 | Sui et al. |
| 7,915,414 B2 | 3/2011 | Chi et al. |
| 8,012,603 B2 | 9/2011 | Doi et al. |
| 8,039,450 B2 | 10/2011 | Akama et al. |
| 8,129,523 B2 | 3/2012 | Wilk et al. |
| 8,168,614 B2 | 5/2012 | Baker et al. |
| 8,178,520 B2 | 5/2012 | Di Francesco et al. |
| 8,308,996 B2 | 11/2012 | Takahashi et al. |
| 8,309,594 B2 | 11/2012 | Wilk et al. |
| 8,410,091 B1 | 4/2013 | Eriksson et al. |
| 8,461,135 B2 | 6/2013 | Akama et al. |
| 8,580,840 B2 | 11/2013 | Sui et al. |
| 8,609,712 B2 | 12/2013 | Wilk et al. |
| 8,680,111 B2 | 3/2014 | Bailey et al. |
| 9,012,431 B2 | 4/2015 | Akama |
| 9,133,168 B2 | 9/2015 | Brollo et al. |
| 9,133,215 B2 | 9/2015 | Bailey et al. |
| 9,181,265 B2 | 11/2015 | Feron et al. |
| 9,221,818 B2 | 12/2015 | Pinto et al. |
| 9,318,714 B2 | 4/2016 | Ise |
| 9,388,161 B2 | 7/2016 | Bair et al. |
| 9,422,292 B2 | 8/2016 | Albrecht et al. |
| 9,446,995 B2 | 9/2016 | Chong |
| 9,502,667 B2 | 11/2016 | Saito et al. |
| 9,518,217 B2 | 12/2016 | Cheng et al. |
| 9,611,274 B2 | 4/2017 | Pinto et al. |
| 9,666,809 B2 | 5/2017 | Lee |
| 9,768,393 B2 | 9/2017 | Shin et al. |

(Continued)

FOREIGN PATENT DOCUMENTS

| | | |
|---|---|---|
| CA | 2160092 | 4/1996 |
| CN | 105669733 A | 6/2016 |

(Continued)

OTHER PUBLICATIONS

Ye et al (Oncotarget 7:12289-12304, 2016) (Year: 2016).*
Hsiao et al (Case Rep Oncol 14:232-238, 2021) (Year: 2021).*
Cognigni et al (Cancers 14:4765-4785, 2022) (Year: 2022).*
Muminovic et al (Cancer Drug Resist 6:332-344, 2023) (Year: 2023).*
Ahn et al., "Entrectinib in patients with locally advanced or metastatic ROS1 fusion-positive non-small cell lung cancer (NSCLC)," IASLC 18th World Conference on Lung Cancer: 16 pages Abstract 8564 (Oct. 15-18, 2017).
Alecensa FDA Approval Media Release., "FDA approves Roche's Alecensa (alectinib) as first-line treatment for people with specific type of lung cancer," Hoffmann-La Roche Ltd.: 6 pages (Nov. 7, 2017).

(Continued)

*Primary Examiner* — Craig D Ricci
(74) *Attorney, Agent, or Firm* — Jones Day

(57) ABSTRACT

Disclosed are heterocyclic heteroaromatic macrocyclic ether compounds, pharmaceutically acceptable salts of the compounds and pharmaceutical compositions thereof. Also disclosed are methods of treating or preventing cancer using the heterocyclic heteroaromatic macrocyclic ether compounds, pharmaceutically acceptable salts of the compounds, and pharmaceutical compositions thereof.

31 Claims, No Drawings

(56) References Cited

U.S. PATENT DOCUMENTS

| | | | |
|---|---|---|---|
| 9,887,372 B2 | 2/2018 | Jun et al. |
| 9,902,742 B2 | 2/2018 | Pinto et al. |
| 9,929,358 B2 | 3/2018 | Hwang et al. |
| 10,147,887 B2 | 12/2018 | Lee |
| 10,189,803 B2 | 1/2019 | Chong |
| 1,020,806 A1 | 2/2019 | Pinto et al. |
| 10,208,068 B2 | 2/2019 | Pinto et al. |
| 10,243,153 B2 | 3/2019 | Ise |
| 10,335,392 B2 | 7/2019 | Xiao et al. |
| 10,336,722 B2 | 7/2019 | Bair et al. |
| 10,487,063 B2 | 11/2019 | Jiang et al. |
| 10,593,889 B1 | 3/2020 | Takahashi et al. |
| 10,611,750 B2 | 4/2020 | Bair et al. |
| 10,774,053 B2 | 9/2020 | Cai et al. |
| 10,800,791 B2 | 10/2020 | Ghosh et al. |
| 10,954,215 B2 | 3/2021 | Hughes et al. |
| 11,008,323 B2 | 5/2021 | Schann et al. |
| 11,111,229 B2 | 9/2021 | Bair et al. |
| 11,352,329 B2 | 6/2022 | Cai et al. |
| 11,542,278 B1 | 1/2023 | Horan et al. |
| 11,548,871 B2 | 1/2023 | Bestvater et al. |
| 11,584,738 B2 | 2/2023 | Bestvater et al. |
| 11,661,437 B2 | 5/2023 | Su et al. |
| 11,667,649 B2 | 6/2023 | Horan et al. |
| 11,702,407 B2 | 7/2023 | Phillips et al. |
| 11,814,367 B2 | 11/2023 | Morgans et al. |
| 11,866,414 B2 | 1/2024 | Spergel et al. |
| 2003/0187272 A1 | 10/2003 | Shimizu et al. |
| 2005/0004074 A1 | 1/2005 | Lyons et al. |
| 2005/0031697 A1 | 2/2005 | Vehige et al. |
| 2005/0059744 A1 | 3/2005 | Donello et al. |
| 2005/0080056 A1 | 4/2005 | Horn |
| 2005/0250766 A1 | 11/2005 | Wilk et al. |
| 2005/0272702 A1 | 12/2005 | Wilk et al. |
| 2006/0116415 A1 | 6/2006 | Sui et al. |
| 2007/0116984 A1 | 5/2007 | Park et al. |
| 2007/0213526 A1 | 9/2007 | Levent et al. |
| 2007/0293457 A1 | 12/2007 | Baker et al. |
| 2008/0125591 A1 | 5/2008 | Chi et al. |
| 2008/0138651 A1 | 6/2008 | Doi et al. |
| 2008/0244838 A1 | 10/2008 | Guerin et al. |
| 2009/0022694 A1 | 1/2009 | Distefano |
| 2009/0042726 A1 | 2/2009 | Black et al. |
| 2009/0054663 A1 | 2/2009 | Wilk et al. |
| 2009/0143577 A1 | 6/2009 | Wilk et al. |
| 2009/0291917 A1 | 9/2009 | Akama et al. |
| 2010/0210658 A1 | 8/2010 | Sui et al. |
| 2010/0216988 A1 | 8/2010 | Alonso et al. |
| 2010/0261719 A1 | 10/2010 | Basarab et al. |
| 2011/0049497 A1 | 3/2011 | Ise |
| 2011/0071136 A1 | 3/2011 | Haddach et al. |
| 2011/0178311 A1 | 7/2011 | Levent et al. |
| 2012/0008068 A1 | 1/2012 | Doi et al. |
| 2012/0121934 A1 | 5/2012 | Takahashi et al. |
| 2012/0157448 A1 | 6/2012 | Cook et al. |
| 2012/0214765 A1 | 8/2012 | Akama et al. |
| 2013/0012702 A1 | 1/2013 | Wilk et al. |
| 2013/0056716 A1 | 3/2013 | Cheng et al. |
| 2013/0196952 A1 | 8/2013 | Bunnage et al. |
| 2013/0252961 A1 | 9/2013 | Bailey et al. |
| 2013/0274253 A1 | 10/2013 | Brollo et al. |
| 2013/0289030 A1 | 10/2013 | Feron et al. |
| 2013/0310555 A1 | 11/2013 | Chong |
| 2014/0011768 A1 | 1/2014 | Akama |
| 2014/0066479 A1 | 3/2014 | Sui et al. |
| 2014/0135316 A1 | 5/2014 | Albrecht et al. |
| 2014/0135339 A1 | 5/2014 | Bailey et al. |
| 2014/0221338 A1 | 8/2014 | Pinto et al. |
| 2015/0045349 A1 | 2/2015 | Nagamiya et al. |
| 2015/0060791 A1 | 3/2015 | Shin et al. |
| 2015/0155497 A1 | 6/2015 | Lee |
| 2015/0207084 A1 | 7/2015 | Hwang et al. |
| 2015/0218441 A1 | 8/2015 | Cho et al. |
| 2015/0232445 A1 | 8/2015 | Bair et al. |
| 2015/0255731 A1 | 9/2015 | Lee |
| 2016/0068544 A1 | 3/2016 | Pinto et al. |
| 2016/0163998 A1 | 6/2016 | Saito et al. |
| 2016/0214996 A1* | 7/2016 | Song .................. C07D 495/18 |
| 2016/0254462 A1 | 9/2016 | Ise |
| 2016/0256448 A1 | 9/2016 | Bair et al. |
| 2016/0257692 A1 | 9/2016 | Bair et al. |
| 2016/0365521 A1 | 12/2016 | Jun et al. |
| 2017/0000886 A1 | 1/2017 | Chong |
| 2017/0008863 A1 | 1/2017 | Chong |
| 2017/0005409 A1 | 2/2017 | Cheng et al. |
| 2017/0054094 A1 | 2/2017 | Cheng et al. |
| 2017/0015871 A1 | 6/2017 | Pinto et al. |
| 2017/0158712 A1 | 6/2017 | Pinto et al. |
| 2018/0029985 A1 | 2/2018 | Shiers et al. |
| 2018/0029999 A1 | 2/2018 | Jiang et al. |
| 2018/0014846 A1 | 5/2018 | Pinto et al. |
| 2018/0148461 A1 | 5/2018 | Pinto et al. |
| 2018/0022134 A1 | 8/2018 | Xiao et al. |
| 2018/0215766 A1 | 8/2018 | Bair et al. |
| 2018/0221344 A1 | 8/2018 | Xiao et al. |
| 2018/0034646 A1 | 12/2018 | Schann et al. |
| 2018/0346468 A1 | 12/2018 | Schann et al. |
| 2019/0127347 A1 | 5/2019 | Bair et al. |
| 2019/0210978 A1 | 7/2019 | Cai et al. |
| 2019/0241582 A1 | 8/2019 | Gjosh et al. |
| 2020/0017519 A1 | 1/2020 | Ghosh et al. |
| 2020/0009899 A1 | 3/2020 | Takahashi et al. |
| 2020/0071298 A1 | 3/2020 | Hughes et al. |
| 2020/0098994 A1 | 3/2020 | Takahashi et al. |
| 2020/0030366 A1 | 9/2020 | Jeon et al. |
| 2020/0303663 A1 | 9/2020 | Jeon et al. |
| 2020/0317646 A1 | 10/2020 | He et al. |
| 2020/0369642 A1 | 11/2020 | Bair et al. |
| 2020/0385396 A1 | 12/2020 | Zhou et al. |
| 2021/0012274 A1 | 1/2021 | Forgatch et al. |
| 2021/0078959 A1 | 3/2021 | Cai et al. |
| 2021/0171500 A1 | 6/2021 | Bestvater et al. |
| 2021/0309682 A1 | 10/2021 | Arefyev et al. |
| 2021/0380561 A1 | 12/2021 | Phillips et al. |
| 2021/0395233 A1 | 12/2021 | Takahashi et al. |
| 2022/0017565 A1 | 1/2022 | Su et al. |
| 2022/0098212 A1 | 3/2022 | Horan et al. |
| 2022/0340586 A9 | 10/2022 | Horan et al. |
| 2022/0402948 A1 | 12/2022 | Liu et al. |
| 2022/0411384 A1 | 12/2022 | Spergel et al. |
| 2022/0411406 A1 | 12/2022 | Bestvater et al. |
| 2023/0012262 A1 | 1/2023 | Bestvater et al. |
| 2023/0020273 A1 | 1/2023 | Spergel et al. |
| 2023/0061891 A1 | 3/2023 | Bair et al. |
| 2023/0076627 A1 | 3/2023 | Horan et al. |
| 2023/0104740 A1 | 4/2023 | Morgans et al. |
| 2023/0107663 A1 | 4/2023 | Horan et al. |
| 2023/0124705 A1 | 4/2023 | Chen et al. |
| 2023/0174513 A1 | 6/2023 | Su et al. |
| 2023/0174553 A1 | 6/2023 | Pandey et al. |
| 2023/0174554 A1 | 6/2023 | Wang et al. |
| 2023/0183264 A1 | 6/2023 | Pandey et al. |
| 2023/0212151 A1 | 7/2023 | Bestvater et al. |
| 2024/0002367 A1 | 1/2024 | Phillips et al. |

FOREIGN PATENT DOCUMENTS

| | | |
|---|---|---|
| CN | 106243096 | 12/2016 |
| CN | 108912175 | 11/2018 |
| CN | 105130966 B | 5/2019 |
| CN | 109912433 | 6/2019 |
| CN | 110357905 | 10/2019 |
| CN | 110734456 A | 1/2020 |
| CN | 111362967 | 7/2020 |
| CN | 111808147 | 10/2020 |
| CN | 112321604 | 2/2021 |
| CN | 112812128 | 5/2021 |
| CN | 113105440 | 7/2021 |
| CN | 113121607 | 7/2021 |
| CN | 111440154 | 4/2022 |
| FR | 2969611 | 6/2012 |
| JP | S60243083 A | 12/1985 |
| JP | 2009-234928 | 10/2009 |
| JP | 2009-266927 | 11/2009 |

(56) References Cited

FOREIGN PATENT DOCUMENTS

| | | |
|---|---|---|
| JP | 2010-278114 | 12/2010 |
| JP | 2018-062496 | 4/2018 |
| KR | 2016-0038813 | 4/2016 |
| KR | 2019-0103769 | 9/2019 |
| WO | WO 1996/022282 | 7/1996 |
| WO | WO 2002/050190 | 6/2002 |
| WO | WO 2004/039859 | 5/2004 |
| WO | WO 2005/105817 | 11/2005 |
| WO | WO 2006/014413 | 2/2006 |
| WO | WO 2006/034090 | 3/2006 |
| WO | WO 2007/047604 | 4/2007 |
| WO | WO 2007/096576 | 8/2007 |
| WO | WO 2009/000412 | 12/2008 |
| WO | WO 2009/004382 | 1/2009 |
| WO | WO 2011/016582 | 2/2011 |
| WO | WO 2011/035019 | 3/2011 |
| WO | WO 2012/016147 | 2/2012 |
| WO | WO 2012/071458 | 5/2012 |
| WO | WO 2012/073143 | 6/2012 |
| WO | WO 2012/085222 | 6/2012 |
| WO | WO 2012/089633 | 8/2012 |
| WO | WO 2012/102409 | 8/2012 |
| WO | WO 2012/138648 | 10/2012 |
| WO | WO 2012/174685 | 12/2012 |
| WO | WO 2013/022818 | 2/2013 |
| WO | WO 2013/127028 | 9/2013 |
| WO | WO 2013/132376 | 9/2013 |
| WO | WO 2014/038867 | 3/2014 |
| WO | WO 2014/138912 | 9/2014 |
| WO | WO 2014/207606 | 12/2014 |
| WO | WO 2015/025197 | 2/2015 |
| WO | WO 2015/050989 | 4/2015 |
| WO | WO 2015/074064 | 5/2015 |
| WO | WO 2015/104711 | 7/2015 |
| WO | WO 2015/175579 | 11/2015 |
| WO | WO 2016/026423 | 2/2016 |
| WO | WO 2016/118774 | 7/2016 |
| WO | WO 2017/023902 | 2/2017 |
| WO | WO 2017/080980 | 5/2017 |
| WO | WO 2017/081483 | 5/2017 |
| WO | WO 2017/148325 | 9/2017 |
| WO | WO 2019/057175 | 3/2019 |
| WO | WO 2019/113071 | 6/2019 |
| WO | WO 2019/120263 | 6/2019 |
| WO | WO 2019/149131 | 8/2019 |
| WO | WO 2019/164301 | 8/2019 |
| WO | WO 2020/021113 | 1/2020 |
| WO | WO 2020/067290 | 4/2020 |
| WO | WO 2020/069106 | 4/2020 |
| WO | WO 2020/085742 A1 | 4/2020 |
| WO | WO 2020/228747 | 11/2020 |
| WO | WO 2021/025371 | 2/2021 |
| WO | WO 2021/058969 | 4/2021 |
| WO | WO 2021/062327 | 4/2021 |
| WO | WO 2021/122868 | 6/2021 |
| WO | WO 2021/125791 | 6/2021 |
| WO | WO 2021/224040 | 11/2021 |
| WO | WO 2021/224320 | 11/2021 |
| WO | WO 2021/225833 | 11/2021 |
| WO | WO 2021/226003 | 11/2021 |
| WO | WO 2021/226168 | 11/2021 |
| WO | WO 2021/226208 | 11/2021 |
| WO | WO 2021/226269 | 11/2021 |
| WO | WO 2022/017408 | 1/2022 |
| WO | WO 2022/194399 | 9/2022 |
| WO | WO 2022/212538 | 10/2022 |
| WO | WO 2023/056405 | 4/2023 |
| WO | WO 2023/056431 | 4/2023 |
| WO | WO 2023/059801 | 4/2023 |
| WO | WO 2023/179600 | 9/2023 |
| WO | WO 2023/196900 | 10/2023 |
| WO | WO 2024/046512 | 3/2024 |

OTHER PUBLICATIONS

Alectinib Prescribing Information., "Alecensa® (alectinib) capsules, for oral use Initial U.S. Approval: 2015," U.S. Food and Drug Administration: 21 pages (Nov. 2017).

Antonescu et al., "Molecular Characterization of Inflammatory Myofibroblastic Tumors with Frequent ALK and ROS1 Fusions and Rare Novel RET Gene Rearrangement," Am. J. Surg. Pathol., 39(7): Author Manuscript pp. 1-19 (2015).

Arai et al., "Mouse Model for ROS1-Rearranged Lung Cancer," Plos One, 8(2): e56010 pp. 1-7 (2013).

Bauer et al., "Clinical Management of Adverse Events Associated with Lorlatinib," The Oncologist, 24: 1103-1110 (Aug. 24, 2019).

Bayliss et al., "Molecular mechanisms that underpin EML4-ALK driven cancers and their response to targeted drugs," Cellular and Molecular Life Sciences, 73: 1209-1224 (2016).

Besse et al., "Clinical Evaluation of NVL-520, a Highly Selective ROS1 Inhibitor, in Patients with Advanced ROS1-Positive Solid Tumors: The Phase 1/2 ARROS-1 Study," European Lung Cancer Congress: Nuvalent Poster Abstract #78TiP (Mar. 30, 2022).

Bestvina et al., "ALK and ROS1 rearrangement in NSCLC: rapidly evolving standards," Oncology, 18: 1555-1556 (Nov. 29, 2017).

Birch et al., "Chromosome 3 Anomalies Investigated by Genome Wide SNP Analysis of Benign, Low Malignant Potential and Low Grade Ovarian Serous Tumours," Plos One, 6(12): e28250 pp. 1-20 (2011).

Bresler et al., "ALK mutations confer differential oncogenic activation and sensitivity to ALK inhibition therapy in neuroblastoma," Cancer Cell., 26(5): Author Manuscript pp. 1-29 (2014).

Camidge et al., "Clinical trial design for systemic agents in patients with brain metastases from solid tumours: a guideline by the Response Assessment in Neuro-Oncology Brain Metastases working group," The Lancet Oncology, 19(1): e20-e32 (Jan. 2018).

Camidge et al., "Exploratory Analysis of Brigatinib Activity in Patients With Anaplastic Lymphoma Kinase-Positive Non-Small-Cell Lung Cancer and Brain Metastases in Two Clinical Trials," Journal of Clinical Oncology, 36(26): 2693-2701 (May 16, 2018).

Charest et al., "Fusion of FIG to the Receptor Tyrosine Kinase ROS in a Glioblastoma with an Interstitial del(6)(q21q21)," Genes, Chromosomes & Cancer, 37: 58-71 (2003).

Chia et al., "Prevalence and natural history of ALK positive non-small-cell lung cancer and the clinical impact of targeted therapy with ALK inhibitors," Clinical Epidemiology, 6: 423-432 (2014).

Cho et al., "Phase 1/2 Trident-1 Study of Repotrectinib in Patients with ROS1+ or NTRK+ Advanced Solid Tumors," 2020 World Conference on Lung Cancer Singapore: 7 pages Abstract #3255 (Jan. 28-31, 2021).

Cho et al., "Safety and Preliminary Clinical Activity of Repotrectinib in Patients with Advanced ROS1 Fusion-Position Non-Small Cell Lung Cancer (Trident-1 Study)," 2019 ASCO Annual Meeting: 13 pages (May 2019).

Chong et al., "Identification of Existing Drugs That Effectively Target NTRK1 and ROS1 Rearrangements in Lung Cancer," Clinical Cancer Research, 23(1): 204-213 (Jan. 1, 2017).

Cocco et al., "NTRK fusion-positive cancers and TRK inhibitor therapy," Nature Reviews Clinical Oncology, 15: 731-747 (Oct. 17, 2018).

Cocco et al., "NTRK fusion-positive cancers and TRK inhibitor therapy," Nat. Rev. Clin. Oncol., 15(12): Author Manuscript pp. 1-34 (2018).

Coleman et al., "Lorlatinib Salvages Central Nervous System Only Relapse on Entrectinib in ROS1-Positive NSCLC," Journal of Thoracic Oncology, 15(8): e142-e144 (Aug. 1, 2020).

Conde et al., "Assessment of a New ROS1 Immunohistrochemistry Clone (SP384) for the Identification of ROS1," Journal of Thoracic Oncology, 14(12): 2120-2132 (Dec. 1, 2019).

Cortinovis et al., "Challenges in ALK inhibition of ALK-positive non-small-cell lung cancer: from ALK positivity detection to treatment strategies after relapse," Future Oncology, 14(22): 2303-2317 (Aug. 8, 2018).

Cui et al., "Abstract 5226: TPX-0131: A next generation macrocyclic ALK inhibitor that overcomes ALK resistant mutations refractory to

(56) References Cited

OTHER PUBLICATIONS current approved ALK inhibitors," American Association for Cancer Research: Poster Abstract#5226 (Aug. 2020).

Dagogo-Jack et al., "MET Alterations Are a Recurring and Actionable Resistance Mechanism in ALK-Positive Lung Cancer," Clinical Cancer Research, 26(11): 2535-2545 (Jun. 1, 2020).

Dagogo-Jack et al., "Tracking the Evolution of Resistance to ALK Tyrosine Kinase Inhibitors Through Longitudinal Analysis of Circulating Tumor DNA," JCO Precision Oncology, 2: pp. 1-14 (Jan. 23, 2018).

Dagogo-Jack et al., "Tracking the Evolution of Resistance to ALK Tyrosine Kinase Inhibitors Through Longitudinal Analysis of Circulating Tumor DNA," JCO Precision Oncology, 2: Supplementary Information pp. 1-9 (Jan. 23, 2018).

Dagogo-Jack et al., "Treatment with Next-Generation ALK Inhibitors Fuels Plasma ALK Mutation Diversity," Clinical Cancer Research, 25(22): 6662-6670 (Nov. 15, 2019).

Davare et al., "Rare but recurrent ROS1 fusions resulting from chromosome 6q22 microdeletions are targetable oncogenes in glioma," Clin. Canc. Res., 24(24): Author Manuscript pp. 1-27 (2018).

Davies et al., "Molecular Pathways: ROS1 Fusion Proteins in Cancer," Clinical Cancer Research, 19(15): 4040-4045 (Aug. 1, 2013).

Dearden et al., "Mutation incidence and coincidence in non smallcell lung cancer: meta-analyses by ethnicity and histology (mutMap)," Annals of Oncology, 24: 2371-2376 (Sep. 1, 2013).

Demicco et al., "New Therapeutic Targets in Soft Tissue Sarcoma," Adv. Anat. Pathol., 19(3): Author Manuscript pp. 1-21 (2012).

Deshpande et al., "Abstract P249: Preclinical antitumor activity of NVL-520 in patient-derived models harboring ROS1 fusions, including G2032R solvent front mutation," Mol. Canc. Ther., 20(Supplement 12): P249 (2021).

Doebele et al., "Genomic landscape of entrectinib resistance from ctDNA analysis in STARTRK-2," Annals of Oncology, 30(Supplement 5): v865 (2019).

Doebele et al., "Trident-1: A Global, Multicenter, Open-label Phase 2 Study Investigating the Activity of Repotrectinib in Advanced Solid Tumors Harboring ROS1 or NTRK1-3 Rearrangements," Turning Point Therapeutics: Poster Abstract #TPS9637 (May 29-Jun. 2, 2020).

Drilon et al., "A Phase 1 Study of the Next-Generation ALK/ROS1/TRK Inhibitor Ropotrectinib (TPX-0005) in Patients with Advanced ALK/ROS1/NTRK+ Cancers (Trident-1)," American Society of Clinical Oncology (ASCO) Annual Meeting: Poster Abstract #2513 (Jun. 1-5, 2018).

Drilon et al., "Entrectinib in ROS1 fusion-positive non-small-cell lung cancer: integrated analysis of three phase 1-2 trials," Lancet Oncology, 21: 261-270 (Dec. 11, 2019).

Drilon et al., "Entrectinib in ROS1 fusion-positive non-small-cell lung cancer: integrated analysis of three phase 1-2 trials," Lancet Oncol., 21(2): Author Manuscript pp. 1-23 (2020).

Drilon et al., "Repotrectinib (TPX-0005) Is a Next-Generation ROS1/TRK/ALK Inhibitor That Potently Inhibits ROS1/TRK/ALK Solvent-Front Mutations," Cancer Discovery, 8: 1227-1236 (Aug. 9, 2018).

Drilon et al., "ROS1—dependent cancers—biology, diagnostics and therapeutics," Nature Reviews Clinical Oncology, 18: 35-55 (Jan. 1, 2021).

Drilon et al., "ROS1—dependent cancers—biology, diagnostics and therapeutics," Nature Reviews Clinical Oncology, 18: Supplementary Information, pp. 1-7 (Jan. 1, 2021).

Drilon et al., "ROS1-dependent cancers—biology, diagnostics and therapeutics," Nat. Rev. Clin. Oncol., 18(1): Author Manuscript pp. 1-45 (2021).

Drilon et al., "Safety and Antitumor Activity of the Multitargeted Pan-TRK, ROS1, and ALK Inhibitor Entrectinib: Combined Results from Two-Phase I Trials (ALKA-372-001 and STARTRK-1)," Cancer Discovery, 7(4): 400-409 (Feb. 9, 2017).

Drilon et al., "Safety and Antitumor Activity of the Multitargeted Pan-TRK, ROS1, and ALK Inhibitor Entrectinib: Combined Results from Two-Phase I Trials (ALKA-372-001 and STARTRK-1)," Cancer Discovery, 7(4): Supplementary Information 1 of 2, pp. 1-2 (Feb. 9, 2017).

Drilon et al., "Safety and Antitumor Activity of the Multitargeted Pan-TRK, ROS1, and ALK Inhibitor Entrectinib: Combined Results from Two-Phase I Trials (ALKA-372-001 and STARTRK-1)," Cancer Discovery, 7(4): Supplementary Information 2 of 2, pp. 1-6 (Feb. 9, 2017).

Drilon et al., "Safety and Preliminary Clinical Activity of Repotrectinib in Patients with Advanced ROS1/TRK Fusion-Positive Solid Tumors (Trident-1 Study)," European Society for Medical Oncology (ESMO): Poster Abstract #4536 (Sep. 27-Oct. 1, 2019).

Eid et al., "KinMap: a web-based tool for interactive navigation through human kinome data," BMC Bioinformatics, 18(16): pp. 1-6 (2017).

Elleraas et al., "Conformational Studies and Atropisomerism Kinetics of the ALK Clinical Candidate Lorlatinib (PF-06463922) and Desmethyl Congeners," Angewandte Chemie, 128(11): 3654-3659 (Feb. 15, 2016).

Entrectinib Multi-Discipline Review., "NDA/BLA Multidisciplinary Review and Evaluation NDA 212725," Center for Drug Evaluation and Research: 632 pages (Feb. 1, 2016).

Entrectinib Prescribing Information Label., "Rozlytrek (entrectinib) capsules, for oral use Initial U.S. Approval: 2019," U.S. Food and Drug Administration: 25 pages (Aug. 2019).

Felip Font et al., "Efficacy and safety of lorlatinib in patients (pts) with ALK+ non-small cell lung cancer (NSCLC) previously treated with 2nd-generation ALK TKIs, " Annals of Oncology, 28(5): 478-479 (Sep. 1, 2017).

Fleuren et al., "Phosphoproteomic Profiling Reveals ALK and MET as Novel Actionable Targets across Synovial Sarcoma Subtypes," Cancer Research, 77(16): 4279-4292 (2017).

Fujiwara et al., "Safety and pharmacokinetics of DS-6051b in Japanese patients with non-small cell lung cancer harboring ROS1 fusions: a phase I study," Oncotarget, 9(34): 23729-23737 (May 4, 2018).

Gadgeel et al., "Cumulative incidence rates for CNS and non-CNS progression in two phase II studies of alectinib in ALK-positive NSCLC," BJC, 118: 38-42 (2018).

Gadgeel et al., "Safety and activity of alectinib against systemic disease and brain metastases in patients with crizotinib-resistant ALK-rearranged non-small-cell lung cancer (AF 002JG): results from the dose-finding portion of a phase 1/2 study," The Lancet Oncology, 15(1): 1119-1128 (Sep. 2014).

Gainor et al., "Molecular Mechanisms of Resistance to First- and Second-Generation ALK Inhibitors in ALK—Rearranged Lung Cancer," Cancer Discovery, 6(10): 1119-1133 (Oct. 2016).

Gainor et al., "Patterns of Metastatic Spread and Mechanisms of Resistance to Crizotinib in ROS1-Positive Non-Small-Cell Lung Cancer," JCO Precision Oncology, 1: pp. 1-13 (2017).

George et al., "Activating mutations in ALK provide a therapeutic target in neuroblastoma," Nature, 455(7215): Author Manuscript pp. 1-11 (2008).

Giacomini et al., "Breakpoint Analysis of Transcriptional and Genomic Profiles Uncovers Novel Gene Fusions Spanning Multiple Human Cancer Types," Plos Genetics, 9(4): e1003464 pp. 1-19 (2013).

Gobbini et al., "Real-world outcomes according to treatment strategies in ALK-rearranged non-small-cell lung cancer (NSCLC) patients: an Italian retrospective study," Clinical and Translational Oncology, 22: 294-301 (Mar. 3, 2020).

Golding et al., "The function and therapeutic targeting of anaplastic lymphoma kinase (ALK) in non-small cell lung cancer (NSCLC)," Molecular Cancer, 17(52): pp. 1-15 (2018).

Gu et al., "Survey of Tyrosine Kinase Signaling Reveals ROS Kinase Fusions in Human Cholangiocarcinoma," Plos One, 6(1): e15640 pp. 1-9 (2011).

Guo et al., "Dual potent ALK and ROS1 inhibitors combating drug-resistant mutants: Synthesis and biological evaluation of aminopyridine containing diarylaminopyrimidine derivatives," European Journal of Medicinal Chemistry, 158: 322-333 (Sep. 6, 2018).

Hallberg et al., "The role of the ALK receptor in cancer biology," Annals of Oncology, 27(Supplement 3): ii4-ii15 (2016).

(56) References Cited

OTHER PUBLICATIONS

Holla et al., "ALK: a tyrosine kinase target for cancer therapy," Cold Spring Harbor Molecular Case Studies, 3: a001115 pp. 1-20 (2017).
Hong et al., "Will the clinical development of 4th-generation "double mutant active" ALK TKIs (TPX-0131 and NVL-655) change the future treatment paradigm of Alk+ NSCLC?," Translational Oncology, 14(11): Article 101191 pp. 1-9 (Aug. 5, 2021).
Horn et al., "Monitoring Therapeutic Response and Resistance: Analysis of Circulating Tumor DNA in Patients With ALK+ Lung Cancer," Journal of Thoracic Oncology, 14(11): 1901-1911 (Nov. 2019).
Hua et al., "Real-world circulating tumor DNA analysis depicts resistance mechanism and clonal evolution in ALK inhibitor-treated lung adenocarcinoma patients, " ESMO Open Cancer Horizons, 7(1): 8 pages (2022).
Huang et al., "Discovery of Brigatinib (AP26113), a Phosphine Oxide-Containing, Potent, Orally Active Inhibitor of Anaplastic Lymphoma Kinase, " Journal of Medicinal Chemistry, 59: 4948-4964 (May 4, 2016).
International Search Report and Written Opinion for International Application No. PCT/CN2020/088589 dated Feb. 10, 2021.
International Search Report and Written Opinion for International Application No. PCT/CN2020/088590 dated Feb. 3, 2021.
International Search Report and Written Opinion for International Application No. PCT/US2021/030842 dated Nov. 5, 2021.
International Search Report and Written Opinion for International Application No. PCT/US2021/030940 mailed Sep. 17, 2021.
Johnson et al., "Discovery of (10R)-7-Amino-12-fluoro-2,10,16-trimethyl-15-oxo-10,15,16,17-tetrahydro-2H-8,4-(metheno)pyrazolo[4,3-h][2,5,11]-benzoxadiazacyclotetradecine-3-carbonitrile (PF-06463922), a Macrocyclic Inhibitor of Anaplastic Lymphoma Kinase (ALK) and c-ros Oncogene 1 (ROS1) with Preclinical Brain Exposure and Broad-Spectrum Potency against ALK-Resistant Mutations," Journal of Medicinal Chemistry, 57(11): 4720-4744 (May 13, 2014).
Johnson et al., "Discovery of PF-06463922, a macrocyclic inhibitor of ALK/ROS1 with pre-clinical brain exposure and broad spectrum potency against ALK-resistant mutations," Journal of Medicinal Chemistry, 57(11): Supporting Information S1-S57 (May 13, 2014).
Jordan et al., "Prospective comprehensive molecular characterization of lung adenocarcinomas for efficient patient matching to approved and emerging therapies," Cancer Discov., 7(6): Author Manuscript pp. 1-21 (2017).
Katayama et al., "The new-generation selective ROS1/NTRK inhibitor DS-6051b overcomes crizotinib resistant ROS1-G2032R mutation in preclinical models," Nature Communications, 10: Article No. 3604 pp. 1-12 (Aug. 9, 2019).
Katayama et al., "Two Novel ALK Mutations Mediate Acquired Resistance to the Next-Generation ALK Inhibitor Alectinib," Clinical Cancer Research, 20(22): 5686-5696 (Nov. 15, 2014).
Keddy et al., "Resistance Profile and Structural Modeling of Next-Generation ROS1 Tyrosine Kinase Inhibitors," Molecular Cancer Therapeutics, 21(2): 336-346 (2022).
Kong et al., "Drug Discovery Targeting Anaplastic Lymphoma Kinase (ALK)," Journal of Medicinal Chemistry: 28 pages (2019).
Ku et al., "Entrectinib resistance mechanisms in ROS1-rearranged non-small cell lung cancer," Investigational New Drugs, 38: 360-368 (Apr. 2020).
Leonetti et al., "COVID-19 in lung cancer patients receiving ALK/ROS1 inhibitor," European Journal of Cancer, 132: 122-124 (Jun. 2020).
Li et al., "Efficacy of Crizotinib among Different Types of ROS1 Fusion Partners in Patients with ROS1-Rearranged Non-Small Cell Lung Cancer," Journal of Thoracic Oncology, 13(7): 987-995 (2018).
Lin et al., "ALK and ROS1 Inhibitors: New Agents Not Yet Approved," 2021 Targeted Therapies of Lung Cancer Meeting: 17 pages (Feb. 17-21, 2021).
Lin et al., "Efficacy of Platinum/Pemetrexed Combination Chemotherapy in ALK-Positive NSCLC Refractory to Second-Generation ALK Inhibitors," Journal of Thoracic Oncology, 15(2): 258-265 (Feb. 2020).
Lin et al., "Impact of EML4-ALK Variant on Resistance Mechanisms and Clinical Outcomes in ALK-Positive Lung Cancer," Journal of Clinical Oncology, 36(12): 1199-1206 (Apr. 20, 2018).
Lin et al., "Recent Advances in Targeting ROS1 in Lung Cancer," Journal of Thoracic Oncology, 12(11): 1611-1625 (Nov. 2017).
Lin et al., "Small cell transformation of ROS1 fusion-positive lung cancer resistant to ROS1 inhibition," NPJ Precision Oncology, 4: Article No. 21 pp. 1-8 (2020).
Lin et al., "Spectrum of Mechanisms of Resistance to Crizotinib and Lorlatinib in ROS1 Fusion-Positive Lung Cancer," Clinical Cancer Research, 27(10): OF1-OF11 (Mar. 8, 2021).
Lin et al., "Spectrum of Mechanisms of Resistance to Crizotinib and Lorlatinib in ROS1 Fusion-Positive Lung Cancer," Clin. Canc. Res., 27(10): Author Manuscript pp. 1-24 (2021).
Liu et al., "Characterization of on-target adverse events caused by TRK inhibitor therapy," Annals of Oncology, 31(9): 1207-1215 (Sep. 2020).
Liu et al., "Characterization of On-Target Adverse Events Caused by TRK Inhibitor Therapy," Ann. Oncol., 31(9): Author Manuscript pp. 1-17 (2020).
Liu et al., "Design, synthesis and biological evaluations of 2-amino-4-(1-piperidine) pyridine derivatives as novel anti crizotinib-resistant ALK/ROS1 dual inhibitors," European Journal of Medicinal Chemistry, 179: 358-375 (Oct. 1, 2019).
Lorbrena (Lorlatinib) Full Prescribing Information and Label Initial U.S. Approval: Nov. 2018.
Lorbrena (lorlatinib) Prescribing Information Label; Food and Drug Administration: 31 pages (2021).
Lorlatinib Multi-Discipline Review., "NDA/BLA Multidisciplinary Review and Evaluation NDA 210868," Center for Drug Evaluation and Research: 302 pages (Feb. 1, 2016).
Lorviqua Public Assessment Report., Published by the European Medicines Agency on Feb. 28, 2019 (148 pages).
Mallinson et al., "Macrocycles in drug discovery," Future Med Chem, 4(11): 1409-1438 (2012).
Marks et al., "ROS1-GOPC/FIG: a novel gene fusion in hepatic angiosarcoma," Oncotarget, 10(2): 245-251 (2019).
Moog-Lutz et al., "Activation and Inhibition of Anaplastic Lymphoma Kinase Receptor Tyrosine Kinase by Monoclonal Antibodies and Absence of Agonist Activity of Pleiotrophin," The Journal of Biological Chemistry, 280(28): 26039-26048 (2005).
Murray et al., "TPX-0131, a Potent CNS-penetrant, Next-generation Inhibitor of Wild-type ALK and ALK-resistant Mutations," Molecular Cancer Therapeutics, 20(9): 1499-1507 (2021).
Murugan et al., "Anaplastic Thyroid Cancers Harbor Novel Oncogenic Mutations of the ALK Gene," Cancer Research, 71(13): Author Manuscript pp. 1-14 (2011).
Neel et al., "Differential subcellular localization regulates oncogenic signaling by ROS1 kinase fusion proteins," Cancer Research, 79(3): Author Manuscript pp. 1-19 (2019).
Noe et al., "ALK Mutation Status Before and After Alectinib Treatment in Locally Advanced or Metastatic ALK-Positive NSCLC: Pooled Analysis of Two Prospective Trials," Journal of Thoracic Oncology, 15(4): 601-608 (Apr. 2020).
Nosaki et al., "P2.06-002 Phase I Study of DS-6051b, a ROS1/NTRK Inhibitor, in Japanese Subjects with Advanced Solid Tumors Harboring Either a ROS1 or NTRK Fusion Gene," Journal of Thoracic Oncology, 12(1): Supplement S1069 (Jan. 1, 2017).
Okubo et al., "Aberrant activation of ALK kinase by a novel truncated form ALK protein in neuroblastoma," Oncogene, 31: 4667-4676 (2012).
Ou et al., "A Catalog of 5' Fusion Partners in ROS1-Positive NSCLC Circa 2020," JTO Clinical and Research Reports, 1(3): pp. 1-5 (2020).
Ou et al., "CNS metastasis in ROS1+ NSCLC: An urgent call to action, to understand, and to overcome," Lung Cancer, 130: 201-207 (Apr. 2019).

(56) References Cited

OTHER PUBLICATIONS

Ou et al., "OA02.03 Clinical Activity of Lorlatinib in Patients with ROS1+ Advanced Non-Small Cell Lung Cancer: Phase 2 Study Cohort EXP-6," Journal of Thoracic Oncology, 13(10): Supplement S322-S323 (Oct. 1, 2018).
Papadopoulos et al., "U.S. Phase I First-in-human Study of Taletrectinib (DS-6051b/AB-106), a ROS1/TRK Inhibitor, in Patients with Advanced Solid Tumors," Clinical Cancer Research, 26(18): 4785-4974 (Sep. 15, 2020).
Patil et al., "The incidence of brain metastases in stage IV ROS1-rearranged non-small cell lung cancer and rate of central nervous system progression on crizotinib," J. Thorac. Oncol., 13(11): Author Manuscript pp. 1-17 (2018).
Pelish et al., "Abstract 1465: NUV-520 (NVL-520) is a brain-penetrant and highly selective ROS1 inhibitor with antitumor activity against the G2032R solvent front mutation," Cancer Res., 81(Supplement 13): Abstract 1465 (2021).
Pelish et al., "NUV-520 is a brain-penetrant and highly selective ROS1 inhibitor with antitumor activity against the G2032R solvent front mutation," American Association for Cancer Research (AACR): Nuvalent Poster Abstract #1465 (Apr. 2021).
Pelish et al., "NUV-655 is a selective, brain-penetrant ALK inhibitor with antitumor activity against the lorlatinib-resistant G1202R/L1196M compound mutation," American Association for Cancer Research (AACR): Nuvalent Poster Abstract #1468 (Apr. 2021).
Perkins et al., "Childhood anaplastic large cell lymphoma has a high incidence of ALK gene rearrangement as determined by immunohistochemical staining and fluorescent in situ hybridisation: a genetic and pathological correlation," British Journal of Haematology, 131(5): 624-627 (2005).
Peters et al., "Alectinib versus Crizotinib in Untreated ALK-Positive Non-Small-Cell Lung Cancer," The New England Journal of Medicine, 377: 829-838 (Aug. 31, 2017).
Pubchem SID 327469789: 7 pages (2017).
Rajan et al., "The mechanism of cancer drug addiction in ALK-positive T-Cell lymphoma," Oncogene, 39: 2103-2117 (Mar. 2020).
Recondo et al., "Diverse Resistance Mechanisms to the Third-Generation ALK Inhibitor Lorlatinib in ALK-Rearranged Lung Cancer," Clinical Cancer Research, 26(1): 242-255 (Oct. 4, 2019).
Rikova et al., "Global Survey of Phosphotyrosine Signaling Identifies Oncogenic Kinases in Lung Cancer," Cell, 131(6): 1190-1203 (2007).
Rimkunas et al., "Analysis of Receptor Tyrosine Kinase ROS1-Positive Tumors in Non-Small Cell Lung Cancer: Identification of a FIG-ROS1 Fusion," Clinical Cancer Research, 18(16): 4449-4457 (2012).
Rizvi et al., "Cholangiocarcinoma—evolving concepts and therapeutic strategies," Nat. Rev. Clin. Oncol., 15(2): Author Manuscript pp. 1-37 (2018).
Rozlytrek (entrectinib) Prescribing Information Label; Food and Drug Administration: 25 pages (2019).
Sabari et al., "The activity, safety, and evolving role of brigatinib in patients with ALK-rearranged non-small cell lung cancers," Onco Targets and Therapy, 10: 1983-1992 (Apr. 6, 2017).
Sakamoto et al., "CH5424802, a Selective ALK Inhibitor Capable of Blocking the Resistant Gatekeeper Mutant," Cancer Cell, 19(5): 679-690 (May 17, 2011).
Sehgal et al., "Cases of ROS1-rearranged lung cancer: when to use crizotinib, entrectinib, lorlatinib, and beyond?" Precis Cancer Med, 3(17): pp. 1-11 (Jun. 15, 2020).
Shaw et al., "ALK in Lung Cancer: Past, Present, and Future," Journal of Clinical Oncology, 31(8): 1105-1111 (2013).
Shaw et al., "ALK Resistance Mutations and Efficacy of Lorlatinib in Advanced Anaplastic Lymphoma Kinase-Positive Non-Small-Cell Lung Cancer," Journal of Clinical Oncology, 37(16): 1370-1379 (Mar. 20, 2019).
Shaw et al., "Crizotinib in ROS1-rearranged advanced non-small-cell lung cancer (NSCLC): updated results, including overall survival, from Profile 1001," Annals of Oncology, 30(7): 1121-1126 (Jul. 2019).

Shaw et al., "First-Line Lorlatinib or Crizotinib in Advanced ALK-Positive Lung Cancer," The New England Journal of Medicine, 383: 2018-2029 (Nov. 19, 2020).
Shaw et al., "First-Line Lorlatinib or Crizotinib in Advanced ALK-Positive Lung Cancer," The New England Journal of Medicine, 383: Supplementary Appendix pp. 1-29 (Nov. 19, 2020).
Shaw et al., "Lorlatinib in ALK- or ROS1-rearranged non-small cell lung cancer: an international, multicenter, open-label phase 1 trial," Lancet Oncology, 18(12): Author Manuscript pp. 1-20 (2017).
Shaw et al., "Lorlatinib in non-small-cell lung cancer with ALK or ROS1 rearrangement: an international, multicentre, open-label, single-arm first-in-man phase 1 trial," Lancet Oncology, 18: 1590-1599 (Dec. 2017).
Shaw et al., "Lorlatinib in non-small-cell lung cancer with ALK or ROS1 rearrangement: an international, multicentre, open-label, single-arm first-in-man phase 1 trial," Supplementary Appendix: 1-305 (Dec. 2017).
Shults et al., "Versatile Fluorescence Probes of Protein Kinase Activity," Journal of the American Chemical Society, 125(47): 14248-14249 (2003).
Soda et al., "Identification of the transforming EML4-ALK fusion gene in non-small-cell lung cancer," Nature, 448: 561-566 (Jul. 11, 2007).
Solomon et al., "Lorlatinib in patients with ALK-positive non-small-cell lung cancer: results from a global phase 2 study," The Lancet Oncology, 19(12): 1654-1667 (Dec. 2018).
Stypinski et al., "Metabolism, Excretion, and Pharmacokinetics of Lorlatinib (PF-06463922) and Evaluation of the Impact of Radiolabel Position and Other Factors on Comparability of Data Across 2 ADME Studies," The Journal of Clinical Pharmacology, 60(9): 1254-1267 (May 22, 2020).
Syed., "Lorlatinib: First Global Approval, " Drugs, 79: 93-98 (Jan. 2, 2019).
Syeda-Mahmood et al., "Shape-based Similarity Retrieval of Doppler Images for Clinical Decision Support," IEEE Computer Society Conference on Computer Vision and Pattern Recognition: 8 pages (Aug. 5, 2010).
Takeuchi et al., "RET, ROS1 and ALK fusions in lung cancer," Nature Medicine, 18(3): 378-381 (2012).
Tangpeerachaikul et al., "Abstract P247: Evaluating TRKB activity of novel preclinical brain-penetrant ROS1 and ALK inhibitors," Mol. Canc. Ther., 20(Supplement 12): P247 (2021).
Tangpeerachaikul et al., "Evaluating TRKB Activity of Novel Preclinical Brain-Penetrant ROS1 and ALK Inhibitors," AACR-NCI-EORTC Virtual International Conference on Molecular Targets and Cancer Therapeutics: 10 pages (Oct. 7-10, 2021).
Tangpeerachaikul et al., "NVL-655 Exhibits Antitumor Activity in Lorlatinib-Resistant Subcutaneous and Intracranial Models of ALK-Rearranged NSCLC" AACR-NCI-EORTC Virtual International Conference on Molecular Targets and Cancer Therapeutics: 9 pages (Oct. 7-10, 2021).
Tangpeerachaikul et al., "Preclinical activity of NVL-520 in ROS1-driven cancer models with diverse fusion partners and kinase-domain mutations," American Association for Cancer Research: Nuvalent Poster Abstract #3336 (Apr. 8, 2022).
Tangpeerachaikul et al., "Preclinical activity of NVL-655 in ALK-driven cancer models beyond non-small cell lung cancer," American Association for Cancer Research: Nuvalent Poster Abstract #3337 (Apr. 8, 2022).
Tangpeerachalkul et al., "NVL-66: a selective, potent 4G ALK TKI; NVL-655: dose-dependent in vivo anti-tumor activity against double mutant ALK; NVL-655: preclinical CNS penetrance and activity," 2022 Targeted Therapies of Lung Cancer Meeting: 3 pages (Feb. 22-26, 2022).
Trigg et al., "ALK in Neuroblastoma: Biological and Therapeutic Implications," Cancers, 10(113): pp. 1-26 (2018).
Tu et al., "Molecular inhibitory mechanism study on the potent inhibitor brigatinib against four crizotinib-resistant ALK mutations," Journal of Cellular Biochemistry, 120(1): 562-574 (Sep. 6, 2018).
Umapathy et al., "Targeting anaplastic lymphoma kinase in neuroblastoma," APMIS Journal of Pathology, Microbiology and Immunology, 127(5): 288-302 (2019).

(56) References Cited

OTHER PUBLICATIONS

Valery et al., "Cholangiocarcinoma with STRN-ALK translocation treated with ALK inhibitors," Digestive and Liver Disease: Article in Press pp. 1-2 (2021).
Weisner et al., "Alternative transcription initiation leads to expression of a novel ALK isoform in cancer," Nature, 56(7573): Author Manuscript pp. 1-35 (2015).
Yamazaki et al., "Mechanistic Understanding of Translational Pharmacokinetic-Pharmacodynamic Relationships in Nonclinical Tumor Models: A Case Study of Orally Available Novel Inhibitors of Anaplastic Lymphoma Kinase," Drug Metabolism and Disposition, 43: 54-62 (Jan. 2015).
Yamazaki et al., "Translational Pharmacokinetic-Pharmacodynamic Modeling for an Orally Available Novel Inhibitor of Anaplastic Lymphoma Kinase and c-Ros Oncogene 1," The Journal of Pharmacology and Experimental Therapeutics, 351: 67-76 (Oct. 2014).
Yoda et al., "Sequential ALK Inhibitors Can Select for Lorlatinib-Resistant Compound ALK Mutations in ALK-Positive Lung Cancer," Cancer Discovery, 8(6): 715-729 (Apr. 12, 2018).
Yoda et al., "Sequential ALK Inhibitors Can Select for Lorlatinib-Resistant Compound ALK Mutations in ALK-Positive Lung Cancer," Cancer Discovery, 8(6): Author Manuscript pp. 1-36 (2018).
Yoda et al., "Sequential ALK Inhibitors Can Select for Lorlatinib-Resistant Compound ALK Mutations in ALK-Positive Lung Cancer," Cancer Discovery, 8(6): Supplementary Figures pp. 1-11 (Apr. 12, 2018).
Yoda et al., "Sequential ALK Inhibitors Can Select for Lorlatinib-Resistant Compound ALK Mutations in ALK-Positive Lung Cancer," Cancer Discovery, 8(6): Supplementary Methods pp. 1-2 (Apr. 12, 2018).
Yun et al., "Repotrectinib Exhibits Potent Antitumor Activity in Treatment-Naïve and Solvent-Front-Mutant ROS1-Rearranged Non-Small Cell Lung Cancer," Clinical Cancer Research, 26(13): OF1-OF9 (Jul. 2020).
Zhang et al., "Determination of the mean pressure gradient in aortic stenosis by Doppler echocardiography," European Heart Journal, 6: 999-1005 (Dec. 1, 1985).
Zhang et al., "The Potent ALK Inhibitor Brigatinib (AP26113) Overcomes Mechanisms of Resistance to First- and Second-Generation ALK Inhibitors in Preclinical Models," Clinical Cancer Research, 22(22): 5527-5538 (Nov. 2016).
Zhao et al., "A Bayesian network meta-analysis regarding the comparative efficacy of therapeutics for ALK-positive, brain metastatic non-small cell lung cancer," Pharmacological Research, 174: 105931 (12 pages)(2021).
Zheng et al., "Investigation on the prognostic impact of concurrent genomic alterations in crizotinib-treated EML4-ALK-rearranged advanced non-small cell lung cancer patients," Lung Cancer, 146: 209-216 (Aug. 2020).
Zhu et al., "A Novel Sequentially Evolved EML4-ALK Variant 3 G1202R/S1206Y Double Mutation in Cis Confers Resistance to Lorlatinib: A Brief Report and Literature Review," JTO Clinical and Research Reports, 2(1): 27 pages (Oct. 25, 2020).
Zhu et al., "An International Real-World Analysis of the Efficacy and Safety of Lorlatinib Through Early or Expanded Access Programs in Patients With Tyrosine Kinase Inhibitor-Refractory ALK-Positive or ROS1-Positive NSCLC," Journal of Thoracic Oncology, 15(9): 1484-1496 (Sep. 2020).
Zou et al., "PF-06463922 is a potent and selective next-generation ROS1/ALK inhibitor capable of blocking crizotinib-resistant ROS1 mutations," PNAS, 112(11): 3493-3498 (Mar. 17, 2015).
Zou et al., "PF-06463922 is a potent and selective next-generation ROS1/ALK inhibitor capable of blocking crizotinib-resistant ROS1 mutations," PNAS, Supporting Information: 1-8 (Mar. 17, 2015).
Zou et al., "The ALK/ROS1 Inhibitor PF-06463922 Has Potency across Resistant ALK Mutants," Cancer Discovery, 5: 902 (Jul. 2, 2015).
Adjei, "JTO Clinical and Research Reports Is Born," JTO Clinical and Research Reports, 1(1):100014 (2020).

Aldea et al., "ALK Inhibitors in ALK-positive NSCLC with Central Nervous System Metastases," Lung Cancer, 4 pages (Sep. 15, 2020).
Anderson, 2000, Practical Process Research & Development, Chapter 11: "Tools for Purifying the Product: Column Chromatography, Crystallization and Reslurrying," pp. 223-224.
Armstrong et al., 2004, "Differential effects of X-ALK fusion proteins of proliferation, transformation, and invasion properties of NIH3T3 cells," Oncgene, 23: 6071-6082.
Basit et al., 2017, "First macrocyclic 3rd-generation ALK inhibitor for treatment of ALK/ROS1 cancer: Clinical and designing strategy update of lorlatinib," European Journal of Medicinal Chemistry, 134:348-356.
Bauer et al., 2020, "Brain Penetration of Lorlatinib: Cumulative Incidences of CNS and Non-CNS Progression with Lorlatinib in Patients with Previously Treated ALK-Positive Non-Small-Cell Lung Cancer," Targeted Oncology, 15:55-65.
Berge et al., 1977, "Pharmaceutical salts," Journal of Pharmaceutical Sciences, 66(1):1-19.
Bertrand et al., 2012, "The Crystal Structures of TrkA and TrkB Suggest Key Regions for Achieving Selective Inhibition," J. Mol. Biol., 423: 439-453.
Byrn et al., 1995, "Pharmaceutical Solids: A Strategic Approach to Regulatory Considerations, " Pharmaceutical Research, 12(7):945-954.
Caira, M, 1998, "Crystalline Polymorphism of Organic Compounds," Topics in Current Chemistry, 198:163-208.
Camidge et al., 2012, "Activity and safety of crizotinib in patients with ALK-positive non-small-cell lung cancer: updated results form a phase 1 study," Lancet Oncol., 13(10): 1011-1019.
Camidge et al., 2020, "Brigatinib Versus Crizotinib in Advanced ALK Inhibitor-Naive ALK-Positive Non-Small Cell Lung Cancer: Second Interim Analysis of the Phase III ALTA-1L Trial," J Clin Oncol, 38:3592-3603.
Camidge, 2021, "Lorlatinib Should Not be Considered as the Preferred First-Line Option in Patients With Advanced ALK Rearranged NSCLC," Journal of Thoracic Oncology, 16(4): 528-531.
Cazes et al., "Characterization of rearrangements involving the ALK gene reveals a novel truncated form associated with tumor aggressiveness in neuroblastoma," Cancer Research, 73(1):195-204 (2013).
Chen et al., 2018, "Molecular Mechanism Behind the Resistance of the G1202R-Mutated Anaplastic Lymphoma Kinase to the Approved Drug Ceritinib," J. Phys. Chem. B, 122:4680-4692.
Chen et al., 2022, "Single-cell DNA-seq depicts clonal evolution of multiple driver alterations in osimertinib-resistant patients," Annals of Oncology, 33(4):434-444.
Childress et al., 2018, "ALK Fusion Partners Impact Response to ALK Inhibition: Differential Effects on Sensitivity, Cellular Phenotypes, and Biochemical Properties," Mol Cancer Res, 16(11): 1724-1736.
Cho et al., "Pivotal topline data from the phase 1/2 Trident-1 trial of repotrectinib in patients with ROS1+ advanced non-small cell lung cancer (NSCLC)," European Journal of Cancer 174S1 (2002) S1-S2.
Chou et al., 2010, "Drug combination studies and their synergy quantification using the Chou-Talalay method," Cancer Research, 70(2):440-446.
ClinicalTrials.gov Identifier: NCT03202940, "A Phase IB/II Study of Alectinib Combined With Cobimetinib in Advanced ALK-Rearranged (ALK+) NSCLC," Last Updated Mar. 9, 2021.
Cooper et al., 2022, "LTK fusions: A new target emerges in non-small cell lung cancer," Cancer Cell, 40(1):23-25.
Debruyne et al., "ALK inhibitor resistance in ALKF1174L-driven neuroblastoma is associated with AXL activation and induction of EMT," Oncogene, 35:3681-3691 (2016).
Delsol et al., 1997, "A New Subtype of Large B-Cell Lymphoma Expressing the ALK Kinase and Lacking the 2; 5 Translocation," Blood, 89(5): 1483-1490.
Drilon et al., 2023, "NVL-520 Is a Selective, TRK-Sparing, and Brain-Penetrant Inhibitor of ROS1 Fusions and Secondary Resistance Mutations," Cancer Discovery, 13(3), 598-615.

(56) References Cited

OTHER PUBLICATIONS

Drilon, 2019, "TRK inhibitors in TRK fusion-positive cancers," Annals of Oncology, 30(8): viii23-viii30.
Eisenhauer et al., 2009, New response evaluation criteria in solid tumours: revised RECIST guideline (version 1.1), European Journal of Cancer, 45(2):228-247.
Enot et al., 2018, "TumGrowth: An open-access web tool for the statistical analysis of tumor growth curves," Oncoimmunology, 7(9) 3 pages.
Ertl et al., 2000, "Fast Calculation of Molecular Polar Surface Area as a Sum of Fragment-Based Contributions and Its Application to the Prediction of Drug Transport Properties," J. Med. Chem., 43: 3714-3717.
Fransson et al., "Intragenic anaplastic lymphoma kinase (ALK) rearrangements:translocations as a novel mechanism of ALK activation in neuroblastoma tumors," Genes, Chromosomes and Cancer, 54(2):99-109 (2014).
Fujino et al., "Preclinical activity of NVL-655 in patient-derived models of ALK cancers, including those with lorlatinib-resistant G1202R/L1196M compound mutation," Abstracts, 34th EORTC-NCI-AACR Symposium (Oct. 27, 2022).
Fukuhara et al., "Partial deletion of the ALK gene in ALK-positive anaplastic large cell lymphoma," Hematological Oncology, 36(1):150-158 (2017).
Gadgeel et al., 2018, "Alectinib versus crizotinib in treatment-naïve anaplastic lymphoma kinase-positive (ALKþ) non-small-cell lung cancer: CNS efficacy results from the ALEX study," Annals of Oncology, 29: 2214-2222.
Griffin et al., 1999, "Recurrent Involvement of 2p23 in Inflammatory Myofibroblastic Tumors," Cancer Research, 59: 2776-2780.
Guerreiro Stucklin et al., 2019, "Alterations in ALK/ROS1/NTRK/MET drive a group of infantile hemispheric gliomas," Nature Communications, 10:4343.
Harwood and Moody, 1989, "Experimental Organic Chemistry—Principles and Practice," Blackwell Science, pp. 127-132.
Hatcher et al., 2015, "Discovery of inhibitors that overcome the G1202R ALK Resistance Mutation," J Med Chem 58(23): 9296-9308.
Heuckmann et al., 2012, "Differential Protein Stability and ALK Inhibitor Sensitivity of EML4-ALK Fusion Variants," Clin Cancer Res, 18(17): 4682-4690.
Horn et al., 2018, "Ensartinib (X-396) in ALK-Positive Non-Small Cell Lung Cancer: Results from a First-in-Human Phase I/II, Multicenter Study," Clin Cancer Res, 24(12): 2771-2779.
Horn et al., 2021, "Ensartinib vs Crizotinib for Patients With Anaplastic Lymphoma Kinase—Positive Non-Small Cell Lung Cancer," JAMA Oncology, 7(11): 1617-1625.
Huang et al., "Extracellular domain shedding of the ALK receptor mediates neuroblastoma cell migration," Cell Reports, 36:109363 (2021).
Inamura et al., 2017, "Association of tumor TROP2 expression with prognosis varies among lung cancer subtypes," Oncotarget, 8(17):28725-28735.
International Search Report and Written Opinion dated Aug. 14, 2023 for PCT/US2023/065434 (30 pages).
International Search Report and Written Opinion dated Jan. 18, 2023 for PCT/US2022/077364 (13 pages).
International Search Report and Written Opinion dated Jan. 26, 2023 for PCT/US2022/077323 (13 pages).
International Search Report and Written Opinion dated Jun. 30, 2023 for PCT/US2023/065449 (11 pages).
Izumi et al., 2021, "The CLIP1-LTK fusion is an oncogenic driver in non-small-cell lung cancer," Nature, 600:319-323.
Keldar et al., 1999, "Polar Molecular Surface as a Dominating Determinant for Oral Absorption and Brain Penetration of Drugs," Pharmaceutical Research, 16(10): 1514-1519.
Kim et al., 2020, "Synergistic Effect of Alectinib and Everolimus on ALK-positive Anaplastic Large Cell Lymphoma Growth Inhibition," Anticancer Research, 40(3):1395-1403.
Koopman et al., 2022, "Actionability of on-target ALK Resistance Mutations inPatients With Non-Small Cell Lung Cancer: Local Experience and Review of the Literature," Clinical Lung Cancer, 23(2): e104-e114.e1.
Lee et al., 2023, "Abstract 4022: Preclinical intracranial activity of NVL-655 in an alectinib-resistant patient derived model harboring EML4-ALK fusion with G1202R mutation," Cancer Res, 23(7_Suppl): Abstract nr 4022.
Lin et al., 2022, "Safety and activity of alectinib plus bevacizumab in patients with advanced ALK-rearranged non-small-cell lung cancer: a phase I/II study," ESMO Open, 7(1):100342.
Lin et al., 2023, "Safety and preliminary activity of the selective ALK inhibitor NVL-655 in patients with ALK fusion-positive solid tumors," AACR-EORTC-NCI International Conference on Molecular Targets and Cancer presentation.
Lu et al., 2020, "Medicinal Chemistry Strategies for the Development of Kinase Inhibitors Targeting Point Mutations," J. Med. Chem., 63:10726-10741.
Lucken et al., 2022, "EML4-ALK Variant 3 Promotes Mitotic Errors and Spindle Assembly Checkpoint Deficiency Leading to Increased Microtubule Poison Sensitivity," Molecular Cancer Research, 20(6):854-866.
Mizuta et al., 2022, "Preclinical Activity of NVL-655 in a Patient-Derived NSCLC Model with Lorlatinib-Resistant ALK G1202R/T1151M Mutation," Journal of Thoracic Oncology, 17(95): S406.
Morris et al., 1994, "Fusion of Kinase Gene, ALK, to a Nucleolar Protein Gene, NPM, in Non-Hodgkin's Lymphoma," Science, 263: 1281-1284.
Mossé et al., 2008, "Identification of ALK as a major familial neuroblastoma predisposition gene," Nature, 455: 930-936.
NCBI Reference Sequence: NP_004295.2, "ALK tyrosine kinase receptor isoform 1 precursor [*Homo sapiens*]".
Oken et al., 1982, "Toxicity and response criteria of the Eastern Cooperative Oncology Group," American Journal of Clinical Oncology, 5(6):649-655.
Ou et al., 2020, "Catalog of 5' Fusion Partners in ALK-positive NSCLC Circa 2020," JTO Clinical and Research Reports, 1(1): 1-10.
Parsons and Flack, "Precise Absolute-Structure Determination in Light-Atom Crystals," Acta Crystallographica, A60:s61 (2004).
Schrock et al., 2018, "Receptor Tyrosine Kinase Fusions and BRAF Kinase Fusions are Rare but Actionable Resistance Mechanisms to EGFR Tyrosine Kinase Inhibitors," Journal of Thoracic Oncology, 13(9):1312-1323.
Taniguchi et al., 2021, "Efficacy of combination treatment using YHO-1701, an orally active STAT3 inhibitor, with molecular-targeted agents on cancer cell lines," Scientific Reports, 11(1):6685.
Tanimoto et al., 2021, "Proteasome Inhibition Overcomes ALK-TKI Resistance in ALK-Rearranged/ TP53-Mutant NSCLC via Noxa Expression," Clinical Cancer Research, 27(5):1410-1420.
Tanimura et al., 2021, "Inhibition of c-Jun N-terminal kinase signaling increased apoptosis and prevented the emergence of ALK-TKI-tolerant cells in ALK-rearranged non-small cell lung cancer," Cancer Letters, 522:119-128.
Tanizaki et al., 2012, "Combined effect of ALK and MEK inhibitors in EML4-ALK-positive non-small-cell lung cancer cells," British Journal of Cancer, 106(4):763-767.
Tsui et al., 2022, "Tumor Shrinkage With Combination of Alectinib and Trastuzumab in a Patient With ALK-Rearranged Non-small Cell Lung Cancer Harboring HER2-Amplification as an Acquired Resistance Mechanism to ALK Inhibitor Therapy, " Clinical Lung Cancer, 23(2):e99-e103.
Tsuji et al., 2020, "YAP1 mediates survival of ALK-rearranged lung cancer cells treated with alectinib via pro-apoptotic protein regulation," Nature Communications, 11:74.
Vippagunta et al., 2001, "Crystalline solids," Advanced Drug Delivery Reviews, 48(1):3-26.
von Buttlar et al., 2021, "EML4-ALK Rearrangement as a Mechanism of Resistance to Osimertinib in Metastatic Lung Adenocarcinoma: A Case Report," JTO Clinical and Research Reports, 2(6):100179.
Wiesner et al., "Alternative transcription initiation leads to expression of a novel ALK isoform in cancer," Nature, 526(7573):453-457 (2015).

(56) References Cited

OTHER PUBLICATIONS

Wilen et al., "Strategies in optical resolutions," Tetrahedron, 33(21):2725-2736 (1977).

Xiao et al., 2022, "Inhibiting ALK-TOPK signaling pathway promotes cell apoptosis of ALK-positive NSCLC," Cell Death & Disease, 13(9):828.

Yu, L., 2001, "Amorphous pharmaceutical solids: preparation, characterization and stabilization," Advanced Drug Delivery Reviews, 48:27-42.

Zhong et al., 2021, "Small molecules in targeted cancer therapy: advances, challenges, and future perspectives," Signal Transduction and Targeted Therapy, 6(1):201.

Ayati et al., 2020, "A review on progression of epidermal growth factor receptor (ECFR) inhibitors as an efficient approach in cancer targeted therapy," Bioorganic Chemistry, 99:103811.

Pacheco et al., 2019, "Natural History and Factors Associated with Overall Survival in Stage IV ALK-Rearranged Non-Small Cell Lung Cancer," J Thorac Oncol., 14(4): 691-700.

Rossari et al., 2018, "Past, present, and future of Bcr-Abl inhibitors: from chemical development to clinical efficacy," Journal of Hematology & Oncology, 11:84.

Shaw et al., "Crizotinib versus Chemotherapy in Advanced ALK-Positive Lung Cancer," 2013, N Engl J Med, 368(25), 2385-2394.

Solomon et al., "Intracranial Efficacy of Crizotinib Versus Chemotherapy in Patients With Advanced ALK-Positive Non-Small-Cell Lung Cancer: Results From Profile 1014, " 2016, J Clin Oncol 24:2858-2865.

Soria et al., "Osimertinib in Untreated EGFR-Mutated Advanced Non-Small-Cell Lung Cancer", 2018, N Engl J Med, 378(2), 113-125.

Wang, et al., 2010, "General Solution to the Synthesis of N-2-Substituted 1,2,3-Triazoles," Org. Lett. 12(20):4632-4635.

Robertson, et al., 2014, "Functionalized thienoacridines: synthesis, optoelectronic, and structural properties," Can. J. Chemistry, 92(11):1106-1110.

Gunasekera et al., 2007, "Practical synthesis and applications of benzoboroxoles," Tetrahedron, 63:9401-9405.

Pirali et al., 2019, "Applications of Deuterium in Medicinal Chemistry," Journal of Medicinal Chemistry, 62(11):5276-5297.

Drilon et al., "Safety and preliminary clinical activity of NVL-520, a highly selective ROS1 inhibitor, in patients with advanced ROS1 fusion-positive solid tumors," 2022, Plenary Session 6: New Drugs on the Horizon, vol. 174, Supplement 1, S6-S7.

Patil et al., 2018, "The incidence of brain metastases in stage IV ROS1-rearranged non-small cell lung cancer and rate of central nervous system progression on crizotinib," J. Thorac. Oncol., 13(11):1717-1726.

Lin et al., 2021, "Spectrum of Mechanisms of Resistance to Crizotinib and Lorlatinib in ROS1 Fusion-Positive Lung Cancer," Clin. Canc. Res., 27(10):2899-2909.

Xalkori Prescribing Information Label (crizotinib), U.S. Food and Drug Administration: 47 pages (Revised Sep. 2023).

Hamilton et al., 2015, "Pharmacokinetics of crizotinib in NSCLC patients," Pharmacokinetics of crizotinib in NSCLC patients, Expert Opinion on Drug Metabolism & Toxicology, 11:5, 835-842.

Entrectinib Prescribing Information Label., U.S. Food and Drug Administration: 33 pages (Revised Jan. 2024).

Repotrectinib Prescribing Information Label., U.S. Food and Drug Administration: 22 pages (Revised Nov. 2023).

Bradeen et al., 2006, "Comparison of imatinib mesylate, dasatinib (BMS-354825), and nilotinib (AMN107) in an N-ethyl-N-nitrosourea (ENU)-based mutagenesis screen: high efficacy of drug combinations," Blood, 108(7):2332-2338.

Davare et al., 2013, "Foretinib is a potent inhibitor of oncogenic ROSI fusion proteins, " PNAS, 110(48):19519-19524.

Katayama et al., 2015, "Cabozantinib Overcomes Crizotinib Resistance in ROS1 Fusion-Positive Cancer," Clin Cancer Res, 21(1):166-174.

Drilon et al., 2024, "Repotrectinib in ROS1 Fusion-Positive Non-Small-Cell Lung Cancer," N Engl J Med, 390(2):118-131.

Mesaros et al., 2014, "Anaplastic lymphoma kinase inhibitors as anticancer therapeutics: a patent review," Expert Opin. Ther. Patents, 24(4):417-442.

\* cited by examiner

HETEROAROMATIC MACROCYCLIC ETHER CHEMOTHERAPEUTIC AGENTS

RELATED APPLICATIONS

This application is a divisional of U.S. patent application Ser. No. 17/524,169, filed Nov. 11, 2021; which is a continuation of International Patent Application No. PCT/US2021/030940, filed May 5, 2021; which claims priority pursuant to 35 U.S.C. § 365(b) to International Patent Application No. PCT/CN2020/088589, filed May 5, 2020; and claims the benefit of priority pursuant to 35 U.S.C. § 119(e) to U.S. Provisional Patent Application Nos. 63/125,747, filed Dec. 15, 2020, and 63/060,331, filed Aug. 3, 2020.

BACKGROUND

Receptor tyrosine kinases (RTKs) are cell surface enzymes that receive outside signals, such as whether to grow and divide, and transmit those signals in the cell through kinase activity. Many RTKs are proto-oncogenes; aberrant RTK activity can drive cell survival, growth and proliferation leading to cancer and related disorders. This aberrant kinase activity can be caused by mutations such as activating mutations in the kinase domain, gene rearrangements that result in fusion proteins containing the intact kinase domain, amplification and other means. RTK proto-oncogenes include ROS1, anaplastic lymphoma kinase (ALK), NTRK1 (encodes TRKA), NTRK2 (encodes TRKB), and NTRK3 (encodes TRKC).

ROS1 is an RTK proto-oncogene, with ROS1 rearrangements detected in non-small cell lung cancer (NSCLC), glioblastoma, inflammatory myofibroblastic tumor (IMT), cholangiocarcinoma, ovarian cancer, gastric cancer, colorectal cancer, angiosarcoma, and spitzoid melanoma. Oncogenic ROS1 gene fusions contain the kinase domain of ROS1 (3' region) fused to the 5' region of a variety of partner genes. Examples of ROS1 fusion partner genes observed in NSCLC include SLC34A2, CD74, TPM3, SDC4, EZR, LRIG3, KDELR2, CEP72, CLTL, CTNND2, GOPC, GPRC6A, LIMA1, LRIG3, MSN, MYO5C, OPRM1, SLC6A17 (putative), SLMAP, SRSF6, TFG, TMEM106B, TPD52L1, ZCCHC8 and CCDC6. Other fusion partners include CAPRIN1, CEP85L, CHCHD3, CLIP1 (putative), EEF1G, KIF21A (putative), KLC1, SART3, ST13 (putative), TRIM24 (putative), ERC1, FIPIL1, HLAA, KIAA1598, MYOSA, PPFIBP1, PWWP2A, FN1, YWHAE, CCDC30, NCOR2, NFKB2, APOB, PLG, RBP4, and GOLGB1.

ALK is an RTK proto-oncogene, with ALK rearrangements detected in many cancers, including NSCLC, anaplastic large cell lymphoma (ALCL), IMT, diffuse large B-cell lymphoma (DLBCL), esophageal squamous cell carcinoma (ESCC), renal medullary carcinoma, renal cell carcinoma, breast cancer, colon cancer, serous ovarian carcinoma, papillary thyroid cancer, and spitzoid tumors, and ALK activating mutations detected in neuroblastoma. Oncogenic ALK gene fusions contain the kinase domain of ALK (3' region) fused to the 5' region of more than 20 different partner genes, the most common being EML4 in NSCLC and NPM in ALCL. Other partner genes include TMP1, WDCP, GTF2IRD1, TPM3, TPM4, CLTC, LMNA, PRKARIA, RANBP2, TFG, FN1, KLC1, VCL, STRN, HIP1, DCTN1, SQSTM1, TPR, CRIM1, PTPN3, FBXO36, ATIC and KIF5B.

NTRK1, NTRK2 and NTRK3 are RTK proto-oncogenes that encode TRK-family kinases, with NTRK1, NTRK2 and NTRK3 chromosomal rearrangements detected at low frequency in many cancers. For treatment of ROS1-positive or ALK-positive patients, however, TRK inhibition, particularly in the central nervous system (CNS), has been associated with adverse reactions, including dizziness/ataxia/gait disturbance, paraesthesia, weight gain and cognitive changes.

Agents in the prior art used to treat oncogenic ROS1 and ALK have substantial deficiencies. These deficiencies may represent one or more of the following: associated TRK inhibition, limited CNS activity, and inadequate activity against resistance mutations.

Treatment of ROS1-positive or ALK-positive patients accompanied by TRK inhibition is associated with adverse reactions, particularly in the CNS, including dizziness/ataxia/gait disturbance, paraesthesia, weight gain and cognitive changes. Additionally, there is a need for CNS-penetrant and TRK-sparing inhibitors of the wild type ROS1 kinase domain and ROS1 with acquired resistance mutations occurring either individually or in combination, including G2032R, D2033N, S1986F, S1986Y, L2026M, L1951R, E1935G, L1947R, G1971E, E1974K, L1982F, F2004C, F2004V, E2020K, C2060G, F2075V, V2089M, V2098I, G2101A, D2113N, D2113G, L2155S, L2032K, and L2086F. Likewise, there is a need for CNS-penetrant and TRK-sparing inhibitors of ALK with acquired resistance mutations. A variety of ALK drug resistance mutations, occurring either individually or in combination, have been reported, including G1202R, L 1196M, G1269A, C1 156Y, I1 171T, 11171N, 11171S, F1174L, V1180L, S1206Y, E1210K, 1151Tins, F1174C, G1202del, D1203N, S1206Y, S1206C, L1152R, L1196Q, L1198P, L1198F, R1275Q, L1152P, C1156T, and F1245V.

SUMMARY

An aspect disclosed herein are compounds of Formula (I) or a pharmaceutically acceptable salt thereof:

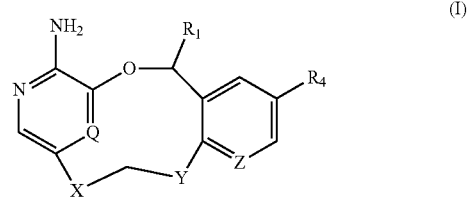

wherein
 Q is CH or N;
 Z is $CR_5$ or N;
 X is a 5-membered heteroarylene, comprising 1 to 3 heteroatoms selected from the group consisting of nitrogen, sulfur and oxygen; wherein the 5-membered heteroarylene is substituted with 0, 1, or 2 occurrences of R2;
 Y is a heteroarylene selected from the group consisting of 2*,3-substituted-furanylene, 2,3*-substituted-furanylene, 3*,4-substituted-furanylene, 1*,2-substituted-imidazolylene, 1*,5-substituted-imidazolylene, 1,5*-substituted-imidazolylene, 4,5*-substituted-1,2,3-oxadiazolylene, 3,4*-substituted-1,2-oxazolylene, 4*,5-substituted-1,2-oxazolylene, 4,5*-substituted-1,2-oxazolylene, 4,5-substituted-1,3-oxazolylene, 1*,2-substituted-phenylene, 1,5*-substituted-pyrazolylene, 4*,5-substituted-pyrazolylene, 3,4*-substituted-pyridazinylene, 4*,5-substituted-pyridazinylene, 2,3*-substituted-pyridinylene, 3*,4-substituted-pyridinylene, 3,4*-substituted-pyridinylene, 4,5*-substituted-pyrimidinylene, 1*,2-substituted-pyrrolylene, 1,2*-substituted-pyrrolylene, 2,3*-substituted-pyrrolylene, 3*,4-substituted-pyrrolylene, 4,5*-substituted-1,2,3-thiadiazolylene, 3,4*-substituted-1,2-thiazolylene, 4*,5-substituted-1,2-thiazolylene, 4,5*-substituted-1,2,3-thiadiazolylene, 3,4*-substituted-1,2-thiazolylene, 4*,5-substituted-1,2-thiazolylene, 4,5*-substituted-1,2-thiazolylene, 4,5*-substituted-1,3-thiazolylene, 2*,3-substituted-thiophenylene, 2,3*-substituted-thiophenylene, 3*,4-substituted-thiophenylene, 4,5*-substituted-1,2,3-triazinylene, 1,5*-substituted-1,2,3-triazolylene, and 3,4*-substituted-1,2,4-triazolylene; wherein the heteroarylene is substituted with 0, 1, or 2 occurrences of $R_3$;

* indicates the point of attachment of X or Y to the methylene group bonded to X and Y;

in Y the heteroarylene ring atom alpha to the point of attachment to the methylene group and beta to the point of attachment to the aromatic ring comprising Z is carbon, oxygen, or sulfur;

$R_1$ is selected from the group consisting of H, methyl, and hydroxymethyl;

each instance of $R_2$ is independently selected from the group consisting of CN, halo, $C_{1-4}$ alkoxy, $C_{1-4}$ alkyl, halo-$C_{1-4}$ alkyl, $C_{3-4}$ cycloalkylmethyl, $C_{3-6}$ cycloalkyl, and $C_{3-6}$ heterocyclyl;

each instance of $R_3$ is independently selected from the group consisting of H, halo, CN, $C_{1-4}$ alkoxy, halo-$C_{1-4}$ alkyl, and $C_{1-4}$ alkyl; and each of $R_4$ and $R_5$ is independently H or F; provided that the compound is not

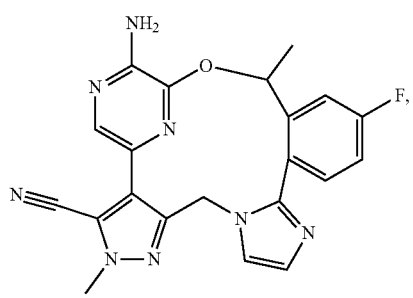

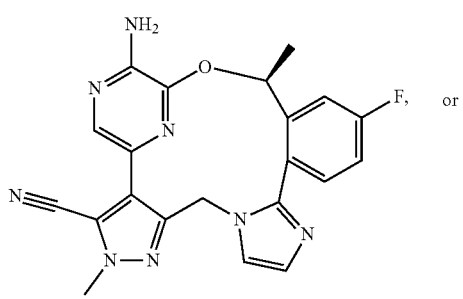

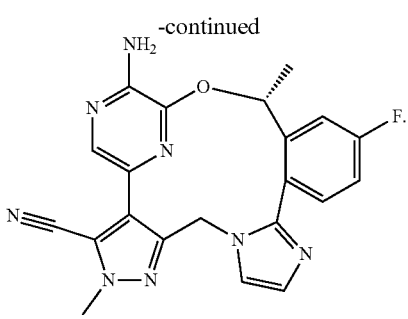

In certain embodiments, the present disclosure provides a pharmaceutical composition suitable for use in a subject in the treatment or prevention of cancer comprising an effective amount of any of the compounds described herein (e.g., a compound of the disclosure, such as a compound of Formula (I), or a pharmaceutically acceptable salt thereof, and one or more pharmaceutically acceptable excipients. In certain embodiments, the pharmaceutical preparations may be for use in treating or preventing a condition or disease as described herein.

An aspect of the disclosure is methods of treating cancer that is characterized by one or more mutations in the ROS1 or ALK genes, comprising administering to a subject in need thereof an effective amount of a compound as disclosed herein (e.g., a compound of Formula (I) or any of the embodiments thereof disclosed herein). In certain embodiments the compound is an inhibitor of ROS1, other embodiments the compound is an inhibitor of ALK, in additional embodiments the compound is an inhibitor of ROS1 and ALK. In certain aspects, the human subject is in need of such treatment.

These cancers include, but are not limited to, non-small cell lung cancer, inflammatory myofibroblastic tumor, ovarian cancer, spitzoid melanoma, glioblastoma, cholangiocarcinoma, gastric cancer, colorectal cancer, angiosarcoma, anaplastic large cell lymphoma, diffuse large B-cell lymphoma, esophageal squamous cell carcinoma, renal medullary carcinoma, renal cell carcinoma, breast cancer, papillary thyroid cancer, and neuroblastoma.

In some embodiments, the method of treating or preventing cancer may comprise administering a compound of Formula (I) conjointly with one or more other chemotherapeutic agent(s).

DETAILED DESCRIPTION

Definitions

Unless defined otherwise, all technical and scientific terms used herein have the meaning commonly understood by a person skilled in the art of the present disclosure. The following references provide one of skill with a general definition of many of the terms used in this disclosure: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

In some embodiments, chemical structures are disclosed with a corresponding chemical name. In case of conflict, the chemical structure controls the meaning, rather than the name.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited are not substantially changed by the presence of more than that which is recited, but excludes prior art embodiments.

Unless specifically stated or obvious from context, as used herein, the term "or" is understood to be inclusive. Unless specifically stated or obvious from context otherwise, as used herein, the terms "a", "an", and "the" are understood to be singular or plural.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-tirfluoroethyl, etc. $C_0$ alkyl indicates a hydrogen where the group is in a terminal position, a bond if internal. The terms "$C_{2-y}$alkenyl" and "$C_{2-y}$ alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

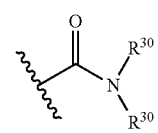

wherein each $R^{30}$ independently represents a hydrogen or hydrocarbyl group, or two $R^{30}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

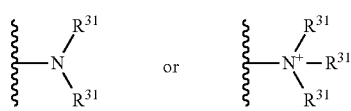

wherein each $R^{31}$ independently represents a hydrogen or a hydrocarbyl group, or two $R^{31}$ are taken together with the N atom to which they are attached complete a heterocycle having from 4 to 8 atoms in the ring structure. The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably, the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

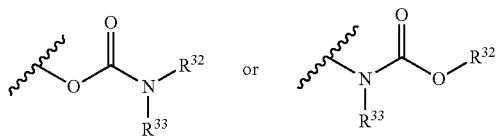

wherein $R^{32}$ and $R^{33}$ independently represent hydrogen or a hydrocarbyl group, such as an alkyl group, or $R^{32}$ and $R^{33}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond.

The term "carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "$C_{3-4}$ cycloalkylmethyl", as used herein, refers to a methyl group substituted with a carbocycle group containing 3 to 4 carbon atoms.

The term "carbonate" is art-recognized and refers to a group —$OCO_2$—$R^{34}$, wherein $R^{34}$ represents a hydrocarbyl group.

The term "carboxy", as used herein, refers to a group represented by the formula —$CO_2H$.

The term "ester", as used herein, refers to a group —$C(O)OR^{35}$ wherein $R^{35}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical.

Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The asterisk (*) notation on a heteroarylene ring moiety corresponding to X or Y in the compound of Formula (I) identifies the ring atom of the moiety bonded to the methylene group between X and Y, as exemplified below:

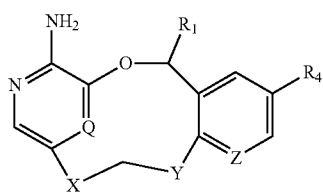

Formula (I)

For example, "1*, 5-substituted-imidazolylene" for Y means substituted:

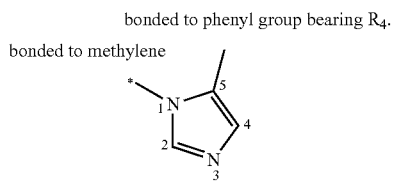

IUPAC numbering rules for heteroarylene rings are used throughout the specification to designate ring atom positions, as shown above. In this example, the 1-position of the imidazolylene is bonded to the methylene group, so it is indicated with the asterisk. The asterisk notation is used in both the names and structures of heteroarylenes for X and Y. Here, for Y the ring atom at the 5-position is not marked because it's bound to the phenyl group bearing variable $R_4$.

For X, an exemplary ring would be "1,5*-substituted-imidazolylene" as shown below.

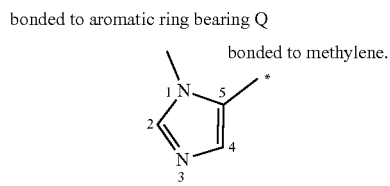

The ring atom bound to the methylene group (the 5-position in this example) is indicated with the asterisk in both the names and structures of ring X heteroarylenes. The ring atom bonded to the aromatic ring bearing Q is not marked.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a=O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a=O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO₃H, or a pharmaceutically acceptable salt thereof.

The term "sulfonamide" is art-recognized and refers to the group represented by the general formulae

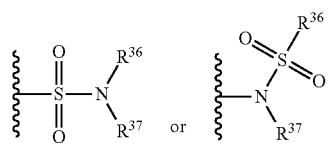

wherein $R^{36}$ and $R^{37}$ independently represent hydrogen or hydrocarbyl, such as alkyl, or $R^{36}$ and $R^{37}$ taken together with the intervening atom(s) complete a heterocycle having from 4 to 8 atoms in the ring structure.

The term "sulfoxide" is art-recognized and refers to the group —S(O)—$R^{38}$, wherein $R^{38}$ represents a hydrocarbyl.

The term "sulfonate" is art-recognized and refers to the group SO₃H, or a pharmaceutically acceptable salt thereof.

The term "sulfone" is art-recognized and refers to the group —S(O)₂—$R^{39}$, wherein $R^{39}$ represents a hydrocarbyl.

The term "thioalkyl", as used herein, refers to an alkyl group substituted with a thiol group.

The term "thioester", as used herein, refers to a group —C(O)S$R^{40}$ or —SC(O)$R^{4o}$ wherein $R^{10}$ represents a hydrocarbyl.

The term "thioether", as used herein, is equivalent to an ether, wherein the oxygen is replaced with a sulfur.

The term "urea" is art-recognized and may be represented by the general formula

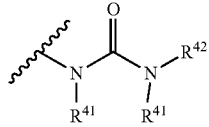

wherein $R^{41}$ and $R^{42}$ independently represent hydrogen or a hydrocarbyl, such as alkyl, or either occurrence of $R^{41}$ taken together with $R^{42}$ and the intervening atom(s) complete a heterocycle having from 4 to 8 atoms in the ring structure.

The term "protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3rd Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

In certain embodiments, compounds of the disclosure may be racemic. In certain embodiments, compounds of the disclosure may be enriched in one enantiomer. For example, a compound of the disclosure may have greater than about 30% ee, about 40% ee, about 50% ee, about 60% ee, about 70% ee, about 80% ee, about 90% ee, or even about 95% or greater ee. In certain embodiments, compounds of the disclosure may have more than one stereocenter. In certain such embodiments, compounds of the disclosure may be enriched in one or more diastereomer. For example, a compound of the disclosure may have greater than about 30% de, about 40% de, about 50% de, about 60% de, about 70% de, about 80% de, about 90% de, or even about 95% or greater de.

In certain embodiments, the therapeutic preparation may be enriched to provide predominantly one enantiomer of a compound (e.g., of Formula (I)). An enantiomerically enriched mixture may comprise, for example, at least about 60 mol percent of one enantiomer, or more preferably at least about 75, about 90, about 95, or even about 99 mol percent. In certain embodiments, the compound enriched in one enantiomer is substantially free of the other enantiomer, wherein substantially free means that the substance in question makes up less than about 10%, or less than about 5%, or less than about 4%, or less than about 3%, or less than about 2%, or less than about 1% as compared to the amount of the other enantiomer, e.g., in the composition or compound mixture. For example, if a composition or compound mixture contains about 98 grams of a first enantiomer and about 2 grams of a second enantiomer, it would be said to contain about 98 mol percent of the first enantiomer and only about 2% of the second enantiomer.

In certain embodiments, the therapeutic preparation may be enriched to provide predominantly one diastereomer of a compound (e.g., of Formula (I)). A diastereomerically enriched mixture may comprise, for example, at least about 60 mol percent of one diastereomer, or more preferably at least about 75, about 90, about 95, or even about 99 mol percent.

In some embodiments, a moiety in a compound exists as a mixture of tautomers. A "tautomer" is a structural isomer of a moiety or a compound that readily interconverts with another structural isomer. For example, a pyrazole ring has two tautomers:

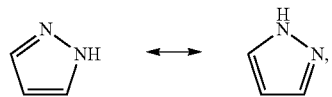

which differ in the positions of the pi-bonds and a hydrogen atom. Unless explicitly stated otherwise, a drawing of one tautomer of a moiety or a compound encompasses all of the possible tautomers.

The term "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys. Preferred subjects are humans.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample. These effects are also called "prophylactic" effects. Thus, as used herein and unless otherwise specified, the terms "prevention" and "preventing" refer to an approach for obtaining beneficial or desired results including, but not limited to, prophylactic benefit. For prophylactic benefit, a therapeutic can be administered to a patient at risk of developing a particular disease, or to a patient reporting one or more of the physiological symptoms of a disease, even though a diagnosis of this disease may not have been made. In one embodiment, a therapeutic is administered prior to clinical manifestation of the unwanted condition (e.g., disease or other unwanted state of the subject) for prophylactic benefit (e.g., it protects the subject against developing the unwanted condition).

As used herein and unless otherwise specified, the terms "treatment" and "treating" refer to therapeutic or palliative measures. Beneficial or desired clinical results include, but are not limited to, alleviation, in whole or in part, of symptoms associated with a disease or disorder or condition, diminishment of the extent of disease, stabilized (i.e., not worsening) state of disease, delay or slowing of disease progression, amelioration or palliation of the disease state (e.g., one or more symptoms of the disease), and remission (whether partial or total), whether detectable or undetectable. "Treatment" can also mean prolonging survival as compared to expected survival if not receiving treatment. In one embodiment, "treatment" comprises administration of a therapeutic after manifestation of the unwanted condition (i.e., it is intended to diminish, ameliorate, or stabilize the existing unwanted condition or side effects thereof).

The term "prodrug" is intended to encompass compounds which, under physiologic conditions, are converted into the therapeutically active agents of the present disclosure (e.g., a compound of Formula (I)). A common method for making a prodrug is to include one or more selected moieties which are hydrolyzed under physiologic conditions to reveal the desired molecule. In other embodiments, the prodrug is converted by an enzymatic activity of the subject. For example, esters or carbonates (e.g., esters or carbonates of alcohols or carboxylic acids) are preferred prodrugs of the present disclosure. In certain embodiments, some or all of the compounds of Formula (I) in a formulation represented above can be replaced with the corresponding suitable prodrug, e.g., wherein a hydroxyl in the parent compound is presented as an ester or a carbonate or carboxylic acid.

An "effective amount", as used herein, refers to an amount that is sufficient to achieve a desired biological effect. A "therapeutically effective amount", as used herein, refers to an amount that is sufficient to achieve a desired therapeutic effect. For example, a therapeutically effective amount can refer to an amount that is sufficient to improve at least one sign or symptom of cancer.

A "response" to a method of treatment can include a decrease in or amelioration of negative symptoms, a decrease in the progression of a disease or symptoms thereof, an increase in beneficial symptoms or clinical outcomes, a lessening of side effects, stabilization of disease, partial or complete remedy of disease, among others.

As used herein and unless otherwise indicated, the term "relapsed" refers to a disorder, disease, or condition that responded to prior treatment (e.g., achieved a complete response) then had progression. The prior treatment can include one or more lines of therapy.

As used herein and unless otherwise indicated, the term "refractory" refers to a disorder, disease, or condition that has not responded to prior treatment that can include one or more lines of therapy.

Compounds

In one aspect, provided herein is a compound of Formula (I), or an enantiomer, a mixture of enantiomers, or a tautomer thereof, or a pharmaceutically acceptable salt thereof:

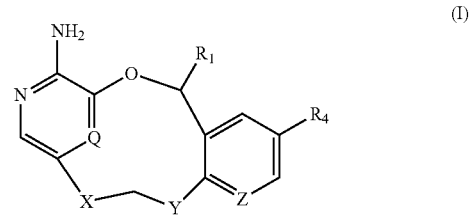

wherein
Q is CH or N;
Z is $CR_5$ or N;
X is a 5-membered heteroarylene, comprising 1 to 3 heteroatoms selected from the group consisting of nitrogen, oxygen and sulfur; wherein the 5-membered heteroarylene is substituted with 0, 1, or 2 occurrences of $R_2$;
Y is a 5- or 6-membered heteroarylene, comprising 1 to 3 heteroatoms selected from the group consisting of nitrogen, oxygen and sulfur; wherein the 5- or 6-membered heteroarylene is substituted with 0, 1, or 2 occurrences of $R_3$;
in Y, the point of attachment to the methylene group bonded to X and Y and the point of attachment to the aromatic ring comprising Z are on adjacent atoms, and the 5- or 6-membered heteroarylene ring atom alpha to the point of attachment to the methylene group and beta to the point of attachment to the aromatic ring comprising Z is carbon, oxygen, or sulfur;
$R_1$ is selected from the group consisting of H, methyl, and hydroxymethyl;
each instance of $R_2$ is independently selected from the group consisting of H, CN, halo, $C_{1-4}$ alkoxy, $C_{1-4}$ alkyl, halo-$C_{1-4}$ alkyl, $C_{3-4}$ cycloalkylmethyl, $C_{3-6}$ cycloalkyl, and $C_{3-6}$ heterocyclyl;
each instance of $R_3$ is independently selected from the group consisting of H, halo, CN, $C_{1-4}$ alkoxy, halo-$C_{1-4}$ alkyl, and $C_{1-4}$ alkyl; and
each of $R_4$ and $R_5$ is independently H or F;
provided that X is not 3*,4-substituted-pyrazolylene, where * indicates the point of attachment of X or Y to the methylene group bonded to X and Y.

In one aspect, disclosed is a compound of Formula (I) or a pharmaceutically acceptable salt thereof:

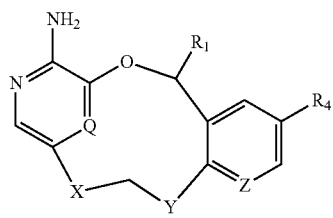

(I)

wherein

Q is CH or N;

Z is CR₅ or N;

X is a 5-membered heteroarylene, comprising 1 to 3 heteroatoms selected from the group consisting of nitrogen, sulfur and oxygen; wherein the 5-membered heteroarylene is substituted with 0, 1, or 2 occurrences of $R_2$;

Y is a heteroarylene selected from the group consisting of 2*,3-substituted-furanylene, 2,3*-substituted-furanylene, 3*,4-substituted-furanylene, 1*,2-substituted-imidazolylene, 1*,5-substituted-imidazolylene, 1,5*-substituted-imidazolylene, 4,5*-substituted-1,2,3-oxadiazolylene, 3,4*-substituted-1,2-oxazolylene, 4*,5-substituted-1,2-oxazolylene, 4,5*-substituted-1,2-oxazolylene, 4,5*-substituted-1,3-oxazolylene, 1*,2-substituted-phenylene, 1,5*-substituted-pyrazolylene, 4*,5-substituted-pyrazolylene, 3,4*-substituted-pyridazinylene, 4*,5-substituted-pyridazinylene, 2,3*-substituted-pyridinylene, 3*,4-substituted-pyridinylene, 3,4*-substituted-pyridinylene, 4,5*-substituted-pyrimidinylene, 1*,2-substituted-pyrrolylene, 1,2*-substituted-pyrrolylene, 2,3*-substituted-pyrrolylene, 3*,4-substituted-pyrrolylene, 4,5*-substituted-1,2,3-thiadiazolylene, 3,4*-substituted-1,2-thiazolylene, 4*,5-substituted-1,2-thiazolylene, 4,5*-substituted-1,2-thiazolylene, 4,5*-substituted-1,3-thiazolylene, 2*,3-substituted-thiophenylene, 2,3*-substituted-thiophenylene, 3*,4-substituted-thiophenylene, 4,5*-substituted-1,2,3-triazinylene, 1,5*-substituted-1,2,3-triazolylene, and 3,4*-substituted-1,2,4-triazolylene; wherein the heteroarylene is substituted with 0, 1, or 2 occurrences of $R_3$;

* indicates the point of attachment of X or Y to the methylene group bonded to X and Y;

in Y the heteroarylene ring atom alpha to the point of attachment to the methylene group and beta to the point of attachment to the aromatic ring comprising Z is carbon, oxygen, or sulfur;

$R_1$ is selected from the group consisting of H, methyl, and hydroxymethyl;

each instance of $R_2$ is independently selected from the group consisting of H, CN, halo, $C_{1-4}$ alkoxy, $C_{1-4}$ alkyl, halo-$C_{1-4}$ alkyl, $C_{3-4}$ cycloalkylmethyl, $C_{3-6}$ cycloalkyl, and $C_{3-6}$ heterocyclyl;

each instance of $R_3$ is independently selected from the group consisting of H, halo, CN, $C_{1-4}$ alkoxy, halo-$C_{1-4}$ alkyl, and $C_{1-4}$ alkyl; and each of $R_4$ and $R_5$ is independently H or F;

provided that the compound is not

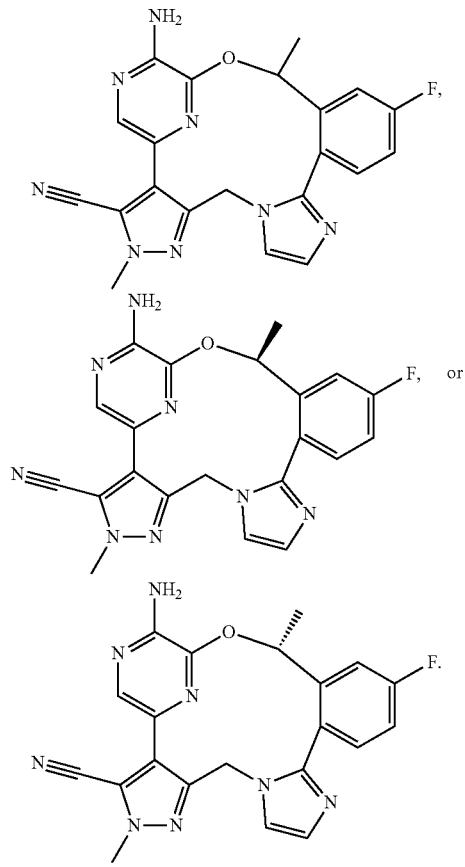

In some embodiments, X is a 5-membered heteroaryl selected from the group consisting of pyrazolylene, isoxazolylene, isothiazolylene, imidazolylene, and triazolylene. In some embodiments, X is selected from the group consisting of pyrazolylene and triazolylene. In certain embodiments, X is selected from the group consisting of 4*,5-substituted-pyrazolylene, 4,5*-substituted-pyrazolylene, 1*,5-substituted-pyrazolylene, 4*,5-substituted-isoxazolylene, 3*,4-substituted-isoxazolylene, 3*,4-substituted-isothiazolylene, 4*,5-substituted-isothiazolylene, 4*,5-substituted-imidazolylene, 1*,5-substituted-imidazolylene, 1*,5-substituted-triazolylene, and 4*,5-substituted-triazolylene.

In some embodiments, X is a 5-membered heteroaryl selected from the group consisting of pyrazolylene, isoxazolylene, isothiazolylene, imidazolylene, and triazolylene. In some embodiments, X is selected from the group consisting of pyrazolylene and triazolylene. In certain embodiments, X is selected from the group consisting of 4*,5-substituted-pyrazolylene, 4,5*-substituted-pyrazolylene, 1*,5-substituted-pyrazolylene, 4*,5-substituted-isoxazolylene, 4,5*-substituted-isoxazolylene, 3*,4-substituted-isoxazolylene, 3*,4-substituted-isothiazolylene, 4*,5-substituted-isothiazolylene, 4*,5-substituted-imidazolylene, 1*,5-substituted-imidazolylene, 1*,5-substituted-triazolylene, and 4*,5-substituted-triazolylene.

In certain embodiments, X is selected from the group consisting of:

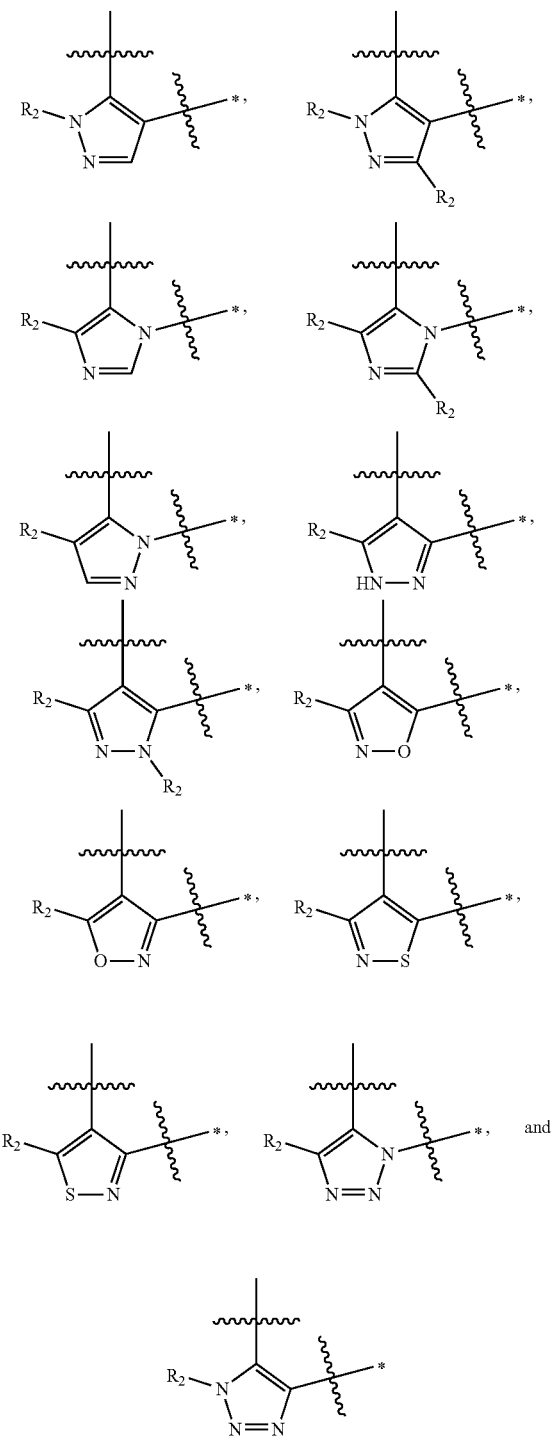

* indicates the point of attachment of X to the methylene group bonded to X and Y; and
$R_2$ is independently selected from the group consisting of H, CN, halo, $C_{1-4}$ alkoxy, $C_{1-4}$ alkyl, halo-$C_{1-4}$ alkyl, $C_{3-4}$ cycloalkylmethyl, $C_{3-6}$ cycloalkyl, and $C_{3-6}$ heterocyclyl.

In one embodiment, X is a pyrazolylene. In one embodiment, X is not 3*,4-$R_2$ substituted-pyrazolylene. In one embodiment, X is not

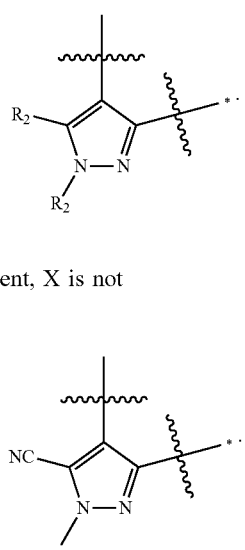

In one embodiment, X is not

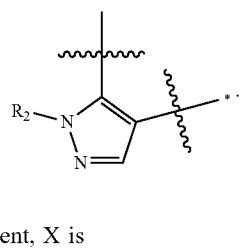

In another embodiment, X is 3*,4-substituted-pyrazolylene.
In another embodiment, X is 4*,5-substituted-pyrazolylene.
In another embodiment, X is 4,5*-substituted-pyrazolylene.
In another embodiment, X is 1*,5-substituted-pyrazolylene.
In one embodiment, X is

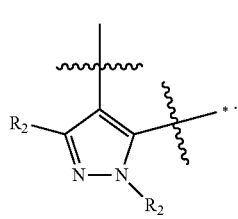

In one embodiment, X is

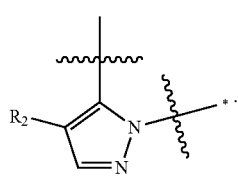

In one embodiment, X is

In one embodiment, X is isoxazolylene. In one embodiment, X is 4*,5-substituted-isoxazolylene. In one embodiment, X is 4,5*-substituted-isoxazolylene. In one embodiment, X is 3*,4-substituted-isoxazolylene. In one embodiment, X is

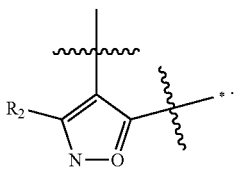

In one embodiment, X is

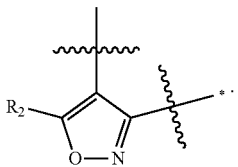

In one embodiment, X is isothiazolylene. In one embodiment, X is 3*,4-substituted-isothiazolylene. In one embodiment, X is 4*,5-substituted-isothiazolylene. In one embodiment, X is 4,5*-substituted-isothiazolylene. In one embodiment, X is

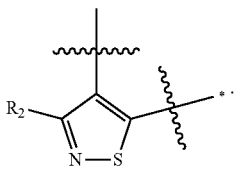

In one embodiment, X is

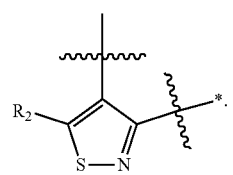

In one embodiment, X is imidazolylene. In one embodiment, X is 4*,5-substituted-imidazolylene. In one embodiment, X is 1*,5-substituted-imidazolylene. In one embodiment, X is

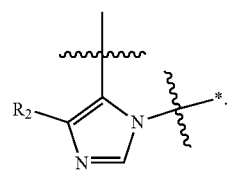

In one embodiment, X is triazolylene. In one embodiment, X is 1*,5-substituted-triazolylene. In one embodiment, X is 4*,5-substituted-triazolylene. In one embodiment, X is

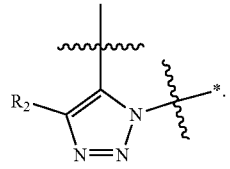

In one embodiment, X is

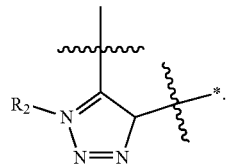

In one embodiment, X is substituted with 0 occurrence of $R_2$ (i.e., all open positions on X are H). In one embodiment, X is substituted with 1 occurrence of $R_2$ that is not H. In one embodiment, X is substituted with 2 occurrences of $R_2$ that are not H.

$R_2$ is independently selected from the group consisting of H, halo, CN, $C_{1-4}$ alkoxy, $C_{1-4}$ alkyl, halo-$C_{1-4}$ alkyl, $C_{3-4}$ cycloalkylmethyl, $C_{3-6}$ cycloalkyl, and $C_{3-6}$ heterocycloalkyl. In one embodiment, $R_2$ is not H. In one embodiment, $R_2$ is $C_{1-4}$ alkyl. In one embodiment, $R_2$ is methyl. In one embodiment, $R_2$ is ethyl. In one embodiment, $R_2$ is isopropyl. In one embodiment, $R_2$ is cyclopropyl. In one embodiment, $R_2$ is cyclobutyl. In one embodiment, $R_2$ is cyclopropylmethyl. In one embodiment, $R_2$ is —$CHF_2$. In one embodiment, $R_2$ is —$CH_2CHF_2$. In one embodiment, $R_2$ is halo. In one embodiment, $R_2$ is fluoro. In one embodiment, $R_2$ is chloro. In one embodiment, $R_2$ is CN. In one embodiment, $R_2$ is methoxy.

In certain embodiments, X is selected from the group consisting of

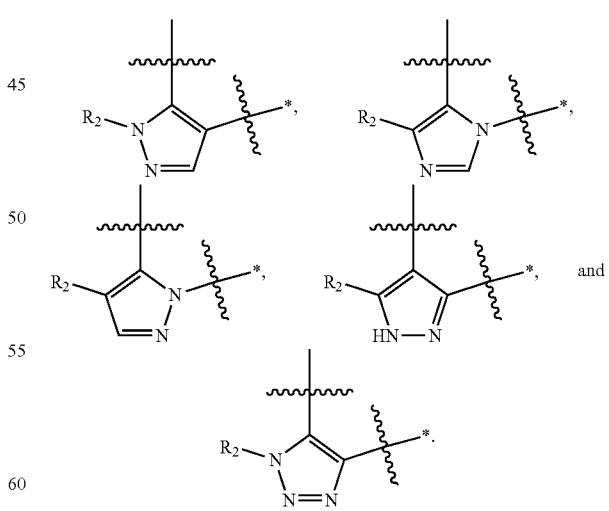

In some embodiments, Y is selected from the group consisting of 4*,5-substituted pyrazolylene, 1,5*-substituted pyrazolylene, 3,4*-substituted pyrazolylene, 1*,2-substituted imidazolylene, 5*,1-substituted imidazolylene, 4,5*-substituted 1,3-thiazolylene, 3,4*-substituted 1,2-oxazolylene, 4*,5-substituted 1,2-oxazolylene, 3,4*-substituted 1,2-thiazolylene, 4*,5-substituted 1,2-thiazolylene, 2,3*-substituted pyridinylene, 3*,4-substituted pyridinylene, 4*,3-substituted pyridinylene, 4,5*-substituted pyrimidinylene, 1,5*-substituted 1,2,3-triazolylene, and 3,4*-substituted 1,2,4-triazolylene.

In certain embodiments, Y is selected from the group consisting of

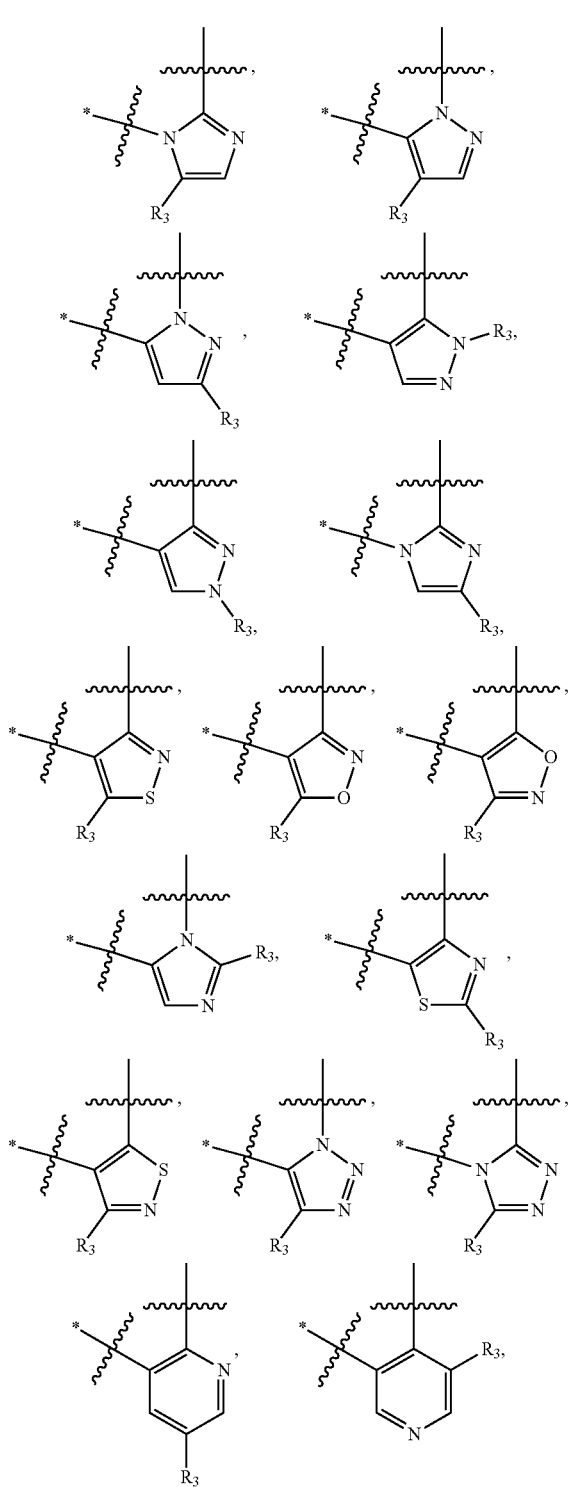

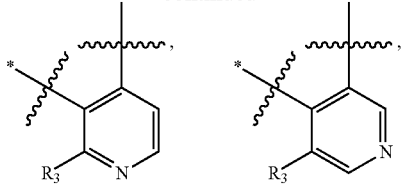

-continued

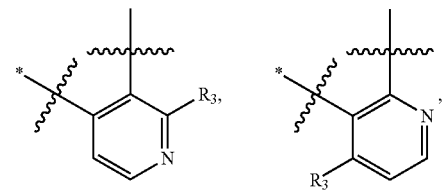

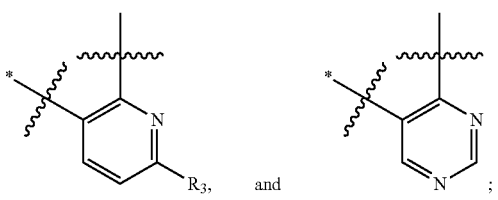

\* indicates the point of attachment of Y to the methylene group bonded to X and Y; and $R_3$ is selected from the group consisting of H, halo, CN, $C_{1-4}$alkoxy, halo-$C_{1-4}$ alkyl, and $C_{1-4}$ alkyl.

In one embodiment, Y is a 5-membered heteroarylene. In one embodiment, Y is pyrazolylene. In one embodiment, Y is 1,5*-substituted pyrazolylene. In one embodiment, Y is 4*,5-substituted pyrazolylene. In one embodiment, Y is 3,4*-substituted pyrazolylene.

In one embodiment, Y is

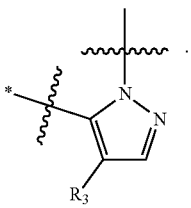

In one embodiment, Y is

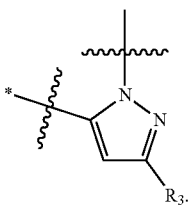

In one embodiment, Y is

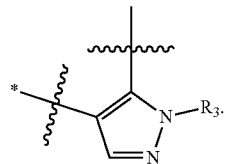

In one embodiment, Y is

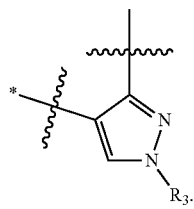

In one embodiment, Y is imidazolylene. In one embodiment, Y is 1*,2-substituted imidazolylene. In one embodiment, Y is 5*,1-substituted imidazolylene. In one embodiment, Y is

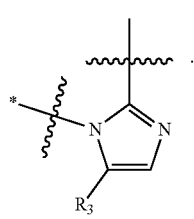

In one embodiment, Y is

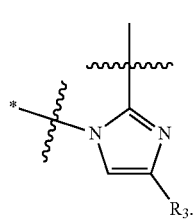

In one embodiment, Y is

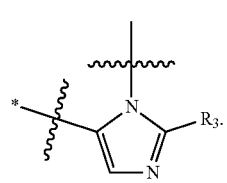

In one embodiment, Y is 1,2-thiazolylene. In one embodiment, Y is 3,4*-substituted 1,2-thiazolylene. In one embodiment, Y is 4*,5-substituted 1,2-thiazolylene. In one embodiment, Y is

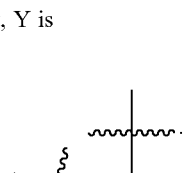

In one embodiment Y is

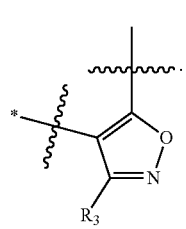

In one embodiment, Y is 1,3-thiazolylene. In one embodiment, Y is 4,5*-substituted 1,3-thiazolylene. In one embodiment, Y is In one embodiment, Y is 1,2-oxazolylene. In one embodiment, Y is 3,4*-substituted 1,2-oxazolylene. In one embodiment, Y is 4*,5-substituted 1,2-oxazolylene. In one embodiment, Y is In one embodiment, Y is In one embodiment, Y is triazolylene. In one embodiment, Y is 1,5*-substituted 1,2,3-triazolylene. In one embodiment, Y is 3,4*-substituted 1,2,4-triazolylene. In one embodiment, Y is

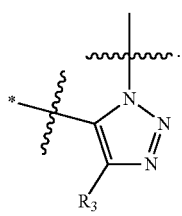

In one embodiment, Y is

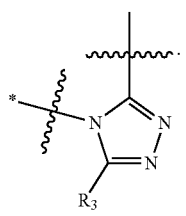

In one embodiment, Y is a 6-membered heteroarylene. In one embodiment, Y is pyridinylene. In one embodiment, Y is 2,3*-substituted pyridinylene. In one embodiment, Y is 3*,4-substituted pyridinylene. In one embodiment, Y is 4*,3-substituted pyridinylene. In one embodiment, Y is

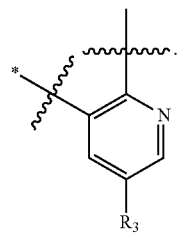

In one embodiment, Y is

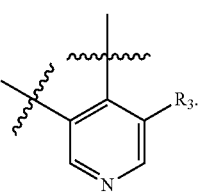

embodiment Y is

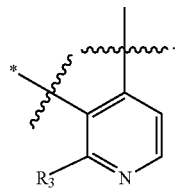

In one embodiment, Y is

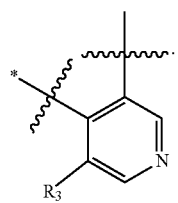

In one embodiment, Y is

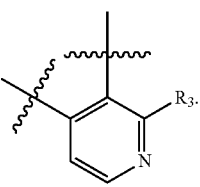

In one embodiment, Y is

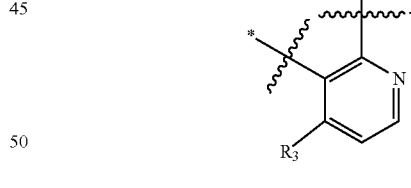

In one embodiment, Y is

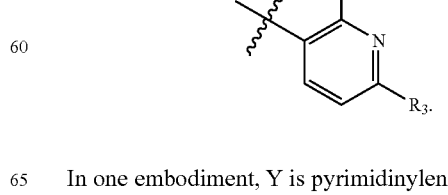

In one embodiment, Y is pyrimidinylene. In one embodiment, Y is 4,5*-substituted pyrimidinylene. In one embodiment, Y is

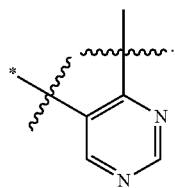

In one embodiment, Y is substituted with 0 occurrence of $R_3$ (i.e., all open positions on Y are H). In one embodiment, Y is substituted with 1 occurrence of $R_3$ that is not H. In one embodiment, Y is substituted with 2 occurrences of $R_3$ that are not H.

In one embodiment, $R_3$ is selected from the group consisting of H, halo, CN, $C_{1-4}$ alkoxy, halo-$C_{1-4}$ alkyl, and $C_{1-4}$ alkyl. In one embodiment, $R_3$ is not H. In one embodiment, $R_3$ is $C_{1-4}$ alkyl. In one embodiment, $R_3$ is methyl. In one embodiment, $R_3$ is ethyl. In one embodiment, $R_3$ is halo. In one embodiment, $R_3$ is flouro. In one embodiment, $R_3$ is chloro. In one embodiment, $R_3$ is CN.

In one embodiment, X is a pyrazolylene provided herein (e.g., a 4*,5-substituted-pyrazolylene provided herein), and Y is a pyrazolylene provided herein. In another embodiment, Y is an imidazolylene provided herein. In another embodiment, Y is a 1,2-thiazolylene provided herein. In another embodiment, Y is a 1,3-thiazolylene provided herein. In another embodiment, Y is a 1,2-oxazolylene provided herein. In another embodiment, Y is a triazolylene provided herein. In another embodiment, Y is a pyridinylene provided herein. In another embodiment, Y is a pyrimidinylene provided herein.

In one embodiment, X is an isoxazolylene provided herein, and Y is a pyrazolylene provided herein. In another embodiment, Y is an imidazolylene provided herein. In another embodiment, Y is a 1,2-thiazolylene provided herein. In another embodiment, Y is a 1,3-thiazolylene provided herein. In another embodiment, Y is a 1,2-oxazolylene provided herein. In another embodiment, Y is a triazolylene provided herein. In another embodiment, Y is a pyridinylene provided herein. In another embodiment, Y is a pyrimidinylene provided herein.

In one embodiment, X is an isothiazolylene provided herein, and Y is a pyrazolylene provided herein. In another embodiment, Y is an imidazolylene provided herein. In another embodiment, Y is a 1,2-thiazolylene provided herein. In another embodiment, Y is a 1,3-thiazolylene provided herein. In another embodiment, Y is a 1,2-oxazolylene provided herein. In another embodiment, Y is a triazolylene provided herein. In another embodiment, Y is a pyridinylene provided herein. In another embodiment, Y is a pyrimidinylene provided herein.

In one embodiment, X is an imidazolylene provided herein, and Y is a pyrazolylene provided herein. In another embodiment, Y is an imidazolylene provided herein. In another embodiment, Y is a 1,2-thiazolylene provided herein. In another embodiment, Y is a 1,3-thiazolylene provided herein. In another embodiment, Y is a 1,2-oxazolylene provided herein. In another embodiment, Y is a triazolylene provided herein. In another embodiment, Y is a pyridinylene provided herein. In another embodiment, Y is a pyrimidinylene provided herein.

In one embodiment, X is a triazolylene provided herein, and Y is a pyrazolylene provided herein. In another embodiment, Y is an imidazolylene provided herein. In another embodiment, Y is a 1,2-thiazolylene provided herein. In another embodiment, Y is a 1,3-thiazolylene provided herein. In another embodiment, Y is a 1,2-oxazolylene provided herein. In another embodiment, Y is a triazolylene provided herein. In another embodiment, Y is a pyridinylene provided herein. In another embodiment, Y is a pyrimidinylene provided herein.

In some embodiments, Q is CH. In other embodiments, Q is N.

In some embodiments, Z is $CR_5$. In particular embodiments, $R_5$ is H. In particular embodiments, $R_5$ is F. In other embodiments, Z is N.

In some embodiments, $R_4$ is H. In other embodiments, $R_4$ is F.

In some embodiments, the compound of Formula (I) has the structure (I-A):

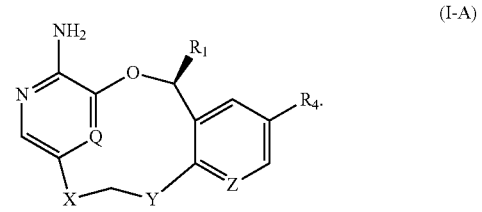

(I-A)

In other embodiments, the compound of Formula (I) has the structure (I-B):

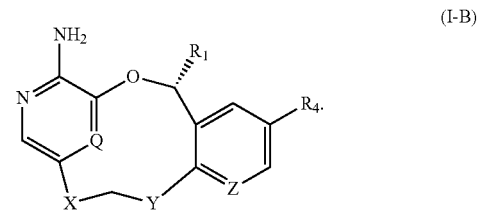

(I-B)

In one embodiment, the compound is a compound of any one of the following formulas, or an enantiomer, a mixture of enantiomers, or a tautomer thereof, or a pharmaceutically acceptable salt thereof:

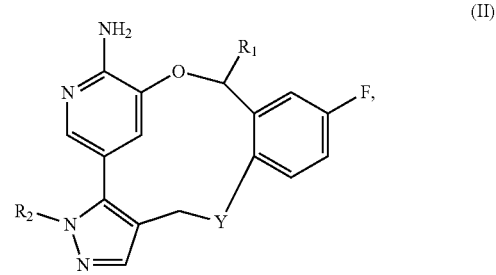

(II)

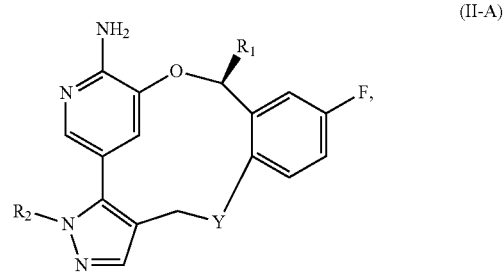

(II-A)

-continued
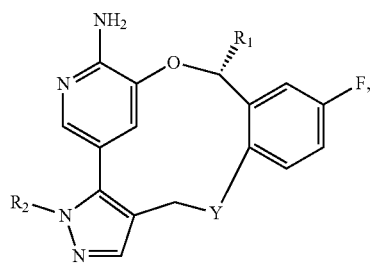
(II-B)
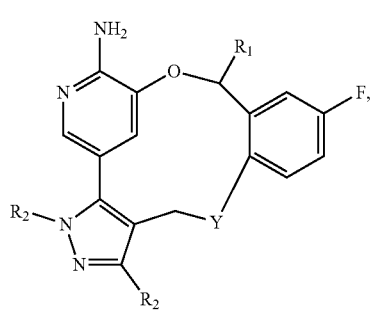
(III)
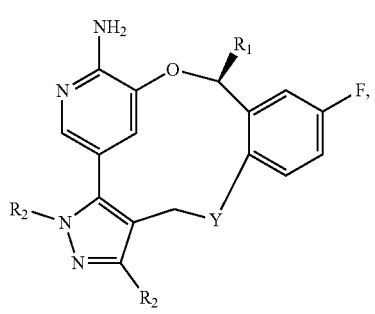
(III-A)
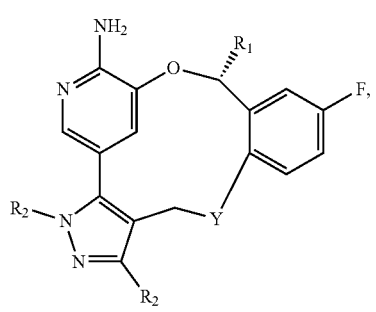
(III-B)
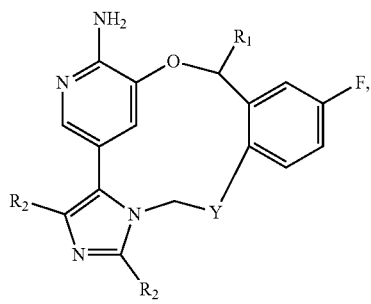
(IV)
-continued
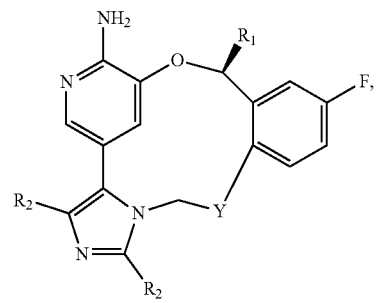
(IV-A)
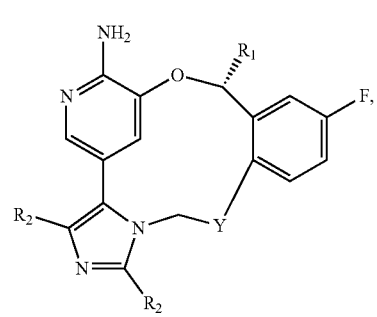
(IV-B)
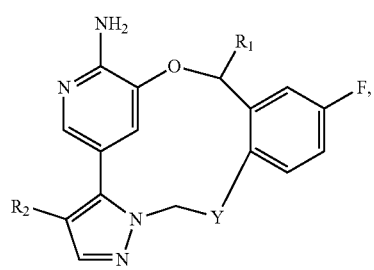
(V)
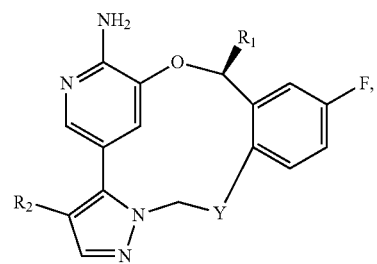
(V-A)
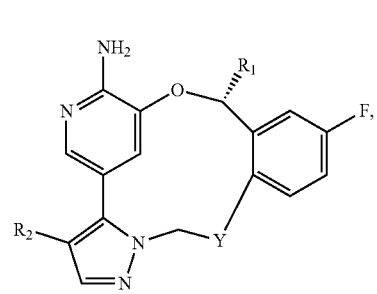
(V-B)

-continued (VI)
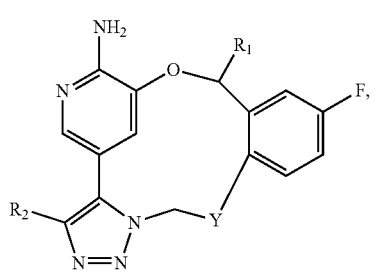

(VI-A)
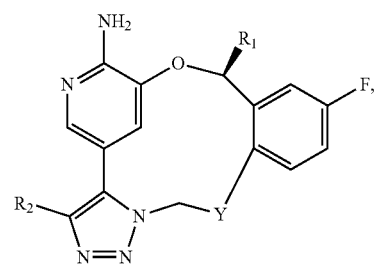

(VI-B)
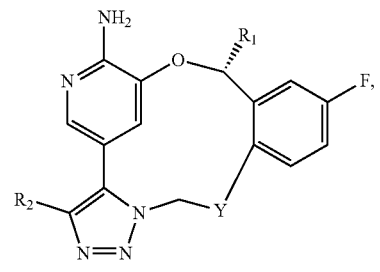

(VII)
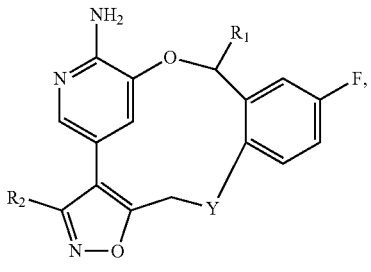

(VII-A)
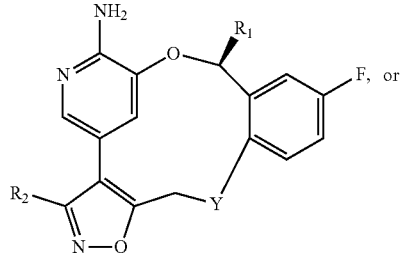

(VII-B)
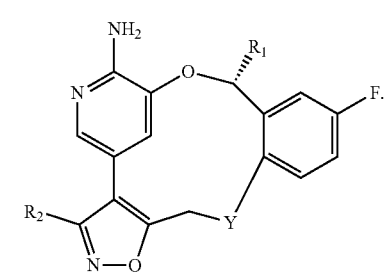

In certain embodiments, $R_2$ is each independently selected from the group consisting of H, CN, methyl, ethyl, isopropyl, chloro, methoxy, trifluoromethyl, 2-fluoroethyl, difluoromethyl, 2,2-difluoroethyl, 2,2,2-trifluoroethyl, cyclopropylmethyl, 5 cyclobutyl, and oxetanyl.

In certain embodiments, $R_3$ is selected from the group consisting of H, fluoro, chloro, bromo, CN, methoxy, difluoromethyl, trifluoromethyl, methyl, and ethyl.

In certain embodiments the compound is selected from the group consisting of:

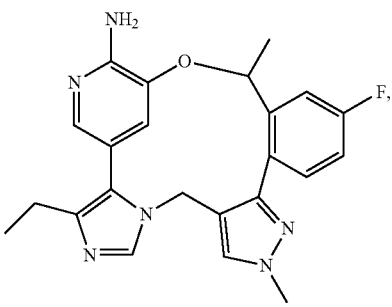

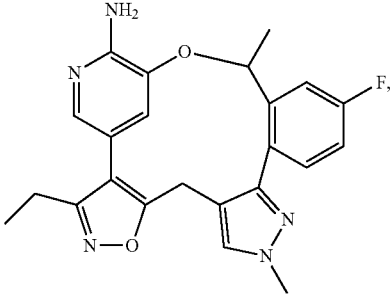

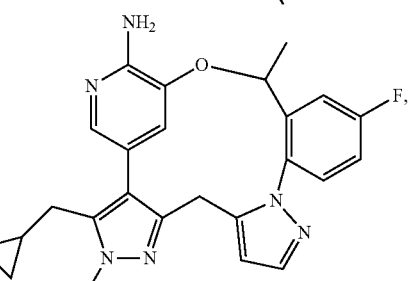

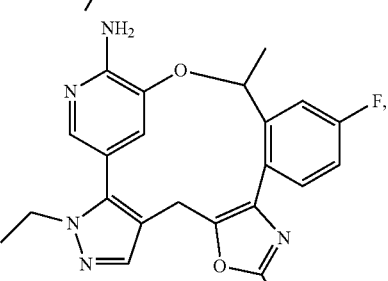

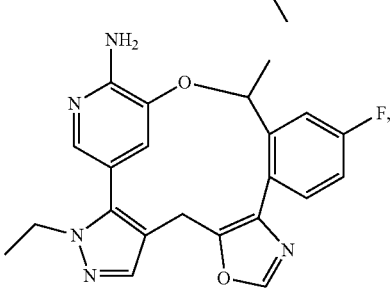

-continued
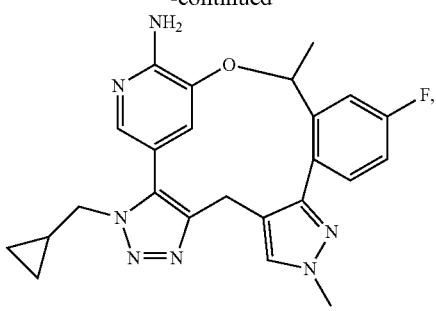
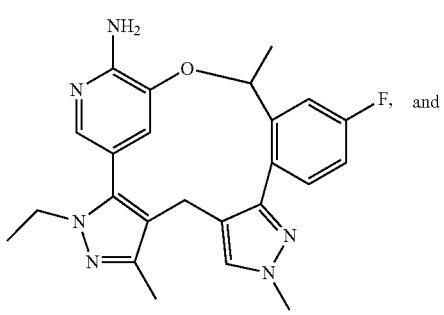
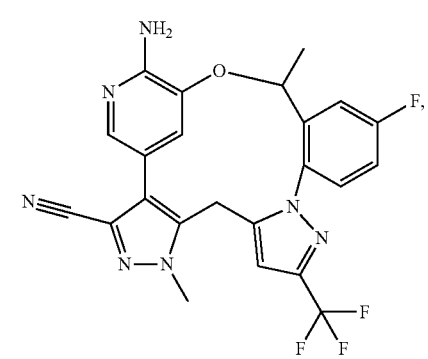
or an enantiomer, a mixture of enantiomers, or a tautomer thereof, or a pharmaceutically acceptable salt thereof.
In certain embodiments the compound is selected from the group consisting of:
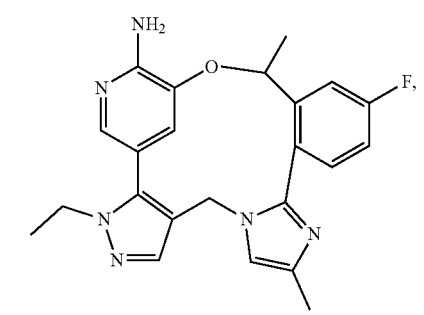
-continued
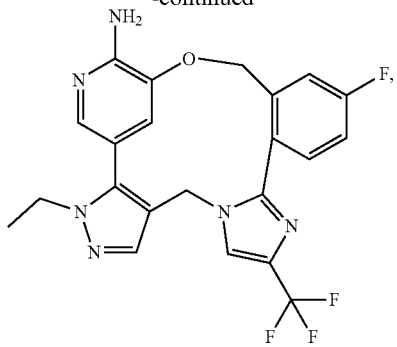
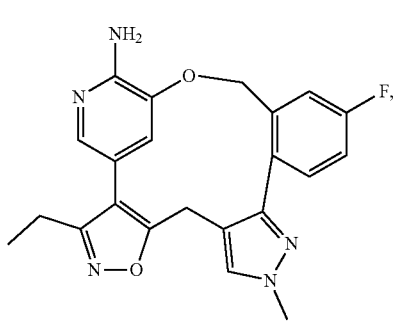
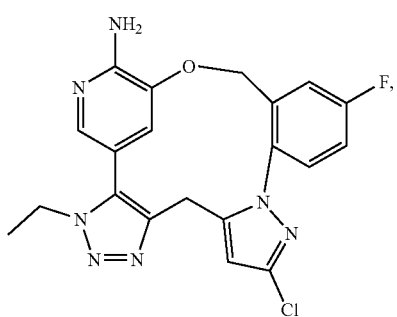
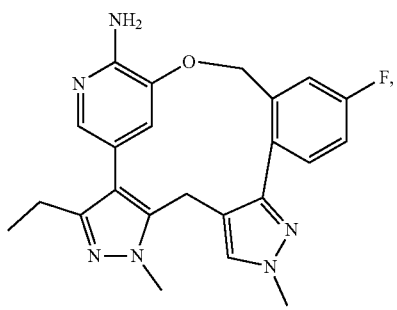
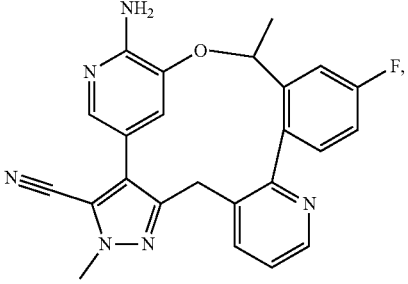

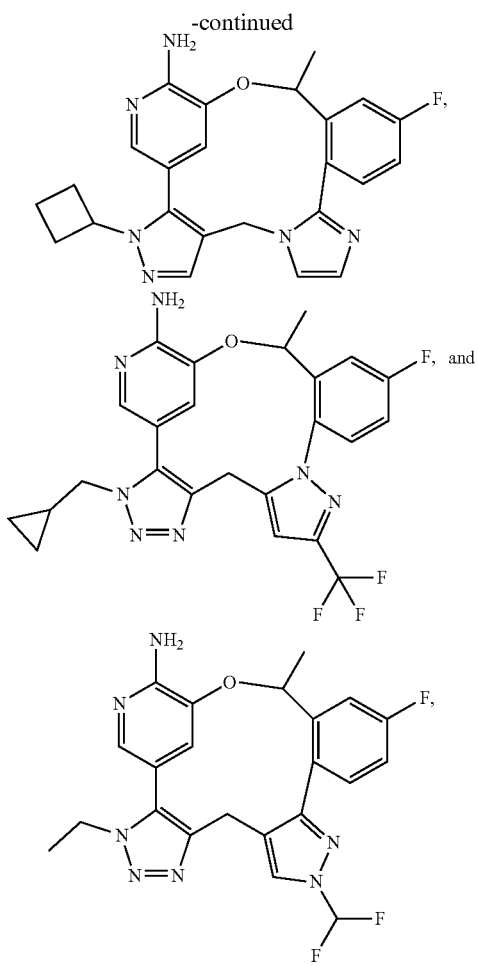
or an enantiomer, a mixture of enantiomers, or a tautomer thereof, or a pharmaceutically acceptable salt thereof.
In certain embodiments the compound is selected from the group consisting of:
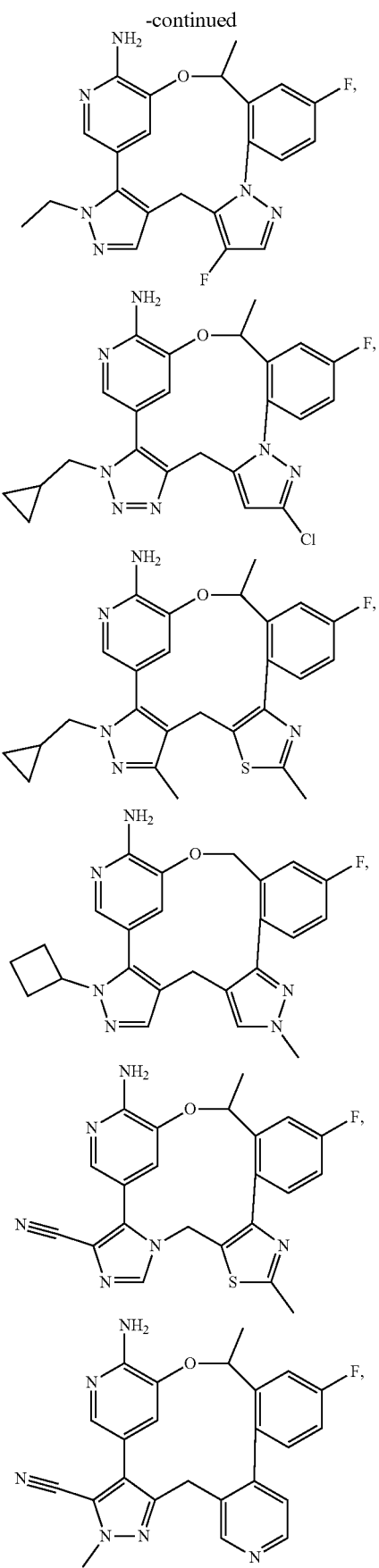

-continued
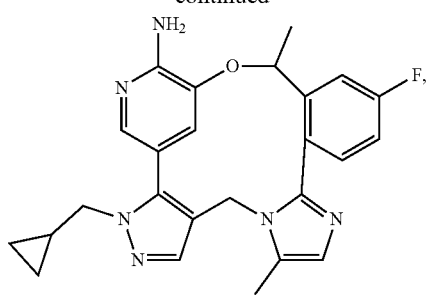
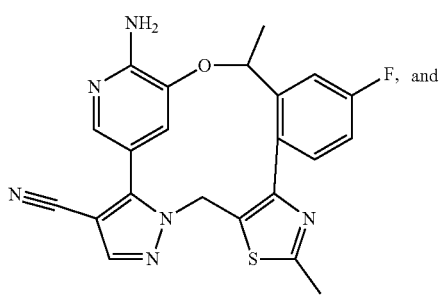
F, and
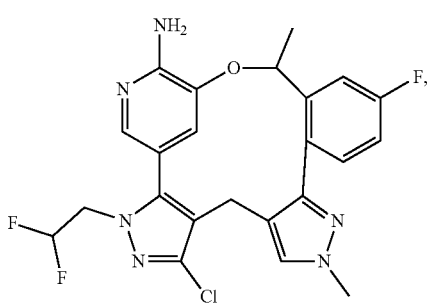 [SMILES: CC1Oc2cc(cnc2N)-c2c(c(Cl)nn2CC(F)F)Cc2cn(C)nc2-c2ccc(F)cc21]
or an enantiomer, a mixture of enantiomers, or a tautomer thereof, or a pharmaceutically acceptable salt thereof.
In certain embodiments the compound is selected from the group consisting of:
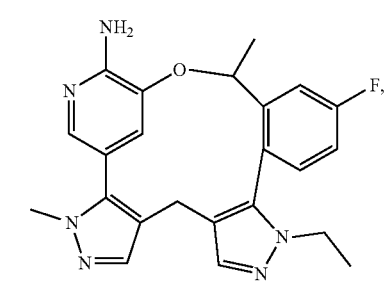
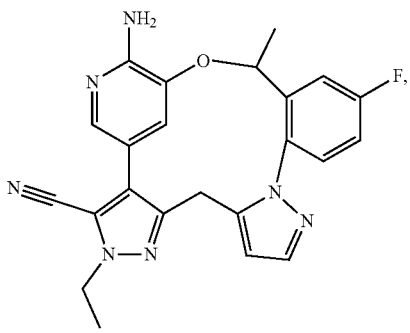
-continued
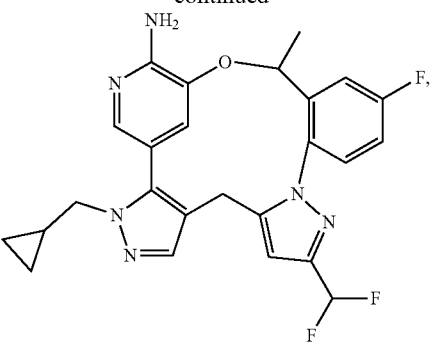
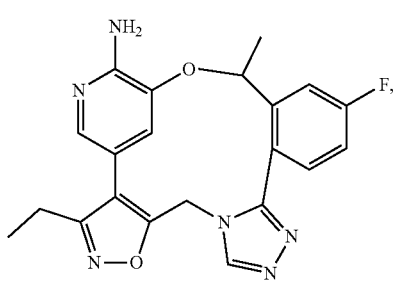
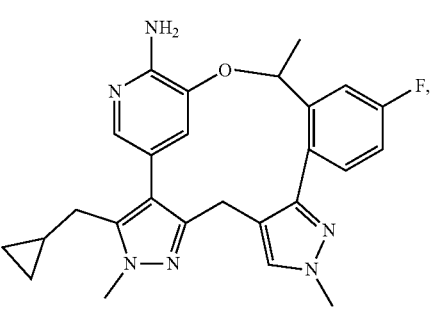
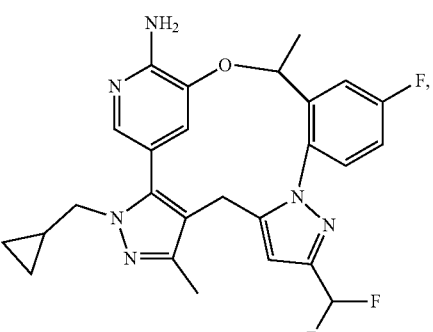
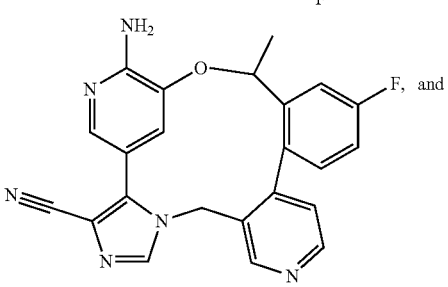
F, and

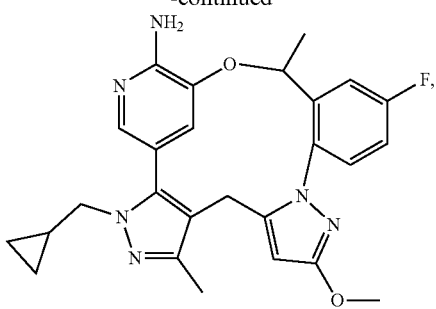
or an enantiomer, a mixture of enantiomers, or a tautomer thereof, or a pharmaceutically acceptable salt thereof.
In certain embodiments the compound is selected from the group consisting of:
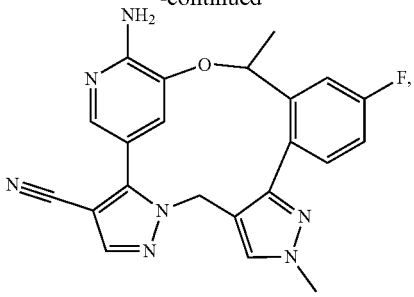
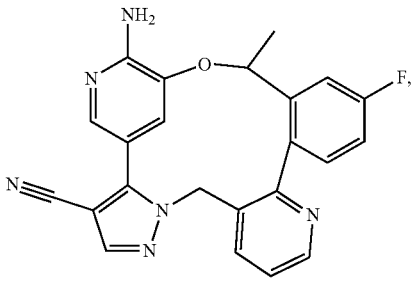
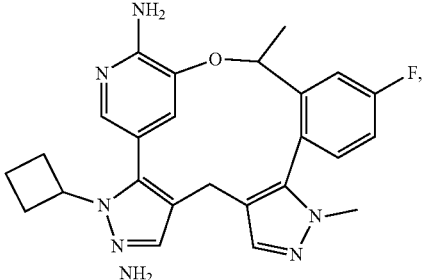
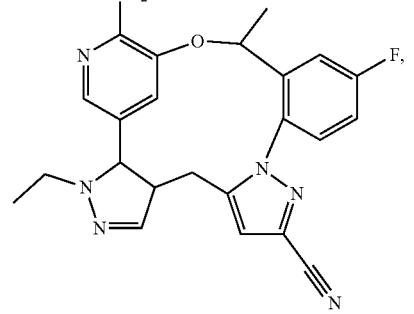

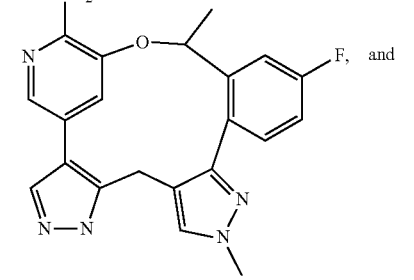

41
-continued
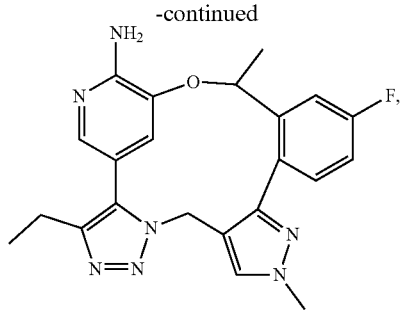
or an enantiomer, a mixture of enantiomers, or a tautomer thereof, or a pharmaceutically acceptable salt thereof.
In certain embodiments the compound is selected from the group consisting of:
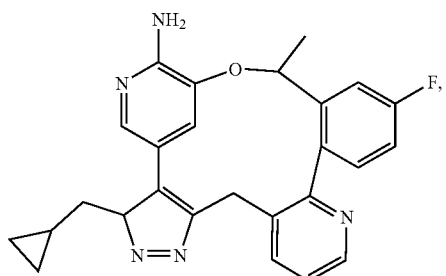
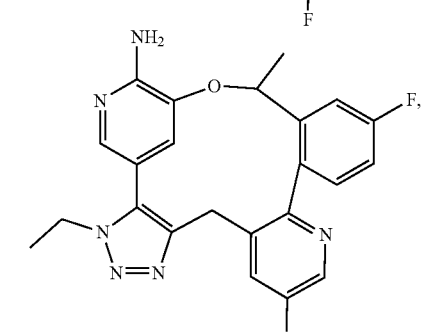
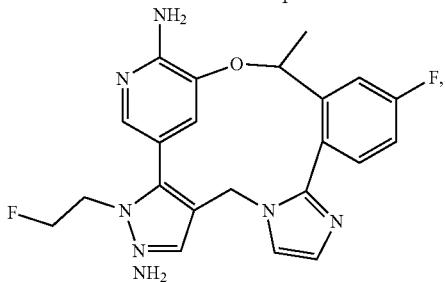
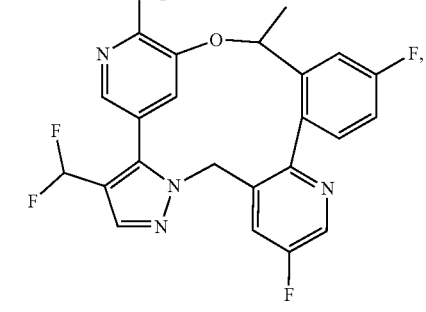
42
-continued
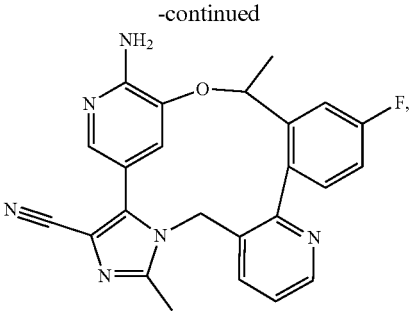
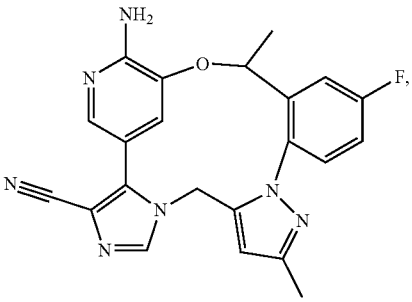
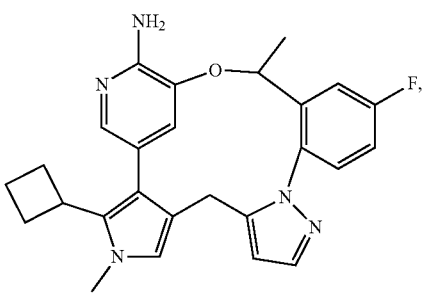
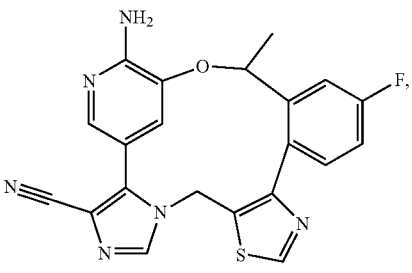
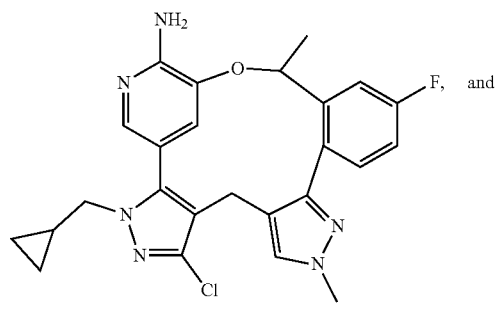
, and

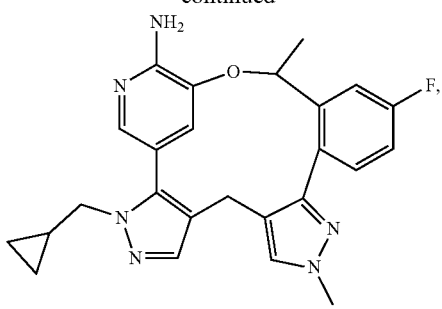
or an enantiomer, a mixture of enantiomers, or a tautomer thereof, or a pharmaceutically acceptable salt thereof.
In certain embodiments the compound is selected from the group consisting of:
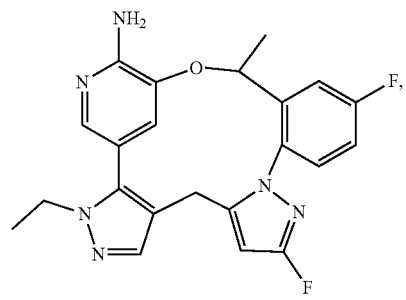
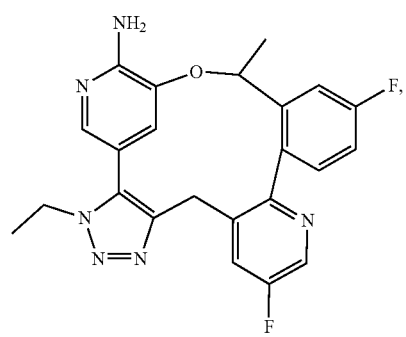
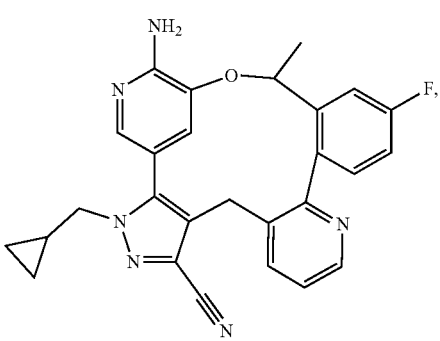
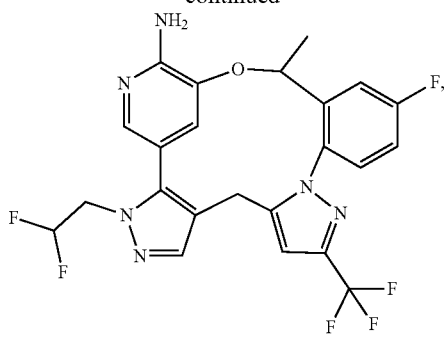
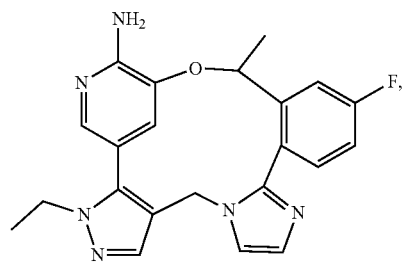
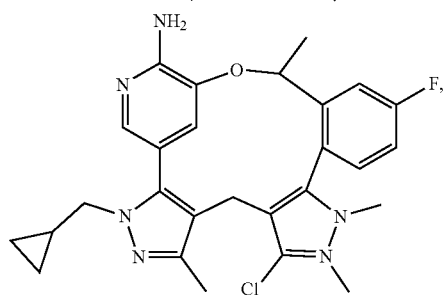
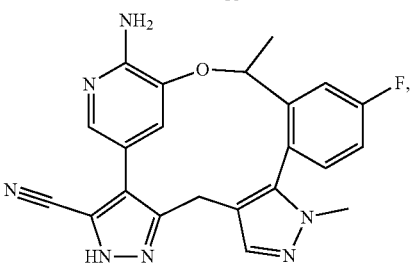
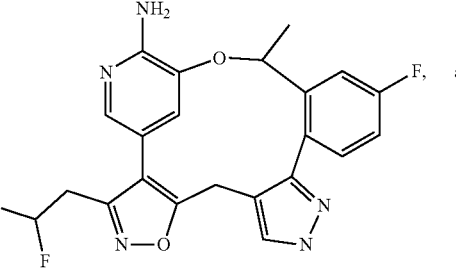
and -continued

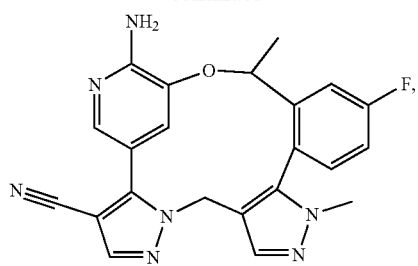

or an enantiomer, a mixture of enantiomers, or a tautomer thereof, or a pharmaceutically acceptable salt thereof.

In certain embodiments the compound is selected from the group consisting of:

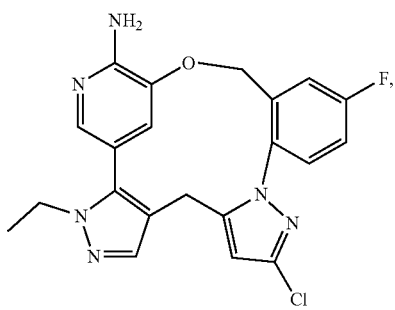

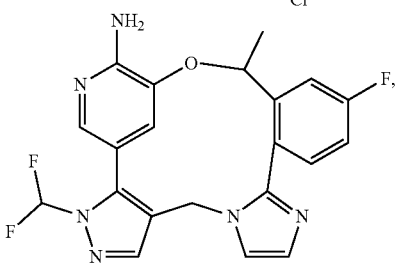

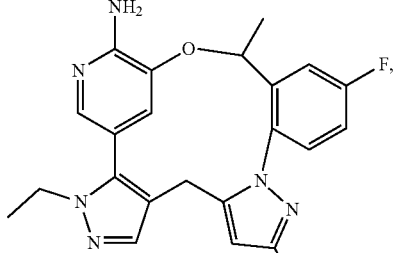

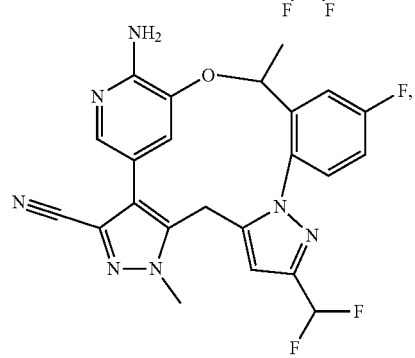

-continued

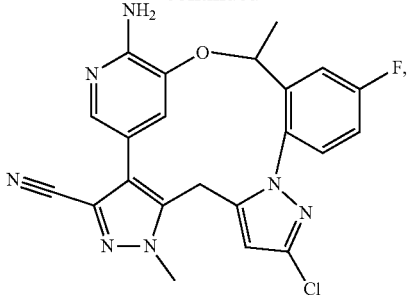

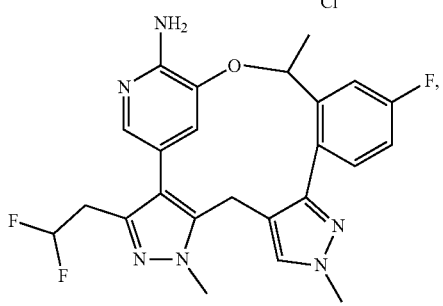

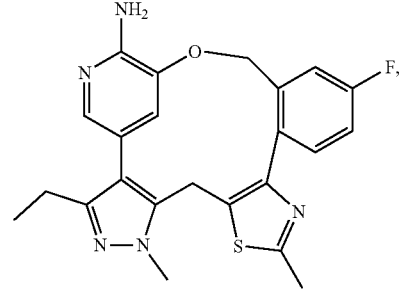

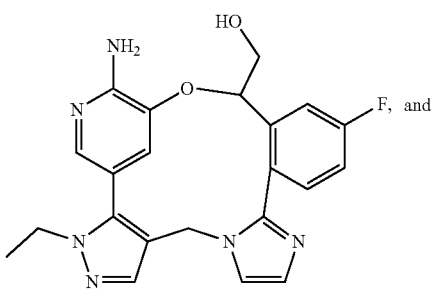

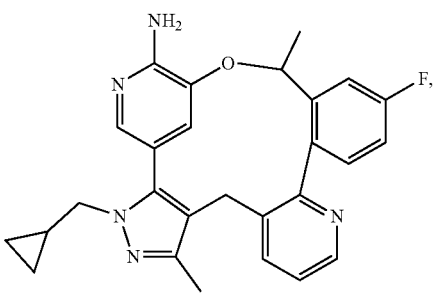

or an enantiomer, a mixture of enantiomers, or a tautomer thereof, or a pharmaceutically acceptable salt thereof.

In certain embodiments the compound is selected from the group consisting of:

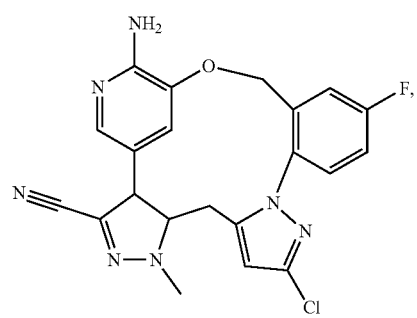
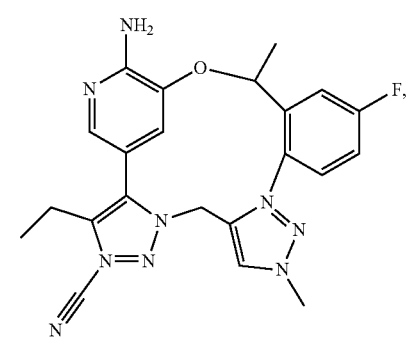
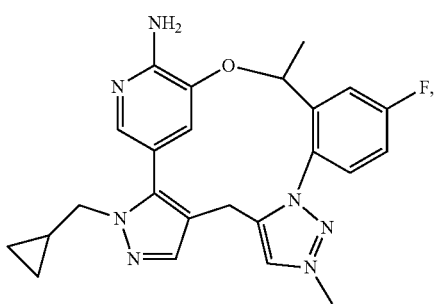
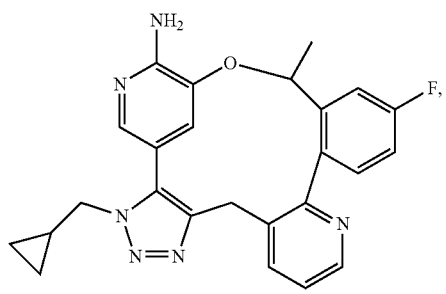
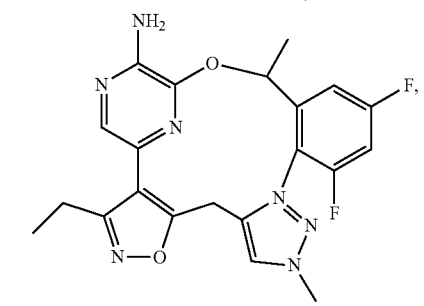
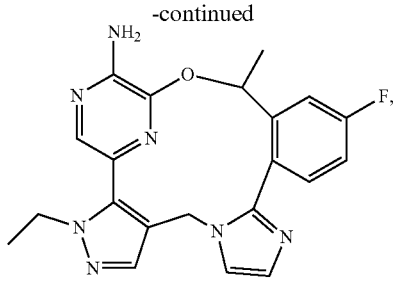
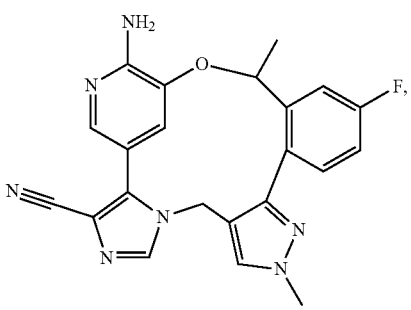
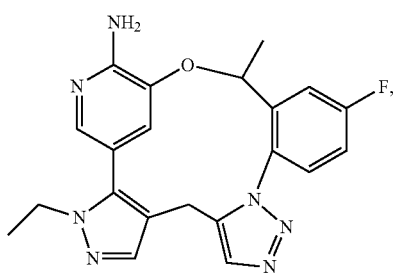
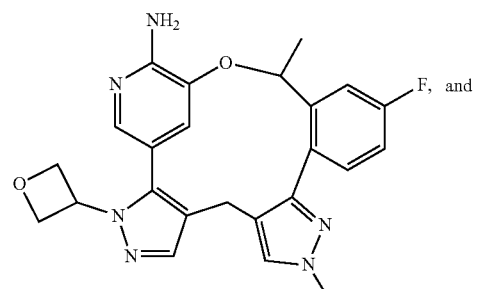
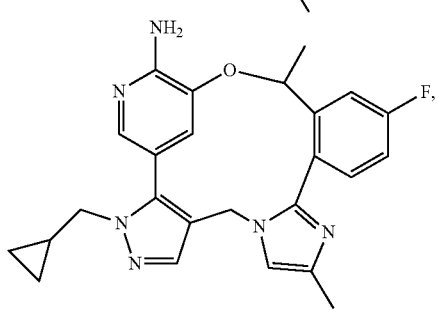
or an enantiomer, a mixture of enantiomers, or a tautomer thereof, or a pharmaceutically acceptable salt thereof.
In certain embodiments the compound is selected from the group consisting of:

or an enantiomer, a mixture of enantiomers, or a tautomer thereof, or a pharmaceutically acceptable salt thereof.

In certain embodiments the compound is selected from the group consisting of:

-continued
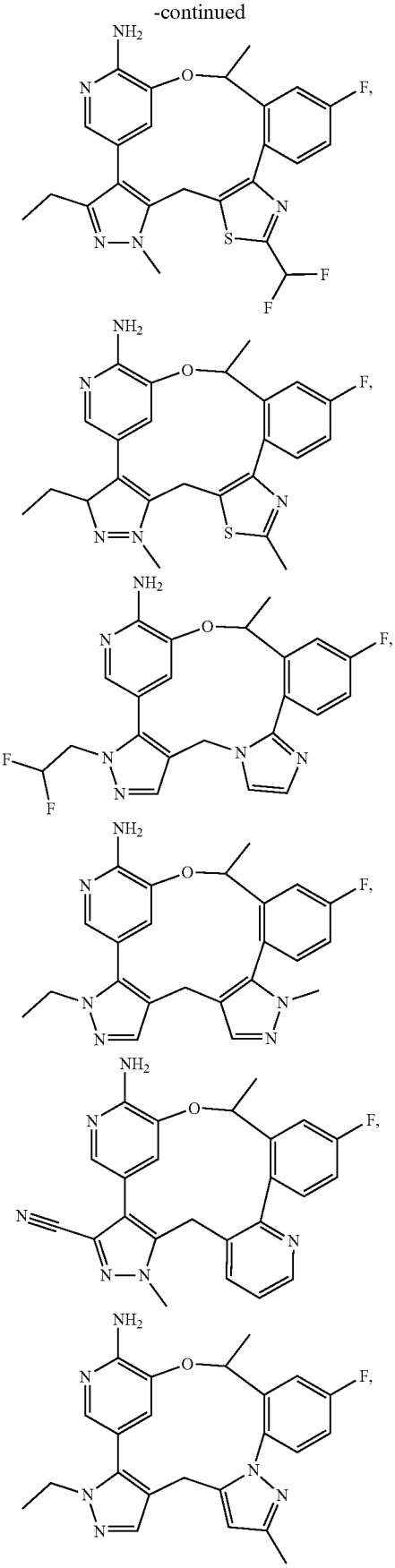
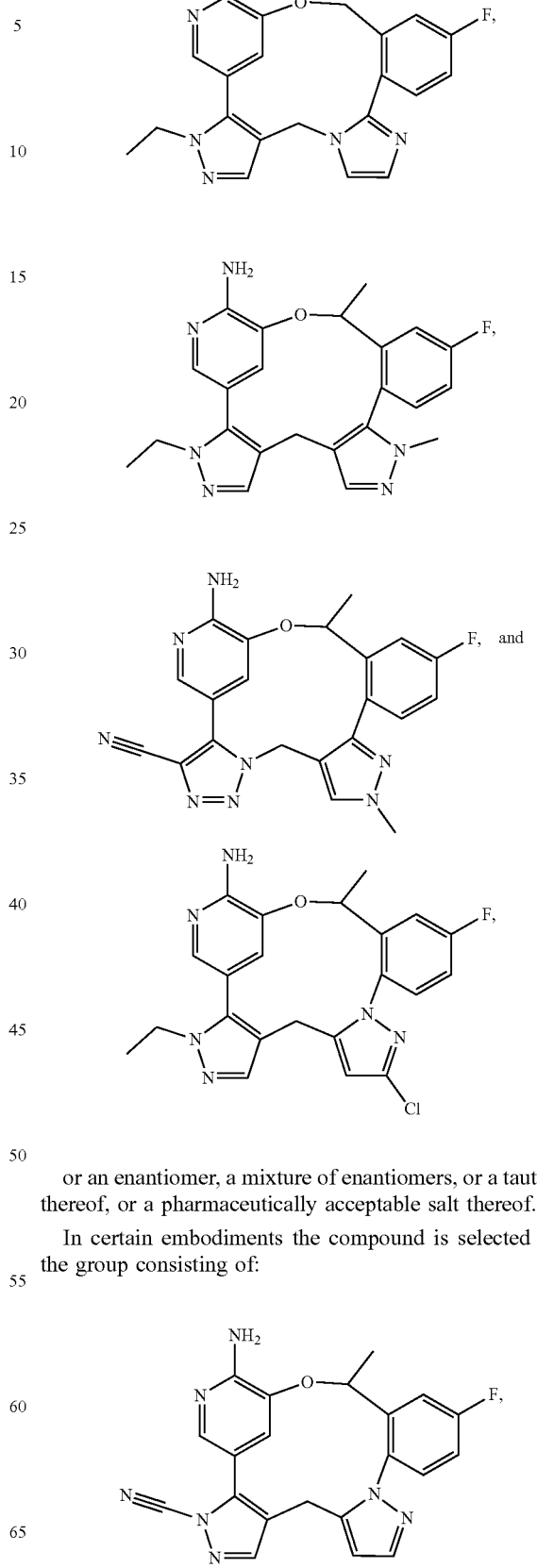
or an enantiomer, a mixture of enantiomers, or a tautomer thereof, or a pharmaceutically acceptable salt thereof.
In certain embodiments the compound is selected from the group consisting of:
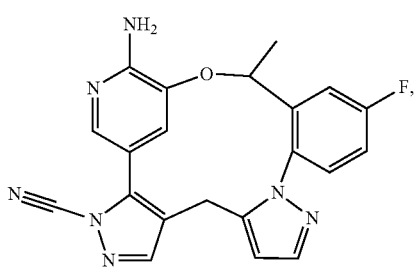

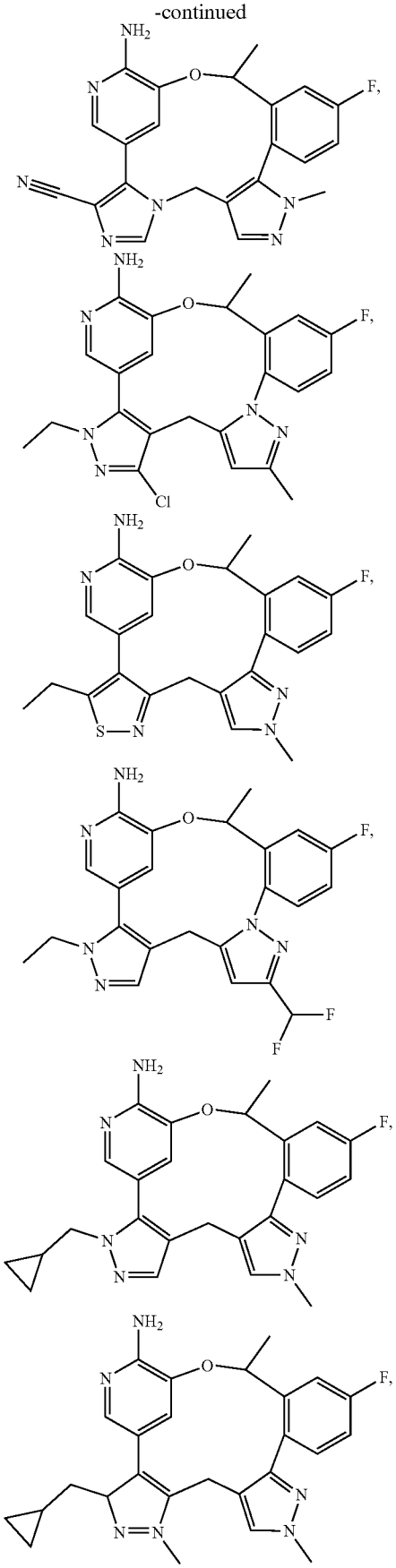
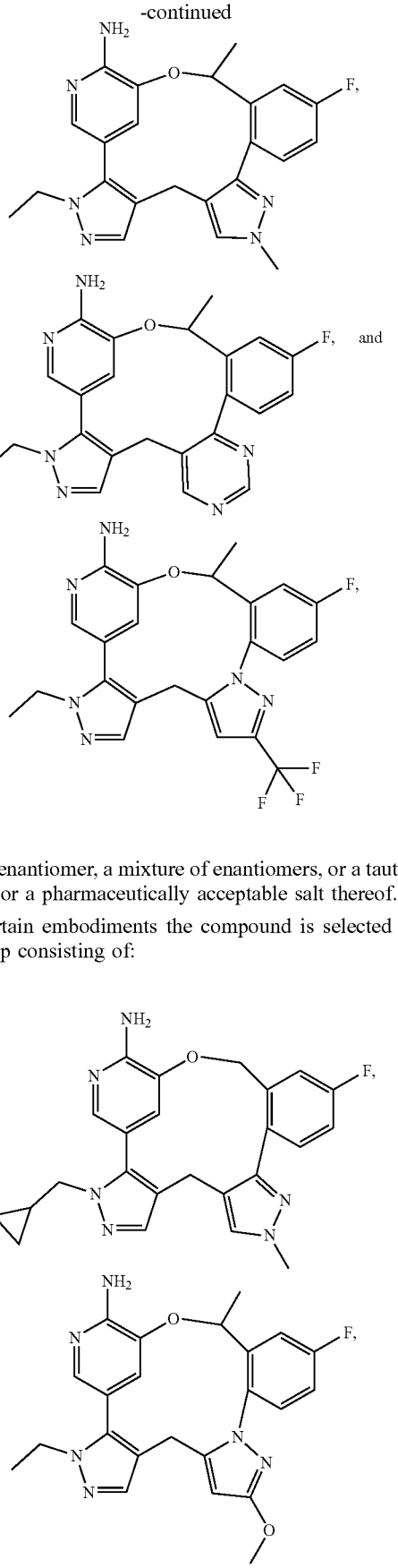
or an enantiomer, a mixture of enantiomers, or a tautomer thereof, or a pharmaceutically acceptable salt thereof.
In certain embodiments the compound is selected from the group consisting of:
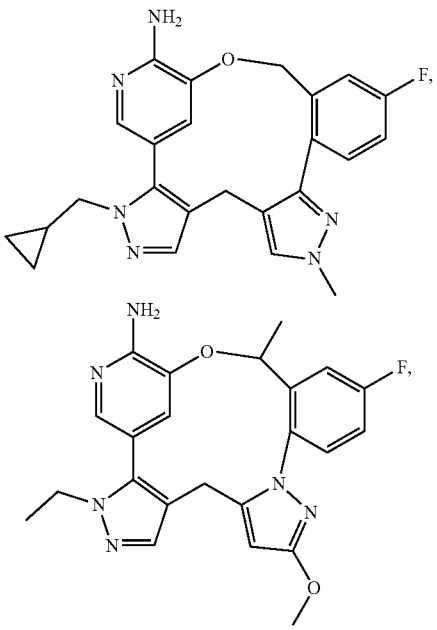

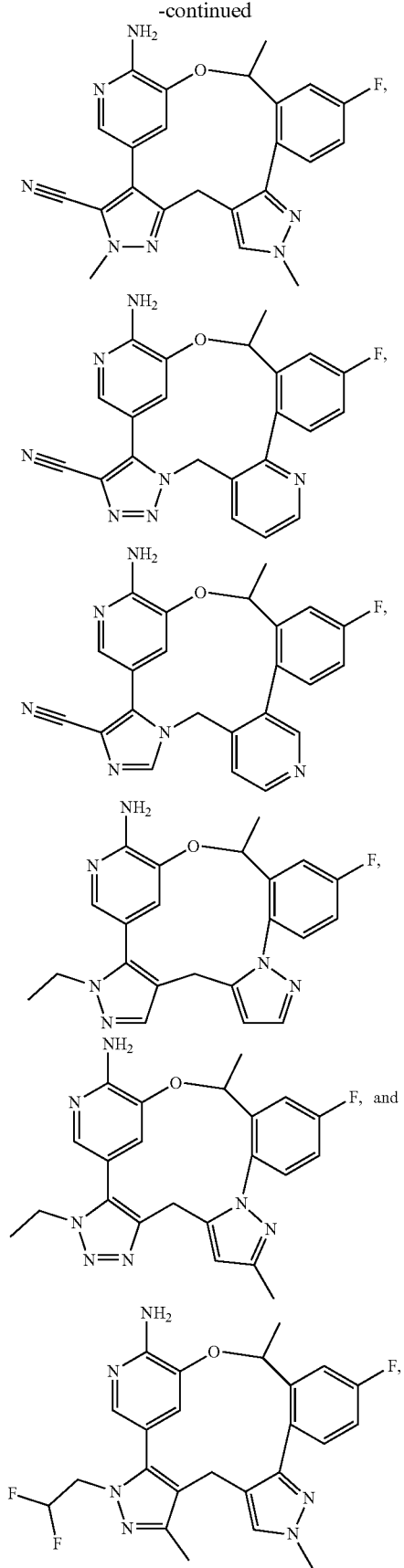
or an enantiomer, a mixture of enantiomers, or a tautomer thereof, or a pharmaceutically acceptable salt thereof.
In certain embodiments the compound is selected from the group consisting of:
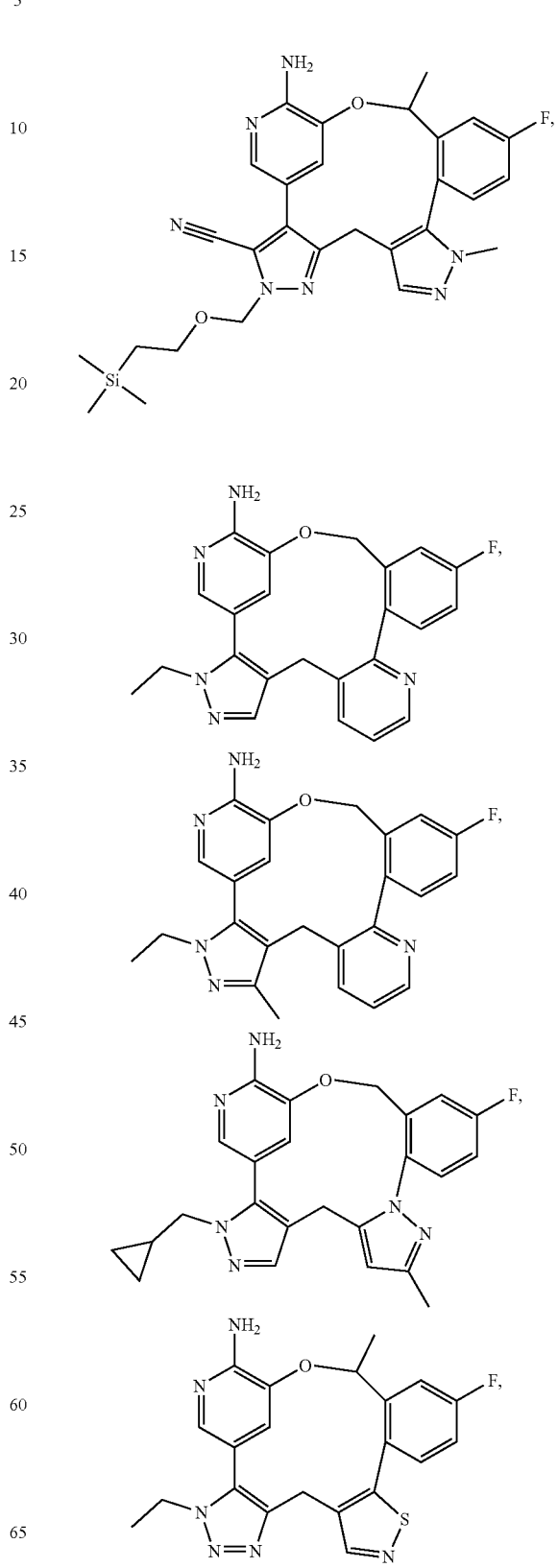

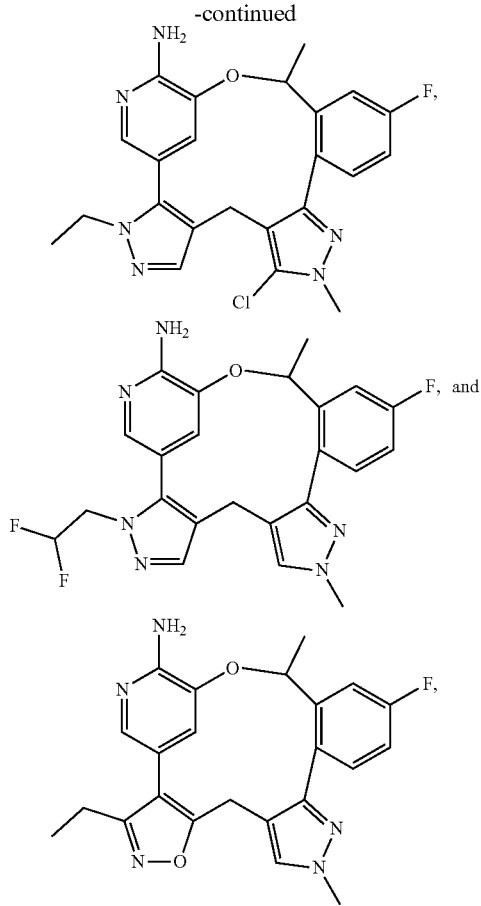
or an enantiomer, a mixture of enantiomers, or a tautomer thereof, or a pharmaceutically acceptable salt thereof.
In certain embodiments the compound is selected from the group consisting of:
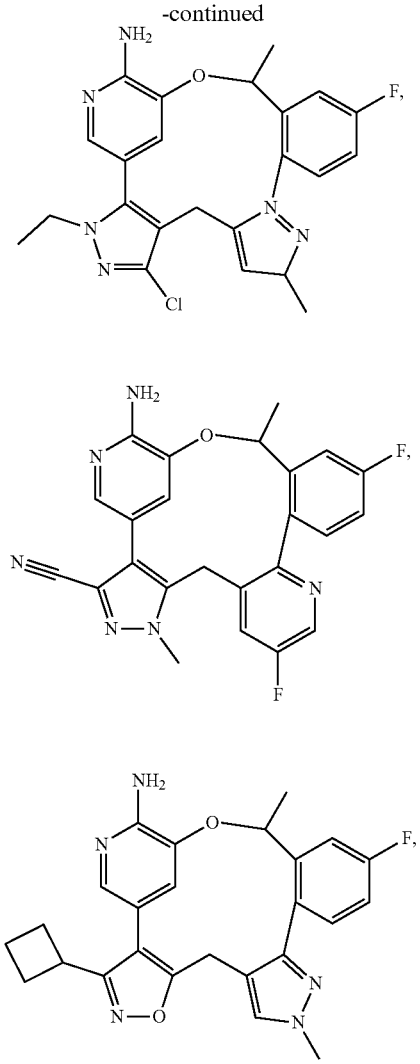
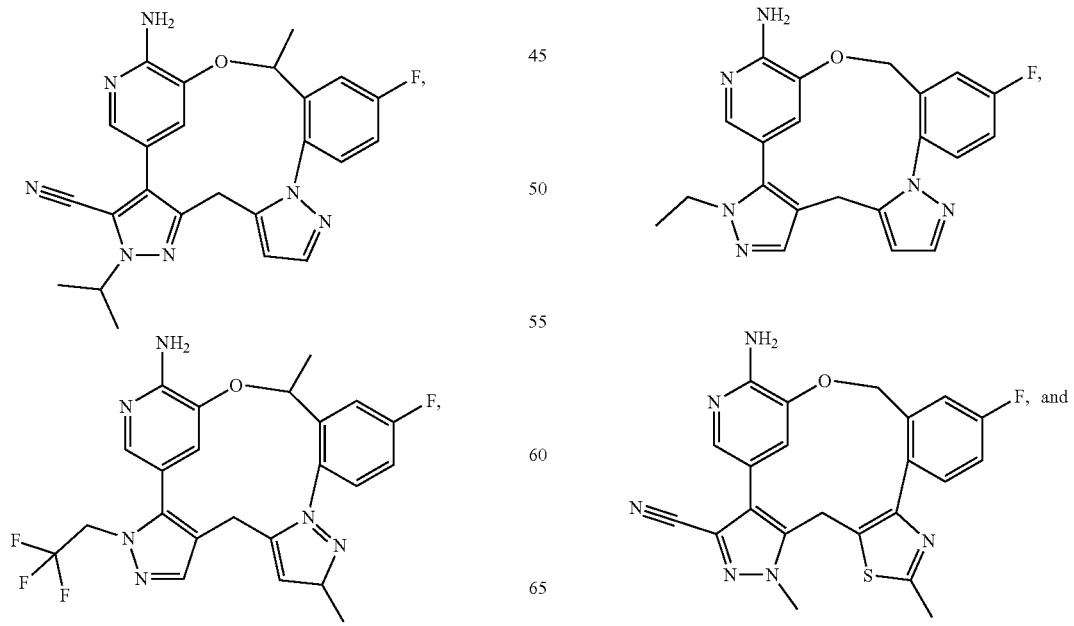

-continued

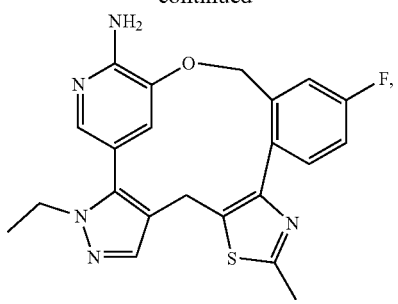

or an enantiomer, a mixture of enantiomers, or a tautomer thereof, or a pharmaceutically acceptable salt thereof.

In certain embodiments the compound is selected from the group consisting of:

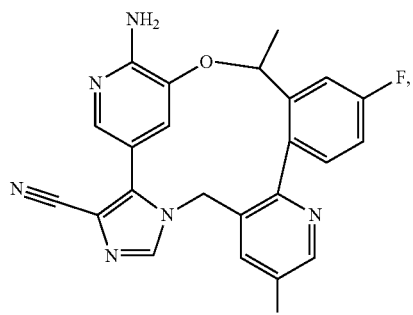

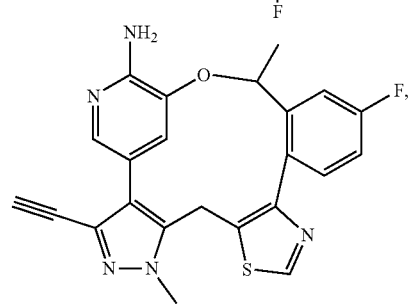

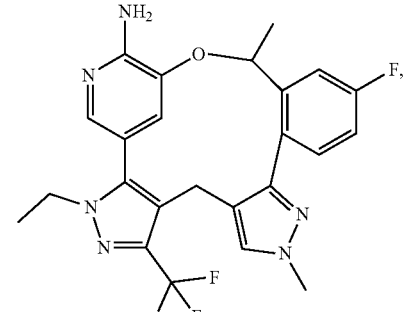

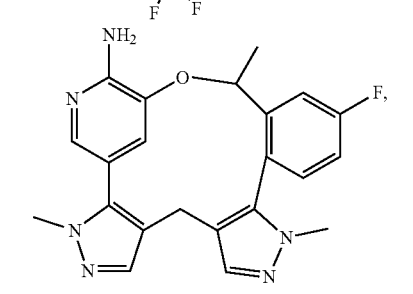

-continued

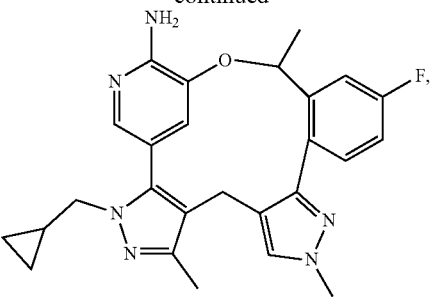

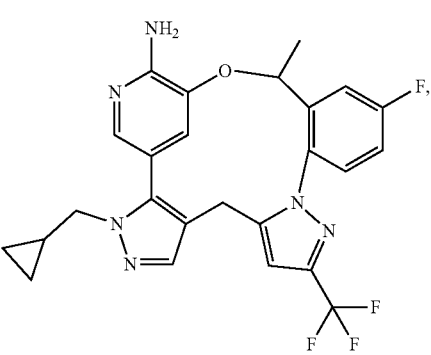

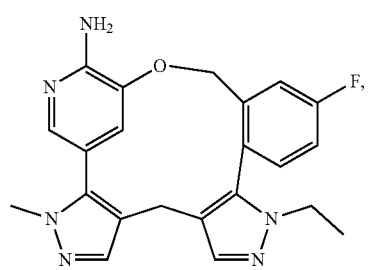

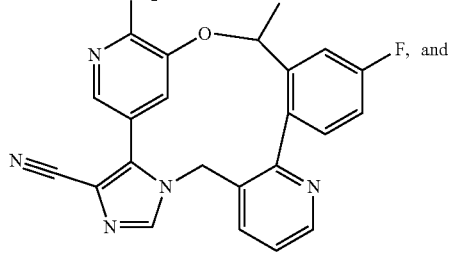

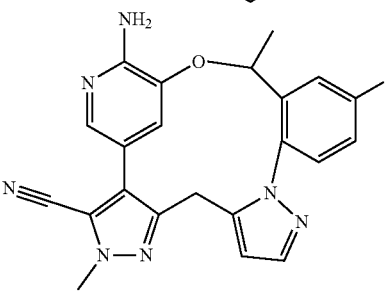

or an enantiomer, a mixture of enantiomers, or a tautomer thereof, or a pharmaceutically acceptable salt thereof.

In certain embodiments the compound is selected from the group consisting of:

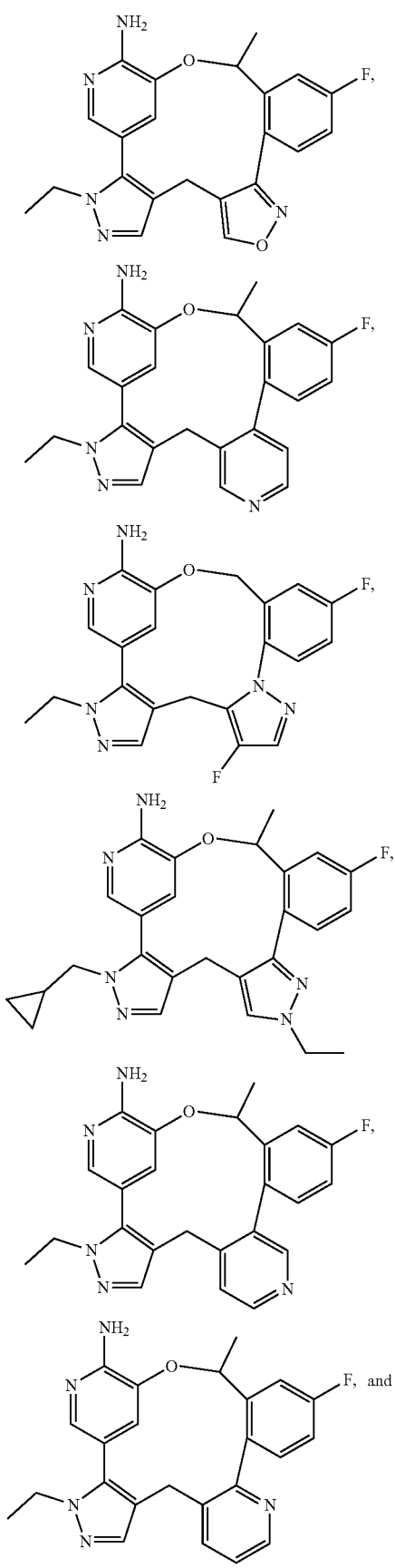
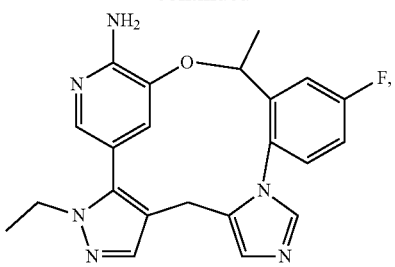
or an enantiomer, a mixture of enantiomers, or a tautomer thereof, or a pharmaceutically acceptable salt thereof.
In certain embodiments the compound is selected from the group consisting of:
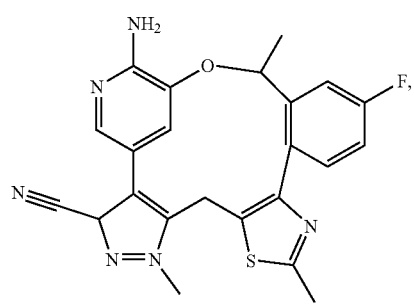
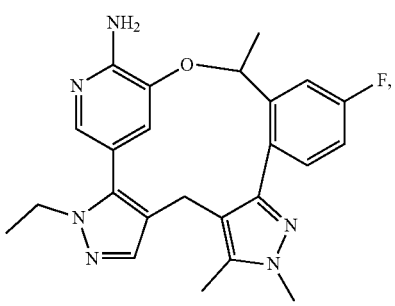
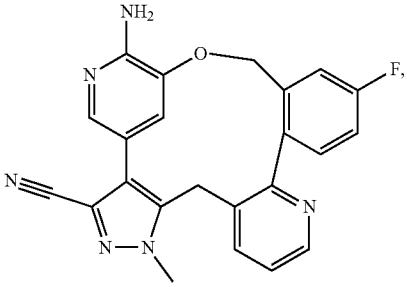
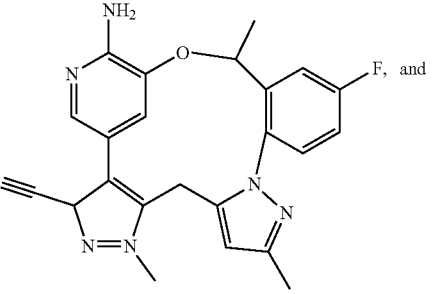

-continued

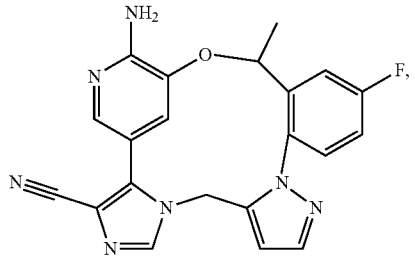

or an enantiomer, a mixture of enantiomers, or a tautomer thereof, or a pharmaceutically acceptable salt thereof.

In certain embodiments the compound is selected from the group consisting of:

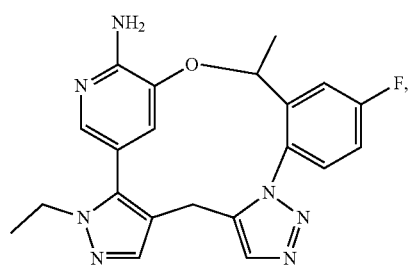

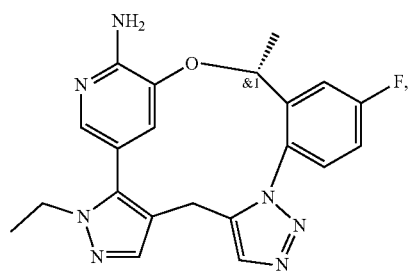

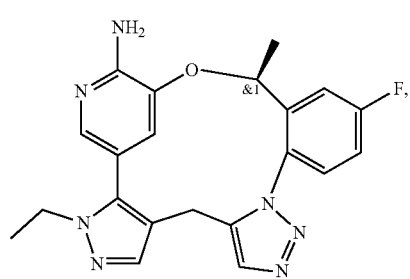

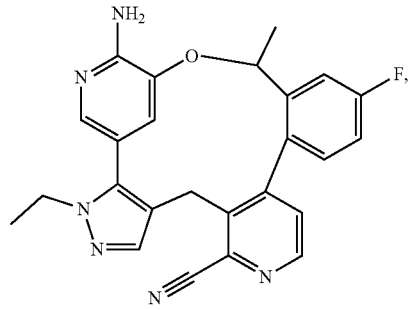

-continued

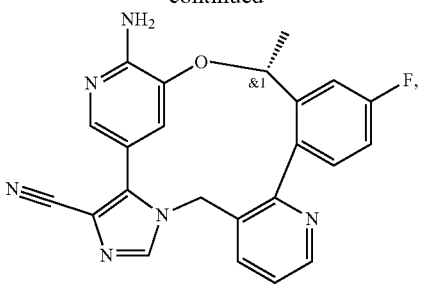

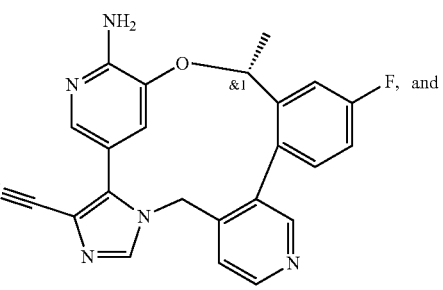

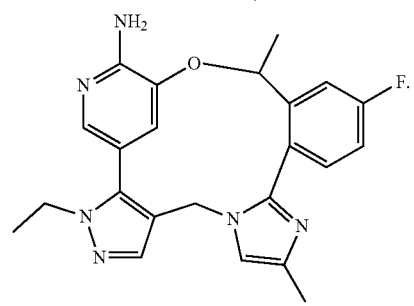

In certain embodiments the compound is selected from the group consisting of:

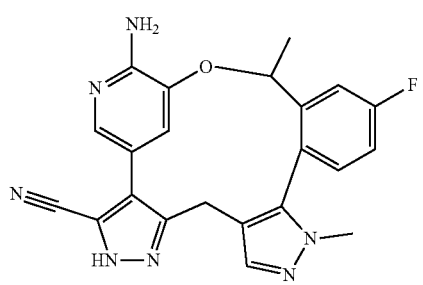

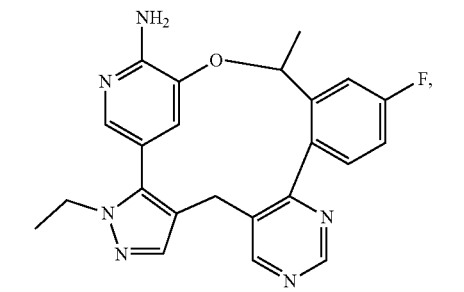

or an enantiomer, a mixture of enantiomers, or a tautomer thereof, or a pharmaceutically acceptable salt thereof.

In certain embodiments the compound is selected from the group consisting of:

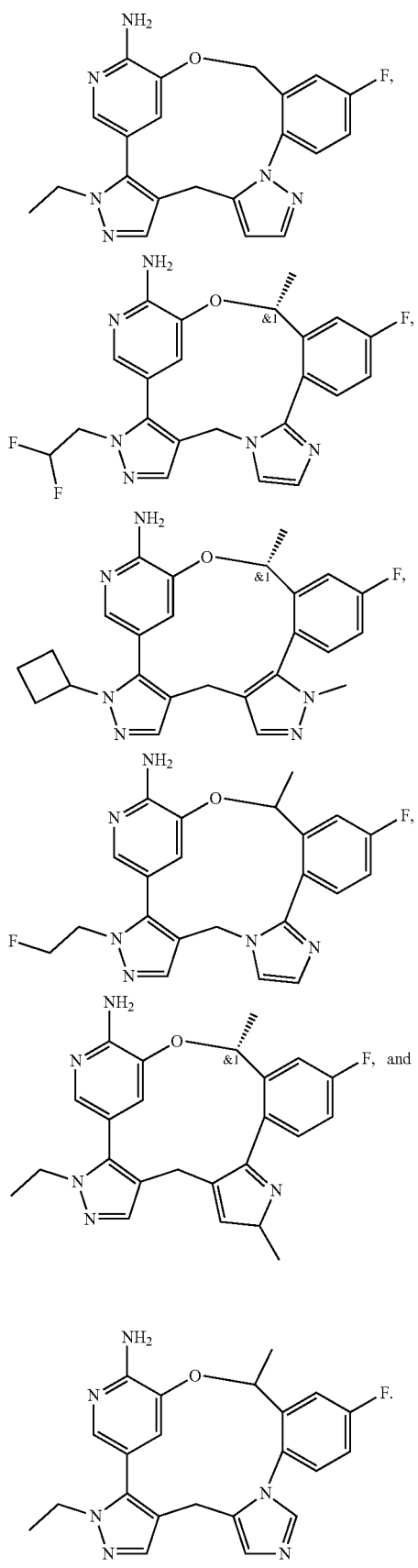
In certain embodiments the compound is selected from the group consisting of
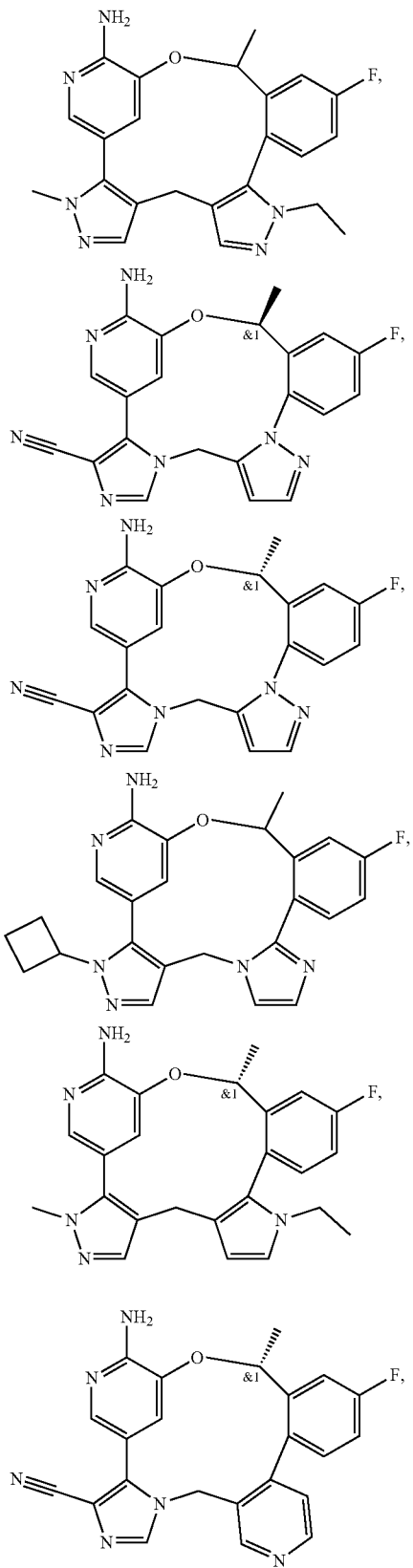

67
-continued
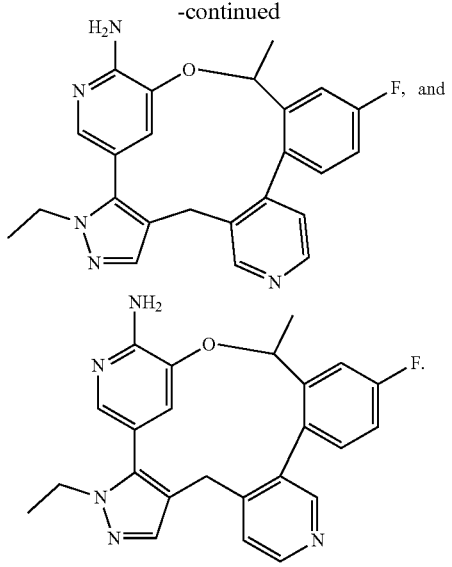
In certain embodiments the compound is selected from the group consisting of
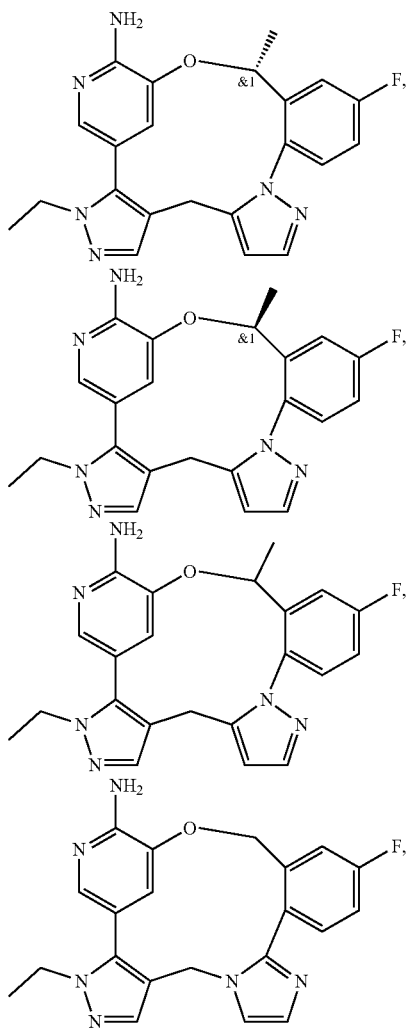
68
-continued
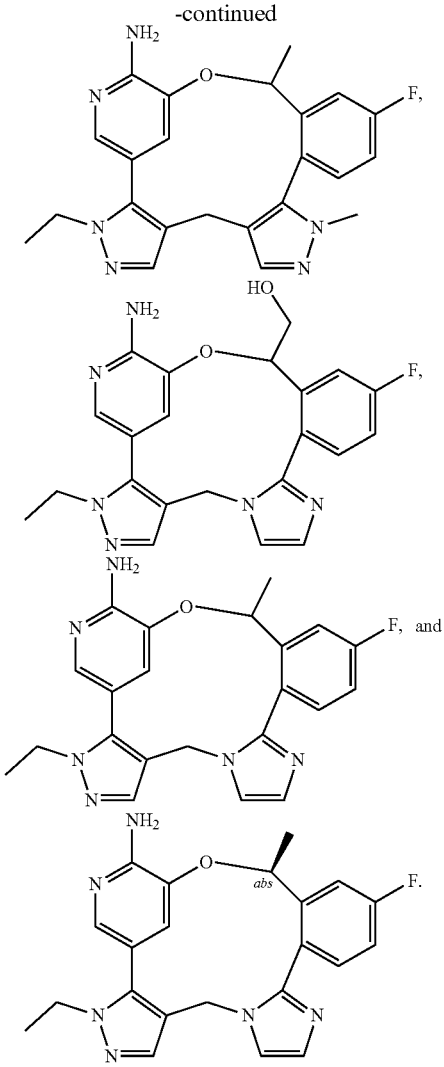
In certain embodiments the compound is selected from the group consisting of
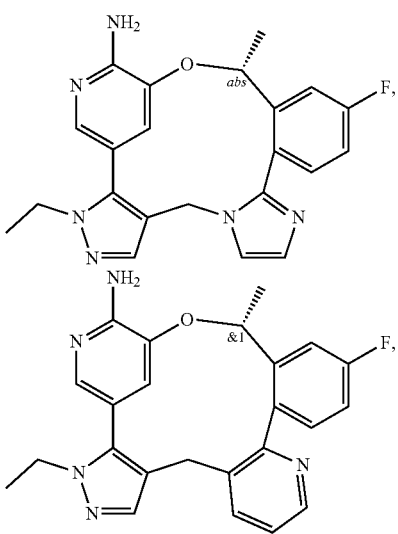

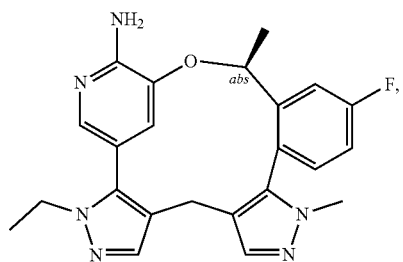
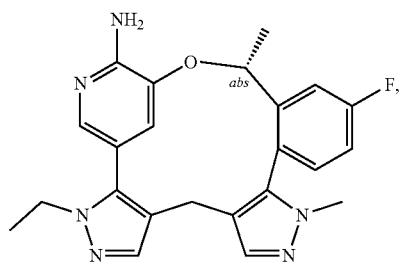
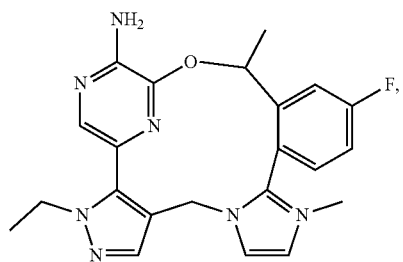

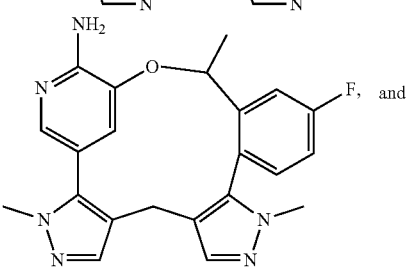
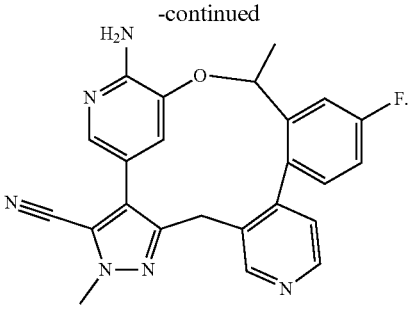
In certain embodiments the compound is selected from the group consisting of
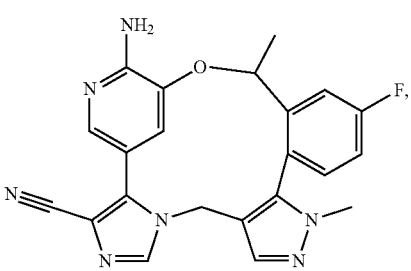
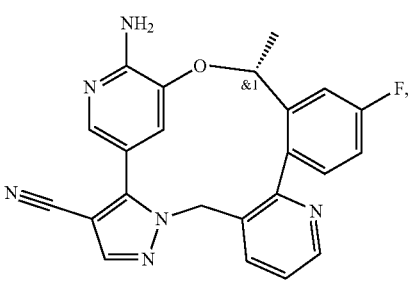
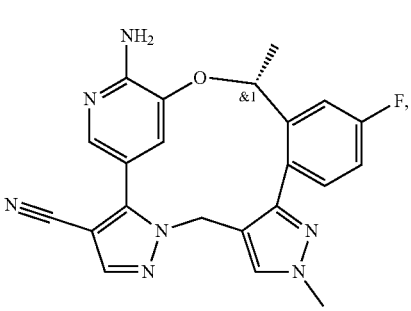
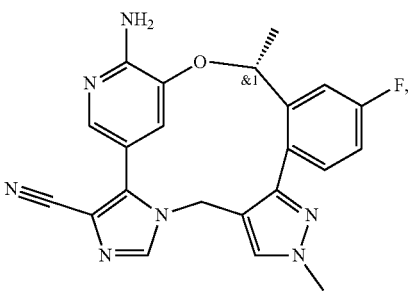

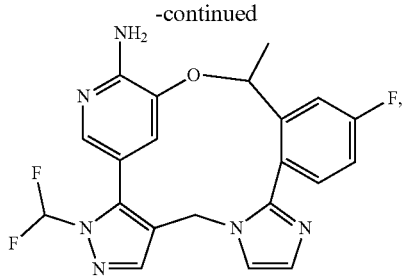
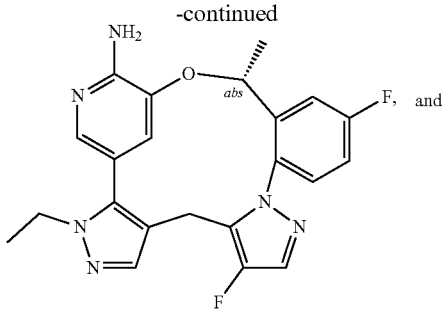
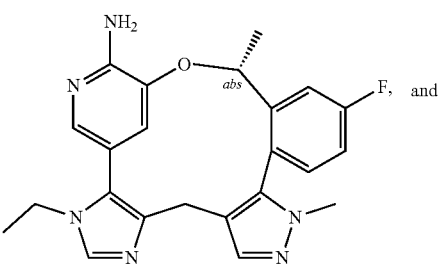
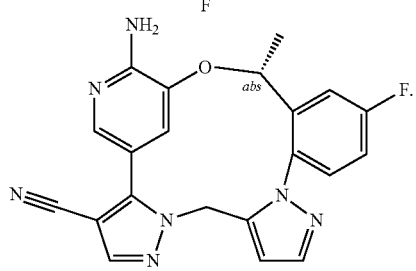
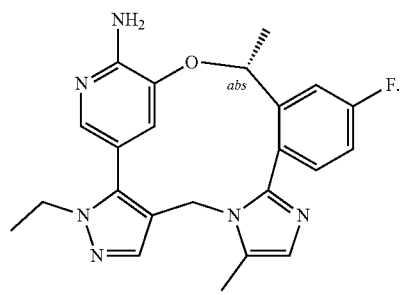
In certain embodiments the compound is selected from—the group consisting of:
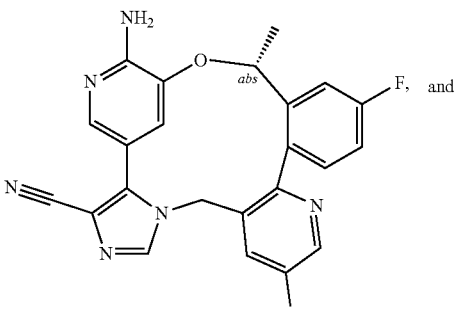
In certain embodiments the compound is selected from the group consisting of
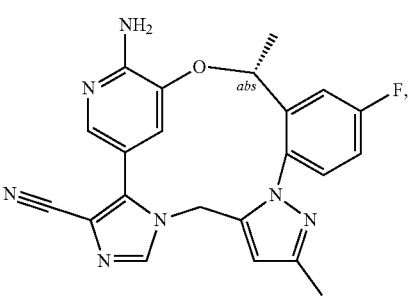
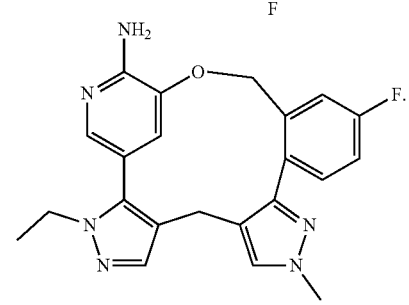
In certain embodiments the compound is selected from the group consisting of:
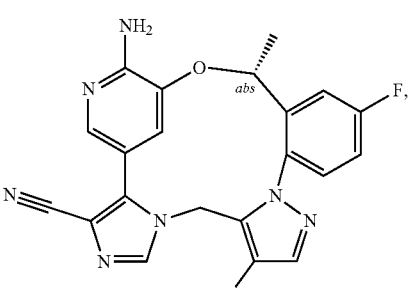
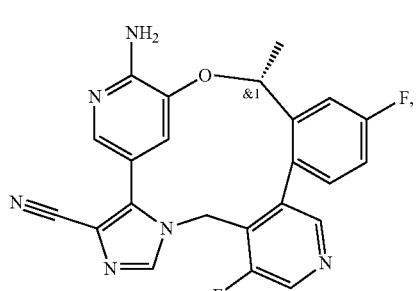

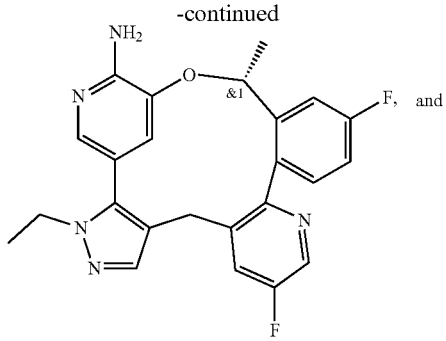
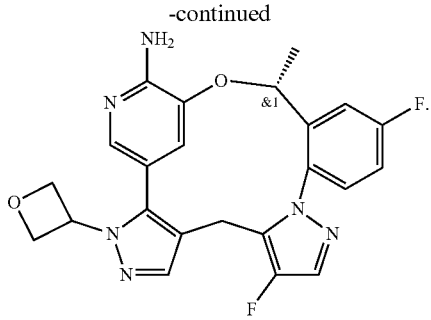 and
In certain embodiments the compound is selected from the group consisting of:
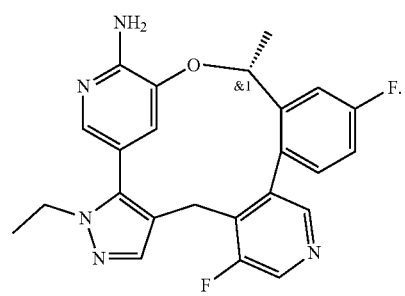
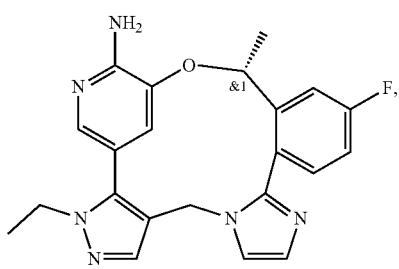
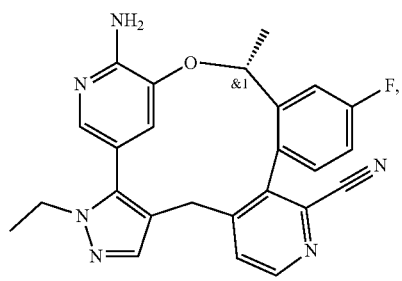
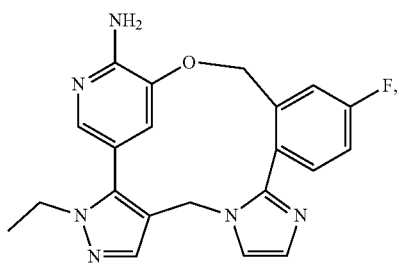
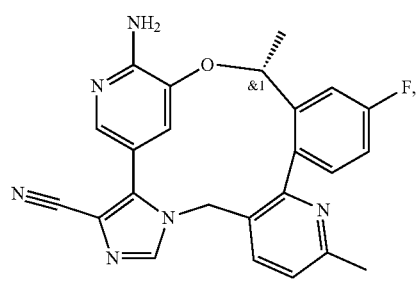
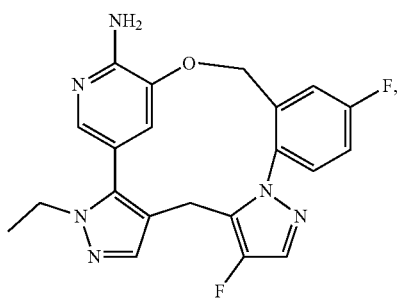
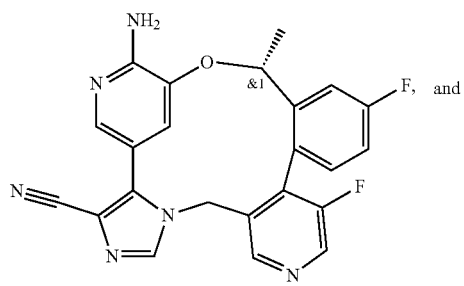, and
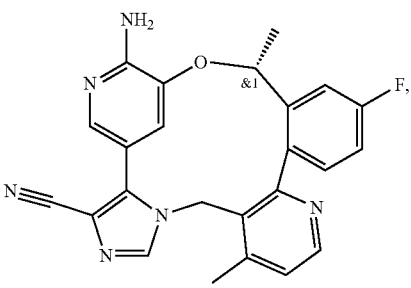

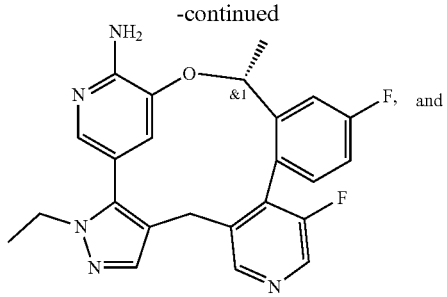
and
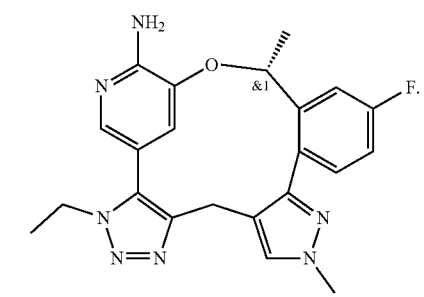
In certain embodiments the compound is selected from the group consisting of
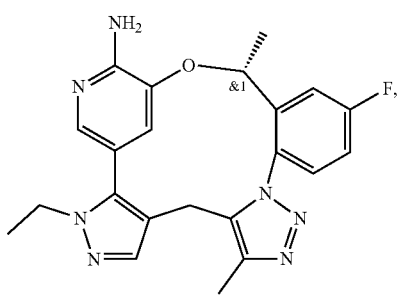
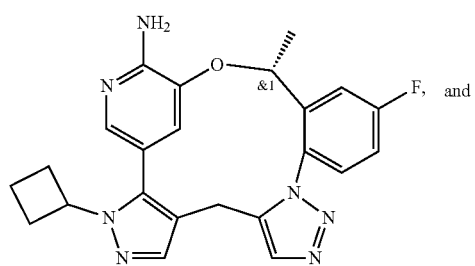
and
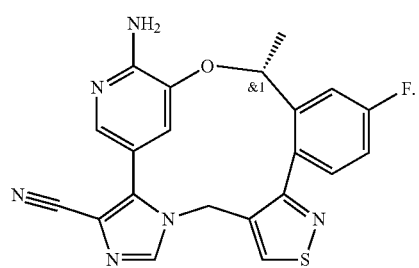
In certain embodiments the compound is selected from the group consisting of:
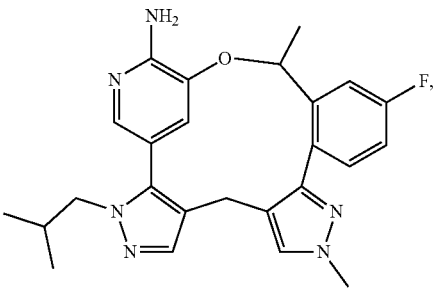
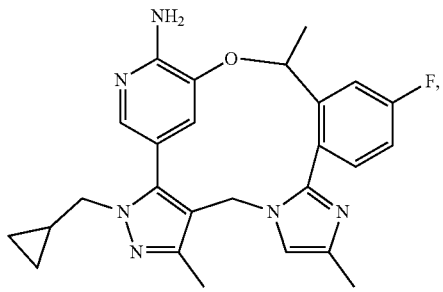
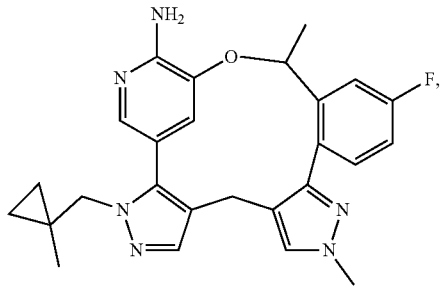
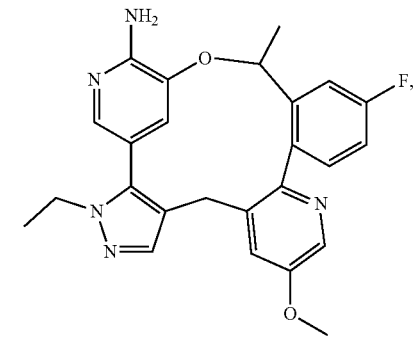
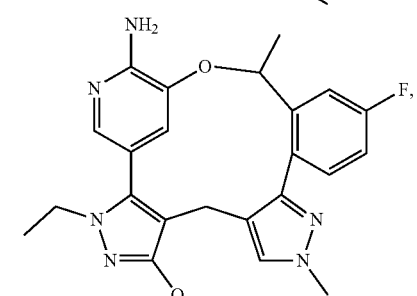

77
-continued
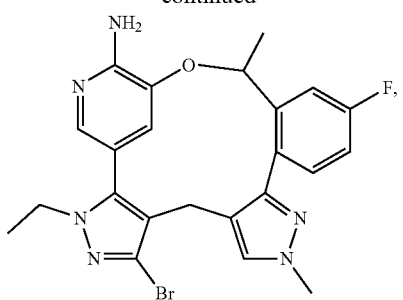
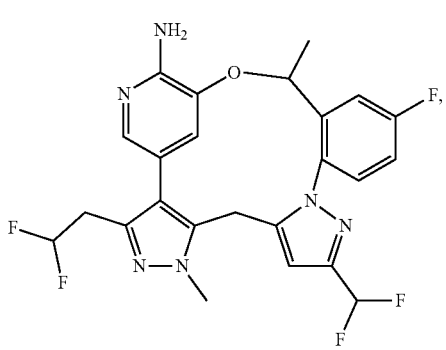
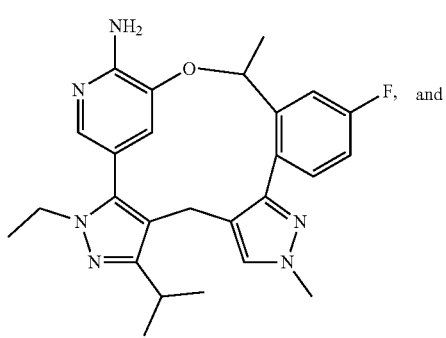
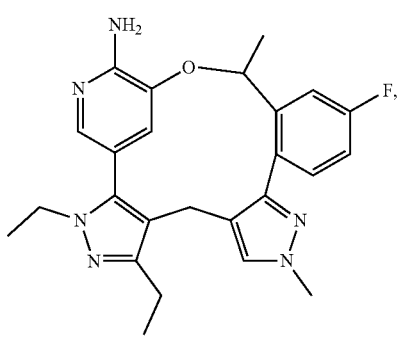
or an enantiomer, a mixture of enantiomers, or a tautomer thereof, or a pharmaceutically acceptable salt thereof.
In certain embodiments the compound is selected from the group consisting of:
78
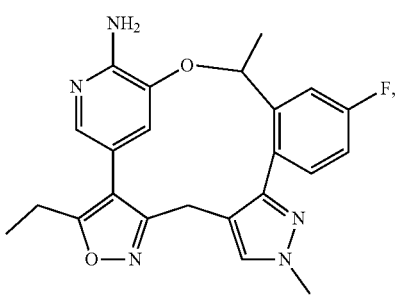
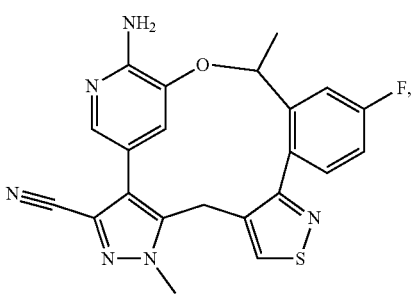
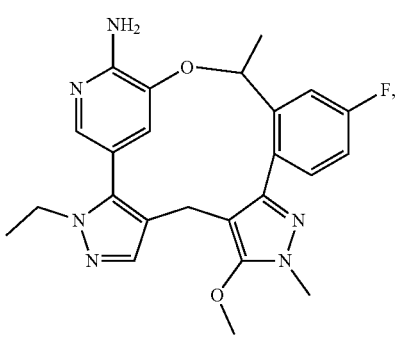
and
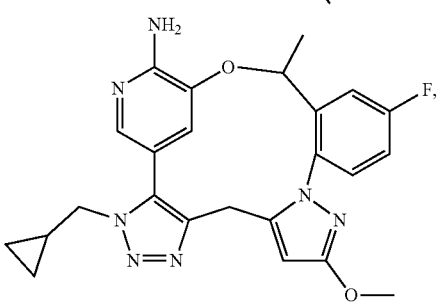

79
-continued
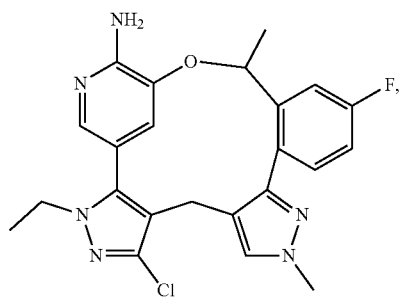
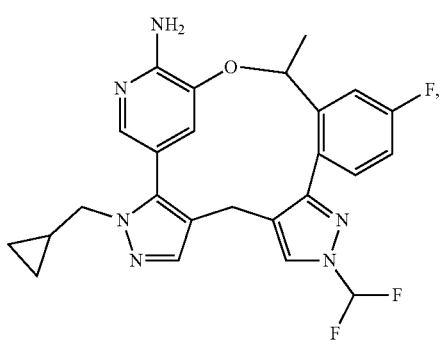
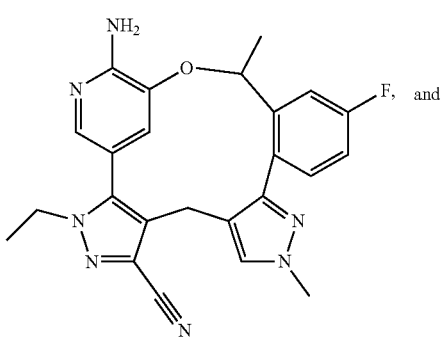, and
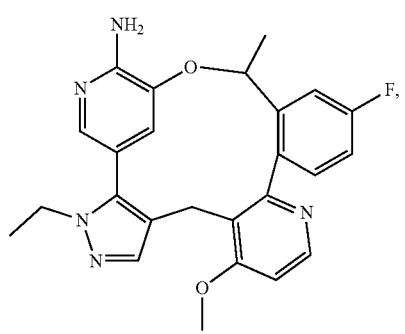
or an enantiomer, a mixture of enantiomers, or a tautomer thereof, or a pharmaceutically acceptable salt thereof.
In certain embodiments the compound is selected from the group consisting of:
80
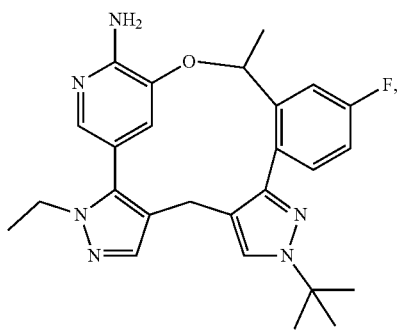
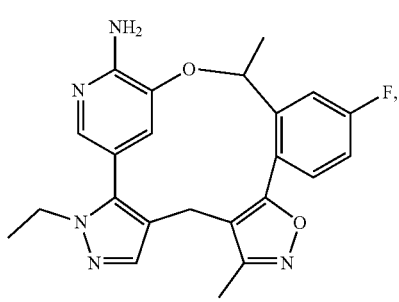
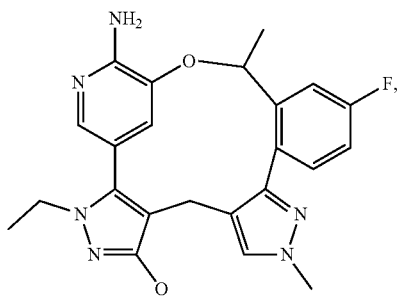
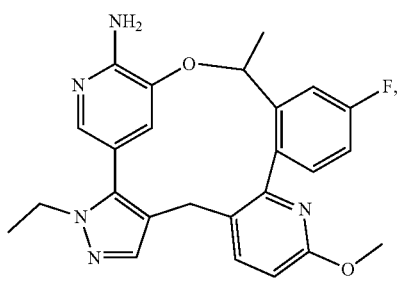
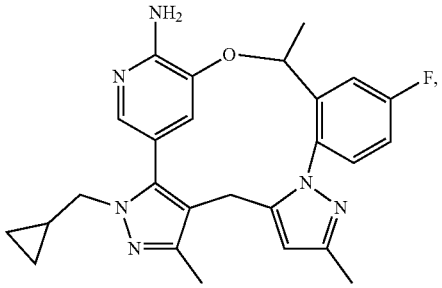

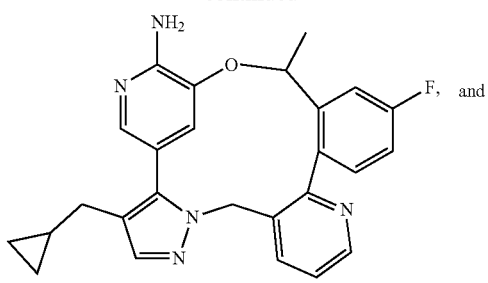
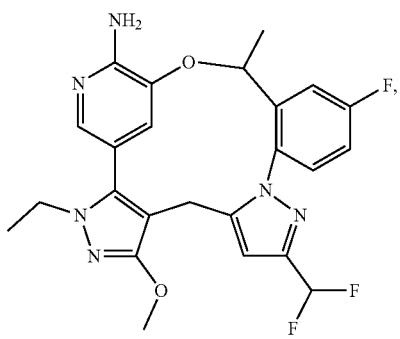
or an enantiomer, a mixture of enantiomers, or a tautomer thereof, or a pharmaceutically acceptable salt thereof.
In certain embodiments, the compound is selected from the group consisting of:
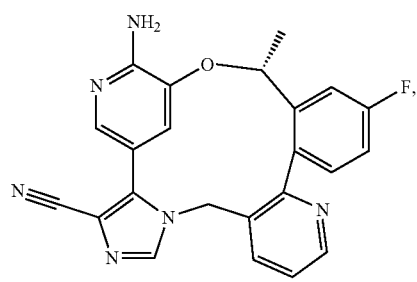
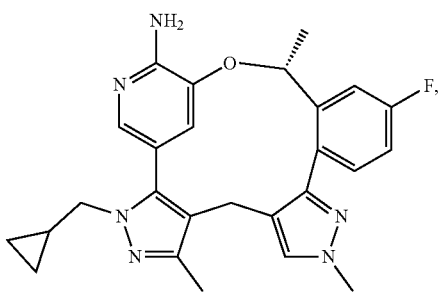
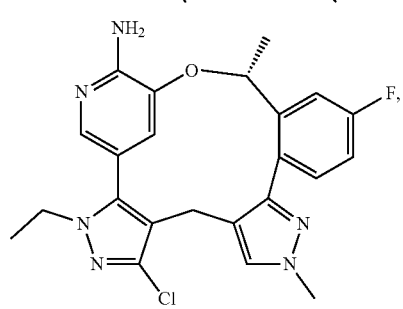
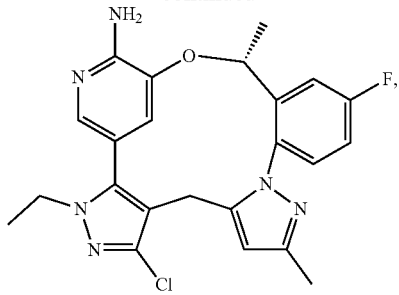
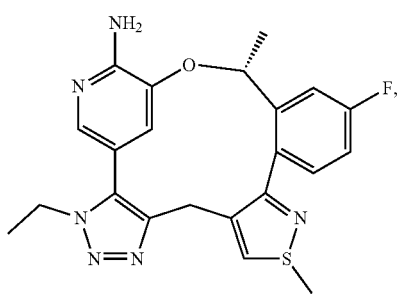
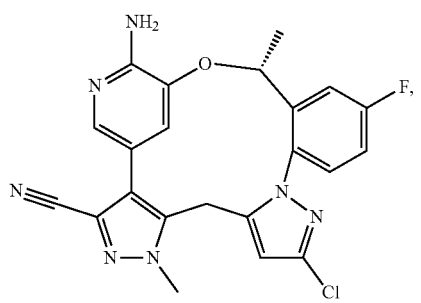
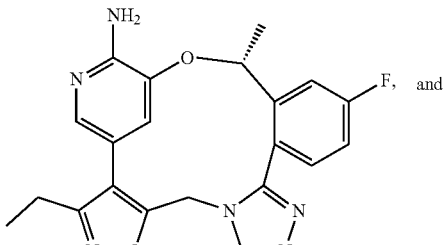
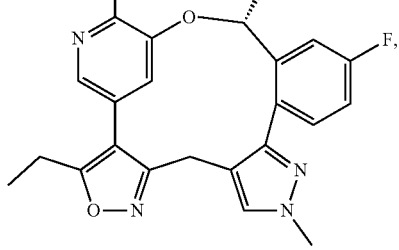
or a pharmaceutically acceptable salt thereof.
In one embodiment, provided herein is a compound in Table 1:

TABLE 1
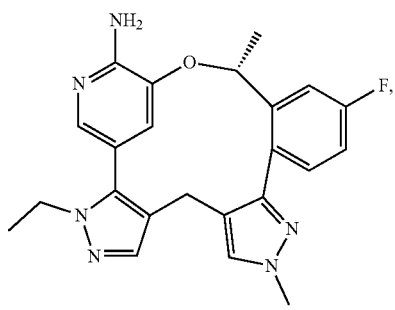 [SMILES: CCn1ncc2c1-c1cnc(N)c(c1)O[C@H](C)c1cc(F)ccc1-c1nn(C)cc1C2] 1
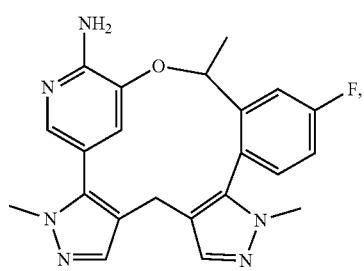 [SMILES: CC1Oc2cc(cnc2N)-c2c(cnn2C)Cc2cnn(C)c2-c2ccc(F)cc21] 2
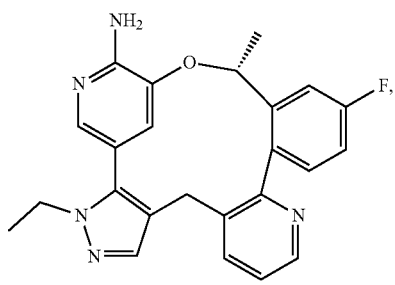 [SMILES: CCn1ncc2c1-c1cnc(N)c(c1)O[C@H](C)c1cc(F)ccc1-c1ncccc1C2] 3
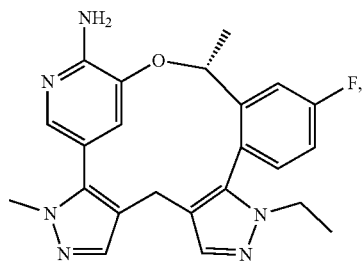 [SMILES: CCn1ncc2c1-c1ccc(F)cc1[C@@H](C)Oc1cc(cnc1N)-c1c(cnn1C)C2] 4
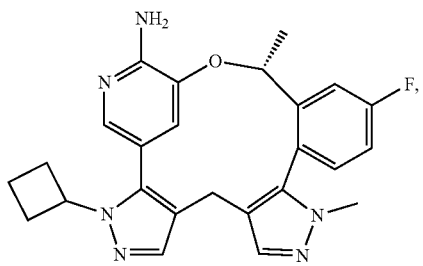 [SMILES: C[C@H]1Oc2cc(cnc2N)-c2c(cnn2C2CCC2)Cc2cnn(C)c2-c2ccc(F)cc21] 5
TABLE 1-continued
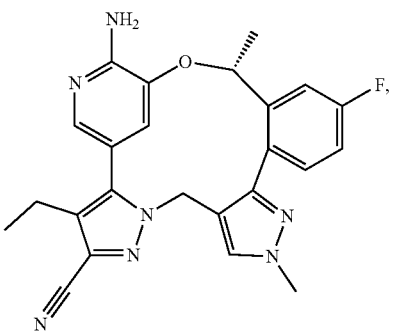 [SMILES: CCc1c(C#N)nn2c1-c1cnc(N)c(c1)O[C@H](C)c1cc(F)ccc1-c1nn(C)cc1C2] 6
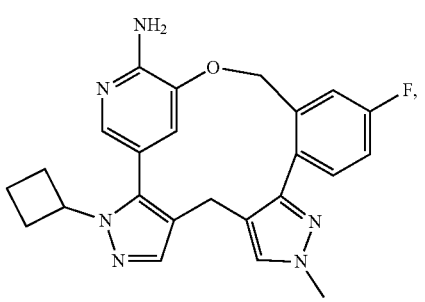 [SMILES: Cn1cc2c(n1)-c1ccc(F)cc1COc1cc(cnc1N)-c1c(cnn1C1CCC1)C2] 7
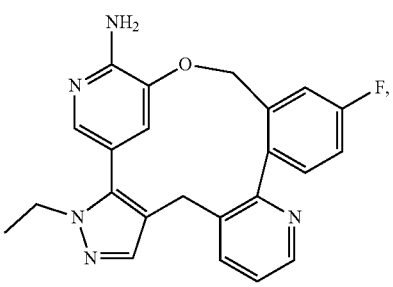 [SMILES: CCn1ncc2c1-c1cnc(N)c(c1)OCc1cc(F)ccc1-c1ncccc1C2] 8
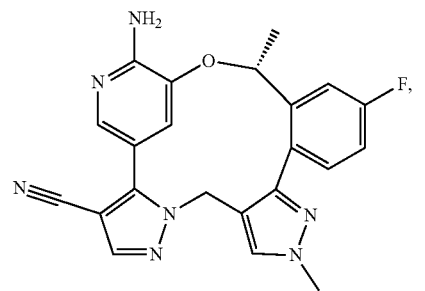 [SMILES: C[C@H]1Oc2cc(cnc2N)-c2c(C#N)cnn2Cc2cn(C)nc2-c2ccc(F)cc21] 9
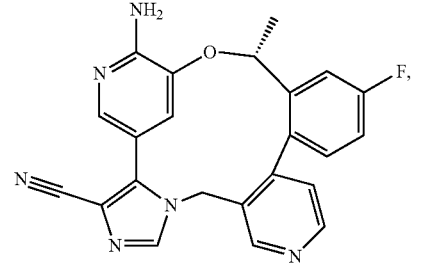 [SMILES: C[C@H]1Oc2cc(cnc2N)-c2c(C#N)ncn2Cc2cnccc2-c2ccc(F)cc21] 10

TABLE 1-continued
11
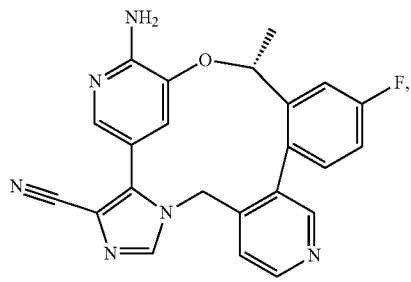 [SMILES: C[C@H]1Oc2cc(cnc2N)-c2c(C#N)ncn2Cc2ccncc2-c2ccc(F)cc21]
12
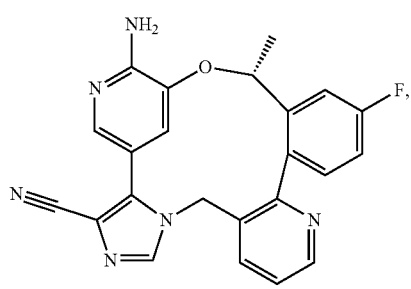 [SMILES: C[C@H]1Oc2cc(cnc2N)-c2c(C#N)ncn2Cc2cccnc2-c2ccc(F)cc21]
13
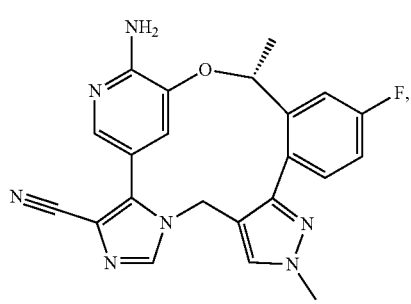
14
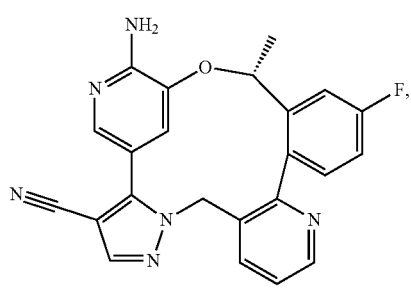 [SMILES: C[C@H]1Oc2cc(cnc2N)-c2c(C#N)cnn2Cc2cccnc2-c2ccc(F)cc21]
15
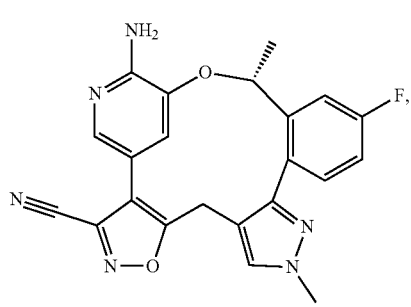 [SMILES: C[C@H]1Oc2cc(cnc2N)-c2c(C#N)noc2Cc2cn(C)nc2-c2ccc(F)cc21]
TABLE 1-continued
16
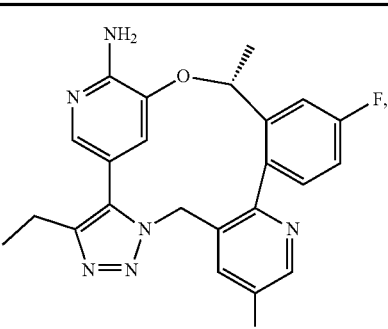
17
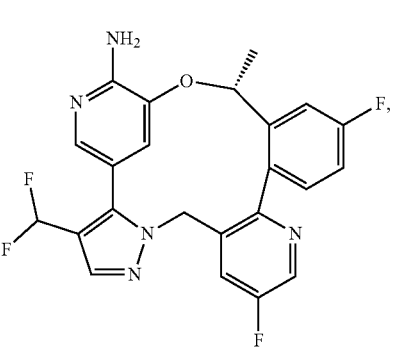 [SMILES: C[C@H]1Oc2cc(cnc2N)-c2c(C(F)F)cnn2Cc2cc(F)cnc2-c2ccc(F)cc21]
18
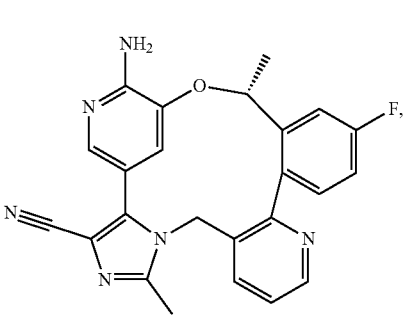 [SMILES: Cc1nc(C#N)c2n1Cc1cccnc1-c1ccc(F)cc1[C@@H](C)Oc1cc-2cnc1N]
19
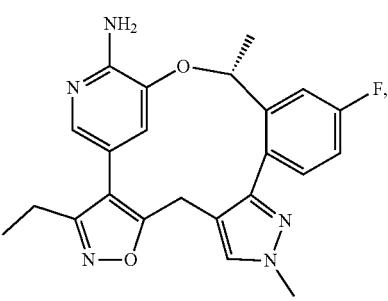
20
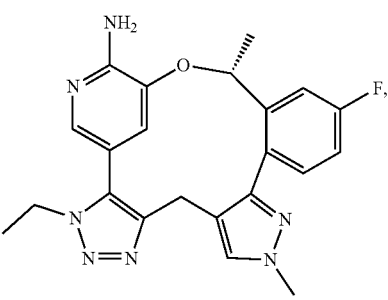 [SMILES: CCn1nnc2c1-c1cnc(N)c(c1)O[C@H](C)c1cc(F)ccc1-c1nn(C)cc1C2]

TABLE 1-continued
| | |
|---|---|
| 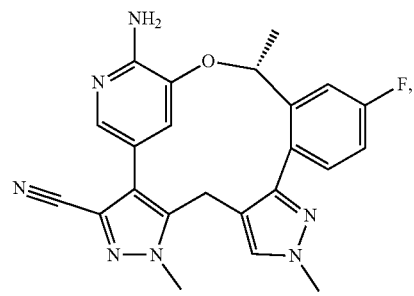 [SMILES: C[C@H]1Oc2cc(cnc2N)-c2c(C#N)nn(C)c2Cc2cn(C)nc2-c2ccc(F)cc21] 21 | 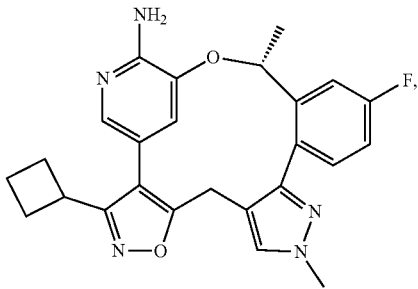 26 |
| 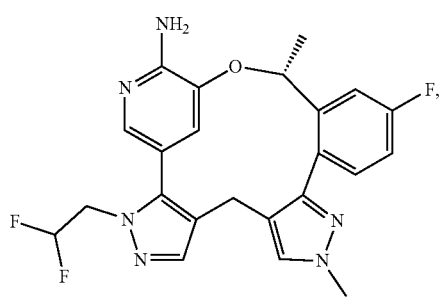 [SMILES: C[C@H]1Oc2cc(cnc2N)-c2c(cnn2CC(F)F)Cc2cn(C)nc2-c2ccc(F)cc21] 22 | 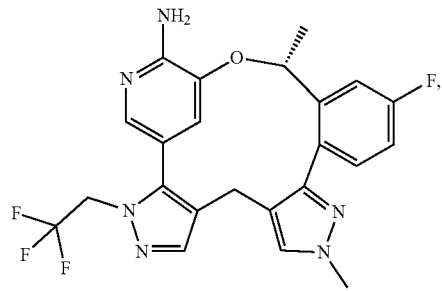 27 |
| 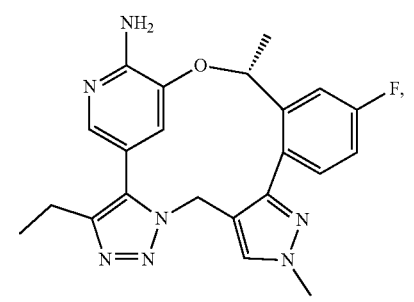 [SMILES: CCc1nnn2c1-c1cnc(N)c(c1)O[C@H](C)c1cc(F)ccc1-c1nn(C)cc1C2] 23 | 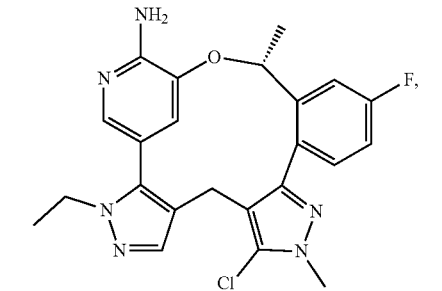 [SMILES: CCn1ncc2c1-c1cnc(N)c(c1)O[C@H](C)c1cc(F)ccc1-c1nn(C)c(Cl)c1C2] 28 |
| 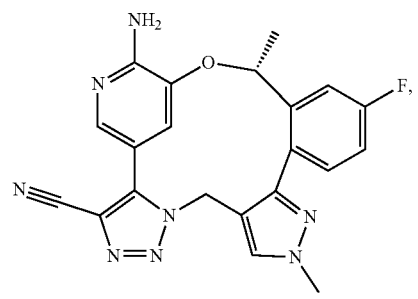 24 | 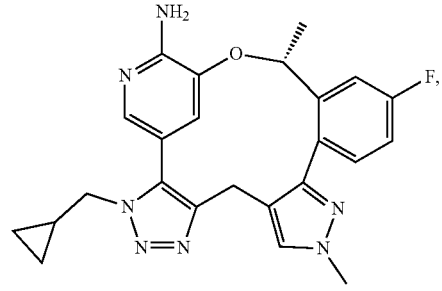 29 |
| 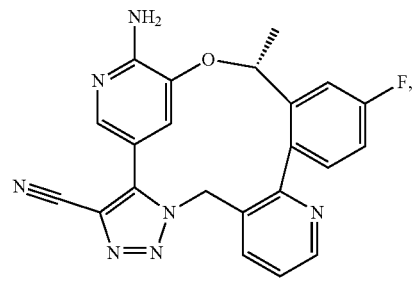 25 | 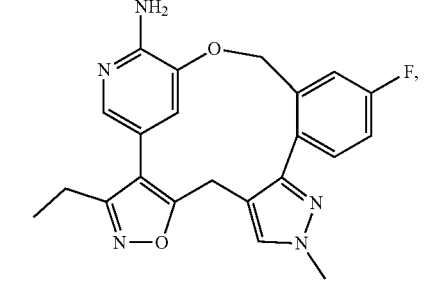 [SMILES: CCc1noc2c1-c1cnc(N)c(c1)OCc1cc(F)ccc1-c1nn(C)cc1C2] 30 |

TABLE 1-continued
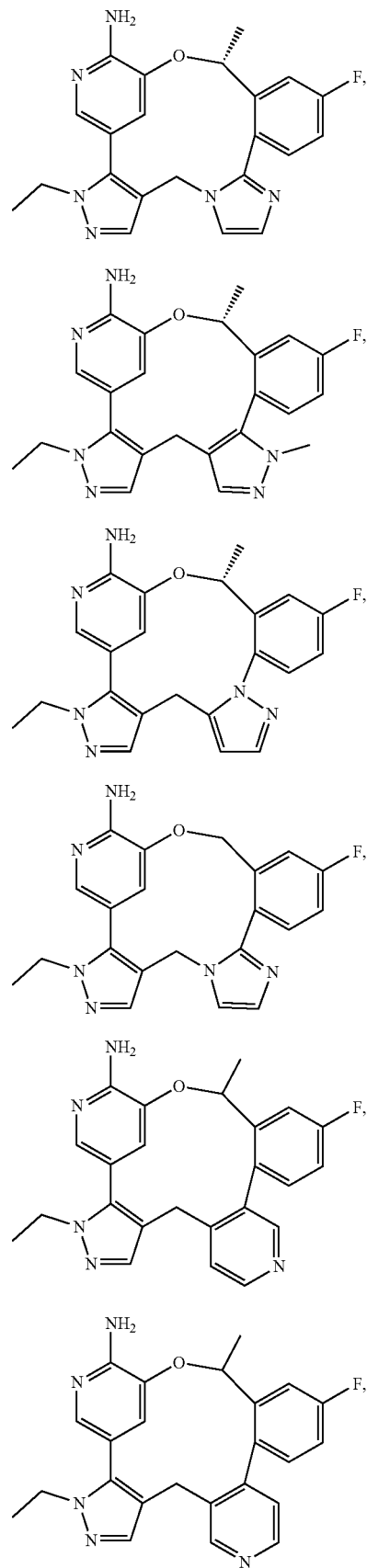
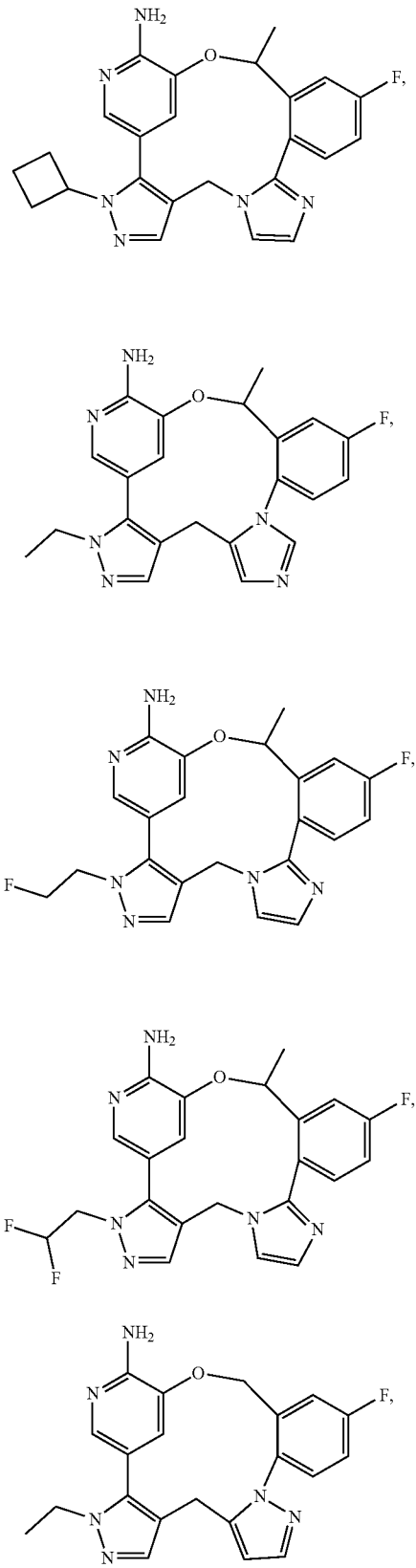

TABLE 1-continued
42
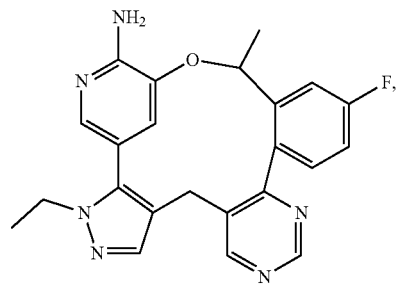 [SMILES: CCn1ncc2c1-c1cnc(N)c(c1)OC(C)c1cc(F)ccc1-c1ncncc1C2]
43
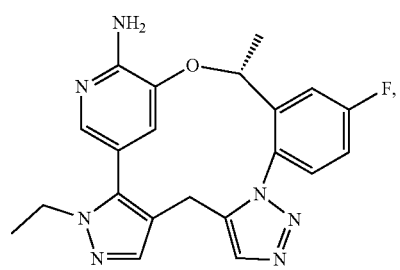 [SMILES: CCn1ncc2c1-c1cnc(N)c(c1)O[C@H](C)c1cc(F)ccc1-n1nncc1C2]
44
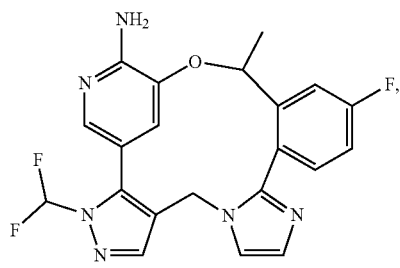 [SMILES: CC1Oc2cc(cnc2N)-c2c(cnn2C(F)F)Cn2ccnc2-c2ccc(F)cc21]
45
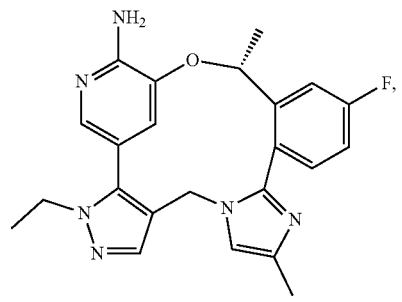 [SMILES: CCn1ncc2c1-c1cnc(N)c(c1)O[C@H](C)c1cc(F)ccc1-c1nc(C)cn1C2]
46
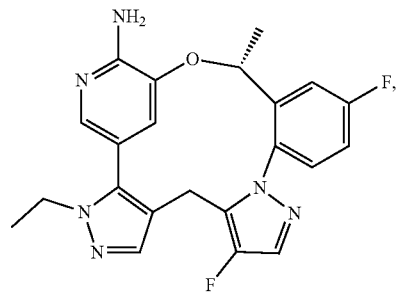 [SMILES: CCn1ncc2c1-c1cnc(N)c(c1)O[C@H](C)c1cc(F)ccc1-n1ncc(F)c1C2]
TABLE 1-continued
47
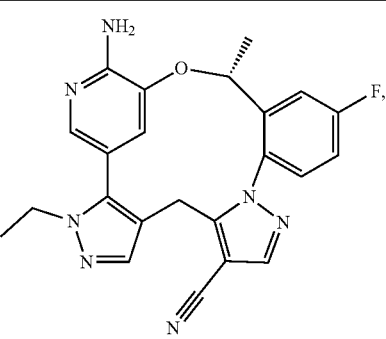
48
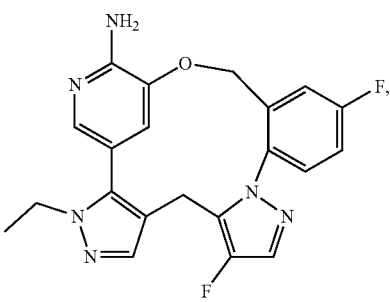 [SMILES: CCn1ncc2c1-c1cnc(N)c(c1)OCc1cc(F)ccc1-n1ncc(F)c1C2]
49
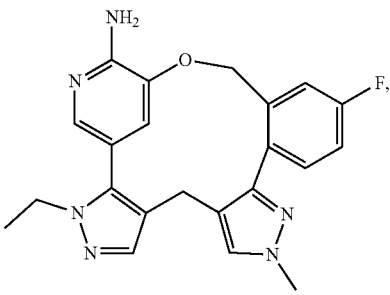 [SMILES: CCn1ncc2c1-c1cnc(N)c(c1)OCc1cc(F)ccc1-c1nn(C)cc1C2]
50
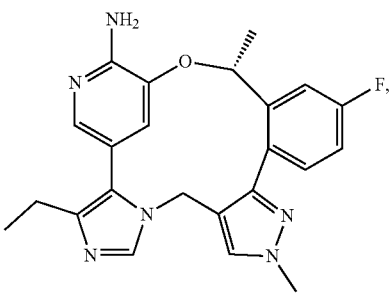 [SMILES: CCc1ncn2c1-c1cnc(N)c(c1)O[C@H](C)c1cc(F)ccc1-c1nn(C)cc1C2]
51
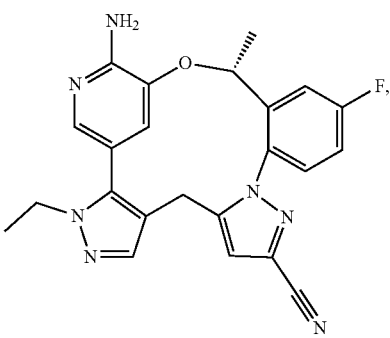 [SMILES: CCn1ncc2c1-c1cnc(N)c(c1)O[C@H](C)c1cc(F)ccc1-n1nc(C#N)cc1C2]

TABLE 1-continued
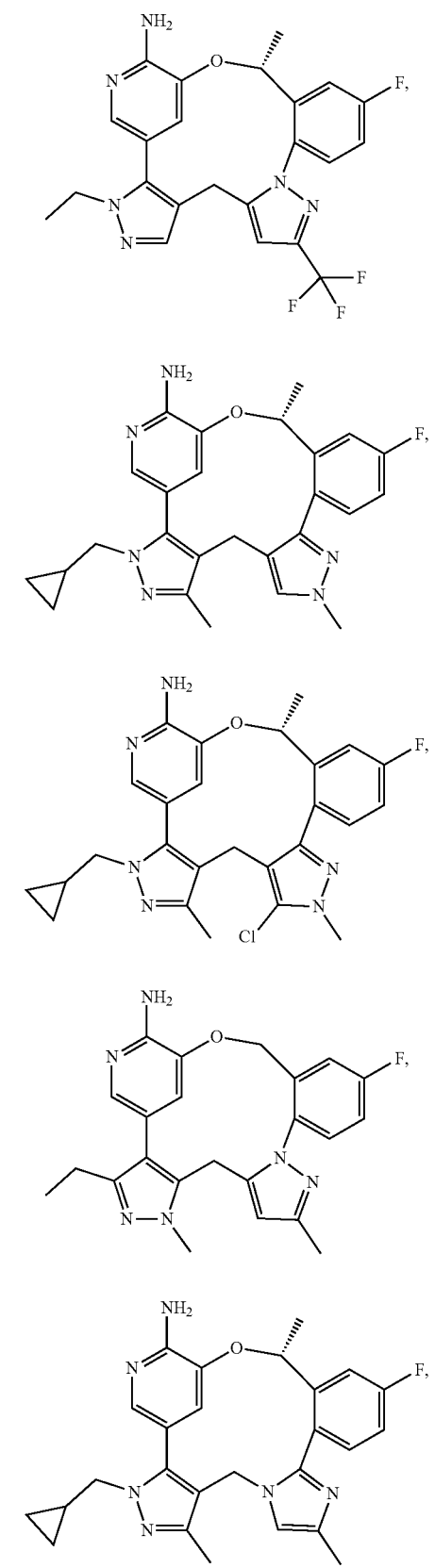
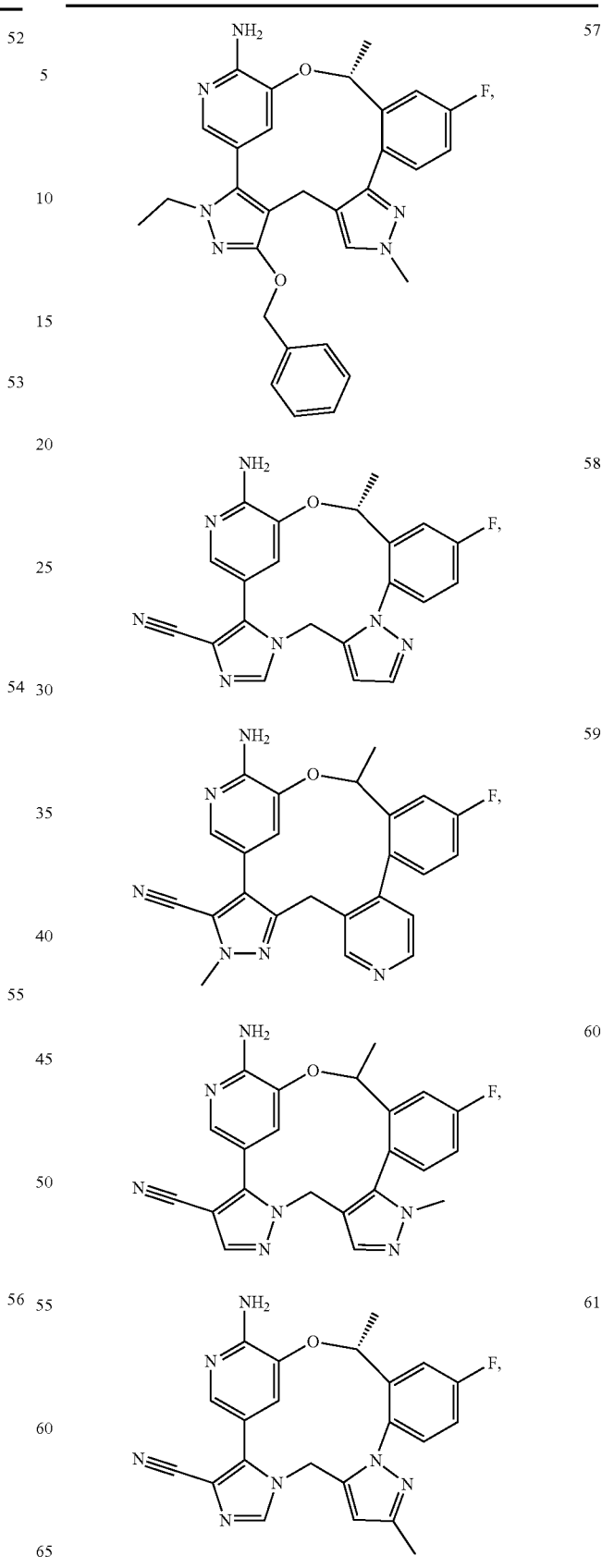

TABLE 1-continued
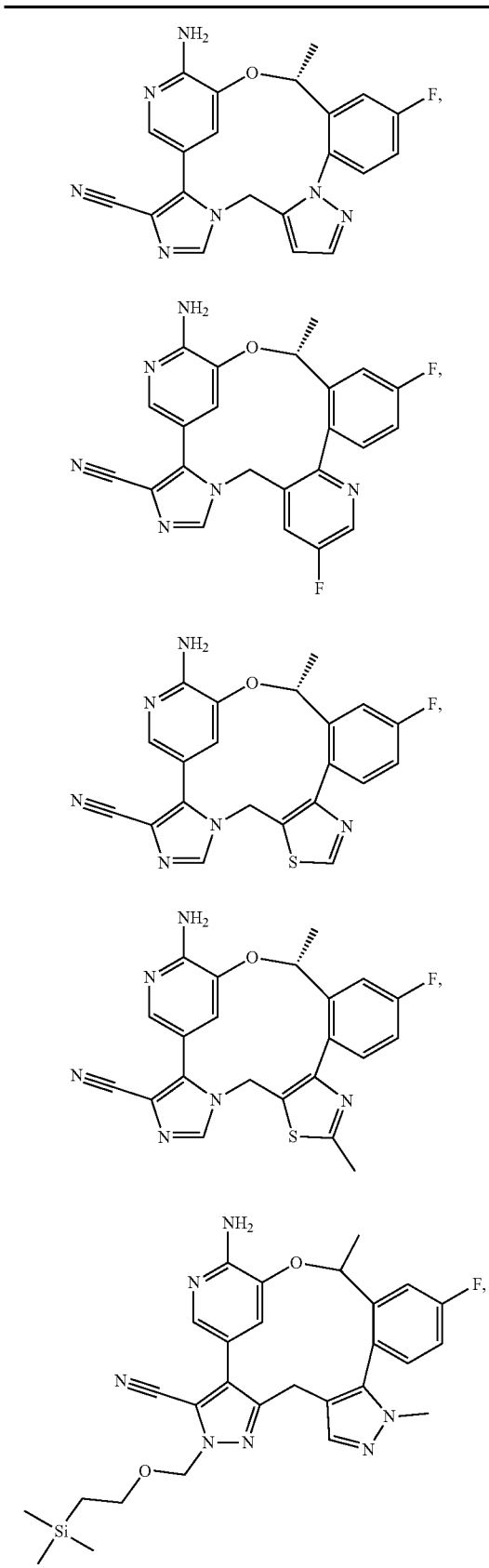
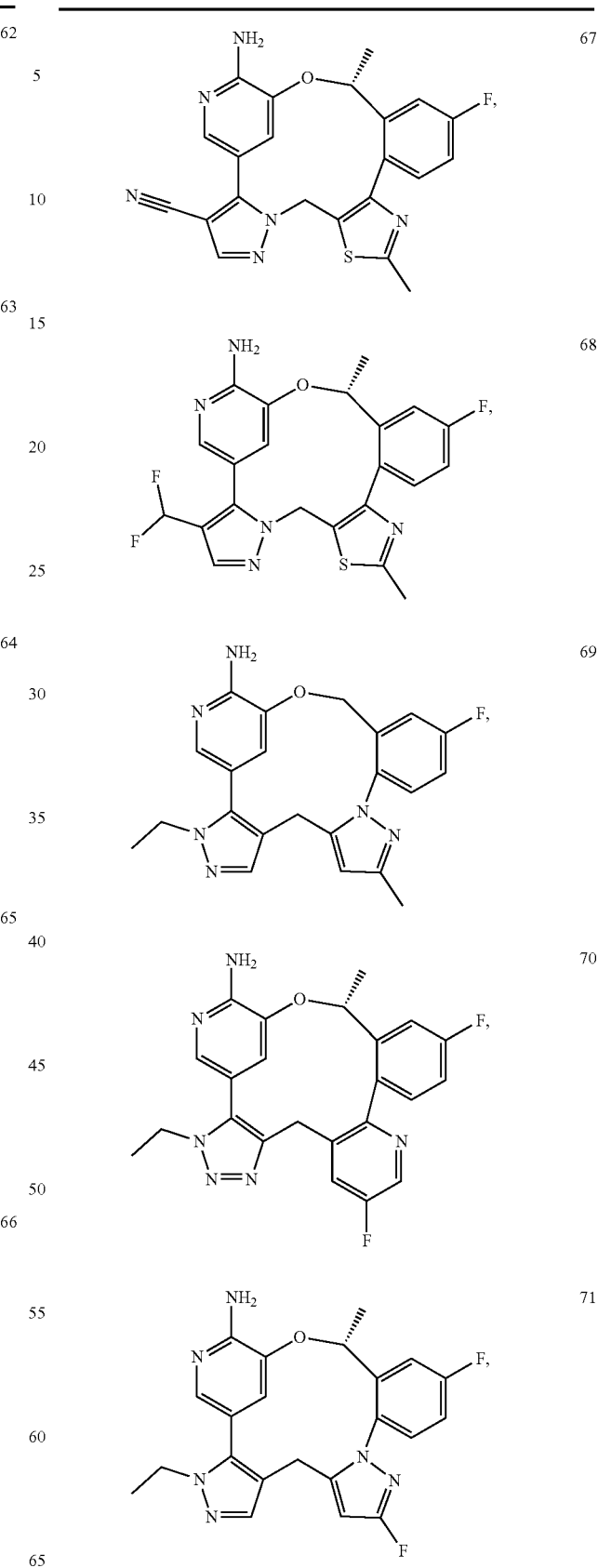

TABLE 1-continued
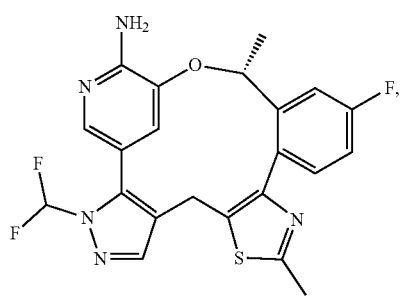 [SMILES: Cc1nc2c(s1)Cc1cnn(C(F)F)c1-c1cnc(N)c(c1)O[C@H](C)c1cc(F)ccc1-2] 72
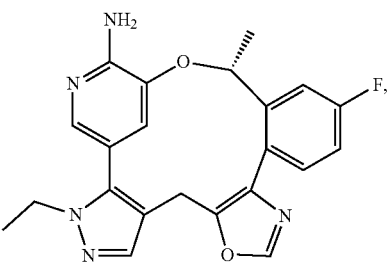 77
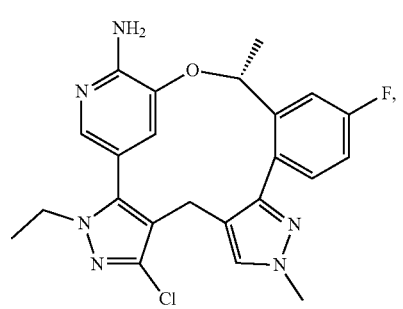 [SMILES: CCn1nc(Cl)c2c1-c1cnc(N)c(c1)O[C@H](C)c1cc(F)ccc1-c1nn(C)cc1C2] 73
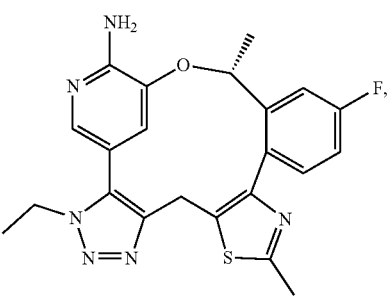 78
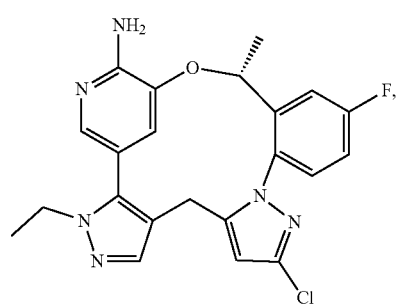 [SMILES: CCn1ncc2c1-c1cnc(N)c(c1)O[C@H](C)c1cc(F)ccc1-n1nc(Cl)cc1C2] 74
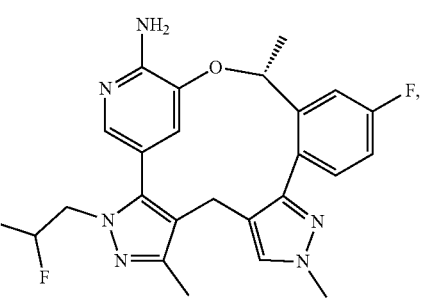 79
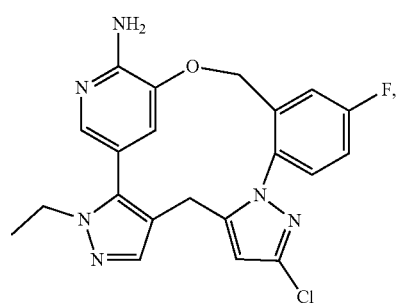 [SMILES: CCn1ncc2c1-c1cnc(N)c(c1)OCc1cc(F)ccc1-n1nc(Cl)cc1C2] 75
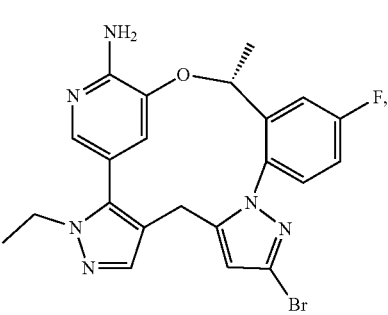 80
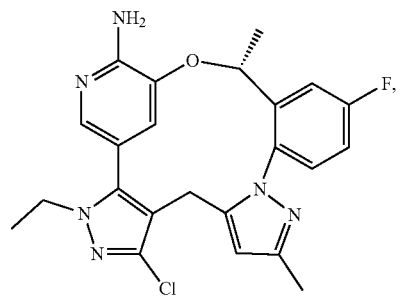 [SMILES: CCn1nc(Cl)c2c1-c1cnc(N)c(c1)O[C@H](C)c1cc(F)ccc1-n1nc(C)cc1C2] 76
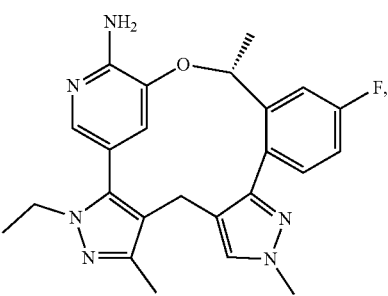 [SMILES: CCn1nc(C)c2c1-c1cnc(N)c(c1)O[C@H](C)c1cc(F)ccc1-c1nn(C)cc1C2] 81

TABLE 1-continued
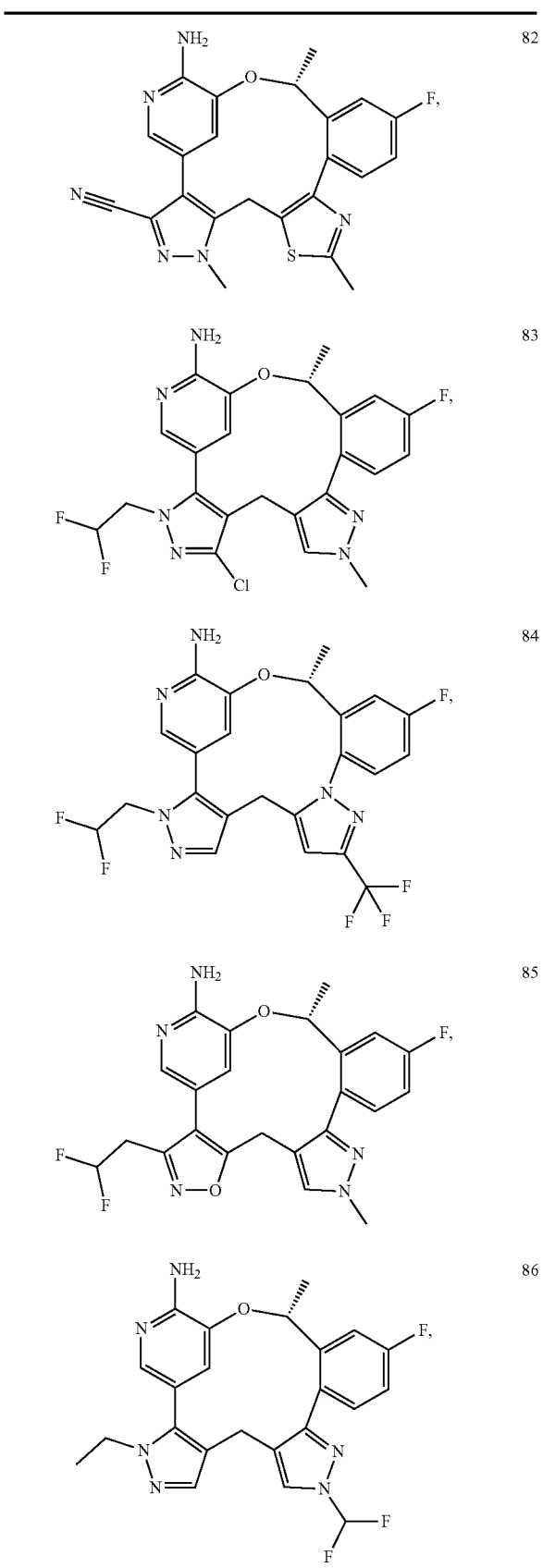
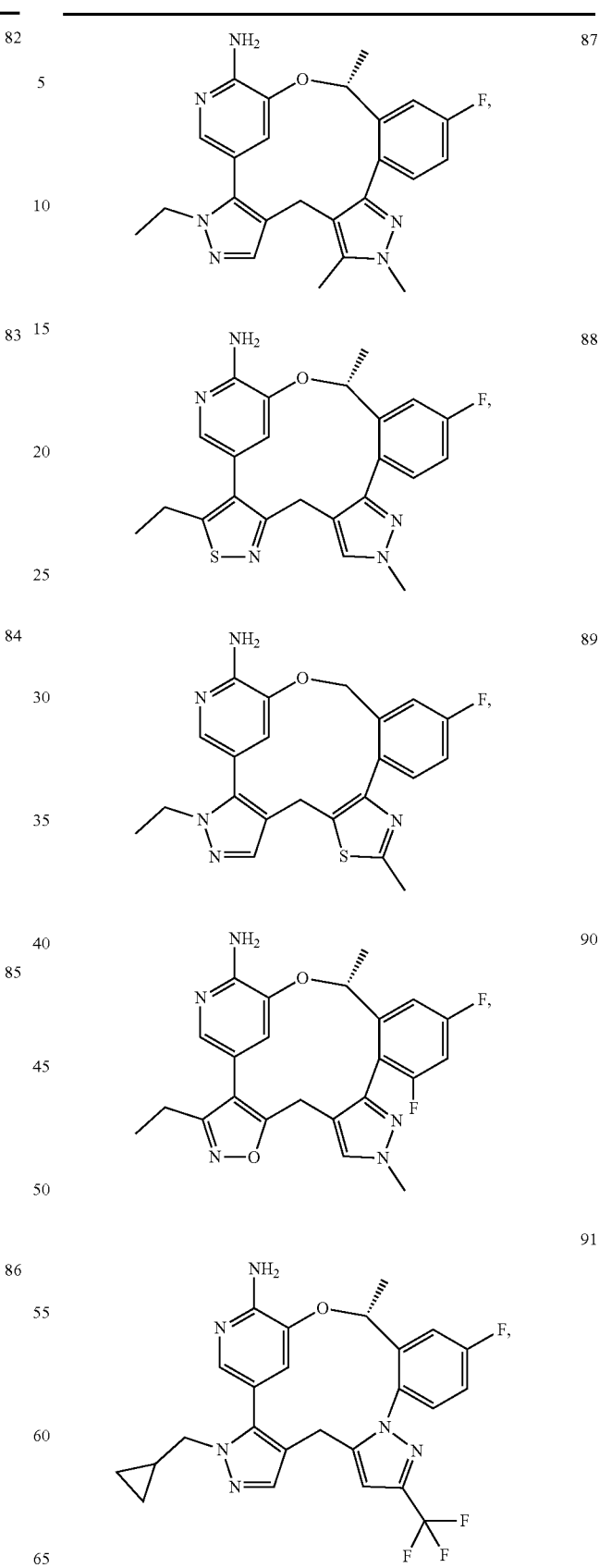

TABLE 1-continued
92
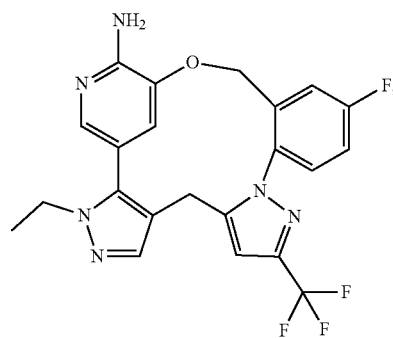 [SMILES: CCn1ncc2c1-c1cnc(N)c(c1)OCc1cc(F)ccc1-n1nc(C(F)(F)F)cc1C2]
93
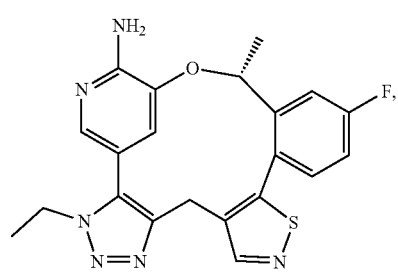 [SMILES: CCn1nnc2c1-c1cnc(N)c(c1)O[C@H](C)c1cc(F)ccc1-c1sncc1C2]
94
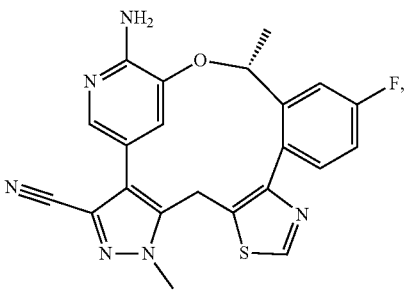 [SMILES: C[C@H]1Oc2cc(cnc2N)-c2c(C#N)nn(C)c2Cc2scnc2-c2ccc(F)cc21]
95
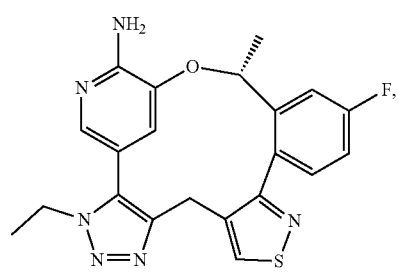 [SMILES: CCn1nnc2c1-c1cnc(N)c(c1)O[C@H](C)c1cc(F)ccc1-c1nscc1C2]
96
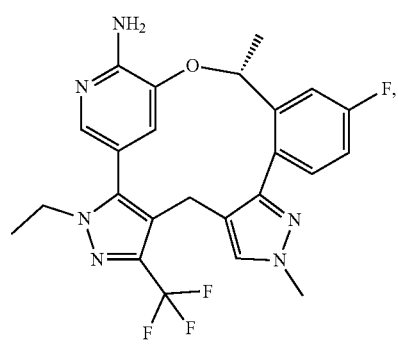 [SMILES: CCn1nc(C(F)(F)F)c2c1-c1cnc(N)c(c1)O[C@H](C)c1cc(F)ccc1-c1nn(C)cc1C2]
TABLE 1-continued
97
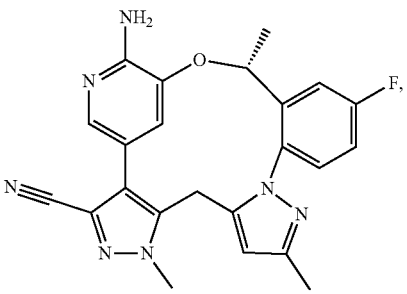 [SMILES: Cc1cc2n(n1)-c1ccc(F)cc1[C@@H](C)Oc1cc(cnc1N)-c1c(C#N)nn(C)c1C2]
98
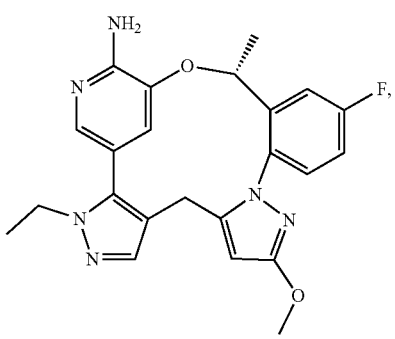 [SMILES: CCn1ncc2c1-c1cnc(N)c(c1)O[C@H](C)c1cc(F)ccc1-n1nc(OC)cc1C2]
99
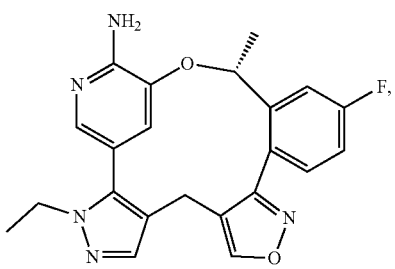 [SMILES: CCn1ncc2c1-c1cnc(N)c(c1)O[C@H](C)c1cc(F)ccc1-c1nocc1C2]
100
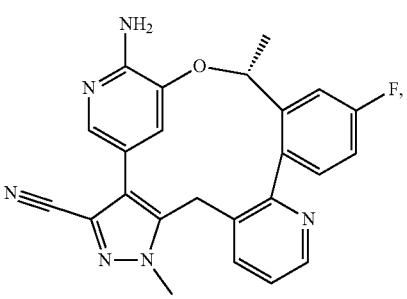 [SMILES: C[C@H]1Oc2cc(cnc2N)-c2c(C#N)nn(C)c2Cc2cccnc2-c2ccc(F)cc21]
101
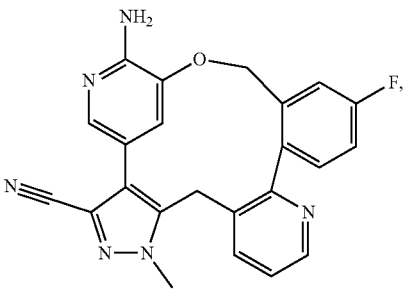 [SMILES: Cn1nc(C#N)c2c1Cc1cccnc1-c1ccc(F)cc1COc1cc-2cnc1N]

TABLE 1-continued
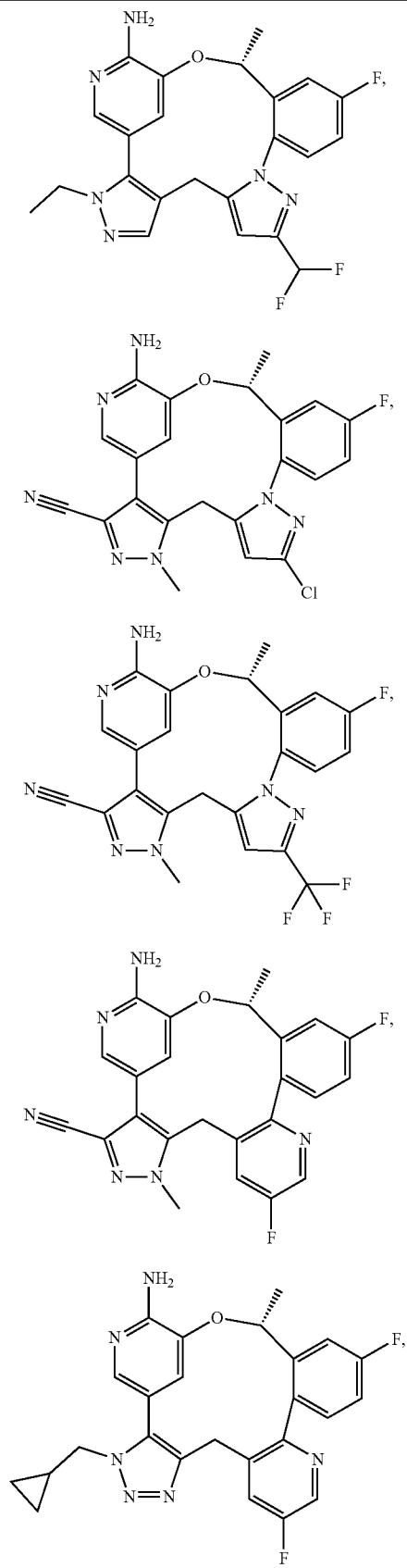
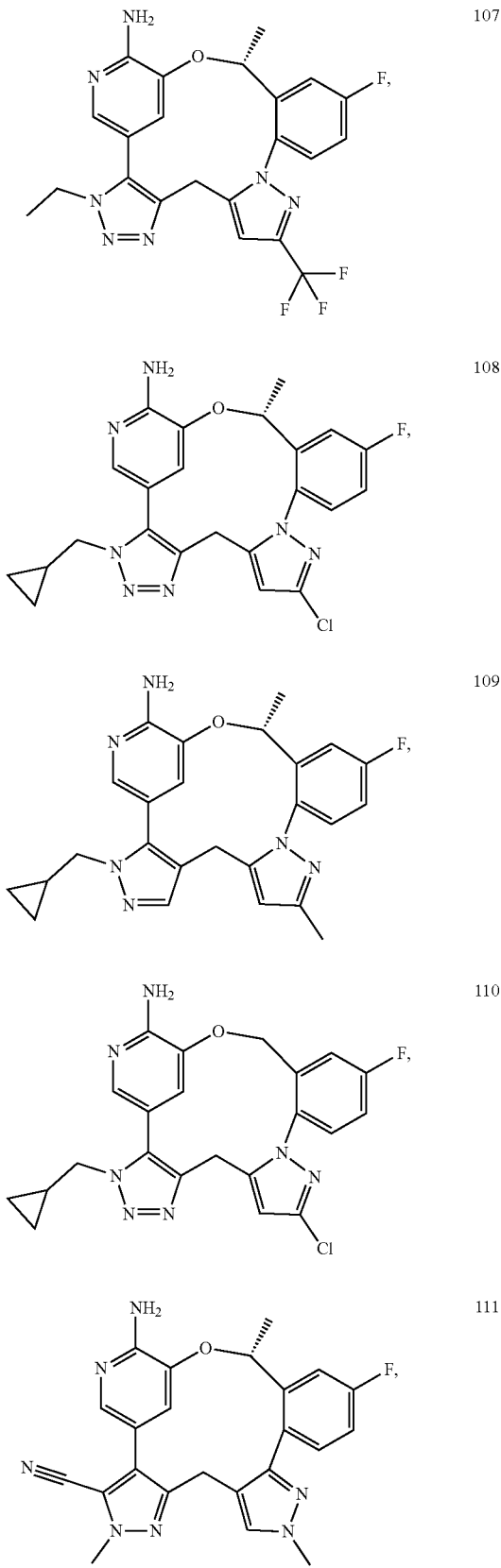

TABLE 1-continued
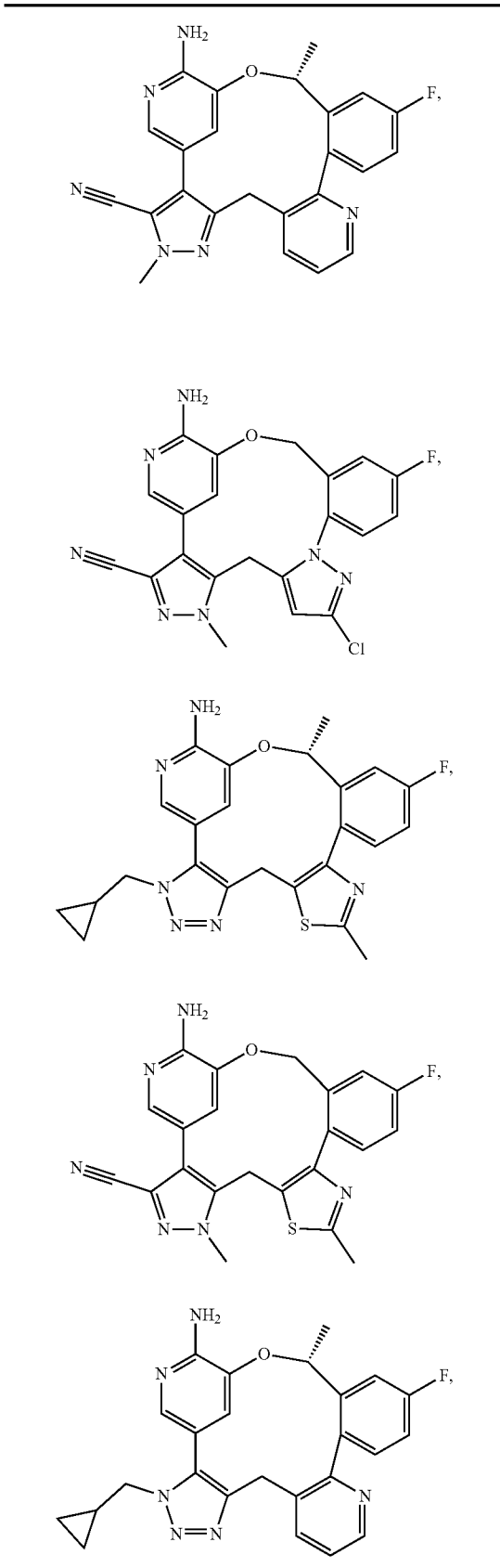

TABLE 1-continued
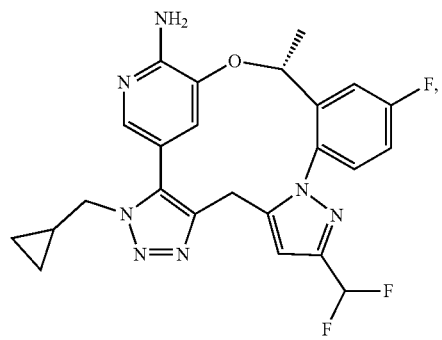 [SMILES: C[C@H]1Oc2cc(cnc2N)-c2c(nnn2CC2CC2)Cc2cc(C(F)F)nn2-c2ccc(F)cc21]
122
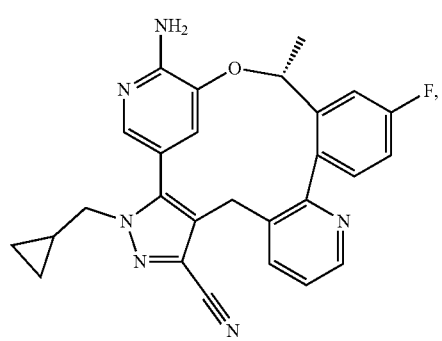 [SMILES: C[C@H]1Oc2cc(cnc2N)-c2c(c(C#N)nn2CC2CC2)Cc2cccnc2-c2ccc(F)cc21]
123
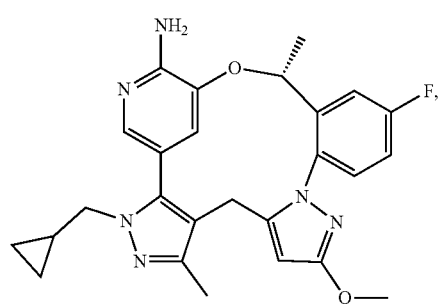 [SMILES: COc1cc2n(n1)-c1ccc(F)cc1[C@@H](C)Oc1cc(cnc1N)-c1c(c(C)nn1CC1CC1)C2]
124
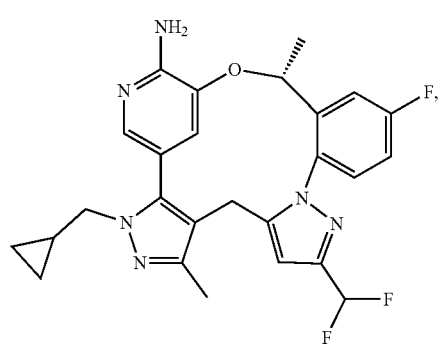 [SMILES: Cc1nn(CC2CC2)c2c1Cc1cc(C(F)F)nn1-c1ccc(F)cc1[C@@H](C)Oc1cc-2cnc1N]
125
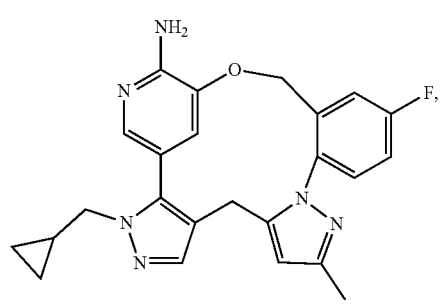 [SMILES: Cc1cc2n(n1)-c1ccc(F)cc1COc1cc(cnc1N)-c1c(cnn1CC1CC1)C2]
126
TABLE 1-continued
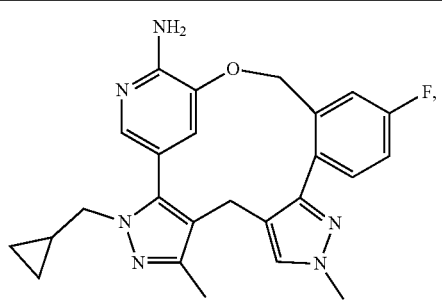
127
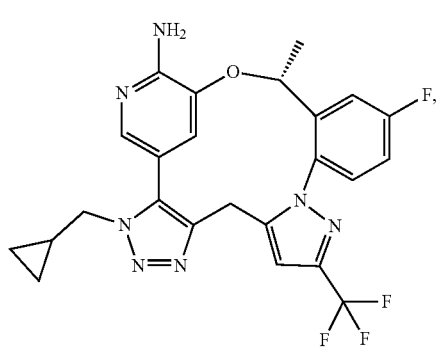 [SMILES: C[C@H]1Oc2cc(cnc2N)-c2c(nnn2CC2CC2)Cc2cc(C(F)(F)F)nn2-c2ccc(F)cc21]
128
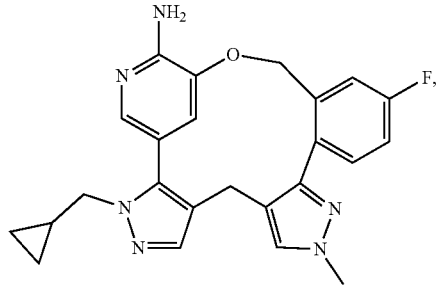 [SMILES: Cn1cc2c(n1)-c1ccc(F)cc1COc1cc(cnc1N)-c1c(cnn1CC1CC1)C2]
129
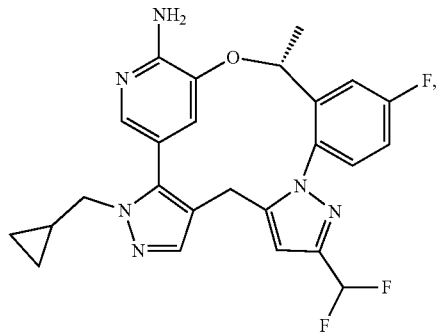 [SMILES: C[C@H]1Oc2cc(cnc2N)-c2c(cnn2CC2CC2)Cc2cc(C(F)F)nn2-c2ccc(F)cc21]
130
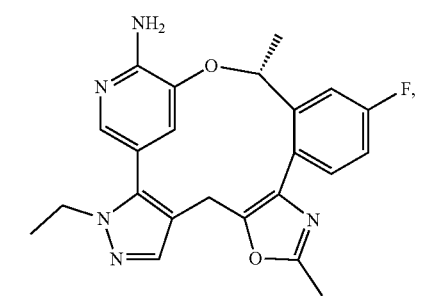 [SMILES: CCn1ncc2c1-c1cnc(N)c(c1)O[C@H](C)c1cc(F)ccc1-c1nc(C)oc1C2]
131

TABLE 1-continued
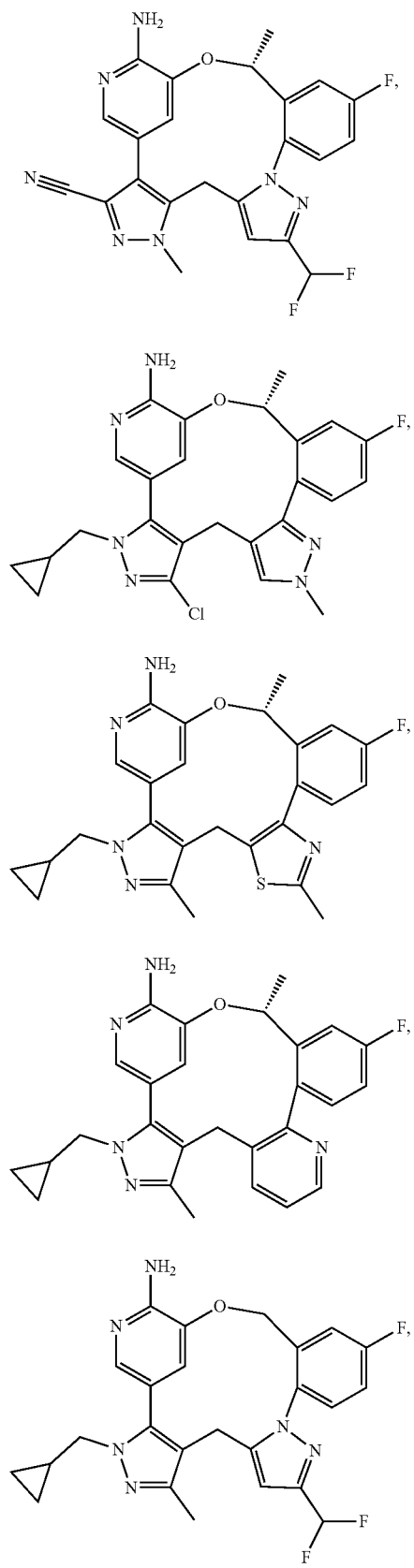
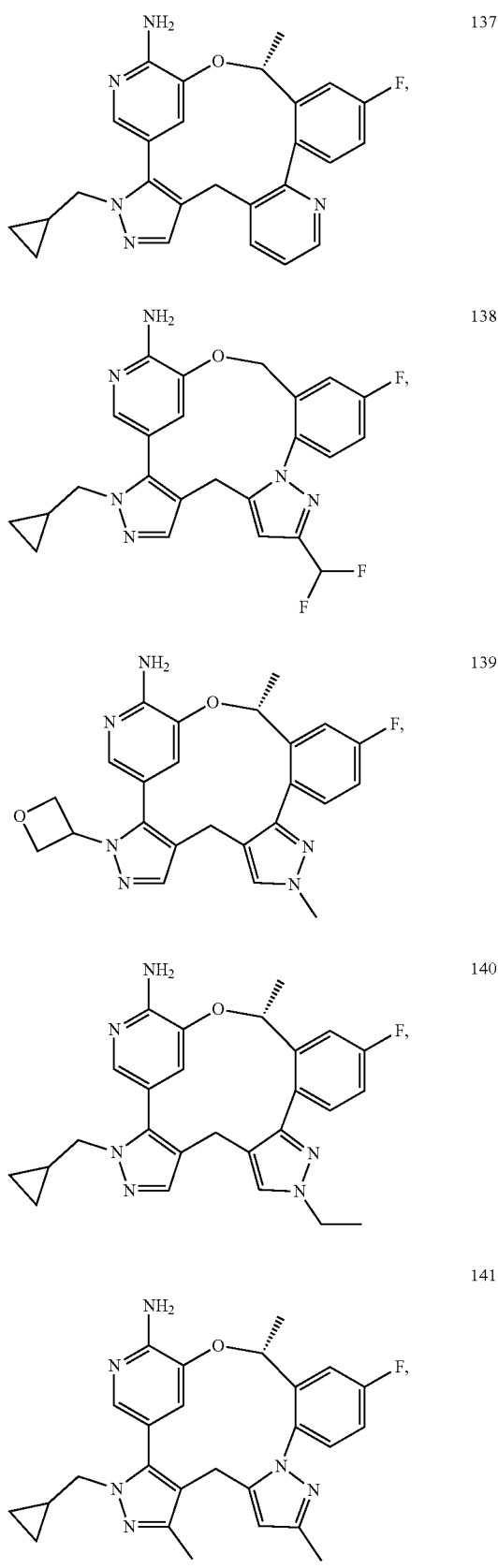

TABLE 1-continued
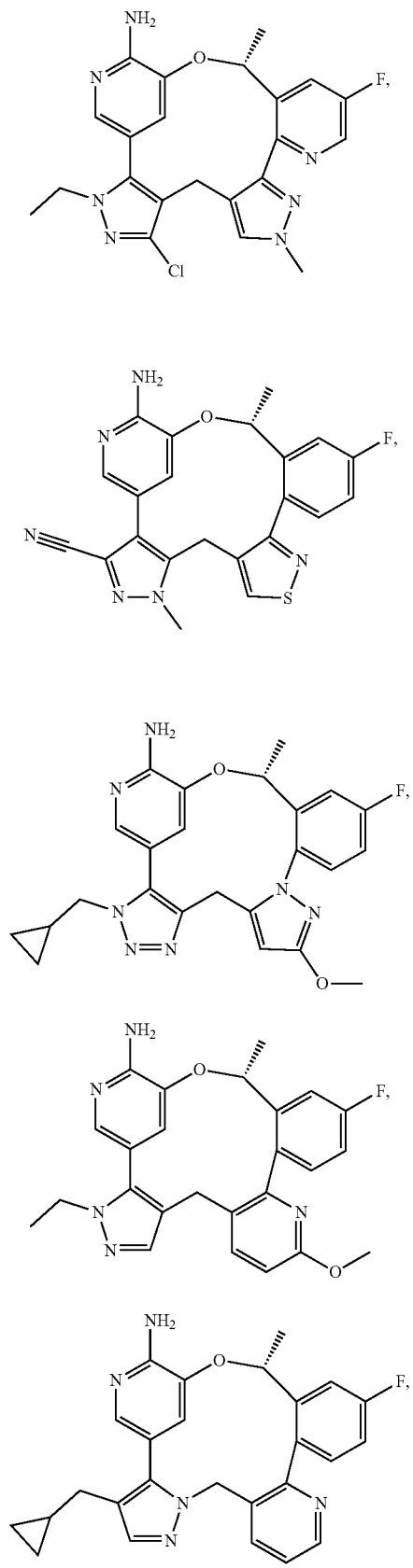
142
143
144
145
146
TABLE 1-continued
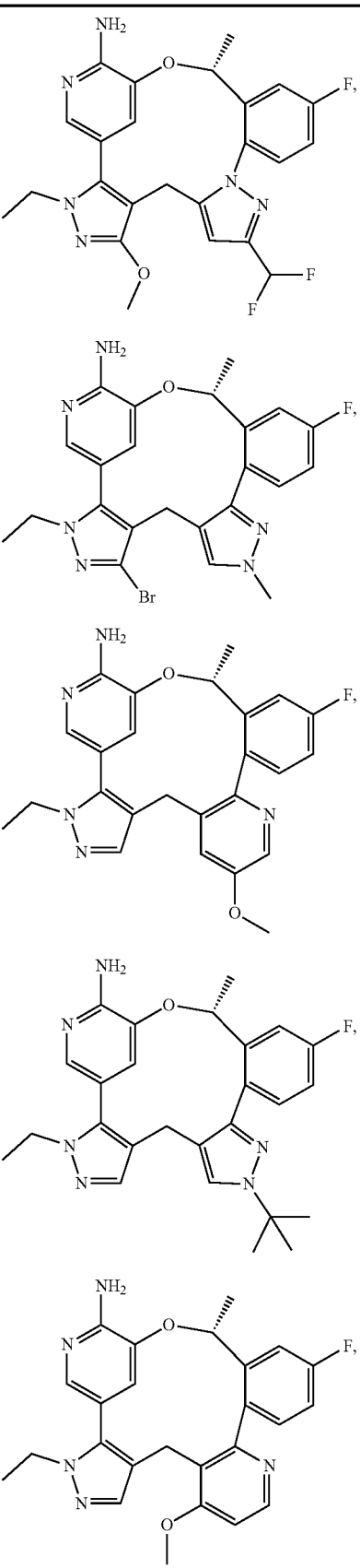
147
148
149
150
151

TABLE 1-continued
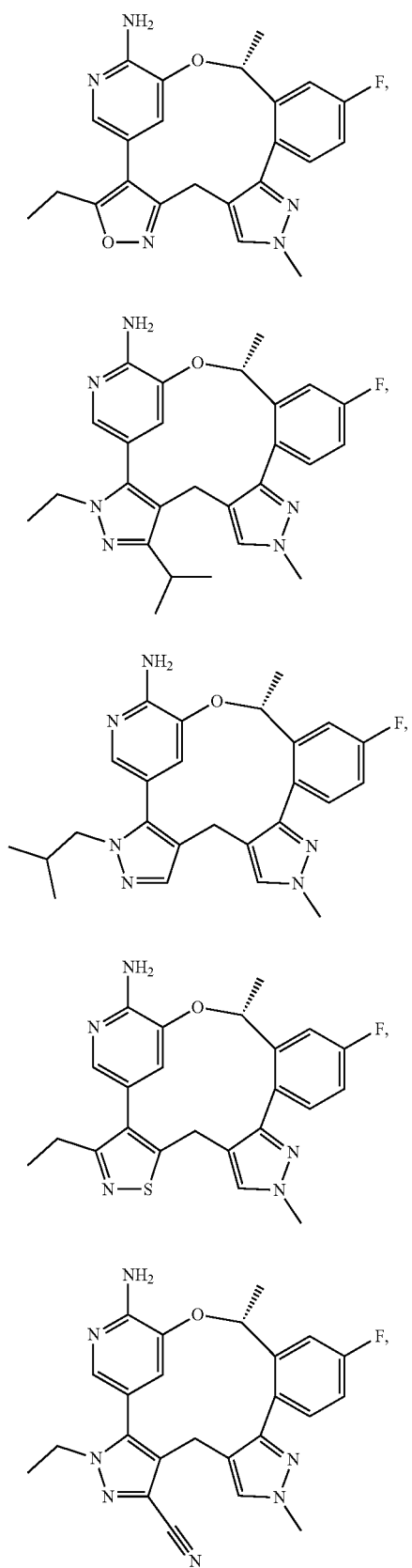
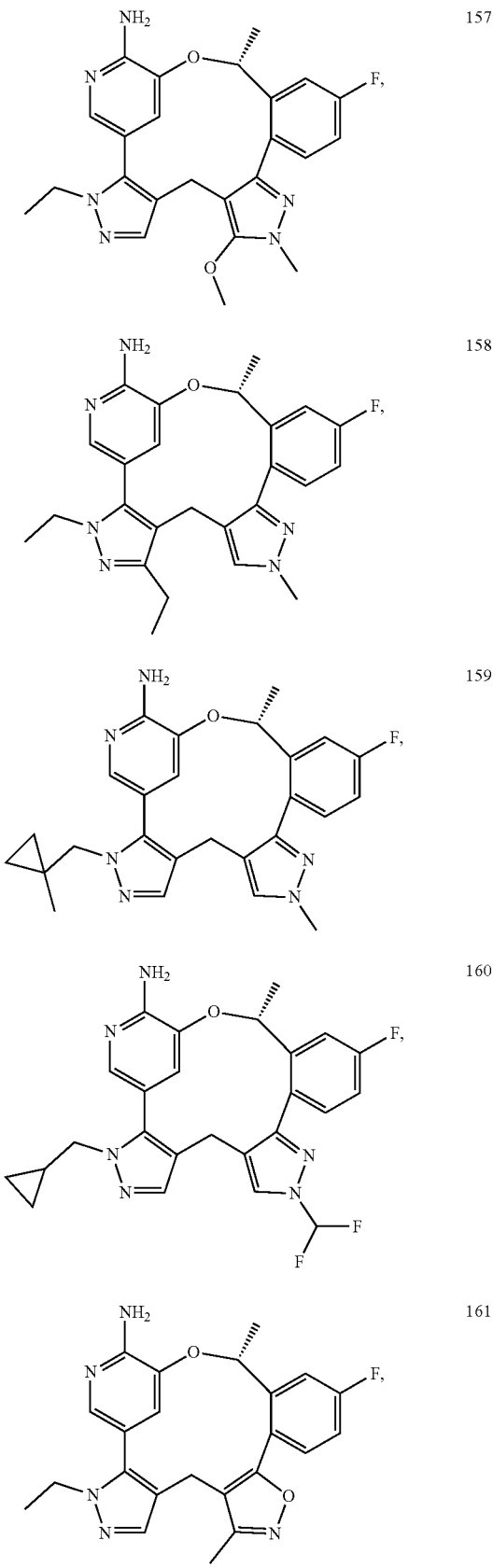

TABLE 1-continued
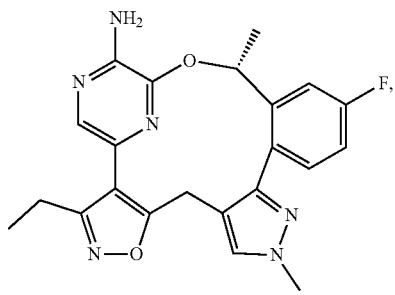
162
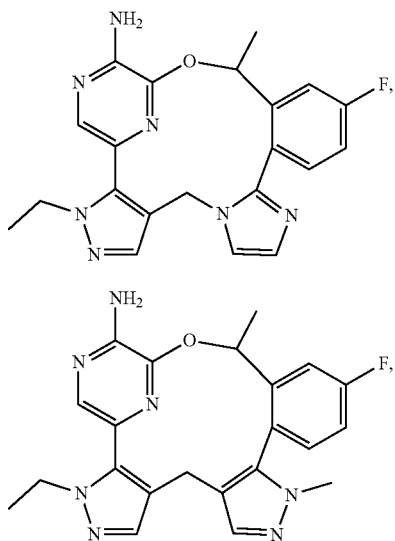
163
164
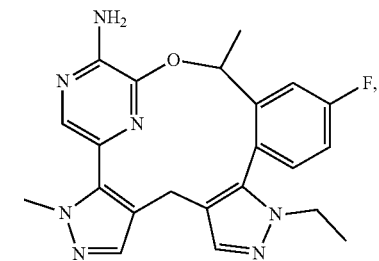 [SMILES: CCn1ncc2c1-c1ccc(F)cc1C(C)Oc1nc(cnc1N)-c1c(cnn1C)C2]
165
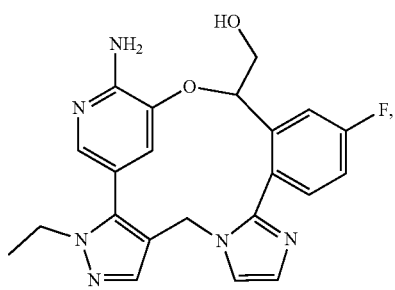 [SMILES: CCn1ncc2c1-c1cnc(N)c(c1)OC(CO)c1cc(F)ccc1-c1nccn1C2]
166
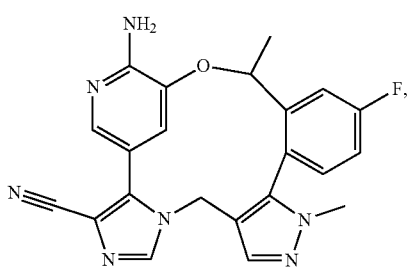 [SMILES: CC1Oc2cc(cnc2N)-c2c(C#N)ncn2Cc2cnn(C)c2-c2ccc(F)cc21]
167
TABLE 1-continued
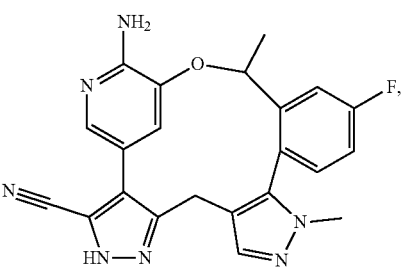 [SMILES: CC1Oc2cc(cnc2N)-c2c(n[nH]c2C#N)Cc2cnn(C)c2-c2ccc(F)cc21]
168
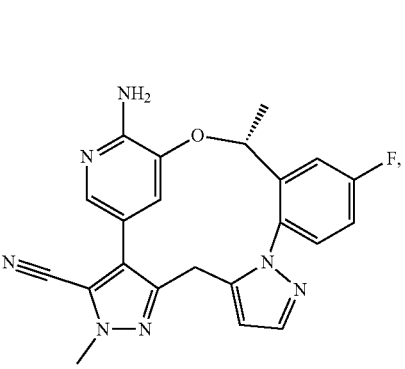 [SMILES: C[C@H]1Oc2cc(cnc2N)-c2c(nn(C)c2C#N)Cc2ccnn2-c2ccc(F)cc21]
169
170
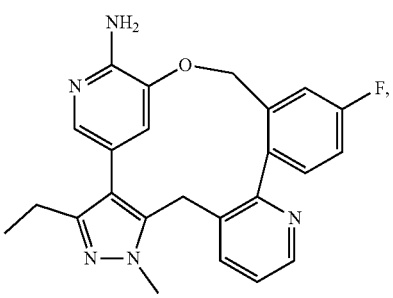 [SMILES: CCc1nn(C)c2c1-c1cnc(N)c(c1)OCc1cc(F)ccc1-c1ncccc1C2]
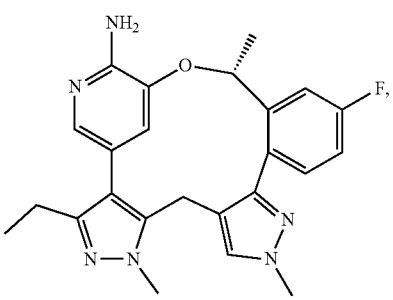 [SMILES: CCc1nn(C)c2c1-c1cnc(N)c(c1)O[C@H](C)c1cc(F)ccc1-c1nn(C)cc1C2]
171
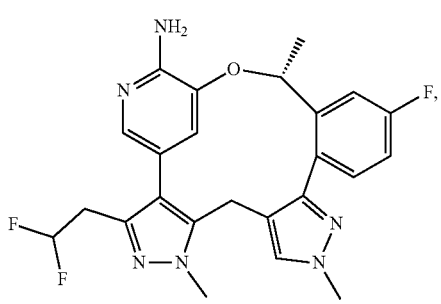 [SMILES: C[C@H]1Oc2cc(cnc2N)-c2c(CC3CC3)nn(C)c2Cc2cn(C)nc2-c2ccc(F)cc21]
172

TABLE 1-continued

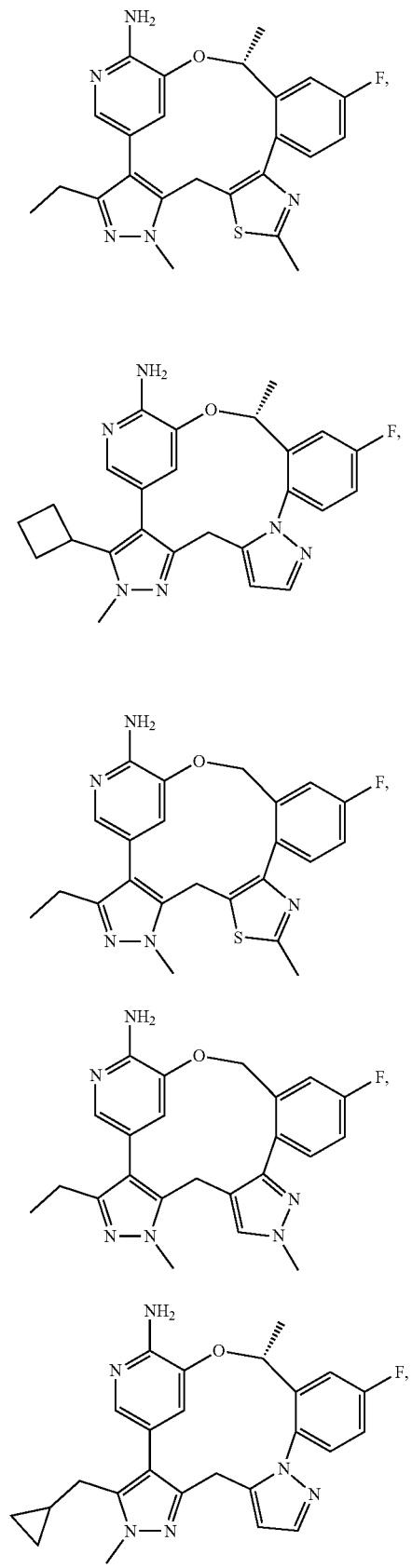

TABLE 1-continued

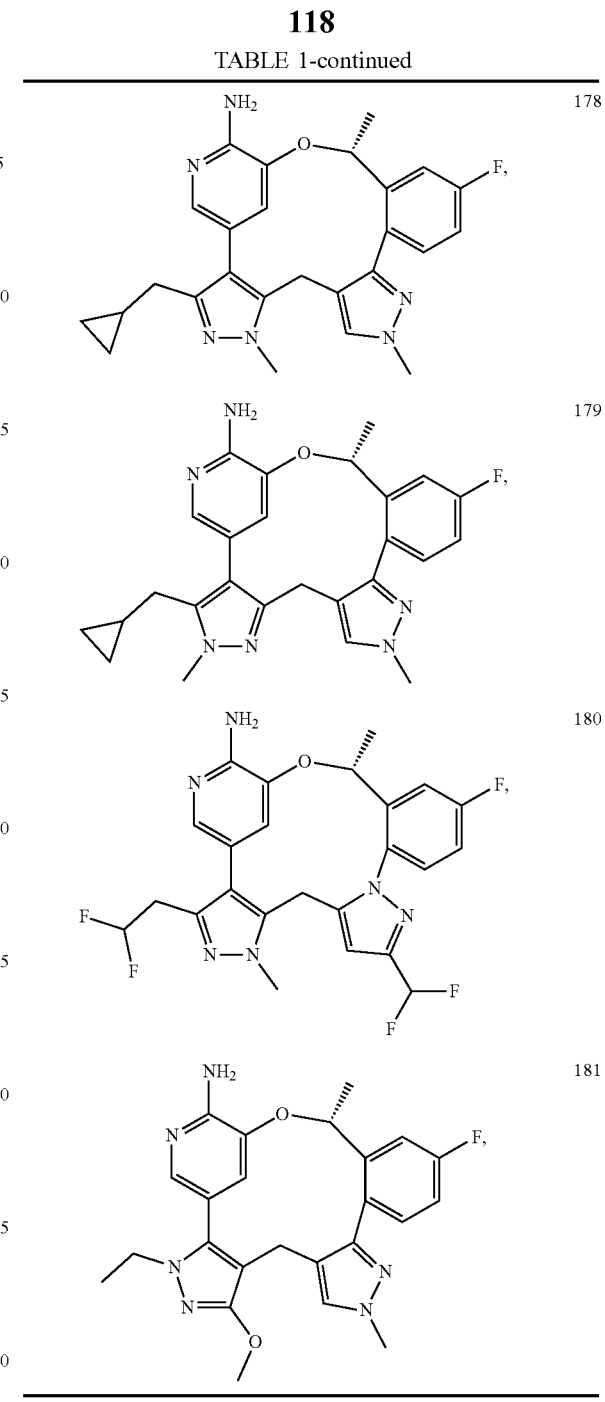

or a pharmaceutically acceptable salt thereof.

For any compound in Table 1 that has a chiral center due to the presence of non-hydrogen R₁, the R-enantiomer, the S-enantiomer, and the racemic compound of such compound are all specifically provided herein, even if not specifically shown in Table 1.

In one embodiment, provided herein is a pharmaceutically acceptable salt of a compound of Formula (I). In one embodiment, provided herein is a pharmaceutically acceptable salt of any compound in Table 1.

In certain embodiments, the pharmaceutically acceptable salt of the compound is selected from the group consisting of alkyl ammonium salts, dialkyl ammonium salts, trialkyl ammonium salts, tetra-alkyl ammonium salts, L-arginine salts, benenthamine salts, benzathine salts, betaine salts, calcium hydroxide salts, choline salts, deanol salts, diethanolamine salts, diethylamine salts, 2-(diethylamino)ethanol salts, ethanolamine salts, ethylenediamine salts, N-methylglucamine salts, hydrabamine salts, 1H-imidazole salts, lithium salts, L-lysine salts, magnesium salts, 4-(2-hydroxyethyl)morpholine salts, piperazine salts, potassium salts, 1-(2-hydroxyethyl)pyrrolidine salts, sodium salts, triethanolamine salts, tromethamine salts, Na salts, Ca salts, K salts, Mg salts, and Zn salts.

In specific embodiments, the pharmaceutically acceptable salt is a solvate selected from the group consisting of water, methanol, ethanol, and dimethylformamide.

In certain embodiments the compound is a pharmaceutical composition including a pharmaceutically acceptable carrier or excipient.

In specific embodiments, the composition is in a form selected from the group consisting of a tablet, a capsule, a granule, a lyophile for reconstitution, a powder, a solution, a syrup, a suppository, an injection, a transdermal delivery system, and a solution suitable for topical administration.

Methods of Use

Provided herein are methods of treating cancer comprising administering a compound of the disclosure, such as a compound of Formula (I), or an enantiomer, a mixture of enantiomers, or a tautomer thereof, or a pharmaceutically acceptable salt thereof.

Cancer is a disease of uncontrolled cell proliferation that results from alterations in certain genes. Some of these alterations occur in genes that encode receptor tyrosine kinases (RTKs), a family of membrane-bound proteins that transmit signals from outside the cell to promote cell survival, growth, and proliferation. Aberrant RTK activation can lead to excessive cell growth and hence cancer. Generally, RTKs contain an N-terminal domain that binds extracellular ligands, a transmembrane domain, and a C-terminal kinase domain that catalyzes intracellular signal transduction.

In some embodiments, the compound of Formula (I) is an inhibitor of human ROS1. ROS1 is an RTK encoded by the ROS1 gene. The ligands and biological functions of human ROS1 are unknown, but its homologs in some other species have been shown to bind extracellular ligands and stimulate cell differentiation. For example, mouse ROS1 is essential for male gamete maturation and reproduction. In humans, ROS1 chromosomal rearrangements are a well-documented cause of cancer, representing 1-2% of non-small cell lung cancer (NSCLC) and a subset of many other cancers. These rearrangements result in the fusion of the C-terminus of ROS1 with the N-terminus of various partner proteins, the most common of which is CD74. ROS1 fusions have constitutive kinase activity that drives tumor growth through MAPK, PI3K, and JAK/STAT signaling pathways. Small-molecule tyrosine kinase inhibitors (TKIs) have been used to target ROS1 fusions in cancer, including crizotinib and entrectinib. Crizotinib was the first FDA-approved TKI for the treatment of ROS1-positive NSCLC, with an overall response rate of 60-80% and median progression-free survival of 9-19 months. Despite an initial response, most patients acquire resistance to crizotinib and relapse. The predominant mechanism of resistance is the G2032R mutation in the solvent front, which dramatically reduces crizotinib affinity. No inhibitors with activity against ROS1-G2032R fusions have been FDA-approved, indicating a need in the art.

In some embodiments, the compound of Formula (I) is an inhibitor of human anaplastic lymphoma kinase (ALK). ALK, also known as cluster of differentiation 246 (CD246), is an RTK encoded by the ALK gene. ALK and ROS1 are evolutionarily related; both belong to the insulin receptor superfamily, and their kinase domains share around 80% sequence similarity. A few ALK ligands in humans have been identified, including pleiotrophin and midkine growth factors. While the roles of ALK in humans remain inconclusive, much evidence from mouse studies suggests that it is important for the development of the nervous system. Like ROS1, ALK chromosomal rearrangements also lead to constitutively active fusion proteins that promote oncogenic transformation through MAPK, JAK/STAT, or other signaling pathways. ALK rearrangements represent 3-5% of NSCLC, roughly half of anaplastic large-cell lymphoma (ALCL), and a subset of many other cancers, with the predominant fusions being EML4-ALK for NSCLC and NPM1-ALK for ALCL. Oncogenic point mutations and amplification of ALK have also been observed, albeit at a much lower frequency than translocations. Crizotinib, ceritinib, alectinib, brigatinib, and lorlatinib are FDA-approved TKIs for the treatment of ALK-positive NSCLC and other cancers, either in front-line or after prior therapy. Crizotinib, for example, shows an overall response rate of 60-80% and median progression-free survival of 8-11 months, which is comparable to its activity in ROS1-positive NSCLC. Despite an initial response, many resistance mutations have emerged to the aforementioned FDA-approved TKIs. Some of these mutations, such as the combined L1196M gatekeeper and G1202R solvent front mutation, are resistant to all of the approved drugs. New treatments of ALK-positive cancer harboring resistance mutations are a need in the art.

In further embodiments, the compound of Formula (I) is an inhibitor of human tropomyosin receptor kinases (TRKs). The TRK family comprises receptor tyrosine kinases TRKA, TRKB, and TRKC, which are encoded by the NTRK1, NTRK2, and NTRK3 genes, respectively. Each TRK is activated by a different but overlapping set of neurotrophin ligands such as NGF, BDNF, and NT-3. All TRKs modulate similar downstream signaling pathways, consistent with sequence divergence in the ligand-binding domain but convergence in the kinase domain (90% similarity). TRKs play crucial roles in the nervous system of developing and adult mammals by regulating processes such as memory, movement, pain, and proprioception. Like ROS1 and ALK, NTRK rearrangements lead to constitutively active TRK fusions that drive oncogenic transformation through MAPK, PI3K, and other pathways. TRK fusions are found in many cancers and represent over 80% of the cases in secretory breast carcinoma, mammary analogue secretory carcinomas, infantile fibrosarcoma, and congenital mesoblastic nephroma. Thus, inhibition of TRKs is advantageous for treating cancers expressing TRK fusions.

Many ROS1 and ALK inhibitors in the prior art also exhibit potent inhibition of native non-oncogenic TRKs. This is a substantial drawback because native TRKs play important functions in the nervous system, and inadvertent inhibition of native TRKs is associated with adverse reactions including dizziness, ataxia, gait disturbance, paraesthesia, weight gain, and cognitive changes. New therapies that spare TRKs while selectively targeting ROS1 and/or ALK, in their non-mutant and/or mutant forms, are a need in the art.

In one embodiment, provided herein is a method of decreasing a level of ROS1 or ALK in a cell, comprising contacting the cell with a compound or a pharmaceutical composition or a pharmaceutical combination provided herein. In an embodiment, such contact occurs in a cell in a mammal such as a human. In an embodiment, such contact occurs in a cell in human patient having a cancer provided herein.

In one embodiment, a compound provided herein selectively inhibits ROS1. In one embodiment, the compound selectively inhibits ROS1 over ALK. By way of non-limiting example, the ratio of selectivity can be greater than a factor of about 1.5, greater than a factor of about 2, greater than a factor of about 3, greater than a factor of about 4, greater than a factor of about 5, greater than a factor of about 10, greater than a factor of about 20, greater than a factor of about 30, greater than a factor of about 50, or greater than a factor of about 100, where selectivity can be measured by ratio of $IC_{50}$ values, among other means. In one embodiment, the selectivity of ROS1 over ALK is measured by the ratio of the $IC_{50}$ value against ALK to the $IC_{50}$ value against ROS1.

In one embodiment, the compound selectively inhibits ROS1 over TRK (e.g., TRKA, TRKB, and/or TRBC). By way of non-limiting example, the ratio of selectivity can be greater than a factor of about 5, greater than a factor of about 10, greater than a factor of about 50, greater than a factor of about 100, greater than a factor of about 200, greater than a factor of about 400, greater than a factor of about 600, greater than a factor of about 800, greater than a factor of about 1000, greater than a factor of about 1500, greater than a factor of about 2000, greater than a factor of about 5000, greater than a factor of about 10,000, or greater than a factor of about 20,000, where selectivity can be measured by ratio of $IC_{50}$ values, among other means. In one embodiment, the selectivity of ROS1 over TRK is measured by the ratio of the $IC_{50}$ value against TRK to the $IC_{50}$ value against ROS1.

In one embodiment, a compound provided herein selectively inhibits ALK. In one embodiment, the compound selectively inhibits ALK over ROS1. By way of non-limiting example, the ratio of selectivity can be greater than a factor of about 1.5, greater than a factor of about 2, than a factor of about 3, greater than a factor of about 4, greater than a factor of about 5, or greater than a factor of about 10, where selectivity can be measured by ratio of $IC_{50}$ values, among other means. In one embodiment, the selectivity of ALK over ROS1 is measured by the ratio of the $IC_{50}$ value against ROS1 to the $IC_{50}$ value against ALK.

In one embodiment, the compound selectively inhibits ALK over TRK (e.g., TRKA, TRKB, and/or TRBC). By way of non-limiting example, the ratio of selectivity can be greater than a factor of about 5, greater than a factor of about 10, greater than a factor of about 50, greater than a factor of about 100, greater than a factor of about 200, greater than a factor of about 400, greater than a factor of about 600, greater than a factor of about 800, greater than a factor of about 1000, greater than a factor of about 1500, greater than a factor of about 2000, greater than a factor of about 5000, or greater than a factor of about 10,000, where selectivity can be measured by ratio of $IC_{50}$ values, among other means. In one embodiment, the selectivity of ALK over TRK is measured by the ratio of the $IC_{50}$ value against TRK to the $IC_{50}$ value against ALK.

In one embodiment, the compound selectively inhibits ROS1 and ALK over TRK (e.g., TRKA, TRKB, and/or TRBC). By way of non-limiting example, the ratio of selectivity can be greater than a factor of about 5, greater than a factor of about 10, greater than a factor of about 50, greater than a factor of about 100, greater than a factor of about 200, greater than a factor of about 400, greater than a factor of about 600, greater than a factor of about 800, greater than a factor of about 1000, greater than a factor of about 1500, greater than a factor of about 2000, greater than a factor of about 5000, greater than a factor of about 10,000, or greater than a factor of about 20,000, where selectivity can be measured by ratio of $IC_{50}$ values, among other means. In one embodiment, the selectivity of ROS1 and ALK over TRK is measured by the ratio of the $IC_{50}$ value against TRK to the $IC_{50}$ value against ROS1 and ALK.

In one embodiment, provided herein is a method for selectively inhibiting ROS1 over ALK wherein the inhibition takes place in a cell. In one embodiment, provided herein is a method for selectively inhibiting ROS1 over TRK (e.g., TRKA, TRKB, and/or TRBC) wherein the inhibition takes place in a cell. In one embodiment, the method comprises contacting ROS1 with an effective amount of a compound provided herein. In an embodiment, such contact occurs in a cell. In an embodiment, such contact occurs in a cell in a mammal such as a human. In an embodiment, such contact occurs in a cell in human patient having a cancer provided herein.

In one embodiment, provided herein is a method for selectively inhibiting ROS1 over ALK wherein the inhibition takes place in a subject suffering from cancer, said method comprising administering an effective amount of a compound or a pharmaceutical composition provided herein to said subject. In certain embodiments, provided herein is a method of treating a subject suffering from a cancer associated with ROS1, said method comprising selectively inhibiting ROS1 over ALK by administering an amount of a compound or a pharmaceutical composition provided herein to said subject, wherein said amount is sufficient for selective inhibiting ROS1 over ALK.

In one embodiment, provided herein is a method for selectively inhibiting ROS1 over TRK (e.g., TRKA, TRKB, and/or TRBC) wherein the inhibition takes place in a subject suffering from cancer, said method comprising administering an effective amount of a compound or a pharmaceutical composition provided herein to said subject. In certain embodiments, provided herein is a method of treating a subject suffering from a cancer associated with ROS1, said method comprising selectively inhibiting ROS1 over TRK (e.g., TRKA, TRKB, and/or TRBC) by administering an amount of a compound or a pharmaceutical composition provided herein to said subject, wherein said amount is sufficient for selective inhibiting ROS1 over TRK (e.g., TRKA, TRKB, and/or TRBC).

In one embodiment, provided herein is a method for selectively inhibiting ALK over ROS1 wherein the inhibition takes place in a cell. In one embodiment, provided herein is a method for selectively inhibiting ALK over TRK (e.g., TRKA, TRKB, and/or TRBC) wherein the inhibition takes place in a cell. In one embodiment, the method comprises contacting ALK with an effective amount of a compound provided herein. In an embodiment, such contact occurs in a cell. In an embodiment, such contact occurs in a cell in a mammal such as a human. In an embodiment, such contact occurs in a cell in human patient having a cancer provided herein.

In one embodiment, provided herein is a method for selectively inhibiting ALK over ROS1 wherein the inhibition takes place in a subject suffering from cancer, said method comprising administering an effective amount of a compound or a pharmaceutical composition provided herein to said subject. In certain embodiments, provided herein is a method of treating a subject suffering from a cancer associated with ALK, said method comprising selectively inhibiting ALK over ROS1 by administering an amount of a compound or a pharmaceutical composition provided herein to said subject, wherein said amount is sufficient for selective inhibiting ALK over ROS1.

In one embodiment, provided herein is a method for selectively inhibiting ALK over TRK (e.g., TRKA, TRKB, and/or TRBC) wherein the inhibition takes place in a subject suffering from cancer, said method comprising administering an effective amount of a compound or a pharmaceutical composition provided herein to said subject. In certain embodiments, provided herein is a method of treating a subject suffering from a cancer associated with ALK, said method comprising selectively inhibiting ALK over TRK (e.g., TRKA, TRKB, and/or TRBC) by administering an amount of a compound or a pharmaceutical composition provided herein to said subject, wherein said amount is sufficient for selective inhibiting ALK over TRK (e.g., TRKA, TRKB, and/or TRBC).

As used herein and unless otherwise specified, inhibition of ROS1 includes inhibition of wild type ROS1, or a mutation thereof; inhibition of ALK includes inhibition of wild type ALK, or a mutation thereof, and inhibition of TRK includes inhibition of wild type TRK, or a mutation thereof.

Cancers treated by methods of the present disclosure include, but are not limited to, lung cancer, e.g., non-small cell lung cancer, inflammatory myofibroblastic tumor, ovarian cancer, e.g., serous ovarian carcinoma, melanoma, e.g., spitzoid melanoma, glioblastoma, bile duct cancer, e.g., cholangiocarcinoma, gastric cancer, colorectal cancer, angiosarcoma, anaplastic large cell lymphoma, diffuse large B-cell lymphoma, large B-cell lymphoma, esophageal cancer, e.g., esophageal squamous cell carcinoma, kidney cancer, e.g., renal medullary carcinoma or renal cell carcinoma, breast cancer, e.g., triple negative breast cancer, thyroid cancer, e.g., papillary thyroid cancer, neuroblastoma, epithelioid hemangioendothelioma, colon cancer, and spitzoid tumor.

Cancers treated by methods of the present disclosure include cancers originating from one or more oncogenic proteins selected from ROS1, ALK, TRKA, TRKB, and TRKC. In certain embodiments, cancers treated by methods of the present disclosure include cancers that are drug resistant to treatments directed at one or more oncogenic proteins selected from ROS1, ALK, TRKA, TRKB, and TRKC.

In one embodiment, the cancer in a method provided herein is anaplastic lymphoma kinase positive (ALK+). As used herein and unless otherwise specified, an "ALK positive" (ALK+) cancer, disease, or disorder refers to a cancer, disease, or disorder characterized by inappropriately high expression of an ALK gene and/or the presence of a mutation in an ALK gene. In one embodiment, the mutation alters the biological activity of an ALK nucleic acid molecule or polypeptide. As used herein and unless otherwise specified, a "mutation" or "mutant" of ALK comprises one or more deletions, substitutions, insertions, inversions, duplications, translocations, or amplifications in the amino acid or nucleotide sequences of ALK, or fragments thereof. As used herein and unless otherwise specified, an ALK "rearrangement" refers to genetic translocations involving the ALK gene that may result in ALK fusion genes and/or ALK fusion proteins. The ALK fusion can also include one or more deletions, substitutions, insertions, inversions, duplications, translocations, or amplifications or a fragment thereof, as long as the mutant retains kinase phosphorylation activity.

In one embodiment, the ALK mutation comprises one or more ALK point mutations. In some embodiments, cancers treated by methods of the present disclosure include one or more mutations in ALK kinase. In one embodiment, the one or more ALK point mutations are selected from point mutations at L1152, C1156, I1171, F1 174, V1180, L1196, L1198, G1202, D1203, S1206, E1210, F1245, G1269, and R1275. In one embodiment, the one or more ALK point mutations are selected from G1202R, G1202K, L1196M, G1269A, C1156Y, I1171T, I1171N, I1171S, F1174L, V1180L, S1206Y, E1210K, 1151Tins, F1174C, G1202del, D1203N, S1206Y, S1206C, L1152R, L1196Q, L1198P, L1198F, R1275Q, L1152P, C1156T, and F1245V. In one embodiment, the ALK mutation is G1202R. In one embodiment, the ALK mutation is L1196M. In one embodiment, the ALK mutation is G1269A. In one embodiment, the ALK mutation is L1198F. In one embodiment, the ALK mutation is co-mutation of G1202R and one or more mutations selected from L1196M, G1269A, and L1198F. In one embodiment, the ALK mutation is G1202R/L1196M dual mutation. In one embodiment, the ALK mutation is G1202R/G1269A dual mutation. In one embodiment, the ALK mutation is G1202R/L1198F dual mutation.

In one embodiment, the ALK mutation comprises one or more ALK rearrangements (in one embodiment, one rearrangement). In one embodiment, the ALK mutation comprises one or more ALK fusions (in one embodiment, one fusion). In some embodiments, cancers treated by methods of the present disclosure include ALK fusions. In one embodiment, the ALK fusion is with one of the fusion partners selected from EML4, TMP1, WDCP, GTF2IRD1, TPM3, TPM4, CLTC, LMNA, PRKARIA, RANBP2, TFG, FN1, KLC1, VCL, STRN, HIP1, NPM1, DCTN1, SQSTM1, TPR, CRIM1, PTPN3, FBXO36, ATIC and KIF5B. In one embodiment, the ALK mutation is EML4-ALK, a fusion between the echinoderm microtubule-associated protein-like 4 (EML4) gene and the ALK tyrosine kinase domain. There are many variants of EML4-ALK that differ by breakpoint junctions, with variant 1 (v1) and variant 3 (v3) being the most prevalent clinically.

In one embodiment, the ALK mutation comprises one ALK rearrangement and one or more ALK point mutations. In one embodiment, the ALK mutation is EML4-ALK wt (variant 1). In one embodiment, the ALK mutation is EML4-ALK G1202R (variant 1). In one embodiment, the ALK mutation is EML4-ALK L1196M/G1202R (variant 1). In one embodiment, the ALK mutation is EML4-ALK G1202R/G1269A (variant 1). In one embodiment, the ALK mutation is EML4-ALK G1202R/L1198F (variant 1).

In one embodiment, the ALK+ cancer is determined by an FDA-approved test or other tests known in the art. The tests that can be used include, e.g., FoundationOne CDx™ (F1CDx) (a sequencing based in vitro diagnostic device for detection of substitutions, insertion and deletion alterations (indels), and copy number alterations (CNAs) in 324 genes and select gene rearrangements, as well as genomic signatures including microsatellite instability (MSI) and tumor mutational burden (TMB) using DNA isolated from formalin-fixed paraffin embedded (FFPE) tumor tissue specimens); VENTANA ALK (D5F3) CDx Assay (qualitative detection of the anaplastic lymphoma kinase (ALK) protein in formalin-fixed, paraffin-embedded (FFPE) non-small cell lung carcinoma (NSCLC) tissue stained with the BenchMark XT or BenchMark ULTRA automated staining instrument); and Vysis ALK Break Apart FISH Probe Kit test (a qualitative test to detect rearrangements involving the ALK gene via fluorescence in situ hybridization (FISH) in formalin-fixed, paraffin-embedded (FFPE) non-small cell lung cancer (NSCLC) tissue specimens). In one embodiment, the test is a fluorescence in situ hybridization (FISH) test, e.g., Vysis ALK Break Apart FISH Probe Kit test. Additional information for FDA-approved tests can be found at, e.g., https://www.fda.gov/MedicalDevices/ProductsandMedicalProcedures/InVitroDiagnostics/ucm303030.htm; and additional information for Vysis ALK Break Apart FISH Probe Kit can be found at, e.g., https://www.molecular.abbott/us/en/products/oncology/vysis-alk-break-apart-fish-probe-kit; the entirety of which are incorporated herein by reference.

Also provided are methods of treating a subject having a cancer (e.g., a ALK positive cancer) that include: determining whether a cancer cell in a sample obtained from a subject having a cancer and previously administered a first ALK inhibitor, has one or more ALK inhibitor resistance mutations; and administering a compound of Formula (I) or a pharmaceutically acceptable salt or solvate thereof as a monotherapy or in combination with another anticancer agent to the subject if the subject has a cancer cell that has one or more ALK inhibitor resistance mutations. In some embodiments, the one or more ALK inhibitor resistance mutations confer increased resistance to a cancer cell or tumor to treatment with the first ALK inhibitor. In some embodiments, the one or more ALK inhibitor resistance mutations include one or more ALK inhibitor resistance mutations. For example, the one or more ALK inhibitor resistance mutations can include a substitution at one or more of amino acid positions 1202, 1196, 1269, 1156, 1171, 1174, 1180, 1206, 1210, 1151, 1174, 1203, 1206, 1152, 1196, 1198, 1275, 1152, 1156, and 1245, e.g., G1202R, L1196M, G1269A, C1156Y, 11171T, 11171N, 11171S, F1174L, V1180L, S1206Y, E1210K, 1151Tins, F1174C, G1202del, D1203N, S1206Y, S1206C, L1152R, L1196Q, L1198P, L1198F, R1275Q, L1152P, C1156T, and F1245V. In some embodiments, another anticancer agent is any anticancer agent known in the art. For example, another anticancer agent can be another ALK inhibitor (e.g., a second ALK inhibitor).

In one embodiment, the cancer in a method provided herein is ROS1 positive (ROS1+). As used herein and unless otherwise specified, a "ROS1 positive" (ROS1+) cancer, disease, or disorder refers to a cancer, disease, or disorder characterized by inappropriately high expression of a ROS1 gene and/or the presence of a mutation in a ROS1 gene. In one embodiment, the mutation alters the biological activity of a ROS1 nucleic acid molecule or polypeptide. As used herein and unless otherwise specified, a "mutation" or "mutant" of ROS1 comprises one or more deletions, substitutions, insertions, inversions, duplications, translocations, or amplifications in the amino acid or nucleotide sequences of ROS1, or fragments thereof. As used herein and unless otherwise specified, a ROS1 "rearrangement" refers to genetic translocations involving the ROS1 gene that may result in ROS1 fusion genes and/or ROS1 fusion proteins. The ROS1 fusion can also include one or more deletions, substitutions, insertions, inversions, duplications, translocations, or amplifications or a fragment thereof, as long as the mutant retains kinase phosphorylation activity.

In one embodiment, the ROS1 mutation comprises one or more ROS1 point mutations. In some embodiments, cancers treated by methods of the present disclosure include one or more mutations in ROS1 kinase. In one embodiment, the one or more ROS1 point mutations are selected from point mutations at E1935, L1947, L1951, G1971, E1974, L1982, 51986, F2004, E2020, L2026, G2032, D2033, C2060, F2075, L2086, V2089, V2098, G2101, D2113, and L2155. In one embodiment, the one or more ROS1 point mutations are selected from G2032R, G2032K, D2033N, S1986F, S1986Y, L2026M, L1951R, E1935G, L1947R, G1971E, E1974K, L1982F, F2004C, F2004V, E2020K, C2060G, F2075V, V2089M, V2098I, G2101A, D2113N, D2113G, L2155S, and L2086F.

In one embodiment, the ROS1 mutation is G2032R. In one embodiment, the ROS1 mutation is S1986F. In one embodiment, the ROS1 mutation is S1986Y. In one embodiment, the ROS1 mutation is L2026M. In one embodiment, the ROS1 mutation is D2033N. In one embodiment, the ROS1 mutation is L2086F. In one embodiment, the ROS1 mutation is F2004C. In one embodiment, the ROS1 mutation is F2004V. In one embodiment, the ROS1 mutation is G2101A. In one embodiment, the ROS1 mutation is L1982F. In one embodiment, the ROS1 mutation is co-mutation of G2032R and one or more of S1986F, S1986Y, F2004C, F2004V, L2026M, or D2033N.

In one embodiment, the ROS1 mutation comprises one or more ROS1 rearrangements (in one embodiment, one rearrangement). In one embodiment, the ROS1 mutation comprises one or more ROS1 fusions (in one embodiment, one fusion). In some embodiments, cancers treated by methods of the present disclosure include ROS1 fusions. In one embodiment, the ROS1 fusion is with one of the fusion partners selected from SLC34A2, CD74, TPM3, SDC4, EZR, LRIG3, KDELR2, CEP72, CLTL, CTNND2, GOPC (e.g., GOPC-S, GOPC-L), GPRC6A, LIMA1, LRIG3, MSN, MYO5C, OPRM1, SLC6A17 SLMAP, SRSF6, TFG, TMEM106B, TPD52L1, ZCCHC8,CCDC6,CAPRIN1, CEP85L, CHCHD3, CLIP1, EEF1G, KIF21A, KLC1, SART3, ST13, TRIM24, ERC1, FIPIL1, HLAA, KIAA1598, MYO5A, PPFIBP1, PWWP2A, FN1, YWHAE, CCDC30, NCOR2, NFKB2, APOB, PLG, RBP4, and GOLGB1. In one embodiment, the ROS1 fusion is CD74-ROS1 fusion. In one embodiment, the ROS1 fusion is SDC4-ROS1 fusion. In one embodiment, the ROS1 fusion is EZR-ROS1 fusion. In one embodiment, the ROS1 fusion is SLC34A2-ROS1 fusion. In one embodiment, the ROS1 fusion is GOPC-ROS1 fusion (e.g., GOPC-ROS1-S, GOPC-ROS1-L). In one embodiment, the ROS1 fusion is CEP85L-ROS1 fusion.

In one embodiment, the ROS1 mutation comprises one ROS1 rearrangements and one or more ROS1 point mutations. In one embodiment, the ROS1 mutation comprises one or more ROS1 rearrangements from CD74-ROS1, EZR-ROS1, SLC34A2-ROS1, GOPC-ROS1 (e.g., GOPC-ROS1-S, GOPC-ROS1-L), and CEP85L-ROS1, and one or more ROS1 point mutations selected from F2004C, F2004V, and G2032R. In one embodiment, the ROS1 mutation comprises one or more ROS1 rearrangements from CD74-ROS1, EZR-ROS1, and SLC34A2-ROS1, and ROS1 point mutation of G2101A.

In one embodiment, the ROS1 mutation is CD74-ROS1 F2004C. In one embodiment, the ROS1 mutation is CD74-ROS1 F2004V. In one embodiment, the ROS1 mutation is CD74-ROS1 G2101A. In one embodiment, the ROS1 mutation is CD74-ROS1 G2032R. In one embodiment, the ROS1 mutation is CD74-ROS1 S1986F. In one embodiment, the ROS1 mutation is CD74-ROS1 L2026M. In one embodiment, the ROS1 mutation is CD74-ROS1 D2033N. In one embodiment, the ROS1 mutation is EZR-ROS1 F2004C. In one embodiment, the ROS1 mutation is EZR-ROS1 F2004V. In one embodiment, the ROS1 mutation is EZR-ROS1 G2101A. In one embodiment, the ROS1 mutation is EZR-ROS1 G2032R. In one embodiment, the ROS1 mutation is SLC34A2-ROS1 F2004C. In one embodiment, the ROS1 mutation is SLC34A2-ROS1 F2004V. In one embodiment, the ROS1 mutation is SLC34A2-ROS1 G2101A. In one embodiment, the ROS1 mutation is SLC34A2-ROS1

G2032R. In one embodiment, the ROS1 mutation is GOPC-ROS1 F2004C (e.g., GOPC-ROS1-S F2004C, GOPC-ROS1-L F2004C). In one embodiment, the ROS1 mutation is GOPC-ROS1 F2004V (e.g., GOPC-ROS1-S F2004V, GOPC-ROS1-L F2004V). In one embodiment, the ROS1 mutation is GOPC-ROS1 G2032R (e.g., GOPC-ROS1-S G2032R, GOPC-ROS1-L G2032R). In one embodiment, the ROS1 mutation is CEP85L-ROS1 F2004C. In one embodiment, the ROS1 mutation is CEP85L-ROS1 F2004V. In one embodiment, the ROS1 mutation is CEP85L-ROS1 G2032R. In one embodiment, the ROS1 mutation is GOPC-ROS1 L1982F (e.g., GOPC-ROS1-S L1982F, GOPC-ROS1-L L1982F). In one embodiment, the ROS1 mutation is CD74-ROS1 L1982F.

In one embodiment, the ROS1+ cancer is determined by an FDA-approved test or other tests known in the art. The tests that can be used include, e.g., Oncomine™ Dx Target Test by Thermo Fisher Scientific. (a qualitative in vitro diagnostic test that uses targeted high-throughput, parallel-sequencing technology to detect sequence variations in 23 genes in DNA and RNA isolated from formalin-fixed, paraffin-embedded tumor (FFPE) tissue samples from patients with non-small cell lung cancer (NSCLC) using the Ion PGM Dx System); Vysis ROS1 Break Apart FISH Probe Kit (a qualitative test to detect rearrangements involving ROS1 gene rearrangements at 6q22 via fluorescence in situ hybridization (FISH) in formalin-fixed, paraffin-embedded (FFPE) non-small cell lung cancer (NSCLC) tissue specimens) or RTReal Time-Polymerase Chain Reaction (RT-PCR) or NGSNext Generation Sequencing via a local diagnostic test.

Also provided are methods of treating a subject having a cancer (e.g., a ROS1 positive cancer) that include: determining whether a cancer cell in a sample obtained from a subject having a cancer and previously administered a first ROS1 inhibitor, has one or more ROS1 inhibitor resistance mutations; and administering a compound of Formula (I) or a pharmaceutically acceptable salt or solvate thereof as a monotherapy or in conjunction with another anticancer agent to the subject if the subject has a cancer cell that has one or more ROS1 inhibitor resistance mutations. In some embodiments, the one or more ROS1 inhibitor resistance mutations confer increased resistance to a cancer cell or tumor to treatment with the first ROS1 inhibitor. In some embodiments, the one or more ROS1 inhibitor resistance mutations include one or more ROS1 inhibitor resistance mutations. For example, the one or more ROS1 inhibitor resistance mutations can include a substitution at one or more of amino acid positions 2032, 2033, 1986, 2026, 1951, 1935, 1947, 1971, 1974, 1982, 2004, 2020, 2060, 2075, 2089, 2098, 2101, 2113, 2155, 2032, and 2086, e.g., G2032R, D2033N, 51986F, 51986Y, L2026M, L1951R, E1935G, L1947R, G1971E, E1974K, L1982F, F2004C, F2004V, E2020K, C2060G, F2075V, V2089M, V2098I, G2101A, D2113N, D2113G, L2155S, L2032K, and L2086F. In some embodiments, another anticancer agent is any anticancer agent known in the art. For example, another anticancer agent can be another ROS1 inhibitor (e.g., a second ROS1 inhibitor).

In one embodiment, a compound provided herein is a CNS-penetrating compound. In one embodiment, after the administration of an effective amount of a compound provided herein (e.g., orally or intravenously), the compound is able to penetrate CNS (e.g., blood-brain barrier) and achieve a concentration in CNS (e.g., brain) that is still sufficient to inhibit (e.g., selectively inhibit) ROS1 or ALK or both.

In one embodiment, provided herein is a method for treating CNS metastases of a cancer, comprising administering to a subject in need thereof an effective amount of a compound provided herein, e.g., a compound of Formula (I), or an enantiomer, a mixture of enantiomers, or a tautomer thereof, or a pharmaceutically acceptable salt thereof. In one embodiment, the CNS metastases is brain metastases. In one embodiment, the cancer is a ROS1+ cancer. In one embodiment, the cancer is an ALK+ cancer.

In some embodiments, the compound is an inhibitor of human tropomyosin receptor kinase A, B, or C. In certain embodiments, the $IC_{50}$ of the compound for inhibition of mutant or non-mutant ROS1 or ALK is no more than one-fifth of the $IC_{50}$ of the compound for inhibition of wild-type tropomyosin receptor kinase A, B, or C. TRK inhibition, particularly in the central nervous system (CNS), has been associated with adverse reactions, including dizziness/ataxia/gait disturbance, paraesthesia, weight gain and cognitive changes.

In some embodiments, provided is a method of minimizing adverse events in a subject in need of treatment for cancer (e.g., a ROS1 positive cancer or an ALK positive cancer), the method comprising administering to the subject a therapeutically effective amount of a compound provided herein, e.g., a compound of Formula (I), an enantiomer, a mixture of enantiomers, or a tautomer thereof, or a pharmaceutically acceptable salt thereof, and wherein the method minimizes adverse events associated with TRK inhibitors. In some embodiments, the cancer is a ROS1-associated cancer or an ALK-associated (or ALK+) cancer. In some embodiments, the adverse events are TRK-related CNS adverse events.

As used herein "minimizing" adverse events refers to a reduction in the incidence of adverse events in a subject or patient population compared to the paradigmatic incidence of adverse events in a subject or patient population treated with TRK inhibitors (e.g., entrectinib, repotrectinib, or lorlatinib). In some embodiments, the incidence of an adverse event refers to the frequency or percentage of a specific adverse event over a subject or patient population. In some embodiments, the incidence of an adverse event refers to the total number of adverse events experienced by an individual subject. In some embodiments, minimizing adverse events refers to minimizing TRK-related CNS adverse events. In some embodiments, minimizing TRK-related CNS adverse events means less than 40% of the patient population has a TRK-related CNS adverse event. In some embodiments, minimizing TRK-related CNS adverse events means less than 35%, less than 30%, less than 25%, less than 20%, less than 15%, less than 10% or less than 5% of the patient population has a TRK-related CNS adverse event. In some embodiments, minimizing TRK-related CNS adverse events means less than 12% of the patient population have more than one TRK-related CNS adverse event. In some embodiments, minimizing TRK-related CNS adverse events means less than 11%, less than 10%, less than 9%, less than 8%, less than 7%, less than 6%, less than 5%, less than 4%, or less than 3% of the patient population have more than one TRK-related CNS adverse event.

In some embodiments, TRK-related CNS adverse events refers to one or more of the following: dizziness, ataxia, gait disturbance, paraesthesia, weight gain, hyperphagia, paresthesias, abnormal movement, cognitive changes, speech effects (e.g, dysarthria, slow speech, or speech disorder), mood disorder (e.g., irritability, anxiety, depression, affect lability, personality change, mood swings, affective disorder, aggression, agitation, mood altered, depressed mood, euphoric mood, or mania), and cognitive disorder (e.g., memory impairment, cognitive disorder, amnesia, confusion, disturbance in attention, delirium, mental impairment, attention deficit/hyperactivity disorder, dementia, or reading disorder).

In one embodiment, provided herein is a method for preventing or limiting TRK-related CNS side effect or adverse event in a cancer treatment, comprising administering to a subject in need thereof an effective amount of a compound provided herein, e.g., a compound of Formula (I), or an enantiomer, a mixture of enantiomers, or a tautomer thereof, or a pharmaceutically acceptable salt thereof. In one embodiment, the method prevents the occurance of the TRK-related CNS adverse event. In one embodiment, the method limits the frequency of occurance of the TRK-related CNS adverse event. In one embodiment, the method limits the severity of the TRK-related side effect. In one embodiment, provided herein is a method for treating CNS metastases of a cancer with reduced TRK-related side effect, comprising administering to a subject in need thereof an effective amount of a compound provided herein, e.g., a compound of Formula (I), or an enantiomer, a mixture of enantiomers, or a tautomer thereof, or a pharmaceutically acceptable salt thereof. In one embodiment, the reduction/ limiting/prevention in CNS side effect or adverse event is determined in a statistical sample, as compared to a standard of care treatment, e.g., an approved ROS1 and/or ALK inhibitor (e.g., crizotinib, entrectinib, lorlatinib, or repotrectinib) for ROS1+ and/or ALK+ cancer. In one embodiment, the TRK-related side effect is a TRKB-related CNS side effect. In one embodiment, the TRK-related CNS side effect or adverse event is dizziness, ataxia, gait disturbance, paraesthesia, weight gain, cognitive impairment, a mood disorder, or sleep disturbance.

In one embodiment, provided herein is a method for treating cancer, comprising administering to a subject in need thereof a therapeutically effective amount of a compound provided herein, e.g., a compound of Formula (I), or an enantiomer, a mixture of enantiomers, or a tautomer thereof, or a pharmaceutically acceptable salt thereof. In one embodiment, the cancer is a ROS1-associated cancer. In one embodiment, the cancer is a ROS1+ cancer. In one embodiment, the cancer is an ALK-associated cancer. In one embodiment, the cancer is an ALK+ cancer. In one embodiment, the cancer is identified to be ROS1+. In one embodiment, the cancer is identified to be ALK+.

In one embodiment, provided herein is a method for treating a ROS1+ cancer, comprising administering to a subject in need thereof a therapeutically effective amount of a compound provided herein, e.g., a compound of Formula (I), or an enantiomer, a mixture of enantiomers, or a tautomer thereof, or a pharmaceutically acceptable salt thereof.

In one embodiment, provided herein is a method for treating an ALK+ cancer, comprising administering to a subject in need thereof a therapeutically effective amount of a compound provided herein, e.g., a compound of Formula (I), or an enantiomer, a mixture of enantiomers, or a tautomer thereof, or a pharmaceutically acceptable salt thereof.

In one embodiment, provided herein is a method for treating cancer in a subject, comprising: (i) identifying the cancer in the subject to be ROS1+, and (ii) administering to the subject a therapeutically effective amount of a compound provided herein, e.g., a compound of Formula (I), or an enantiomer, a mixture of enantiomers, or a tautomer thereof, or a pharmaceutically acceptable salt thereof.

In one embodiment, provided herein is a method for treating cancer in a subject, comprising: (i) identifying the cancer in the subject to be ALK+, and (ii) administering to the subject a therapeutically effective amount of a compound provided herein, e.g., a compound of Formula (I), or an enantiomer, a mixture of enantiomers, or a tautomer thereof, or a pharmaceutically acceptable salt thereof.

In one embodiment, the cancer (or ROS1+ cancer, or ALK+ cancer) is a solid tumor. In one embodiment, the cancer (or ROS1+ cancer, or ALK+ cancer) is lung cancer, e.g., non-small cell lung cancer (NSCLC), glioblastoma, inflammatory myofibroblastic tumor (IMT), bile duct cancer, e.g., cholangiocarcinoma, ovarian cancer, e.g., serous ovarian carcinoma, gastric cancer, colorectal cancer, angiosarcoma, melanoma, e.g., spitzoid melanoma, epithelioid hemangioendothelioma, esophageal cancer, e.g., esophageal squamous cell carcinoma (ESCC), kidney cancer, e.g., renal medullary carcinoma or renal cell carcinoma, breast cancer, e.g., triple negative breast cancer, colon cancer, thyroid cancer, e.g., papillary thyroid cancer, spitzoid tumor, or neuroblastoma.

In one embodiment, the cancer is lung cancer. In one embodiment, the cancer is non-small cell lung cancer. In one embodiment, the cancer is ROS1+non-small cell lung cancer. In one embodiment, the cancer is ALK+non-small cell lung cancer. In one embodiment, the cancer is relapsed or refractory non-small cell lung cancer. In one embodiment, the cancer is relapsed or refractory ROS1+non-small cell lung cancer. In one embodiment, the cancer is relapsed or refractory ALK+non-small cell lung cancer. In one embodiment, the cancer is newly diagnosed non-small cell lung cancer. In one embodiment, the cancer is newly diagnosed ROS1+non-small cell lung cancer. In one embodiment, the cancer is newly diagnosed ALK+non-small cell lung cancer.

In one embodiment, the cancer is glioblastoma. In one embodiment, the cancer is ROS1+glioblastoma. In one embodiment, the cancer is ALK+glioblastoma. In one embodiment, the cancer is relapsed or refractory glioblastoma. In one embodiment, the cancer is relapsed or refractory ROS1+glioblastoma. In one embodiment, the cancer is relapsed or refractory ALK+glioblastoma. In one embodiment, the cancer is newly diagnosed glioblastoma. In one embodiment, the cancer is newly diagnosed ROS1+glioblastoma. In one embodiment, the cancer is newly diagnosed ALK+glioblastoma.

In one embodiment, the cancer is IMT. In one embodiment, the cancer is ROS1+IMT. In one embodiment, the cancer is ALK+IMT. In one embodiment, the cancer is relapsed or refractory IMT. In one embodiment, the cancer is relapsed or refractory ROS1+IMT. In one embodiment, the cancer is relapsed or refractory ALK+IMT. In one embodiment, the cancer is newly diagnosed IMT. In one embodiment, the cancer is newly diagnosed ROS1+IMT. In one embodiment, the cancer is newly diagnosed ALK+IMT.

In one embodiment, the cancer is bile duct cancer. In one embodiment, the cancer is cholangiocarcinoma. In one embodiment, the cancer is ROS1+cholangiocarcinoma. In one embodiment, the cancer is ALK+cholangiocarcinoma. In one embodiment, the cancer is relapsed or refractory cholangiocarcinoma. In one embodiment, the cancer is relapsed or refractory ROS1+cholangiocarcinoma. In one embodiment, the cancer is relapsed or refractory ALK+cholangiocarcinoma. In one embodiment, the cancer is newly diagnosed cholangiocarcinoma. In one embodiment, the cancer is newly diagnosed ROS1+cholangiocarcinoma. In one embodiment, the cancer is newly diagnosed ALK+cholangiocarcinoma.

In one embodiment, the cancer is ovarian cancer. In one embodiment, the cancer is ROS1+ovarian cancer. In one embodiment, the cancer is ALK+ovarian cancer. In one embodiment, the cancer is relapsed or refractory ovarian cancer. In one embodiment, the cancer is relapsed or refractory ROS1+ovarian cancer. In one embodiment, the cancer is relapsed or refractory ALK+ovarian cancer. In one embodiment, the cancer is newly diagnosed ovarian cancer. In one embodiment, the cancer is newly diagnosed ROS1+ovarian cancer. In one embodiment, the cancer is newly diagnosed ALK+ovarian cancer. In one embodiment, the ovarian cancer is serous ovarian carcinoma. In one embodiment, the ovarian cancer is high grade serous ovarian carcinoma.

In one embodiment, the cancer is gastric cancer. In one embodiment, the cancer is ROS1+gastric cancer. In one embodiment, the cancer is ALK+gastric cancer. In one embodiment, the cancer is relapsed or refractory gastric cancer. In one embodiment, the cancer is relapsed or refractory ROS1+gastric cancer. In one embodiment, the cancer is relapsed or refractory ALK+gastric cancer. In one embodiment, the cancer is newly diagnosed gastric cancer. In one embodiment, the cancer is newly diagnosed ROS1+gastric cancer. In one embodiment, the cancer is newly diagnosed ALK+gastric cancer.

In one embodiment, the cancer is colorectal cancer. In one embodiment, the cancer is ROS1+colorectal cancer. In one embodiment, the cancer is ALK+colorectal cancer. In one embodiment, the cancer is relapsed or refractory colorectal cancer. In one embodiment, the cancer is relapsed or refractory ROS1+colorectal cancer. In one embodiment, the cancer is relapsed or refractory ALK+colorectal cancer. In one embodiment, the cancer is newly diagnosed colorectal cancer. In one embodiment, the cancer is newly diagnosed ROS1+colorectal cancer. In one embodiment, the cancer is newly diagnosed ALK+colorectal cancer.

In one embodiment, the cancer is angiosarcoma. In one embodiment, the cancer is ROS1+angiosarcoma. In one embodiment, the cancer is ALK+angiosarcoma. In one embodiment, the cancer is relapsed or refractory angiosarcoma. In one embodiment, the cancer is relapsed or refractory ROS1+angiosarcoma. In one embodiment, the cancer is relapsed or refractory ALK+angiosarcoma. In one embodiment, the cancer is newly diagnosed angiosarcoma. In one embodiment, the cancer is newly diagnosed ROS1+angiosarcoma. In one embodiment, the cancer is newly diagnosed ALK+angiosarcoma.

In one embodiment, the cancer is melanoma. In one embodiment, the cancer is spitzoid tumor. In one embodiment, the cancer is spitzoid melanoma. In one embodiment, the cancer is ROS1+spitzoid melanoma. In one embodiment, the cancer is ALK+spitzoid melanoma. In one embodiment, the cancer is relapsed or refractory spitzoid melanoma. In one embodiment, the cancer is relapsed or refractory ROS1+spitzoid melanoma. In one embodiment, the cancer is relapsed or refractory ALK+spitzoid melanoma. In one embodiment, the cancer is newly diagnosed spitzoid melanoma. In one embodiment, the cancer is newly diagnosed ROS1+spitzoid melanoma. In one embodiment, the cancer is newly diagnosed ALK+spitzoid melanoma.

In one embodiment, the cancer is epithelioid hemangioendothelioma. In one embodiment, the cancer is ROS1+epithelioid hemangioendothelioma. In one embodiment, the cancer is ALK+epithelioid hemangioendothelioma. In one embodiment, the cancer is relapsed or refractory epithelioid hemangioendothelioma. In one embodiment, the cancer is relapsed or refractory ROS1+epithelioid hemangioendothelioma. In one embodiment, the cancer is relapsed or refractory ALK+epithelioid hemangioendothelioma. In one embodiment, the cancer is newly diagnosed epithelioid hemangioendothelioma. In one embodiment, the cancer is newly diagnosed ROS1+epithelioid hemangioendothelioma. In one embodiment, the cancer is newly diagnosed ALK+epithelioid hemangioendothelioma.

In one embodiment, the cancer is esophageal cancer. In one embodiment, the cancer is ESCC. In one embodiment, the cancer is ROS1+ESCC. In one embodiment, the cancer is ALK+ESCC. In one embodiment, the cancer is relapsed or refractory ESCC. In one embodiment, the cancer is relapsed or refractory ROS1+ESCC. In one embodiment, the cancer is relapsed or refractory ALK+ESCC. In one embodiment, the cancer is newly diagnosed ESCC. In one embodiment, the cancer is newly diagnosed ROS1+ESCC. In one embodiment, the cancer is newly diagnosed ALK+ESCC.

In one embodiment, the cancer is kidney cancer. In one embodiment, the cancer is renal medullary carcinoma. In one embodiment, the cancer is ROS1+renal medullary carcinoma. In one embodiment, the cancer is ALK+renal medullary carcinoma. In one embodiment, the cancer is relapsed or refractory renal medullary carcinoma. In one embodiment, the cancer is relapsed or refractory ROS1+renal medullary carcinoma. In one embodiment, the cancer is relapsed or refractory ALK+renal medullary carcinoma.

In one embodiment, the cancer is newly diagnosed renal medullary carcinoma. In one embodiment, the cancer is newly diagnosed ROS1+renal medullary carcinoma. In one embodiment, the cancer is newly diagnosed ALK+renal medullary carcinoma. In one embodiment, the cancer is renal cell carcinoma. In one embodiment, the cancer is ROS1+renal cell carcinoma. In one embodiment, the cancer is ALK+renal cell carcinoma. In one embodiment, the cancer is relapsed or refractory renal cell carcinoma.

In one embodiment, the cancer is relapsed or refractory ROS1+renal cell carcinoma. In one embodiment, the cancer is relapsed or refractory ALK+renal cell carcinoma. In one embodiment, the cancer is newly diagnosed renal cell carcinoma. In one embodiment, the cancer is newly diagnosed ROS1+renal cell carcinoma. In one embodiment, the cancer is newly diagnosed ALK+renal cell carcinoma.

In one embodiment, the cancer is breast cancer. In one embodiment, the cancer is ROS1+breast cancer. In one embodiment, the cancer is ALK+breast cancer. In one embodiment, the cancer is relapsed or refractory breast cancer. In one embodiment, the cancer is relapsed or refractory ROS1+breast cancer. In one embodiment, the cancer is relapsed or refractory ALK+breast cancer. In one embodiment, the cancer is newly diagnosed breast cancer. In one embodiment, the cancer is newly diagnosed ROS1+breast cancer. In one embodiment, the cancer is newly diagnosed ALK+breast cancer.

In one embodiment, the breast cancer is triple negative breast cancer.

In one embodiment, the cancer is colon cancer. In one embodiment, the cancer is ROS1+colon cancer. In one embodiment, the cancer is ALK+colon cancer. In one embodiment, the cancer is relapsed or refractory colon cancer. In one embodiment, the cancer is relapsed or refractory ROS1+colon cancer. In one embodiment, the cancer is relapsed or refractory ALK+colon cancer. In one embodiment, the cancer is newly diagnosed colon cancer. In one embodiment, the cancer is newly diagnosed ROS1+colon cancer. In one embodiment, the cancer is newly diagnosed ALK+colon cancer.

In one embodiment, the cancer is thyroid cancer. In one embodiment, the cancer is papillary thyroid cancer. In one embodiment, the cancer is ROS1+papillary thyroid cancer. In one embodiment, the cancer is ALK+papillary thyroid cancer. In one embodiment, the cancer is relapsed or refractory papillary thyroid cancer. In one embodiment, the cancer is relapsed or refractory ROS1+papillary thyroid cancer. In one embodiment, the cancer is relapsed or refractory ALK+ papillary thyroid cancer. In one embodiment, the cancer is newly diagnosed papillary thyroid cancer. In one embodiment, the cancer is newly diagnosed ROS1+papillary thyroid cancer. In one embodiment, the cancer is newly diagnosed ALK+papillary thyroid cancer.

In one embodiment, the cancer is neuroblastoma. In one embodiment, the cancer is ROS1+neuroblastoma. In one embodiment, the cancer is ALK+neuroblastoma. In one embodiment, the cancer is relapsed or refractory neuroblastoma. In one embodiment, the cancer is relapsed or refractory ROS1+neuroblastoma. In one embodiment, the cancer is relapsed or refractory ALK+neuroblastoma. In one embodiment, the cancer is newly diagnosed neuroblastoma. In one embodiment, the cancer is newly diagnosed ROS1+ neuroblastoma. In one embodiment, the cancer is newly diagnosed ALK+neuroblastoma.

In one embodiment, the cancer (or ROS1+ cancer, or ALK+ cancer) is a hematological cancer. In one embodiment, the cancer (or ROS1+ cancer, or ALK+cancer) is lymphoma. In one embodiment, the lymphoma is non-Hodgkin lymphoma. In one embodiment, the lymphoma is anaplastic large cell lymphoma (ALCL), diffuse large B-cell lymphoma (DLBCL), or large B-cell lymphoma. In addition to hematological cancer, methods for treating other blood disorder or hematologic malignancy that is ROS1+ or ALK+ are also provided herein.

In one embodiment, the cancer is ALCL. In one embodiment, the cancer is ROS1+ALCL. In one embodiment, the cancer is ALK+ALCL. In one embodiment, the cancer is relapsed or refractory ALCL. In one embodiment, the cancer is relapsed or refractory ROS1+ALCL. In one embodiment, the cancer is relapsed or refractory ALK+ALCL. In one embodiment, the cancer is newly diagnosed ALCL. In one embodiment, the cancer is newly diagnosed ROS1+ALCL. In one embodiment, the cancer is newly diagnosed ALK+ ALCL.

In one embodiment, the cancer is DLBCL. In one embodiment, the cancer is ROS1+DLBCL. In one embodiment, the cancer is ALK+DLBCL. In one embodiment, the cancer is relapsed or refractory DLBCL. In one embodiment, the cancer is relapsed or refractory ROS1+DLBCL. In one embodiment, the cancer is relapsed or refractory ALK+ DLBCL. In one embodiment, the cancer is newly diagnosed DLBCL. In one embodiment, the cancer is newly diagnosed ROS1+DLBCL. In one embodiment, the cancer is newly diagnosed ALK+DLBCL.

In one embodiment, the cancer is large B-cell lymphoma. In one embodiment, the cancer is ROS1+large B-cell lymphoma. In one embodiment, the cancer is ALK+large B-cell lymphoma. In one embodiment, the cancer is relapsed or refractory large B-cell lymphoma. In one embodiment, the cancer is relapsed or refractory ROS1+large B-cell lymphoma. In one embodiment, the cancer is relapsed or refractory ALK+large B-cell lymphoma. In one embodiment, the cancer is newly diagnosed large B-cell lymphoma.

In one embodiment, the cancer is newly diagnosed ROS1+large B-cell lymphoma. In one embodiment, the cancer is newly diagnosed ALK+large B-cell lymphoma.

In one embodiment, the cancer (or ROS1+ cancer, or ALK+ cancer) is new diagnosed. In one embodiment, the cancer (or ROS1+ cancer, or ALK+ cancer) is previously untreated.

In one embodiment, the cancer (or ROS1+ cancer, or ALK+ cancer) is relapsed or refractory. In one embodiment, the cancer is relapsed. In one embodiment, the cancer (or ROS1+ cancer, or ALK+ cancer) is refractory.

In one embodiment, the subject is previously untreated. In one embodiment, the subject is treatment naïve to tyrosine kinase inhibitor (TKI) therapy. In one embodiment, the subject has received one or more prior lines of therapy. In one embodiment, the subject has received two or more prior lines of therapy. In one embodiment, the subject has developed resistance to one or more of the prior line of therapy. In one embodiment, the prior therapy comprises a tyrosine kinase inhibitor (TKI). In one embodiment, the prior therapy comprises one or more of crizotinib, ceritinib, alectinib, brigatinib, lorlatinib, entrectinib, repotrectinib, cabozantinib, foretinib, taletrectinib, merestinib, masitinib, and ensartinib. In one embodiment, the prior therapy comprises one or more chemotherapies. In one embodiment, the one or more chemotherapies are in addition to the TKI therapy.

In one embodiment, the cancer (or ROS1+ cancer, or ALK+ cancer) is resistant to a tyrosine kinase inhibitor (TKI).

In one embodiment, the cancer is resistant lung cancer. In one embodiment, the cancer is resistant non-small cell lung cancer. In one embodiment, the cancer is non-small cell lung cancer resistant to a TKI. In one embodiment, the cancer is ROS1+non-small cell lung cancer resistant to a TKI. In one embodiment, the cancer is ALK+non-small cell lung cancer resistant to a TKI.

In one embodiment, the cancer is lung cancer (e.g., NSCLC), and the cancer is relapsed after, or refractory to, prior treatment by a TKI.

In one embodiment, a compound provided herein is administered as first-line treatment. In one embodiment, a compound provided herein is administered as second-line treatment. In one embodiment, a compound provided herein is administered as third or fourth-line treatment.

In one embodiment, the cancer (or ROS1+ cancer, or ALK+ cancer) is metastatic. In one embodiment, the cancer has CNS metastases. In one embodiment, the cancer has brain metastases. In one embodiment, the cancer is metastatic non-small cell lung cancer (NSCLC). In one embodiment, the cancer is metastatic ROS1+NSCLC. In one embodiment, the cancer is metastatic ALK+NSCLC.

In one embodiment, provided herein is a method for treating a patient with metastatic ALK+non-small cell lung cancer (NSCLC), comprising administering to the patient a therapeutically effective amount of a compound provided herein, e.g., a compound of Formula (I), or an enantiomer, a mixture of enantiomers, or a tautomer thereof, or a pharmaceutically acceptable salt thereof.

In one embodiment, provided herein is a method for treating a patient with metastatic ROS1+non-small cell lung cancer (NSCLC), comprising administering to the patient a therapeutically effective amount of a compound provided herein, e.g., a compound of Formula (I), or an enantiomer, a mixture of enantiomers, or a tautomer thereof, or a pharmaceutically acceptable salt thereof.

In one embodiment, the patient is an adult patient. In one embodiment, the patient is a pediatric patient.

In one embodiment, provided herein is a method for treating an adult patient with metastatic ROS1+NSCLC, comprising administering to the patient a therapeutically effective amount of a compound provided herein, e.g., a compound of Formula (I), or an enantiomer, a mixture of enantiomers, or a tautomer thereof, or a pharmaceutically acceptable salt thereof.

In one embodiment, provided herein is a method for treating an adult patient with metastatic ROS1+NSCLC, comprising administering to the patient a therapeutically effective amount of a compound provided herein, e.g., a compound of Formula (I), or an enantiomer, a mixture of enantiomers, or a tautomer thereof, or a pharmaceutically acceptable salt thereof, wherein the patient has progressed on or is intolerant of at least 1 prior TKI therapy.

In one embodiment, provided herein is a method for treating an adult patient with metastatic NSCLC that is ROS1+with solvent front mutation G2032R, comprising administering to the patient a therapeutically effective amount of a compound provided herein, e.g., a compound of Formula (I), or an enantiomer, a mixture of enantiomers, or a tautomer thereof, or a pharmaceutically acceptable salt thereof, wherein the patient has progressed on or is intolerant of at least 1 prior TKI therapy.

In one embodiment, provided herein is a method for treating a ROS1-associated (or ROS1+) cancer in a subject in need thereof, wherein the cancer has developed resistance to a tyrosine kinase inhibitor (TKI), the method comprising administering to the subject a therapeutically effective amount of a compound provided herein, e.g., a compound of Formula (I), or an enantiomer, a mixture of enantiomers, or a tautomer thereof, or a pharmaceutically acceptable salt thereof.

In one embodiment, provided herein is a method for treating a ROS1-associated (or ROS1+) cancer in a subject in need thereof, wherein the cancer has developed resistance to a tyrosine kinase inhibitor (TKI), and wherein the cancer has been identified as having one or more ROS1 inhibitor resistance mutations, the method comprising administering to the subject a therapeutically effective amount of a compound provided herein, e.g., a compound of Formula (I), or an enantiomer, a mixture of enantiomers, or a tautomer thereof, or a pharmaceutically acceptable salt thereof. In one embodiment, the one or more ROS1 inhibitor resistance mutations comprise one or more amino acid substitutions at an amino acid position selected from 1986, 2004, 2026, 2032, and 2033. In one embodiment, the one or more ROS1 inhibitor resistance mutations comprise one or more amino acid substitutions selected from S1986F, S1986Y, F2004C, F2004V, L2026M, G2032R, D2033N, L2086F, and G2101A. In one embodiment, the one or more ROS1 inhibitor resistance mutations is G2032R. In one embodiment, the one or more ROS1 inhibitor resistance mutations comprise G2032R and one or more of S1986F, S1986Y, F2004C, F2004V, L2026M, D2033N, or G2101A. In one embodiment, the ROS1 inhibitor resistance mutation is L2086F.

In one embodiment, provided herein is a method for treating a ALK-associated (or ALK+) cancer in a subject in need thereof, wherein the cancer has developed resistance to a tyrosine kinase inhibitor (TKI), the method comprising administering to the subject a therapeutically effective amount of a compound provided herein, e.g., a compound of Formula (I), or an enantiomer, a mixture of enantiomers, or a tautomer thereof, or a pharmaceutically acceptable salt thereof.

In one embodiment, provided herein is a method for treating a ALK-associated (or ALK+) cancer in a subject in need thereof, wherein the cancer has developed resistance to a tyrosine kinase inhibitor (TKI), and wherein the cancer has been identified as having one or more ALK inhibitor resistance mutations, the method comprising administering o the subject a therapeutically effective amount of a compound provided herein, e.g., a compound of Formula (I), or an enantiomer, a mixture of enantiomers, or a tautomer thereof, or a pharmaceutically acceptable salt thereof. In one embodiment, the one or more ALK inhibitor resistance mutations comprise one or more amino acid substitutions at an amino acid position selected from 1196, 1198, 1202, and 1269. In one embodiment, the one or more ALK inhibitor resistance mutations comprise one or more amino acid substitutions selected from L1196M, L1198F, G1202R, and G1269A. In one embodiment, the one or more ALK inhibitor resistance mutations is G1202R. In one embodiment, the one or more ALK inhibitor resistance mutations comprise G1202R and one or more of L1196M, L1198F, and G1269A.

In one embodiment, provided herein is a method for treating an adult patient with metastatic NSCLC that is ALK+with mutation G1202R, comprising administering to the patient a therapeutically effective amount of a compound provided herein, e.g., a compound of Formula (I), or an enantiomer, a mixture of enantiomers, or a tautomer thereof, or a pharmaceutically acceptable salt thereof, wherein the patient has progressed on or is intolerant of at least 1 prior TKI therapy.

In one embodiment, provided herein is a method for treating a ALK-associated (or ALK+) cancer in a subject in need thereof, wherein the cancer has developed resistance to a tyrosine kinase inhibitor (TKI), the method comprising administering to the subject a therapeutically effective amount of a compound provided herein, e.g., a compound of Formula (I), or an enantiomer, a mixture of enantiomers, or a tautomer thereof, or a pharmaceutically acceptable salt thereof.

In one embodiment, the TKI is a ROS1 inhibitor. In one embodiment, the TKI is an ALK inhibitor. In one embodiment, the TKI is crizotinib, ceritinib, alectinib, brigatinib, lorlatinib, entrectinib, repotrectinib, cabozantinib, foretinib, merestinib, taletrectinib, masitinib, or ensartinib. In one embodiment, the TKI is crizotinib. In one embodiment, the TKI is entrectinib.

In certain embodiments, the subject has relapsed after first-line treatment of the cancer. In other embodiments, the subject has relapsed after second-line treatment of the cancer.

In one embodiment, the cancer or disease is in a pediatric patient (including an infantile patient). In one embodiment, the cancer is systemic anaplastic large cell lymphoma (ALCL) that is ALK+ in pediatric patients 1 year of age or older, and young adults. In another embodiment, the cancer is relapsed or refractory systemic anaplastic large cell lymphoma (ALCL) that is ALK+ in pediatric patients 1 year of age or older, and young adults. In one embodiment, the cancer is systemic anaplastic large cell lymphoma (ALCL) that is ROS1+ in pediatric patients 1 year of age or older, and young adults. In another embodiment, the cancer is relapsed or refractory systemic anaplastic large cell lymphoma (ALCL) that is ROS1+ in pediatric patients 1 year of age or older, and young adults.

In certain embodiments, the methods for treating or preventing cancer can be demonstrated by one or more responses such as increased apoptosis, inhibition of tumor growth, reduction of tumor metastasis, inhibition of tumor metastasis, reduction of microvessel density, decreased neovascularization, inhibition of tumor migration, tumor regression, and increased survival of the subject.

Combination Treatments

In some embodiments, the method of treating or preventing cancer may comprise administering a compound of Formula (I) conjointly with one or more other chemotherapeutic agent(s).

As used herein and unless otherwise specified, by "conjointly" or "in combination with", it is not intended to imply that the other agent and the compound of Formula (I) must be administered at the same time and/or formulated for delivery together, although these methods of delivery are within the scope of this disclosure. The compound provided herein can be administered concurrently with, prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks before), or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks after), one or more other agents (e.g., one or more other additional agents). In general, each therapeutic agent is administered at a dose and/or on a time schedule determined for that particular agent. The other therapeutic agent can be administered with the compound provided herein in a single composition or separately in a different composition. Triple therapy is also contemplated herein.

Chemotherapeutic agents that may be conjointly administered with compounds of the disclosure include: 1-amino-4-phenylamino-9,10-dioxo-9,10-dihydroanthracene-2-sulfonate (acid blue 25), 1-amino-4-[4-hydroxyphenyl-amino]-9,10-dioxo-9,10-dihydroanthracene-2-sulfonate, 1-amino-4-[4-aminophenylamino]-9,10-dioxo-9,10-dihydroanthracene-2-sulfonate, 1-amino-4-[1-naphthylamino]-9,10-dioxo-9,10-dihydroanthracene-2-sulfonate, 1-amino-4-[4-fluoro-2-carboxyphenylamino]-9,10-dioxo-9,10-dihydroanthracene-2-sulfonate, 1-amino-4-[2-anthracenylamino]-9,10-dioxo-9,10-dihydroanthracene-2-sulfonate, ABT-263, afatinib dimaleate, axitinib, aminoglutethimide, amsacrine, anastrozole, APCP, asparaginase, AZD5363, *Bacillus* Calmette-Guerin vaccine (bcg), bicalutamide, bleomycin, bortezomib, β-methylene-ADP (AOPCP), buserelin, busulfan, cabazitaxel, cabozantinib, campothecin, capecitabine, carboplatin, carfilzomib, carmustine, ceritinib, chlorambucil, chloroquine, cisplatin, cladribine, clodronate, cobimetinib, colchicine, crizotinib, cyclophosphamide, cyproterone, cytarabine, dacarbazine, dactinomycin, daunorubicin, demethoxyviridin, dexamethasone, dichloroacetate, dienestrol, diethylstilbestrol, docetaxel, doxorubicin, epirubicin, eribulin, erlotinib, estradiol, estramustine, etoposide, everolimus, exemestane, filgrastim, fludarabine, fludrocortisone, fluorouracil, fluoxymesterone, flutamide, gefitinib, gemcitabine, genistein, goserelin, GSK1120212, hydroxyurea, idarubicin, ifosfamide, imatinib, interferon, irinotecan, ixabepilone, lenalidomide, letrozole, leucovorin, leuprolide, levamisole, lomustine, lonidamine, mechlorethamine, medroxyprogesterone, megestrol, melphalan, mercaptopurine, mesna, metformin, methotrexate, miltefosine, mitomycin, mitotane, mitoxantrone, MK-2206, mutamycin, N-(4-sulfamoylphenylcarbamothioyl) pivalamide, NF279, NF449, nilutamide, nocodazole, octreotide, olaparib, oxaliplatin, paclitaxel, pamidronate, pazopanib, pemexetred, pentostatin, perifosine, PF-04691502, plicamycin, pomalidomide, porfimer, PPADS, procarbazine, quercetin, raltitrexed, ramucirumab, reactive blue 2, rituximab, rolofylline, romidepsin, rucaparib, selumetinib, sirolimus, sodium 2,4-dinitrobenzene-sulfonate, sorafenib, streptozocin, sunitinib, suramin, talazoparib, tamoxifen, temozolomide, temsirolimus, teniposide, testosterone, thalidomide, thioguanine, thiotepa, titanocene dichloride, tonapofylline, topotecan, trametinib, trastuzumab, tretinoin, veliparib, vinblastine, vincristine, vindesine, vinorelbine, and vorinostat (SAHA). In other embodiments, chemotherapeutic agents that may be conjointly administered with compounds of the disclosure include: ABT-263, dexamethasone, 5-fluorouracil, PF-04691502, romidepsin, and vorinostat (SAHA). In other embodiments, chemotherapeutic agents that may be conjointly administered with compounds of the disclosure include: 1-amino-4-phenylamino-9,10-dioxo-9,10-dihydroanthracene-2-sulfonate (acid blue 25), 1-amino-4-[4-hydroxyphenyl-amino]-9,10-dioxo-9,10-dihydroanthracene-2-sulfonate, 1-amino-4-[4-aminophenylamino]-9,10-dioxo-9,10-dihydroanthracene-2-sulfonate, 1-amino-4-[1-naphthylamino]-9,10-dioxo-9,10-dihydroanthracene-2-sulfonate, 1-amino-4-[4-fluoro-2-carboxyphenylamino]-9,10-dioxo-9,10-dihydroanthracene-2-sulfonate, 1-amino-4-[2-anthracenylamino]-9,10-dioxo-9,10-dihydroanthracene-2-sulfonate, APCP, O-methylene-ADP (AOPCP), capecitabine, cladribine, cytarabine, fludarabine, doxorubicin, gemcitabine, N-(4-sulfamoylphenylcarbamothioyl) pivalamide, NF279, NF449, PPADS, quercetin, reactive blue 2, rolofylline sodium 2,4-dinitrobenzenesulfonate, sumarin, and tonapofylline.

Many combination therapies have been developed for the treatment of cancer. In certain embodiments, compounds of the disclosure (e.g., compounds of Formula (I)) may be conjointly administered with one or more combination therapies. Examples of combination therapies with which compounds of the disclosure may be conjointly administered are included in Table 2.

TABLE 2

Exemplary combinatorial therapies for the treatment of cancer

| Name | Therapeutic agents |
|---|---|
| ABV | Doxorubicin, Bleomycin, Vinblastine |
| ABVD | Doxorubicin, Bleomycin, Vinblastine, Dacarbazine |
| AC (Breast) | Doxorubicin, Cyclophosphamide |
| AC (Sarcoma) | Doxorubicin, Cisplatin |
| AC (Neuroblastoma) | Cyclophosphamide, Doxorubicin |
| ACE | Cyclophosphamide, Doxorubicin, Etoposide |
| ACe | Cyclophosphamide, Doxorubicin |
| AD | Doxorubicin, Dacarbazine |
| AP | Doxorubicin, Cisplatin |
| ARAC-DNR | Cytarabine, Daunorubicin |
| B-CAVe | Bleomycin, Lomustine, Doxorubicin, Vinblastine |
| BCVPP | Carmustine, Cyclophosphamide, Vinblastine, Procarbazine, Prednisone |
| BEACOPP | Bleomycin, Etoposide, Doxorubicin, Cyclophosphamide, Vincristine, Procarbazine, Prednisone, Filgrastim |

TABLE 2-continued

Exemplary combinatorial therapies for the treatment of cancer

| Name | Therapeutic agents |
|---|---|
| BEP | Bleomycin, Etoposide, Cisplatin |
| BIP | Bleomycin, Cisplatin, Ifosfamide, Mesna |
| BOMP | Bleomycin, Vincristine, Cisplatin, Mitomycin |
| CA | Cytarabine, Asparaginase |
| CABO | Cisplatin, Methotrexate, Bleomycin, Vincristine |
| CAF | Cyclophosphamide, Doxorubicin, Fluorouracil |
| CAL-G | Cyclophosphamide, Daunorubicin, Vincristine, Prednisone, Asparaginase |
| CAMP | Cyclophosphamide, Doxorubicin, Methotrexate, Procarbazine |
| CAP | Cyclophosphamide, Doxorubicin, Cisplatin |
| CAV | Cyclophosphamide, Doxorubicin, Vincristine |
| CAVE ADD | CAV and Etoposide |
| CA-VP16 | Cyclophosphamide, Doxorubicin, Etoposide |
| CC | Cyclophosphamide, Carboplatin |
| CDDP/VP-16 | Cisplatin, Etoposide |
| CEF | Cyclophosphamide, Epirubicin, Fluorouracil |
| CEPP(B) | Cyclophosphamide, Etoposide, Prednisone, with or without/Bleomycin |
| CEV | Cyclophosphamide, Etoposide, Vincristine |
| CF | Cisplatin, Fluorouracil or Carboplatin Fluorouracil |
| CHAP | Cyclophosphamide or Cyclophosphamide, Altretamine, Doxorubicin, Cisplatin |
| ChlVPP | Chlorambucil, Vinblastine, Procarbazine, Prednisone |
| CHOP | Cyclophosphamide, Doxorubicin, Vincristine, Prednisone |
| CHOP-BLEO | Add Bleomycin to CHOP |
| CISCA | Cyclophosphamide, Doxorubicin, Cisplatin |
| CLD-BOMP | Bleomycin, Cisplatin, Vincristine, Mitomycin |
| CMF | Methotrexate, Fluorouracil, Cyclophosphamide |
| CMFP | Cyclophosphamide, Methotrexate, Fluorouracil, Prednisone |
| CMFVP | Cyclophosphamide, Methotrexate, Fluorouracil, Vincristine, Prednisone |
| CMV | Cisplatin, Methotrexate, Vinblastine |
| CNF | Cyclophosphamide, Mitoxantrone, Fluorouracil |
| CNOP | Cyclophosphamide, Mitoxantrone, Vincristine, Prednisone |
| COB | Cisplatin, Vincristine, Bleomycin |
| CODE | Cisplatin, Vincristine, Doxorubicin, Etoposide |
| COMLA | Cyclophosphamide, Vincristine, Methotrexate, Leucovorin, Cytarabine |
| COMP | Cyclophosphamide, Vincristine, Methotrexate, Prednisone |
| Cooper Regimen | Cyclophosphamide, Methotrexate, Fluorouracil, Vincristine, Prednisone |
| COP | Cyclophosphamide, Vincristine, Prednisone |
| COPE | Cyclophosphamide, Vincristine, Cisplatin, Etoposide |
| COPP | Cyclophosphamide, Vincristine, Procarbazine, Prednisone |
| CP(Chronic lymphocytic leukemia) | Chlorambucil, Prednisone |
| CP (Ovarian Cancer) | Cyclophosphamide, Cisplatin |
| CVD | Cisplatin, Vinblastine, Dacarbazine |
| CVI | Carboplatin, Etoposide, Ifosfamide, Mesna |
| CVP | Cyclophosphamide, Vincristine, Prednisome |
| CVPP | Lomustine, Procarbazine, Prednisone |
| CYVADIC | Cyclophosphamide, Vincristine, Doxorubicin, Dacarbazine |
| DA | Daunorubicin, Cytarabine |
| DAT | Daunorubicin, Cytarabine, Thioguanine |
| DAV | Daunorubicin, Cytarabine, Etoposide |
| DCT | Daunorubicin, Cytarabine, Thioguanine |
| DHAP | Cisplatin, Cytarabine, Dexamethasone |
| DI | Doxorubicin, Ifosfamide |
| DTIC/Tamoxifen | Dacarbazine, Tamoxifen |
| DVP | Daunorubicin, Vincristine, Prednisone |
| EAP | Etoposide, Doxorubicin, Cisplatin |
| EC | Etoposide, Carboplatin |
| EFP | Etoposie, Fluorouracil, Cisplatin |
| ELF | Etoposide, Leucovorin, Fluorouracil |
| EMA 86 | Mitoxantrone, Etoposide, Cytarabine |
| EP | Etoposide, Cisplatin |
| EVA | Etoposide, Vinblastine |
| FAC | Fluorouracil, Doxorubicin, Cyclophosphamide |
| FAM | Fluorouracil, Doxorubicin, Mitomycin |
| FAMTX | Methotrexate, Leucovorin, Doxorubicin |
| FAP | Fluorouracil, Doxorubicin, Cisplatin |
| F-CL | Fluorouracil, Leucovorin |
| FEC | Fluorouracil, Cyclophosphamide, Epirubicin |

TABLE 2-continued

Exemplary combinatorial therapies for the treatment of cancer

| Name | Therapeutic agents |
|---|---|
| FED | Fluorouracil, Etoposide, Cisplatin |
| FL | Flutamide, Leuprolide |
| FZ | Flutamide, Goserelin acetate implant |
| HDMTX | Methotrexate, Leucovorin |
| Hexa-CAF | Altretamine, Cyclophosphamide, Methotrexate, Fluorouracil |
| IDMTX/6-MP | Methotrexate, Mercaptopurine, Leucovorin |
| IE | Ifosfamide, Etoposie, Mesna |
| IfoVP | Ifosfamide, Etoposide, Mesna |
| IPA | Ifosfamide, Cisplatin, Doxorubicin |
| M-2 | Vincristine, Carmustine, Cyclophosphamide, Prednisone, Melphalan |
| MAC-III | Methotrexate, Leucovorin, Dactinomycin, Cyclophosphamide |
| MACC | Methotrexate, Doxorubicin, Cyclophosphamide, Lomustine |
| MACOP-B | Methotrexate, Leucovorin, Doxorubicin, Cyclophosphamide, Vincristine, Bleomycin, Prednisone |
| MAID | Mesna, Doxorubicin, Ifosfamide, Dacarbazine |
| m-BACOD | Bleomycin, Doxorubicin, Cyclophosphamide, Vincristine, Dexamethasone, Methotrexate, Leucovorin |
| MBC | Methotrexate, Bleomycin, Cisplatin |
| MC | Mitoxantrone, Cytarabine |
| MF | Methotrexate, Fluorouracil, Leucovorin |
| MICE | Ifosfamide, Carboplatin, Etoposide, Mesna |
| MINE | Mesna, Ifosfamide, Mitoxantrone, Etoposide |
| mini-BEAM | Carmustine, Etoposide, Cytarabine, Melphalan |
| MOBP | Bleomycin, Vincristine, Cisplatin, Mitomycin |
| MOP | Mechlorethamine, Vincristine, Procarbazine |
| MOPP | Mechlorethamine, Vincristine, Procarbazine, Prednisone |
| MOPP/ABV | Mechlorethamine, Vincristine, Procarbazine, Prednisone, Doxorubicin, Bleomycin, Vinblastine |
| MP (multiple myeloma) | Melphalan, Prednisone |
| MP (prostate cancer) | Mitoxantrone, Prednisone |
| MTX/6-MO | Methotrexate, Mercaptopurine |
| MTX/6-MP/VP | Methotrexate, Mercaptopurine, Vincristine, Prednisone |
| MTX-CDDPAdr | Methotrexate, Leucovorin, Cisplatin, Doxorubicin |
| MV (breast cancer) | Mitomycin, Vinblastine |
| MV (acute myelocytic leukemia) | Mitoxantrone, Etoposide |
| M-VAC Methotrexate | Vinblastine, Doxorubicin, Cisplatin |
| MVP Mitomycin | Vinblastine, Cisplatin |
| MVPP | Mechlorethamine, Vinblastine, Procarbazine, Prednisone |
| NFL | Mitoxantrone, Fluorouracil, Leucovorin |
| NOVP | Mitoxantrone, Vinblastine, Vincristine |
| OPA | Vincristine, Prednisone, Doxorubicin |
| OPPA | Add Procarbazine to OPA. |
| PAC | Cisplatin, Doxorubicin |
| PAC-I | Cisplatin, Doxorubicin, Cyclophosphamide |
| PA-CI | Cisplatin, Doxorubicin |
| PCV | Lomustine, Procarbazine, Vincristine |
| PFL | Cisplatin, Fluorouracil, Leucovorin |
| POC | Prednisone, Vincristine, Lomustine |
| ProMACE | Prednisone, Methotrexate, Leucovorin, Doxorubicin, Cyclophosphamide, Etoposide |
| ProMACE/cytaBOM | Prednisone, Doxorubicin, Cyclophosphamide, Etoposide, Cytarabine, Bleomycin, Vincristine, Methotrexate, Leucovorin, Cotrimoxazole |
| PRoMACE/MOPP | Prednisone, Doxorubicin, Cyclophosphamide, Etoposide, Mechlorethamine, Vincristine, Procarbazine, Methotrexate, Leucovorin |
| Pt/VM | Cisplatin, Teniposide |
| PVA | Prednisone, Vincristine, Asparaginase |
| PVB | Cisplatin, Vinblastine, Bleomycin |
| PVDA | Prednisone, Vincristine, Daunorubicin, Asparaginase |
| SMF | Streptozocin, Mitomycin, Fluorouracil |
| TAD | Mechlorethamine, Doxorubicin, Vinblastine, Vincristine, Bleomycin, Etoposide, Prednisone |
| TTT | Methotrexate, Cytarabine, Hydrocortisone |
| Topo/CTX | Cyclophosphamide, Topotecan, Mesna |
| VAB-6 | Cyclophosphamide, Dactinomycin, Vinblastine, Cisplatin, Bleomycin |
| VAC | Vincristine, Dactinomycin, Cyclophosphamide |
| VACAdr | Vincristine, Cyclophosphamide, Doxorubicin, Dactinomycin, Vincristine |

TABLE 2-continued

Exemplary combinatorial therapies for the treatment of cancer

| Name | Therapeutic agents |
|---|---|
| VAD | Vincristine, Doxorubicin, Dexamethasone |
| VATH | Vinblastine, Doxorubicin, Thiotepa, Flouxymesterone |
| VBAP | Vincristine, Carmustine, Doxorubicin, Prednisone |
| VBCMP | Vincristine, Carmustine, Melphalan, Cyclophosphamide, Prednisone |
| VC | Vinorelbine, Cisplatin |
| VCAP | Vincristine, Cyclophosphamide, Doxorubicin, Prednisone |
| VD | Vinorelbine, Doxorubicin |
| VelP | Vinblastine, Cisplatin, Ifosfamide, Mesna |
| VIP | Etoposide, Cisplatin, Ifosfamide, Mesna |
| VM | Mitomycin, Vinblastine |
| VMCP | Vincristine, Melphalan, Cyclophosphamide, Prednisone |
| VP | Etoposide, Cisplatin |
| V-TAD | Etoposide, Thioguanine, Daunorubicin, Cytarabine |
| 5 + 2 | Cytarabine, Daunorubicin, Mitoxantrone |
| 7 + 3 | Cytarabine with/, Daunorubicin or Idarubicin or Mitoxantrone |
| "8 in 1" | Methylprednisolone, Vincristine, Lomustine, Procarbazine, Hydroxyurea, Cisplatin, Cytarabine, Dacarbazine |

In certain embodiments, the conjoint therapies of the disclosure comprise conjoint administration with other types of chemotherapeutic agents, such as immuno-oncology agents. Cancer cells often have specific cell surface antigens that can be recognized by the immune system. Thus, immuno-oncology agents, such as monoclonal antibodies, can selectively bind to cancer cell antigens and effect cell death. Other immuno-oncology agents can suppress tumor-mediated inhibition of the native immune response or otherwise activate the immune response and thus facilitate recognition of the tumor by the immune system. Exemplary antibody immuno-oncology agents, include, but are not limited to, abagovomab, adecatumumab, afutuzumab, alemtuzumab, anatumomab mafenatox, apolizumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, and tremelimumab. In some embodiments, the antibody immuno-oncology agents are selected from anti-CD73 monoclonal antibody (mAb), anti-CD39 mAb, anti-PD-1 mAb, and anti-CTLA4 mAb. Thus, in some embodiments, the methods of the disclosure comprise conjoint administration of one or more immuno-oncology agents, such as the agents mentioned above.

In some embodiments, the combination therapy comprises conjoint administration of a compound of the disclosure, such as a compound of Formula (I), with SH2 inhibitors, such as CGP78850, CPG85793, C90, C126, G7-18NATE, G7-B1, and NSC642056.

In some embodiments, the combination therapy comprises conjoint administration of a compound of the disclosure, such as a compound of Formula (I), with MEK inhibitors, such as trametinib, cobimetinib, binimetinib, selumetinib, PD-325901, CI-1040, and TAK-733.

In some embodiments, the combination therapy comprises conjoint administration of a compound of the disclosure, such as a compound of Formula (I), with a MET inhibitor selected from JNJ-38877605, PF-04217903, foretinib, AMG 458, tivantinib, cabozantinib, crizotinib, capmatinib hydrochloride, tepotinib hydrochloride, and savolitinib.

In some embodiments, the combination therapy comprises conjoint administration of a compound of the disclosre, such as Formula (I), with a SHP2 inhibitor selected from TNO-155, RMC-4630, JAB-3068, or RLY-1971.

In some embodiments, the combination therapy comprises conjoint administration of a compound of the disclosure, such as a compound of Formula (I), with a RAS inhibitor selected from aliskiren, captopril, losartan, irbesartan, olmesartan, candesartan, valsartan, fimasartan, azilsartan, telmisartan, eprosartan, benazepril, enalapril, lisinopril, perindopril, quinapril, ramipril, and trandolapril.

In some embodiment, the combination therapy comprises administration of a compound provided herein, e.g., a compound of Formula (I), in combination with a TKI.

In one embodiment, the TKI is a ROS1 inhibitor. In one embodiment, the TKI is an ALK inhibitor. In one embodiment, the TKI is crizotinib, ceritinib, alectinib, brigatinib, lorlatinib, entrectinib, repotrectinib, cabozantinib, foretinib, merestinib, taletrectinib, masitinib, or ensartinib. In one embodiment, the TKI is crizotinib. In one embodiment, the TKI is entrectinib. In one embodiment, the TKI is alectinib. In one embodiment, the TKI is brigatinib.

In some embodiments, the combination therapy comprises conjoint administration of a compound of the disclosure, such as a compound of Formula (I), with anti-PD-1 therapy. In certain embodiments, the combination therapy comprises conjoint administration of a compound of the disclosure, such as a compound of Formula (I), with oxaliplatin. In other embodiments, the combination therapy comprises conjoint administration of a compound of the disclosure, such as a compound of Formula (I), with doxorubicin.

In certain embodiments, a compound of the disclosure may be conjointly administered with non-chemical methods of cancer treatment. In certain embodiments, a compound of the disclosure may be conjointly administered with radiation therapy. In certain embodiments, a compound of the disclosure may be conjointly administered with surgery, with thermoablation, with focused ultrasound therapy, with cryotherapy, or with any combination of these.

In certain embodiments, compounds of the disclosure may be conjointly administered with one or more other compounds of the disclosure. Moreover, such combinations may be conjointly administered with other therapeutic agents, such as other agents suitable for the treatment of cancer, immunological or neurological diseases, such as the agents identified above. In certain embodiments, conjointly administering one or more additional chemotherapeutic agents with a compound of the disclosure provides a synergistic effect. In certain embodiments, conjointly administering one or more additional chemotherapeutic agents provides an additive effect.

Pharmaceutical Compositions

In certain embodiments, the present disclosure provides a pharmaceutical preparation suitable for use in a human patient, comprising any of the compounds shown above (e.g., a compound of the disclosure, such as a compound of Formula (I), and one or more pharmaceutically acceptable excipients. In certain embodiments, the pharmaceutical preparations may be for use in treating or preventing a condition or disease as described herein. Any of the disclosed compounds may be used in the manufacture of medicaments for the treatment of any diseases or conditions disclosed herein.

The compositions and methods of the present disclosure may be utilized to treat a subject in need thereof. In certain embodiments, the subject is a mammal such as a human, or a non-human mammal. When administered to subject, such as a human, the composition or the compound is preferably administered as a pharmaceutical composition comprising, for example, a compound of the disclosure and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the disclosure. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the disclosure. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of a subject without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the subject. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the subject being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the disclosure, with the carrier and, optionally, one or more accessory ingredients. In general, the formulations are prepared by uniformly and intimately bringing into association a compound of the present disclosure with liquid carriers, or finely divided solid carriers, or both, and then, if necessary, shaping the product.

Formulations of the disclosure suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present disclosure as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof, (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present disclosure to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this disclosure. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatible with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate.

Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this disclosure, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the subject being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the subject's condition, the disorder being treated, the stability of the compound, and, if desired, another type of therapeutic agent being administered with the compound of the disclosure. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the disclosure will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present disclosure, the active compound may be administered two or three times daily. In certain embodiments, the active compound will be administered once daily.

In certain embodiments, compounds of the disclosure may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the subject, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, a subject who receives such treatment can benefit from a combined effect of different therapeutic compounds.

In certain embodiments, conjoint administration of compounds of the disclosure with one or more additional therapeutic agent(s) (e.g., one or more additional chemotherapeutic agent(s)) provides improved efficacy relative to each individual administration of the compound of the disclosure (e.g., compound of Formula I or Ia) or the one or more additional therapeutic agent(s). In certain such embodiments, the conjoint administration provides an additive effect, wherein an additive effect refers to the sum of each of the effects of individual administration of the compound of the disclosure and the one or more additional therapeutic agent(s).

This disclosure includes the use of pharmaceutically acceptable salts of compounds of the disclosure in the compositions and methods of the present disclosure. In certain embodiments, contemplated salts of the disclosure include, but are not limited to, alkyl, dialkyl, trialkyl or tetra-alkyl ammonium salts. In certain embodiments, contemplated salts of the disclosure include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the disclosure include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Pharmaceutically acceptable anionic salts include acetate, aspartate, benzenesulfonate, benzoate, besylate, bicarbonate, bitartrate, bromide, camsylate, carbonate, chloride, citrate, decanoate, edetate, esylate, fumarate, gluceptate, gluconate, glutamate, glycolate, hexanoate, hydroxynaphthoate, iodide, isethionate, lactate, lactobionate, malate, maleate, mandelate, mesylate, methylsulfate, mucate, napsylate, nitrate, octanoate, oleate, pamoate, pantothenate, phosphate, polygalacturonate, propionate, salicylate, stearate, acetate, succinate, sulfate, tartrate, teoclate, and tosylate.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

The disclosure now being generally described, it will be more readily understood by reference to the following examples which are included merely for purposes of illustration of certain aspects and embodiments of the present disclosure, and are not intended to limit the disclosure.

General Synthetic Procedures

The starting materials and reagents used in preparing these compounds are either available from commercial supplier such as Aldrich Chemical Co., Bachem, etc., or can be made by methods well known in the art. The schemes are merely illustrative of some methods by which the compounds disclosed herein can be synthesized and various modifications to these schemes can be made and will be suggested to one of skill in the art having referred to this disclosure. The starting materials and the intermediates and the final products of the reaction may be isolated and purified if desired using convential techniques, including but not limited to filtration, distillation, crystallization, chromatography, and the like and may be characterized using conventional means, including physical constants and spectral data. In some instances, reactions may produce more than one regioisomeric product. In these cases, chromatography may be used to separate the isomers and NOE or NOESY NMR spectroscopy may be used to aid structural assignment.

Unless specified otherwise, the reactions described herein take place at atmospheric pressure over a temperature range from about −78° C. to about 150° C.

| Abbreviations | Definition |
|---|---|
| Solvents | |
| EA, EtOAc | ethyl acetate |
| PE, pet. ether | petroleum ether |
| THF | tetrahydrofuran |
| DCM | dichloromethane |
| DMF | N,N-dimethylformamide |
| DMA | N,N-dimethylacetamide |
| NMP | N-methyl-2-pyrrolidone |
| DMSO | dimethyl sulfoxide |
| IPA | isopropyl alcohol |
| DME | dimethoxyethane |
| MeCN, ACN | acetonitrile |
| DCE | dichloroethane |
| Reagents | |
| DAST | diethylaminosulfur trifluoride |
| DIAD | diisopropyl azodicarboxylate |
| DEAD | diethyl azodicarboxylate |
| DBAD | di-tert-butyl azodicarboxylate |
| DIPEA, DIEA | N,N-diisopropylethylamine |
| TEA | triethylamine |
| ATP | adenosine triphosphate |
| TFA | trifluoroacetic acid |
| FA | formic acid |
| DIBAL, DIBAL-H, DIBALH | diisobutylaluminium hydride |
| AcOH, HOAc | acetic acid |
| TES | triethylsilane |
| n-BuLi, BuLi | n-butyllithium |
| LDA | lithium diisopropylamide |
| NBS | N-bromosuccinimide |
| NIS | N-iodosuccinimide |
| NCS | N-chlorosuccinimide |
| DMP | Dess-Martin periodinane |
| DEA | diethylamine |
| DMF-DMA | 1,1-dimethoxy-N,N-dimethylmethanamine |
| TMP | 2,2,6,6-tetramethylpiperidine |
| NMO | N-methylmorpholine N-oxide |
| TBSCl | tert-butyldimethylsilyl chloride |
| KOAc, AcOK | potassium acetate |
| NaOAc, AcONa | sodium acetate |
| SEMCl | 2-(trimethylsilyl)ethoxymethyl chloride |
| tBuLi, t-BuLi | tert-butyllithium |
| NFSI | N-fluorobenzenesulfonimide |
| AIBN | azobisisobutyronitrile |
| EDCI | 1-ethyl-3-(3-dimethylaminopropyl)carbodiimide |
| HOBT | hydroxybenzotriazole |
| TBAF | tetra-n-butylammonium fluoride |
| HATU | 1-[bis(dimethylamino)methylene]-1H-1,2,3-triazolo[4,5-b]pyridinium 3-oxide hexafluorophosphate |
| XPhos | 2-dicyclohexylphosphino-2',4',6'-triisopropylbiphenyl |
| cataCXium A | di(1-adamantyl)-n-butylphosphine |
| DPPP | 1,3-bis(diphenylphosphino)propane |
| DPPF | 1,1'-bis(diphenylphosphino)ferrocene |
| TfOH | triflic acid |
| HMTA | 1,3,5,7-tetraazaadamantane |
| PMBCl | p-methoxybenzyl chloride |
| HEPES | 4-(2-hydroxyethyl)-1-piperazineethanesulfonic acid |
| EGTA | ethylene glycol-bis(2-aminoethylether)-N,N,N',N'-tetraacetic acid |
| Other | |
| HPLC | high-pressure liquid chromatography |
| Prep | preparative |
| wt | wild-type |
| rt, r.t., RT | room-temperature |
| SFC | supercritical fluid chromatography |
| V/V | volume/volume |
| LC/MS, LC-MS, LCMS | liquid chromatography-mass spectrometry |
| MS | mass spectrometry |
| ESI, ES+, ES– | electrospray ionization |
| NMR | nuclear magnetic resonance |
| ppm | parts per million |
| sat | saturated |
| aq | aqueous |
| TLC | thin layer chromatography |
| $t_R$ | retention time |

The compounds of the invention can be prepared by a variety of synthetic methods, as further described and illustrated herein. It will be understood by those with skill in the art that the following general synthetic methods are representative and not intended to be limiting. Racemic compounds can be enantiomerically enriched via chiral, preparative, SFC or TIPLC separation. Variable A denotes a carbon, nitrogen or sulfur atom that can be the same or different as another instance of variable A. Variable X denotes a chloride, bromide or iodide atom that can be the same or different as another instance of variable X.

Variable Z denotes a nitrogen atom, or C—H or C—F group that can be the same or different as another instance of variable Z.

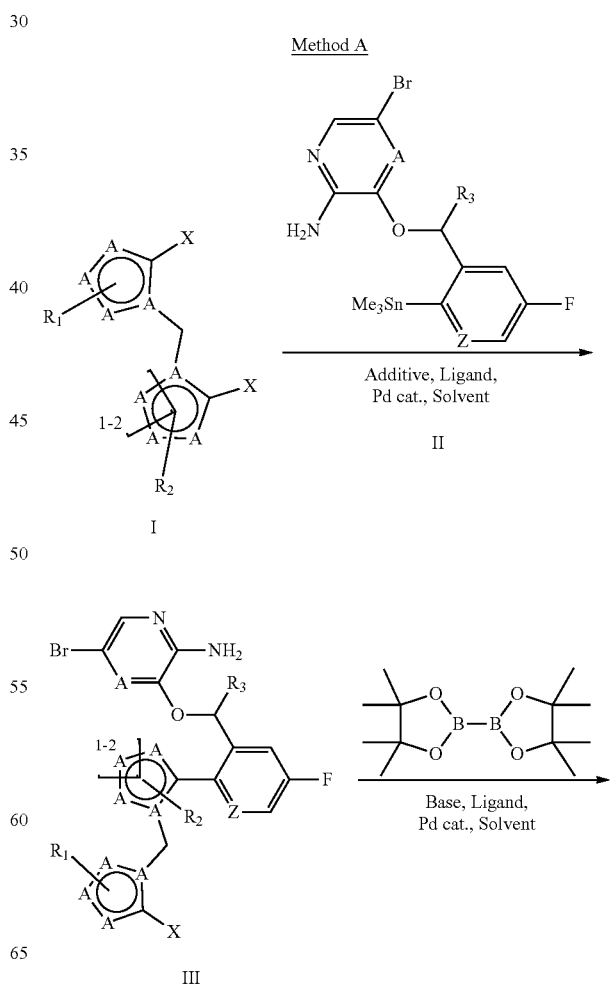

Method A

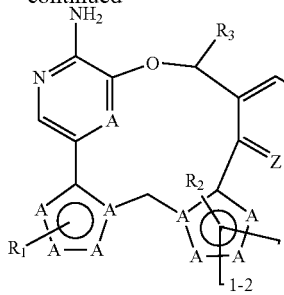

IV

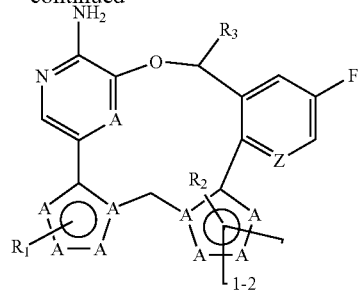

IV

Poly-halide I may be coupled with stannane II using Stille coupling conditions to provide compounds of type III. Various additives including (but not limited to) LiCl or CuI may be optionally employed to facilitate this reaction. Intramolecular ring closure of poly-halide 10 III may be effected using two-step, one-pot borylation/Suzuki cross-coupling conditions to afford compounds of type IV.

Halide V may be coupled with stannane II using Stille coupling conditions to provide compounds of type VI. Various additives including (but not limited to) LiCl or CuI may be optionally employed to facilitate this reaction. Intramolecular ring closure of halide VI may be effected using C—H insertion cross-coupling conditions to afford compounds of type IV. Potassium acetate or potassium pivalate are effective bases for the macrocyclization step.

Method B

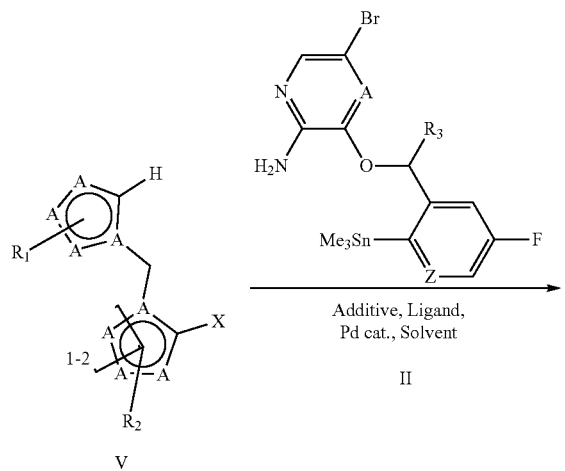

Method C

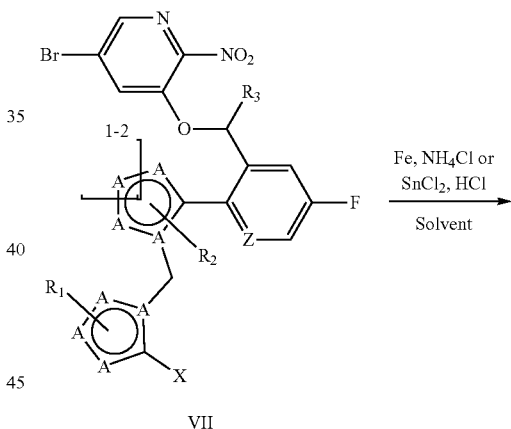

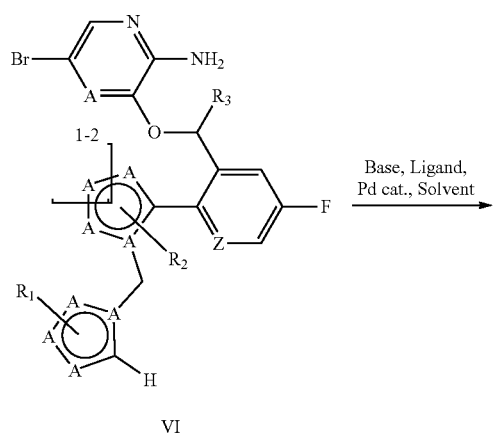

VI

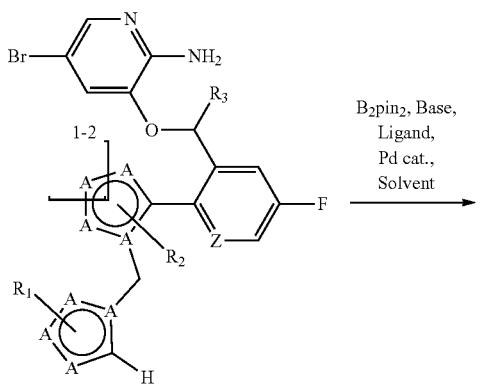

VIII

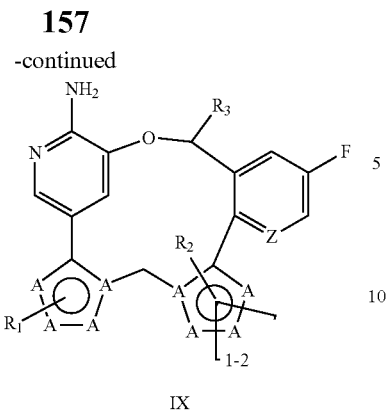

Nitropyridine VII may be reduced using Fe metal conditions to provide aminopyridines of type VIII. In cases where the substrate contains an isoxazole moiety, yields can be improved by using $SnCl_2$ conditions instead. Intramolecular ring closure of VIII may be effected using two-step, one-pot borylation/Suzuki cross-coupling conditions to afford compounds of type IX.

Nitropyridine X may be reduced using Fe metal conditions to provide aminopyridines of type XI. In cases where the substrate contains an isoxazole moiety, yields can be improved by using $SnCl_2$ conditions instead. Intramolecular ring closure of XI may be effected using C—H insertion cross-coupling conditions to afford compounds of type IX. Potassium acetate or potassium pivalate are effective bases for the macrocyclization step.

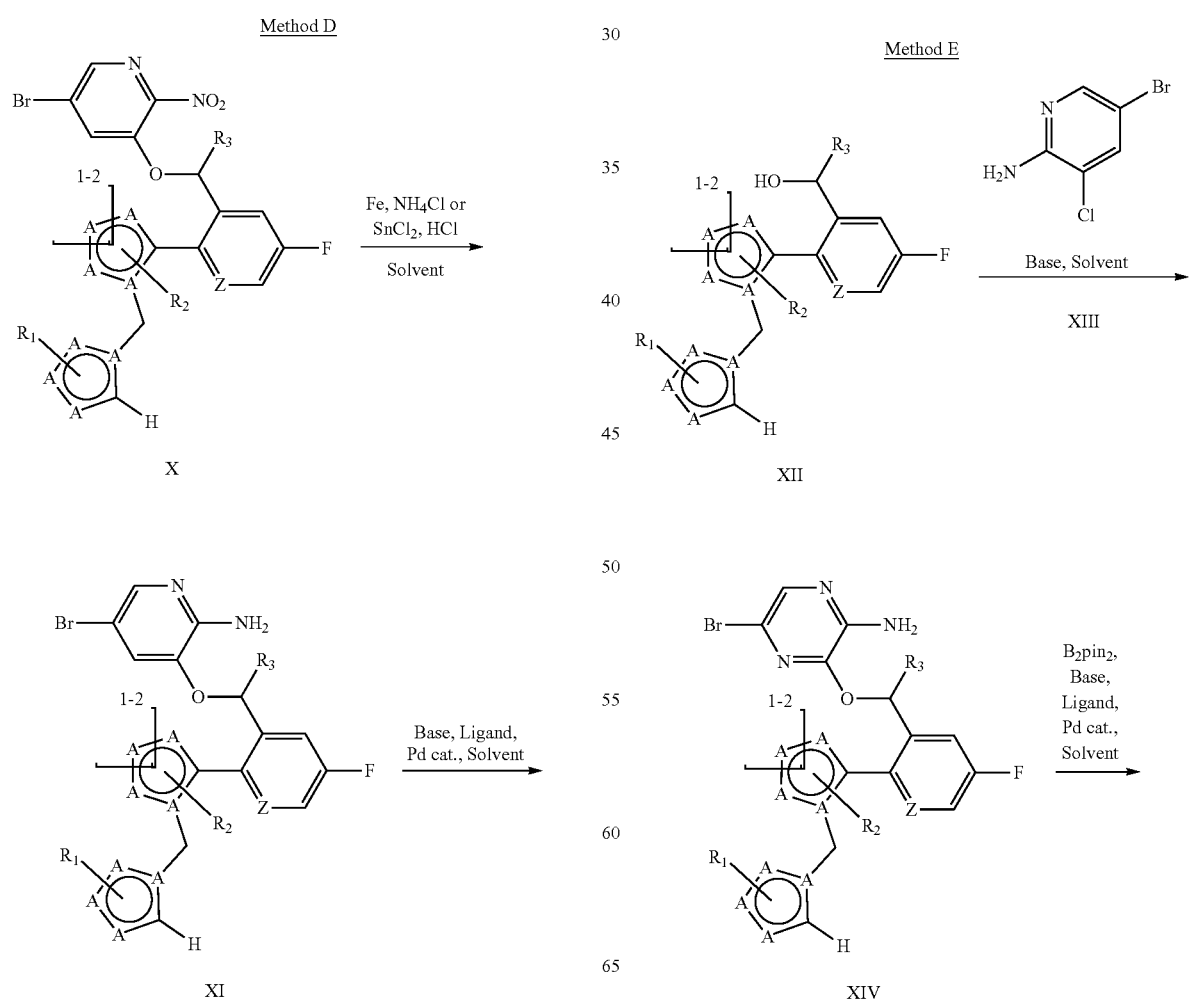

159

-continued

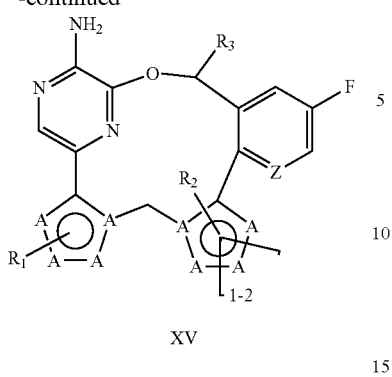

XV

Alcohol XII may be reacted with chloropyrazine XIII using SNAr coupling conditions to form ether XIV. Intramolecular ring closure of XIV may be effected using two-step, one-pot borylation/Suzuki cross-coupling conditions to afford compounds of type XV.

160

-continued

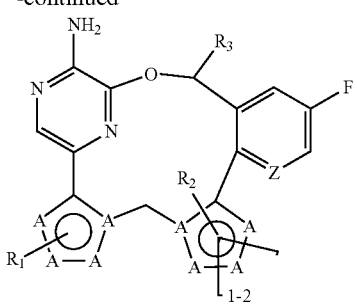

XV

Alcohol XVI may be reacted with chloropyrazine XIII using SNAr coupling conditions to form ether XVII. Intramolecular ring closure of XVII may be effected using C—H insertion cross-coupling conditions to afford compounds of type XV. Potassium acetate or potassium pivalate are effective bases for the macrocyclization step.

Method F

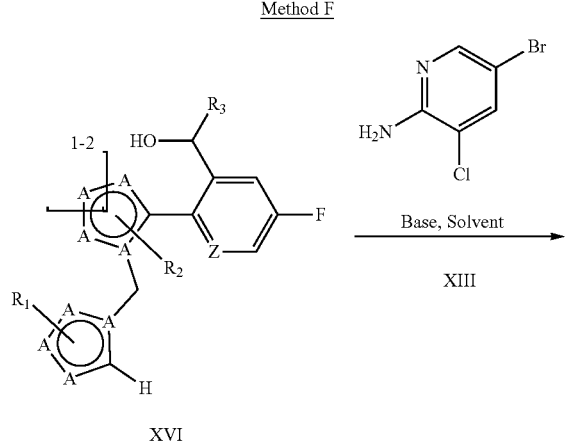

XVI

Method G

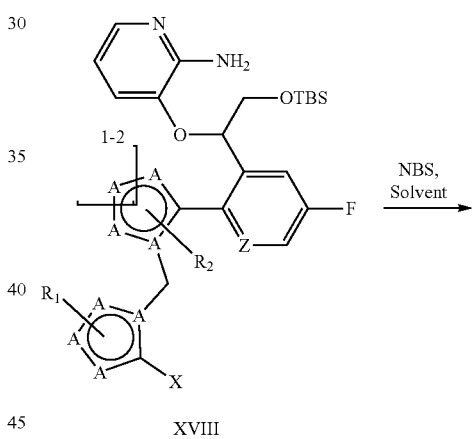

XVIII

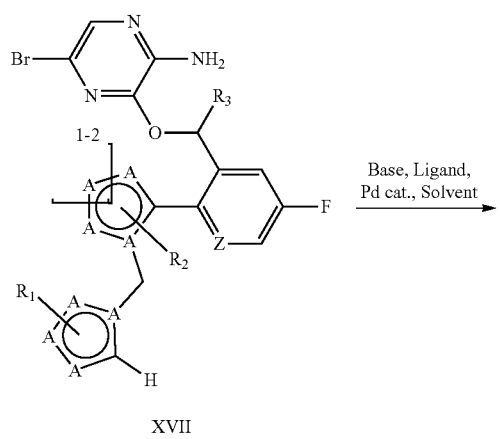

XVII

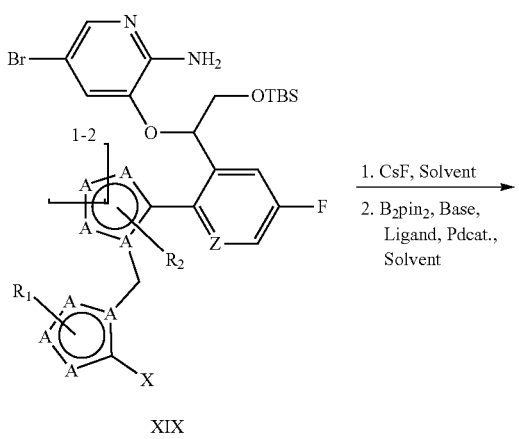

XIX

161
-continued

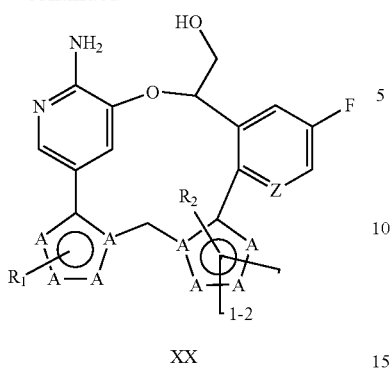

XX

162
-continued

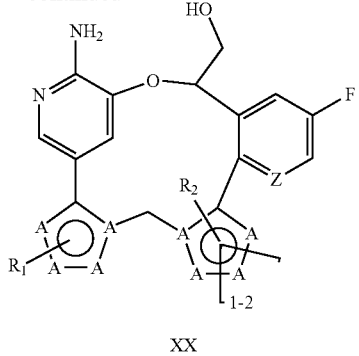

XX

Aminopyridine XVIII may be brominated with a suitable brominating reagent to provide bromide XIX. Desilylation of XIX using a suitable fluoride ion source, followed by intramolecular ring closure using two-step, one-pot borylation/Suzuki cross-coupling conditions may afford compounds of type XX.

Nitropyridine XXI may be reduced using Fe metal conditions to provide aminopyridines of type XXII. In cases where the substrate contains an isoxazole moiety, yields can be improved by using $SnCl_2$ conditions instead. Intramolecular ring closure of XXII using C—H insertion cross-coupling conditions, followed by TBAF desilylation affords compounds of type XX. Potassium acetate or potassium pivalate are effective bases for the macrocyclization step.

Method H

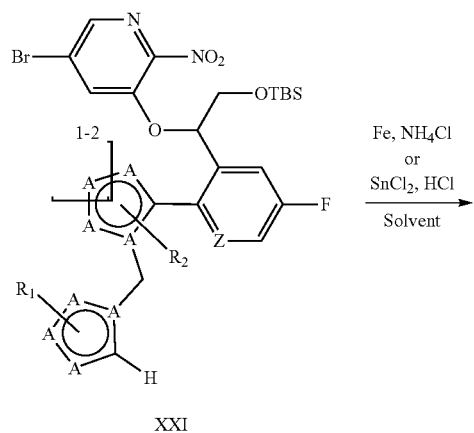

XXI

Method I

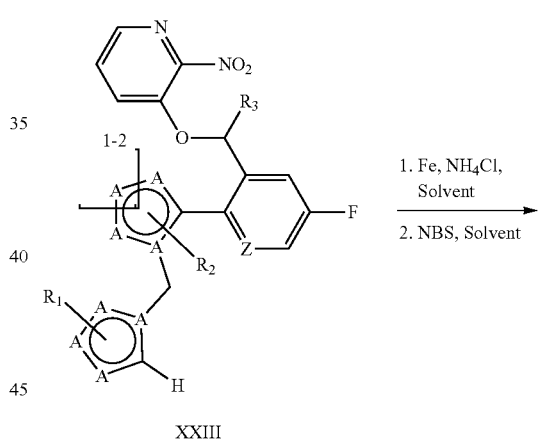

XXIII

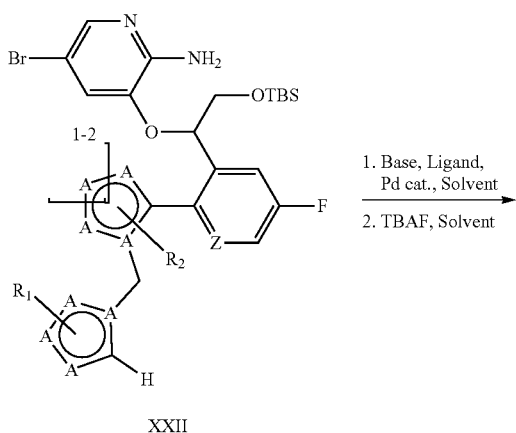

XXII

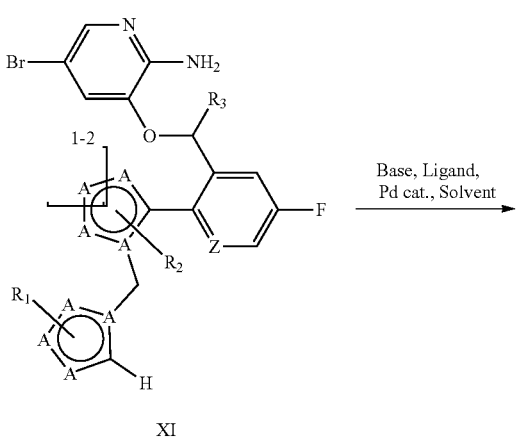

XI

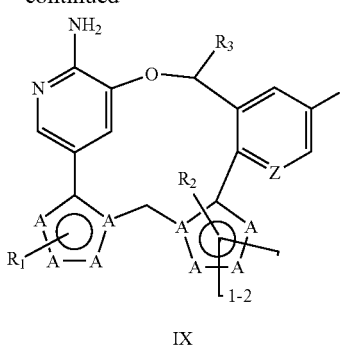

IX

Nitropyridine XXIII may be converted to compound XI by reduction using Fe metal conditions followed by bromination with a suitable brominating reagent. Intramolecular ring closure of XI may be effected using C—H insertion cross-coupling conditions to afford compounds of type IX. Potassium acetate or potassium pivalate are effective bases for the macrocyclization step.

Method J

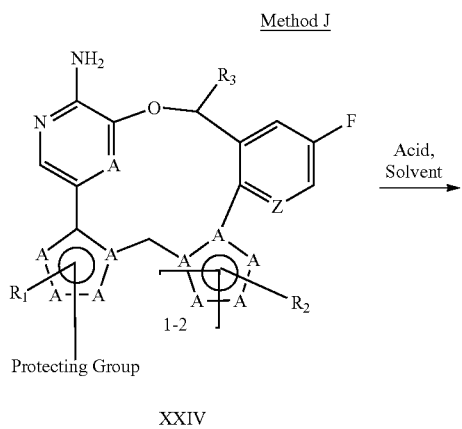

XXIV

Compounds of type XXIV may be deprotected to provide compounds of type IV by treatment with a suitable acid in solution (e.g. TFA or HCl). Protecting groups amenable to this method include, but are not limited to, the methoxymethyl, 2-(trimethylsilyl)ethoxymethyl, tetrahydropyranyl, and p-methoxybenzyl groups.

Method K

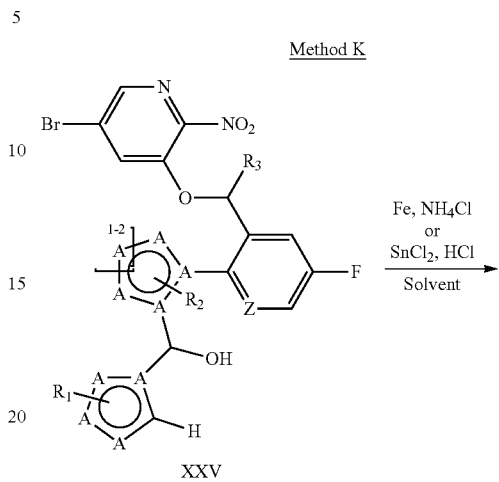

XXV

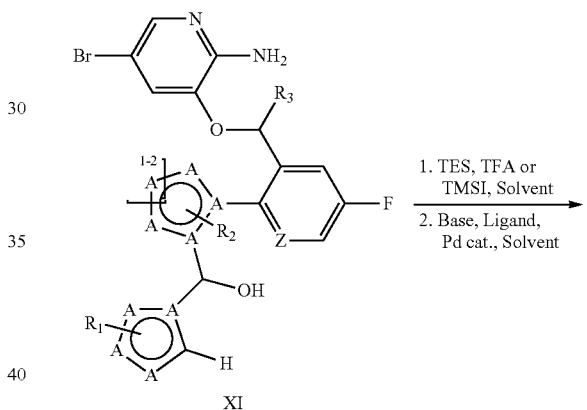

XI

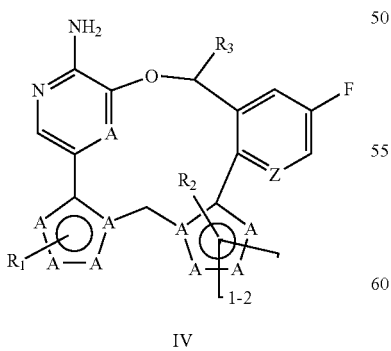

IV

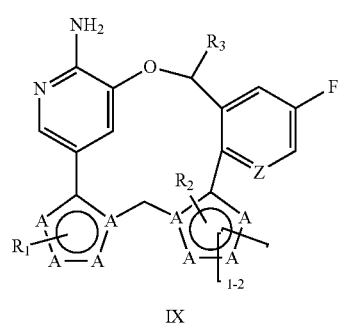

IX

Nitropyridine XXV may be reduced using Fe metal conditions to provide aminopyridines of type XI. In cases where the substrate contains an isoxazole moiety, yields can be improved by using $SnCl_2$ conditions instead. Intramolecular ring closure of XI may be effected using C—H insertion cross-coupling conditions to afford compounds of type IX.

Potassium acetate or potassium pivalate are effective bases for the macrocyclization step.

Method L

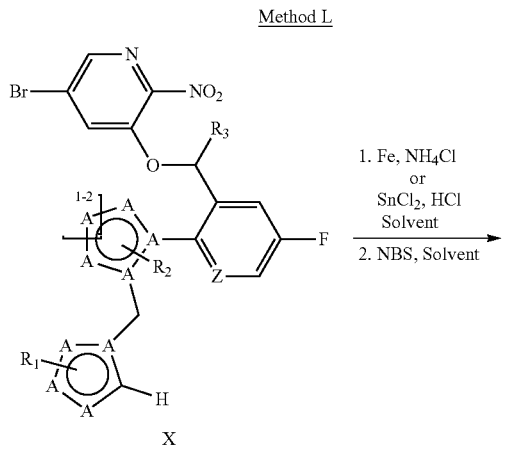

X

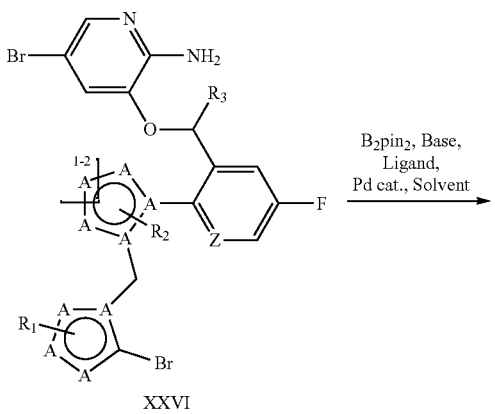

XXVI

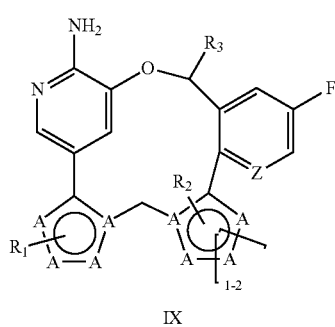

IX

Nitropyridine X may be reduced using iron metal, and then brominated with NBS to provide aminopyridines of type XXVI. In cases where the substrate contains an isoxazole moiety, yields can be improved by using $SnCl_2$ reducing conditions instead of iron. Intramolecular ring closure of XXVI may be effected using two-step, one-pot borylation/Suzuki cross-coupling conditions to afford compounds of type IX.

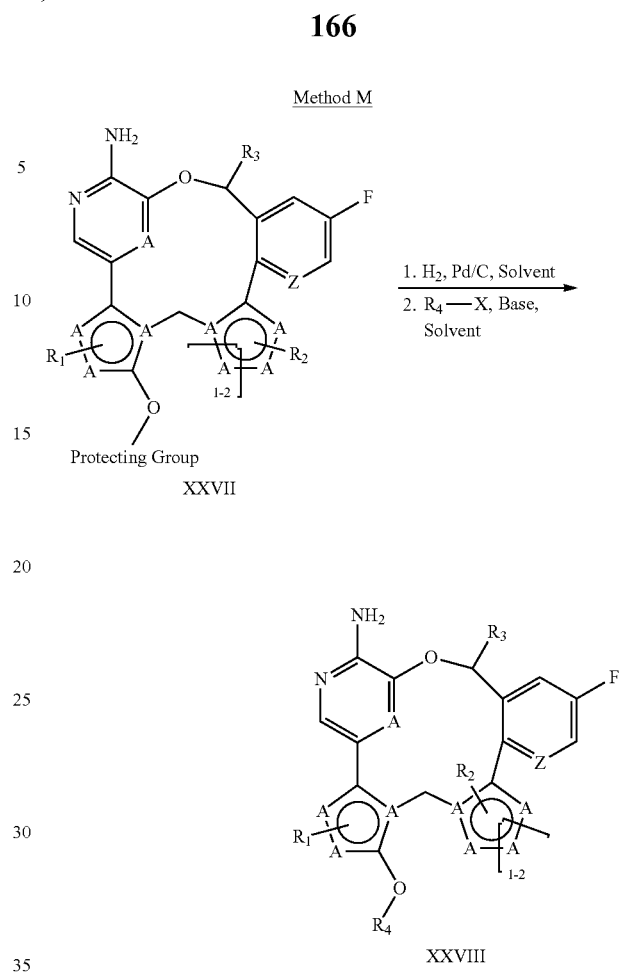

Compounds of type XXVII may be first deprotected by hydrogenolysis using palladium on carbon under a hydrogen atmosphere, followed by alkylation of the resulting hydroxyl group with an alkyl halide (e.g. methyl iodide) to provide compounds of type XXVIII. Protecting groups amenable to this method include, but are not limited to, the benzyl and p-methoxybenzyl groups.

Method N

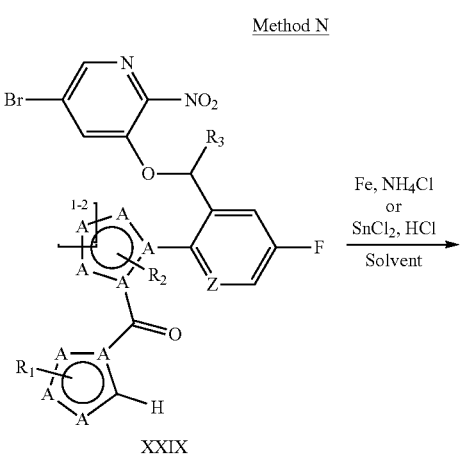

XXIX

-continued

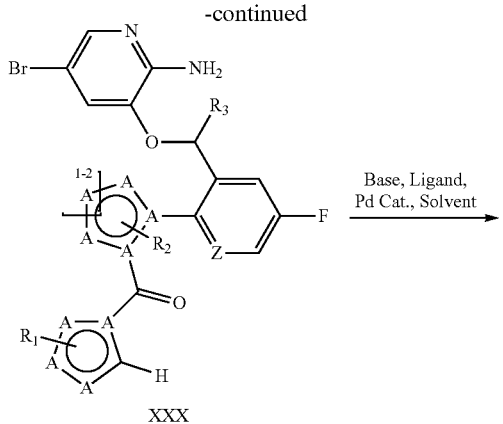

XXX

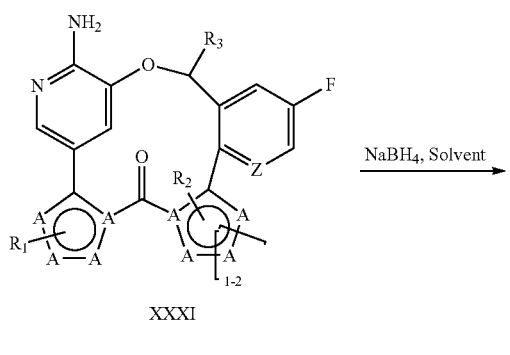

XXXI

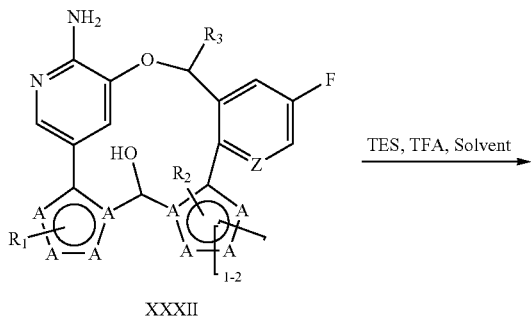

XXXII

-continued

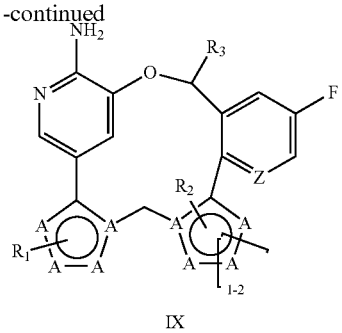

IX

Nitropyridine XXIX may be reduced using Fe metal conditions to provide aminopyridines of type XXX. In cases where the substrate contains an isoxazole moiety, yields can be improved by using $SnCl_2$ conditions instead. Intramolecular ring closure of XXX may be effected using C—H insertion cross-coupling conditions to afford ketones of type XXXI. Potassium acetate or potassium pivalate are effective bases for the macrocyclization step. Reduction of the ketone XXXI to the alcohols of type XXXII can be effected using sodium borohydride. Finally, deoxygenation may be performed using triethylsilane and trifluoroacetic acid to afford compounds of type IX.

Those having skill in the art will recognize that the starting materials and reaction conditions may be varied, the sequence of the reactions altered, and additional steps employed to produce compounds encompassed by the present disclosure, as demonstrated by the following examples. In some cases, protection of certain reactive functionalities may be necessary to achieve some of the above transformations. In general, the need for such protecting groups as well as the conditions necessary to attach and remove such groups will be apparent to experienced organic chemists. The disclosures of all articles and references mentioned in this application, including patents, are incorporated herein by reference.

The preparation of the compounds of the present disclosure is illustrated further by the following examples, which are not to be construed as limiting the disclosure in scope or spirit to the specific procedures and compounds described in them.

Analytical Methods

LCMS data was collected using one of the following methods:

| LCMS Method | Method Details |
|---|---|
| A | Instrument: Agilent1260-6125B |
| | Column: YMC Triart C18, 50 × 4.6 mm, 5 μm |
| | Mobile phase: A is $H_2O$ (+0.05% FA) and B is $CH_3CN$ (+0.05% FA) |
| | Run Time: 20% B (0.1 min); 20-95% B (1.4 min); 95% B (0.7 min); 20% B (0.5 min) |
| | Flow rate: 2.5 mL/min |
| | Column temperature: 35° C. |
| | Wavelength: 220 nm/254 nm |
| B | Instrument: SHIMADZU 2020 |
| | Column: Inertsustain C18, 50 × 4.6 mm, 5 μm |
| | Mobile phase: A is $H_2O$ (+0.1% FA) and B is $CH_3CN$ |
| | Run Time: 15% B (0.6 min); 15-95% B (3.2 min); 95% B (0.5 min); 15% B (0.7 min) |
| | Flow rate: 2.5 mL/min |
| | Column temperature: 35° C. |
| | Wavelength: 220 nm/254 nm |
| C | Instrument: SHIMADZU 2020 |
| | Column: YMC-Triart C18, 50 × 4.6 mm, 5 μm |
| | Mobile phase: A is $H_2O$ (+0.1% FA) and B is $CH_3CN$ |
| | Run Time: 20% B (0.1 min); 20-95% B (1.7 min); 95% B (0.7 min); 20% B (0.4 min) |

| LCMS Method | Method Details |
|---|---|
| | Flow rate: 2.5 mL/min |
| | Column temperature: 35° C. |
| | Wavelength: 220 nm/254 nm |
| D | Instrument: SHIMADZU 2020 |
| | Column: YMC-Triart C18, 50 × 4.6 mm, 5 μm |
| | Mobile phase: A is $H_2O$ (+0.1% FA) and B is $CH_3CN$ |
| | Run Time: 0% B (0.6 min); 0-50% B (3.2 min); 50% B (0.5 min); 0% B (0.4 min) |
| | Flow rate: 2.5 mL/min |
| | Column temperature: 35° C. |
| | Wavelength: 220 nm/254 nm |
| E | Instrument: SHIMADZU 2020 |
| | Column: Inertsustain C18, 50 × 4.6 mm, 5 μm |
| | Mobile phase: A is $H_2O$ (+0.1% FA) and B is $CH_3CN$ |
| | Run Time: 0% B (0.1 min); 0-50% B (1.7 min); 50% B (0.7 min); 0% B (0.4 min) |
| | Flow rate: 2.5 mL/min |
| | Column temperature: 35° C. |
| | Wavelength: 220 nm/254 nm |
| F | Instrument: SHIMADZU 2020 |
| | Column: Shim-pack GIST C18, 50 × 4.6 mm, 5 μm |
| | Mobile phase: A is $H_2O$ (+0.1% FA) and B is $CH_3CN$ |
| | Run Time: 20% B (0.1 min); 20-95% B (1.7 min); 95% B (0.7 min); 20% B (0.4 min) |
| | Flow rate: 2.5 mL/min |
| | Column temperature: 35° C. |
| | Wavelength: 220 nm/254 nm |
| G | Instrument: SHIMADZU 2020 |
| | Column: Shim-pack GIST C18, 50 × 4.6 mm, 5 μm |
| | Mobile phase: A is $H_2O$ (+0.1% FA) and B is $CH_3CN$ |
| | Run Time: 0% B (0.6 min); 0-50% B (3.2 min); 50% B (0.5 min); 0% B (0.4 min) |
| | Flow rate: 2.5 mL/min |
| | Column temperature: 35° C. |
| | Wavelength: 220 nm/254 nm |
| H | Instrument: SHIMADZU 2020 |
| | Column: Inertsil ODS-3 C18, 50 × 4.6 mm, 5 μm |
| | Mobile phase: A is $H_2O$ (+0.04% aq. $NH_3$) and B is $CH_3CN$ |
| | Run Time: 20% B (0.1 min); 20-95% B (1.7 min); 95% B (0.7 min); 20% B (0.4 min) |
| | Flow rate: 2.5 mL/min |
| | Column temperature: 35° C. |
| | Wavelength: 220 nm/254 nm |
| I | Instrument: SHIMADZU 2010 |
| | Column: Shim-pack GIST C18, 50 × 4.6 mm, 5 μm |
| | Mobile phase: A is 10% $CH_3CN$ in $H_2O$ + 0.05% FA and B is $CH_3CN$ |
| | Run Time: 20-95% B (1.8 min); 95% B (0.9 min) |
| | Flow rate: 2.3 mL/min |
| | Column temperature: 40° C. |
| | Wavelength: 220 nm/254 nm |
| J | Instrument: SHIMADZU 2020 |
| | Column: Inertsil ODS-3 C18, 50 × 4.6 mm, 5 μm |
| | Mobile phase: A is $H_2O$ (+0.04% aq. $NH_3$) and B is $CH_3CN$ |
| | Run Time: 15% B (0.6 min); 15-95% B (3.2 min); 95% B (0.5 min); 15% B (0.4 min) |
| | Flow rate: 2.5 mL/min |
| | Column temperature: 35° C. |
| | Wavelength: 220 nm/254 nm |
| K | Instrument: SHIMADZU 2020 |
| | Column: Kromasil Eternity XT C18, 50 × 4.6 mm, 5 μm |
| | Mobile phase: A is $H_2O$ (+0.1% FA) and B is $CH_3CN$ |
| | Run Time: 20% B (0.1 min); 20-95% B (1.7 min); 95% B (0.7 min); 20% B (0.4 min) |
| | Flow rate: 2.5 mL/min |
| | Column temperature: 35° C. |
| | Wavelength: 220 nm/254 nm |
| L | Instrument: SHIMADZU 2020 |
| | Column: YMC Triart C18, 50 × 4.6 mm, 5 μm |
| | Mobile phase: A is $H_2O$ (+0.1% FA) and B is $CH_3CN$ |
| | Run Time: 15% B (0.6 min); 15-95% B (3.2 min); 95% B (0.5 min); 15% B (0.4 min) |
| | Flow rate: 2.5 mL/min |
| | Column temperature: 35° C. |
| | Wavelength: 220 nm/254 nm |
| M | Instrument: SHIMADZU 2020 |
| | Column: Shim-pack GIST C18, 50 × 4.6 mm, 5 μm |
| | Mobile phase: A is $H_2O$ (+0.05% FA) and B is $CH_3CN$ |
| | Run Time: 0% B (0.6 min); 0-70% B (3.2 min); 70% B (0.5 min); 0% B (0.4 min) |
| | Flow rate: 2.5 mL/min |
| | Column temperature: 35° C. |
| | Wavelength: 220 nm/254 nm |

Synthetic Examples

Intermediates

Synthesis of 3-chloro-4-iodo-1H-pyrazole

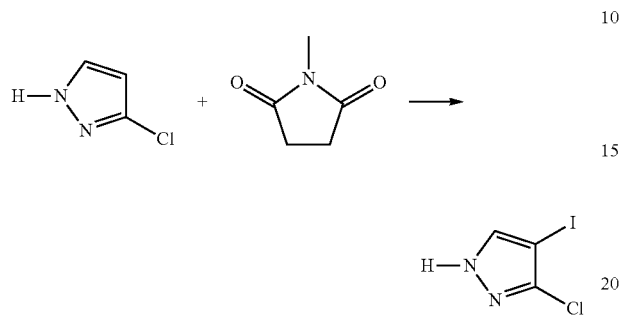

To a stirred solution of 3-chloro-1H-pyrazole (25.00 g, 243.8 mmol) in DMF (250 mL) was added NIS (71.3 g, 317 mmol) portion-wise at 0° C. over 30 min. After the addition, the mixture was stirred at 25° C. for 1 h and then concentrated by oil pump to remove DMF. The residue was diluted with EtOAc, washed with sat. NaHCO$_3$ (250 mL×2) and brine (250 mL×2), dried over Na$_2$SO$_4$ and concentrated to dryness to give crude 3-chloro-4-iodo-1H-pyrazole (55.7 g, 96%) as a brown oil. LC/MS (ESI) m/z: 229 [M+H]$^+$.

The following intermediates were synthesized using a similar experimental protocol:

3-(benzyloxy)-5-bromo-1-ethyl-4-iodo-1H-pyrazole

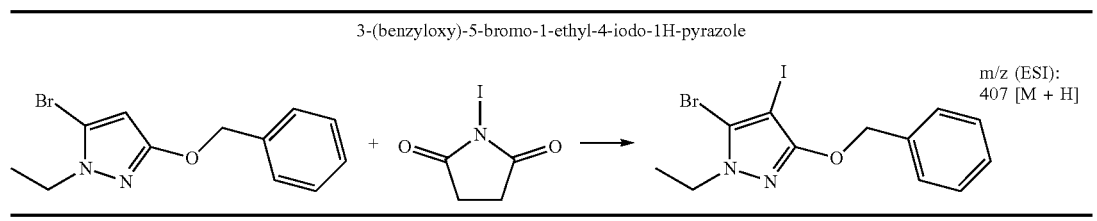

m/z (ESI): 407 [M + H]

Synthesis of 1-methyl-3-vinyl-1H-pyrazole

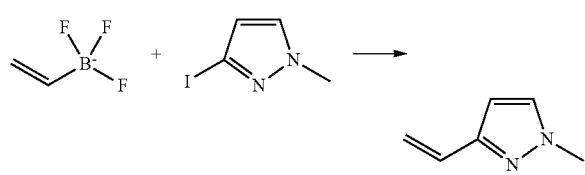

To a mixture of 3-iodo-1-methyl-1H-pyrazole (14.00 g, 67.31 mmol) and potassium vinyltrifluoroborate (27.06 g, 201.9 mmol) in 1,4-dioxane (200 mL) and water (50 mL) were added K$_2$CO$_3$ (27.9 g, 202 mmol) and Pd(dppf)Cl$_2$ (0.98 g, 1.4 mmol) at r.t. The mixture was degassed for three times under N$_2$ atmosphere, and this mixture was stirred at 100° C. for 12 h. The mixture was filtered, and the filtrate was diluted with EtOAc (100 mL), washed with water (100 mL) and brine (100 mL), dried over anhydrous Na$_2$SO$_4$ and concentrated to dryness. The residue was purified by column chromatography on silica gel (PE:EtOAc=20:1) to give 1-methyl-3-vinyl-1H-pyrazole (4.25 g, 58% yield) as a yellow oil. LC/MS (ESI) (m/z): 109 [M+H]$^+$.

The following intermediates were synthesized using a similar experimental protocol:

1-ethyl-3-vinyl-1H-pyrazole

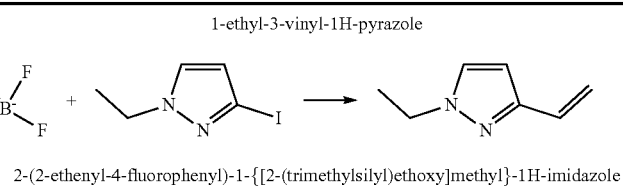

m/z (ESI): 123 [M + H]

2-(2-ethenyl-4-fluorophenyl)-1-{[2-(trimethylsilyl)ethoxy]methyl}-1H-imidazole

-continued

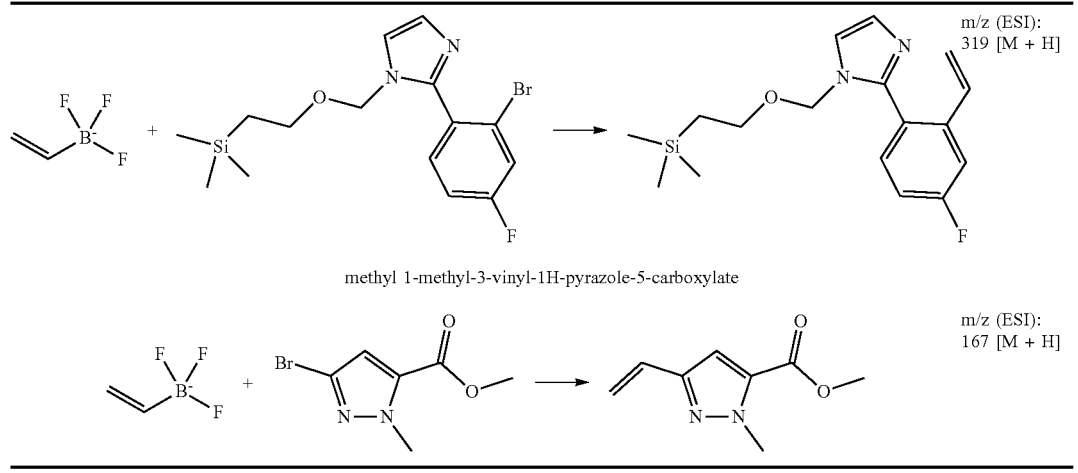

methyl 1-methyl-3-vinyl-1H-pyrazole-5-carboxylate

Synthesis of (4-bromooxazol-5-yl)methanol

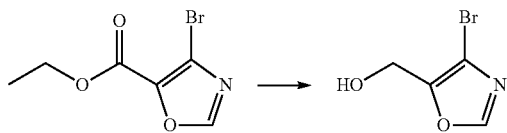

To a solution of ethyl 4-bromooxazole-5-carboxylate (5.0 g, 22.7 mmol) in THF (100 mL) was added diisobutylaluminium hydride (1.5 M in THF, 45.5 mL, 68.2 mmol) dropwise at 0° C. The mixture was stirred at 0° C. for 2 h and then diluted with EA (50 mL). To this mixture was first added water (3 mL), then aq. NaOH solution (15%, 3 mL), followed again by water (27 mL), all at 0° C. After warming to r.t., the mixture was stirred for 15 min, anhydrous MgSO₄ was added and stirring continued for another 15 min, then the mixture was filtered to remove solids. The filtrate was concentrated in vacuo to give crude (4-bromooxazol-5-yl)methanol (2.9 g, 72%) as a yellow solid. LC/MS ESI (m/z): 178 [M+H]⁺.

The following intermediates were synthesized using a similar experimental protocol:

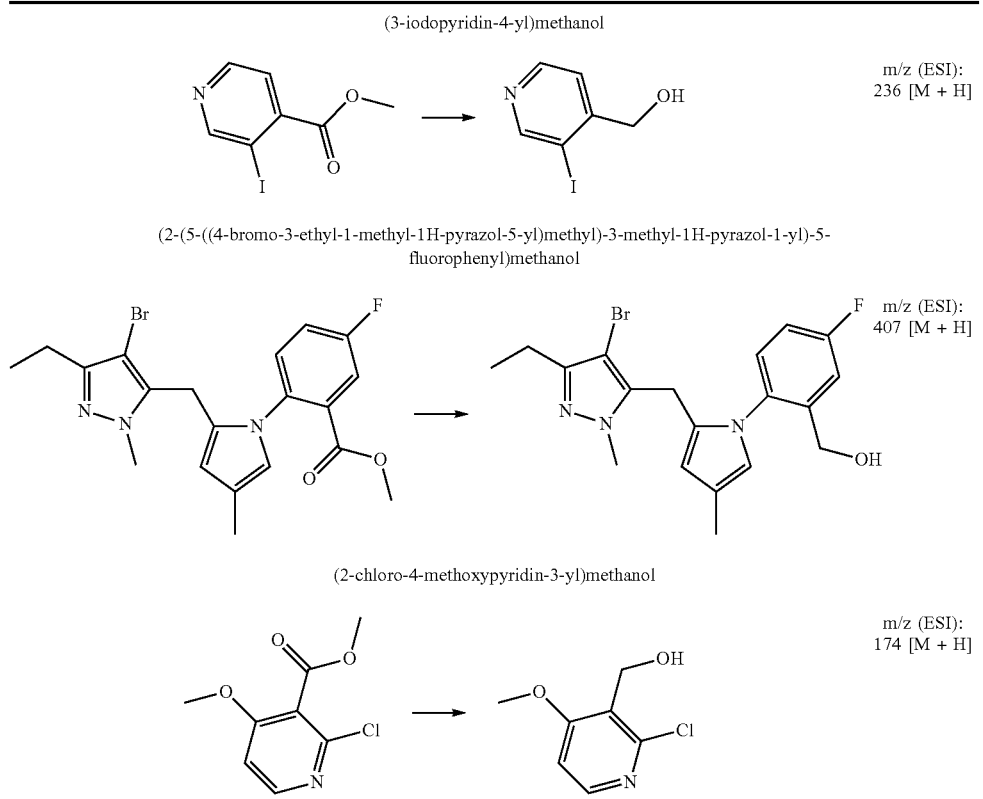

(3-bromo-1-(4-fluoro-2-iodophenyl)-1H-pyrazol-5-yl)methanol

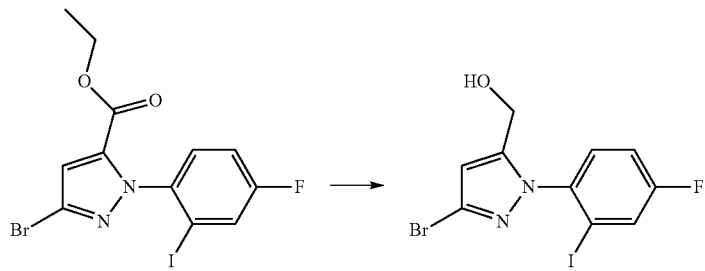 [SMILES: CCOC(=O)c1cc(Br)nn1-c1ccc(F)cc1I ; OCc1cc(Br)nn1-c1ccc(F)cc1I]

m/z (ESI): 397 [M + H]

[3-(4-fluoro-2-iodophenyl)-1,2-thiazol-4-yl]methanol

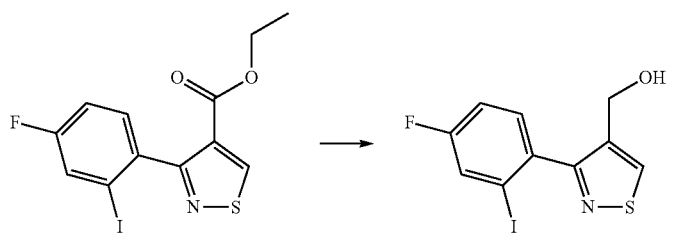 [SMILES: CCOC(=O)c1csnc1-c1ccc(F)cc1I ; OCc1csnc1-c1ccc(F)cc1I]

m/z (ESI): 336 [M + H]

[5-(2-bromo-4-fluorophenyl)-3-methyl-1,2-oxazol-4-yl]methanol

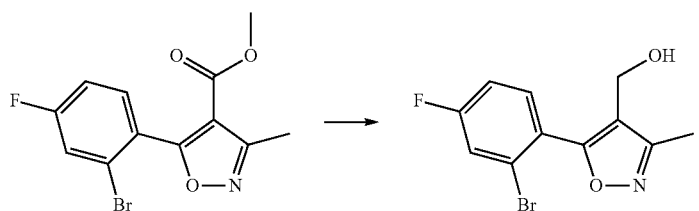 [SMILES: COC(=O)c1c(C)noc1-c1ccc(F)cc1Br ; Cc1noc(-c2ccc(F)cc2Br)c1CO]

m/z (ESI): 286 [M + H]

(5-(cyclopropylmethyl)-1-methyl-1H-pyrazol-3-yl)methanol

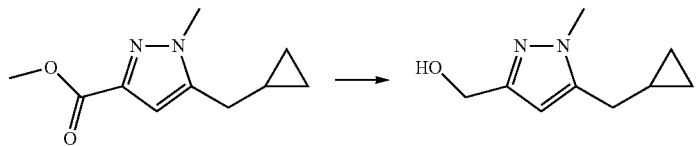

m/z (ESI): 167 [M + H]

Synthesis of 1-ethyl-3-iodo-1H-pyrazole

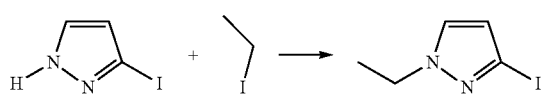

To a solution of 3-iodo-1H-pyrazole (10 g, 51.5 mmol) in DMF (50 mL) was added iodoethane (12.4 mL, 155 mmol) and $K_2CO_3$ (21.4 g, 155 mmol) at 25° C. After stirring at 25° C. for 16 h, the reaction mixture was filtered, and the filtrate was diluted with EtOAc (100 mL). This solution was washed with brine (3×30 mL), dried over anhydrous $Na_2SO_4$ and concentrated. The residue was purified by column chromatography on silica gel (0→20% EA in PE) to give 1-ethyl-3-iodo-H-pyrazole (8.4 g, yield: 73% yield) as a colorless oil. LC/MS (ESI) (m/z): 223 [M+H]$^+$.

3-bromo-1-ethyl-4-iodo-1H-pyrazole m/z (ESI): 301 [M + H]

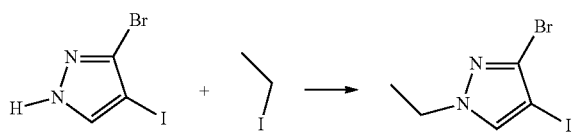

-continued l-ethyl-3-methyl-1H-pyrazole-4-carbaldehyde

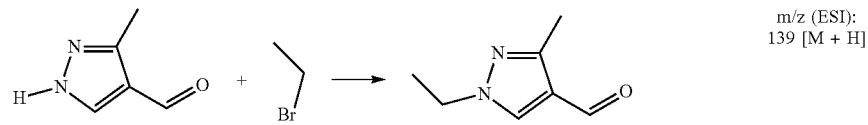

m/z (ESI): 139 [M + H]

l-(cyclopropylmethyl)-3-methyl-lH-pyrazole-4-carbaldehyde

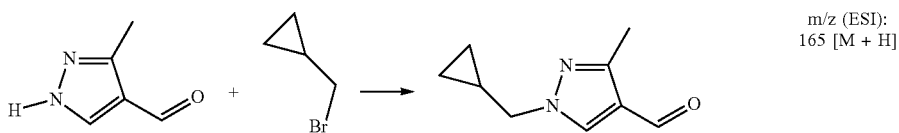

m/z (ESI): 165 [M + H]

1-((3-iodo-1-methyl-1H-pyrazol-4-yl)methyl)-1H-pyrazole-4-carbonitrile

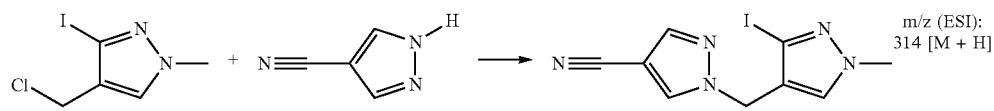

m/z (ESI): 314 [M + H]

1-((2-bromo-5-fluoropyridin-3-yl)methyl)-1H-pyrazole-4-carbaldehyde

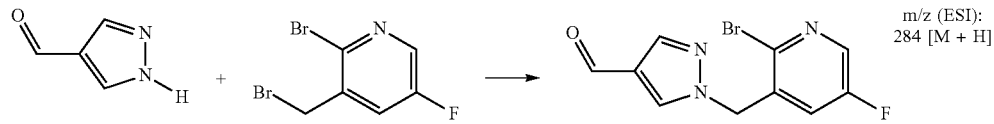

m/z (ESI): 284 [M + H]

3-(benzyloxy)-1-ethyl-1H-pyrazole

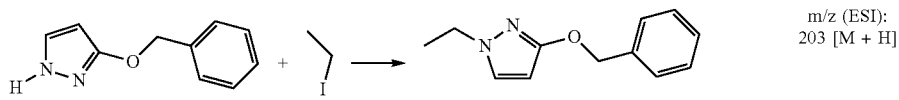

m/z (ESI): 203 [M + H]

l-(2,2-difluoroethyl)-3-methyl-lH-pyrazole-4-carbaldehyde

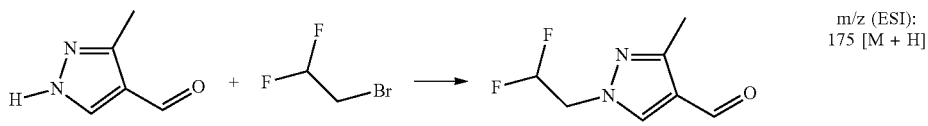

m/z (ESI): 175 [M + H]

4-bromo-1-(cyclopropylmethyl)-1H-pyrazole-3-carbonitrile

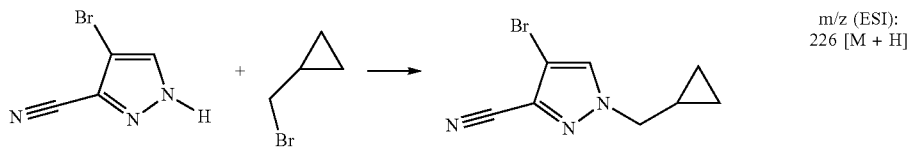

m/z (ESI): 226 [M + H]

l-((2-chloropyridin-3-yl)methyl)-lH-pyrazole-4-carbaldehyde

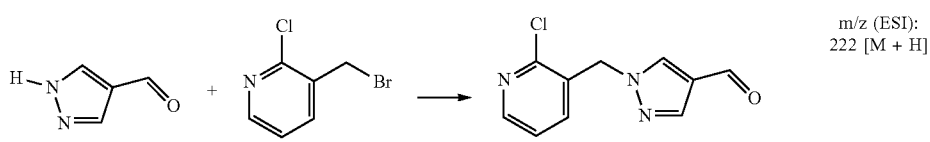

m/z (ESI): 222 [M + H]

4-iodo-1-isobutyl-1H-pyrazole

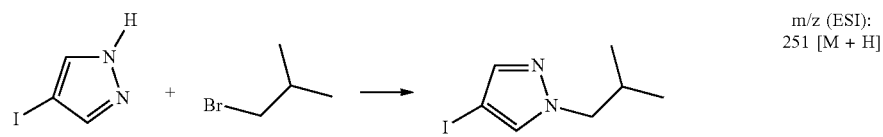

m/z (ESI): 251 [M + H]

1-((1-(4-fluoro-2-iodophenyl)-1H-pyrazol-5-yl)methyl)-1H-pyrazole-4-carbonitrile

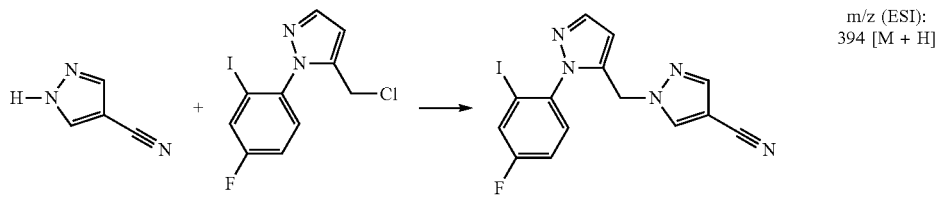

m/z (ESI): 394 [M + H]

1-((2,4-dibromothiazol-5-yl)methyl)-1H-pyrazole-4-carbonitrile

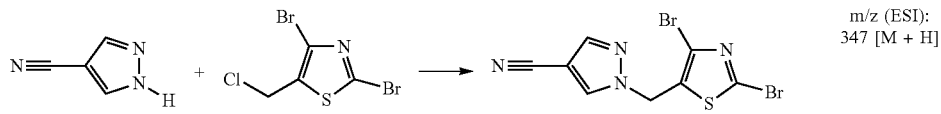

m/z (ESI): 347 [M + H]

1-((4-bromo-2-methylthiazol-5-yl)methyl)-1H-pyrazole-4-carbaldehyde

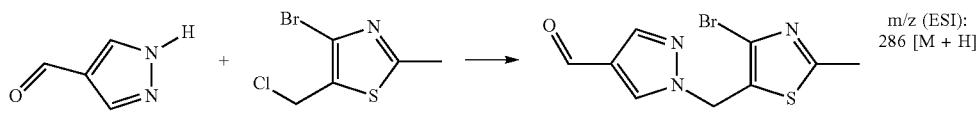

m/z (ESI): 286 [M + H]

1-(cyclopropylmethyl)-4-iodo-3-methyl-1H-pyrazole

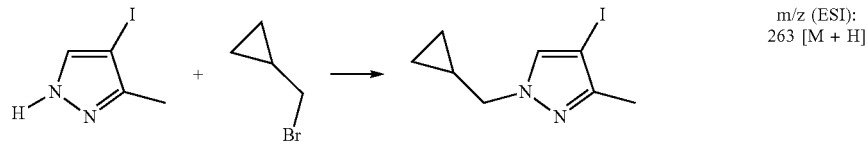

m/z (ESI): 263 [M + H]

1-(cyclopropylmethyl)-3-methyl-1H-pyrazole

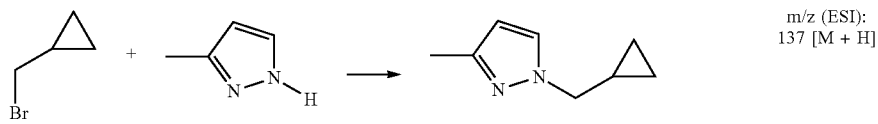

m/z (ESI): 137 [M + H]

Synthesis of 5-chloro-3-iodo-1-methyl-1H-pyrazole

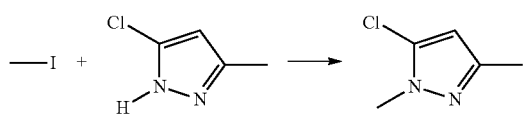

To a mixture of 5-chloro-3-iodo-1H-pyrazole (100 mg, 0.440 mmol) and $K_2CO_3$ (121 mg, 0.880 mmol) in DMF (8 mL) was added methyl iodide (0.03 mL, 0.5 mmol) at 25° C. The mixture was then stirred at r.t. for 30 min. The reaction mixture was quenched with ice water, extracted twice into EA, washed with brine, dried over anhydrous $Na_2SO_4$, filtered and concentrated to give crude 5-chloro-3-iodo-1-methyl-1H-pyrazole (100 mg, 94% yield) as a yellow liquid. The material can be used as—is, or further purified by flash-, high-pressure-, or supercritical fluid-chromatography to separate possible regioisomer. LC/MS (ESI) m/z: 243 [M+H]$^+$.

The following intermediates were synthesized using a similar experimental protocol:

ethyl 5-bromo-1-(2,2-difluoroethyl)-1H-pyrazole-4-carboxylate

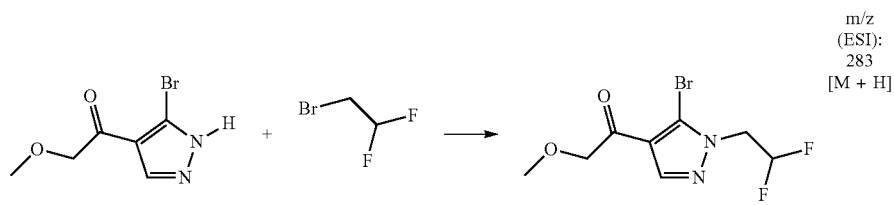

m/z (ESI): 283 [M + H]

3-((3-iodo-1-methyl-1H-pyrazol-4-yl)methyl)-1-methyl-1H-pyrazole-5-carbonitrile

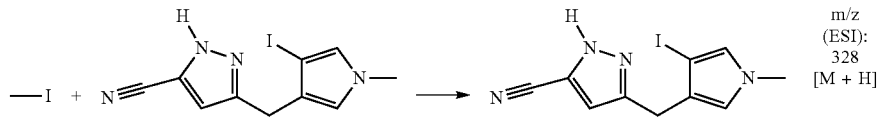

m/z (ESI): 328 [M + H]

(R)-3-((1-(2-(1-((5-bromo-2-nitropyridin-3-yl)oxy)ethyl)-4-fluorophenyl)-1H-pyrazol-5-yl)methyl)-1-ethyl-1H-pyrazole-5-carbonitrile

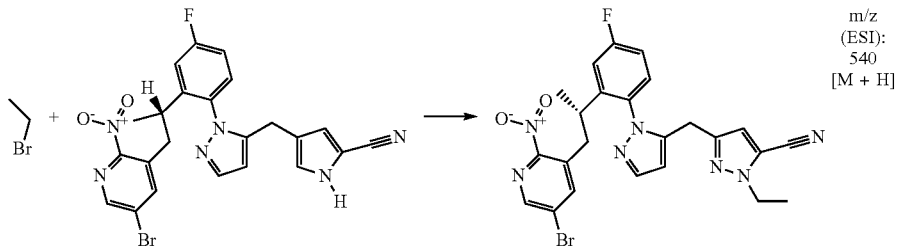

m/z (ESI): 540 [M + H]

3-(1-(2-(1,3-dioxolan-2-yl)-4-fluorophenyl)-1H-pyrazole-5-carbonyl)-1-methyl-1H-pyrazole-5-carbonitrile

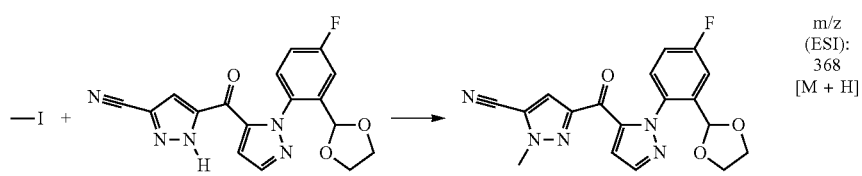

m/z (ESI): 368 [M + H]

Synthesis of 5-bromo-4-iodo-1-methyl-1H-pyrazole

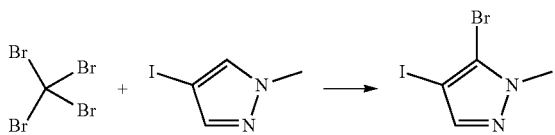

To a solution of 4-iodo-1-methyl-1H-pyrazole (10.00 g, 48.08 mmol) in dry THF (100 mL) at −70° C. was added LDA (2.0 M in THF, 28.8 mL, 57.7 mmol) dropwise under N₂ atmosphere over 20 min. After the addition, the mixture was stirred at −70° C. for 30 min, then a solution of CBr₄ (19.0 g, 57.7 mmol) in THF (40 mL) was added dropwise. The resulting mixture was stirred at −70° C. for 1 h. The mixture was quenched with sat. NH₄Cl solution, and then diluted with EA (200 mL). The organic layer was separated, washed with brine, dried over anhydrous Na₂SO₄, filtered and concentrated. The residue was purified by column chromatography on silica gel (2% EA in PE) to give the target product as a brown oil (11 g, yield: 80%). LC/MS ESI (m/z): 287 [M+H]⁺.

The following intermediates were synthesized using a similar experimental protocol:

5-bromo-1-cyclobutyl-4-iodo-1H-pyrazole

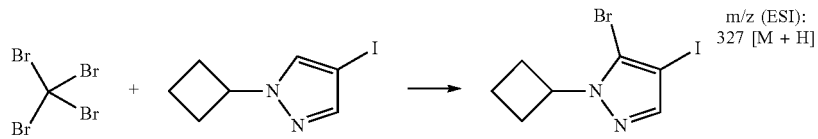

m/z (ESI): 327 [M + H]

5-bromo-1-ethyl-4-iodo-1H-pyrazole

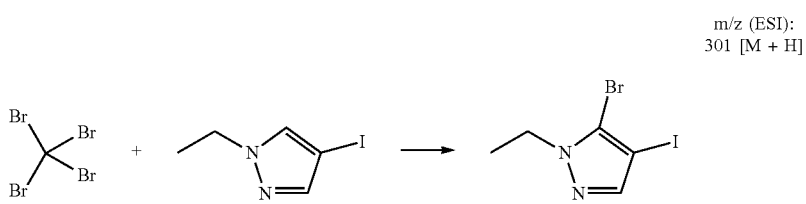

m/z (ESI): 301 [M + H]

| 5-bromo-1-(cyclopropylmethyl)-3-methyl-1H-pyrazole |
|---|
| 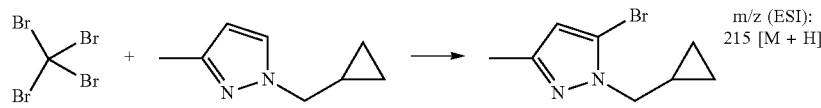 m/z (ESI): 215 [M + H] |

Synthesis of 3-bromo-4-iodo-1-methyl-1H-pyrazole

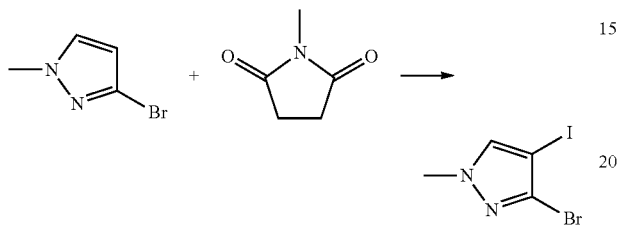

To a solution of 3-bromo-1-methyl-1H-pyrazole (10.0 g, 62.1 mmol) in DMF (32 mL) was added NIS (16.8 g, 74.5 mmol). After the addition, the resulting solution was stirred at 50° C. for 5 h. The mixture was diluted with water and extracted into EA., The combined organic phase was washed with brine (30 mL×4), dried over anhydrous $Na_2SO_4$, and concentrated in vacuum. The residue was purified by flash chromatography (0→10% EA in PE) to give 3-bromo-4-iodo-1-methyl-1H-pyrazole (15.0 g, 76% yield) as a yellow solid. LC/MS (ESI) m/z: 287 [M+H]$^+$.

| 1-ethyl-4-iodo-1H-pyrazole-3-carbonitrile |
|---|
| 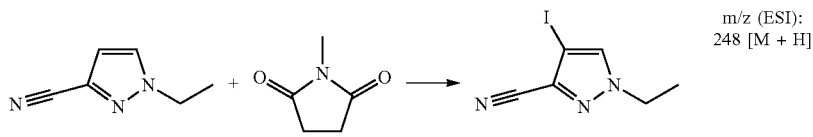 m/z (ESI): 248 [M + H] |
| 5-bromo-1-(cyclopropylmethyl)-4-iodo-3-methyl-1H-pyrazole |
| 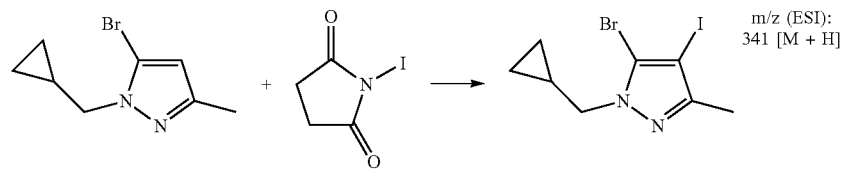 m/z (ESI): 341 [M + H] |

Synthesis of 3-ethylisoxazole-5-carbaldehyde

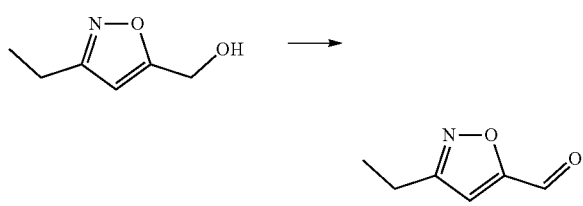

To a solution of (3-ethylisoxazol-5-yl)methanol (4.00 g, 31.5 mmol) in DCM (100 mL) was added DMP (16.01 g, 37.75 mmol) at 0° C. and the mixture was stirred at r.t. for 1 h (additional equivalents of oxidizing agent may be added to ensure complete oxidation of substrates containing multiple alcohol groups). The mixture was washed with sat. $Na_2S_2O_3$ (100 mL) and sat. $NaHCO_3$ (100 mL), dried over anhydrous $Na_2SO_4$ and concentrated to dryness. The residue was purified by flash chromatography on silica gel (20% EtOAc in PE) to give 3-ethylisoxazole-5-carbaldehyde (3.37 g, yield: 86%) as a yellow oil. LC/MS (ESI): m/z=126 [M+H]$^+$.

The following intermediates were synthesized using a similar experimental protocol:

1-((2-(trimethylsilyl)ethoxy)methyl)-1H-pyrazole-3,5-dicarbaldehyde

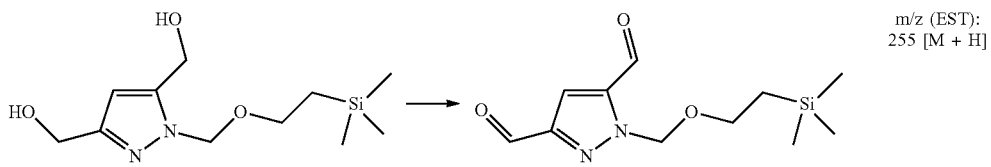

m/z (ESI): 255 [M + H]

2-chloro-5-fluoropyridine-3-carbaldehyde

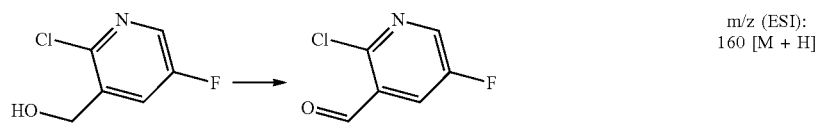

m/z (ESI): 160 [M + H]

2-(5-((tetrahydro-2H-pyran-2-yloxy)methyl)isoxazol-3-yl)acetaldehyde

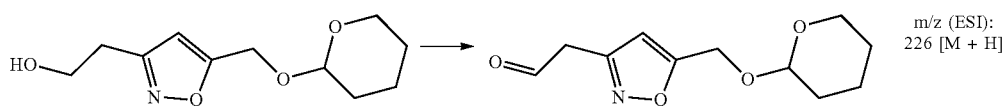

m/z (ESI): 226 [M + H]

3-bromo-1-(4-fluoro-2-iodophenyl)-1H-pyrazole-5-carbaldehyde


m/z (ESI): 395 [M + H]

5-(2-bromo-4-fluorophenyl)-3-methylisoxazole-4-carbaldehyde

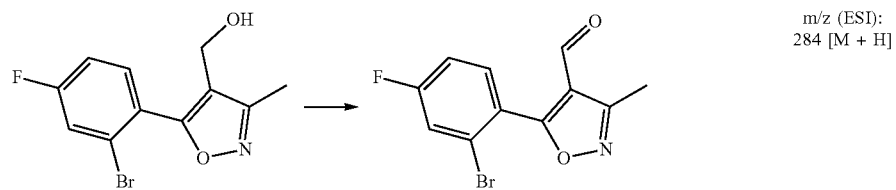

m/z (ESI): 284 [M + H]

methyl 1-methyl-3-(2-oxoethyl)-1H-pyrazole-5-carboxylate

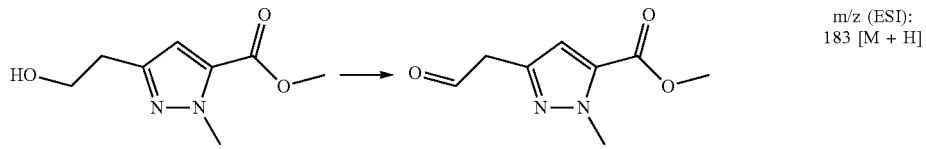

m/z (ESI): 183 [M + H]

methyl 3-formyl-1-methyl-1H-pyrazole-5-carboxylate

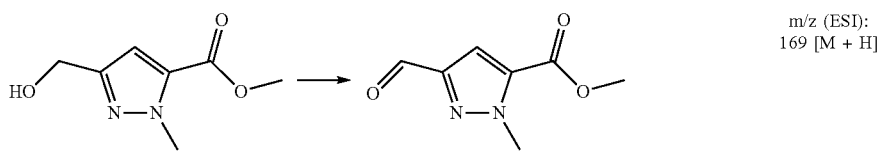

m/z (ESI): 169 [M + H]

3-(cyclopropylmethyl)-1-methyl-1H-pyrazole-5-carbaldehyde

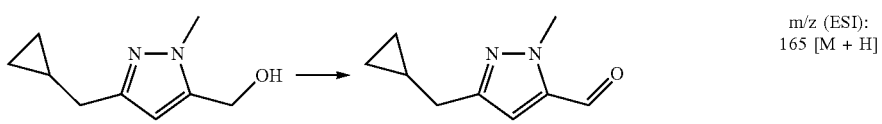

m/z (ESI): 165 [M + H]

| 5-(cyclopropylmethyl)-1-methyl-1H-pyrazole-3-carbaldehyde | |
|---|---|
| 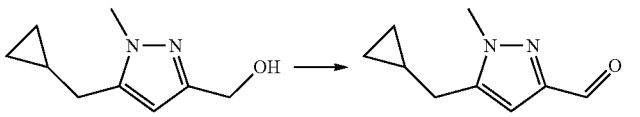 | m/z (ESI): 165 [M + H] |

Synthesis of 4-(chloromethyl)-1-ethyl-1H-pyrazole

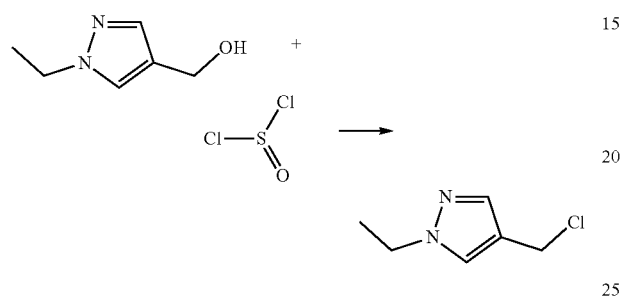

To a solution of (1-ethyl-1H-pyrazol-4-yl)methanol (1.40 g, 11.1 mmol) in DCM (15 mL) at 0° C. was added SOCl$_2$ (3.96 g, 33.3 mmol) dropwise under an N$_2$ atmosphere. After the addition, the mixture was stirred at 0° C. for 2 h. The mixture was concentrated to dryness to give crude 4-(chloromethyl)-1-ethyl-1H-pyrazole (1.60 g, 100% yield) as a yellow oil. LC/MS (ESI) m/z: 145 [M+H]$^+$.

The following intermediates were synthesized using a similar experimental protocol:

| 5-bromo-4-(chloromethyl)-1-ethyl-1H-pyrazole | |
|---|---|
| 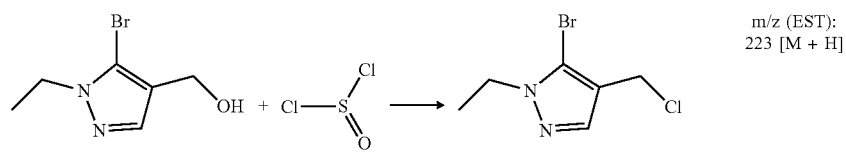 | m/z (EST): 223 [M + H] |

| 5-bromo-4-(chloromethyl)-1-(difluoromethyl)-1H-pyrazole | |
|---|---|
| 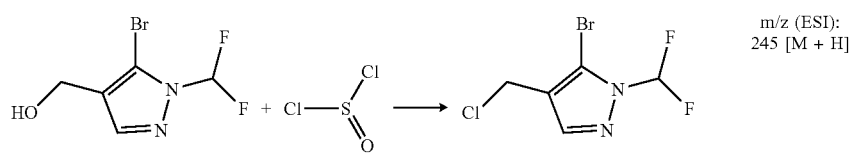 | m/z (ESI): 245 [M + H] |

| 5-(chloromethyl)-1-(4-fluoro-2-iodophenyl)-IH-pyrazole | |
|---|---|
| 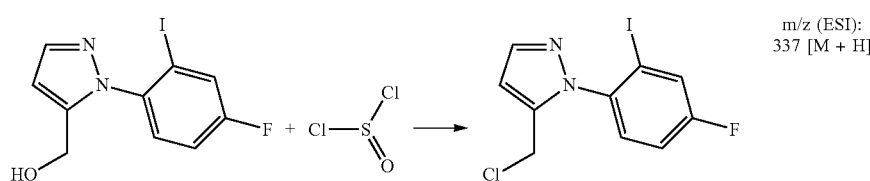 | m/z (ESI): 337 [M + H] |

Synthesis of 5-(chloromethyl)-3-ethylisoxazole

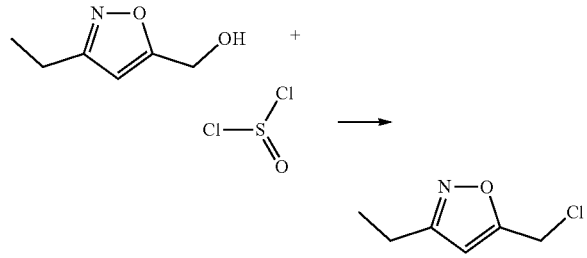

To a stirred solution of (3-ethyl-1,2-oxazol-5-yl)methanol (4.10 g, 32.3 mmol) in dry DCM (10 mL) was added triethylamine (5.8 mL, 42 mmol), followed by the addition of thionyl chloride (2.8 mL, 39 mmol) at 0° C. over a period of 10 min. After the addition, the reaction mixture was stirred at r.t. for 5.0 h under $N_2$. The reaction mixture was cooled to 0° C. and quenched with 10% aq. NaCl.

The mixture was then extracted with DCM twice, and the combined extracts were washed with sat. aq. $NaHCO_3$, dried over anhydrous $Na_2SO_4$ and concentrated in vacuo. The residue was purified by column chromatography on silica gel (10→30% EA in PE) to give 5-(chloromethyl)-3-ethyl-1,2-oxazole (4.20 g, yield: 90%) as a yellow oil. LC/MS ESI (m/z): 146 [M+H]$^+$.

Synthesis of 3-bromo-1-methylpyrazole-4-carbaldehyde

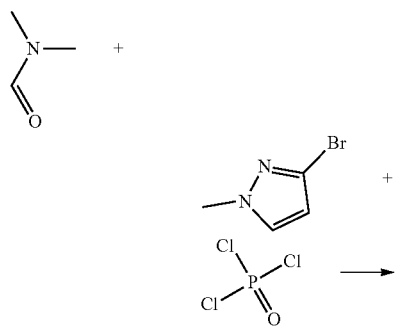

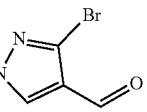

To a flask of DMF (12.00 mL) was added $POCl_3$ (12.00 mL) dropwise at 0° C. The resulting mixture was stirred for 30 min at rt. To the above mixture was added 3-bromo-1-methylpyrazole (4.00 g, 24.8 mmol) dropwise at r.t. The resulting mixture was then stirred for 3 h at 95° C. The reaction was quenched with $H_2O$ at rt. The resulting mixture was concentrated under reduced pressure. The residue was purified by reverse-phase flash chromatography (C18, 0→30% MeCN in water+0.1% FA) to afford 3-bromo-1-methylpyrazole-4-carbaldehyde (3.94 g, 84%) as a light brown solid.
LC/MS ESI (m/z): 189 [M+H]$^+$.

Synthesis of 4-bromo-2-methylthiazole-5-carbaldehyde

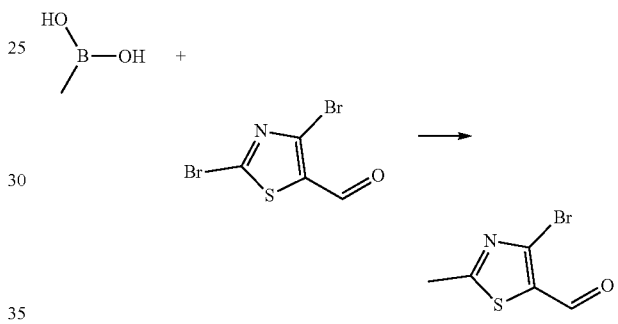

To a mixture of 2,4-dibromo-1,3-thiazole-5-carbaldehyde (2.00 g, 7.38 mmol) and methylboronic acid (486 mg, 8.12 mmol) in 1,4-dioxane (20 mL) was added $K_2CO_3$ (2.00 g, 14.8 mmol) and Pd(PPh$_3$)$_4$ (853 mg, 0.740 mmol) at r.t. The mixture was thrice degassed under $N_2$ and then stirred at 110° C. under an $N_2$ atmosphere for 12 h. The reaction was cooled to r.t., filtered, and concentrated to dryness. The residue was purified on flash chromatography (silica gel, 25% EtOAc in PE) to give 4-bromo-2-methyl-1,3-thiazole-5-carbaldehyde (728 mg, 31% yield) as a yellow solid. LC/MS (ESI) (m/z): 206 [M+H]$^+$.

The following intermediates were synthesized using a similar experimental protocol:

---

5-[(4-bromo-2-methyl-1,3-thiazol-5-yl)methyl]-1-methyl-1H-pyrazole-3-carbonitrile m/z (ESI): 297 [M + H]

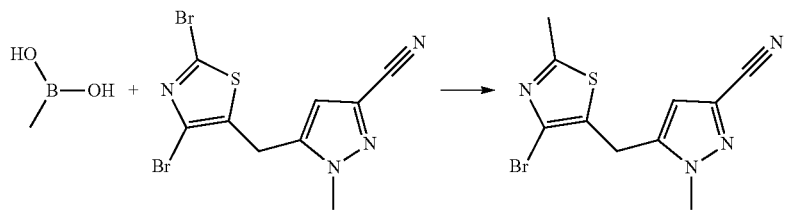

-continued 4-bromo-5-((3-ethyl-1-methyl-1H-pyrazol-5-yl)methyl)-2-methylthiazole

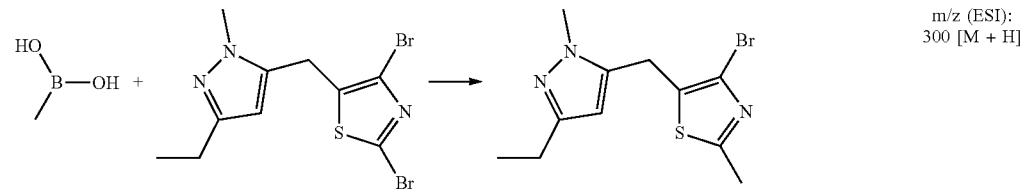

m/z (ESI): 300 [M + H]

4-[4-bromo-2-methyl-1,3-thiazol-5-yl)methyl]-1-ethyl-1H-1,2,3-triazole

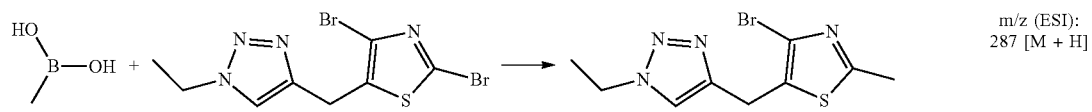

m/z (ESI): 287 [M + H]

4-[(4-bromo-2-methyl-1,3-thiazol-5-yl)methyl]-1-(cyclopropylmethyl)-1H-1,2,3-triazole

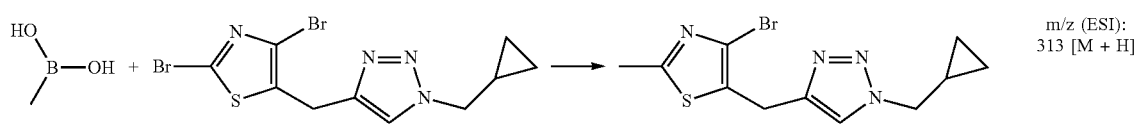

m/z (ESI): 313 [M + H]

4-bromo-5-((1-(cyclopropylmethyl)-3-methyl-1H-pyrazol-4-yl)methyl)-2-methylthiazole

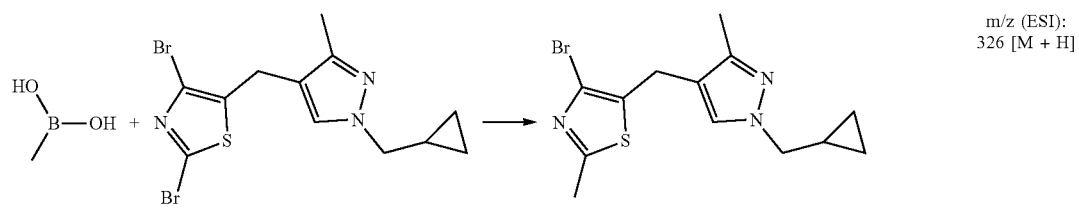

m/z (ESI): 326 [M + H]

1-[(4-bromo-2-methyl-1,3-thiazol-5-yl)methyl]-1H-imidazole-4-carbonitrile

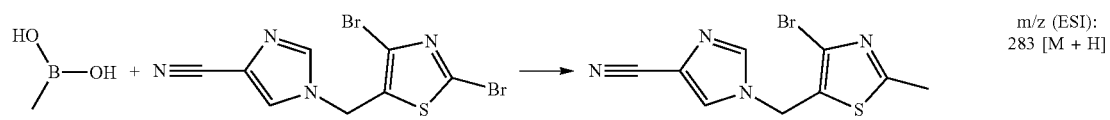

m/z (ESI): 283 [M + H]

1-((4-bromo-2-methylthiazol-5-yl)methyl)-1H-pyrazole-4-carbonitrile

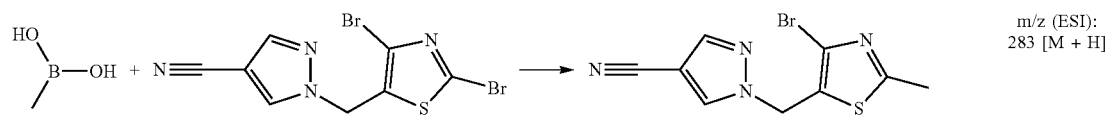

m/z (ESI): 283 [M + H]

4-bromo-5-{[1-(difluoromethyl)-1H-pyrazol-4-yl]methyl}-2-methyl-1,3-thiazole

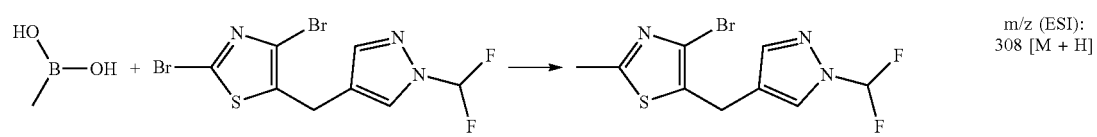

m/z (ESI): 308 [M + H]

4-bromo-5-[(1-ethyl-1H-pyrazol-4-yl)methyl]-2-methyl-1,3-thiazole

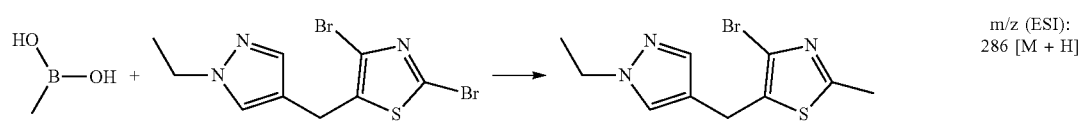

m/z (ESI): 286 [M + H]

Synthesis of 5-bromoisothiazole-4-carboxylic acid

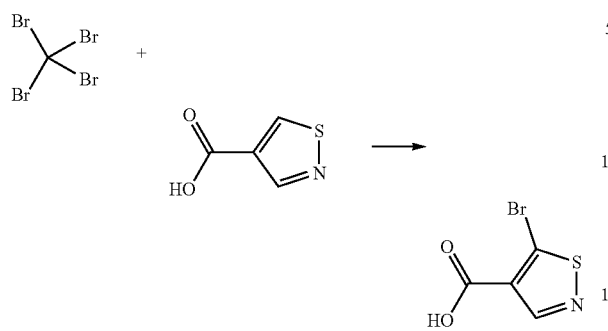

To a solution of isothiazole-4-carboxylic acid (800 mg, 6.20 mmol) in THF (15 mL) was added t-BuLi (1.3 M in heptane, 10.9 mL, 14.3 mmol) at −78° C. Then a solution of $CBr_4$ (4.10 g, 12.4 mmol) in THF (10 mL) was added dropwise. The mixture was stirred at −78° C. for 2 h. This reaction solution was quenched with addition of sat. aq. $NH_4Cl$ and extracted with EtOAc. The aq. layer was adjusted to pH 1 by addition of aq. HCl (1M) and then extracted with EtOAc. This second organic layer was dried over anhydrous $MgSO_4$, filtered, and concentrated in vacuo to give crude 5-bromoisothiazole-4-carboxylic acid (750 mg) as a pale-yellow oil. LC/MS ESI (m/z): 208 $[M+H]^+$.

Synthesis of 5-iodo-1-methyl-3-vinyl-1H-pyrazole

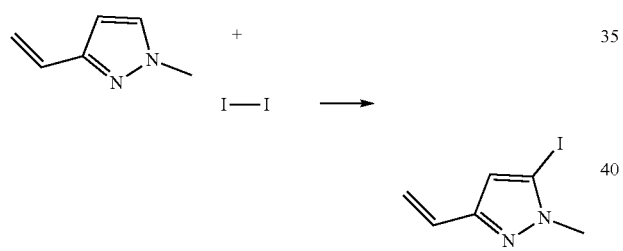

To a stirred solution of 1-methyl-3-vinyl-1H-pyrazole (4.25 g, 39.30 mmol) in THF (40 mL) was added n-BuLi (24 mL, 58.95 mmol, 2.5 M in THF) dropwise via syringe at −78° C. under $N_2$. After stirring at −78° C. for 1 h, a solution of iodine (14.97 g, 58.95 mmol) in THF (25 mL) was added and the reaction was stirred at −78° C. under $N_2$ for another 2 h. The reaction was allowed to warm to 0° C., quenched with sat. aq. $NH_4Cl$ (25 mL) and extracted with EtOAc (25 mL×2). The combined organic phases were washed with $Na_2S_2O_3$ (20 mL), dried over anhydrous $Na_2SO_4$ and concentrated to dryness. The residue was purified by column chromatography on silica gel (5% EtOAc in PE) to give 5-iodo-1-methyl-3-vinyl-1H-pyrazole (2.70 g, 29% yield) as a yellow oil.

LC/MS (ESI) (m/z): 235.0 $[M+H]^+$.

Synthesis of (5-iodo-1-methyl-1H-pyrazol-4-yl)methanol

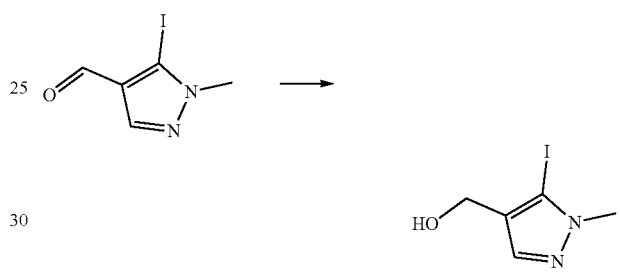

To a mixture of 5-iodo-1-methyl-1H-pyrazole-4-carbaldehyde (2.00 g, 8.47 mmol) in MeOH (30 mL) was added $NaBH_4$ (84 mg, 2.5 mmol) at −10° C. The mixture was stirred at 20° C. for 1 h. The mixture was quenched with sat. $NH_4Cl$ (10 mL) and extracted with EA (60 mL×3). The combined organic layers were dried over anhydrous $Na_2SO_4$, filtered and concentrated. The residue was purified by column chromatography on silica gel (5% MeOH in DCM) to afford (5-iodo-1-methyl-1H-pyrazol-4-yl)methanol as a light-yellow solid (840 mg, yield: 41%). LC/MS ESI (m/z): 239 $[M+H]^+$.

| (1-(cyclopropylmethyl)-1H-pyrazol-4-yl)methanol | |
|---|---|
| 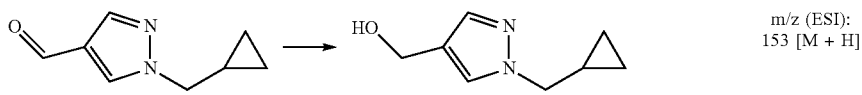 | m/z (ESI): 153 [M + H] |

| [1-(cyclopropylmethyl)-3-methyl-1H-pyrazol-4-yl]methanol | |
|---|---|
| 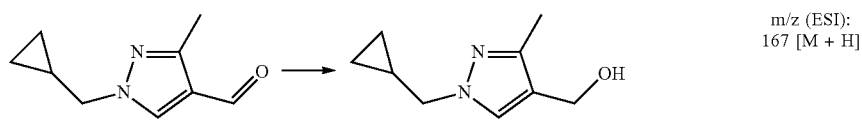 | m/z (ESI): 167 [M + H] |

| (3-bromo-1-methylpyrazol-4-yl)methanol | |
|---|---|
| 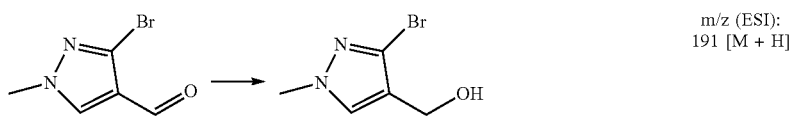 | m/z (ESI): 191 [M + H] |

-continued (5-bromo-1-ethyl-1H-pyrazol-4-yl)(1-(4-fluoro-2-(hydroxymethyl)phenyl)-1H-pyrazol-5-yl)methanol

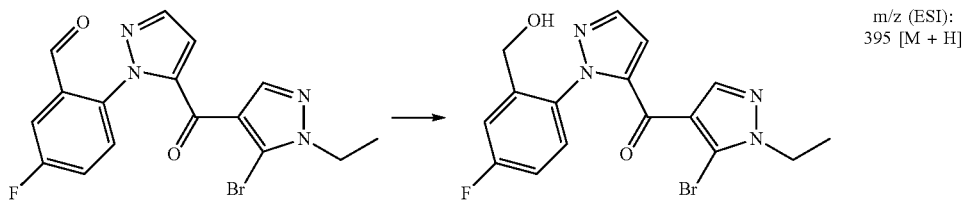

m/z (ESI): 395 [M + H]

(5-bromo-1-ethyl-1H-pyrazol-4-yl)(4-fluoro-1-(4-fluoro-2-(hydroxymethyl)phenyl)-1H-pyrazol-5-yl)methanol

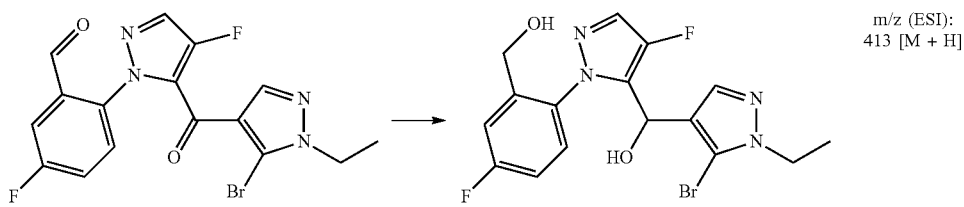

m/z (ESI): 413 [M + H]

[1-(4-fluoro-2-iodophenyl)-3-methyl-1H-pyrazol-5-yl]methanol

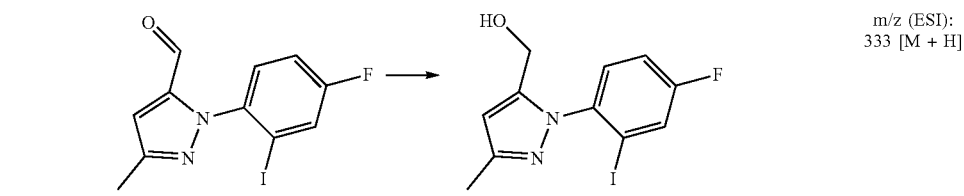

m/z (ESI): 333 [M + H]

(1-ethyl-1H-pyrazol-4-yl)(1-(4-fluoro-2-(hydroxymethyl)phenyl)-3-methyl-1H-pyrazol-5-yl)methanol

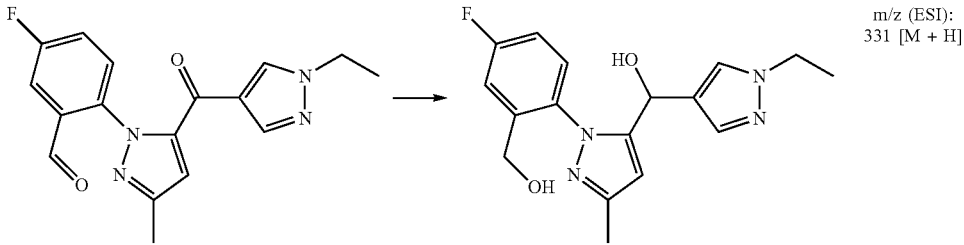

m/z (ESI): 331 [M + H]

(4-bromo-2-methylthiazol-5-yl)methanol

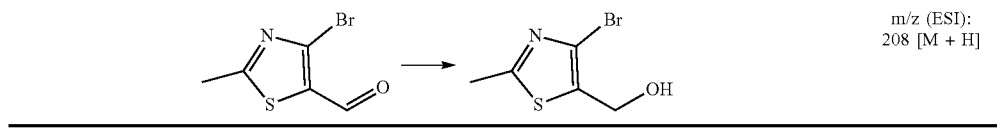

m/z (ESI): 208 [M + H]

Synthesis of (3-iodo-1-methyl-1H-pyrazol-4-yl)methanol

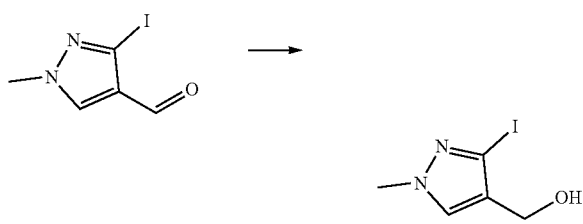

To a solution of 3-iodo-1-methyl-1H-pyrazole-4-carbaldehyde (2.00 g, 8.47 mmol) in dry THF (20 mL) was added DIBAL-H (1.0 M in toluene, 12 mL, 12 mmol) dropwise at −70° C. (additional equivalents of reducing agent may be utilized in cases where more than one hydride transfer is required). The mixture was stirred at −70° C. for 2 h before quenching with sat. aq. NH$_4$Cl. The resulting mixture was filtered, and the filter cake was washed with THF. The combined filtrates were concentrated under reduced pressure; the residue was diluted with DCM, washed with water and brine, dried over anhydrous Na$_2$SO$_4$ and concentrated. The residue was purified by column chromatography on silica gel (0→20% of EA in PE) to give (3-iodo-1-methyl-1H-pyrazol-4-yl)methanol (1.6 g, 79% yield) as a yellow oil. LC/MS ESI (m/z): 239 [M+H]$^+$.

The following intermediates were synthesized using a similar experimental protocol:

1-(4-fluoro-2-iodophenyl)-3-methyl-1H-pyrazole-5-carbaldehyde

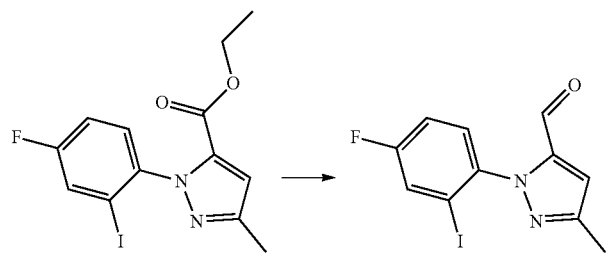 [SMILES: CCOC(=O)c1cc(C)nn1-c1ccc(F)cc1I ; Cc1cc(C=O)n(-c2ccc(F)cc2I)n1]

m/z (ESI): 331 [M + H]

5-bromoisothiazole-4-carbaldehyde

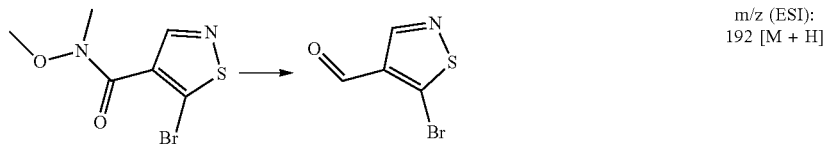

m/z (ESI): 192 [M + H]

[3-(2-bromo-4-fluorophenyl)-1,2-oxazol-4-yl]methanol

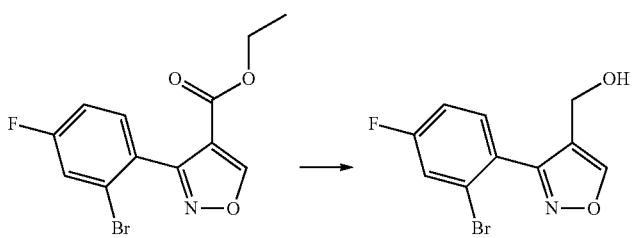 [SMILES: CCOC(=O)c1conc1-c1ccc(F)cc1Br ; OCc1conc1-c1ccc(F)cc1Br]

m/z (ESI): 272 [M + H]

(2-(5-((1-(cyclopropylmethyl)-1H-pyrazol-4-yl)methyl)-3-methyl-1H-pyrazol-1-yl)-5-fluorophenyl)methanol

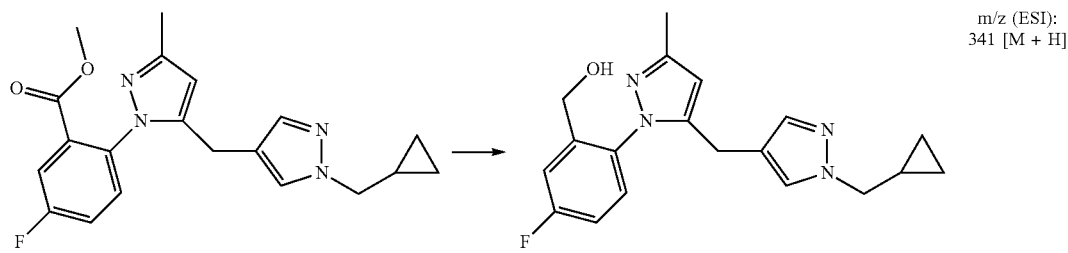

m/z (ESI): 341 [M + H]

Synthesis 3choro-1-ethyl-4-iodo-1H-pyrazole IC33C

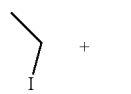

To a stirred mixture of 3-chloro-4-iodo-1H-pyrazole (55.34 g, 242.2 mmol) and Cs$_2$CO$_3$ (118.7 g, 364.1 mmol) in DMF (150 mL) was added EtI (29.3 mL, 370 mmol) dropwise at −10° C. After stirring at −10° C. for 3 h, the reaction was concentrated. The residue was diluted with EtOAc, washed with brine (150 mL×2), dried over Na$_2$SO$_4$ and concentrated to dryness. The residue was purified by column chromatography on silica gel (0→20% EA in PE) to give 3-chloro-1-ethyl-4-iodo-1H-pyrazole (37.5 g, 60%) as a yellow oil. LC/MS (ESI) m/z: 257 [M+H]$^+$.

Synthesis of 4-(chloromethyl)-3-iodo-1-methyl-1H-pyrazole

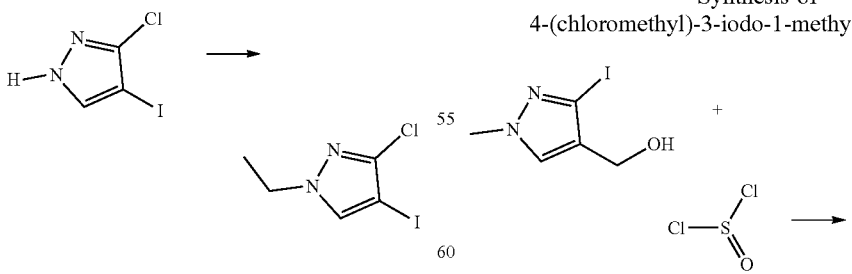

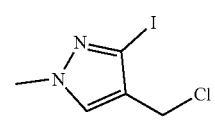

To a solution of (3-iodo-1-methyl-1H-pyrazol-4-yl)methanol (1.00 g, 4.20 mmol) in DCM (20 mL) was added thionyl chloride (0.90 mL, 13 mmol) at 0° C. After addition, the mixture was stirred at r.t. for 3 h, and then concentrated to give crude 4-(chloromethyl)-3-iodo-1-methyl-1H-pyrazole (1.0 g, 93%) as a yellow oil. LCMS (ESI): m/z=257 [M+H]⁺.

The following intermediates were synthesized using a similar experimental protocol:

4-(chloromethyl)-1-(cyclopropylmethyl)-1H-pyrazole

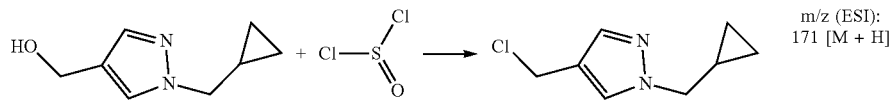

m/z (ESI): 171 [M + H]

4-(chloromethyl)-1-(cyclopropylmethyl)-3-methyl-1H-pyrazole

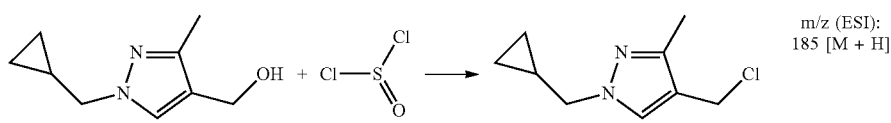

m/z (ESI): 185 [M + H]

5-bromo-4-(chloromethyl)-1-(cyclopropylmethyl)-3-methyl-1H-pyrazole

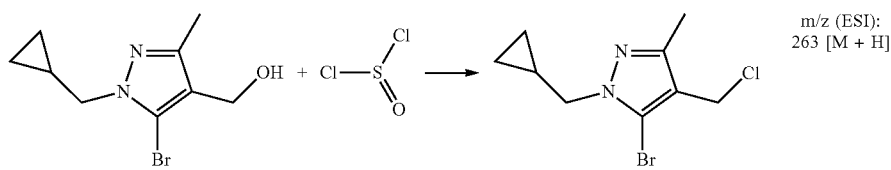

m/z (ESI): 263 [M + H]

3-bromo-4-(chloromethyl)-1-methylpyrazole

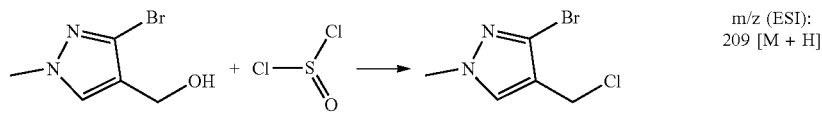

m/z (ESI): 209 [M + H]

2,4-dibromo-5-(chloromethyl)thiazole

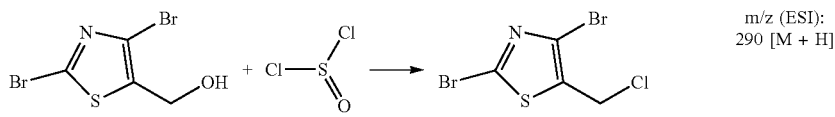

m/z (ESI): 290 [M + H]

4-bromo-5-(chloromethyl)-2-methylthiazole

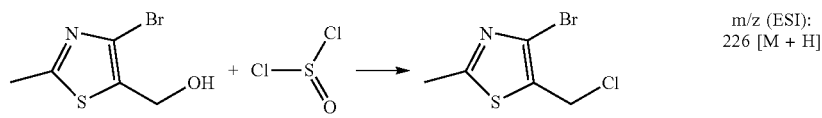

m/z (ESI): 226 [M + H]

Synthesis of 1-ethyl-3-(propan-2-yl)-1H-pyrazole

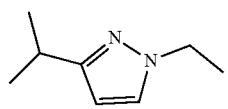

To a solution of 1-ethyl-3-iodo-1H-pyrazole (3.20 g, 14.4 mmol) in H₂O (0.5 mL) and 1,4-dioxane (2.5 mL) in a sealed tube were added K₂CO₃ (7.97 g, 57.6 mmol), Pd(dppf)Cl₂ (1.05 g, 1.44 mmol). The mixture was stirred at 100° C. for 16 h, then poured into water (80 mL) and extracted with EA (80 mL). The organic layer was washed with brine (60 mL), dried over anhydrous Na₂SO₄ and concentrated in vacuo. The residue was purified by column chromatography on silica gel (PE/EA=10/1 to 1/1) to give 1-ethyl-3-(prop-1-en-2-yl)-1H-pyrazole (1.2 g, yield: 61% yield) as a white solid. LC/MS (ESI): m/z=137.1 [M+H]⁺.

To a solution of 1-ethyl-3-(prop-1-en-2-yl)-1H-pyrazole (1.0 g, 7.3 mmol) in EtOAc (15 mL) was added PtO₂ (0.17 g, 0.73 mmol) and then this mixture was stirred at r.t. for 16 h under H₂ (15 psi).

The reaction mixture was filtered, and the filtrate was concentrated to afford crude 1-ethyl-3-(propan-2-yl)-1H-pyrazole (800 mg, yield: 79%) as a white solid. LC/MS (ESI): m/z=139.1[M+H]⁺.

Synthesis of 1-(difluoromethyl)-1H-pyrazole-4-carbaldehyde

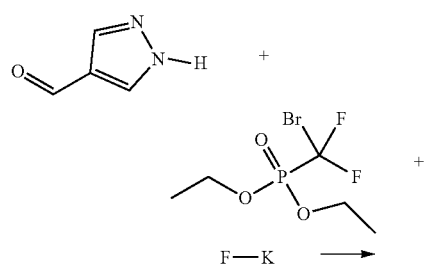

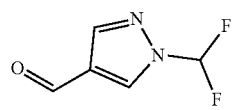

A mixture of 1H-pyrazole-4-carbaldehyde (2.00 g, 20.8 mmol), diethyl (bromodifluoromethyl)phosphonate (9.45 g, 35.3 mmol) and KF (3.63 g, 62.4 mmol) in MeCN (20 mL) was stirred at r.t. overnight. The mixture was filtered and concentrated in vacuo to give a residue, which was purified by column chromatography on silica gel (10% EtOAc in PE) to give 1-(difluoromethyl)-1H-pyrazole-4-carbaldehyde (2.1 g, 69%) as a light-yellow oil. LC/MS (ESI) m/z: 147 [M+H]$^+$.

The following intermediates were synthesized using a similar experimental protocol:

ethyl 5-bromo-1-(difluoromethyl)-1H-pyrazole-4-carboxylate

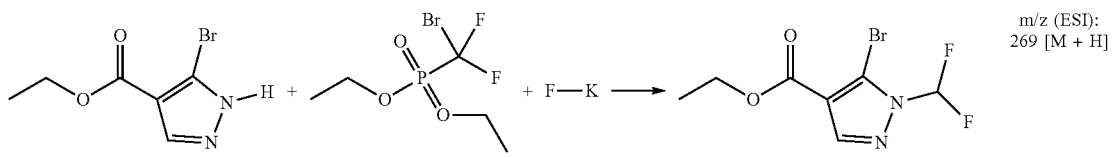

m/z (ESI): 269 [M + H]

Synthesis of 3-chloro-1-(cyclopropylmethyl)-1H-pyrazole

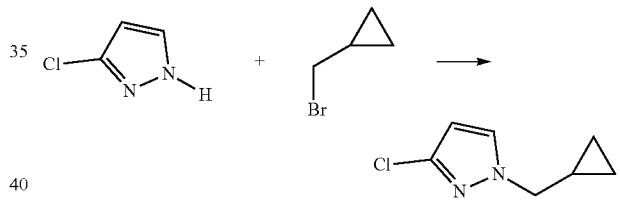

To a solution of 3-chloro-1H-pyrazole (2.00 g, 19.5 mmol) in MeCN (50 mL) was added K$_2$CO$_3$ (5.40 g, 39.0 mmol) and (bromomethyl)cyclopropane (2.90 g, 21.5 mmol). The reaction mixture was stirred at 80° C. for 12 h. The reaction mixture was cooled and filtered, and the filtrate was concentrated under reduced pressure. The residue was purified by flash column chromatography (0→30% EtOAc in PE) to give 3-chloro-1-(cyclopropylmethyl)-1H-pyrazole (2.3 g, 75%) as a colorless oil. LC/MS (ESI) (m/z): 157 [M+H]$^+$.

The following intermediates were synthesized using a similar experimental protocol:

3-chloro-1-(2,2-difluoroethyl)-1H-pyrazole m/z (ESI): 167 [M + H]

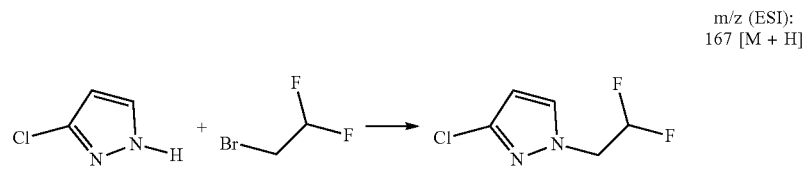

| 1-ethyl-4-iodo-3-(trifluoromethyl)-1H-pyrazole | |
|---|---|
| 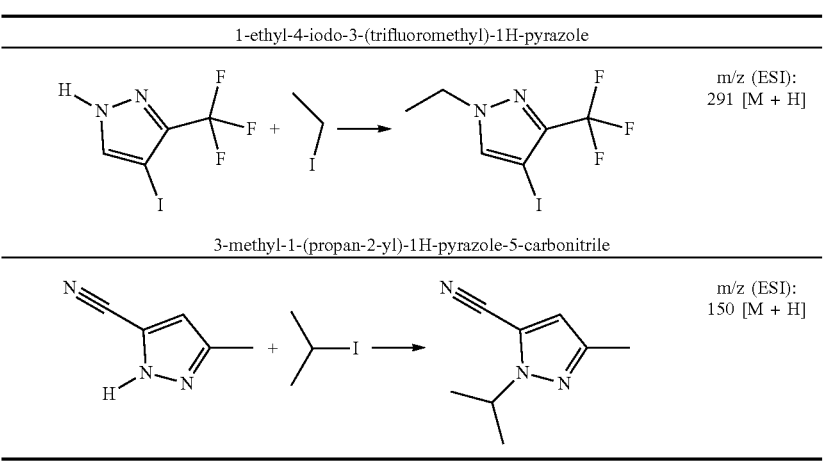 | m/z (ESI): 291 [M + H] |
| 3-methyl-1-(propan-2-yl)-1H-pyrazole-5-carbonitrile | |
| | m/z (ESI): 150 [M + H] |

Synthesis of 5-bromo-1-ethyl-1H-pyrazole-4-carbaldehyde

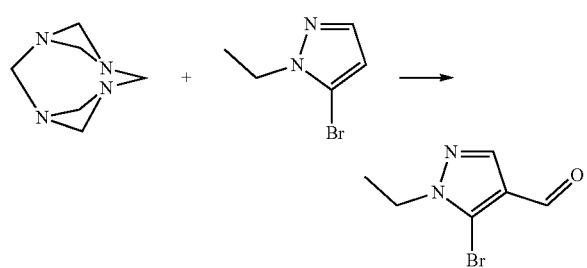

To a solution of 5-bromo-1-ethyl-1H-pyrazole (100 g, 571 mmol) in TFA (700 mL) at 0° C. was added 1,3,5,7-tetraazaadamantane (120 g, 857 mmol). The resulting mixture was stirred at 90° C. for 16 h. After cooling to r.t., the mixture was concentrated under reduced pressure to remove most of the TFA. The residue was diluted with DCM (600 mL), washed with sat. NaHCO$_3$ and brine, dried over anhydrous Na$_2$SO$_4$, filtered and concentrated. The residue was purified by column chromatography on silica gel (10% EtOAc in PE) to give 5-bromo-1-ethyl-1H-pyrazole-4-carbaldehyde as a white solid (60 g, yield: 52%). LC/MS ESI (m/z): 203 [M+H]$^+$.

The following intermediates were synthesized using a similar experimental protocol:

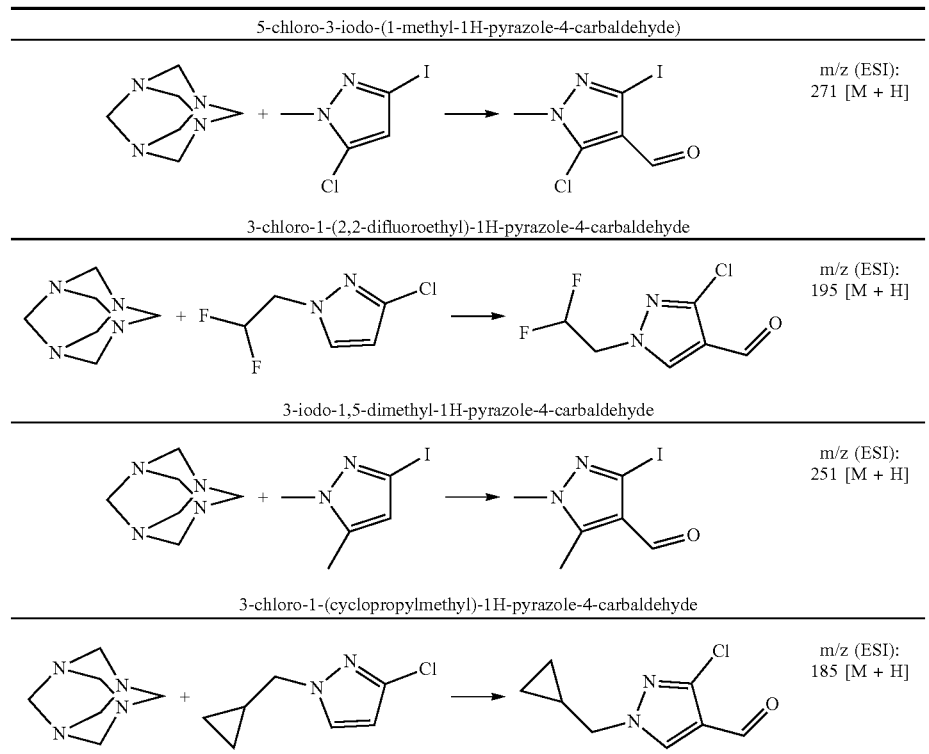

| 3,5-dibromo-1-methyl-1H-pyrazole-4-carbaldehyde | |
|---|---|
| 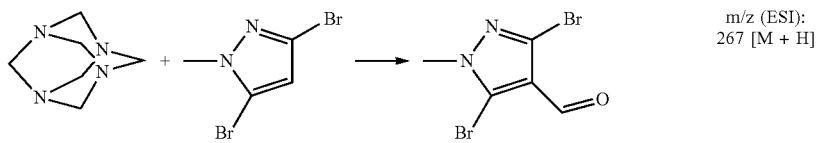 | m/z (ESI): 267 [M + H] |

| 3-bromo-1-(tert-butyl)-1H-pyrazole-4-carbaldehyde | |
|---|---|
| 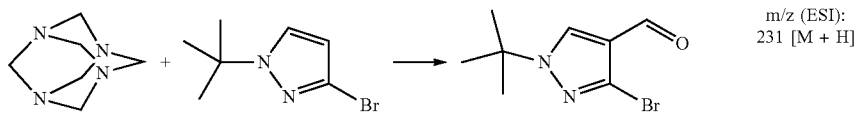 | m/z (ESI): 231 [M + H] |

| 1-ethyl-3-(propan-2-yl)-1H-pyrazole-4-carbaldehyde | |
|---|---|
| 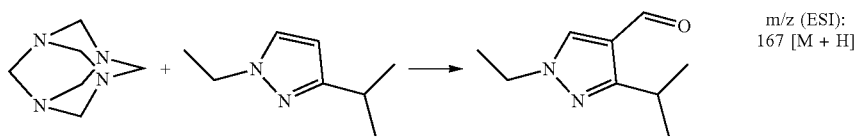 | m/z (ESI): 167 [M + H] |

| 1,3-diethyl-1H-pyrazole-4-carbaldehyde | |
|---|---|
| 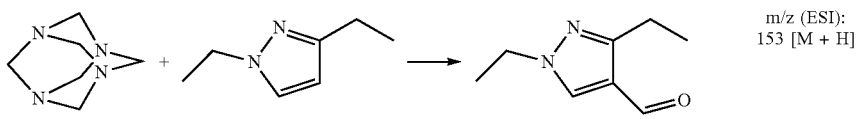 | m/z (ESI): 153 [M + H] |

Synthesis of 3-bromo-1-(tert-butyl)-1H-pyrazole

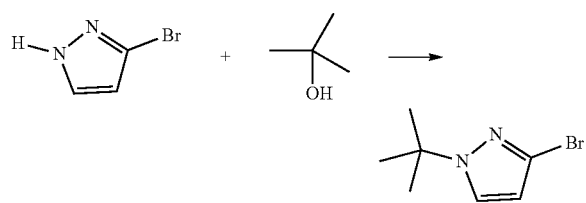

To a mixture of 3-bromo-1H-pyrazole (3.00 g, 20.4 mmol) and 2-methylpropan-2-ol (5 mL) was added $H_2SO_4$ (1.98 mL, 20.4 mmol) slowly at r.t. The mixture was heated at 100° C. for 16 h. reaction mixture was diluted with $H_2O$ (20 mL) and then extracted with ethyl acetate (20 mL). The organic layer was washed with brine (20 mL), dried over anhydrous $Na_2SO_4$, filtered, concentrated, and then purified by silica gel chromatography (0→100% EtOAc in PE) to give 3-bromo-1-tert-butyl-1H-pyrazole (1.4 g, 34% yield) as a yellow oil. LC/MS (ESI) m/z: 203.0 [M+H]*.

Synthesis of 1,3-diethyl-1H-pyrazole

A mixture of 3-ethenyl-1-ethyl-1H-pyrazole (1.00 g, 8.18 mmol) and platinum dioxide (0.190 g, 0.82 mmol) in EtOAc (10 mL) was stirred at r.t. under $H_2$ (15 psi) overnight. This mixture was filtered, and the filtrate was concentrated. The residue was purified by column chromatography on silica gel (0→100% of EtOAc in PE) to give 1,3-diethyl-1H-pyrazole (1.00 g, 98% yield) as a colorless oil. LC/MS (ESI) (m/z): 125 [M+H]$^+$.

The following intermediates were synthesized using a similar experimental protocol:

| 3-ethyl-5-iodo-1-methyl-1H-pyrazole | |
|---|---|
| 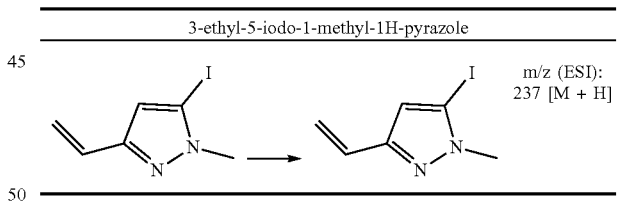 | m/z (ESI): 237 [M + H] |

Synthesis of 3-(bromomethyl)-2-chloro-5-fluoropyridine

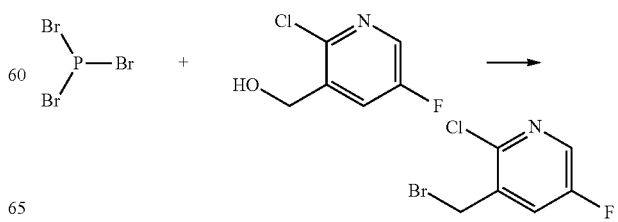

To a solution of (2-chloro-5-fluoropyridin-3-yl)methanol (4.0 g, 25 mmol) in DMF (20 mL) was added tribromophosphane (2.4 mL, 26 mmol) dropwise at 0° C. After stirring at 25° C. for 1 h, the mixture was basified to pH 7 with sat. NaHCO$_3$, and extracted with EA (30 mL×3). The combined organic phase was dried over anhydrous Na$_2$SO$_4$ and concentrated in vacuo. The residue was purified by prep-TLC (8% EA in PE) to give 3-(bromomethyl)-2-chloro-5-fluoropyridine (2.7 g, 46% yield) as a colorless oil. LC/MS ESI (m/z): 224 [M+H]$^+$.

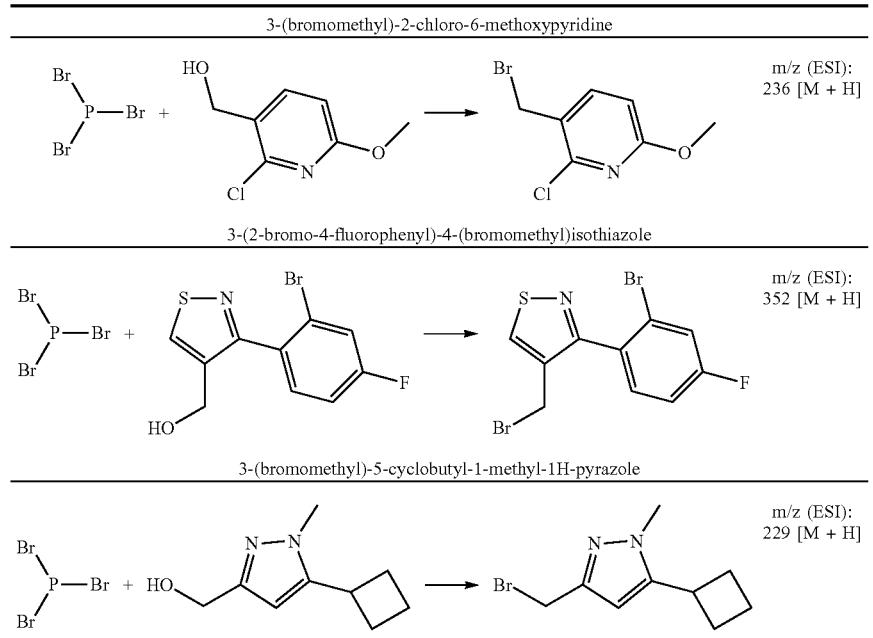

Synthesis of 1-cyclobutyl-4-iodo-1H-pyrazole

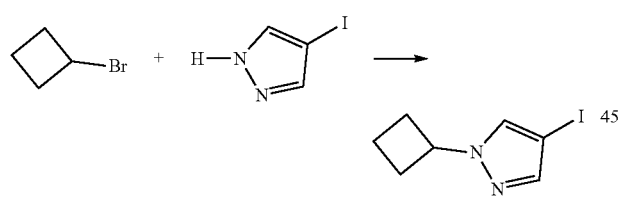

A mixture of 4-iodo-1H-pyrazole (10.0 g, 51.6 mmol), bromocyclobutane (20.9g 155 mmol) and K$_2$CO$_3$ (28.5 g, 206 mmol) in DMF (200 mL) was heated at 70° C. for 12 h. The reaction mixture was filtered, and the filtrate was extracted with EA (300 ml×2). The combined organic layers were washed with brine, dried over anhydrous Na$_2$SO$_4$ and concentrated. The residue was purified by column chromatography on silica gel (0→5% EtOAc in PE) to give the target product (9.73 g, 76% o yield) as a yellow oil. LC/MS ESI (m/z): 249 [M+H]$^+$.

The following intermediates were synthesized using a similar experimental protocol:

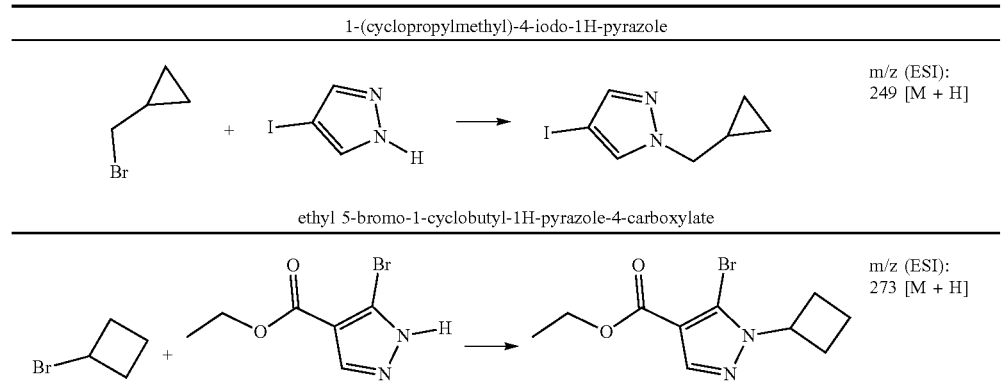

| ethyl 5-bromo-1-(2-fluoroethyl)-1H-pyrazole-4-carboxylate |
|---|

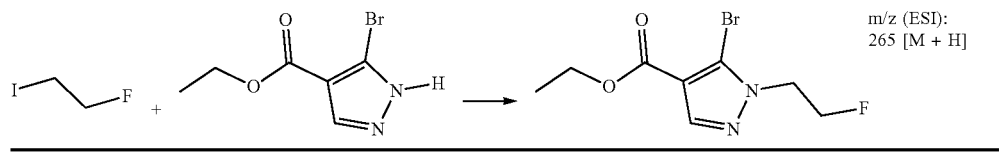

m/z (ESI): 265 [M + H]

Synthesis of (4-fluoro-2-iodophenyl)hydrazine

Synthesis of 5-bromo-4-(bromomethyl)-1-ethyl-1H-pyrazole

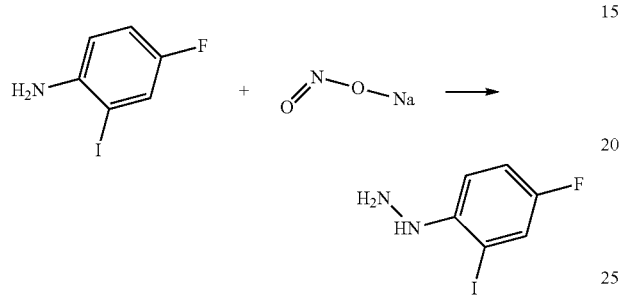

To a mechanically stirred solution of 4-fluoro-2-iodoaniline (5.0 g, 21 mmol) in AcOH (10 mL) was slowly added conc. HCl (40 mL). The solution quickly became a thick suspension. The reaction was then cooled to 0° C. in an ice bath and treated slowly dropwise with a solution of sodium nitrite (1.63 g, 23.6 mmol) in water (8 mL). The reaction was stirred for 1 h, then a solution of SnCl$_2$ (8.46 g, 44.5 mmol) in conc. HCl (8 mL) was added slowly. The reaction was allowed to warm to r.t. over 2 h. The suspension was filtered, washed with water and dried under vacuum to give crude (4-fluoro-2-iodophenyl)hydrazine hydrochloride (4.1 g, yield: 77%) as a gray solid. LC/MS (ESI) m/z: 253 [M+H]$^+$.

To a stirred solution of (5-bromo-1-ethyl-1H-pyrazol-4-yl)methanol (4.00 g, 19.5 mmol) and triphenylphosphine (6.14 g, 23.4 mmol) in dry DCM (50 mL) was added a solution of tetrabromomethane (7.76 g, 23.4 mmol) in DCM dropwise at 0° C. After the addition, the reaction mixture was stirred at r.t. for 24 h. The reaction mixture was concentrated in vacuo and the residue was purified by silica gel column chromatography (eluent: PE/EtOAc 50/1 to 10/1) to give 5-bromo-4-(bromomethyl)-1-ethyl-1H-pyrazole (3.0 g, 57% yield) as a white solid. LC/MS ESI (m/z): 267 [M+H]$^+$.

The following intermediates were synthesized using a similar experimental protocol:

| 5-bromo-4-(bromomethyl)-1-cyclobutyl-1H-pyrazole |
|---|

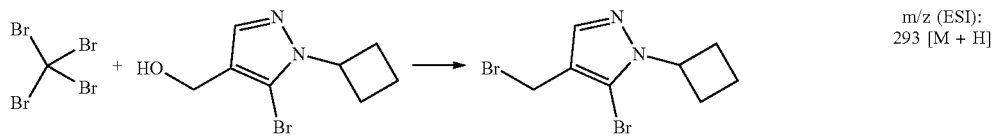

m/z (ESI): 293 [M + H]

| 5-bromo-4-(bromomethyl)-1-(2,2-difluoroethyl)-1H-pyrazole |
|---|

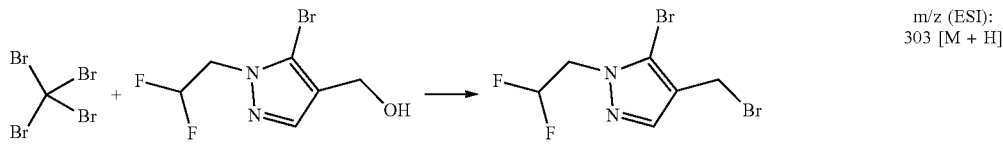

m/z (ESI): 303 [M + H]

| 5-bromo-4-(bromomethyl)-1-(2-fluoroethyl)-1H-pyrazole |
|---|

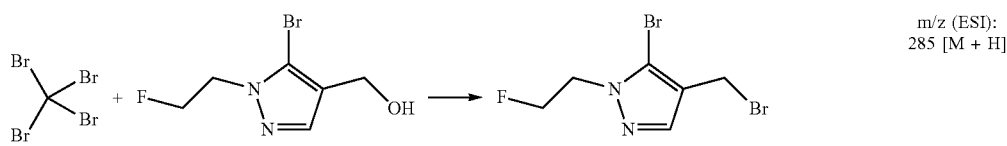

m/z (ESI): 285 [M + H]

| 3-(bromomethyl)-1-((2-(trimethylsilyl)ethoxy)methyl)-1H-pyrazole-5-carbonitrile | |
|---|---|
| 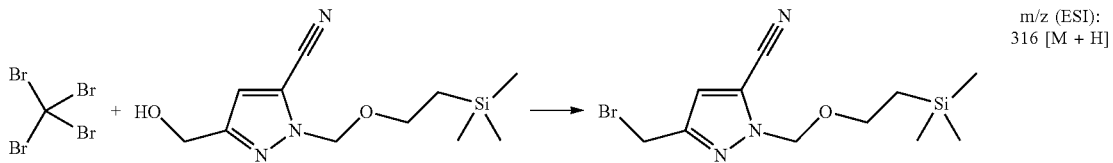 | m/z (ESI): 316 [M + H] |

Synthesis of
2-bromo-3-(bromomethyl)-5-fluoropyridine

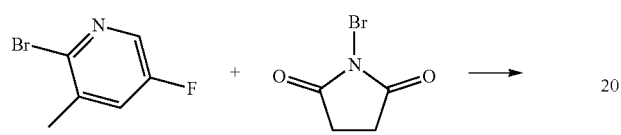

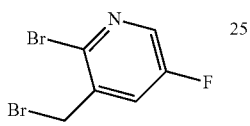

A mixture consisting of 2-bromo-5-fluoro-3-methylpyridine (2.00 g, 10.5 mmol), AIBN (52 mg, 0.32 mmol) and NBS (2.44 g, 13.7 mmol) in DCE (20 mL) was thrice degassed with N₂ and heated to 85° C. with stirring for 1 h. After cooling to r.t., the mixture was quenched with water, diluted with EtOAc, and washed with brine. The final organic layer was dried over Na₂SO₄, filtered, and the filtrate was concentrated in vacuo to provide a residue, which was purified by silica gel flash column chromatography (PE: EA=50:1) to give 2-bromo-3-(bromomethyl)-5-fluoropyridine (1.20 g, 42%) as a white solid. LC-MS ESI (m/z): 268 [M+H]$^+$.

The following intermediates were synthesized using a similar experimental protocol:

| 4-bromo-3-(bromomethyl)-1-isopropyl-1H-pyrazole-5-carbonitrile | |
|---|---|
| 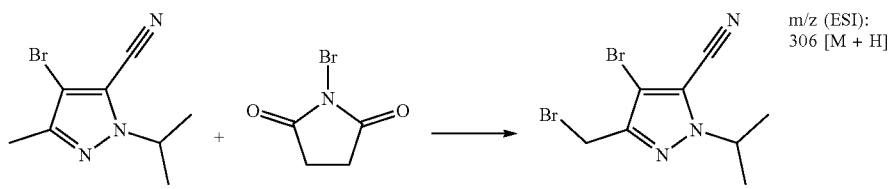 | m/z (ESI): 306 [M + H] |

| 4-bromo-3-(bromomethyl)-1-methyl-1H-pyrazole-5-carbonitrile | |
|---|---|
| 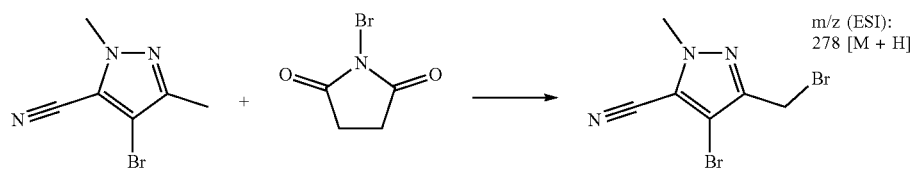 | m/z (ESI): 278 [M + H] |

Synthesis of 3-bromo-1-(difluoromethyl)-4-iodo-1H-pyrazole

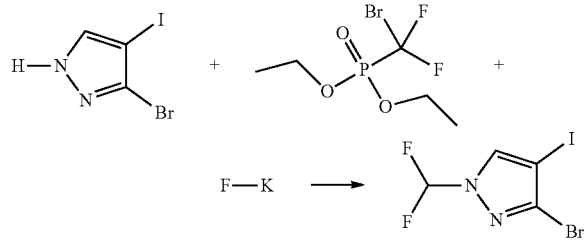

To a solution of 3-bromo-4-iodo-1H-pyrazole (5.42 g, 19.9 mmol) and diethyl (bromodifluoromethyl)phosphonate (7.95 g, 29.8 mmol) in acetonitrile (50 mL) was added potassium fluoride (2.3 g, 40 mmol). The reaction was stirred at 40° C. for 3 h. The reaction was cooled to r.t., diluted with DCM (50 mL), washed with water (50 mL) and brine (50 mL), dried over Na$_2$SO$_4$ and concentrated to dryness. The residue was purified by chromatography on silica gel (15% EtOAc in PE) to give 3-bromo-1-(difluoromethyl)-4-iodo-1H-pyrazole (5.12 g, 80% yield) as a white solid. LC/MS (ESI) m/z: 323 [M+H]$^+$.

Synthesis of (3-cyano-1-methyl-1H-pyrazol-5-yl)boronic acid

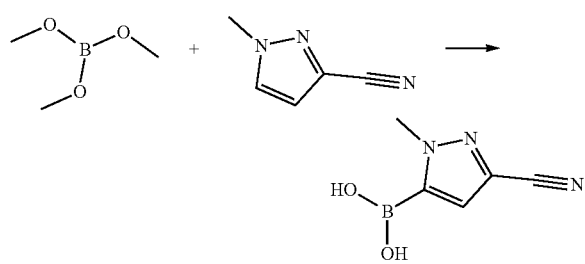

To a solution of 1-methyl-1H-pyrazole-3-carbonitrile (1.0 g, 9.3 mmol) in THF (15 mL) was added LDA (2 M in THF, 4.7 mL, 9.3 mmol) dropwise under the atmosphere of N$_2$ at −78° C. After stirring for 0.5 h at −78° C., trimethyl borate (1.9 g, 19 mmol) in THF (2 mL) was added dropwise. After stirring at −78° C. for 1 h, the reaction was quenched with sat. aq. ammonium chloride. The reaction was diluted with EtOAc and washed first with H$_2$O and then brine. The organic layer was dried over anhydrous Na$_2$SO$_4$, filtered, and concentrated under vacuum. The residue was purified by silica gel column chromatography (0→80% EtOAc in PE) to give (3-cyano-1-methyl-1H-pyrazol-5-yl)boronic acid (800 mg, 57% yield) as a yellow oil. LC/MS ESI (m/z): 152 [M+H]$^+$.

Synthesis of 3-(azidomethyl)-2-bromopyridine

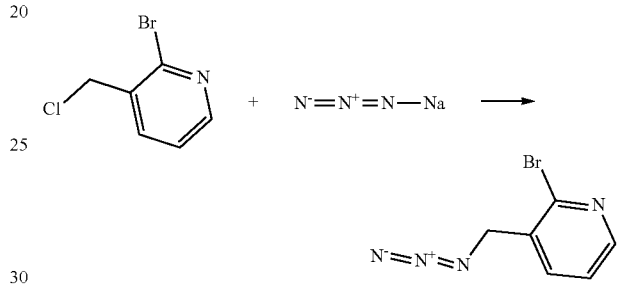

To a solution of 2-bromo-3-(chloromethyl)pyridine (1.15 g, 5.58 mmol) in MeCN (20 mL) was added NaN$_3$ (1.09 g, 16.8 mmol) at r.t. The mixture was stirred at 40° C. overnight, then partitioned between EtOAc (20 mL) and water (20 mL). The organic phase was washed with brine (20 mL), dried over anhydrous Na$_2$SO$_4$, filtered and concentrated. The residue was purified by flash chromatography (silica gel, 0→33% EA in PE) to give 3-(azidomethyl)-2-bromopyridine (955 mg, 80% yield over 2 steps) as a yellow oil. LC/MS (ESI) m/z: 213 [M+H]$^+$.

The following intermediates were synthesized using a similar experimental protocol:

4-(azidomethyl)-3-iodo-1-methyl-1H-pyrazole

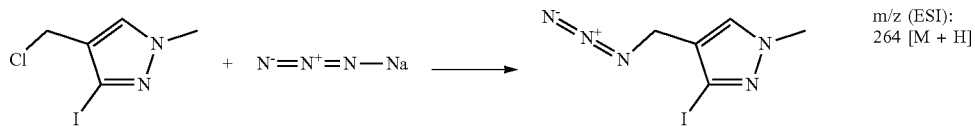

m/z (ESI): 264 [M + H]

3-(azidomethyl)-2-bromo-5-fluoropyridine

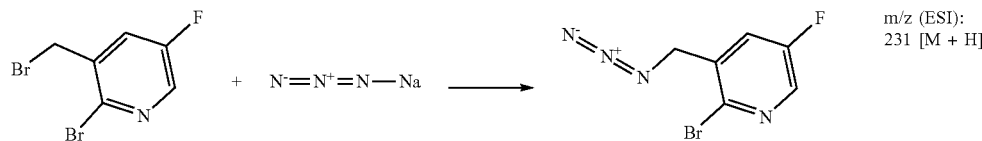

m/z (ESI): 231 [M + H]

5-(azidomethyl)-3-ethyl-1,2-oxazole

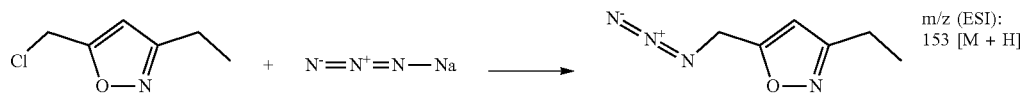

m/z (ESI): 153 [M + H]

215

Synthesis of
2-(5-bromo-1-ethyl-1H-pyrazol-4-yl)acetonitrile

216

Synthesis of
1-(5-bromo-1-ethyl-1H-pyrazol-4-yl)ethanol

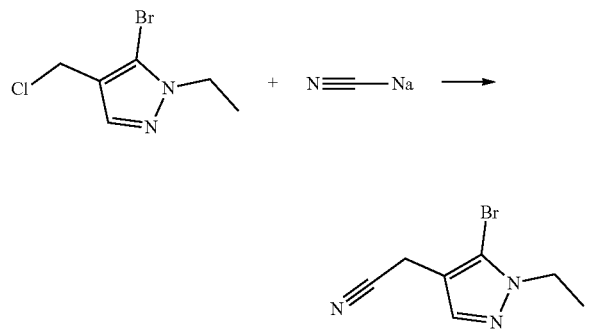

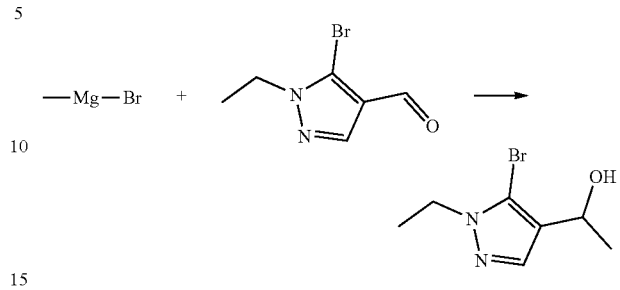

To a solution of 5-bromo-4-(chloromethyl)-1-ethyl-1H-pyrazole (5.00 g, 22.4 mmol) in DMSO (50 mL) was added NaCN (2.20 g, 44.7 mmol) at 25° C. After stirring at 25° C. for 2 h, the mixture was treated with EtOAc and H₂O. The organic layer was separated, washed with brine, dried over anhydrous Na₂SO₄, filtered, and concentrated. The residue was purified by column chromatography on silica gel (20% EtOAc in PE) to give 2-(5-bromo-1-ethyl-1H-pyrazol-4-yl)acetonitrile (4.5 g, yield: 94%) as a light-yellow oil. LC/MS ESI (m/z): 214 [M+H]⁺.

To a solution of 5-bromo-1-ethyl-1H-pyrazole-4-carbaldehyde (10.00 g, 49.25 mmol) in THF (120 mL) was added methylmagnesium bromide (18.8 mL, 56.4 mmol, 3.0 M in THF) dropwise at 0° C. over 10 min. The resulting mixture was stirred at 0° C. for 1 h. The mixture was quenched with sat. NH₄Cl (30 mL) at 0° C. and then extracted with EA (100 mL×3), the combined extracts were dried over anhydrous Na₂SO₄, filtered and concentrated in vacuo. The residue was purified by column chromatography on silica gel (20% EtOAc in PE) to give 1-(5-bromo-1-ethyl-1H-pyrazol-4-yl)ethanol as a light-yellow solid (9.28 g, 86% yield). LC/MS ESI (m/z): 219 [M+H]⁺.

The following intermediates were synthesized using a similar experimental protocol:

cyclopropyl(3-iodo-1-methyl-1H-pyrazol-5-yl)methanol

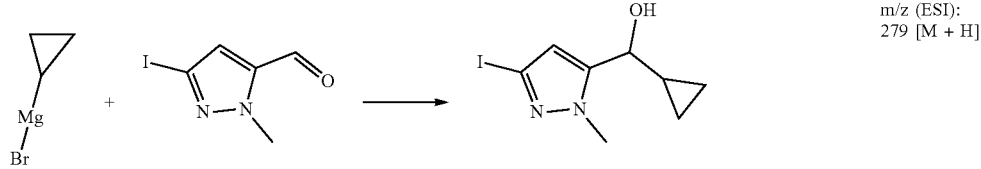

m/z (ESI): 279 [M + H]

1-(2-(1-((5-bromo-1-(difluoromethyl)-1H-pyrazol-4-yl)methyl)-1H-imidazol-2-yl)-5-fluorophenyl)ethan-1-ol

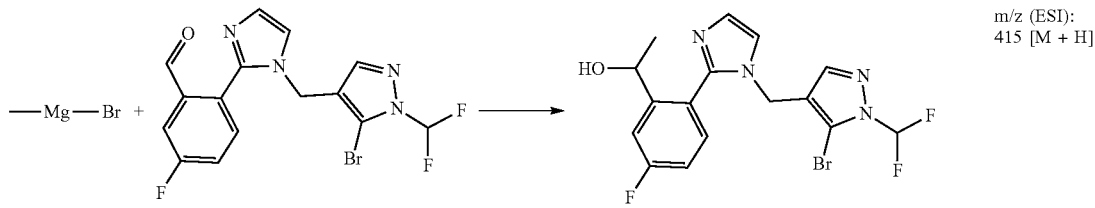

m/z (ESI): 415 [M + H]

(5-bromo-1-ethyl-1H-pyrazol-4-yl)(4-fluoro-1-(4-fluoro-2-(1-hydroxyethyl)phenyl)-1H-pyrazol-5-yl)methanone

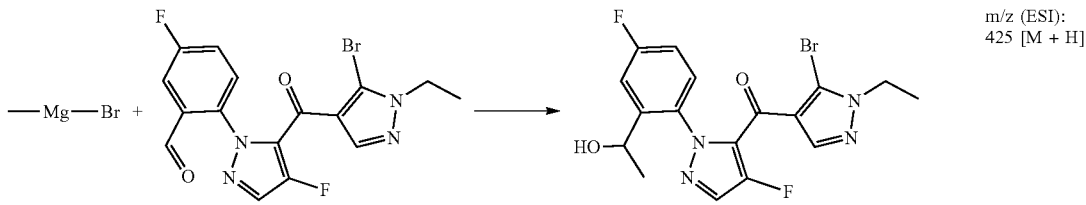

m/z (ESI): 425 [M + H]

1-(5-bromoisothiazol-4-yl)prop-2-yn-1-ol

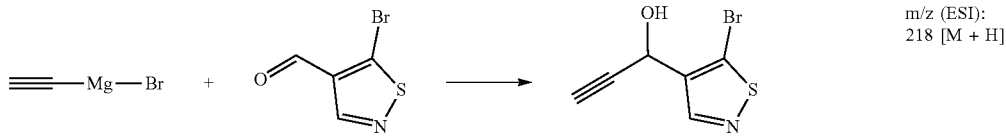

m/z (ESI): 218 [M + H]

| | |
|---|---|
| (1-ethyl-1H-pyrazol-4-yl)(3-fluoro-1-(4-fluoro-2-(1-hydroxyethyl)phenyl)-1H-pyrazol-5-yl)methanone | |
| 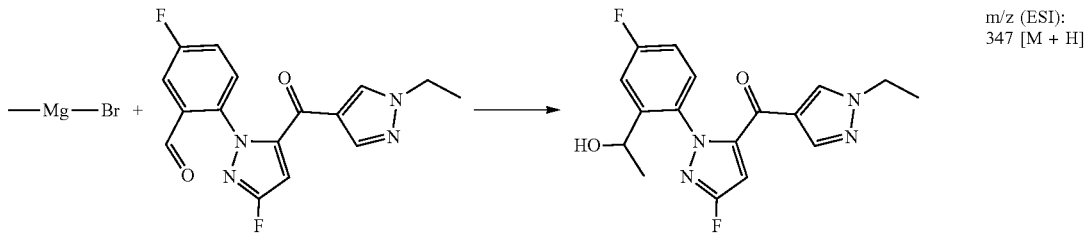 | m/z (ESI): 347 [M + H] |
| 1-[3-(4-fluoro-2-iodophenyl)-1,2-thiazol-4-yl]prop-2-yn-1-ol | |
| 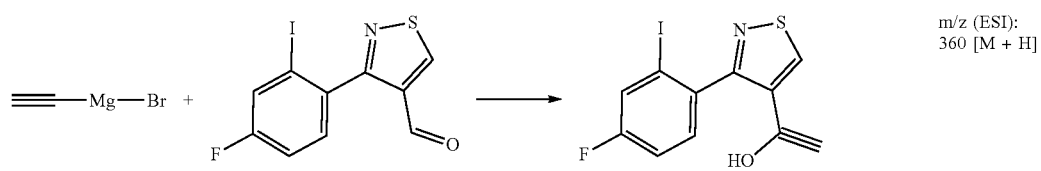 | m/z (ESI): 360 [M + H] |
| 1-((5-(4-fluoro-2-(1-hydroxyethyl)phenyl)-1-methyl-1H-pyrazol-4-yl)methyl)-1H-imidazole-4-carbonitrile | |
| 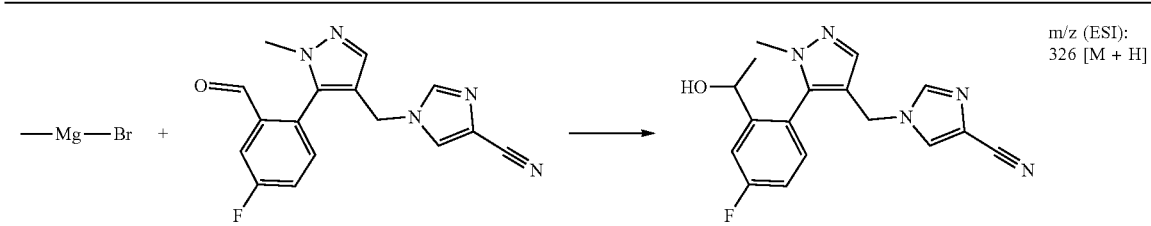 | m/z (ESI): 326 [M + H] |
| 3-(1-(4-fluoro-2-(1-hydroxyethyl)phenyl)-1H-pyrazole-5-carbonyl)-1-methyl-1H-pyrazole-5-carbonitrile | |
| 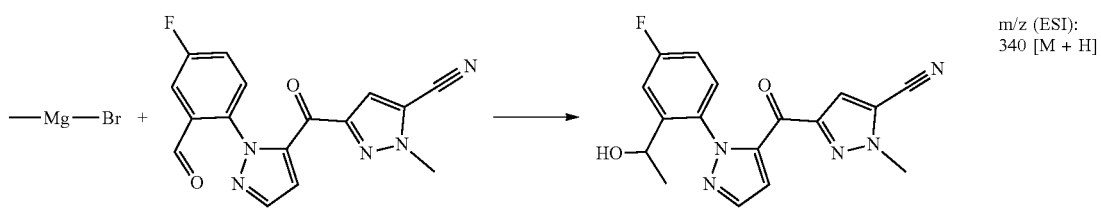 | m/z (ESI): 340 [M + H] |

Synthesis of 3-(bromomethyl)-2-chloro-5-methoxy pyridine

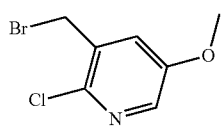

To a solution of 2-chloro-5-methoxy-3-methylpyridine (500 mg, 3.17 mmol) in CCl$_4$ (12 mL) was added NBS (565 mg, 3.17 mmol) and benzoyl peroxide (76.8 mg, 0.317 mmol). The mixture was stirred at 80° C. for 3 h, then poured into water (80 mL), and the extracted with EA (80 mL×3). The combined organic layers were washed with brine (60 mL), dried over Na$_2$SO$_4$, filtered, and concentrated in vacuo. The residue was purified by column chromatography on silica gel eluted (1→10% EtOAc in PE) to give 2-chloro-3-(dibromomethyl)-5-methoxypyridine (200 mg, yield:20%) as a white solid. LC/MS (ESI): m/z=315.8 [M+H]$^+$.

To a solution of 2-chloro-3-(dibromomethyl)-5-methoxy-pyridine (200 mg, 0.634 mmol) in THF (4 mL) was added diethoxyphosphinous acid (0.161 mL, 1.27 mmol), DIPEA (164 mg, 1.27 mmol) and then this mixture was stirred at r.t. for 16 h. The mixture was poured into water (80 mL) and extracted with EA (80 mL×3). The combined organic layers were washed with brine (60 mL), dried with Na$_2$SO$_4$, filtered, and concentrated in vacuo This residue was purified by column chromatography on silica gel eluted (1→10% EtOAc in PE) to give 3-(bromomethyl)-2-chloro-5-methoxypyridine (100 mg, yield: 67%) as a white solid. LC/MS (ESI): m/z=236 [M+H]$^+$.

Synthesis of 1-(3-iodo-1-methyl-H-pyrazol-4-yl)-prop-2-yn-1-ol

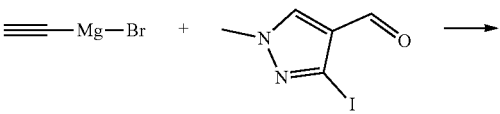

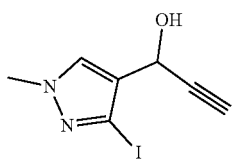

To a solution of 3-iodo-1-methyl-1H-pyrazole-4-carbaldehyde (1.00 g, 4.24 mmol) in THF (7 mL) at 0° C. was added ethynylmagnesium bromide (12.7 mL, 6.36 mmol) dropwise. The mixture was stirred at r.t. for 2 h. The reaction was quenched with sat. aq. NH$_4$Cl (13 mL) and extracted with EA (15 mL×3). The organic layer was separated, washed with brine, dried over anhydrous Na$_2$SO$_4$, filtered and concentrated. The residue was purified by column chromatography on silica gel (20→90% EA in PE) to give 1-(3-iodo-1-methyl-H-pyrazol-4-yl)prop-2-yn-1-ol (780 mg, 70) as a white solid. LC-MS (ESI) m/z: 262.9 [M+H]$^+$.

The following intermediates were synthesized using a similar experimental protocol:

| 1-(2-chloro-5-fluoropyridin-3-yl)prop-2-yn-1-ol | |
|---|---|
| 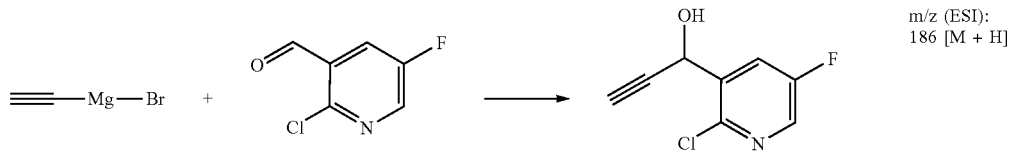 | m/z (ESI): 186 [M + H] |

| 1-(2-bromo-4-fluorophenyl)prop-2-yn-1-ol | |
|---|---|
| 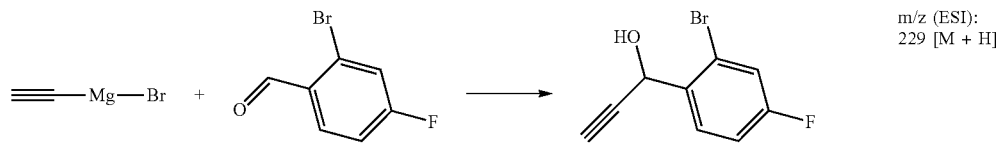 | m/z (ESI): 229 [M + H] |

| 1-(2-(1-((5-bromo-1-cyclobutyl-1H-pyrazol-4-yl)methyl)-1H-imidazol-2-yl)-5-fluorophenyl)ethan-1-ol | |
|---|---|
| 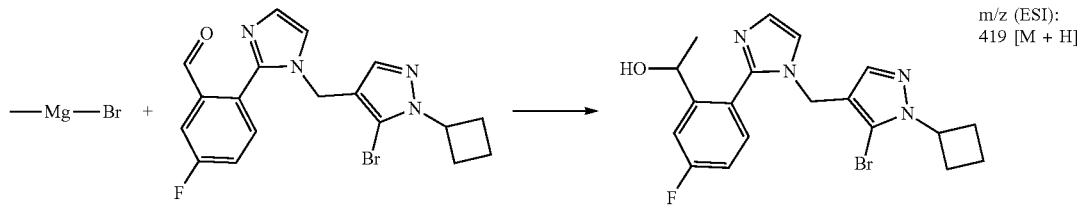 | m/z (ESI): 419 [M + H] |

| 1-(2-(1-((5-bromo-1-(2,2-difluoroethyl)-1H-pyrazol-4-yl)methyl)-1H-imidazol-2-yl)-5-fluorophenyl)ethan-1-ol | |
|---|---|
| 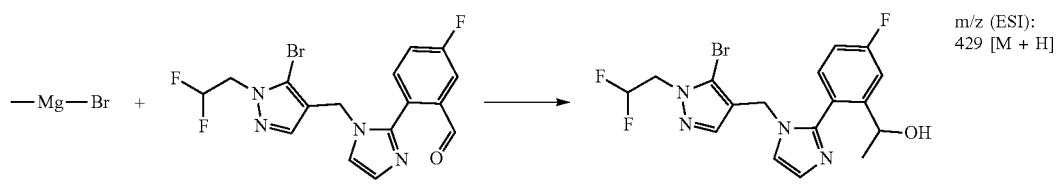 | m/z (ESI): 429 [M + H] |

| 1-[2-(1-{[5-bromo-1-(2-fluoroethyl)-1H-pyrazol-4-yl]methyl}-1H-imidazol-2-yl)-5-fluorophenyl]ethan-1-ol | |
|---|---|
| 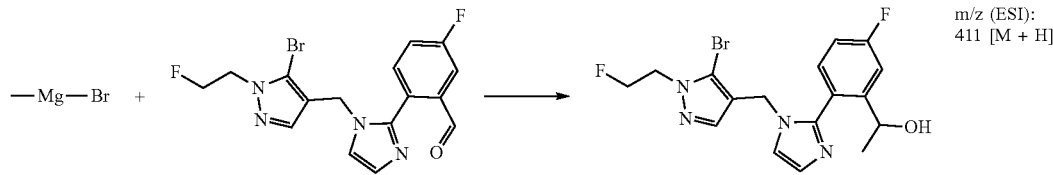 | m/z (ESI): 411 [M + H] |

| (5-bromo-1-ethyl-1H-pyrazol-4-yl)(1-(4-fluoro-2-(1-hydroxyethyl)phenyl)-1H-pyrazol-5-yl)methanone | |
|---|---|
| 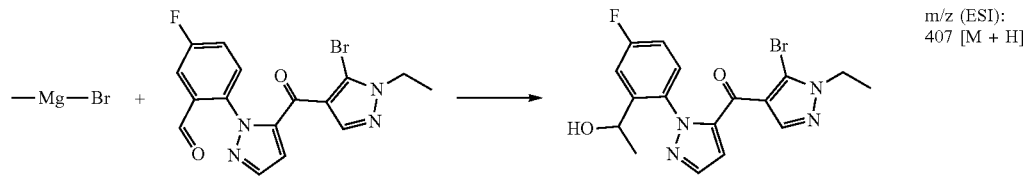 | m/z (ESI): 407 [M + H] |

1-(3-chloro-1-(4-fluoro-2-((R)-1-((4-methoxybenzyl)oxy)ethyl)phenyl)-1H-pyrazol-5-yl)prop-2-yn-1-ol

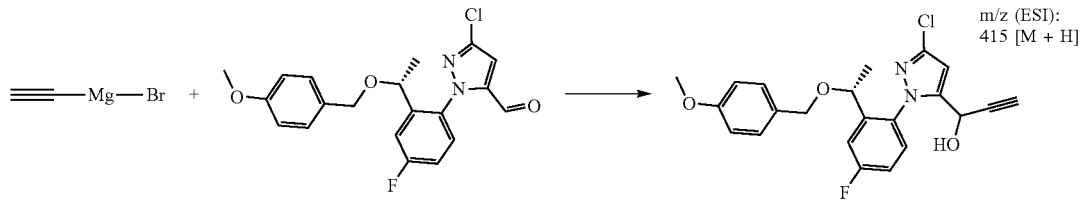

m/z (ESI): 415 [M + H]

(1-((2-chloropyridin-3-yl)methyl)-1H-pyrazol-4-yl)(cyclopropyl)methanol

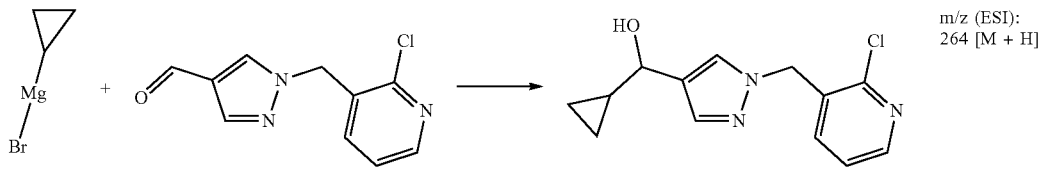

m/z (ESI): 264 [M + H]

1-(2-(1-((5-bromo-1-ethyl-1H-pyrazol-4-yl)methyl)-1H-imidazol-2-yl)-5-fluorophenyl)ethanol

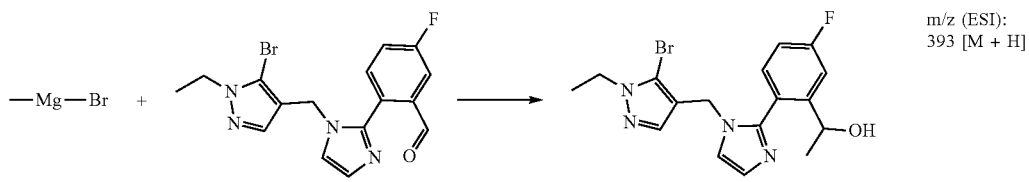

m/z (ESI): 393 [M + H]

methyl 3-(cyclopropyl(hydroxy)methyl)-1-methyl-1H-pyrazole-5-carboxylate

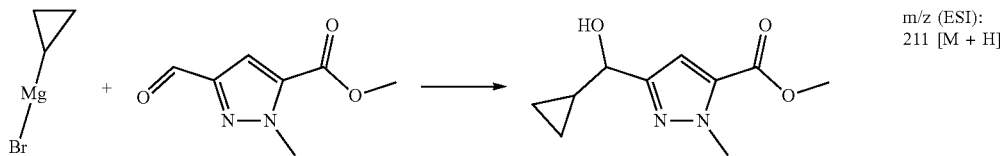

m/z (ESI): 211 [M + H]

Synthesis of 4-fluoro-2-iodobenzamide

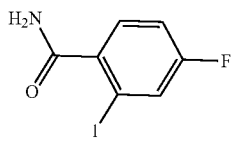

To a solution of 4-fluoro-2-iodobenzoic acid (5.00 g, 18.8 mmol) in DCM (100 mL) was added oxalyl chloride (5.00 g, 39.4 mmol), followed by the addition of DMF (0.07 mL, 0.9 mmol) at 0° C. After the addition, the resulting mixture was stirred at 25° C. for 2 h. The mixture was concentrated in vacuo to dryness to give crude 4-fluoro-2-iodobenzoyl chloride as a yellow oil.

To a solution of 4-fluoro-2-iodobenzoyl chloride in dry DCM (50 mL) cooled to 0° C., was added a pre-cooled solution of aq. NH$_3$ (14 mL, 370 mmol, 28% in H$_2$O) dropwise over 10 min. The internal temperature was maintained below 5° C. during the addition. The resulting mixture was stirred at r.t. for 4 h and then concentrated to dryness. The residual white solids were triturated with water and PE, and then dried in a vacuum oven to give target product 4-fluoro-2-iodobenzamide (11 g, 92% yield over 2 steps) as a white solid. LC/MS (ESI): m/z=266 [M+H]$^+$.

Synthesis of 3-bromo-5-methoxy-1-methyl-1H-pyrazole-4-carbaldehyde

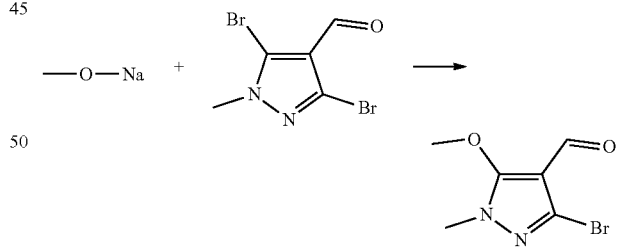

To a stirred solution of 3,5-dibromo-1-methyl-1H-pyrazole-4-carbaldehyde (5.00 g, 20.8 mmol) in MeOH (40 mL), was added sodium methanolate (12.5 mL, 62.5 mmol, 5.0 M in methanol) and the resulting mixture was stirred at 60° C. for 1 h. After 1 h, the reaction mixture was concentrated in vacuo to remove the solvent. The residue was diluted with sat. aq. NH$_4$Cl (30 mL) and EtOAc (30 mL), and then extracted with EtOAc (3×30 mL). The organic phases were combined, washed with brine (30 mL), dried over anhydrous Na$_2$SO$_4$, filtered and concentrated in vacuo to give crude 3-bromo-5-methoxy-1-methyl-1H-pyrazole-4-carbaldehyde (3.31 g, yield: 59%) as a light-yellow solid. LC/MS (ESI) (m/z): 219 [M+H]$^+$.

Synthesis of 1-(2,4-dibromothiazol-5-yl)prop-2-yn-1-ol

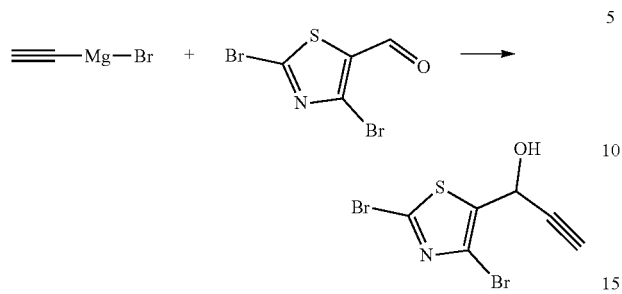

To a solution of 2,4-dibromo-1,3-thiazole-5-carbaldehyde (2.0 g, 7.3 mmol) in THF (20 mL) at −78° C. was added ethynylmagnesium bromide (7.3 mL, 7.3 mmol, 1 M in THF) under an $N_2$ atmosphere. After the addition, the mixture was stirred at −78° C. for 2 h. The reaction was quenched with sat. aq. solution of ammonium chloride (30 mL). The reaction mixture was concentrated in vacuo and diluted with DCM (30 mL). Then the mixture was washed with brine (30 mL) and dried over anhydrous $Na_2SO_4$, filtered and concentrated in vacuo to give the residue, which was purified by flash chromatography (30% EtOAc in PE) to give 1-(2,4-dibromothiazol-5-yl)prop-2-yn-1-ol (1.5 g, 68%) as a white solid. LC/MS ESI (m/z): 296 [M+H]$^+$.

The following intermediates were synthesized using a similar experimental protocol:

| 1-(3,5-difluoro-2-iodophenyl)ethan-1-ol |
|---|
| 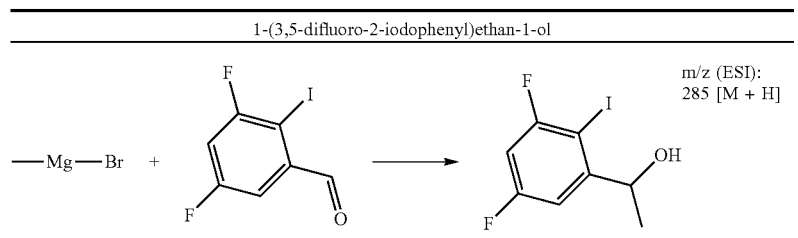 m/z (ESI): 285 [M + H] |

Synthesis of 1-[(1-methylcyclopropyl)methyl]-1H-pyrazole-4-carbaldehyde

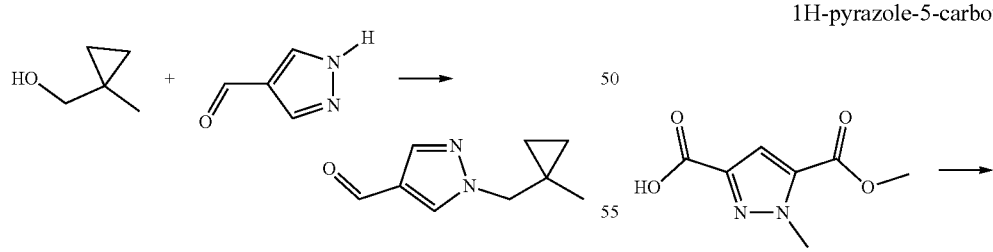

To a solution of (1-methylcyclopropyl)methanol (0.56 mL, 5.8 mmol) and TEA (0.89 mL, 6.4 mmol) in DCM (20 mL) was added methanesulfonyl chloride (0.49 mL, 6.4 mmol). The mixture was stirred at 0° C. for 1 h. This solution was added to a mixture of 1H-pyrazole-4-carbaldehyde (836 mg, 8.70 mmol) and $K_2CO_3$ (1.60 g, 11.6 mmol) in DMF (10 mL) and the reaction was stirred at 0° C. for 2 h. The mixture was filtered and concentrated in vacuo to give a residue which was purified by column chromatography on silica gel (25% EtOAc in PE) to give 1-[(1-methylcyclopropyl) methyl]-1H-pyrazole-4-carbaldehyde (350 mg, yield: 37%) as a light-yellow solid. LC/MS ESI (m/z): 165 [M+H]$^+$.

Synthesis of methyl 3-(hydroxymethyl)-1-methyl-1H-pyrazole-5-carboxylate

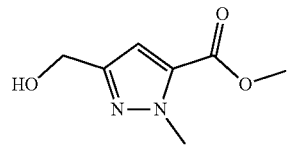

To a solution of 5-(methoxycarbonyl)-1-methyl-1H-pyrazole-3-carboxylic acid (5.70 g, 30.9 mmol) in THF (80 mL) at 0° C. under $N_2$, was slowly added $BH_3$·THF (61.9 mL, 61.9 mmol, 1 N). The reaction was allowed to warm to r.t.

over 30 min and then heated to 65° C. for 4 h. After cooling to r.t., MeOH (12 mL) was slowly added, and then the solvent was removed under reduced pressure. The residue was re-dissolved in MeOH (12 mL), stirred for 20 min at r.t., and then then evaporated to dryness. The residue was diluted with water and extracted with DCM (50.0 mL×3). The combined organic phases were washed with brine (50 mL), dried over anhydrous sodium sulfate, filtered, and concentrated. The crude mixture was then purified via silica gel chromatography (33→100% EA in PE) to give methyl 3-(hydroxymethyl)-1-methyl-1H-pyrazole-5-carboxylate (3.2 g, yield: 61%) as a white solid. LC-MS ESI (m/z): 171 [M+H]$^+$.

Synthesis of ethyl 5-ethyl-1,2-thiazole-3-carboxylate

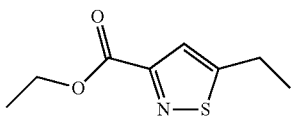

To a solution of ethyl 2,4-dioxohexanoate (3.00 g, 17.4 mmol) in toluene (30 mL) was added ammonium acetate (3.36 g, 43.6 mmol), AcOH (3.0 mL, 52 mmol). The reaction mixture was stirred at 80° C. for 18 h, allowed to cool, and then concentrated under reduced pressure. The residue was diluted with water, and the pH was adjusted to 8 with 10% aq. Na$_2$CO$_3$. The resulting mixture was extracted with EtOAc (2×50 mL). The combined organic extracts were dried over Na$_2$SO$_4$ and concentrated under reduced pressure. The residue was purified by flash column chromatography on silica gel (0→20% EtOAc in PE) to give ethyl 4-amino-2-oxohex-3-enoate (1.2 g, 40%) as a pale-yellow oil. LC/MS (ESI): m/z=172 [M+H]$^+$.

To a solution of ethyl 4-amino-2-oxohex-3-enoate (1.30 g, 7.59 mmol) in THF (15 mL) was added phosphorus pentasulfide (0.84 g, 3.8 mmol). The reaction mixture was stirred at r.t. overnight. The mixture was concentrated, and the residue was dissolved in EA (50 mL). This solution was cooled to 0° C. and H$_2$O$_2$(30%, 5 mL) was added. The mixture was stirred at r.t. for 10 min and then extracted with EtOAc (50 mL×2). The combined organic extracts were dried over Na$_2$SO$_4$ and concentrated under reduced pressure. The residue was purified by flash column chromatography on silica gel (0→30% EtOAc in PE) to give ethyl 5-ethyl-1,2-thiazole-3-carboxylate (0.75 g, 53%) as a white solid. LC/MS (ESI): m/z=186 [M+H]$^+$.

Synthesis of 1-(5-bromo-1-ethyl-1H-pyrazol-4-yl)ethanone

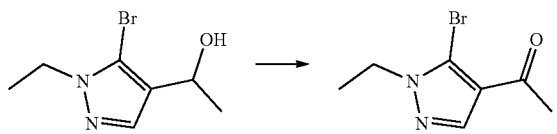

To a solution of 1-(5-bromo-1-ethyl-1H-pyrazol-4-yl) ethanol (9.28 g, 42.4 mmol) in DCM (50 mL) was added DMP (21.5 g, 50.8 mmol) portion-wise at 0° C. over 10 min. After the addition, the mixture was stirred at 0° C. for another 10 min. The mixture was adjusted to pH 8 with sat. NaHCO$_3$ and then extracted with EA (100 mL×3). The combined organic layers were dried over Na$_2$SO$_4$, filtered, and concentrated in vacuo. The residue was purified by column chromatography on silica gel (20% EtOAc in PE) to give 1-(5-bromo-1-ethyl-1H-pyrazol-4-yl)ethanone as light-yellow oil (8.6 g, yield: 93%). LC/MS ESI (m/z): 217 [M+H]$^+$.

Synthesis of 4-bromo-3-methyl-1-(propan-2-yl)-1H-pyrazole-5-carbonitrile

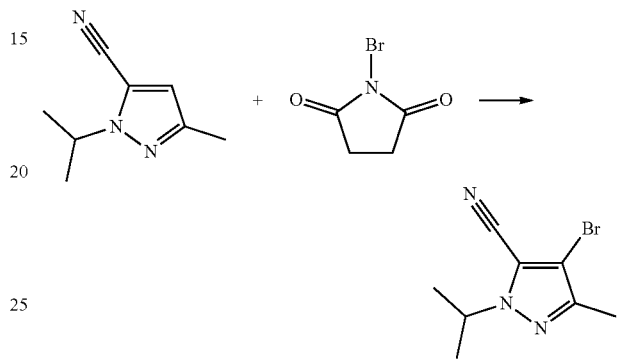

A mixture of 3-methyl-1-(propan-2-yl)-1H-pyrazole-5-carbonitrile (470 mg, 3.15 mmol), TFA (0.25 mL, 3.4 mmol) and NBS (673 mg, 3.78 mmol) in MeCN (20 mL) was stirred at r.t. for 1 h. The reaction mixture was diluted with EtOAc (30 mL), washed with sat. Na$_2$S$_2$O$_3$ (20 mL), dried over Na$_2$SO$_4$, filtered, and concentrated to dryness. The residue was purified by flash chromatography on silica gel (25% EtOAc in PE) to give 4-bromo-3-methyl-1-(propan-2-yl)-1H-pyrazole-5-carbonitrile (460 mg, 64% yield) as a light-yellow solid. LC/MS (ESI) m/z: 228 [M+H]$^+$.

Synthesis of 5-bromo-N-methoxy-N-methylisothiazole-4-carboxamide

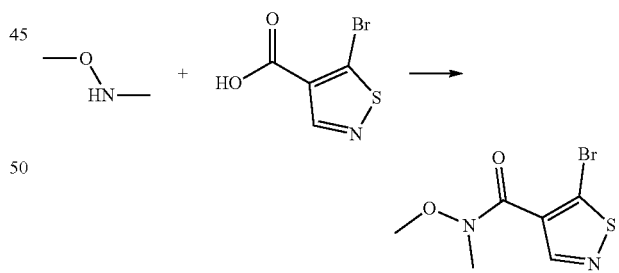

To a solution of 5-bromoisothiazole-4-carboxylic acid (700 mg, crude) in DCM (15 mL), were added HATU (1.6 g, 4.4 mmol), TEA (1.0 g, 10 mmol) and N,O-dimethylhydroxylamine hydrochloride (427 mg, 4.40 mmol). After stirring at 25° C. for 16 h, the reaction was diluted with DCM. The resulting mixture was washed with H$_2$O, and then brine. The organic layer was dried over anhydrous Na$_2$SO$_4$, filtered, and concentrated under vacuum. The residue was purified by silica gel column chromatography, (0→17% EtOAc in PE) to give 5-bromo-N-methoxy-N-methylisothiazole-4-carboxamide (220 mg, 14% yield over 2 steps) as a yellow oil. LC/MS ESI (m/z): 251 [M+H]$^+$.

5-ethyl-N-methoxy-N-methylisoxazole-3-carboxamide

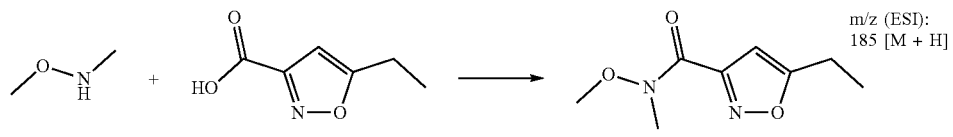

m/z (ESI): 185 [M + H]

Synthesis of 3-bromo-5-fluoro-2-(trimethylstannyl)pyridine

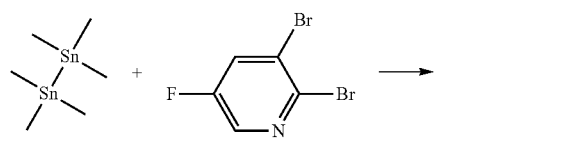

A mixture of 2,3-dibromo-5-fluoropyridine (1.0 g, 3.9 mmol), hexamethyldistannane (1.35 g, 4.12 mmol) and Pd(PPh$_3$)$_4$(0.23 g, 0.20 mmol) in toluene (50 mL) was heated to 110° C. under N$_2$ for 16 h. The mixture was concentrated, diluted with EtOAc (50 mL), washed with brine (30 mL), dried over anhydrous Na$_2$SO$_4$ and concentrated. The residue was purified by neutral Al$_2$O$_3$ chromatography (100% petroleum ether) to afford 3-bromo-5-fluoro-2-(trimethylstannyl)pyridine (1.2 g, 90% yield) as a colorless oil. LC/MS (ESI) m/z: 340 [M+H]$^+$.

Synthesis of methyl 3-(2-hydroxyethyl)-1-methyl-1H-pyrazole-5-carboxylate

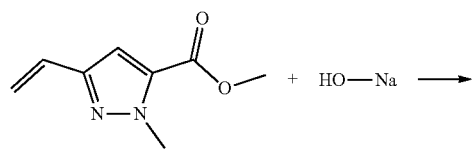

Under a nitrogen atmosphere, 9-borabicyclo[3.3.1] nonane (31.34 mL, 15.67 mmol) was added to a solution of methyl 3-ethenyl-1-methyl-1H-pyrazole-5-carboxylate (1.50 g, 9.04 mmol) in dioxane (50 mL) at 0° C., and the mixture was stirred at 100° C. for 1 h. Water (10 mL), aq. sodium hydroxide (3.50 mL, 31.0 mmol, 10% in water) and hydrogen peroxide (3.2 mL, 10% in water) were successively added dropwise to the reaction mixture at 0° C. The mixture was stirred at r.t. for 0.5 h, then water (20 mL) and ethyl acetate (30 mL) were added. The layers were separated, and the aq. layer was extracted with ethyl acetate (20 mL). The combined organic layers were washed with brine (20 mL), dried over anhydrous sodium sulfate, filtered, and concentrated in vacuo. The residue was purified by column chromatography on silica gel (1.6% MeOH in DCM) to afford methyl 3-(2-hydroxyethyl)-1-methyl-1H-pyrazole-5-carboxylate (1.10 g, 66%) as a white solid. LC/MS ESI (m/z): 185 [M+H]$^+$.

Synthesis of methyl 2-chloro-4-methoxynicotinate

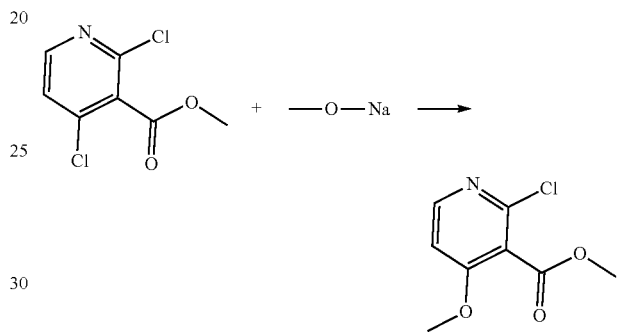

A mixture of methyl 2,4-dichloropyridine-3-carboxylate (2.40 g, 11.6 mmol) and sodium methoxide (2.06 g, 11.6 mmol) in MeOH (20 mL) was refluxed under N$_2$ for 16 h. The mixture was filtered through celite and the filtrate was diluted with EA (30 mL). This solution was washed with brine, dried over anhydrous Na$_2$SO$_4$, and concentrated. The residue was purified by column chromatography on silica gel (0→30% EA in PE) to give methyl 2-chloro-4-methoxynicotinate (1.70 g, yield: 72%) as a white solid. LC/MS (ESI) (m/z): 202 [M+H]$^+$.

Synthesis of potassium (E)-3-cyano-1-ethoxy-1-oxopent-2-en-2-olate

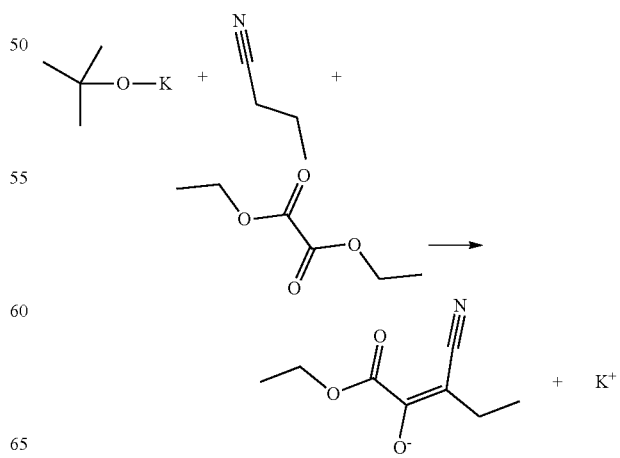

To a stirred solution of t-BuOK (8.10 g, 72.4 mmol) and 18-crown-6 (1.91 g, 7.24 mmol) in THF (60 mL) was added a solution of diethyl oxalate (10.57 g, 72.35 mmol) in THF (10 mL) via syringe at 0° C. under $N_2$. The reaction was heated to 60° C., and then a solution of butyronitrile (5.00 g, 72.3 mmol) in THF (10 mL) was added and stirring continued at 60° C. for 30 min. The reaction was evaporated to dryness to give crude potassium (E)-3-cyano-1-ethoxy-1-oxopent-2-en-2-olate (14.20 g, yield: 93%) as a yellow solid. LC/MS ESI (m/z): 170 [M+H]$^+$.

Synthesis of 2-(2-bromo-4-fluorophenyl)-1H-imidazole

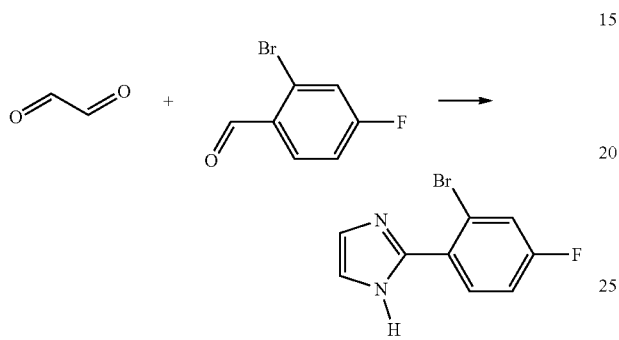

To a mixture of 2-bromo-4-fluorobenzaldehyde (50.00 g, 246.3 mmol) and oxalaldehyde (52.56 mL, 492.6 mmol, 40% in $H_2O$) in EtOH (200 mL) was added $NH_3H_2O$ (113.8 mL, 738.9 mmol, 25% in $H_2O$) dropwise under $N_2$ atmosphere at r.t. After the addition, the resulting mixture was degassed, heated to 50° C. and stirred for 72 h. The reaction mixture was concentrated in vacuo and the residue was diluted with EA, washed with brine, dried over anhydrous $Na_2SO_4$ and concentrated in vacuo. The residue was purified by flash column chromatography on silica gel (PE/EA=3:1 to 2:1) to afford 2-(2-bromo-4-fluorophenyl)-1H-imidazole (35.0 g, 59% yield) as a yellow solid.
LC/MS ESI (m/z): 241 [M+H]$^+$.

| 2-(4-fluoro-2-iodophenyl)-4-methyl-1H-imidazole |
|---|
| 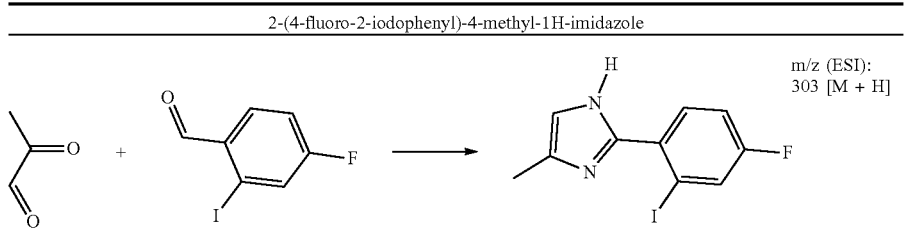 m/z (ESI): 303 [M + H] |

Synthesis of [5-bromo-1-(cyclopropylmethyl)-3-methyl-1H-pyrazol-4-yl]methanol

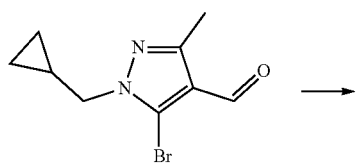

-continued

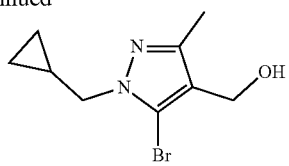

To a solution of 5-bromo-1-(cyclopropylmethyl)-3-methyl-1H-pyrazole-4-carbaldehyde (1.80 g, 7.41 mmol) in EtOH (15 mL) was added $NaBH_4$ (0.33 g, 9.6 mmol) at 0° C. This mixture was stirred at 0° C. for 1 h. The reaction mixture was concentrated, diluted with $H_2O$ (10 mL) and extracted with EtOAc (15 mL×3). The combined organic solutions were washed with brine (15 mL), dried over anhydrous Na$_2$SO$_4$, and then concentrated to give crude (5-bromo-1-(cyclopropylmethyl)-3-methyl-1H-pyrazol-4-yl)methanol (1.4 g, yield: 77%) as a light-yellow solid. LC-MS (ESI) m/z: 245 [M+H]$^+$.

The following intermediates were synthesized using a similar experimental protocol:

| [1-(4-fluoro-2-iodophenyl)-1H-pyrazol-5-yl]methanol |
|---|

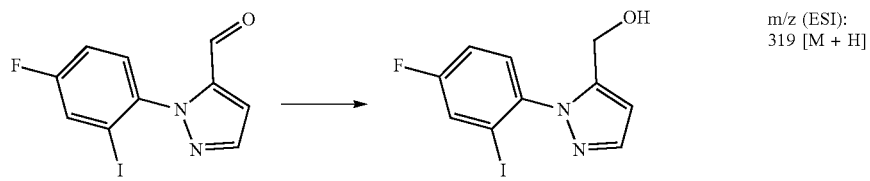

m/z (ESI): 319 [M + H]

| 3-(hydroxymethyl)-1-((2-(trimethylsilyl)ethoxy)methyl)-1H-pyrazole-5-carbonitrile |
|---|

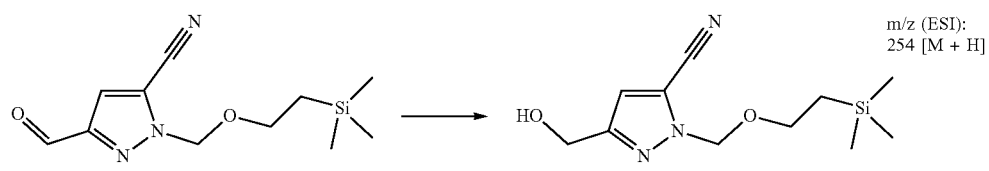

m/z (ESI): 254 [M + H]

Synthesis of 2-(2-bromo-5-fluorophenyl)-1,3-dioxolane

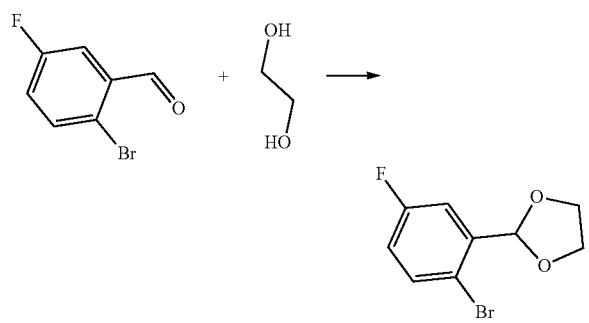

To a mixture of 2-bromo-5-fluorobenzaldehyde (10.0 g, 49.3 mmol) and ethane-1,2-diol (9.16 g, 148 mmol) in toluene (100 mL) at 25° C. was added 4-methylbenzenesulfonic acid (1.69 g, 9.87 mmol) in one portion under an N$_2$ atmosphere. After the addition, the mixture was stirred at 120° C. for 16 h. The resulting mixture was cooled to 2-5° C., and then diluted with water and EtOAc. The organic layer was separated, washed with brine, dried over anhydrous Na$_2$SO$_4$, filtered and concentrated in vacuo. The residue was purified by column chromatography on silica gel (20-30% EtOAc in PE) to give the target product as a yellow oil (10.0 g, yield: 82%). LC/MS ESI (m/z): 247 [M+H]$^+$.

Synthesis of 5-(cyclopropylmethyl)-3-iodo-1-methyl-1H-pyrazole

To a stirred solution of cyclopropyl(3-iodo-1-methyl-1H-pyrazol-5-yl)methanol (1.0 g, 3.6 mmol) in DCM (18 mL) was added TES (4.20 g, 36.0 mmol) and TFA (2.7 mL, 36 mmol) at 0° C. The reaction was stirred at r.t. overnight. The reaction was concentrated to dryness. The residue was purified by flash chromatography (0→10% EtOAc in PE) to give 5-(cyclopropylmethyl)-3-iodo-1-methyl-1H-pyrazole (0.60 g, 51% yield) as a yellow solid. LC/MS (ESI) (m/z): 263 [M+H]$^+$.

The following intermediates were synthesized using a similar experimental protocol:

| methyl 3-(cyclopropylmethyl)-1-methyl-1H-pyrazole-5-carboxylate |
|---|

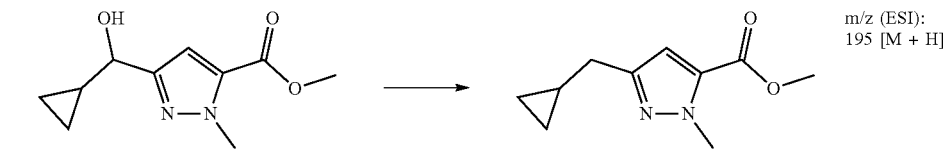

m/z (ESI): 195 [M + H]

Synthesis of (5-ethyl-1,2-thiazol-3-yl)methanol

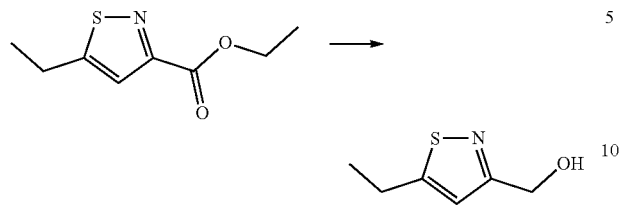

To a solution of ethyl 5-ethyl-1,2-thiazole-3-carboxylate (750 mg, 4.05 mmol) in THF (15 mL) was added DIBAL-H (13.5 mL, 20.2 mmol) at 0° C. The reaction mixture was stirred at r.t. for 2 h and then quenched by sequential addition of MeOH (0.5 mL) and then water (15 mL). The resulting mixture was extracted with EtOAc (2×50 mL). The combined organic extracts were dried over $Na_2SO_4$ and concentrated under reduced pressure. The residue was purified by flash column chromatography on silica gel (0→50% EtOAc in PE) to give (5-ethyl-1,2-thiazol-3-yl)methanol (510 mg, 88%) as a colorless oil. LC/MS (ESI): m/z=144 $[M+H]^+$.

The following intermediates were synthesized using a similar experimental protocol:

(1-((2-(trimethylsilyl)ethoxy)methyl)-1H-pyrazole-3,5-diyl)dimethanol

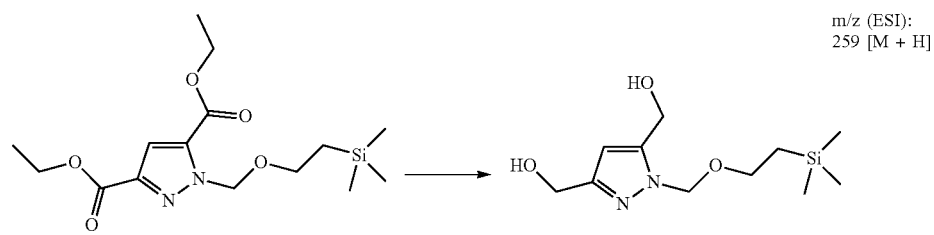

m/z (ESI): 259 [M + H]

(1-(4-fluoro-2-iodophenyl)-1H-imidazol-5-yl)methanol

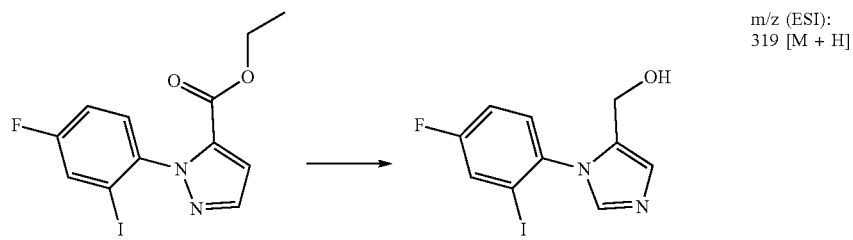

m/z (ESI): 319 [M + H]

(3-(2-bromo-4-fluorophenyl)isothiazol-4-yl)methanol

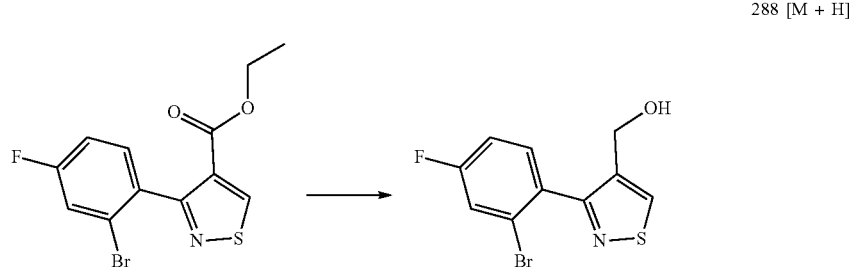

m/z (ESI): 288 [M + H]

(3-(cyclopropylmethyl)-1-methyl-1H-pyrazol-5-yl)methanol

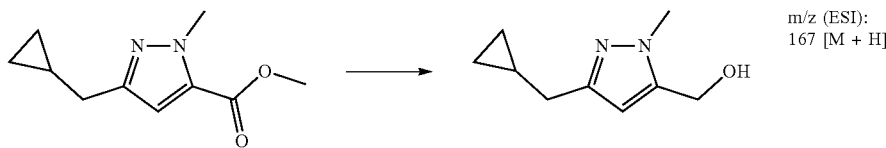

m/z (ESI): 167 [M + H]

Synthesis of
5-fluoro-2-(1H-imidazol-2-yl)benzaldehyde

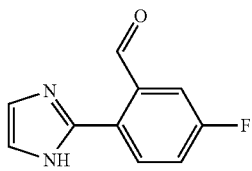 [SMILES: O=Cc1cc(F)ccc1-c1ncc[nH]1]

n-BuLi (21.54 mL, 53.86 mmol, 2.5 N) and N,N-dimethylformamide (6.25 mL, 80.79 mmol) were added dropwise simultaneously via two different syringes over 30 min to a solution of 2-(2-bromo-4-fluorophenyl)-1-{[2-(trimethylsilyl)ethoxy]methyl}-1H-imidazole (10.00 g, 26.93 mmol) in anhydrous THF (20 mL) while maintaining the internal temperature at −78° C. After the addition, the mixture was stirred at −78° C. for 10 min before quenching with sat. aq. NH$_4$Cl. The resulting mixture was warmed slowly to r.t. and acidified to pH 6 with 2 N HCl. The mixture was then extracted with ether (150 mL). The organic layer was washed with water and brine, dried over MgSO$_4$, filtered, and concentrated in vacuo. The residue was purified by flash column chromatography on silica-gel (30% EtOAc in PE) to afford 5-fluoro-2-(1-{[2(trimethylsilyl)ethoxy]methyl}-1H-imidazol-2-yl)benzaldehyde (6.0 g, 70% yield) as an orange oil. LC/MS ESI (m/z): 321 [M+H]$^+$.

To a flask of TFA (209 mL) was added 5-fluoro-2-(1-{[2(trimethylsilyl)ethoxy]methyl}-1H-imidazol-2-yl)benzaldehyde (45.0 g, 141 mmol) portion-wise at 20° C. The resulting solution was stirred at r.t. for 6 h, and the reaction mixture was concentrated in vacuo to remove most of the TFA. The residue was poured slowly into sat. aq. NaHCO$_3$ at 0° C. The resulting mixture was then extracted with EA (3×200 mL), and the combined extracts were dried over anhydrous Na$_2$SO$_4$, and concentrated in vacuo. The residue was purified by flash column chromatography on silica-gel (0→3% MeOH in DCM) to give 5-fluoro-2-(1H-imidazol-2-yl)benzaldehyde (23.0 g, 86% yield) as a white solid. LC/MS ESI (m/z): 191 [M+H]$^+$.

Synthesis of methyl 5-(cyclopropylmethyl)-1-methyl-1H-pyrazole-3-carboxylate

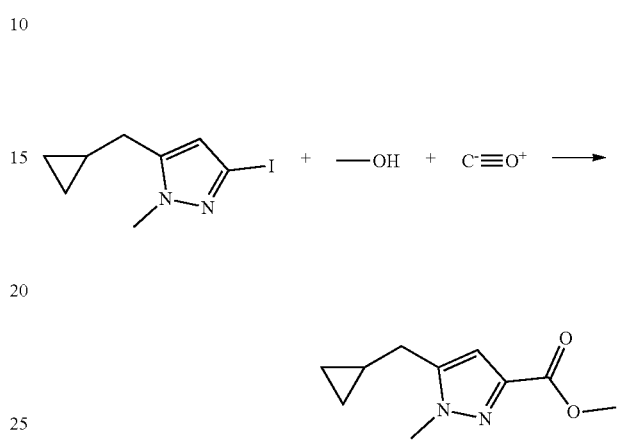

A mixture of 5-(cyclopropylmethyl)-3-iodo-1-methyl-1H-pyrazole (2.50 g, 9.54 mmol), triethylamine (2.90 g, 28.6 mmol), MeOH (50 mL), and Pd(dppf)Cl$_2$ (698 mg, 0.950 mmol) was thrice degassed under a CO atmosphere and then stirred under a CO balloon at 60° C. for 12 h. The mixture was cooled to r.t., filtered, and concentrated to dryness. The residue was purified by column chromatography on silica gel (PE:EA=5:1) to give methyl 5-(cyclopropylmethyl)-1-methyl-1H-pyrazole-3-carboxylate (1.50 g, 81% yield) as a brown oil. LC/MS (ESI) (m/z): 195.1 [M+H]$^+$.

The following intermediates were synthesized using a similar experimental protocol:

| methyl 2-(5-((4-bromo-3-ethyl-1-methyl-1H-pyrazol-5-yl)methyl)-3-methyl-1H-pyrazol-1-yl)-5-fluorobenzoate |
|---| m/z (ESI): 435 [M + H]

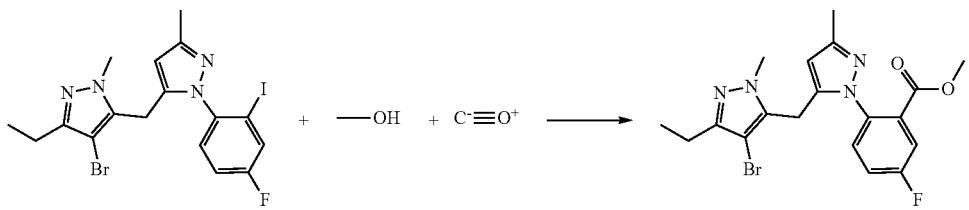

Synthesis of 1-((4-bromothiazol-5-yl)methyl)-1H-imidazole-4-carbonitrile

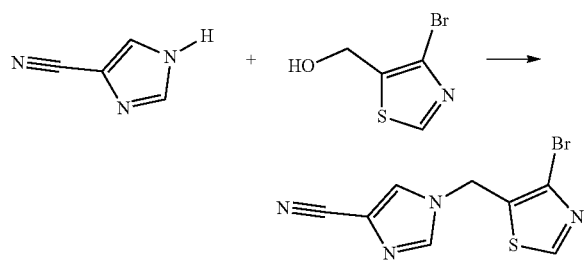

To a mixture of (4-bromo-1,3-thiazol-5-yl)methanol (480 mg, 2.40 mmol), 1H-imidazole-4-carbonitrile (276 mg, 2.90 mmol) and triphenylphosphine (1.3 g, 4.9 mmol) in dry THF (30 mL) was added DIAD (0.98 mL, 4.9 mmol) dropwise at 0° C. over 10 min. After the addition, the reaction mixture was stirred at r.t. for 2 h. The mixture was concentrated in vacuo and the residue was purified by flash chromatography on silica gel (30% EtOAc in PE) to give 1-((4-bromothiazol-5-yl)methyl)-1H-imidazole-4-carbonitrile (220 mg, yield: 33%) as a light-yellow solid. LC/MS ESI (m/z): 269 [M+H]$^+$.

The following intermediates were synthesized using a similar experimental protocol:

1-((4-bromopyridin-3-yl)methyl)-1H-imidazole-4-carbonitrile

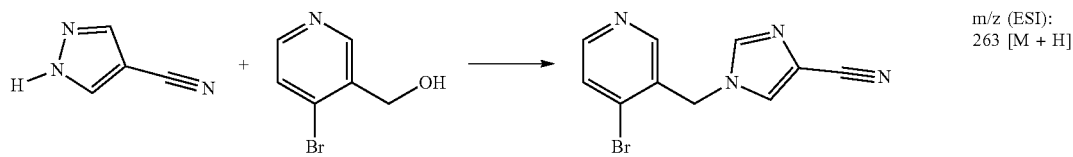

m/z (ESI): 263 [M + H]

1-((2-bromopyridin-3-yl)methyl)-1H-imidazole-4-carbonitrile

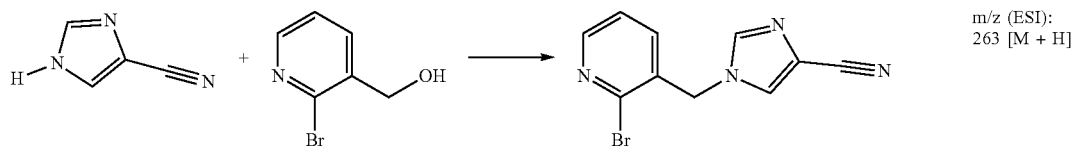

m/z (ESI): 263 [M + H]

1-((2-bromopyridin-3-yl)methyl)-1H-pyrazole-4-carbonitrile

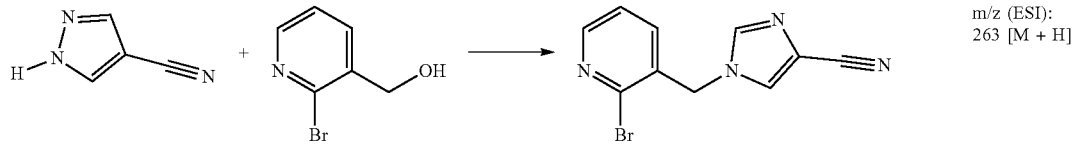

m/z (ESI): 263 [M + H]

1-((2-bromopyridin-3-yl)methyl)-2-methyl-1H-imidazole-4-carbonitrile

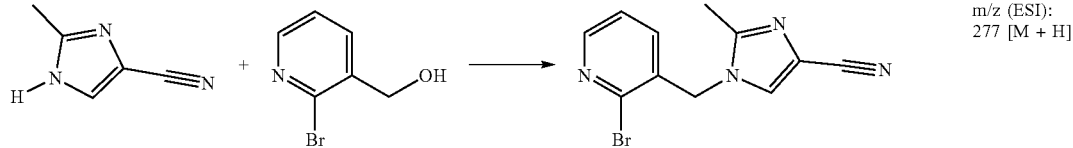

m/z (ESI): 277 [M + H]

1-{[1-(4-fluoro-2-iodophenyl)-1H-pyrazol-5-yl]methyl}-1H-imidazole-4-carbonitrile

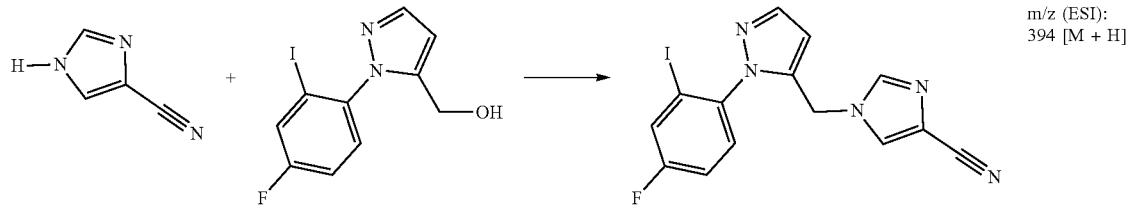

m/z (ESI): 394 [M + H]

| 1-[(5-iodo-1-methyl-1H-pyrazol-4-yl)methyl]-1H-pyrazole-4-carbonitrile |
|---|

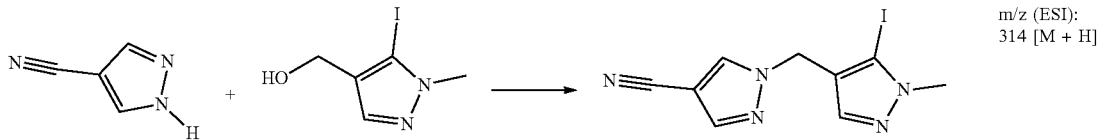

m/z (ESI): 314 [M + H]

Synthesis of
5-(2-bromo-4-fluorophenyl)-1,3,4-oxathiazol-2-one

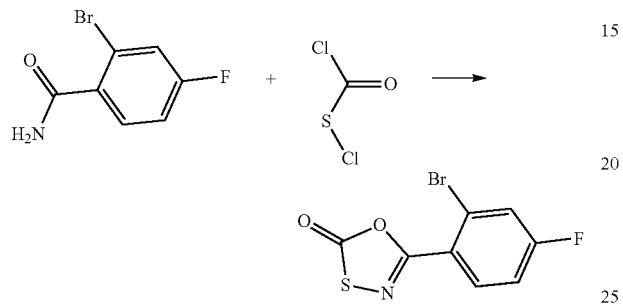

To a solution of 2-bromo-4-fluorobenzamide (4.43 g, 20.3 mmol) in toluene (50 mL) was added chloro(chlorosulfanyl)methanone (2.53 mL, 30.5 mmol). The mixture was stirred at 100° C. for 2 h, concentrated in vacuo, and the residue was purified by column chromatography on silica gel (0→50% EtOAc in PE) to give 5-(2-bromo-4-fluorophenyl)-1,3,4-oxathiazol-2-one (3.90 g, 69% o yield) as a white solid. LC/MS (ESI) m/z: 276 [M+H]$^+$.

| 5-(4-fluoro-2-iodophenyl)-1,3,4-oxathiazol-2-one |
|---|

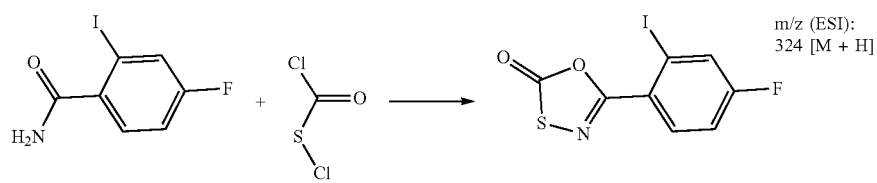

m/z (ESI): 324 [M + H]

Synthesis of 5-ethyl-1,2-thiazole-3-carbaldehyde

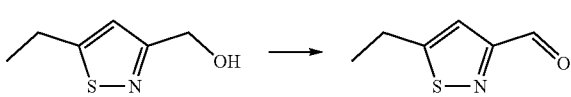

To a solution of (5-ethyl-1,2-thiazol-3-yl)methanol (510 mg, 3.56 mmol) in DCM (15 mL) was added MnO$_2$ (3.10 g, 35.6 mmol). The reaction mixture was stirred at r.t. for 20 h. After filtration, the filtrate was concentrated under reduced pressure to give 5-ethyl-1,2-thiazole-3-carbaldehyde (120 mg, 24%) as a pale-yellow oil. LC/MS (ESI): m/z=142 [M+H]$^+$.

The following intermediates were synthesized using a similar experimental protocol:

| 1-(4-fluoro-2-iodophenyl)-1H-imidazole-5-carbaldehyde |
|---|

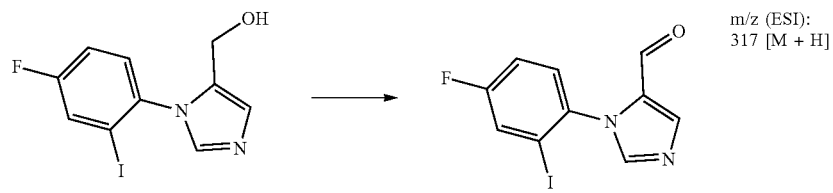

m/z (ESI): 317 [M + H]

| 3-(2-bromo-4-fluorophenyl)-1,2-oxazole-4-carbaldehyde |
|---|
| 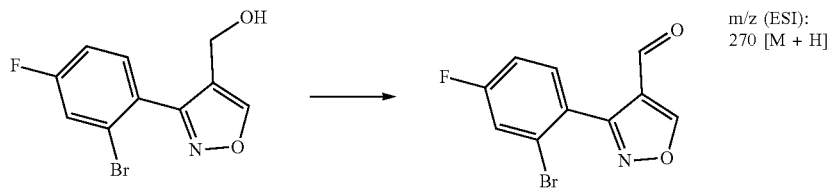 m/z (ESI): 270 [M + H] |

| 3-(2,2-difluoroethyl)-1-methyl-1H-pyrazole-5-carbaldehyde |
|---|
| 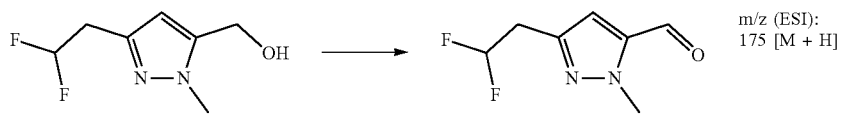 m/z (ESI): 175 [M + H] |

Synthesis of methyl 3-(2,2-difluoroethyl)-1-methyl-1H-pyrazole-5-carboxylate

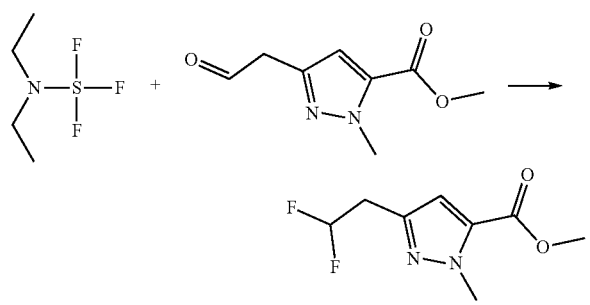

Under a nitrogen atmosphere, diethylaminosulfur trifluoride (0.40 mL, 3.0 mmol) was slowly added to a crude solution of methyl 1-methyl-3-(2-oxoethyl)-1H-pyrazole-5-carboxylate (1.5 g, 2.9 mmol) in DCM (20 mL) at 0° C. The reaction was stirred at this temperature for 0.5 h, then quenched with sat. aq. NaHCO₃ (50 mL). The resulting mixture was extracted with DCM (3×10 mL). The combined extracts were washed sequentially with water (1×30 mL) and brine (30 mL), dried over sodium sulfate, filtered, and concentrated under reduced pressure. The residue was purified by prep-TLC (0→50% EtOAc in PE) to provide methyl 3-(2,2-difluoroethyl)-1-methyl-1H-pyrazole-5-carboxylate (500 mg, 85%) as a white solid. LC/MS ESI (m/z): 205 [M+H]⁺.

The following intermediates were synthesized using a similar experimental protocol:

| 2-bromo-3-((4-(difluoromethyl)-1H-pyrazol-1-yl)methyl)-5-fluoropyridine |
|---|
| 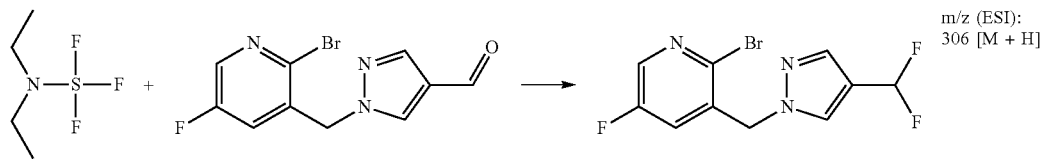 m/z (ESI): 306 [M + H] |

| (R)-1-(2-(1-(benzyloxy)ethyl)-4-fluorophenyl)-3-(difluoromethyl)-1H-pyrazole |
|---|
| 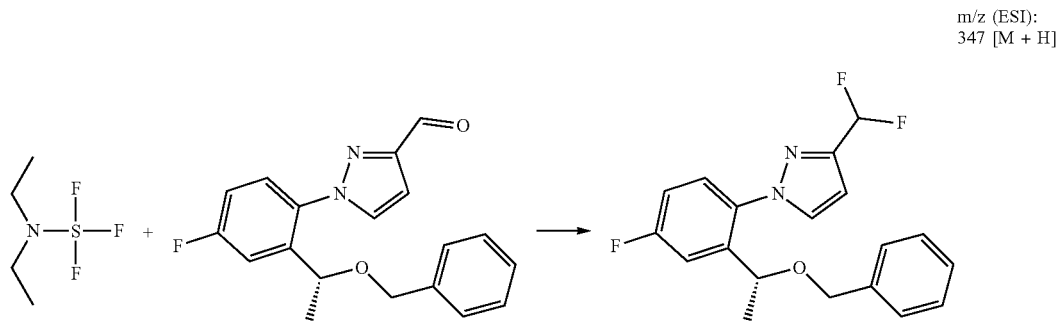 m/z (ESI): 347 [M + H] |

Synthesis of (R)-1-(5-fluoro-2-(1H-pyrazol-1-yl)phenyl)ethan-1-ol

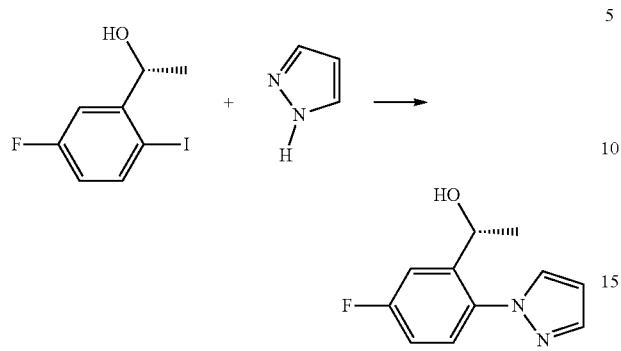

A mixture of methyl[2-(methylamino)ethyl]amine (0.41 mL, 3.8 mmol), (1R)-1-(5-fluoro-2-iodophenyl)ethan-1-ol (5.0 g, 19 mmol), 1H-pyrazole (1.09 mL, 22.6 mmol), $K_2CO_3$ (5.19 g, 37.6 mmol) and CuI (60 mg, 1.9 mmol) in NMP (150 mL) in a sealed tube was stirred at 120° C. under $N_2$ for 18 h. The reaction mixture was poured into water (100 mL) and then extracted with EtOAc (100 mL×2). The combined organic layers were washed with brine, dried over anhydrous $Na_2SO_4$ and concentrated. The residue was purified by column chromatography (silica gel, 1→10% ethyl acetate in petroleum ether) to afford (1R)-1-[5-fluoro-2-(1H-pyrazol-1-yl)phenyl]ethan-1-ol (3.6 g, 93%) as a yellow oil. LC/MS (ESI) m/z: 207.1 [M+H]$^+$.

The following intermediates were synthesized using a similar experimental protocol:

(R)-1-(2-(3-chloro-1H-pyrazol-1-yl)-5-fluorophenyl)ethan-1-ol

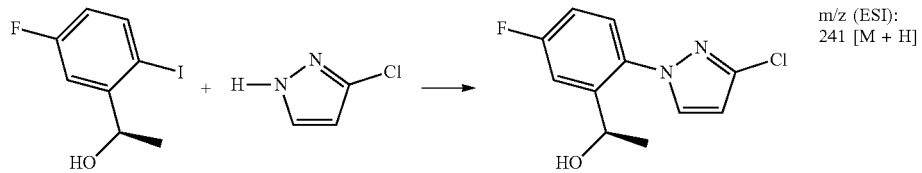

m/z (ESI): 241 [M + H]

(R)-1-(5-fluoro-2-(3-methoxy-1H-pyrazol-1-yl)phenyl)ethan-1-ol

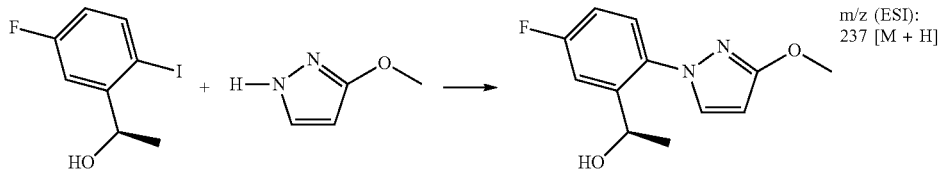

m/z (ESI): 237 [M + H]

Synthesis of ethyl 5-cyclobutyl-1-methyl-1H-pyrazole-3-carboxylate

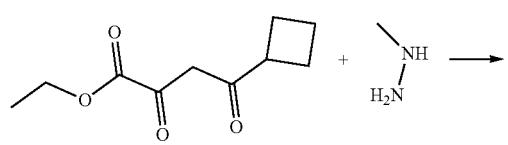

-continued

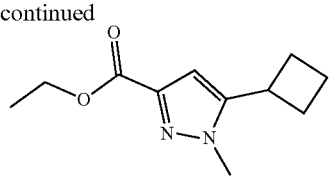

To a solution of ethyl 4-cyclobutyl-2,4-dioxobutanoate (6.2 g, 31 mmol) in acetic acid (15 mL) was added methylhydrazine (3.6 g, 31 mmol) and the resulting mixture was stirred at 100° C. for 3 h. After 3 h, the reaction mixture was cooled to r.t. and concentrated in vacuo to remove the solvent to give the residue, which was diluted with toluene (20 mL) and concentrated in vacuo. The residue was purified by silica gel chromatography (0→50% EA in PE) to give ethyl 5-cyclobutyl-1-methyl-1H-pyrazole-3-carboxylate (4.2 g, 20%) as a yellow oil. LC/MS ESI (m/z): 209 [M+H]⁺.

Synthesis of 3-ethyl-5-(((tetrahydro-2H-pyran-2-yl)oxy)methyl)isoxazole

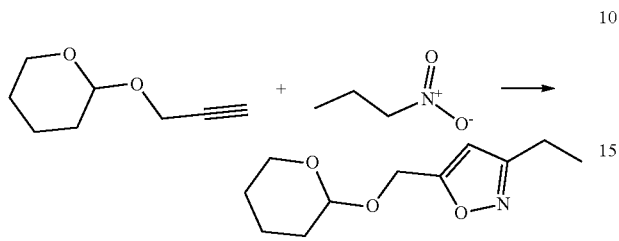

To a stirred solution of 2-(prop-2-yn-1-yloxy)tetrahydro-2H-pyran (5.00 g, 36.7 mmol) and 1-nitropropane (7.00 g, 78.6 mmol) in toluene (40 mL) was added phenyl isocyanate (17.0 mL, 119 mmol), followed by the addition of triethylamine (2.94 mL, 21.2 mmol). The reaction mixture was heated to 120° C. and stirred for 24 h. After cooling to r.t., the reaction mixture was quenched with 1 mL of water, and the mixture was stirred at r.t. for 1 h. The precipitates were removed by filtration, and the filtrate was concentrated. The residue was purified by column chromatography on silica gel (0→20% EtOAc in PE) to give 3-ethyl-5-(((tetrahydro-2H-pyran-2-yl)oxy)methyl)isoxazole (10.0 g, 61% yield) as a yellow syrup. LC/MS ESI (m/z): 212 [M+H]⁺.

The following intermediates were synthesized using a similar experimental protocol: IDC-1074 TRE 3-(cyclopropylmethyl)-5-(((tetrahydro-2H-pyran-2-yl)oxy)methyl)isoxazole

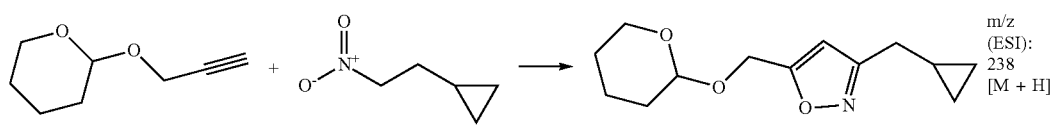

m/z (ESI): 238 [M + H]

3-(2-((tert-butyldimethylsilyl)oxy)ethyl)-5-(((tetrahydro-2H-pyran-2-yl)oxy)methyl)isoxazole

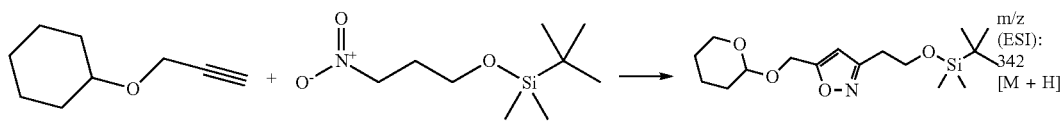

m/z (ESI): 342 [M + H]

Synthesis of (2-(3-chloro-1H-pyrazol-1-yl)-5-fluorophenyl)methanol

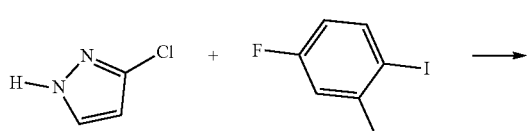

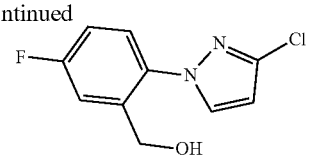

-continued

To a solution of (5-fluoro-2-iodophenyl)methanol (25.0 g, 99.2 mmol) in toluene (250 mL) were added 3-chloro-1H-pyrazole (11.2 g, 109 mmol), K₂CO₃ (27.4 g, 198.4 mmol) and CuI (1.9 g, 9.9 mmol). The reaction was stirred at 120° C. under N₂ for 12 h. The reaction was filtered and concentrated. The residue was purified by flash chromatography (5→25% EtOAc in PE) to give (2-(3-chloro-1H-pyrazol-1-yl)-5-fluorophenyl)methanol (21.1 g, 85% yield) as a white solid.
LC/MS (ESI) (m/z): 227 [M+H]⁺.

Synthesis of 1-[(2-bromopyridin-3-yl)methyl]-1H-1,2,3-triazole-4-carbonitrile

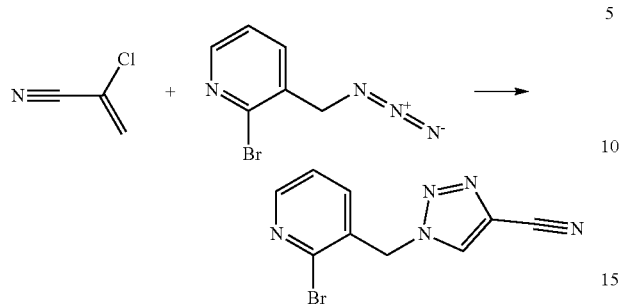

A mixture of 3-(azidomethyl)-2-bromopyridine (955 mg, 4.48 mmol) and 2-chloroprop-2-enenitrile (0.90 mL, 11 mmol) in water (30 mL) was stirred at 80° C. for 12 h. The reaction was cooled to r.t., extracted with DCM (20 mL), washed with sat. brine (20 mL), dried over anhydrous $Na_2SO_4$, filtered and concentrated. The residue was purified by flash chromatography (silica gel, 0→100% EA in PE) to give 1-[(2-bromopyridin-3-yl)methyl]-1H-1,2,3-triazole-4-carbonitrile (639 mg, 54% yield) as a white solid. LC/MS (ESI) m/z: 264 [M+H]$^+$.

The following intermediates were synthesized using a similar experimental protocol:

1-((3-iodo-1-methyl-1H-pyrazol-4-yl)methyl)-1H-1,2,3-triazole-4-carbonitrile

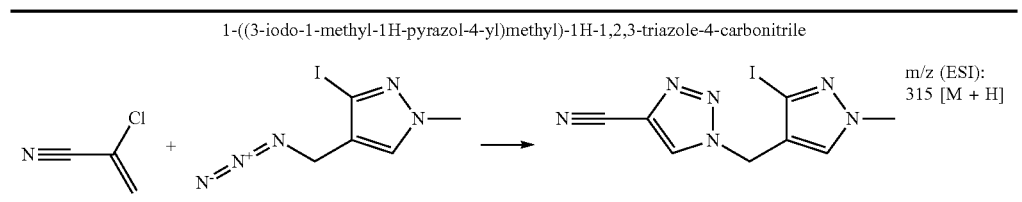

m/z (ESI): 315 [M + H]

Synthesis of [5-bromo-1-(2-fluoroethyl)-1H-pyrazol-4-yl]methanol

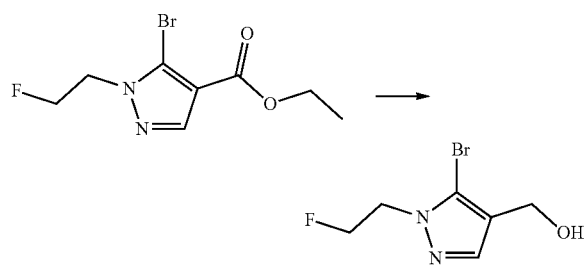

To a solution of ethyl 5-bromo-1-(2-fluoroethyl)-1H-pyrazole-4-carboxylate (3.10 g, 11.3 mmol) in THF (50 mL) was added DIBAL-H (22.6 mL, 22.6 mmol, 1 M in toluene) dropwise at 0° C. over 10 min. After the addition, the resulting solution was stirred at r.t. for another 3 h. After cooling to 0° C., the reaction mixture was treated with EtOAc (100 mL) and 1 N HCl (100 mL), and the organic layer was separated, and the aq. layer was extracted with EtOAc (150 mL). The combined organics were concentrated in vacuo and the residue was purified by flash chromatography (silica gel, 0→50% of EtOAc in PE) to give [5-bromo-1-(2-fluoroethyl)-1H-pyrazol-4-yl]methanol (2.1 g, 83% yield) as a white solid. LC-MS(ESI) found: 223 [M+H]$^+$.

The following intermediates were synthesized using a similar experimental protocol:

(3-(2,2-difluoroethyl)-1-methyl-1H-pyrazol-5-yl)methanol

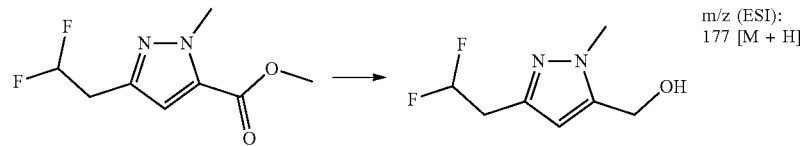

m/z (ESI): 177 [M + H]

Synthesis of 3-bromo-4-[(4-ethylimidazol-1-yl)methyl]-1-methylpyrazole

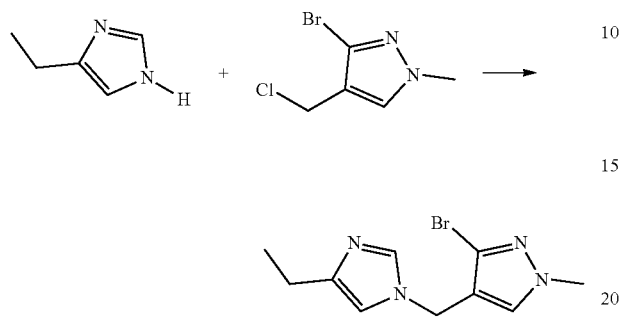

To a stirred mixture of 4-ethyl-1H-imidazole (0.73 g, 7.6 mmol) in DMF (5.00 mL) was added NaH (0.22 g, 9.1 mmol) in portions at 0° C. The resulting mixture was stirred for 30 min at 0° C. To the above mixture was added 3-bromo-4-(chloromethyl)-1-methylpyrazole (1.91 g, 9.11 mmol) in DMF (5 mL) dropwise at 0° C. The resulting mixture was stirred for additional 1 h at r.t., then quenched with H$_2$O. The resulting mixture was purified directly by reverse-phase flash chromatography (C18, 0→40% MeCN in water+1% aq. NH$_3$) to afford 3-bromo-4-[(4-ethylimidazol-1-yl)methyl]-1-methylpyrazole (1.9 g, 93%) as a light brown oil. LC-MS (ESI) m/z: 269 [M+H]$^+$.

Synthesis of (5-bromo-1-(difluoromethyl)-1H-pyrazol-4-yl)methanol

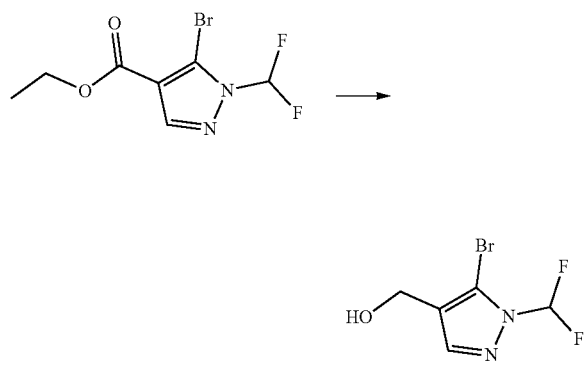

To a solution of ethyl 5-bromo-1-(difluoromethyl)-1H-pyrazole-4-carboxylate (2.00 g, 7.43 mmol) in THF (30 mL) was added DIBAL-H (18.6 mL, 18.6 mmol, 1 M in toluene) at −78° C. over 30 min. During the addition, the internal temperature was monitored to stay below −60° C. The reaction was stirred for 1 h at −78° C., then quenched by slowly adding into aq. HCl (1M) at 0° C. The mixture was extracted with EtOAc twice. The combined extracts were washed with brine, dried over anhydrous Na$_2$SO$_4$, filtered, and concentrated in vacuo. The residue was purified by flash chromatography on silica gel (30% of EtOAc in PE) to give (5-bromo-1-(difluoromethyl)-1H-pyrazol-4-yl)methanol (1.5 g, 89% yield) as a colorless oil. LC/MS ESI (m/z): 227 [M+H]$^+$.

Synthesis of (4-bromooxazol-5-yl)(1-ethyl-1H-pyrazol-4-yl)methanol

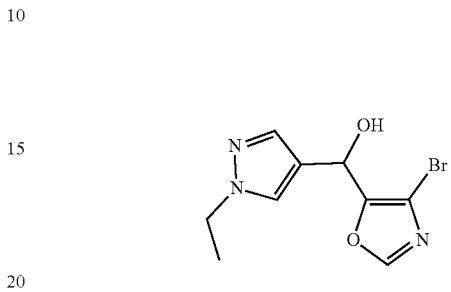

To a solution of (4-bromooxazol-5-yl)methanol (2.90 g, 16.3 mmol) in DCM (5 mL) was added Dess-Martin periodinane (10.4 g, 24.4 mmol). The reaction was stirred at r.t. for 2 h, filtered, and the filtrate was concentrated in vacuo. The residue was purified by flash chromatography (0-30% EtOAc in PE) to give 4-bromooxazole-5-carbaldehyde (2.49 g, 87% yield) as a light-yellow solid.

To a solution of 1-ethyl-4-iodo-1H-pyrazole (3.14 g, 14.2 mmol) in THF (30 mL) was added isopropylmagnesium chloride-lithium chloride complex (13.1 mL, 17.0 mmol, 1.3 M in THF) dropwise at −10° C. The mixture was stirred at r.t. for 1 h, then cooled to −10° C. A solution of 4-bromooxazole-5-carbaldehyde (2.49 g, 14.2 mmol) in 10 mL THF was added dropwise. The ice bath was removed and stirring was continued at r.t. for 1 h. The reaction was quenched with sat. aq. NH$_4$Cl (20 mL), and then extracted with EA (3×20 mL). The combined organic phases were washed with water (20 mL) and brine (20 mL), dried over anhydrous Na$_2$SO$_4$, filtered and concentrated in vacuo. The residue was purified by flash chromatography (0→10% MeOH in DCM) to give (4-bromooxazol-5-yl)(1-ethyl-1H-pyrazol-4-yl)methanol (1.21 g, 31% yield) as a light-yellow solid. LC/MS ESI (m/z): 272 [M+H]$^+$.

Synthesis of (E)-1-(5-bromo-1-ethyl-1H-pyrazol-4-yl)-3-(dimethylamino)prop-2-en-1-one

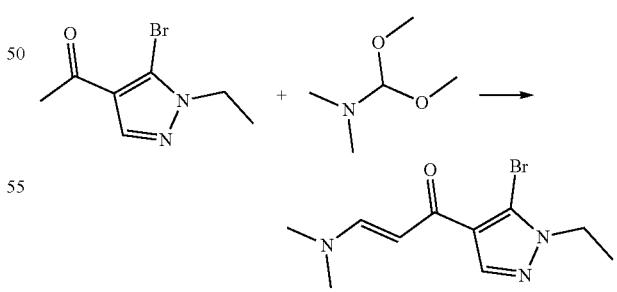

A mixture of 1-(5-bromo-1-ethyl-1H-pyrazol-4-yl)ethan-1-one (4.00 g, 18.4 mmol) and DMF-DMA (80 mL) was stirred at 110° C. for 12 h. After cooling to r.t., the mixture was concentrated in vacuo by oil pump to obtain crude (E)-1-(5-bromo-1-ethyl-1H-pyrazol-4-yl)-3-(dimethylamino)prop-2-en-1-one as a light-yellow solid (2.6 g, yield: 51%). LC/MS ESI (m/z): 272 [M+H]$^+$.

The following intermediates were synthesized using a similar experimental protocol:

(E)-N'-(4-fluoro-2-iodobenzoyl)-N,N-dimethylformohydrazonamide

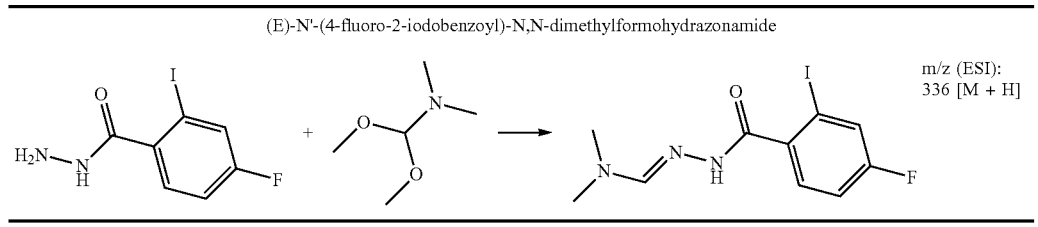

m/z (ESI): 336 [M + H]

Synthesis of 5-((4-bromothiazol-5-yl)methyl)-1-methyl-1H-pyrazole-3-carbonitrile

Synthesis of (5-bromoisothiazol-4-yl)(1-ethyl-1H-1,2,3-triazol-4-yl)methanol

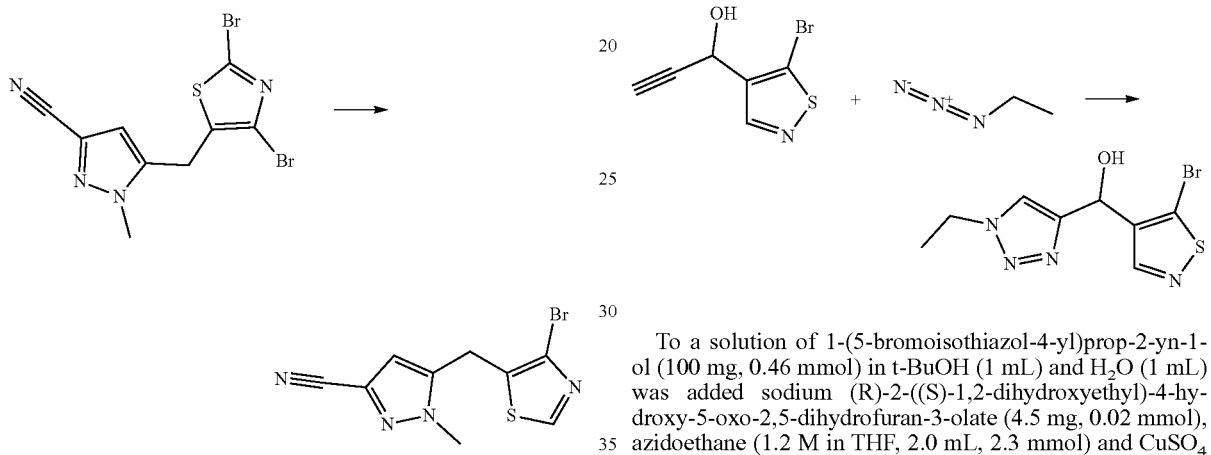

A mixture of 5-[(dibromo-1,3-thiazol-5-yl)methyl]-1-methyl-1H-pyrazole-3-carbonitrile (0.700 g, 1.93 mmol), Pd/C (0.07 g, 10% wt) in MeOH (20 mL) was stirred at 50° C. for 2 h under 1 atm of $H_2$. The reaction mixture was filtered, and the filtrate was concentrated in vacuo. The residue was purified by flash chromatography (0→25% EA in PE) to give 5-((4-bromothiazol-5-yl)methyl)-1-methyl-1H-pyrazole-3-carbonitrile (0.45 g, 78% yield) as a colorless oil. LC/MS (ESI) (m/z): 283 [M+H]$^+$.

To a solution of 1-(5-bromoisothiazol-4-yl)prop-2-yn-1-ol (100 mg, 0.46 mmol) in t-BuOH (1 mL) and $H_2O$ (1 mL) was added sodium (R)-2-((S)-1,2-dihydroxyethyl)-4-hydroxy-5-oxo-2,5-dihydrofuran-3-olate (4.5 mg, 0.02 mmol), azidoethane (1.2 M in THF, 2.0 mL, 2.3 mmol) and $CuSO_4$ (3.6 mg, 0.02 mmol) under $N_2$ at 25° C. After stirring at 50° C. for 16 h, the reaction was diluted with EtOAc. The resulting mixture was washed with $H_2O$, brine and dried over anhydrous $Na_2SO_4$. After filtration, the filtrate was concentrated. The residue was purified by flash chromatography (silica gel, 0→100% EA in PE) to give (5-bromoisothiazol-4-yl)(1-ethyl-1H-1,2,3-triazol-4-yl)methanol (60 mg, 45% yield) as a yellow oil. LC/MS (ESI) m/z: 289 [M+H]$^+$.

The following intermediates were synthesized using a similar experimental protocol:

(1-ethyl-1H-1,2,3-triazol-4-yl)(3-iodo-1-methyl-1H-pyrazol-4-yl)methanol 4-ethyl-1-((3-iodo-1-methyl-1H-pyrazol-4-yl)methyl)-1H-1,2,3-triazole

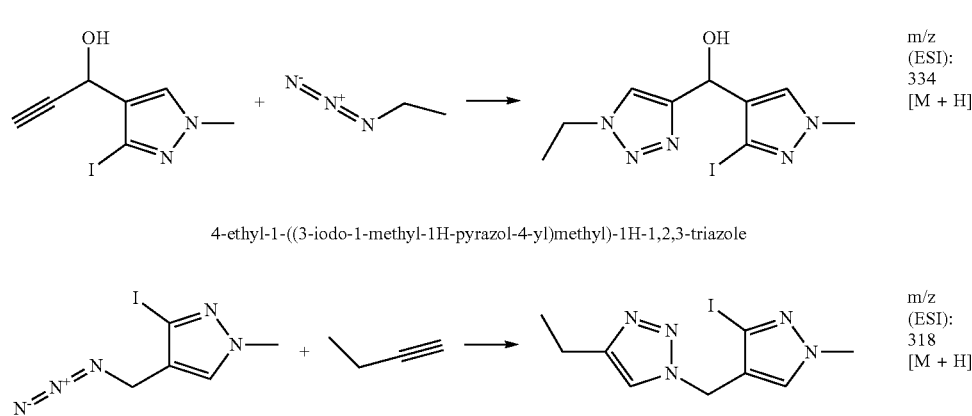

m/z (ESI): 334 [M + H]

m/z (ESI): 318 [M + H]

-continued (1-(cyclopropylmethyl)-1H-1,2,3-triazol-4-yl)(3-iodo-1-methyl-1H-pyrazol-4-yl)methanol

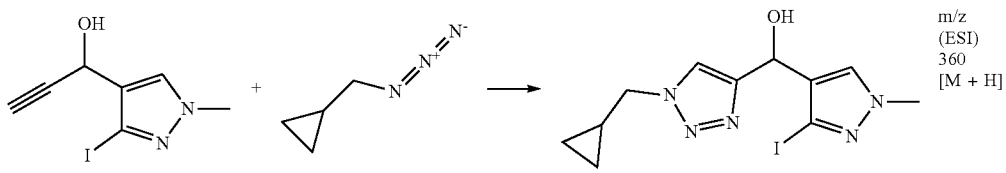

m/z (ESI) 360 [M + H]

(2-chloro-5-fluoropyridin-3-yl)(1-ethyl-1H-1,2,3-triazol-4-yl)methanol

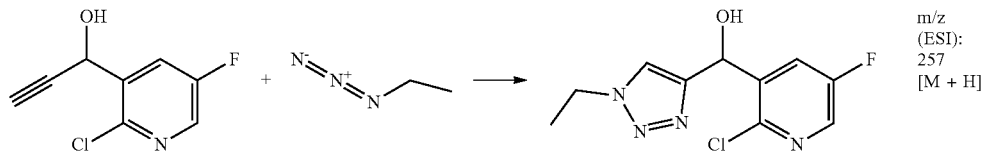

m/z (ESI): 257 [M + H]

(2,4-dibromothiazol-5-yl)(1-ethyl-1H-1,2,3-triazol-4-yl)-methanol

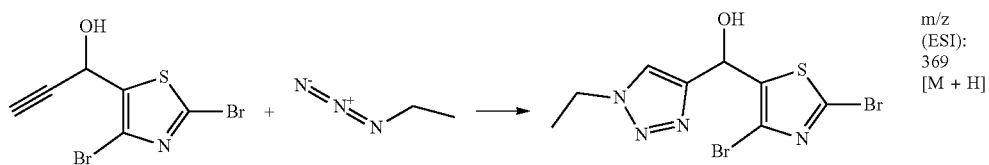

m/z (ESI): 369 [M + H]

(2-chloro-5-fluoropyridin-3-yl)[1-(cyclopropylmethyl)-1H-1,2,3-triazol-4-yl]methanol

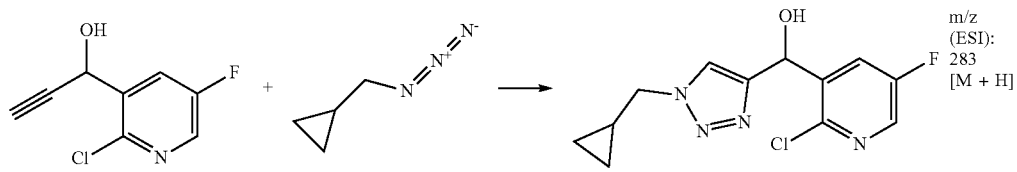

m/z (ESI): 283 [M + H]

(3-chloro-1-(4-fluoro-2-((R)-1-((4-methoxybenzyl)oxy)ethyl)phenyl)-1H-pyrazol-5-yl)(1-(cyclopropylmethyl)-1H-1,2,3-triazol-4-yl)methanol

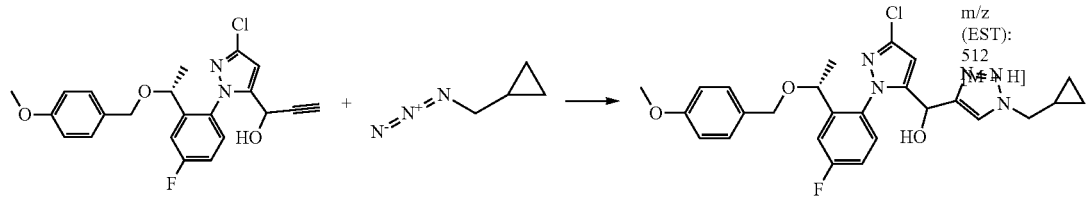

m/z (ESI): 512 [M + H]

[1-(cyclopropylmethyl)-1H-1,2,3-triazol-4-yl](dibromo-1,3-thiazol-5-yl)methanol

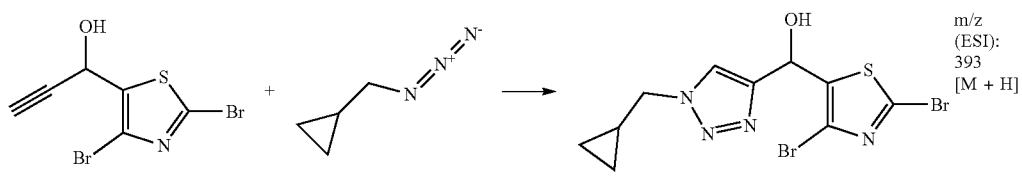

m/z (ESI): 393 [M + H]

(1-ethyl-1H-1,2,3-triazol-4-yl)[3-(4-fluoro-2-iodophenyl)-1,2-thiazol-4-yl]methanol

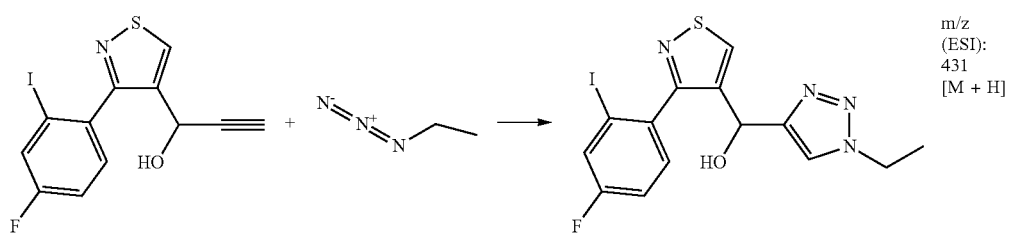

m/z (ESI): 431 [M + H]

Synthesis of 1-((3-iodopyridin-4-yl)methyl)-1H-imidazole-4-carbonitrile

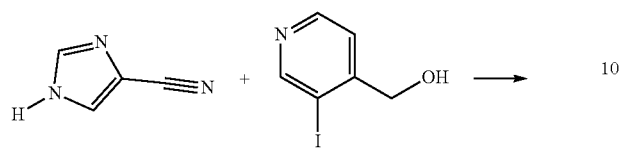

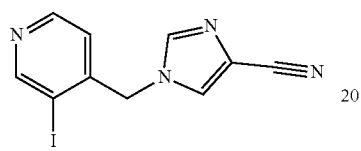

To a solution of PPh$_3$ (1.43 g, 5.45 mmol) in THF (16 mL) at 0° C. was added a solution of DIAD (1.1 g, 5.45 mmol) in THF (16 mL) under N$_2$ atmosphere. After the addition, the mixture was stirred at 0° C. until a white solid precipitated. To this mixture was added 1H-imidazole-4-carbonitrile (304 mg, 3.27 mmol) in THF (8 mL), followed by (3-iodopyridin-4-yl)methanol (640 mg, 2.72 mmol) in THF (8 mL). The resulting mixture was stirred at r.t. for 3 h. The mixture was concentrated under reduced pressure. The residue was diluted with DCM (60 mL), then washed with water and brine, dried over anhydrous Na$_2$SO$_4$, filtered and concentrated. The residue was purified by column chromatography on silica gel (50% EtOAc in PE) to 1-((3-iodopyridin-4-yl)methyl)-1H-imidazole-4-carbonitrile (890 mg, yield: 53%) as a pale-yellow oil. LC-MS (ESI): m/z 311 [M+H]$^+$.

The following intermediates were synthesized using a similar experimental protocol:

1-((3-iodo-1-methyl-1H-pyrazol-4-yl)methyl)-1H-imidazole-4-carbonitrile

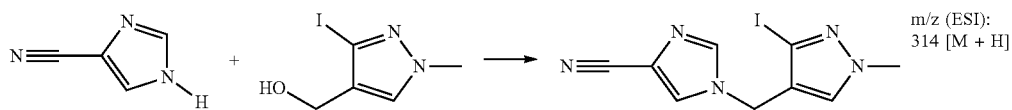

m/z (ESI): 314 [M + H]

1-((2-chloro-5-fluoropyridin-3-yl)methyl)-1H-imidazole-4-carbonitrile

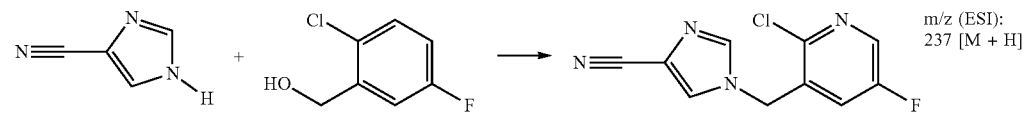

m/z (ESI): 237 [M + H]

1-[(dibromo-1,3-thiazol-5-yl)methyl]-1H-imidazole-4-carbonitrile

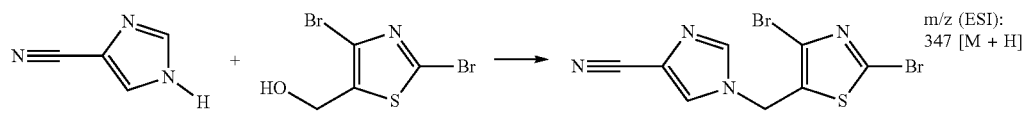

m/z (ESI): 347 [M + H]

Synthesis of 1-(4-fluoro-2-iodophenyl)-1H-pyrazole-3-carbonitrile

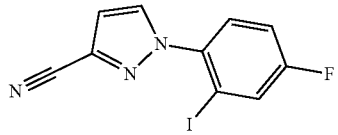 [SMILES: N#Cc1ccn(-c2ccc(F)cc2I)n1]

To a stirred flask of conc. H₂SO₄ (25 mL) was added NaNO₂ (2.93 g, 42.5 mmol) at 0° C. in several portions. The mixture was heated to 50° C. and stirred at this temperature for 1 h. This nitrite mixture was cooled to 0° C. and set aside. Separately, conc. H₂SO₄ (3.97 g, 40.5 mmol) was added to a solution of 4-fluoro-2-iodoaniline (9.60 g, 40.5 mmol) in AcOH (40 mL) at r.t. This solution was added dropwise to the original nitrite mixture at 0° C. After addition was complete, the mixture was heated to 50° C. for 1 h. The reaction mixture was then added to a suspension of ethyl 2,3-dicyanopropanoate (9.24 g, 60.8 mmol) and anhydrous NaOAc (49.82 g, 607.6 mmol) in H₂O (100 mL) at 5° C. After stirring for 15 h at 15° C., the reaction mixture was diluted with water and extracted with DCM (250 mL). The organic layer was stirred vigorously with 30% aq. NH₄OH (150 mL) for 2 h. The organic phase separated, dried over anhydrous Na₂SO₄, filtered and concentrated under vacuum. The residue was purified by flash chromatography (0-70% EtOAc in PE) to give 5-amino-1-(4-fluoro-2-iodophenyl)-1H-pyrazole-3-carbonitrile (11 g, 83%) as a brown solid. LC/MS ESI (m/z): 329 [M+H]⁺.

A solution of 5-amino-1-(4-fluoro-2-iodophenyl)-1H-pyrazole-3-carbonitrile (12.0 g, 36.6 mmol) and isopentyl nitrite (12.8 g, 110 mmol) in THF (150 mL) at 25° C. was heated to 70° C. and stirred for 16 h. The reaction was diluted with EtOAc. The resulting mixture was washed with H₂O, and then brine. The organic layer was dried over anhydrous Na₂SO₄. After filtration, the filtrate was concentrated under vacuum. The residue was purified by silica gel column chromatography, eluted with PE/EA (0→20%) to give 1-(4-fluoro-2-iodophenyl)-1H-pyrazole-3-carbonitrile (6.0 g, 52% yield) as a clear oil. LC/MS ESI (m/z): 314 [M+H]⁺.

Synthesis of 1-(4-fluoro-2-iodophenyl)-1H-pyrazole-5-carbaldehyde

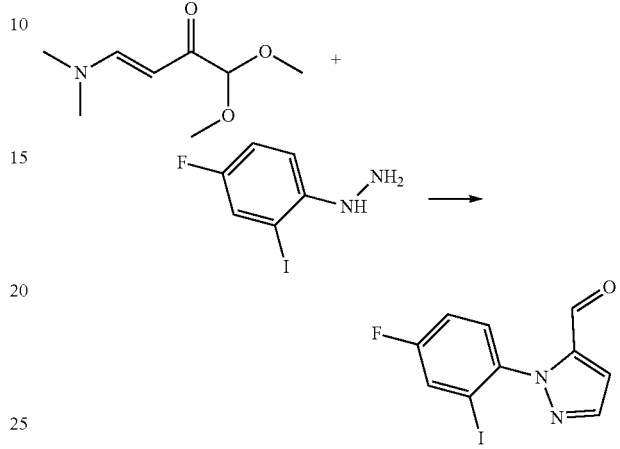

To a suspension of (4-fluoro-2-iodophenyl)hydrazine (4.10 g, 16.3 mmol) in EtOH (100 mL) was added [(1E)-4,4-dimethoxy-3-oxobut-1-en-1-yl]dimethylamine (2.82 g, 16.3 mmol). The resulting mixture was heated at reflux for 48 h and then concentrated. To a solution of the crude residue in acetone (50 mL) was added 6 N HCl (10 mL). The resulting solution was stirred at r.t. for 30 min, and then was partitioned between ethyl acetate and water. The organic extract was washed with water, sat. sodium bicarbonate, and brine, and then dried over anhydrous sodium sulfate. The residue was concentrated to dryness to give crude 1-(4-fluoro-2-iodophenyl)-1H-pyrazole-5-carbaldehyde (4.50 g, yield: 88%) as a black oil. LC/MS (ESI) m/z: 317 [M+H]⁺.

The following intermediates were synthesized using a similar experimental protocol:

ethyl 1-(4-fluoro-2-iodophenyl)-3-methyl-1H-pyrazole-5-carboxylate

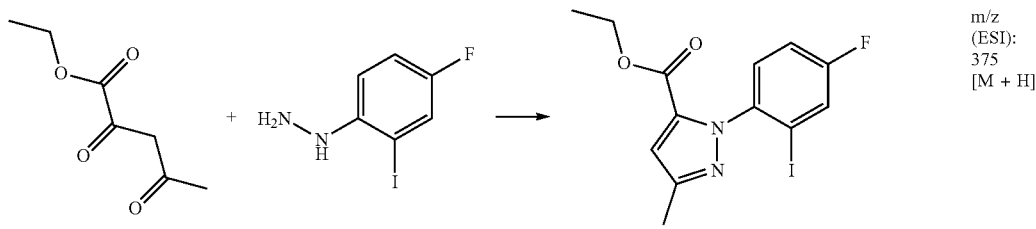

m/z (ESI): 375 [M + H]

5-((5-bromo-1-ethyl-1H-pyrazol-4-yl)methyl)-1-(4-fluoro-2-iodophenyl)-1H-pyrazole-4-carbonitrile

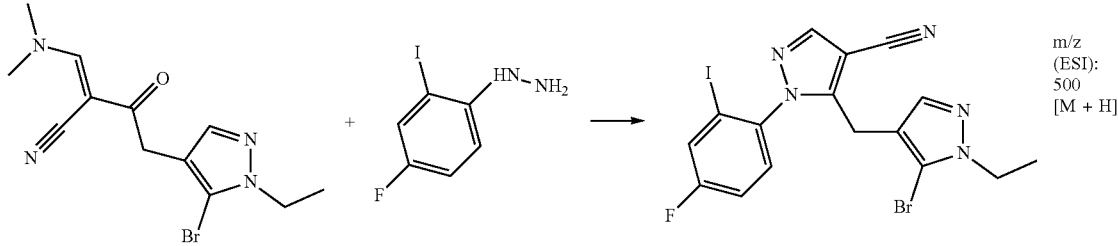

m/z (ESI): 500 [M + H]

Synthesis of 3,5-difluoro-2-iodo-N-methoxy-N-methylbenzamide

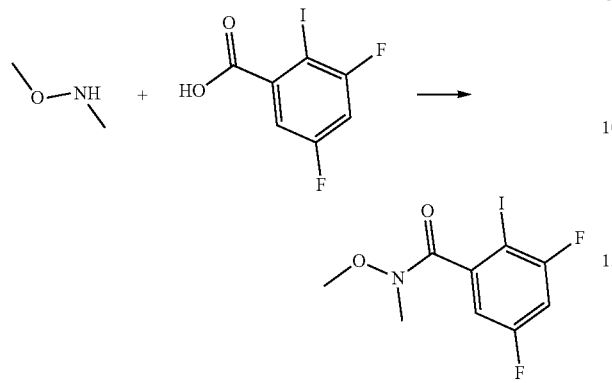

A mixture of 3,5-difluoro-2-iodobenzoic acid (11.3 g, 39.8 mmol), EDCI (9.92 g, 51.7 mmol), HOBt (6.99 g, 51.7 mmol), methoxy(methyl)amine (2.92 g, 47.9 mmol) and DIPEA (15.40 g, 119.4 mmol) in DMF (40 mL) was stirred at r.t. for 2 h. The mixture was concentrated, diluted with EA (80 mL) and washed with sat. NaHCO$_3$ (40 mL×3). The combined organic layers were separated, washed by brine, dried over anhydrous Na$_2$SO$_4$, filtered and concentrated. The residue was purified by flash column chromatography on silica gel to give 3,5-difluoro-2-iodo-N-methoxy-N-methylbenzamide (12 g, 92%) as light-yellow solid. LC-MS (ESI): m/z 328 [M+H]$^+$.

Synthesis of (5-cyclobutyl-1-methyl-1H-pyrazol-3-yl)methanol

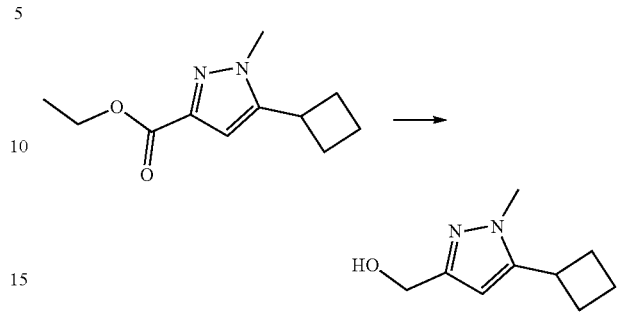

To a solution of ethyl 5-cyclobutyl-1-methyl-1H-pyrazole-3-carboxylate (4.20 g, 20.2 mmol) in THF (40 mL) was added diisobutylaluminium hydride (33.6 mL, 50.4 mmol, 1.5 M in THF) dropwise at −78° C. The mixture was stirred at −78° C. for 1 h. After 1 h, the reaction mixture was diluted by EA (20 mL), then water (2 mL), aq. NaOH solution (15%, 2 mL) and water (5 mL) was added in sequence at 0° C. After warming to r.t., anhydrous MgSO$_4$ was added, and stirring was continued for 15 min. The mixture was filtered, and the filtrate was concentrated in vacuo to give crude (5-cyclobutyl-1-methyl-1H-pyrazol-3-yl)methanol (2.86 g, 85%) as a yellow oil. LC/MS ESI (m/z): 167 [M+H]$^+$.

The following intermediates were synthesized using a similar experimental protocol:

(5-bromo-1-(2,2-difluoroethyl)-1H-pyrazol-4-yl)methanol

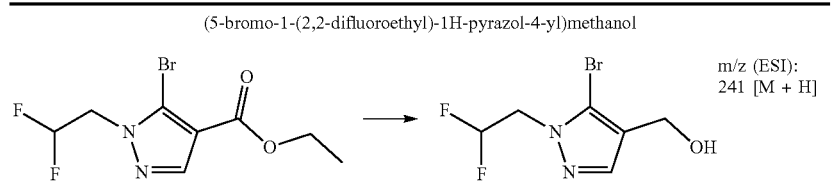

m/z (ESI): 241 [M + H]

Synthesis of (3-ethylisoxazol-5-yl)methanol

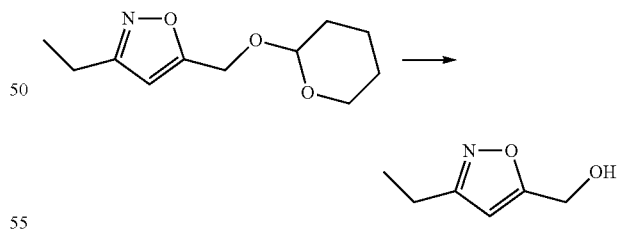

To a solution of 3-ethyl-5-[(oxan-2-yloxy)methyl]-1,2-oxazole (17.4 g, 82.4 mmol) in MeOH (10 mL) was added Amberlyst 15 (26 mg, 83 mmol). The mixture was stirred vigorously at 45° C. for 6 h. Filtration and removal of solvent in vacuum gave a red residue, which was purified by column chromatography on silica gel (15→30% EtOAc in PE) to give (3-ethyl-1,2-oxazol-5-yl)methanol (8.05 g, yield: 77%) as a pale-yellow oil. LC/MS ESI (m/z): 128 [M+H]$^+$.

The following intermediates were synthesized using a similar experimental protocol:

(3-(cyclopropylmethyl)isoxazol-5-yl)methanol

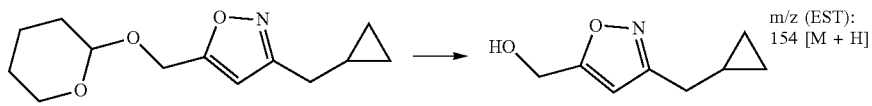

m/z (ESI): 154 [M + H]

(3-(2,2-difluoroethyl)isoxazol-5-yl)methanol

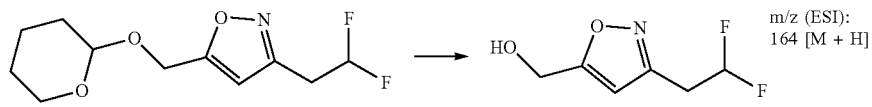

m/z (ESI): 164 [M + H]

Synthesis of 3-(bromomethyl)-5-(cyclopropylmethyl)-1-methyl-1H-pyrazole

Synthesis of 5-((2-chloropyridin-3-yl)methyl)-1-methyl-1H-pyrazole-3-carbonitrile

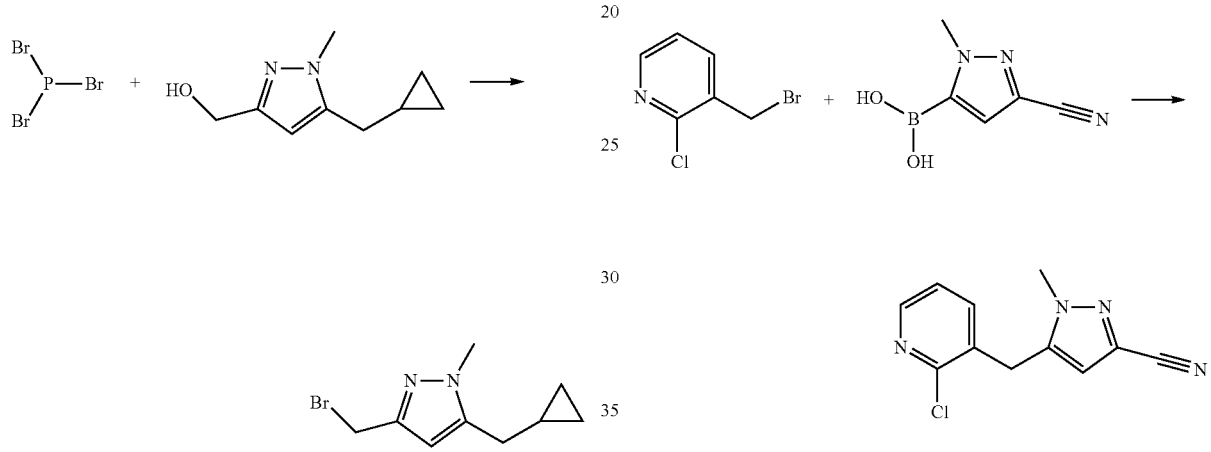

To a stirred solution of (5-(cyclopropylmethyl)-1-methyl-1H-pyrazol-3-yl)methanol (410 mg, 2.47 mmol) in DCM (10 mL) was added dropwise a solution of phosphorous tribromide (2.00 g, 7.40 mmol) in DCM (5 mL) at 0° C. under N$_2$. The reaction was stirred at 0° C. for 2 h, washed with sat. NaHCO$_3$ (30 mL), dried over anhydrous Na$_2$SO$_4$ and evaporated to dryness. The residue was purified by column chromatography on silica gel eluted with PE/EtOAc (9:1→4:1) to give 3-(bromomethyl)-5-(cyclopropylmethyl)-1-methyl-1H-pyrazole (285 mg, 50% yield) as a yellow oil.

LC/MS (ESI) (m/z): 229 [M+H]$^+$.

To a solution of 3-(bromomethyl)-2-chloropyridine (2.07 g, 10.1 mmol), (3-cyano-1-methyl-1H-pyrazol-5-yl)boronic acid (1.52 g, 10.0 mmol), Pd(PPh$_3$)$_4$(0.81 g, 0.70 mmol) in toluene (20 mL) and EtOH (4 mL), was added Na$_2$CO$_3$ (2.13 g, 20.1 mmol). The reaction was thrice degassed with N$_2$, and then stirred at 100° C. overnight. The mixture was cooled to r.t., filtered, and concentrated in vacuo. The residue was purified by flash chromatography (0→50% EtOAc in PE) to give 5-((2-chloropyridin-3-yl)methyl)-1-methyl-1H-pyrazole-3-carbonitrile (675 mg, 29%) as a yellow solid.

LC/MS ESI (m/z): 233 [M+H]$^+$.

The following intermediates were synthesized using a similar experimental protocol:

5-((2-chloro-5-fluoropyridin-3-yl)methyl)-1-methyl-1H-pyrazole-3-carbonitrile m/z (ESI): 251 [M + H]

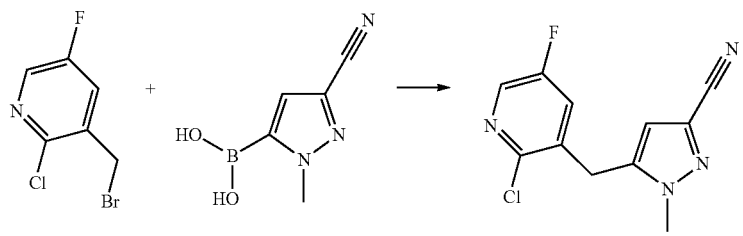 [SMILES: Fc1cnc(Cl)c(CBr)c1 ; Cn1nc(C#N)cc1B(O)O ; Cn1nc(C#N)cc1Cc1cc(F)cnc1Cl]

4-bromo-3-((2-chloropyridin-3-yl)methyl)-1-methyl-1H-pyrazole-5-carbonitrile

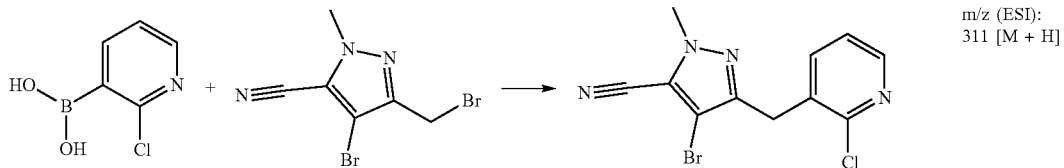

m/z (ESI): 311 [M + H]

5-(2-bromobenzyl)-1-methyl-1H-pyrazole-3-carbonitrile

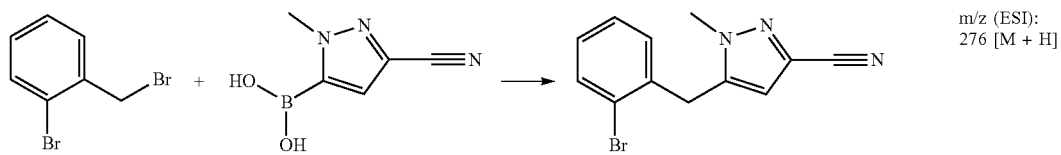

m/z (ESI): 276 [M + H]

5-((3-(2-bromo-4-fluorophenyl)isothiazol-4-yl)methyl)-1-methyl-1H-pyrazole-3-carbonitrile

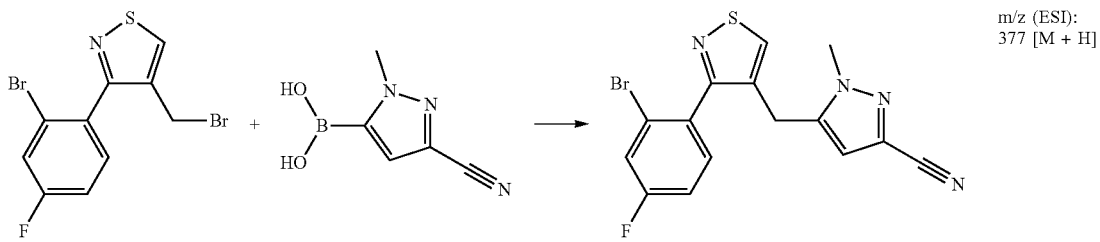

m/z (ESI): 377 [M + H]

Synthesis of (5-bromo-1-cyclobutyl-1H-pyrazol-4-yl)methanol

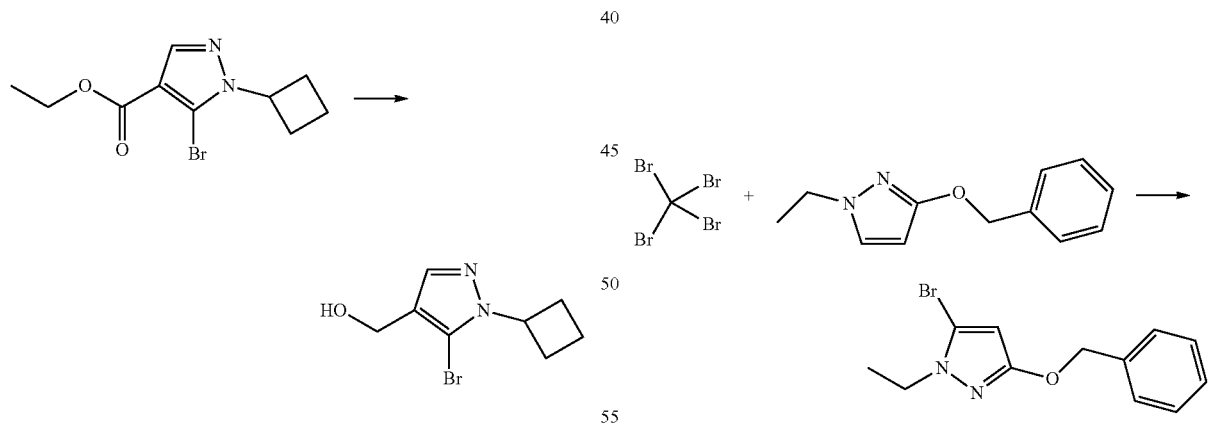

At −60° C., to a solution of ethyl 5-bromo-1-cyclobutyl-1H-pyrazole-4-carboxylate (1.9 g, 7.0 mmol) in THF (20 mL), was added DIBAL-H (1M in toluene, 20.9 mL, 20.9 mmol) dropwise at −60° C. Then the mixture was stirred at 0° C. for 3 h. The reaction mixture was diluted with EA (20 mL), and water (1 mL), and then 15% sodium hydroxide solution (1 mL) and water (2.5 mL) were added sequentially. After warming to r.t., anhydrous magnesium sulfate was added and stirring was continued for 15 min. The resulting mixture was filtered, the filtrate was washed with sat. aq. NH$_4$Cl and brine, dried over anhydrous Na$_2$SO$_4$, filtered, and concentrated in vacuo. The residue was purified by column chromatography on silica gel (0→10% EtOAc in PE) to give (5-bromo-1-cyclobutyl-1H-pyrazol-4-yl)methanol (1.6 g, 15%) as a light-yellow oil. LC/MS ESI (m/z): 231 [M+H]$^+$.

Synthesis of 3-(benzyloxy)-5-bromo-1-ethyl-1H-pyrazole

To a stirred solution of 3-(benzyloxy)-1-ethyl-1H-pyrazole (11.5 g, 56.9 mmol) in THF (200 mL) was added n-BuLi (27.3 mL, 68.3 mmol, 2.5 M in THF) at −78° C. under N$_2$. After stirring at −78° C. for 1 h, a solution of CBr$_4$ (22.6 g, 68.2 mmol) in THF (50 mL) was added. The reaction was stirred at −78° C. for another 1.5 h, then quenched with sat. NH$_4$Cl (50 mL) and concentrated in vacuo. The residue was purified by flash chromatography (0→25% EtOAc in PE) to give 3-(benzyloxy)-5-bromo-1-ethyl-1H-pyrazole (8.3 g, 52% yield) as a yellow oil. LC/MS ESI (m/z): 281.0 [M+H]f.

The following intermediates were synthesized using a similar experimental protocol:

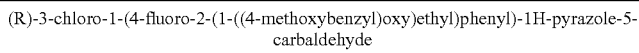
(R)-3-chloro-1-(4-fluoro-2-(1-((4-methoxybenzyl)oxy)ethyl)phenyl)-1H-pyrazole-5-carbaldehyde

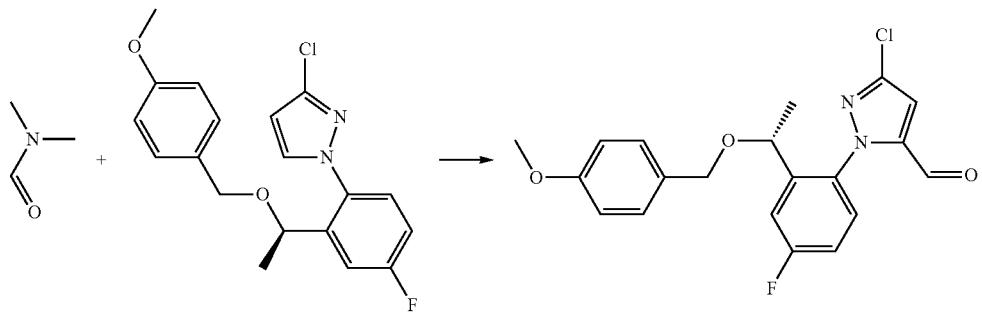

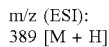
m/z (ESI): 389 [M + H]

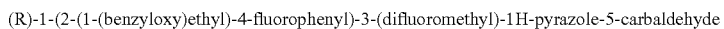
(R)-1-(2-(1-(benzyloxy)ethyl)-4-fluorophenyl)-3-(difluoromethyl)-1H-pyrazole-5-carbaldehyde

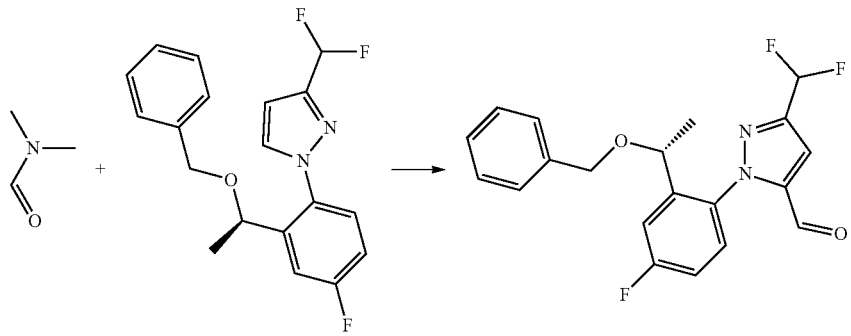

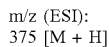
m/z (ESI): 375 [M + H]

Synthesis of (3-bromo-1-methyl-1H-pyrazol-4-yl)(5-ethylisoxazol-3-yl)methanone

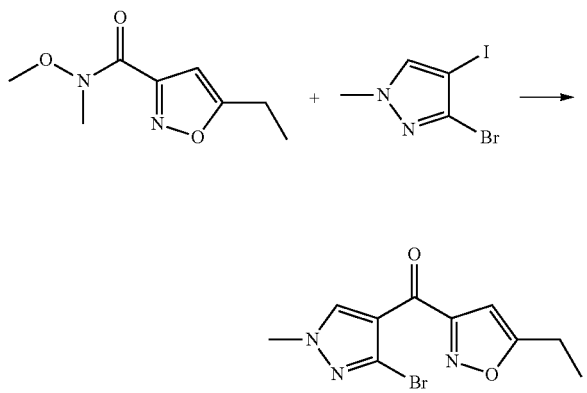

To a stirred solution of 3-bromo-4-iodo-1-methyl-1H-pyrazole (500 mg, 1.74 mmol) in THF (10 mL) was added i-PrMgBr (2.1 mL, 2.1 mmol, 1 M in THF) at 0° C. under $N_2$. After stirring at 0° C. for 1 h, a solution of 5-ethyl-N-methoxy-N-methyl-1,2-oxazole-3-carboxamide (360 mg, 1.95 mmol) in THF (2 mL) was added dropwise. The reaction was stirred at 0° C. for another 1 h, then quenched with sat. $NH_4Cl$ (10 mL) and extracted with EtOAc (30 mL×2). The combined organic phases were washed with brine (20 mL), dried over anhydrous $Na_2SO_4$ and concentrated. The residue was purified by column chromatography on silica gel (25% EtOAc in PE) to give 3-(3-bromo-1-methyl-1H-pyrazole-4-carbonyl)-5-ethyl-1,2-oxazole (400 mg, 77% yield) as a yellow oil.
LC/MS (ESI) (m/z): 284.3 [M+H]$^+$.

Synthesis of 2-bromo-3-((4-ethyl-1H-1,2,3-triazol-1-yl)methyl)-5-fluoropyridine

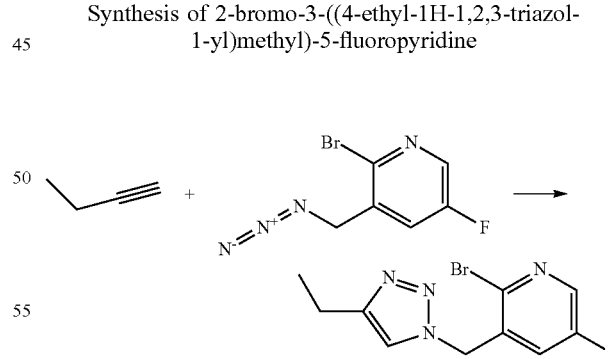

To a solution of 1-butyne (ca. 0.2 M, 12 mL) was added 3-(azidomethyl)-2-bromo-5-fluoropyridine (350 mg, 1.52 mmol) and CuI (57 mg, 0.30 mmol). The mixture was stirred at r.t. for 1 h then filtered through celite. The filtrate was concentrated in vacuo to get a residue, which was purified by silica gel column chromatography (PE:EA=10:1 to 3:1) to give 2-bromo-3-[(4-ethyl-1H-1,2,3-triazol-1-yl)methyl]-5-fluoropyridine (130.0 mg, 30% yield) as a white solid.
LC/MS (ESI): m/z=285 [M+H]f.

Synthesis of (3-bromo-1-methyl-1H-pyrazol-4-yl)(3-ethylisoxazol-5-yl)methanol

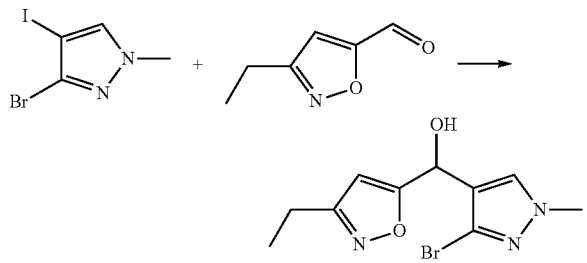

To the mixture of 3-bromo-4-iodo-1-methyl-1H-pyrazole (1.43 g, 4.98 mmol) in THF (10 mL) was added isopropylmagnesium bromide (1 M in THF, 5.48 mL, 5.48 mmol) slowly under $N_2$ at 0° C. The mixture was stirred at 0° C. for 1 h. To this mixture was added a solution of 3-ethylisoxazole-5-carbaldehyde (0.62 g, 5.0 mmol) in dry THF (3 mL) dropwise at 0° C. over 10 min and the resulting mixture was stirred at 0° C. for another 1 h. The reaction mixture was quenched by ice-water and then extracted with EtOAc twice. The combined extracts were concentrated and the residue was purified by column chromatography on silica gel (PE: EA=3:1) to give (3-bromo-1-methyl-1H-pyrazol-4-yl)(3-ethylisoxazol-5-yl)methanol (900 mg, yield: 63%) as a yellow oil.

LC/MS ESI (m/z): 286 [M+H]$^+$.

The following intermediates were synthesized using a similar experimental protocol:

(5-bromo-1-ethyl-1H-pyrazol-4-yl)(5-iodo-1-methyl-1H-pyrazol-4-yl)methanol

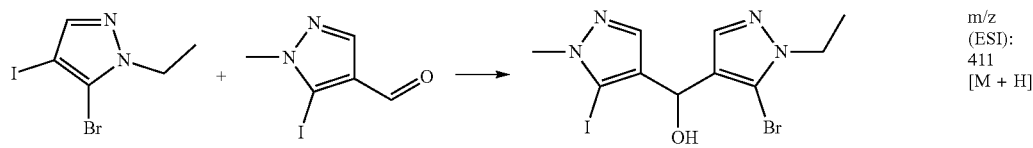

m/z (ESI): 411 [M + H]

(5-bromo-1-ethyl-1H-pyrazol-4-yl)(2-bromopyridin-3-yl)methanol

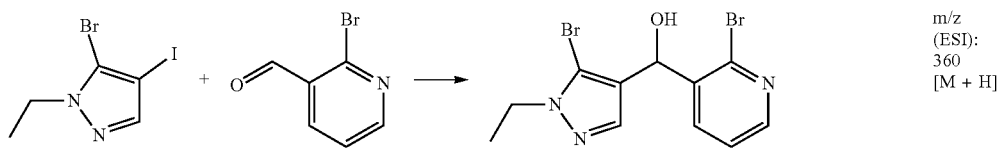

m/z (ESI): 360 [M + H]

(3-bromo-1-methyl-1H-pyrazol-4-yl)(3-ethyl-1-methyl-1H-pyrazol-5-yl)methanol

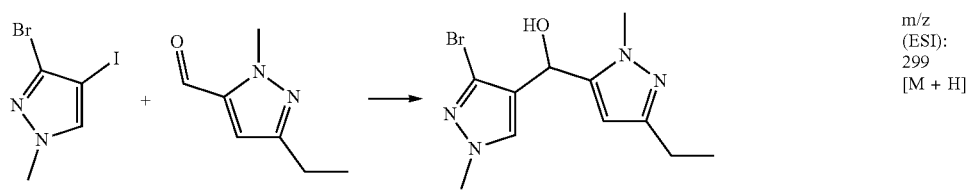

m/z (ESI): 299 [M + H]

5-[(dibromo-1,3-thiazol-5-yl)(hydroxy)methyl]-1-methyl-1H-pyrazole-3-carbonitrile

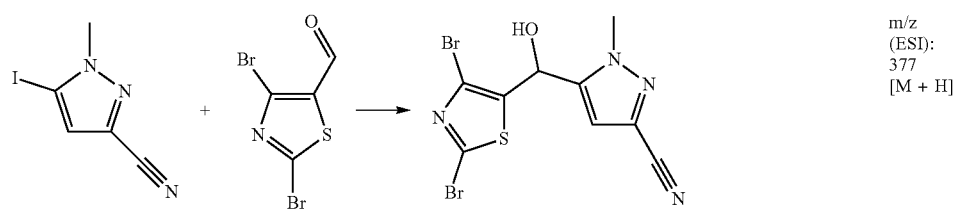

m/z (ESI): 377 [M + H]

(3-chloro-1-ethyl-1H-pyrazol-4-yl)(3-iodo-1-methyl-1H-pyrazol-4-yl)methanol

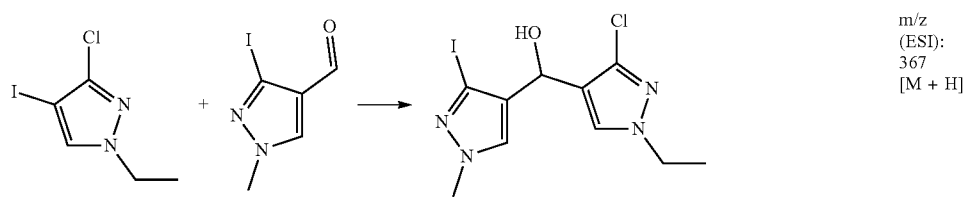

m/z (ESI): 367 [M + H]

-continued (5-bromo-1-cyclobutyl-1H-pyrazol-4-yl)(5-iodo-1-methyl-1H-pyrazol-4-yl)methanol

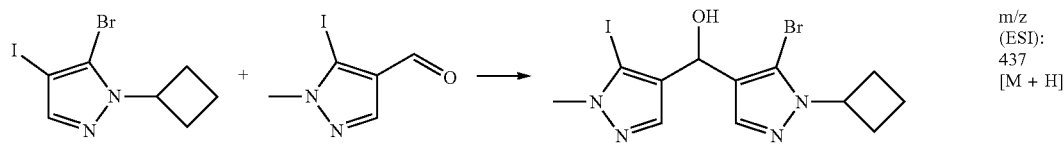

m/z (ESI): 437 [M + H]

ethyl 5-((3-bromo-1-methyl-1H-pyrazol-4-yl)(hydroxy)methyl)isoxazole-3-carboxylate

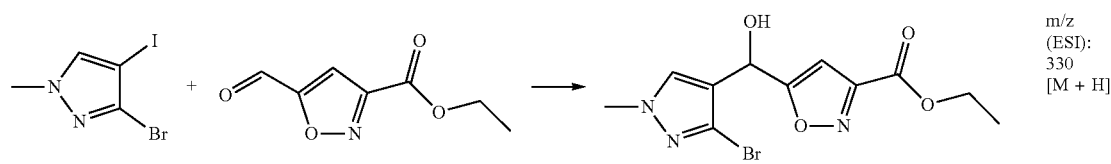

m/z (ESI): 330 [M + H]

(3-(benzyloxy)-5-bromo-1-ethyl-1H-pyrazol-4-yl)(3-iodo-1-methyl-1H-pyrazol-4-yl)methanol

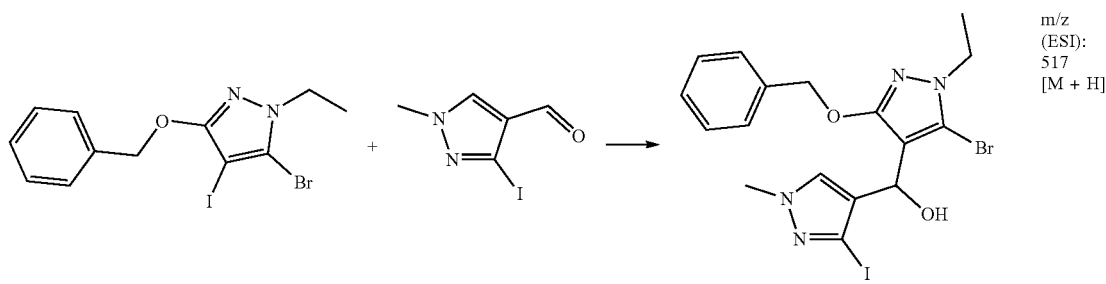

m/z (ESI): 517 [M + H]

[5-bromo-1-(cyclopropylmethyl)-3-methyl-1H-pyrazol-4-yl](5-chloro-3-iodo-1-methyl-1H-pyrazol-4-yl)methanol

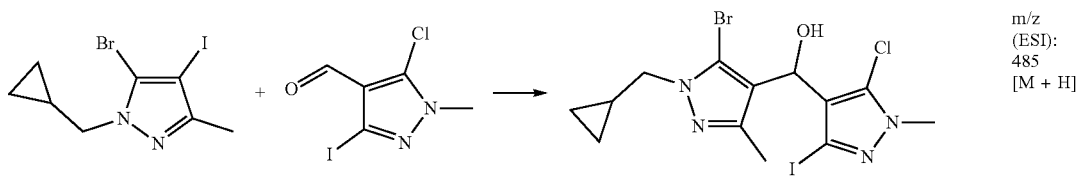

m/z (ESI): 485 [M + H]

(3-ethyl-1-methyl-1H-pyrazol-5-yl)(1-(4-fluoro-2-iodophenyl)-3-methyl-1H-pyrazol-5-yl)methanol

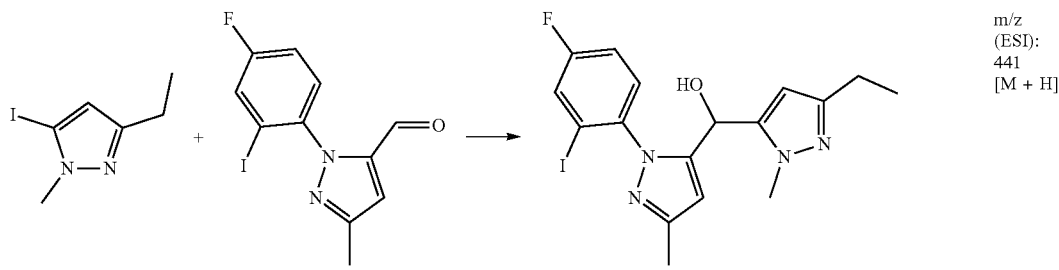

m/z (ESI): 441 [M + H]

(5-bromo-1-ethyl-1H-pyrazol-4-yl)(3-iodopyridin-4-yl)methanol

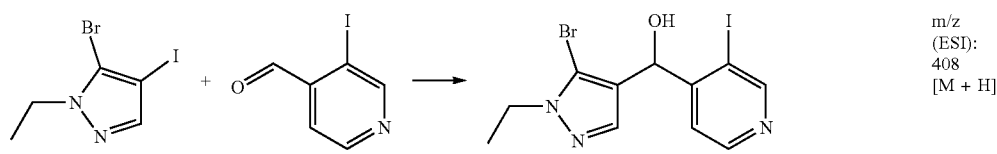

m/z (ESI): 408 [M + H]

-continued (5-bromo-1-ethyl-1H-pyrazol-4-yl)(1-(4-fluoro-2-iodophenyl)-1H-imidazol-5-yl)methanol

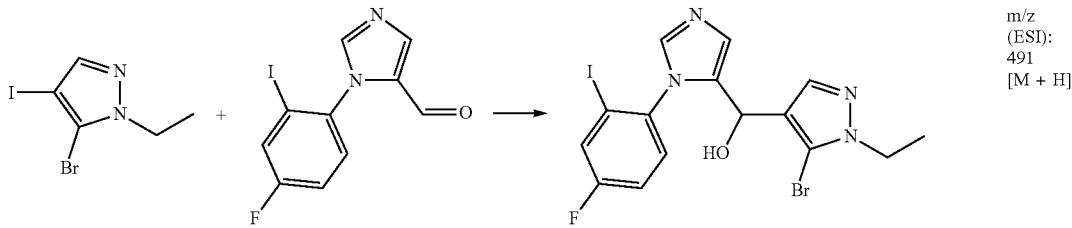

m/z (ESI): 491 [M + H]

(3-bromo-1-methyl-1H-pyrazol-4-yl)(1-ethyl-3-methyl-1H-pyrazol-4-yl)methanol

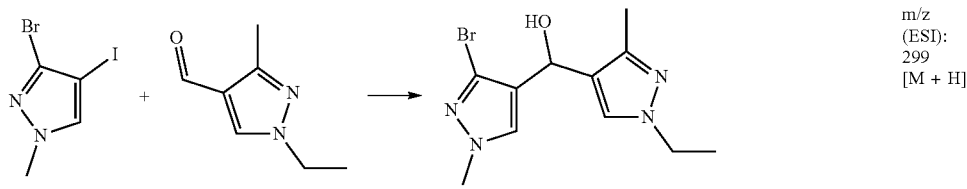

m/z (ESI): 299 [M + H]

(1-ethyl-1H-pyrazol-4-yl)(3-iodo-1,5-dimethyl-1H-pyrazol-4-yl)methanol

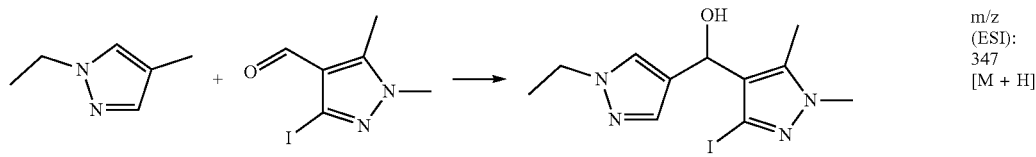

m/z (ESI): 347 [M + H]

(3-bromo-1-methyl-1H-pyrazol-4-yl)(5-ethyl-1,2-thiazol-3-yl)methanol

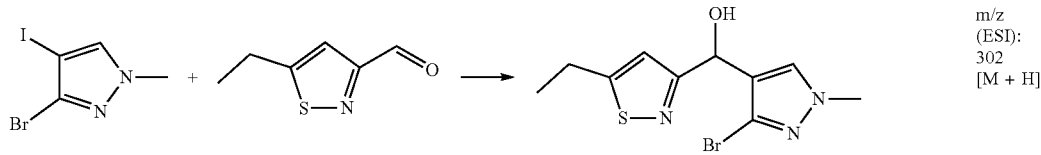

m/z (ESI): 302 [M + H]

(2-chloropyridin-3-yl)(1-(cyclopropylmethyl)-1H-1,2,3-triazol-4-yl)methanol

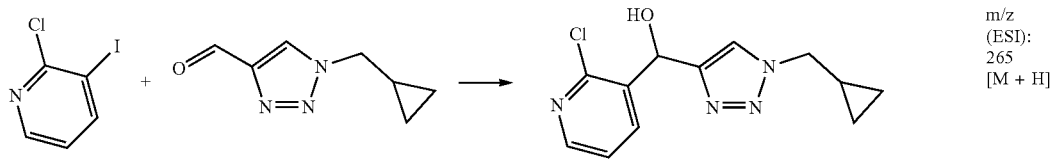

m/z (ESI): 265 [M + H]

(3-bromo-1-methyl-1H-pyrazol-4-yl)(3-ethylisothiazol-5-yl)methanol

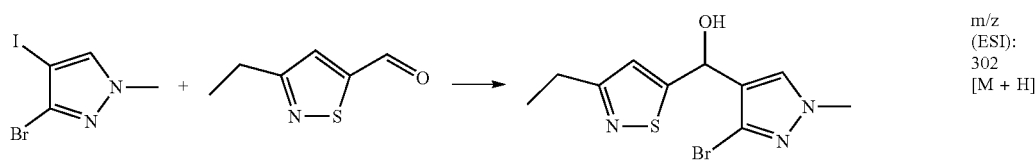

m/z (ESI): 302 [M + H]

(2-chloropyridin-3-yl)(1-(cyclopropylmethyl)-3-methyl-1H-pyrazol-4-yl)methanol

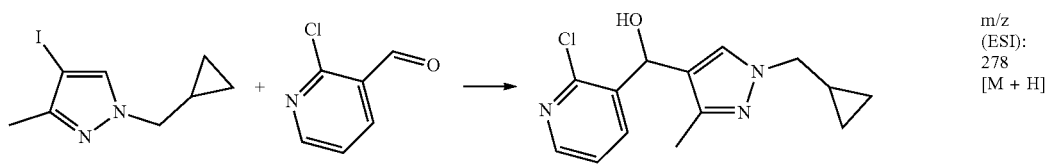

m/z (ESI): 278 [M + H]

-continued (1-(2-((R)-1-(benzyloxy)ethyl)-4-fluorophenyl)-3-(difluoromethyl)-1H-pyrazol-5-yl)(1-ethyl-3-methoxy-1H-pyrazol-4-yl)methanol

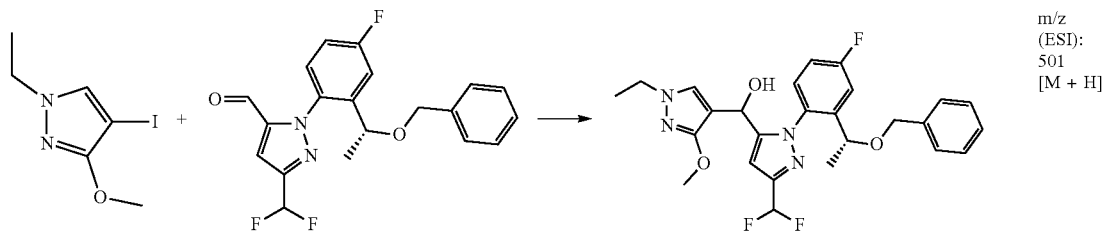

m/z (ESI): 501 [M + H]

(3-bromo-1-ethyl-1H-pyrazol-4-yl)(3-iodo-1-methyl-1H-pyrazol-4-yl)methanol

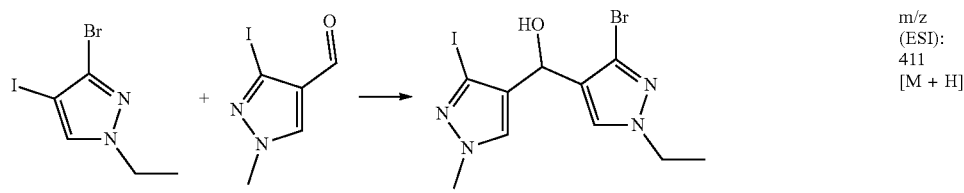

m/z (ESI): 411 [M + H]

(3-bromo-1-methyl-1H-pyrazol-4-yl)(1,3-diethyl-1H-pyrazol-4-yl)methanol

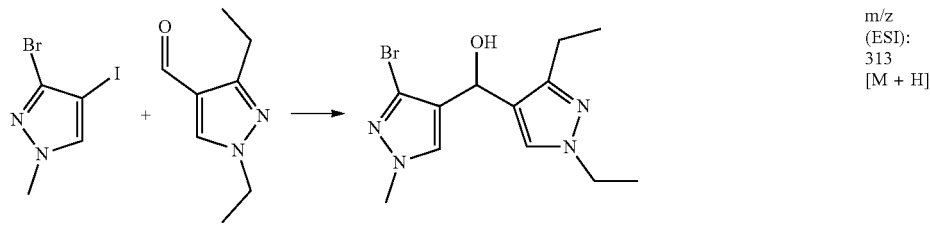

m/z (ESI): 313 [M + H]

(3-bromo-1-(difluoromethyl)-1H-pyrazol-4-yl)(1-(cyclopropylmethyl)-1H-pyrazol-4-yl)methanol

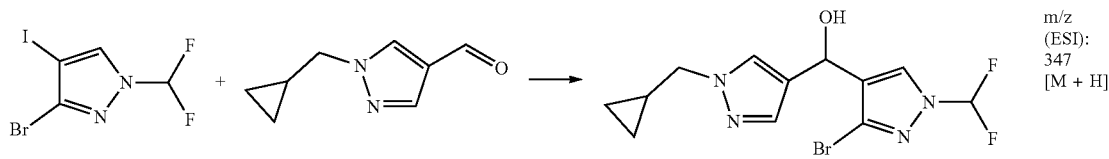

m/z (ESI): 347 [M + H]

(3-bromo-1-methyl-1H-pyrazol-4-yl)(1-isobutyl-1H-pyrazol-4-yl)methanol

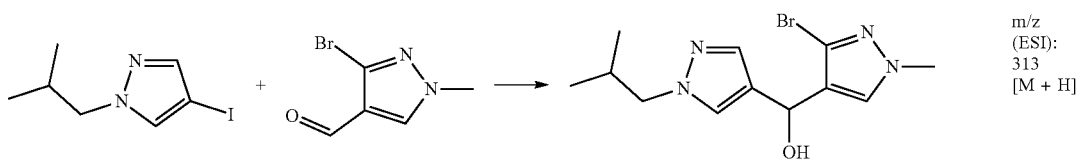

m/z (ESI): 313 [M + H]

(3-bromo-1-(4-fluoro-2-iodophenyl)-1H-pyrazol-5-yl)(1-ethyl-1H-pyrazol-4-yl)methanol

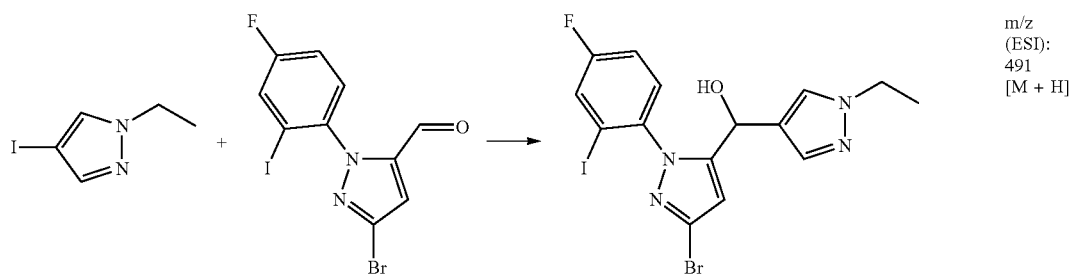

m/z (ESI): 491 [M + H]

-continued (dibromo-1,3-thiazol-5-yl)(1-ethyl-1H-pyrazol-4-yl)methanol

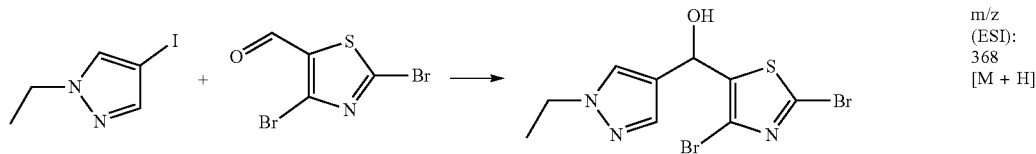

m/z (ESI): 368 [M + H]

5-((1-(4-fluoro-2-iodophenyl)-3-methyl-1H-pyrazol-5-yl)(hydroxy)methyl)-1-methyl-1H-pyrazole-3-carbonitrile

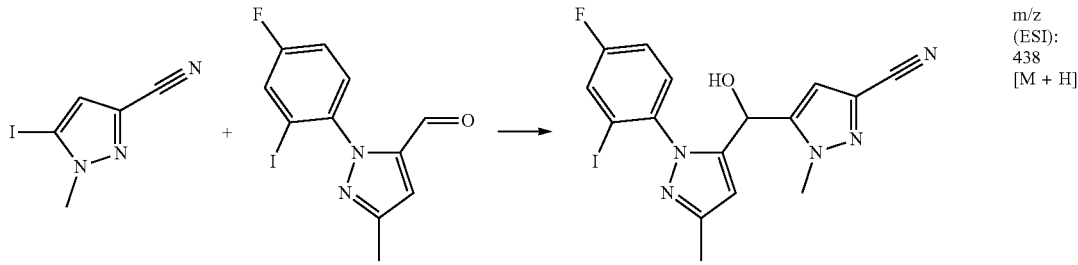

m/z (ESI): 438 [M + H]

3-((5-bromo-1-methyl-1H-pyrazol-4-yl)(hydroxy)methyl)-1-((2-(trimethylsilyl)ethoxy)methyl)-1H-pyrazole-5-carbaldehyde

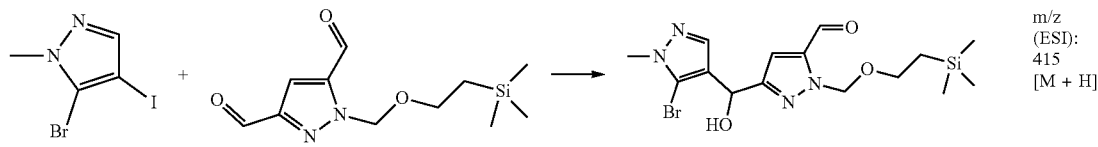

m/z (ESI): 415 [M + H]

(5-bromo-1-methyl-1H-pyrazol-4-yl)(1-ethyl-5-iodo-1H-pyrazol-4-yl)methanol

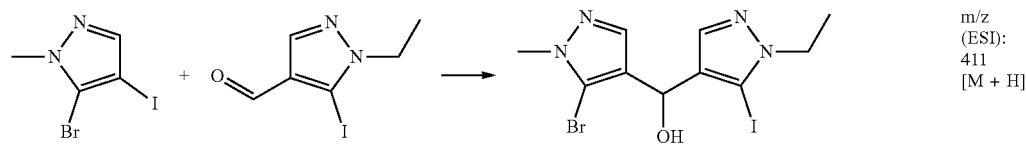

m/z (ESI): 411 [M + H]

(3-bromo-1-methyl-1H-pyrazol-4-yl)(5-(cyclopropylmethyl)-1-methyl-1H-pyrazol-3-yl)methanol

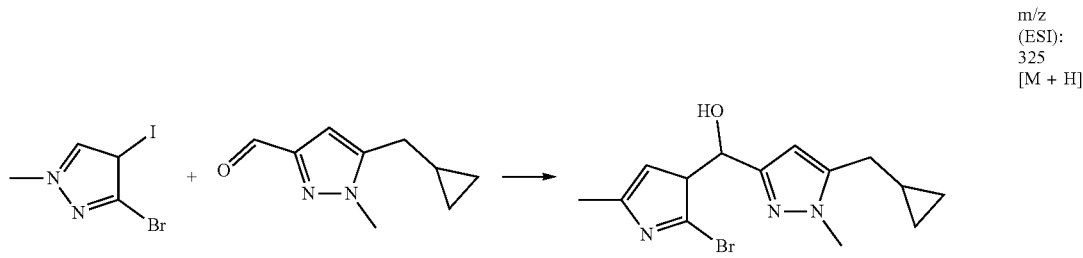

m/z (ESI): 325 [M + H]

Synthesis of 5-bromo-4-((1-ethyl-H-1,2,3-triazol-4-yl)methyl)isothiazole

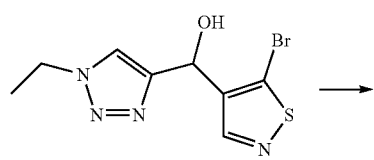

-continued

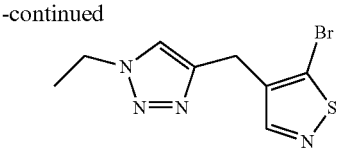

To a solution of (5-bromoisothiazol-4-yl)(1-ethyl-H-1,2,3-triazol-4-yl)methanol (60 mg, 0.20 mmol) in TFA (3 mL) was added TES (193 mg, 1.60 mmol). The mixture was heated to 70° C. and stirred for 2 h. The reaction mixture was concentrated, diluted with sat. aq. NaHCO₃, and extracted with EtOAc. The combined organic phases were washed with brine, dried over anhydrous Na₂SO₄, filtered and concentrated. The residue was purified by flash chromatography (silica gel, 0→40% o EA in PE) to give 5-bromo-4-((1-ethyl-1H-1,2,3-triazol-4-yl)methyl)isothiazole (50 mg, 88% o yield) as a yellow oil. LC/MS (ESI) m/z: 273 [M+H]⁺.

The following intermediates were synthesized using a similar experimental protocol:

4-((1-(cyclopropylmethyl)-1H-pyrazol-4-yl)methyl)-3-iodo-1-methyl-1H-pyrazole

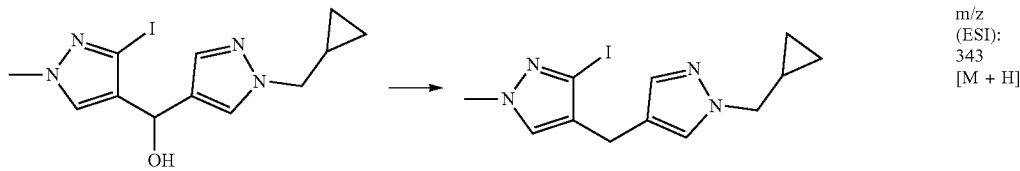

m/z (ESI): 343 [M + H]

3-bromo-4-((3-ethyl-1-methyl-1H-pyrazol-5-yl)methyl)-1-methyl-1H-pyrazole

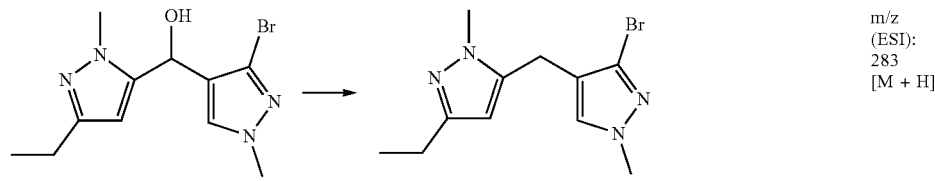

m/z (ESI): 283 [M + H]

5-[(dibromo-1,3-thiazol-5-yl)methyl]-1-methyl-1H-pyrazole-3-carbonitrile

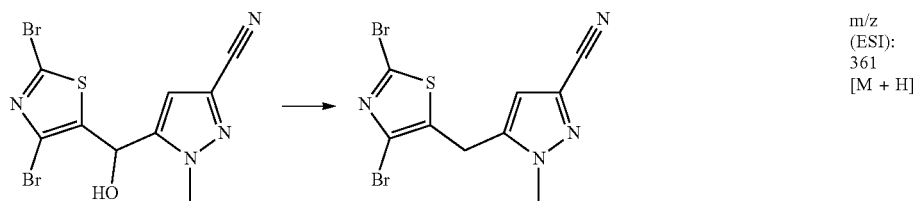

m/z (ESI): 361 [M + H]

3-chloro-1-ethyl-4-((3-iodo-1-methyl-1H-pyrazol-4-yl)methyl)-1H-pyrazole

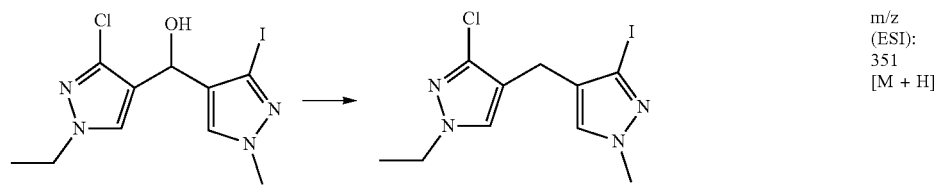

m/z (ESI): 351 [M + H]

2,4-dibromo-5-((3-ethyl-1-methyl-1H-pyrazol-5-yl)methyl)thiazole

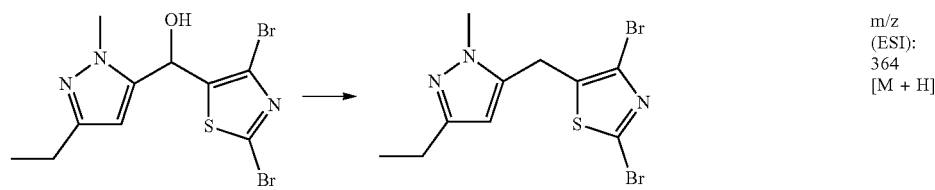

m/z (ESI): 364 [M + H]

5-bromo-1-ethyl-4-((3-iodo-1-methyl-1H-pyrazol-4-yl)methyl)-1H-pyrazole

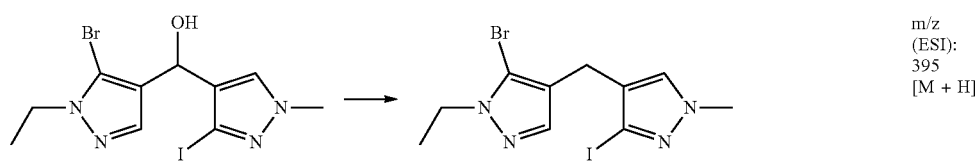

m/z (ESI): 395 [M + H]

1-ethyl-4-((3-iodo-1-methyl-1H-pyrazol-4-yl)methyl)-1H-1,2,3-triazole

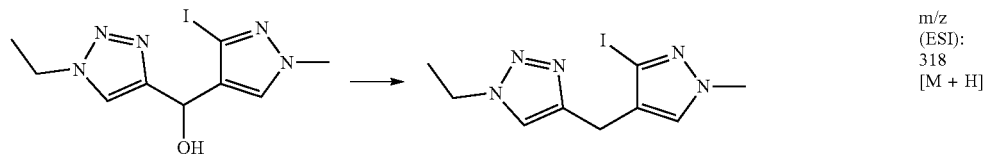

m/z (ESI): 318 [M + H]

5-((3-iodo-1-methyl-1H-pyrazol-4-yl)methyl)-1-methyl-1H-pyrazole-3-carbonitrile

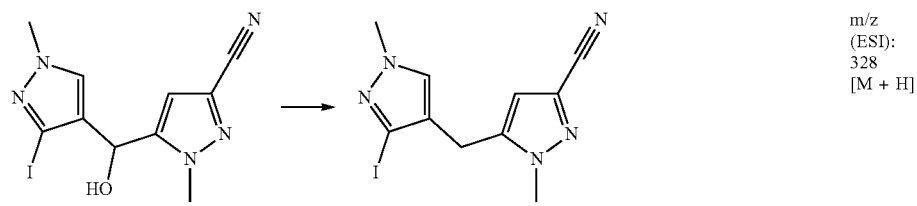

m/z (ESI): 328 [M + H]

3-iodo-1-methyl-4-((1-(2,2,2-trifluoroethyl)-1H-pyrazol-4-yl)methyl)-1H-pyrazole

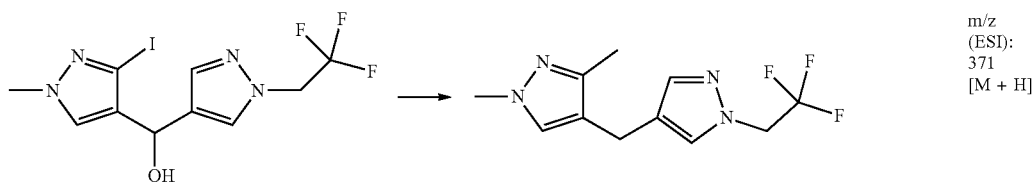

m/z (ESI): 371 [M + H]

1-(cyclopropylmethyl)-4-((3-iodo-1-methyl-1H-pyrazol-4-yl)methyl)-1H-1,2,3-triazole

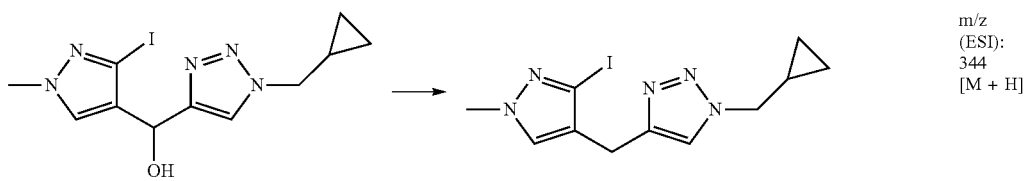

m/z (ESI): 344 [M + H]

5-bromo-1-(cyclopropylmethyl)-4-[(3-iodo-1-methyl-1H-pyrazol-4-yl)methyl]-3-methyl-1H-pyrazole

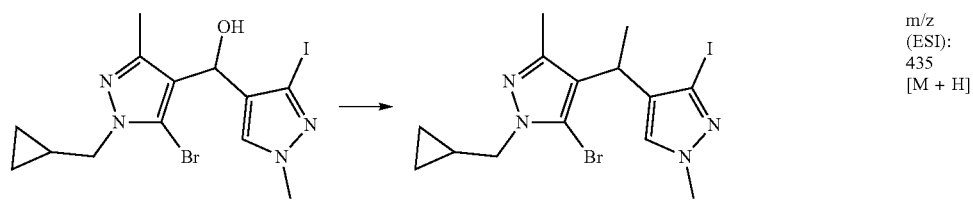

m/z (ESI): 435 [M + H]

5-bromo-4-((5-chloro-3-iodo-1-methyl-1H-pyrazol-4-yl)methyl)-1-(cyclopropylmethyl)-3-methyl-1H-pyrazole

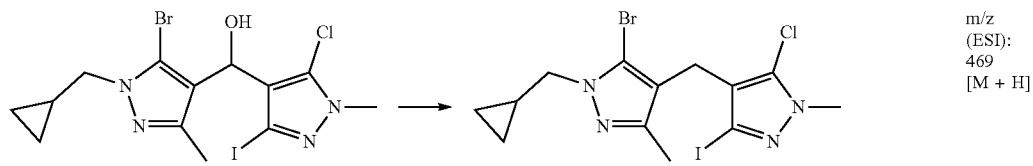

m/z (ESI): 469 [M + H]

-continued 5-((5-bromo-1-ethyl-1H-pyrazol-4-yl)methyl)-1-(4-fluoro-2-iodophenyl)-1H-1,2,3-triazole

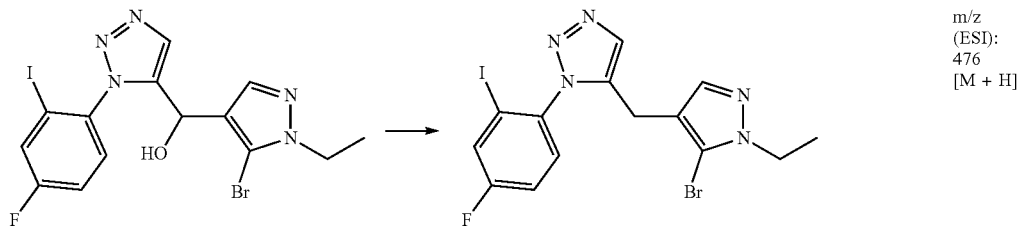

m/z (ESI): 476 [M + H]

5-((5-bromo-1-ethyl-1H-pyrazol-4-yl)methyl)-1-(4-fluoro-2-iodophenyl)-1H-pyrazole-3-carbonitrile

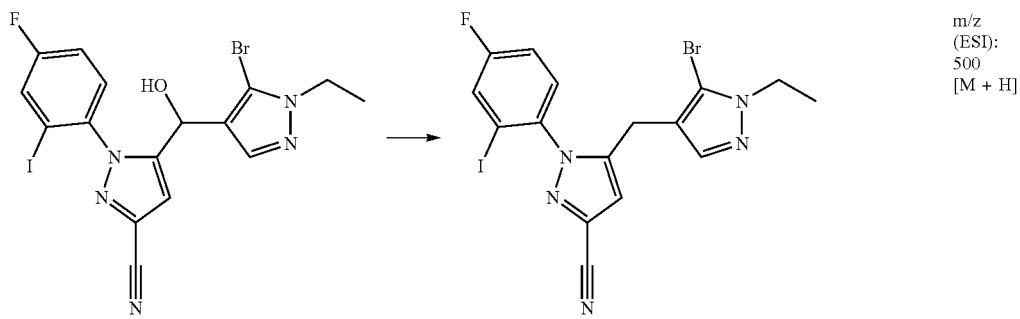

m/z (ESI): 500 [M + H]

4-bromo-3-ethyl-5-((1-(4-fluoro-2-iodophenyl)-3-methyl-1H-pyrazol-5-yl)methyl)-1-methyl-1H-pyrazole

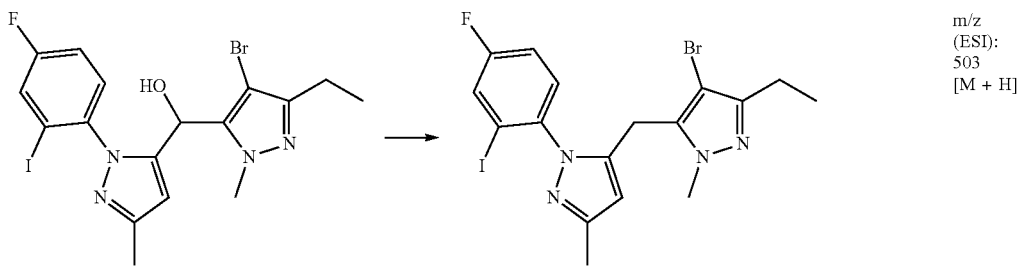

m/z (ESI): 503 [M + H]

4-((5-bromo-1-ethyl-1H-pyrazol-4-yl)methyl)-3-iodopyridine

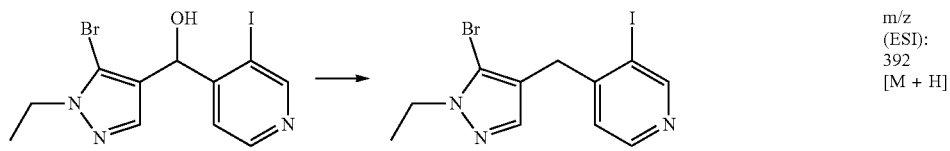

m/z (ESI): 392 [M + H]

4-bromo-3-((5-bromo-1-ethyl-1H-pyrazol-4-yl)methyl)pyridine

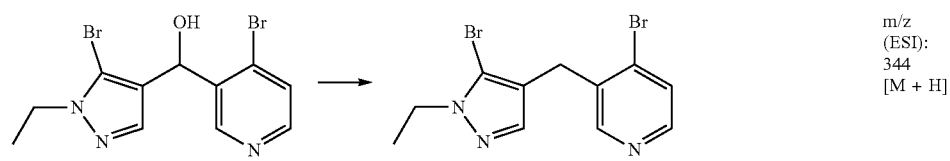

m/z (ESI): 344 [M + H]

5-((5-bromo-1-ethyl-1H-pyrazol-4-yl)methyl)pyrimidin-4-ol

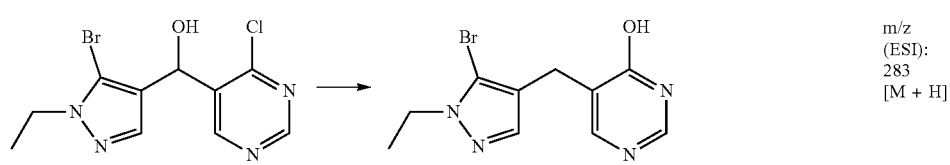

m/z (ESI): 283 [M + H]

5-bromo-3-(1-(2-(5-((5-bromo-1-ethyl-1H-pyrazol-4-yl)methyl)-1H-pyrazol-1-yl)-5-fluorophenyl)ethoxy)-2-nitropyridine

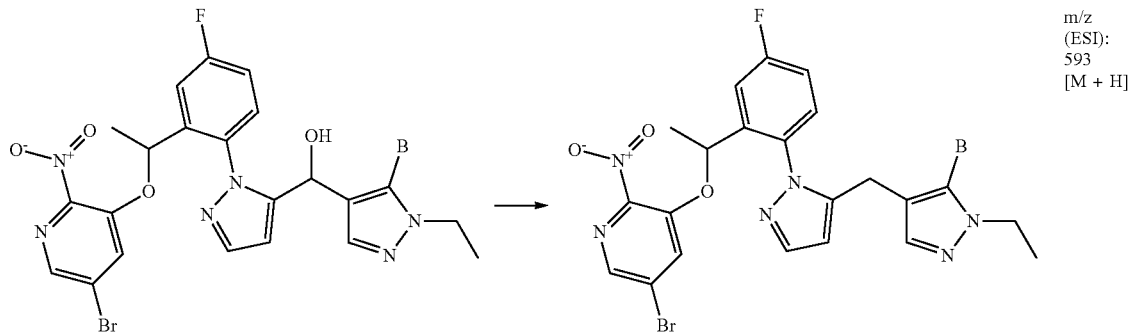

m/z (ESI): 593 [M + H]

5-bromo-3-((2-(5-((5-bromo-1-ethyl-1H-pyrazol-4-yl)methyl)-1H-pyrazol-1-yl)-5-fluorobenzyl)oxy)-2-nitropyridine

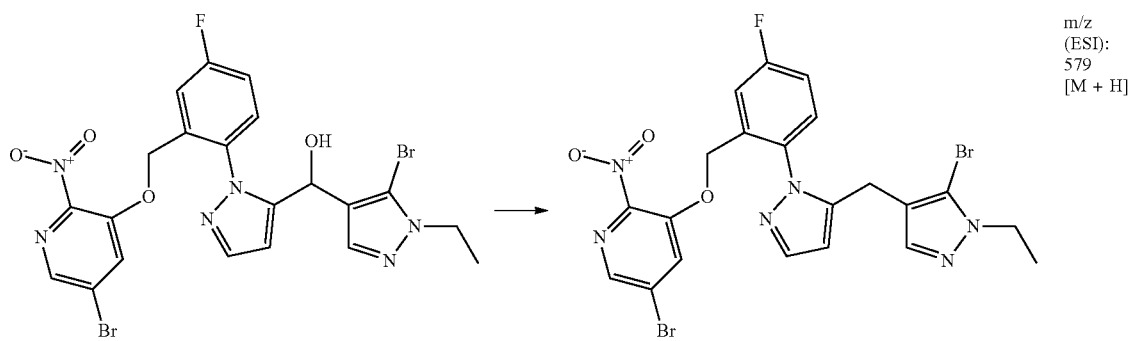

m/z (ESI): 579 [M + H]

5-bromo-3-(1-(2-(5-((5-bromo-1-ethyl-1H-pyrazol-4-yl)methyl)-4-fluoro-1H-pyrazol-1-yl)-5-fluorophenyl)ethoxy)-2-nitropyridine

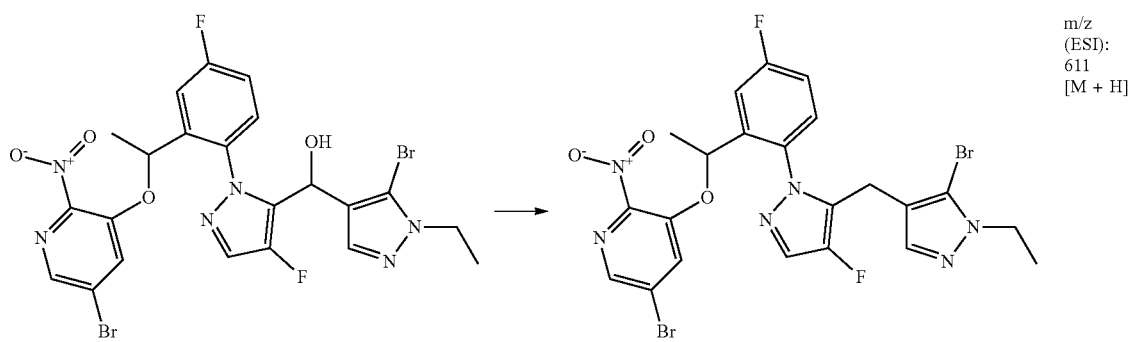

m/z (ESI): 611 [M + H]

5-bromo-3-((2-(5-((5-bromo-1-ethyl-1H-pyrazol-4-yl)methyl)-4-fluoro-1H-pyrazol-1-yl)-5-fluorobenzyl)oxy)-2-nitropyridine

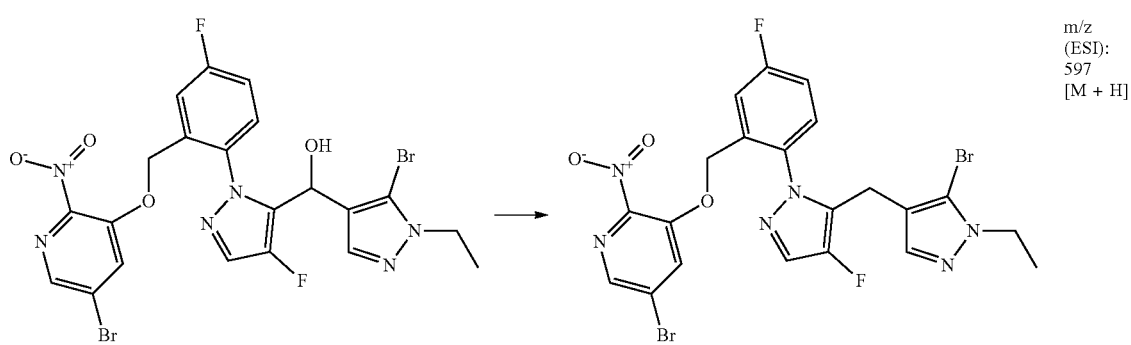

m/z (ESI): 597 [M + H]

-continued 2-chloro-3-((1-ethyl-1H-1,2,3-triazol-4-yl)methyl)-5-fluoropyridine

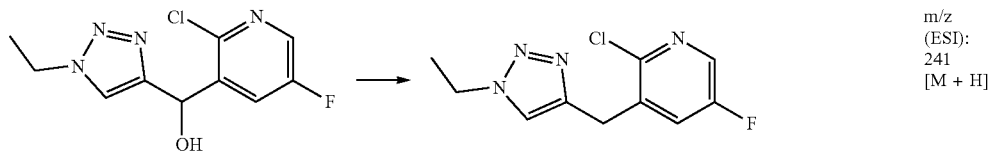

m/z (ESI): 241 [M + H]

3-chloro-1-ethyl 4-((1-(4-fluoro-2-iodophenyl)-3-methyl-1H-pyrazol-5-yl)methyl)-1H-pyrazole

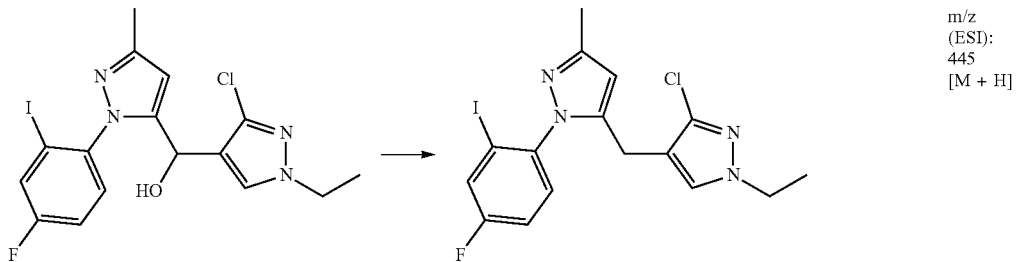

m/z (ESI): 445 [M + H]

4-[(dibromo-1,3-thiazol-5-yl)methyl]-1-ethyl-1H-1,2,3-triazole

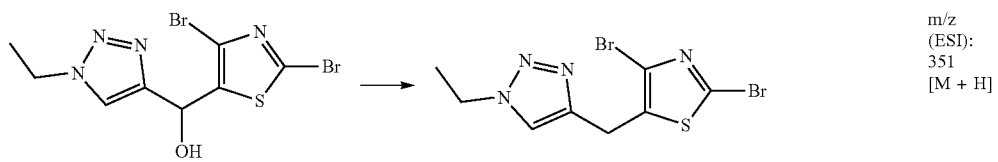

m/z (ESI): 351 [M + H]

3-bromo-4-((3-chloro-1-(2,2-difluoroethyl)-1H-pyrazol-4-yl)methyl)-1-methyl-1H-pyrazole

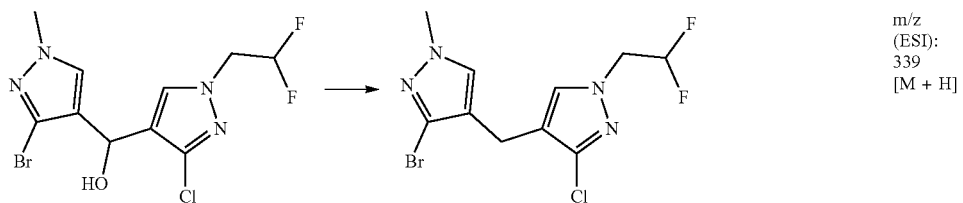

m/z (ESI): 339 [M + H]

4-[(3-bromo-1-methyl-1H-pyrazol-4-yl)methyl]-1-(2,2-difluoroethyl)-3-methyl-1H-pyrazole

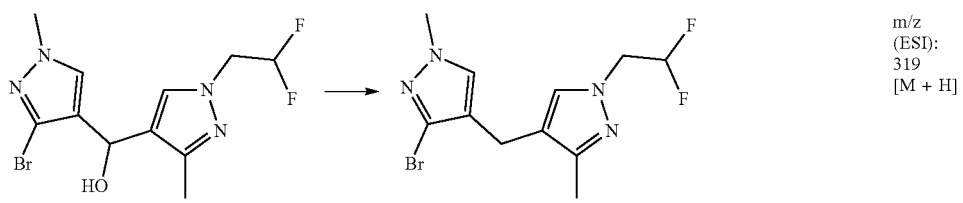

m/z (ESI): 319 [M + H]

3-bromo-1-(difluoromethyl)-4-[(1-ethyl-1H-pyrazol-4-yl)methyl]-1H-pyrazole

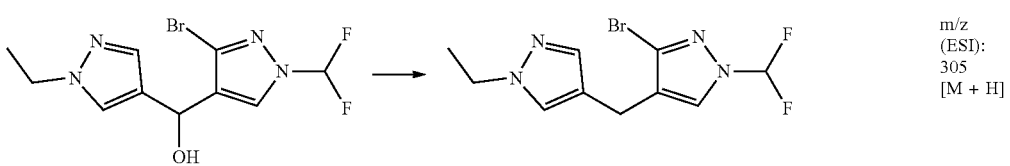

m/z (ESI): 305 [M + H]

3-[(3-bromo-1-methyl-1H-pyrazol-4-yl)methyl]-5-ethyl-1,2-thiazole

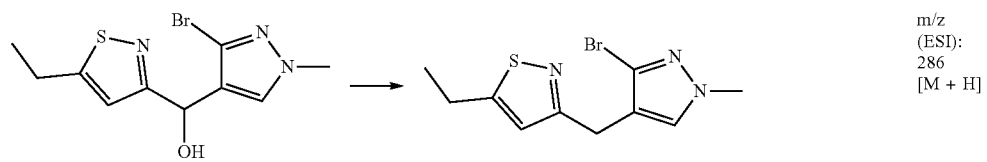

m/z (ESI): 286 [M + H]

-continued (R)-1-(2-(1-(benzyloxy)ethyl)-4-fluorophenyl)-5-((1-(cyclopropylmethyl)-1H-pyrazol-4-yl)methyl)-3-(trifluoromethyl)-1H-pyrazole

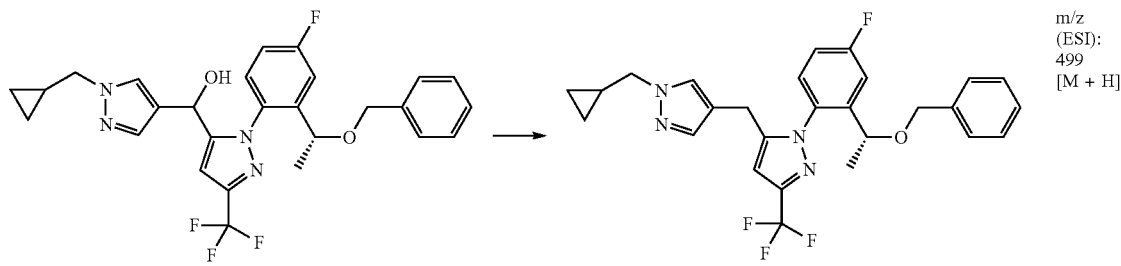

m/z (ESI): 499 [M + H]

1-ethyl-4-((3-iodo-1-methyl-1H-pyrazol-4-yl)methyl)-3-(trifluoromethyl)-1H-pyrazole

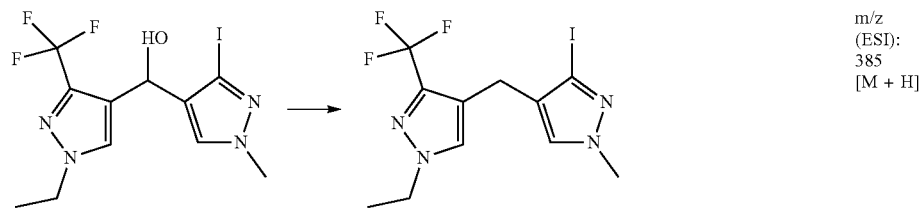

m/z (ESI): 385 [M + H]

2-chloro-3-{[1-(cyclopropylmethyl)-1H-1,2,3-triazol-4-yl]methyl}-5-fluoropyridine

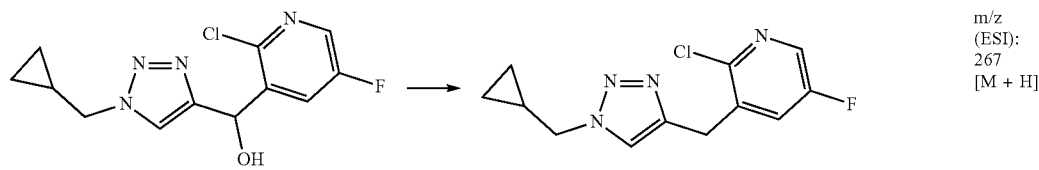

m/z (ESI): 267 [M + H]

1-(cyclopropylmethyl)-4-[(dibromo-1,3-thiazol-5-yl)methyl]-1H-1,2,3-triazole

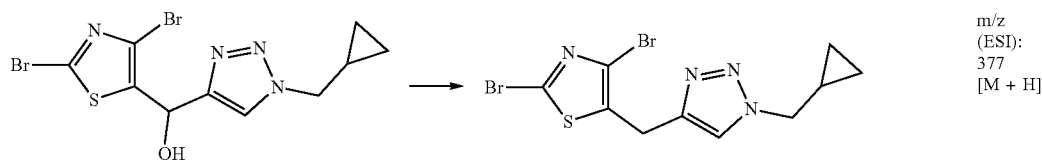

m/z (ESI): 377 [M + H]

2-chloro-3-((1-(cyclopropylmethyl)-1H-1,2,3-triazol-4-yl)methyl)pyridine

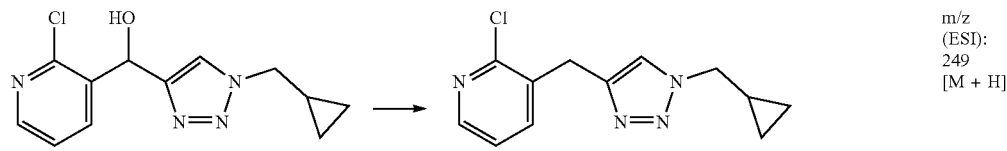

m/z (ESI): 249 [M + H]

(R)-4-((1-(2-(1-(benzyloxy)ethyl)-4-fluorophenyl)-3-(difluoromethyl)-1H-pyrazol-5-yl)methyl)-1-(cyclopropylmethyl)-1H-1,2,3-triazole

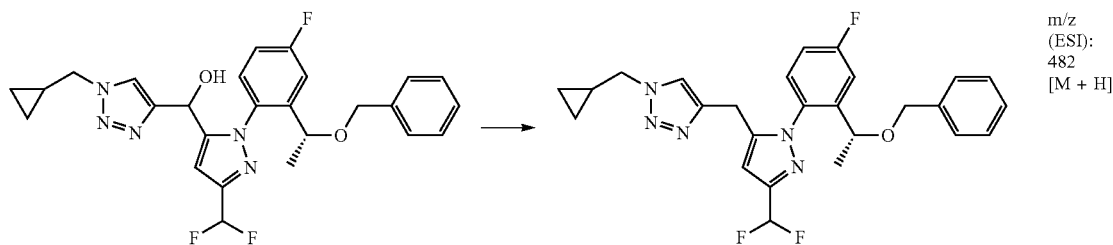

m/z (ESI): 482 [M + H]

(R)-1-(2-(1-(benzyloxy)ethyl)-4-fluorophenyl)-5-((1-(cyclopropylmethyl)-3-methyl-1H-pyrazol-4-yl)methyl)-3-(difluoromethyl)-1H-pyrazole

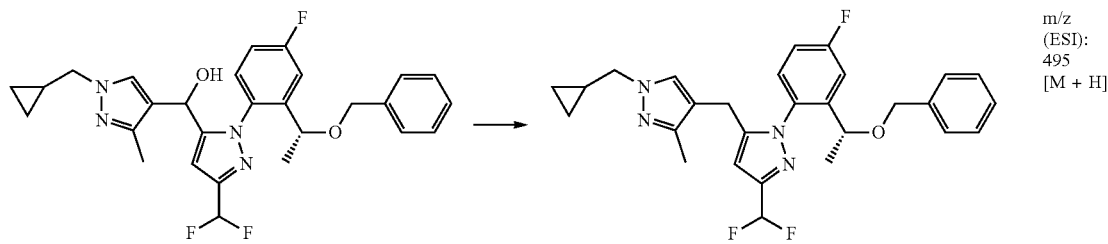

m/z (ESI): 495 [M + H]

2,4-dibromo-5-{[1-(cyclopropylmethyl)-3-methyl-1H-pyrazol-4-yl]methyl}-1,3-thiazole

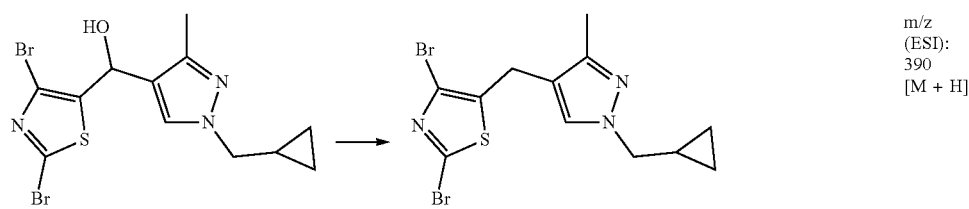

m/z (ESI): 390 [M + H]

(R)-1-(2-(1-(benzyloxy)ethyl)-4-fluorophenyl)-5-((1-(cyclopropylmethyl)-1H-pyrazol-4-yl)methyl)-3-(difluoromethyl)-1H-pyrazole

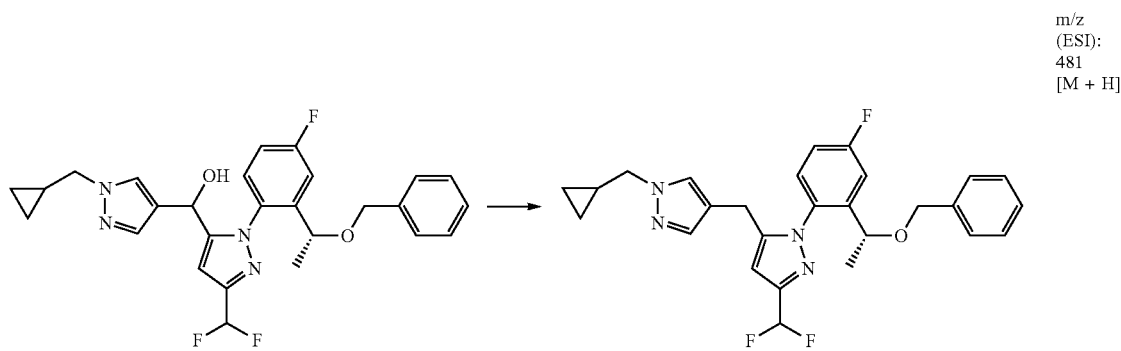

m/z (ESI): 481 [M + H]

3-bromo-4-{[3-chloro-1-(cyclopropylmethyl)-1H-pyrazol-4-yl]methyl}-1-methyl-1H-pyrazole

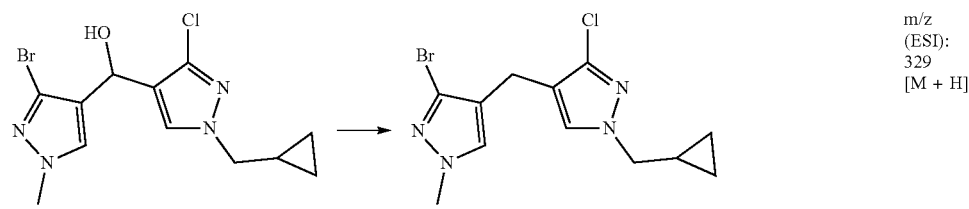

m/z (ESI): 329 [M + H]

2-chloro-3-((1-(cyclopropylmethyl)-3-methyl-1H-pyrazol-4-yl)methyl)pyridine

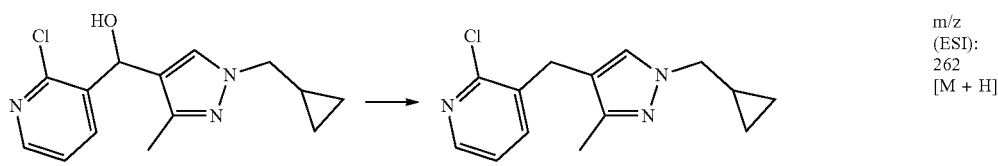

m/z (ESI): 262 [M + H]

(R)-1-(2-(1-(benzyloxy)ethyl)-4-fluorophenyl)-3-(difluoromethyl)-5-((1-ethyl-3-methoxy-1H-pyrazol-4-yl)methyl)-1H-pyrazole

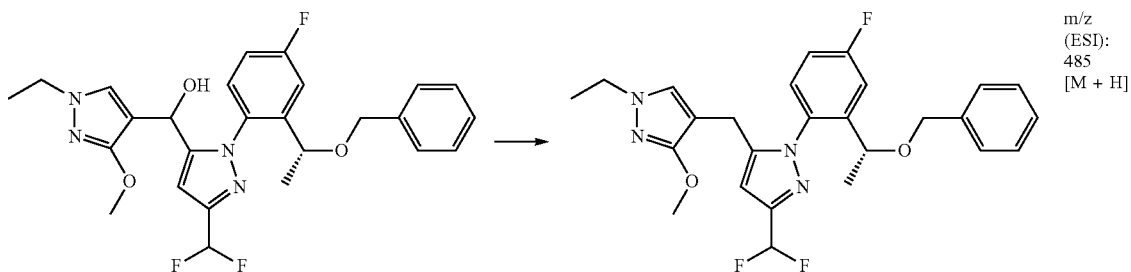

m/z (ESI): 485 [M + H]

2-chloro-3-((1-(cyclopropylmethyl)-1H-pyrazol-4-yl)methyl)pyridine

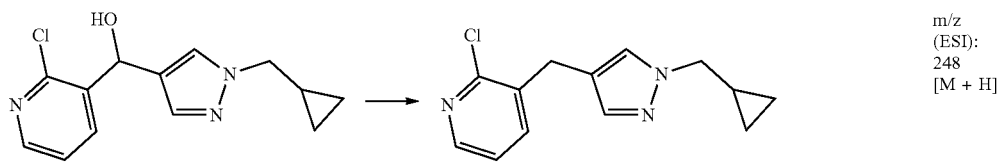

m/z (ESI): 248 [M + H]

3-bromo-4-{[1-ethyl-3-(propan-2-yl)-1H-pyrazol-4-yl]methyl}-1-methyl-1H-pyrazole

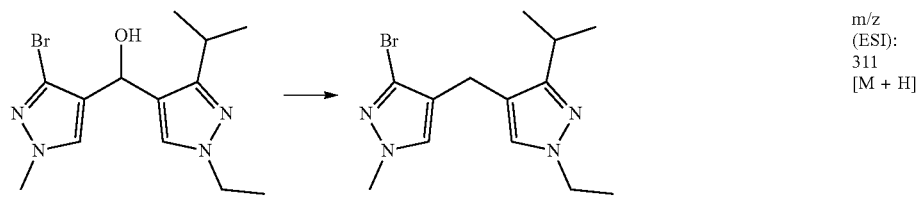

m/z (ESI): 311 [M + H]

3-((3-bromo-1-methyl-1H-pyrazol-4-yl)methyl)-5-ethylisoxazole m/z (ESI): 270 [M + H]

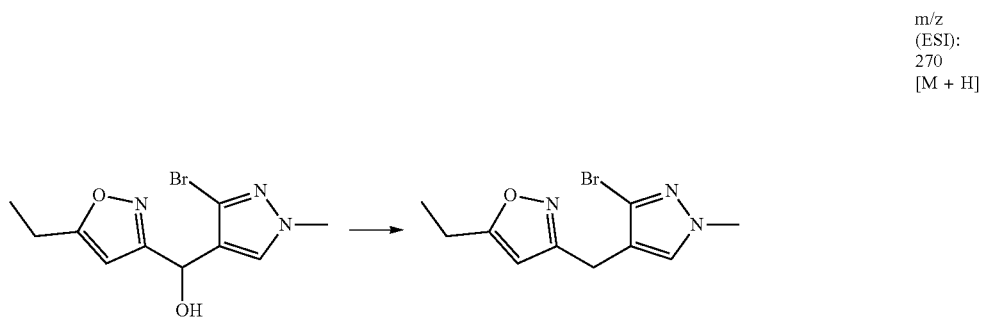

4-((3-bromo-1-methyl-1H-pyrazol-4-yl)methyl)-1-ethyl-1H-pyrazole-3-carbonitrile

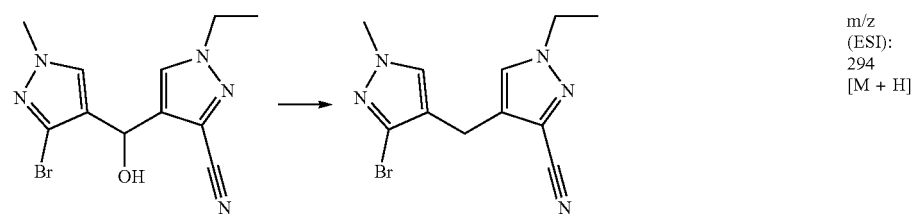

m/z (ESI): 294 [M + H]

5-bromo-3-((2-(5-((1-ethyl-1H-pyrazol-4-yl)methyl)-3-methyl-1H-pyrazol-1-yl)-5-fluorobenzyl)oxy)-2-nitropyridine

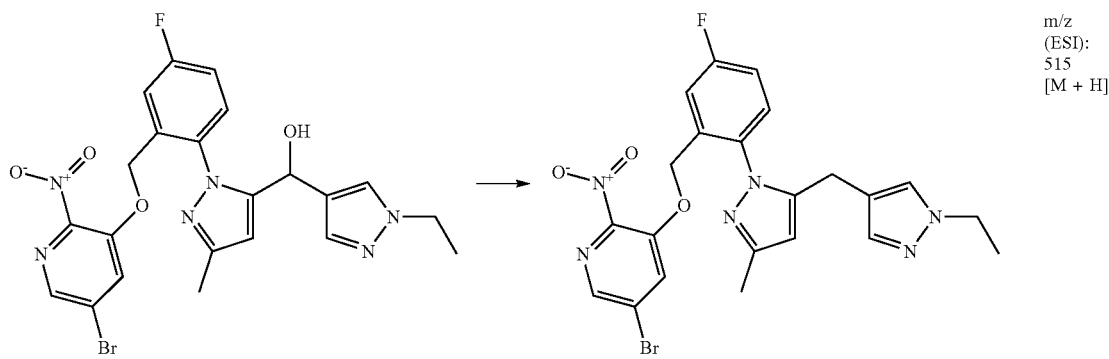
5-bromo-3-(1-(2-(5-((1-ethyl-1H-pyrazol-4-yl)methyl)-3-fluoro-1H-pyrazol-1-yl)-5-fluorophenyl)ethoxy)-2-nitropyridine
m/z (ESI): 515 [M + H]
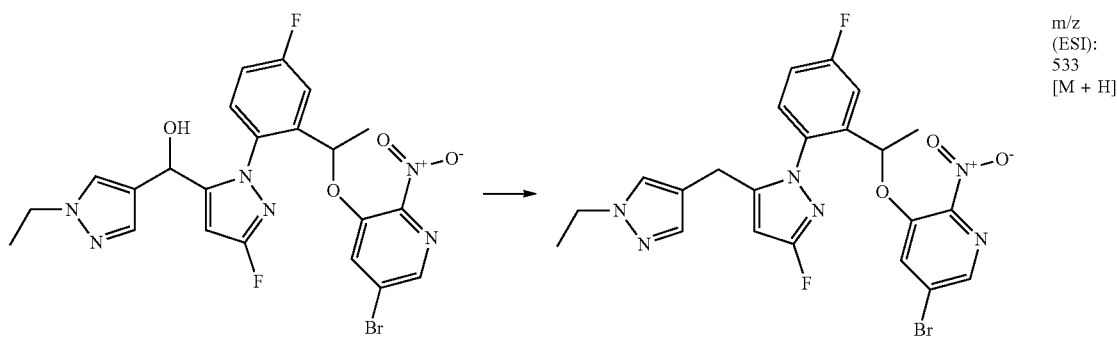
5-bromo-3-((2-(3-chloro-5-((1-ethyl-1H-pyrazol-4-yl)methyl)-1H-pyrazol-1-yl)-5-fluorobenzyl)oxy)-2-nitropyridine
m/z (ESI): 533 [M + H]
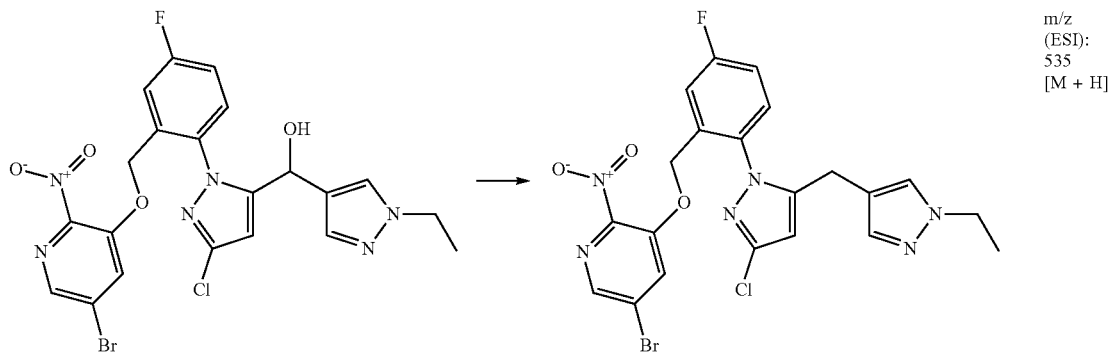
3-bromo-5-((1-ethyl-1H-pyrazol-4-yl)methyl)-1-(4-fluoro-2-iodophenyl)-1H-pyrazole
m/z (ESI): 535 [M + H]
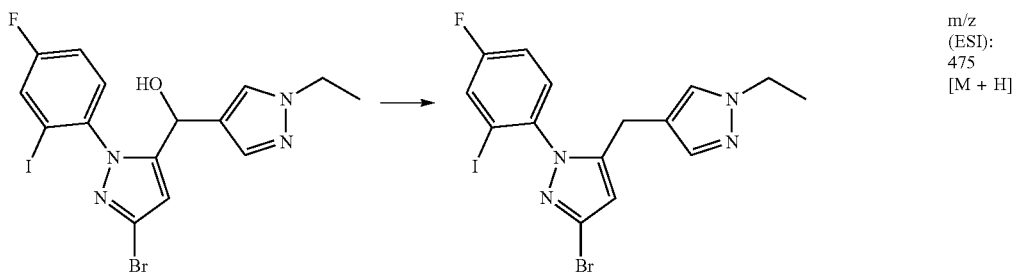
m/z (ESI): 475 [M + H]

-continued 2,4-dibromo-5-[(1-ethyl-1H-pyrazol-4-yl)methyl]-1,3-thiazole

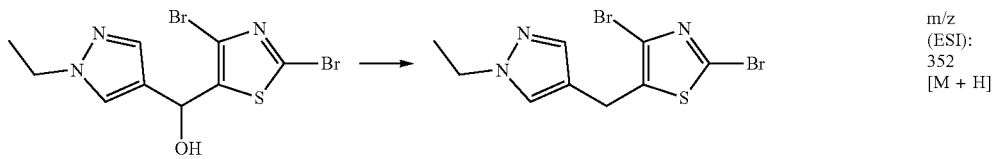

m/z (ESI): 352 [M + H]

5-((1-(4-fluoro-2-iodophenyl)-3-methyl-1H-pyrazol-5-yl)methyl)-1-methyl-1H-pyrazole-3-carbonitrile

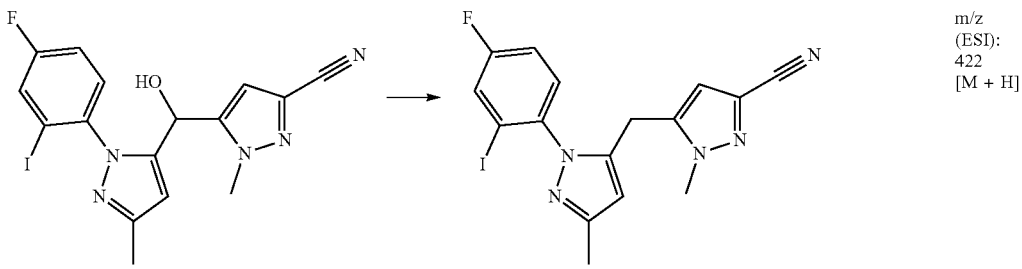

m/z (ESI): 422 [M + H]

3-((5-bromo-1-methyl-1H-pyrazol-4-yl)methyl)-1H-pyrazole-5-carbonitrile

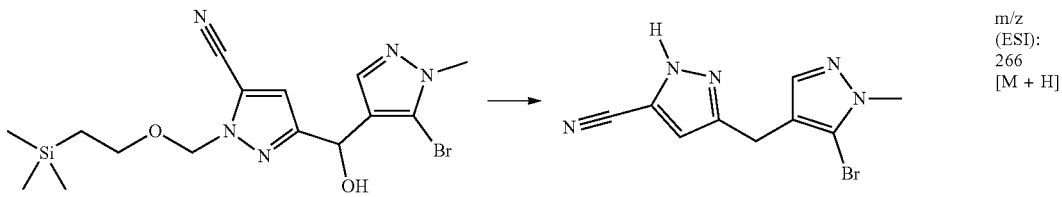

m/z (ESI): 266 [M + H]

3-bromo-4-((3-(2,2-difluoroethyl)-1-methyl-1H-pyrazol-5-yl)methyl)-1-methyl-1H-pyrazole

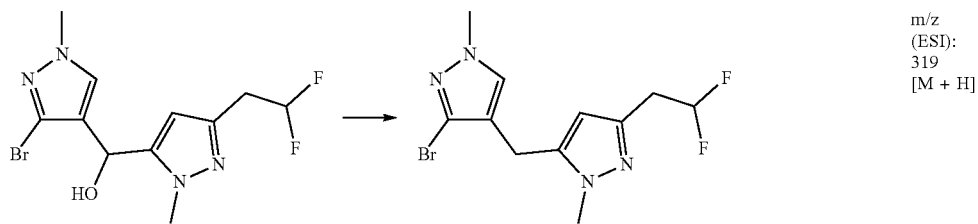

m/z (ESI): 319 [M + H]

3-bromo-4-((3-(cyclopropylmethyl)-1-methyl-1H-pyrazol-5-yl)methyl)-1-methyl-1H-pyrazole

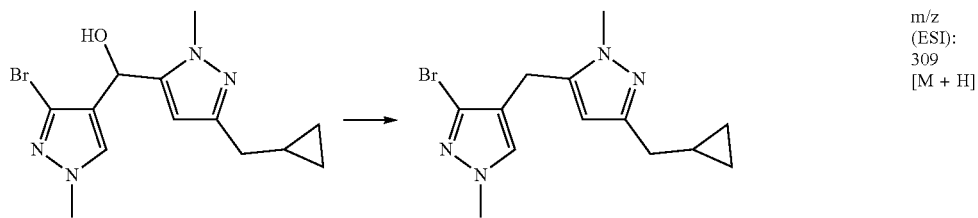

m/z (ESI): 309 [M + H]

Synthesis of 4-bromo-5-((4-(difluoromethyl)-1H-pyrazol-1-yl)methyl)-2-methylthiazole

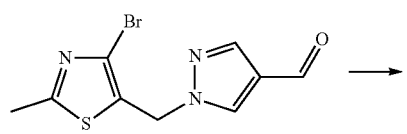

-continued

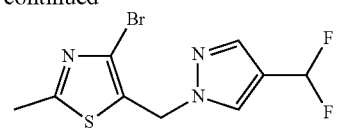

A solution of 1-((4-bromo-2-methylthiazol-5-yl)methyl)-1H-pyrazole-4-carbaldehyde (580 mg, 2.03 mmol) in DAST (5 mL) was stirred at 30° C. for 12 h under $N_2$. The reaction was quenched with sat. aq. $NaHCO_3$ (50 mL) at 0° C., and then extracted with EtOAc (15 mL). The organic phase was dried over Na$_2$SO$_4$, filtered, and concentrated in vacuo. The residue was purified by column chromatography on silica gel (10→25% EtOAc in PE) to give 4-bromo-5-((4-(difluoromethyl)-1H-pyrazol-1-yl)methyl)-2-methylthiazole (426 mg, 68% yield) as a yellow oil. LC/MS (ESI) (m/z): 308 [M+H]$^+$.

Synthesis of 3,5-difluoro-2-iodobenzaldehyde

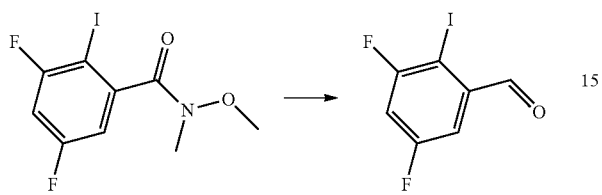

To a solution of 3,5-difluoro-2-iodo-N-methoxy-N-methylbenzamide (8.00 g, 24.5 mmol) in THF (60 mL) at −78° C. was added dropwise DIBAL-H (36.7 mL, 39.7 mmol, 1.0 M) under N$_2$ atmosphere. After the addition, the mixture was stirred at 0° C. for 2 h. The mixture was quenched with ice-water and then extracted with DCM (40 mL×2). The combined organic layers were washed with brine, dried over anhydrous Na$_2$SO$_4$, filtered and concentrated. The residue was purified by flash column chromatography on silica gel (5% DCM in MeOH) to give 3,5-difluoro-2-iodobenzaldehyde (6.0 g, 92%) as a yellow oil. LC-MS (ESI): m/z 269 [M+H]$^+$.

The following intermediates were synthesized using a similar experimental protocol:

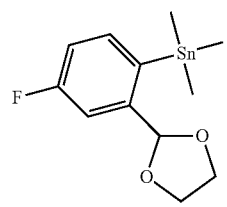

To a mixture of 2-(2-bromo-5-fluorophenyl)-1,3-dioxolane (1.0 g, 4.0 mmol) in THF (20 mL) was added n-BuLi (1.78 mL, 4.45 mmol, 2.5 M) dropwise at −78° C. The mixture was stirred at −78° C. for 1 h. Then, trimethyltin chloride (4.45 mL, 4.45 mmol, 1.0 M in THF) was added dropwise to the mixture. The resulting mixture was stirred at −78° C. for 15 min. The mixture was quenched with sat. NH$_4$Cl (50 mL) at 0° C. and extracted with EtOAc (50 mL×3). The combined extracts were washed with brine (20 mL×2), dried over anhydrous Na$_2$SO$_4$, filtered and concentrated. The residue was purified by flash chromatography on silica gel (10% EtOAc in PE) to give [2-(1,3-dioxolan-2-yl)-4-fluorophenyl]trimethylstannane (600 mg, yield: 44%) as a colorless oil. LC/MS ESI (m/z): 333 [M+H]$^+$.

1-(2-(3-bromo-5-(((1-ethyl-1H-pyrazol-4-yl)methyl)-1H-pyrazol-1-yl)-5-fluorophenyl)ethan-1-ol m/z (ESI): 393 [M + H]

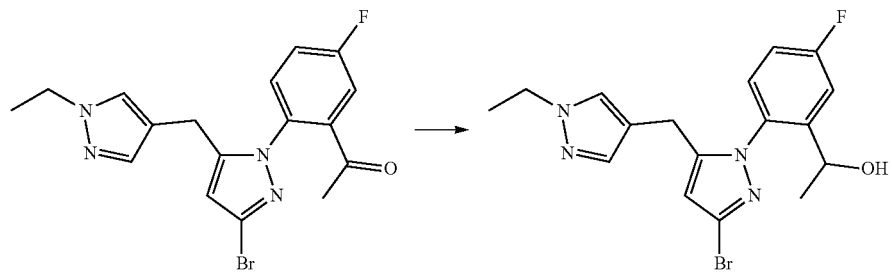 [SMILES: CCn1cc(Cc2cc(Br)nn2-c2ccc(F)cc2C(C)=O)cn1 ; CCn1cc(Cc2cc(Br)nn2-c2ccc(F)cc2C(C)O)cn1]

Synthesis of [2-(1,3-dioxolan-2-yl)-4-fluorophenyl]trimethylstannane

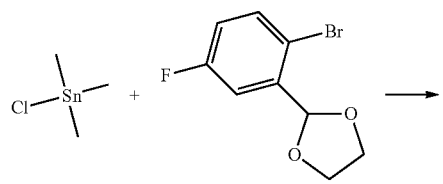

Synthesis of (5-bromo-1-methyl-1H-pyrazol-4-yl)(5-iodo-1-methyl-1H-pyrazol-4-yl)methanol

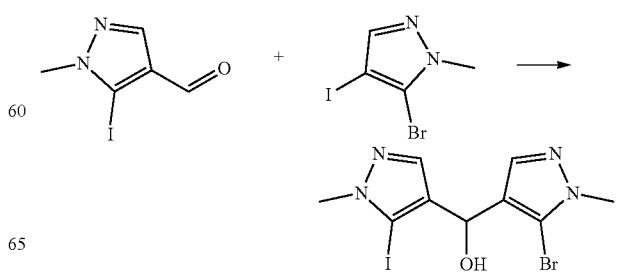

To a solution of 5-bromo-4-iodo-1-methyl-1H-pyrazole (2.00 g, 6.99 mmol) in THF (35 mL) at −70° C. was added isopropylmagnesium bromide (1.0 M in THF, 13.9 mL, 13.9 mmol) dropwise under an N₂ atmosphere. After the addition, the mixture was stirred at −70° C. for 30 min, then a solution of 5-iodo-1-methyl-1H-pyrazole-4-carbaldehyde (2.14 g, 9.09 mmol) in THF (15 mL) was added dropwise at −70° C. over 10 min. The resulting mixture was stirred at −70° C. for another 2 h before being quenched with sat. NH₄Cl solution (60 mL). The mixture was extracted with DCM (2×100 mL). The combined extracts were washed with brine, dried over anhydrous Na₂SO₄, filtered and concentrated. The residue was purified by column chromatography on silica gel (30% EtOAc in PE) to give (5-bromo-1-methyl-1H-pyrazol-4-yl)(5-iodo-1-methyl-1H-pyrazol-4-yl)methanol as a yellow oil (785 mg, yield: 29%). LC/MS ESI (m/z): 397 [M+H]⁺.

The following intermediates were synthesized using a similar experimental protocol:

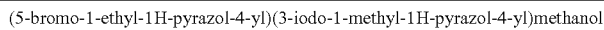
(5-bromo-1-ethyl-1H-pyrazol-4-yl)(3-iodo-1-methyl-1H-pyrazol-4-yl)methanol

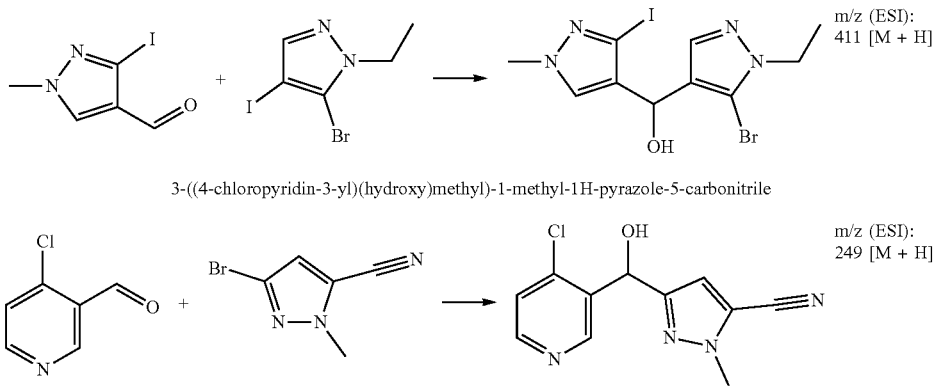

3-((4-chloropyridin-3-yl)(hydroxy)methyl)-1-methyl-1H-pyrazole-5-carbonitrile

Synthesis of 1-(2-(1,3-dioxolan-2-yl)-4-fluorophenyl)-1H-pyrazole

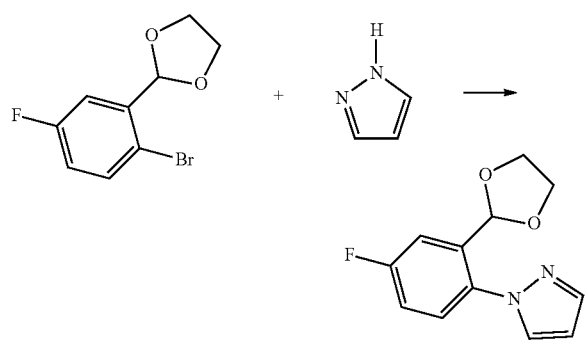

To a solution of 2-(2-bromo-5-fluorophenyl)-1,3-dioxolane (3.0 g, 12.1 mmol) in 1-methylpyrrolidine (50 mL), was added copper oxide (348 mg, 2.43 mmol) at r.t., then followed by the addition of 1H-pyrazole (868 mg, 12.8 mmol). After stirring at 120° C. overnight, the reaction mixture was diluted with EtOAc and water. The organic layer was separated, washed with sat. aq. NH₄Cl three times, brine once and concentrated in vacuo. The residue was purified by flash chromatography on silica gel (PE:EA=10:1 to 1:1, V/V) to give 1-(2-(1,3-dioxolan-2-yl)-4-fluorophenyl)-1H-pyrazole (2.0 g, 70% yield) as a yellow oil. TLC: R_f=0.3 (PE/EA=5:1), LC/MS ESI (m/z): 235 [M+H]⁺.

The following intermediates were synthesized using a similar experimental protocol:

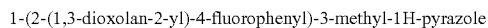
1-(2-(1,3-dioxolan-2-yl)-4-fluorophenyl)-3-methyl-1H-pyrazole

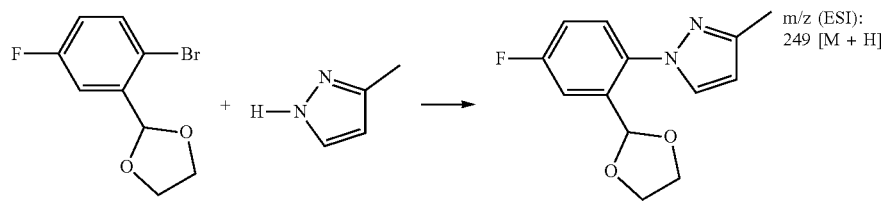

Synthesis of 5-fluoro-2-(4-(hydroxymethyl)-1-methyl-1H-pyrazol-5-yl)benzaldehyde

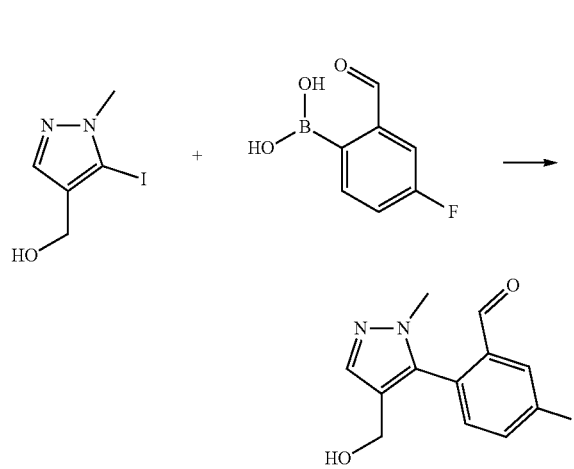

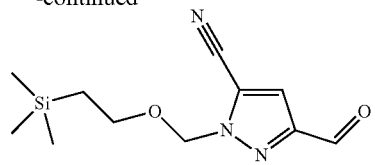

To a solution of 1-((2-(trimethylsilyl)ethoxy)methyl)-1H-pyrazole-5-carbonitrile (5.40 g, 24.2 mmol) in THF (50 mL) was added LiTMP MgCl$_2$ (1.0 M in THF, 36.3 mL, 36.3 mmol) dropwise at −16° C. under nitrogen. The resulting solution was stirred at −16° C. for 1 h. N,N-dimethylformamide (3.7 mL, 48.4 mmol) was then added and the mixture stirred for 1 h. The reaction was quenched by the addition of brine, extracted with EtOAc (2×30 mL), dried and concentrated. The residue was purified by flash chromatography (silica gel, 0→5% ethyl acetate in petroleum ether) to afford 3-formyl-1-((2-(trimethylsilyl)ethoxy)methyl)-1H-pyrazole-5-carbonitrile (3.4 g, 60%) as a brown liquid. LC/MS (ESI) m/z: 252 [M+H]$^+$.

The following intermediates were synthesized using a similar experimental protocol:

3-(hydroxy(3-iodo-1-methyl-1H-pyrazol-4-yl)methyl)-1-((2-(trimethylsilyl)ethoxy)methyl)-1H-pyrazole-5-carbonitrile

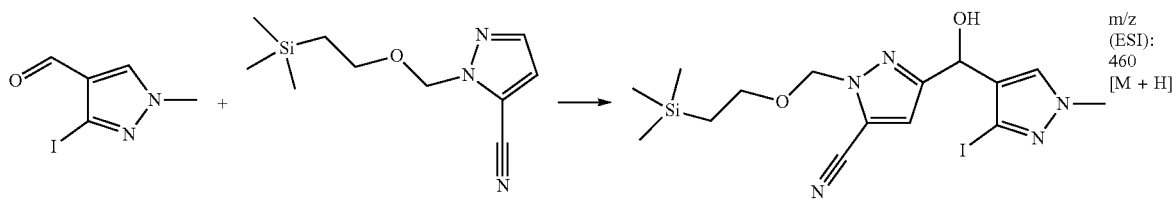

m/z (ESI): 460 [M + H]

To a solution of (5-iodo-1-methyl-1H-pyrazol-4-yl)methanol (1.6 g, 6.7 mmol) in dioxane (15 mL) and H$_2$O (5 mL) were added (4-fluoro-2-formylphenyl)boronic acid (1.69 g, 10.1 mmol), disodium carbonate (2.14 g, 20.2 mmol) and Pd(dppf)Cl$_2$ (492 mg, 0.670 mmol). After stirring at 80° C. for 2 h, the reaction was diluted with water and extracted with EtOAc twice. The combined organic layers were dried over anhydrous Na$_2$SO$_4$, filtered and concentrated. The residue was purified by flash chromatography (silica gel, EtOAc/PE=1/1) to afford 5-fluoro-2-[4-(hydroxymethyl)-1-methyl-1H-pyrazol-5-yl]benzaldehyde (1.2 g, 76% yield) as a white solid. LC/MS ESI (m/z): 235 [M+H]$^+$.

Synthesis of 3-formyl-1-((2-(trimethylsilyl)ethoxy)methyl)-1H-pyrazole-5-carbonitrile

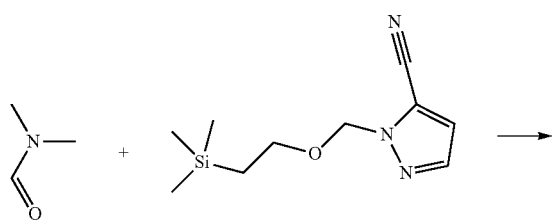

Synthesis of (2-chloropyridin-3-yl)(3-ethyl-1-methyl-1H-pyrazol-5-yl)methanol

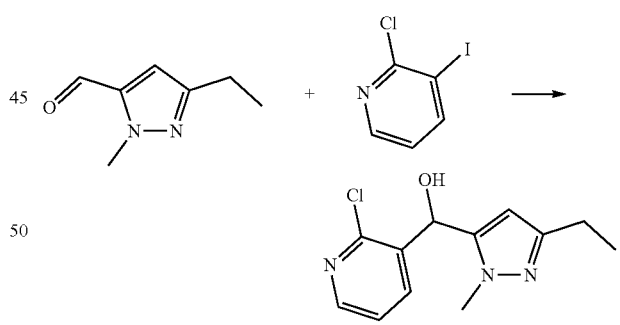

To a solution of 2-chloro-3-iodopyridine (1.04 g, 4.34 mmol) in THF (17 mL) was added isopropylmagnesium bromide (5.21 mL, 3.43 mmol) at −5° C. After stirring at r.t. for 0.5 h, 3-ethyl-1-methyl-1H-pyrazole-5-carbaldehyde (600 mg, 4.34 mmol) was added. Stirring was continued at r.t. for 0.5 h, then the mixture was poured into water (80 mL) and extracted with EA (80 mL×3). The organic layer was washed with sat. NaCl (60 mL×2), dried over anhydrous Na$_2$SO$_4$, filtered, and concentrated in vacuo. The residue was purified by column chromatography on silica gel (30% EtOAc in PE) to afford (2-chloropyridin-3-yl)(3-ethyl-1-methyl-1H-pyrazol-5-yl)methanol (850 mg, 78%) as a light-yellow solid. LC/MS (ESI): m/z=252 [M+H]$^+$.

The following intermediates were synthesized using a similar experimental protocol:

(1-(cyclopropylmethyl)-1H-pyrazol-4-yl)(3-iodo-1-methyl-1H-pyrazol-4-yl)methanol

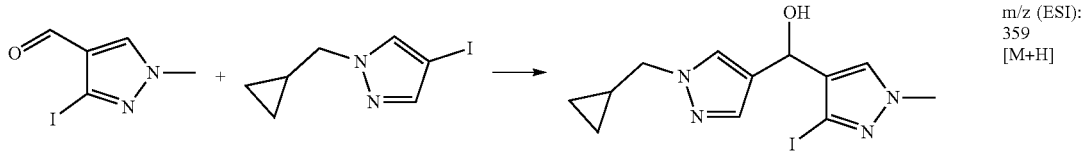

m/z (ESI): 359 [M+H]

(1-(cyclopropylmethyl)-1H-pyrazol-4-yl)(1-(4-fluoro-2-iodophenyl)-3-methyl-1H-pyrazol-5-yl)methanol

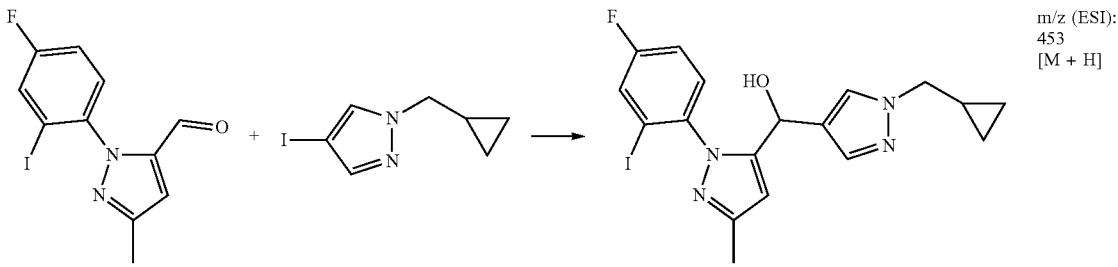

m/z (ESI): 453 [M + H]

(5-bromo-1-(cyclopropylmethyl)-3-methyl-1H-pyrazol-4-yl)(3-iodo-1-methyl-1H-pyrazol-4-yl)methanol

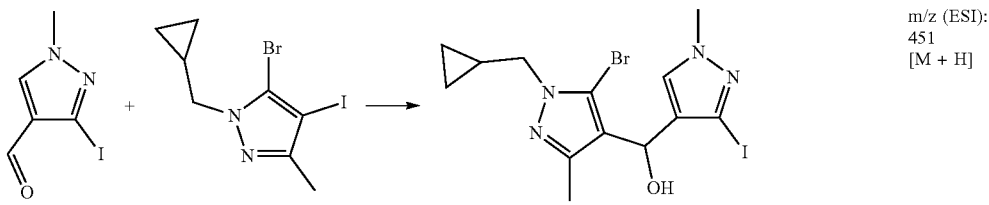

m/z (ESI): 451 [M + H]

(5-bromo-1-ethyl-1H-pyrazol-4-yl)(1-(4-fluoro-2-iodophenyl)-3-(trifluoromethyl)-1H-pyrazol-5-yl)methanol

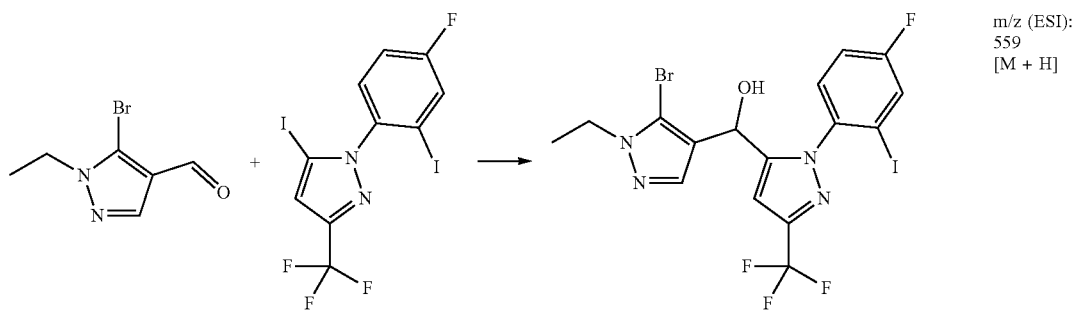

m/z (ESI): 559 [M + H]

(3-chloro-1-ethyl-1H-pyrazol-4-yl)(1-(4-fluoro-2-iodophenyl)-3-methyl-1H-pyrazol-5-yl)methanol

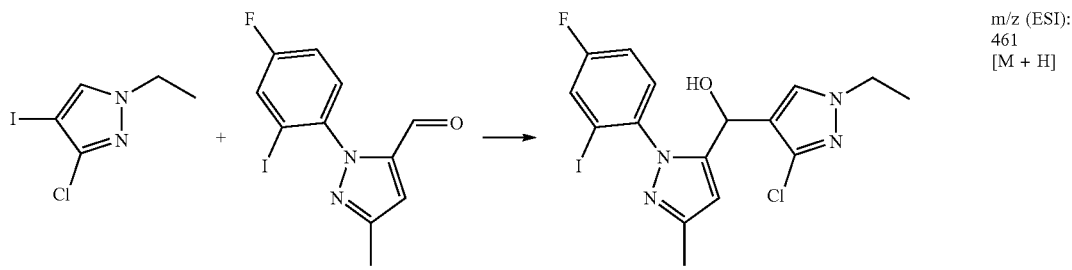

m/z (ESI): 461 [M + H]

(3-bromo-1-methyl-1H-pyrazol-4-yl)(3-chloro-1-(2,2-difluoroethyl)-1H-pyrazol-4-yl)methanol

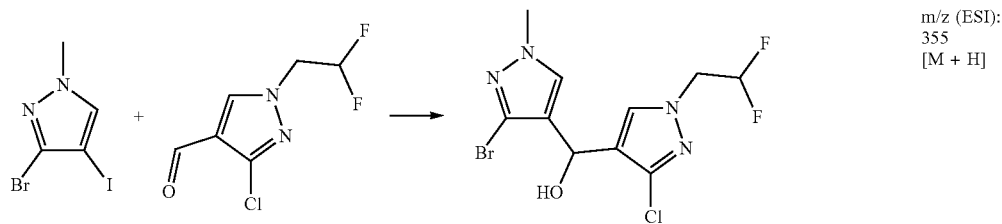

m/z (ESI): 355 [M + H]

(1-ethyl-3-(trifluoromethyl)-1H-pyrazol-4-yl)(3-iodo-1-methyl-1H-pyrazol-4-yl)methanol

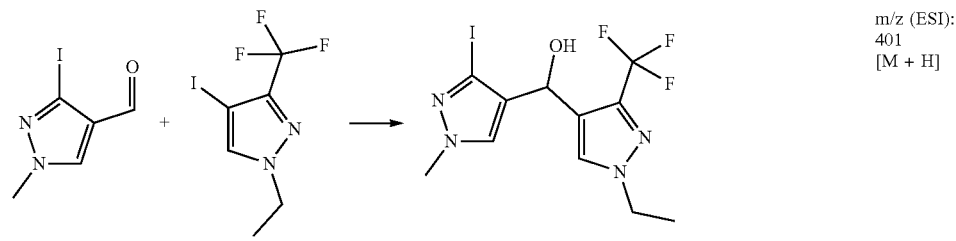

m/z (ESI): 401 [M + H]

(1-(cyclopropylmethyl)-3-methyl-1H-pyrazol-4-yl)(2,4-dibromothiazol-5-yl)methanol

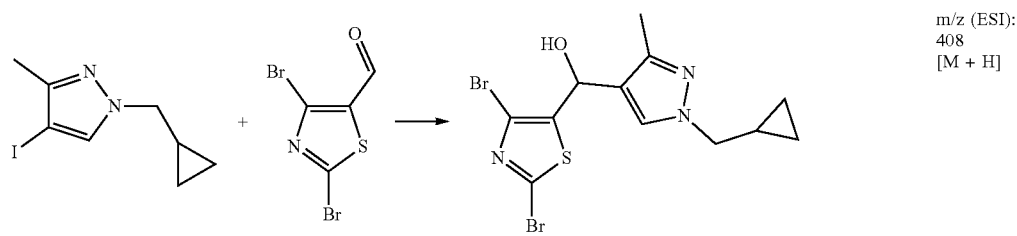

m/z (ESI): 408 [M + H]

(3-bromo-1-methyl-1H-pyrazol-4-yl)[3-chloro-1-(cyclopropylmethyl)-1H-pyrazol-4-yl]methanol

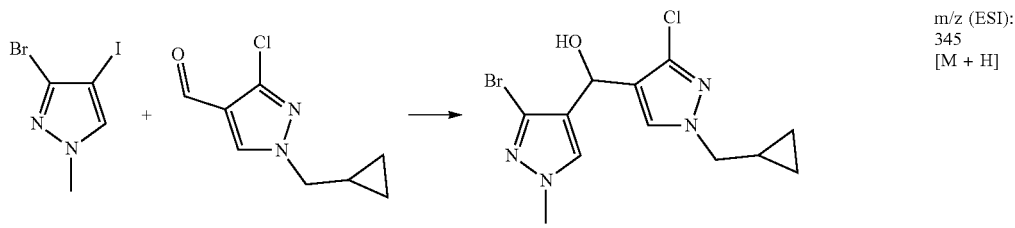

m/z (ESI): 345 [M + H]

(2-chloropyridin-3-yl)(1-(cyclopropylmethyl)-1H-pyrazol-4-yl)methanol

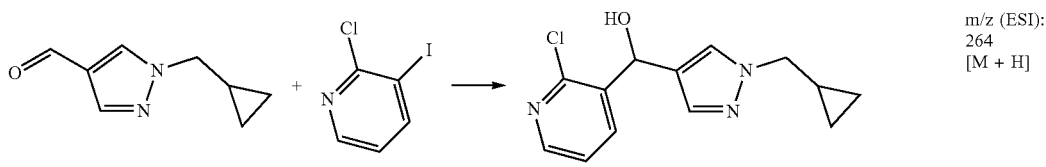

m/z (ESI): 264 [M + H]

(3-bromo-1-methyl-1H-pyrazol-4-yl)[1-ethyl-3-(propan-2-yl)-1H-pyrazol-4-yl]methanol

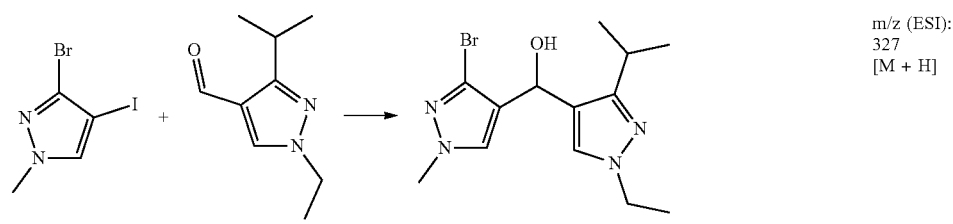

m/z (ESI): 327 [M + H]

(1-(2,2-difluoroethyl)-1H-pyrazol-4-yl)(1-(4-fluoro-2-iodophenyl)-3-(trifluoromethyl)-1H-pyrazol-5-yl)methanol

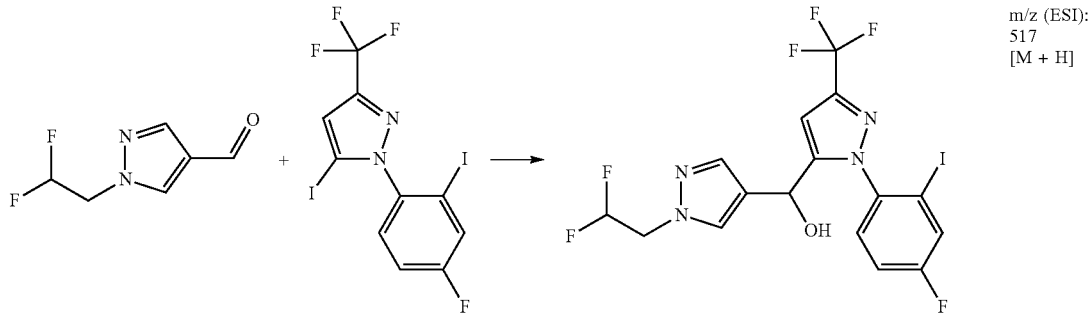

m/z (ESI): 517 [M + H]

[1-(cyclopropylmethyl)-3-methyl-1H-pyrazol-4-yl](3-iodo-1-methyl-1H-pyrazol-4-yl)methanol

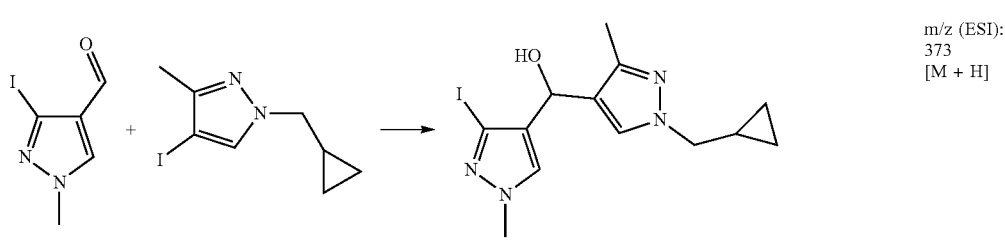

m/z (ESI): 373 [M + H]

(3-bromo-1-methyl-1H-pyrazol-4-yl)(3-(2,2-difluoroethyl)-1-methyl-1H-pyrazol-5-yl)methanol

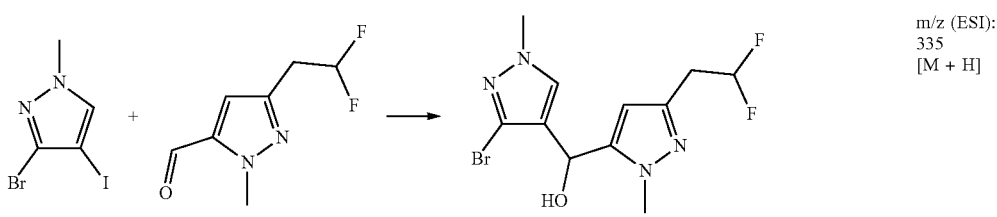

m/z (ESI): 335 [M + H]

(3-bromo-1-methyl-1H-pyrazol-4-yl)(3-(cyclopropylmethyl)-1-methyl-1H-pyrazol-5-yl)methanol

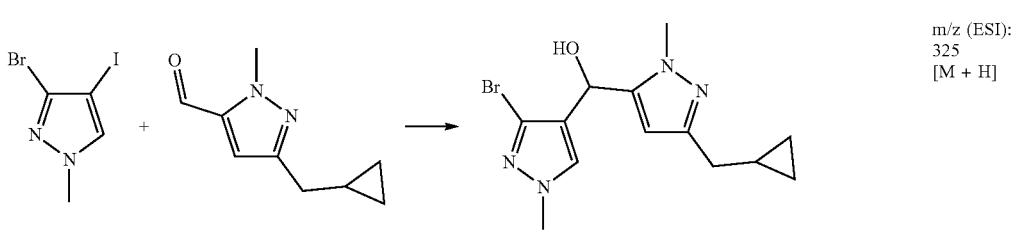

m/z (ESI): 325 [M + H]

Synthesis of 2-chloro-3-((1-ethyl-1H-pyrazol-4-yl)methyl)-5-methoxypyridine

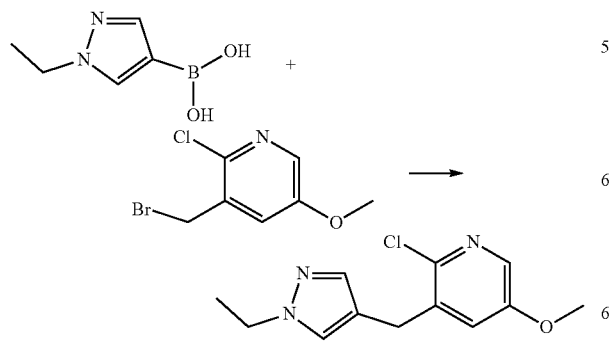

To a solution of 3-(bromomethyl)-2-chloro-5-methoxypyridine (100 mg, 0.423 mmol) in THF (2.5 mL) and H₂O (0.5 mL) was added (1-ethyl-1H-pyrazol-4-yl)boronic acid (59 mg, 0.42 mmol), K₃PO₄ (269 mg, 1.27 mmol), and 1,1'-bis(di-t-butylphosphino)ferrocene palladium dichloride (28 mg, 0.042 mmol). The mixture was stirred at 70° C. for 16 h, then poured into water (80 mL) and extracted with EA (80 mL×3). The combined organic layers were washed with brine (60 mL), dried with Na₂SO₄, filtered and concentrated. The residue was purified by column chromatography on silica gel (10→50% EtOAc in PE) to give 2-chloro-3-[(1-ethyl-1H-pyrazol-4-yl)methyl]-5-methoxypyridine (100 mg, yield: 94%) as a white solid. LC/MS (ESI): m/z=252 [M+H]⁺.

The following intermediates were synthesized using a similar experimental protocol:

---

2-chloro-3-((1-ethyl-1H-pyrazol-4-yl)methyl)-6-methoxypyridine

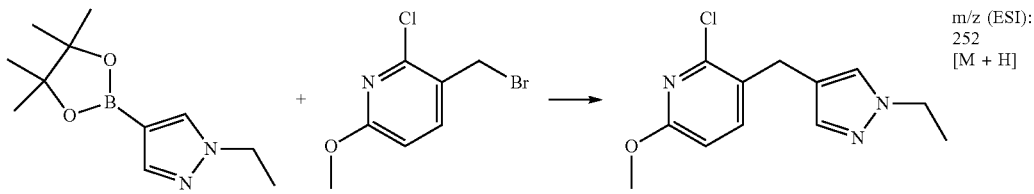

m/z (ESI): 252 [M + H]

---

Synthesis of 2-chloro-3-((1-ethyl-1H-pyrazol-4-)thyl)-4-methoxypyridine

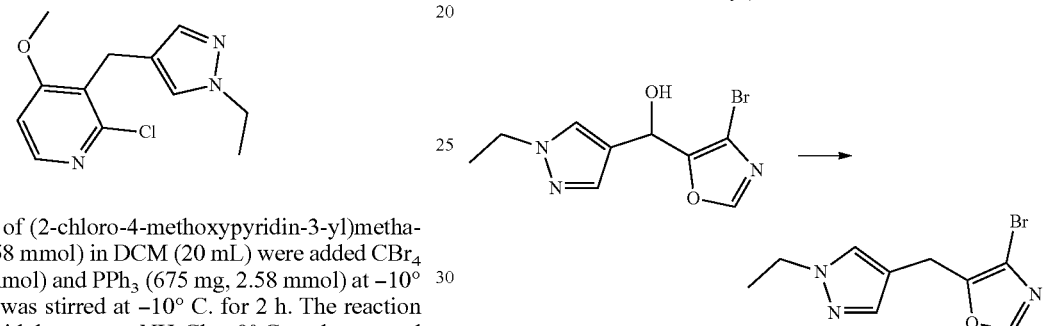

To a solution of (2-chloro-4-methoxypyridin-3-yl)methanol (447 mg, 2.58 mmol) in DCM (20 mL) were added $CBr_4$ (853 mg, 2.58 mmol) and $PPh_3$ (675 mg, 2.58 mmol) at −10° C. The mixture was stirred at −10° C. for 2 h. The reaction was quenched with by sat. aq. $NH_4Cl$ at 0° C. and extracted with DCM (30 mL). The organic layer was washed with brine, dried over anhydrous $Na_2SO_4$ and concentrated. The residue was purified by column chromatography on silica gel (25% of EA in PE) to give 3-(bromomethyl)-2-chloro-4-methoxypyridine (350 mg, yield: 58%) as a yellow oil. LC/MS (ESI) (m/z): 236 [M+H]⁺.

A mixture of 3-(bromomethyl)-2-chloro-4-methoxypyridine (250 mg, 1.06 mmol), 1-ethyl-4-(tetramethyl-1,3,2-dioxaborolan-2-yl)-1H-pyrazole (234 mg, 1.06 mmol), $K_3PO_4$ (179 mg, 0.846 mmol) and $Pd(dppf)Cl_2$ (28 mg, 0.042 mmol) in water (1 mL) and THF (5 mL) was stirred at 95° C. under an $N_2$ atmosphere for 4 h. The reaction mixture was filtered, and the filtrate was diluted with EA (50 mL). This solution was washed with brine (20 mL), dried over anhydrous $Na_2SO_4$ and concentrated. The residue was purified by flash column chromatography (0→30% of EtOAc in PE) to give 2-chloro-3-((1-ethyl-1H-pyrazol-4-yl) methyl)-4-methoxypyridine (120 mg, yield: 45%) as a colorless oil. LC/MS (ESI) (m/z): 252 [M+H]⁺.

Synthesis of 4-bromo-5-((-ethyl-1H-pyrazol-4-yl)methyl)oxazole

To a solution of (4-bromooxazol-5-yl)(1-ethyl-1H-pyrazol-4-yl)methanol (1.21 g, 4.45 mmol) in trifluoroacetic acid (12 mL), was added triethylsilane (3.60 mL, 22.2 mmol) and stirred at r.t. for 1.5 h. The reaction mixture was then concentrated in vacuo to give a residue, which was diluted with EA (20 mL) and basified to pH 7 with sat. aq. $NaHCO_3$. The layers were separated, and the aq. phase was extracted with EA (3×20 mL). The combined organic phases were washed with brine (10 mL), dried over anhydrous $Na_2SO_4$, filtered and concentrated in vacuo. The residue was purified by flash chromatography (0-40% EtOAc in PE) to give 4-bromo-5-((1-ethyl-1H-pyrazol-4-yl)methyl)oxazole (678 mg, 60% yield) as a yellow oil. LC/MS ESI (m/z): 256 [M+H]⁺.

The following intermediates were synthesized using a similar experimental protocol:

--- ethyl 5-((3-bromo-1-methyl-1H-pyrazol-4-yl)methyl)isoxazole-3-carboxylate

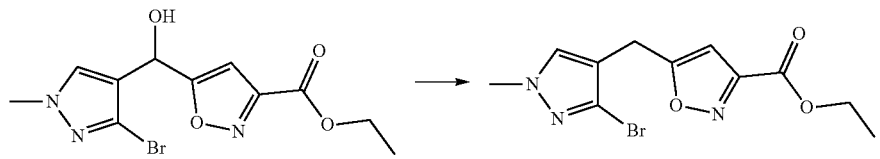 [SMILES: CCOC(=O)c1cc(C(O)c2cn(C)nc2Br)on1 ; CCOC(=O)c1cc(Cc2cn(C)nc2Br)on1]

m/z (ESI): 314 [M + H]

-continued 3-(benzyloxy)-5-bromo-1-ethyl-4-((3-iodo-1-methyl-1H-pyrazol-4-yl)methyl)-1H-pyrazole

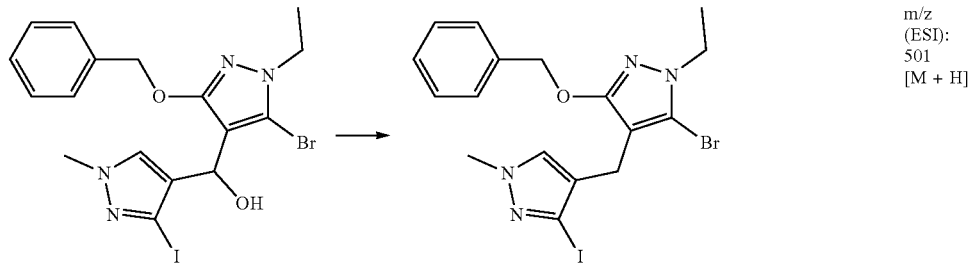

m/z (ESI): 501 [M + H]

5-bromo-1-ethyl-4-((1-(4-fluoro-2-iodophenyl)-1H-imidazol-5-yl)methyl)-1H-pyrazole

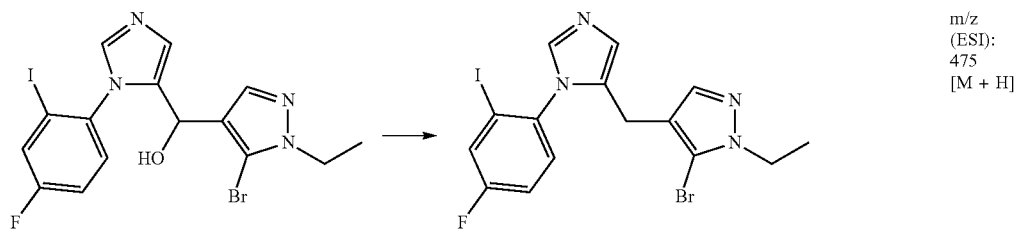

m/z (ESI): 475 [M + H]

(R)-1-(2-(1-(benzyloxy)ethyl)-4-fluorophenyl)-3-(difluoromethyl)-5-((1-ethyl-1H-pyrazol-4-yl)methyl)-1H-pyrazole

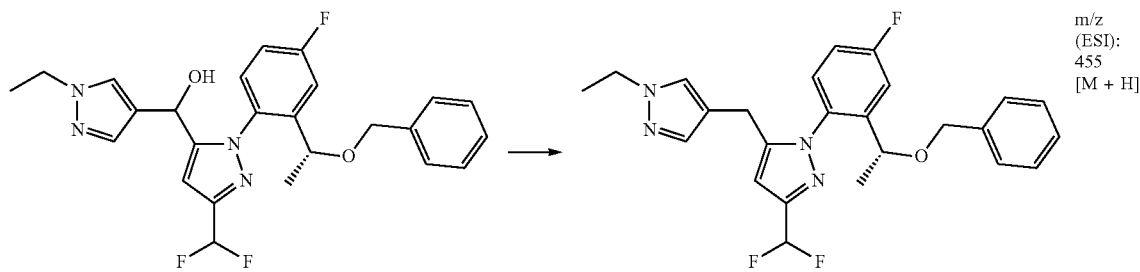

m/z (ESI): 455 [M + H]

5-((3-bromo-1-methyl-1H-pyrazol-4-yl)methyl)-3-(2,2-difluoroethyl)isoxazole

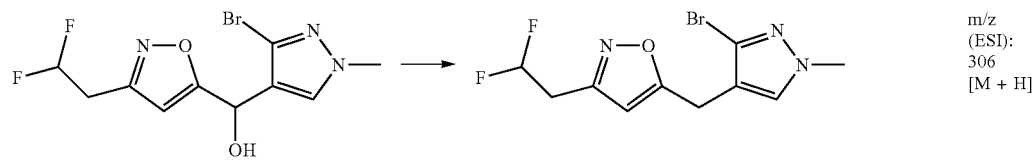

m/z (ESI): 306 [M + H]

3-bromo-4-((1-ethyl-3-methyl-1H-pyrazol-4-yl)methyl)-1-methyl-1H-pyrazole

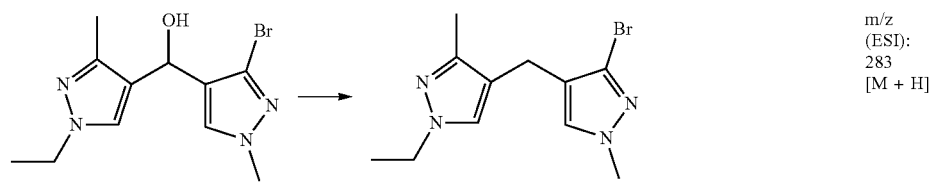

m/z (ESI): 283 [M + H]

4-[(1-ethyl-1H-pyrazol-4-yl)methyl]-3-iodo-1,5-dimethyl-1H-pyrazole

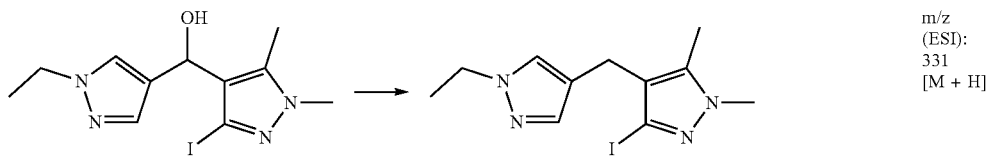

m/z (ESI): 331 [M + H]

(R)-1-(2-(1-(benzyloxy)ethyl)-4-fluorophenyl)-5-((1-(cyclopropylmethyl)-3-methyl-1H-pyrazol-4-yl)methyl)-3-methoxy-1H-pyrazole

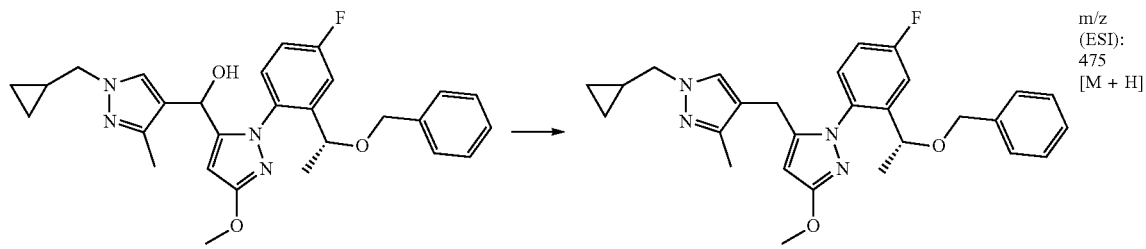

m/z (ESI): 475 [M + H]

5-((3-bromo-1-methyl-1H-pyrazol-4-yl)methyl)-3-ethylisothiazole

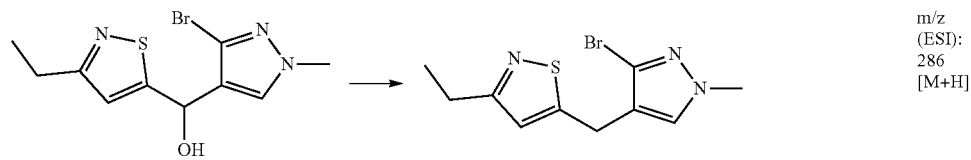

m/z (ESI): 286 [M+H]

3-iodo-1-methyl-4-((1-(oxetan-3-yl)-1H-pyrazol-4-yl)methyl)-1H-pyrazole

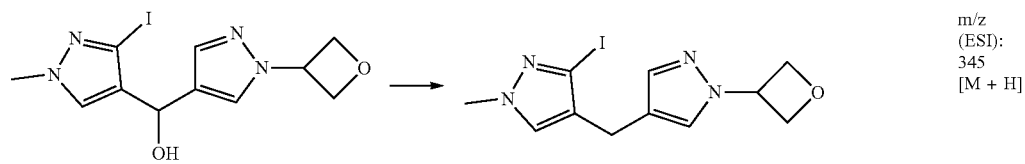

m/z (ESI): 345 [M + H]

3-bromo-1-ethyl-4-((3-iodo-1-methyl-1H-pyrazol-4-yl)methyl)-1H-pyrazole

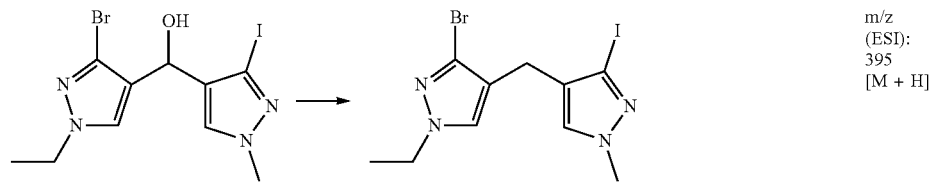

m/z (ESI): 395 [M + H]

3-bromo-4-((1-ethyl-1H-pyrazol-4-yl)methyl)-5-methoxy-1-methyl-1H-pyrazole

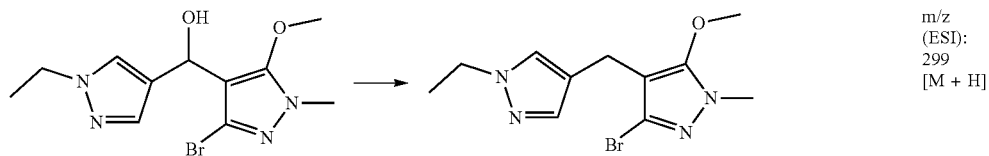

m/z (ESI): 299 [M + H]

3-bromo-1-(tert-butyl)-4-((1-ethyl-1H-pyrazol-4-yl)methyl)-1H-pyrazole

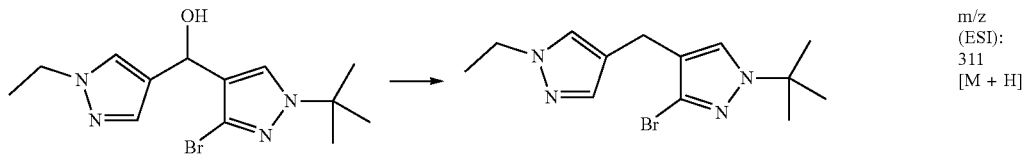

m/z (ESI): 311 [M + H]

3-bromo-4-((1-isobutyl-1H-pyrazol-4-yl)methyl)-1-methyl-1H-pyrazole

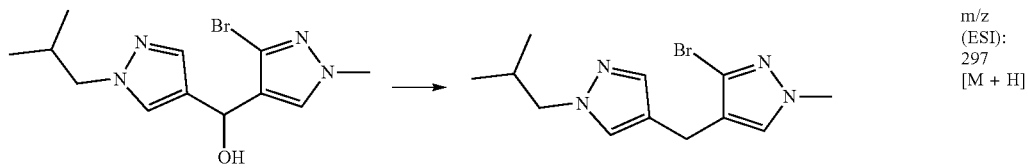

m/z (ESI): 297 [M + H]

-continued 3-bromo-1-methyl-4-({1-[(1-methylcyclopropyl)methyl]-1H-pyrazol-4-yl}methyl)-1H-pyrazole

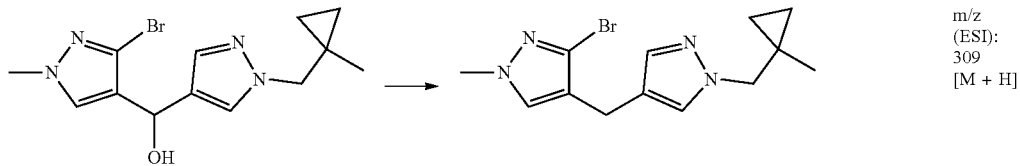

m/z (ESI): 309 [M + H]

2,4-dibromo-5-{[1-(difluoromethyl)-1H-pyrazol-4-yl]methyl}-1,3-thiazole

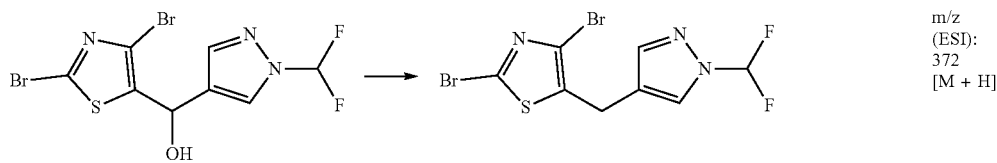

m/z (ESI): 372 [M + H]

5-((1-(2,2-difluoroethyl)-1H-pyrazol-4-yl)methyl)-1-(4-fluoro-2-iodophenyl)-3-(trifluoromethyl)-1H-pyrazole

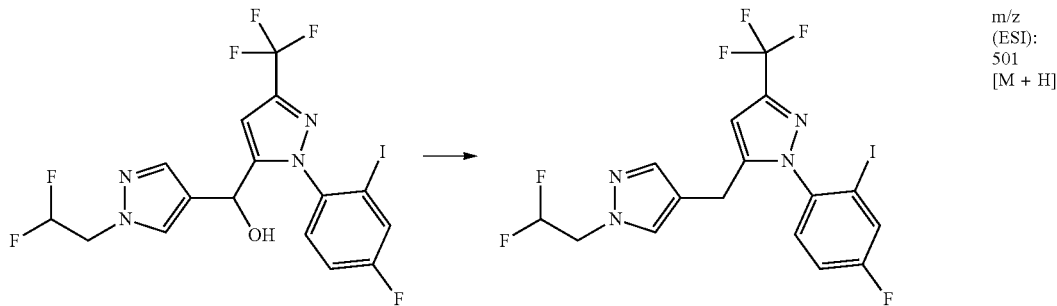

m/z (ESI): 501 [M + H]

3-(2-bromo-4-fluorophenyl)-4-((1-ethyl-1H-pyrazol-4-yl)methyl)isoxazole

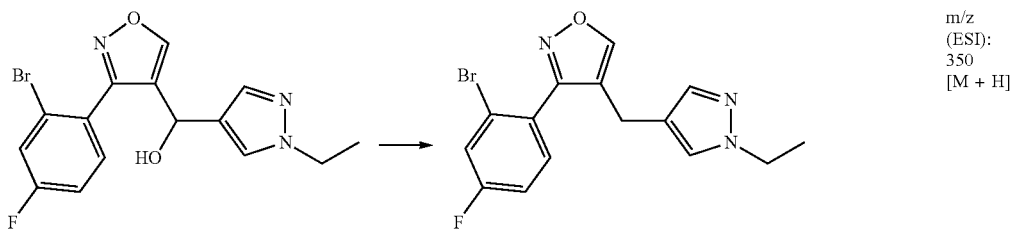

m/z (ESI): 350 [M + H]

1-ethyl-4-{[3-(4-fluoro-2-iodophenyl)-1,2-thiazol-4-yl]methyl}-1H-1,2,3-triazole

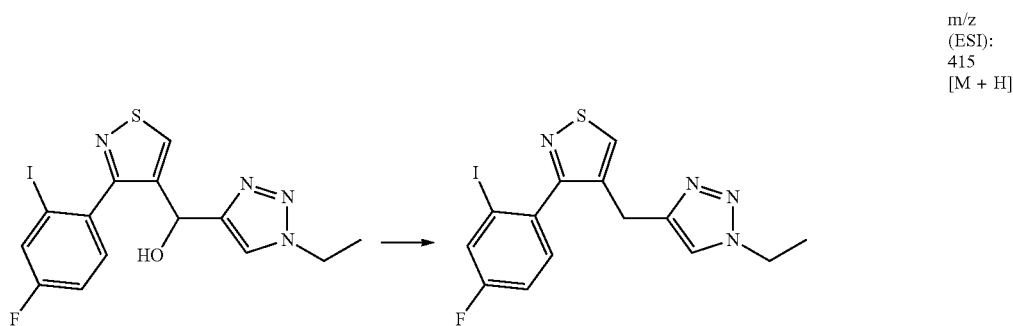

m/z (ESI): 415 [M + H]

-continued 1-(2-((benzyloxy)methyl)-4-fluorophenyl)-5-(((1-(cyclopropylmethyl)-1H-pyrazol-4-yl)methyl)-3-(difluoromethyl)-1H-pyrazole

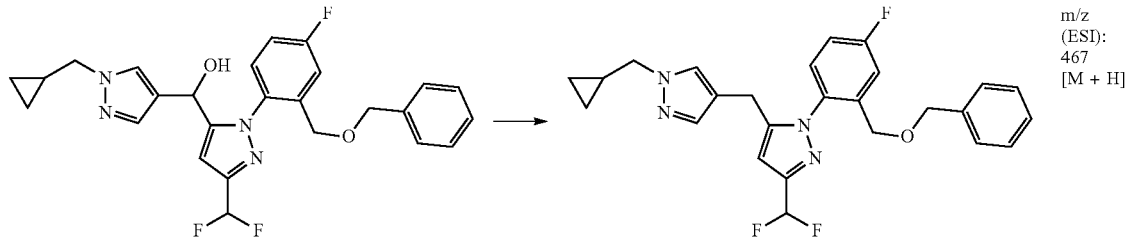

m/z (ESI): 467 [M + H]

1-(cyclopropylmethyl)-4-[(3-iodo-1-methyl-1H-pyrazol-4-yl)methyl]-3-methyl-1H-pyrazole

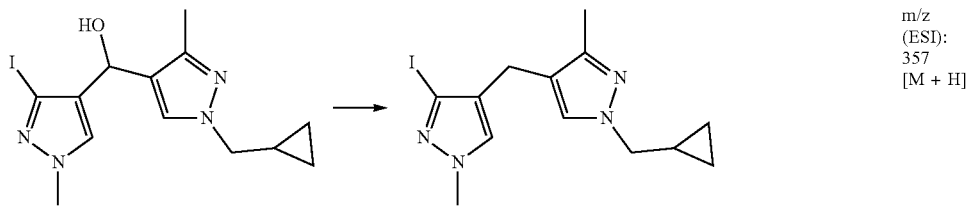

m/z (ESI): 357 [M + H]

1-(2-((benzyloxy)methyl)-4-fluorophenyl)-5-(((1-(cyclopropylmethyl)-3-methyl-1H-pyrazol-4-yl)methyl)-3-(difluoromethyl)-1H-pyrazole

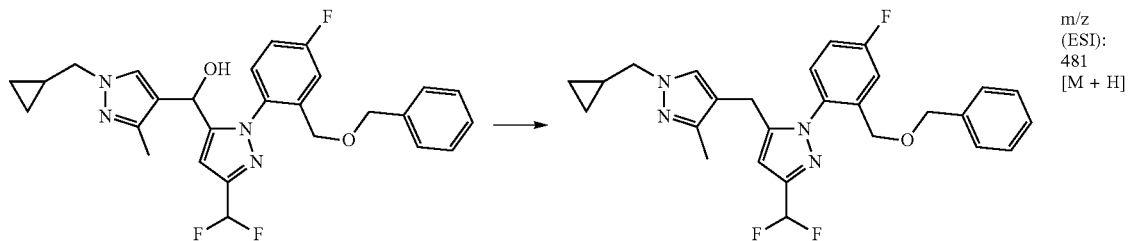

m/z (ESI): 481 [M + H]

1-(cyclopropylmethyl)-4-((1-(4-fluoro-2-iodophenyl)-3-methyl-1H-pyrazol-5-yl)methyl)-3-methyl-1H-pyrazole

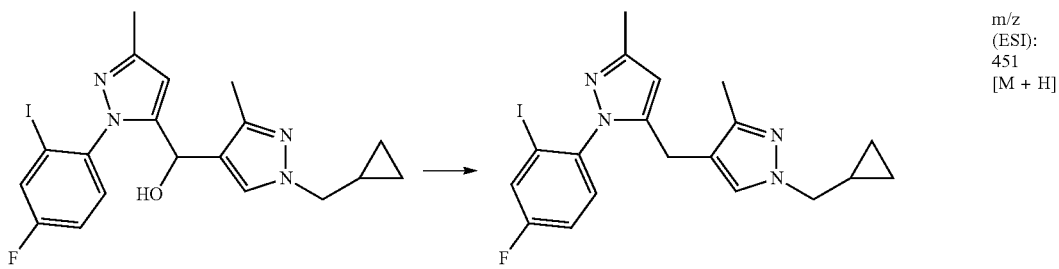

m/z (ESI): 451 [M + H]

2-chloro-3-[(3-ethyl-1-methyl-1H-pyrazol-5-yl)methyl]pyridine

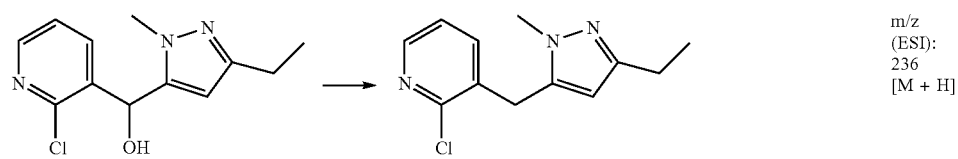

m/z (ESI): 236 [M + H]

3-bromo-4-((5-(cyclopropylmethyl)-1-methyl-1H-pyrazol-3-yl)methyl)-1-methyl-1H-pyrazole

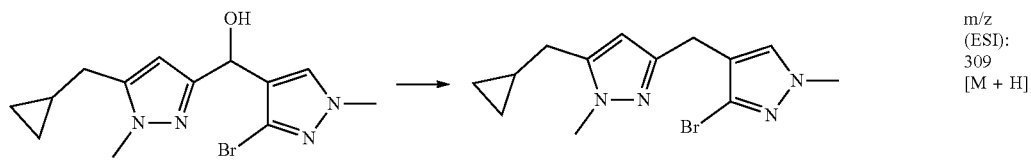

m/z (ESI): 309 [M + H]

319

Synthesis of (3-bromo-1-methyl-1H-pyrazol-4-yl)(5-ethylisoxazol-3-yl)methanol

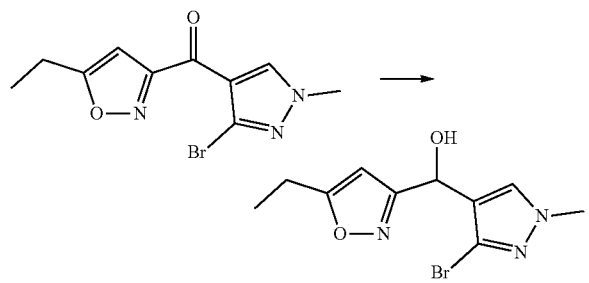

320

To a stirred solution of 3-(3-bromo-1-methyl-1H-pyrazole-4-carbonyl)-5-ethyl-1,2-oxazole (400 mg, 1.41 mmol) in methanol (10 mL) was added NaBH$_4$ (65 mg, 1.9 mmol) at 0° C. The reaction was stirred at 0° C. for 1 h, then concentrated to dryness. The residue was purified by column chromatography on silica gel (PE:EtOAc=1:1, V/V) to give (3-bromo-1-methyl-1H-pyrazol-4-yl)(5-ethyl-1,2-oxazol-3-yl)methanol (360 mg, 85% yield) as a white solid. LC/MS (ESI) (m/z): 286.0 [M+H]$^+$.

The following intermediates were synthesized using a similar experimental protocol:

5-((5-bromo-1-ethyl-1H-pyrazol-4-yl)methyl)-1-(4-fluoro-2-(1-hydroxyethyl)phenyl)-1H-pyrazole-4-carbonitrile

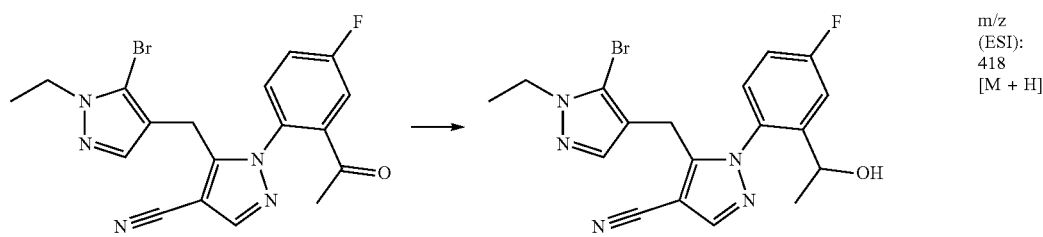

m/z (ESI): 418 [M + H]

1-(2-(5-((5-bromo-1-ethyl-1H-pyrazol-4-yl)methyl)-3-(trifluoromethyl)-1H-pyrazol-1-yl)-5-fluorophenyl)ethan-1-ol

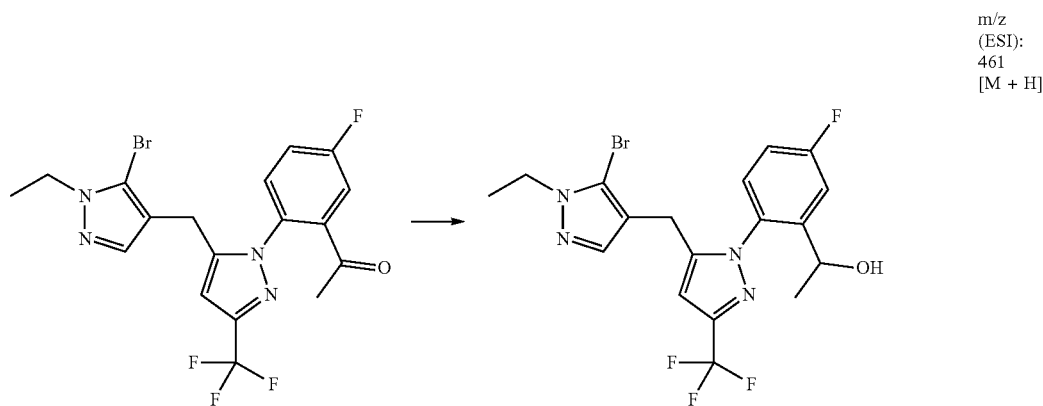

m/z (ESI): 461 [M + H]

1-({1-[4-fluoro-2-(1-hydroxyethyl)phenyl]-1H-pyrazol-5-yl}methyl)-1H-imidazole-4-carbonitrile

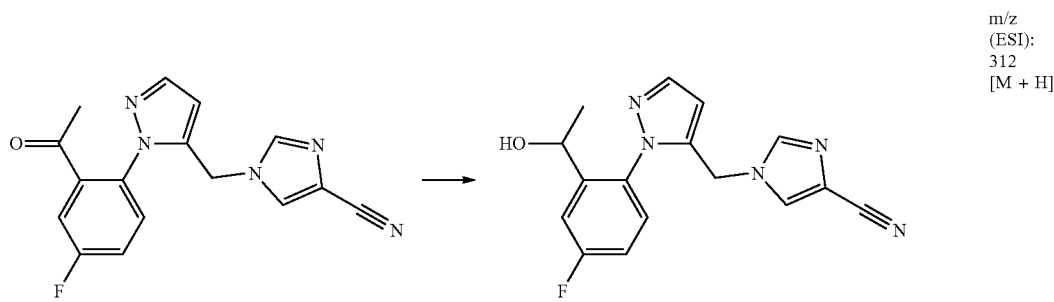

m/z (ESI): 312 [M + H]

1-({1-[4-fluoro-2-(1-hydroxyethyl)phenyl]-3-methyl-1H-pyrazol-5-yl}methyl)-1H-imidazole-4-carbonitrile

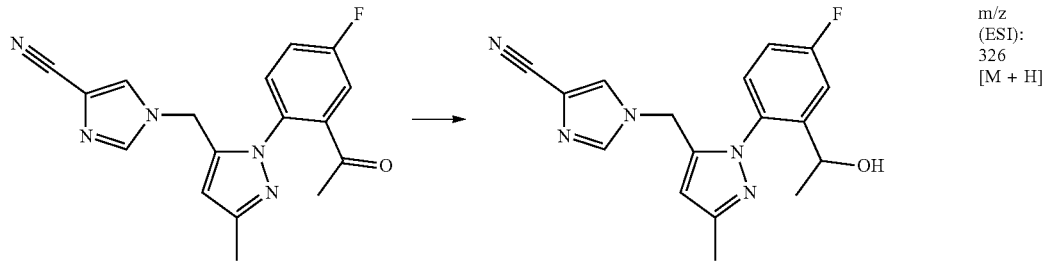

m/z (ESI): 326 [M + H]

(1-(2-(1-((5-bromo-2-nitropyridin-3-yl)oxy)ethyl)-4-fluorophenyl)-3-chloro-1H-pyrazol-5-yl)(1-ethyl-1H-pyrazol-4-yl)methanol

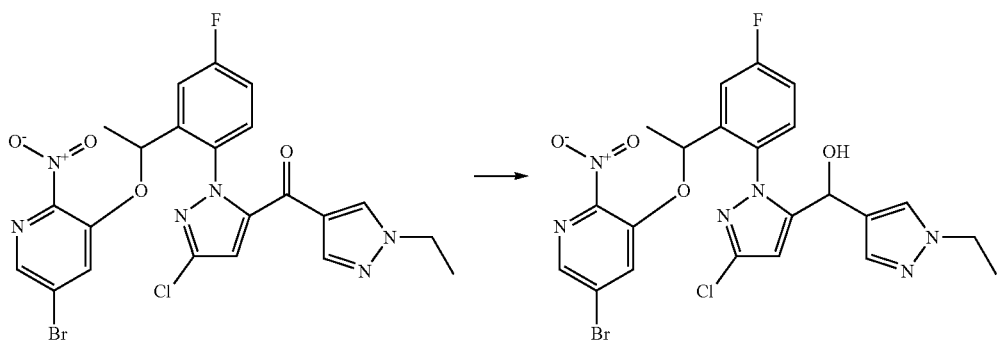 [SMILES: CCn1cc(C(=O)c2cc(Cl)nn2-c2ccc(F)cc2C(C)Oc2cc(Br)cnc2[N+](=O)[O-])cn1 ; CCn1cc(C(O)c2cc(Cl)nn2-c2ccc(F)cc2C(C)Oc2cc(Br)cnc2[N+](=O)[O-])cn1]

m/z (ESI): 565 [M + H]

1-(2-(5-((1-(2,2-difluoroethyl)-1H-pyrazol-4-yl)methyl)-3-(trifluoromethyl)-1H-pyrazol-1-yl)-5-fluorophenyl)ethan-1-ol

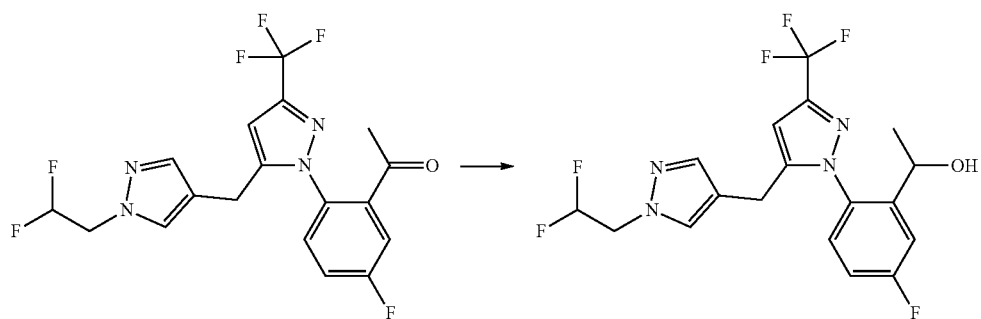 [SMILES: CC(=O)c1cc(F)ccc1-n1nc(C(F)(F)F)cc1Cc1cnn(CC(F)F)c1 ; CC(O)c1cc(F)ccc1-n1nc(C(F)(F)F)cc1Cc1cnn(CC(F)F)c1]

m/z (ESI): 419 [M + H]

Synthesis of 5-((3-bromo-1-methyl-1H-pyrazol-4-yl)methyl)-3-ethylisoxazole

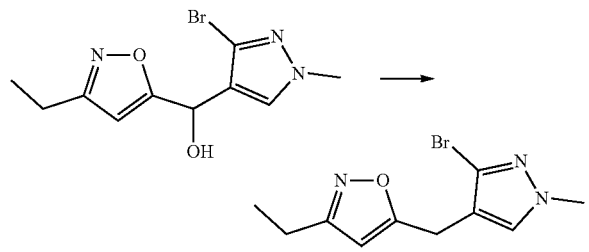

To a solution of (3-bromo-1-methyl-1H-pyrazol-4-yl)(3-ethylisoxazol-5-yl)methanol (900 mg, 3.15 mmol) in dichloromethane (8 mL) were added triethylsilane (4.06 mL, 25.2 mmol) and trifluoroacetic acid (2.34 mL, 31.5 mmol) at 0'° C. The mixture was stirred at r.t. for 2 h. The solvent was removed in vacuum and the residue was treated with water and EA. The organic layer was separated and concentrated in vacuo to give 5-((3-bromo-1-methyl-1H-pyrazol-4-yl)methyl)-3-ethylisoxazole as a brown oil (680 mg, yield: 80%). LC/MS ESI (m/z): 270 [M+H]⁺.

The following intermediates were synthesized using a similar experimental protocol:

5-bromo-1-ethyl-4-((5-iodo-1-methyl-1H-pyrazol-4-yl)methyl)-1H-pyrazole

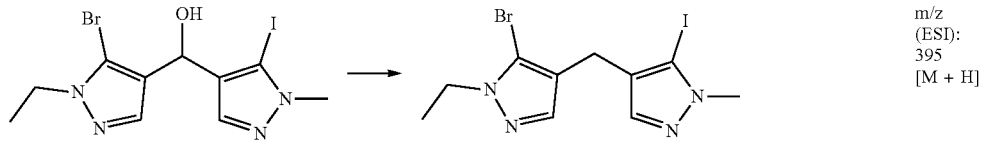

m/z (ESI): 395 [M + H]

2-bromo-3-((5-bromo-1-ethyl-1H-pyrazol-4-yl)methyl)pyridine

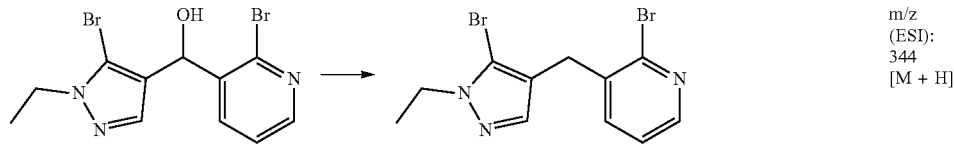

m/z (ESI): 344 [M + H]

5-bromo-4-((5-iodo-1-methyl-1H-pyrazol-4-yl)methyl)-1-methyl-1H-pyrazole

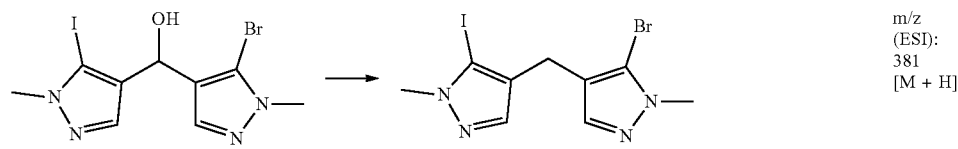

m/z (ESI): 381 [M + H]

5-bromo-1-cyclobutyl-4-((5-iodo-1-methyl-1H-pyrazol-4-yl)methyl)-1H-pyrazole

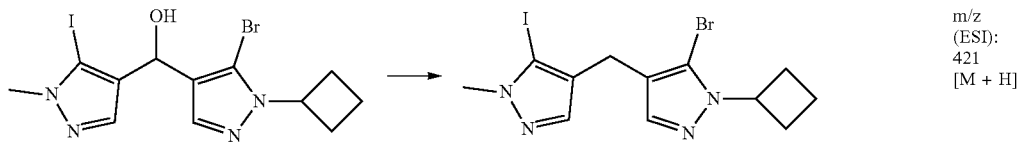

m/z (ESI): 421 [M + H]

5-chloro-4-((1-ethyl-1H-pyrazol-4-yl)methyl)-3-iodo-1-methyl-1H-pyrazole

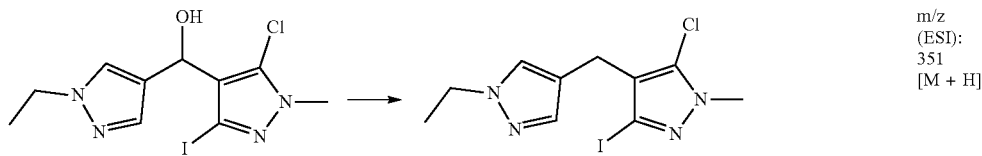

m/z (ESI): 351 [M + H]

5-bromo-1-ethyl-4-((1-(4-fluoro-2-iodophenyl)-3-(trifluoromethyl)-1H-pyrazol-5-yl)methyl)-1H-pyrazole

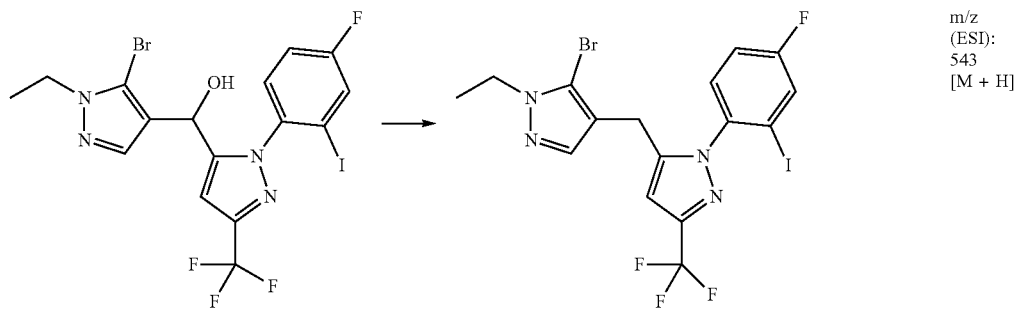

m/z (ESI): 543 [M + H]

3-bromo-4-{[1-(cyclopropylmethyl)-1H-pyrazol-4-yl]methyl}-1-ethyl-1H-pyrazole

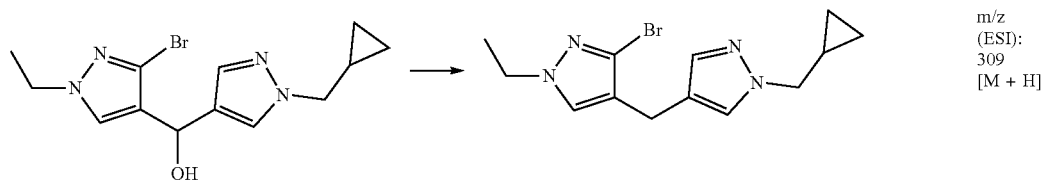

m/z (ESI): 309 [M + H]

-continued 3-bromo-4-((1,3-diethyl-1H-pyrazol-4-yl)methyl)-1-methyl-1H-pyrazole

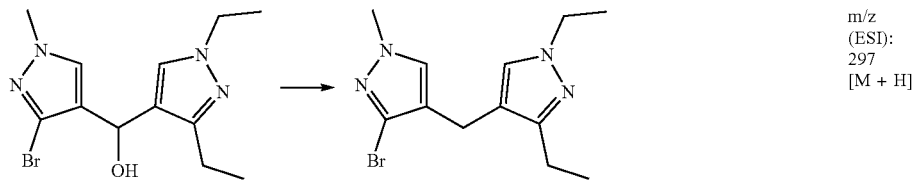

m/z (ESI): 297 [M + H]

5-bromo-3-(2-(5-((1-ethyl-1H-pyrazol-4-yl)methyl)-3-(trifluoromethyl)-1H-pyrazol-1-yl)-5-fluorobenzyloxy)-2-nitropyridine

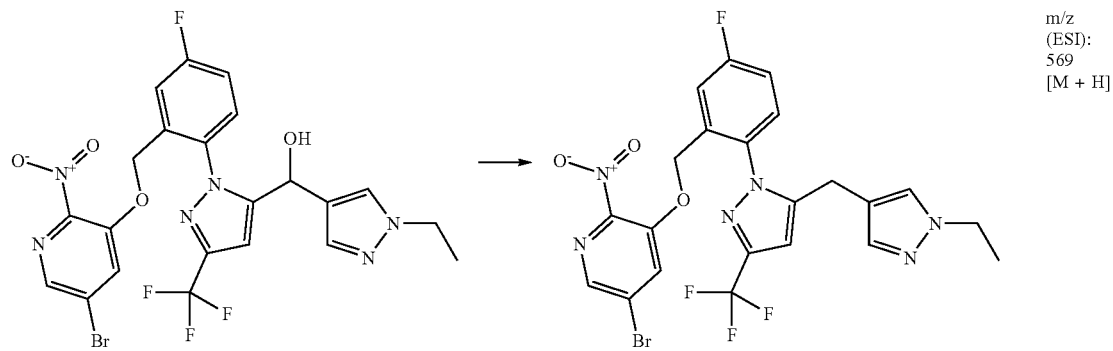

m/z (ESI): 569 [M + H]

5-bromo-3-{[2-(3-chloro-5-{[1-(cyclopropylmethyl)-1H-1,2,3-triazol-4-yl]methyl}-1H-pyrazol-1-yl)-5-fluorophenyl]methoxy}-2-nitropyridine

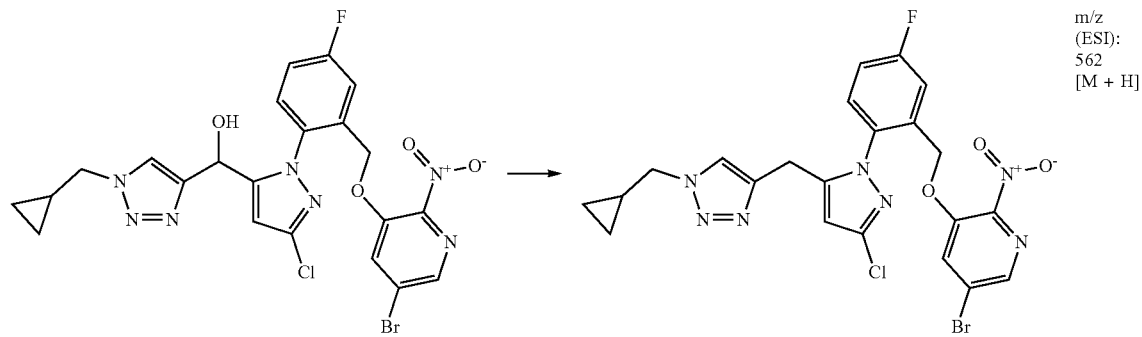

m/z (ESI): 562 [M + H]

1-{2-[(1R)-1-(benzyloxy)ethyl]-4-fluorophenyl}-5-[(1-ethyl-1H-pyrazol-4-yl)methyl]-3-methoxy-1H-pyrazolE

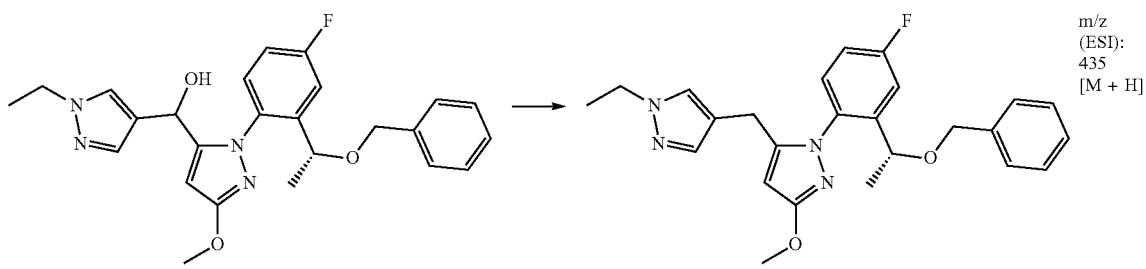

m/z (ESI): 435 [M + H]

5-(2-bromo-4-fluorophenyl)-4-((1-ethyl-1H-pyrazol-4-yl)methyl)-3-methylisoxazole

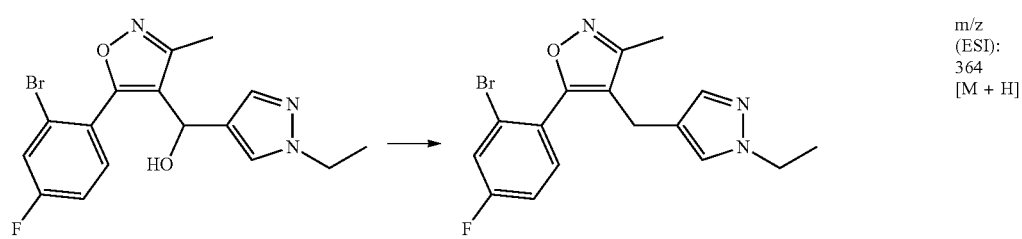

m/z (ESI): 364 [M + H]

5-bromo-4-((1-ethyl-5-iodo-1H-pyrazol-4-yl)methyl)-1-methyl-1H-pyrazole

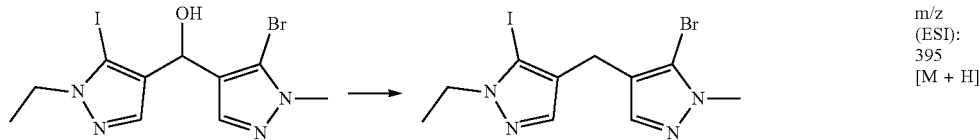

m/z (ESI): 395 [M + H]

Synthesis of (5-bromo-1-ethyl-1H-pyrazol-4-yl)(4-chloropyrimidin-5-yl)methanol

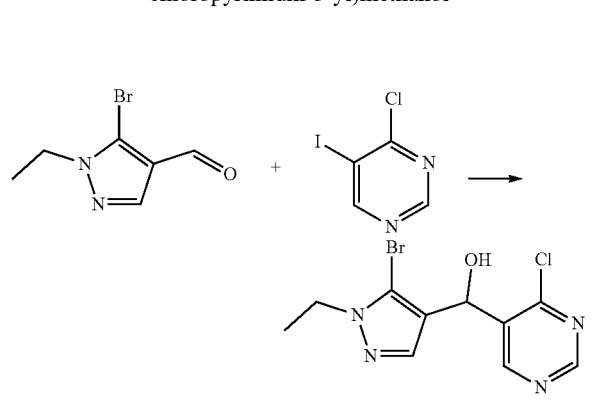

Synthesis of 5-(hydroxy(3-iodo-1-methyl-1H-pyrazol-4-yl)methyl)-1-methyl-1H-pyrazole-3-carbonitrile

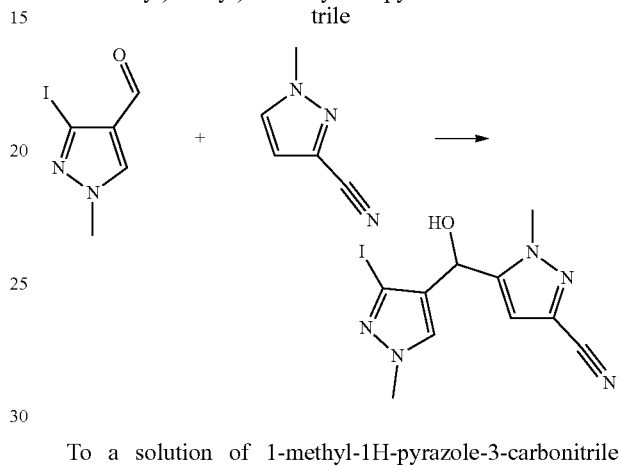

To a solution of 4-chloro-5-iodopyrimidine (2.60 g, 10.8 mmol) in THF (50 mL) at −78° C. was added n-BuLi (2.5 M in THF, 8.65 mL, 21.6 mmol) dropwise under $N_2$ atmosphere. The mixture was stirred at −78° C. for 10 min, and then a solution of 5-bromo-1-ethyl-1H-pyrazole-4-carbaldehyde (1.98 g, 9.73 mmol) in THF (10 mL) was added dropwise at −78° C. The resulting mixture was stirred at −78° C. for 30 min. The reaction was quenched with sat. aq. $NH_4Cl$, then extracted with EA (100 mL×2). The organic layers were washed with brine, dried over anhydrous $Na_2SO_4$ and concentrated. The residue was purified by column chromatography (silica gel, 30% EtOAc in PE) to give (5-bromo-1-ethyl-1H-pyrazol-4-yl)(4-chloropyrimidin-5-yl)methanol as a yellow oil (1.4 g, yield: 41%). LC/MS ESI (m/z): 317 [M+H]$^+$.

To a solution of 1-methyl-1H-pyrazole-3-carbonitrile (600 mg, 5.60 mmol) in THF (20 mL), was added lithium diisopropylamide (4.20 mL, 8.40 mmol, 2.0 M in THF) dropwise at −78° C. for 1 h. After 1 h, a solution of 3-iodo-1-methyl-1H-pyrazole-4-carbaldehyde (1.98 g, 8.40 mmol) in THF (15 mL) was added dropwise and the resulting mixture was stirred at −78° C. for 2 h. The reaction mixture was quenched by adding sat. aq. $NH_4Cl$ (20 mL), and then extracted with EA (3×20 mL). The combined organic phases were washed with brine (10 mL), dried over anhydrous $Na_2SO_4$, filtered, and concentrated in vacuo. The residue was purified by flash chromatography with MeOH in DCM (0→5%, V/V) to give 5-(hydroxy(3-iodo-1-methyl-1H-pyrazol-4-yl)methyl)-1-methyl-1H-pyrazole-3-carbonitrile (0.94 g, 82%) as a yellow solid. LC/MS ESI (m/z): 344 [M+H]$^+$.

The following intermediates were synthesized using a similar experimental protocol:

5-((5-bromo-1-ethyl-1H-pyrazol-4-yl)(hydroxy)methyl)-1-(4-fluoro-2-iodophenyl)-1H-pyrazole-3-carbonitrile

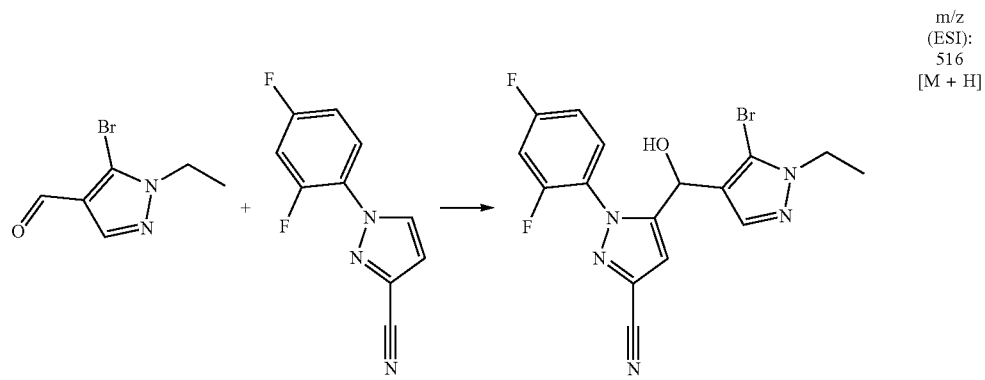

m/z (ESI): 516 [M + H]

(5-bromo-1-ethyl-1H-pyrazol-4-yl)(4-bromopyridin-3-yl)methanol

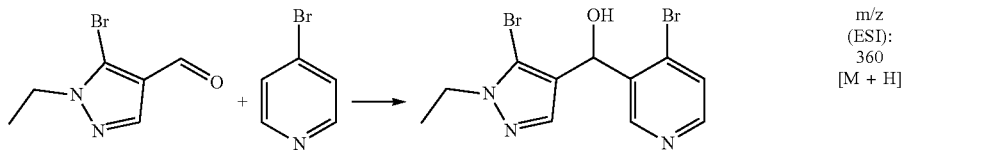

m/z (ESI): 360 [M + H]

(1-(2-((1R)-1-(benzyloxy)ethyl)-4-fluorophenyl)-3-methoxy-1H-pyrazol-5-yl)(1-(cyclopropylmethyl)-1H-1,2,3-triazol-4-yl)methanol

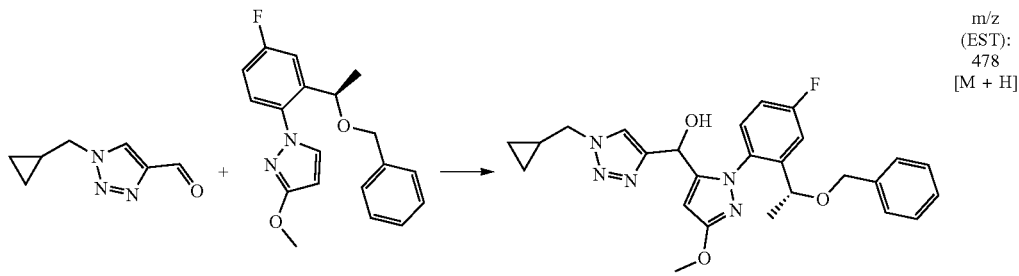

m/z (EST): 478 [M + H]

(dibromo-1,3-thiazol-5-yl)[1-(difluoromethyl)-1H-pyrazol-4-yl]methanol

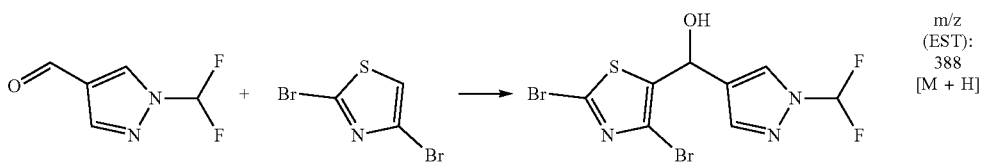

m/z (EST): 388 [M + H]

Synthesis of 3-cyclobutyl-5-((3-iodo-1-methyl-1H-pyrazol-4-yl)methyl)isoxazole

A mixture of 5-((3-bromo-1-methyl-1H-pyrazol-4-yl)methyl)-3-cyclobutylisoxazole (230 mg, 0.78 mmol), methyl[2-(methylamino)ethyl]amine (30 mg, 0.39 mmol) and CuI (40 mg, 0.21 mmol), KI (1.29 g, 7.79 mmol) in dioxane (5.0 mL) was stirred at 100° C. for 5 h under $N_2$. The mixture was diluted with water and extracted with EA (50 mL×3). The combined extracts were washed with brine twice, dried over anhydrous $Na_2SO_4$, filtered and concentrated. The residue was purified by flash chromatography (0→50% EA in PE) to give 3-cyclobutyl-5-((3-iodo-1-methyl-1H-pyrazol-4-yl)methyl)isoxazole (220 mg, 78% yield) as a yellow oil. LC-MS(ESI): 344 [M+H]$^+$.

The following intermediates were synthesized using a similar experimental protocol:

3-ethyl-5-((3-iodo-1-methyl-1H-pyrazol-4-yl)methyl)isoxazole

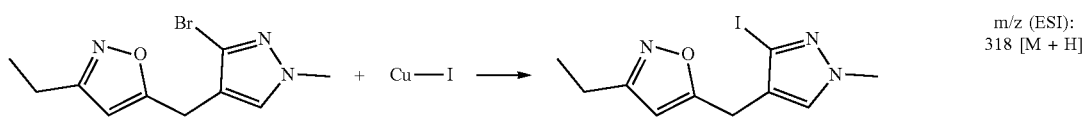

m/z (ESI): 318 [M + H]

5-((3-iodo-1-methyl-1H-pyrazol-4-yl)methyl)isoxazole-3-carbonitrile

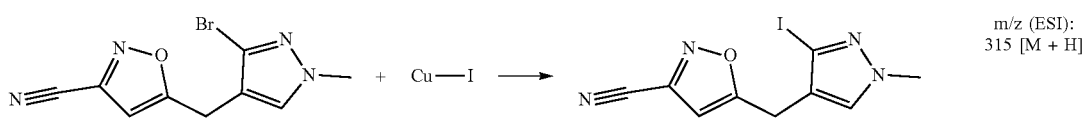

m/z (ESI): 315 [M + H]

3-(2,2-difluoroethyl)-5-((3-iodo-1-methyl-1H-pyrazol-4-yl)methyl)isoxazole

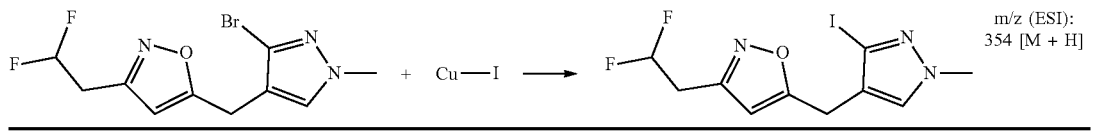

m/z (ESI): 354 [M + H]

Synthesis of tert-butyl 2-((3-iodo-1-methyl-1H-pyrazol-4-yl)methyl)hydrazine-1-carboxylate

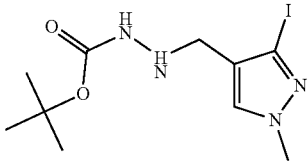 [SMILES: Cn1cc(CNNC(=O)OC(C)(C)C)c(I)n1]

A solution of 3-iodo-1-methyl-1H-pyrazole-4-carbaldehyde (4.70 g, 19.9 mmol) and tert-butyl carbazate (2.63 g, 19.9 mmol) in MeOH (20 mL) was stirred at 25° C. for 12 h. The mixture was concentrated under reduced pressure to give crude tert-butyl (E)-2-((3-iodo-1-methyl-1H-pyrazol-4-yl)methylene)hydrazine-1-carboxylate (6.80 g, 98% yield) as a yellow oil. LC/MS ESI (m/z): 351 [M+H]⁺.

To a solution of tert-butyl (E)-2-((3-iodo-1-methyl-1H-pyrazol-4-yl)methylene)hydrazine-1-carboxylate (6.80 g, 19.4 mmol) in AcOH (20 mL) was added NaBH₃CN (1.22 g, 19.4 mmol) at 0° C. The reaction mixture was stirred for 12 h at 25° C. The mixture was concentrated under reduced pressure. The residue was dissolved in EtOAc (20 mL), washed with sat. Na₂CO₃ (20 mL), dried over anhydrous Na₂SO₄ and concentrated under reduced pressure. The residue was purified by column chromatography on silica gel (10→30% EA in PE) to give tert-butyl 2-((3-iodo-1-methyl-1H-pyrazol-4-yl)methyl)hydrazine-1-carboxylate (5.00 g, 73% yield) as a white solid. LC/MS ESI (m/z): 353 [M+H]⁺.

Synthesis of 5-chloro-3-iodo-(1-methyl-1H-pyrazol-4-yl)(1-ethyl-1H-pyrazol-4-yl)methanol

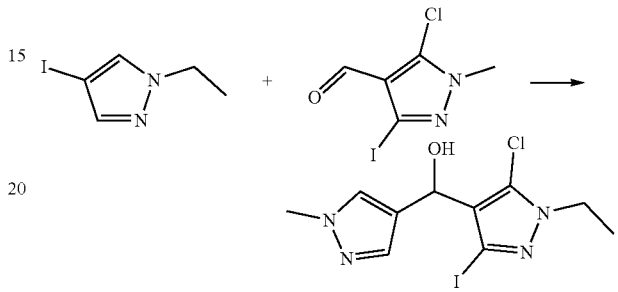

Isopropylmagnesium chloride-lithium chloride complex (1.88 mL, 2.45 mmol, 1.3 M in THF) was added to the solution of 1-ethyl-4-iodo-1H-pyrazole (502 mg, 2.26 mmol) dropwise in THF (4 mL) at 0° C. under N₂. The mixture was stirred for 1 h and then 5-chloro-3-iodo-1-methyl-1H-pyrazole-4-carbaldehyde (510 mg, 1.89 mmol) in THF (1 mL) was added to the mixture dropwise at 0° C. The mixture was warmed to r.t. and stirred for 2 h under N₂. The reaction mixture was poured into water (100 mL) and then extracted with EA (100 mL×2). The combined organic layers were washed with brine, dried over anhydrous Na₂SO₄ and concentrated. The residue was purified by column chromatography (silica gel, 1→10% EA in PE) to afford 5-chloro-3-iodo-(1-methyl-1H-pyrazol-4-yl)(1-ethyl-1H-pyrazol-4-yl)methanol (420 mg, 61%) as a yellow solid. LC/MS (ESI) m/z: 367 [M+H]⁺.

The following intermediates were synthesized using a similar experimental protocol:

(3-bromo-1-ethyl-1H-pyrazol-4-yl)[1-(cyclopropylmethyl)-1H-pyrazol-4-yl]methanol

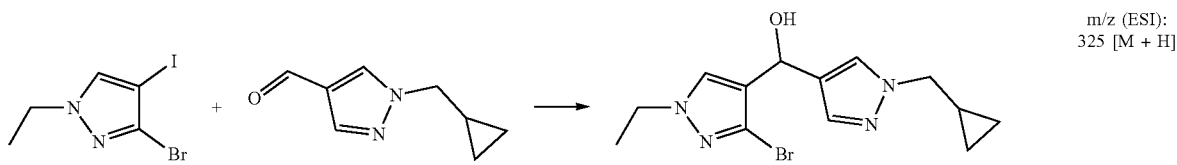

m/z (ESI): 325 [M + H]

(1-(cyclopropylmethyl)-3-methyl-1H-pyrazol-4-yl)(1-(4-fluoro-2-iodophenyl)-3-methyl-1H-pyrazol-5-yl)methanol

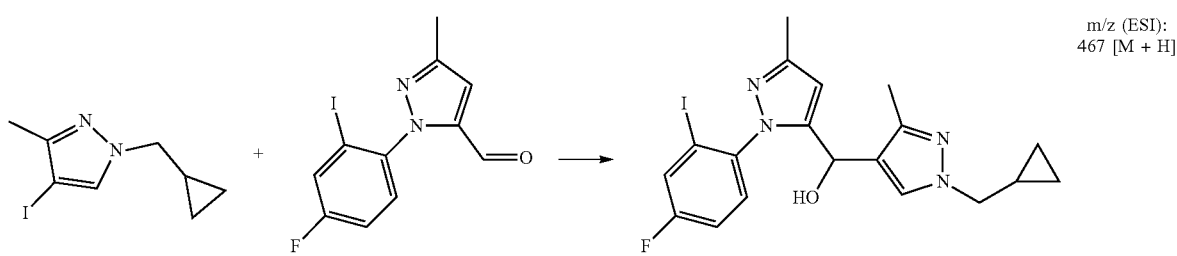

m/z (ESI): 467 [M + H]

Synthesis of (2,4-dibromothiazol-5-yl)(3-ethyl-1-methyl-1H-pyrazol-5-yl)methanol

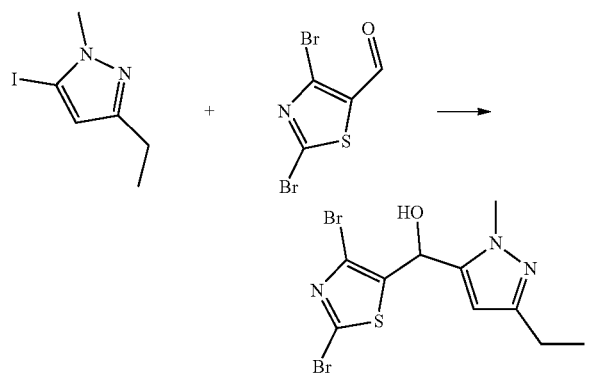

To a stirred solution of 3-ethyl-5-iodo-1-methyl-1H-pyrazole (1.40 g, 5.93 mmol) in THF (20 mL) was added i-PrMgCl·LiCl (4.6 mL, 1.3 M in THF, 5.93 mmol) dropwise at 0° C. under $N_2$. After stirring at 0° C. for 1 h, a solution of 2,4-dibromothiazole-5-carbaldehyde (1.77 g, 6.52 mmol) in THF (5 mL) was added at 0° C. The reaction was stirred at 0° C. for 2 h and LCMS showed the reaction was complete. The reaction was quenched with sat. $NH_4Cl$ (15 mL), extracted with EtOAc (10 mL), dried over anhydrous $Na_2SO_4$ and concentrated to dryness. The residue was purified by column chromatography on silica gel (PE:EtOAc=1:1) to give (2,4-dibromothiazol-5-yl)(3-ethyl-1-methyl-1H-pyrazol-5-yl)methanol (1.10 g, 49N-yield) as a yellow oil. LC/MS (ESI) (m/z):379.9 $[M+H]^+$.

The following intermediates were synthesized using a similar experimental protocol:

(3-iodo-1-methyl-1H-pyrazol-4-yl)(1-(2,2,2-trifluoroethyl)-1H-pyrazol-4-yl)methanol

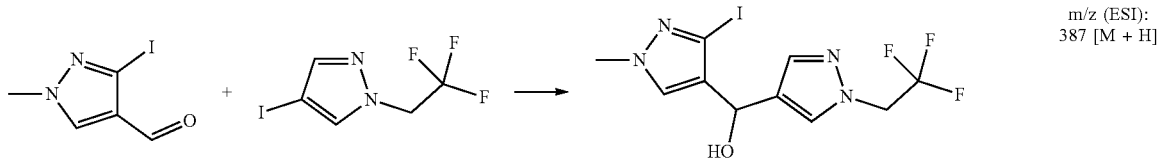

m/z (ESI): 387 [M + H]

(3-bromo-1-methyl-1H-pyrazol-4-yl)(3-(2,2-difluoroethyl)isoxazol-5-yl)methanol

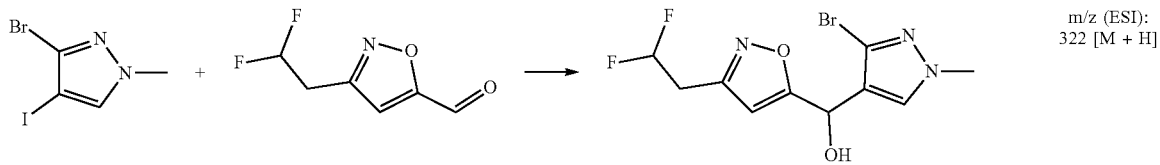

m/z (ESI): 322 [M + H]

(3-bromo-1-methyl-1H-pyrazol-4-yl)[1-(2,2-difluoroethyl)-3-methyl-1H-pyrazol-4-yl]methanol

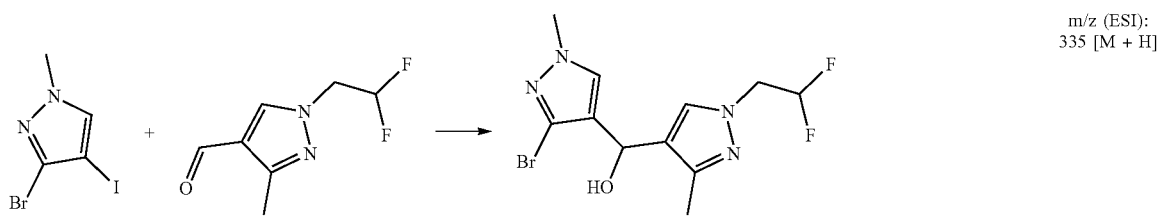

m/z (ESI): 335 [M + H]

[3-bromo-1-(difluoromethyl)-1H-pyrazol-4-yl](1-ethyl-1H-pyrazol-4-yl)methanol

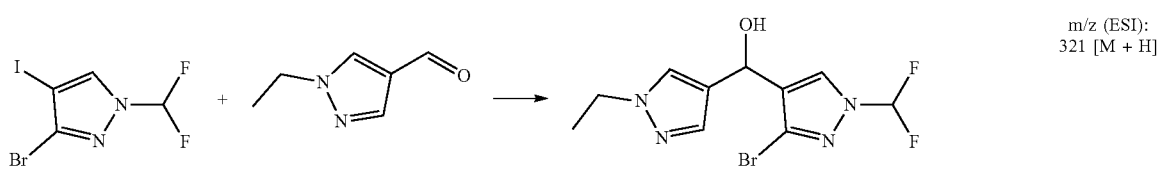

m/z (ESI): 321 [M + H]

(3-iodo-1-methyl-1H-pyrazol-4-yl)(1-(oxetan-3-yl)-1H-pyrazol-4-yl)methanol

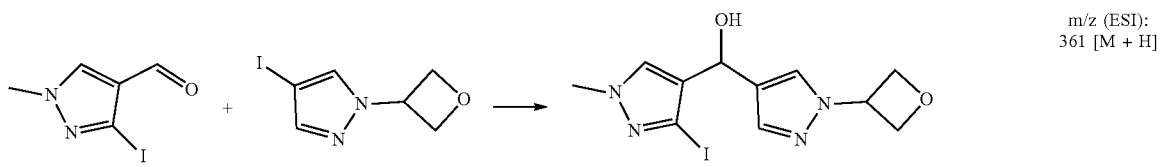

m/z (ESI): 361 [M + H]

(3-bromo-5-methoxy-1-methyl-1H-pyrazol-4-yl)(1-ethyl-1H-pyrazol-4-yl)methanol


m/z (ESI): 315 [M + H]

(3-bromo-1-methyl-1H-pyrazol-4-yl)({1-[(1-methylcyclopropyl)methyl]-1H-pyrazol-4-yl})methanol


m/z (ESI): 325 [M + H]

4-((3-bromo-1-methyl-1H-pyrazol-4-yl)(hydroxy)methyl)-1-ethyl-1H-pyrazole-3-carbonitrile

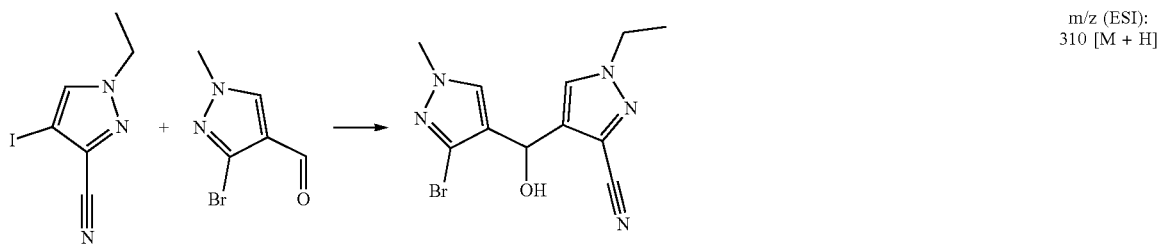

m/z (ESI): 310 [M + H]

[3-(2-bromo-4-fluorophenyl)-1,2-oxazol-4-yl](1-ethyl-1H-pyrazol-4-yl)methanol

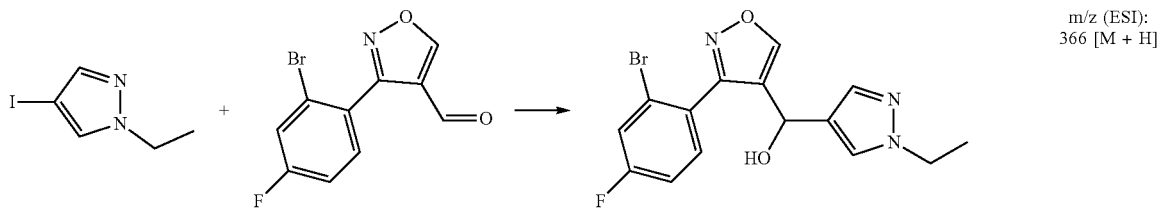

m/z (ESI): 366 [M + H]

(5-(2-bromo-4-fluorophenyl)-3-methylisoxazol-4-yl)(1-ethyl-1H-pyrazol-4-yl)methanol

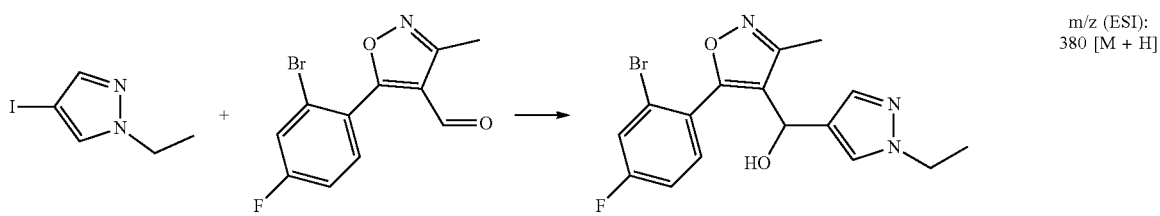

m/z (ESI): 380 [M + H]

Synthesis of 1-(2-(1,3-dioxolan-2-yl)-4-fluorophenyl)-4-fluoro-1H-pyrazole

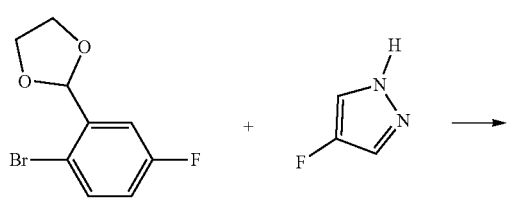

-continued

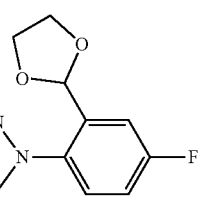

To a solution of 2-(2-bromo-5-fluorophenyl)-1,3-dioxolane (4.62 g, 18.7 mmol) in DMF (20 mL) at r.t. was added 4-fluoro-1H-pyrazole (1.77 g, 20.6 mmol), cesium carbonate (9.14 g, 28.1 mmol), CuI (0.71 g, 3.7 mmol) and L-proline (0.43 g, 3.4 mmol). The mixture was degassed under $N_2$ for three times and stirred at 120° C. overnight. After cooling to r.t., the reaction mixture was filtered, the filtrate was diluted with sat. aq. NH₄Cl (50 mL) and extracted with EtOAc (3×50 mL). Then the combined organic extracts were washed with sat. aq. NH₄Cl (3×30 mL) and brine (30 mL), dried over anhydrous Na₂SO₄, filtered, and concentrated. The residue was purified by flash chromatography (silica gel, 0→10% EtOAc in PE) to give 1-(2-(1,3-dioxolan-2-yl)-4-fluorophenyl)-4-fluoro-1H-pyrazole as a brown oil (2.62 g, yield: 56%). LC/MS (ESI) m/z: 253 [M+H]⁺.

Synthesis of 1-(2-(1,3-dioxolan-2-yl)-4-fluorophenyl)-3-fluoro-1H-pyrazole

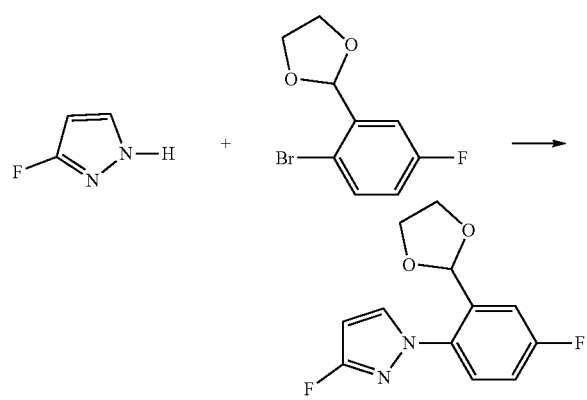

To a solution of 2-(2-bromo-5-fluorophenyl)-1,3-dioxolane (1.37 g, 5.54 mmol) in 1-methyl-2-pyrrolidinone (5 mL) was added 3-fluoro-1H-pyrazole (0.53 g, 6.1 mmol), cesium carbonate (2.71 g, 8.32 mmol) and cuprous oxide (0.16 g, 1.1 mmol), the resulting mixture was stirred at 120° C. overnight. The reaction mixture was cooled to r.t., diluted with EA (5 mL) and sat. aq. NH₄Cl solution (5 mL). The layers were separated, and the aq. phase was extracted with EA (3×5 mL). The combined organic phases were washed with sat. aq. NH₄Cl (5 mL) and brine (5 mL), dried over anhydrous Na₂SO₄, filtered, and concentrated in vacuo. The residue was purified by flash chromatography (0→10% EA in PE) to give 1-(2-(1,3-dioxolan-2-yl)-4-fluorophenyl)-3-fluoro-1H-pyrazole (486 mg, 35%) as a light-yellow oil. LC/MS ESI (m/z): 253 [M+H]⁺.

Synthesis of (Z)-4-(5-bromo-1-ethyl-1H-pyrazol-4-yl)-2-((dimethylamino)methylene)-3-oxobutanenitrile

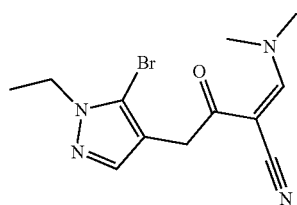 [SMILES: CCn1ncc(CC(=O)/C(C#N)=C\N(C)C)c1Br]

To a mixture of 2-(5-bromo-1-ethyl-1H-pyrazol-4-yl)acetonitrile (4.50 g, 21.0 mmol) and MeOH (50 mL) was added conc. H₂SO₄ (10 mL) dropwise at 25° C. After stirring at 80° C. for 16 h, the mixture was slowly neutralized to pH 8 with sat. NaHCO₃ at 0° C. The resulting mixture was extracted with EtOAc twice. The combined extracts were washed with H₂O and brine, dried over anhydrous Na₂SO₄, filtered, and concentrated under vacuum. The residue was purified by column chromatography on silica gel (0→20% EA in PE) to give methyl 2-(5-bromo-1-ethyl-1H-pyrazol-4-yl)acetate (3.3 g, yield: 64%) as a yellow oil. LC/MS ESI (m/z): 247 [M+H]⁺.

To a solution of potassium 2-methylbutan-2-olate (10.0 mL, 20.0 mmol, 2 M in THF) in dry THF (50 mL) was added acetonitrile (822 mg, 20.0 mmol) and methyl 2-(5-bromo-1-ethyl-1H-pyrazol-4-yl)acetate (3.30 g, 13.4 mmol) at 0° C. After stirring at 25° C. for 16 h, the mixture was filtered, and the filter cake was collected and rinsed with hexane. The filter cake was dissolved in water and adjusted to pH 3 with aq. HCl (1 N). The resulting mixture was then extracted with EtOAc twice. The combined organic extracts were washed with H₂O and brine, dried over anhydrous Na₂SO₄, filtered, and concentrated. The residue was purified by column chromatography on silica gel to give 4-(5-bromo-1-ethyl-1H-pyrazol-4-yl)-3-oxobutanenitrile (1.9 g, yield: 56%) as a brown oil. LC/MS ESI (m/z): 256 [M+H]⁺.

To a solution of 4-(5-bromo-1-ethyl-1H-pyrazol-4-yl)-3-oxobutanenitrile (1.6 g, 6.3 mmol) in THF (20 mL) was added DMF-DMA (1.50 g, 12.5 mmol) at 25° C. After stirring at 25° C. for 2 h, the reaction mixture was diluted with EtOAc, washed with H₂O and brine, dried over anhydrous Na₂SO₄, filtered and concentrated. The residue was purified by column chromatography on silica gel to give (Z)-4-(5-bromo-1-ethyl-1H-pyrazol-4-yl)-2-((dimethylamino)methylene)-3-oxobutanenitrile (1.1 g, yield: 56%) as a yellow solid. LC/MS (ESI) m/z: 311 [M+H]⁺.

Synthesis of 3-((2-chloropyridin-3-yl)methyl)-1-methyl-1H-pyrazole-5-carbonitrile

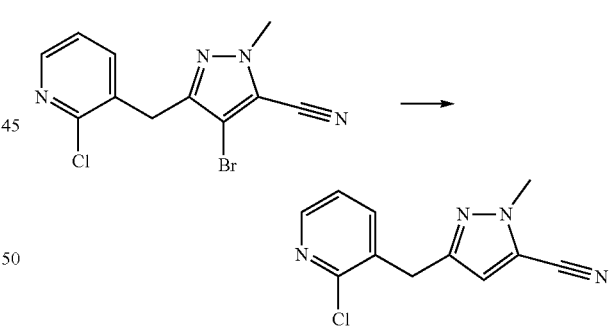

A mixture of 4-bromo-3-[(2-chloropyridin-3-yl)methyl]-1-methyl-1H-pyrazole-5-carbonitrile (270 mg, 0.87 mmol), PPh₃ (46 mg, 0.17 mmol), K₂CO₃ (240 mg, 1.73 mmol) and Pd(OAc)₂ (20 mg, 0.087 mmol) in n-BuOH (20 mL) was stirred at 80° C. under N₂ overnight. After cooling to r.t., the mixture was filtered and the filtrate was concentrated. The residue was treated with water and 15 extracted with EA (2×100 mL). The combined organic extracts were washed with brine, dried over Na₂SO₄ and concentrated. The residue was purified by flash column chromatography on silica gel (PE:EA=5:1) to give 3-((2-chloropyridin-3-yl)methyl)-1-methyl-1H-pyrazole-5-carbonitrile (70 mg, 31%) as a colorless oil. LC/MS (ESI): m/z=233 [M+H]⁺.

Synthesis of ethyl 3-(2-bromo-4-fluorophenyl)-1,2-oxazole-4-carboxylate

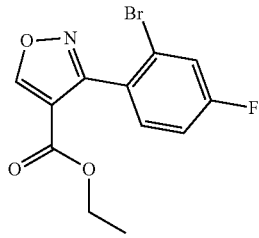 [SMILES: CCOC(=O)c1conc1-c1ccc(F)cc1Br]

To a solution of 2-bromo-4-fluorobenzaldehyde (5.9 mL, 49 mmol) and hydroxylamine hydrochloride (10.0 g, 145 mmol) in EtOH (120 mL) and water (120 mL) was added sodium hydroxide (4.40 g, 110 mmol). The mixture was stirred at r.t. overnight. The reaction mixture was acidified with 1 N HCl to pH 5, then concentrated to remove EtOH. The residue was dissolved in EtOAc (120 mL), washed with brine (120 mL), dried over $Na_2SO_4$, filtered, and concentrated to dryness. The residue was purified by column chromatography on silica gel (PE:EA=5:1) to give N-[(2-bromo-4-fluorophenyl)methylidene]hydroxylamine (10.74 g, 100% yield) as a white solid.

LC/MS (ESI) m/z: 218 $[M+H]^+$.

To a solution of N-[(2-bromo-4-fluorophenyl)methylidene]hydroxylamine (10.74 g, 49.25 mmol) in N,N-dimethylformamide (50 mL) was added NCS (8.55 g, 64.0 mmol) at 0° C. After stirring at r.t. for 2 h, the reaction was concentrated. The residue was diluted with EtOAc (50 mL), washed with sat. $NaHCO_3$ (50 mL) and brine (50 mL), dried over $Na_2SO_4$, filtered, and concentrated to give crude (Z)-2-bromo-4-fluoro-N-hydroxybenzimidoyl chloride (12.44 g, 100% yield) as a yellow oil.

LC/MS (ESI) m/z: 252 $[M+H]^+$.

To a solution of 2-bromo-4-fluoro-N-hydroxybenzimidoyl chloride (5.0 g, 20 mmol) and ethyl prop-2-ynoate (1.94 g, 19.8 mmol) in toluene (50 mL) was added TEA (6.00 g, 59.4 mmol). The mixture was stirred at 50° C. overnight, and then the reaction was concentrated. The residue was diluted with EtOAc (50 mL), washed with brine (50 mL), dried over $Na_2SO_4$, filtered, and concentrated to dryness. The residue was purified by column chromatography on silica gel (PE:EtOAc=5:1) to give ethyl 3-(2-bromo-4-fluorophenyl)isoxazole-4-carboxylate (as a mixture containing both regioisomers, 4.62 g, 74% yield) as a yellow oil. LC/MS (ESI) m/z: 314 $[M+H]^+$.

Synthesis of methyl 5-(2-bromo-4-fluorophenyl)-3-methyl-1,2-oxazole-4-carboxylate

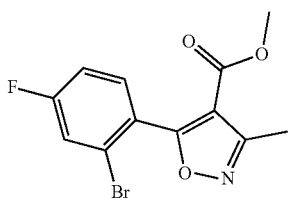 [SMILES: COC(=O)c1c(C)noc1-c1ccc(F)cc1Br]

To a stirred solution of methyl 3-oxobutanoate (20.0 g, 172 mmol) in MeOH (20 mL) was added methanamine (17.4 g, 224 mmol, 40% in water). The reaction was stirred at r.t. overnight. The reaction was concentrated under reduced pressure to give crude methyl (2E)-3-(methylamino)but-2-enoate (18.0 g, 81% yield) as a colorless oil. LC/MS (ESI) m/z: 130 $[M+H]^+$.

To a solution of 2-bromo-4-fluorobenzoic acid (2.0 g, 9.1 mmol) in $SOCl_2$ (10 mL) was added DMF (0.07 mL) dropwise at 0° C. The reaction was stirred for 1 h at 80° C. The reaction was cooled to r.t. and concentrated under reduced pressure to give crude 2-bromo-4-fluorobenzoyl chloride (2.0 g, 92% yield) as a colorless oil.

To a solution of methyl (2E)-3-(methylamino)but-2-enoate (1.0 g, 7.7 mmol) in THF (10 mL) was added pyridine (0.94 mL, 12 mmol) and 2-bromo-4-fluorobenzoyl chloride (1.80 g, 7.74 mmol). The reaction mixture was stirred overnight at 20° C. and then concentrated under reduced pressure. The residue was purified by flash column chromatography (0→30% EA in PE) to give methyl (3E)-2-(2-bromo-4-fluorobenzoyl)-3-(methylimino)butanoate (0.40 g, 16% yield) as a colorless oil.

LC/MS (ESI) m/z: 330 $[M+H]^+$.

A mixture of methyl (3E)-2-(2-bromo-4-fluorobenzoyl)-3-(methylimino)butanoate (400 mg, 1.21 mmol) and hydroxylamine hydrochloride (126 mg, 1.82 mmol) in AcOH (5 mL) was stirred at 110° C. for 1 h. The reaction mixture was cooled to r.t. and concentrated under reduced pressure. The residue was purified by flash column chromatography (0→20% EA in PE) to give methyl 5-(2-bromo-4-fluorophenyl)-3-methyl-1,2-oxazole-4-carboxylate (300 mg, 79% yield) as a colorless oil.

LC/MS (ESI): m/z=314 $[M+H]^+$.

Synthesis of 5,7-difluoro-3-methylbenzo[c][1,2]oxaborol-1(3H)-ol

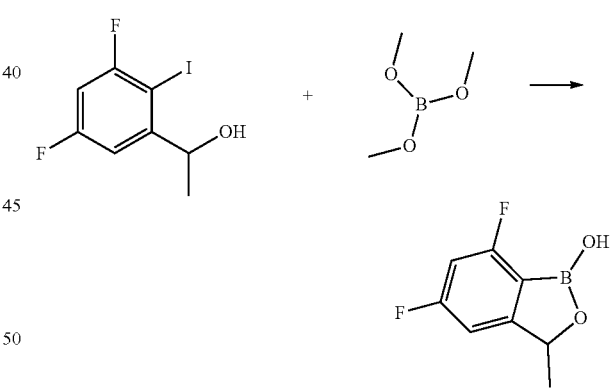

To a solution of 1-(3,5-difluoro-2-iodophenyl)ethan-1-ol (1.00 g, 3.52 mmol) in THF (30 mL) at −40° C. was added i-PrMgBr (6.8 mL, 6.8 mmol, 1 M) dropwise under an $N_2$ atmosphere. After the addition, the mixture was stirred at −10° C. for 0.5 h, then a solution of trimethyl borate (1.0 M in THF, 8.8 mL, 8.8 mmol) was added at −10° C. The resulting mixture was stirred at r.t. for 16 h. The mixture was quenched with ice-water and then extracted with EA (100 mL×2). The combined organic layers were washed with brine, dried over anhydrous $Na_2SO_4$, filtered and concentrated. The residue was purified by flash column chromatography on silica gel (PE:EA=2:1) to give 5,7-difluoro-3-methyl-1,3-dihydro-2,1-benzoxaborol-1-ol (700 mg, 95%) as a colorless oil. LC-MS (ESI): m/z 185 $[M+H]^+$.

341

Synthesis of ethyl 3-(2-bromo-4-fluorophenyl)isothiazole-4-carboxylate

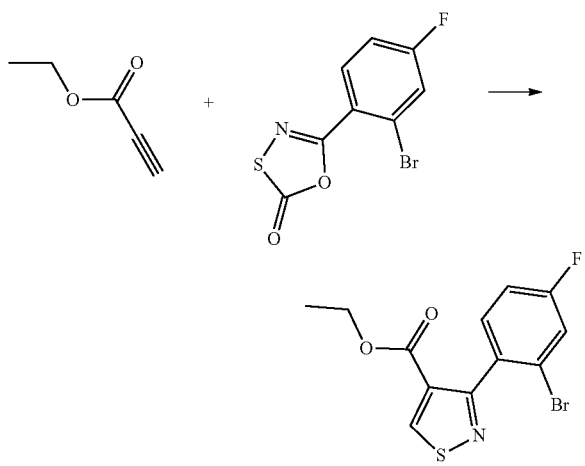

Ethyl prop-2-ynoate (3.48 g, 35.5 mmol) was dropwise added to a solution of 5-(2-bromo-4-fluorophenyl)-2H-1,3,4-oxathiazol-2-one (4.90 g, 17.8 mmol) in toluene (50 mL) at r.t. The reaction was stirred for 16 h at 120° C., concentrated in vacuo, and the residue was purified by flash chromatography (0→30% EA in PE) to give ethyl 3-(2-bromo-4-fluorophenyl)isothiazole-4-carboxylate (1.7 g, 29% yield) as a white solid. LC/MS (ESI) m/z: 330 [M+H]⁺.

Synthesis of ethyl 1-(4-fluoro-2-iodophenyl)-1H-imidazole-5-carboxylate

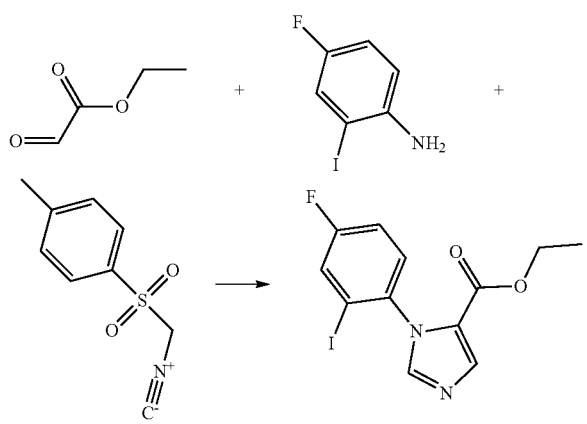

342

To a solution of 4-fluoro-2-iodoaniline (10.00 g, 42.19 mmol) in MeOH (100 mL) was added ethyl 2-oxoacetate (10.01 mL, 50.63 mmol, 50% in toluene) and the resulting mixture was heated at reflux for 3.5 h. The mixture was concentrated in vacuo and the resulting residue was dissolved in anhydrous ethanol (100 mL) and treated with 1-isocyanomethanesulfonyl-4-methylbenzene (12.35 g, 63.28 mmol) and K₂CO₃ (11.66 g, 84.38 mmol). The resulting mixture was heated to 65° C. and stirred for 4 h, then cooled to r.t. and poured into water and EtOAc. The organic layer was separated, concentrated under reduced pressure, and purified by flash chromatography on silica gel (0→30% EtOAc in PE) to give ethyl 1-(4-fluoro-2-iodophenyl)-1H-imidazole-5-carboxylate (11 g, 72% yield) as a yellow solid. LC/MS (ES+): m/z=361 [M+H]⁺.

Synthesis of 1-(4-fluoro-2-iodophenyl)-3-(trifluoromethyl)-1H-pyrazol-5-amine

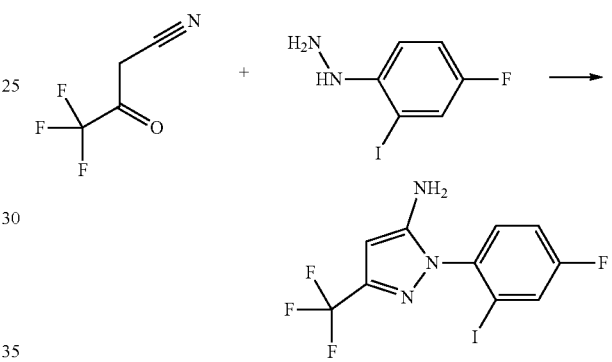

To a solution of 4,4,4-trifluoro-3-oxobutanenitrile (4.00 g, 29.2 mmol) and (4-fluoro-2-iodophenyl)hydrazine hydrochloride (10.1 g, 35.0 mmol) in EtOH (100 mL) was added conc. HCl (10 mL) dropwise at 25° C. After being stirred at 80° C. for 16 h, the reaction was neutralized to pH 8 with NaHCO₃ and then diluted with EtOAc. The resulting mixture was washed with H₂O and brine. The organic layer was dried over anhydrous Na₂SO₄. After filtration, the filtrate was concentrated under vacuum. The residue was purified by silica gel column chromatography, eluted with PE/EA (0--17%) to give 1-(4-fluoro-2-iodophenyl)-3-(trifluoromethyl)-1H-pyrazol-5-amine (5 g, 38% yield) as a brown solid. LC/MS ESI (m/z): 372 [M+H]⁺.

The following intermediates were synthesized using a similar experimental protocol:

ethyl 5-amino-4-ethyl-1-((3-iodo-1-methyl-1H-pyrazol-4-yl)methyl)-1H-pyrazole-3-carboxylate

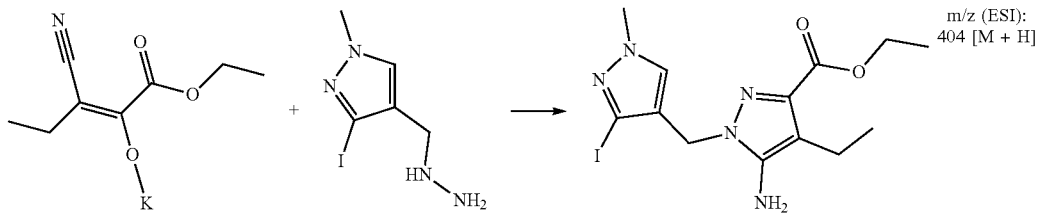

m/z (ESI): 404 [M + H]

Synthesis of ethyl 3-(4-fluoro-2-iodophenyl)isothiazole-4-carboxylate

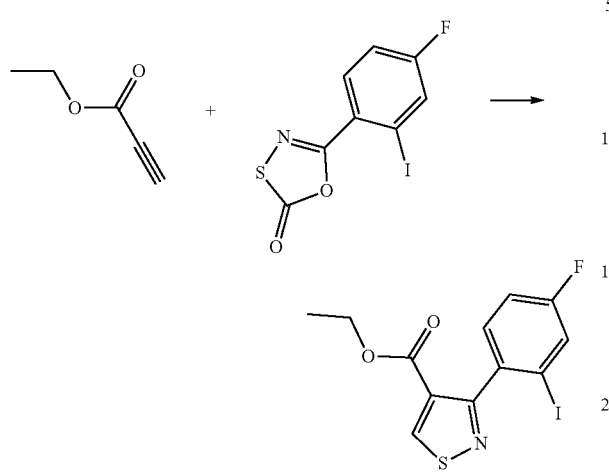

To a solution of 5-(4-fluoro-2-iodophenyl)-2H-1,3,4-oxathiazol-2-one (2.80 g, 8.66 mmol) in toluene (30 mL) was added ethyl prop-2-ynoate (1.76 mL, 17.3 mmol). The resulting solution was stirred at 120° C. in a sealed tube for 16 h. The mixture was concentrated under vacuum and the residue was purified by flash chromatography on silica gel (EA/PE=⅕) to give ethyl 3-(4-fluoro-2-iodophenyl)-1,2-thiazole-4-carboxylate (650 mg, 20%) as a colorless oil. LC/MS (ESI): m/z=378 [M+H]⁺.

Synthesis of 2-chloro-3-((4-(cyclopropylmethyl)-1H-pyrazol-1-yl)methyl)pyridine

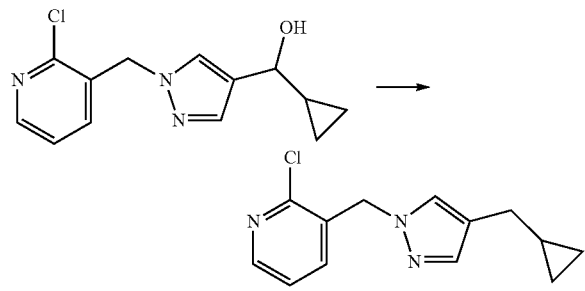

To a solution of (1-((2-chloropyridin-3-yl)methyl)-1H-pyrazol-4-yl)(cyclopropyl)methanol (400 mg, 1.5 mmol) in TFA (2 mL) was added triethylsilane (2.4 mL, 15.1 mmol). The resulting mixture was stirred at 60° C. for 2 h. The reaction mixture was cooled down to r.t. and concentrated under reduced pressure. The residue was basified with sat. aq. NaHCO₃ solution to pH 7 and extracted with DCM (2×10 ml). The combined organic layers were washed with brine (10 mL), dried over anhydrous Na₂SO₄, filtered and concentrated. The residue was purified by flash column chromatography on silica gel (PE:EtOAc=1:1, V/V) to give 2-chloro-3-((4-(cyclopropylmethyl)-1H-pyrazol-1-yl)methyl)pyridine (250 mg, 67%) as a yellow oil. LC/MS (ESI) (m/z): 248 [M+H]⁺.

Synthesis of 5-((5-bromo-1-ethyl-1H-pyrazol-4-yl)methyl)-4-chloropyrimidine

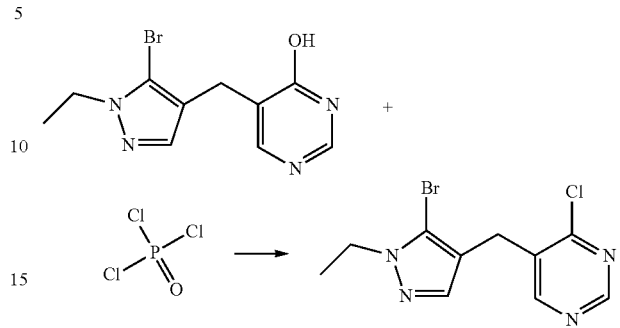

To a solution of 5-((5-bromo-1-ethyl-1H-pyrazol-4-yl)methyl)pyrimidin-4-ol (970 mg, 3.43 mmol) in MeCN (30 mL) at 0° C. was added POCl₃ (1.58 g, 10.3 mmol) dropwise under N₂ atmosphere. After the addition, the mixture was stirred at 80° C. for 3 h. The reaction mixture was quenched with sat. NaHCO₃ and extracted with DCM (100 ml×2). The combined organic layers were washed with brine, dried over anhydrous Na₂SO₄, filtered and concentrated. The residue was purified by column chromatography on silica gel (30% EtOAc in PE) to give 5-((5-bromo-1-ethyl-1H-pyrazol-4-yl)methyl)-4-chloropyrimidine as a yellow solid (587 mg, yield: 57%). LC/MS ESI (m/z): 301 [M+H]⁺.

Synthesis of (3-bromo-1-(tert-butyl)-1H-pyrazol-4-yl)(1-ethyl-1H-pyrazol-4-yl)methanol

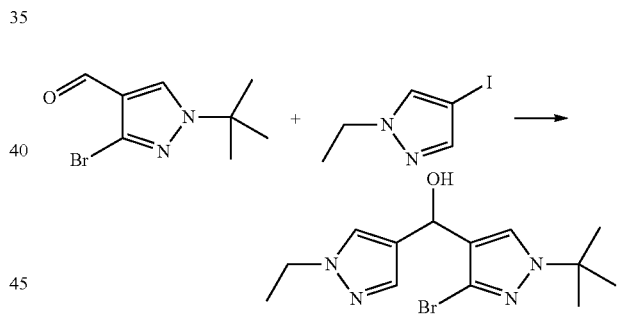

n-BuLi (1.30 mL, 3.25 mmol, 2.5 M in THF) was added slowly to a solution of 1-ethyl-4-iodo-1H-pyrazole (961 mg, 4.33 mmol) in THF (10 mL) at −78° C. and the reaction mixture was stirred for 40 min at −78° C. (additional equivalents of base can be used in cases where substrates contain additional acidic protons). Then 3-bromo-1-(tert-butyl)-1H-pyrazole-4-carbaldehyde (500 mg, 2.16 mmol) in THF (5 mL) was dropwise added at −78° C. and the reaction mixture was stirred for 0.5 h at −78° C. This reaction was quenched with sat. NH₄Cl (10 mL) and extracted with EtOAc (20 mL×2). The combined organic phases were washed with brine (20 mL), dried over anhydrous Na₂SO₄ and concentrated. The residue was purified by flash column chromatography on silica gel (PE:EtOAc=1:1) to give (3-bromo-1-(tert-butyl)-1H-pyrazol-4-yl)(1-ethyl-1H-pyrazol-4-yl)methanol (283 mg, 40% yield) as a yellow oil. LC/MS ESI (m/z): 327 [M+H]⁺.

The following intermediates were synthesized using a similar experimental protocol:

(1-(2-(1,3-dioxolan-2-yl)-4-fluorophenyl)-1H-pyrazol-5-yl)(5-bromo-1-ethyl-1H-pyrazol-4-yl)methanol

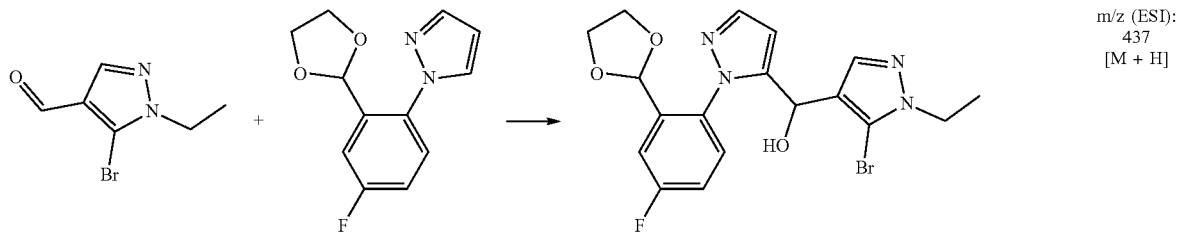

m/z (ESI): 437 [M + H]

(1-(2-(1,3-dioxolan-2-yl)-4-fluorophenyl)-4-fluoro-1H-pyrazol-5-yl)(5-bromo-1-ethyl-1H-pyrazol-4-yl)methanol

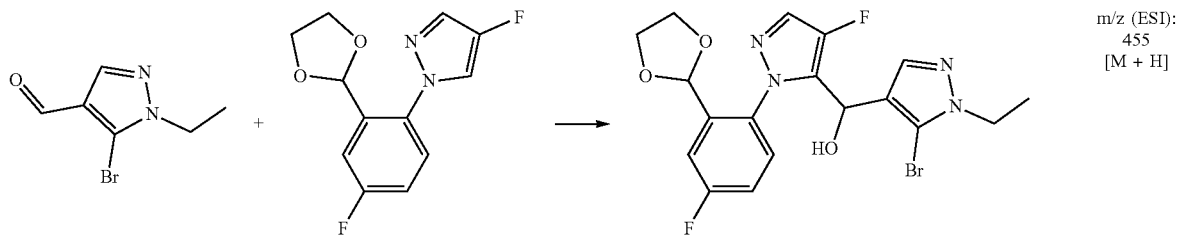

m/z (ESI): 455 [M + H]

(1-(2-((R)-1-(benzyloxy)ethyl)-4-fluorophenyl)-3-(difluoromethyl)-1H-pyrazol-5-yl)(1-ethyl-1H-pyrazol-4-yl)methanol


m/z (ESI): 471 [M + H]

(1-(2-((R)-1-(benzyloxy)ethyl)-4-fluorophenyl)-3-(trifluoromethyl)-1H-pyrazol-5-yl)(1-(cyclopropylmethyl)-1H-pyrazol-4-yl)methanol

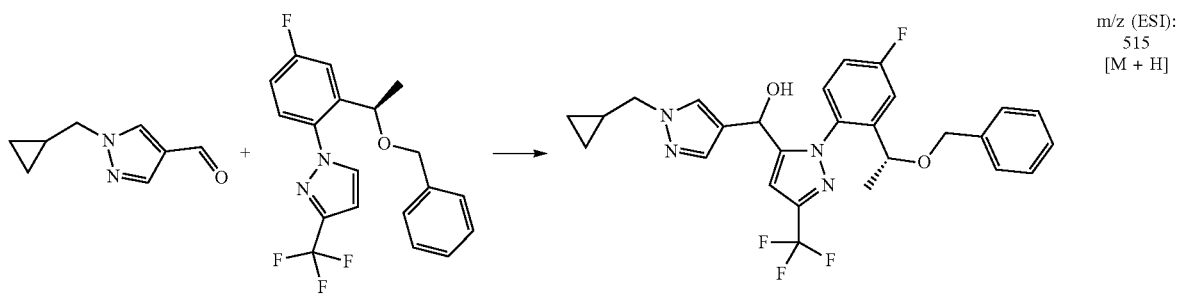

m/z (ESI): 515 [M + H]

(1-ethyl-1H-1,2,3-triazol-4-yl)(1-(4-fluoro-2-((R)-1-(4-methoxybenzyloxy)ethyl)phenyl)-3-(trifluoromethyl)-1H-pyrazol-5-yl)methanol

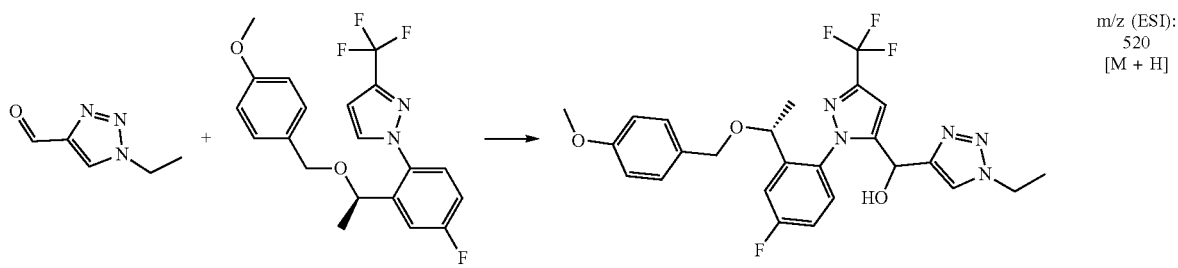

m/z (ESI): 520 [M + H]

5-((3-chloro-1-(4-fluoro-2-((R)-1-((4-methoxybenzyl)oxy)ethyl)phenyl)-1H-pyrazol-5-yl)(hydroxy)methyl)-1-methyl-1H-pyrazole-3-carbonitrile

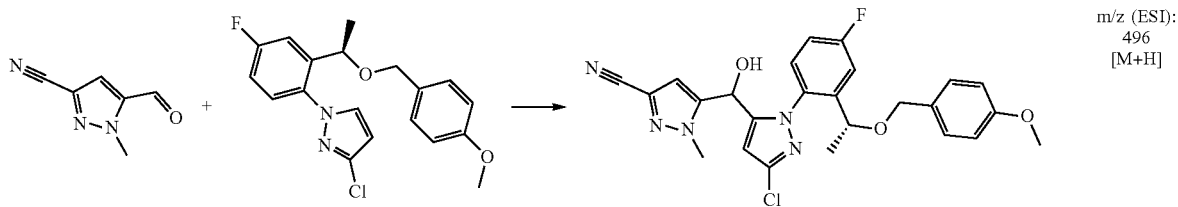

m/z (ESI): 496 [M+H]

5-((1-(4-fluoro-2-((R)-1-((4-methoxybenzyl)oxy)ethyl)phenyl)-3-(trifluoromethyl)-1H-pyrazol-5-yl)(hydroxy)methyl)-1-methyl-1H-pyrazole-3-carbonitrile

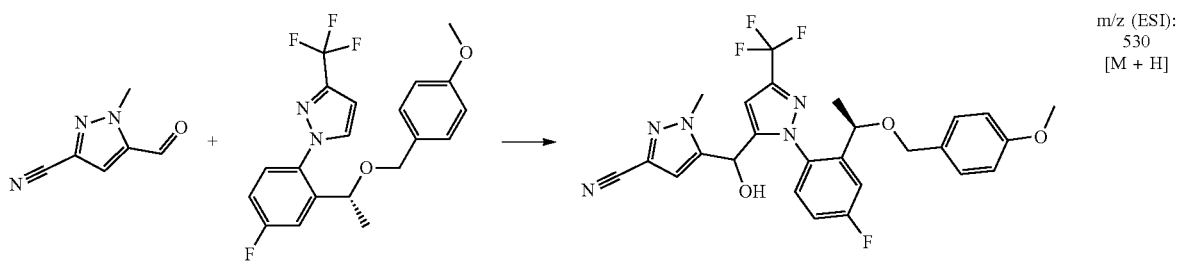

m/z (ESI): 530 [M + H]

(1-(2-((R)-1-(benzyloxy)ethyl)-4-fluorophenyl)-3-(difluoromethyl)-1H-pyrazol-5-yl)(1-(cyclopropylmethyl)-1H-1,2,3-triazol-4-yl)methanol

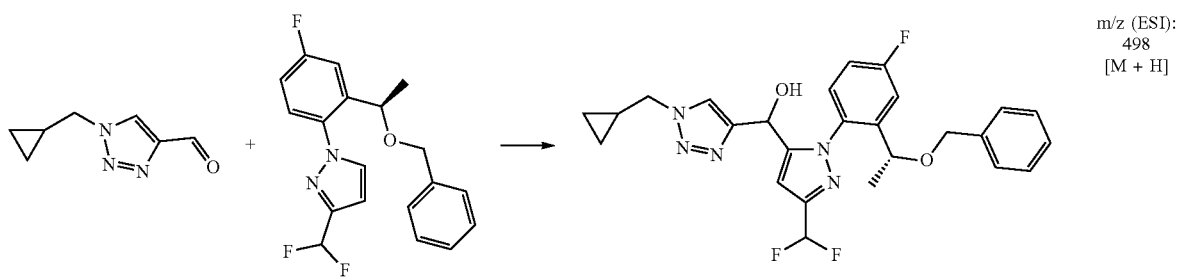

m/z (ESI): 498 [M + H]

5-((3-(difluoromethyl)-1-(4-fluoro-2-((R)-1-((4-methoxybenzyl)oxy)ethyl)phenyl)-1H-pyrazol-5-yl)(hydroxy)methyl)-1-methyl-1H-pyrazole-3-carbonitrile

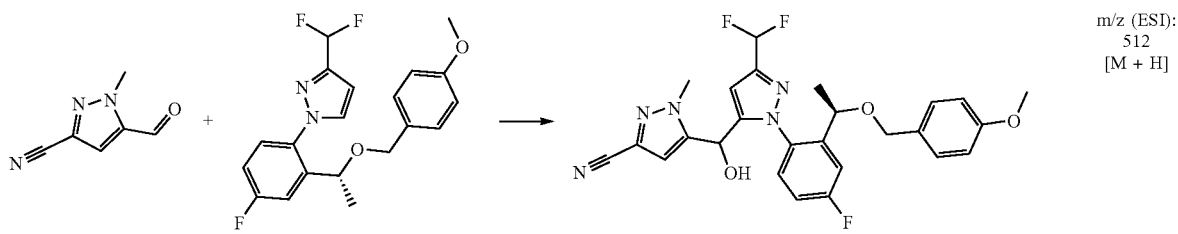

m/z (ESI): 512 [M + H]

4-((2-chloropyridin-3-yl)(hydroxy)methyl)-1-(cyclopropylmethyl)-1H-pyrazole-3-carbonitrile

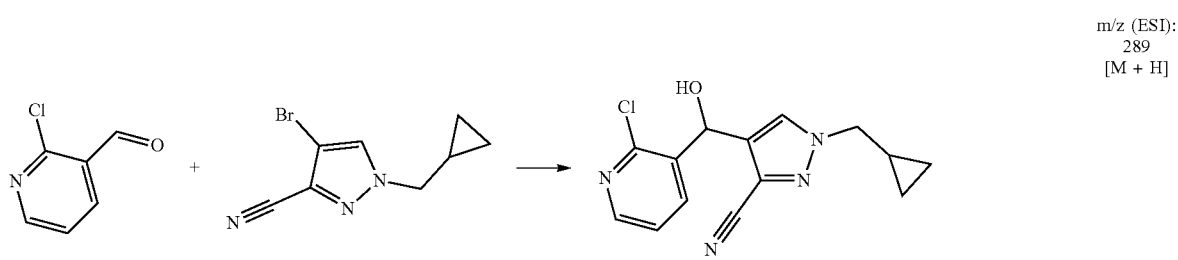

m/z (ESI): 289 [M + H]

(1-(2-((R)-1-(benzyloxy)ethyl)-4-fluorophenyl)-3-methoxy-1H-pyrazol-5-yl)(1-(cyclopropylmethyl)-3-methyl-1H-pyrazol-4-yl)methanol

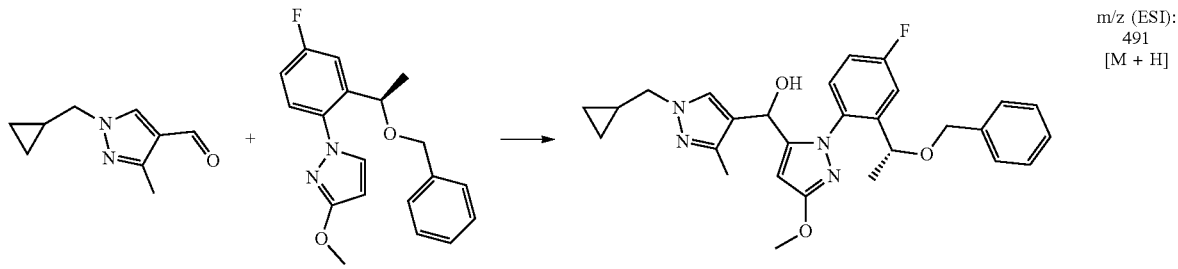

m/z (ESI): 491 [M + H]

(1-(2-((R)-1-(benzyloxy)ethyl)-4-fluorophenyl)-3-(difluoromethyl)-1H-pyrazol-5-yl)(1-(cyclopropylmethyl)-3-methyl-1H-pyrazol-4-yl)methanol

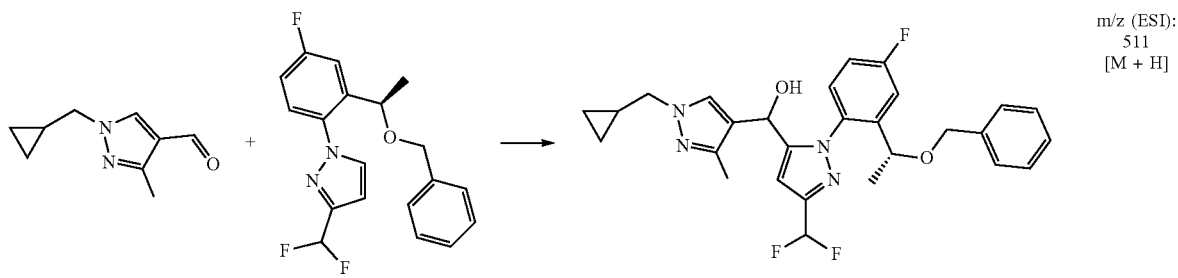

m/z (ESI): 511 [M + H]

(1-(2-((R)-1-(benzyloxy)ethyl)-4-fluorophenyl)-3-(difluoromethyl)-1H-pyrazol-5-yl)(1-(cyclopropylmethyl)-1H-pyrazol-4-yl)methanol

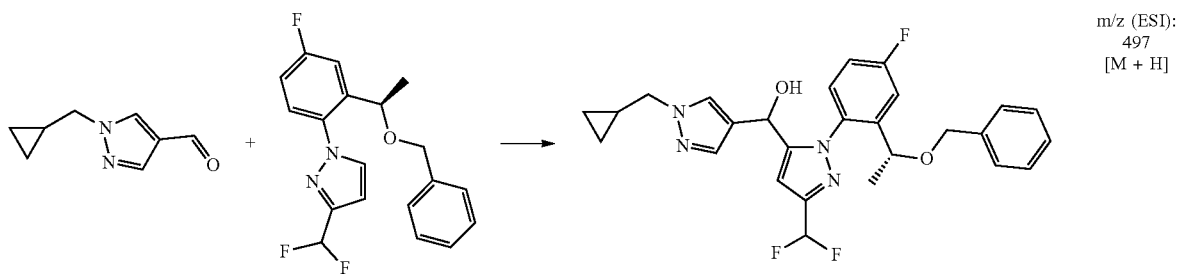

m/z (ESI): 497 [M + H]

[1-(cyclopropylmethyl)-1H-1,2,3-triazol-4-yl](1-{4-fluoro-2-[(1R)-1-[(4-methoxyphenyl)methoxy]ethyl]phenyl}-3-(trifluoromethyl)-1H-pyrazol-5-yl)methanol

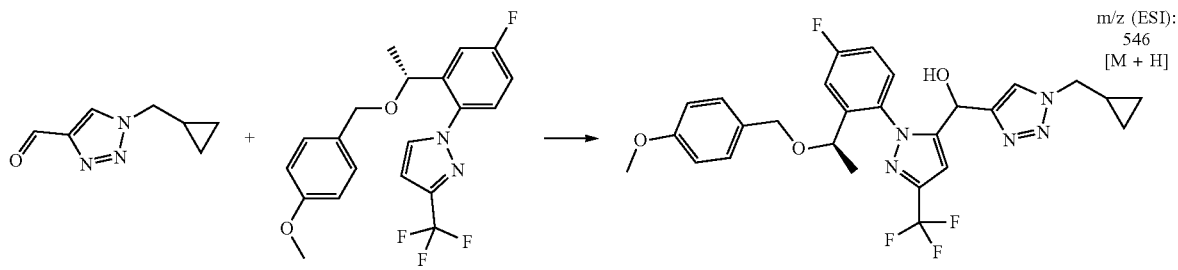

m/z (ESI): 546 [M + H]

(1-(2-(1,3-dioxolan-2-yl)-4-fluorophenyl)-3-methyl-1H-pyrazol-5-yl)(1-ethyl-1H-pyrazol-4-yl)methanol

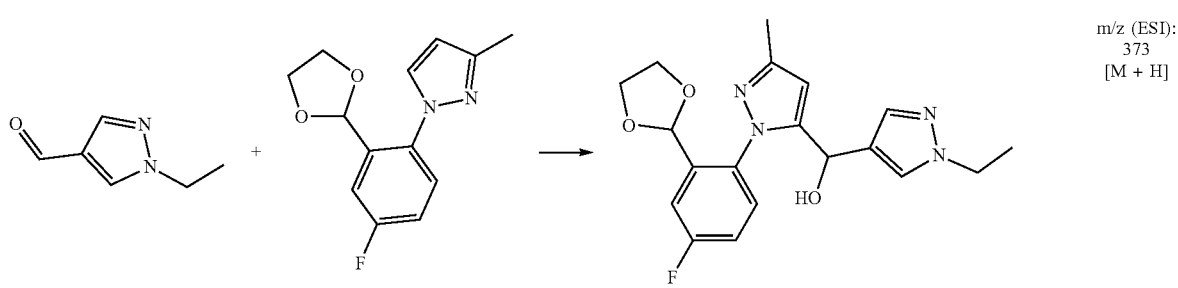

m/z (ESI): 373 [M + H]

-continued (1-(2-(1,3-dioxolan-2-yl)-4-fluorophenyl)-3-fluoro-1H-pyrazol-5-yl)(1-ethyl-1H-pyrazol-4-yl)methanol

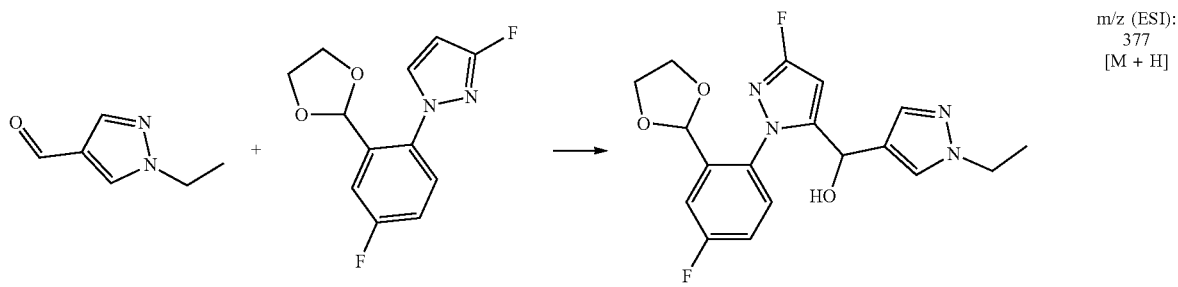

m/z (ESI): 377 [M + H]

(3-chloro-1-(4-fluoro-2-(hydroxymethyl)phenyl)-1H-pyrazol-5-yl)(1-ethyl-1H-pyrazol-4-yl)methanol

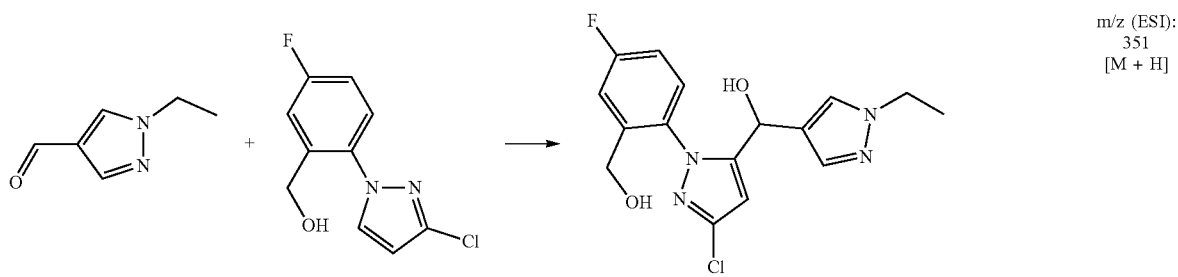

m/z (ESI): 351 [M + H]

(3-chloro-1-(4-fluoro-2-(hydroxymethyl)phenyl)-1H-pyrazol-5-yl)(1-(cyclopropylmethyl)-1H-1,2,3-triazol-4-yl)methanol

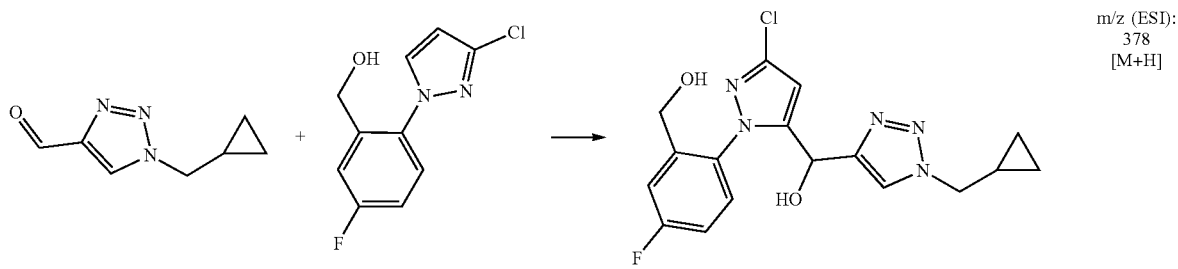

m/z (ESI): 378 [M+H]

(1-(2-((R)-1-(benzyloxy)ethyl)-4-fluorophenyl)-3-methoxy-1H-pyrazol-5-yl)(1-ethyl-1H-pyrazol-4-yl)methanol

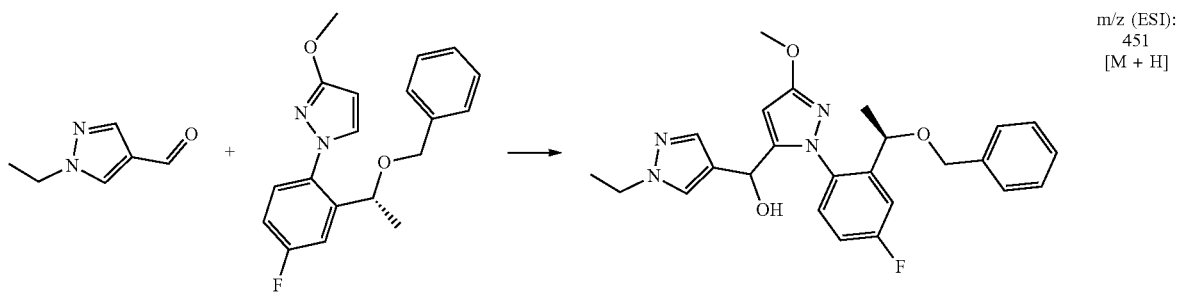

m/z (ESI): 451 [M + H]

5-((3-chloro-1-(4-fluoro-2-(((4-methoxybenzyl)oxy)methyl)phenyl)-1H-pyrazol-5-yl)(hydroxy)methyl)-1-methyl-1H-pyrazole-3-carbonitrile

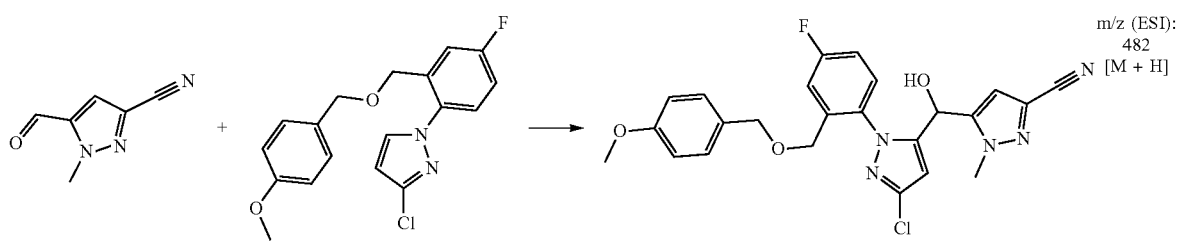

m/z (ESI): 482 [M + H]

(1-(2-((benzyloxy)methyl)-4-fluorophenyl)-3-(difluoromethyl)-1H-pyrazol-5-yl)(1-(cyclopropylmethyl)-1H-pyrazol-4-yl)methanol m/z (ESI): 483 [M + H]

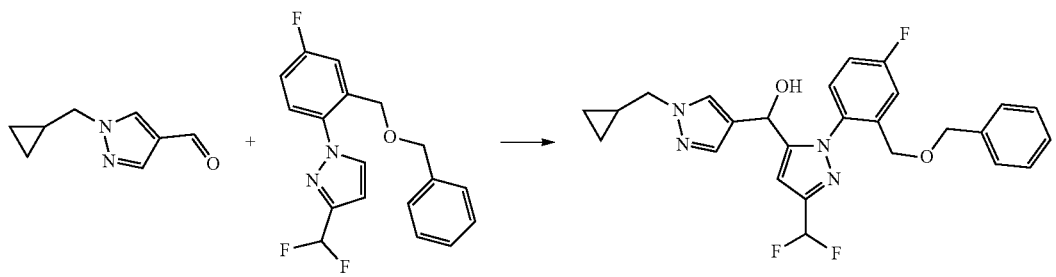 [SMILES: O=Cc1cnn(CC2CC2)c1 ; Fc1ccc(-n2ccc(C(F)F)n2)c(COCc2ccccc2)c1 ; OC(c1cnn(CC2CC2)c1)c1cc(C(F)F)nn1-c1ccc(F)cc1COCc1ccccc1]

(1-(2-((benzyloxy)methyl)-4-fluorophenyl)-3-(difluoromethyl)-1H-pyrazol-5-yl)(1-(cyclopropylmethyl)-3-methyl-1H-pyrazol-4-yl)methanol m/z (ESI): 497 [M + H]

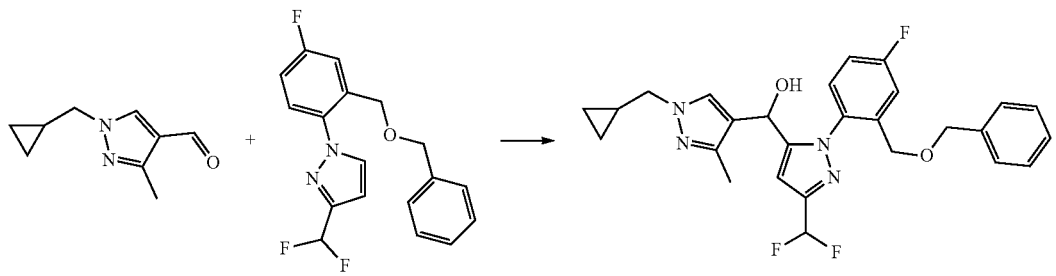 [SMILES: Cc1nn(CC2CC2)cc1C=O ; Fc1ccc(-n2ccc(C(F)F)n2)c(COCc2ccccc2)c1 ; Cc1nn(CC2CC2)cc1C(O)c1cc(C(F)F)nn1-c1ccc(F)cc1COCc1ccccc1]

5-((1-(2-(1,3-dioxolan-2-yl)-4-fluorophenyl)-1H-pyrazol-5-yl)(hydroxy)methyl)-1-((2-(trimethylsilyl)ethoxy)methyl)-1H-pyrazole-3-carbaldehyde m/z (ESI): 489 [M + H]

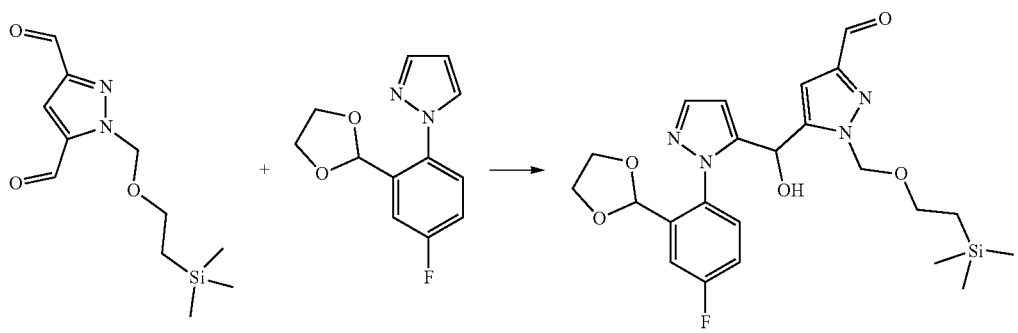 [SMILES: C[Si](C)(C)CCOCn1nc(C=O)cc1C=O ; Fc1ccc(-n2cccn2)c(C2OCCO2)c1 ; C[Si](C)(C)CCOCn1nc(C=O)cc1C(O)c1ccnn1-c1ccc(F)cc1C1OCCO1]

Synthesis of 4-(hydrazinylmethyl)-3-iodo-1-methyl-1H-pyrazole hydrochloride

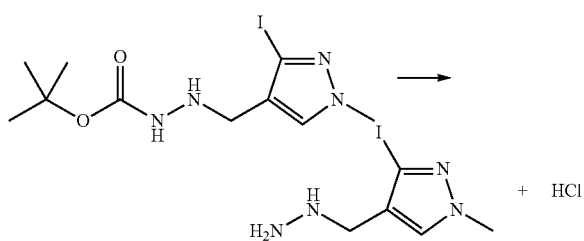

To a solution of tert-butyl 2-((3-iodo-1-methyl-1H-pyrazol-4-yl)methyl)hydrazine-1-carboxylate (5.00 g, 14.2 mmol) in MeOH (20 mL) was added HCl (30 mL, 4 N in dioxane) at r.t. The mixture was stirred for 12 h at 25° C., and then concentrated under reduced pressure to give 4-(hydrazinylmethyl)-3-iodo-1-methyl-1H-pyrazole hydrochloride (3.30 g, 75% yield) as a white solid. LC/MS ESI (m/z): 253 [M+H]⁺.

The following intermediates were synthesized using a similar experimental protocol:

4-fluoro-2-iodobenzohydrazide

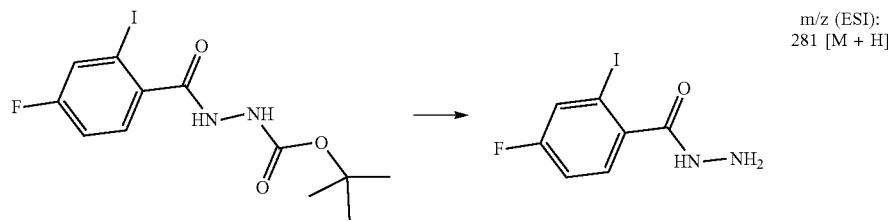

m/z (ESI): 281 [M + H]

Synthesis of (R)-1-(5-fluoro-2-iodophenyl)ethyl benzoate

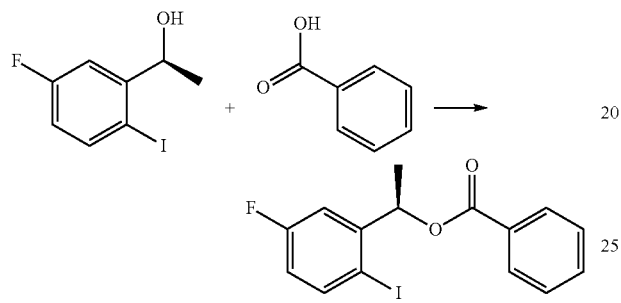

To a mixture of (1S)-1-(5-fluoro-2-iodophenyl)ethan-1-ol (1.00 g, 3.76 mmol), benzoic acid (0.550 g, 4.51 mmol) and triphenylphosphine (1.18 g, 4.51 mmol) in THF (30 mL) was added DIAD (0.89 mL, 4.5 mmol) dropwise at 0° C. under $N_2$. The resulting mixture was stirred at r.t. overnight, poured into water, and then extracted with EtOAc (50 mL×2). The combined organic layers were washed with brine, dried over anhydrous $Na_2SO_4$ and concentrated. The residue was purified by column chromatography (silica gel, 1→5% ethyl acetate in petroleum ether) to afford (1R)-1-(5-fluoro-2-iodophenyl)ethyl benzoate (1.2 g, 86%) as a yellow solid. LC/MS (ESI): m/z=371 [M+H]$^+$.

The following intermediates were synthesized using a similar experimental protocol:

(R)-3-(1-(5-fluoro-2-iodophenyl)ethoxy)-2-nitropyridine

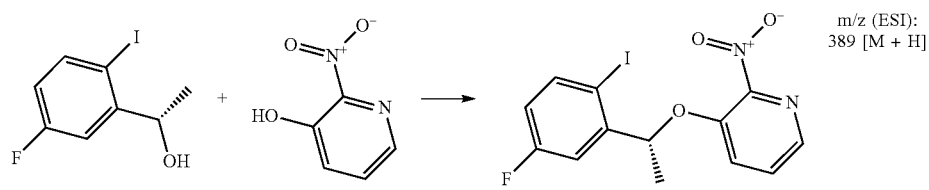

m/z (ESI): 389 [M + H]

Synthesis of tert-butyl 2-(4-fluoro-2-iodobenzoyl)hydrazine-1-carboxylate

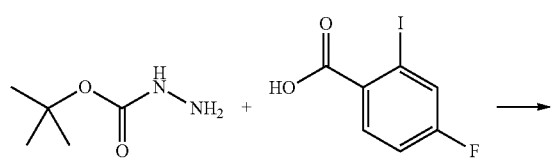

-continued

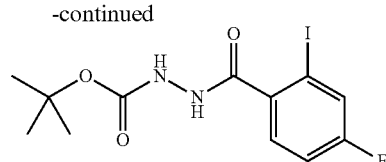

To a solution of 4-fluoro-2-iodobenzoic acid (8.50 g, 32.0 mmol) in DCM (50 mL) were added EDCI (6.14 g, 32.0 mmol), HOBT (4.32 g, 3.02 mmol) and TEA (6.46 g, 64.0 mmol). The mixture was stirred at r.t. for 0.5 h. Then tert-butyl hydrazinecarboxylate (5.07 g, 38.3 mmol) was added.

357

The reaction mixture was stirred at r.t. for 16 h, quenched with water and extracted with EA (100 mL). The organic layer was concentrated under reduced pressure. The residue was purified by flash column chromatography on silica gel (0→30% EA in PE) to give tert-butyl 2-(4-fluoro-2-iodo-benzoyl)hydrazine-1-carboxylate (7.6 g, 63%) as a white solid. LC/MS (ESI): m/z=381 [M+H]$^+$.

Synthesis of 5-bromo-1-(cyclopropylmethyl)-4-[(2-iodo-4-methyl-1H-imidazol-1-yl)methyl]-3-methyl-1H-pyrazole

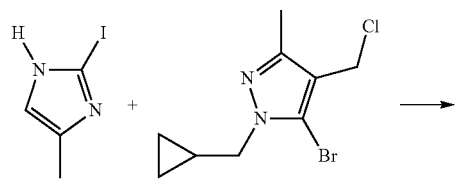

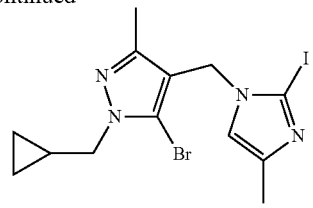

To a solution of 5-bromo-4-(chloromethyl)-1-(cyclopropylmethyl)-3-methyl-1H-pyrazole (639 mg, 2.42 mmol) and 2-iodo-4-methyl-1H-imidazole (420 mg, 2.02 mmol) in DMF (5 mL) was added K$_2$CO$_3$ (1.12 g, 8.08 mmol). This mixture was stirred at 25° C. for 16 h. The reaction was concentrated, and the residue was diluted with EtOAc (45 mL). The mixture was washed with brine (15 mL), dried over Na$_2$SO$_4$, and then concentrated. The residue was purified by flash column chromatography (silica gel, 30→85% EtOAc in PE) to give 5-bromo-1-(cyclopropylmethyl)-4-[(2-iodo-4-methyl-1H-imidazol-1-yl)methyl]-3-methyl-1H-pyrazole (500 mg, yield: 57%) as a light-yellow solid. LC-MS (ESI) m/z: 435 [M+H]$^+$.

The following intermediates were synthesized using a similar experimental protocol:IC12TE 5-bromo-1-ethyl-4-((2-(4-fluoro-2-iodophenyl)-4-methyl-1H-imidazol-1-yl)methyl)-1H-pyrazole

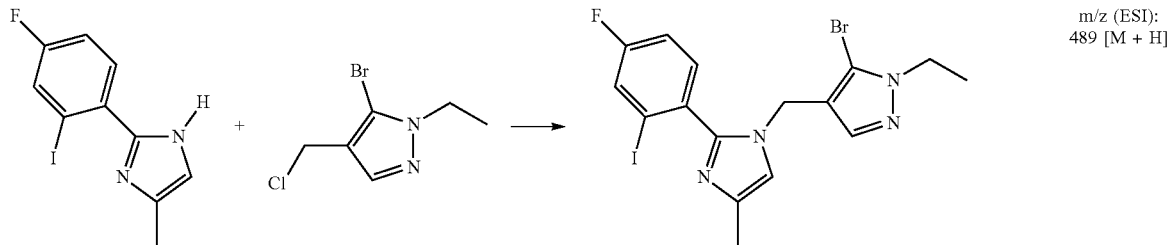

m/z (ESI): 489 [M + H]

2-(1-((5-bromo-1-(2,2-difluoroethyl)-1H-pyrazol-4-yl)methyl)-1H-imidazol-2-yl)-5-fluorobenzaldehyde

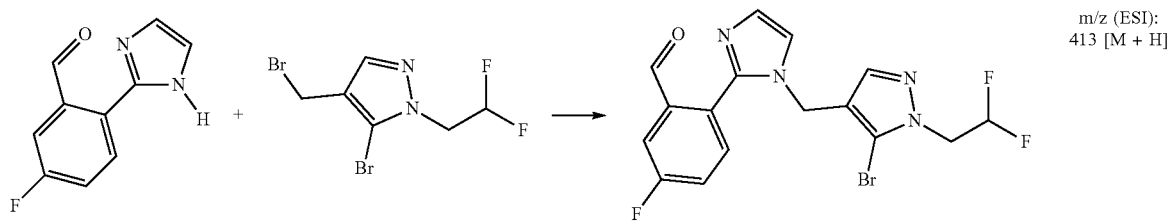

m/z (ESI): 413 [M + H]

2-(1-{[5-bromo-1-(2-fluoroethyl)-1H-pyrazol-4-yl]methyl}-1H-imidazol-2-yl)-5-fluorobenzaldehyde

m/z (ESI): 395 [M + H]

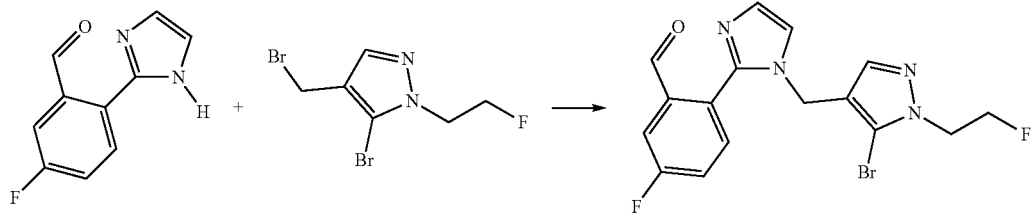 [SMILES: O=Cc1cc(F)ccc1-c1ncc[nH]1 ; FCCn1ncc(CBr)c1Br ; O=Cc1cc(F)ccc1-c1nccn1Cc1cnn(CCF)c1Br]

2-(1-((5-bromo-1-(difluoromethyl)-1H-pyrazol-4-yl)methyl)-1H-imidazol-2-yl)-5-fluorobenzaldehyde

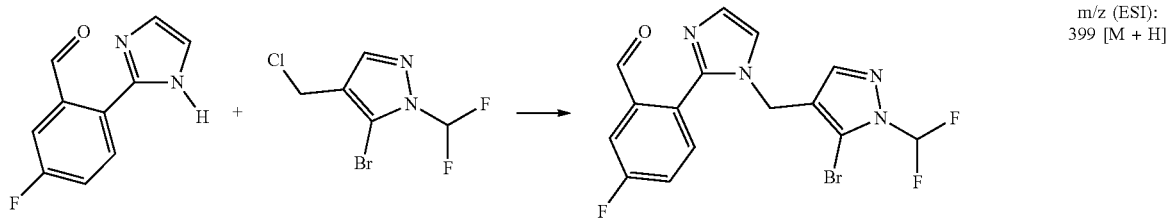

m/z (ESI): 399 [M + H]

Synthesis of ethyl 3-bromo-1-(4-fluoro-2-iodophenyl)-1H-pyrazole-5-carboxylate

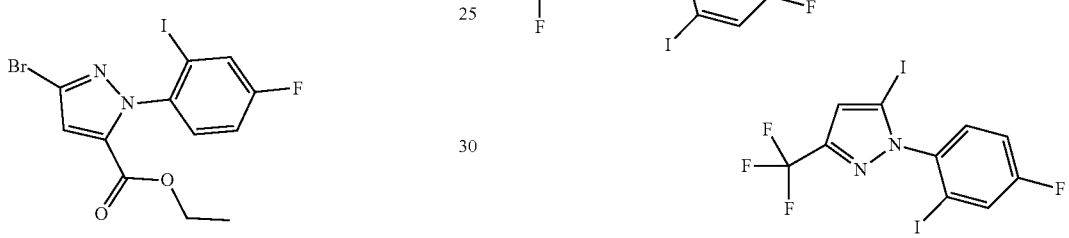

To a solution of (4-fluoro-2-iodophenyl)hydrazine hydrochloride (600 mg, 2.08 mmol) in H₂O (10 mL) was added conc. HCl (257 mg, 2.50 mmol), followed by the addition of a 50% aq. solution of 2-oxoacetic acid (339 mg, 2.29 mmol) dropwise at 15° C. The resulting mixture was stirred at 15° C. for 0.5 h. The resulting precipitate was collected by filtration, washed with H₂O, and dried in vacuo to give crude (2E)-2-[2-(4-fluoro-2-iodophenyl)hydrazin-1-ylidene]acetic acid (500 mg, 78%) as a pale-yellow solid. LC/MS (ESI) m/z: 309 [M+H]⁺.

To a solution of (E)-2-(2-(4-fluoro-2-iodophenyl)hydrazono)acetic acid (4.50 g, 14.6 mmol) in DMF (30 mL) was added NBS (5.20 g, 29.2 mmol) at −10° C. and the mixture was stirred −10° C. for 30 min. The reaction was filtered and concentrated in vacuo. The residue was purified by flash chromatography (0→5% EtOAc in PE) to give (dibromomethyl)(4-fluoro-2-iodophenyl)diazene (1.78 g, 27% yield) as an off-white solid. LC/MS (ESI) m/z: 421 [M+H]⁺.

To a solution of (dibromomethyl)(4-fluoro-2-iodophenyl)diazene (1.76 g, 4.17 mmol) and TEA (1.26 g, 12.5 mmol) in DMF (30 mL) was added a solution of ethyl propiolate (0.75 mL, 4.5 mmol) in DCM (2 mL) dropwise at −10° C. The reaction was stirred at −10° C. for 10 min, and then filtered and concentrated in vacuo. The residue was purified by flash chromatography (0→20% EtOAc in PE) to give ethyl 3-bromo-1-(4-fluoro-2-iodophenyl)-1H-pyrazole-5-carboxylate (1.2 g, 62% yield) as an off-white solid. LC-MS (ESI): 439 [M+H]⁺.

Synthesis of 1-(4-fluoro-2-iodophenyl)-5-iodo-3-(trifluoromethyl)-1H-pyrazole To a mixture of KI (6.70 g, 40.4 mmol) and isopentyl nitrite (4.70 g, 40.4 mmol) in THF (100 mL) was added a solution of 1-(4-fluoro-2-iodophenyl)-3-(trifluoromethyl)-1H-pyrazol-5-amine (5.00 g, 13.4 mmol) in THF (80 mL) dropwise at 0° C. After stirring at 85° C. for 16 h, the reaction was diluted with EtOAc. The resulting mixture was washed with H₂O and brine. The organic layer was dried over anhydrous Na₂SO₄. After filtration, the filtrate was concentrated under vacuum. The residue was purified by silica gel column chromatography (0→40% EtOAc in PE) to give 1-(4-fluoro-2-iodophenyl)-5-iodo-3-(trifluoromethyl)-1H-pyrazole (3.7 g, 57% yield) as a clear oil.
LC/MS ESI (m/z): 483 [M+H]⁺.

Synthesis of (R)-5-fluoro-3-methylbenzo[c][1,2]oxaborol-1(3H)-ol

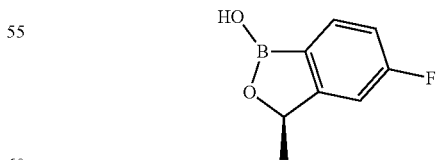

To a solution of (1R)-1-(5-fluoro-2-iodophenyl)ethyl benzoate (300 mg, 0.81 mmol) in methanol (8 mL) was added a solution of NaOH (32 mg, 0.81 mmol) in water (8 mL). The mixture was stirred at r.t. overnight. The reaction mixture was poured into water and then extracted with EtOAc (50 mL×2). The combined organic layers were washed with brine, dried over anhydrous Na₂SO₄ and concentrated. The residue was purified by column chromatography (silica gel, 1→5% ethyl acetate in petroleum ether) to afford (1R)-1-(5-fluoro-2-iodophenyl)ethan-1-ol (150 mg, 70%) as a white solid. LC/MS (ESI): m/z=267 [M+H]⁺.

Isopropylmagnesium chloride-lithium chloride complex, 1.3M solution in THF (72.3 mL, 94.0 mmol) was added to the mixture of (1R)-1-(5-fluoro-2-iodophenyl)ethan-1-ol (10.00 g, 37.59 mmol) in THF (120 mL) at −40° C. under N₂ dropwise. The mixture was stirred at −40° C. under N₂ for 1 h, then warmed to −10° C. for another 0.5 h before trimethyl borate (10.67 mL, 93.97 mmol) was added dropwise over 10 min at −10° C. After stirring at r.t. overnight under N₂, The reaction mixture was poured into sat. NH₄Cl solution (100 mL) and then extracted with EtOAc (50 mL×2). The combined organic layers were washed with brine, dried over anhydrous Na₂SO₄ and concentrated. The residue was purified by column chromatography (silica gel, 1→10% ethyl acetate in petroleum ether) to afford (R)-5-fluoro-3-methylbenzo[c][1,2]oxaborol-1(3H)-ol (4.0 g, 64%) as a colorless oil. LC/MS (ESI): m/z=167 [M+H]⁺.

Synthesis of 3-(4-fluoro-2-iodophenyl)-1,2-thiazole-4-carbaldehyde

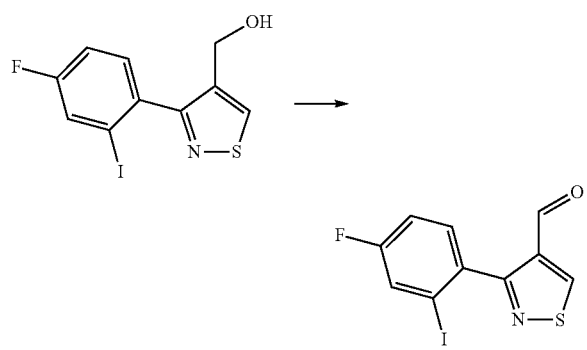

To a solution of [3-(4-fluoro-2-iodophenyl)-1,2-thiazol-4-yl]methanol (550 mg, 1.64 mmol) in DCM (20 mL), was added MnO₂ (1.42 g, 16.4 mmol) at r.t. Then this mixture was stirred at 40° C. for 32 h. The reaction mixture was filtered, and the filtrate was concentrated. The residue was purified by column chromatography on silica gel (30% EtOAc in PE) to afford 3-(4-fluoro-2-iodophenyl)-1,2-thiazole-4-carbaldehyde (400 mg, 73%) as a light-yellow solid. LC/MS (ESI): m/z=334 [M+H]⁺.

Synthesis of 3-(1-(5-fluoro-2-iodophenyl)ethoxy)-2-nitropyridine

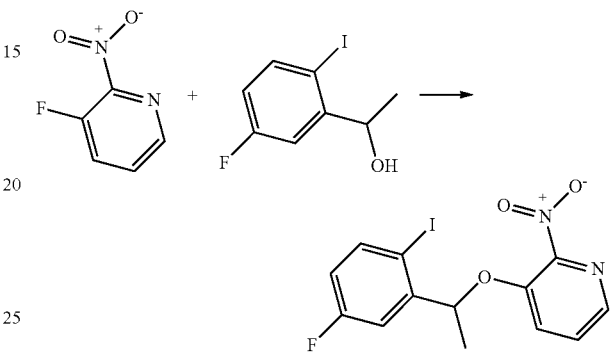

To a solution of 1-(5-fluoro-2-iodophenyl)ethan-1-ol (9.20 g, 34.6 mmol) in THF (180 mL) at 0° C. was added portion-wise NaH (1.38 g, 34.6 mmol, 60% in mineral oil) over 10 min. After the addition, the mixture was stirred at 0° C. for 15 min, and then a solution of 3-fluoro-2-nitropyridine (4.91 g, 34.6 mmol) in THF (20 mL) was added dropwise. The ice bath was removed, and the mixture was stirred at r.t. for 3 h. The reaction mixture was partitioned between DCM (200 mL) and water (200 mL). The organic layer was separated, washed with brine, and concentrated in vacuo. The residue was purified by flash chromatography (eluent: 0→30% EtOAc in PE) to give 3-(1-(5-fluoro-2-iodophenyl)ethoxy)-2-nitropyridine (5.3 g, yield: 39%) as a white solid. LC/MS ESI (m/z): 389 [M+H]⁺.

The following intermediates were synthesized using a similar experimental protocol:

(R)-3-chloro-1-(4-fluoro-2-(1-((4-methoxybenzyl)oxy)ethyl)phenyl)-1H-pyrazole

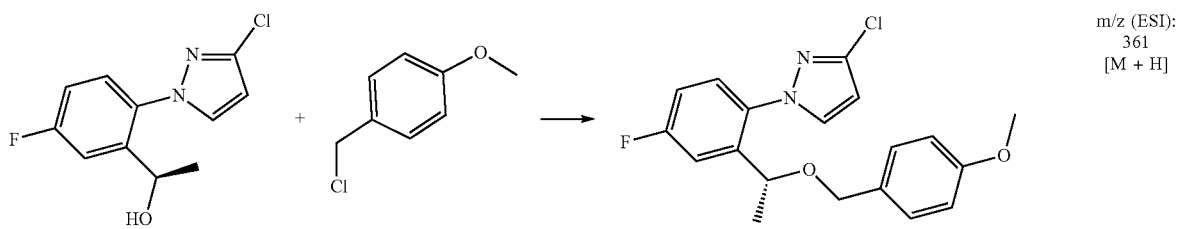

m/z (ESI): 361 [M + H]

(R)-1-(4-fluoro-2-(1-((4-methoxybenzyl)oxy)ethyl)phenyl)-1H-pyrazole

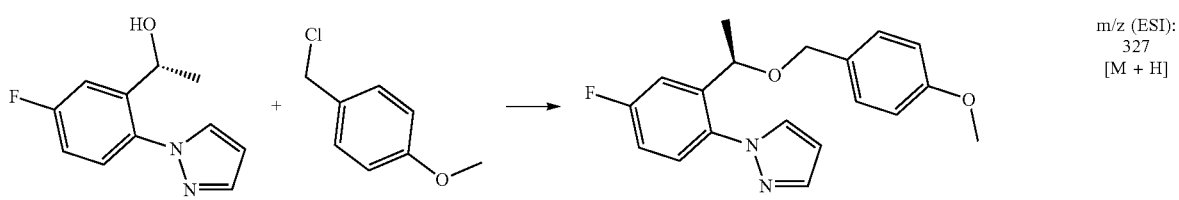

m/z (ESI): 327 [M + H]

-continued (R)-1-(2-(1-(benzyloxy)ethyl)-4-fluorophenyl)-3-methoxy-1H-pyrazole

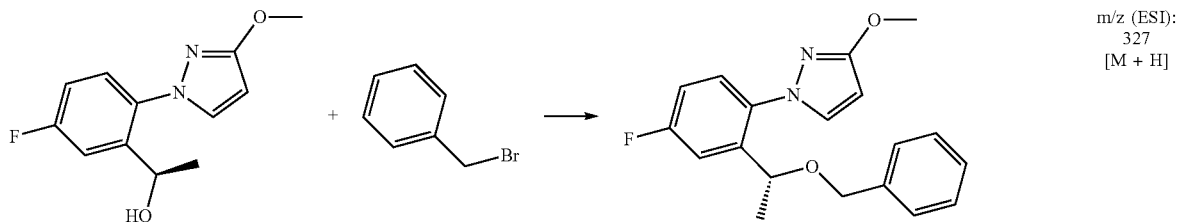

m/z (ESI): 327 [M + H]

(R)-3-(1-(2-(4-((3-(benzyloxy)-5-bromo-1-ethyl-1H-pyrazol-4-yl)methyl)-1-methyl-1H-pyrazol-3-yl)-5-fluorophenyl)ethoxy)-5-bromo-2-nitropyridine

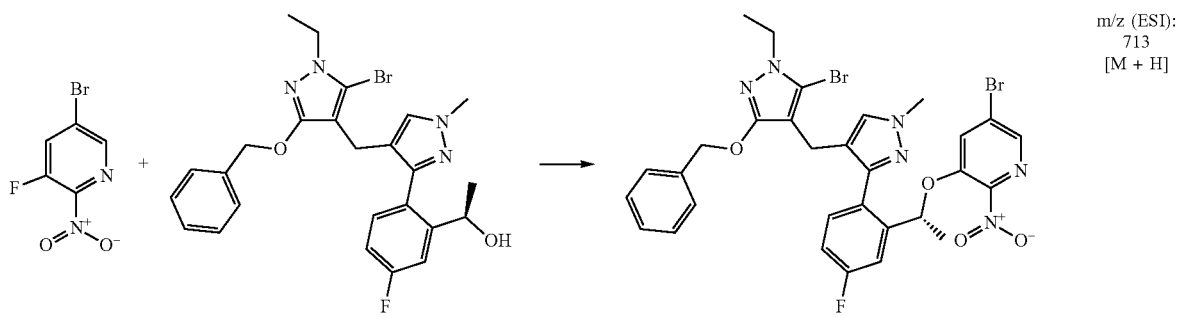

m/z (ESI): 713 [M + H]

(R)-5-bromo-3-(1-(2-(4-((5-bromo-1-(cyclopropylmethyl)-3-methyl-1H-pyrazol-4-yl)methyl)-1-methyl-1H-pyrazol-3-yl)-5-fluorophenyl)ethoxy)-2-nitropyridine

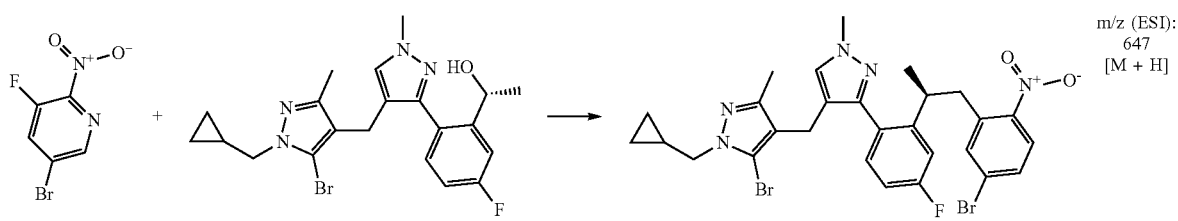

m/z (ESI): 647 [M + H]

5-bromo-3-[(1R)-1-[2-(1-{[5-bromo-1-(cyclopropylmethyl)-3-methyl-1H-pyrazol-4-yl]methyl}-4-methyl-1H-imidazol-2-yl)-5-fluorophenyl]ethoxy]-2-nitropyridine

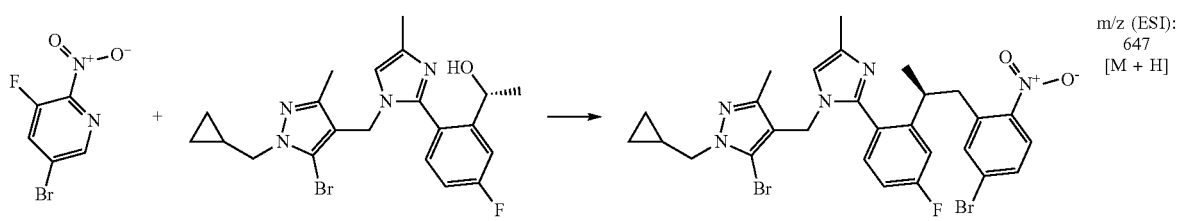

m/z (ESI): 647 [M + H]

5-bromo-3-(1-(2-(4-((5-bromo-1-ethyl-1H-pyrazol-4-yl)methyl)-1-methyl-1H-pyrazol-5-yl)-5-fluorophenyl)ethoxy)-2-nitropyridine

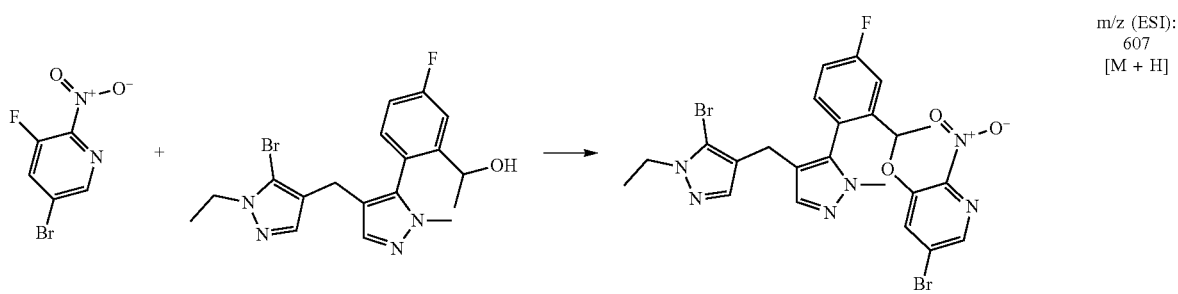

m/z (ESI): 607 [M + H]

5-bromo-3-(1-(2-(1-((5-bromo-1-ethyl-1H-pyrazol-4-yl)methyl)-1H-imidazol-2-yl)-5-fluorophenyl)ethoxy)-2-nitropyridine

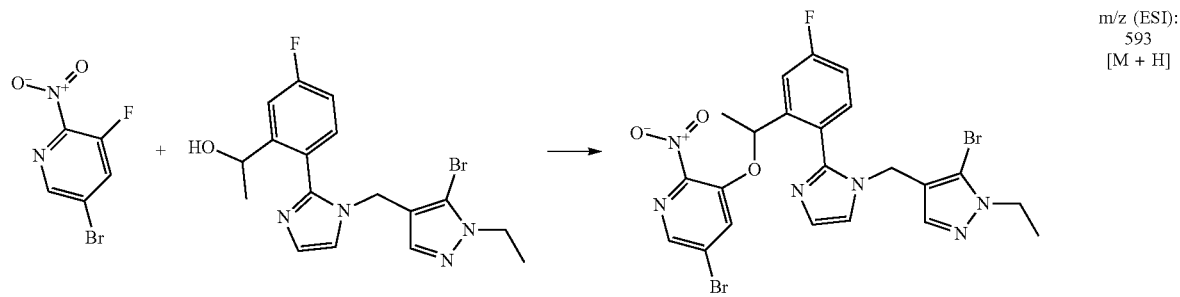

m/z (ESI): 593 [M + H]

5-bromo-3-[1-(2-[4-(5-bromo-4-ethylimidazol-1-yl)methyl]-1-methylpyrazol-3-yl]-5-fluorophenyl)ethoxy]-2-nitropyridine

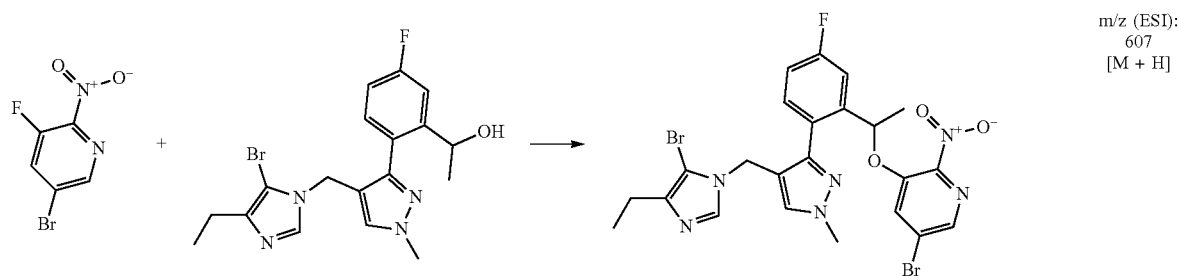

m/z (ESI): 607 [M + H]

5-((5-bromo-1-ethyl-1H-pyrazol-4-yl)methyl)-1-(2-(1-(5-bromo-2-nitropyridin-3-yloxy)ethyl)-4-fluorophenyl)-1H-pyrazole-4-carbonitrile

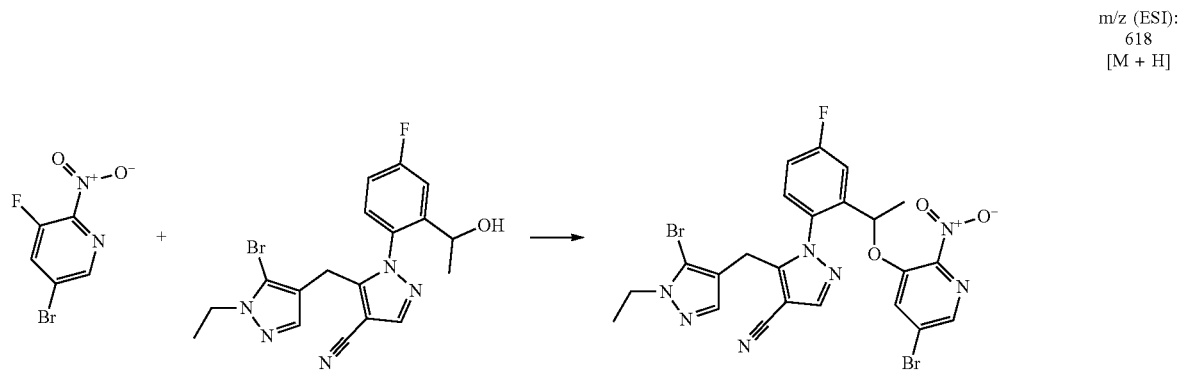

m/z (ESI): 618 [M + H]

5-((5-bromo-1-ethyl-1H-pyrazol-4-yl)methyl)-1-(2-(1-((5-bromo-2-nitropyridin-3-yl)oxy)ethyl)-4-fluorophenyl)-1H-pyrazole-3-carbonitrile

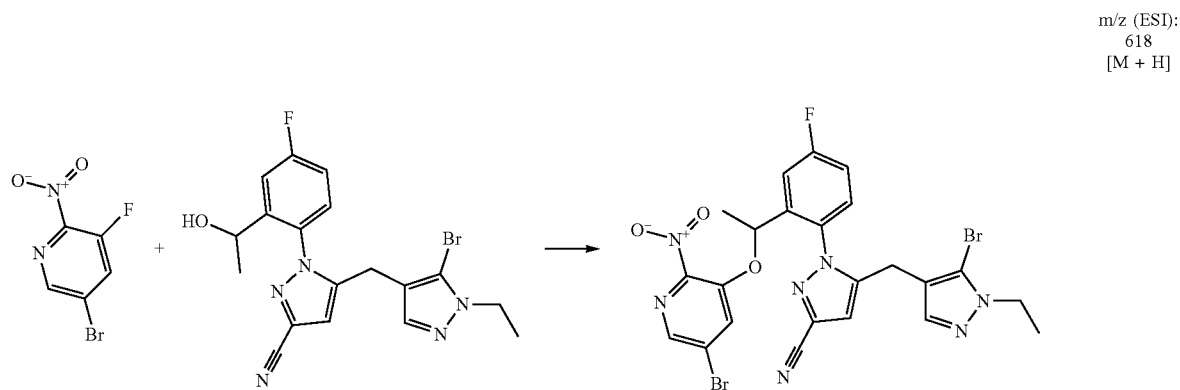

m/z (ESI): 618 [M + H]

-continued 5-bromo-3-(1-(2-(5-((5-bromo-1-ethyl-1H-pyrazol-4-yl)methyl)-3-(trifluoromethyl)-1H-pyrazol-1-yl)-5-fluorophenyl)ethoxy)-2-nitropyridine

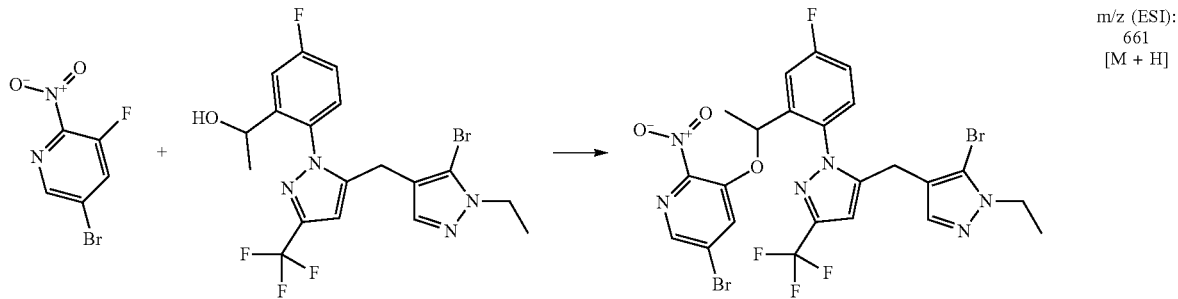

m/z (ESI): 661 [M + H]

5-bromo-3-((2-(5-((4-bromo-3-ethyl-1-methyl-1H-pyrazol-5-yl)methyl)-3-methyl-1H-pyrazol-1-yl)-5-fluorobenzyl)oxy)-2-nitropyridine

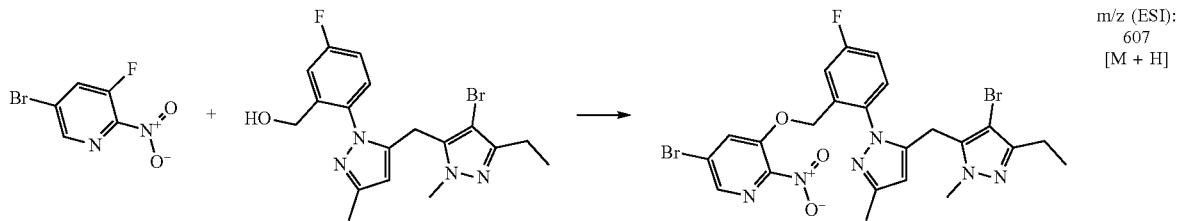

m/z (ESI): 607 [M + H]

5-bromo-3-(1-(2-(4-((5-bromo-1-ethyl-1H-pyrazol-4-yl)methyl)pyridin-3-yl)-5-fluorophenyl)ethoxy)-2-nitropyridine

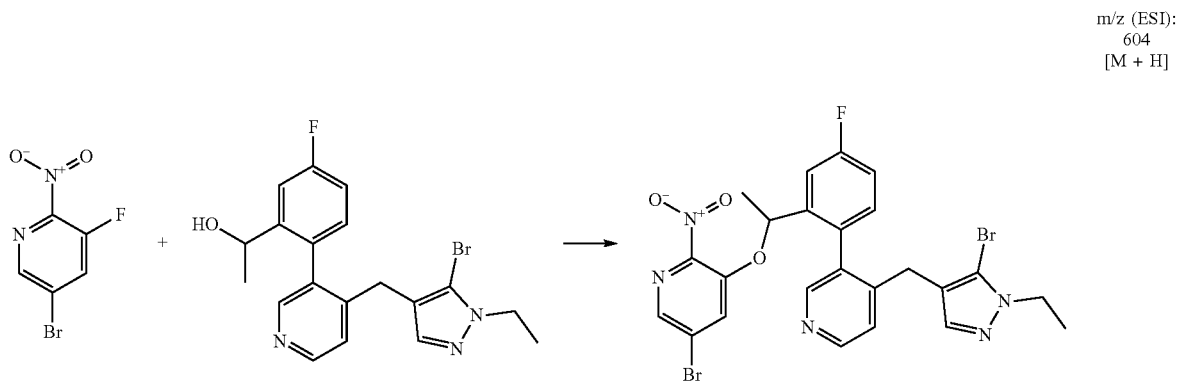

m/z (ESI): 604 [M + H]

5-bromo-3-(1-(2-(5-((5-bromo-1-ethyl-1H-pyrazol-4-yl)methyl)-1H-imidazol-1-yl)-5-fluorophenyl)ethoxy)-2-nitropyridine

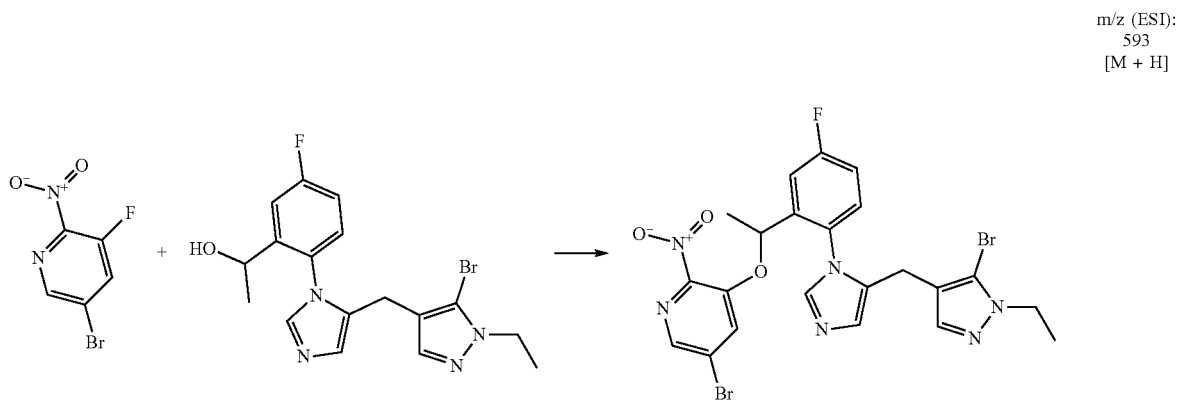

m/z (ESI): 593 [M + H]

5-bromo-3-((2-(1-((5-bromo-1-ethyl-1H-pyrazol-4-yl)methyl)-1H-imidazol-2-yl)-5-fluorobenzyl)oxy)-2-nitropyridine

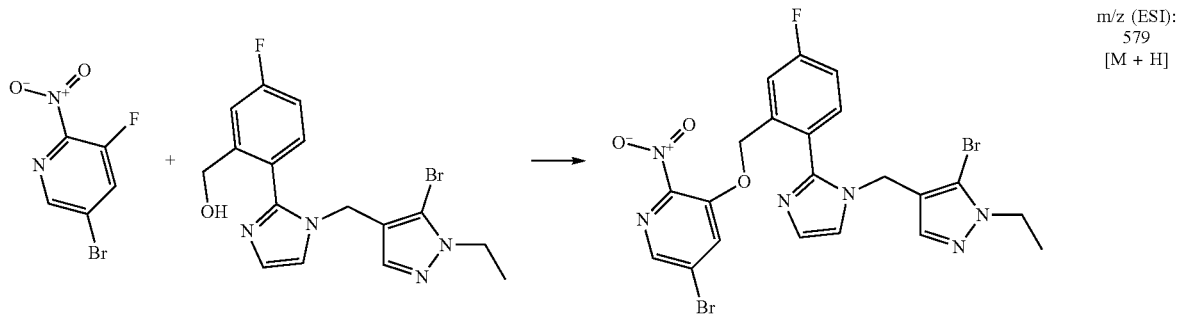

m/z (ESI): 579 [M + H]

5-bromo-3-(1-(2-(3-((5-bromo-1-ethyl-1H-pyrazol-4-yl)methyl)pyridin-4-yl)-5-fluorophenyl)ethoxy)-2-nitropyridine

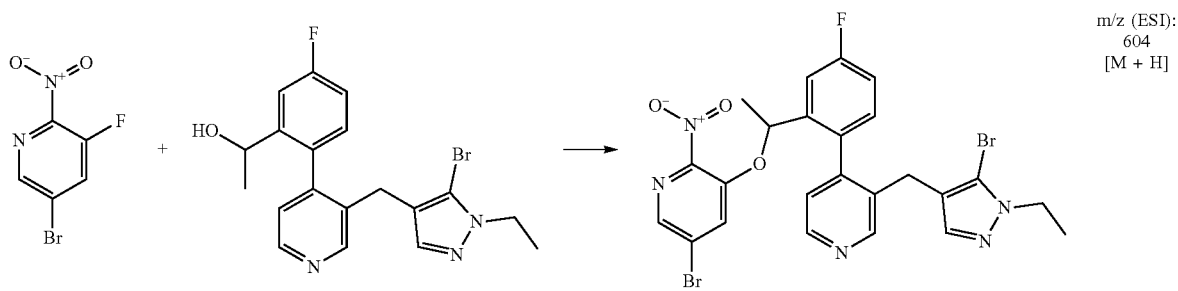

m/z (ESI): 604 [M + H]

5-bromo-3-(1-(2-(1-((5-bromo-1-cyclobutyl-1H-pyrazol-4-yl)methyl)-1H-imidazol-2-yl)-5-fluorophenyl)ethoxy)-2-nitropyridine

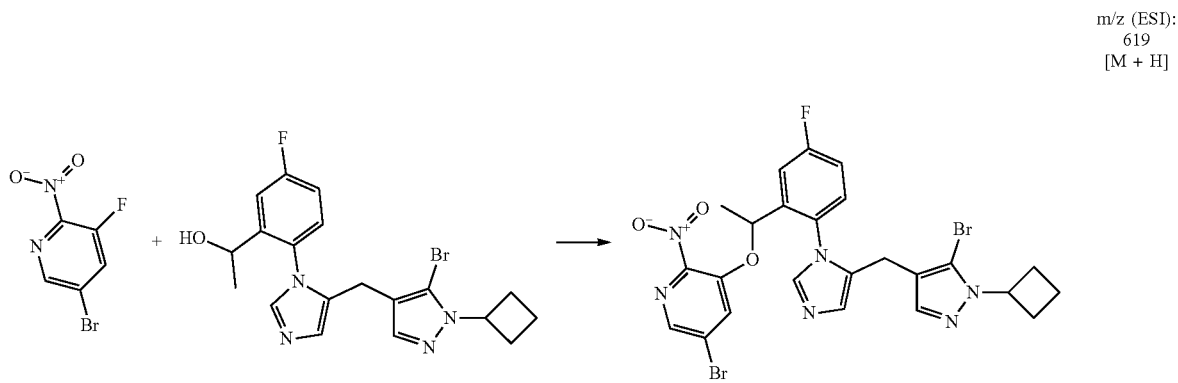

m/z (ESI): 619 [M + H]

5-bromo-3-(1-(2-(1-((5-bromo-1-ethyl-1H-pyrazol-4-yl)methyl)-4-methyl-1H-imidazol-2-yl)-5-fluorophenyl)ethoxy)-2-nitropyridine

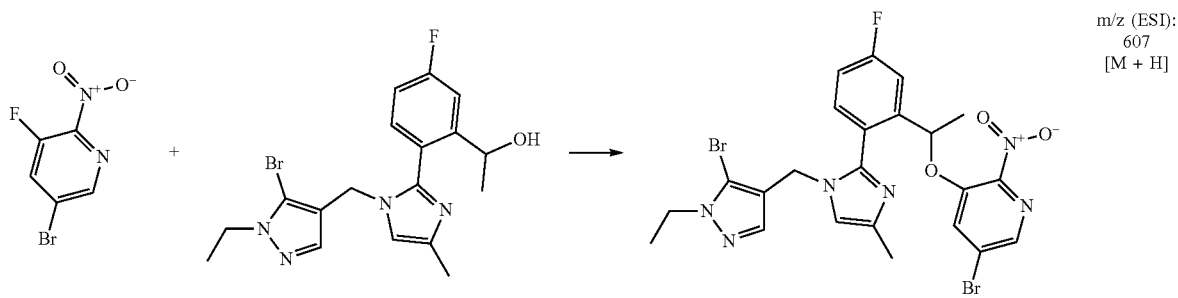

m/z (ESI): 607 [M + H]

5-((5-bromo-1-ethyl-1H-pyrazol-4-yl)methyl)-4-(2-(1-((5-bromo-2-nitropyridin-3-yl)oxy)ethyl)-4-fluorophenyl)pyrimidine

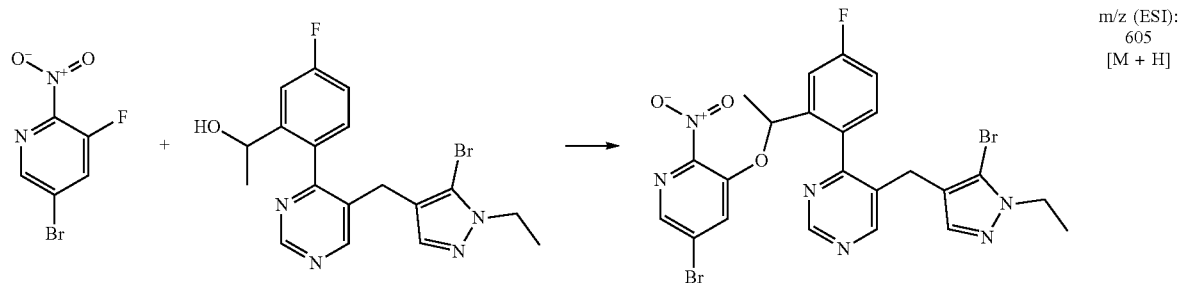

m/z (ESI): 605 [M + H]

5-bromo-3-{1-[2-(1-{[5-bromo-1-(2-fluoroethyl)-1H-pyrazol-4-yl]methyl}-1H-imidazol-2-yl)-5-fluorophenyl]ethoxy}-2-nitropyridine

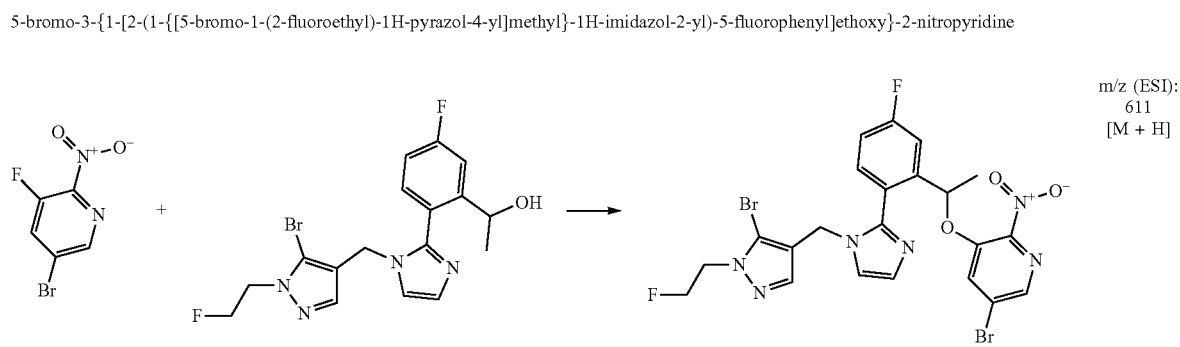

m/z (ESI): 611 [M + H]

5-bromo-3-(2-(4-((5-bromo-1-ethyl-1H-pyrazol-4-yl)methyl)-1-methyl-1H-pyrazol-3-yl)-5-fluorobenzyloxy)-2-nitropyridine

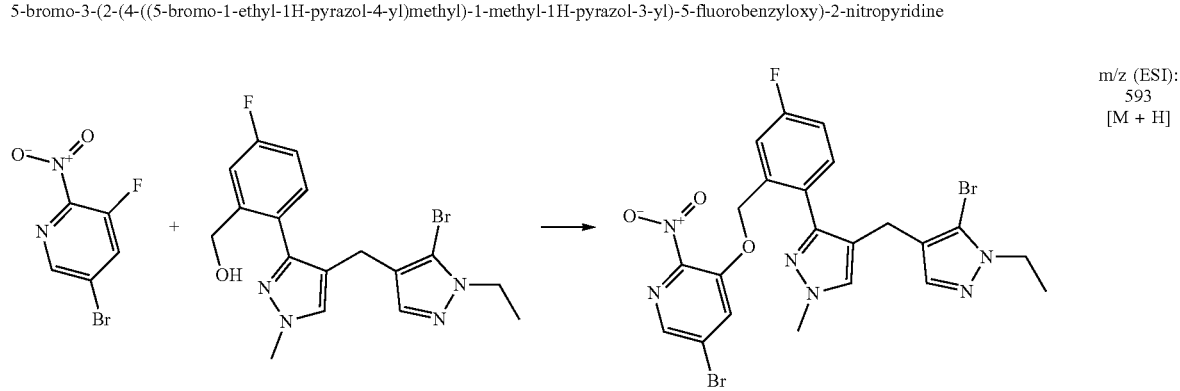

m/z (ESI): 593 [M + H]

(5-bromo-1-ethyl-1H-pyrazol-4-yl)(1-(2-(1-((5-bromo-2-nitropyridin-3-yl)oxy)ethyl)-4-fluorophenyl)-4-fluoro-1H-pyrazol-5-yl)methanone

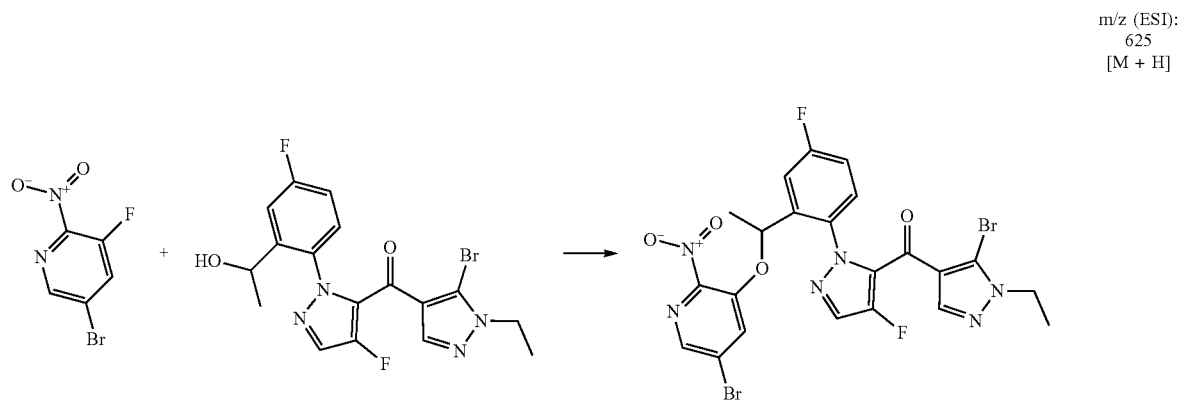

m/z (ESI): 625 [M + H]

-continued (R)-5-bromo-3-(1-(2-(3-(difluoromethyl)-5-((1-ethyl-1H-pyrazol-4-yl)methyl)-1H-pyrazol-1-yl)-5-fluorophenyl)ethoxy)-2-nitropyridine

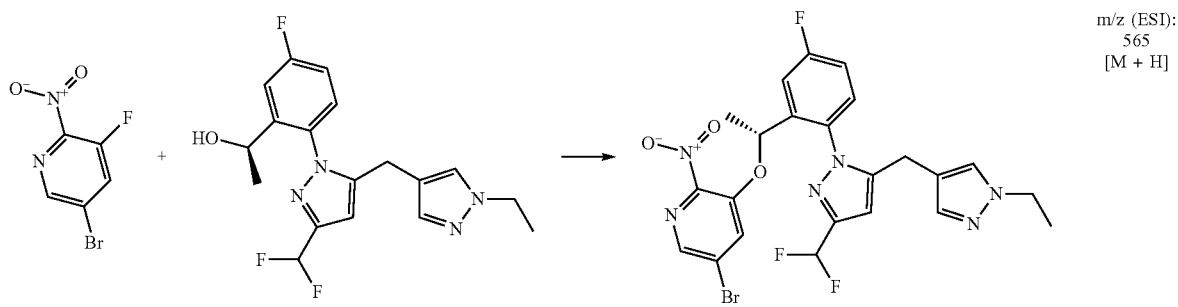

m/z (ESI): 565 [M + H]

5-bromo-3-[(1R)-1-(2-{5-[(1-ethyl-1H-1,2,3-triazol-4-yl)methyl]-2-methyl-1,3-thiazol-4-yl}-5-fluorophenyl)ethoxy]-2-nitropyridine

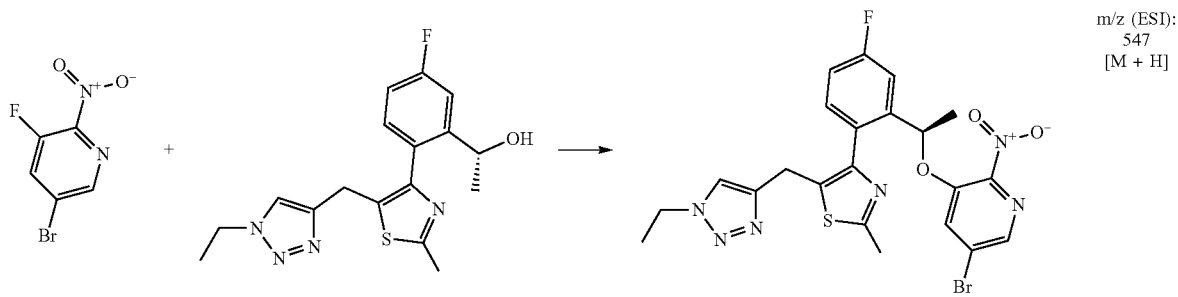

m/z (ESI): 547 [M + H]

(R)-5-bromo-3-(1-(2-(4-((1-ethyl-3-methyl-1H-pyrazol-4-yl)methyl)-1-methyl-1H-pyrazol-3-yl)-5-fluorophenyl)ethoxy)-2-nitropyridine

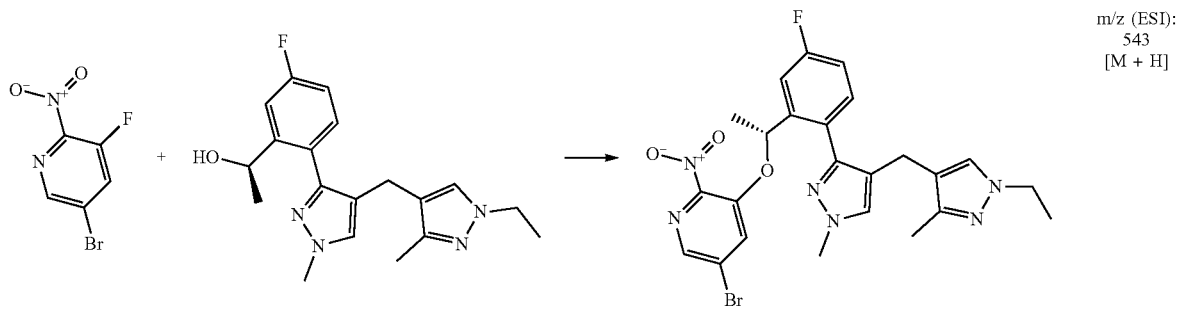

m/z (ESI): 543 [M + H]

5-bromo-3-[(1R)-1-(2-{4-[(1-ethyl-1H-pyrazol-4-yl)methyl]-1,5-dimethyl-1H-pyrazol-3-yl}-5-fluorophenyl)ethoxy]-2-nitropyridine

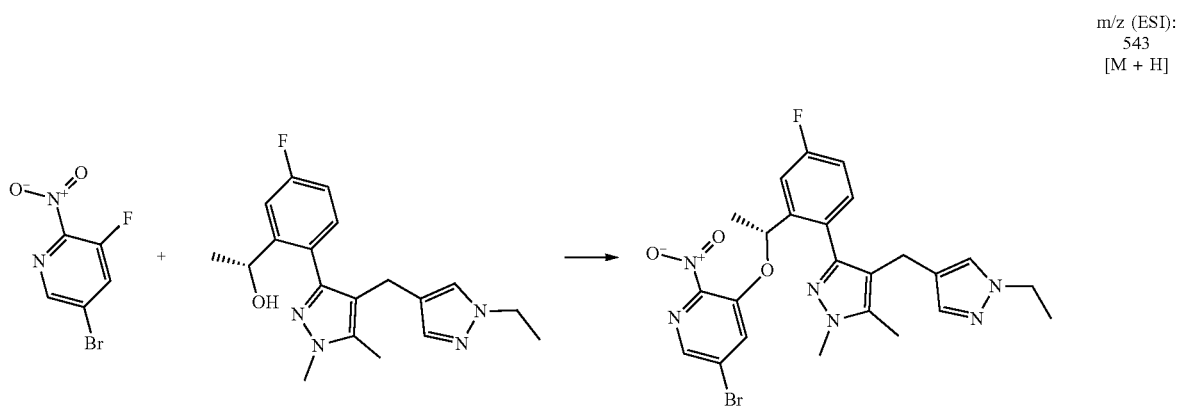

m/z (ESI): 543 [M + H]

(R)-5-((2-(2-(1-((5-bromo-2-nitropyridin-3-yl)oxy)ethyl)-4-fluorophenyl)pyridin-3-yl)methyl)-1-methyl-1H-pyrazole-3-carbonitrile

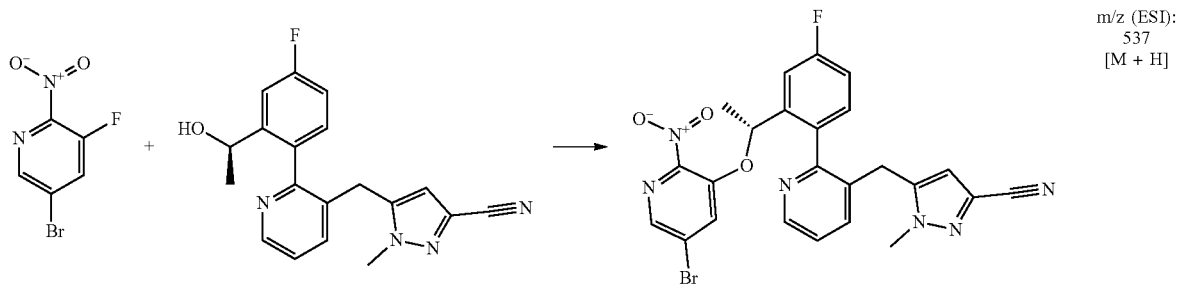

m/z (ESI): 537 [M + H]

5-bromo-3-[(1R)-1-(2-{4-[(5-ethyl-1,2-thiazol-3-yl)methyl]-1-methyl-1H-pyrazol-3-yl}-5-fluorophenyl)ethoxy]-2-nitropyridine

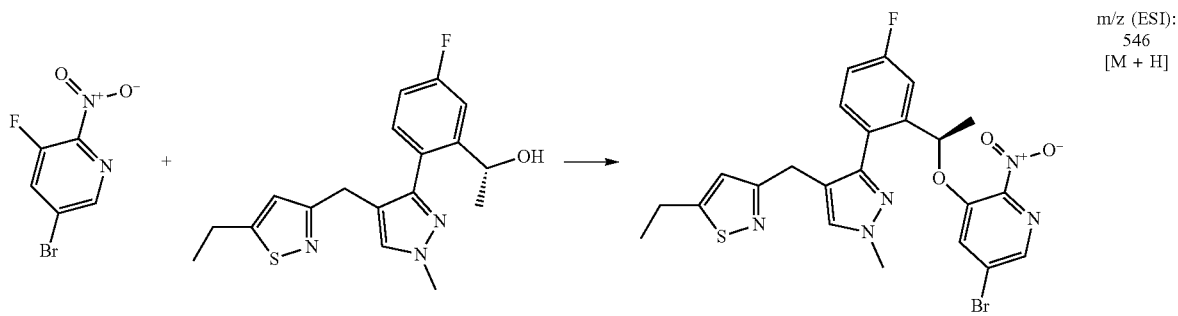

m/z (ESI): 546 [M + H]

(R)-5-bromo-3-(1-(2-(5-((1-(cyclopropylmethyl)-1H-pyrazol-4-yl)methyl)-3-(trifluoromethyl)-1H-pyrazol-1-yl)-5-fluorophenyl)ethoxy)-2-nitropyridine

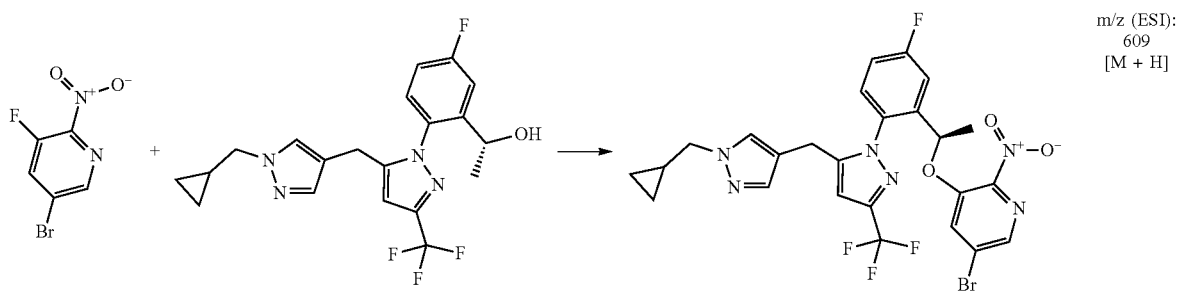

m/z (ESI): 609 [M + H]

5-bromo-3-[(1R)-1-(2-{5-[(1-ethyl-1H-1,2,3-triazol-4-yl)methyl]-3-(trifluoromethyl)-1H-pyrazol-1-yl}-5-fluorophenyl)ethoxy]-2-nitropyridine

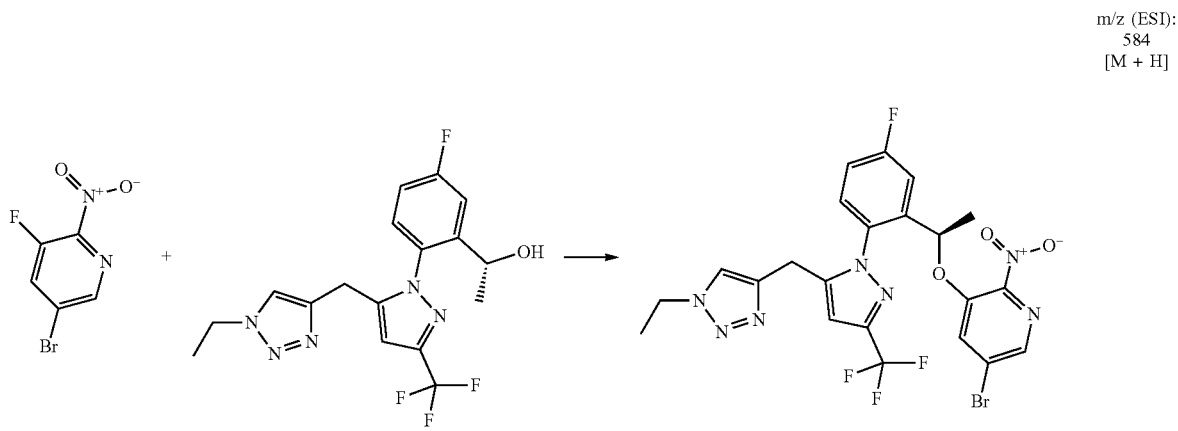

m/z (ESI): 584 [M + H]

(R)-5-(2-(1-((5-bromo-2-nitropyridin-3-yl)oxy)ethyl)-4-fluorophenyl)-4-((1-ethyl-1H-1,2,3-triazol-4-yl)methyl)isothiazole

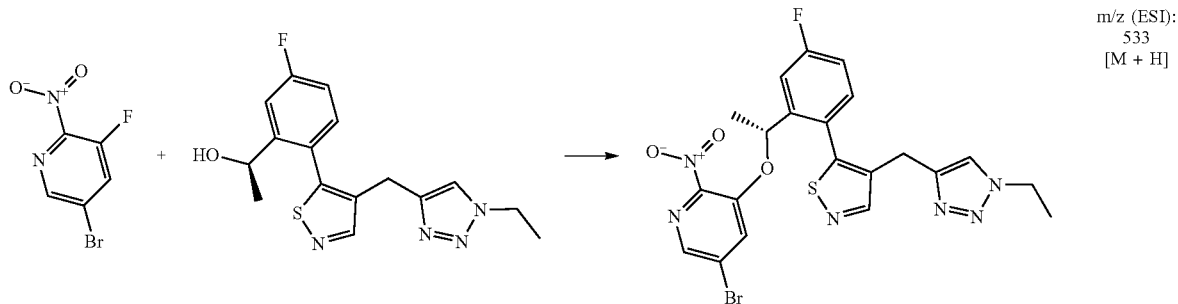

m/z (ESI): 533 [M + H]

(R)-5-((1-(2-(1-((5-bromo-2-nitropyridin-3-yl)oxy)ethyl)-4-fluorophenyl)-3-chloro-1H-pyrazol-5-yl)methyl)-1-methyl-1H-pyrazole-3-carbonitrile

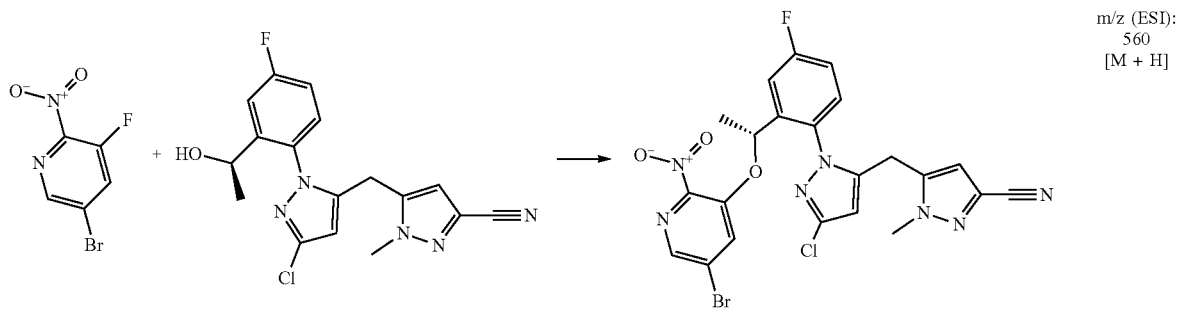

m/z (ESI): 560 [M + H]

(R)-1-(4-fluoro-2-(1-((4-methoxybenzyl)oxy)ethyl)phenyl)-3-(trifluoromethyl)-1H-pyrazole

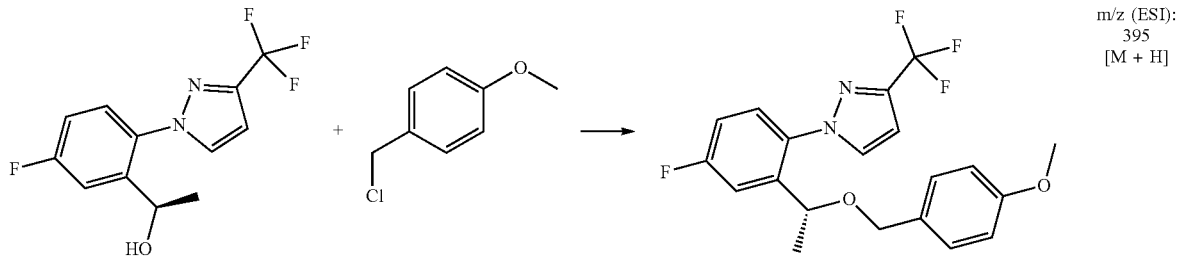

m/z (ESI): 395 [M + H]

(R)-5-((1-(2-(1-((5-bromo-2-nitropyridin-3-yl)oxy)ethyl)-4-fluorophenyl)-3-(trifluoromethyl)-1H-pyrazol-5-yl)methyl)-1-methyl-1H-pyrazole-3-carbonitrile m/z (ESI): 594 [M + H]

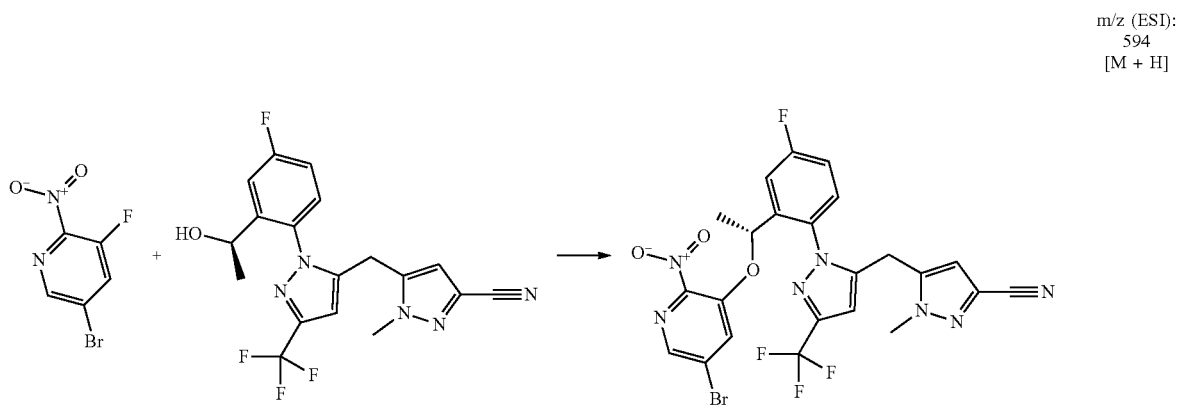

2-{2-[(1R)-1-[(5-bromo-2-nitropyridin-3-yl)oxy]ethyl]-4-fluorophenyl}-3-{[1-(cyclopropylmethyl)-1H-1,2,3-triazol-4-yl]methyl}-5-fluoropyridine


m/z (ESI): 571 [M + H]

(R)-5-bromo-3-(1-(2-(3-chloro-5-((1-(cyclopropylmethyl)-1H-1,2,3-triazol-4-yl)methyl)-1H-pyrazol-1-yl)-5-fluorophenyl)ethoxy)-2-nitropyridine

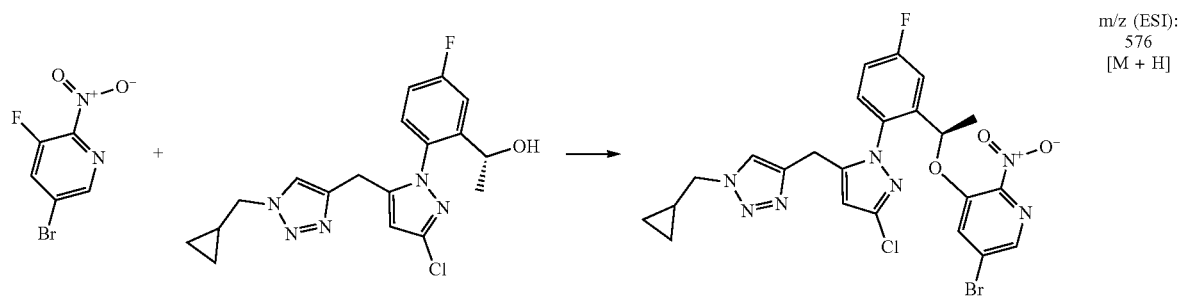

m/z (ESI): 576 [M + H]

(R)-3-((3-(2-(1-((5-bromo-2-nitropyridin-3-yl)oxy)ethyl)-4-fluorophenyl)-1-methyl-1H-pyrazol-4-yl)methyl)-1-methyl-1H-pyrazole-5-carbonitrile

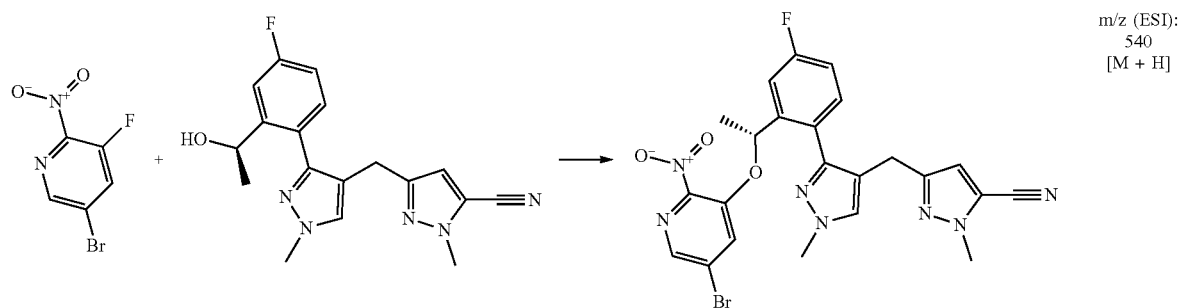

m/z (ESI): 540 [M + H]

(R)-3-((2-(2-(1-((5-bromo-2-nitropyridin-3-yl)oxy)ethyl)-4-fluorophenyl)pyridin-3-yl)methyl)-1-methyl-1H-pyrazole-5-carbonitrile

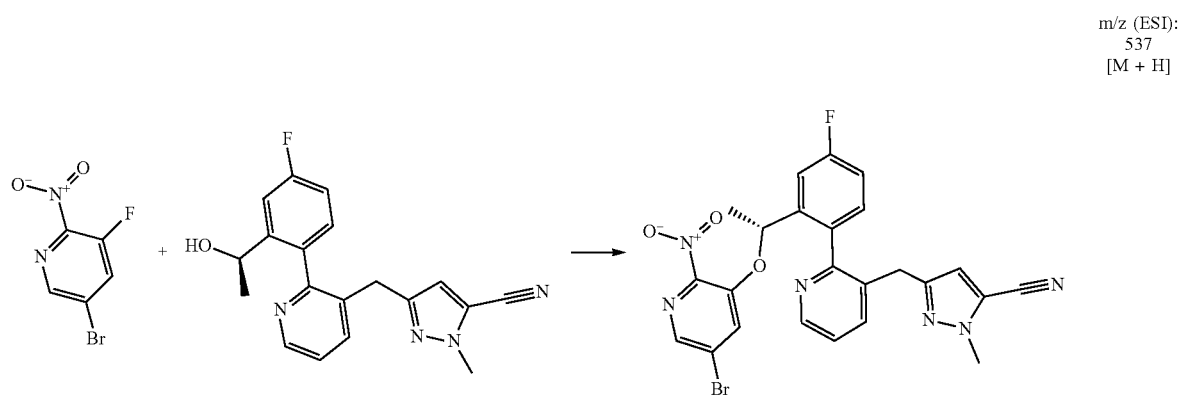

m/z (ESI): 537 [M + H]

5-bromo-3-[(1R)-1-[2-(5-{[1-(cyclopropylmethyl)-1H-1,2,3-triazol-4-yl]methyl}-2-methyl-1,3-thiazol-4-yl)-5-fluorophenyl]ethoxy]-2-nitropyridine

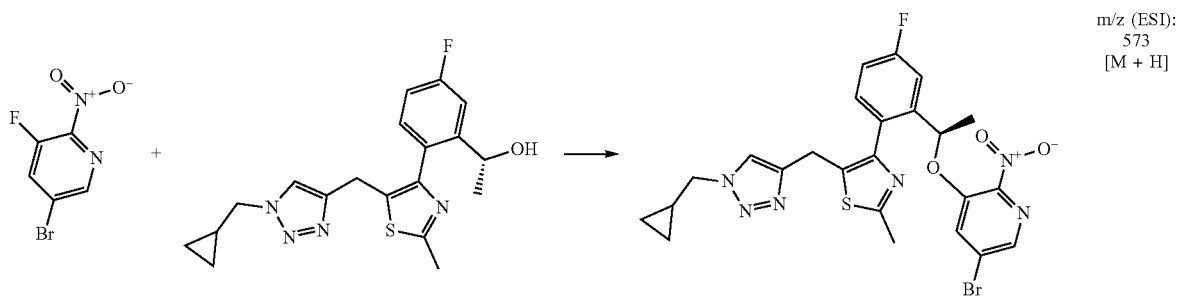

m/z (ESI): 573 [M + H]

(R)-5-bromo-3-(1-(2-(3-((1-(cyclopropylmethyl)-1H-1,2,3-triazol-4-yl)methyl)pyridin-2-yl)-5-fluorophenyl)ethoxy)-2-nitropyridine

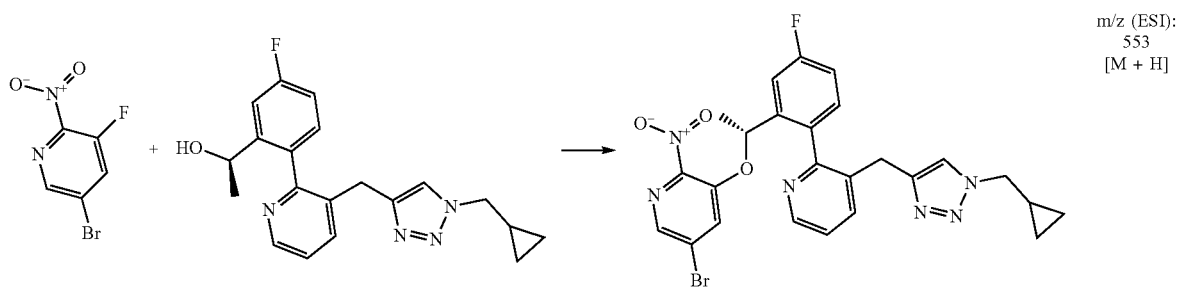

m/z (ESI): 553 [M + H]

(R)-5-((2'-(1-((5-bromo-2-nitropyridin-3-yl)oxy)ethyl)-4'-fluoro-[1,1'-biphenyl]-2-yl)methyl)-1-methyl-1H-pyrazole-3-carbonitrile

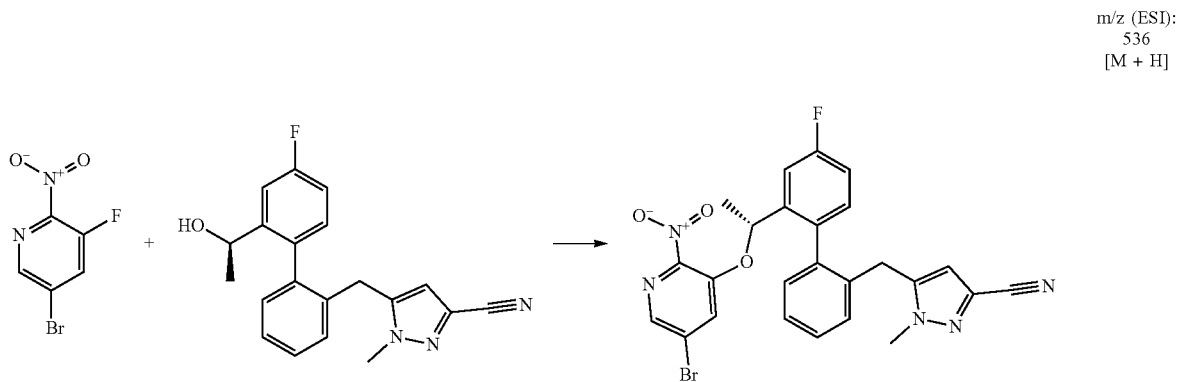

m/z (ESI): 536 [M + H]

(R)-5-((1-(2-(1-((5-bromo-2-nitropyridin-3-yl)oxy)ethyl)-4-fluorophenyl)-3-(difluoromethyl)-1H-pyrazol-5-yl)methyl)-1-methyl-1H-pyrazole-3-carbonitrile

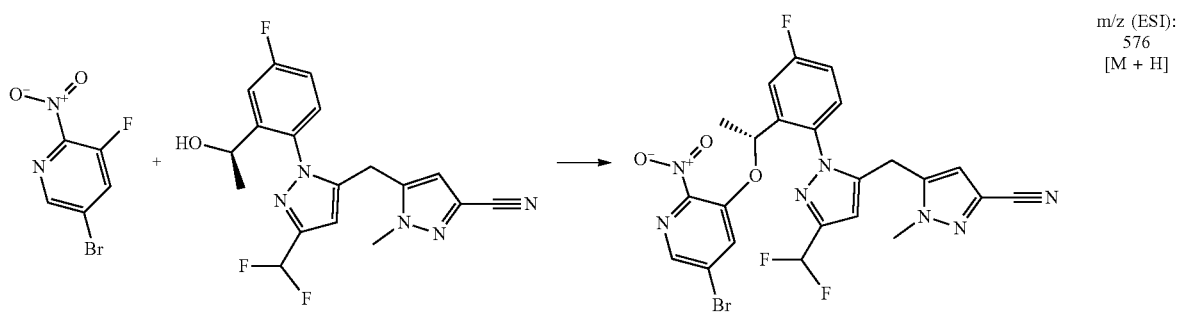

m/z (ESI): 576 [M + H]

-continued (R)-4-((2-(2-(1-((5-bromo-2-nitropyridin-3-yl)oxy)ethyl)-4-fluorophenyl)pyridin-3-yl)methyl)-1-(cyclopropylmethyl)-1H-pyrazole-3-carbonitrile

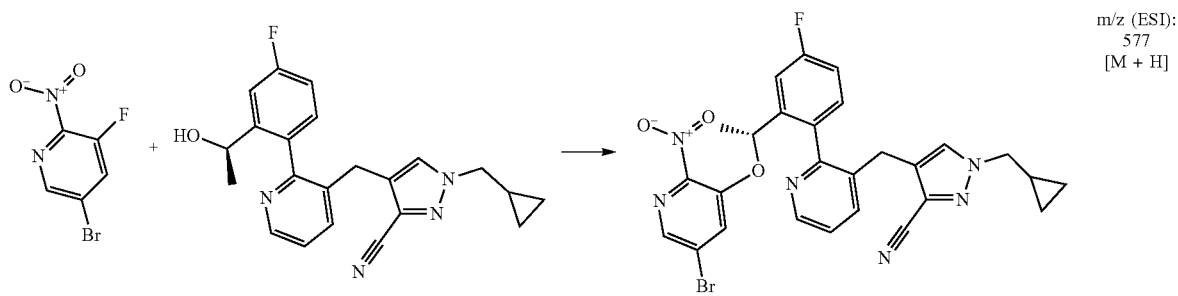

m/z (ESI): 577 [M + H]

(R)-5-bromo-3-(1-(2-(5-(((1-(cyclopropylmethyl)-3-methyl-1H-pyrazol-4-yl)methyl)-3-methoxy-1H-pyrazol-1-yl)-5-fluorophenyl)ethoxy)-2-nitropyridine

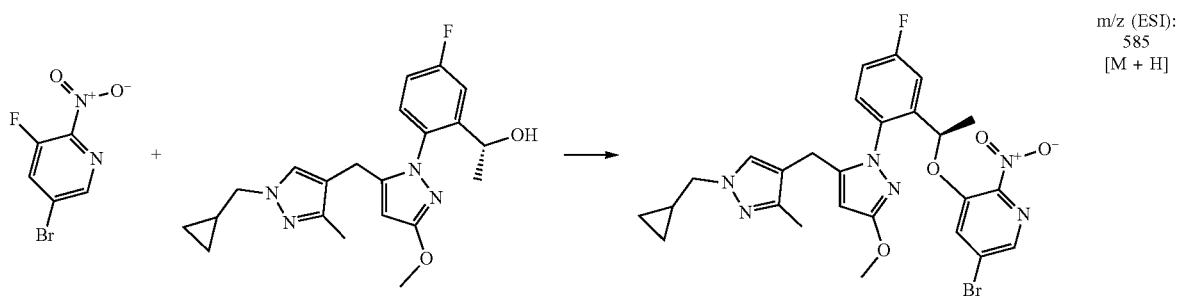

m/z (ESI): 585 [M + H]

(R)-5-bromo-3-(1-(2-(5-(((1-(cyclopropylmethyl)-3-methyl-1H-pyrazol-4-yl)methyl)-3-(difluoromethyl)-1H-pyrazol-1-yl)-5-fluorophenyl)ethoxy)-2-nitropyridine

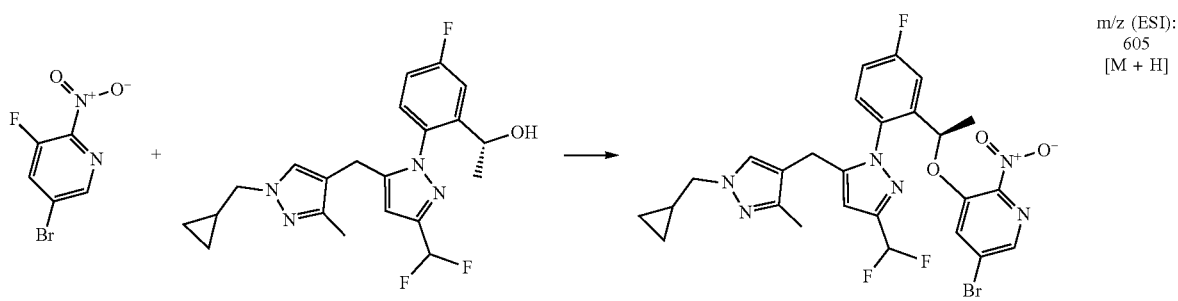

m/z (ESI): 605 [M + H]

(R)-4-(2-(1-((5-bromo-2-nitropyridin-3-yl)oxy)ethyl)-4-fluorophenyl)-5-(((1-(cyclopropylmethyl)-3-methyl-1H-pyrazol-4-yl)methyl)-2-methylthiazole m/z (ESI): 586 [M + H]

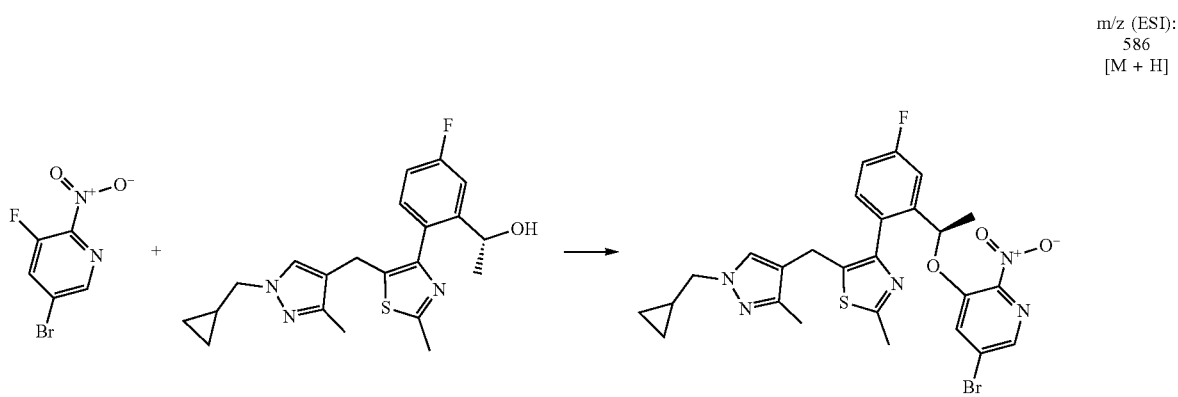

(R)-5-bromo-3-(1-(2-(5-((1-(cyclopropylmethyl)-1H-pyrazol-4-yl)methyl)-3-(difluoromethyl)-1H-pyrazol-1-yl)-5-fluorophenyl)ethoxy)-2-nitropyridine

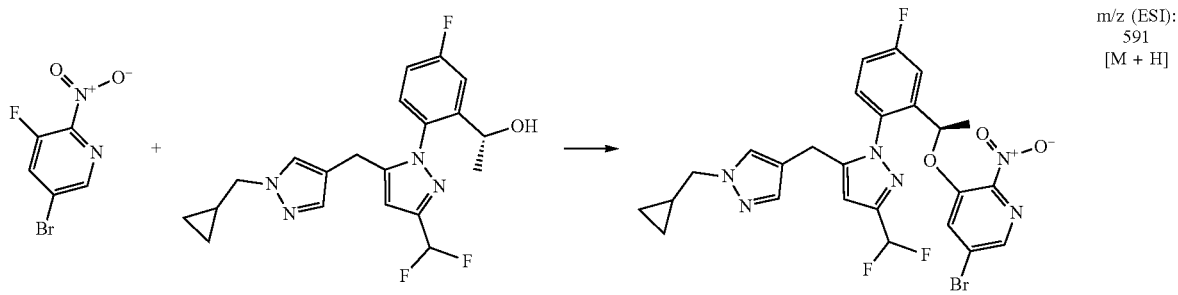

m/z (ESI): 591 [M + H]

(R)-5-((3-(2-(1-((5-bromo-2-nitropyridin-3-yl)oxy)ethyl)-4-fluorophenyl)-1-methyl-1H-pyrazol-4-yl)methyl)-3-ethylisothiazole

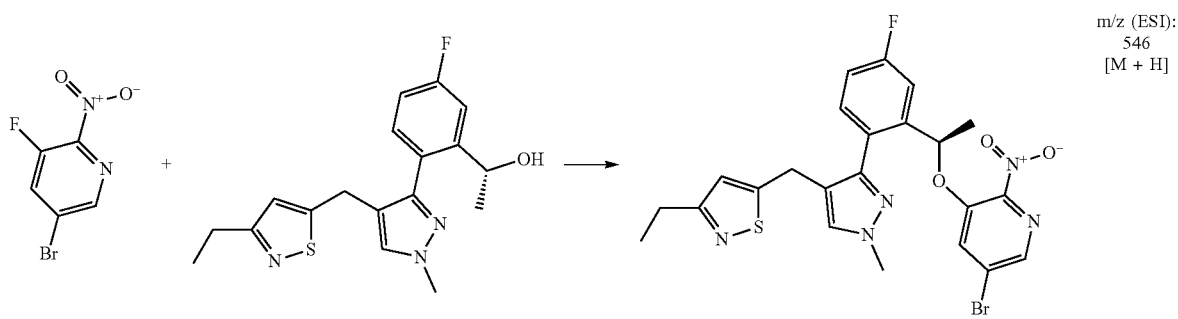

m/z (ESI): 546 [M + H]

(R)-5-bromo-3-(1-(5-fluoro-2-(1-methyl-4-((1-(oxetan-3-yl)-1H-pyrazol-4-yl)methyl)-1H-pyrazol-3-yl)phenyl)ethoxy)-2-nitropyridine

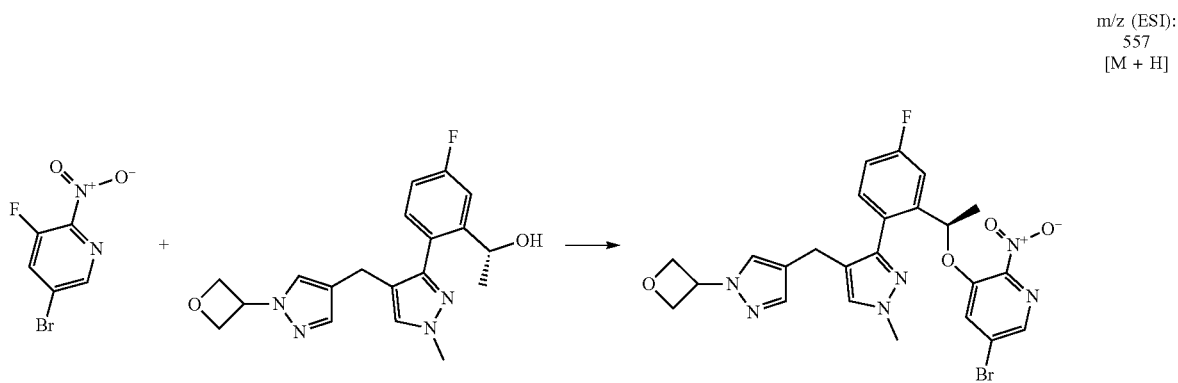

m/z (ESI): 557 [M + H]

(R)-5-bromo-3-(1-(2-(3-(difluoromethyl)-5-((1-ethyl-3-methoxy-1H-pyrazol-4-yl)methyl)-1H-pyrazol-1-yl)-5-fluorophenyl)ethoxy)-2-nitropyridine

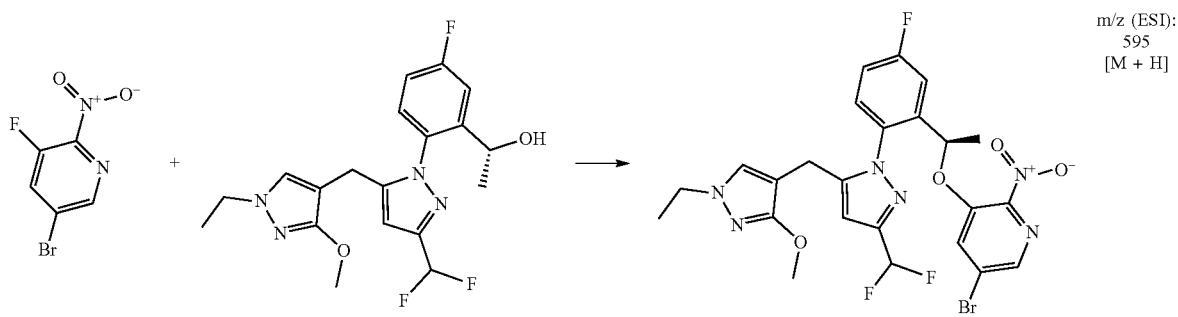

m/z (ESI): 595 [M + H]

-continued (R)-5-bromo-3-(1-(2-(5-((1-(cyclopropylmethyl)-1H-1,2,3-triazol-4-yl)methyl)-3-methoxy-1H-pyrazol-1-yl)-5-fluorophenyl)ethoxy)-2-nitropyridine

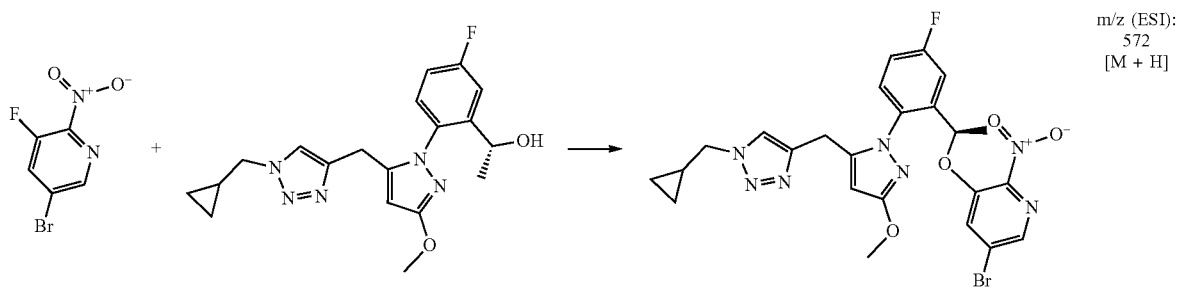

m/z (ESI): 572 [M + H]

(R)-5-bromo-3-(1-(2-(3-((1-(cyclopropylmethyl)-1H-pyrazol-4-yl)methyl)pyridin-2-yl)-5-fluorophenyl)ethoxy)-2-nitropyridine

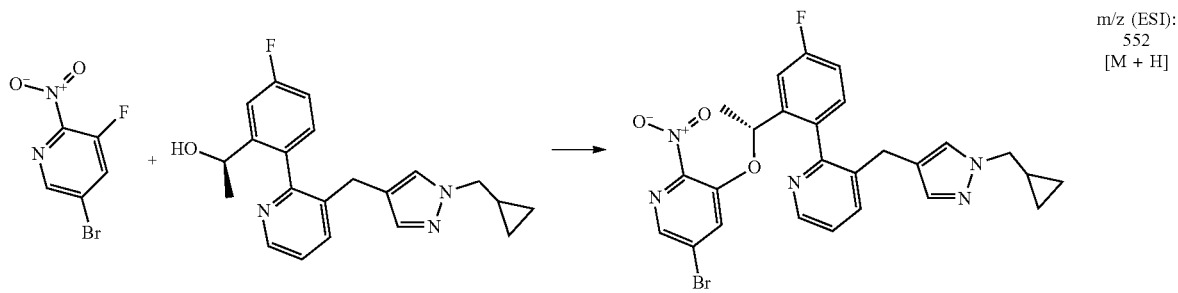

m/z (ESI): 552 [M + H]

(R)-5-bromo-3-(1-(2-(4-((3-bromo-1-ethyl-1H-pyrazol-4-yl)methyl)-1-methyl-1H-pyrazol-3-yl)-5-fluorophenyl)ethoxy)-2-nitropyridine

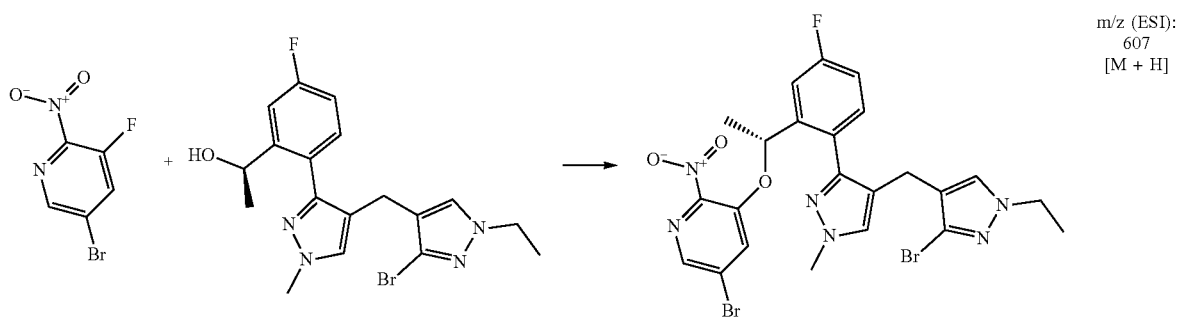

m/z (ESI): 607 [M + H]

(R)-5-bromo-3-(1-(2-(4-((1-ethyl-1H-pyrazol-4-yl)methyl)-5-methoxy-1-methyl-1H-pyrazol-3-yl)-5-fluorophenyl)ethoxy)-2-nitropyridine

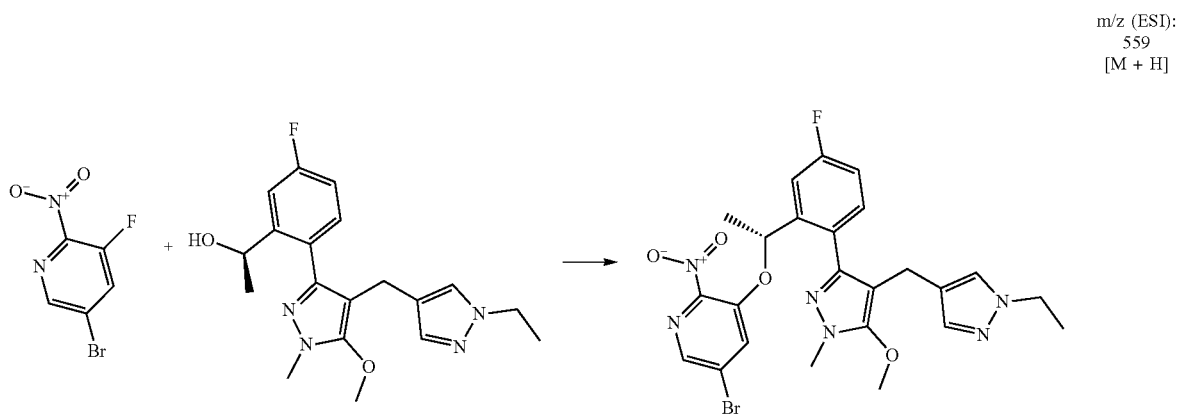

m/z (ESI): 559 [M + H]

-continued (R)-5-bromo-3-(1-(2-(1-(tert-butyl)-4-((1-ethyl-1H-pyrazol-4-yl)methyl)-1H-pyrazol-3-yl)-5-fluorophenyl)ethoxy)-2-nitropyridine

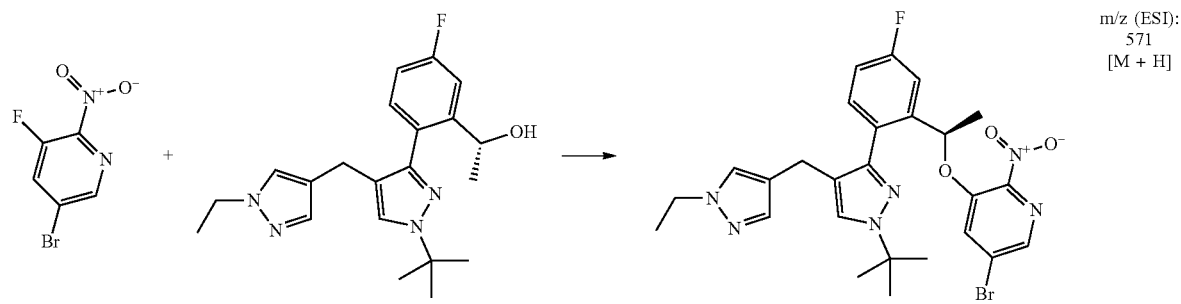

m/z (ESI): 571 [M + H]

(R)-5-bromo-3-(1-(2-(3-((1-ethyl-1H-pyrazol-4-yl)methyl)-5-methoxypyridin-2-yl)-5-fluorophenyl)ethoxy)-2-nitropyridine

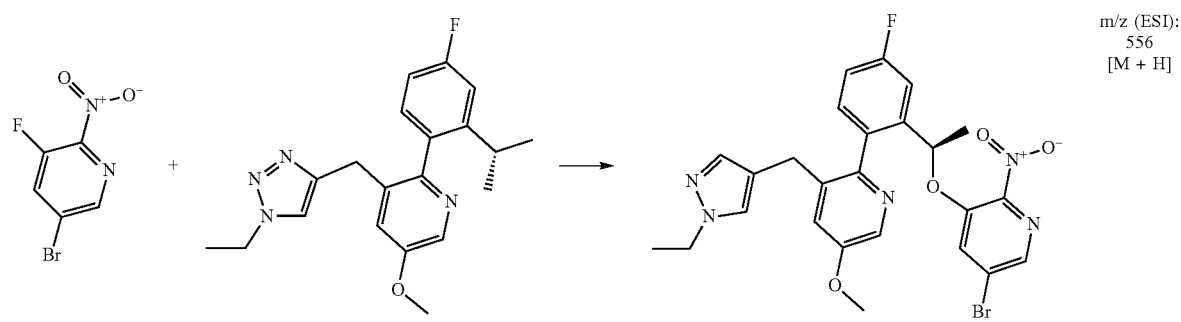

m/z (ESI): 556 [M + H]

(R)-5-bromo-3-(1-(2-(4-((1-ethyl-3-isopropyl-1H-pyrazol-4-yl)methyl)-1-methyl-1H-pyrazol-3-yl)-5-fluorophenyl)ethoxy)-2-nitropyridine

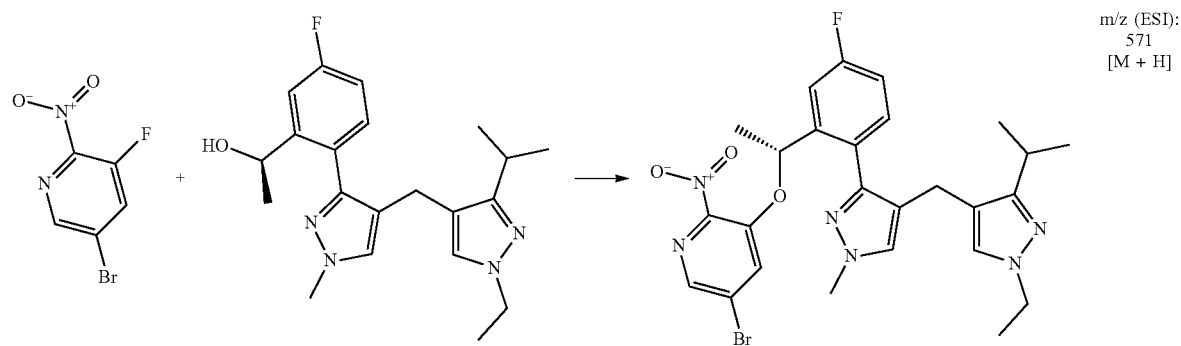

m/z (ESI): 571 [M + H]

(R)-3-((3-(2-(1-((5-bromo-2-nitropyridin-3-yl)oxy)ethyl)-4-fluorophenyl)-1-methyl-1H-pyrazol-4-yl)methyl)-5-ethylisoxazole

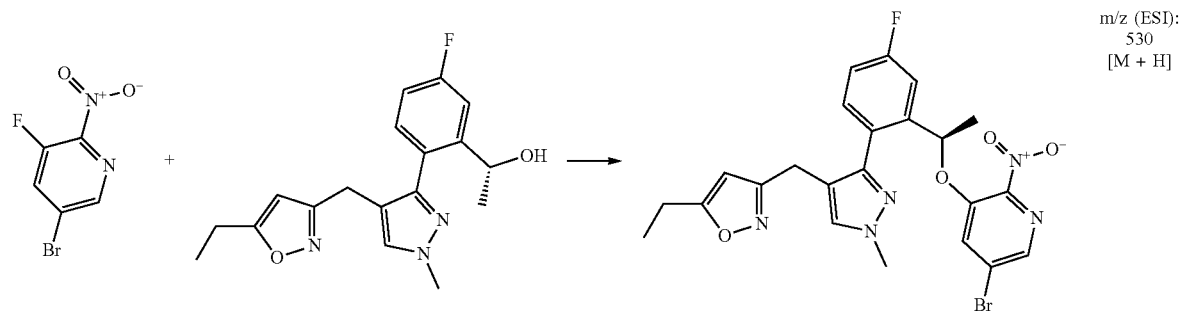

m/z (ESI): 530 [M + H]

-continued (R)-5-bromo-3-(1-(5-fluoro-2-(4-((1-isobutyl-1H-pyrazol-4-yl)methyl)-1-methyl-1H-pyrazol-3-yl)phenyl)ethoxy)-2-nitropyridine

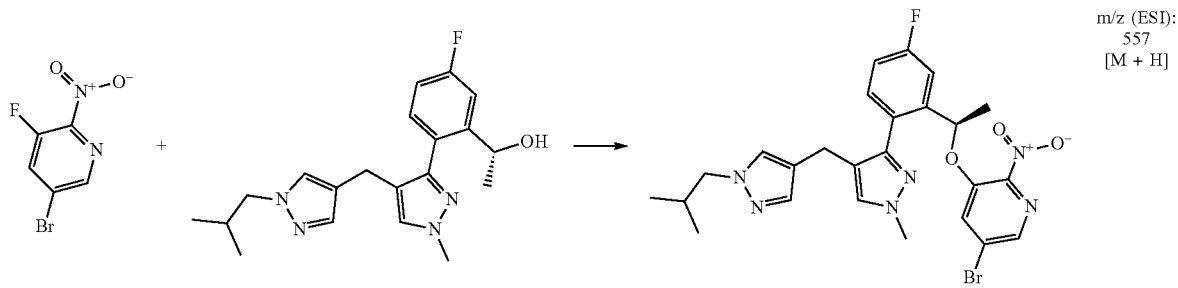

m/z (ESI): 557 [M + H]

(R)-4-((3-(2-(1-((5-bromo-2-nitropyridin-3-yl)oxy)ethyl)-4-fluorophenyl)-1-methyl-1H-pyrazol-4-yl)methyl)-1-ethyl-1H-pyrazole-3-carbonitrile

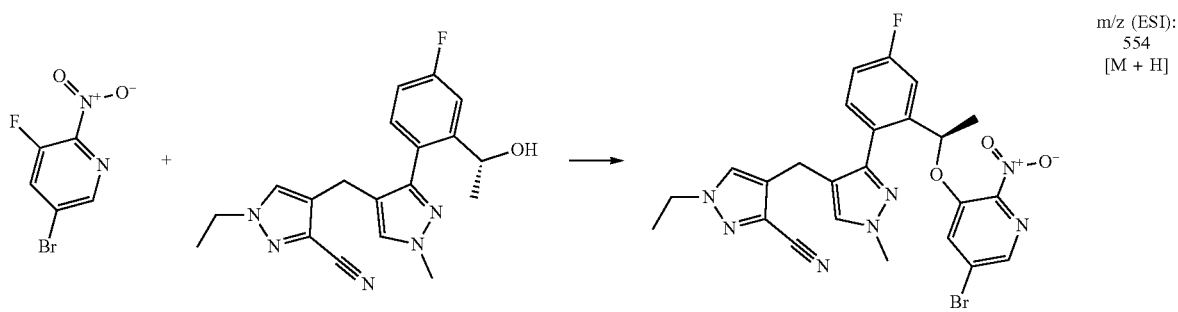

m/z (ESI): 554 [M + H]

1-{[1-(2-{1-[(5-bromo-2-nitropyridin-3-yl)oxy]ethyl}-4-fluorophenyl)-1H-pyrazol-5-yl]methyl}-1H-imidazole-4-carbonitrile

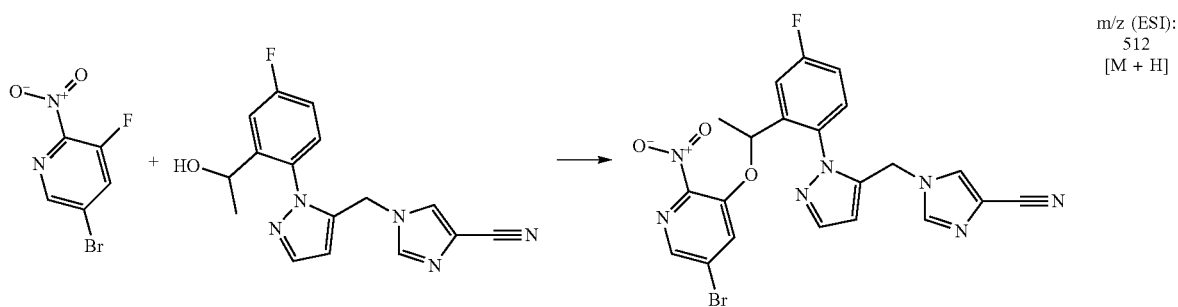

m/z (ESI): 512 [M + H]

1-{[1-(2-{1-[(5-bromo-2-nitropyridin-3-yl)oxy]ethyl}-4-fluorophenyl)-3-methyl-1H-pyrazol-5-yl]methyl}-1H-imidazole-4-carbonitrile m/z (ESI): 526 [M + H]

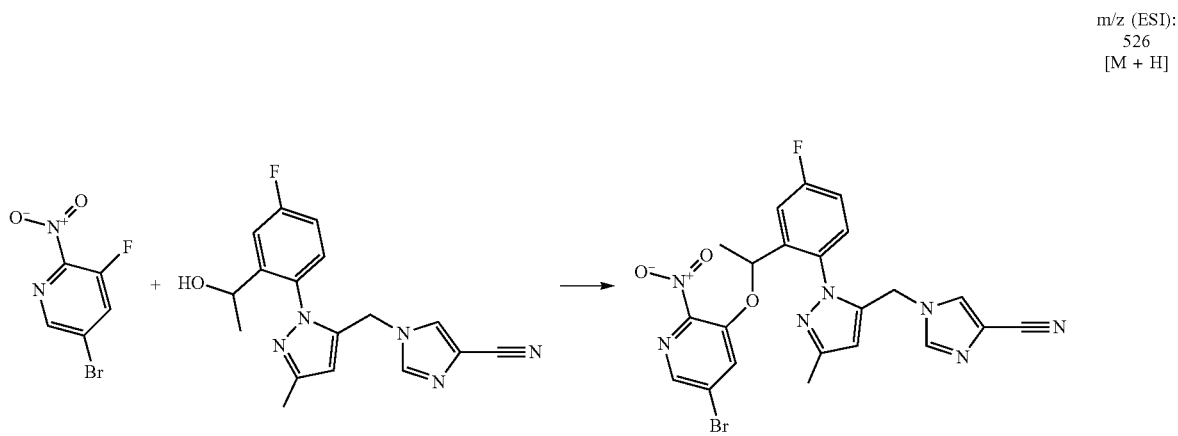

1-((1-(2-(1-(5-bromo-2-nitropyridin-3-yloxy)ethyl)-4-fluorophenyl)-1H-pyrazol-5-yl)methyl)-1H-pyrazole-4-carbonitrile

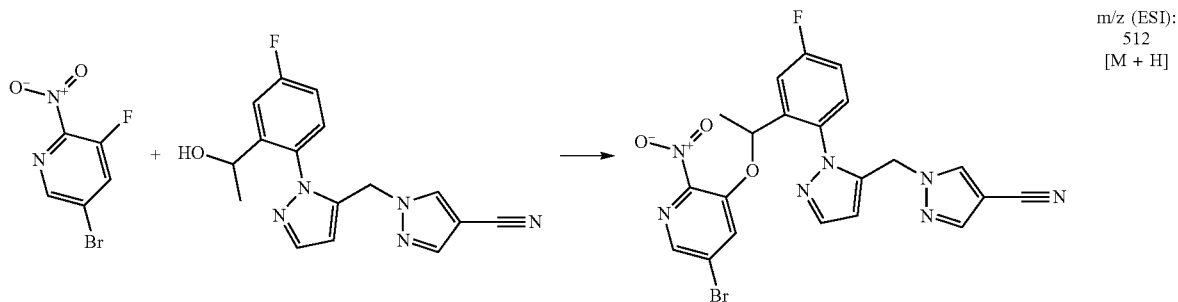

m/z (ESI): 512 [M + H]

1-((2-(2-(1-(5-bromo-2-nitropyridin-3-yloxy)ethyl)-4-fluorophenyl)-5-fluoropyridin-3-yl)methyl)-1H-imidazole-4-carbonitrile

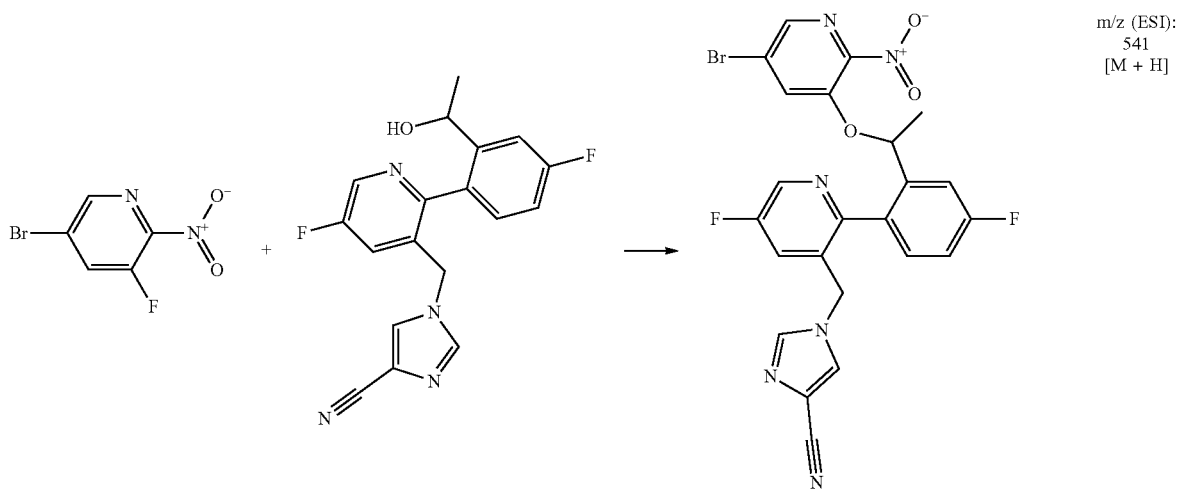

m/z (ESI): 541 [M + H]

1-{[4-(2-{1-[(5-bromo-2-nitropyridin-3-yl)oxy]ethyl}-4-fluorophenyl)-2-methyl-1,3-thiazol-5-yl]methyl}-1H-imidazole-4-carbonitrile

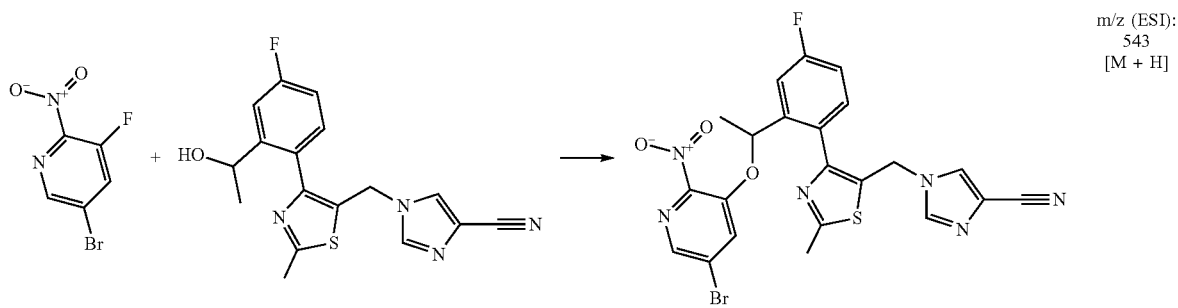

m/z (ESI): 543 [M + H]

(1-(2-(1-((5-bromo-2-nitropyridin-3-yl)oxy)ethyl)-4-fluorophenyl)-3-fluoro-1H-pyrazol-5-yl)(1-ethyl-1H-pyrazol-4-yl)methanone

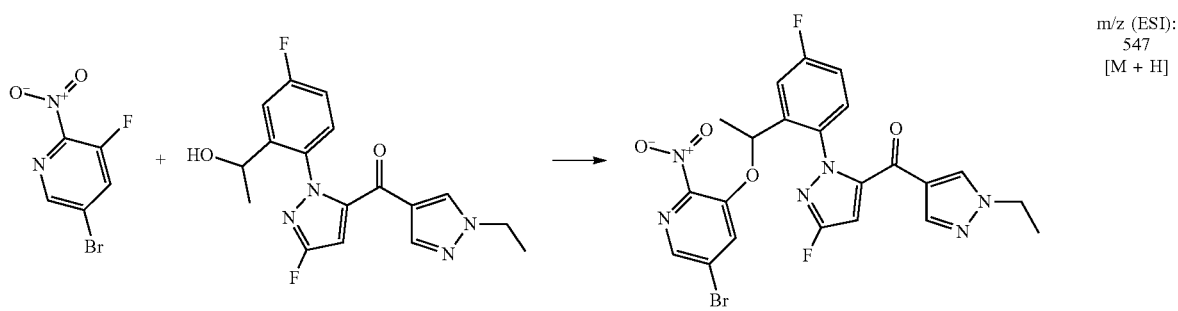

m/z (ESI): 547 [M + H]

(R)-3-((1-(2-(1-((5-bromo-2-nitropyridin-3-yl)oxy)ethyl)-4-fluorophenyl)-1H-pyrazol-5-yl)methyl)-1-((2-(trimethylsilyl)ethoxy)methyl)-1H-pyrazole-5-carbonitrile

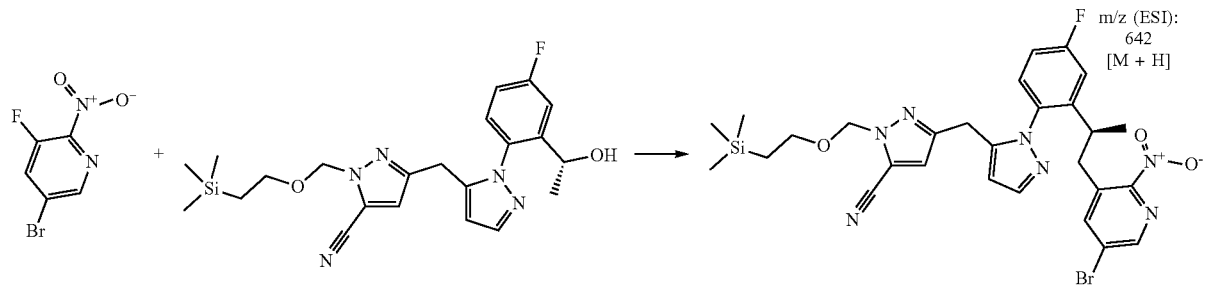 [SMILES: O=[N+]([O-])c1ncc(Br)cc1F ; C[C@@H](O)c1cc(F)ccc1-n1nccc1Cc1cc(C#N)n(COCC[Si](C)(C)C)n1 ; C[C@@H](Cc1cc(Br)cnc1[N+](=O)[O-])c1cc(F)ccc1-n1nccc1Cc1cc(C#N)n(COCC[Si](C)(C)C)n1]

m/z (ESI): 642 [M + H]

5-bromo-3-{1-[2-(5-{[1-(difluoromethyl)-1H-pyrazol-4-yl]methyl}-2-methyl-1,3-thiazol-4-yl)-5-fluorophenyl]ethoxy}-2-nitropyridine

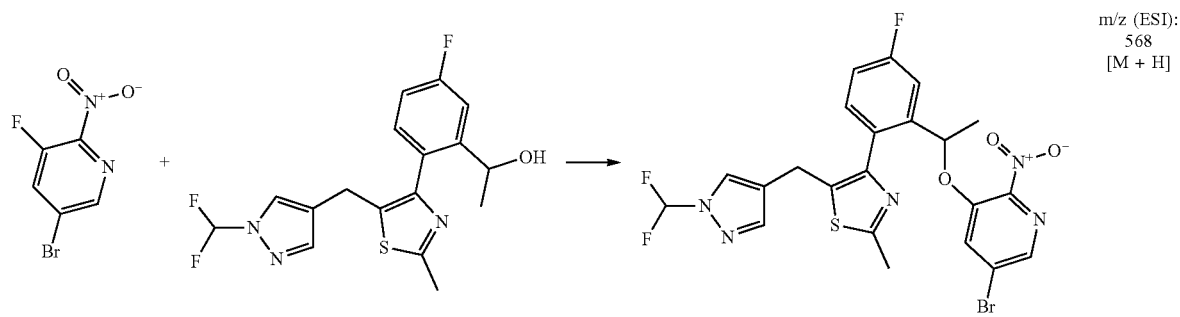

m/z (ESI): 568 [M + H]

5-bromo-3-(1-(2-(5-((1-(2,2-difluoroethyl)-1H-pyrazol-4-yl)methyl)-3-(trifluoromethyl)-1H-pyrazol-1-yl)-5-fluorophenyl)ethoxy)-2-nitropyridine

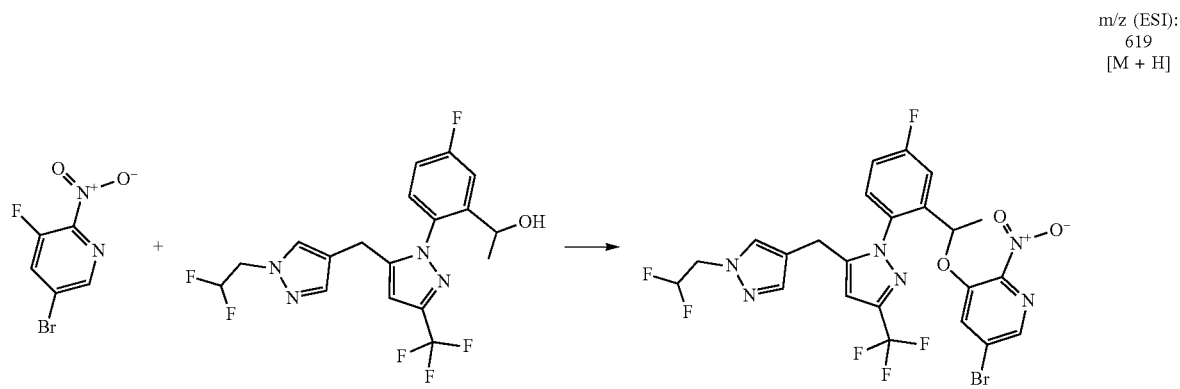

m/z (ESI): 619 [M + H]

5-((3-(2-(1-((5-bromo-2-nitropyridin-3-yl)oxy)ethyl)-4,6-difluorophenyl)-1-methyl-1H-pyrazol-4-yl)methyl)-3-ethylisoxazole

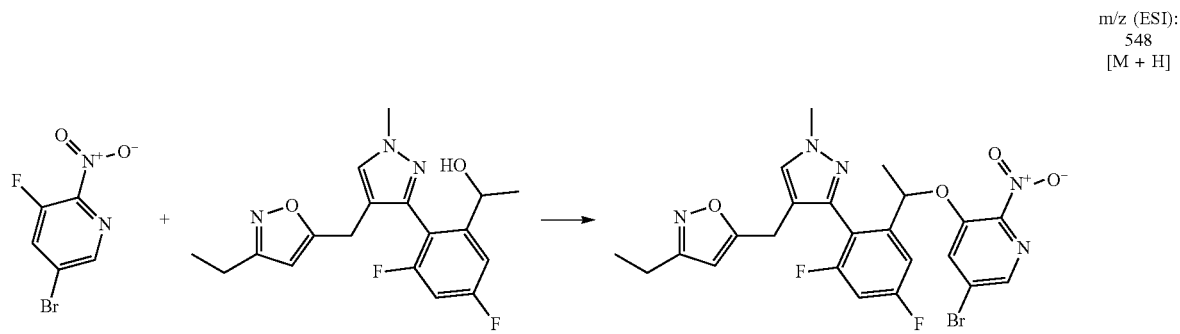

m/z (ESI): 548 [M + H]

-continued 5-((2-(2-(((5-bromo-2-nitropyridin-3-yl)oxy)methyl)-4-fluorophenyl)pyridin-3-yl)methyl)-1-methyl-1H-pyrazole-3-carbonitrile

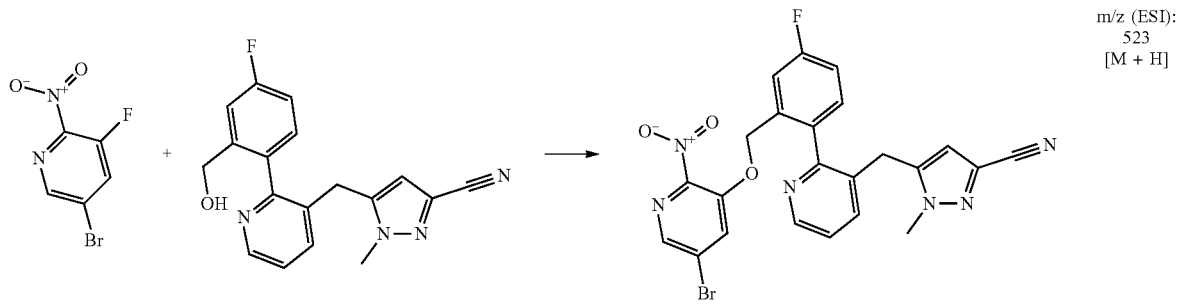

m/z (ESI): 523 [M + H]

5-bromo-3-[1-(2-{4-[(1-ethyl-1H-1,2,3-triazol-4-yl)methyl]-1,2-thiazol-3-yl}-5-fluorophenyl)ethoxy]-2-nitropyridine

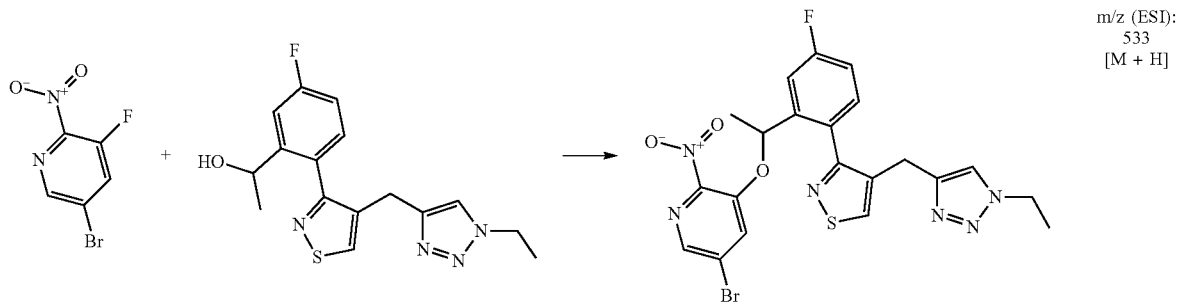

m/z (ESI): 533 [M + H]

5-(((1-(2-(((5-bromo-2-nitropyridin-3-yl)oxy)methyl)-4-fluorophenyl)-3-chloro-1H-pyrazol-5-yl)methyl)-1-methyl-1H-pyrazole-3-carbonitrile

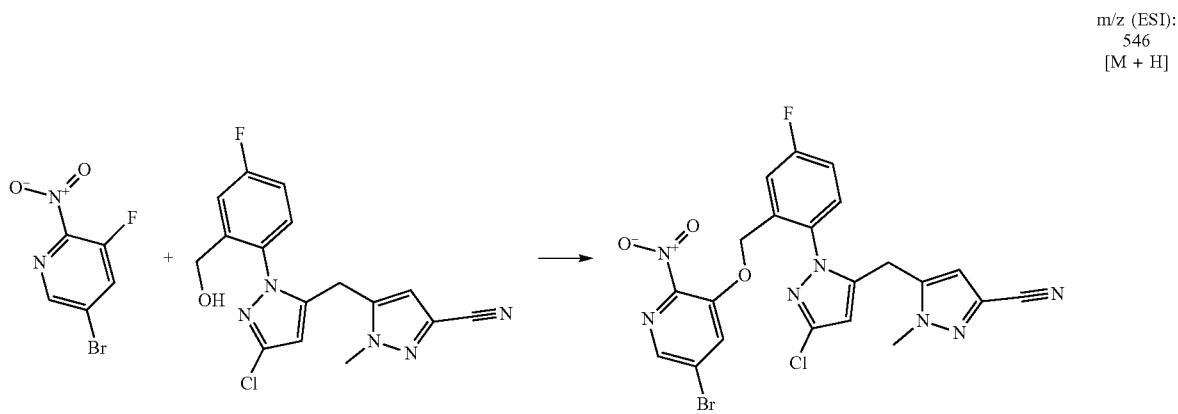

m/z (ESI): 546 [M + H]

5-bromo-3-(1-(2-(5-(((1-(cyclopropylmethyl)-1H-pyrazol-4-yl)methyl)-3-methyl-1H-pyrazol-1-yl)-5-fluorophenyl)ethoxy)-2-nitropyridine

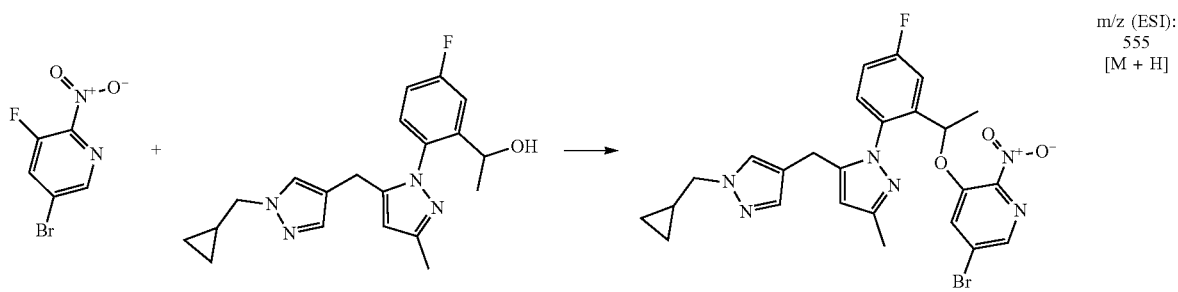

m/z (ESI): 555 [M + H]

-continued

5-{[4-(2-{[(5-bromo-2-nitropyridin-3-yl)oxy]methyl}-4-fluorophenyl)-2-methyl-1,3-thiazol-5-yl]methyl}-1-methyl-1H-pyrazole-3-carbonitrile

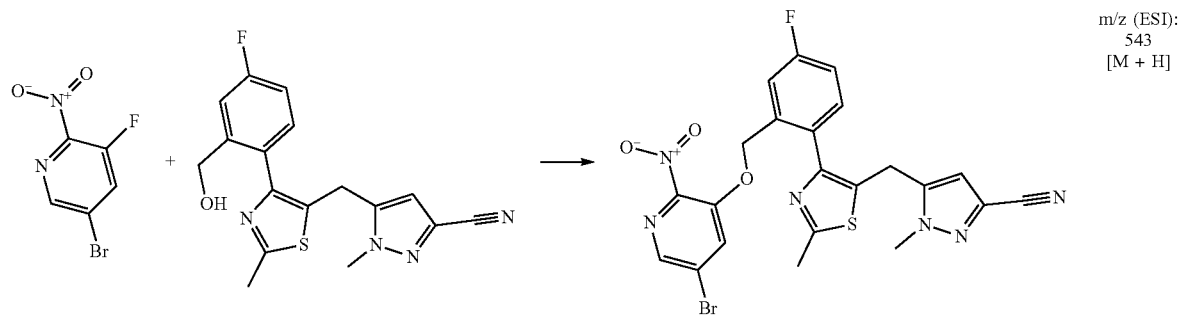

m/z (ESI): 543 [M + H]

4-(2-(1-((5-bromo-2-nitropyridin-3-yl)oxy)ethyl)-4-fluorophenyl)-5-((1-ethyl-1H-pyrazol-4-yl)methyl)-2-methyloxazole

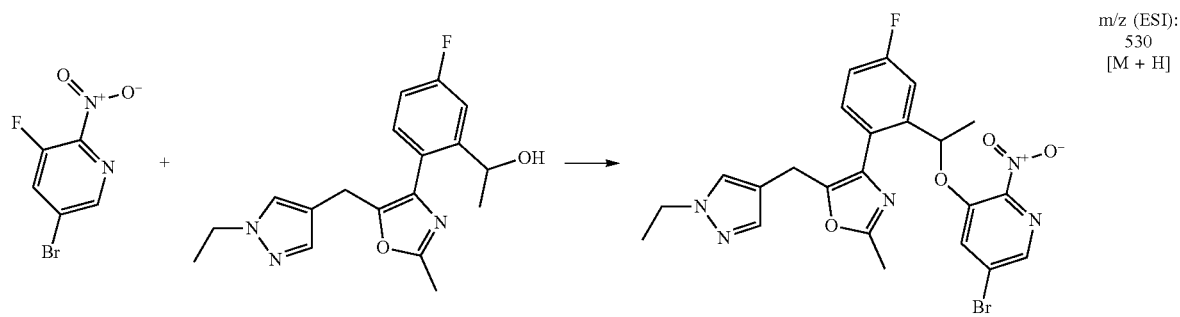

m/z (ESI): 530 [M + H]

5-bromo-3-((2-(5-((1-(cyclopropylmethyl)-1H-pyrazol-4-yl)methyl)-3-(difluoromethyl)-1H-pyrazol-1-yl)-5-fluorobenzyl)oxy)-2-nitropyridine

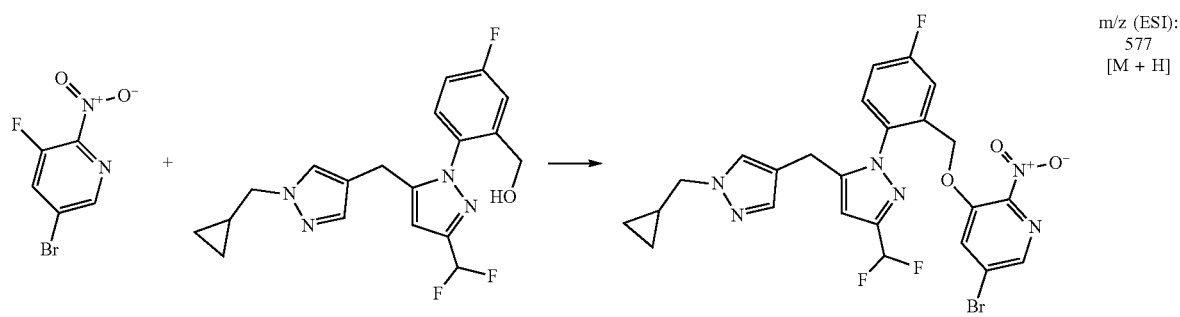

m/z (ESI): 577 [M + H]

5-bromo-3-((2-(5-((1-(cyclopropylmethyl)-1H-pyrazol-4-yl)methyl)-3-methyl-1H-pyrazol-1-yl)-5-fluorobenzyl)oxy)-2-nitropyridine

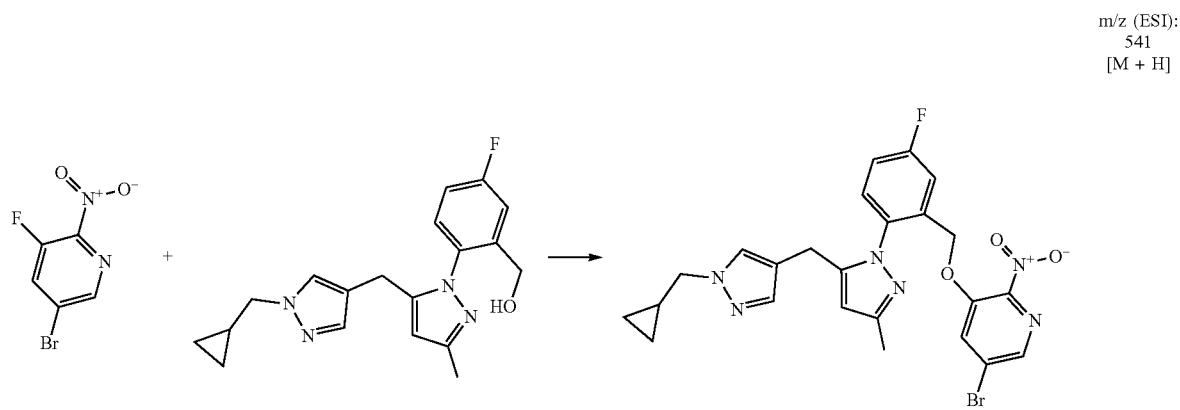

m/z (ESI): 541 [M + H]

5-bromo-3-((2-(5-((1-(cyclopropylmethyl)-3-methyl-1H-pyrazol-4-yl)methyl)-3-(difluoromethyl)-1H-pyrazol-1-yl)-5-fluorobenzyl)oxy)-2-nitropyridine

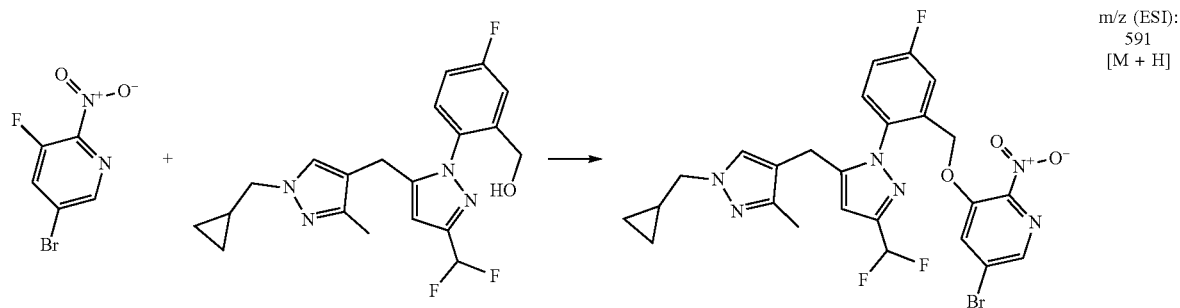

m/z (ESI): 591 [M + H]

5-bromo-3-(1-(2-(5-((1-(cyclopropylmethyl)-3-methyl-1H-pyrazol-4-yl)methyl)-3-methyl-1H-pyrazol-1-yl)-5-fluorophenyl)ethoxy)-2-nitropyridine

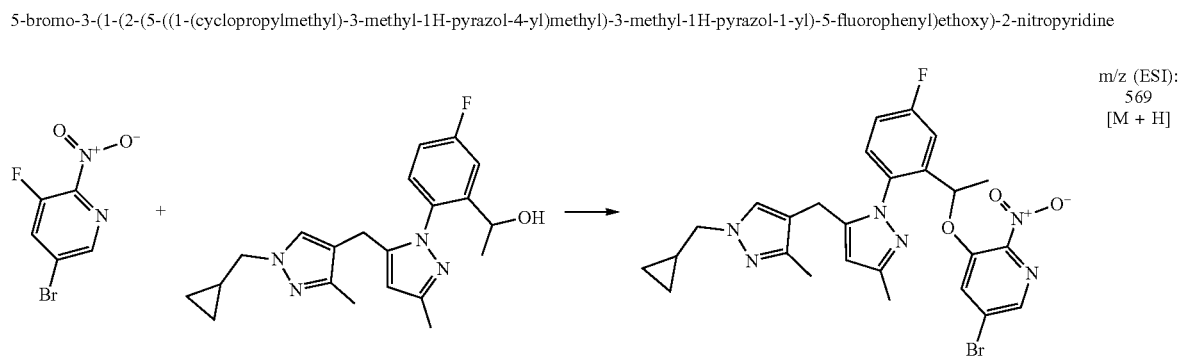

m/z (ESI): 569 [M + H]

5-bromo-3-(1-(2-(4-((3-chloro-1-ethyl-1H-pyrazol-4-yl)methyl)-1-methyl-1H-pyrazol-3-yl)-5-fluoropyridin-3-yl)ethoxy)-2-nitropyridine

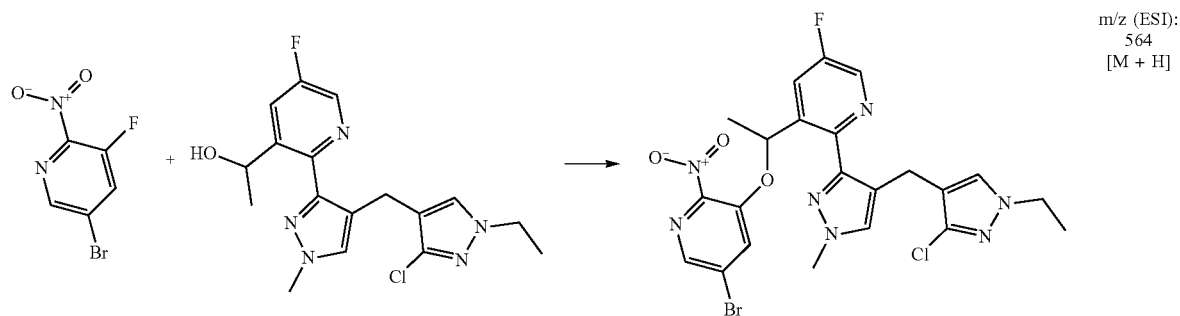

m/z (ESI): 564 [M + H]

5-((3-(2-(1-((5-bromo-2-nitropyridin-3-yl)oxy)ethyl)-4-fluorophenyl)isothiazol-4-yl)methyl)-1-methyl-1H-pyrazole-3-carbonitrile m/z (ESI): 543 [M + H]

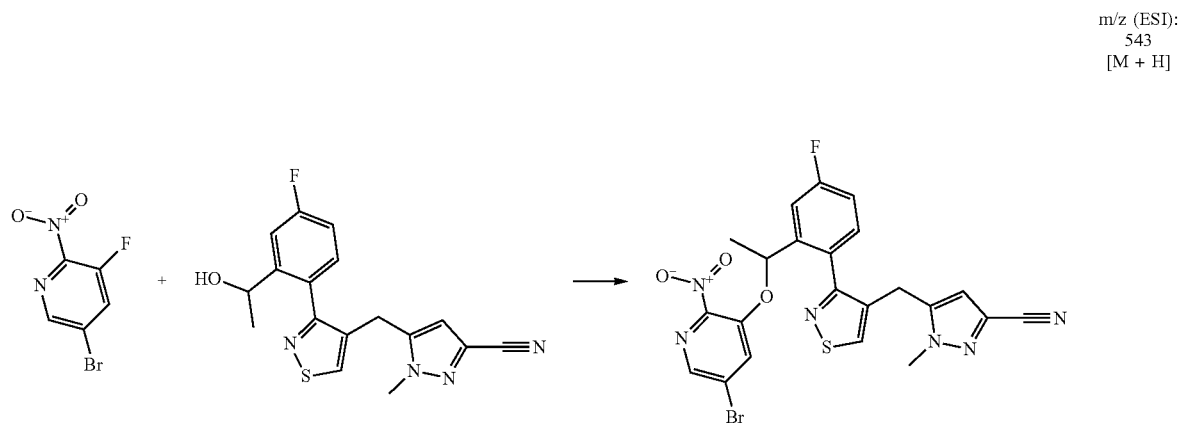

-continued 5-(2-(1-((5-bromo-2-nitropyridin-3-yl)oxy)ethyl)-4-fluorophenyl)-4-((1-ethyl-1H-pyrazol-4-yl)methyl)-3-methylisoxazole

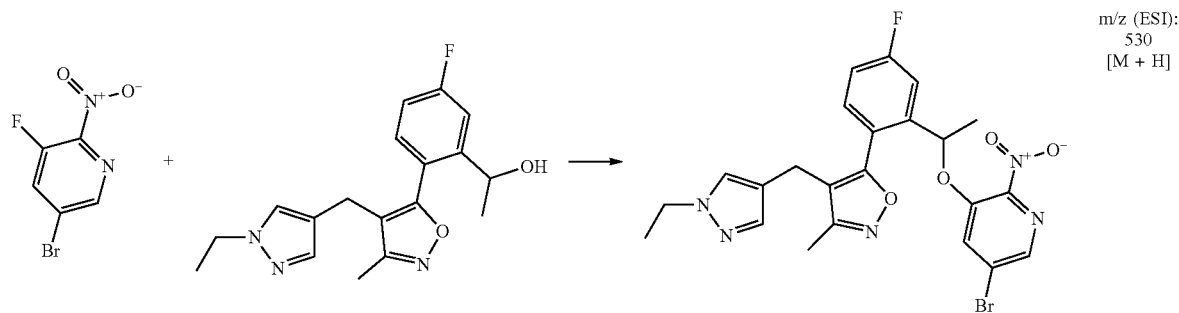

m/z (ESI): 530 [M + H]

3-((4-(2-(1-((5-bromo-2-nitropyridin-3-yl)oxy)ethyl)-4-fluorophenyl)pyridin-3-yl)methyl)-1-methyl-1H-pyrazole-5-carbonitrile

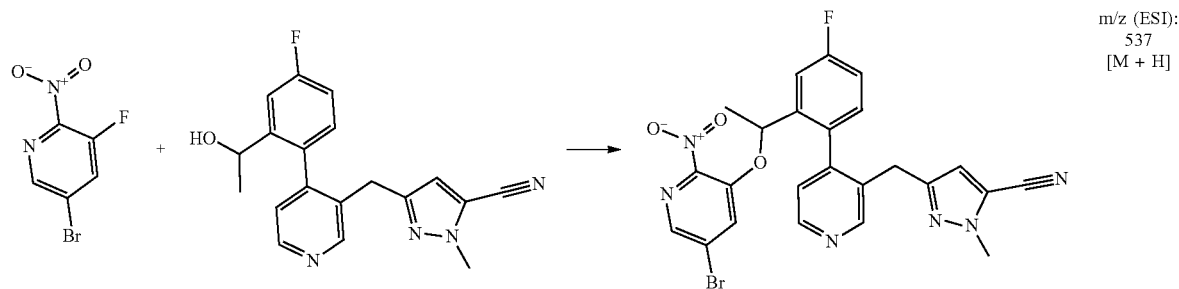

m/z (ESI): 537 [M + H]

3-((5-(2-(1-((5-bromo-2-nitropyridin-3-yl)oxy)ethyl)-5-fluorophenyl)-1-methyl-1H-pyrazol-4-yl)methyl)-1-((2-(trimethylsilyl)ethoxy)methyl)-1H-pyrazole-5-carbonitrile

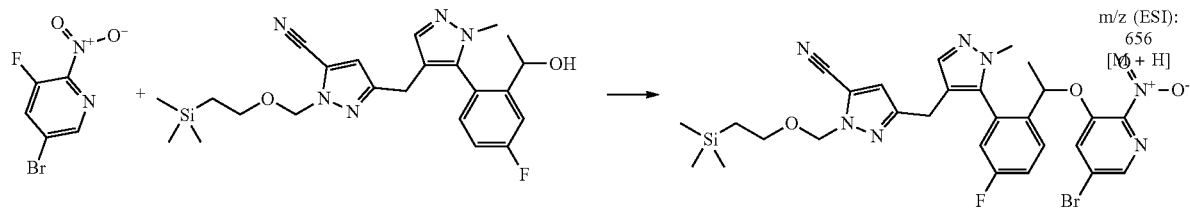

m/z (ESI): 656 [M + H]

1-((5-(4-fluoro-2-(1-(2-nitropyridin-3-yloxy)ethyl)phenyl)-1-methyl-1H-pyrazol-4-yl)methyl)-1H-imidazole-4-carbonitrile

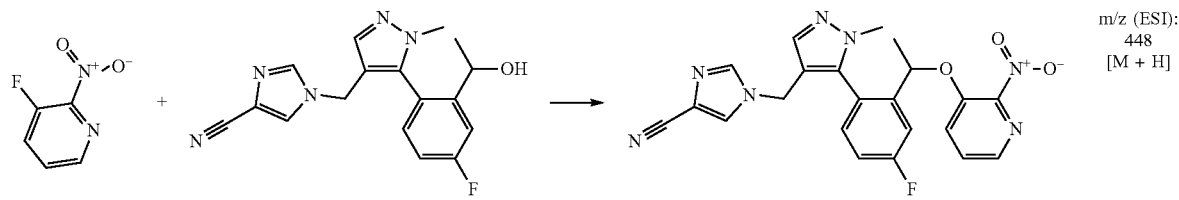

m/z (ESI): 448 [M + H]

3-(1-(2-(1-((5-bromo-2-nitropyridin-3-yl)oxy)ethyl)-4-fluorophenyl)-1H-pyrazole-5-carbonyl)-1-methyl-1H-pyrazole-5-carbonitrile

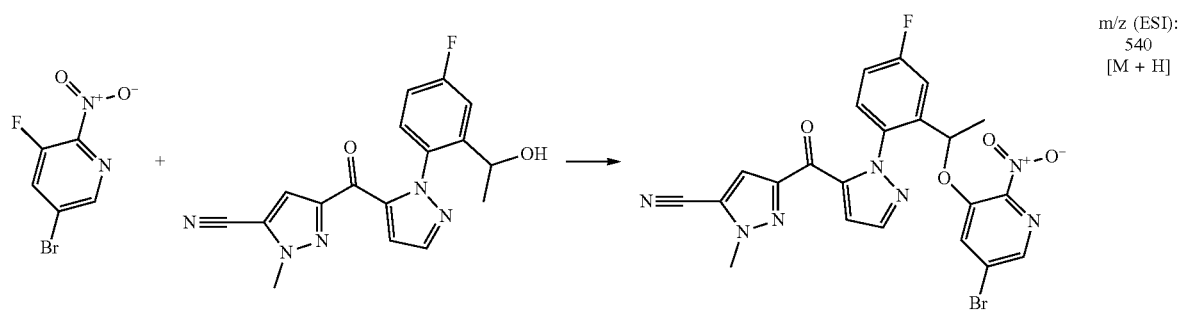

m/z (ESI): 540 [M + H]

-continued 5-bromo-3-((2-(3-((3-ethyl-1-methyl-1H-pyrazol-5-yl)methyl)pyridin-2-yl)-5-fluorobenzyl)oxy)-2-nitropyridine

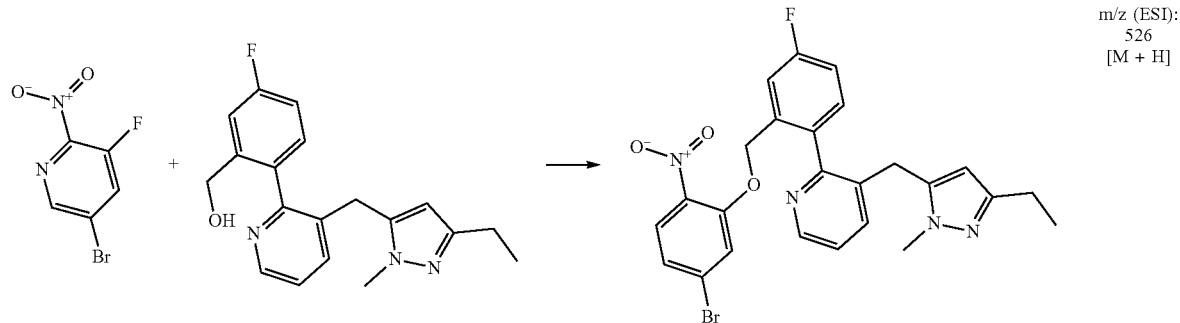

m/z (ESI): 526 [M + H]

4-(2-(((5-bromo-2-nitropyridin-3-yl)oxy)methyl)-4-fluorophenyl)-5-((3-ethyl-1-methyl-1H-pyrazol-5-yl)methyl)-2-methylthiazole

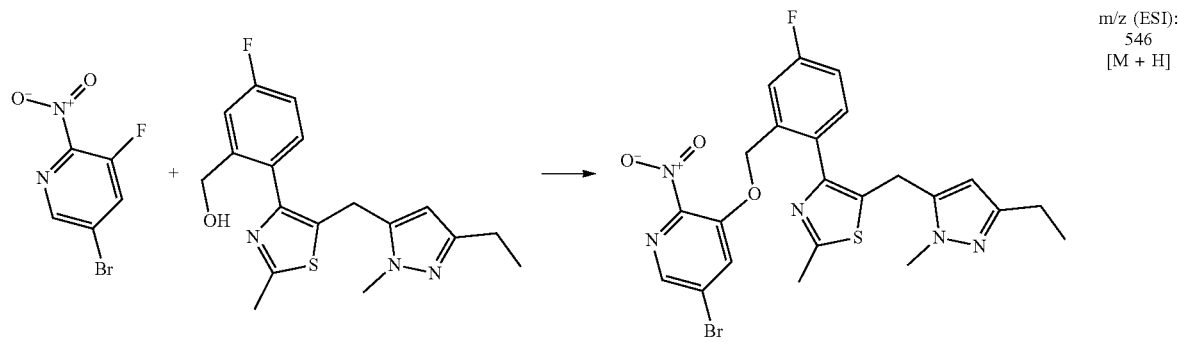

m/z (ESI): 546 [M + H]

5-bromo-3-((2-(4-((3-ethyl-1-methyl-1H-pyrazol-5-yl)methyl)-1-methyl-1H-pyrazol-3-yl)-5-fluorobenzyl)oxy)-2-nitropyridine

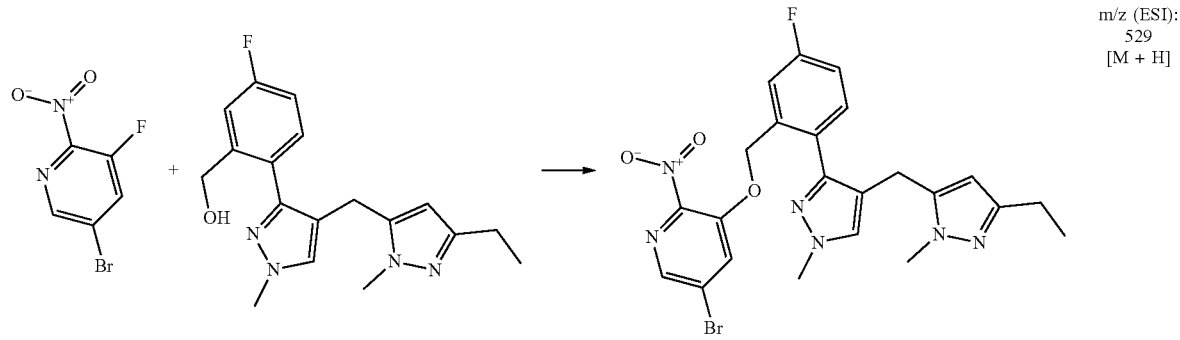

m/z (ESI): 529 [M + H]

(R)-5-bromo-3-(1-(2-(5-((5-cyclobutyl-1-methyl-1H-pyrazol-3-yl)methyl)-1H-pyrazol-1-yl)-5-fluorophenyl)ethoxy)-2-nitropyridine

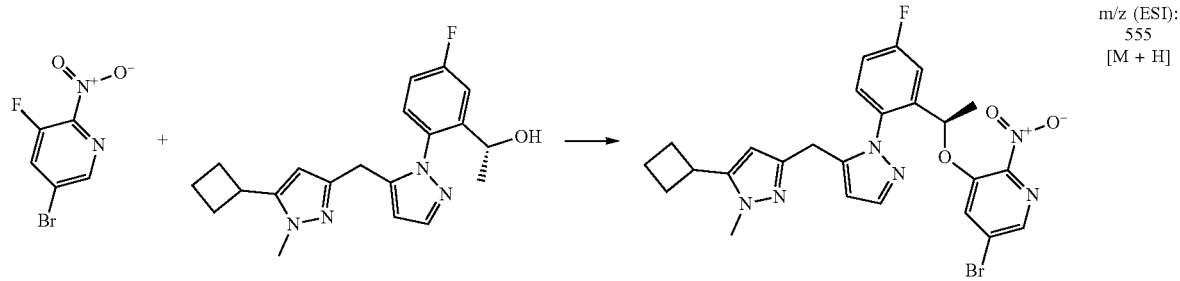

m/z (ESI): 555 [M + H]

-continued (R)-5-bromo-3-(1-(2-(5-((5-(cyclopropylmethyl)-1-methyl-1H-pyrazol-3-yl)methyl)-1H-pyrazol-1-yl)-5-fluorophenyl)ethoxy)-2-nitropyridine


m/z (ESI): 555 [M + H]

(R)-5-bromo-3-(1-(2-(4-((5-(cyclopropylmethyl)-1-methyl-1H-pyrazol-3-yl)methyl)-1-methyl-1H-pyrazol-3-yl)-5-fluorophenyl)ethoxy)-2-nitropyridine

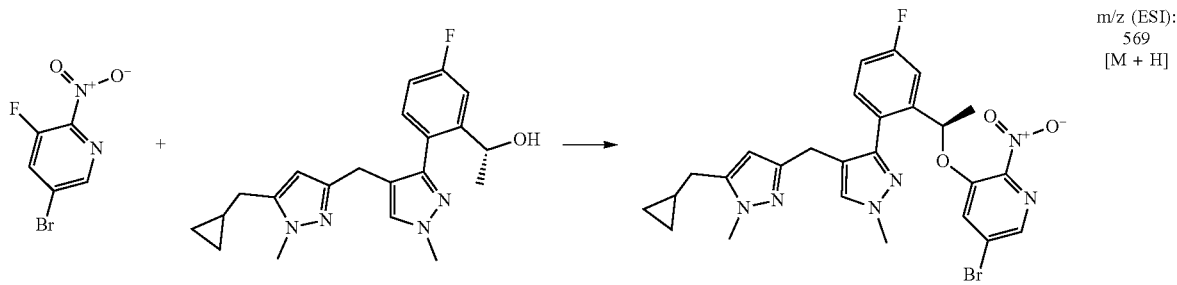

m/z (ESI): 569 [M + H]

(R)-5-bromo-3-(1-(2-(5-((3-(2,2-difluoroethyl)-1-methyl-1H-pyrazol-5-yl)methyl)-3-(difluoromethyl)-1H-pyrazol-1-yl)-5-fluorophenyl)ethoxy)-2-nitropyridine

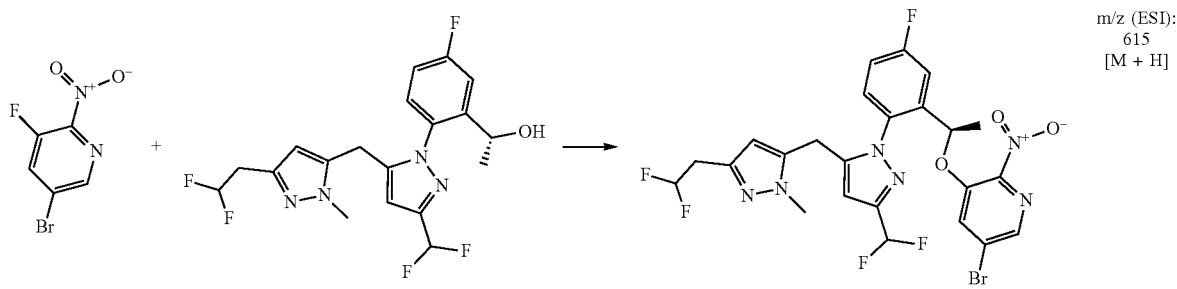

m/z (ESI): 615 [M + H]

Synthesis of 4-((2-chloropyridin-3-yl)methyl)-1-(cyclopropylmethyl)-1H-pyrazole-3-carbonitrile

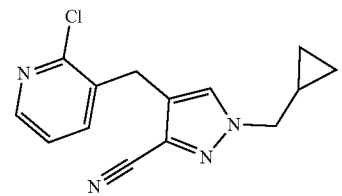 [SMILES: N#Cc1nn(CC2CC2)cc1Cc1cccnc1Cl]

To a solution of 4-((2-chloropyridin-3-yl)(hydroxy)methyl)-1-(cyclopropylmethyl)-1H-pyrazole-3-carbonitrile (450 mg, 1.56 mmol) in DCM (15 mL) was added $SOCl_2$ (0.34 mL, 4.7 mmol) at 0° C. under $N_2$. After stirring at r.t. for 2 h, the reaction was concentrated to afford crude 4-(chloro(2-chloropyridin-3-yl)methyl)-1-(cyclopropylmethyl)-1H-pyrazole-3-carbonitrile (478 mg, 99% yield) as a colorless oil.

To a stirred solution of 4-(chloro(2-chloropyridin-3-yl)methyl)-1-(cyclopropylmethyl)-1H-pyrazole-3-carbonitrile (478 mg, 1.56 mmol) in AcOH (12 mL) was added Zn powder (1.08 g, 15.6 mmol). The reaction mixture was stirred at r.t. for 2 h under $N_2$ and then concentrated in vacuo. The residue was purified by flash column chromatography on silica gel (30% EtOAc in PE) to afford 4-((2-chloropyridin-3-yl)methyl)-1-(cyclopropylmethyl)-1H-pyrazole-3-carbonitrile (160 mg, 38% yield) as a white solid. LC/MS (ESI)(m/z): 273 [M+H]V.

Synthesis of (5-(4-fluoro-2-formylphenyl)-1-methyl-1H-pyrazol-4-yl)methyl methanesulfonate

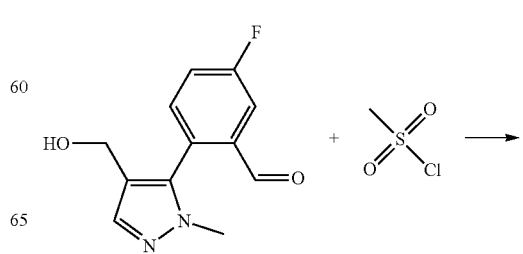

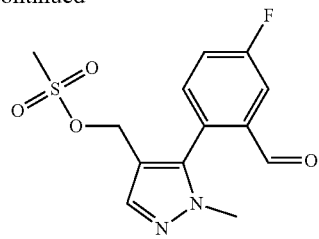

To a solution of 5-fluoro-2-[4-(hydroxymethyl)-1-methyl-1H-pyrazol-5-yl]benzaldehyde (50 mg, 0.20 mmol) in DCM (5 mL) was added TEA (65 mg, 0.64 mmol), followed by the addition of MsCl (37 mg, 0.32 mmol) at 0° C. After stirring at r.t. for 1 h, the reaction was quenched with water and extracted with DCM twice, the combined organic layers were dried over anhydrous $Na_2SO_4$, filtered and concentrated. The residue was purified by flash chromatography (silica gel, EtOAc/PE=2/1) to afford (5-(4-fluoro-2-formylphenyl)-1-methyl-1H-pyrazol-4-yl)methyl methanesulfonate (25 mg, 38% yield) as a yellow solid. LC/MS ESI (m/z): 313 $[M+H]^+$.

The following intermediates were synthesized using a similar experimental protocol:

To a stirred solution of ethyl 5-((3-bromo-1-methyl-1H-pyrazol-4-yl)methyl)isoxazole-3-carboxylate (1.10 g, 3.50 mmol) in MeOH (2 mL) was added a solution of $NH_3$ in MeOH (8 mL, 7 N) dropwise via syringe at r.t. After stirring at r.t. for 3 h in a sealed tube, the reaction was evaporated to give crude 5-((3-bromo-1-methyl-1H-pyrazol-4-yl)methyl)isoxazole-3-carboxamide (920 mg, 92% yield) as a white solid. LC/MS (ESI) (m/z): 285 $[M+H]^+$.

Synthesis of 3-bromo-4-((1-(cyclopropylmethyl)-1H-pyrazol-4-yl)methyl)-1-(difluoromethyl)-1H-pyrazole

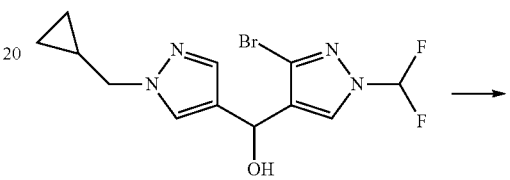

(3-cyano-1-methyl-1H-pyrazol-5-yl)(3-(difluoromethyl)-1-(4-fluoro-2-((R)-1-((4-methoxybenzyl)oxy)ethyl)phenyl)-1H-pyrazol-5-yl)methyl methanesulfonate

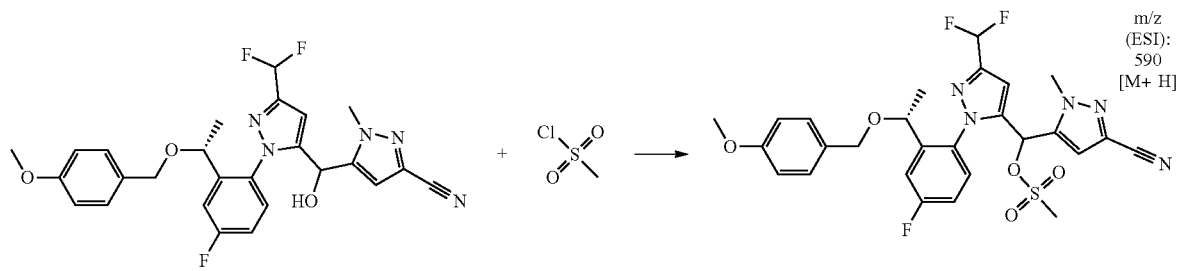

m/z (ESI): 590 [M+ H]

(4-chloropyridin-3-yl)(5-cyano-1-methyl-1H-pyrazol-3-yl)methyl methanesulfonate

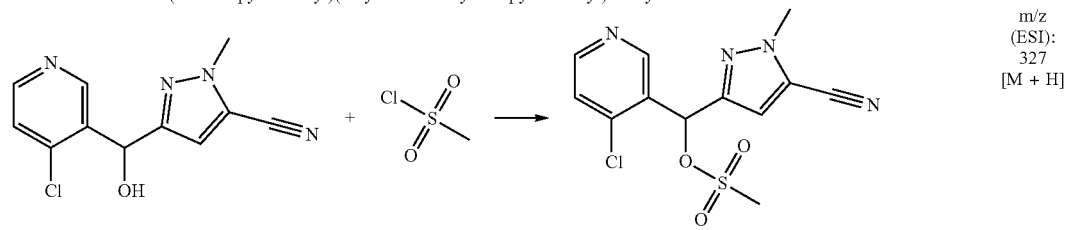

m/z (ESI): 327 [M + H]

Synthesis of 5-((3-bromo-1-methyl-1H-pyrazol-4-yl)methyl)isoxazole-3-carboxamide

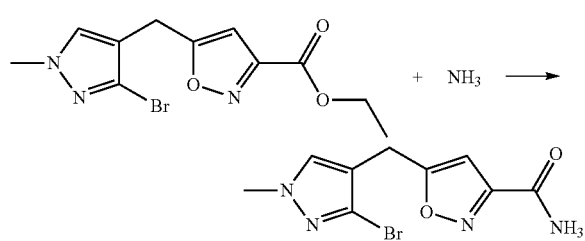

-continued

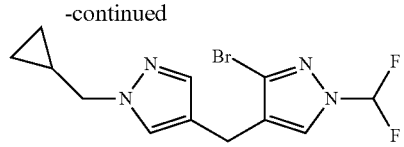

A solution of (3-bromo-1-(difluoromethyl)-1H-pyrazol-4-yl)(1-(cyclopropylmethyl)-1H-pyrazol-4-yl)methanol (340 mg, 0.979 mmol) in TFA (2.0 mL) and TES (1.0 mL) was stirred at r.t. for 1 h. The reaction was concentrated. The residue was diluted with EtOAc (15 mL), washed with sat. $NaHCO_3$ (20 mL) and brine (15 mL), dried over anhydrous $Na_2SO_4$ and concentrated to dryness. The residue was purified by column chromatography on silica gel (PE:EtOAc=3:

1) to give 3-bromo-4-((1-(cyclopropylmethyl)-1H-pyrazol-4-yl)methyl)-1-(difluoromethyl)-1H-pyrazole (300 mg, yield: 93%) as a yellow oil. LC/MS (ESI) m/z: 331 [M+H]$^+$.

Synthesis of 2-(2-bromo-4-fluorophenyl)-1-{[2-(trimethylsilyl)ethoxy]methyl}-1H-imidazole

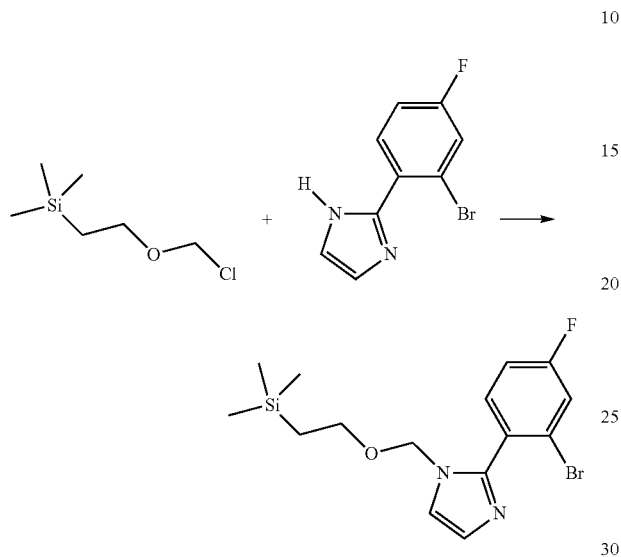

To a solution of 2-(2-bromo-4-fluorophenyl)-1H-imidazole (65.0 g, 270 mmol) in DMF (300 mL) was added NaH (12.94 g, 323.6 mmol, 60% in mineral oil) portion-wise at 0° C. over 0.5 h. After the addition, the mixture was stirred at 0° C. for another 30 min and then warmed to r.t. with stirring over 1 h. After cooling to 0° C., [2-(chloromethoxy)ethyl]trimethylsilane (50.21 mL, 283.1 mmol) was added dropwise, and the resulting mixture was stirred at r.t. for 3 h. The reaction mixture was quenched with sat. aq. NH$_4$Cl (200 mL) at 0° C. and then extracted with EA (2×300 mL). The combined organic extracts were washed with brine, dried over anhydrous Na$_2$SO$_4$, filtered, and concentrated. The residue was purified by flash column chromatography on silica-gel (30% EtOAc in PE) to afford 2-(2-bromo-4-fluorophenyl)-1-{[2-(trimethylsilyl)ethoxy]methyl}-1H-imidazole (64 g, 64% yield) as a yellow solid. LC/MS ESI (m/z): 371 [M+H]$^+$.

The following intermediates were synthesized using a similar experimental protocol-1/I1TRE 3-(1-(2-(1-((5-bromo-1-ethyl-1H-pyrazol-4-yl)methyl)-1H-imidazol-2-yl)-5-fluorophenyl)-2-(tert-butyldimethylsilyloxy)ethoxy)-2-nitropyridine

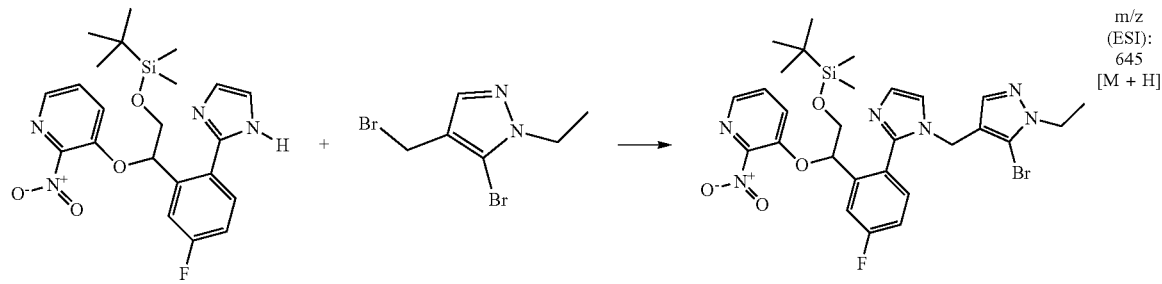

m/z (ESI): 645 [M + H]

Synthesis of 3-[(1R)-1-(5-fluoro-2-iodophenyl)ethoxy]pyridin-2-amine

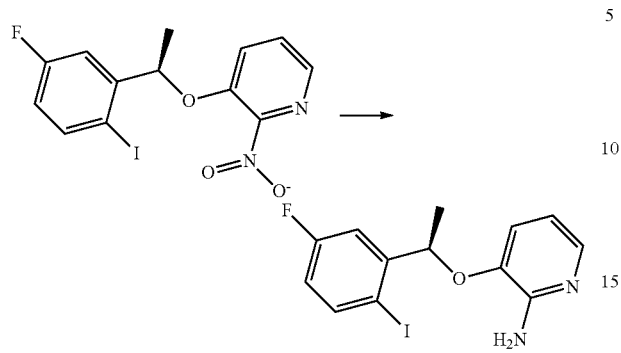

A mixture of (R)-3-(1-(5-fluoro-2-iodophenyl)ethoxy)-2-nitropyridine (15.5 g, 40.0 mmol), iron powder (22.4 g, 400 mmol) and NH$_4$Cl (21.6 g, 400 mmol) in co-solvent of EtOH (550 mL) and H$_2$O (110 mL) was stirred at 80° C. for 1 h. After cooling to r.t., the mixture was filtered, the filtrate was concentrated under reduced pressure. The residue was diluted with DCM (500 mL), then washed with water and brine, dried over anhydrous Na$_2$SO$_4$, filtered and concentrated. The residue was purified by column chromatography on silica gel (50% EtOAc in PE) to give 3-[(1R)-1-(5-fluoro-2-iodophenyl)ethoxy]pyridin-2-amine as a white solid (10.5 g, yield: 73%). LC/MS ESI (m/z): 359 [M+H]$^+$.

The following intermediates were synthesized using a similar experimental protocol:

3-(1-(5-fluoro-2-iodophenyl)ethoxy)pyridin-2-amine

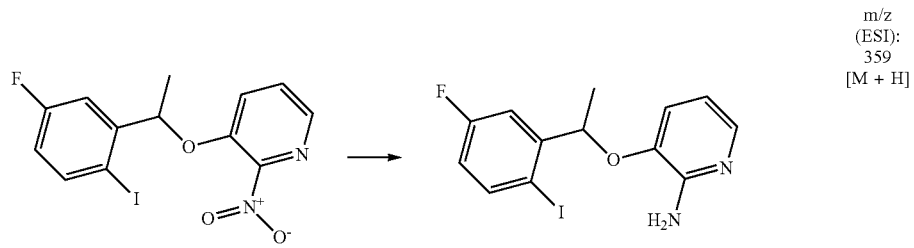

m/z (ESI): 359 [M + H]

3-[1-(2-{1-1(5-bromo-1-ethyl-1H-pyrazol-4-yl)methyl]-1H-imidazol-2-yl}-5-fluorophenyl)-2-[(tert-butyldimethylsilyl)oxy]ethoxy]pyridin-2-amine m/z (ESI): 615 [M + H]

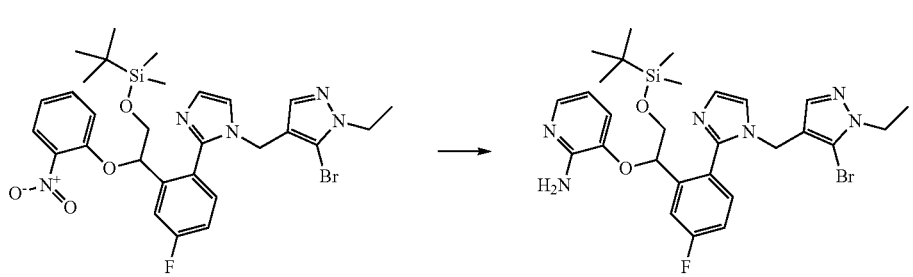 [SMILES: CCn1ncc(Cn2ccnc2-c2ccc(F)cc2C(CO[Si](C)(C)C(C)(C)C)Oc2ccccc2[N+](=O)[O-])c1Br ; CCn1ncc(Cn2ccnc2-c2ccc(F)cc2C(CO[Si](C)(C)C(C)(C)C)Oc2cccnc2N)c1Br]

415

Synthesis of 3-((4-chloropyridin-3-yl)methyl)-1-methyl-1H-pyrazole-5-carbonitrile

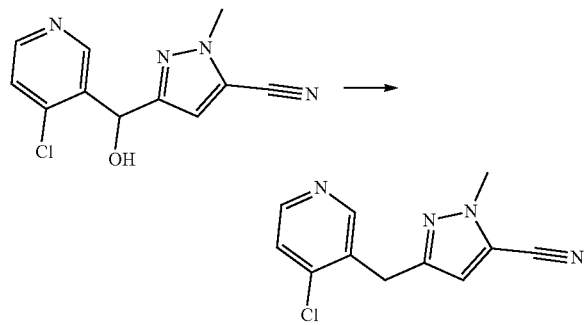

416

A mixture of 3-((4-chloropyridin-3-yl)(hydroxy)methyl)-1-methyl-1H-pyrazole-5-carbonitrile (500 mg, 2.01 mmol) and Pd/C (50 mg, 40%) in MeOH (8 mL) was stirred at 25° C. under atmosphere of H$_2$ for 30 min. Then, the mixture was filtered through celite. The filtrate was concentrated in vacuo and the residue was purified by column chromatography on silica gel (PE:EA=1:2, V/V) to give the target product as a yellow oil (100 mg, yield: 21%). LC/MS ESI (m/z): 233 [M+H]$^+$.

The following intermediates were synthesized using a similar experimental protocol:

1-ethyl-4-[(1-{4-fluoro-2-[(1R)-1-[(4-methoxyphenyl)methoxy]ethyl]phenyl}-3-(trifluoromethyl)-1H-pyrazol-5-yl)methyl]-1H-1,2,3-triazole

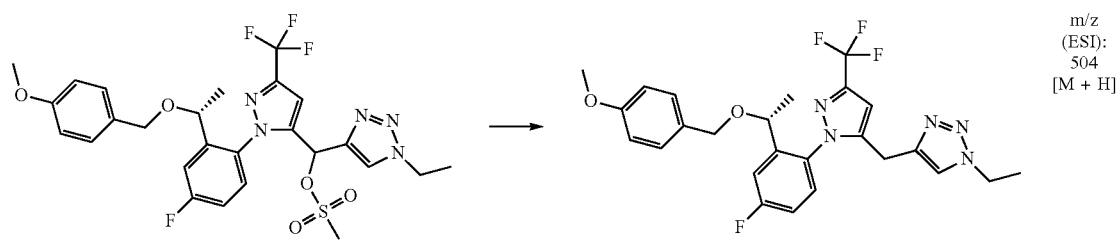

m/z (ESI): 504 [M + H]

(R)-5-((3-(difluoromethyl)-1-(4-fluoro-2-(1-((4-methoxybenzyl)oxy)ethyl)phenyl)-1H-pyrazol-5-yl)methyl)-1-methyl-1H-pyrazole-3-carbonitrile

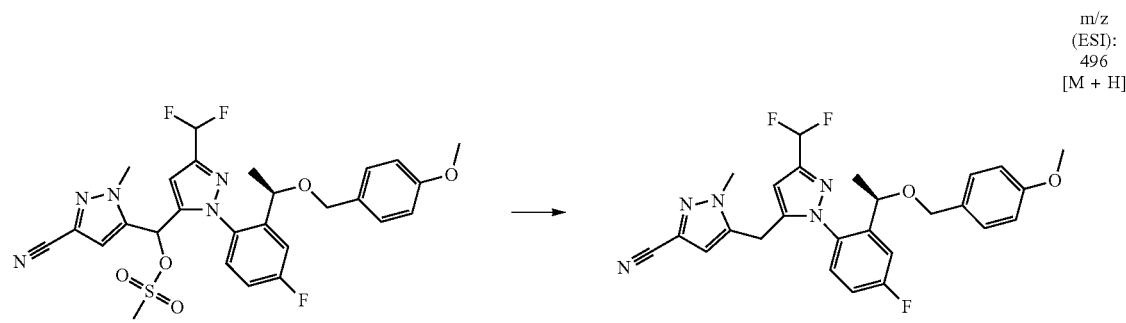

m/z (ESI): 496 [M + H]

5-((3-chloro-1-(4-fluoro-2-(((4-methoxybenzyl)oxy)methyl)phenyl)-1H-pyrazol-5-yl)methyl)-1-methyl-1H-pyrazole-3-carbonitrile

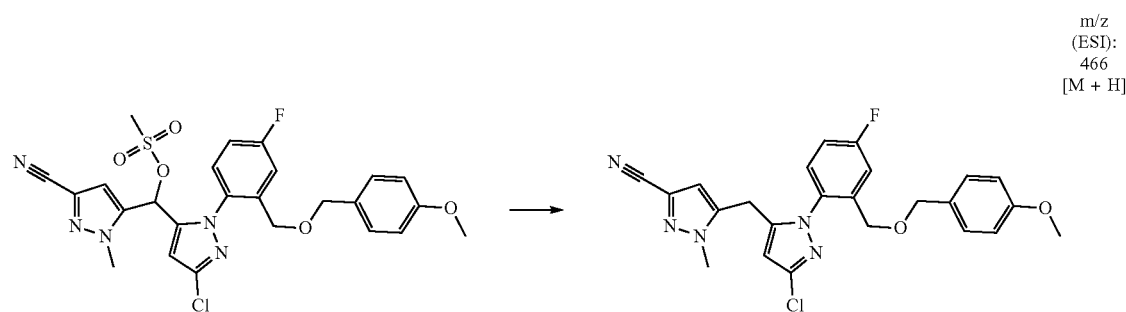

m/z (ESI): 466 [M + H]

Synthesis of 5-((3-bromo-1-methyl-1H-pyrazol-4-yl)methyl)isoxazole-3-carbonitrile

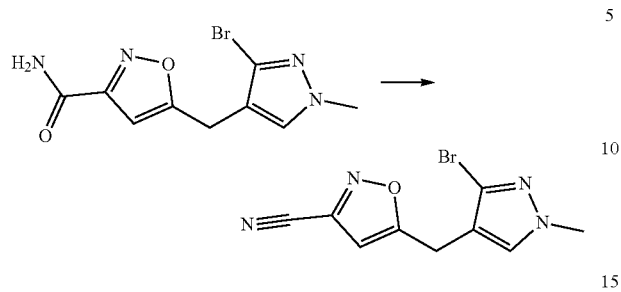

A solution of 5-((3-bromo-1-methyl-1H-pyrazol-4-yl)methyl)isoxazole-3-carboxamide (920 mg, 3.23 mmol) in POCl$_3$ (10 mL) was stirred at 110° C. for 3 h, then concentrated. The residue was partitioned between EtOAc (15 mL) and sat. NaHCO$_3$ (30 mL), the organic layer was washed with brine (30 mL), dried (MgSO$_4$) and evaporated. The residue was purified by column chromatography on silica gel eluted (PE:EA=1:1) to give 5-((3-bromo-1-methyl-1H-pyrazol-4-yl)methyl)isoxazole-3-carbonitrile (750 mg, 870% yield) as a colorless oil. LC/MS (ESI) (m/z): 267 [M+H]$^+$.

5-bromo-4-ethyl-1-((3-iodo-1-methyl-1H-pyrazol-4-yl)methyl)-1H-pyrazole-3-carbonitrile

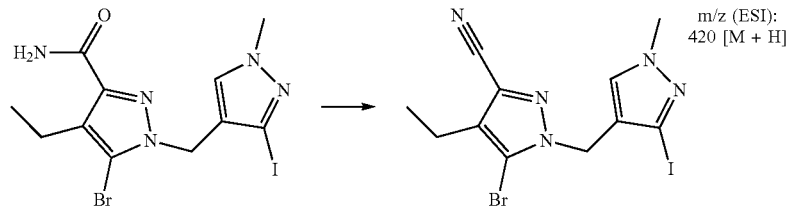

m/z (ESI): 420 [M + H]

Synthesis of 4-(2-bromo-4-fluorophenyl)-5-((1-ethyl-1H-pyrazol-4-yl)methyl)-2-methyloxazole

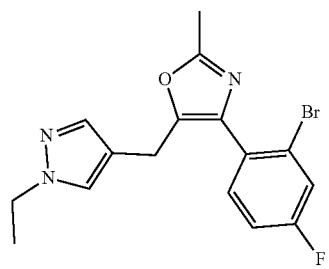 [SMILES: CCn1cc(Cc2oc(C)nc2-c2ccc(F)cc2Br)cn1]

To a solution of 1-(2-bromo-4-fluorophenyl)-3-(1-ethyl-1H-pyrazol-4-yl)propan-1-one (1.00 g, 3.09 mmol) in CH$_3$Cl (20 mL) was added hydrobromic acid (0.4 mL, 33% in acetic acid) dropwise at 0° C. followed by the addition of Br$_2$ (494 mg, 3.09 mmol) at 0° C. The reaction was stirred at 2 5° C. for 1.5 h. The reaction mixture was quenched with sat. aq. NH$_4$Cl and then partitioned between EtOAc and water. The organic layer was separated, washed with brine, dried over anhydrous Na$_2$SO$_4$ and concentrated in vacuo. The residue was purified by flash column chromatography (PE/EA=3/1) to give 2-bromo-1-(2-bromo-4-fluorophenyl)-3-(1-ethyl-1H-pyrazol-4-yl)propan-1-one (1.1 g, yield: 88%) as a yellow oil. LC/MS (ES+): m/z=403 [M+H]$^+$.

To a solution of 2-bromo-1-(2-bromo-4-fluorophenyl)-3-(1-ethyl-1H-pyrazol-4-yl)propan-1-one (1.10 g, 2.72 mmol) in MeOH (20 mL) was added sodium acetate (450 mg, 5.44 mmol) at 25° C., and the mixture was stirred at 70° C. for 3 h. The reaction was quenched by adding water (5 mL). The mixture was then extracted with EA (3×10 mL), washed with sat. NH$_4$Cl (5 mL) and brine (5 mL), dried over anhydrous Na$_2$SO$_4$ and concentrated in vacuo to give crude 1-(2-bromo-4-fluorophenyl)-3-(1-ethyl-1H-pyrazol-4-yl)-1-oxopropan-2-yl acetate (1.0 g, purity: ca. 50%) as a yellow gum.

To a solution of crude 1-(2-bromo-4-fluorophenyl)-3-(1-ethyl-1H-pyrazol-4-yl)-1-oxopropan-2-yl acetate (1.0 g, 1.3 mmol, purity: ca. 50%) in acetic acid (5.0 mL) was added ammonium acetate (840 mg, 10.9 mmol) at 25° C., and the mixture was stirred at 120° C. for 3 h. The reaction was quenched by adding water (5 mL). The mixture was then extracted with EA (3×10 mL), washed with sat. NH$_4$Cl (5 mL) and brine (5 mL), dried over anhydrous Na$_2$SO$_4$ and concentrated in vacuo. The residue was purified by flash column chromatography on silica gel (EA in PE=0→50%) to give 4-(2-bromo-4-fluorophenyl)-5-[(1-ethyl-1H-pyrazol-4-yl)methyl]-2-methyl-1,3-oxazole (380 mg, yield: 38%) as a yellow gum. LC/MS (ES+): m/z=364 [M+H]$^+$.

Synthesis of 1-{[1-(4-fluoro-2-iodophenyl)-3-methyl-1H-pyrazol-5-yl]methyl}-1H-imidazole-4-carbonitrile

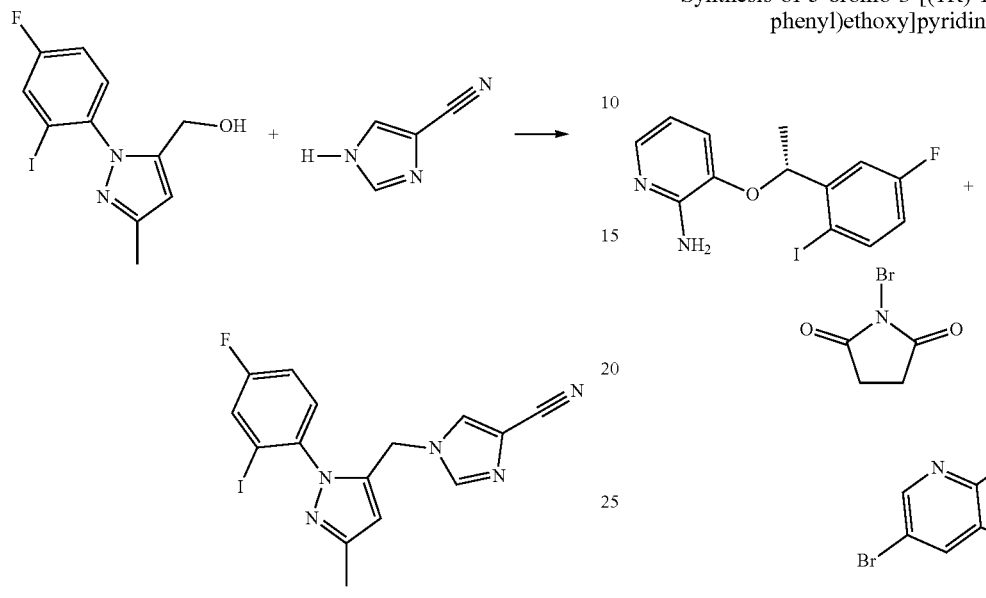

To a solution of [1-(4-fluoro-2-iodophenyl)-3-methyl-1H-pyrazol-5-yl]methanol (600 mg, 1.81 mmol) in DCM (20 mL) was added $SOCl_2$ (0.260 mL, 3.61 mmol), and then the mixture was stirred at 0° C. for 1 h. The mixture was concentrated to dryness. To the residue were added DMF (10 mL), $K_2CO_3$ (749 mg, 5.42 mmol) and 1H-imidazole-4-carbonitrile (336 mg, 3.61 mmol). The resulting mixture was stirred at r.t. for 16 h. The reaction mixture was quenched by ice water and then diluted with EtOAc. The organic layer was separated, washed with sat. aq. $NH_4Cl$ solution and brine, dried over anhydrous $Na_2SO_4$, filtered and concentrated to dryness. The residue was purified by flash chromatography (silica gel, 0→50% EtOAc in PE) to give 1-{[1-(4-fluoro-2-iodophenyl)-3-methyl-1H-pyrazol-5-yl]methyl}-1H-imidazole-4-carbonitrile (720 mg, 98%) as a yellow solid.

LC/MS (ESI) m/z: 408 [M+H]$^+$.

Synthesis of 5-bromo-3-[(1R)-1-(5-fluoro-2-iodophenyl)ethoxy]pyridin-2-amine

To a solution of 3-[(1R)-1-(5-fluoro-2-iodophenyl)ethoxy]pyridin-2-amine (21.0 g, 58.6 mmol) in HOAc (2000 mL) at 0° C. was added the solution of N-bromosuccinimide (12.52 g, 70.36 mmol) in HOAc (360 mL) dropwise over 30 min. After the addition, the mixture was stirred at r.t. for 16 h. The reaction mixture was directly concentrated in vacuo and the residue was purified by flash chromatography (0→20% EtOAc in PE) to give 5-bromo-3-[(1R)-1-(5-fluoro-2-iodophenyl)ethoxy]pyridin-2-amine (10.5 g, 41% yield) as a white solid. LC/MS ESI (m/z): 437 [M+H]$^+$.

The following intermediates were synthesized using a similar experimental protocol:

5-bromo-3-(1-(5-fluoro-2-iodophenyl)ethoxy)pyridin-2-amine

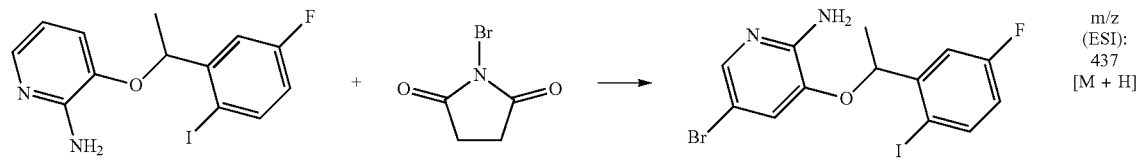

m/z (ESI): 437 [M + H]

1-(2-[4-[(5-bromo-4-ethylimidazol-1-yl)methyl]-1-methylpyrazol-3-yl]-5-fluorophenyl)ethanol

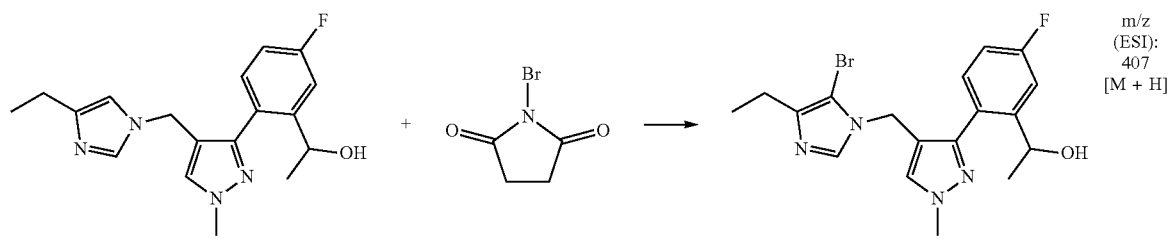

m/z (ESI): 407 [M + H]

Synthesis of 5-bromo-4-ethyl-1-((3-iodo-1-methyl-1H-pyrazol-4-yl)methyl)-1H-pyrazole-3-carboxamide

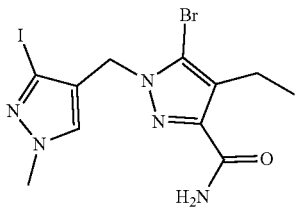 [SMILES: CCc1c(C(N)=O)nn(Cc2cn(C)nc2I)c1Br]

To a stirred solution of isoamyl nitrite (1.13 g, 9.67 mmol) and CuBr$_2$ (1.73 g, 7.74 mmol) in MeCN (28 mL) was added a solution of ethyl 5-amino-4-ethyl-1-((3-iodo-1-methyl-1H-pyrazol-4-yl)methyl)-1H-pyrazole-3-carboxylate (2.60 g, 6.45 mmol) in ACN (2 mL) at 0° C. under N$_2$. After stirring at r.t. for 12 h, the reaction was separated between EtOAc (30 mL) and water (30 mL), the organic phase was dried over Na$_2$SO$_4$, then concentrated. The residue was purified by column chromatography on silica gel eluted with PE/EtOAc (5:1→3:1) to give ethyl 5-bromo-4-ethyl-1-((3-iodo-1-methyl-1H-pyrazol-4-yl)methyl)-1H-pyrazole-3-carboxylate (2.10 g, yield: 70%) as a yellow oil. LC/MS (ESI) (m/z): 467 [M+H]$^+$.

To a solution of ethyl 5-bromo-4-ethyl-1-((3-iodo-1-methyl-1H-pyrazol-4-yl)methyl)-1H-pyrazole-3-carboxylate (2.10 g, 4.50 mmol) in MeOH (10 mL), THF (10 mL) and water (10 mL) was added lithium hydroxide monohydrate (566 mg, 13.5 mmol) and the mixture was stirred at 40° C. for 2 h. The mixture was concentrated, diluted with water (20 mL), and washed with EtOAc (15 mL). The aq. layer was acidified with 1N aq. HCl to pH 3, the resulting solid was filtered and dried under reduced pressure to give 5-bromo-4-ethyl-1-((3-iodo-1-methyl-1H-pyrazol-4-yl)methyl)-1H-pyrazole-3-carboxylic acid (1.60 g, yield: 81%) as white solid. LC/MS (ESI) (m/z): 439 [M+H]$^+$.

To a mixture of compound 5-bromo-4-ethyl-1-((3-iodo-1-methyl-1H-pyrazol-4-yl)methyl)-1H-pyrazole-3-carboxylic acid (1.98 g, 4.50 mmol) and NH$_4$Cl (2.41 g, 45.0 mmol) in DMF (20 mL) was added TEA (1.37 g, 13.5 mmol) and HATU (2.05 g, 5.40 mmol) at 0° C. The mixture was stirred at r.t. for 12 h, diluted with EtOAc (30 mL) and washed with water (30 mL) and brine (15 mL), dried over anhydrous Na$_2$SO$_4$, filtered and concentrated to give compound 5-bromo-4-ethyl-1-((3-iodo-1-methyl-1H-pyrazol-4-yl)methyl)-1H-pyrazole-3-carboxamide (1.50 g, yield: 76%) as a yellow oil. LC/MS (ESI) (m/z): 438 [M+H]$^+$.

Synthesis of 1-((5-(4-fluoro-2-formylphenyl)-1-methyl-1H-pyrazol-4-yl)methyl)-1H-imidazole-4-carbonitrile

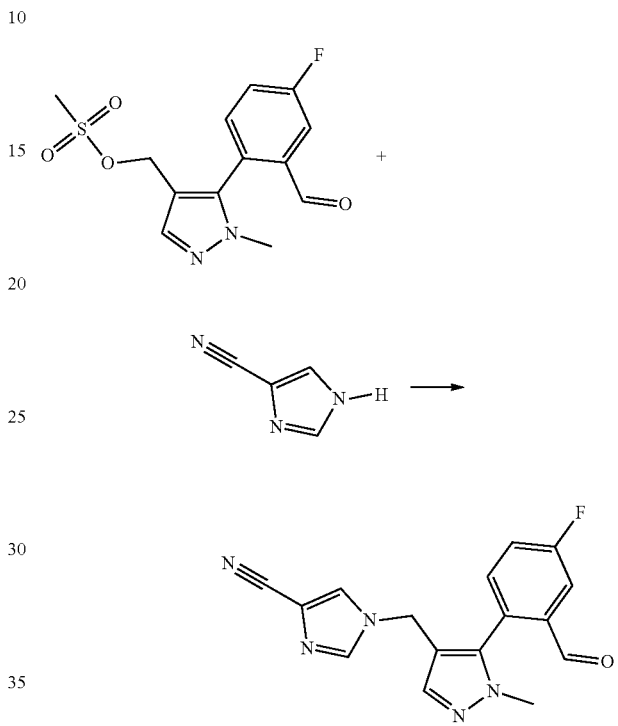

To a solution of (5-(4-fluoro-2-formylphenyl)-1-methyl-1H-pyrazol-4-yl)methyl methanesulfonate (50 mg, 0.16 mmol) in DMF (3 mL) were added 1H-imidazole-4-carbonitrile (18 mg, 0.19 mmol) and Cs$_2$CO$_3$ (104 mg, 0.320 mmol). After stirring at 80° C. for 2 h, the reaction was quenched with water and extracted twice with EtOAc. The combined organic layers were dried over anhydrous Na$_2$SO$_4$, filtered and concentrated. The residue was purified by flash chromatography (silica gel, EtOAc/PE=1/1) to afford 1-((5-(4-fluoro-2-formylphenyl)-1-methyl-1H-pyrazol-4-yl)methyl)-1H-imidazole-4-carbonitrile (12 mg, 24% yield) as a white solid. LC/MS ESI (m/z): 310 [M+H]$^+$.

The following intermediates were synthesized using a similar experimental protocol:

2-(1-((5-bromo-1-ethyl-1H-pyrazol-4-yl)methyl)-1H-imidazol-2-yl)-5-fluorobenzaldehyde

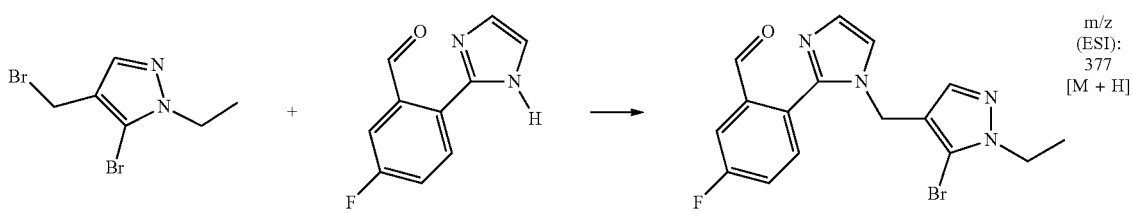

m/z (ESI): 377 [M + H]

2-(1-((5-bromo-1-cyclobutyl-1H-pyrazol-4-yl)methyl)-1H-imidazol-2-yl)-5-fluorobenzaldehyde m/z (ESI): 403 [M + H]

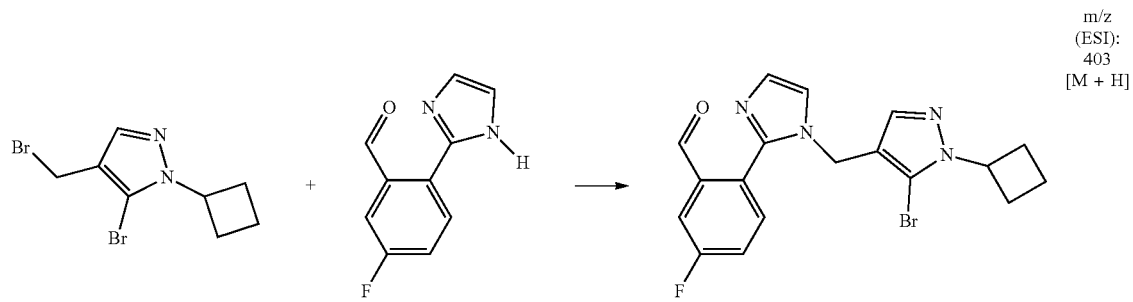

Synthesis of (R)-1-(2-(5-((1-ethyl-1H-pyrazol-4-yl)methyl)oxazol-4-yl)-5-fluorophenyl)ethan-1-ol

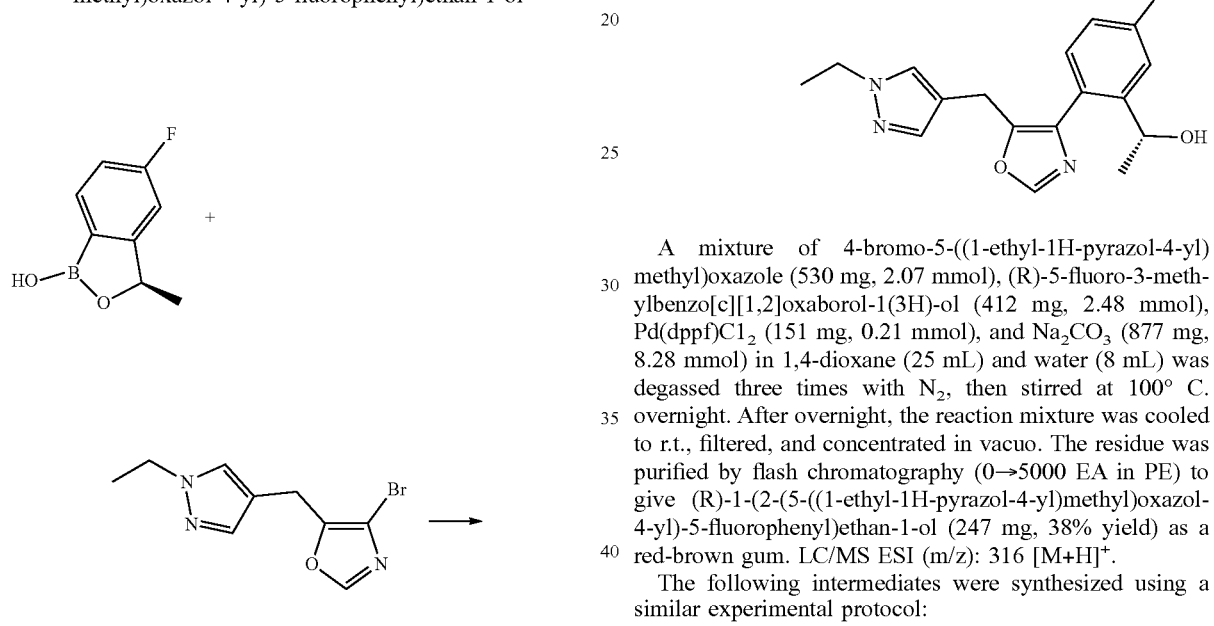

A mixture of 4-bromo-5-((1-ethyl-1H-pyrazol-4-yl)methyl)oxazole (530 mg, 2.07 mmol), (R)-5-fluoro-3-methylbenzo[c][1,2]oxaborol-1(3H)-ol (412 mg, 2.48 mmol), Pd(dppf)Cl$_2$ (151 mg, 0.21 mmol), and Na$_2$CO$_3$ (877 mg, 8.28 mmol) in 1,4-dioxane (25 mL) and water (8 mL) was degassed three times with N$_2$, then stirred at 100° C. overnight. After overnight, the reaction mixture was cooled to r.t., filtered, and concentrated in vacuo. The residue was purified by flash chromatography (0→5000 EA in PE) to give (R)-1-(2-(5-((1-ethyl-1H-pyrazol-4-yl)methyl)oxazol-4-yl)-5-fluorophenyl)ethan-1-ol (247 mg, 38% yield) as a red-brown gum. LC/MS ESI (m/z): 316 [M+H]$^+$.

The following intermediates were synthesized using a similar experimental protocol:

1-(2-(4-((5-bromo-1-ethyl-1H-pyrazol-4-yl)methyl)-1-methyl-1H-pyrazol-5-yl)-5-fluorophenyl)ethan-1-ol m/z (ESI): 407 [M + H]

(R)-1-(2-(4-((3-(benzyloxy)-5-bromo-1-ethyl-1H-pyrazol-4-yl)methyl)-1-methyl-1H-pyrazol-3-yl)-5-fluorophenyl)ethan-1-ol

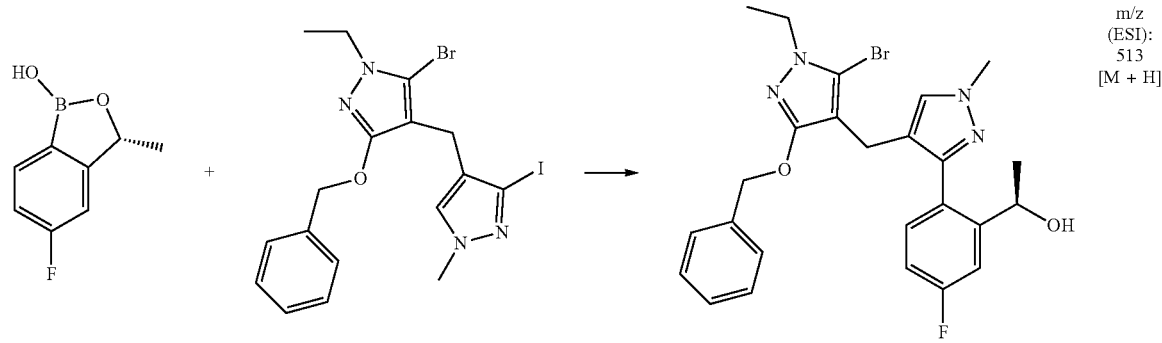

m/z (ESI): 513 [M + H]

(1R)-1-[2-(4-{[5-bromo-1-(cyclopropylmethyl)-3-methyl-1H-pyrazol-4-yl]methyl}-1-methyl-1H-pyrazol-3-yl)-5-fluorophenyl]ethan-1-ol

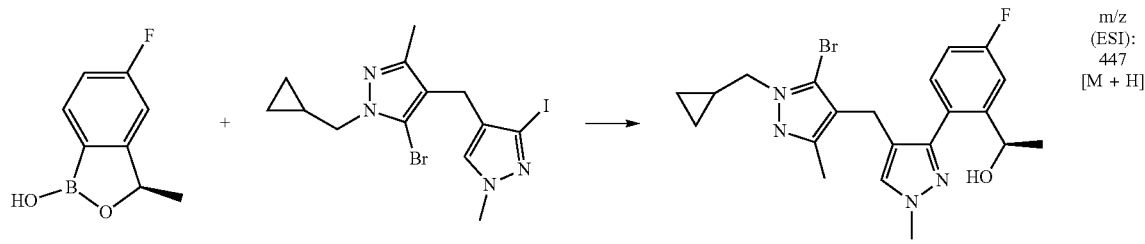

m/z (ESI): 447 [M + H]

(1R)-1-[2-(1-{[5-bromo-1-(cyclopropylmethyl)-3-methyl-1H-pyrazol-4-yl]methyl}-4-methyl-1H-imidazol-2-yl)-5-fluorophenyl]ethan-1-ol

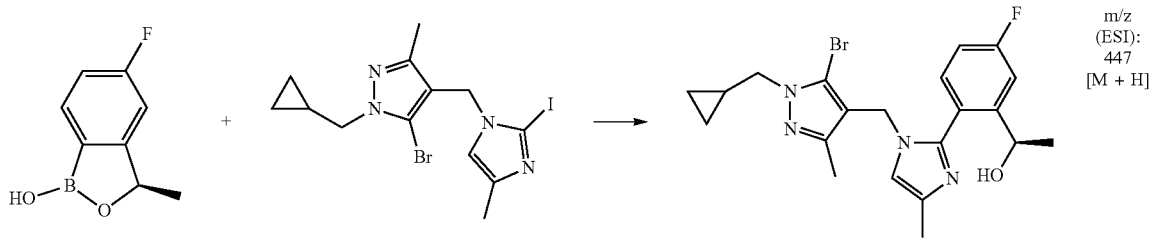

m/z (ESI): 447 [M + H]

(R)-1-(2-(4-((5-bromo-1-(cyclopropylmethyl)-3-methyl-1H-pyrazol-4-yl)methyl)-5-chloro-1-methyl-1H-pyrazol-3-yl)-5-fluorophenyl)ethan-1-ol

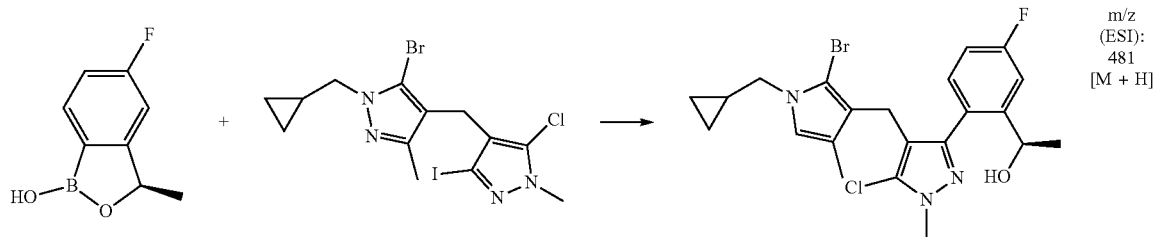

m/z (ESI): 481 [M + H]

1-(2-[4-[(4-ethylimidazol-1-yl)methyl]-1-methylpyrazol-3-yl]-5-fluorophenyl)ethanol

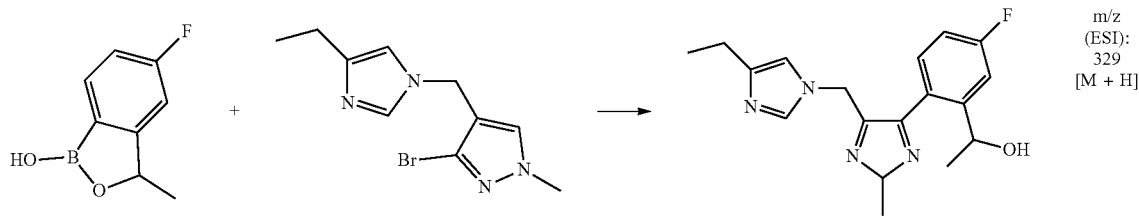

m/z (ESI): 329 [M + H]

-continued 1-(2-(4-((5-bromo-1-ethyl-1H-pyrazol-4-yl)methyl)pyridin-3-yl)-5-fluorophenyl)ethan-1-ol

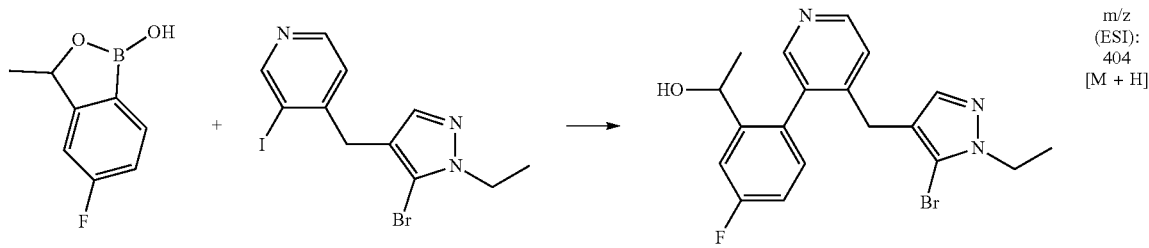

m/z (ESI): 404 [M + H]

1-(2-(3-((5-bromo-1-ethyl-1H-pyrazol-4-yl)methyl)pyridin-4-yl)-5-fluorophenyl)ethanol

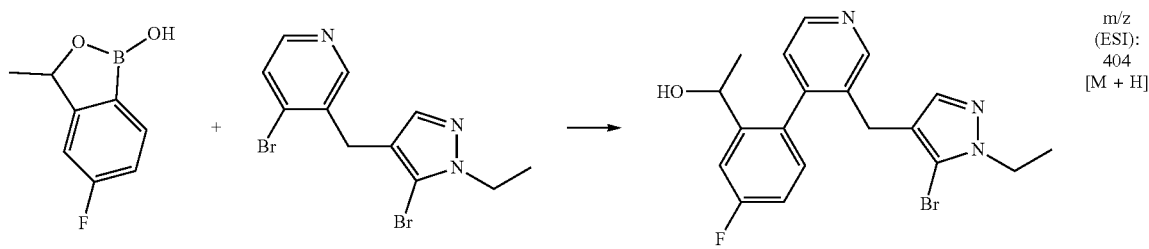

m/z (ESI): 404 [M + H]

1-(2-(5-((5-bromo-1-ethyl-1H-pyrazol-4-yl)methyl)pyrimidin-4-yl)-5-fluorophenyl)ethan-1-ol

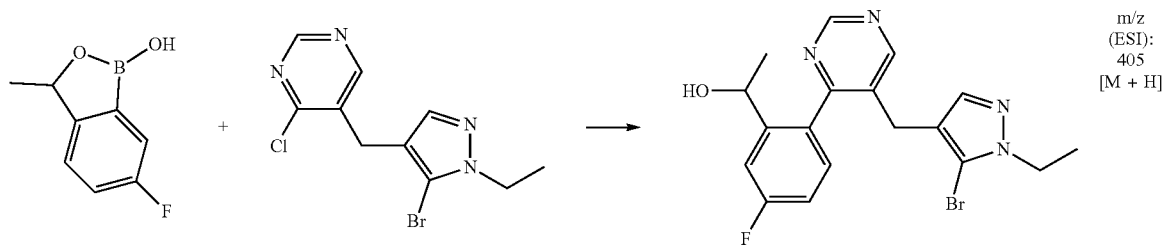

m/z (ESI): 405 [M + H]

1-(2-(3-((1-ethyl-1H-1,2,3-triazol-4-yl)methyl)-5-fluoropyridin-2-yl)-5-fluorophenyl)ethanol

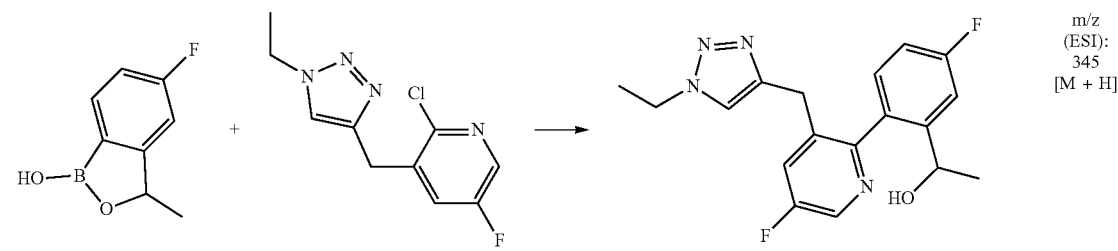

m/z (ESI): 345 [M + H]

(R)-1-(2-(4-((3-chloro-1-ethyl-1H-pyrazol-4-yl)methyl)-1-methyl-1H-pyrazol-3-yl)-5-fluorophenyl)ethan-1-ol

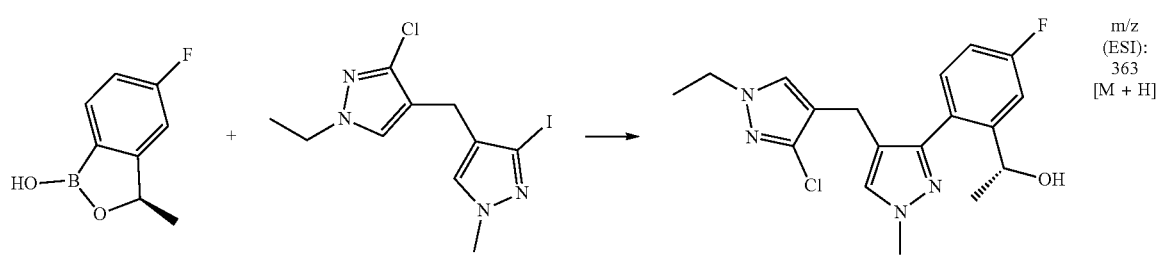

m/z (ESI): 363 [M + H]

-continued (1R)-1-(2-{5-[(1-ethyl-1H-1,2,3-triazol-4-yl)methyl]-2-methyl-1,3-thiazol-4-yl}-5-fluorophenyl)ethan-1-ol

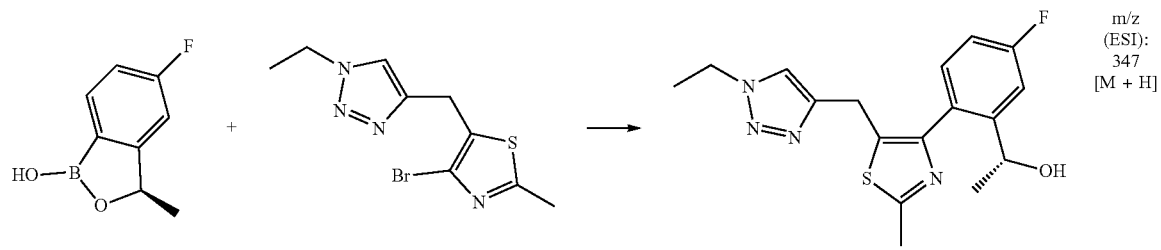

m/z (ESI): 347 [M + H]

(R)-1-(2-(4-((1-ethyl-3-methyl-1H-pyrazol-4-yl)methyl)-1-methyl-1H-pyrazol-3-yl)-5-fluorophenyl)ethan-1-ol


m/z (ESI): 343 [M + H]

(R)-5-((4-(4-fluoro-2-(1-hydroxyethyl)phenyl)-2-methylthiazol-5-yl)methyl)-1-methyl-1H-pyrazole-3-carbonitrile

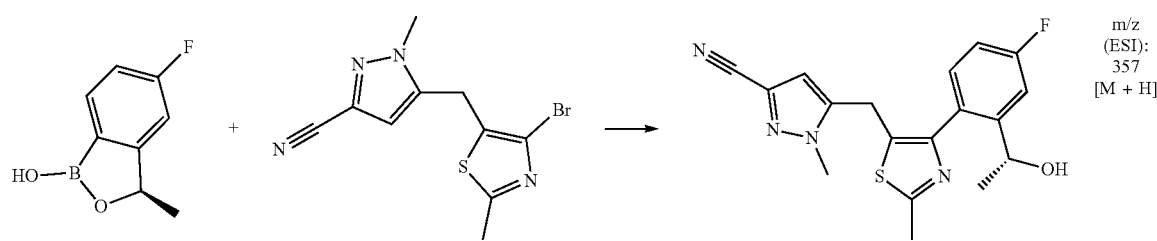

m/z (ESI): 357 [M + H]

(R)-1-(2-(4-((3-chloro-1-(2,2-difluoroethyl)-1H-pyrazol-4-yl)methyl)-1-methyl-1H-pyrazol-3-yl)-5-fluorophenyl)ethan-1-ol

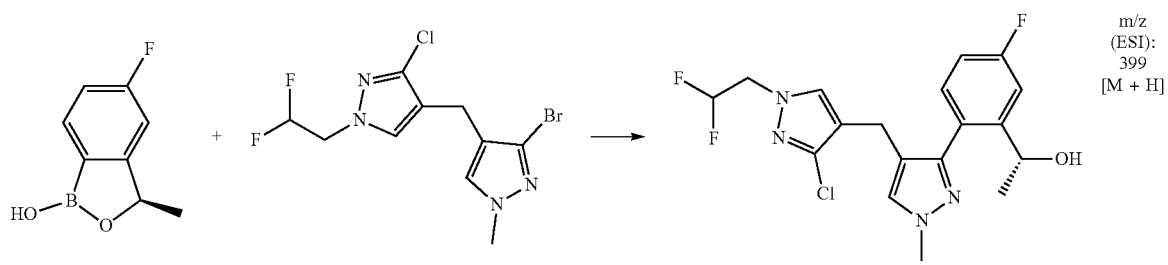

m/z (ESI): 399 [M + H]

(1R)-1-[2-(4-{[1-(2,2-difluoroethyl)-3-methyl-1H-pyrazol-4-yl]methyl}-1-methyl-1H-pyrazol-3-yl)-5-fluorophenyl]ethan-1-ol

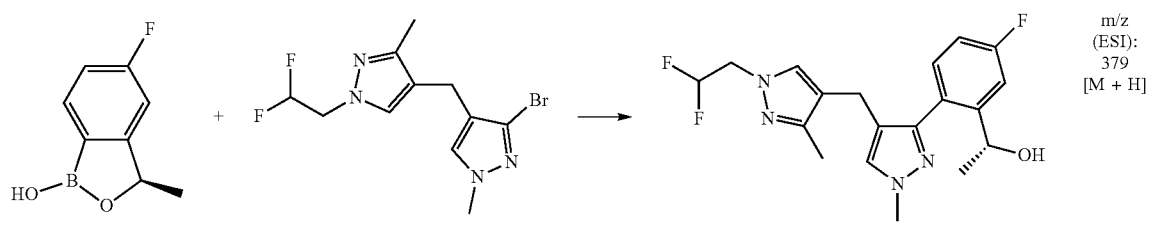

m/z (ESI): 379 [M + H]

-continued (1R)-1-{2-[1-(difluoromethyl)-4-[(1-ethyl-1H-pyrazol-4-yl)methyl]-1H-pyrazol-3-yl]-5-fluorophenyl}ethan-1-ol

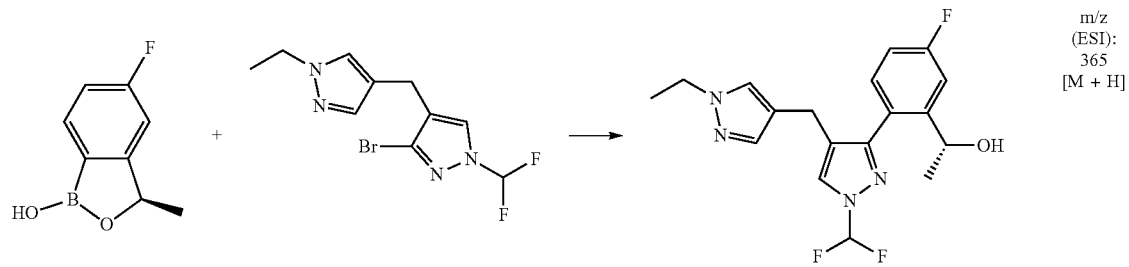

m/z (ESI): 365 [M + H]

(1R)-1-(2-{4-[(1-ethyl-1H-pyrazol-4-yl)methyl]-1,5-dimethyl-1H-pyrazol-3-yl}-5-fluorophenyl)ethan-1-ol

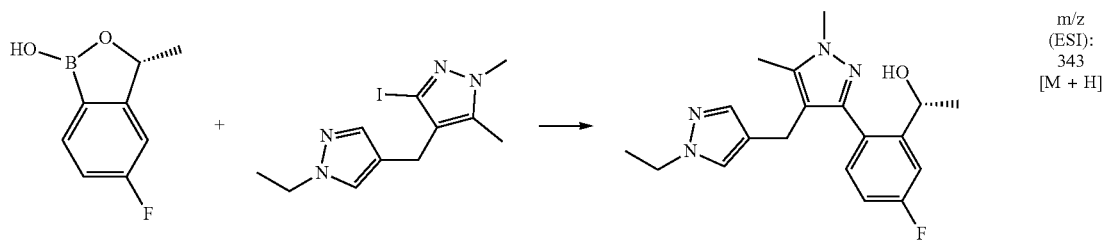

m/z (ESI): 343 [M + H]

5-({2-[4-fluoro-2-(1-hydroxyethyl)phenyl]pyridine-3-yl}methyl)-1-methyl-1H-pyrazole-3-carbonitrile

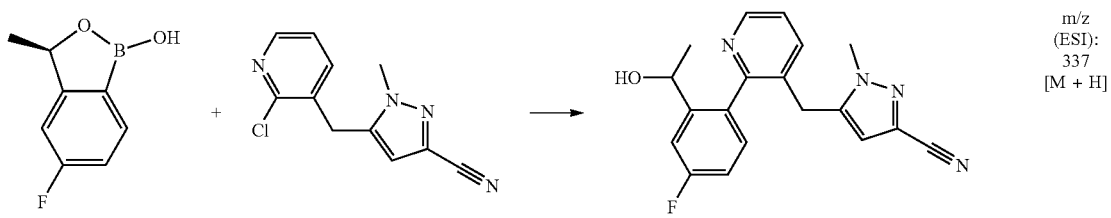

m/z (ESI): 337 [M + H]

(1R)-1-(2-{4-[(5-ethyl-1,2-thiazol-3-yl)methyl]-1-methyl-1H-pyrazol-3-yl}-5-fluorophenyl)ethan-1-ol

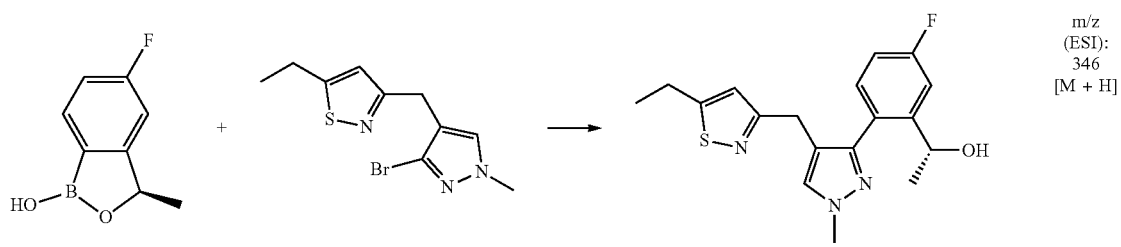

m/z (ESI): 346 [M + H]

(R)-1-(2-(4-((1-ethyl-1H-1,2,3-triazol-4-yl)methyl)isothiazol-5-yl)-5-fluorophenyl)ethan-1-ol

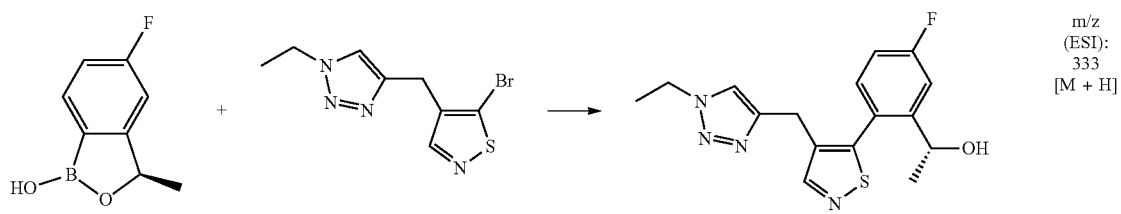

m/z (ESI): 333 [M + H]

-continued (R)-1-(2-(4-((1-ethyl-3-(trifluoromethyl)-1H-pyrazol-4-yl)methyl)-1-methyl-1H-pyrazol-3-yl)-5-fluorophenyl)ethan-1-ol

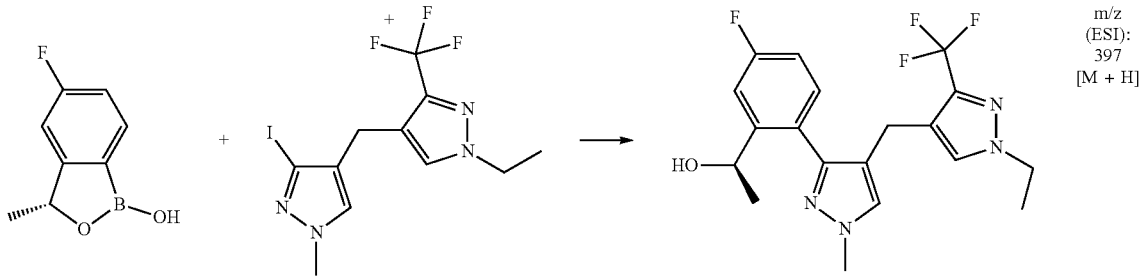

m/z (ESI): 397 [M + H]

(R)-5-((4-(4-fluoro-2-(1-hydroxyethyl)phenyl)thiazol-5-yl)methyl)-1-methyl-1H-pyrazole-3-carbonitrile

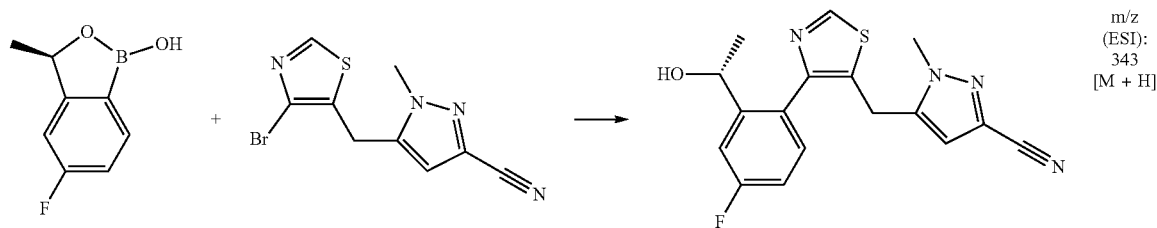

m/z (ESI): 343 [M + H]

(R)-1-(2-(4-((1-(cyclopropylmethyl)-1H-pyrazol-4-yl)methyl)-1-methyl-1H-pyrazol-3-yl)-5-fluorophenyl)ethan-1-ol

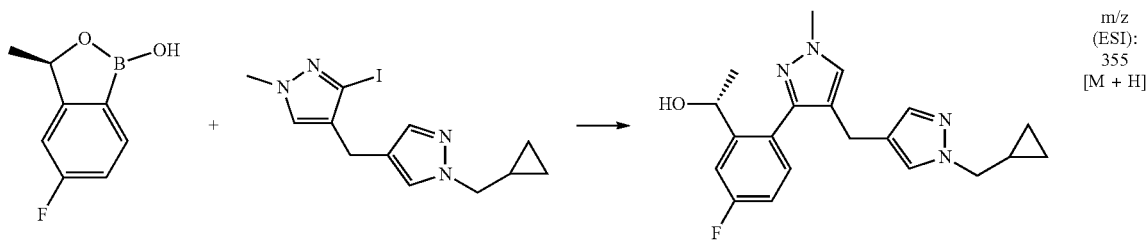

m/z (ESI): 355 [M + H]

(R)-5-((5-fluoro-2-(4-fluoro-2-(1-hydroxyethyl)phenyl)pyridin-3-yl)methyl)-1-methyl-1H-pyrazole-3-carbonitrile

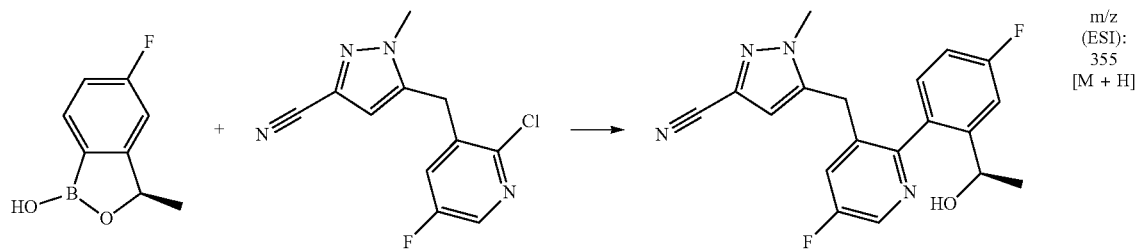

m/z (ESI): 355 [M + H]

(1R)-1-[2-(3-{[1-(cyclopropylmethyl)-1H-1,2,3-triazol-4-yl]methyl}-5-fluoropyridin-2-yl)-5-fluorophenyl]ethan-1-ol

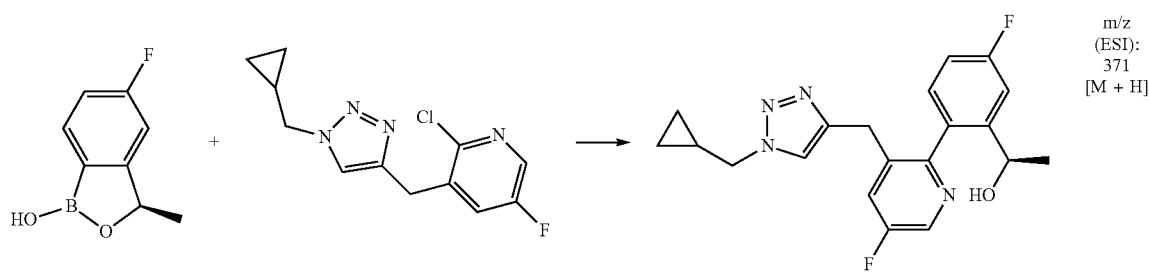

m/z (ESI): 371 [M + H]

-continued (R)-3-((3-(4-fluoro-2-(1-hydroxyethyl)phenyl)-1-methyl-1H-pyrazol-4-yl)methyl)-1-methyl-1H-pyrazole-5-carbonitrile

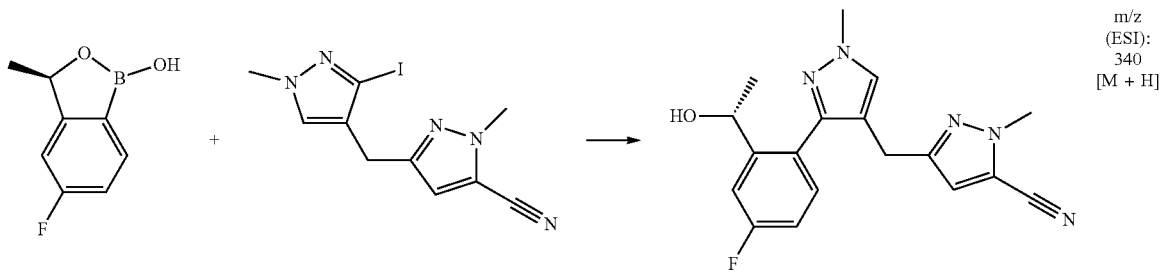

m/z (ESI): 340 [M + H]

(R)-3-((2-(4-fluoro-2-(1-hydroxyethyl)phenyl)pyridin-3-yl)methyl)-1-methyl-1H-pyrazole-5-carbonitrile

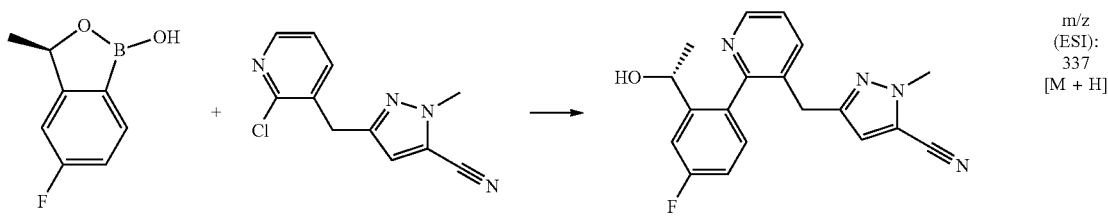

m/z (ESI): 337 [M + H]

(1R)-1-[2-(5-{[1-(cyclopropylmethyl)-1H-1,2,3-triazol-4-yl]methyl}-2-methyl-1,3-thiazol-4-yl)-5-fluorophenyl]ethan-1-ol

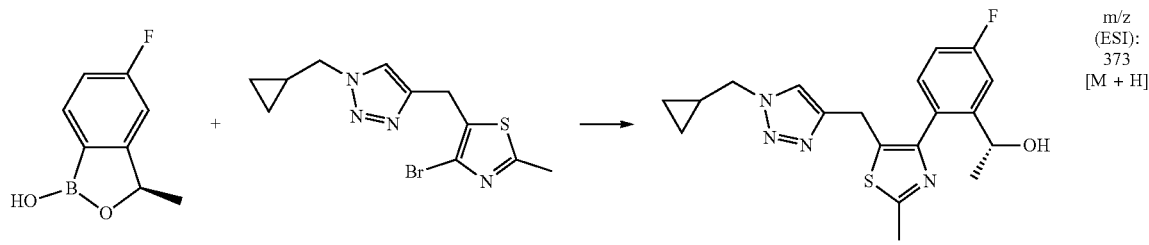

m/z (ESI): 373 [M + H]

(R)-1-(2-(3-((1-(cyclopropylmethyl)-1H-1,2,3-triazol-4-yl)methyl)pyridin-2-yl)-5-fluorophenyl)ethan-1-ol

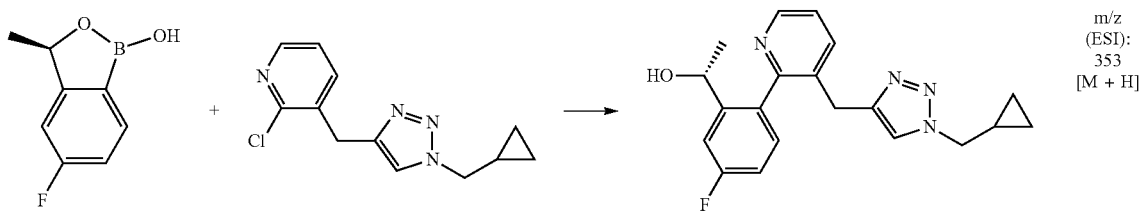

m/z (ESI): 353 [M + H]

(R)-5-((4'-fluoro-2'-(1-hydroxyethyl)-1,1'-biphenyl]-2-yl)methyl)-1-methyl-1H-pyrazole-3-carbonitrile

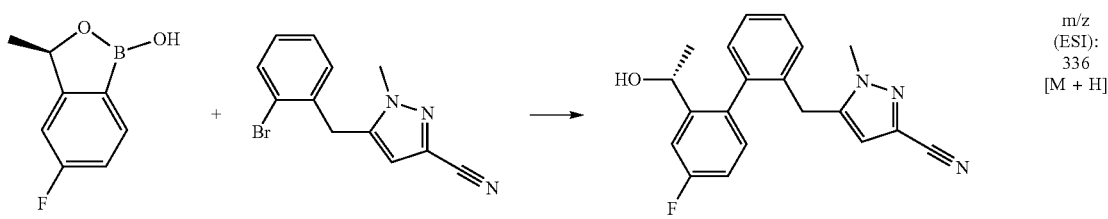

m/z (ESI): 336 [M + H]

(R)-1-(cyclopropylmethyl)-4-((2-(4-fluoro-2-(1-hydroxyethyl)phenyl)pyridin-3-yl)methyl)-1H-pyrazole-3-carbonitrile

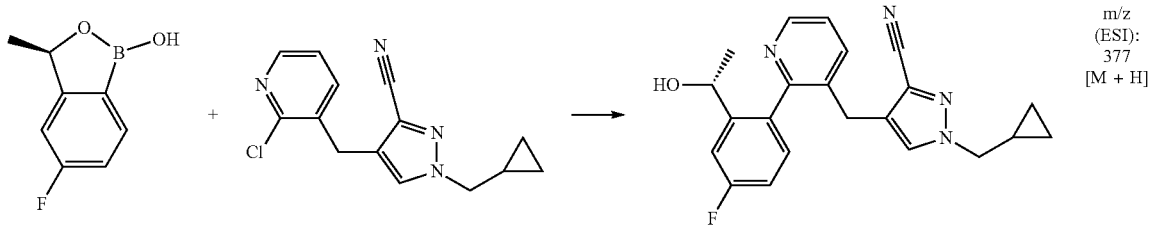

m/z (ESI): 377 [M + H]

(R)-1-(2-(5-(((1-(cyclopropylmethyl)-3-methyl-1H-pyrazol-4-yl)methyl)-2-methylthiazol-4-yl)-5-fluorophenyl)ethan-1-ol

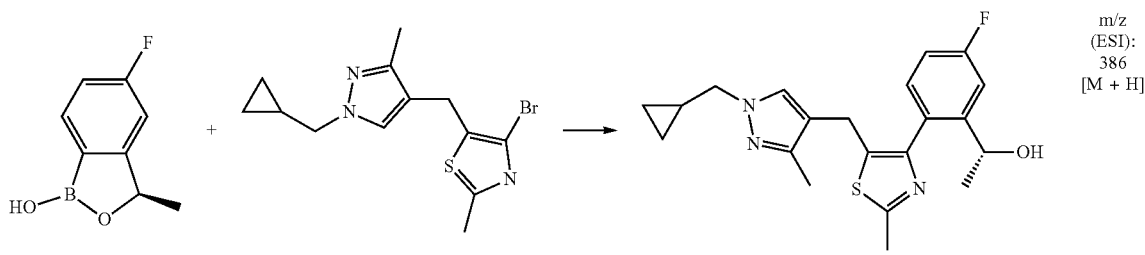

m/z (ESI): 386 [M + H]

(1R)-1-[2-(4-{[3-chloro-1-(cyclopropylmethyl)-1H-pyrazol-4-yl]methyl}-1-methyl-1H-pyrazol-3-yl)-5-fluorophenyl]ethan-1-ol

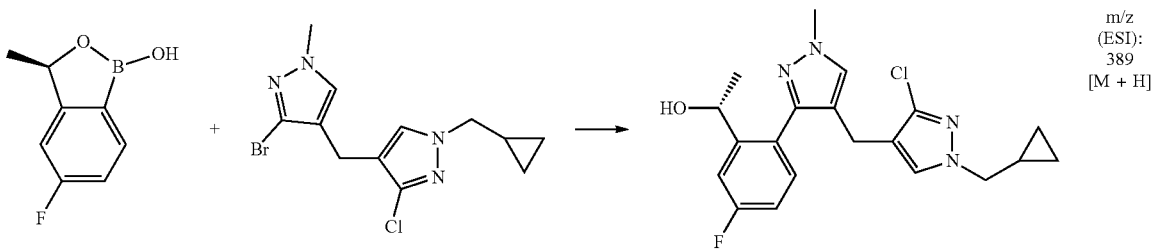

m/z (ESI): 389 [M + H]

(R)-1-(2-(4-((3-ethylisothiazol-5-yl)methyl)-1-methyl-1H-pyrazol-3-yl)-5-fluorophenyl)ethan-1-ol

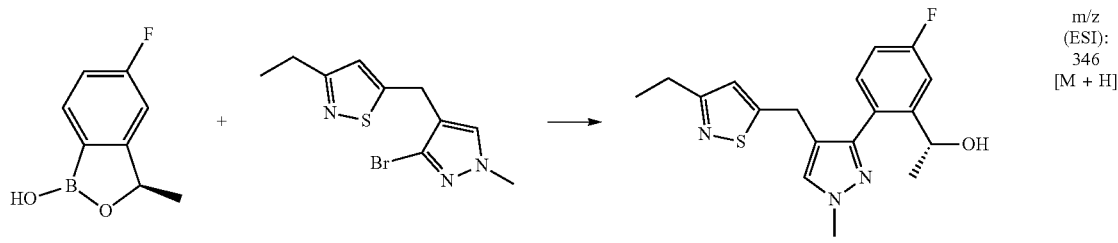

m/z (ESI): 346 [M + H]

(R)-1-(5-fluoro-2-(1-methyl-4-((1-(oxetan-3-yl)-1H-pyrazol-4-yl)methyl)-1H-pyrazol-3-yl)phenyl)ethan-1-ol

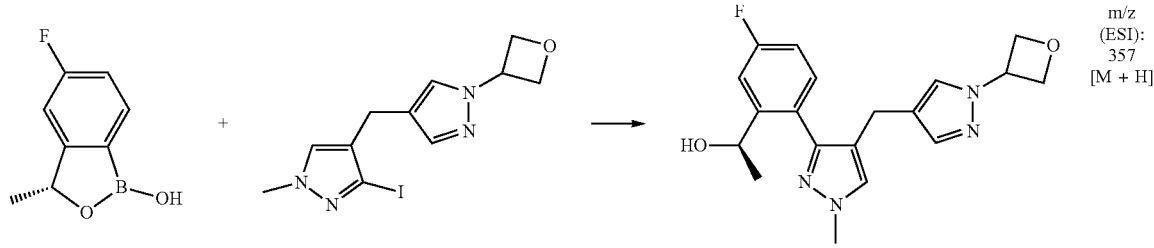

m/z (ESI): 357 [M + H]

-continued (R)-1-(2-(3-((1-(cyclopropylmethyl)-3-methyl-1H-pyrazol-4-yl)methyl)pyridin-2-yl)-5-fluorophenyl)ethan-1-ol

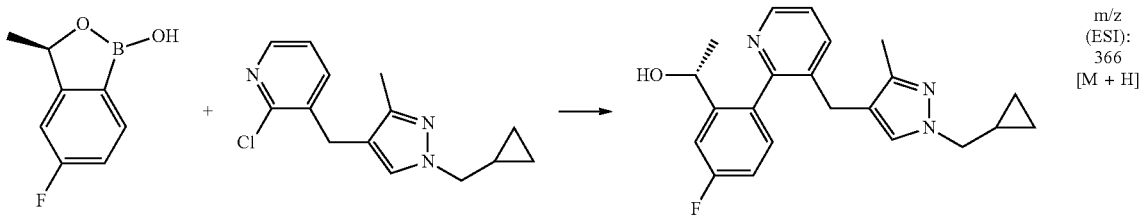

m/z (ESI): 366 [M + H]

(1R)-1-[2-(4-{[1-(cyclopropylmethyl)-1H-pyrazol-4-yl]methyl}-1-ethyl-1H-pyrazol-3-yl)-5-fluorophenyl]ethan-1-ol

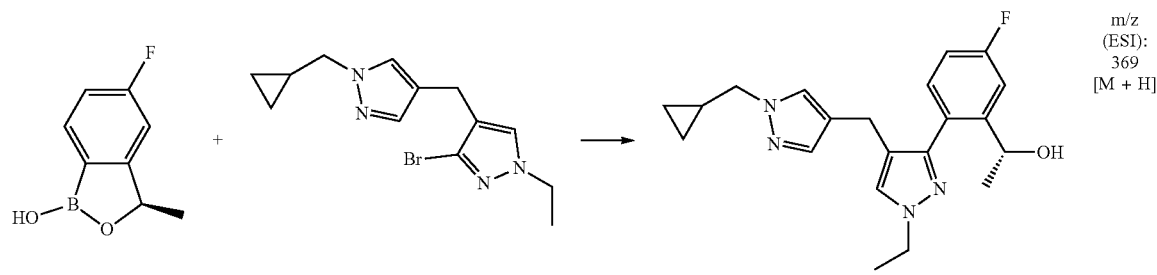

m/z (ESI): 369 [M + H]

(R)-1-(2-(3-((1-(cyclopropylmethyl)-1H-pyrazol-4-yl)methyl)pyridin-2-yl)-5-fluorophenyl)ethan-1-ol

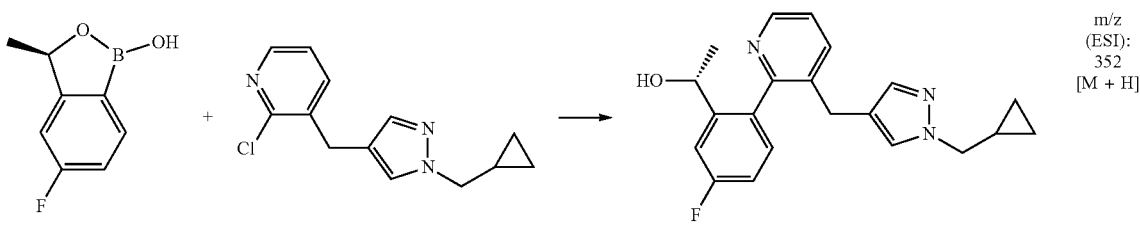

m/z (ESI): 352 [M + H]

(R)-1-(2-(4-((3-bromo-1-ethyl-1H-pyrazol-4-yl)methyl)-1-methyl-1H-pyrazol-3-yl)-5-fluorophenyl)ethan-1-ol

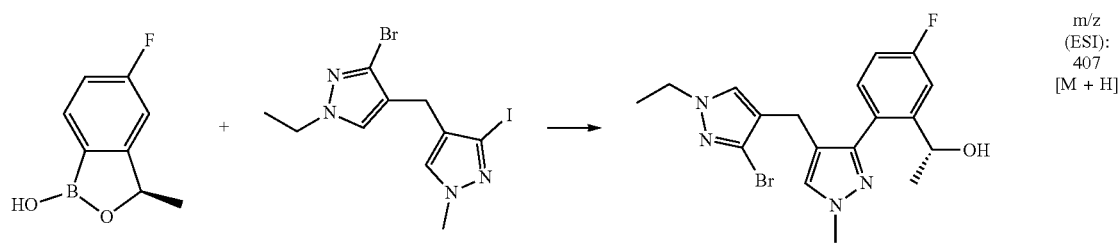

m/z (ESI): 407 [M + H]

(R)-1-(2-(4-((1-ethyl-1H-pyrazol-4-yl)methyl)-5-methoxy-1-methyl-1H-pyrazol-3-yl)-5-fluorophenyl)ethan-1-ol

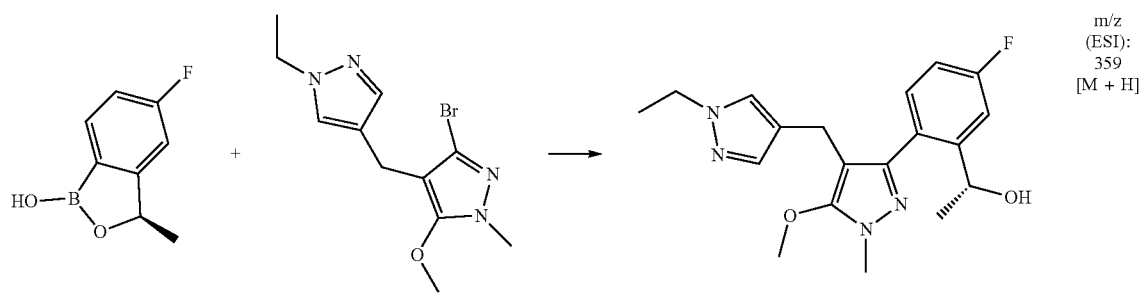

m/z (ESI): 359 [M + H]

-continued (R)-1-(2-(1-(tert-butyl)-4-((1-ethyl-1H-pyrazol-4-yl)methyl)-1H-pyrazol-3-yl)-5-fluorophenyl)ethan-1-ol

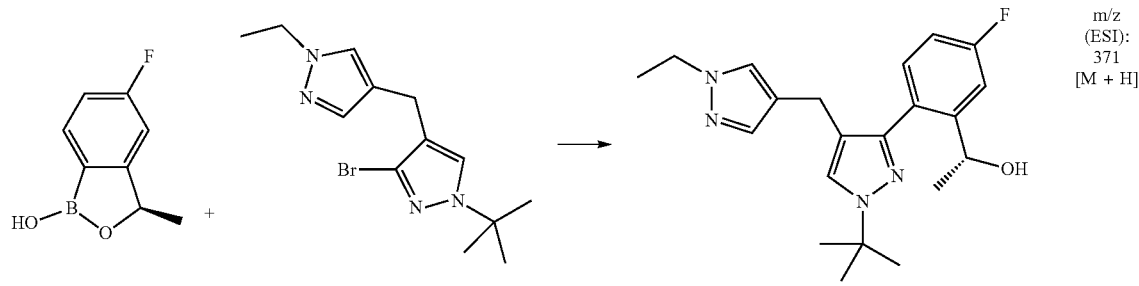

m/z (ESI): 371 [M + H]

(1R)-1-(2-{3-[(1-ethyl-1H-pyrazol-4-yl)methyl]-5-methoxypyridin-2-yl}-5-fluorophenyl)ethan-1-ol

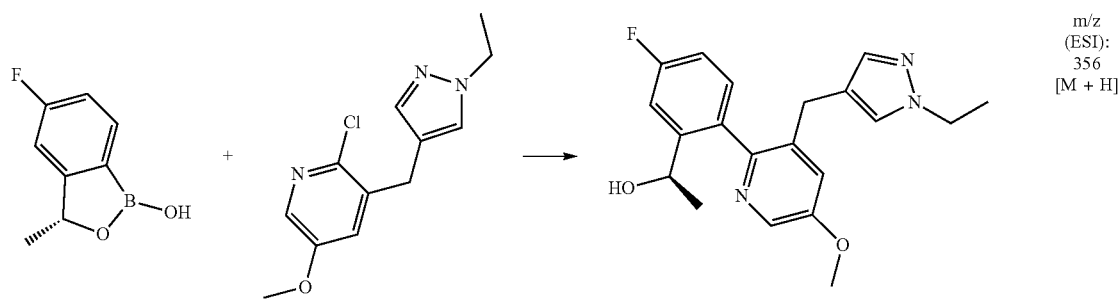

m/z (ESI): 356 [M + H]

(R)-1-(2-(3-((1-ethyl-1H-pyrazol-4-yl)methyl)-4-methoxypyridin-2-yl)-5-fluorophenyl)ethan-1-ol

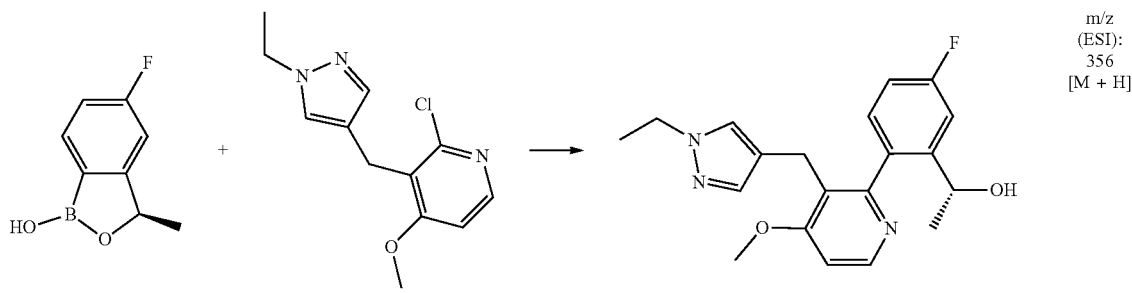

m/z (ESI): 356 [M + H]

(R)-1-(2-(3-((4-(cyclopropylmethyl)-1H-pyrazol-1-yl)methyl)pyridin-2-yl)-5-fluorophenyl)ethan-1-ol

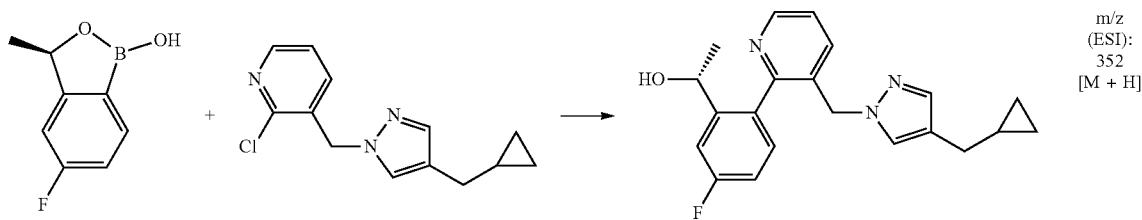

m/z (ESI): 352 [M + H]

(1R)-1-[2-(4-{[1-ethyl-3-(propan-2-yl)-1H-pyrazol-4-yl]methyl}-1-methyl-1H-pyrazol-3-yl)-5-fluorophenyl]ethan-1-ol

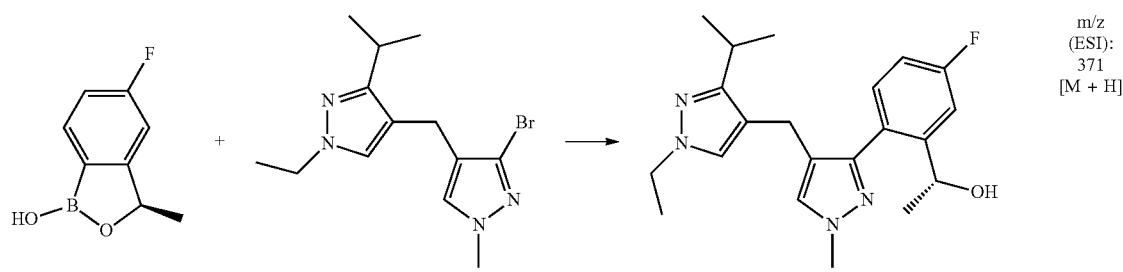

m/z (ESI): 371 [M + H]

-continued (R)-1-(2-(4-((1,3-diethyl-1H-pyrazol-4-yl)methyl)-1-methyl-1H-pyrazol-3-yl)-5-fluorophenyl)ethan-1-ol

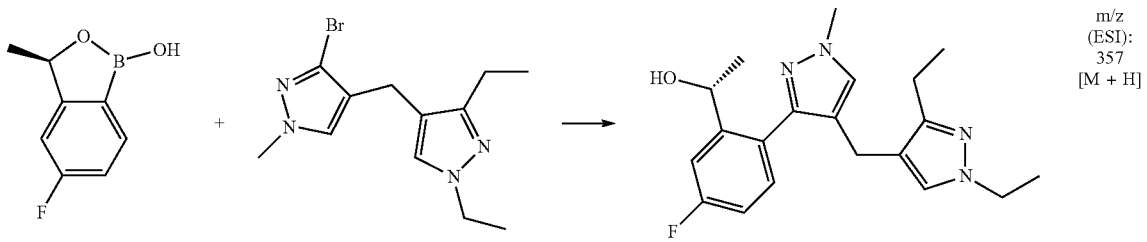

m/z (ESI): 357 [M + H]

(R)-1-(2-(4-((5-ethylisoxazol-3-yl)methyl)-1-methyl-1H-pyrazol-3-yl)-5-fluorophenyl)ethan-1-ol

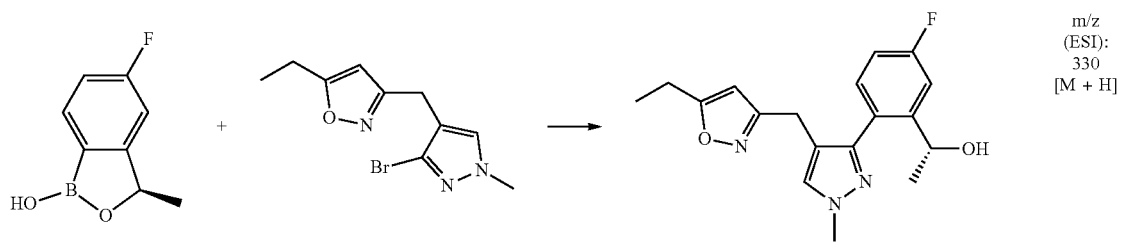

m/z (ESI): 330 [M + H]

(R)-1-(2-(4-((1-(cyclopropylmethyl)-1H-pyrazol-4-yl)methyl)-1-(difluoromethyl)-1H-pyrazol-3-yl)-5-fluorophenyl)ethan-1-ol

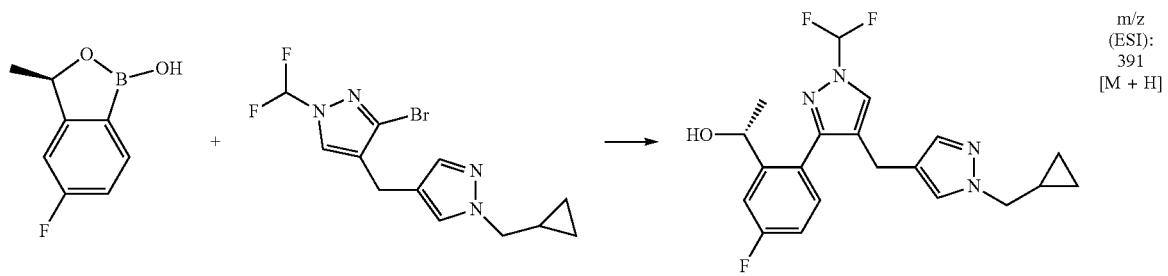

m/z (ESI): 391 [M + H]

(R)-1-(5-fluoro-2-(4-((1-isobutyl-1H-pyrazol-4-yl)methyl)-1-methyl-1H-pyrazol-3-yl)phenyl)ethan-1-ol

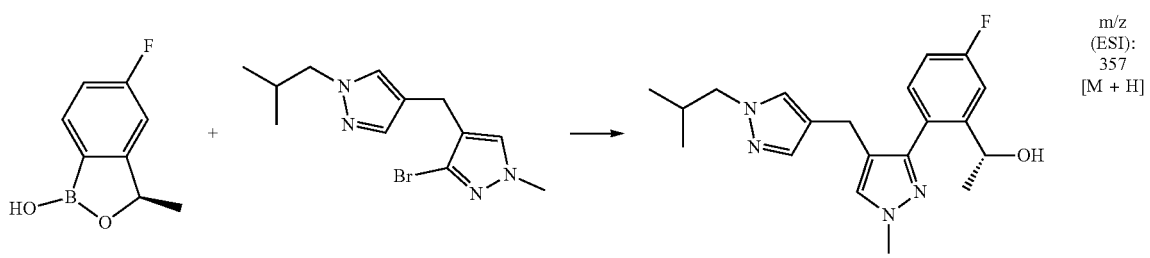

m/z (ESI): 357 [M + H]

(1R)-1-{5-fluoro-2-[1-methyl-4-({1-[(1-methylcyclopropyl)methyl]-1H-pyrazol-4-yl}methyl)-1H-pyrazol-3-yl]phenyl}ethan-1-ol

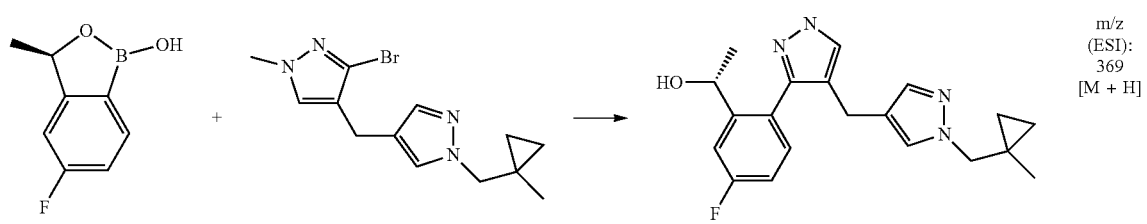

m/z (ESI): 369 [M + H]

-continued (R)-1-ethyl-4-((3-(4-fluoro-2-(1-hydroxyethyl)phenyl)-1-methyl-1H-pyrazol-4-yl)methyl)-1H-pyrazole-3-carbonitrile

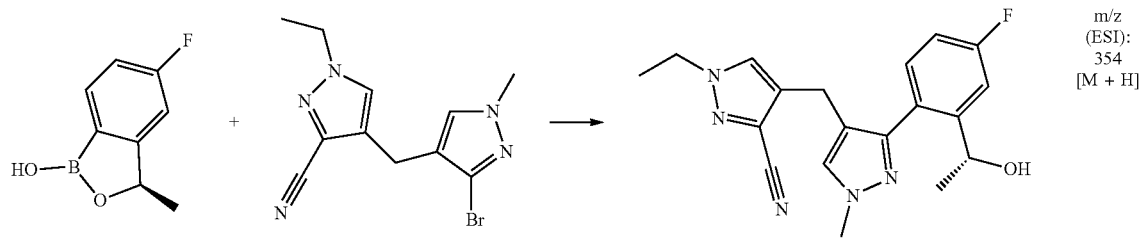

m/z (ESI): 354 [M + H]

1-((5-fluoro-2-(4-fluoro-2-(1-hydroxyethyl)phenyl)pyridin-3-yl)methyl)-1H-imidazole-4-carbonitrile

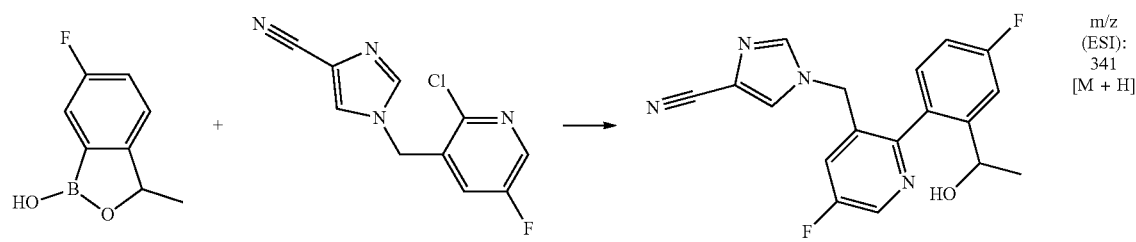

m/z (ESI): 341 [M + H]

1-((4-(4-fluoro-2-(1-hydroxyethyl)phenyl)thiazol-5-yl)methyl)-1H-imidazole-4-carbonitrile

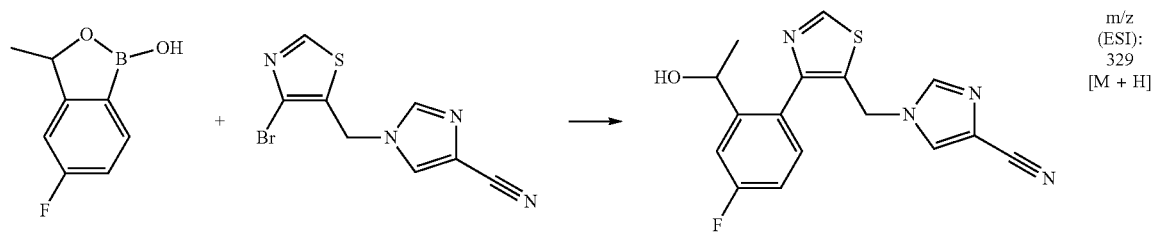

m/z (ESI): 329 [M + H]

1-({4-[4-fluoro-2-(1-hydroxyethyl)phenyl]-2-methyl-1,3-thiazol-5-yl}methyl)-1H-imidazole-4-carbonitrile

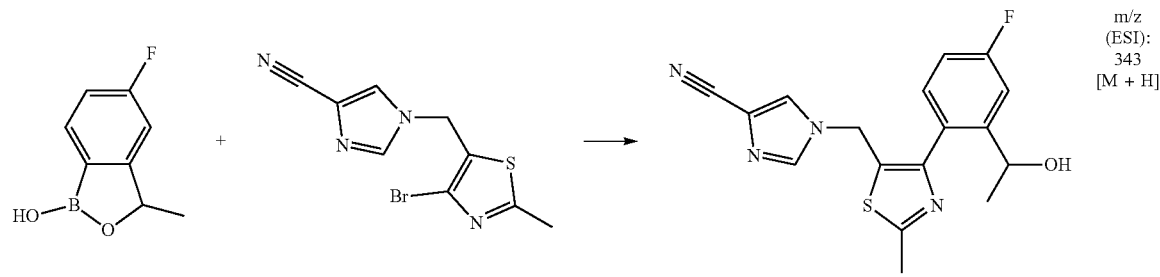

m/z (ESI): 343 [M + H]

1-((4-(4-fluoro-2-(1-hydroxyethyl)phenyl)-2-methylthiazol-5-yl)methyl)-1H-pyrazole-4-carbonitrile

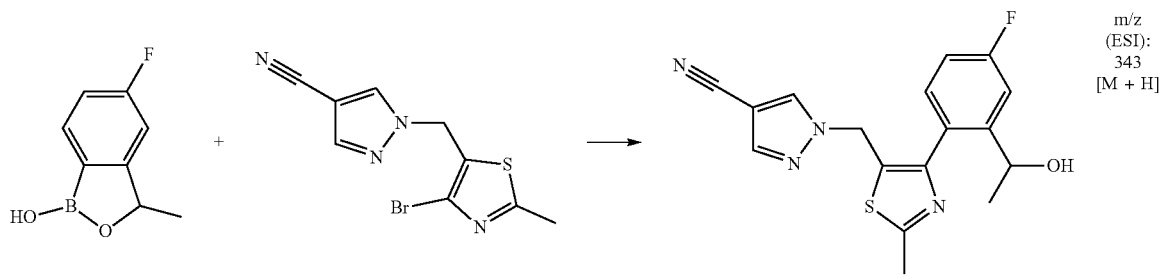

m/z (ESI): 343 [M + H]

-continued (R)-3-((1-(4-fluoro-2-(1-hydroxyethyl)phenyl)-1H-pyrazol-5-yl)methyl)-1-((2-(trimethylsilyl)ethoxy)methyl)-1H-pyrazole-5-carbonitrile

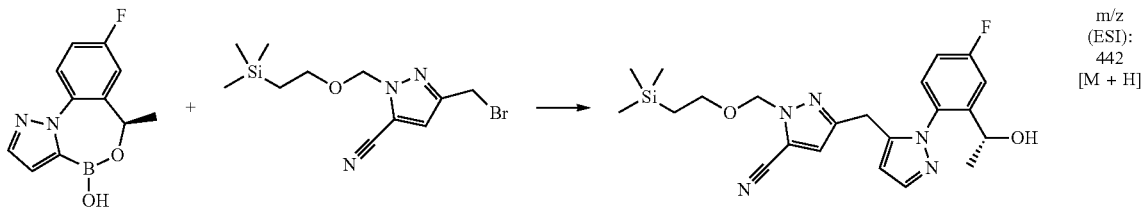

m/z (ESI): 442 [M + H]

1-(2-(5-((4-(difluoromethyl)-1H-pyrazol-1-yl)methyl)-2-methylthiazol-4-yl)-5-fluorophenyl)ethan-1-ol

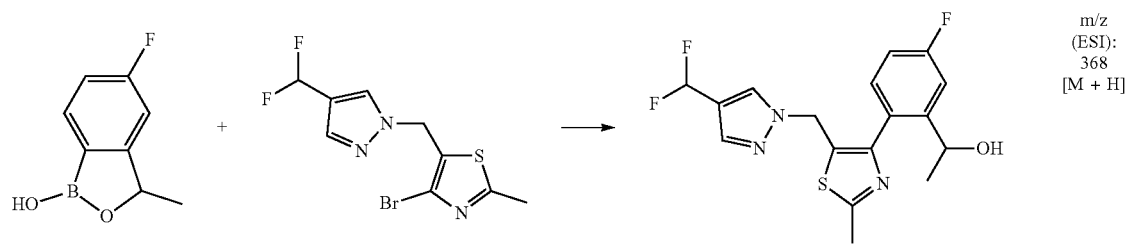

m/z (ESI): 368 [M + H]

1-[2-(5-{[1-(difluoromethyl)-1H-pyrazol-4-yl]methyl}-2-methyl-1,3-thiazol-4-yl)-5-fluorophenyl]ethan-1-ol

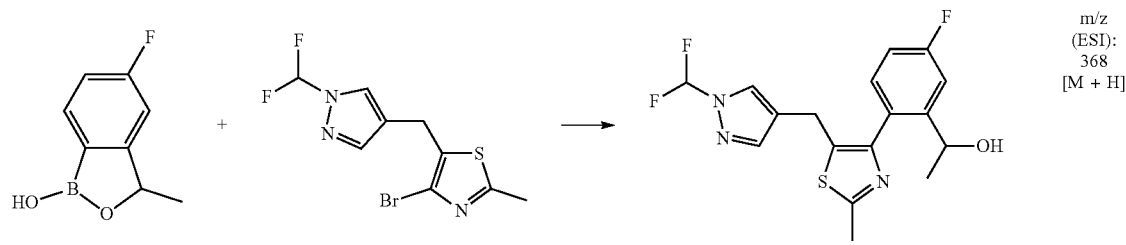

m/z (ESI): 368 [M + H]

1-(2-(4-((3-ethylisoxazol-5-yl)methyl)-1-methyl-1H-pyrazol-3-yl)-3,5-difluorophenyl)ethan-1-ol

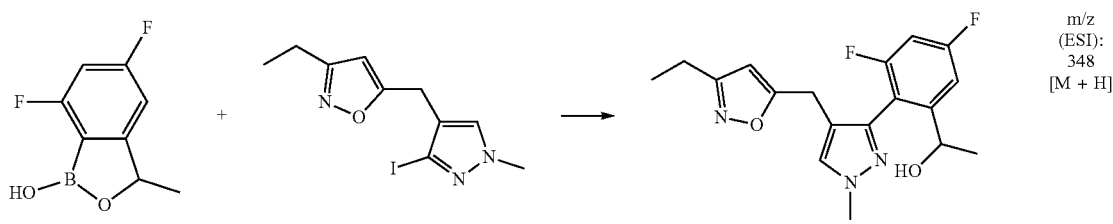

m/z (ESI): 348 [M + H]

1-((5-(4-fluoro-2-(1-hydroxyethyl)phenyl)-1-methyl-1H-pyrazol-4-yl)methyl)-1H-pyrazole-4-carbonitrile

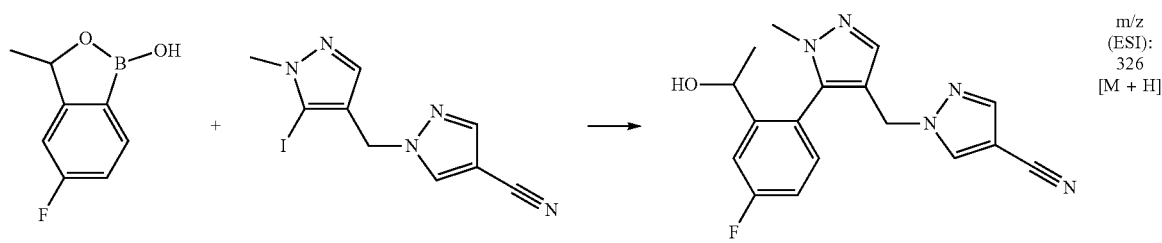

m/z (ESI): 326 [M + H]

3-((5-(5-fluoro-2-(1-hydroxyethyl)phenyl)-1-methyl-1H-pyrazol-4-yl)methyl)-1-((2-(trimethylsilyl)ethoxy)methyl)-1H-pyrazole-5-carbonitrile

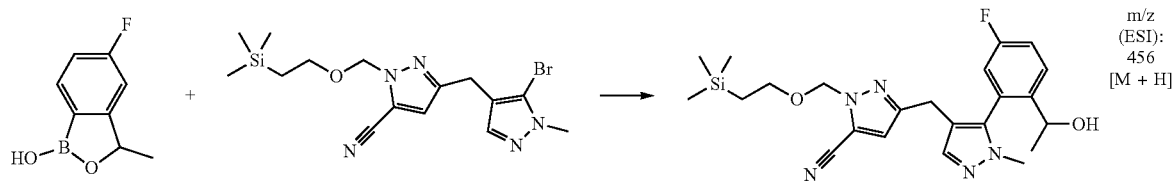

m/z (ESI): 456 [M + H]

(R)-1-(2-(4-((3-ethylisoxazol-5-yl)methyl)-1-methyl-1H-pyrazol-3-yl)-5-fluorophenyl)ethan-1-ol

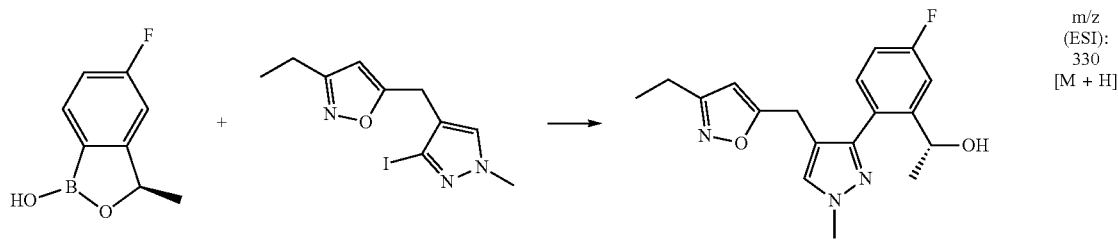

m/z (ESI): 330 [M + H]

1-(2-(4-((5-bromo-1-methyl-1H-pyrazol-4-yl)methyl)-1-ethyl-1H-pyrazol-5-yl)-5-fluorophenyl)ethan-1-ol

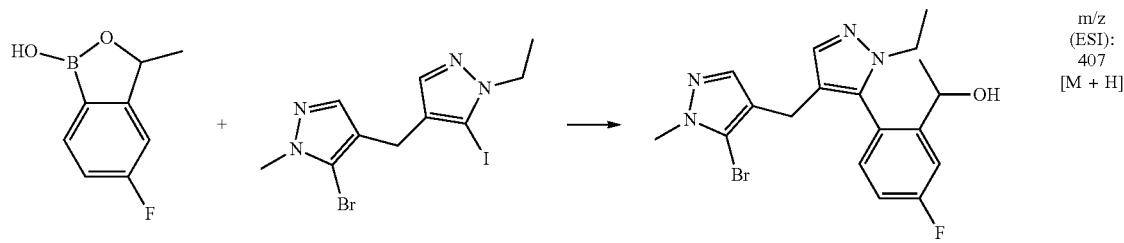

m/z (ESI): 407 [M + H]

(R)-1-(2-(4-((3-ethyl-1-methyl-1H-pyrazol-5-yl)methyl)-1-methyl-1H-pyrazol-3-yl)-5-fluorophenyl)ethan-1-ol

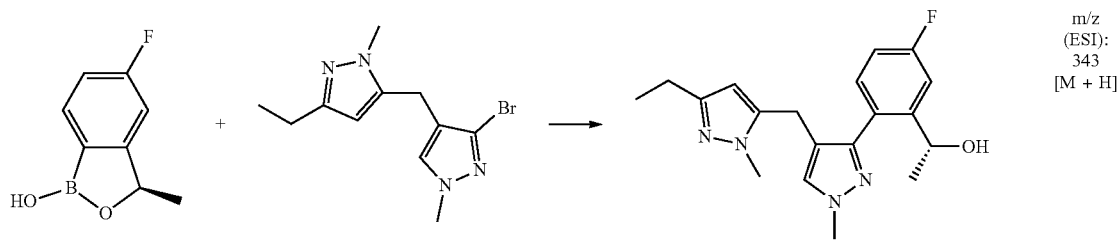

m/z (ESI): 343 [M + H]

(R)-1-(2-(4-((3-(2,2-difluoroethyl)-1-methyl-1H-pyrazol-5-yl)methyl)-1-methyl-1H-pyrazol-3-yl)-5-fluorophenyl)ethan-1-ol

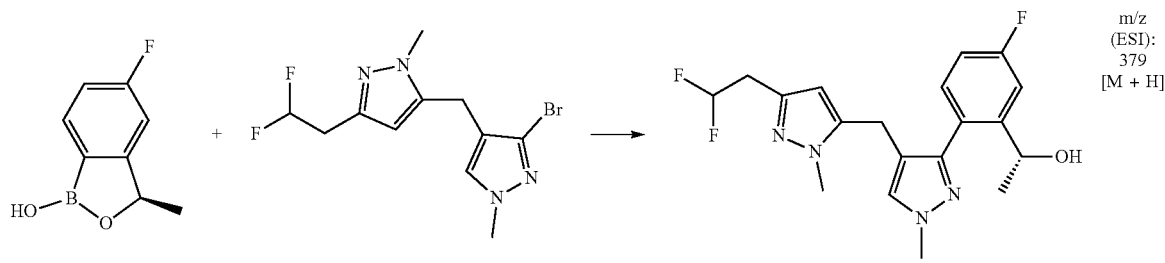

m/z (ESI): 379 [M + H]

-continued (R)-1-(2-(5-((3-ethyl-1-methyl-1H-pyrazol-5-yl)methyl)-2-methylthiazol-4-yl)-5-fluorophenyl)ethan-1-ol

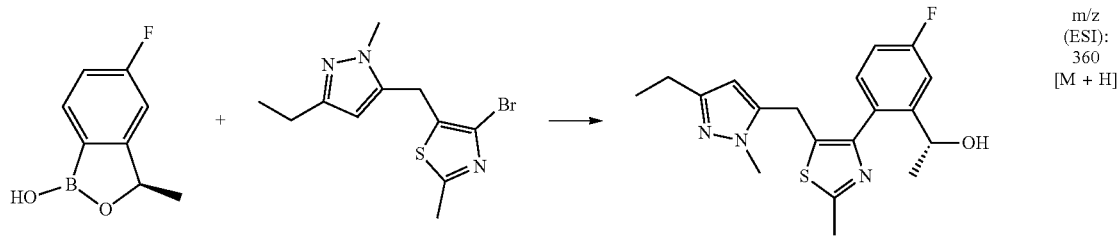

m/z (ESI): 360 [M + H]

(R)-1-(2-(5-((5-cyclobutyl-1-methyl-1H-pyrazol-3-yl)methyl)-1H-pyrazol-1-yl)-5-fluorophenyl)ethan-1-ol

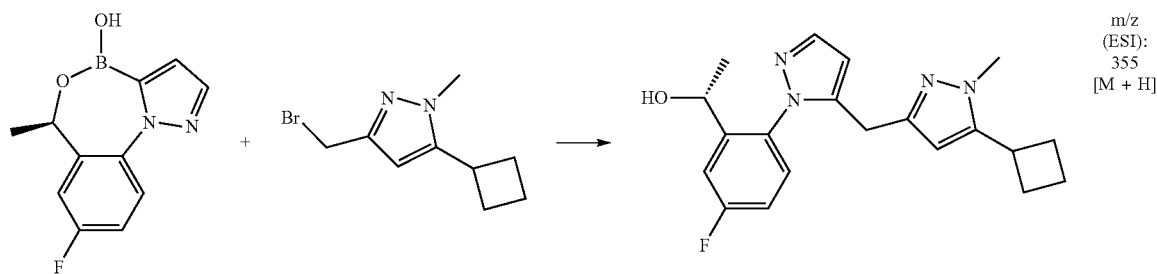

m/z (ESI): 355 [M + H]

(R)-1-(2-(4-((3-(cyclopropylmethyl)-1-methyl-1H-pyrazol-5-yl)methyl)-1-methyl-1H-pyrazol-3-yl)-5-fluorophenyl)ethan-1-ol

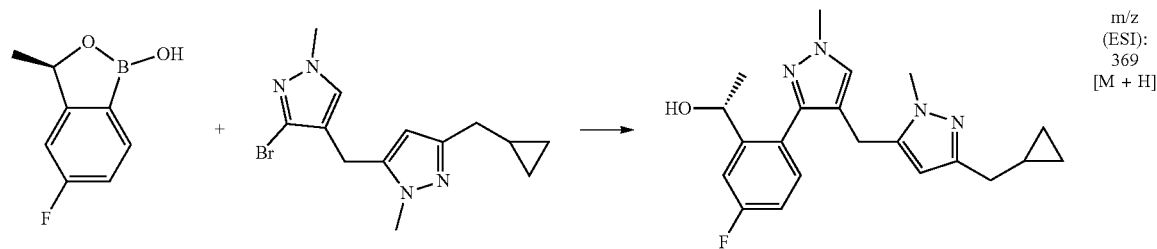

m/z (ESI): 369 [M + H]

(R)-1-(2-(5-((5-(cyclopropylmethyl)-1-methyl-1H-pyrazol-3-yl)methyl)-1H-pyrazol-1-yl)-5-fluorophenyl)ethan-1-ol

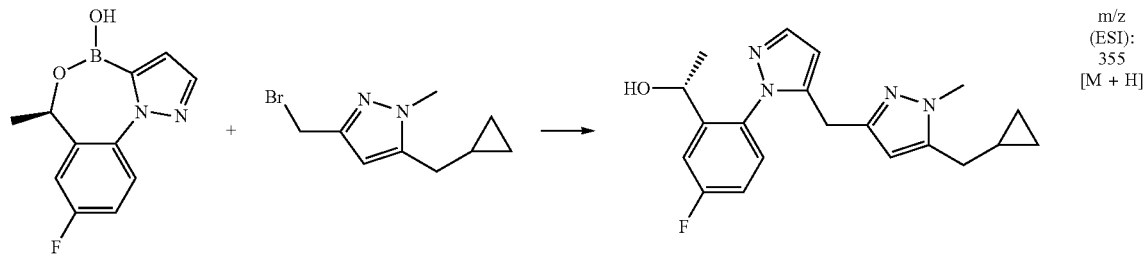

m/z (ESI): 355 [M + H]

(R)-1-(2-(4-((5-(cyclopropylmethyl)-1-methyl-1H-pyrazol-3-yl)methyl)-1-methyl-1H-pyrazol-3-yl)-5-fluorophenyl)ethan-1-ol

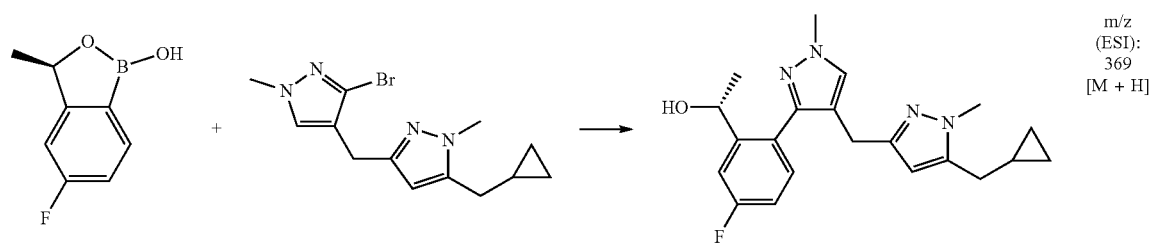

m/z (ESI): 369 [M + H]

453

Synthesis of diethyl 1-((2-(trimethylsilyl)ethoxy)methyl)-1H-pyrazole-3,5-dicarboxylate

454

Synthesis of (2-{5-[(1-ethyl-1H-pyrazol-4-yl)methyl]-2-methyl-1,3-thiazol-4-yl}-5-fluorophenyl)methanol

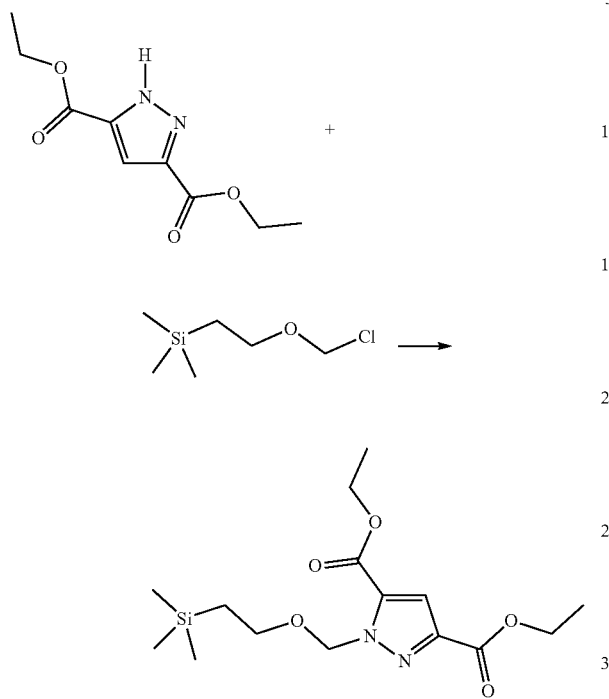

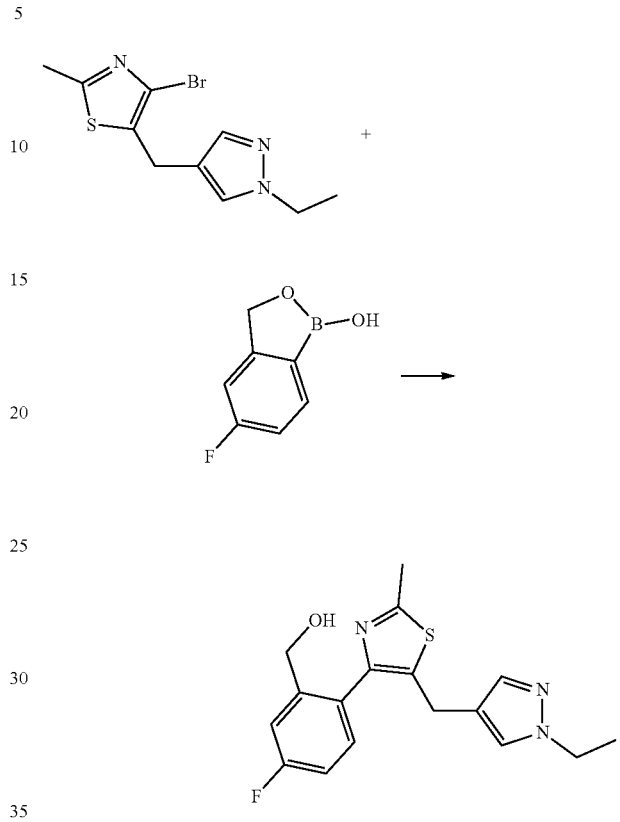

To a solution of diethyl 1H-pyrazole-3,5-dicarboxylate (10.0 g, 47.1 mmol) in THF (150 mL), was added sodium hydride (60%, dispersion in mineral oil, 2.07 g, 51.8 mmol) in portions at 0° C., and the resulting mixture was stirred at 0° C. for 30 min. Then a solution of (2-(chloromethoxy)ethyl)trimethylsilane (9.2 mL, 52 mmol) in THF (150 mL) was added dropwise and the reaction mixture was stirred at r.t. for 2 h. After 2 h, the reaction mixture was quenched by adding sat. aq. NH$_4$Cl solution (100 mL), extracted with EA (3×100 mL), combined all organic phases, washed with brine (100 mL), dried over anhydrous Na$_2$SO$_4$, filtered and concentrated in vacuo. The residue was purified by column chromatography on silica gel with EA in PE (0→10%, V/V) to give diethyl 1-((2-(trimethylsilyl)ethoxy)methyl)-1H-pyrazole-3,5-dicarboxylate (10.0 g, 62%) as a yellow solid. LC/MS ESI (m/z): 343 [M+H]$^+$.

The following intermediates were synthesized using a similar experimental protocol:

A mixture of 4-bromo-5-[(1-ethyl-1H-pyrazol-4-yl)methyl]-2-methyl-1,3-thiazole (210 mg, 0.73 mmol), 5-fluoro-1,3-dihydro-2,1-benzoxaborol-1-ol (223 mg, 1.47 mmol), Pd(PPh$_3$)$_4$ (85 mg, 0.073 mmol) and disodium carbonate (156 mg, 1.47 mmol), in EtOH (5 mL), water (2.5 mL), and toluene (1 mL) was stirred at 95° C. for 4 h under an N$_2$ atmosphere. The reaction was filtered, and the filtrate was diluted with EA (50 mL), washed with brine (2×20 mL), dried over anhydrous Na$_2$SO$_4$ and concentrated. The residue was purified by flash chromatography (0→30% EtOAc in PE) to give (2-{5-[(1-ethyl-1H-pyrazol-4-yl)methyl]-2-methyl-1,3-thiazol-4-yl}-5-fluorophenyl)methanol (220 mg, 47%). LC/MS ESI (m/z): 332 [M+H]$^+$.

The following intermediates were synthesized using a similar experimental protocol:

3-((5-bromo-1-methyl-1H-pyrazol-4-yl)methyl)-1-((2-(trimethylsilyl)ethoxy)methyl)-1H-pyrazole-5-carbonitrile m/z (ESI): 396 [M + H]

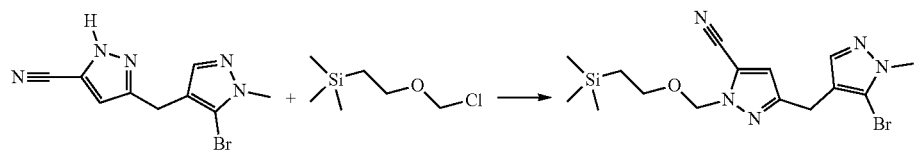

5-((2-(4-fluoro-2-(hydroxymethyl)phenyl)pyridin-3-yl)methyl)-1-methyl-1H-pyrazole-3-carbonitrile

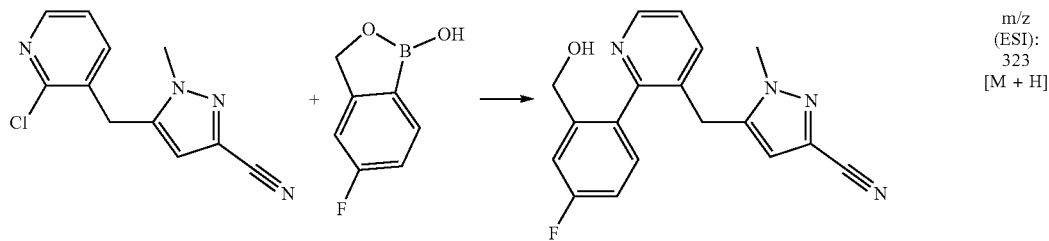

m/z (ESI): 323 [M + H]

5-({4-[4-fluoro-2(hydroxymethyl)phenyl]-2-methyl-1,3-thiazol-5-yl}methyl)-1-methyl-1H-pyrazole-3-carbonitrile

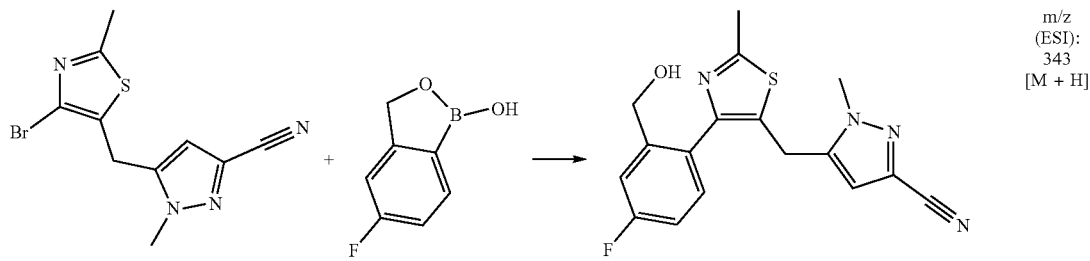

m/z (ESI): 343 [M + H]

(2-(4-((1-(cyclopropylmethyl)-3-methyl-1H-pyrazol-4-yl)methyl)-1-methyl-1H-pyrazol-3-yl)-5-fluorophenyl)methanol

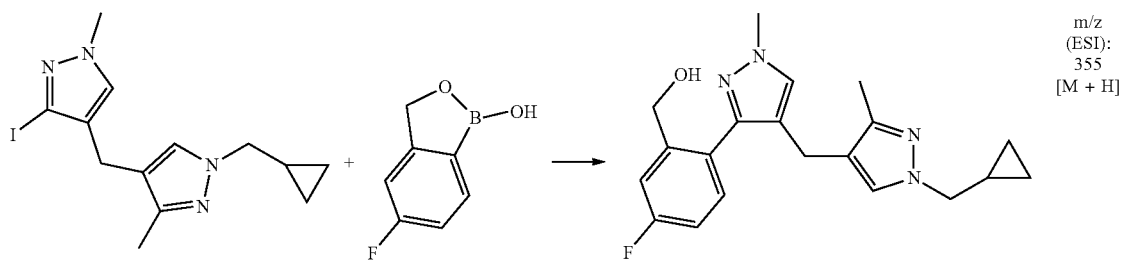

m/z (ESI): 355 [M + H]

(2-(4-((1-(cyclopropylmethyl)-1H-pyrazol-4-yl)methyl)-1-methyl-1H-pyrazol-3-yl)-5-fluorophenyl)methanol

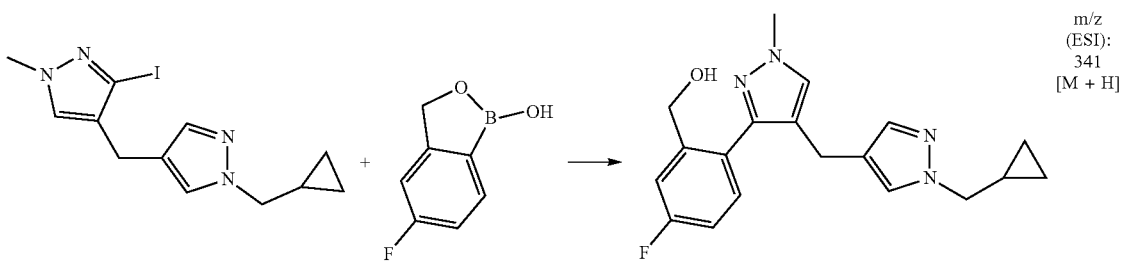

m/z (ESI): 341 [M + H]

(2-(3-((3-ethyl-1-methyl-1H-pyrazol-5-yl)methyl)pyridin-2-yl)-5-fluorophenyl)methanol

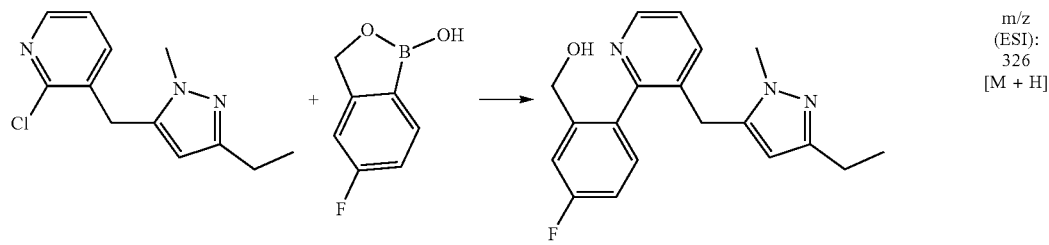

m/z (ESI): 326 [M + H]

(2-(5-((3-ethyl-1-methyl-1H-pyrazol-5-yl)methyl)-2-methylthiazol-4-yl)-5-fluorophenyl)methanol

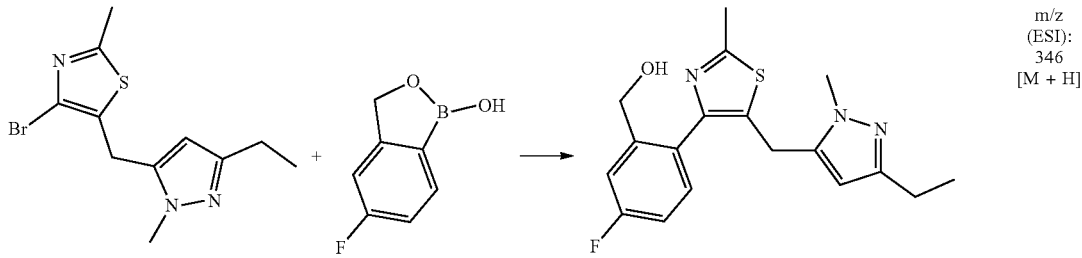

m/z (ESI): 346 [M + H]

(2-(4-((3-ethyl-1-methyl-1H-pyrazol-5-yl)methyl-1-methyl-1H-pyrazol-3-yl)-5-fluorophenyl)methanol

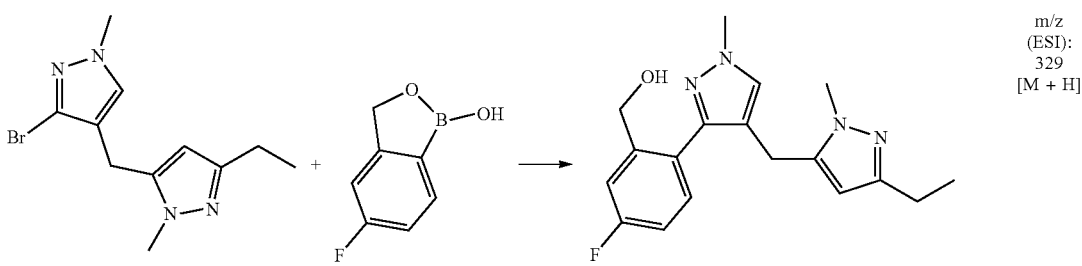

m/z (ESI): 329 [M + H]

Synthesis of (2-(1-((5-bromo-1-ethyl-1H-pyrazol-4-yl)methyl)-1H-imidazol-2-yl)-5-fluorophenyl)methanol

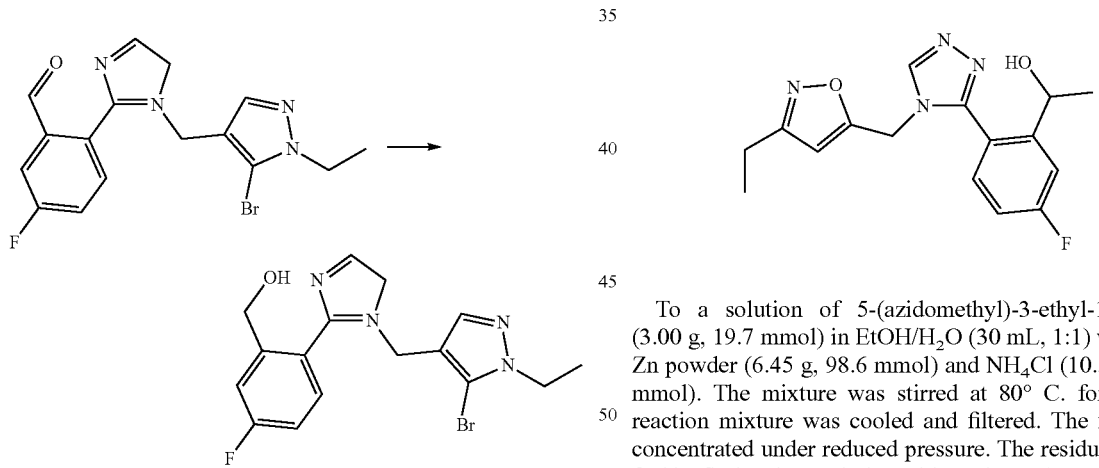

To a mixture of 2-(1-((5-bromo-1-ethyl-1H-pyrazol-4-yl)methyl)-1H-imidazol-2-yl)-5-fluorobenzaldehyde (380 mg, 1.01 mmol) in CH$_3$OH (5 mL) was added NaBH$_4$ (76.2 mg, 2.01 mmol) at 0° C. The reaction was stirred at 25° C. overnight. The mixture was concentrated under reduced pressure. EtOH (9 mL) and H$_2$O (1 mL) were added to this residue and the mixture was refluxed for 1 h. The mixture concentrated under reduced pressure to give a residue, which was purified by column chromatography on silica gel eluted with PE/EtOAc (100:1--1:1) to give (2-(1-((5-bromo-1-ethyl-1H-pyrazol-4-yl)methyl)-1H-imidazol-2-yl)-5-fluorophenyl)methanol (0.3 g, yield: 79%) as a yellow oil. LC/MS ESI (m/z): 379 [M+H]$^+$.

Synthesis of 1-(2-{4-[(3-ethyl-1,2-oxazol-5-yl)methyl]-4H-1,2,4-triazol-3-yl}-5-fluorophenyl)ethan-1-ol To a solution of 5-(azidomethyl)-3-ethyl-1,2-oxazole (3.00 g, 19.7 mmol) in EtOH/H$_2$O (30 mL, 1:1) were added Zn powder (6.45 g, 98.6 mmol) and NH$_4$Cl (10.55 g, 197.2 mmol). The mixture was stirred at 80° C. for 1 h. The reaction mixture was cooled and filtered. The filtrate was concentrated under reduced pressure. The residue was purified by flash column eluting with EA in PE (0→50%) to give (3-ethyl-1,2-oxazol-5-yl)methanamine (1.8 g, 72%) as a pale-yellow oil.

LC/MS (ESI): m/z=127 [M+H]$^+$.

A solution of (E)-N'-(4-fluoro-2-iodobenzoyl)-N,N-dimethylformohydrazonamide (2.80 g, 8.36 mmol) and (3-ethyl-1,2-oxazol-5-yl)methanamine (1.05 g, 8.36 mmol) in AcOH (30 mL) was stirred for 16 h at 80° C. The reaction mixture was concentrated under reduced pressure and the residue was dissolved in EA (50 mL). The organic layer was washed with aq. NaHCO$_3$, dried over Na$_2$SO$_4$, filtered, and concentrated. The residue was purified by flash column eluting with EA in PE (0→50%) to give 4-[(3-ethyl-1,2-oxazol-5-yl)methyl]-3-(4-fluoro-2-iodophenyl)-4H-1,2,4-triazole (360 mg, 11%) as a yellow solid. MS (ESI): m/z=399 [M+H]$^+$.

To a solution of 4-[(3-ethyl-1,2-oxazol-5-yl)methyl]-3-(4-fluoro-2-iodophenyl)-4H-1,2,4-triazole (360 mg, 0.90 mmol), tributyl(1-ethoxyethenyl)stannane (327 mg, 0.900 mmol), and CuI (17 mg, 0.09 mmol) in toluene (30 mL) was added Pd(PPh₃)₄(105 mg, 0.09 mmol). The reaction mixture was stirred for 16 h at 90° C., cooled, and filtered. The filtrate was concentrated under reduced pressure. The residue was dissolved in THF (10 mL) and 1 N aq. HCl (5 mL) was added. The mixture was stirred for 1 h at r.t., neutralized with Na₂CO₃ to pH 8, and thrice extracted with EA (20 mL). The extracts were dried over Na₂SO₄, and concentrated under reduced pressure. The residue was purified by flash chromatography with EA in PE (0→50%). The concentrate was dissolved in MeOH (10 mL) and NaBH₄ (61.1 mg, 1.81 mmol) was added. The mixture was stirred for 0.5 h, then quenched with sat. aq. NH₄Cl, and extracted with EA (50 mL). The organic layer was dried over Na₂SO₄, and concentrated under reduced pressure. The residue was purified by flash column eluting with MeOH in DCM (0→3%) to give 1-(2-{4-[(3-ethyl-1,2-oxazol-5-yl)methyl]-4H-1,2,4-triazol-3-yl}-5-fluorophenyl)ethan-1-ol (80 mg, 28%) as a colorless oil. MS (ESI) m/z=317 [M+H]⁺.

Synthesis of 1-{[1-(2-acetyl-4-fluorophenyl)-1H-pyrazol-5-yl]methyl}-1H-imidazole-4-carbonitrile

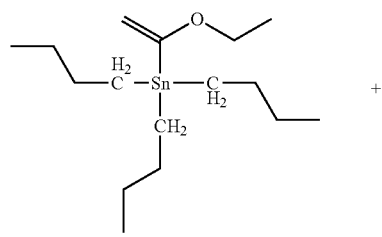

+

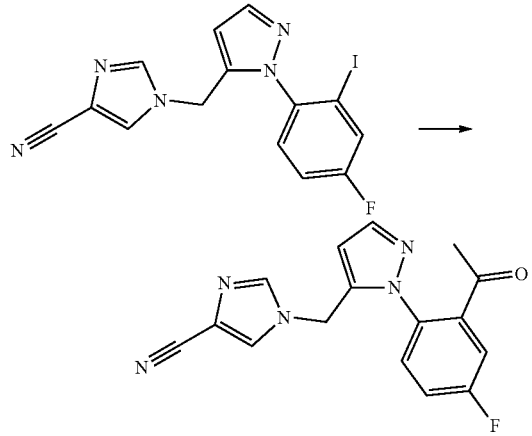

To a solution of 1-{[1-(4-fluoro-2-iodophenyl)-1H-pyrazol-5-yl]methyl}-1H-imidazole-4-carbonitrile (1.70 g, 4.32 mmol) in toluene (20 mL) was added Pd(PPh₃)₄(500 mg, 0.430 mmol), tributyl(1-ethoxyethenyl)stannane (3.12 g, 8.64 mmol), and catalytic CuI. The mixture was thrice degassed under N₂ and then stirred at 120° C. for 16 h. The reaction mixture was quenched with an aq. KF solution and extracted with EtOAc. The separated organic layer was concentrated to dryness. Aq. HCl (10 mL, 1N) and THF (10 mL) were added, and the mixture was stirred at r.t. for 1 h. The mixture was twice extracted with EtOAc, and the combined organic layers were washed with brine, dried with anhydrous Na₂SO₄ and concentrated. The residue was purified by flash chromatography (0-4% MeOH in DCM) to give 1-{[1-(2-acetyl-4-fluorophenyl)-1H-pyrazol-5-yl]methyl}-1H-imidazole-4-carbonitrile (1.21 g, yield: 90%) as yellow oil. LC/MS (ESI) m/z: 310 [M+H]⁺.

The following intermediates were synthesized using a similar experimental protocol:

1-(2-(5-((5-bromo-1-ethyl-1H-pyrazol-4-yl)methyl)-1H-1,2,3-triazol-1-yl)-5-fluorophenyl)ethanone

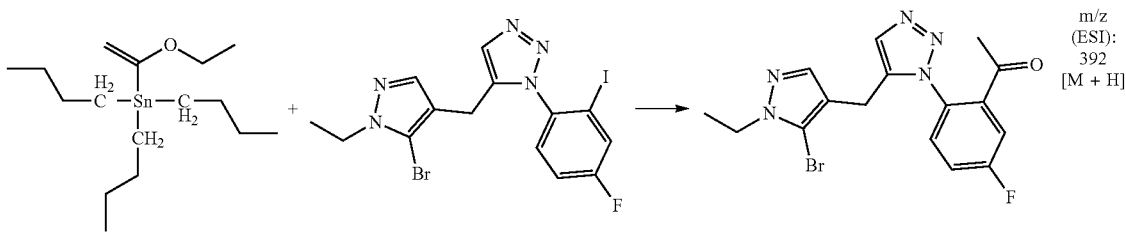

m/z (ESI): 392 [M + H]

1-(2-(1-((5-bromo-1-ethyl-1H-pyrazol-4-yl)methyl)-4-methyl-1H-imidazol-2-yl)-5-fluorophenyl)ethanone

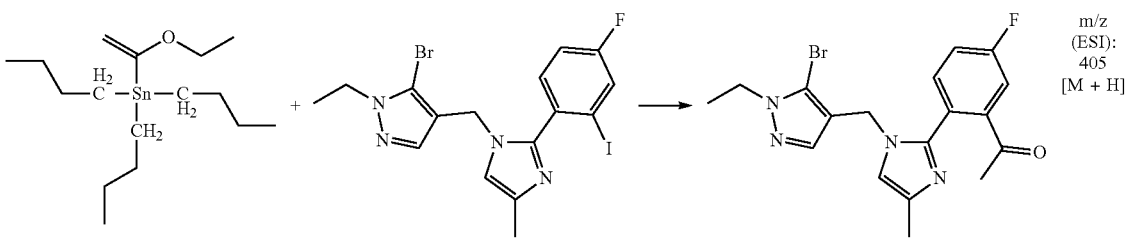

m/z (ESI): 405 [M + H]

1-{[1-(2-acetyl-4-fluorophenyl)-3-methyl-1H-pyrazol-5-yl]methyl}-1H-imidazole-4-carbonitrile

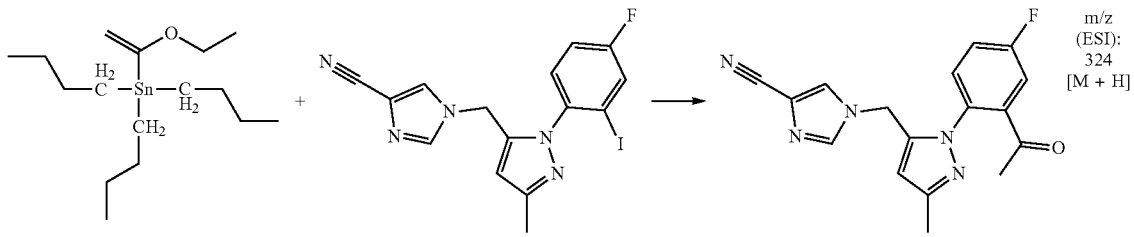

m/z (ESI): 324 [M + H]

1-{[1-(2-acetyl-4-fluorophenyl)-1H-pyrazol-5-yl]methyl}-1H-pyrazole-4-carbonitrile

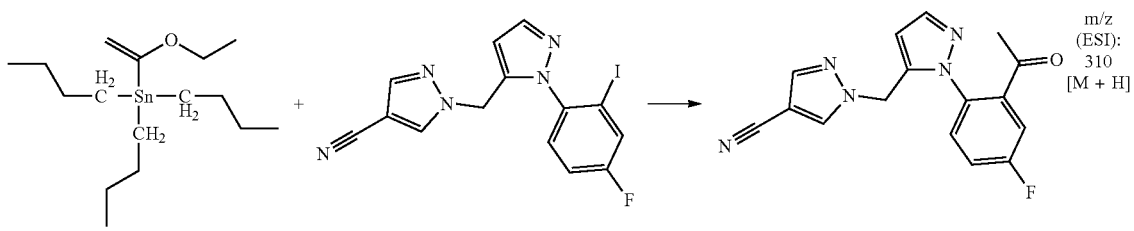

m/z (ESI): 310 [M + H]

1-(2-(5-(((1-(cyclopropylmethyl)-1H-pyrazol-4-yl)methyl)-3-methyl-1H-pyrazol-1-yl)-5-fluorophenyl)ethan-1-one

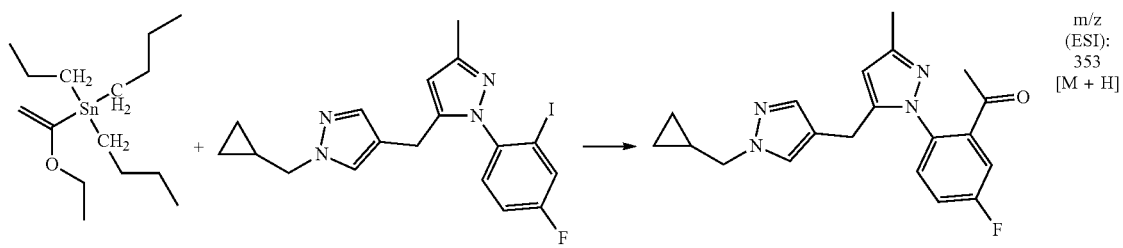

m/z (ESI): 353 [M + H]

1-(2-(5-(((1-ethyl-1H-pyrazol-4-yl)methyl)-2-methyloxazol-4-yl)-5-fluorophenyl)ethan-1-one

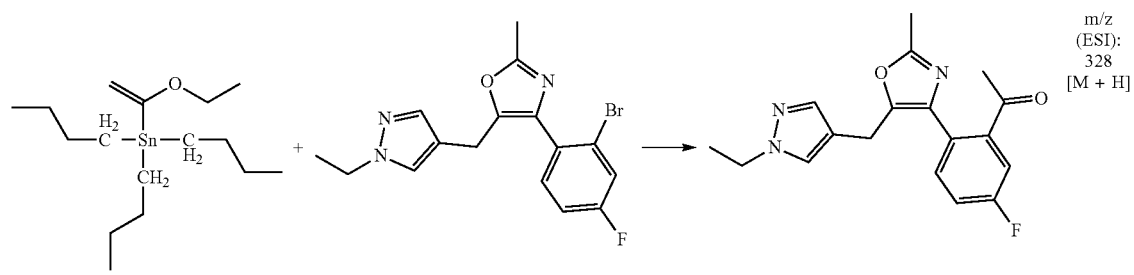

m/z (ESI): 328 [M + H]

1-(2-(4-((1-ethyl-1H-pyrazol-4-yl)methyl)-3-methylisoxazol-5-yl)-5-fluorophenyl)ethan-1-one

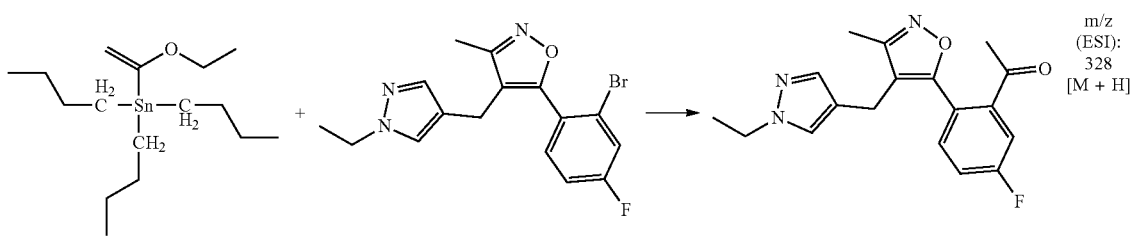

m/z (ESI): 328 [M + H]

463

Synthesis of 3-bromo-2-(4-((3-chloro-1-ethyl-1H-pyrazol-4-yl)methyl)-1-methyl-1H-pyrazol-3-yl)-5-fluoropyridine

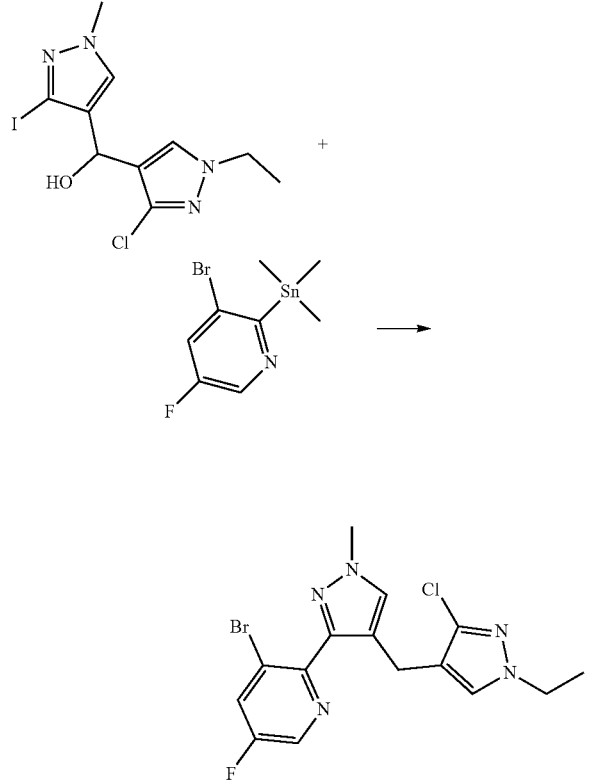

A mixture of (3-chloro-1-ethyl-1H-pyrazol-4-yl)(3-iodo-1-methyl-1H-pyrazol-4-yl)methanol (500 mg,1.36 mmol), 3-bromo-5-fluoro-2-(trimethylstannyl)pyridine (555 mg, 1.63 mmol) and Pd(PPh₃)₄(158 mg, 0.136 mmol) in toluene (20 mL) was heated to 110° C. under N₂ for 16 h. Toluene was removed by reduced pressure and this mixture was diluted by EtOAc (100 mL). This organic solution was washed by brine (30 mL), dried over anhydrous Na₂SO₄ and concentrated. The residue was purified by column chromatography on silica gel (PE:EtOAc=1:1) to give 3-bromo-2-(4-((3-chloro-1-ethyl-1H-pyrazol-4-yl)methyl)-1-methyl-1H-pyrazol-3-yl)-5-fluoropyridine (230 mg, yield: 28.7%) as colorless oil. LC/MS (ESI) (m/z): 398 [M+H]⁺.

464

Synthesis of (R)-5-bromo-3-(1-(5-fluoro-2-(trimethylstannyl)phenyl)ethoxy)pyridin-2-amine

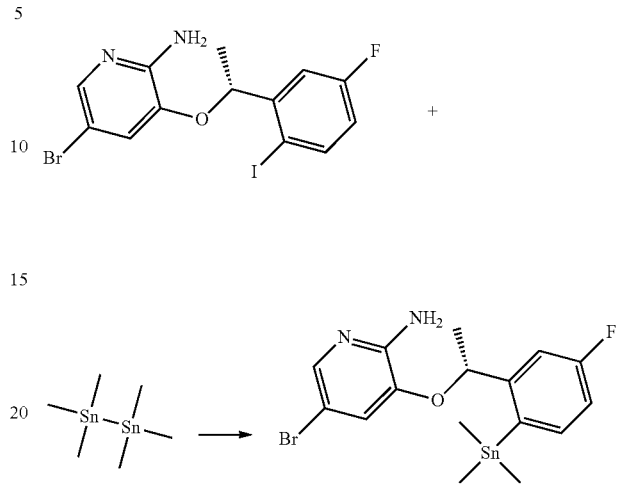

To a solution of 5-bromo-3-[(1R)-1-(5-fluoro-2-iodophenyl)ethoxy]pyridin-2-amine (4.60 g, 10.5 mmol) in toluene (200 mL) was added tetrakis(triphenylphosphine) palladium (1.36 g, 1.18 mmol) and hexamethyldistannane (2.40 mL, 11.6 mmol). The mixture was stirred at 110° C. for 12 h under an N₂ atmosphere. After cooling to r.t., the mixture was treated with aq. KF and EtOAc and separated. The organic layer was washed with brine, dried over anhydrous Na₂SO₄, filtered and concentrated. The residue was purified by column chromatography on silica gel (PE:EA=10:1, V/V) to give the target product (1.95 g, yield: 39%) as a white solid. LC/MS ESI (m/z): 475 [M+H]⁺.

The following intermediates were synthesized using a similar experimental protocol:

5-bromo-3-(1-(5-fluoro-2-(trimethylstannyl)phenyl)ethoxy)pyridin-2-amine

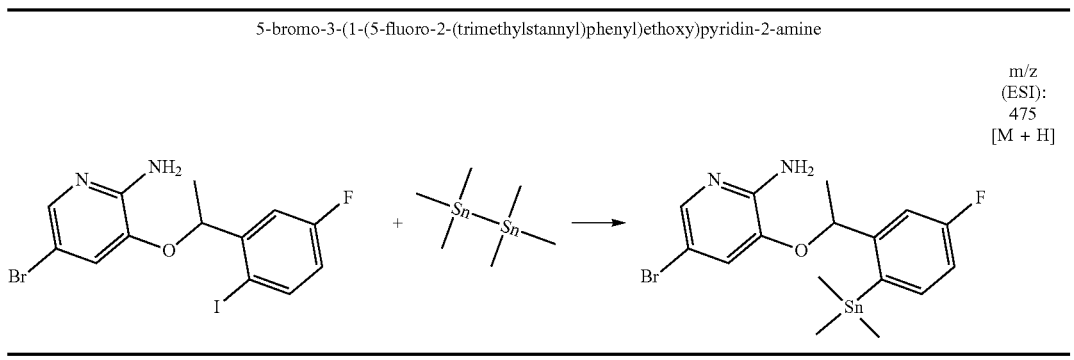

m/z (ESI): 475 [M + H]

Synthesis of (5-bromo-1-ethyl-1H-pyrazol-4-yl)(1-(4-fluoro-2-iodophenyl)-1H-1,2,3-triazol-5-yl)methanone

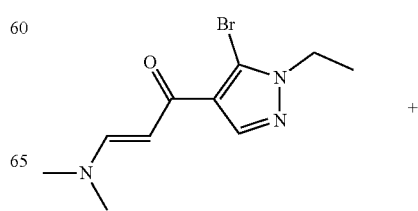

465

-continued

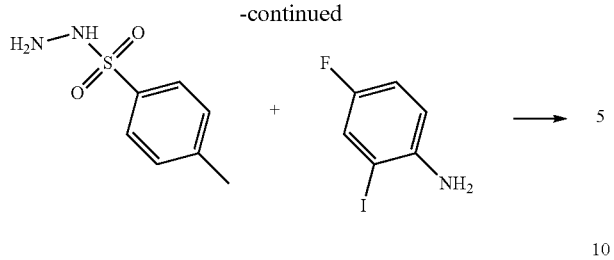

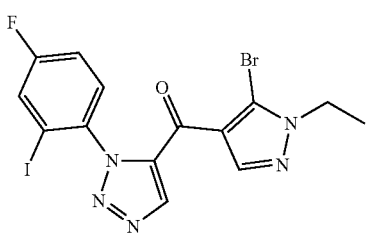

A mixture of (E)-1-(5-bromo-1-ethyl-1H-pyrazol-4-yl)-3-(dimethylamino)prop-2-en-1-one (1.00 g, 3.67 mmol), 4-fluoro-2-iodoaniline (0.870 g, 3.67 mmol), I2 (0.470 g, 1.83 mmol) and 4-methylbenzene-1-sulfonohydrazide (1.03 g, 5.51 mmol) in DMSO (20 mL) was stirred at 110° C. under air for 12 h. After cooling to rt, the mixture was quenched with ice water and extracted with EA twice, the combined extracts were wash with brine twice, dried over Na$_2$SO$_4$, filtered and concentrated in vacuo to give a residue which was purified by silica gel column chromatography (DCM:MeOH=10:1, V/V) to give (5-bromo-1-ethyl-1H-pyrazol-4-yl)(1-(4-fluoro-2-iodophenyl)-1H-1,2,3-triazol-5-yl)methanone as brown oil (700 mg, yield: 38%). LC/MS ESI (m/z): 490 [M+H]$^+$.

Synthesis of (R)-1-(2-(1-(benzyloxy)ethyl)-4-fluoro-phenyl)-1H-pyrazole-3-carbaldehyde

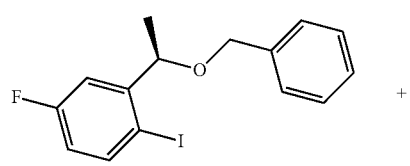

+

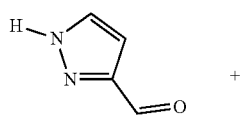

+

466

-continued

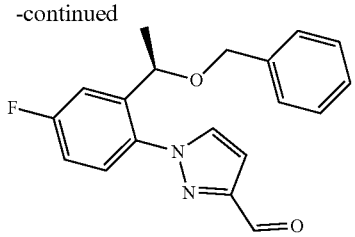

To a solution of 1H-pyrazole-3-carbaldehyde (2.00 g, 20.8 mmol), (R)-2-(1-(benzyloxy)ethyl)-4-fluoro-1-iodo-benzene (8.10 g, 22.9 mmol), N,N'-dimethylcyclohexane-1,2-diamine (592 mg, 4.20 mmol) and K$_2$CO$_3$ (5.70 g, 41.6 mmol) in NMP (30 mL) was added CuI (396 mg, 2.10 mmol). The mixture was stirred at 150° C. for 16 h. The reaction was diluted with EtOAc and washed first with H$_2$O, and then with brine. The organic layer was dried over anhydrous Na$_2$SO$_4$, filtered, and concentrated. The residue was purified by flash chromatography (silica gel, 0→11% EA in PE) to give (R)-1-(2-(1-(benzyloxy)ethyl)-4-fluoro-phenyl)-1H-pyrazole-3-carbaldehyde (500 mg, 7% yield) as a yellow oil. LC/MS (ESI) m/z: 325 [M+H]$^+$.

Synthesis of 2-(5-((tetrahydro-2H-pyran-2-yloxy)methyl)isoxazol-3-yl)ethanol

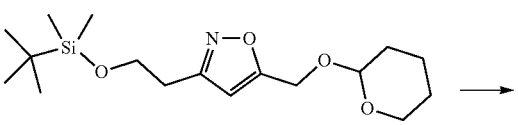

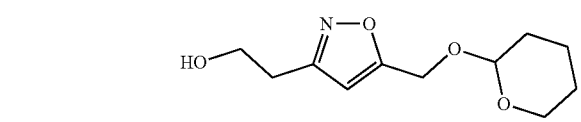

To a solution of 3-{2-[(tert-butyldimethylsilyl)oxy]ethyl}-5-[(oxan-2-yloxy)methyl]-1,2-oxazole (3.40 g, 9.96 mmol) in THF (30 mL) was added TBAF (1 M in THF, 9.96 mL, 9.96 mmol) dropwise over 5 min at 0° C. The resulting solution was stirred at 25° C. for 1 h. Then, the solution was diluted with EtOAc (50 mL) and washed with sat. NH$_4$Cl (50 mL×2). The organic phase was concentrated in vacuo and the residue was purified by flash chromatography (0→20% MeOH in DCM) to give 2-{5-[(oxan-2-yloxy)methyl]-1,2-oxazol-3-yl}ethan-1-ol (1.8 g, 80% yield) as a pale-yellow oil.

LC/MS (ESI): m/z=228[M+H]$^+$.

The following intermediates were synthesized using a similar experimental protocol:

(2-{3-chloro-5-[1-(cyclopropylmethyl)-1H-1,2,3-triazole-4-carbonyl]-1H-pyrazol-1-yl}-5-fluorophenyl)methanol

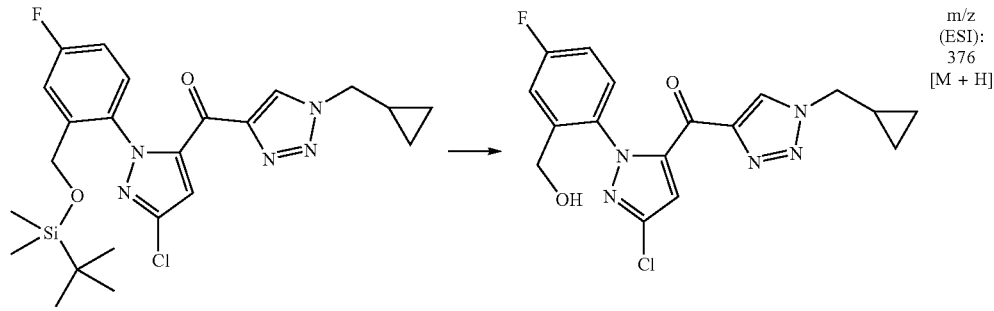

m/z (ESI): 376 [M + H]

Synthesis of 1-[5-fluoro-2-(1-{[2-(trimethylsilyl)ethoxy]methyl}-1H-imidazol-2-yl)phenyl]ethane-1,2-diol Synthesis of 5-((3-(2-acetyl-4-fluorophenyl)isothiazol-4-yl)methyl)-1-methyl-1H-pyrazole-3-carbonitrile

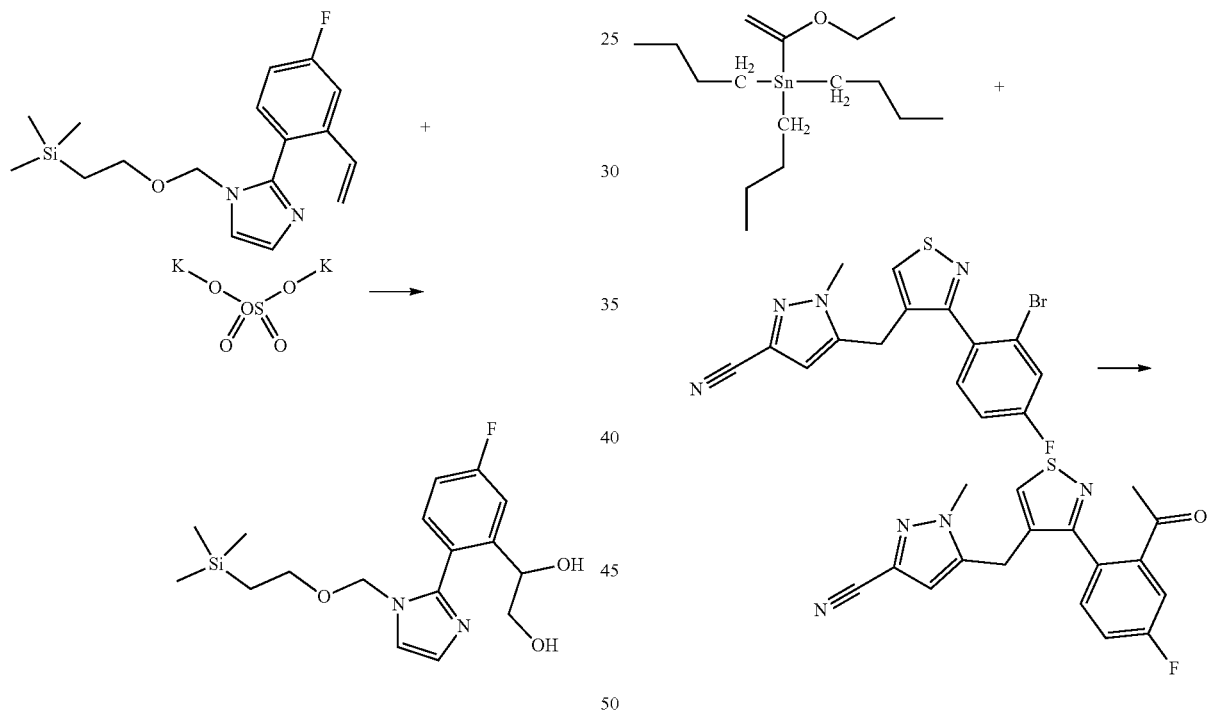

To a solution of 2-(2-ethenyl-4-fluorophenyl)-1-{[2-(trimethylsilyl)ethoxy]methyl}-1H-imidazole (5.00 g, 15.5 mmol) and pyridine (1.24 g, 15.5 mmol) in acetone (50 mL) and H₂O (10 mL) were added NMO (7.28 g, 31.1 mmol) and K₂OsO₄·2H₂O (60 mg, 0.16 mmol). The reaction mixture was heated to reflux and stirred for 18 h. The mixture was evaporated under reduced pressure and the residue was partitioned between EtOAc and water. The layers were separated, and the aq. layer was thrice extracted with EtOAc. The combined organic layers were washed with brine, dried over anhydrous Na₂SO₄, and concentrated under reduced pressure. The residue was purified by column chromatography on silica gel eluted with PE:EA=1:1 to give 1-[5-fluoro-2-(1-{[2-(trimethylsilyl)ethoxy]methyl}-1H-imidazol-2-yl)phenyl]ethane-1,2-diol (3.50 g, 63%) as an oil.

LC/MS ESI (m/z): 353 [M+H]⁺.

To a solution of 5-((3-(2-bromo-4-fluorophenyl)-1,2-thiazol-4-yl)methyl)-1-methyl-1H-pyrazole-3-carbonitrile (0.91 g, 2.4 mmol) in toluene (10 mL) were added tributyl (1-ethoxyethenyl)stannane (1.47 g, 4.08 mmol) and Pd(PPh₃)₄(0.28 g, 0.24 mmol). The reaction mixture stirred at 100° C. for 18 h under N₂. This mixture was concentrated and then diluted with THF (10 mL) and HCl (2 mL, 1 N). The mixture was stirred at r.t. for 2 h. The reaction mixture was diluted with ethyl acetate (20 mL) and washed with water (3×20 mL). The organic layer was washed with brine (20 mL), dried over anhydrous Na₂SO₄ and concentrated under reduced pressure. The residue was purified by column chromatography on silica gel (30% to 50% of EA in PE) to give 5-((3-(2-acetyl-4-fluorophenyl)isothiazol-4-yl)methyl)-1-methyl-1H-pyrazole-3-carbonitrile (779 mg, 95% yield) as a colorless oil. LC/MS (ESI) m/z: 341.0 [M+H]⁺.

Synthesis of (2-(4-((5-bromo-1-ethyl-1H-pyrazol-4-yl)methyl)-1-methyl-1H-pyrazol-3-yl)-5-fluorophenyl)methanol

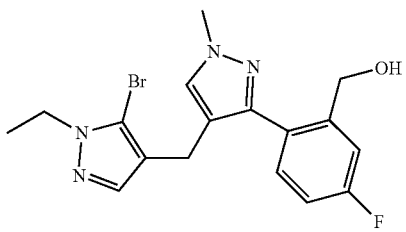 [SMILES: CCn1ncc(Cc2cn(C)nc2-c2ccc(F)cc2CO)c1Br]

To a mixture of 5-bromo-1-ethyl-4-((4-iodo-1-methyl-1H-pyrazol-3-yl)methyl)-1H-pyrazole (200 mg, 0.510 mmol) and (2-(1,3-dioxolan-2-yl)-4-fluorophenyl)trimethylstannane (184 mg, 0.560 mmol) in DMF (8 mL) was added LiCl (43 mg, 1.0 mmol), CuCl (100 mg, 1.01 mmol) and Pd(PPh$_3$)$_4$(59 mg, 0.051 mmol). The mixture was thrice degassed with N$_2$ and stirred at 100° C. under a N$_2$ atmosphere for 8 h. After cooling to r.t., the mixture was poured into water (50 mL) and EtOAc (20 mL). The aq. layer was twice extracted with EtOAc (10 mL). The combined extracts were washed with brine (2×20 mL), dried over anhydrous Na$_2$SO$_4$, filtered, and concentrated. The residue was purified by column chromatography on silica gel (10→25% EtOAc in PE) to give 3-(2-(1,3-dioxolan-2-yl)-4-fluorophenyl)-4-((5-bromo-1-ethyl-1H-pyrazol-4-yl)methyl)-1-methyl-1H-pyrazole as a white solid (170 mg, yield: 69%). LC/MS ESI (m/z): 435 [M+H]$^+$.

To a solution of 3-(2-(1,3-dioxolan-2-yl)-4-fluorophenyl)-4-((5-bromo-1-ethyl-1H-pyrazol-4-yl)methyl)-1-methyl-1H-pyrazole (300 mg, 0.62 mmol) in THF (2 mL) was added conc. HCl (0.26 mL, 3.1 mmol, 12 N) at 0° C. The mixture was stirred at r.t. for 3 h. The reaction mixture was treated with sat. aq. Na$_2$CO$_3$ solution (10 mL) and extracted with EtOAc (2×10 mL). The combined extracts were washed with brine (20 mL), dried over anhydrous Na$_2$SO$_4$, filtered, and concentrated.

The residue was dissolved in MeOH (2 mL). To this solution was added NaBH$_4$(32 mg, 0.93 mmol) at 0° C., and the resulting mixture was stirred at r.t. for 3 h. The mixture was diluted with water (20 mL) and extracted with EtOAc (2×10 mL). The combined extracts were washed with brine (20 mL), dried over anhydrous Na$_2$SO$_4$, filtered, and concentrated. The residue was purified by column chromatography on silica gel (euent: 25→50% EtOAc in PE) to give (2-(4-((5-bromo-1-ethyl-1H-pyrazol-4-yl)methyl)-1-methyl-1H-pyrazol-3-yl)-5-fluorophenyl)methanol as a colorless oil (190 mg, yield: 78%). LC/MS ESI (m/z): 393 [M+H]$^+$.

Synthesis of 1-((1-(4-fluoro-2-(1-hydroxyethyl)phenyl)-1H-pyrazol-5-yl)methyl)-1H-pyrazole-4-carbonitrile

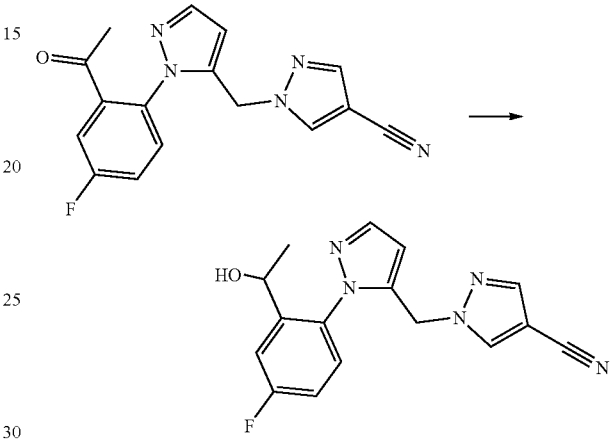

To a solution of 1-((1-(2-acetyl-4-fluorophenyl)-1H-pyrazol-5-yl)methyl)-1H-pyrazole-4-carbonitrile (480 mg, 1.55 mmol) in MeOH (10 mL) was added NaBH$_4$ (117 mg, 3.11 mmol) at 0° C. under N$_2$ atmosphere. After the addition, the resulting solution was stirred at r.t. for 3 h. After cooling to 0° C., the reaction mixture was treated with DCM (20 mL) and water (20 mL), the organic layer was separated, and the aq. layer was extracted with DCM (20 mL). The combined organic layers were washed with brine, dried over anhydrous Na$_2$SO$_4$, filtered and concentrated. The residue was purified by flash chromatography (0→100% EtOAc in PE) to give 1-((1-(4-fluoro-2-(1-hydroxyethyl)phenyl)-1H-pyrazol-5-yl)methyl)-1H-pyrazole-4-carbonitrile (380 mg, yield: 79%) as a colorless oil. LC/MS ESI (m/z): 312 [M+H]$^+$.

The following intermediates were synthesized using a similar experimental protocol.

(5-bromo-1-ethyl-1H-pyrazol-4-yl)(1-(4-fluoro-2-iodophenyl)-1H-1,2,3-triazol-5-yl)methanol m/z (ESI): 492 [M + H]

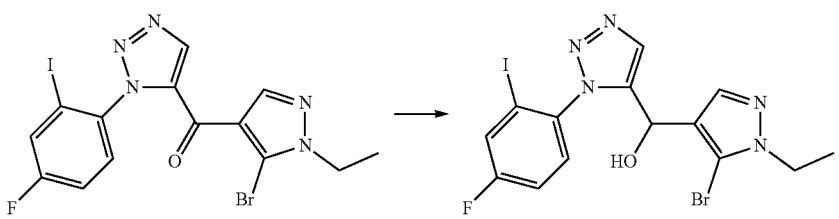 [SMILES: CCn1ncc(C(=O)c2cnnn2-c2ccc(F)cc2I)c1Br ; CCn1ncc(C(O)c2cnnn2-c2ccc(F)cc2I)c1Br]

-continued
1-(2-(5-((5-bromo-1-ethyl-1H-pyrazol-4-yl)methyl)-1H-1,2,3-triazol-1-yl)-5-fluorophenyl)ethan-1-ol
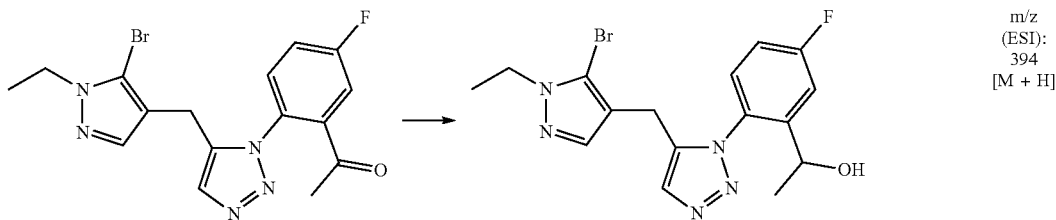
m/z (ESI): 394 [M + H]
5-((5-bromo-1-ethyl-1H-pyrazol-4-yl)methyl)-1-(4-fluoro-2-(1-hydroxyethyl)phenyl)-1H-pyrazole-3-carbonitrile
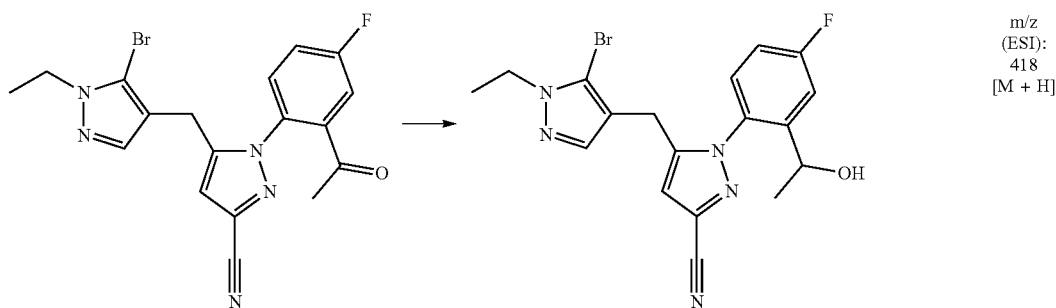
m/z (ESI): 418 [M + H]
1-(2-(5-((5-bromo-1-ethyl-1H-pyrazol-4-yl)methyl)-1H-imidazol-1-yl)-5-fluorophenyl)ethan-1-ol
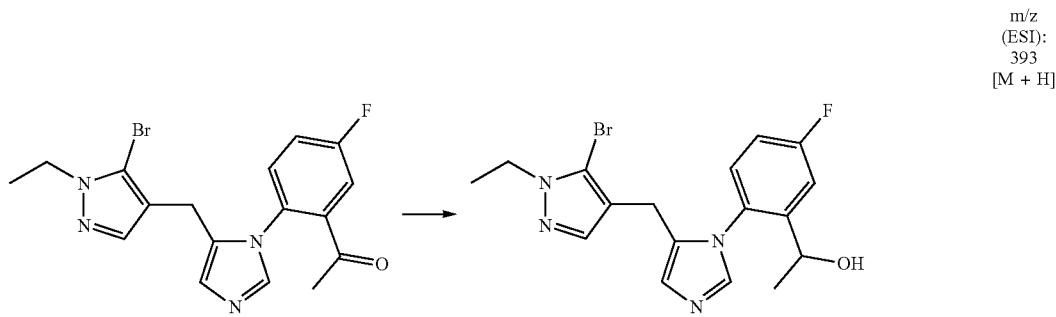
m/z (ESI): 393 [M + H]
1-(2-(1-((5-bromo-1-ethyl-1H-pyrazol-4-yl)methyl)-4-methyl-1H-imidazol-2-yl)-5-fluorophenyl)ethanol
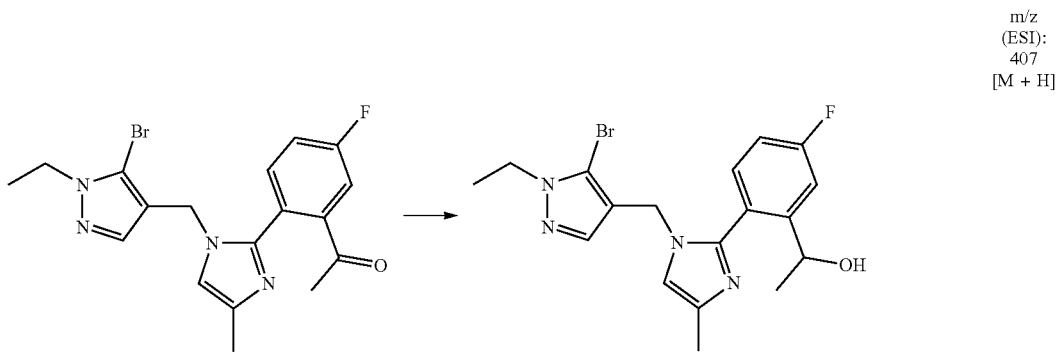
m/z (ESI): 407 [M + H]

(5-bromo-1-ethyl-1H-pyrazol-4-yl)(1-(2-(1-((5-bromo-2-nitropyridin-3-yl)oxy)ethyl)-4-fluorophenyl)-1H-pyrazol-5-yl)methanol

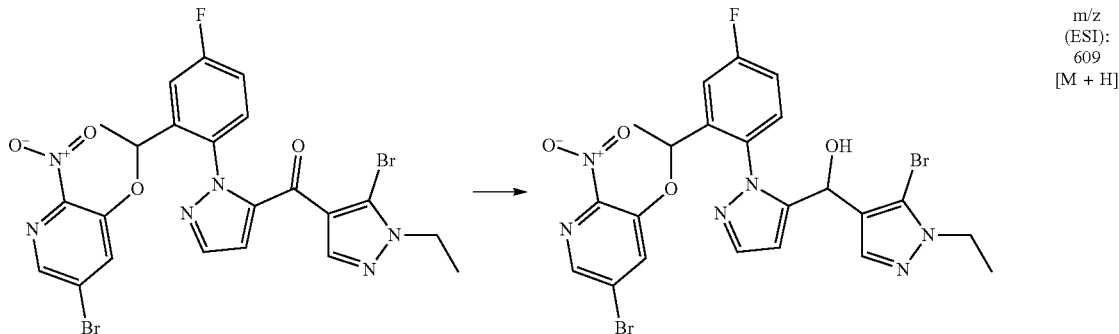

m/z (ESI): 609 [M + H]

(5-bromo-1-ethyl-1H-pyrazol-4-yl)(1-(2-(1-((5-bromo-2-nitropyridin-3-yl)oxy)ethyl)-4-fluorophenyl)-4-fluoro-1H-pyrazol-5-yl)methanol

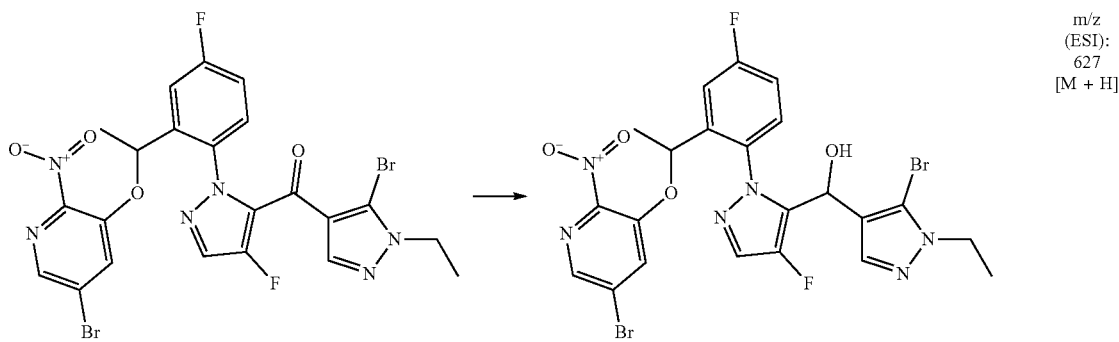

m/z (ESI): 627 [M + H]

1-(2-(5-((3-chloro-1-ethyl-1H-pyrazol-4-yl)methyl)-3-methyl-1H-pyrazol-1-yl)-5-fluorophenyl)ethan-1-ol

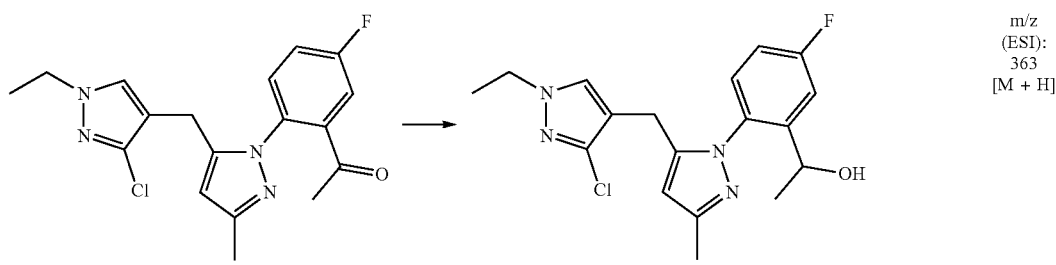

m/z (ESI): 363 [M + H]

(1-(2-(1-((5-bromo-2-nitropyridin-3-yl)oxy)ethyl)-4-fluorophenyl)-3-fluoro-1H-pyrazol-5-yl)(1-ethyl-1H-pyrazol-4-yl)methanol

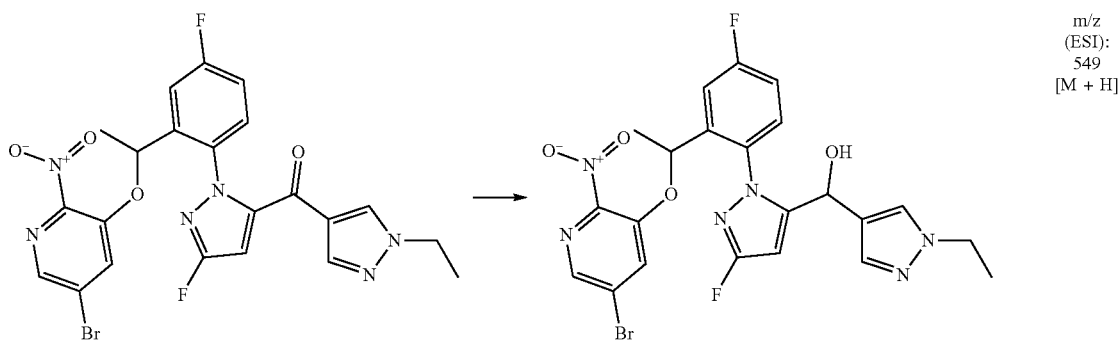

m/z (ESI): 549 [M + H]

-continued (1-(2-(((5-bromo-2-nitropyridin-3-yl)oxy)methyl)-4-fluorophenyl)-3-chloro-1H-pyrazol-5-yl)(1-ethyl-1H-pyrazol-4-yl)methanol

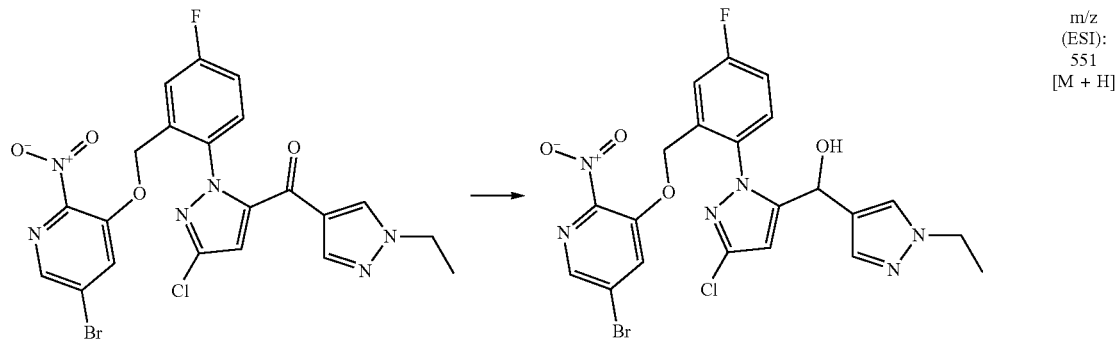

m/z (ESI): 551 [M + H]

[1-(2-{[(5-bromo-2-nitropyridin-3-yl)oxy]methyl}-4-fluorophenyl)-3-chloro-1H-pyrazol-5-yl][1-(cyclopropylmethyl)-1H-1,2,3-triazol-4-yl]methanol

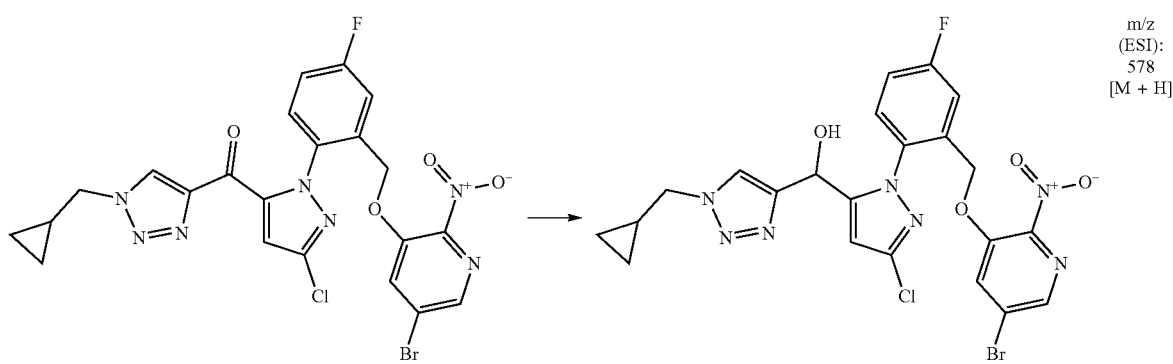

m/z (ESI): 578 [M + H]

1-(2-{4-[(1-ethyl-1H-pyrazol-4-yl)methyl]-1,2-oxazol-3-yl}-5-fluorophenyl)ethan-1-ol

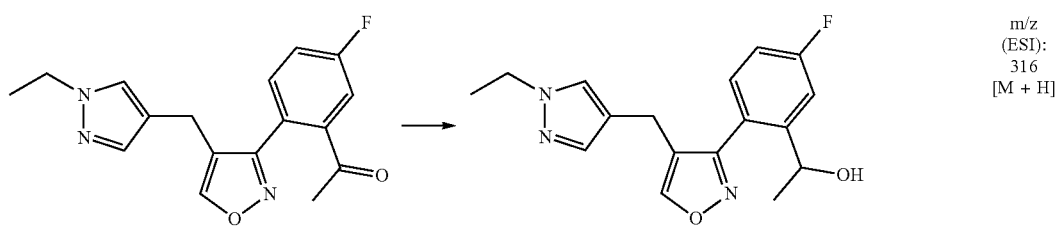

m/z (ESI): 316 [M + H]

1-(2-{4-[(1-ethyl-1H-1,2,3-triazol-4-yl)methyl]-1,2-thiazol-3-yl}-5-fluorophenyl)ethan-1-ol

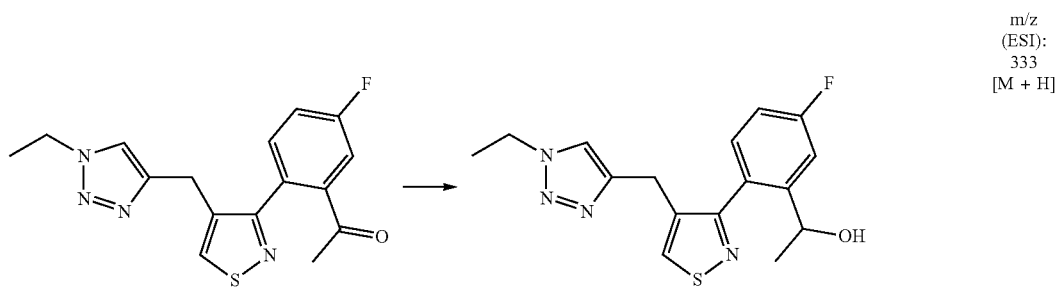

m/z (ESI): 333 [M + H]

5-((1-(4-fluoro-2-(1-hydroxyethyl)phenyl)-3-methyl-1H-pyrazol-5-yl)methyl)-1-methyl-1H-pyrazole-3-carbonitrile

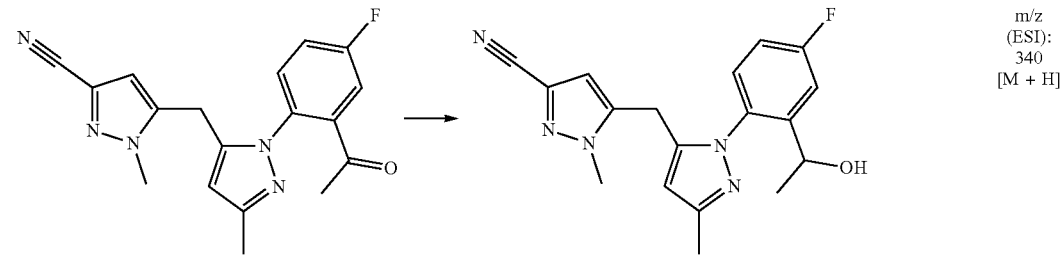

m/z (ESI): 340 [M + H]

1-(2-(5-((1-(cyclopropylmethyl)-1H-pyrazol-4-yl)methyl)-3-methyl-1H-pyrazol-1-yl)-5 fluorophenyl)ethan-1-ol

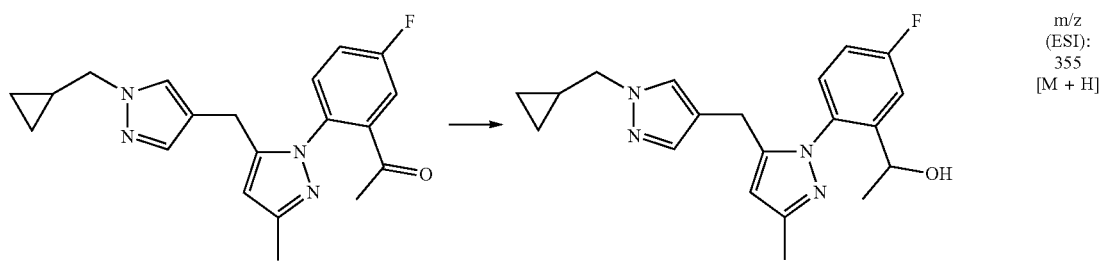

m/z (ESI): 355 [M + H]

1-(2-(5-((1-ethyl-1H-pyrazol-4-yl)methyl)-2-methyloxazol-4-yl)-5-fluorophenyl)ethan-1-ol

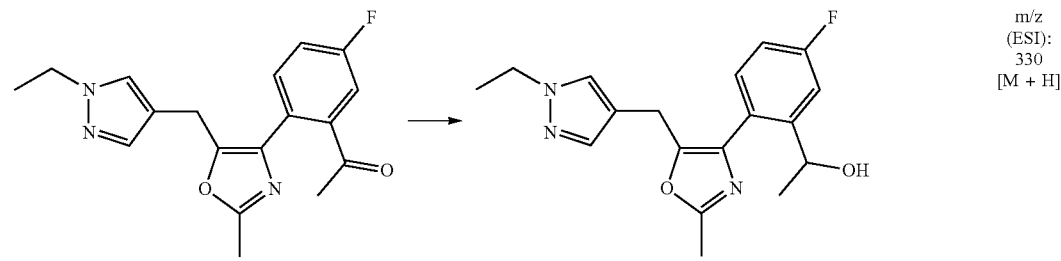

m/z (ESI): 330 [M + H]

1-(2-(5-((1-(cyclopropylmethyl)-3-methyl-1H-pyrazol-4-yl)methyl)-3-methyl-1H-pyrazol-1-yl)-5-fluorophenyl)ethan-1-ol

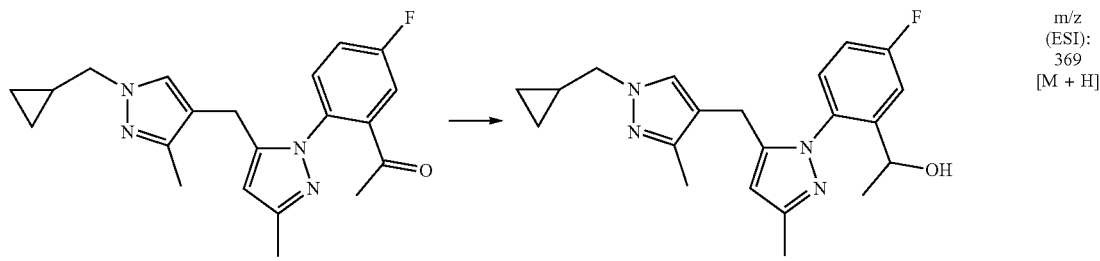

m/z (ESI): 369 [M + H]

1-(2-(4-((3-chloro-1-ethyl-1H-pyrazol-4-yl)methyl)-1-methyl-1H-pyrazol-3-yl)-5-fluoropyridin-3-yl)ethan-1-ol

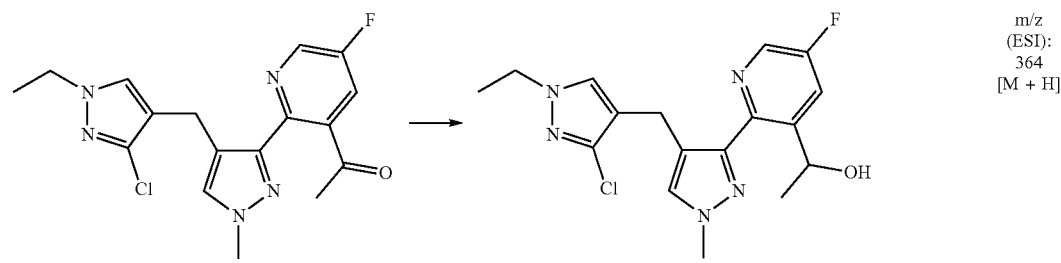

m/z (ESI): 364 [M + H]

5-((3-(4-fluoro-2-(1-hydroxyethyl)phenyl)isothiazol-4-yl)methyl)-1-methyl-1H-pyrazole-3-carbonitrile

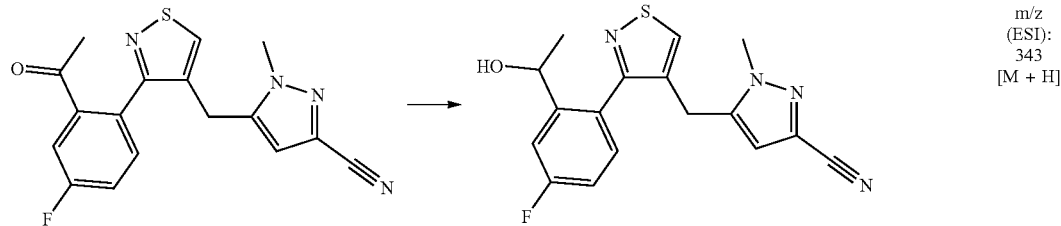

m/z (ESI): 343 [M + H]

1-(2-{4-[(1-ethyl-1H-pyrazol-4-yl)methyl]-3-methyl-1,2-oxazol-5-yl}-5-fluorophenyl)ethan-1-ol

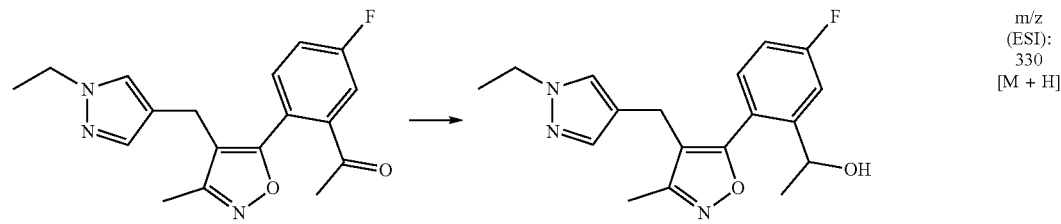

m/z (ESI): 330 [M + H]

3-((1-(2-(1-((5-bromo-2-nitropyridin-3-yl)oxy)ethyl)-4-fluorophenyl)-1H-pyrazol-5-yl)(hydroxy)methyl)-1-methyl-1H-pyrazole-5-carbonitrile

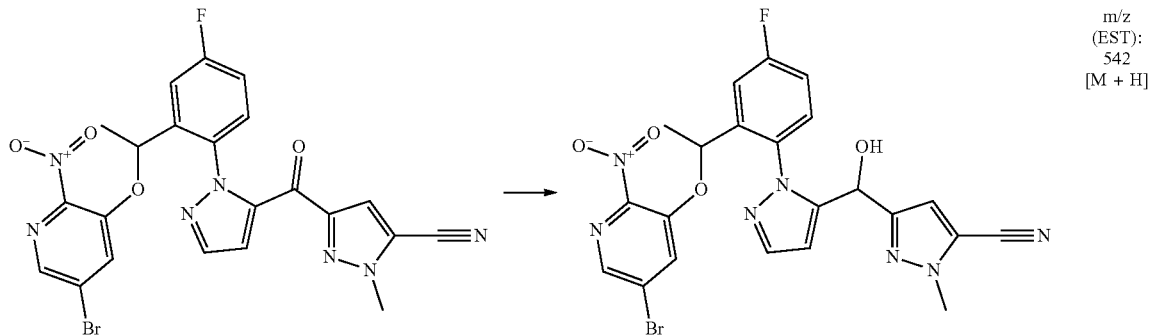

m/z (ESI): 542 [M + H]

Synthesis of 1-(2-{4-[(1-ethyl-1H-1,2,3-triazol-4-yl)methyl]-1,2-thiazol-3-yl}-5-fluorophenyl)ethan-1-one

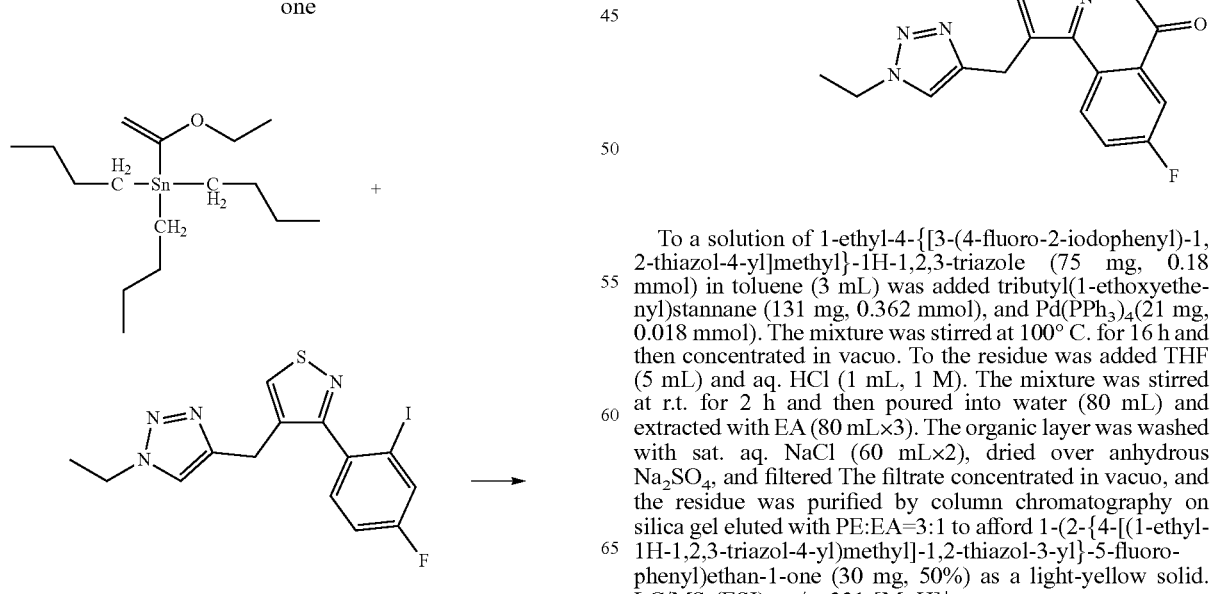

To a solution of 1-ethyl-4-{[3-(4-fluoro-2-iodophenyl)-1,2-thiazol-4-yl]methyl}-1H-1,2,3-triazole (75 mg, 0.18 mmol) in toluene (3 mL) was added tributyl(1-ethoxyethenyl)stannane (131 mg, 0.362 mmol), and Pd(PPh$_3$)$_4$ (21 mg, 0.018 mmol). The mixture was stirred at 100° C. for 16 h and then concentrated in vacuo. To the residue was added THF (5 mL) and aq. HCl (1 mL, 1 M). The mixture was stirred at r.t. for 2 h and then poured into water (80 mL) and extracted with EA (80 mL×3). The organic layer was washed with sat. aq. NaCl (60 mL×2), dried over anhydrous Na$_2$SO$_4$, and filtered The filtrate concentrated in vacuo, and the residue was purified by column chromatography on silica gel eluted with PE:EA=3:1 to afford 1-(2-{4-[(1-ethyl-1H-1,2,3-triazol-4-yl)methyl]-1,2-thiazol-3-yl}-5-fluorophenyl)ethan-1-one (30 mg, 50%) as a light-yellow solid. LC/MS (ESI): m/z=331 [M+H]$^+$.

The following intermediates were synthesized using a similar experimental protocol:

1-(2-(3-bromo-5-((1-ethyl-1H-pyrazol-4-yl)methyl)-1H-pyrazol-1-yl)-5-fluorophenyl)ethan-1-one

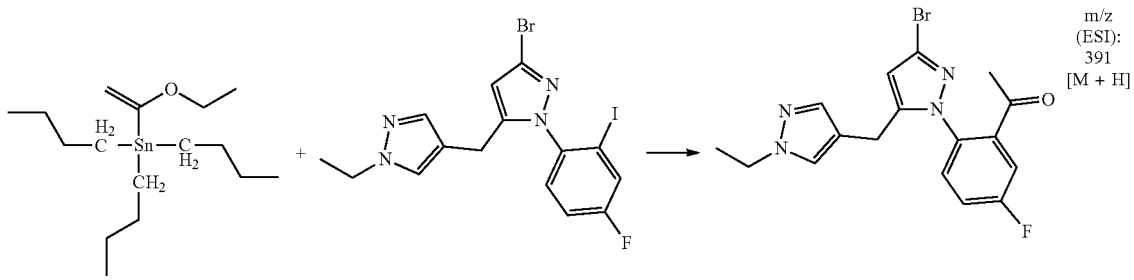

m/z (ESI): 391 [M + H]

5-((1-(2-acetyl-4-fluorophenyl)-3-methyl-1H-pyrazol-5-yl)methyl)-1-methyl-1H-pyrazole-3-carbonitrile

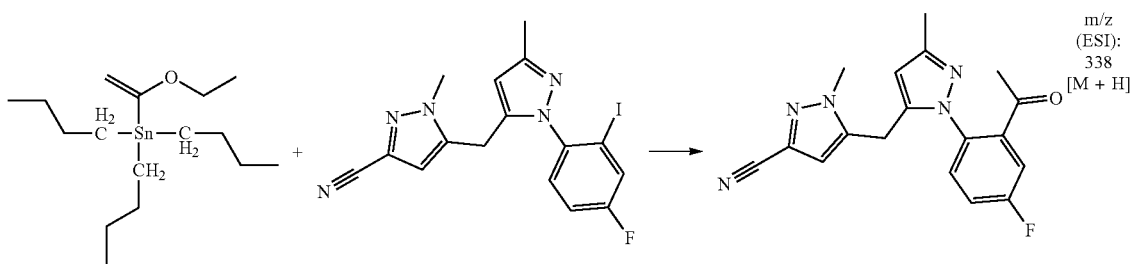

m/z (ESI): 338 [M + H]

1-(2-(4-((3-chloro-1-ethyl-1H-pyrazol-4-yl)methyl)-1-methyl-1H-pyrazol-3-yl)-5-fluoropyridin-3-yl)ethan-1-one

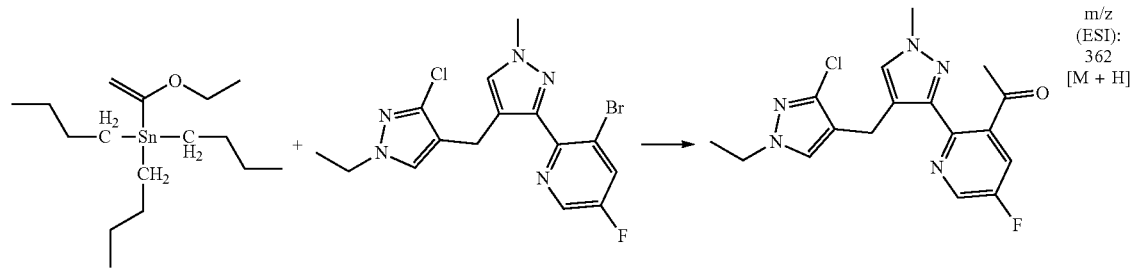

m/z (ESI): 362 [M + H]

Synthesis of (R)-8-fluoro-6-methyl-4H,6H-benzo[e]pyrazolo[5,1-c][1,4,2]oxazaborepin-4-ol

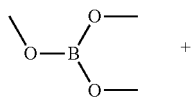

+

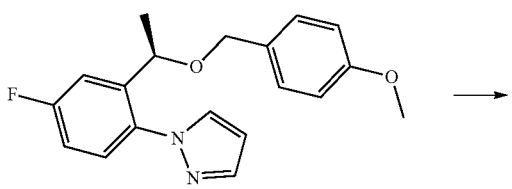

→

-continued

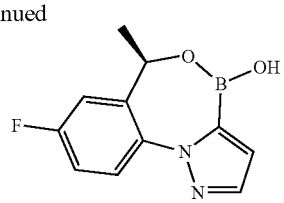

LDA (5.52 mL, 5.52 mmol, 1.0 N in THF) was added dropwise to a solution of 1-{4-fluoro-2-[(1R)-1-[(4-methoxyphenyl)methoxy]ethyl]phenyl}-1H-pyrazole (1.80 g, 5.52 mmol) in THF (80 mL) at −78° C. over 5 min. After the addition, the mixture was stirred at −78° C. under N₂ for 1 h. Trimethyl borate (0.480 g, 4.60 mmol) was added dropwise at −78° C. and the reaction mixture was warmed slowly to r.t. with stirring overnight under N₂. The mixture was poured into ice-water and twice extracted with EtOAc. The combined organic layers were washed with brine, dried over anhydrous Na₂SO₄, filtered, and concentrated. The residue was dissolved in DCM (100 mL), followed by the addition of TFA (10 mL). The resulting mixture was stirred

Synthesis of 3-((4-(4-fluoro-2-(1-hydroxyethyl)phenyl)pyridin-3-yl)methyl)-1-methyl-1H-pyrazole-5-carbonitrile at r.t. for 1 h. The mixture was concentrated and the residue was purified by column chromatography (silica gel, 1→10% ethyl acetate in petroleum ether) to afford (9R)-12-fluoro-9-methyl-8-oxa-2,3-diaza-7-boratricyclo[8.4.0.0{2,6}]tetradeca-1(14),3,5,10,12-pentaen-7-ol (1.1 g, 86%) as a white solid.

LC/MS (ESI) m/z: 233 [M+H]+.

Synthesis of 3-((4-(4-fluoro-2-(1-hydroxyethyl)phenyl)pyridin-3-yl)methyl)-1-methyl-1H-pyrazole-5-carbonitrile

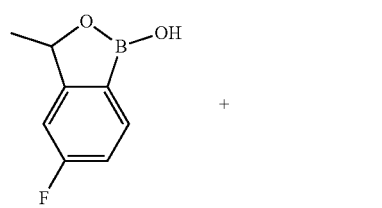

+

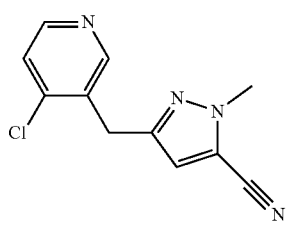

→

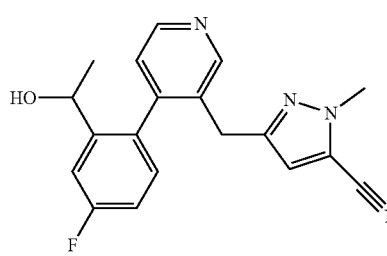

To a solution of 3-((4-chloropyridin-3-yl)methyl)-1-methyl-1H-pyrazole-5-carbonitrile (100 mg, 0.258 mmol) in DME (3 mL) was added 5-fluoro-3-methylbenzo[c][1,2]oxaborol-1(3H)-ol (107 mg, 0.644 mmol), X-Phos (43 mg, 0.086 mmol), Pd(dppf)Cl$_2$ (21 mg, 0.025 mmol), Cs$_2$CO$_3$ (420 mg, 1.29 mmol) and H$_2$O (1 mL). After degassing with N$_2$ three times, the mixture was stirred at 90° C. for 4 h. The mixture was allowed to cool to 25° C. and then diluted with DCM and water. The organic layer was separated, washed with brine, dried over anhydrous Na$_2$SO$_4$, filtered and concentrated. The residue was purified by column chromatography on silica gel (PE:EA=1:3, V/V) to give the target product as a white solid (60 mg, yield: 41%). LC/MS ESI (m/z): 337 [M+H]+.

Synthesis of (3-chloro-1-(4-fluoro-2-(1-hydroxyethyl)phenyl)-1H-pyrazol-5-yl)(1-ethyl-1H-pyrazol-4-yl)methanone

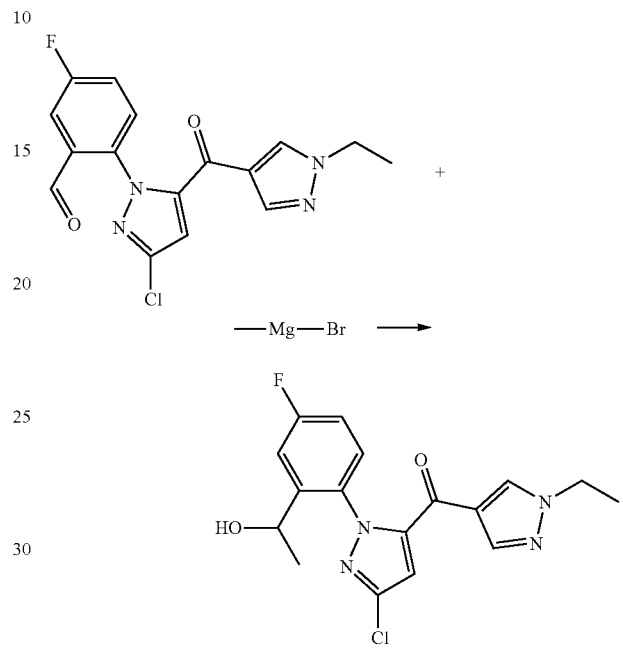

To a solution of 2-(3-chloro-5-(1-ethyl-1H-pyrazole-4-carbonyl)-1H-pyrazol-1-yl)-5-fluorobenzaldehyde (400 mg, 1.15 mmol) in anhydrous THF (20 mL) was added bromo(methyl)magnesium (1.92 mL, 1.15 mmol, 0.6 M in THF) dropwise at −30° C. After the addition, the resulting mixture was stirred at −30° C. for 0.5 h. The reaction mixture was quenched with sat. aq. NH$_4$Cl solution (20 mL) and then extracted with EA (20 mL). The extract was washed with brine (20 mL) and concentrated in vacuo to give the residue, which was purified by flash chromatography (0→100% EA in PE, V/V) to give (3-chloro-1-(4-fluoro-2-(1-hydroxyethyl)phenyl)-1H-pyrazol-5-yl)(1-ethyl-1H-pyrazol-4-yl)methanone (350 mg, 84%) as a white solid. LC/MS (ESI): m/z=363 [M+H]+.

Synthesis of 1-(2-{4-[(1-ethyl-1H-pyrazol-4-yl)methyl]-1,2-oxazol-3-yl}-5-fluorophenyl)ethan-1-one

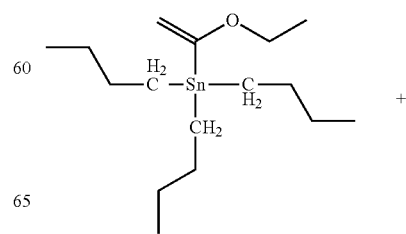

+

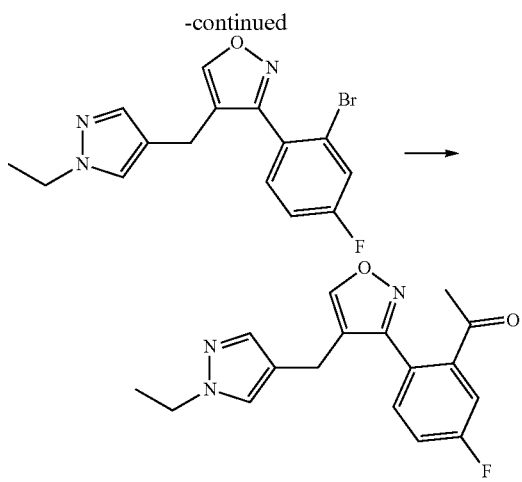

To a solution of 3-(2-bromo-4-fluorophenyl)-4-[(1-ethyl-1H-pyrazol-4-yl)methyl]-1,2-oxazole (313 mg, 0.894 mmol) in toluene (8 mL) was added Pd(PPh$_3$)$_4$ (103 mg, 0.089 mmol), CuI (17 mg, 0.089 mmol) and tributyl(1-ethoxyethenyl)stannane (484 mg, 1.34 mmol) at r.t. The reaction was thrice degassed under N$_2$ atmosphere and stirred at 100° C. for 16 h. The reaction mixture was concentrated, and the residue was stirred in THF (8 mL) and conc. HCl (3.6 mL) for 1 h. sat. aq. KF solution (20 mL) was added, and the reaction was stirred for another 1 h. The resulting solid was filtered, the residue was diluted with EtOAc (10 mL), washed with sat. NaHCO$_3$ (10 mL) and brine (15 mL), dried over Na$_2$SO$_4$ and concentrated to dryness to give crude 1-(2-{4-[(1-ethyl-1H-pyrazol-4-yl)methyl]-1,2-oxazol-3-yl}-5-fluorophenyl)ethan-1-one (629 mg) as a brown oil.

LC/MS (ESI) m/z: 314 [M+H]$^+$.

Synthesis of 3-((5-bromo-1-methyl-1H-pyrazol-4-yl)(hydroxy)methyl)-1-((2-(trimethylsilyl)ethoxy)methyl)-1H-pyrazole-5-carbonitrile

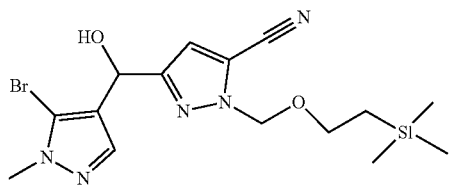

A mixture of 3-[(5-bromo-1-methyl-1H-pyrazol-4-yl)(hydroxy)methyl]-1-{[2-(trimethylsilyl)ethoxy]methyl}-1H-pyrazole-5-carbaldehyde (1.30 g, 3.13 mmol), hydroxylamine hydrochloride (0.390 g, 5.63 mmol) and NaOAc (0.770 g, 5.63 mmol) in EtOH (40 mL) was stirred at 50° C. for 2 h. After cooling to r.t., the mixture was concentrated under reduced pressure. The residue was diluted with DCM (40 mL), then washed with water and brine, dried over anhydrous Na$_2$SO$_4$, filtered and concentrated to give crude 3-((5-bromo-1-methyl-1H-pyrazol-4-yl)(hydroxy)methyl)-1-((2-(trimethylsilyl)ethoxy)methyl)-1H-pyrazole-5-carbaldehyde oxime (1.33 g, yield: 94%). LC-MS (ESI): m/z 430 [M+H]$^+$.

To a solution of 3-((5-bromo-1-methyl-1H-pyrazol-4-yl)(hydroxy)methyl)-1-((2-(trimethylsilyl)ethoxy)methyl)-1H-pyrazole-5-carbaldehyde oxime (1.2 g, 2.8 mmol) in THF (30 mL) at 0° C. was added SOCl$_2$ (1.26 g, 10.6 mmol) dropwise. After the addition, the mixture was stirred at r.t. for 2 h. The mixture was concentrated under reduced pressure to give crude 3-((5-bromo-1-methyl-1H-pyrazol-4-yl)(hydroxy)methyl)-1-((2-(trimethylsilyl)ethoxy)methyl)-1H-pyrazole-5-carbonitrile (1.2 g, yield: 99%). LC-MS (ESI): m/z 412 [M+H]$^+$.

Synthesis of 3-[(3-iodo-1-methyl-1H-pyrazol-4-yl)methyl]-1H-pyrazole-5-carbonitrile

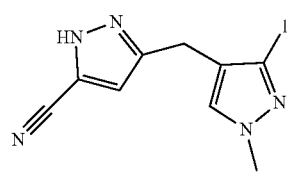

To a solution of 3-(hydroxy(3-iodo-1-methyl-1H-pyrazol-4-yl)methyl)-1-((2-(trimethylsilyl)ethoxy)methyl)-1H-pyrazole-5-carbonitrile (638 mg, 1.39 mmol) in DCM (15 mL) was added Et$_3$SiH (0.67 mL, 4.2 mmol) at 0° C. and TFA (0.41 mL, 5.6 mmol) and then the mixture was stirred at 0° C. for 1 h. The reaction was concentrated. The residue was diluted with EtOAc (15 mL), washed with sat. NaHCO$_3$ (20 mL) and brine (15 mL), dried over anhydrous Na$_2$SO$_4$ and concentrated to dryness. The residue was purified by flash column chromatography on silica gel (PE:EtOAc=3:1) to give 3-((3-iodo-1-methyl-1H-pyrazol-4-yl)methyl)-1-((2-(trimethylsilyl)ethoxy)methyl)-1H-pyrazole-5-carbonitrile (600 mg, yield: 97%) as a colorless oil.

LC/MS (ESI) m/z: 444.1 [M+H]$^+$.

To a solution of 3-((3-iodo-1-methyl-1H-pyrazol-4-yl)methyl)-1-((2-(trimethylsilyl)ethoxy)methyl)-1H-pyrazole-5-carbonitrile (276 mg, 0.623 mmol) in DCM (3 mL) was added TFA (3.0 mL, 40.4 mmol) and then the mixture was stirred at 25° C. for 16 h. The mixture was concentrated, and the residue was diluted with CH$_3$CN (3 mL). Aq. ammonia (1 mL) was added to this solution at 0° C. and the mixture was stirred at 25° C. for 1 h. The reaction was concentrated, diluted with EtOAc (15 mL). The organic solution was washed with brine (15 mL), dried over anhydrous Na$_2$SO$_4$ and then concentrated. The residue was purified by flash column chromatography (silica gel, 50→75% EtOAc in PE) to give 3-[(3-iodo-1-methyl-1H-pyrazol-4-yl)methyl]-1H-pyrazole-5-carbonitrile (103 mg, yield: 53% yield) as a white solid. LC/MS (ESI) m/z: 314.0 [M+H]$^+$.

Synthesis of 1-(2-(5-((5-bromo-1-ethyl-1H-pyrazol-4-yl)methyl)-1H-imidazol-1-yl)-5-fluorophenyl)ethanone

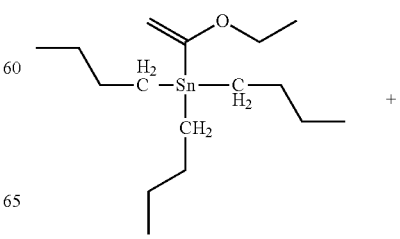

487

-continued

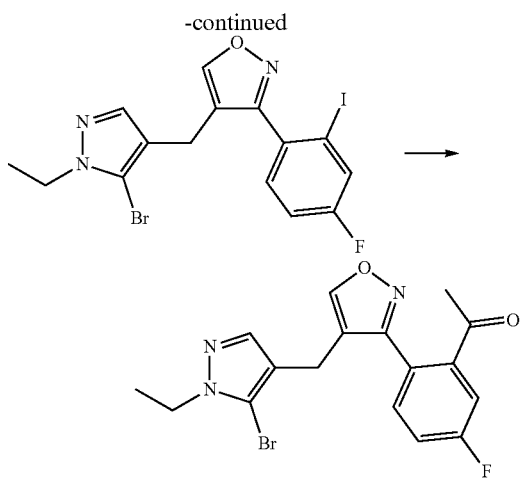

To a solution of 5-bromo-1-ethyl-4-((1-(4-fluoro-2-iodophenyl)-1H-imidazol-5-yl)methyl)-1H-pyrazole (500 mg, 1.05 mmol), tributyl(1-ethoxyethenyl)stannane (760 mg, 2.10 mmol) and CuI (10 mg, 0.052 mmol) in toluene (50 mL) was added Pd(PPh$_3$)$_4$ (243 mg, 0.210 mmol) under N$_2$. The resulting mixture was stirred at 100° C. under N$_2$ for 48 h. The mixture was cooled to r.t., then 1 N aq. HCl (20 mL) and THF (30 mL) were added. The resulted mixture was stirred at r.t. for another 2 h before neutralization with sat. Na$_2$CO$_3$ to pH 8. The organic layer was separated, dried over anhydrous Na$_2$SO$_4$ and concentrated under reduced pressure. The residue was purified by flash chromatography on silica gel (0→5% MeOH in DCM) to give 1-(2-(5-((5-bromo-1-ethyl-1H-pyrazol-4-yl)methyl)-1H-imidazol-1-yl)-5-fluorophenyl)ethanone (80 mg, 19% yield) as a yellow solid. LC/MS (ESI): m/z=391 [M+H]$^+$.

Synthesis of (4-bromo-3-ethyl-1-methyl-1H-pyrazol-5-yl)(1-(4-fluoro-2-iodophenyl)-3-methyl-1H-pyrazol-5-yl)methanol

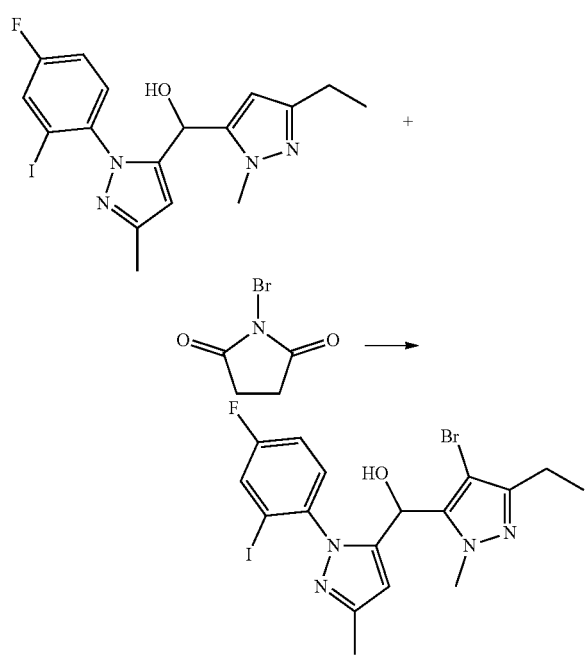

488

To a stirred solution of (3-ethyl-1-methyl-1H-pyrazol-5-yl)(1-(4-fluoro-2-iodophenyl)-3-methyl-1H-pyrazol-5-yl)methanol (350 mg, 0.79 mmol) in N,N-dimethylformamide (8 mL) was added a solution of 1-bromopyrrolidine-2,5-dione (142 mg, 0.79 mmol) in N,N-dimethylformamide (1 mL) at 0° C. The reaction was stirred at 0° C. for 1 h. The reaction mixture was poured into water (10 mL) and extracted with EtOAc (20 mL×3). The combined organic phases were washed with brine (30 mL), dried over anhydrous Na$_2$SO$_4$ and concentrated to dryness. The residue was purified by flash column chromatography on silica gel (PE:EtOAc=1:1, V/V) to give (4-bromo-3-ethyl-1-methyl-1H-pyrazol-5-yl)(1-(4-fluoro-2-iodophenyl)-3-methyl-1H-pyrazol-5-yl)methanol (0.40 g, 87% yield) as a yellow oil. LC/MS (ESI) (m/z): 519.0 [M+H]$^+$.

Synthesis of 3-(2,2-difluoroethyl)-5-((tetrahydro-2H-pyran-2-yloxy)methyl)isoxazole

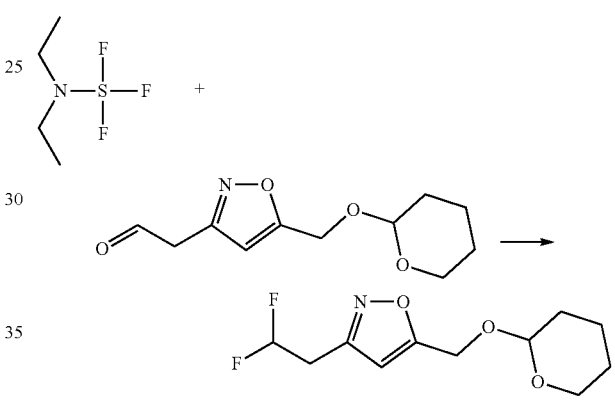

To a solution of crude 2-{5-[(oxan-2-yloxy)methyl]-1,2-oxazol-3-yl}acetaldehyde (3.19 g, 7.50 mmol) in dry DCM (60 mL) was added DAST (2.4 mL, 18 mmol) dropwise at 0° C. over 5 min. The resulting mixture was stirred at 0° C. for 2 h, then the solution was slowly poured into cold sat. aq. NaHCO$_3$ (100 mL) with vigorous stirring. After 10 min, the mixture was extracted twice with DCM. The combined extracts were washed with brine, concentrated and purified by column chromatography on silica gel (0→40% EA in PE) to give 3-(2,2-difluoroethyl)-5-((tetrahydro-2H-pyran-2-yloxy)methyl)isoxazole (900 mg, 49% yield over 2 steps) as a colorless oil. LC/MS (ESI): m/z=248 [M+H]$^+$.

Synthesis of (R)-3-((1-(4-fluoro-2-(1-hydroxyethyl)phenyl)-1H-pyrazol-5-yl)methyl)-1-isopropyl-1H-pyrazole-5-carbonitrile

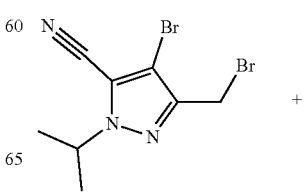

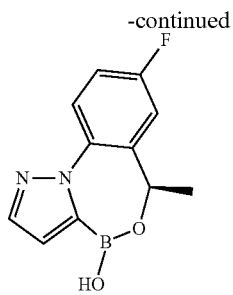

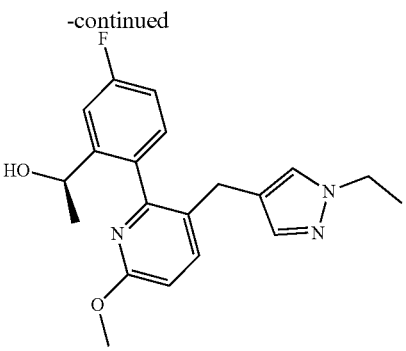

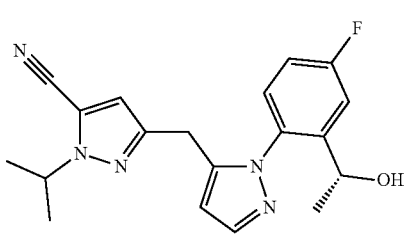

To a solution of 4-bromo-3-(bromomethyl)-1-isopropyl-1H-pyrazole-5-carbonitrile (100 mg, 0.33 mmol) and (R)-8-fluoro-6-methyl-4H,6H-benzo[e]pyrazolo[5,1-c][1,4,2]oxazaborepin-4-ol (83 mg, 0.36 mmol) in toluene (10 mL) and EtOH (2 mL) were added potassium phosphate (207 mg, 0.98 mmol) and Pd(PPh$_3$)$_4$(38 mg, 0.03 mmol) at r.t. The mixture was thrice degassed under N$_2$ atmosphere and stirred at 90° C. for 12 h. The reaction mixture was filtered, and the filtrate was concentrated to dryness. The residue was purified by prep-TLC (PE:EtOAc=3:1, V/V) to give (R)-3-((1-(4-fluoro-2-(1-hydroxyethyl)phenyl)-1H-pyrazol-5-yl)methyl)-1-isopropyl-1H-pyrazole-5-carbonitrile (20 mg, 14% yield) as a yellow oil. LC/MS (ESI) (m/z): 354 [M+H]$^+$.

Synthesis of (R)-1-(2-(3-((1-ethyl-1H-pyrazol-4-yl)methyl)-6-methoxypyridin-2-yl)-5-fluorophenyl)ethan-1-ol

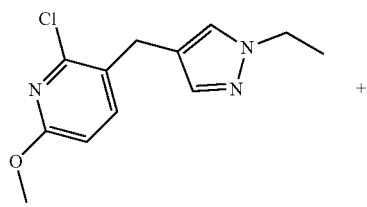

+

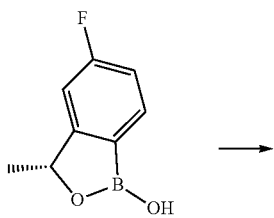

→

To a solution of 2-chloro-3-[(1-ethyl-1H-pyrazol-4-yl)methyl]-6-methoxypyridine (140 mg, 0.56 mmol) and (3R)-5-fluoro-3-methyl-1,3-dihydro-2,1-benzoxaborol-1-ol (92 mg, 0.56 mmol) in THF (5 mL) and H$_2$O (1 mL) was added K$_3$PO$_4$ (236 mg, 1.11 mmol). The mixture was degassed with N$_2$ three times and then [1,1'-bis(di-tert-butylphosphino)ferrocene]dichloropalladium (36 mg, 0.056 mmol) was added. The mixture was degassed with N$_2$ once again and stirred at 70° C. overnight. After cooling to r.t. and concentration in vacuo, the residue was purified by flash column chromatography (silica gel, 0→50% EA in PE) to give (1R)-1-(2-{3-[(1-ethyl-1H-pyrazol-4-yl)methyl]-6-methoxypyridin-2-yl}-5-fluorophenyl)ethan-1-ol (140 mg, yield: 71%) as a yellow foam. LC/MS ESI (m/z): 356 [M+H]$^+$.

Synthesis of 5-((1-(cyclopropylmethyl)-1H-pyrazol-4-yl)methyl)-1-(4-fluoro-2-iodophenyl)-3-methyl-1H-pyrazole

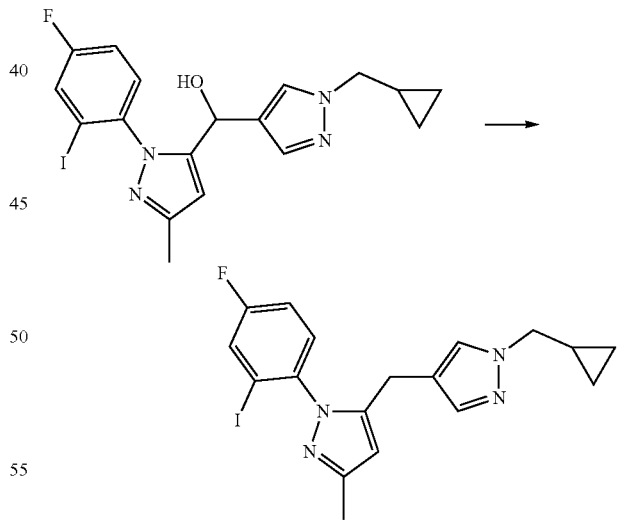

To a solution of (1-(cyclopropylmethyl)-1H-pyrazol-4-yl)(1-(4-fluoro-2-iodophenyl)-3-methyl-1H-pyrazol-5-yl)methanol (460 mg, 1.02 mmol) in CH$_3$CN (5 mL) was added iodotrimethylsilane (1.45 mL, 10.2 mmol) at r.t. The mixture was stirred at 90° C. for 2 h. After concentration to remove CH$_3$CN, the resulting residue was treated with EtOAc and aq. Na$_2$CO$_3$. The organic layer was separated, concentrated under reduced pressure and purified by flash chromatography on silica gel (10→50% EA in PE) to give 5-((1-

(cyclopropylmethyl)-1H-pyrazol-4-yl)methyl)-1-(4-fluoro-2-iodophenyl)-3-methyl-1H-pyrazole (300 mg, 67% yield) as a white solid. LC/MS (ESI): m/z=437 [M+H]$^+$.

Synthesis of 1-(2-(5-((3-chloro-1-ethyl-1H-pyrazol-4-yl)methyl)-3-methyl-1H-pyrazol-1-yl)-5-fluorophenyl)ethan-1-one

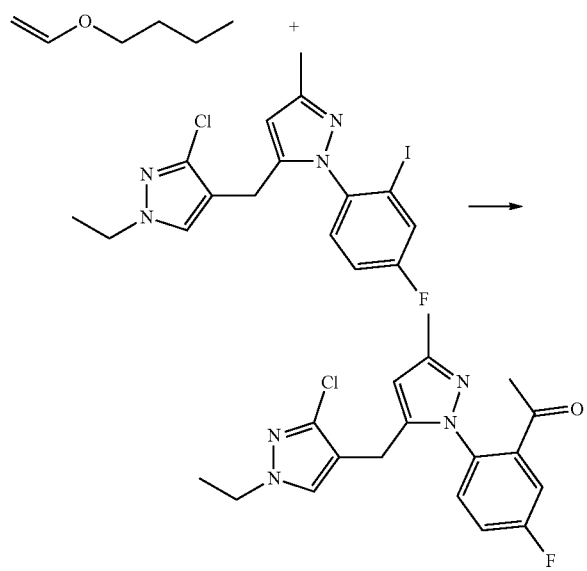

A suspension of 5-[(3-chloro-1-ethyl-1H-pyrazol-4-yl)methyl]-1-(4-fluoro-2-iodophenyl)-3-methyl-1H-pyrazole (19.5 g, 43.9 mmol) and Pd(OAc)$_2$ (247 mg, 1.10 mmol), 1,3-bis(diphenylphosphino)propane (905 mg, 2.19 mmol) in 1-butyl-3-methylimidazolium tetrafluoroborate (150 mL) was stirred for 10 min. After the mixture was degassed three times, 1-(vinyloxy)butane (21.96 g, 219.6 mmol) and TEA (7.31 mL, 52.7 mmol) were added sequentially. The mixture was stirred for 24 h at 115° C. The mixture cooled to r.t., and then 1N aq. HCl was added. After stirring for 0.5 h, dichloromethane was added. The organic layer was washed with brine, dried over anhydrous magnesium sulfate, filtered, and concentrated under reduced pressure. The crude residue was purified by flash column chromatography on silica gel to give 1-(2-{5-[(3-chloro-1-ethyl-1Hpyrazol-4-yl)methyl]-3-methyl-1H-pyrazol-1-yl}-5-fluorophenyl)ethan-1-one (11.1 g, yield: 70%) as a white foam. LC/MS (ESI): m/z=361 [M+H]$^+$.

Synthesis of methyl 2-(5-((1-(cyclopropylmethyl)-1H-pyrazol-4-yl)methyl)-3-methyl-1H-pyrazol-1-yl)-5-fluorobenzoate

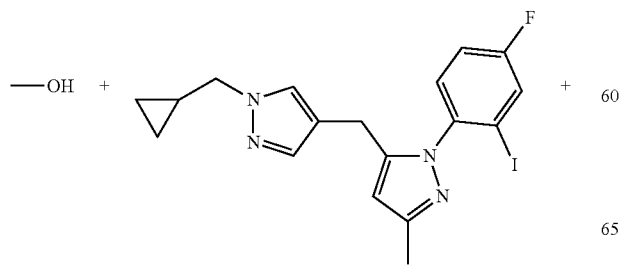

-continued

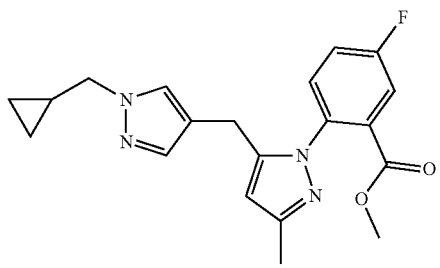

A mixture of 5-{[1-(cyclopropylmethyl)-1H-pyrazol-4-yl]methyl}-1-(4-fluoro-2-iodophenyl)-3-methyl-1H-pyrazole (340 mg, 0.779 mmol), MeOH (10 mL), Pd(dppf)Cl$_2$ (57 mg, 0.078 mmol) and TEA (236 mg, 2.33 mmol) was stirred for 16 h under a CO balloon at 25° C. The reaction mixture was concentrated and diluted with DCM. This solution was washed with brine, dried over anhydrous Na$_2$SO$_4$, filtered and concentrated. The residue was purified by flash column chromatography (silica gel, 0→50% EA in PE) to give methyl 2-(5-{[1-(cyclopropylmethyl)-1H-pyrazol-4-yl]methyl}-3-methyl-1H-pyrazol-1-yl)-5-fluorobenzoate (280 mg, 98%) as a colorless oil. LC/MS (ESI) m/z: 369 [M+H]$^+$.

Synthesis of (1-ethyl-1H-pyrazol-4-yl)(1-(4-fluoro-2-(hydroxymethyl)phenyl)-3-(trifluoromethyl)-1H-pyrazol-5-yl)methanol

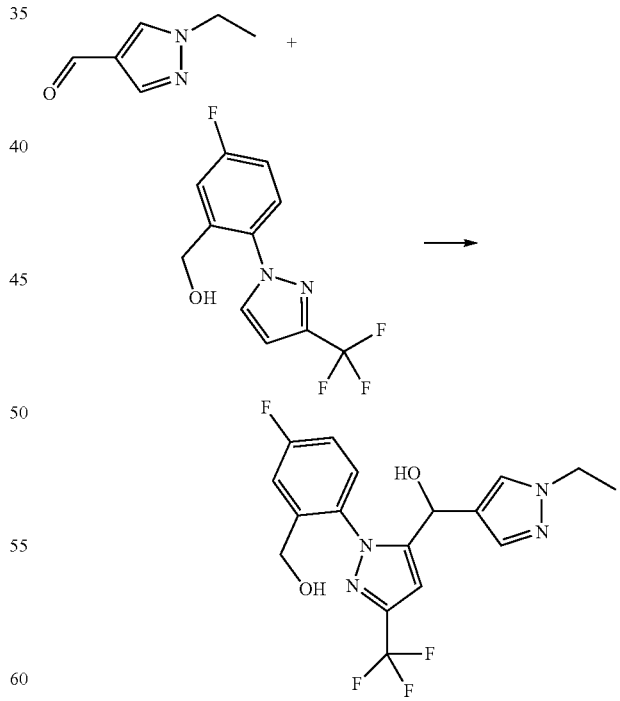

To a solution of {5-fluoro-2-[3-(trifluoromethyl)-1H-pyrazol-1-yl]phenyl}methanol (260 mg, 0.990 mmol) in dry THF (2 mL) was added n-BuLi (0.990 mL, 2.49 mmol, 2.5 M) dropwise at −78° C. over 5 min. The solution was stirred at −70° C. for 1 h. To this solution was added 1-ethyl-1H- pyrazole-4-carbaldehyde (186 mg, 1.49 mmol) in THF (2 mL) dropwise. The solution was warmed slowly to 0° C. while stirring over 0.5 h. The mixture was poured into cold sat. NH$_4$Cl and then extracted with EA twice. The combined extracts were washed with brine, concentrated under vacuum and purified by flash chromatography (0→100% EtOAc in PE) to give (1-ethyl-1H-pyrazol-4-yl)({1-[4-fluoro-2-(hydroxymethyl)phenyl]-3-(trifluoromethyl)-1H-pyrazol-5-yl})methanol (270 mg, 70%) as a colorless syrup. LC/MS (ESI): m/z=385 [M+H]$^+$.

The following intermediates were synthesized using a similar experimental protocol:

(1-{2-[(1R)-1-(benzyloxy)ethyl]-4-fluorophenyl}-3-(difluoromethyl)-1H-pyrazol-5-yl)[3-(2,2-difluoroethyl)-1-methyl-1H-pyrazol-5-yl]methanol m/z (ESI): 521 [M + H]

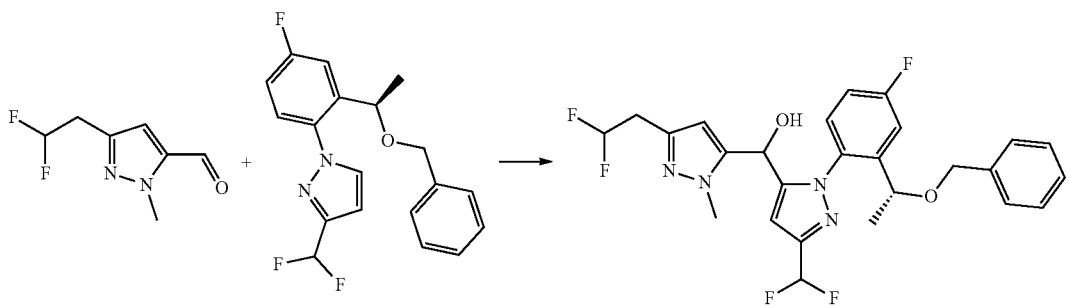 [SMILES: Cn1nc(CC(F)F)cc1C=O ; C[C@@H](OCc1ccccc1)c1cc(F)ccc1-n1ccc(C(F)F)n1 ; C[C@@H](OCc1ccccc1)c1cc(F)ccc1-n1nc(C(F)F)cc1C(O)c1cc(CC(F)F)nn1C]

Synthesis of 3-(2,2-difluoroethyl)isoxazole-5-carbaldehyde

Synthesis of (1-(2-(1,3-dioxolan-2-yl)-4-fluorophenyl)-3-methyl-1H-pyrazol-5-yl)(1-ethyl-1H-pyrazol-4-yl)methanone

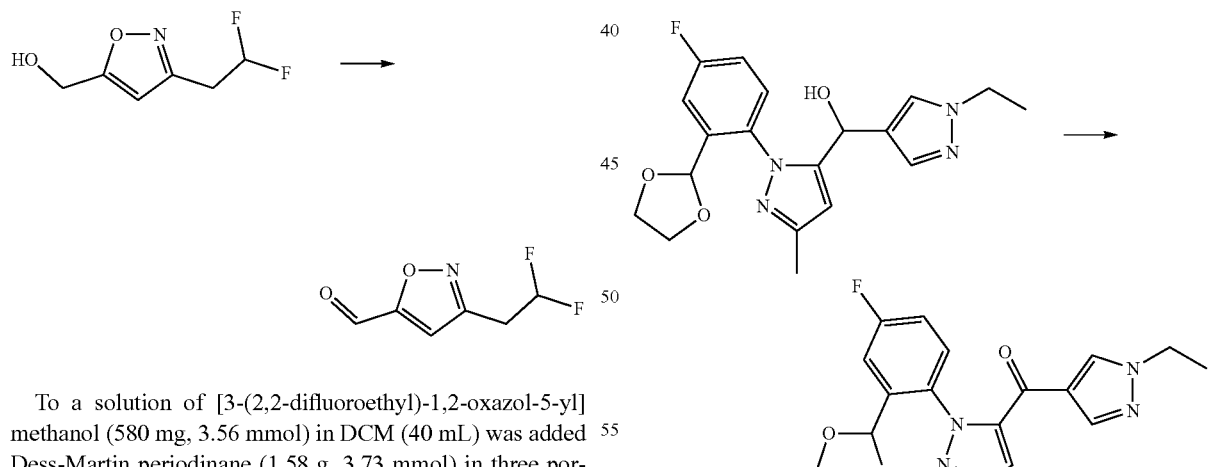

To a solution of [3-(2,2-difluoroethyl)-1,2-oxazol-5-yl]methanol (580 mg, 3.56 mmol) in DCM (40 mL) was added Dess-Martin periodinane (1.58 g, 3.73 mmol) in three portions at 0° C. The resulting mixture was stirred at 0° C. for 1 h. The mixture was diluted with DCM (100 mL), and washed with sat. NaHCO$_3$ (50 mL×2) and brine (30 mL). The organic layer was concentrated in vacuo and the residue was purified by column chromatography on silica gel (20% EtOAc in PE) to give 3-(2,2-difluoroethyl)-1,2-oxazole-5-carbaldehyde (330 mg, 58% over 2 steps) as a light-yellow oil.

LC/MS (ESI): m/z=162 [M+H]$^+$.

To a solution of (1-(2-(1,3-dioxolan-2-yl)-4-fluorophenyl)-3-methyl-1H-pyrazol-5-yl)(1-ethyl-1H-pyrazol-4-yl)methanol (2.18 g, 5.87 mmol) in dioxane (15 mL) was added MnO$_2$ (2.01 g, 29.3 mmol) in one portion. The reaction mixture was then warmed to 100° C. and stirred at that temperature for 16 h. The reaction mixture was filtered and the filtrate was concentrated in vacuo to give the crude product, which was purified by column chromatography on silica gel (0→20% EtOAc in PE) to give (1-(2-(1,3-dioxolan-2-yl)-4-fluorophenyl)-3-methyl-1H-pyrazol-5-yl)(1-ethyl-1H-pyrazol-4-yl)methanone (1.84 g, 85% yield) as a yellow solid. TLC: $R_f$=0.3 (PE/EA=2:1), LC/MS ESI (m/z): 371 [M+H]$^+$.

Synthesis of (-(2-(1,3-dioxolan-2-yl)-4-fluorophenyl)-3-fluoro-H-pyrazol-5-yl)(1-ethyl-H-pyrazol-4-yl)methanone

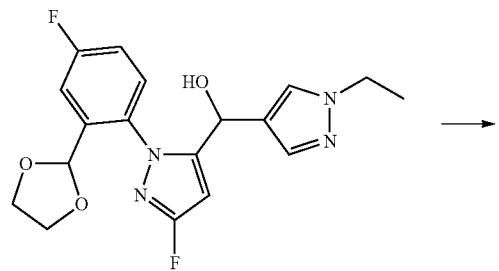

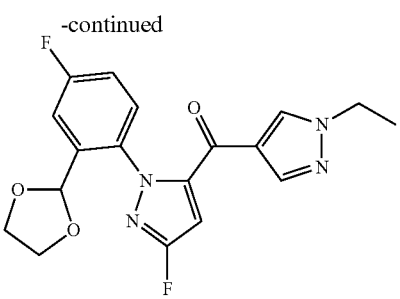

To a solution of (1-(2-(1,3-dioxolan-2-yl)-4-fluorophenyl)-3-fluoro-H-pyrazol-5-yl)(-ethyl-1H-pyrazol-4-yl)methanol (941 mg, 2.50 mmol) in DCM (30 mL) was added Dess-Martin periodinane (1.59 g, 3.75 mmol). Then the mixture was stirred at r.t. for 1 h. After 1 h, the reaction mixture was filtered, the filtrate was concentrated in vacuo to give the crude product. The crude product was purified by prep-TLC (MeOW/DCM=1/30, V/V) to give (1-(2-(1,3-dioxolan-2-yl)-4-fluorophenyl)-3-fluoro-1H-pyrazol-5-yl)(1-ethyl-1H-pyrazol-4-yl)methanone (2.49 g, 870%) as a light yellow gum. LC/MS ESI (m/z): 375 [M+H]$^+$.

The following intermediates were synthesized using a similar experimental protocol:

(1-(2-(1,3-dioxolan-2-yl)-4-fluorophenyl)-1H-pyrazol-5-yl)(5-bromo-1-ethyl-1H-pyrazol-4-yl)methanone

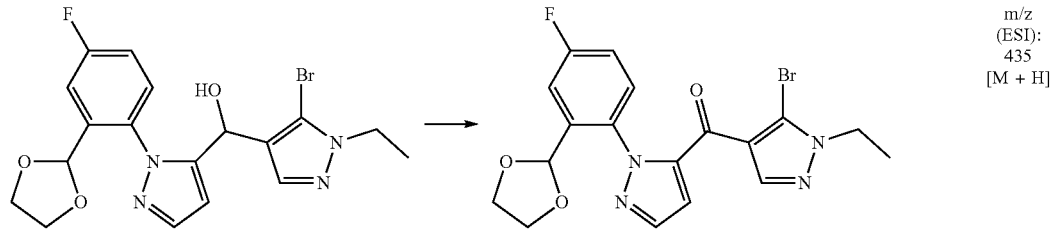

m/z (ESI): 435 [M + H]

(1-(2-(1,3-dioxolan-2-yl)-4-fluorophenyl)-4-fluoro-1H-pyrazol-5-yl)(5-bromo-1-ethyl-1H-pyrazol-4-yl)methanone

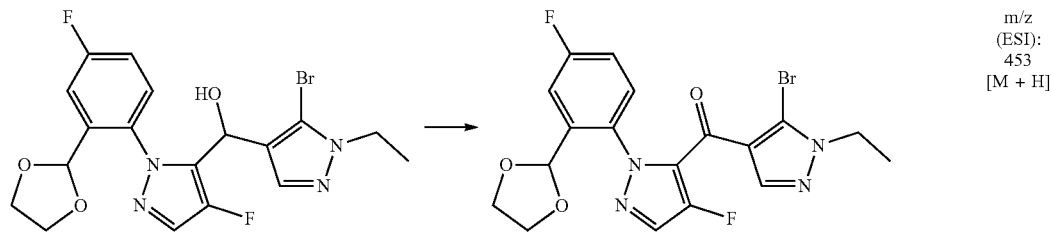

m/z (ESI): 453 [M + H]

5-(1-(2-(1,3-dioxolan-2-yl)-4-fluorophenyl)-1H-pyrazole-5-carbonyl)-1-((2-(trimethylsilyl)ethoxy)methyl)-1H-pyrazole-3-carbaldehyde

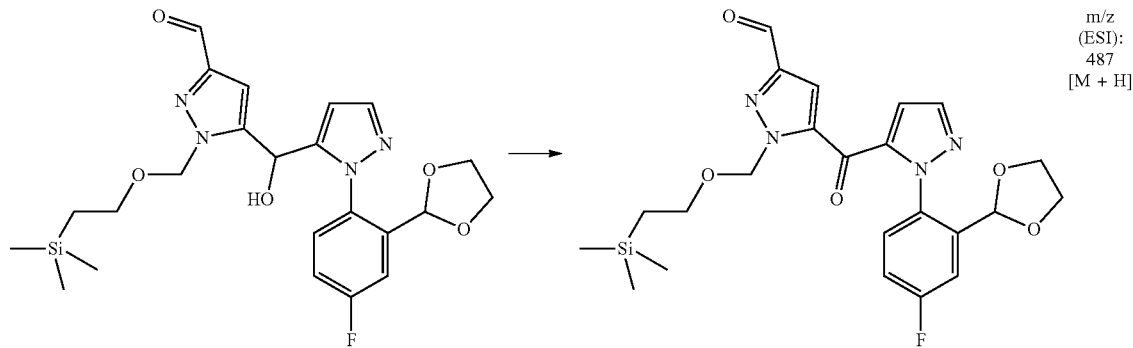

m/z (ESI): 487 [M + H]

497

Synthesis of 1-(2-(5-((1-(cyclopropylmethyl)-3-methyl-1H-pyrazol-4-yl)methyl)-3-methyl-1H-pyrazol-1-yl)-5-fluorophenyl)ethan-1-one

498

Synthesis of 5-((5-bromo-1-ethyl-1H-pyrazol-4-yl)methyl)-1-(2-(1-ethoxyvinyl)-4-fluorophenyl)-1H-pyrazole-4-carbonitrile

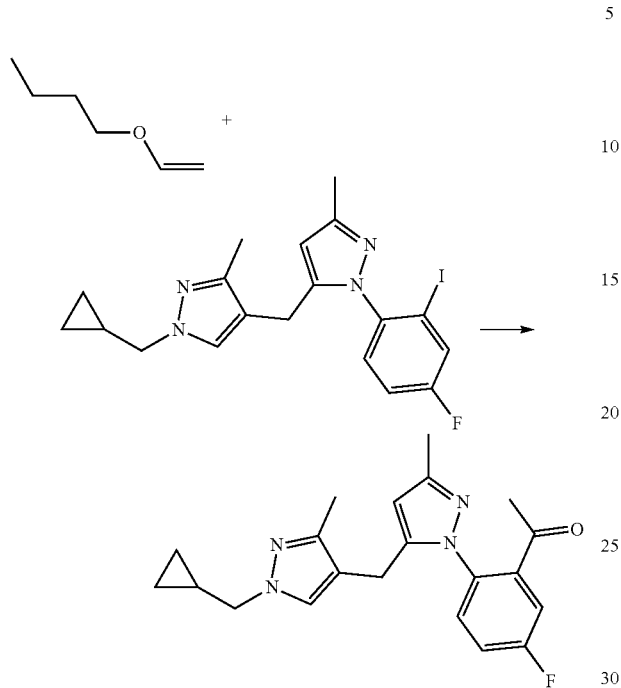

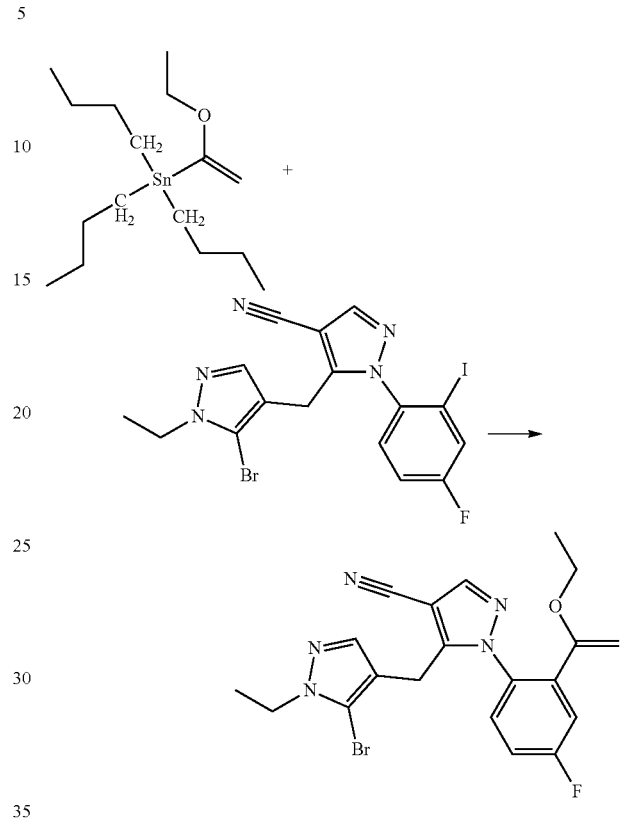

To a solution of 1-(cyclopropylmethyl)-4-((1-(4-fluoro-2-iodophenyl)-3-methyl-1H-pyrazol-5-yl)methyl)-3-methyl-1H-pyrazole (1.70 g, 3.80 mmol) in ionic liquid (10 mL) were added [3-(diphenylphosphanyl)propyl]diphenylphosphane (0.08 g, 0.19 mmol), triethylamine (0.60 mL, 4.5 mmol), Pd(OAc)$_2$ (30 mg, 0.11 mmol) and 1-(ethenyloxy)butane (2.5 mL, 19 mmol) under N$_2$ atmosphere. The mixture was thrice degassed under N$_2$ atmosphere and stirred at 115° C. under N$_2$ atmosphere for 24 h. The mixture was diluted with EtOAc (15 mL), washed with water (5 mL) and brine (5 mL), dried over anhydrous Na$_2$SO$_4$ and concentrated to dryness. The residue was purified by flash column chromatography on silica gel (PE:EtOAc=1:1, V/V) to give 1-(2-(5-((1-(cyclopropylmethyl)-3-methyl-1H-pyrazol-4-yl)methyl)-3-methyl-1H-pyrazol-1-yl)-5-fluorophenyl)ethan-1-one (300 mg, 22%) as a yellow oil. LC/MS (ESI) (m/z): 367 [M+H]$^+$.

To a solution of 5-((5-bromo-1-ethyl-1H-pyrazol-4-yl)methyl)-1-(4-fluoro-2-iodophenyl)-1H-pyrazole-4-carbonitrile (200 mg, 0.390 mmol) and tributyl(1-ethoxyvinyl)stannane (159 mg, 0.440 mmol) in toluene (10 mL) was added Pd(PPh$_3$)$_2$Cl$_2$ (14 mg, 0.02 mmol) at 25° C. The mixture was degassed with N$_2$ for three times and then stirred at 100° C. for 16 h. The mixture was concentrated under reduced pressure to give crude 5-((5-bromo-1-ethyl-1H-pyrazol-4-yl)methyl)-1-(2-(1-ethoxyvinyl)-4-fluorophenyl)-1H-pyrazole-4-carbonitrile (175 mg, yield: 100%) as a brown solid without further purification for the next step. LC/MS (ESI) m/z: 444 [M+H]$^+$.

The following intermediates were synthesized using a similar experimental protocol:

5-((5-bromo-1-ethyl-1H-pyrazol-4-yl)methyl)-1-(2-(1-ethoxyvinyl)-4-fluorophenyl)-1H-pyrazole-3-carbonitrile

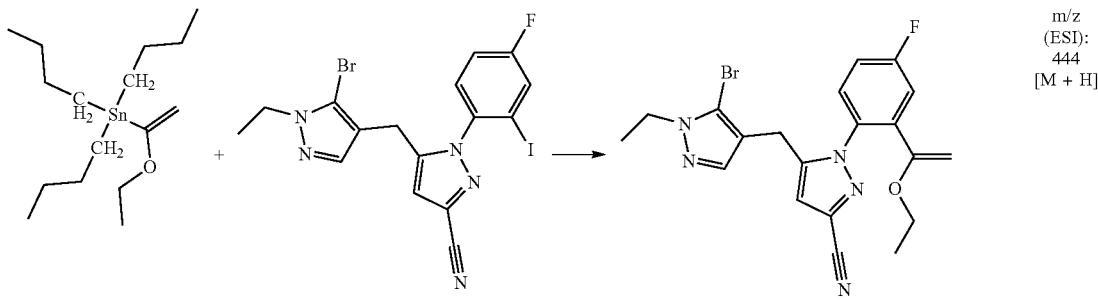

m/z (ESI): 444 [M + H]

5-bromo-4-((1-(2-(1-ethoxyvinyl)-4-fluorophenyl)-3-(trifluoromethyl)-1H-pyrazol-5-yl)methyl)-1-ethyl-1H-pyrazole m/z (ESI): 487 [M + H]

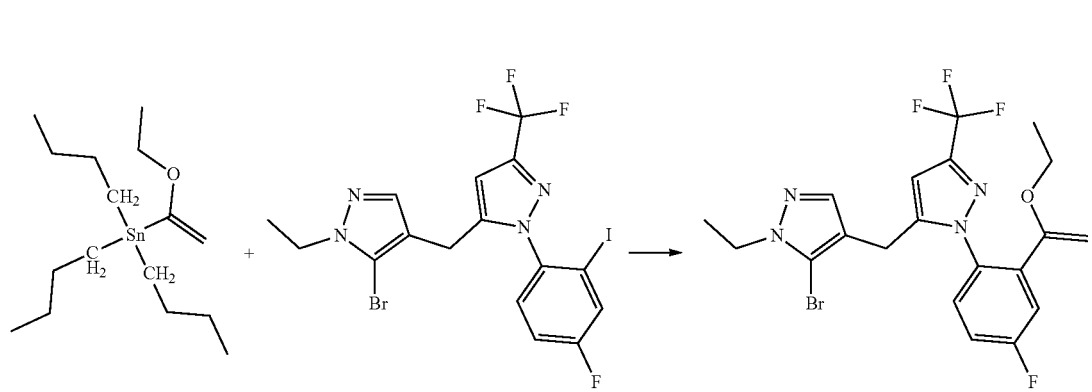 [SMILES: C=[C](OCC)[Sn]([CH2]CCC)([CH2]CCC)[CH2]CCC ; CCn1ncc(Cc2cc(C(F)(F)F)nn2-c2ccc(F)cc2I)c1Br ; C=C(OCC)c1cc(F)ccc1-n1nc(C(F)(F)F)cc1Cc1cnn(CC)c1Br]

5-((1-(2,2-difluoroethyl)-1H-pyrazol-4-yl)methyl)-1-(2-(1-ethoxyvinyl)-4-fluorophenyl)-3-(trifluoromethyl)-1H-pyrazole m/z (ESI): 445 [M + H]

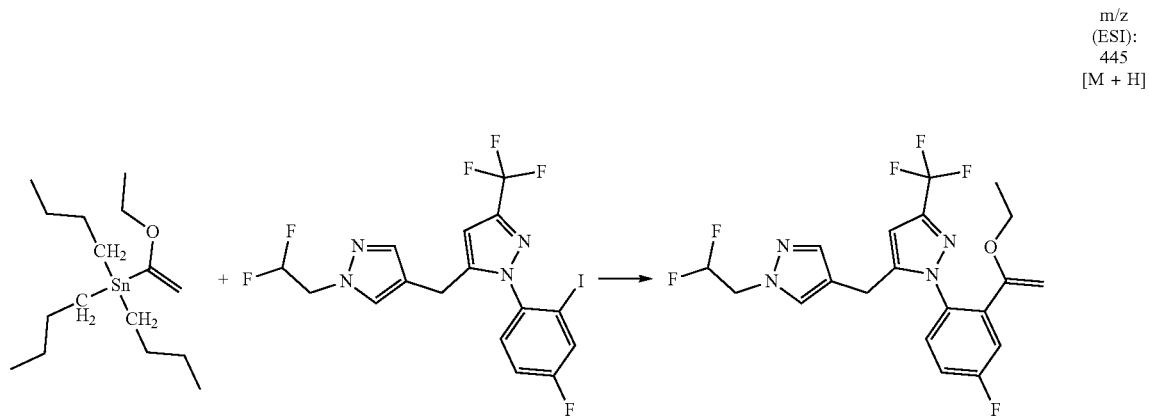

Synthesis of 2-(5-(1-ethyl-1H-pyrazole-4-carbonyl)-3-methyl-1H-pyrazol-1-yl)-5-fluorobenzaldehyde

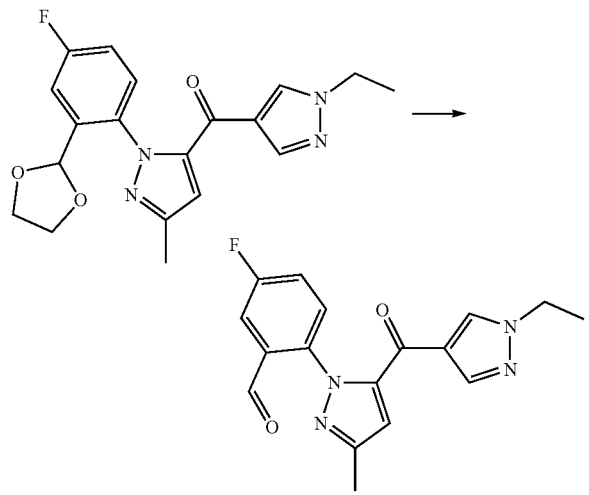

To a solution of (1-(2-(1,3-dioxolan-2-yl)-4-fluorophenyl)-3-methyl-1H-pyrazol-5-yl)(1-ethyl-1H-pyrazol-4-yl)methanone (1.84 g, 4.98 mmol) in THF (20 mL) and $H_2O$ (5 mL) was added conc. HCl (5.0 mL) in one portion at 0° C. The resulting solution was stirred at 20° C. for 1 h. Then the reaction mixture was quenched with sat. aq. $NaHCO_3$ and partitioned between EtOAc and water. The organic layer was separated, washed with sat. $NH_4Cl$ and brine, dried over anhydrous $Na_2SO_4$, filtered, and concentrated in vacuo. The residue was purified by column chromatography on silica gel (50% of EtOAc in PE, V/V) to give 2-(5-(1-ethyl-1H-pyrazole-4-carbonyl)-3-methyl-1H-pyrazol-1-yl)-5-fluorobenzaldehyde (650 mg, 40% yield) as a yellow solid. TLC: $R_f$=0.5 (PE/EA=1:1), LC/MS ESI (m/z): 327 [M+H]$^+$.

The following intermediates were synthesized using a similar experimental protocol:

2-(5-(5-bromo-1-ethyl-1H-pyrazole-4-carbonyl)-1H-pyrazol-1-yl)-5-fluorobenzaldehyde

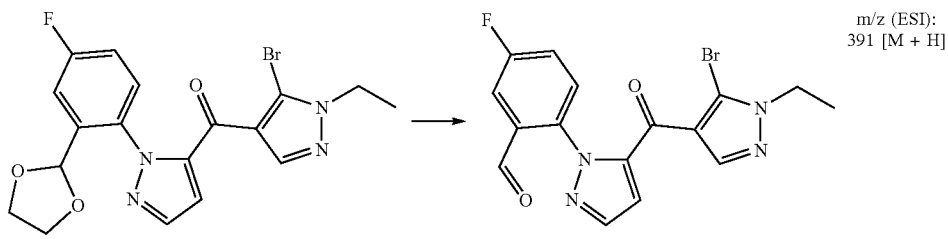

m/z (ESI): 391 [M + H]

2-(5-(5-bromo-1-ethyl-1H-pyrazole-4-carbonyl)-4-fluoro-1H-pyrazol-1-yl)-5-fluorobenzaldehyde

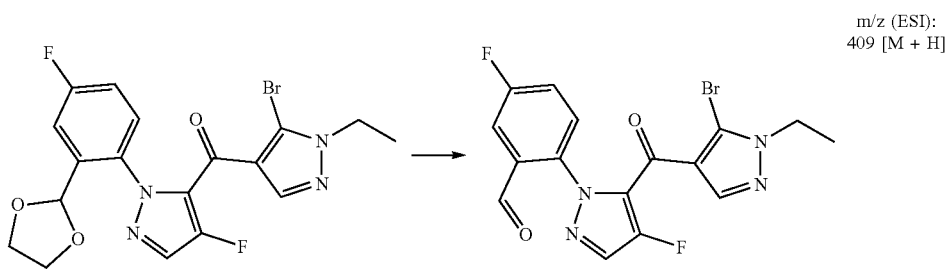

m/z (ESI): 409 [M + H]

2-(5-(1-ethyl-1H-pyrazole-4-carbonyl)-3-fluoro-1H-pyrazol-1-yl)-5-fluorobenzaldehyde

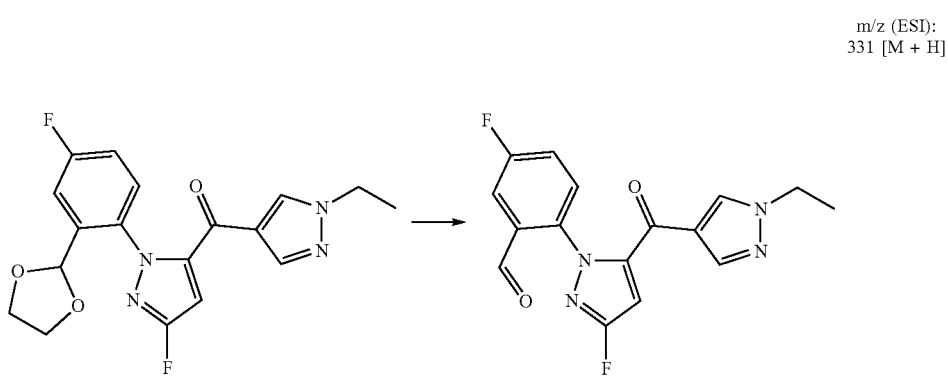

m/z (ESI): 331 [M + H]

Synthesis of 1-(2-acetyl-4-fluorophenyl)-5-((5-bromo-1-ethyl-1H-pyrazol-4-yl)methyl)-1H-pyrazole-4-carbonitrile

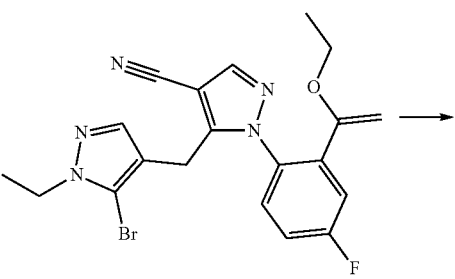

-continued

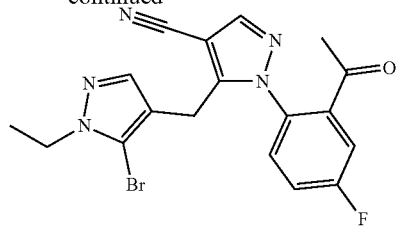

To a solution of 5-((5-bromo-1-ethyl-1H-pyrazol-4-yl)methyl)-1-(2-(1-ethoxyvinyl)-4-fluorophenyl)-1H-pyrazole-4-carbonitrile (200 mg, 0.390 mmol) in THF (2 mL) was added aq. HCl (1 M, 2.0 mL) at 25° C. After stirring at 30° C. for 2 h, the mixture was neutralized to pH 8 with sat. aq. NaHCO$_3$ and then extracted with EtOAc twice. The combined extracts were washed with H$_2$O and brine, dried over anhydrous Na$_2$SO$_4$, filtered and concentrated. The residue was purified by column chromatography on silica gel (0→35% EA in PE) to give 1-(2-acetyl-4-fluorophenyl)-5-((5-bromo-1-ethyl-1H-pyrazol-4-yl)methyl)-1H-pyrazole-4-carbonitrile (100 mg, yield: 530%) as a yellow oil. LC/MS (ESI) m/z: 416 [M+H]$^+$.

The following intermediates were synthesized using a similar experimental protocol:

1-(2-acetyl-4-fluorophenyl)-5-((5-bromo-1-ethyl-1H-pyrazol-4-yl)methyl)-1H-pyrazole-3-carbonitrile

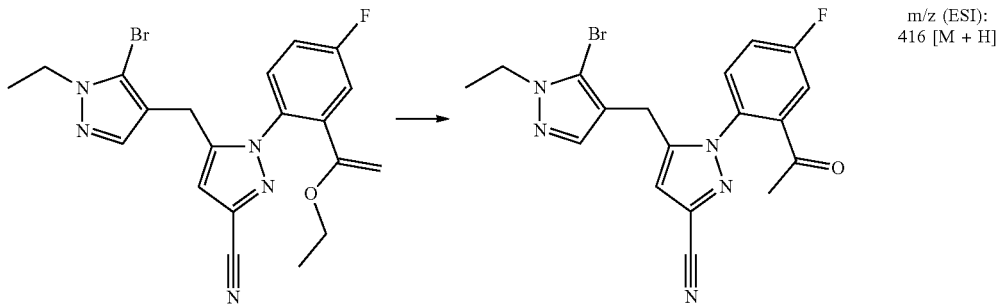

m/z (ESI): 416 [M + H]

1-(2-(5-((5-bromo-1-ethyl-1H-pyrazol-4-yl)methyl)-3-(trifluoromethyl)-1H-pyrazol-1-yl)-5-fluorophenyl)ethan-1-one

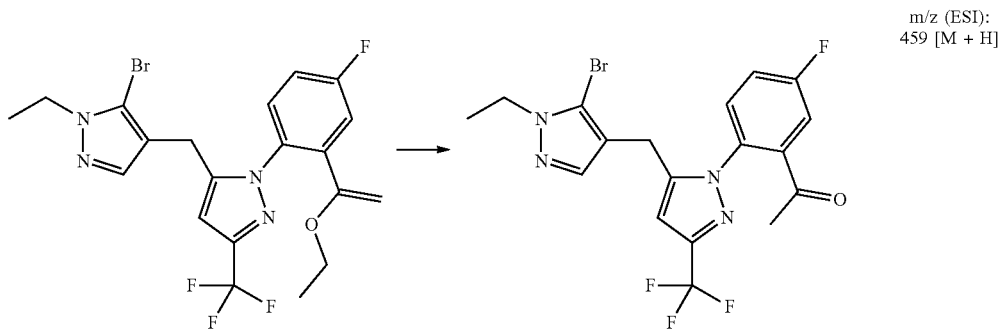

m/z (ESI): 459 [M + H]

1-(2-(5-((1-(2,2-difluoroethyl)-1H-pyrazol-4-yl)methyl)-3-(trifluoromethyl)-1H-pyrazol-1-yl)-5-fluorophenyl)ethan-1-one

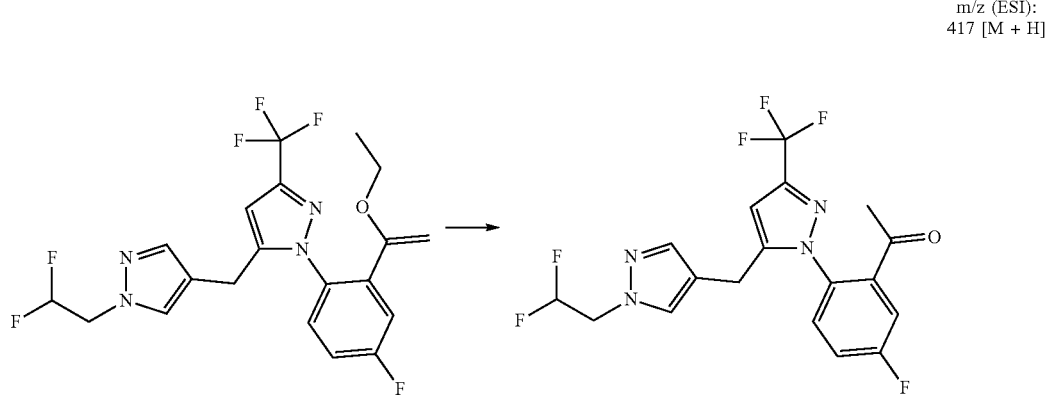

m/z (ESI): 417 [M + H]

Synthesis of (1-(2-(((tert-butyldimethylsilyl)oxy)methyl)-4-fluorophenyl)-3-chloro-1H-pyrazol-5-yl)(1-ethyl-1H-pyrazol-4-yl)methanol

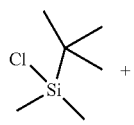 +

-continued

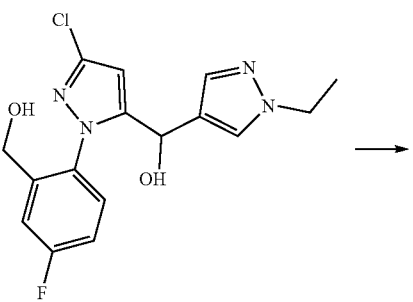

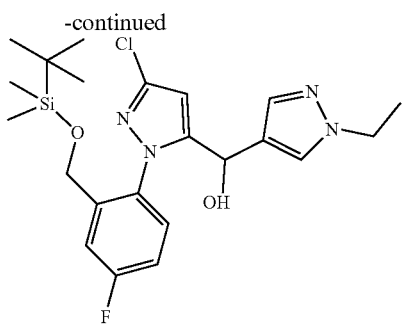

To a stirred solution of (3-chloro-1-(4-fluoro-2-(hydroxymethyl)phenyl)-1H-pyrazol-5-yl)(1-ethyl-1H-pyrazol-4-yl)methanol (19.1 g, 54.5 mmol) and imidazole (7.40 g, 109 mmol) in THF (200 mL) was added a solution of tert-butyl(chloro)dimethylsilane (7.50 g, 49.6 mmol) dropwise in THF (20 mL) at 0° C. After addition, the reaction was stirred at r.t. for 18 h. The mixture was concentrated and purified by flash chromatography (10→50% EtOAc in PE) to give [1-(2-{[(tert-butyldimethylsilyl)oxy]methyl}-4-fluorophenyl)-3-chloro-1H-pyrazol-5-yl](1-ethyl-1H-pyrazol-4-yl)methanol (20.5 g, 81% yield) as a yellow oil. LC/MS (ESI) (m/z): 465 [M+H]$^+$.

The following intermediates were synthesized using a similar experimental protocol:

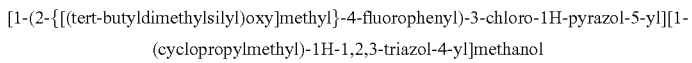

[1-(2-{[(tert-butyldimethylsilyl)oxy]methyl}-4-fluorophenyl)-3-chloro-1H-pyrazol-5-yl][1-(cyclopropylmethyl)-1H-1,2,3-triazol-4-yl]methanol

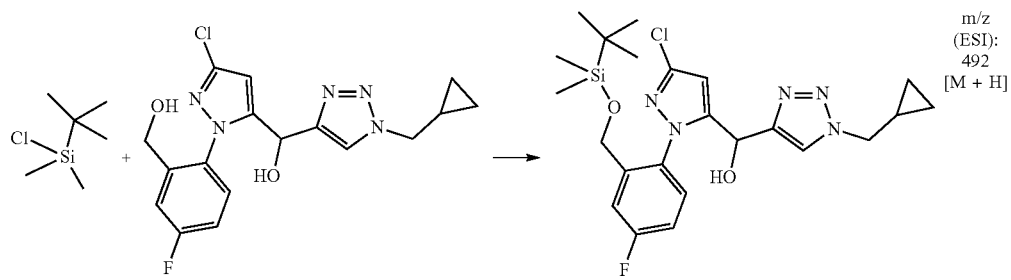

m/z (ESI): 492 [M + H]

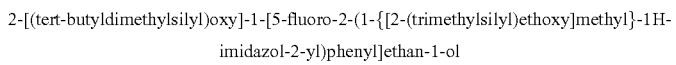

2-[(tert-butyldimethylsilyl)oxy]-1-[5-fluoro-2-(1-{[2-(trimethylsilyl)ethoxy]methyl}-1H-imidazol-2-yl)phenyl]ethan-1-ol

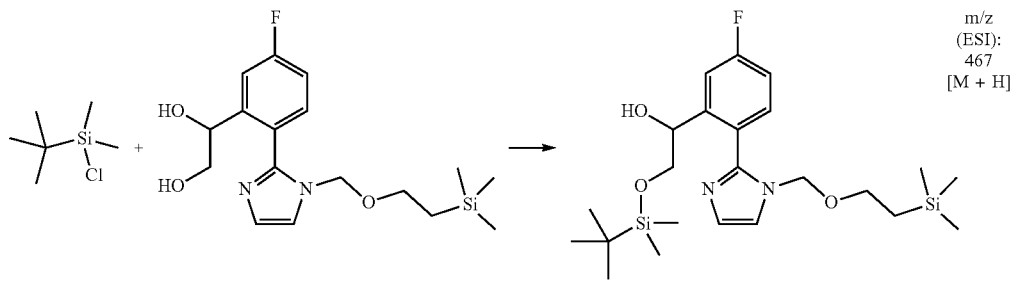

m/z (ESI): 467 [M + H]

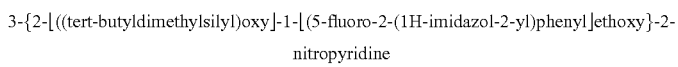

3-{2-[((tert-butyldimethylsilyl)oxy]-1-[(5-fluoro-2-(1H-imidazol-2-yl)phenyl]ethoxy}-2-nitropyridine

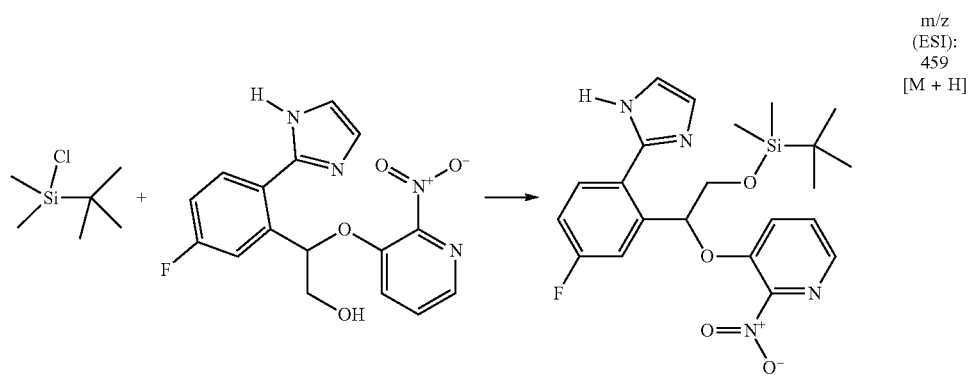

m/z (ESI): 459 [M + H]

507

Synthesis of (1-(2-(((tert-butyldimethylsilyl)oxy) methyl)-4-fluorophenyl)-3-chloro-1H-pyrazol-5-yl) (1-ethyl-1H-pyrazol-4-yl)methanone

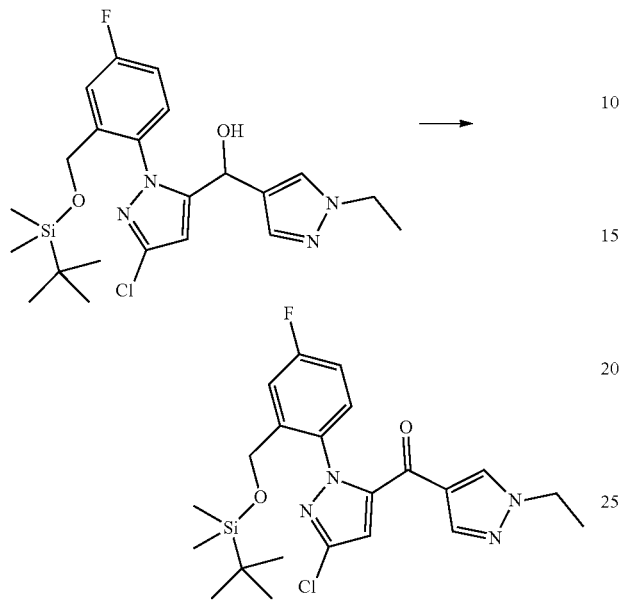

To a stirred solution of [1-(2-{[(tert-butyldimethylsilyl) oxy]methyl}-4-fluorophenyl)-3-chloro-1H-pyrazol-5-yl](1-ethyl-1H-pyrazol-4-yl)methanol (20.5 g, 44.2 mmol) in DCM (250 mL) was added $MnO_2$ (40.0 g, 460 mmol). After addition, the mixture was stirred at r.t. for 2 h. The reaction was filtered and concentrated to give (1-(2-(((tert-butyldimethylsilyl)oxy)methyl)-4-fluorophenyl)-3-chloro-1H-pyrazol-5-yl)(1-ethyl-1H-pyrazol-4-yl)methanone (20.4 g, 99% yield) as a yellow solid.

LC/MS (ESI) (m/z): 463 [M+H]$^+$.

The following intermediates were synthesized using a similar experimental protocol:

508

Synthesis of (3-chloro-1-(4-fluoro-2-(hydroxymethyl)phenyl)-1H-pyrazol-5-yl)(1-ethyl-1H-pyrazol-4-yl)methanone

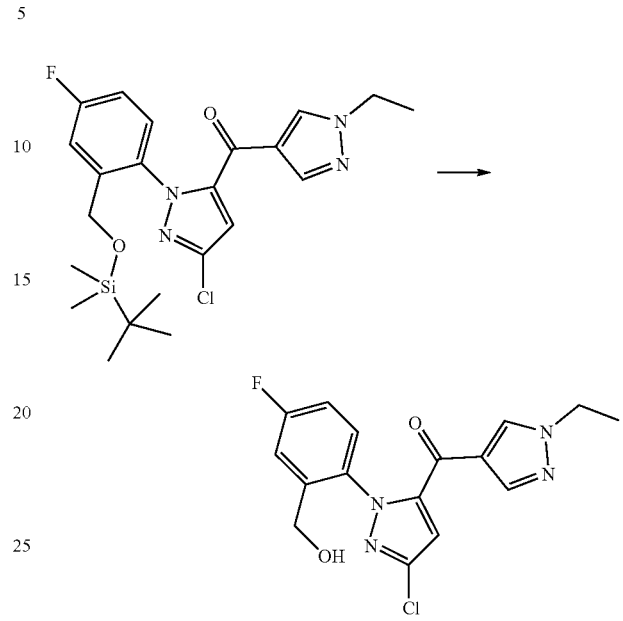

To a stirred solution of (1-(2-(((tert-butyldimethylsilyl) oxy)methyl)-4-fluorophenyl)-3-chloro-1H-pyrazol-5-yl)(1-ethyl-1H-pyrazol-4-yl)methanone (20.4 g, 44.1 mmol) in THF (150 mL) was added TBAF (135 mL, 135 mmol, 1 M in THF) at r.t. The mixture was stirred at 70° C. for 1.5 h. The reaction was poured into water (200 mL) and extracted with EtOAc (100 mL×2). The combined organic layers were washed with brine (200 mL), dried over anhydrous $Na_2SO_4$ and concentrated. The residue was purified by flash chromatography (10→50% EtOAc in PE) to give (3-chloro-1-(4-fluoro-2-(hydroxymethyl)phenyl)-1H-pyrazol-5-yl)(1-ethyl-1H-pyrazol-4-yl)methanone (12.6 g, 82%) as a yellow oil. LC/MS (ESI) (m/z): 349 [M+H]$^+$.

---

4-[1-(2-{[(tert-butyldimethylsilyl)oxy]methyl}-4-fluorophenyl)-3-chloro-1H-pyrazole-5-carbonyl]-1-(cyclopropylmethyl)-1H-1,2,3-triazole m/z (ESI): 490 [M + H]

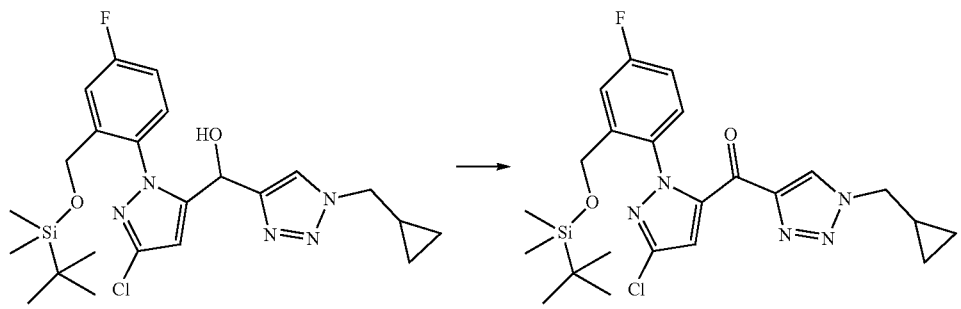 [SMILES: CC(C)(C)[Si](C)(C)OCc1cc(F)ccc1-n1nc(Cl)cc1C(O)c1cn(CC2CC2)nn1 ; CC(C)(C)[Si](C)(C)OCc1cc(F)ccc1-n1nc(Cl)cc1C(=O)c1cn(CC2CC2)nn1]

Synthesis of (R)-4-(2-(1-((5-bromo-2-nitropyridin-3-yl)oxy)ethyl)-4-fluorophenyl)-5-((1-ethyl-1H-pyrazol-4-yl)methyl)oxazole

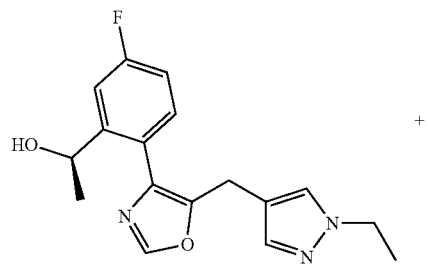

+

To a solution of (R)-1-(2-(5-((1-ethyl-1H-pyrazol-4-yl)methyl)oxazol-4-yl)-5-fluorophenyl)ethan-1-ol (247 mg, 0.780 mmol) in THF (4 mL), was added NaH (47 mg, 1.2 mmol, 60%, in mineral oil) in portions at 0° C. The resulting mixture was stirred at 0° C. for 30 min, then 5-bromo-3-fluoro-2-nitropyridine (208 mg, 0.940 mmol) was added. The reaction as heated to 80° C. and stirring was continued for 3 h. The mixture was cooled to r.t., quenched with water (5 mL), and extracted with EA (3×5 mL). The combined organic phases were washed with sat. aq. NH$_4$Cl (5 mL) and brine (5 mL), dried over anhydrous Na$_2$SO$_4$, filtered, and concentrated in vacuo. The residue was purified by flash chromatography (0→40% EtOAc in PE) to give (R)-4-(2-(1-((5-bromo-2-nitropyridin-3-yl)oxy)ethyl)-4-fluorophenyl)-5-((1-ethyl-1H-pyrazol-4-yl)methyl)oxazole (144 mg, 36% yield) as a yellow gum. LC/MS ESI (m/z): 516 [M+H]$^+$.

The following intermediates were synthesized using a similar experimental protocol:

(R)-4-(2-(1-((5-bromo-2-nitropyridin-3-yl)oxy)ethyl)-4-fluorophenyl)-5-((3-ethyl-1-methyl-1H-pyrazol-5-yl)methyl)-2-methylthiazole

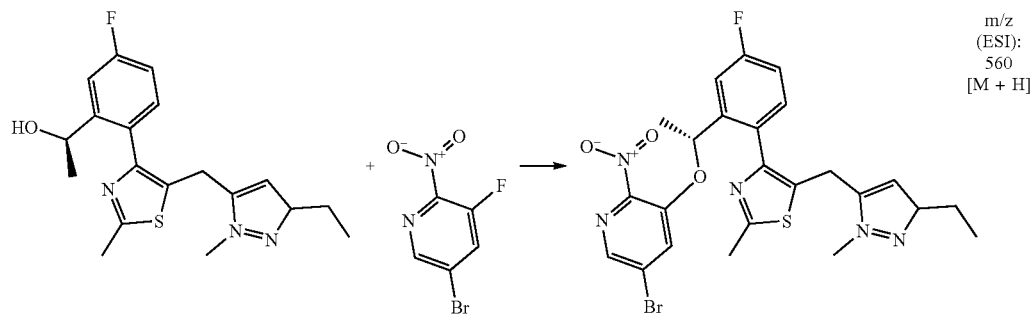

m/z (ESI): 560 [M + H]

Synthesis of 5-bromo-3-[1-(2-{4-[(1-ethyl-1H-pyrazol-4-yl)methyl]-1,2-oxazol-3-yl}-5-fluorophenyl)ethoxy]-2-nitropyridine

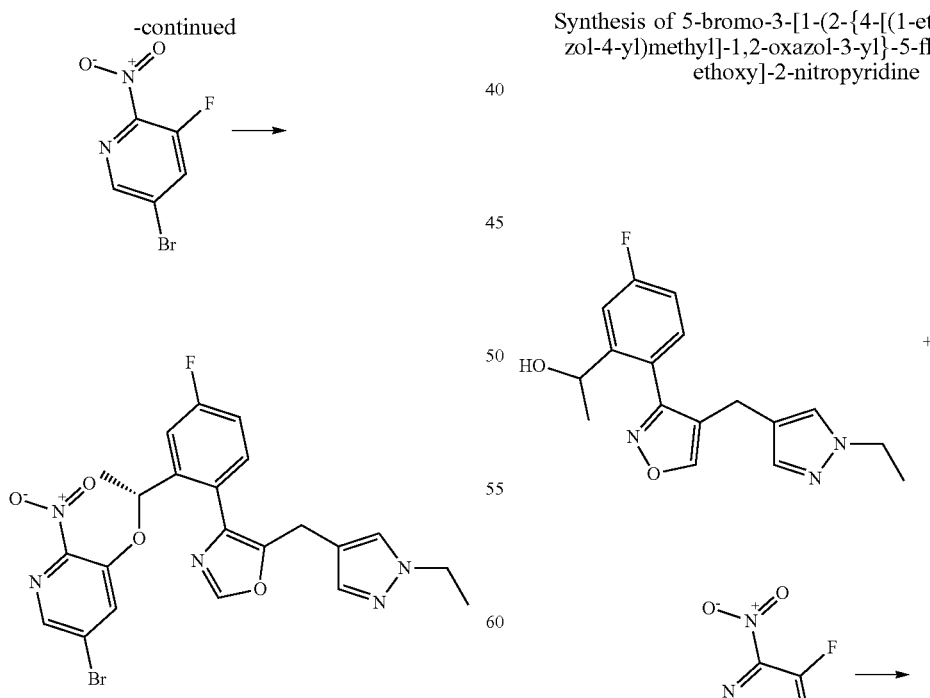

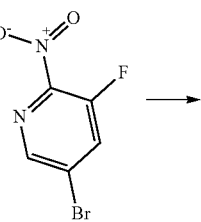

-continued

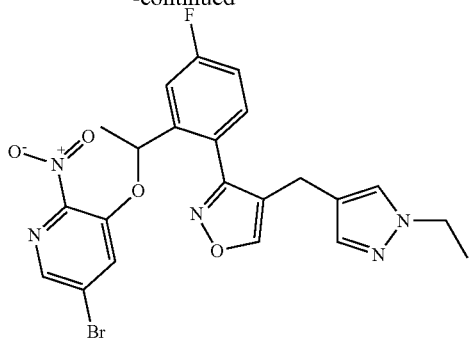

To a stirred solution of 1-(2-{4-[(1-ethyl-1H-pyrazol-4-yl)methyl]-1,2-oxazol-3-yl}-5-fluorophenyl)ethan-1-ol (113 mg, 0.358 mmol) in THF (4 mL) was added NaH (22 mg, 0.54 mmol, 60% in mineral oil) at 0° C. under $N_2$. After stirring at 0° C. for 50 min, a solution of 5-bromo-3-fluoro-2-nitropyridine (87 mg, 0.39 mmol) in THF (4 mL) was added dropwise at 0° C. The ice bath was removed, and the reaction was stirred at 25° C. for 12 h. The mixture was quenched with sat. aq. $NH_4Cl$ (10 mL), extracted with EtOAc (10 mL), dried over $Na_2SO_4$, filtered, and concentrated. The residue was purified by silica gel chromatography (50% EtOAc in PE) to give 5-bromo-3-[1-(2-{4-[(1-ethyl-1H-pyrazol-4-yl)methyl]-1,2-oxazol-3-yl}-5-fluorophenyl)ethoxy]-2-nitropyridine (83 mg, 45% yield) as a yellow oil. LC/MS (ESI) m/z: 516 [M+H]⁺.

The following intermediates were synthesized using a similar experimental protocol:

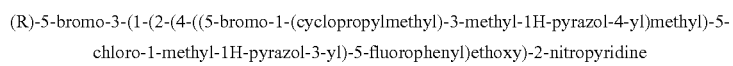

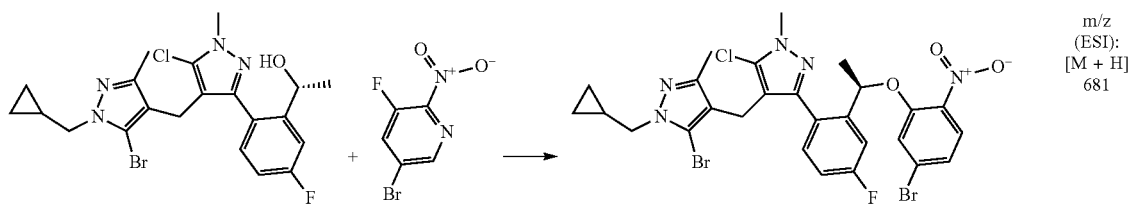

m/z (ESI): [M + H] 681

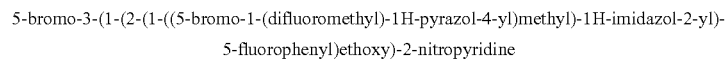

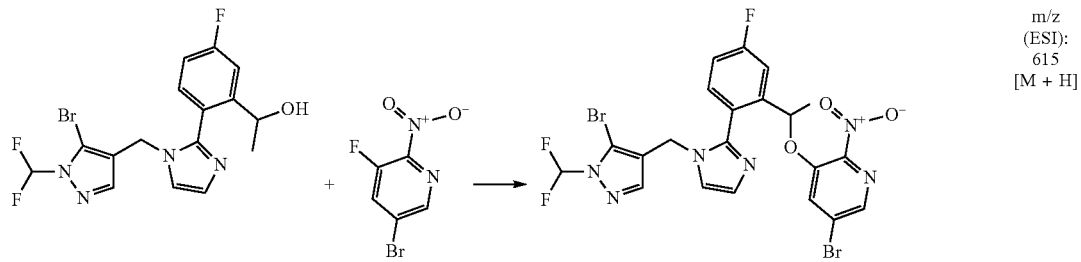

m/z (ESI): 615 [M + H]

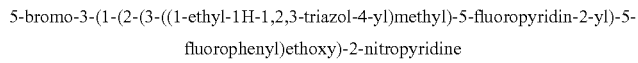

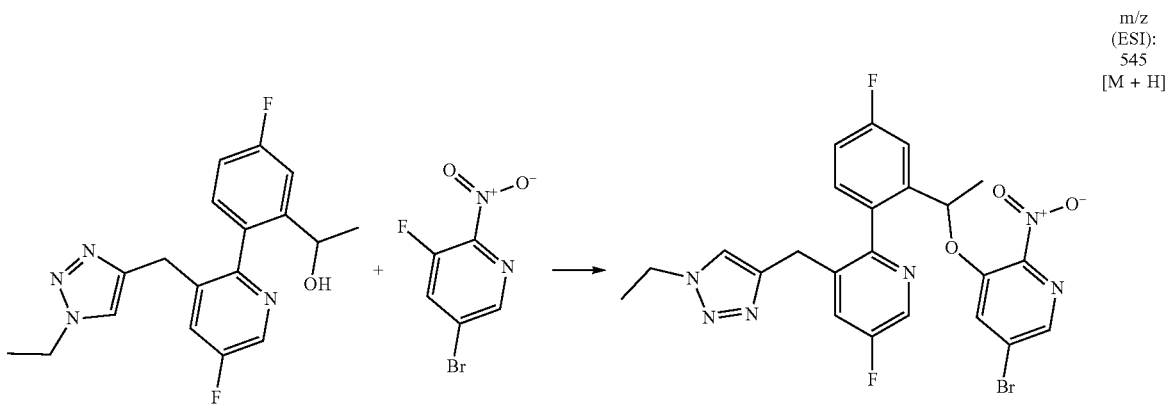

m/z (ESI): 545 [M + H]

-continued (R)-5-bromo-3-(1-(2-(4-((3-chloro-1-ethyl-1H-pyrazol-4-yl)methyl)-1-methyl-1H-pyrazol-3-yl)-5-fluorophenyl)ethoxy)-2-nitropyridine

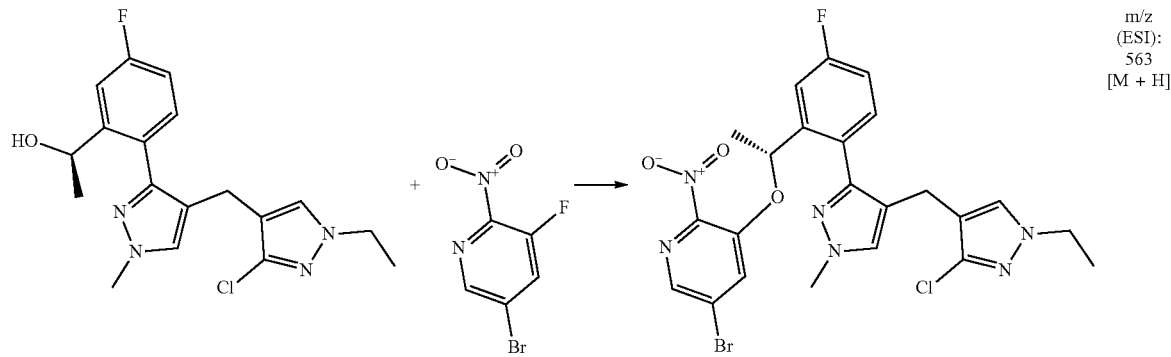

m/z (ESI): 563 [M + H]

(R)-5-bromo-3-(1-(2-(5-((3-chloro-1-ethyl-1H-pyrazol-4-yl)methyl)-3-methyl-1H-pyrazol-1-yl)-5-fluorophenyl)ethoxy)-2-nitropyridine

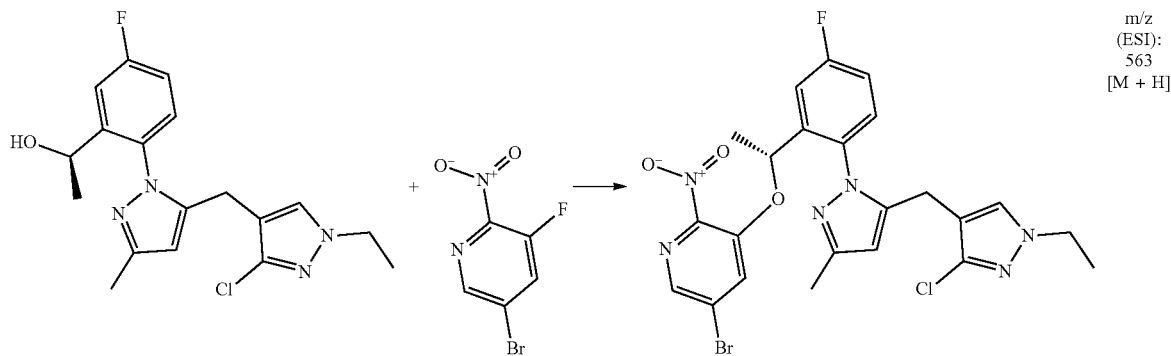

m/z (ESI): 563 [M + H]

(R)-5-((4-(2-(1-((5-bromo-2-nitropyridin-3-yl)oxy)ethyl)-4-fluorophenyl)-2-methylthiazol-5-yl)methyl)-1-methyl-1H-pyrazole-3-carbonitrile

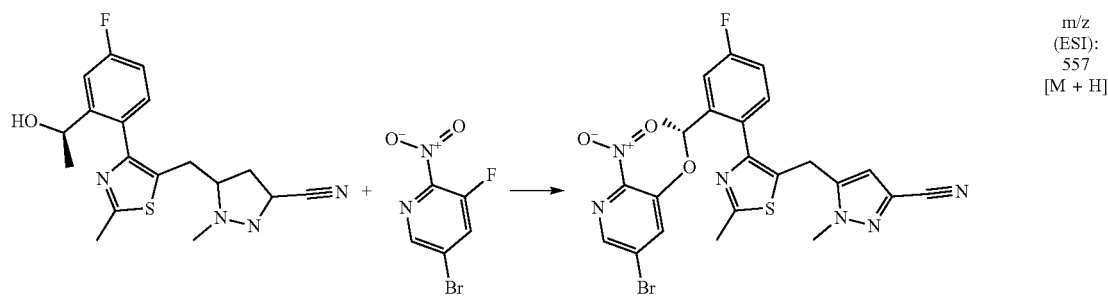

m/z (ESI): 557 [M + H]

(R)-5-bromo-3-(1-(2-(4-((3-chloro-1-(2,2-difluoroethyl)-1H-pyrazol-4-yl)methyl)-1-methyl-1H-pyrazol-3-yl)-5-fluorophenyl)ethoxy)-2-nitropyridine

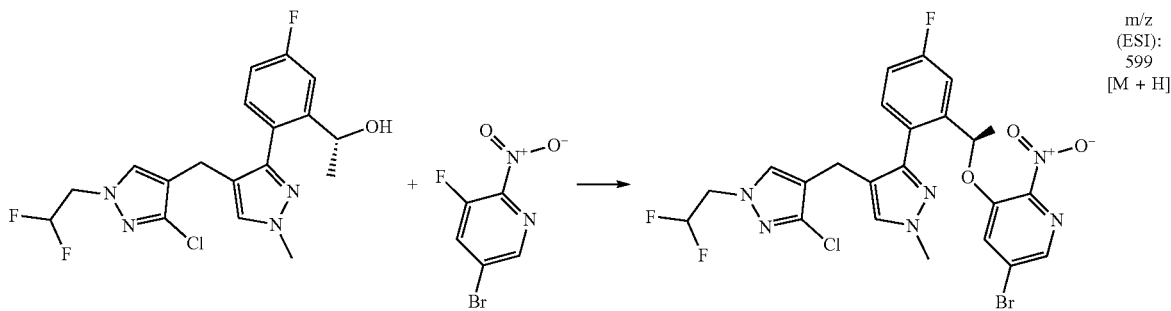

m/z (ESI): 599 [M + H]

-continued 5-bromo-3-[(1R)-1-[2-(4-{[1-(2,2-difluoroethyl)-3-methyl-1H-pyrazol-4-yl]methyl}-1-methyl-1H-pyrazol-3-yl)-5-fluorophenyl]ethoxy]-2-nitropyridine

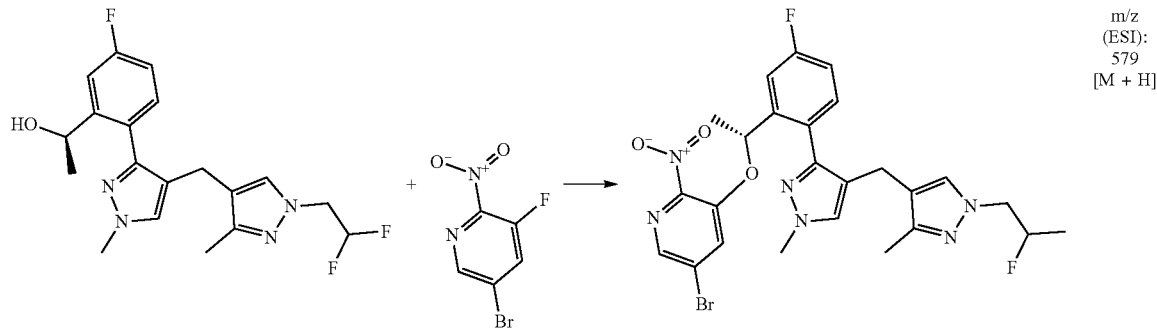

m/z (ESI): 579 [M + H]

5-bromo-3-[(1R)-1-{2-[1-(difluoromethyl)-4-[(1-ethyl-1H-pyrazol-4-yl)methyl]-1H-pyrazol-3-yl]-5-fluorophenyl}ethoxy]-2-nitropyridine

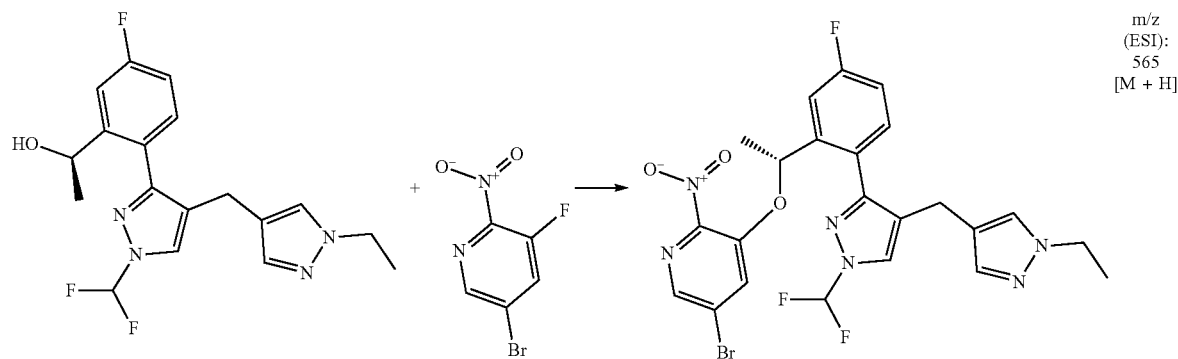

m/z (ESI): 565 [M + H]

(R)-5-bromo-3-(1-(2-(4-((1-ethyl-3-(trifluoromethyl)-1H-pyrazol-4-yl)methyl)-1-methyl-1H-pyrazol-3-yl)-5-fluorophenyl)ethoxy)-2-nitropyridine

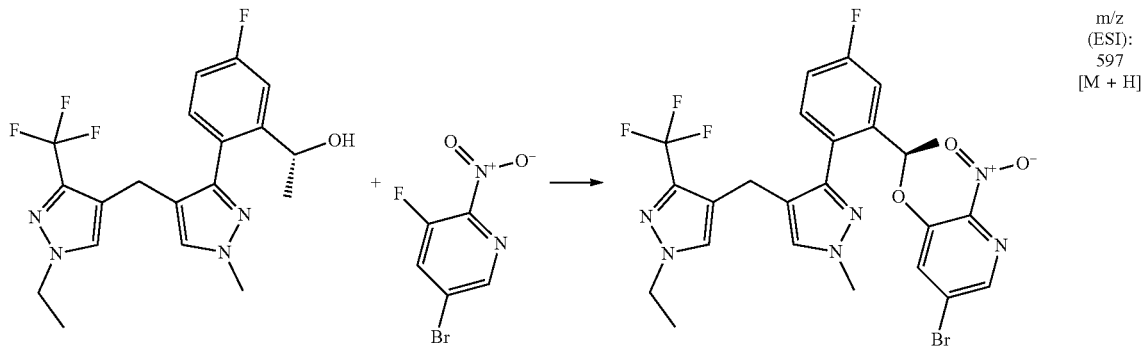

m/z (ESI): 597 [M + H]

(R)-5-((4-(2-(1-((5-bromo-2-nitropyridin-3-yl)oxy)ethyl)-4-fluorophenyl)thiazol-5-yl)methyl)-1-methyl-1H-pyrazole-3-carbonitrile

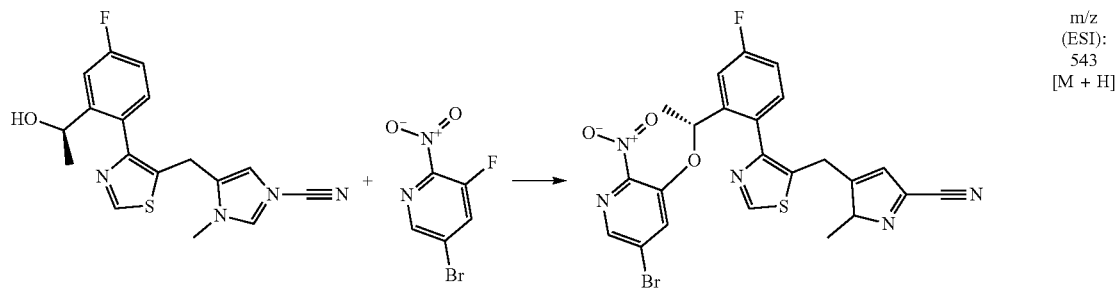

m/z (ESI): 543 [M + H]

-continued (R)-5-bromo-3-(1-(2-(4-((1-(cyclopropylmethyl)-1H-pyrazol-4-yl)methyl)-1-methyl-1H-pyrazol-3-yl)-5-fluorophenyl)ethoxy)-2-nitropyridine

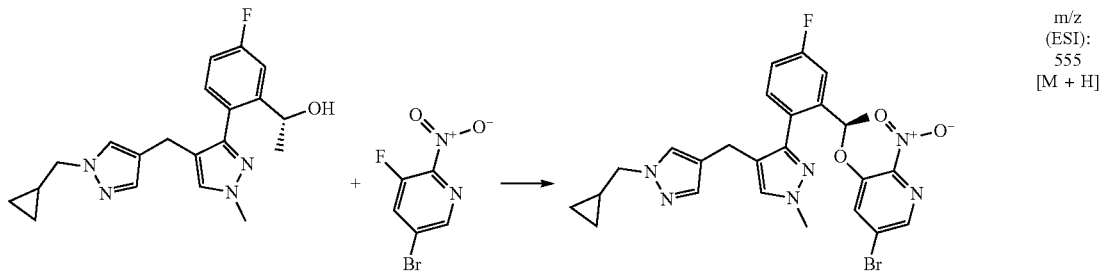

m/z (ESI): 555 [M + H]

(R)-5-((2-(2-(1-((5-bromo-2-nitropyridin-3-yl)oxy)ethyl)-4-fluorophenyl)-5-fluoropyridin-3-yl)methyl)-1-methyl-1H-pyrazole-3-carbonitrile

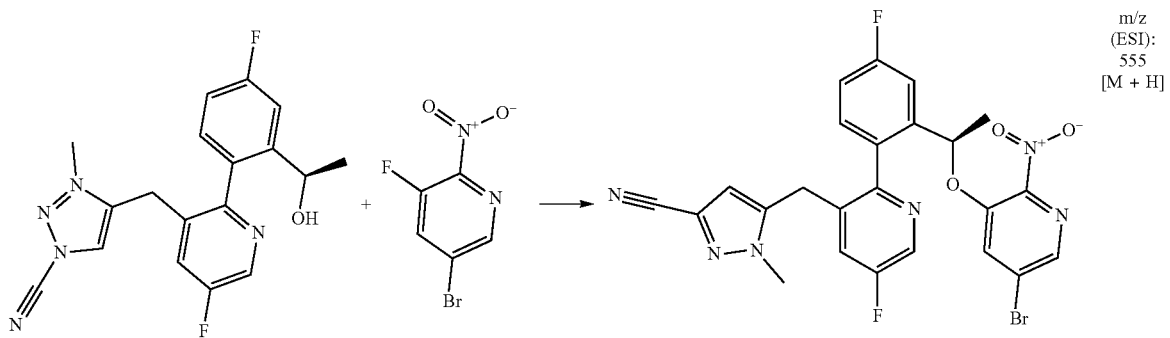

m/z (ESI): 555 [M + H]

(R)-3-((1-(2-(1-((5-bromo-2-nitropyridin-3-yl)oxy)ethyl)-4-fluorophenyl)-1H-pyrazol-5-yl)methyl)-1-isopropyl-1H-pyrazole-5-carbonitrile

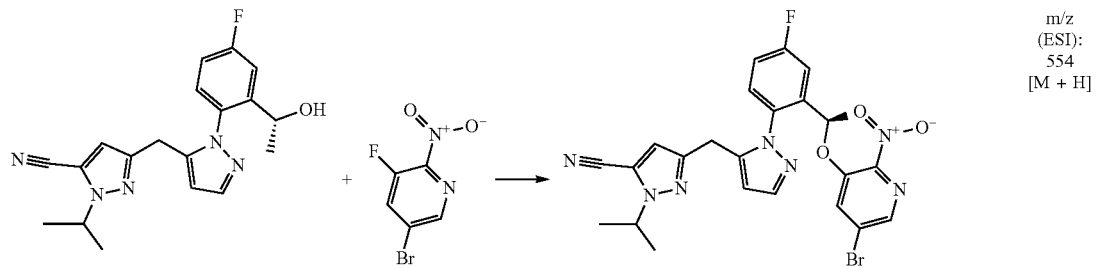

m/z (ESI): 554 [M + H]

(R)-5-bromo-3-(1-(2-(5-((1-(cyclopropylmethyl)-1H-1,2,3-triazol-4-yl)methyl)-3-(difluoromethyl)-1H-pyrazol-1-yl)-5-fluorophenyl)ethoxy)-2-nitropyridine

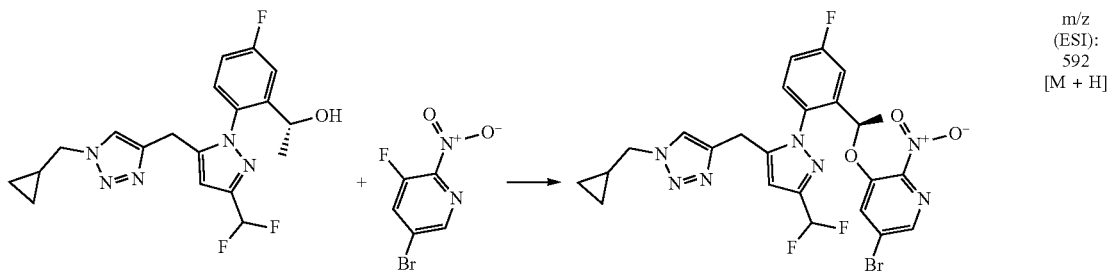

m/z (ESI): 592 [M + H]

5-bromo-3-[(1R)-1-[2-(5-{[1-(cyclopropylmethyl)-1H-1,2,3-triazol-4-yl]methyl}-3-(trifluoromethyl)-1H-pyrazol-1-yl)-5-fluorophenyl]ethoxy]-2-nitropyridine

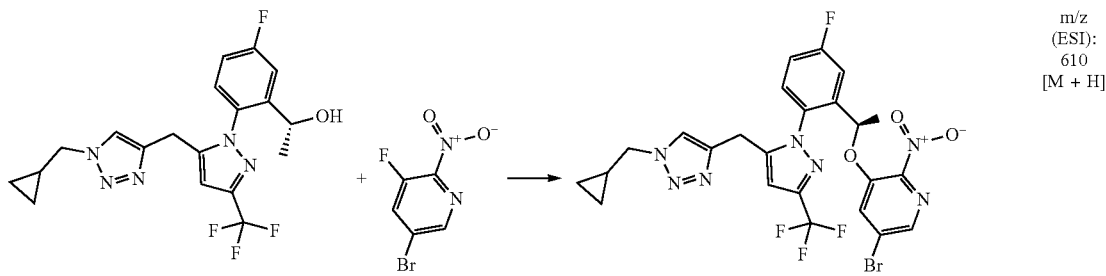

m/z (ESI): 610 [M + H]

5-bromo-3-[(1R)-1-[2-(4-{[3-chloro-1-(cyclopropylmethyl)-1H-pyrazol-4-yl]methyl}-1-methyl-1H-pyrazol-3-yl)-5-fluorophenyl]ethoxy]-2-nitropyridine

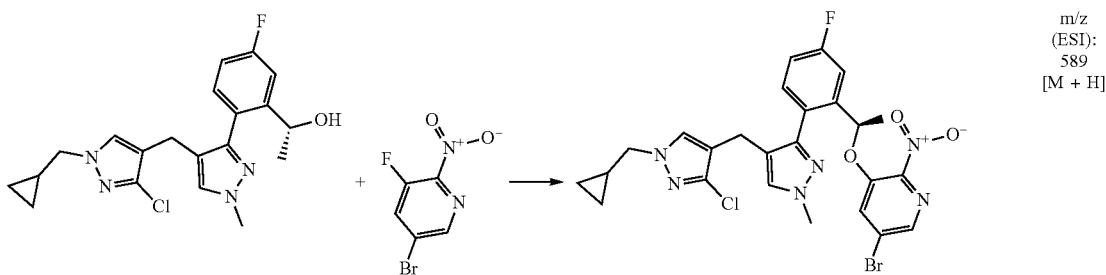

m/z (ESI): 589 [M + H]

(R)-5-bromo-3-(1-(2-(3-((1-(cyclopropylmethyl)-3-methyl-1H-pyrazol-4-yl)methyl)pyridin-2-yl)-5-fluorophenyl)ethoxy)-2-nitropyridine

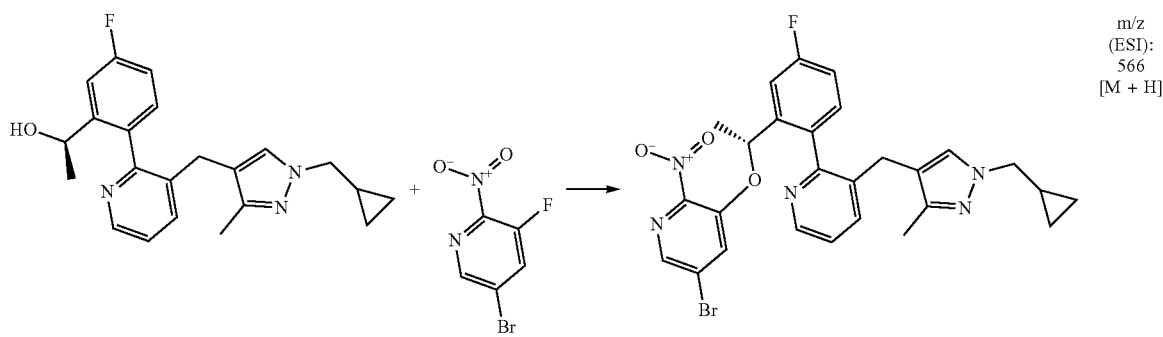

m/z (ESI): 566 [M + H]

(R)-5-bromo-3-(1-(2-(4-((1-(cyclopropylmethyl)-1H-pyrazol-4-yl)methyl)-1-ethyl-1H-pyrazol-3-yl)-5-fluorophenyl)ethoxy)-2-nitropyridine

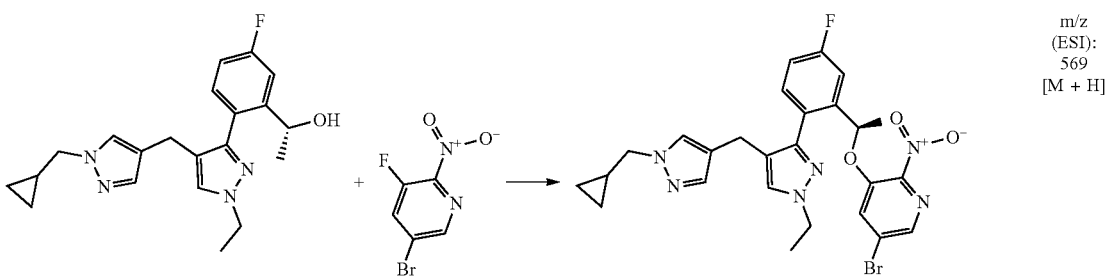

m/z (ESI): 569 [M + H]

(R)-5-bromo-3-(1-(2-(3-((1-ethyl-1H-pyrazol-4-yl)methyl)-6-methoxypyridin-2-yl)-5-fluorophenyl)ethoxy)-2-nitropyridine

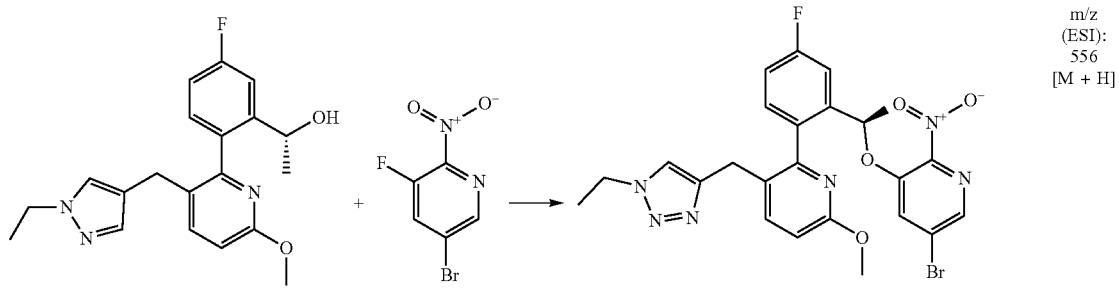

m/z (ESI): 556 [M + H]

(R)-2-(2-(1-((5-bromo-2-nitropyridin-3-yl)oxy)ethyl)-4-fluorophenyl)-3-((1-ethyl-1H-pyrazol-4-yl)methyl)-4-methoxypyridine

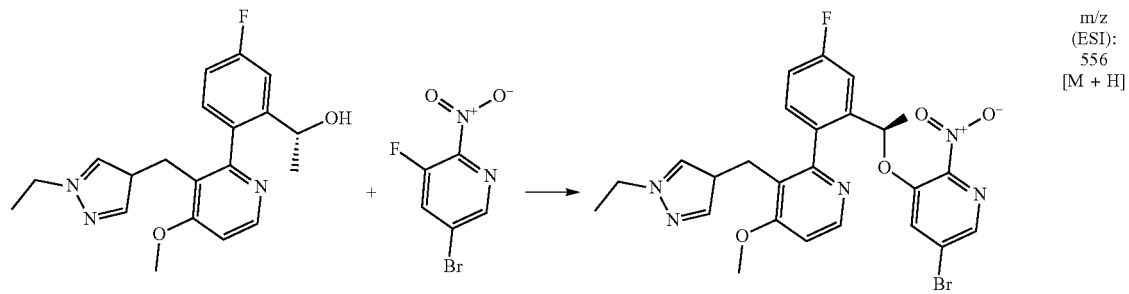

m/z (ESI): 556 [M + H]

(R)-5-bromo-3-(1-(2-(3-((4-(cyclopropylmethyl)-1H-pyrazol-1-yl)methyl)pyridin-2-yl)-5-fluorophenyl)ethoxy)-2-nitropyridine

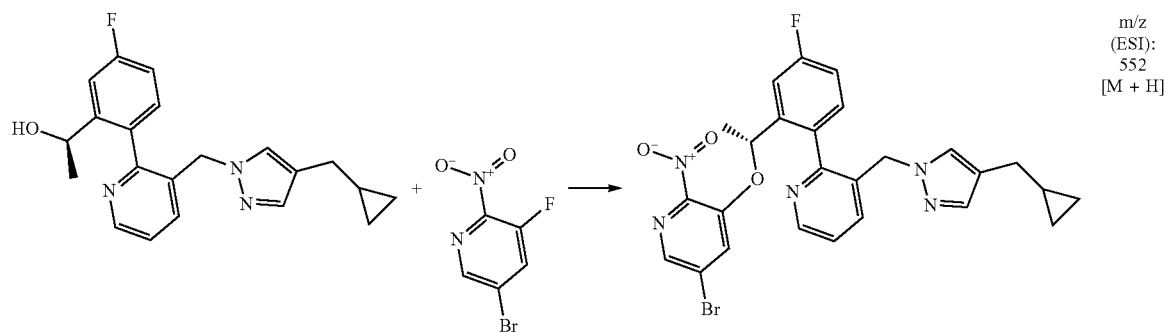

m/z (ESI): 552 [M + H]

(R)-5-bromo-3-(1-(2-(4-((1,3-diethyl-1H-pyrazol-4-yl)methyl)-1-methyl-1H-pyrazol-3-yl)-5-fluorophenyl)ethoxy)-2-nitropyridine

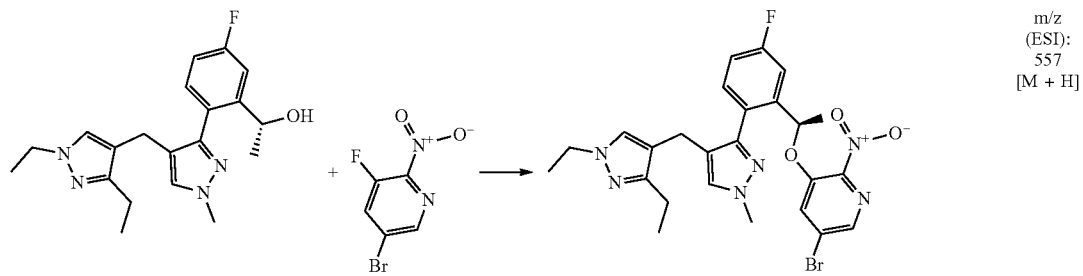

m/z (ESI): 557 [M + H]

-continued (R)-5-bromo-3-(1-(2-(4-((1-(cyclopropylmethyl)-1H-pyrazol-4-yl)methyl)-1-(difluoromethyl)-
1H-pyrazol-3-yl)-5-fluorophenyl)ethoxy)-2-nitropyridine

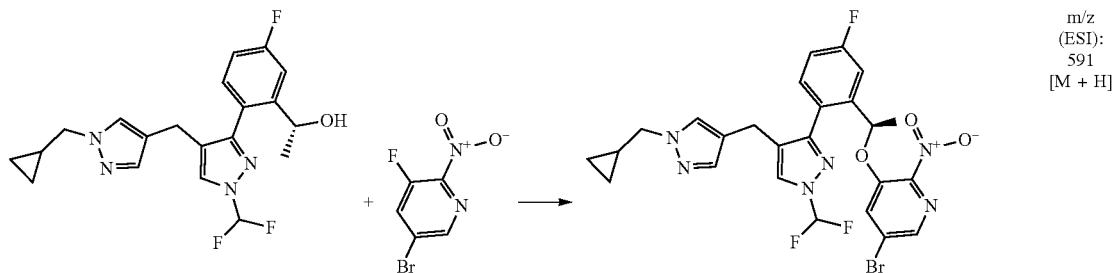

m/z (ESI): 591 [M + H]

5-bromo-3-[(1R)-1-{5-fluoro-2-[1-methyl-4-({1-[(1-methylcyclopropyl)methyl]-1H-pyrazol-4-
yl}methyl)-1H-pyrazol-3-yl]phenyl}ethoxy]-2-nitropyridine

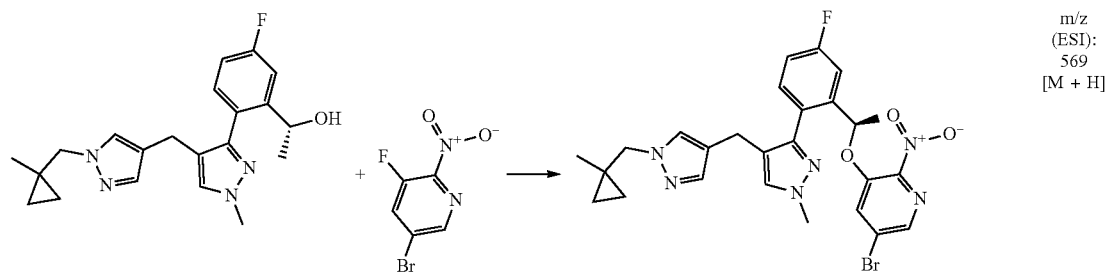

m/z (ESI): 569 [M + H]

1-((4-(2-(1-(5-bromo-2-nitropyridin-3-yloxy)ethyl)-4-fluorophenyl)thiazol-5-yl)methyl)-1H-
imidazole-4-carbonitrile

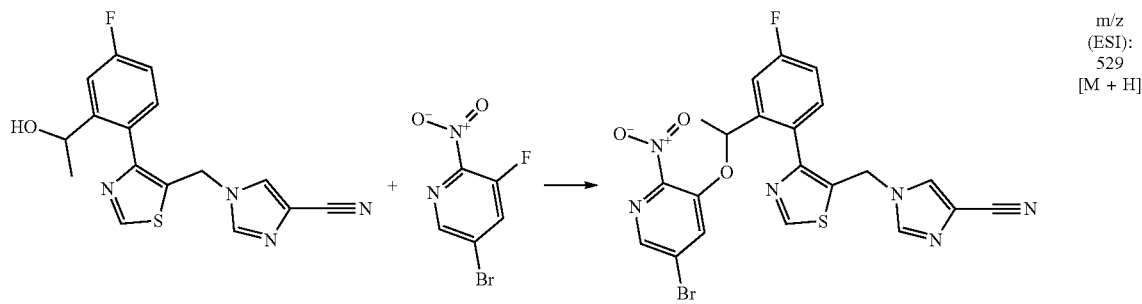

m/z (ESI): 529 [M + H]

1-((4-(2-(1-((5-bromo-2-nitropyridin-3-yl)oxy)ethyl)-4-fluorophenyl)-2-methylthiazol-5-
yl)methyl)-1H-pyrazole-4-carbonitrile

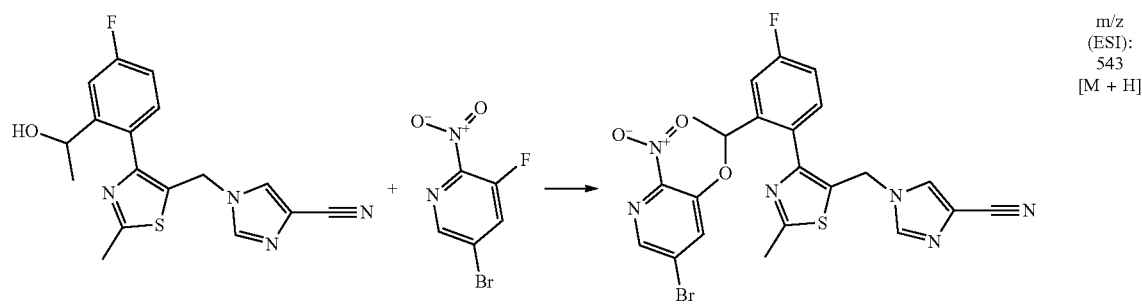

m/z (ESI): 543 [M + H]

(1-(2-(((5-bromo-2-nitropyridin-3-yl)oxy)methyl)-4-fluorophenyl)-3-chloro-1H-pyrazol-5-yl)(1-ethyl-1H-pyrazol-4-yl)methanone

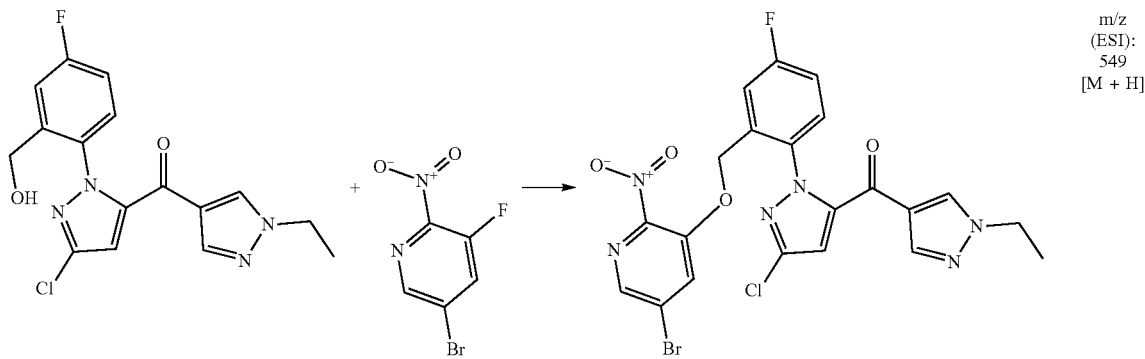

m/z (ESI): 549 [M + H]

(1-(2-((5-bromo-2-nitropyridin-3-yloxy)methyl)-4-fluorophenyl)-3-(trifluoromethyl)-1H-pyrazol-5-yl)(1-ethyl-1H-pyrazol-4-yl)methanol

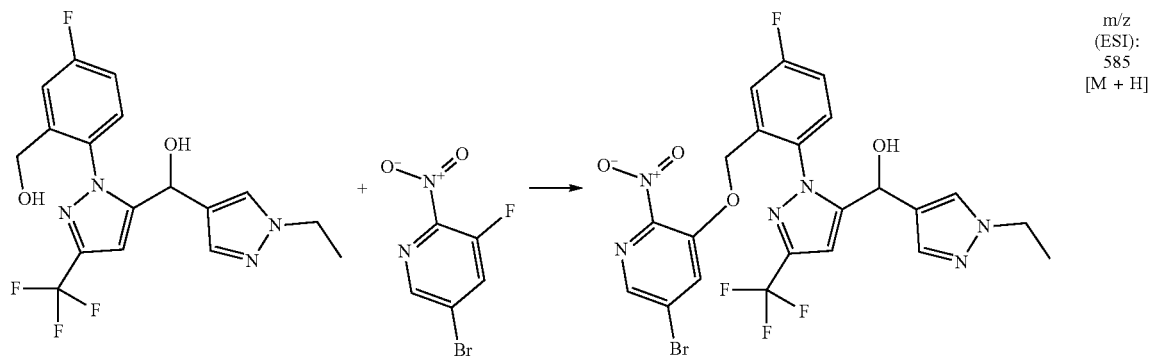

m/z (ESI): 585 [M + H]

5-bromo-3-[(2-{3-chloro-5-[1-(cyclopropylmethyl)-1H-1,2,3-triazole-4-carbonyl]-1H-pyrazol-1-yl}-5-fluorophenyl)methoxy]-2-nitropyridine

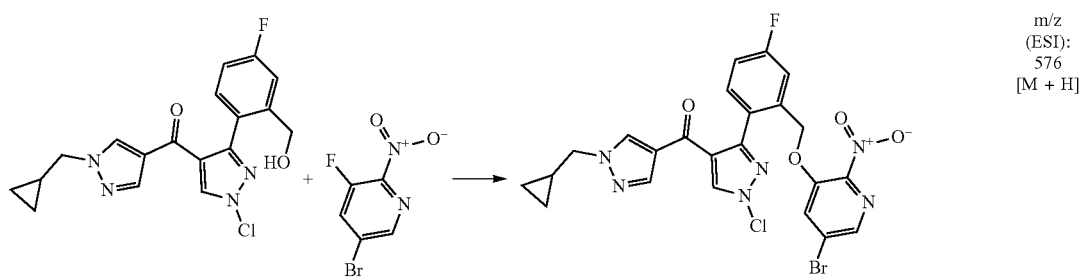

m/z (ESI): 576 [M + H]

4-(2-(1-((5-bromo-2-nitropyridin-3-yl)oxy)ethyl)-4-fluorophenyl)-5-((4-(difluoromethyl)-1H-pyrazol-1-yl)methyl)-2-methylthiazole

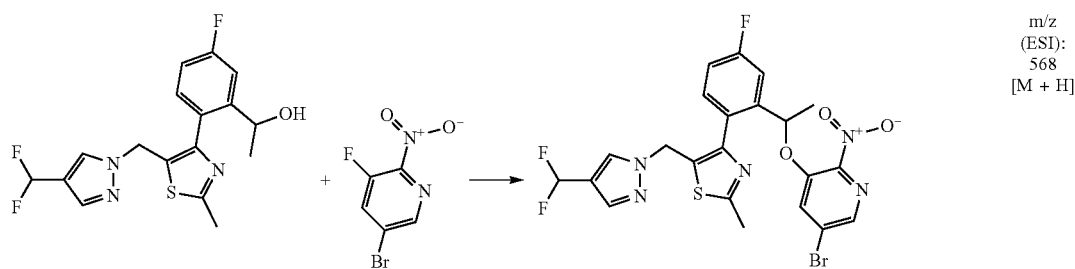

m/z (ESI): 568 [M + H]

5-bromo-3-(1-(2-(3-bromo-5-((1-ethyl-1H-pyrazol-4-yl)methyl)-1H-pyrazol-1-yl)-5-fluorophenyl)ethoxy)-2-nitropyridine

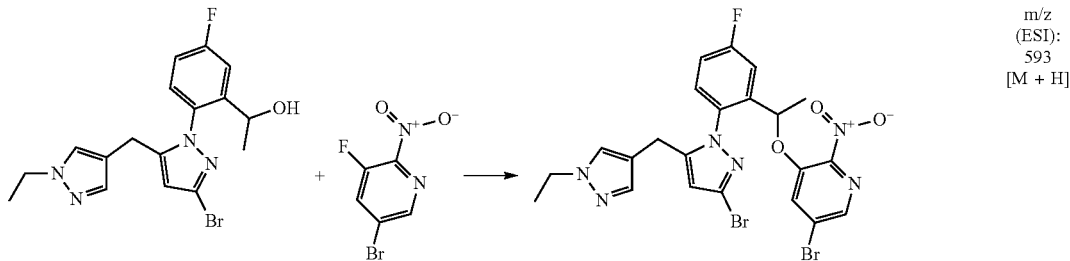

m/z (ESI): 593 [M + H]

5-bromo-3-[(1R)-1-(2-{5-[(1-ethyl-1H-pyrazol-4-yl)methyl]-3-methoxy-1H-pyrazol-1-yl}-5-fluorophenyl)ethoxy]-2-nitropyridine

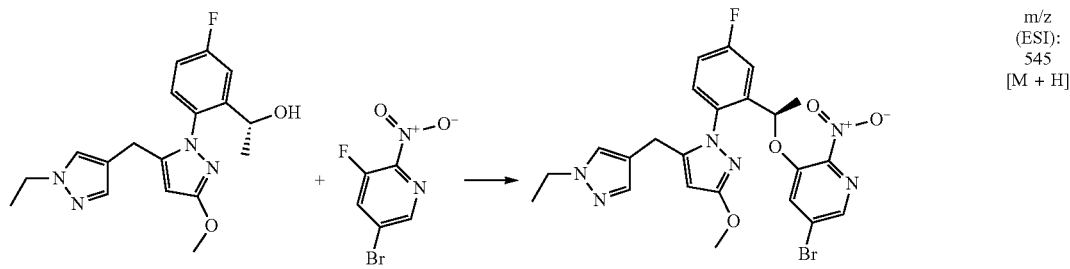

m/z (ESI): 545 [M + H]

5-bromo-3-[(2-{5-[(1-ethyl-1H-pyrazol-4-yl)methyl]-2-methyl-1,3-thiazol-4-yl}-5-fluorophenyl)methoxy]-2-nitropyridine

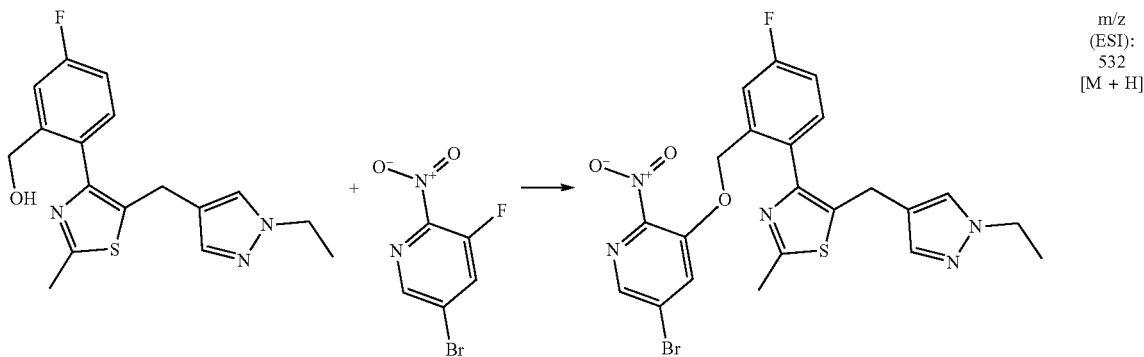

m/z (ESI): 532 [M + H]

5-bromo-3-[1-(2-{4-[(3-ethyl-1,2-oxazol-5-yl)methyl]-4H-1,2,4-triazol-3-yl}-5-fluorophenyl)ethoxy]-2-nitropyridine

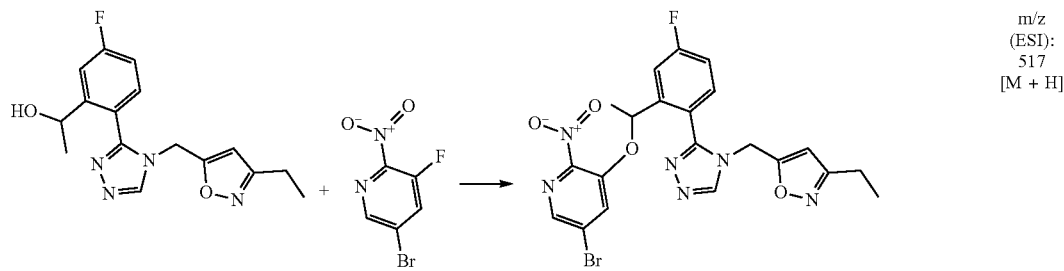

m/z (ESI): 517 [M + H]

5-((1-(2-(1-((5-bromo-2-nitropyridin-3-yl)oxy)ethyl)-4-fluorophenyl)-3-methyl-1H-pyrazol-5-yl)methyl)-1-methyl-1H-pyrazole-3-carbonitrile

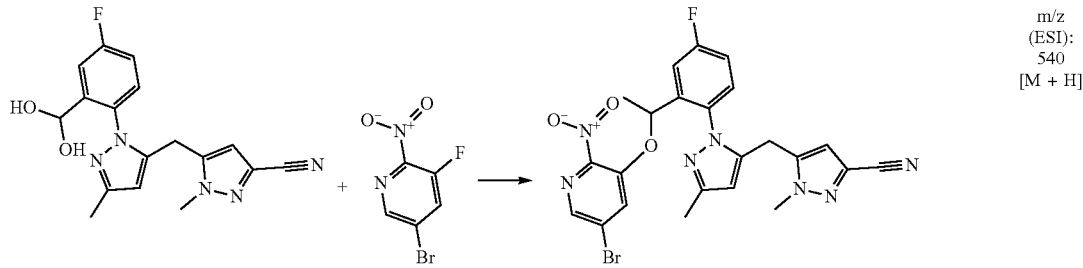

m/z (ESI): 540 [M + H]

5-bromo-3-((2-(4-((1-(cyclopropylmethyl)-3-methyl-1H-pyrazol-4-yl)methyl)-1-methyl-1H-pyrazol-3-yl)-5-fluorobenzyl)oxy)-2-nitropyridine

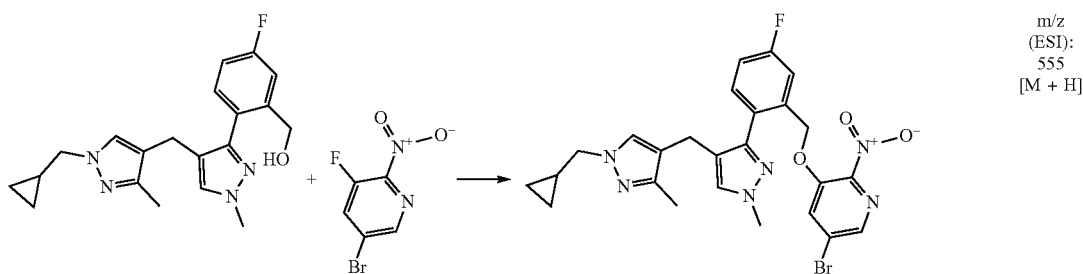

m/z (ESI): 555 [M + H]

5-bromo-3-((2-(4-((1-(cyclopropylmethyl)-1H-pyrazol-4-yl)methyl)-1-methyl-1H-pyrazol-3-yl)-5-fluorobenzyl)oxy)-2-nitropyridine

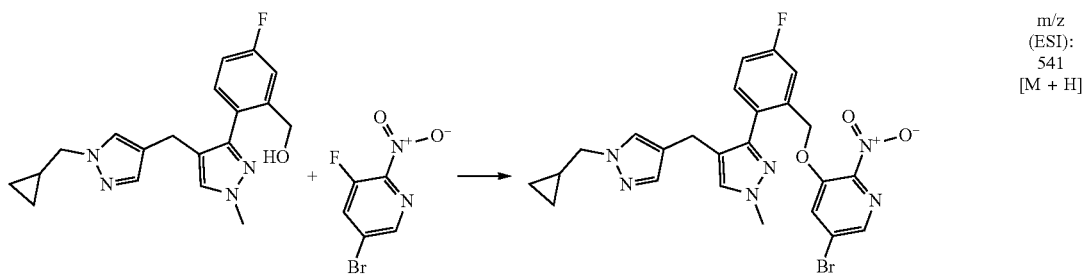

m/z (ESI): 541 [M + H]

1-((5-(2-(1-((5-bromo-2-nitropyridin-3-yl)oxy)ethyl)-4-fluorophenyl)-1-methyl-1H-pyrazol-4-yl)methyl)-1H-pyrazole-4-carbonitrile

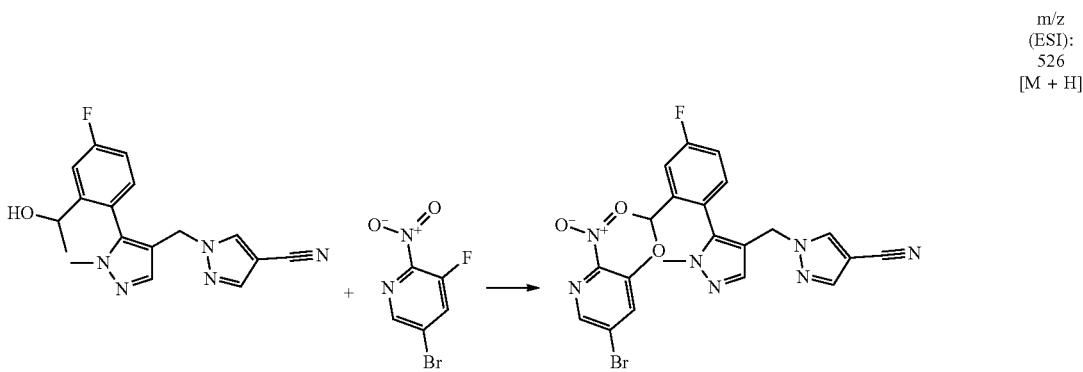

m/z (ESI): 526 [M + H]

-continued

3-{2-[(tert-butyldimethylsilyl)oxy]-1-[5-fluoro-2-(1-{[2-(trimethylsilyl)ethoxy]methyl}-1H-imidazol-2-yl)phenyl]ethoxy}-2-nitropyridine

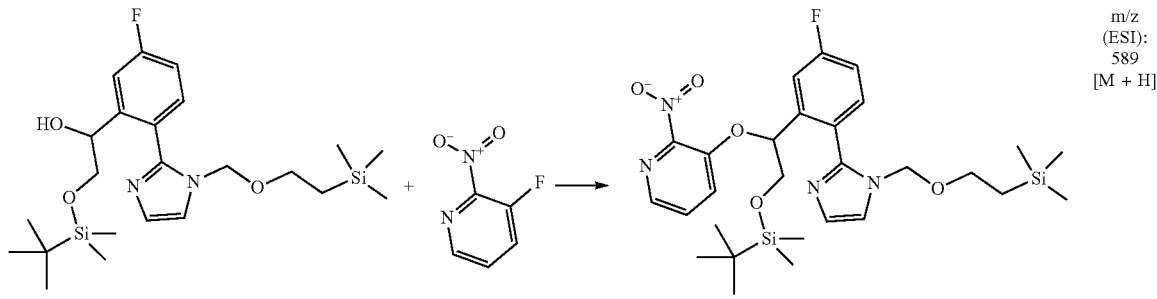

m/z (ESI): 589 [M + H]

(R)-5-bromo-3-(1-(2-(4-((3-ethyl-1-methyl-1H-pyrazol-5-yl)methyl)-1-methyl-1H-pyrazol-3-yl)-5-fluorophenyl)ethoxy)-2-nitropyridine

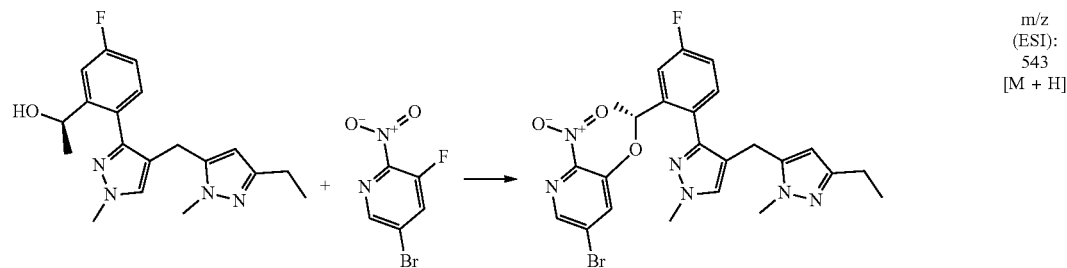

m/z (ESI): 543 [M + H]

(R)-5-bromo-3-(1-(2-(4-((3-(2,2-difluoroethyl)-1-methyl-1H-pyrazol-5-yl)methyl)-1-methyl-1H-pyrazol-3-yl)-5-fluorophenyl)ethoxy)-2-nitropyridine

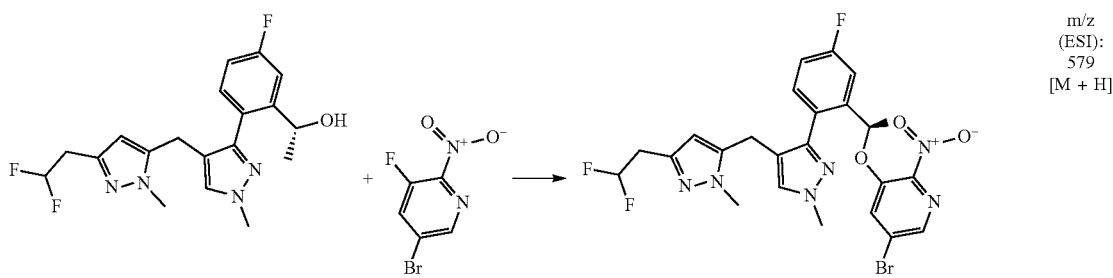

m/z (ESI): 579 [M + H]

(R)-5-bromo-3-(1-(2-(4-((3-(cyclopropylmethyl)-1-methyl-1H-pyrazol-5-yl)methyl)-1-methyl-1H-pyrazol-3-yl)-5-fluorophenyl)ethoxy)-2-nitropyridine

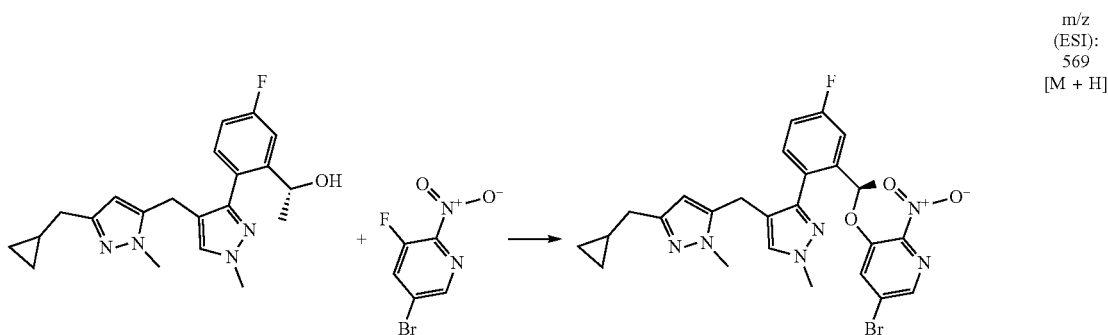

m/z (ESI): 569 [M + H]

533

Synthesis of (1-(2-(((5-bromo-2-nitropyridin-3-yl)oxy)methyl)-4-fluorophenyl)-3-methyl-1H-pyrazol-5-yl)(1-ethyl-1H-pyrazol-4-yl)methanol

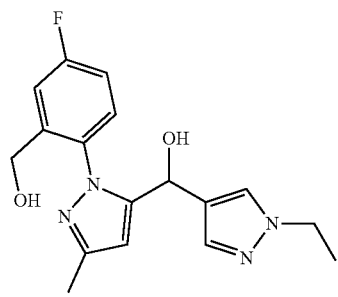

+

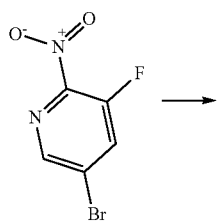

534

-continued

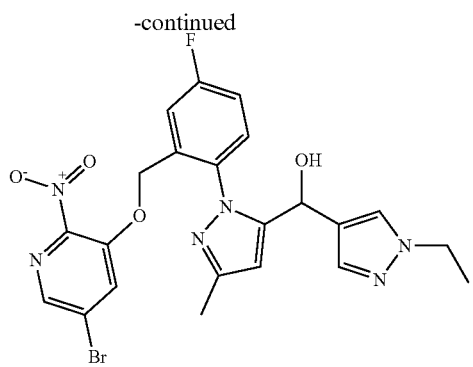

The mixture of (1-ethyl-1H-pyrazol-4-yl)(1-(4-fluoro-2-(hydroxymethyl)phenyl)-3-methyl-1H-pyrazol-5-yl)methanol (320 mg, 0.99 mmol), 5-bromo-3-fluoro-2-nitropyridine (241 mg, 1.09 mmol), Cs$_2$CO$_3$ (968 mg, 2.97 mmol) and dry THF (15 mL) was stirred at 60° C. for 16 h. The reaction mixture was filtered through celite and the filtrate was partitioned between EtOAc and water. The organic layer was separated, dried over anhydrous Na$_2$SO$_4$, filtered, and concentrated in vacuo. The residue was purified by flash chromatography (15→40% EtOAc in PE) to give (1-(2-(((5-bromo-2-nitropyridin-3-yl)oxy)methyl)-4-fluorophenyl)-3-methyl-1H-pyrazol-5-yl)(1-ethyl-1H-pyrazol-4-yl)methanol (210 mg, 40% yield) as a yellow solid. TLC: R$_f$=0.3 (PE/EA=1/1).

LC/MS ESI (m/z): 531 [M+H]$^+$.

The following intermediates were synthesized using a similar experimental protocol:

5-bromo-3-(1-(2-(5-((5-bromo-1-ethyl-1H-pyrazol-4-yl)methyl)-1H-1,2,3-triazol-1-yl)-5-fluorophenyl)ethoxy)-2-nitropyridine

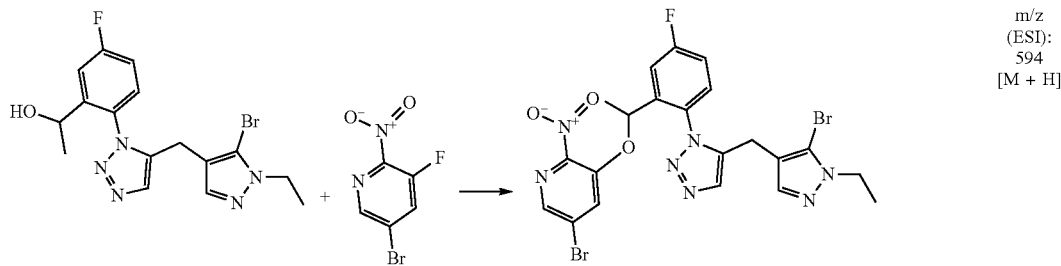

m/z (ESI): 594 [M + H]

5-bromo-3-(1-(2-(1-((5-bromo-1-(2,2-difluoroethyl)-1H-pyrazol-4-yl)methyl)-1H-imidazol-2-yl)-5-fluorophenyl)ethoxy)-2-nitropyridine

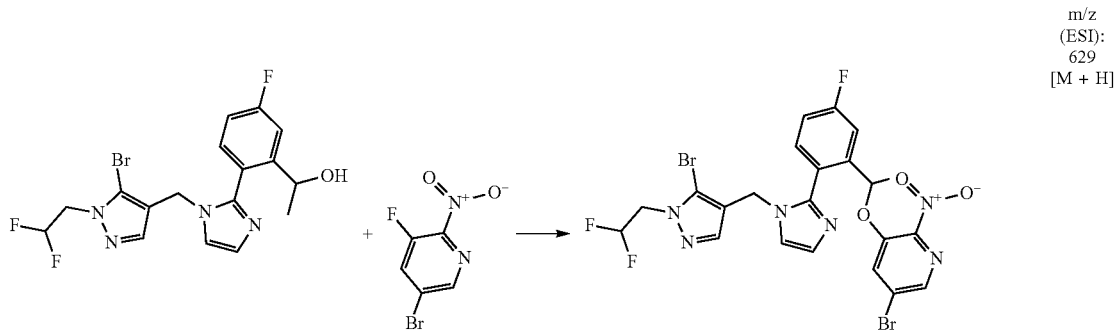

m/z (ESI): 629 [M + H]

-continued (5-bromo-1-ethyl-1H-pyrazol-4-yl)(1-(2-(1-(((5-bromo-2-nitropyridin-3-yl)oxy)ethyl)-4-fluorophenyl)-1H-pyrazol-5-yl)methanone

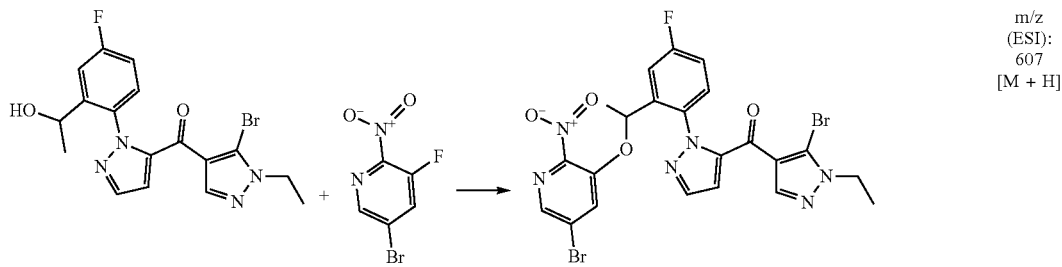

m/z (ESI): 607 [M + H]

(5-bromo-1-ethyl-1H-pyrazol-4-yl)(1-(2-(((5-bromo-2-nitropyridin-3-yl)oxy)methyl)-4-fluorophenyl)-1H-pyrazol-5-yl)methanol

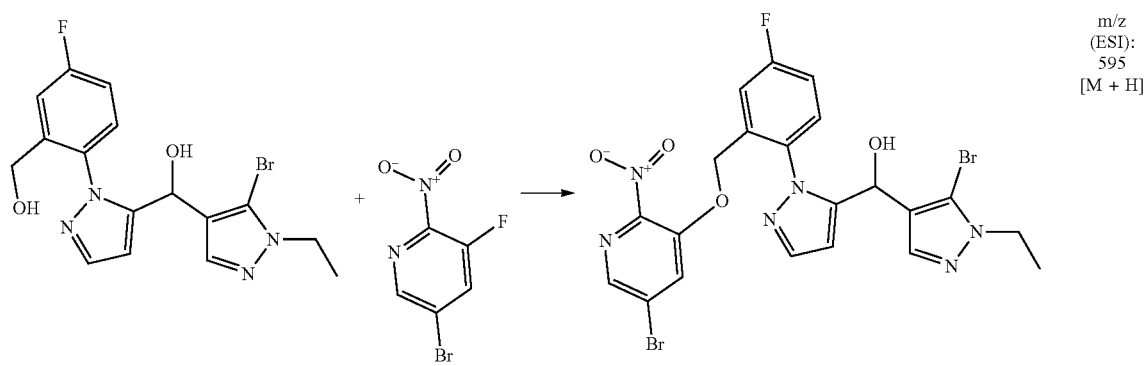

m/z (ESI): 595 [M + H]

(5-bromo-1-ethyl-1H-pyrazol-4-yl)(1-(2-(((5-bromo-2-nitropyridin-3-yl)oxy)methyl)-4-fluorophenyl)-4-fluoro-1H-pyrazol-5-yl)methanol

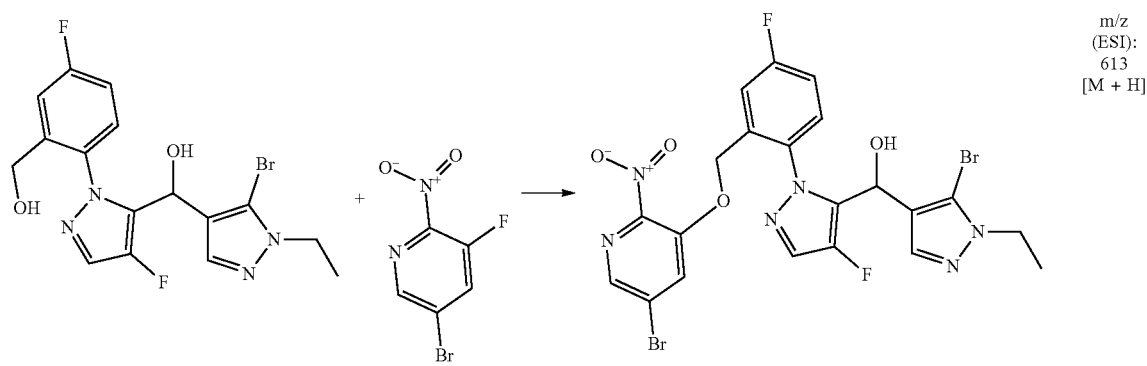

m/z (ESI): 613 [M + H]

(1-(2-(1-(5-bromo-2-nitropyridin-3-yloxy)ethyl)-4-fluorophenyl)-3-chloro-1H-pyrazol-5-yl)(1-ethyl-1H-pyrazol-4-yl)methanone

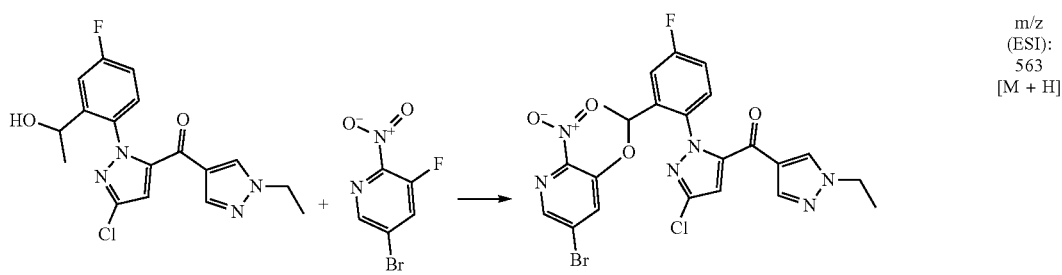

m/z (ESI): 563 [M + H]

537

Synthesis of (1R)-1-(2-{5-[(1-ethyl-1H-pyrazol-4-yl)methyl]-3-methoxy-1H-pyrazol-1-yl}-5-fluorophenyl)ethan-1-ol

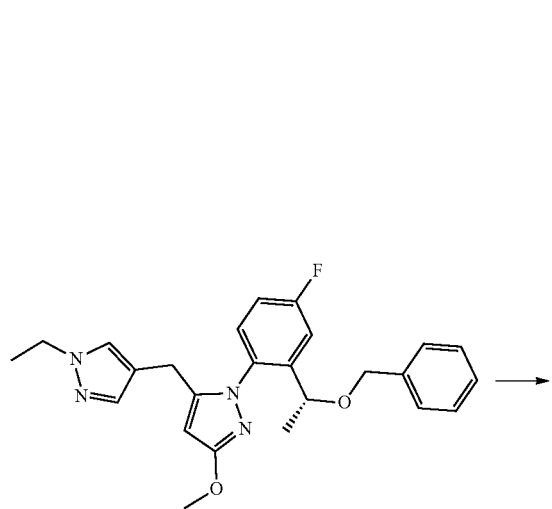

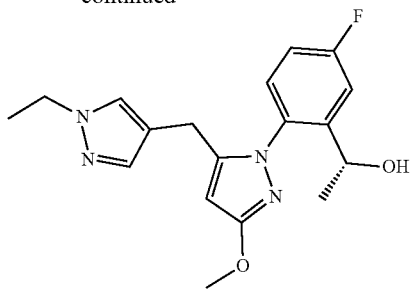

A mixture of 1-{2-[(1R)-1-(benzyloxy)ethyl]-4-fluorophenyl}-5-[(1-ethyl-1H-pyrazol-4-yl)methyl]-3-methoxy-1H-pyrazole (350 mg, 0.81 mmol), and Pd/C (30 mg, 10% wt.) in MeOH (20 mL) was stirred for 12 h at 50° C. under an $H_2$ atmosphere. The reaction mixture was cooled and then filtered. The filtrate was concentrated under reduced pressure and the residue was purified by flash column chromatography on silica gel (0→80% EtOAc in PE) to give (1R)-1-(2-{5-[(1-ethyl-1H-pyrazol-4-yl)methyl]-3-methoxy-1H-pyrazol-1-yl}-5-fluorophenyl)ethan-1-ol (220 mg, 79%) as a colorless oil. LC/MS (ESI): m/z=345 [M+H]$^+$.

The following intermediates were synthesized using a similar experimental protocol:

(R)-1-(2-(3-(difluoromethyl)-5-((1-ethyl-1H-pyrazol-4-yl)methyl)-1H-pyrazol-1-yl)-5-fluorophenyl)ethan-1-ol

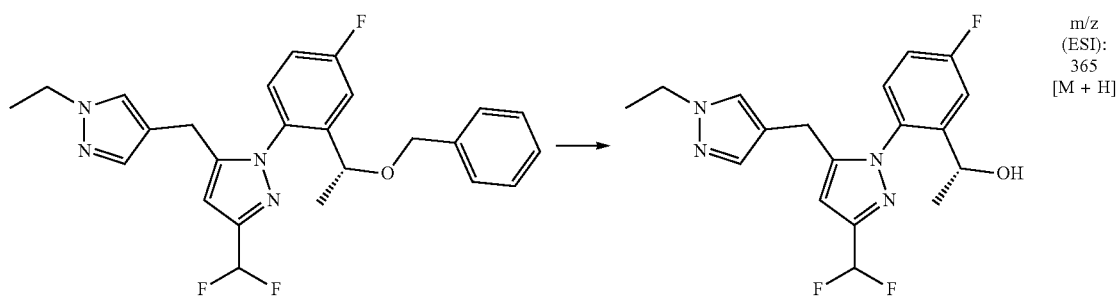

m/z (ESI): 365 [M + H]

(R)-1-(2-(5-((1-(cyclopropylmethyl)-1H-pyrazol-4-yl)methyl)-3-(trifluoromethyl)-1H-pyrazol-1-yl)-5-fluorophenyl)ethan-1-ol m/z (ESI): 409 [M + H]

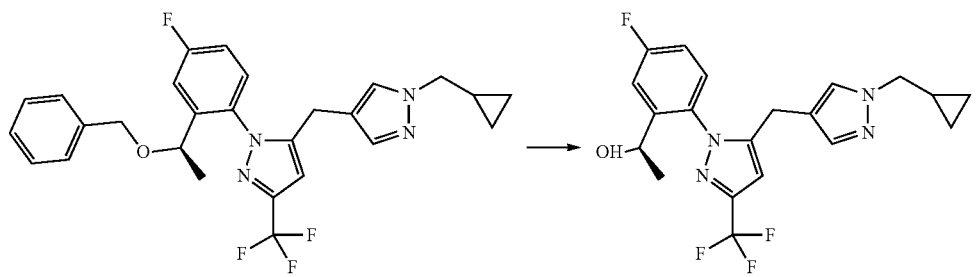 [SMILES: C[C@@H](OCc1ccccc1)c1cc(F)ccc1-n1nc(C(F)(F)F)cc1Cc1cnn(CC2CC2)c1 ; C[C@@H](O)c1cc(F)ccc1-n1nc(C(F)(F)F)cc1Cc1cnn(CC2CC2)c1]

(R)-1-(2-(5-((1-(cyclopropylmethyl)-1H-1,2,3-triazol-4-yl)methyl)-3-(difluoromethyl)-1H-pyrazol-1-yl)-5-fluorophenyl)ethan-1-ol

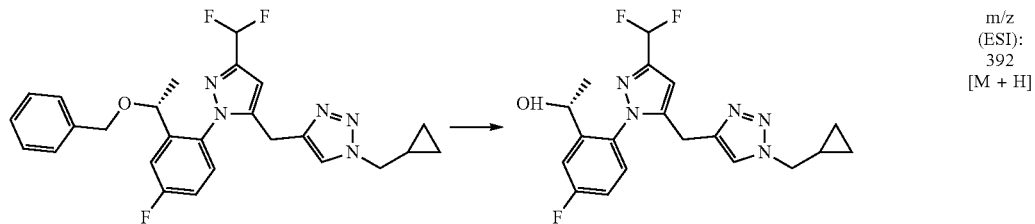

m/z (ESI): 392 [M + H]

(R)-1-(2-(5-((1-(cyclopropylmethyl)-3-methyl-1H-pyrazol-4-yl)methyl)-3-(difluoromethyl)-1H-pyrazol-1-yl)-5-fluorophenyl)ethan-1-ol

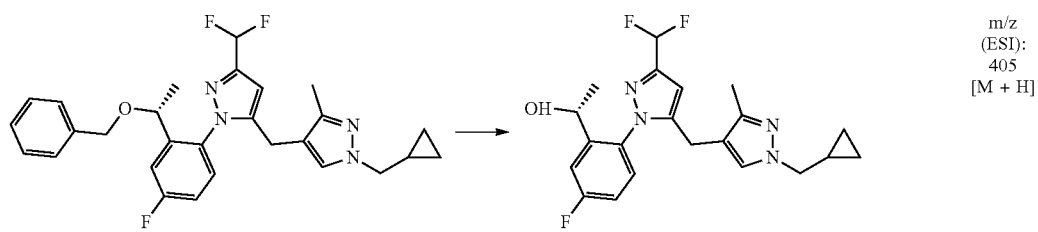

m/z (ESI): 405 [M + H]

(R)-1-(2-(5-((1-(cyclopropylmethyl)-1H-pyrazol-4-yl)methyl)-3-(difluoromethyl)-1H-pyrazol-1-yl)-5-fluorophenyl)ethan-1-ol

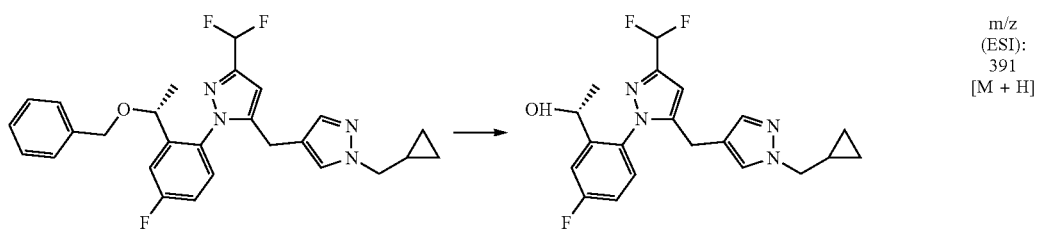

m/z (ESI): 391 [M + H]

(R)-1-(2-(3-(difluoromethyl)-5-((1-ethyl-3-methoxy-1H-pyrazol-4-yl)methyl)-1H-pyrazol-1-yl)-5-fluorophenyl)ethan-1-ol

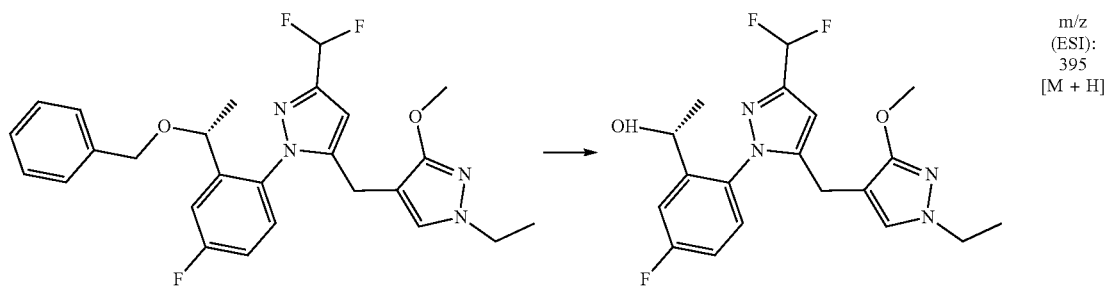

m/z (ESI): 395 [M + H]

(R)-1-(2-(5-((1-(cyclopropylmethyl)-1H-1,2,3-triazol-4-yl)methyl)-3-methoxy-1H-pyrazol-1-yl)-5-fluorophenyl)ethan-1-ol

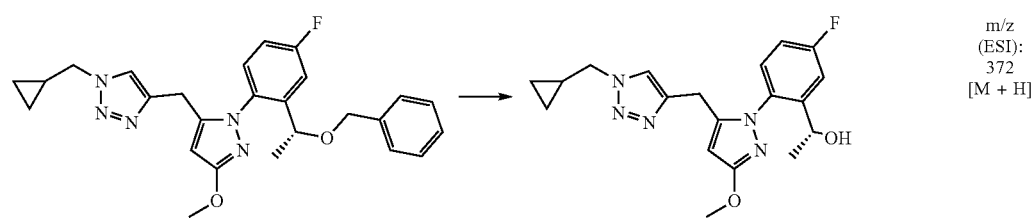

m/z (ESI): 372 [M + H]

-continued (2-(5-((1-(cyclopropylmethyl)-1H-pyrazol-4-yl)methyl)-3-(difluoromethyl)-1H-pyrazol-1-yl)-5-fluorophenyl)methanol

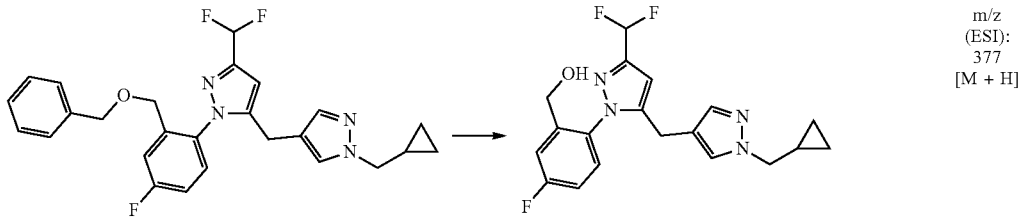

m/z (ESI): 377 [M + H]

(2-(5-((1-(cyclopropylmethyl)-3-methyl-1H-pyrazol-4-yl)methyl)-3-(difluoromethyl)-1H-pyrazol-1-yl)-5-fluorophenyl)methanol

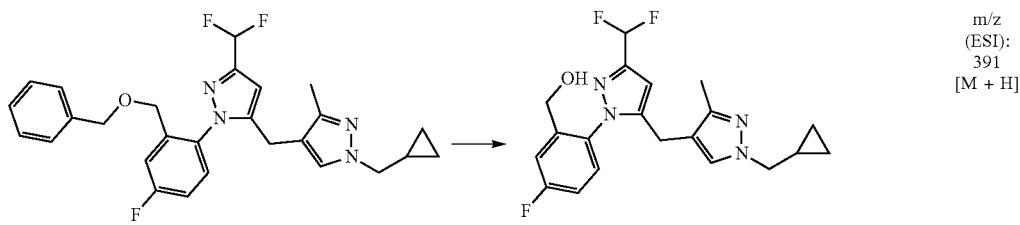

m/z (ESI): 391 [M + H]

Synthesis of (R)-4-((1-(2-(1-(benzyloxy)ethyl)-4-fluorophenyl)-3-methoxy-1H-pyrazol-5-yl)methyl)-1-(cyclopropylmethyl)-1H-1,2,3-triazole

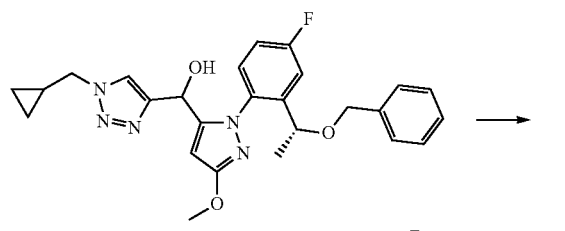

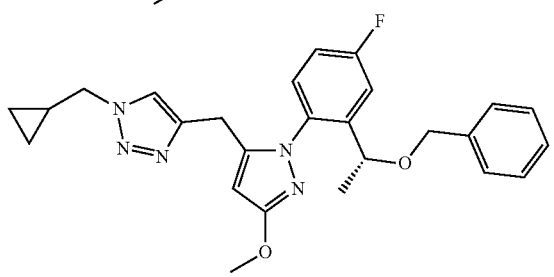

To a stirred solution of (1-(2-((1R)-1-(benzyloxy)ethyl)-4-fluorophenyl)-3-methoxy-1H-pyrazol-5-yl)(1-(cyclopropylmethyl)-1H-1,2,3-triazol-4-yl)methanol (652 mg, 1.37 mmol) in DCM (10 mL) were added TFA (1.56 g, 13.7 mmol) and TES (1.58 g, 13.7 mmol) at r.t. The reaction was stirred at 45° C. for 12 h, concentrated, and the residue was diluted with EtOAc (10 mL). The resulting solution was washed with sat. NaHCO₃ (10 mL) and brine (15 mL), dried over anhydrous Na₂SO₄ and concentrated to dryness. The residue was purified by column chromatography on silica gel (PE:EA=2:1) to give (R)-4-((1-(2-(1-(benzyloxy)ethyl)-4-fluorophenyl)-3-methoxy-1H-pyrazol-5-yl)methyl)-1-(cyclopropylmethyl)-1H-1,2,3-triazole (541 mg, 8600yield) as a yellow oil. LC/MS (ESI) (m/z):462.2 [M+H]⁺.

Synthesis of 5-(1-(2-(1,3-dioxolan-2-yl)-4-fluorophenyl)-1H-pyrazole-5-carbonyl)-1H-pyrazole-3-carbonitrile

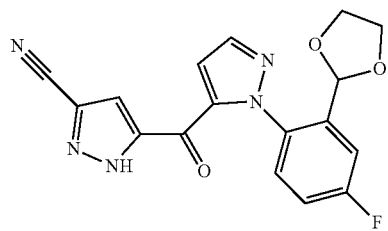 [SMILES: N#Cc1cc(C(=O)c2ccnn2-c2ccc(F)cc2C2OCCO2)[nH]n1]

To a solution of hydroxyl ammonium hydrochloride (0.250 g, 3.60 mmol) in EtOH (10 mL) was added sodium acetate (0.300 g, 3.66 mmol) and the reaction was stirred at r.t. for 30 min. To this mixture was then added a solution of 5-(1-(2-(1,3-dioxolan-2-yl)-4-fluorophenyl)-1H-pyrazole-5-carbonyl)-1-((2-(trimethylsilyl)ethoxy)methyl)-1H-pyrazole-3-carbaldehyde (1.00 g, 2.05 mmol) in EtOH (10 mL), and stirring was continued at r.t. for 1 h. The reaction mixture was poured into ice water (50 mL), and then extracted with EA (2×30 mL). The combined organic phases were washed with water (20 mL) and brine (20 mL), dried over anhydrous Na₂SO₄, filtered, and concentrated in vacuo to give the crude aldoxime. To this residue in DCM (10 mL) was added SOCl₂ (0.98 g, 8.2 mmol) at 0° C. and the reaction was stirred at r.t. for 1 h. The mixture was poured into ice water (10 mL), and then extracted with EA (2×5 mL). The combined organic phases were washed with brine (10 mL), dried over anhydrous Na₂SO₄, filtered, and concentrated in vacuo. The residue was purified by prep-TLC (25% EtOAc in PE) to give 5-(1-(2-(1,3-dioxolan-2-yl)-4-fluorophenyl)-1H-pyrazole-5-carbonyl)-1-((2-(trimethylsilyl)ethoxy)methyl)-1H-pyrazole-3-carbonitrile (0.55 g, 55% yield over 2 steps) as a yellow oil. LC/MS ESI (m/z): 484 [M+H]V.

To a solution of 5-(1-(2-(1,3-dioxolan-2-yl)-4-fluorophenyl)-1H-pyrazole-5-carbonyl)-1-((2-(trimethylsilyl)ethoxy)methyl)-1H-pyrazole-3-carbonitrile (600 mg, 1.24 mmol) in THF (5 mL), was added TBAF (1.0 M in THF, 5.00 mL, 5.00 mmol) and the reaction was stirred at 70° C. for 3 h. The mixture was concentrated in vacuo, and the residue was purified by flash chromatography (0→25% EtOAc in PE) to give 5-(1-(2-(1,3-dioxolan-2-yl)-4-fluorophenyl)-1H-pyrazole-5-carbonyl)-1H-pyrazole-3-carbonitrile (350 mg, 80%) as a white solid. LC/MS ESI (m/z): 354 [M+H]⁺.

Synthesis of (R)-5-((3-chloro-1-(4-fluoro-2-(1-((4-methoxybenzyl)oxy)ethyl)phenyl)-1H-pyrazol-5-yl)methyl)-1-methyl-1H-pyrazole-3-carbonitrile Synthesis of 5-bromo-3-(1-(2-(3-chloro-5-(((1-ethyl-1H-pyrazol-4-yl)methyl)-1H-pyrazol-1-yl)-5-fluorophenyl)ethoxy)-2-nitropyridine

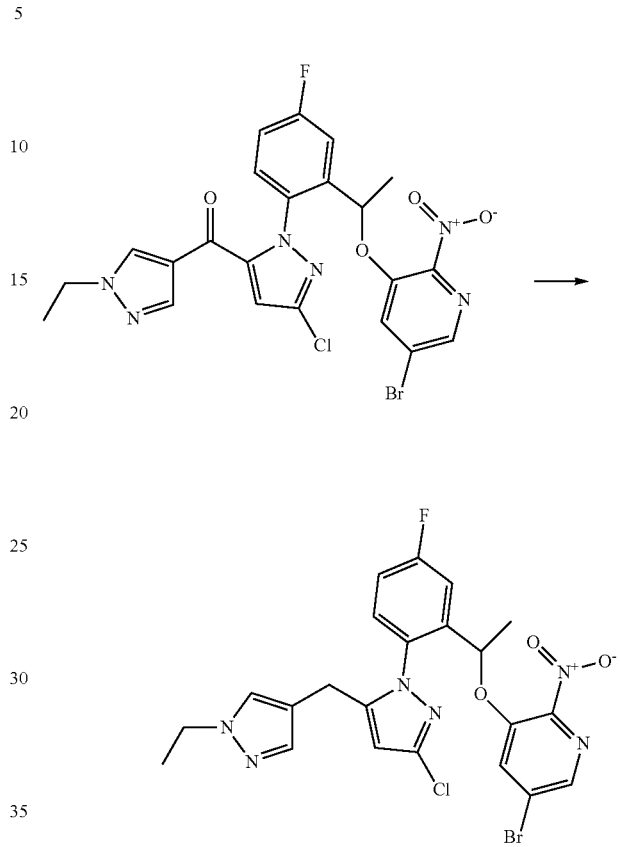

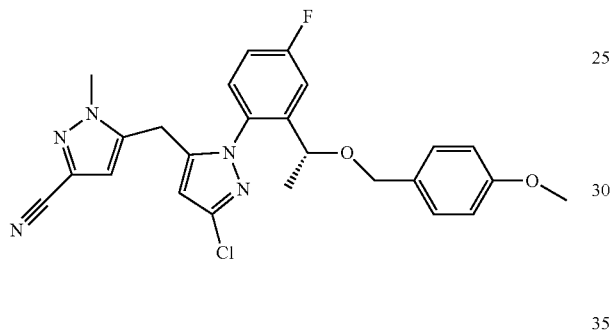

To a solution of 5-((3-chloro-1-(4-fluoro-2-((R)-1-((4-methoxybenzyl)oxy)ethyl)phenyl)-1H-pyrazol-5-yl)(hydroxy)methyl)-1-methyl-1H-pyrazole-3-carbonitrile (600 mg, 1.21 mmol) and DIPEA (1.0 mL, 6.05 mmol) in DCM (20 mL) was added MsCl (415 mg, 3.63 mmol) at 0° C. The reaction mixture was stirred at r.t. for 2 h. The reaction mixture was slowly poured into ice-water and extracted with DCM twice. The combined organic layers were washed with brine, dried (MgSO₄) and concentrated to afford crude (3-chloro-1-(4-fluoro-2-((R)-1-((4-methoxybenzyl)oxy)ethyl)phenyl)-1H-pyrazol-5-yl)(3-cyano-1-methyl-1H-pyrazol-5-yl)methyl methanesulfonate (680 mg, 98%) as a yellow oil.

To a solution of (3-chloro-1-(4-fluoro-2-((R)-1-((4-methoxybenzyl)oxy)ethyl)phenyl)-1H-pyrazol-5-yl)(3-cyano-1-methyl-1H-pyrazol-5-yl)methyl methanesulfonate (680 mg, 1.18 mmol) in EA (20 mL) were added Pd/C (126 mg, 10% wt.). The reaction mixture was degassed with H₂ three times. Then the reaction mixture was stirred at r.t. under H₂ (15 psi) overnight. The reaction mixture was filtered through celite and the filtrate was concentrated. The residue was purified by flash chromatography (silica gel, 0→15% ethyl acetate in petroleum ether) to give (R)-5-((3-chloro-1-(4-fluoro-2-(1-((4-methoxybenzyl)oxy)ethyl)phenyl)-1H-pyrazol-5-yl)methyl)-1-methyl-1H-pyrazole-3-carbonitrile (330 mg, 58%) as a yellow oil. LC/MS ESI (m/z):480 [M+H]⁺.

To a solution of (1-(2-(1-(5-bromo-2-nitropyridin-3-yloxy)ethyl)-4-fluorophenyl)-3-chloro-1H-pyrazol-5-yl)(1-ethyl-1H-pyrazol-4-yl)methanone (390 mg, 0.69 mmol) in TFA (5 mL) was added Et₃SiH (1.1 mL, 6.9 mmol). The resulting mixture was stirred at 25° C. for 1 h. After concentration in vacuo, the residue was partitioned between DCM (10 mL) and sat. aq. NaHCO₃ (10 mL), The organic layer was separated, washed with brine (10 mL) and concentrated in vacuo to give crude 5-bromo-3-(1-(2-(3-chloro-5-((1-ethyl-1H-pyrazol-4-yl)methyl)-1H-pyrazol-1-yl)-5-fluorophenyl)ethoxy)-2-nitropyridine (300 mg, 7%) as a white solid. LC/MS (ESI): m/z=549 [M+H]⁺.

Synthesis of (R)-1-(2-(5-(((1-(cyclopropylmethyl)-3-methyl-1H-pyrazol-4-yl)methyl)-3-methoxy-1H-pyrazol-1-yl)-5-fluorophenyl)ethan-1-ol

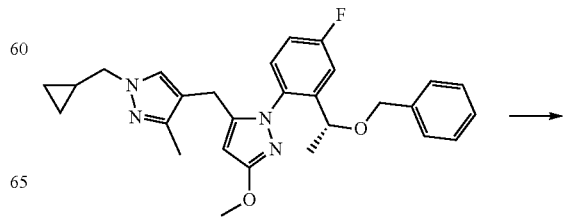

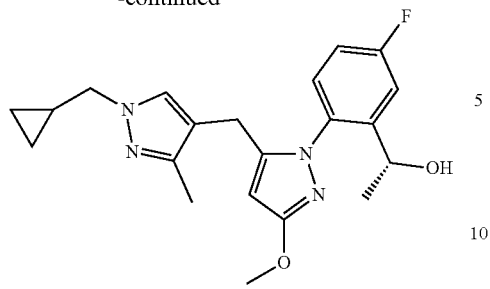

To a solution of (R)-1-(2-(1-(benzyloxy)ethyl)-4-fluorophenyl)-5-((1-(cyclopropylmethyl)-3-methyl-1H-pyrazol-4-yl)methyl)-3-methoxy-1H-pyrazole (610 mg, 1.24 mmol) in MeOH (10 mL) was added Pd/C (100 mg, 10% wt) at r.t. The mixture was thrice degassed under $H_2$ and stirred at r.t. for 12 h under an $H_2$ atmosphere. The mixture was filtered, and the filtrate was concentrated to dryness. The residue was purified by column chromatography on silica gel (PE:EA=1:1) to give (R)-1-(2-(5-((1-(cyclopropylmethyl)-3-methyl-1H-pyrazol-4-yl)methyl)-3-methoxy-1H-pyrazol-1-yl)-5-fluorophenyl)ethan-1-ol (228 mg, 39% yield) as a yellow oil. LC/MS (ESI) (m/z): 385.2 $[M+H]^+$.

The following intermediates were synthesized using a similar experimental protocol:

(R)-1-(2-(5-((3-(2,2-difluoroethyl)-1-methyl-1H-pyrazol-5-yl)methyl)-3-(difluoromethyl)-1H-pyrazol-1-yl)-5-fluorophenyl)ethan-1-ol

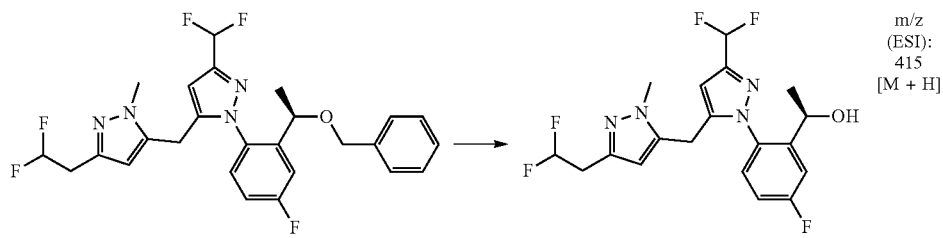

m/z (ESI): 415 [M + H]

Synthesis of (R)-5-((3-chloro-1-(4-fluoro-2-(1-hydroxyethyl)phenyl)-1H-pyrazol-5-yl)methyl)-1-methyl-1H-pyrazole-3-carbonitrile

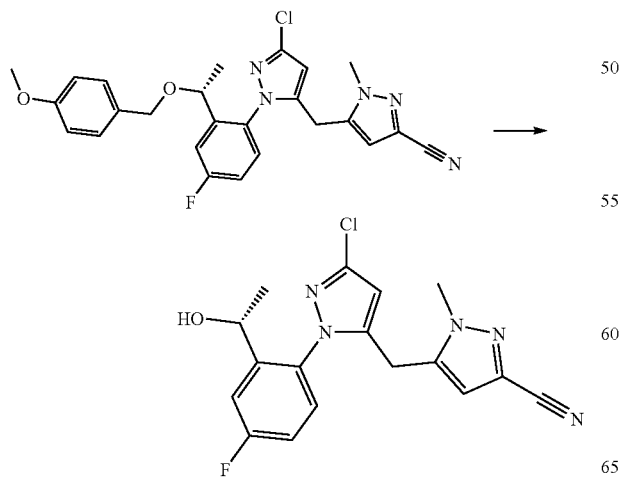

To a solution of (R)-5-((3-chloro-1-(4-fluoro-2-(1-((4-methoxybenzyl)oxy)ethyl)phenyl)-1H-pyrazol-5-yl)methyl)-1-methyl-1H-pyrazole-3-carbonitrile (330 mg, 0.680 mmol) in DCM (10 mL) was added TFA (1 mL) at r.t. and the reaction mixture was stirred at r.t. for 30 min. Then the reaction mixture was slowly poured into sat. NaHCO$_3$ and extracted with DCM twice. The combined organic layers were washed with brine, dried (MgSO$_4$) and concentrated. The residue was purified by flash column chromatography (silica gel, 0→30% EtOAc in petroleum ether) to afford (R)-5-((3-chloro-1-(4-fluoro-2-(1-hydroxyethyl)phenyl)-1H-pyrazol-5-yl)methyl)-1-methyl-1H-pyrazole-3-carbonitrile (215 mg, 87%) as a white solid. LC/MS ESI (m/z): 360 [M+H]$^+$.

The following intermediates were synthesized using a similar experimental protocol:

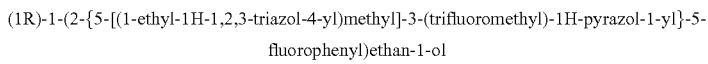
(1R)-1-(2-{5-[(1-ethyl-1H-1,2,3-triazol-4-yl)methyl]-3-(trifluoromethyl)-1H-pyrazol-1-yl}-5-fluorophenyl)ethan-1-ol

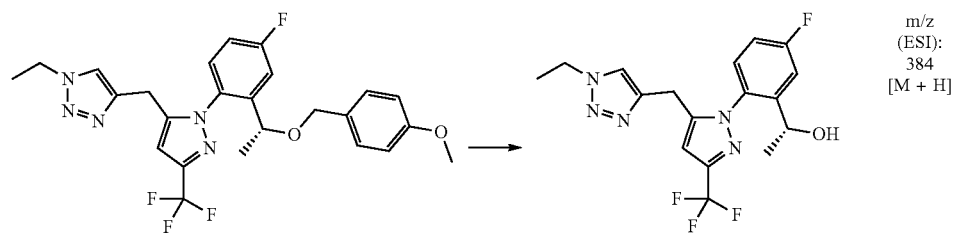

m/z (ESI): 384 [M + H]

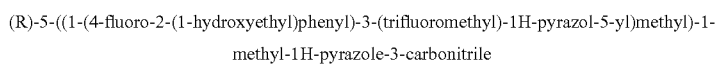
(R)-5-((1-(4-fluoro-2-(1-hydroxyethyl)phenyl)-3-(trifluoromethyl)-1H-pyrazol-5-yl)methyl)-1-methyl-1H-pyrazole-3-carbonitrile

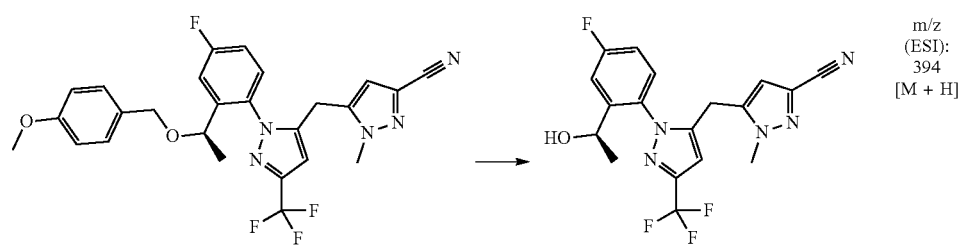

m/z (ESI): 394 [M + H]

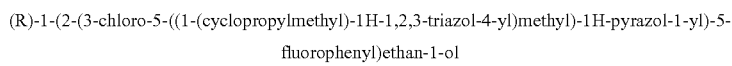
(R)-1-(2-(3-chloro-5-((1-(cyclopropylmethyl)-1H-1,2,3-triazol-4-yl)methyl)-1H-pyrazol-1-yl)-5-fluorophenyl)ethan-1-ol

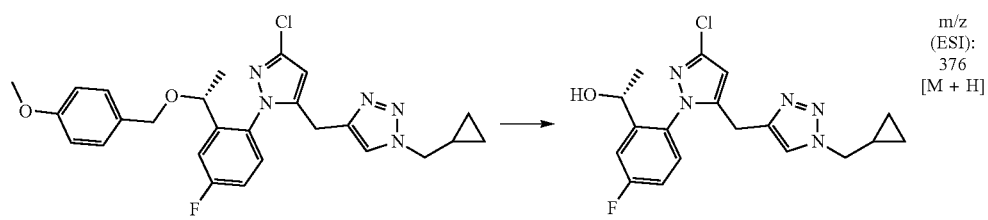

m/z (ESI): 376 [M + H]

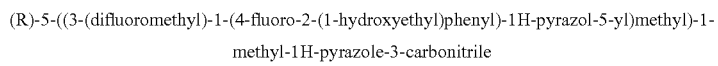
(R)-5-((3-(difluoromethyl)-1-(4-fluoro-2-(1-hydroxyethyl)phenyl)-1H-pyrazol-5-yl)methyl)-1-methyl-1H-pyrazole-3-carbonitrile

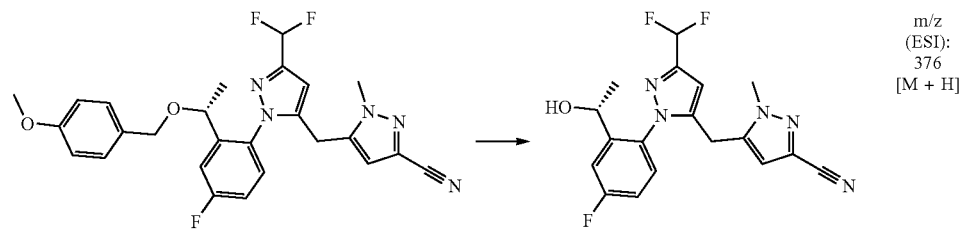

m/z (ESI): 376 [M + H]

549

Synthesis of 1-{2-[(1R)-1-(benzyloxy)ethyl]-4-fluorophenyl}-5-{[3-(2,2-difluoroethyl)-1-methyl-1H-pyrazol-5-yl]methyl}-3-(difluoromethyl)-1H-pyrazole

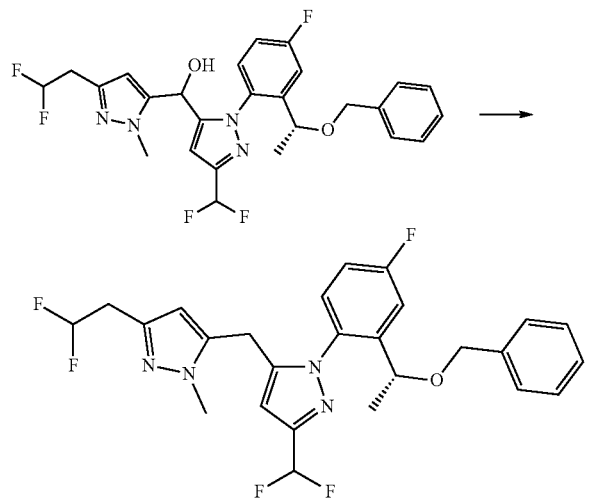

To a solution of (1-{2-[(1R)-1-(benzyloxy)ethyl]-4-fluorophenyl}-3-(difluoromethyl)-1H-pyrazol-5-yl)[3-(2,2-difluoroethyl)-1-methyl-1H-pyrazol-5-yl]methanol (0.45 g, 0.86 mmol) in DCM (8 mL) was added SOCl$_2$ (0.20 mL, 2.8 mmol) dropwise at 0° C. The mixture was stirred r.t. for 1 h, and then concentrated. The residue was dissolved in acetic acid (4 mL) and then Zn powder (0.50 g, 7.6 mmol) was added at 0° C. The mixture was stirred at r.t. for 2 h, and then filtered. The filtrate was concentrated, the residue was diluted with sat. aq. NaHCO$_3$, and then extracted with EA (20 mL×2). The combined organic layers were dried over anhydrous Na$_2$SO$_4$, filtered, and concentrated. The residue was purified by column chromatography on silica gel (25% EtOAc in PE) to give 1-{2-[(1R)-1-(benzyloxy)ethyl]-4-fluorophenyl}-5-{[3-(2,2-difluoroethyl)-1-methyl-1H-pyrazol-5-yl]methyl}-3-(difluoromethyl)-1H-pyrazole (0.35 g, 76% yield) as a colorless oil.

550

LC/MS (ESI) m/z: 505[M+H]$^+$.

Synthesis of (3-chloro-1-(4-fluoro-2-(((4-methoxybenzyl)oxy)methyl)phenyl)-1H-pyrazol-5-yl)(3-cyano-1-methyl-1H-pyrazol-5-yl)methyl methanesulfonate

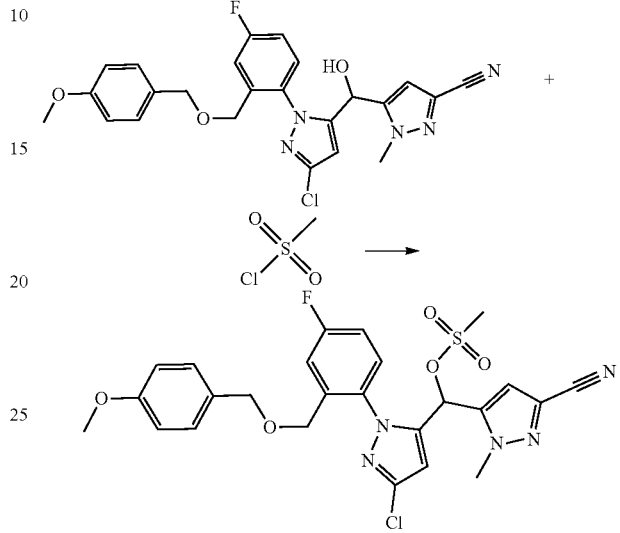

To a solution of 5-((3-chloro-1-(4-fluoro-2-(((4-methoxybenzyl)oxy)methyl)phenyl)-1H-pyrazol-5-yl)(hydroxy)methyl)-1-methyl-1H-pyrazole-3-carbonitrile (550 mg, 1.10 mmol) and DIPEA (442 mg, 3.40 mmol) in DCM (8 mL) was added MsCl (261 mg, 2.20 mmol) under the atmosphere of N$_2$ at 0° C. After stirring at 0° C. for 2 h, the reaction was extracted with EA. The combined organic phase was washed with sat. aq. NaCl, dried over anhydrous Na$_2$SO$_4$, filtered and concentrated to give crude (3-chloro-1-(4-fluoro-2-(((4-methoxybenzyl)oxy)methyl)phenyl)-1H-pyrazol-5-yl)(3-cyano-1-methyl-1H-pyrazol-5-yl)methyl methanesulfonate (700 mg) as a yellow oil. LC/MS (ESI) m/z: 560 [M+H]$^+$.

The following intermediates were synthesized using a similar experimental protocol:

(1-ethyl-1H-1,2,3-triazol-4-yl)(1-(4-fluoro-2-((R)-1-((4-methoxybenzyl)oxy)ethyl)phenyl)-3-(trifluoromethyl)-1H-pyrazol-5-yl)methylmethanesulfonate m/z (ESI): 598 [M + H]

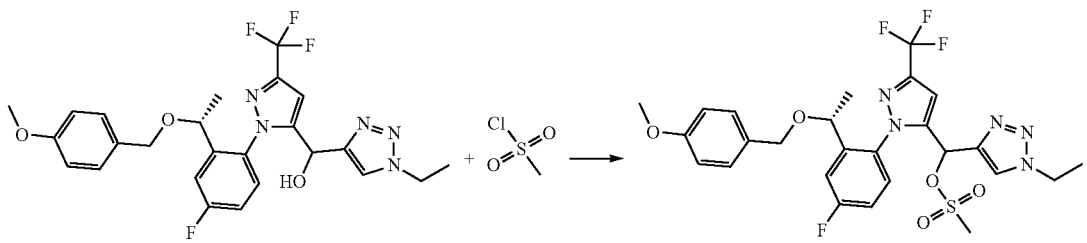

(3-chloro-1-(4-fluoro-2-((R)-1-((4-methoxybenzyl)oxy)ethyl)phenyl)-1H-pyrazol-5-yl)(1-(cyclopropylmethyl)-1H-1,2,3-triazol-4-yl)methyl methanesulfonate

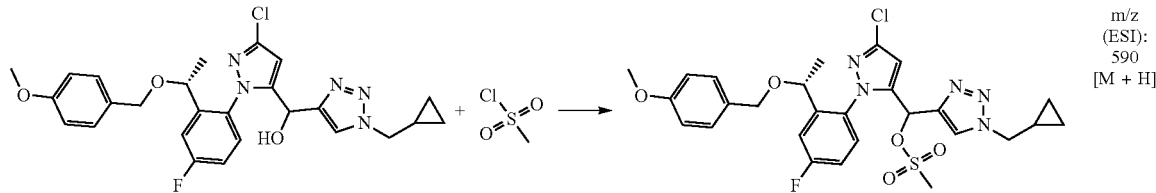

m/z (ESI): 590 [M + H]

Synthesis of 3-(1-(4-fluoro-2-formylphenyl)-1H-pyrazole-5-carbonyl)-1-methyl-1H-pyrazole-5-carbonitrile

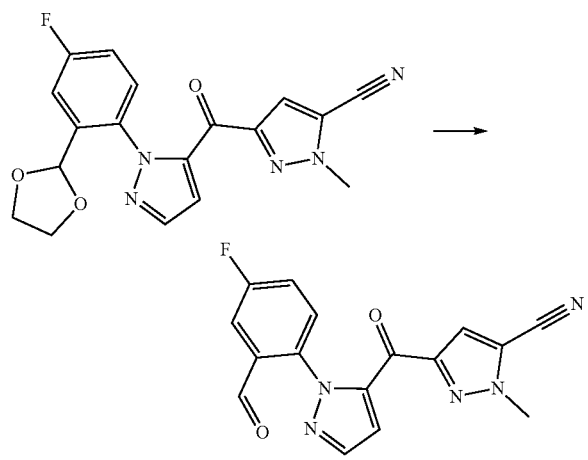

To a solution of 3-(1-(2-(1,3-dioxolan-2-yl)-4-fluorophenyl)-1H-pyrazole-5-carbonyl)-1-methyl-1H-pyrazole-5-carbonitrile (155 mg, 0.420 mmol) in acetone (3 mL) was added ferric chloride (21 mg, 0.13 mmol), then the mixture was stirred at r.t. for 4 h. After 4 h, the reaction mixture was concentrated in vacuo to give the crude product. The crude product was purified by flash chromatography (0→40% EtOAc in PE) to give 3-(1-(4-fluoro-2-formylphenyl)-1H-pyrazole-5-carbonyl)-1-methyl-1H-pyrazole-5-carbonitrile (98 mg, 72%) as a white solid. LC/MS ESI (m/z): 324 [M+H]+.

Synthesis of (R)-5-((1-(4-fluoro-2-(1-((4-methoxybenzyl)oxy)ethyl)phenyl)-3-(trifluoromethyl)-1H-pyrazol-5-yl)methyl)-1-methyl-1H-pyrazole-3-carbonitrile To a solution of 5-((1-(4-fluoro-2-((R)-1-((4-methoxybenzyl)oxy)ethyl)phenyl)-3-(trifluoromethyl)-1H-pyrazol-5-yl)(hydroxy)methyl)-1-methyl-1H-pyrazole-3-carbonitrile (800 mg, 1.51 mmol) and DIPEA (976 mg, 7.55 mmol) in DCM (20 mL) was added MsCl (519 mg, 4.53 mmol) at 0° C. The reaction mixture was stirred at r.t. for 2 h, and then slowly poured into ice-water and extracted twice with DCM. The combined organic layers were washed with brine, dried over anhydrous MgSO4 and concentrated to afford crude (3-cyano-1-methyl-1H-pyrazol-5-yl)(1-(4-fluoro-2-((R)-1-((4-methoxybenzyl)oxy)ethyl)phenyl)-3-(trifluoromethyl)-1H-pyrazol-5-yl)methyl methanesulfonate (900 mg, 98%) as a yellow oil.

To a solution of (3-cyano-1-methyl-1H-pyrazol-5-yl)(1-(4-fluoro-2-((R)-1-((4-methoxybenzyl)oxy)ethyl)phenyl)-3-(trifluoromethyl)-1H-pyrazol-5-yl)methyl methanesulfonate (900 mg, 1.48 mmol) in EA (20 mL) was added Pd/C (100 mg, 0.94 mmol, 10% wt.). The mixture was degassed with H2 three times and stirred at r.t. under H2 (15 psi) overnight. The mixture was filtered through celite and the filtrate was concentrated. The residue was purified by flash column chromatography (silica gel, 0→20% ethyl acetate in petroleum ether) to give (R)-5-((1-(4-fluoro-2-(1-((4-methoxybenzyl)oxy)ethyl)phenyl)-3-(trifluoromethyl)-1H-pyrazol-5-yl)methyl)-1-methyl-1H-pyrazole-3-carbonitrile (350 mg, 46%) as a yellow oil. LC/MS ESI (m/z): 514 [M+H]+.

Synthesis of (1R)-1-[2-(5-{[1-(cyclopropylmethyl)-1H-1,2,3-triazol-4-yl]methyl}-3-(trifluoromethyl)-1H-pyrazol-1-yl)-5-fluorophenyl]ethan-1-ol

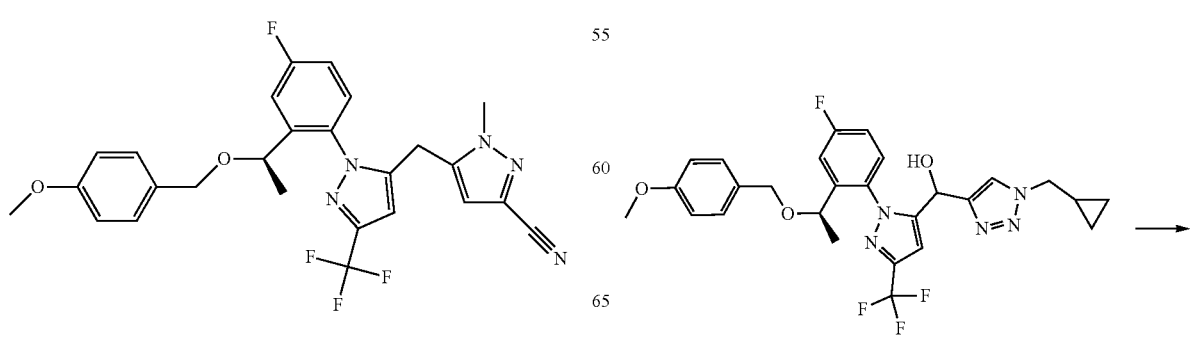

-continued

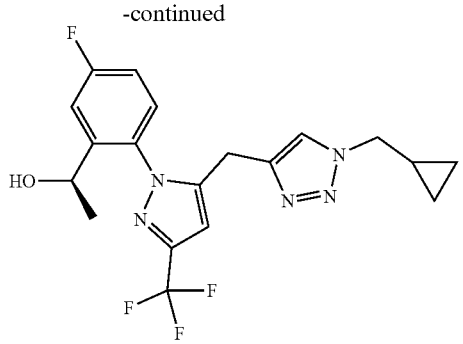

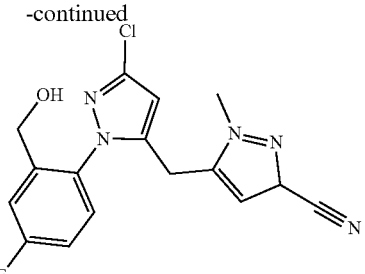

To a solution of [1-(cyclopropylmethyl)-1H-1,2,3-triazol-4-yl](1-{4-fluoro-2-[(1R)-1-[(4-methoxyphenyl)methoxy]ethyl]phenyl}-3-(trifluoromethyl)-1H-pyrazol-5-yl)methanol (400 mg, 0.730 mmol) in DCM (10 mL) was added TEA (0.10 mL, 0.73 mmol) and MsCl (84 mg, 0.73 mmol) at 0° C. The reaction was stirred for 1 h at r.t. The mixture was diluted with water (10 mL) and extracted with DCM (3×10 mL). The combined organic layers were dried over anhydrous Na$_2$SO$_4$, filtered, and concentrated in vacuo. The residue was dissolved in EtOAc (20 mL) and to this solution was added Pd/C (40 mg, 10% wt.). The mixture was stirred under 1 atm. of H$_2$ at r.t. overnight. The reaction mixture was filtered, and the filtrate was concentrated under reduced pressure. The residue was purified by flash column chromatography (0→5% MeOH in DCM) to give (1R)-1-[2-(5-{[1-(cyclopropylmethyl)-1H-1,2,3-triazol-4-yl]methyl}-3-(trifluoromethyl)-1H-pyrazol-1-yl)-5-fluorophenyl]ethan-1-ol (75 mg, 25%) as a colorless oil. LC/MS (ESI) (m/z): 410 [M+H]$^+$.

Synthesis of 5-((3-chloro-1-(4-fluoro-2-(hydroxymethyl)phenyl)-1H-pyrazol-5-yl)methyl)-1-methyl-1H-pyrazole-3-carbonitrile A solution of 5-((3-chloro-1-(4-fluoro-2-(((4-methoxybenzyl)oxy)methyl)phenyl)-1H-pyrazol-5-yl)methyl)-1-methyl-1H-pyrazole-3-carbonitrile (150 mg, 0.320 mmol) in DCM (5 mL) and TFA (0.5 mL) was stirred at 25° C. for 0.5 h. The mixture was diluted with NaHCO$_3$ and EtOAc. The layers were separated, and the organic phase was washed with H$_2$O, brine. The organic layer was dried over anhydrous Na$_2$SO$_4$, filtered, After and concentrated under vacuum. The residue was purified by flash chromatography (silica gel, 0-40% EA in PE) to give 5-((3-chloro-1-(4-fluoro-2-(hydroxymethyl)phenyl)-1H-pyrazol-5-yl)methyl)-1-methyl-1H-pyrazole-3-carbonitrile (110 mg, 99% yield) as a yellow oil. LC/MS (ESI) m/z: 346 [M+H]$^+$.

The following intermediates were synthesized using a similar experimental protocol:

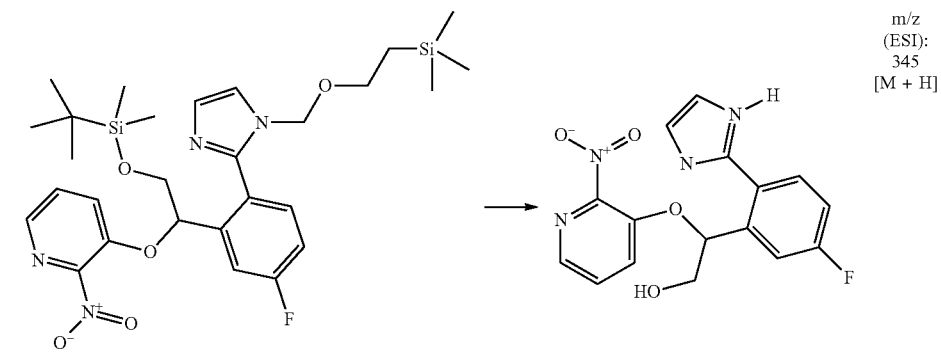

2-[5-fluoro-2-(1H-imidazol-2-yl)phenyl]-2-[(2-nitropyridin-3-yl)oxy]ethan-1-ol m/z (ESI): 345 [M + H]

Synthesis of (R)-4-((3-chloro-1-(4-fluoro-2-(1-((4-methoxybenzyl)oxy)ethyl)phenyl)-1H-pyrazol-5-yl)methyl)-1-(cyclopropylmethyl)-1H-1,2,3-triazole

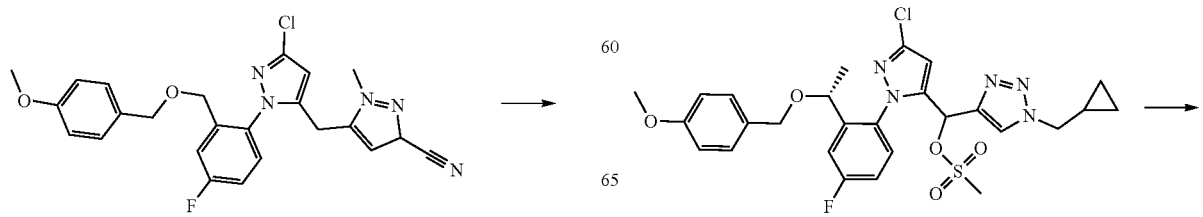

-continued

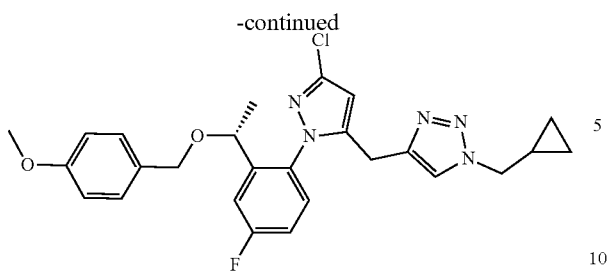

To a solution of crude (3-chloro-1-(4-fluoro-2-((R)-1-((4-methoxybenzyl)oxy)ethyl)phenyl)-1H-pyrazol-5-yl)(1-(cyclopropylmethyl)-1H-1,2,3-triazol-4-yl)methyl methanesulfonate (690 mg, 1.17 mmol) in DCM (8 mL) were added Pd/C (100 mg, 10% wt.) and EtOAc (80 mL). The resulting mixture was degassed with H$_2$ three times and then stirred at 40° C. under 1 atm of H$_2$ overnight. The mixture was filtered through celite, and the filtrate was concentrated and purified by flash column chromatography to afford (R)-4-((3-chloro-1-(4-fluoro-2-(1-(4-methoxybenzyloxy)ethyl)phenyl)-1H-pyrazol-5-yl)methyl)-1-(cyclopropylmethyl)-1H-1,2,3-triazole (250 mg, 43%) as a white solid. LC/MS (ESI) m/z: 496 [M+H]$^+$.

Synthesis of (R)-3-((1-(2-(1-((5-bromo-2-nitropyridin-3-yl)oxy)ethyl)-4-fluorophenyl)-1H-pyrazol-5-yl)methyl)-1H-pyrazole-5-carbonitrile

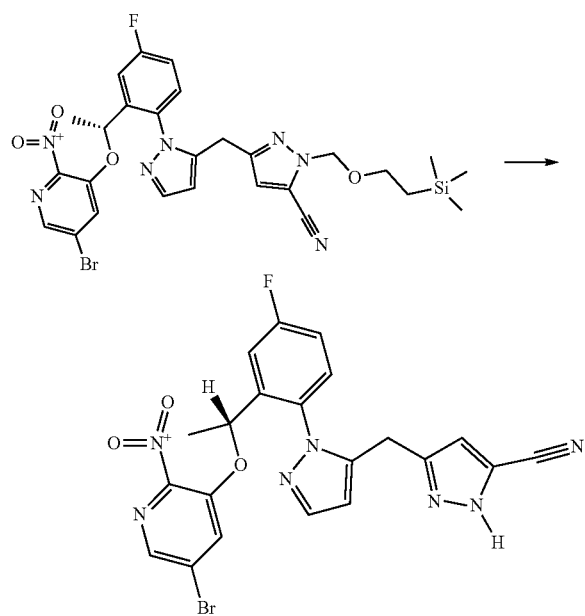

To a solution of (R)-3-((1-(2-(1-((5-bromo-2-nitropyridin-3-yl)oxy)ethyl)-4-fluorophenyl)-1H-Pyrazol-5-yl)methyl)-1-((2-(trimethylsilyl)ethoxy)methyl)-1H-pyrazole-5-carbonitrile (230 mg, 0.40 mmol) in DCM (10 mL) was added TFA (5 mL) at r.t. The mixture was stirred at r.t. overnight, and then concentrated to afford crude (R)-3-((1-(2-(1-((5-bromo-2-nitropyridin-3-yl)oxy)ethyl)-4-fluorophenyl)-1H-pyrazol-5-yl)methyl)-1H-pyrazole-5-carbonitrile (180 mg, 98%) as a yellow oil.
LC/MS ESI (m/z): 512 [M+H]$^+$.

Compounds

Example 1 (Method A)

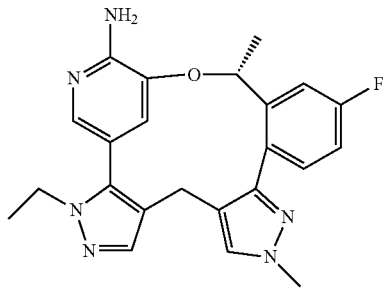 [SMILES: CCn1ncc2c1-c1cnc(N)c(c1)O[C@H](C)c1cc(F)ccc1-c1nn(C)cc1C2]

Name: (19R)-3-ethyl-16-fluoro-10,19-dimethyl-20-oxa-3,4,10,11,23-pentaazapentacyclo[19.3.1.0$^{2,6}$,0$^{8,12}$,0$^{3,18}$]pentacosa-1(24),2(6),4,8,11,13,15,17,21(25),22-decaen-22-amine NMR: 1H NMR (400 MHz, CDCl3) δ 7.58 (s, 1H), 7.51 (d, J=1.8 Hz, 1H), 7.30 (dd, J=10.7, 3.5 Hz, 2H), 7.12 (dd, J=8.5, 5.8 Hz, 1H), 7.00 (td, J=8.3, 2.7 Hz, 1H), 6.52 (d, J=1.6 Hz, 1H), 5.41 (m, 1H), 4.78 (s, 2H), 4.14 (qd, J=7.1, 1.5 Hz, 2H), 3.91 (s, 3H), 3.61 (d, J=16.1 Hz, 1H), 2.96 (d, J=15.7 Hz, 1H), 1.80 (d, J=6.3 Hz, 3H), 1.41 (t, J=7.2 Hz, 3H).

LCMS: Method D; t$_R$: 1.54 min; m/z 419 [m+H]

To a solution of 4-[(5-bromo-1-ethyl-1H-pyrazol-4-yl)methyl]-3-iodo-1-methyl-1H-pyrazole (500 mg, 1.27 mmol) and 5-bromo-3-[(1R)-1-[5-fluoro-2-(trimethylstannyl)phenyl]ethoxy]pyridin-2-amine (1.2 g, 2.53 mmol) in DMF (5 mL) was added AsPh$_3$ (775 mg, 2.53 mmol), CuI (4 mg, 0.03 mmol) and Pd$_2$(dba)$_3$ (116 mg, 0.127 mmol). The mixture was stirred under N$_2$ at 100° C. overnight.

The mixture was concentrated in vacuo to remove DMF, and the residue was purified by column chromatography on silica gel (0→100% EtOAc in PE) to give (R)-5-bromo-3-(1-(2-(4-((5-bromo-1-ethyl-1H-pyrazol-4-yl)methyl)-1-methyl-1H-pyrazol-3-yl)-5-fluorophenyl)ethoxy)pyridin-2-amine (300 mg, 41% yield) as a light-yellow solid. LC/MS ESI (m/z): 577 [M+H]$^+$.

To a mixture of 5-bromo-3-[(1R)-1-(2-{4-[(5-bromo-1-ethyl-1H-pyrazol-4-yl)methyl]-1-methyl-1H-pyrazol-3-yl}-5-fluorophenyl)ethoxy]pyridin-2-amine (250 mg, 0.432 mmol), 4,4,5,5-tetramethyl-2-(tetramethyl-1,3,2-dioxaborolan-2-yl)-1,3,2-dioxaborolane (329 mg, 1.3 mmol), Pd(OAc)$_2$ (19 mg, 0.086 mmol) and cataCXium A (62 mg, 0.17 mmol) in MeOH (10 mL) was added a solution of aq. NaOH (2.0 M, 0.43 mL, 0.86 mmol). The mixture was twice flushed with N$_2$ and then stirred at 80° C. for 12 h. After cooling to r.t., the mixture was filtered through celite, and the filtrate was concentrated under reduced pressure. The residue was diluted with DCM (50 mL), washed with water and brine, dried over anhydrous Na$_2$SO$_4$, filtered, and concentrated. The residue was purified by prep-HPLC (Gemini 5 um C18 250*21.2 mm, MeCN in H$_2$+0.100 FA) to give the target product (19 mg, ~65 yield) as a white solid. LC/MS ESI (m/z): 419 [M+H].

The following compounds were prepared in a similar manner:

| Example | | |
|---|---|---|
| Example 2 | 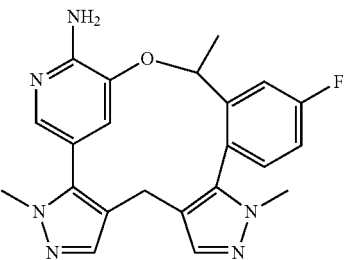 | 16-fluoro-3,11,19-trimethyl-20-oxa-3,4,10,11,23-pentaazapentacyclo[19.3.1.0²,⁶.0⁸,¹².0¹³,¹⁸]pentacosa-1(24),2(6),4,8(12),9,13,15,17,21(25),22-decaen-22-amine<br>1H NMR (400 MHz, DMSO) δ 7.81 (dd, J = 10.3, 2.7 Hz, 1H), 7.59 (s, 1H), 7.55 (d, J = 1.7 Hz, 1H), 7.37 (s, 1H), 7.27 (td, J = 8.4, 2.7 Hz, 1H), 7.20-7.14 (m, 1H), 6.48 (d, J = 1.6 Hz, 1H), 6.13 (s, 2H), 5.08-4.95 (m, 1H), 3.75 (s, 3H), 3.67 (d, J = 7.8 Hz, 1H), 3.58 (s, 3H), 2.62 (d, J = 15.4 Hz, 1H), 1.79 (d, J = 6.2 Hz, 3H).<br>LCMS Method C; $t_R$: 0.98 min; m/z: 405 [M + H] |
| Example 3 | 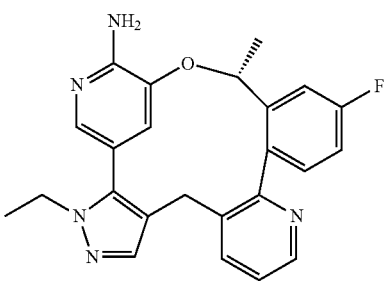 [SMILES: CCn1ncc2c1-c1cnc(N)c(c1)O[C@H](C)c1cc(F)ccc1-c1ncccc1C2] | (20R)-3-ethyl-17-fluoro-20-methyl-21-oxa-3,4,12,24-tetraazapentacyclo[20.3.1.0²,⁶.0⁸,¹³.0¹⁴,¹⁹]hexacosa-1(25),2(6),4,8(13),9,11,14,16,18,22(26),23-undecaen-23-amine<br>1H NMR (400 MHz, DMSO) δ 8.55-8.50 (m, 1H), 7.89 (d, J = 7.2 Hz, 1H), 7.78 (s, 1H), 7.69 (dd, J = 10.4, 2.7 Hz, 1H), 7.47-7.42 (m, 2H), 7.22 (dd, J = 8.5, 5.9 Hz, 1H), 7.15 (td, J = 8.4, 2.7 Hz, 1H), 6.14 (s, 2H), 6.01 (d, J = 1.7 Hz, 1H), 5.12 (d, J = 4.4 Hz, 1H), 4.06 (tt, J = 13.9, 7.0 Hz, 2H), 3.83 (d, J = 15.7 Hz, 1H), 3.09 (d, J = 15.5 Hz, 1H), 1.74 (d, J = 6.2 Hz, 3H), 1.28 (t, J = 7.2 Hz, 3H).<br>LCMS Method C; $t_R$: 1.06 min; m/z: 416 [M + H] |
| Example 4 | 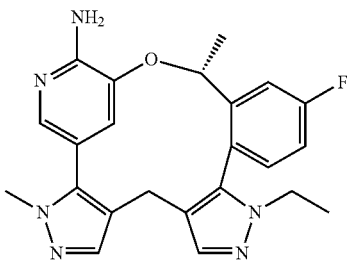 [SMILES: CCn1ncc2c1-c1ccc(F)cc1[C@@H](C)Oc1cc(cnc1N)-c1c(cnn1C)C2] | (19R)-11-ethyl-16-fluoro-3,19-dimethyl-20-oxa-3,4,10,11,23-pentaazapentacyclo[19.3.1.0²,⁶.0⁸,¹².0¹³,¹⁸]pentacosa-1(24),2(6),4,8(12),9,13,15,17,21(25),22-decaen-22-amine<br>1H NMR (400 MHz, DMSO-d6) δ 7.82 (dd, J = 10.3, 2.8 Hz, 1H), 7.58 (s, 1H), 7.55 (d, J = 1.8 Hz, 1H), 7.40 (s, 1H), 7.27 (td, J = 8.3, 2.8 Hz, 1H), 7.19 (dd, J = 8.5, 5.9 Hz, 1H), 6.49 (dd, J = 2.0 Hz, 1H), 6.14 (s, 2H), 4.99 (dd, J = 6.4, 2.1 Hz, 1H), 3.90 (dt, J = 14.3, 7.1 Hz, 1H), 3.75 (s, 3H), 3.71 (dd, J = 13.8, 7.1 Hz, 1H), 3.55 (d, J = 15.6 Hz, 1H), 2.62 (d, J = 15.4 Hz, 1H), 1.77 (d, J = 6.1 Hz, 3H), 1.25 (s, 3H).<br>LCMS Method C; $t_R$: 1.07 min; m/z: 419 [M + H] |
| Example 5 | 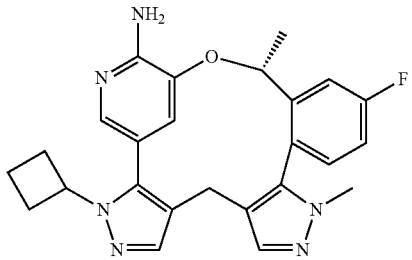 [SMILES: C[C@H]1Oc2cc(cnc2N)-c2c(cnn2C2CCC2)Cc2cnn(C)c2-c2ccc(F)cc21] | (19R)-3-cyclobutyl-16-fluoro-11,19-dimethyl-20-oxa-3,4,10,11,23-pentaazapentacyclo19.3.1.0²,⁶.0⁸,¹².0¹³,¹⁸]pentacosa-1(24),2(6),4,8(12),9,13,15,17,21(25),22-decaen-22-amine<br>1H NMR (400 MHz, DMSO) δ 7.82 (dd, J = 10.3, 2.6 Hz, 1H), 7.68 (s, 1H), 7.38 (s, 1H), 7.35 (d, J = 1.6 Hz, 1H), 7.25 (td, J = 8.4, 2.8 Hz, 1H), 7.16 (dd, J = 8.5, 5.9 Hz, 1H), 6.46 (s, 1H), 6.14 (s, 2H), 5.10-4.97 (m, 1H), 4.82-4.69 (m, 1H), 3.57 (s, 3H), 3.52 (s, 1H), 2.65 (d, J = 9.6 Hz, 1H), 2.61 (d, J = 2.6 Hz, 1H), 2.47-2.38 (m, 2H), 2.12-2.04 (m, 1H), 1.78 (d, J = 6.2 Hz, 3H), 1.76-1.66 (m, 2H).<br>LCMS Method C; $t_R$: 1.18 min; m/z: 445 [M + H] |
| Example 6 | 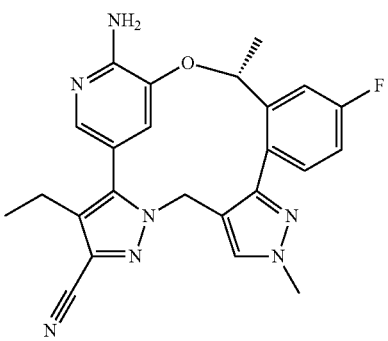 [SMILES: CCc1c(C#N)nn2c1-c1cnc(N)c(c1)O[C@H](C)c1cc(F)ccc1-c1nn(C)cc1C2] | (19R)-22-amino-3-ethyl-16-fluoro-10,19-dimethyl-20-oxa-5,6,10,11,23-pentaazapentacyclo[19.3.1.0²,⁶.0⁸,¹².0¹³,¹⁸]pentacosa-1(24),2,4,8,11,13,15,17,21(25),22-decaene-4-carbonitrile<br>1H NMR (400 MHz, DMSO) δ 7.85 (s, 1H), 7.76 (d, J = 10.2 Hz, 1H), 7.41 (s, 1H), 7.15 (d, J = 6.4 Hz, 2H), 6.33 (s, 1H), 6.28 (s, 2H), 5.47-5.37 (m, 1H), 5.32 (d, J = 15.9 Hz, 1H), 4.26 (d, J = 15.7 Hz, 1H), 3.89 (s, 3H), 2.41-2.28 (m, 2H), 1.73 (d, J = 6.2 Hz, 3H), 1.08 (t, J = 7.5 Hz, 3H).<br>LCMS Method F; $t_R$: 1.08 min; m/z: 444 [M + H] |

| Example | | |
|---|---|---|
| 7 | 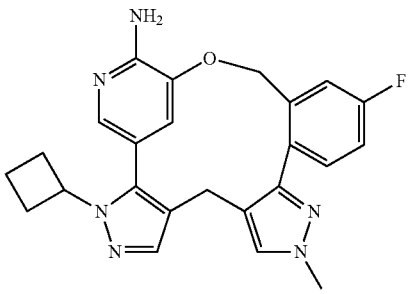 [SMILES: Cn1cc2c(n1)-c1ccc(F)cc1COc1cc(cnc1N)-c1c(cnn1C1CCC1)C2] | 3-cyclobutyl-16-fluoro-10-methyl-20-oxa-3,4,10,11,23-pentaazapentacyclo[19.3.1.0$^{2,6}$.0$^{8,12}$.0$^{13,18}$]pentacosa-1(24),2(6),4,8,11,13,15,17,21(25),22-decaen-22-amine<br>1H NMR (400 MHz, DMSO) δ 7.68-7.61 (m, 2H), 7.56 (s, 1H), 7.31 (s, 1H), 7.21-7.15 (m, 2H), 6.28 (s, 1H), 6.12 (s, 2H), 5.08 (dd, J = 26.2, 13.1 Hz, 2H), 4.77-4.67 (m, 1H), 3.83 (s, 3H), 3.61 (d, J = 16.2 Hz, 1H), 2.73 (d, J = 14.7 Hz, 1H), 2.70-2.64 (m, 1H), 2.44-2.36 (m, 2H), 2.10-2.03 (m, 1H), 1.77-1.65 (m, 2H).<br>LCMS Method I; t$_R$: 1.16 min; m/z: 431 [M + H] |
| 8 | 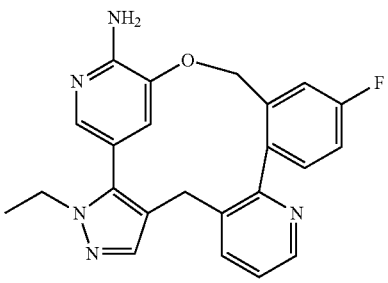 [SMILES: CCn1ncc2c1-c1cnc(N)c(c1)OCc1cc(F)ccc1-c1ncccc1C2] | 3-ethyl-17-fluoro-21-oxa-3,4,12,24-tetraazapentacyclo[20.3.1.0$^{2,6}$.0$^{5,13}$.0$^{14,19}$]hexacosa-1(25),2(6),4,8(13),9,11,14,16,18,22(26),23-undecaen-23-amine<br>1H NMR (400 MHz, DMSO) δ 8.51 (d, J = 3.5 Hz, 1H), 7.90 (d, J = 7.3 Hz, 1H), 7.79 (s, 1H), 7.66 (dd, J = 10.1, 2.5 Hz, 1H), 7.50-7.40 (m, 2H), 7.28-7.13 (m, 2H), 6.15 (s, 2H), 6.03 (s, 1H), 5.21 (d, J = 13.3 Hz, 1H), 4.87 (d, J = 14.1 Hz, 1H), 4.07 (q, J = 7.1 Hz, 2H), 3.87 (d, J = 15.6 Hz, 1H), 3.13 (d, J = 15.4 Hz, 1H), 1.29 (t, J = 7.2 Hz, 3H).<br>LCMS Method F; t$_R$: 0.79 min; m/z: 402 [M + H] |

Example 9 (Method B)

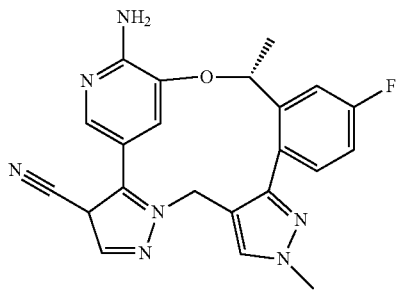

Name: (19R)-22-amino-16-fluoro-10,19-dimethyl-20-oxa-5,6,10,11,23-pentaazapentacyclo[19.3.1.0$^{2,6}$,0$^{8,12}$,0$^{13,18}$]pentacosa-1(24),2,4,8,11,13,15,17,21(25),22-decaene-3-carbonitrile NMR: 1H NMR (400 MHz, DMSO) δ 8.16 (s, 1H), 7.83 (s, 1H), 7.71 N $_{N\,(d,\,J=}$9.9 Hz, 1H), 7.61 (d, J=1.9 Hz, 1H), 7.21-7.17 (m, 2H), 6.48-6.41 (m, 3H), 5.41-5.32 (m, 2H), 4.27 (d, J=15.8 Hz, 1H), 3.89 (s, 3H), 1.74 (d, J=6.2 Hz, 3H).

LCMS: Method D; t$_R$; 1.72 min; m/z: 416 [M+H]

To a solution of 1-((3-iodo-1-methyl-1H-pyrazol-4-yl)methyl)-1H-pyrazole-4-carbonitrile (600 mg, 1.92 mmol) and (R)-5-bromo-3-(1-(5-fluoro-2-(trimethylstannyl)phenyl)ethoxy)pyridin-2-amine (1.36 g, 2.87 mmol) in DMF (10 mL) was added AsPh$_3$ (586 mg, 1.92 mmol), CuI (4 mg, 0.02 mmol) and Pd$_2$(dba)$_3$ (150 mg, 0.190 mmol). The mixture was thrice degassed with N$_2$ and then stirred at 100° C. overnight. After concentration under reduced pressure, the residue was purified by column chromatography on silica gel (0→100% EA in PE) to give (R)-1-((3-(2-(1-((2-amino-5-bromopyridin-3-yl)oxy)ethyl)-4-fluorophenyl)-1-methyl-1H-pyrazol-4-yl)methyl)-1H-pyrazole-4-carbonitrile (80 mg, 8.4%) as a pale-yellow solid. LC/MS ESI (m/z): 496 [M+H]$^+$.

To a solution of (R)-1-((3-(2-(1-((2-amino-5-bromopyridin-3-yl)oxy)ethyl)-4-fluorophenyl)-1-methyl-1H-pyrazol-4-yl)methyl)-1H-pyrazole-4-carbonitrile (80 mg, 0.16 mmol) in 2-methyl-2-butanol (5 mL) was added KOAc (79 mg, 0.80 mmol), cataCXium A (23 mg, 0.60 mmol) and Pd(OAc)$_2$ (7 mg, 0.03 mmol). The mixture was thrice degassed with N$_2$ and then stirred in a sealed tube at 120° C. overnight. After concentration under reduced pressure, the residue was purified by prep-HPLC (Gemini 5 um C18 250*21.2 mm, MeCN in H$_2$O+0.1% FA) to give the target product (10 mg, 15% yield) as a white solid. LC/MS ESI (m/z): 416 [M+H]$^+$.

The following compounds were prepared in a similar manner:

| Example | | |
|---|---|---|
| 10 | 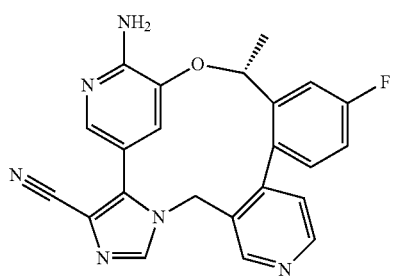 [SMILES: C[C@H]1Oc2cc(cnc2N)-c2c(C#N)ncn2Cc2cnccc2-c2ccc(F)cc21] | (20R)-23-amino-17-fluoro-20-methyl-21-oxa-4,6,10,24-tetraazapentacyclo[20.3.1.0$^{2,6}$.0$^{8,13}$.0$^{14,19}$]hexacosa-1(25),2,4,8(13),9,11,14,16,18,22(26),23-undecaene-3-carbonitrile<br>1H NMR (400 MHz, DMSO) δ 8.80 (s, 1H), 8.65 (d, J = 4.9 Hz, 1H), 8.54 (s, 1H), 7.73 (dd, J = 10.3, 2.3 Hz, 1H), 7.61 (d, J = 1.9 Hz, 1H), 7.37 (d, J = 5.0 Hz, 1H), 7.26-7.17 (m, 2H), 6.43 (s, 2H), 6.17 (d, J = 1.7 Hz, 1H), 5.56 (d, J = 16.2 Hz, 1H), 5.20 (d, J = 4.6 Hz, 1H), 4.34 (d, J = 16.1Hz, 1H), 1.82 (d, J = 6.2 Hz, 3H).<br>LCMS Method C; t$_R$: 1.03 min; m/z: 413 [M + H] |

| Example | Structure | Name / Data |
|---|---|---|
| Example 11 | 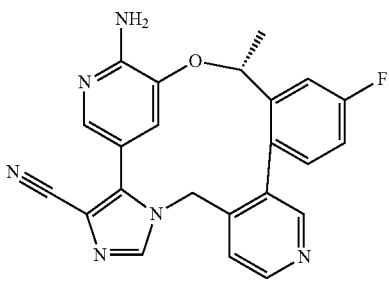 [SMILES: C[C@H]1Oc2cc(cnc2N)-c2c(C#N)ncn2Cc2ccncc2-c2ccc(F)cc21] | (20R)-23-amino-17-fluoro-20-methyl-21-oxa-4,6,11,24-tetraazapentacyclo [20.3.1.0²,⁶.0⁸,¹³.0¹⁴,¹⁹]hexacosa-1(25),2,4,8(13),9,11,14,16,18,22(26),23-undecaene-3-carbonitrile<br>1H NMR (400 MHz, DMSO) δ 8.73 (d, J = 5.2 Hz, 1H), 8.54 (s, 1H), 8.47 (s, 1H), 7.75-7.70 (m, 1H), 7.61 (d, J = 1.9 Hz, 1H), 7.53 (d, J = 5.3 Hz, 1H), 7.27-7.22 (m, 2H), 6.47 (s, 2H), 6.05 (d, J = 1.9 Hz, 1H), 5.49 (d, J = 16.5 Hz, 1H), 5.17-5.09 (m, 1H), 4.30 (d, J = 16.2 Hz, 1H), 1.83 (d, J = 6.3 Hz, 3H).<br>LCMS Method C; $t_R$: 0.96 min; m/z: 413 [M + H] |
| Example 12 | 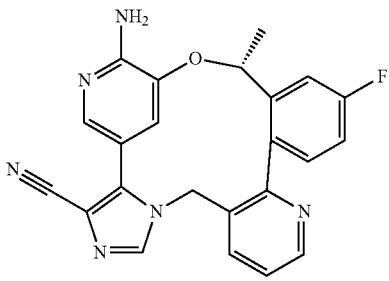 [SMILES: C[C@H]1Oc2cc(cnc2N)-c2c(C#N)ncn2Cc2cccnc2-c2ccc(F)cc21] | (20R)-23-amino-17-fluoro-20-methyl-21-oxa-4,6,12,24-tetraazapentacyclo[20.3.1.0²,⁶.0⁸,¹³.0¹⁴,¹⁹]hexacosa-1(25),2,4,8(13),9,11,14,16,18,22(26),23-undecaene-3-carbonitrile<br>1H NMR (400 MHz, DMSO) δ 8.75-8.65 (m, 1H), 8.47 (s, 1H), 7.99 (d, J = 8.0 Hz, 1H), 7.70 (dd, J = 10.3, 2.5 Hz, 1H), 7.66-7.52 (m, 2H), 7.21 (td, J = 8.5, 2.5 Hz, 2H), 6.42 (s, iment2H), 6.09 (d, J = 1.7 Hz, 1H), 5.54 (d, J = 16.1 Hz, 1H), 5.15 (d, J = 4.7 Hz, 1H), 4.35 (d, J = 16.0 Hz, 1H), 1.77 (d, J = 6.2 Hz, 3H).<br>LCMS Method C; $t_R$: 0.95 min; m/z: 413 [M + H] |
| Example 13 | 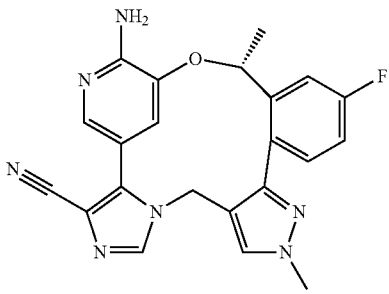 [SMILES: C[C@H]1Oc2cc(cnc2N)-c2c(C#N)ncn2Cc2cn(C)nc2-c2ccc(F)cc21] | (19R)-22-amino-16-fluoro-10,19-dimethyl-20-oxa-4,6,10,11,23-pentaazapentacyclo[19.3.1.0²,⁶.0⁸,¹².0¹³,¹⁸]pentacosa-1(24),2,4,8,11,13,15,17,21(25),22-decaene-3-carbonitrile<br>1H NMR (400 MHz, DMSO) δ 8.28 (s, 1H), 7.94 (s, 1H), 7.70 (dd, J = 10.3, 2.3 Hz, 1H), 7.55 (d, J = 1.7 Hz, 1H), 7.21-7.11 (m, 2H), 6.37 (s, 3H), 5.42-5.30 (m, 2H), 4.01 (d, J = 15.8 Hz, 1H), 3.90 (s, 3H), 1.73 (d, J = 6.2 Hz, 3H).<br>LCMS Method C; $t_R$: 0.93 min; m/z: 416 [M + H] |
| Example 14 | 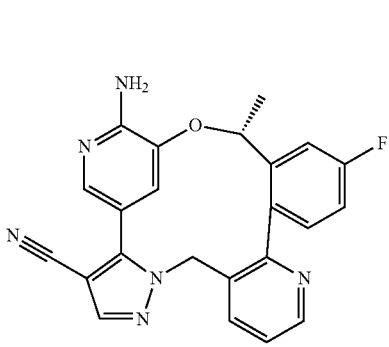 [SMILES: C[C@H]1Oc2cc(cnc2N)-c2c(C#N)cnn2Cc2cccnc2-c2ccc(F)cc21] | (20R)-23-amino-17-fluoro-20-methyl-21-oxa-5,6,12,24-tetraazapentacyclo[20.3.1.0²,⁶.0⁸,¹³.0¹⁴,¹⁹]hexacosa-1(25),2,4,8(13),9,11,14,16,18,22(26),23-undecaene-3-carbonitrile<br>1H NMR (400 MHz, DMSO-d6) δ 8.62 (dd, J = 4.7, 1.4 Hz, 1H), 8.18 (s, 1H), 8.05 (d, J = 7.2 Hz, 1H), 7.64 (dd, J = 10.3, 2.7 Hz, 1H), 7.58 (s, 1H), 7.49 (dd, J = 8.0, 4.7 Hz, 1H), 7.23 (dd, J = 8.5, 5.8 Hz, 1H), 7.16-7.05 (m, 1H), 6.45 (s, 2H), 6.09 (s, 1H), 5.55 (d, J = 16.1 Hz, 1H), 5.09 (d, J = 4.5 Hz, 1H), 4.49 (d, J = 16.0 Hz, 1H), 1.70 (d, J = 6.2 Hz, 3H)<br>LCMS Method C; $t_R$: 1.29 min; m/z: 413 [M + H] |
| Example 15 | 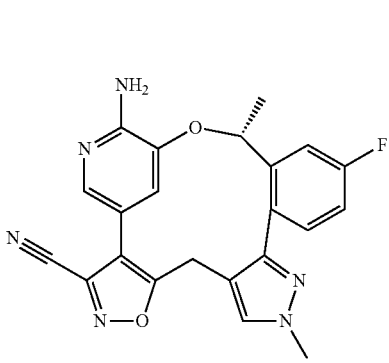 [SMILES: C[C@H]1Oc2cc(cnc2N)-c2c(C#N)noc2Cc2cn(C)nc2-c2ccc(F)cc21] | (19R)-22-amino-16-fluoro-10,19-dimethyl-5,20-dioxa-4,10,11,23-tetraazapentacyclo[19.3.1.0²,⁶.0⁸,¹².0¹³,¹⁸]pentacosa-1(24),2(6),3,8,11,13(18),14,16,21(25),22-decaene-3-carbonitrile<br>1H NMR (400 MHz, DMSO) δ 7.84 (s, 1H), 7.64 (d, J = 9.7 Hz, 1H), 7.61 (d, J = 1.8 Hz, 1H), 7.23 (d, J = 7.4 Hz, 2H), 6.31-6.16 (m, 3H), 5.26 (d, J = 4.9 Hz, 1H), 4.27 (d, J = 16.2 Hz, 1H), 3.88 (s, 3H), 3.31 (d, J = 1H), 1.73 (d, J = 6.3 Hz, 3H).<br>LCMS Method H; $t_R$: 1.06 min; m/z: 417 [M + H] |

| Example | | |
|---|---|---|
| Example 16 | 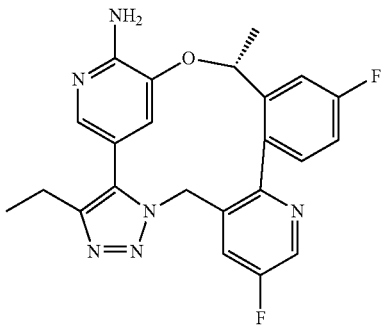 [SMILES: CCc1nnn2c1-c1cnc(N)c(c1)O[C@H](C)c1cc(F)ccc1-c1ncc(F)cc1C2] | (20R)-3-ethyl-10,17-difluoro-20-methyl-21-oxa-4,5,6,12,24-pentaazapentacyclo[20.3.1.0$^{2,6}$.0$^{8,13}$.0$^{14,19}$]hexacosa-1(25),2,4,8(13),9,11,14,16,18,22(26),23-undecaen-23-amine<br>1H NMR (400 MHz, DMSO) δ 8.72 (d, J = 2.7 Hz, 1H), 7.79-7.71 (m, 2H), 7.45 (d, J = 1.8 Hz, 1H), 7.30 (dd, J = 8.6, 5.8 Hz, 1H), 7.22-7.16 (m, 1H), 6.28 (s, 2H), 6.12 (s, 1H), 5.85 (d, J = 16.2 Hz, 1H), 5.24-5.15 (m, 1H), 4.53 (d, J = 15.6 Hz, 1H), 2.62 (q, J = 7.5 Hz, 2H), 1.73 (d, J = 6.1 Hz, 3H), 1.18 (t, J = 7.5 Hz, 3H).<br>LCMS Method F; t$_R$: 1.06 min; m/z: 435 [M + H] |
| Example 17 | 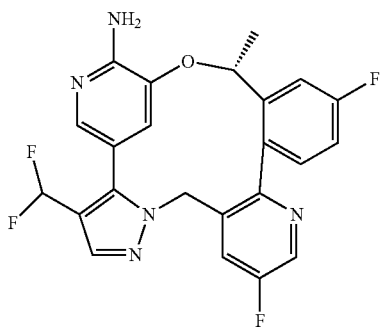 [SMILES: C[C@H]1Oc2cc(cnc2N)-c2c(C(F)F)cnn2Cc2cc(F)cnc2-c2ccc(F)cc21] | (20R)-3-(difluoromethyl)-10,17-difluoro-20-methyl-21-oxa-5,6,12,24-tetraazapentacyclo[20.3.1.0$^{2,6}$.0$^{8,13}$.0$^{14,19}$]hexacosa-1(25),2,4,8(13),9,11,14,16,18,22(26),23-undecaen-23-amine<br>1H NMR (400 MHz, DMSO) δ 8.70 (d, J = 2.8 Hz, 1H), 7.94 (s, 1H), 7.91 (dd, J = 9.6, 2.6 Hz, 1H), 7.76 (dd, J = 10.4, 2.7 Hz, 1H), 7.45 (d, J = 1.7 Hz, 1H), 7.27 (dd, J = 8.5, 5.8 Hz, 1H), 7.18 (td, J = 8.4, 2.7 Hz, 1H), 7.04-6.71 (m, 1H), 6.36 (s, 2H), 6.21 (s, 1H), 5.54 (d, J = 16.1 Hz, 1H), 5.22 (d, J = 8.0 Hz, 1H), 4.49 (d, J = 16.3 Hz, 1H), 1.74 (d, J = 6.2 Hz, 3H).<br>LCMS Method F; t$_R$: 1.34 min; m/z: 456 [M + H] |
| Example 18 | 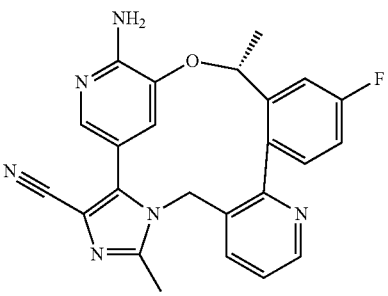 [SMILES: Cc1nc(C#N)c2n1Cc1cccnc1-c1ccc(F)cc1[C@@H](C)Oc1cc-2cnc1N] | (20R)-23-amino-17-fluoro-5,20-dimethyl-21-oxa-4,6,12,24-tetraazapentacyclo[20.3.1.0$^{2,6}$.0$^{8,13}$.0$^{14,19}$]hexacosa-1(25),2,4,8(13),9,11,14,16,18,22(26),23-undecaene-3-carbonitrile<br>1H NMR (400 MHz, DMSO-d6) δ 8.71 (d, J = 4.4 Hz, 1H), 7.68 (s, 2H), 7.56 (t, J = 2.9 Hz, 2H), 7.38 (dd, J = 8.6, 5.7 Hz, 1H), 7.27-7.18 (m, 1H), 6.40 (s, 2H), 6.07 (s, 1H), 5.50 (d, J = 16.7 Hz, 1H), 5.03 (s, 1H), 4.23 (d, J = 17.2 Hz, 1H), 2.64 (s, 3H), 1.74 (d, J = 6.2 Hz, 3H).<br>LCMS Method F; t$_R$: 0.88 min; m/z: 427 [M + H] |
| Example 19 | 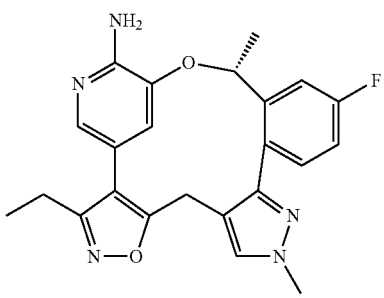 | (19R)-3-ethyl-16-fluoro-10,19-dimethyl-5,20-dioxa-4,10,11,23-tetraazapentacyclo[19.3.1.0$^{2,6}$.0$^{8,12}$.0$^{13,18}$]pentacosa-1(24),2(6),3,8,11,13,15,17,21(25),22-decaen-22-amine<br>1H NMR (400 MHz, DMSO) δ 7.76 (s, 1H), 7.67 (d, J = 10.2 Hz, 1H), 7.44 (s, 1H), 7.19 (d, J = 7.1 Hz, 2H), 6.21 (s, 1H), 5.94 (s, 2H), 5.28 (d, J = 4.6 Hz, 1H), 3.98 (d, J = 16.0 Hz, 1H), 3.89-3.83 (m, 3H), 3.15 (d, J = 15.7 Hz, 1H), 2.78-2.64 (m, 1H), 2.63-2.54 (m, 1H), 1.71 (d, J = 6.3 Hz, 3H), 1.11 (t, J = 7.5 Hz, 3H).<br>LCMS Method F; t$_R$: 0.70 min; m/z: 420 [M + H] |
| Example 20 | 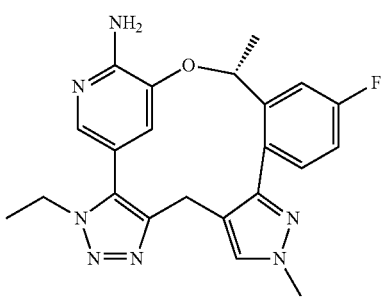 [SMILES: CCn1nnc2c1-c1cnc(N)c(c1)O[C@H](C)c1cc(F)ccc1-c1nn(C)cc1C2] | (19R)-3-ethyl-16-fluoro-10,19-dimethyl-20-oxa-3,4,5,10,11,23-hexaazapentacyclo[19.3.1.0$^{2,6}$.0$^{8,12}$.0$^{13,18}$]pentacosa-1(24),2(6),4,8,11,13,15,17,21(25),22-decaen-22-amine<br>1H NMR (400 MHz, DMSO-d6) δ 7.68 (dd, J = 10.3, 2.5 Hz, 1H), 7.60 (s, 1H), 7.54 (d, J = 1.9 Hz, 1H), 7.24-7.14 (m, 2H), 6.25 (d, J = 1.9 Hz, 1H), 6.22 (s, 2H), 5.36 - 5.28 (m, 1H), 4.29 (qd, J = 7.1, 4.0 Hz, 2H), 3.93 (d, J = 15.6 Hz, 1H), 3.85 (s, 3H), 2.96 (d, J = 15.4 Hz, 1H), 1.72 (d, J = 6.2 Hz, 3H), 1.34 (t, J = 7.3 Hz, 3H).<br>LCMS Method G; t$_R$: 2.25 min; m/z: 420 [M + H] |

| Example 21 | 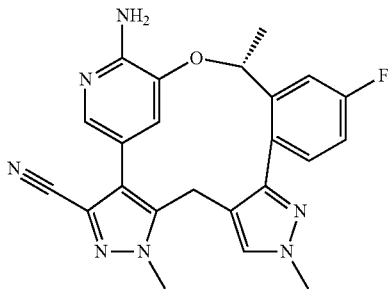 [SMILES: C[C@H]1Oc2cc(cnc2N)-c2c(C#N)nn(C)c2Cc2cn(C)nc2-c2ccc(F)cc21] | (19R)-22-amino-16-fluoro-5,10,19-trimethyl-20-oxa-4,5,10,11,23-pentaazapentacyclo[19.3.1.0$^{2,6}$.0$^{8,12}$.0$^{13,18}$]pentacosa-1(24),2(6),3,8,11,13,15,17,21(25),22-decaene-3-carbonitrile<br>1H NMR (400 MHz, DMSO-d6) δ 7.89 (s, 1H), 7.66 (dd, J = 9.8, 1.3 Hz, 1H), 7.50 (d, J = 1.8 Hz, 1H), 7.25-7.17 (m, 2H), 6.27 (d, J = 2.0 Hz, 1H), 6.04 (s, 2H), 5.29-5.18 (m, 1H), 4.14 (s, 3H), 4.04 (d, J = 16.5 Hz, 1H), 3.88 (s, 3H), 3.03 (d, J = 16.4 Hz, 1H), 1.72 (d, J = 6.2 Hz, 3H).<br>LCMS Method G; $t_R$: 2.88 min; m/z: 430 [M + H] |
|---|---|---|
| Example 22 | 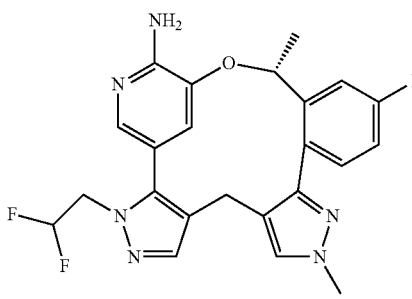 | (19R)-3-(2,2-difluoroethyl)-16-fluoro-10,19-dimethyl-20-oxa-3,4,10,11,23-pentaazapentacyclo[19.3.1.0$^{2,6}$.0$^{8,12}$.0$^{13,18}$]pentacosa-1(24),2(6),4,8,11,13,15,17,21(25),22-decaen-22-amine<br>1H NMR (400 MHz, DMSO) δ 7.70 (d, J = 8.2 Hz, 2H), 7.60 (s, 1H), 7.45 (d, J = 1.7 Hz, 1H), 7.18-7.09 (m, 2H), 6.41 (dt, J = 55.3, 4.1 Hz, 1H), 6.27 (d, J = 1.5 Hz, 1H), 6.23-6.11 (m, 2H), 5.42-5.24 (m, 1H), 4.56-4.31 (m, 2H), 3.86 (s, 3H), 3.62 (d, J = 15.6 Hz, 1H), 2.72 (d, J = 14.5 Hz, 1H), 1.71 (d, J = 6.2 Hz, 3H).<br>LCMS Method F; $t_R$: 0.89 min; m/z: 455 [M + H] |
| Example 23 | 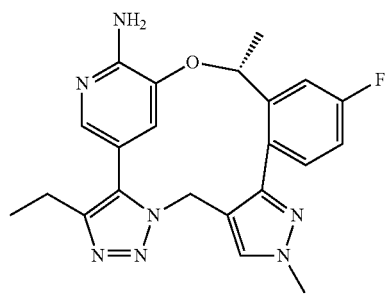 [SMILES: CCc1nnn2c1-c1cnc(N)c(c1)O[C@H](C)c1cc(F)ccc1-c1nn(C)cc1C2] | (19R)-3-ethyl-16-fluoro-10,19-dimethyl-20-oxa-4,5,6,10,11,23-hexaazapentacyclo[19.3.1.0$^{2,6}$.0$^{8,12}$.0$^{13,18}$]pentacosa-1(24),2,4,8,11,13,15,17,21(25),22-decaen-22-amine<br>1H NMR (400 MHz, DMSO-d6) δ 7.82 (s, 1H), 7.73 (d, J = 10.6 Hz, 1H), 7.41 (s, 1H), 7.22-7.17 (m, 2H), 6.31 (s, 1H), 6.21 (s, 2H), 5.62 (d, J = 15.7 Hz, 1H), 5.38 (d, J = 6.5 Hz, 1H), 4.26 (d, J = 15.7 Hz, 1H), 3.88 (s, 3H), 2.56 (dd, J = 7.6, 2.7 Hz, 2H), 1.72 (d, J = 6.2 Hz, 3H), 1.14 (t, J = 7.5 Hz, 3H).<br>LCMS Method F; $t_R$: 0.65 min; m/z: 420 [M + H] |
| Example 24 | 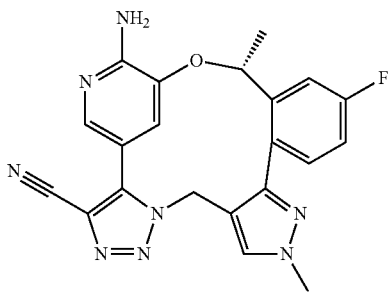 [SMILES: C[C@H]1Oc2cc(cnc2N)-c2c(C#N)nnn2Cc2cn(C)nc2-c2ccc(F)cc21] | (19R)-22-amino-16-fluoro-10,19-dimethyl-20-oxa-4,5,6,10,11,23-hexaazapentacyclo[19.3.1.0$^{2,6}$.0$^{8,12}$.0$^{13,18}$]pentacosa-1(24),2,4,8,11,13,15,17,21(25),22-decaene-3-carbonitrile<br>1H NMR (400 MHz, DMSO) δ 7.92 (s, 1H), 7.70 (dd, J = 10.3, 2.3 Hz, 1H), 7.67 (d, J = 1.9 Hz, 1H), 7.27-7.18 (m, 2H), 6.60 (s, 2H), 6.44 (d, J = 1.8 Hz, 1H), 5.85 (d, J = 16.1 Hz, 1H), 5.40-5.32 (m, 1H), 4.43 (d, J = 15.9 Hz, 1H), 3.90 (s, 3H), 1.75 (d, J = 6.3 Hz, 3H).<br>LCMS Method F; $t_R$: 1.09 min; m/z: 417 [M + H] |
| Example 25 | 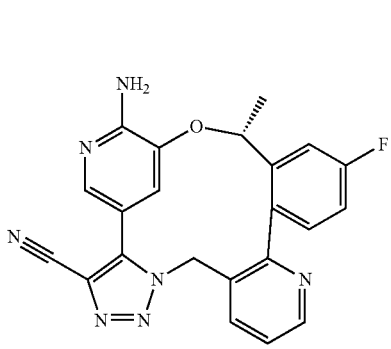 [SMILES: C[C@H]1Oc2cc(cnc2N)-c2c(C#N)nnn2Cc2cccnc2-c2ccc(F)cc21] | (20R)-23-amino-17-fluoro-20-methyl-21-oxa-4,5,6,12,24-pentaazapentacyclo[20.3.1.0$^{2,6}$.0$^{8,13}$.0$^{14,19}$]hexacosa-1(25),2,4,8(13),9,11,14,16,18,22(26),23-undecaene-3-carbonitrile<br>1H NMR (400 MHz, DMSO) δ 8.73 (d, J = 3.3 Hz, 1H), 8.00 (d, J = 7.6 Hz, 1H), 7.70 (dd, J = 9.5, 2.2 Hz, 2H), 7.59 (dd, J = 8.0, 4.7 Hz, 1H), 7.36 (dd, J = 8.5, 5.8 Hz, 1H), 7.24 (td, J = 8.4, 2.6 Hz, 1H), 6.68 (s, 2H), 6.17 (s, 1H), 6.08 (d, J = 15.9 Hz, 1H), 5.15 (d, J = 4.1 Hz, 1H), 4.70 (d, J = 16.1 Hz, 1H), 1.78 (d, J = 6.2 Hz, 3H).<br>LCMS Method 1; $t_R$: 1.16 min; m/z: 414 [M + H] |

-continued

| Example 26 | 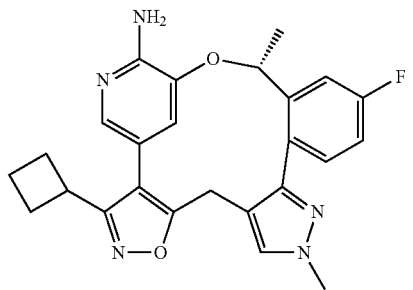 [SMILES: C[C@H]1Oc2cc(cnc2N)-c2c(C3CCC3)noc2Cc2cn(C)nc2-c2ccc(F)cc21] | (19R)-3-cyclobutyl-16-fluoro-10,19-dimethyl-5,20-dioxa-4,10,11,23-tetraazapentacyclo[19.3.1.0$^{2,6}$.0$^{8,12}$.0$^{13,18}$]pentacosa-1(24),2(6),3,8,11,13,15,17,21(25),22-decaen-22-amine<br>1H NMR (400 MHz, DMSO) δ 7.76 (s, 1H), 7.65 (d, J = 10.1 Hz, 1H), 7.30 (s, 1H), 7.19 (d, J = 7.1 Hz, 2H), 6.20 (s, 1H), 5.92 (s, 2H), 5.26 (q, J = 8.0 Hz, 1H), 3.98 (d, J = 15.7 Hz, 1H), 3.88 (s, 3H), 3.14 (d, J = 15.8 Hz, 1H), 2.40-2.28 (m, 2H), 2.28-2.18 (m, 1H), 2.14-2.02 (m, 2H), 1.97 (dd, J = 19.4, 7.2 Hz, 1H), 1.82 (qd, J = 12.2, 8.8 Hz, 1H), 1.71 (d, J = 6.3 Hz, 3H).<br>LCMS Method F; t$_R$: 0.83 min; m/z: 446 [M + H] |
| --- | --- | --- |
| Example 27 | 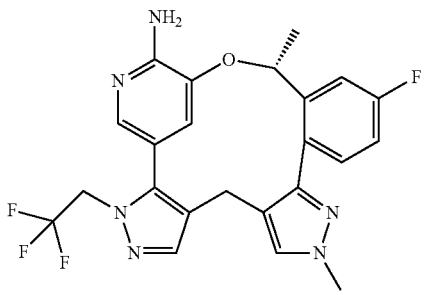 [SMILES: C[C@H]1Oc2cc(cnc2N)-c2c(cnn2CC(F)(F)F)Cc2cn(C)nc2-c2ccc(F)cc21] | (19R)-16-fluoro-10,19-dimethyl-3-(2,2,2-trifluoroethyl)-20-oxa-3,4,10,11,23-pentaazapentacyclo[19.3.1.0$^{2,6}$.0$^{8,12}$.0$^{13,18}$]pentacosa-1(24),2(6),4,8,11,13,15,17,21(25),22-decaen-22-amine<br>1H NMR (400 MHz, DMSO) δ 7.76 (s, 1H), 7.70 (d, J = 9.9 Hz, 1H), 7.62 (s, 1H), 7.45 (d, J = 1.6 Hz, 1H), 7.14 (d, J = 7.2 Hz, 2H), 6.24 (s, 1H), 6.17 (s, 2H), 5.32 (d, J = 4.6 Hz, 1H), 4.98 (dt, J = 17.4, 8.7 Hz, 1H), 4.88-4.75 (m, 1H), 3.85 (s, 3H), 3.62 (d, J = 15.4 Hz, 1H), 2.71 (d, J = 15.4 Hz, 1H), 1.71 (d, J = 6.2 Hz, 3H).<br>LCMS Method F; t$_R$: 0.76 min; m/z: 473 [M + H] |
| Example 28 | 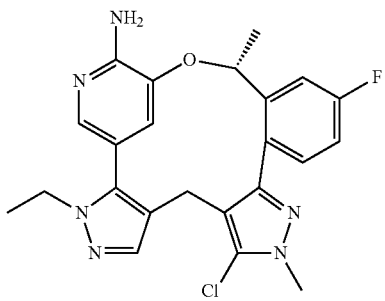 [SMILES: CCn1ncc2c1-c1cnc(N)c(c1)O[C@H](C)c1cc(F)ccc1-c1nn(C)c(Cl)c1C2] | (19R)-9-chloro-3-ethyl-16-fluoro-10,19-dimethyl-20-oxa-3,4,10,11,23-pentaazapentacyclo[19.3.1.0$^{2,6}$.0$^{8,12}$.0$^{13,18}$]pentacosa-1(24),2(6),4,8,11,13,15,17,21(25),22-decaen-22-amine<br>1H NMR (400 MHz, DMSO) δ 7.72 (d, J = 10.1 Hz, 1H), 7.60 (s, 1H), 7.39 (d, J = 1.8 Hz, 1H), 7.16-7.11 (m, 2H), 6.35 (d, J = 1.7 Hz, 1H), 6.09 (s, 2H), 5.47 (dd, J = 6.4, 1.8 Hz, 1H), 3.98 (q, J = 7.1 Hz, 2H), 3.81 (s, 3H), 3.63 (d, J = 15.7 Hz, 1H), 2.91 (d, J = 15.7 Hz, 1H), 1.72 (d, J = 6.2 Hz, 3H), 1.26 (t, J = 7.2 Hz, 3H).<br>LCMS Method F; t$_R$: 0.66 min; m/z: 453 [M + H] |
| Example 29 | 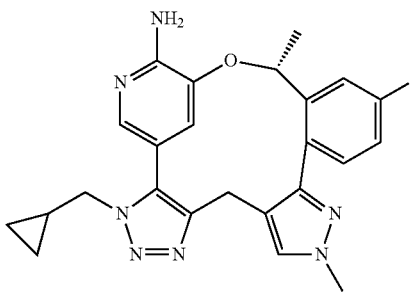 | (19R)-3-(cyclopropylmethyl)-16-fluoro-10,19-dimethyl-20-oxa-3,4,5,10,11,23-hexaazapentacyclo[19.3.1.0$^{2,6}$.0$^{8,12}$.0$^{13,18}$]pentacosa-1(24),2(6),4,8,11,13,15,17,21(25),22-decaen-22-amine<br>1H NMR (400 MHz, DMSO-d6) δ 7.68 (dd, J = 10.4, 2.5 Hz, 1H), 7.62 (s, 1H), 7.56 (d, J = 1.8 Hz, 1H), 7.22-7.13 (m, 2H), 6.24 (d, J = 1.8 Hz, 1H), 6.21 (s, 2H), 5.32 (qd, J = 6.3, 2.1 Hz, 1H), 4.15 (qd, J = 14.5, 7.0 Hz, 2H), 3.91 (d, J = 15.5 Hz, 1H), 3.85 (s, 3H), 2.96 (d, J = 15.4 Hz, 1H), 1.71 (d, J = 6.2 Hz, 3H), 1.11 (ddt, J = 10.5, 7.5, 3.8 Hz, 1H), 0.49-0.38 (m, 2H), 0.33-0.26 (m, 1H), 0.16 (dq, J = 9.7, 4.6 Hz, 1H).<br>LCMS Method F; t$_R$: 1.12 min; m/z: 446 [M + H] |
| Example 30 | 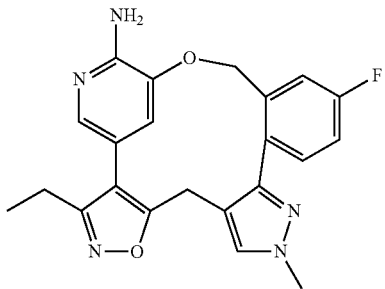 [SMILES: CCc1noc2c1-c1cnc(N)c(c1)OCc1cc(F)ccc1-c1nn(C)cc1C2] | 3-ethyl-16-fluoro-10-methyl-5,20-dioxa-4,10,11,23-tetraazapentacyclo[19.3.1.0$^{2,6}$.0$^{8,12}$.0$^{13,18}$]pentacosa-1(24),2(6),3,8,11,13,15,17,21(25),22-decaen-22-amine<br>1H NMR (400 MHz, CDCl3) δ 7.51 (d, J = 1.2 Hz, 1H), 7.46 (s, 1H), 7.37 (dd, J = 9.3, 2.4 Hz, 1H), 7.16 (dd, J = 8.4, 5.7 Hz, 1H), 7.07 (td, J = 8.2, 2.5 Hz, 1H), 6.44 (s, 1H), 5.16 (q, J = 13.6 Hz, 2H), 4.93 (br s, 2H), 3.99 (d, J = 15.7 Hz, 1H), 3.94 (s, 3H), 3.40 (d, J = 15.6 Hz, 1H), 2.83-2.61 (m, 2H), 1.24 (t, J = 7.5 Hz, 3H).<br>LCMS Method F; t$_R$: 0.86 min; m/z: 406 [M + H] |

Example 31 (Method C)

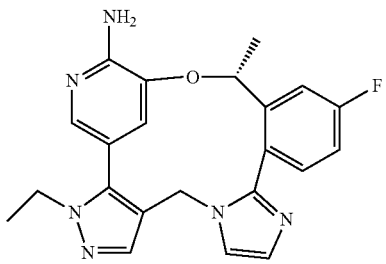 [SMILES: CCn1ncc2c1-c1cnc(N)c(c1)O[C@H](C)c1cc(F)ccc1-c1nccn1C2]

Name: (19R)-3-ethyl-16-fluoro-19-methyl-20-oxa-3,4,8,11,23-pentaazapentacyclo[19.3.1.0$^{2,6}$,0$^{8,12}$,0$^{3,18}$]pentacosa-1(24),2(6),4,9,11,13,15,17,21(25),22-decaen-22-amine NMR: 1H NMR (400 MHz, DMSO-d6) δ 7.88 (s, 1H), 7.75 (dd, J=10.4, 2.8 Hz, 1H), 7.48 (d, J=1.8 Hz, 1H), 7.38 (dd, J=8.6, 5.7 Hz, 1H), 7.26 (d, J=1.3 Hz, 1H), 7.21 (td, J=8.5, 2.9 Hz, 1H), 7.10 (d, J=1.2 Hz, 1H), 6.20 (s, 2H), 5.65 (s, 1H), 5.52 (q, J=7.4, 6.5 Hz, 1H), 5.01 (d, J=14.7 Hz, 1H), 4.19 (d, J=14.7 Hz, 1H), 4.14-3.99 (m, 2H), 1.74 (d, J=6.2 Hz, 3H), 1.28 (t, J=7.2 Hz, 3H).

LCMS: Method D; $t_R$: 2.21 min; m/z: 405 [m+H]

To a solution of 5-bromo-3-(1-(2-(1-((5-bromo-1-ethyl-1H-pyrazol-4-yl)methyl)-1H-imidazol-2-yl)-5-fluorophenyl)ethoxy)-2-nitropyridine (560 mg, 0.94 mmol) in EtOH (10 mL) and water (2.5 mL) was added iron powder (263 mg, 4.71 mmol) and NH$_4$Cl (504 mg, 9.42 mmol). The resulting mixture was stirred at 75° C. for 3 h. The reaction mixture was concentrated in vacuo, and the residue was purified by column chromatography (silica gel, 0→50% EtOAc in PE) to give 5-bromo-3-(1-(2-(1-((5-bromo-1-ethyl-1H-pyrazol-4-yl)methyl)-1H-imidazol-2-yl)-5-fluorophenyl)ethoxy)pyridin-2-amine (421 mg, 79% yield) as a brown solid. LC/MS ESI (m/z): 563 [M+H]$^+$.

To a solution of 5-bromo-3-(1-(2-(1-((5-bromo-1-ethyl-1H-pyrazol-4-yl)methyl)-1H-imidazol-2-yl)-5-fluorophenyl)ethoxy)pyridin-2-amine (338 mg, 0.600 mmol), 4,4,5,5-tetramethyl-2-(tetramethyl-1,3,2-dioxaborolan-2-yl)-1,3,2-dioxaborolane (456 mg, 1.80 mmol), Pd(OAc)$_2$ (27 mg, 0.12 mmol) and cataCXium A (54 mg, 0.15 mmol) in MeOH (10 mL) was added a solution of aq. NaOH (2.0 M, 0.60 mL, 1.2 mmol). The mixture was thrice degassed with N$_2$, and then stirred at 75° C. for 3 h. After cooling to r.t., the mixture was filtered, and the filtrate was concentrated in vacuo. The residue was diluted with EA, washed with water and brine, dried over anhydrous sodium sulfate, filtered, and concentrated in vacuo. The residue was purified by column chromatography (silica gel, 0→90% EtOAc in PE) to give the racemic product as a white solid. This was further purified by chiral SFC (ChiralCel OJ 21.2 mm×250 mm 5 m, 20% MeOH+0.1% aq. NH$_3$ in CO$_2$, eutomer $t_R$: 4.90 min, distomer $t_R$: 4.68 min) to obtain the eutomer as a white solid (25 mg, yield: 10%). LC/MS ESI (m/z): 405 [M+H]$^+$.

The following compounds were prepared in a similar manner:

Example 32

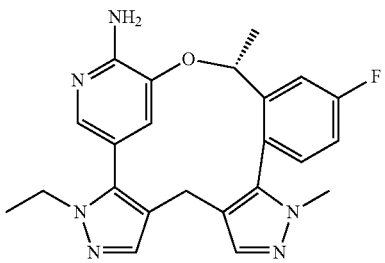 [SMILES: CCn1ncc2c1-c1cnc(N)c(c1)O[C@H](C)c1cc(F)ccc1-c1c(cnn1C)C2]

(19R)-3-ethyl-16-fluoro-11,19-dimethyl-20-oxa-3,4,10,11,23-pentaazapentacyclo[19.3.1.0$^{2,6}$,0$^{8,12}$,0$^{13,18}$]pentacosa-1(24),2(6),4,8(12),9,13,15,17,21(25),22-decaen-22-amine
1H NMR (400 MHz, DMSO-d6) δ 7.83 (dd, J = 10.3, 2.8 Hz, 1H), 7.63 (s, 1H), 7.47 (d, J = 1.8 Hz, 1H), 7.38 (s, 1H), 7.28-7.24 (m, 1H), 7.17 (dd, J = 8.5, 5.9 Hz, 1H), 6.48 (d, J = 1.9 Hz, 1H), 6.23 (s, 2H), 5.05 (dd, J = 6.4, 2.1 Hz, 1H), 4.11-4.00 (m, 2H), 3.57 (s, 3H), 3.52 (s, 1H), 2.61 (d, J = 15.4 Hz, 1H), 1.79 (d, J = 6.1 Hz, 3H), 1.26(t, J = 7.2 Hz, 3H).
LCMS Method C; $t_R$: 0.97 min; m/z: 419 [M + H]

Example 33

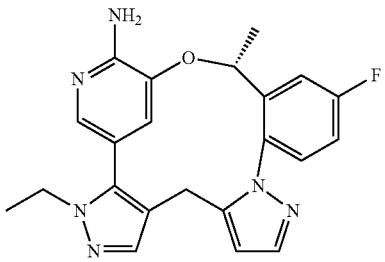 [SMILES: CCn1ncc2c1-c1cnc(N)c(c1)O[C@H](C)c1cc(F)ccc1-n1nccc1C2]

(19R)-3-ethyl-16-fluoro-19-methyl-20-oxa-3,4,11,12,23-pentaazapentacyclo[19.3.1.0$^{2,6}$,0$^{8,12}$,0$^{13,18}$]pentacosa-1(24),2(6),4,8,10,13,15,17,21(25),22-decaen-22-amine
1H NMR (400 MHz, DMSO-d6) δ 7.83 (d, J = 10.2 Hz, 1H), 7.67 (d, J = 6.1 Hz, 2H), 7.49 (d, J = 1.6 Hz, 1H), 7.39-7.34 (m, 1H), 7.27 (t, J = 7.1 Hz, 1H), 6.24 (d, J = 1.6 Hz, 1H), 6.19 (s, 2H), 6.03 (s, 1H), 5.14 (d, J = 6.9 Hz, 1H), 4.07 (t, J = 6.9 Hz, 2H), 3.91 (s, 1H), 2.92 (d, J = 16.0 Hz, 1H), 1.71 (d, J = 6.2 Hz, 3H), 1.29 (t, J = 7.2 Hz, 3H).
LCMS Method D; $t_R$: 3.35 min; m/z: 405 [M + H]

Example 34

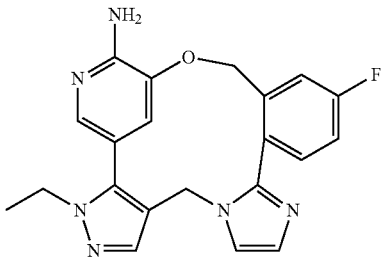 [SMILES: CCn1ncc2c1-c1cnc(N)c(c1)OCc1cc(F)ccc1-c1nccn1C2]

3-ethyl-16-fluoro-20-oxa-3,4,8,11,23-pentaazapentacyclo[19.3.1.0$^{2,6}$,0$^{8,12}$,0$^{13,18}$]pentacosa-1(24),2(6),4,9,11,13,15,17,21(25),22-decaen-22-amine
1H NMR (400 MHz, DMSO) δ 7.89 (s, 1H), 7.69 (s, 1H), 7.49 (d, J = 1.8 Hz, 1H), 7.45-7.40 (m, 1H), 7.26 (t, J = 2.4 Hz, 2H), 7.09 (d, J= 1.2 Hz, 1H), 6.21 (s, 2H), 5.63 (d, J = 1.8 Hz, 1H), 5.27 (s, 1H), 5.16 (d, J = 13.2 Hz, 1H), 5.05 (d, J = 14.7 Hz, 1H), 4.24 (d, J = 14.6 Hz, 1H), 4.08 (dd, J = 7.2, 3.3 Hz, 2H), 1.30 (t, J = 7.2 Hz, 3H).
LCMS Method B; $t_R$: 2.40 min; m/z: 391 [M + H]

| Example 35 | 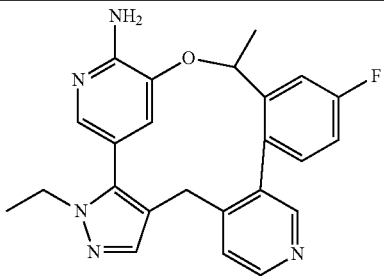 | 3-ethyl-17-fluoro-20-methyl-21-oxa-3,4,11,24-tetraazapentacyclo[20.3.1.0$^{2,6}$.0$^{8,13}$.0$^{14,19}$]hexacosa-1(25),2(6),4,8(13),9,11,14,16,18,22(26),23-undecaen-23-amine<br>1H NMR (400 MHz, DMSO) δ 8.57 (d, J = 5.2 Hz, 1H), 8.37 (s, 1H), 7.79 (s, 1H), 7.73 (dd, J = 10.4, 2.2 Hz, 1H), 7.47 (t, J = 4.1 Hz, 2H), 7.23-7.17 (m, 2H), 6.16 (s, 2H), 5.98 (d, J = 1.7 Hz, 1H), 5.13 (q, J = 6.7 Hz, 1H), 4.12-4.03 (m, 2H), 3.77 (d, J = 15.7 Hz, 1H), 3.06 (d, J = 15.6 Hz, 1H), 1.80 (d, J = 6.3 Hz, 3H), 1.28 (t, J = 7.2 Hz, 3H).<br>LCMS Method C; t$_R$: 0.96 min; m/z: 416 [M + H] |
| --- | --- | --- |
| Example 36 | 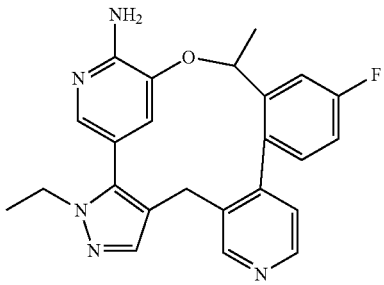 [SMILES: CCn1ncc2c1-c1cnc(N)c(c1)OC(C)c1cc(F)ccc1-c1ccncc1C2] | 3-ethyl-17-fluoro-20-methyl-21-oxa-3,4,10,24-tetraazapentacyclo[20.3.1.0$^{2,6}$.0$^{8,13}$.0$^{14,19}$]hexacosa-1(25),2(6),4,8(13),9,11,14,16,18,22(26),23-undecaen-23-amine<br>1H NMR (400 MHz, DMSO) δ 8.71 (s, 1H), 8.47 (d, J = 4.9 Hz, 1H), 7.83 (s, 1H), 7.72 (d, J = 9.8 Hz, 1H), 7.47 (d, J = 1.8 Hz, 1H), 7.26-7.14 (m, 3H), 6.15 (s, 2H), 6.06 (d, J = 1.5 Hz, 1H), 5.21-5.11 (m, 1H), 4.07 (m, 2H), 3.83 (d, J = 15.7 Hz, 1H), 3.05 (d, J = 15.6 Hz, 1H), 1.79 (d, J = 6.2 Hz, 3H), 1.28 (t, J = 7.2 Hz, 3H).<br>LCMS Method C; t$_R$: 0.80 min; m/z: 416 [M + H] |
| Example 37 | 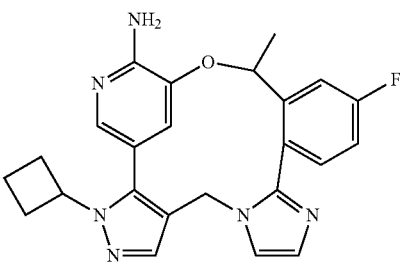 [SMILES: CC1Oc2cc(cnc2N)-c2c(cnn2C2CCC2)Cn2ccnc2-c2ccc(F)cc21] | 3-cyclobutyl-16-fluoro-19-methyl-20-oxa-3,4,8,11,23-pentaazapentacyclo[19.3.1.0$^{2,6}$.0$^{8,12}$.0$^{13,18}$]pentacosa-1(24),2(6),4,9,11,13,15,17,21(25),22-decaen-22-amine<br>1H NMR (400 MHz, DMSO-d6) δ 7.92 (s, 1H), 7.75 (dd, J = 10.3, 2.8 Hz, 1H), 7.38 (dd, J = 8.5, 5.7 Hz, 1H), 7.35 (d, J = 1.8 Hz, 1H), 7.26 (d, J = 1.3 Hz, 1H), 7.21 (td, J = 8.4, 2.8 Hz, 1H), 7.09 (d, J = 1.2 Hz, 1H), 6.21 (s, 2H), 5.63 (d, J = 1.8 Hz, 1H), 5.57-5.48 (m, 1H), 5.02 (d, J = 14.8 Hz, 1H), 4.78 (p, J = 8.3 Hz, 1H), 4.18 (d, J = 14.7 Hz, 1H), 2.65 (p, J = 10.2 Hz, 1H), 2.48-2.36 (m, 2H), 2.16-2.03 (m, 1H), 1.80-1.65(m, 5H).<br>LCMS Method D; t$_R$: 2.67 min; m/z: 431 [M + H] |
| Example 38 | 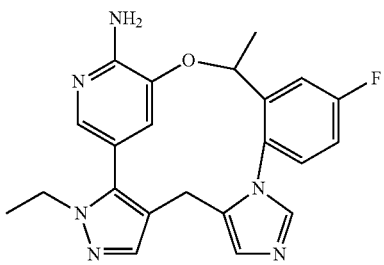 [SMILES: CCn1ncc2c1-c1cnc(N)c(c1)OC(C)c1cc(F)ccc1-n1cncc1C2] | 3-ethyl-16-fluoro-19-methyl-20-oxa-3,4,10,12,23-pentaazapentacyclo[19.3.1.0$^{2,6}$.0$^{8,12}$.0$^{13,18}$]pentacosa-1(24),2(6),4,8,10,13,15,17,21(25),22-decaen-22-amine<br>1H NMR (400 MHz, DMSO) δ 7.86-7.81 (m, 2H), 7.65 (s, 1H), 7.50 (s, 1H), 7.41-7.28 (m, 2H), 6.81 (s, 1H), 6.20 (br s, 3H), 5.18-5.09 (m, 1H), 4.14-4.01 (m, 2H), 3.77 (d, J = 16.7 Hz, 1H), 2.73 (d, J = 16.2 Hz, 1H), 1.78 (d, J = 6.3 Hz, 3H), 1.29 (t, J = 7.2 Hz, 3H).<br>LCMS Method D; t$_R$: 1.94 min; m/z: 405 [M + H] |
| Example 39 | 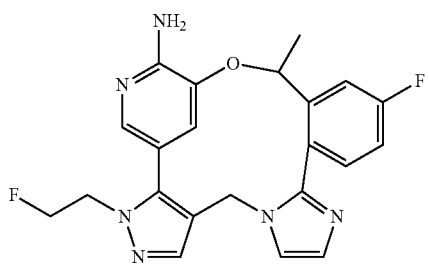 [SMILES: CC1Oc2cc(cnc2N)-c2c(cnn2CCF)Cn2ccnc2-c2ccc(F)cc21] | 16-fluoro-3-(2-fluoroethyl)-19-methyl-20-oxa-3,4,8,11,23-pentaazapentacyclo[19.3.1.0$^{2,6}$.0$^{8,12}$.0$^{13,18}$]pentacosa-1(24),2(6),4,9,11,13,15,17,21(25),22-decaen-22-amine<br>1H NMR (400 MHz, DMSO) δ 7.97 (s, 1H), 7.79-7.72 (m, 1H), 7.49 (d, J = 1.6 Hz, 1H), 7.38 (dd, J = 8.6, 5.7 Hz, 1H), 7.28 (d, J = 1.2 Hz, 1H), 7.24-7.19 (m, 1H), 7.11 (d, J = 1.2 Hz, 1H), 6.22 (s, 2H), 5.66 (s, 1H), 5.51 (s, 1H), 5.04 (d, J = 14.8 Hz, 1H), 4.81 (ddd, J = 31.2, 18.1, 4.4 Hz, 2H), 4.40-4.35 (m, 2H), 4.22 (s, 1H), 1.75 (d, J = 6.3 Hz, 3H).<br>LCMS Method C; t$_R$: 1.16 min; m/z: 423 [M + H] |
| Example 40 | 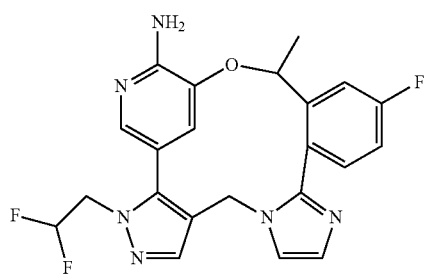 [SMILES: CC1Oc2cc(cnc2N)-c2c(cnn2CC(F)F)Cn2ccnc2-c2ccc(F)cc21] | 3-(2,2-difluoroethyl)-16-fluoro-19-methyl-20-oxa-3,4,8,11,23-pentaazapentacyclo[19.3.1.0$^{2,6}$.0$^{8,12}$.0$^{13,18}$]pentacosa-1(24),2(6),4,9,11,13,15,17,21(25),22-decaen-22-amine<br>1H NMR (400 MHz, DMSO-d6) δ 8.01 (s, 1H), 7.76 (dd, J = 10.3, 2.8 Hz, 1H), 7.50 (d, J = 1.9 Hz, 1H), 7.38 (dd, J = 8.6, 5.7 Hz, 1H), 7.28 (d, J = 1.3 Hz, 1H), 7.22 (td, J = 8.5, 2.8 Hz, 1H), 7.11 (d, J = 1.3 Hz, 1H), 6.52-6.20 (m, 3H), 5.64 (d, J = 2.0 Hz, 1H), 5.58-5.47 (m, 1H), 5.04 (d, J = 14.8 Hz, 1H), 4.51 (qd, J = 14.8, 4.0 Hz, 2H), 4.21 (d, J = 14.7 Hz, 1H), 1.74 (d, J = 6.2 Hz, 3H).<br>LCMS Method D; t$_R$: 0.60 min; m/z: 441 [M + H] |

| Example 41 | 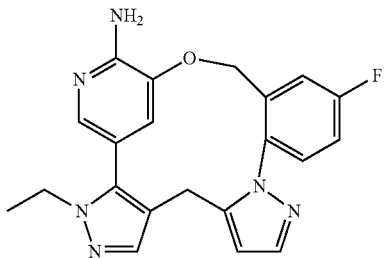 [SMILES: CCn1ncc2c1-c1cnc(N)c(c1)OCc1cc(F)ccc1-n1nccc1C2] | 3-ethyl-16-fluoro-20-oxa-3,4,11,12,23-pentaazapentacyclo[19.3.1.0$^{2,6}$.0$^{8,12}$.0$^{13,18}$]pentacosa-1(24),2(6),4,8,10,13,15,17,21(25),22-decaen-22-amine<br>1H NMR (400 MHz, DMSO-d6) δ 7.77 (dd, J = 9.4, 2.9 Hz, 1H), 7.66 (d, J = 2.3 Hz, 2H), 7.50 (d, J = 1.7 Hz, 1H), 7.40 (dd, J = 8.8, 5.2 Hz, 1H), 7.31 (td, J = 8.4, 3.0 Hz, 1H), 6.22 (d, J = 1.8 Hz, 1H), 6.19 (s, 2H), 6.00 (d, J = 1.8 Hz, 1H), 5.14 (d, J = 13.5 Hz, 1H), 4.90 (d, J = 13.6 Hz, 1H), 4.07 (qd, J = 7.0, 3.7 Hz, 2H), 3.91 (d, J = 16.2 Hz, 1H), 2.95 (d, J = 16.1 Hz, 1H), 1.29 (t, J = 7.2 Hz, 3H).<br>LCMS Method D; $t_R$: 2.82 min; m/z: 391 [M + H] |
|---|---|---|
| Example 42 | 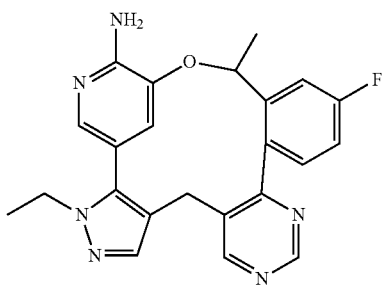 [SMILES: CCn1ncc2c1-c1cnc(N)c(c1)OC(C)c1cc(F)ccc1-c1ncncc1C2] | 3-ethyl-17-fluoro-20-methyl-21-oxa-3,4,10,12,24-pentaazapentacyclo[20.3.1.0$^{2,6}$.0$^{8,13}$.0$^{14,19}$]hexacosa-1(25),2(6),4,8(13),9,11,14,16,18,22(26),23-undecaen-23-amine<br>1H NMR (400 MHz, DMSO) δ 9.10 (s, 1H), 8.92 (s, 1H), 7.85 (s, 1H), 7.76 (dd, J = 10.4, 2.6 Hz, 1H), 7.45 (d, J = 1.8 Hz, 1H), 7.29-7.15 (m, 2H), 6.15 (s, 2H), 6.07 (d, J = 1.7 Hz, 1H), 5.37-5.23 (m, 1H), 4.13-3.98 (m, 2H), 3.93 (d, J = 15.7 Hz, 1H), 3.04 (d, J = 15.6 Hz, 1H), 1.75 (d, J = 6.2 Hz, 3H), 1.27 (t, J = 7.2 Hz, 3H).<br>LCMS Method C; $t_R$: 0.97 min; m/z: 417 [M + H] |
| Example 43 | 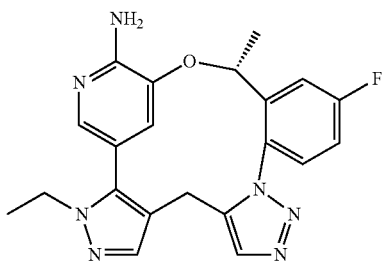 [SMILES: CCn1ncc2c1-c1cnc(N)c(c1)O[C@H](C)c1cc(F)ccc1-n1nncc1C2] | (19R)-3-ethyl-16-fluoro-19-methyl-20-oxa-3,4,10,11,12,23-hexaazapentacyclo[19.3.1.0$^{2,6}$.0$^{8,12}$.0$^{13,18}$]pentacosa-1(24),2(6),4,8,10,13,15,17,21(25),22-decaen-22-amine<br>1H NMR (400 MHz, MeOD) δ 7.79-7.75 (m, 2H), 7.72 (s, 1H), 7.48 (d, J = 1.8 Hz, 1H), 7.39 (dd, J = 8.8, 5.0 Hz, 1H), 7.28 (ddd, J = 8.8, 7.7, 2.9 Hz, 1H), 6.09 (d, J = 1.7 Hz, 1H), 5.20 (dd, J = 6.4, 1.9 Hz, 1H), 4.59 (s, 2H), 4.16 (ddt, J = 21.3, 14.1, 7.1 Hz, 2H), 4.03 (d, J = 17.2 Hz, 1H), 3.16 (d, J = 16.4 Hz, 1H), 1.83 (d, J = 6.3 Hz, 3H), 1.36 (t, J = 7.2 Hz, 3H).<br>LCMS Method C; $t_R$: 0.87 min; m/z: 406 [M + H] |
| Example 44 | 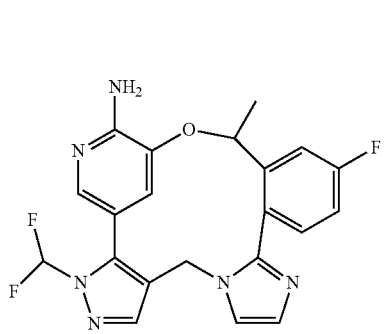 [SMILES: CC1Oc2cc(cnc2N)-c2c(cnn2C(F)F)Cn2ccnc2-c2ccc(F)cc21] | 3-(difluoromethyl)-16-fluoro-19-methyl-20-oxa-3,4,8,11,23-pentaazapentacyclo[19.3.1.0$^{2,6}$.0$^{8,12}$.0$^{13,18}$]pentacosa-1(24),2(6),4,9,11,13,15,17,21(25),22-decaen-22-amine<br>1H NMR (400 MHz, DMSO) δ 8.29 (s, 1H), 7.75 (dd, J = 10.3, 2.7 Hz, 1H), 7.68-7.66 (t, 1H), 7.42 (s, 1H), 7.39 (dd, J = 8.6, 5.8 Hz, 1H), 7.31 (d, J = 1.3 Hz, 1H), 7.23 (td, J = 8.4, 2.7 Hz, 1H), 7.13 (d, J = 1.3 Hz, 1H), 6.38 (s, 2H), 5.67 (s, 1H), 5.57-5.49 (m, 1H), 5.10 (d, J = 14.8 Hz, 1H), 4.23 (d, J = 14.7 Hz, 1H), 1.75 (d, J = 6.3 Hz, 3H).<br>LCMS Method C; $t_R$: 2.56 min; m/z: 427 [M + H] |
| Example 45 | 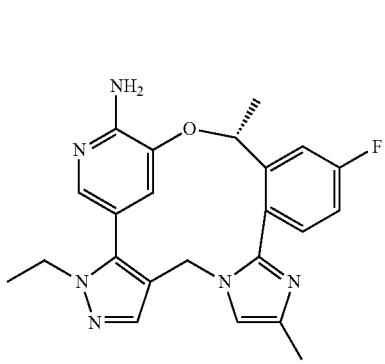 [SMILES: CCn1ncc2c1-c1cnc(N)c(c1)O[C@H](C)c1cc(F)ccc1-c1nc(C)cn1C2] | (19R)-3-ethyl-16-fluoro-10,19-dimethyl-20-oxa-3,4,8,11,23-pentaazapentacyclo[19.3.1.0$^{2,6}$.0$^{8,12}$.0$^{13,18}$]pentacosa-1(24),2(6),4,9,11,13,15,17,21(25),22-decaen-22-amine<br>1H NMR (400 MHz, DMSO-d6) δ 7.84 (s, 1H), 7.74 (dd, J = 10.4, 2.8 Hz, 1H), 7.47 (d, J = 1.8 Hz, 1H), 7.34 (dd, J = 8.6, 5.8 Hz, 1H), 7.22-7.17 (m, 1H), 6.96 (d, J = 1.2 Hz, 1H), 6.19 (s, 2H), 5.73 (s, 1H), 5.56 (d, J = 7.3 Hz, 1H), 4.93 (d, J = 14.6 Hz, 1H), 4.13-4.04 (m, 3H), 2.14 (d, J = 1.0 Hz, 3H), 1.74 (d, J = 6.2 Hz, 3H), 1.29 (t, J = 7.2 Hz, 3H).<br>LCMS Method D; $t_R$: 2.04 min; m/z: 419 [M + H] |

| Example 46 | 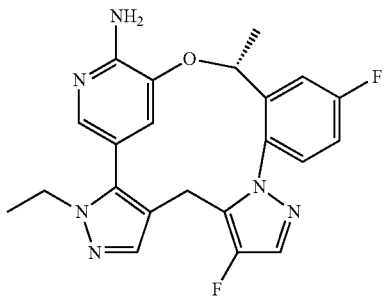 [SMILES: CCn1ncc2c1-c1cnc(N)c(c1)O[C@H](C)c1cc(F)ccc1-n1ncc(F)c1C2] | (19R)-3-ethyl-9,16-difluoro-19-methyl-20-oxa-3,4,11,12,23-pentaazapentacyclo[19.3.1.0$^{2,6}$.0$^{8,12}$.0$^{13,18}$]pentacosa-1(24),2(6),4,8,10,13,15,17,21(25),22-decaen-22-amine<br>1H NMR (400 MHz, DMSO-d6) δ 7.85 (dd, J = 9.8, 2.9 Hz, 1H), 7.79 (d, J = 3.9 Hz, 1H), 7.58 (d, J = 1.4 Hz, 1H), 7.49 (d, J = 1.8 Hz, 1H), 7.35 (dd, J = 8.7, 5.2 Hz, 1H), 7.27 (td, J = 8.4, 2.9 Hz, 1H), 6.20 (s, 2H), 6.17 (d, J = 1.9 Hz, 1H), 5.31 (q, J = 6.0 Hz, 1H), 409-3.99 (m, 3H), 2.96 (d, J = 16.3 Hz, 1H), 1.72 (d, J = 6.2 Hz, 3H), 1.29 (t, J = 7.2 Hz, 3H).<br>LCMS Method G; t$_R$: 3.35 min; m/z: 423 [M + H] |
|---|---|---|
| Example 47 | 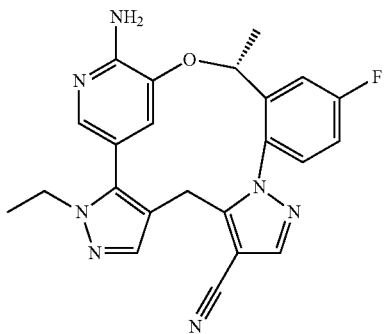 [SMILES: CCn1ncc2c1-c1cnc(N)c(c1)O[C@H](C)c1cc(F)ccc1-n1ncc(C#N)c1C2] | (19R)-22-amino-3-ethyl-16-fluoro-19-methyl-20-oxa-3,4,11,12,23-pentaazapentacyclo[19.3.1.0$^{2,6}$.0$^{8,12}$.0$^{13,18}$]pentacosa-1(24),2(6),4,8,10,13,15,17,21(25),22-decaene-9-carbonitrile<br>1H NMR (400 MHz, DMSO) δ 8.30 (s, 1H), 7.90 (dd, J = 9.8, 2.9 Hz, 1H), 7.67 (s, 1H), 7.48 (d, J = 1.8 Hz, 1H), 7.44 (dd, J = 8.8, 5.1 Hz, 1H), 7.34-7.29 (m, 1H), 6.23 (s, 2H), 6.11 (s, 1H), 5.29 (d, J = 5.4 Hz, 1H), 4.21 (d, J = 16.5 Hz, 1H), 4.12-4.02 (m, 2H), 3.12 (d, J = 16.2 Hz, 1H), 1.71 (d, J = 6.2 Hz, 3H), 1.31 (t, J = 7.2 Hz, 3H).<br>LCMS Method F; t$_R$: 0.96 min; m/z: 430 [M + H] |
| Example 48 | 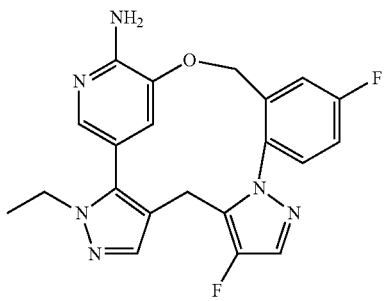 [SMILES: CCn1ncc2c1-c1cnc(N)c(c1)OCc1cc(F)ccc1-n1ncc(F)c1C2] | 3-ethyl-9,16-difluoro-20-oxa-3,4,11,12,23-pentaazapentacyclo[19.3.1.0$^{2,6}$.0$^{8,12}$.0$^{13,18}$]pentacosa-1(24),2(6),4,8,10,13,15,17,21(25),22-decaen-22-amine<br>1H NMR (400 MHz, DMSO-d6) δ 7.79 (dd, J = 9.9, 3.3 Hz, 2H), 7.59 (d, J = 1.5 Hz, 1H), 7.51 (d, J = 1.9 Hz, 1H), 7.39 (dd, J = 8.9, 5.3 Hz, 1H), 7.32 (td, J = 8.2, 2.9 Hz, 1H), 6.20 (s, 2H), 6.16 (d, J = 1.7 Hz, 1H), 5.16 (d, J = 13.5 Hz, 1H), 5.07 (d, J = 13.6 Hz, 1H), 4.13-4.00 (m, 3H), 3.00 (d, J = 16.3 Hz, 1H), 1.31 (t, J = 7.2 Hz, 3H).<br>LCMS Method G; t$_R$: 2.93 min; m/z: 409 [M + H] |
| Example 49 | 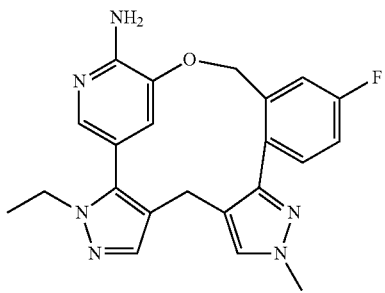 [SMILES: CCn1ncc2c1-c1cnc(N)c(c1)OCc1cc(F)ccc1-c1nn(C)cc1C2] | 3-ethyl-16-fluoro-10-methyl-20-oxa-3,4,10,11,23-pentaazapentacyclo[19.3.1.0$^{2,6}$.0$^{8,12}$.0$^{13,18}$]pentacosa-1(24),2(6),4,8,11,13,15,17,21(25),22-decaen-22-amine<br>1H NMR (400 MHz, DMSO-d6) δ 7.65 (d, J = 8.6 Hz, 1H), 7.58 (d, J = 10.7 Hz, 2H), 7.44 (d, J = 1.7 Hz, 1H), 7.18 (d, J = 7.2 Hz, 2H), 6.29 (s, 1H), 6.09 (s, 2H), 5.08 (dd, J = 28.5, 13.6 Hz, 2H), 4.02 (d, J = 7.3 Hz, 2H), 3.84 (s, 3H), 3.63-3.61 (m, 1H), 2.72 (s, 1H), 1.28 (t, J = 7.2 Hz, 3H)<br>LCMS Method F; t$_R$: 0.81 min; m/z: 405 [M + H] |
| Example 50 | 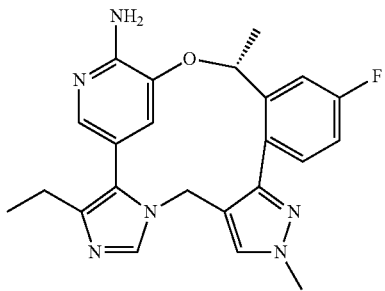 [SMILES: CCc1ncn2c1-c1cnc(N)c(c1)O[C@H](C)c1cc(F)ccc1-c1nn(C)cc1C2] | (19R)-3-ethyl-16-fluoro-10,19-dimethyl-20-oxa-4,6,10,11,23-pentaazapentacyclo[19.3.1.0$^{2,6}$.0$^{8,12}$.0$^{13,18}$]pentacosa-1(24),2,4,8,11,13,15,17,21(25),22-decaen-22-amine<br>1H NMR (300 MHz, DMSO-d6) δ 7.95 (s, 1H), 7.86 (s, 1H), 7.73 (dd, J = 10.4, 2.5 Hz, 1H), 7.30 (d, J = 1.7 Hz, 1H), 7.19-7.08 (m, 2H), 6.28 (s, 1H), 5.98 (s, 2H), 5.45-5.33 (m, 1H), 5.19 (d, J = 15.8 Hz, 1H), 3.90 (s, 3H), 3.89 (d, J = 15.7 Hz, 1H), 2.46-2.31 (m, 2H), 1.72 (d, J = 6.1 Hz, 3H), 1.09 (t, J = 7.6 Hz, 3H).<br>LCMS Method I; t$_R$: 0.99 min; m/z: 419 [M + H] |

| Example 51 | 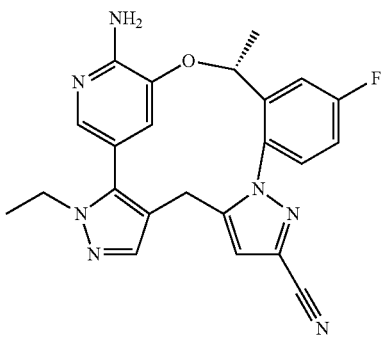 [SMILES: CCn1ncc2c1-c1cnc(N)c(c1)O[C@H](C)c1cc(F)ccc1-n1nc(C#N)cc1C2] | (19R)-22-amino-3-ethyl-16-fluoro-19-methyl-20-oxa-3,4,11,12,23-pentaazapentacyclo[19.3.1.0$^{2,6}$.0$^{8,12}$.0$^{13,18}$]pentacosa-1(24),2(6),4,8,10,13,15,17,21(25),22-decaene-10-carbonitrile<br>1H NMR (400 MHz, DMSO) δ 7.52 (s, 1H), 7.46 (d, J = 1.7 Hz, 1H), 7.14 (t, J = 8.7 Hz, 2H), 6.99-6.92 (m, 2H), 6.65 (s, 1H), 6.01 (q, J = 6.4 Hz, 1H), 5.89 (s, 2H), 4.45 (d, J = 16.8 Hz, 1H), 4.25-4.11 (m, 2H), 3.80 (d, J = 17.0 Hz, 1H), 1.99 (d, J = 6.6 Hz, 3H), 1.31 (t, J = 6.7 Hz, 3H).<br>LCMS Method H; t$_R$: 0.67 min; m/z: 430 [M + H] |
| --- | --- | --- |
| Example 52 | 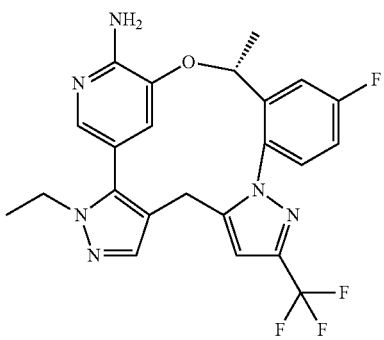 [SMILES: CCn1ncc2c1-c1cnc(N)c(c1)O[C@H](C)c1cc(F)ccc1-n1nc(C(F)(F)F)cc1C2] | (19R)-3-ethyl-16-fluoro-19-methyl-10-(trifluoromethyl)-20-oxa-3,4,11,12,23-pentaazapentacyclo[19.3.1.0$^{2,6}$.0$^{8,12}$.0$^{13,18}$]pentacosa-1(24),2(6),4,8,10,13,15,17,21(25),22-decaen-22-amine<br>1H NMR (400 MHz, DMSO) δ 7.91 (dd, J = 9.8, 2.9 Hz, 1H), 7.71 (s, 1H), 7.55-7.49 (m, 2H), 7.33 (td, J = 8.3, 2.9 Hz, 1H), 6.73 (s, 1H), 6.25 (s, 2H), 6.04 (d, J = 1.5 Hz, 1H), 5.08 (d, J = 4.9 Hz, 1H), 4.13-4.02 (m, 2H), 3.96 (d, J = 16.5 Hz, 1H), 2.93 (d, J = 16.2 Hz, 1H), 1.71 (d, J = 6.2 Hz, 3H), 1.30 (t, J = 7.2 Hz, 3H).<br>LCMS Method H; t$_R$: 1.29 min; m/z: 473 [M + H] |
| Example 53 | 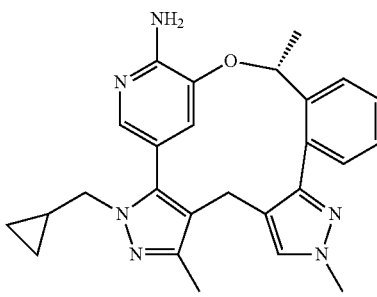 | (19R)-3-(cyclopropylmethyl)-16-fluoro-5,10,19-trimethyl-20-oxa-3,4,10,11,23-pentaazapentacyclo[19.3.1.0$^{2,6}$.0$^{8,12}$.0$^{13,18}$]pentacosa-1(24),2(6),4,8,11,13,15,17,21(25),22-decaen-22-amine<br>1H NMR (400 MHz, DMSO) δ 7.69 (d, J = 10.3 Hz, 1H), 7.62 (s, 1H), 7.42 (d, J = 1.8 Hz, 1H), 7.17-7.11 (m, 2H), 6.29 (d, J = 1.6 Hz, 1H), 6.15 (s, 2H), 5.31 (m, 1H), 3.92-3.87 (m, 1H), 3.86 (s, 3H), 3.73 (dd, J = 14.4, 7.4 Hz, 1H), 3.48 (d, J = 15.8 Hz, 1H), 2.66 (d, J = 15.6 Hz, 1H), 2.33 (s, 3H), 1.70 (d, J = 6.3 Hz, 3H), 1.08 (m, 1H), 0.47-0.31 (m, 2H), 0.22 (td, J = 9.1, 4.8 Hz, 1H), 0.05 (td, J = 9.3, 5.1 Hz, 1H).<br>LCMS Method H; t$_R$: 0.88 min; m/z: 459 [M + H] |
| Example 54 | 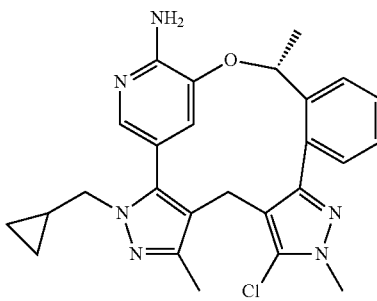 | (19R)-9-chloro-3-(cyclopropylmethyl)-16-fluoro-5,10,19-trimethyl-20-oxa-3,4,10,11,23-pentaazapentacyclo[19.3.1.0$^{2,6}$.0$^{8,12}$.0$^{13,18}$]pentacosa-1(24),2(6),4,8,11,13,15,17,21(25),22-decaen-22-amine<br>1H NMR (400 MHz, MeOD) δ 7.55 (dd, J = 10.0, 2.6 Hz, 1H), 7.37 (d, J = 1.7 Hz, 1H), 7.29 (dd, J = 8.6, 5.7 Hz, 1H), 7.15 (td, J = 8.4, 2.7 Hz, 1H), 6.88 (d, J = 1.6 Hz, 1H), 5.79-5.71 (m, 1H), 4.00 (dd, J = 14.7, 6.3 Hz, 1H), 3.95-3.86 (m, 4H), 3.71 (d, J = 16.3 Hz, 1H), 3.17-3.10 (m, 1H), 2.46 (s, 3H), 1.89 (d, J = 6.4 Hz, 3H), 1.13-1.02 (m, 1H), 0.51-0.38 (m, 2H), 0.26 (dt, J = 8.7, 5.0 Hz, 1H), 0.11-0.03 (m, 1H).<br>LCMS Method F; t$_R$: 1.14 min; m/z: 493 [M + H] |
| Example 55 | 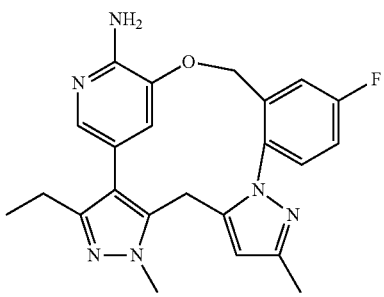 [SMILES: CCc1nn(C)c2c1-c1cnc(N)c(c1)OCc1cc(F)ccc1-n1nc(C)cc1C2] | 3-ethyl-16-fluoro-5,10-dimethyl-20-oxa-4,5,11,12,23-pentaazapentacyclo[19.3.1.0$^{2,6}$.0$^{8,12}$.0$^{13,18}$]pentacosa-1(24),2(6),3,8,10,13,15,17,21(25),22-decaen-22-amine<br>1H NMR (400 MHz, DMSO) δ 7.74 (dd, J = 9.4, 2.8 Hz, 1H), 7.41-7.35 (m, 2H), 7.35-7.28 (m, 1H), 6.13 (s, 1H), 6.01 (d, J = 1.5 Hz, 1H), 5.80 (s, 2H), 5.13 (d, J = 13.5 Hz, 1H), 4.92 (d, J = 14.1 Hz, 1H), 4.19 (d, J = 16.7 Hz, 1H), 3.96 (s, 3H), 3.13 (d, J = 16.6 Hz, 1H), 2.56 (dd, J = 15.1, 7.6 Hz, 2H), 2.22 (s, 3H), 1.12 (t, J = 7.5 Hz, 3H).<br>LCMS Method F; t$_R$: 0.45 min; m/z: 419 [M + H] |

| Example | | |
|---|---|---|
| Example 56 | 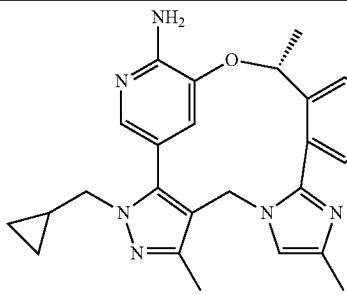 | (19R)-3-(cyclopropylmethyl)-16-fluoro-5,10,19-trimethyl-20-oxa-3,4,8,11,23-pentaazapentacyclo[19.3.1.0²,⁶.0⁸,¹².0¹³,¹⁸]pentacosa-1(24),2(6),4,9,11,13,15,17,21(25),22-decaen-22-amine<br>1H NMR (400 MHz, DMSO) δ 7.57 (s, 1H), 7.48 (s, 1H), 7.37 (d, J = 1.5 Hz, 1H), 7.15 (d, J = 9.9 Hz, 1H), 7.10-7.05 (m, 2H), 6.14 (s, 2H), 5.83 (d, J = 6.0 Hz, 1H), 4.84 (d, J = 14.8 Hz, 1H), 4.51 (d, J = 14.8 Hz, 1H), 3.42 (dd, J = 14.3, 6.1 Hz, 1H), 2.92 (dd, J = 13.9, 7.9 Hz, 1H), 2.09 (s, 3H), 2.02 (s, 3H), 1.23 (d, J = 6.1 Hz, 3H), 0.38 (s, 1H), 0.06-0.01 (m, 2H), −0.22−−0.33 (m, 2H).<br>LCMS Method K; $t_R$: 1.13 min; m/z: 459 [M + H] |
| Example 57 | | (19R)-5-(benzyloxy)-3-ethyl-16-fluoro-10,19-dimethyl-20-oxa-3,4,10,11,23-pentaazapentacyclo[19.3.1.0²,⁶.0⁸,¹².0¹³,¹⁸]pentacosa-1(24),2(6),4,8,11,13,15,17,21(25),22-decaen-22-amine<br>LCMS Method M; $t_R$: 3.35 min; m/z: 525 [M + H] |
| | 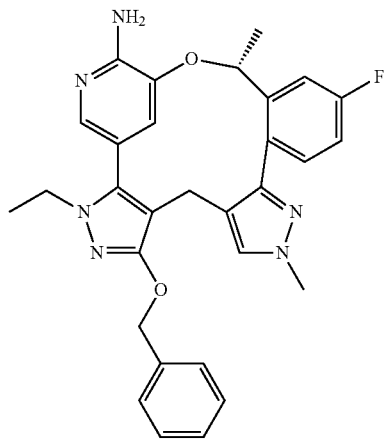 [SMILES: CCn1nc(OCc2ccccc2)c2c1-c1cnc(N)c(c1)O[C@H](C)c1cc(F)ccc1-c1nn(C)cc1C2] | |

Example 58 (Method D)

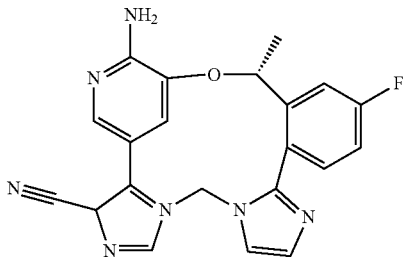

Name: (19R)-22-amino-16-fluoro-19-methyl-20-oxa-4,6,11,12,23-pentaazapentacyclo[19.3.1.0²,⁶,0⁸,¹²,0³,¹⁸]pentacosa-1(24),2,4,8,10,13,15,17,21(25),22-decaene-3-carbonitrile NMR: 1H NMR (400 MHz, DMSO) δ 8.35 (s, 1H), 7.89-7.76 (m, 2H), 7.60 (d, J=1.7 Hz, 1H), 7.41 (dd, J=8.7, 5.2 Hz, 1H), 7.35-7.26 (m, 1H), 6.58 (s, 1H), 6.46 (br s, 2H), 6.02 (s, 1H), 5.63 (d, J=16.7 Hz, 1H), 5.28-5.17 (m, 1H), 4.27 (d, J=16.7 Hz, 1H), 1.74 (d, J=6.1 Hz, 3H).

LCMS: Method C; $t_R$: 1.04 min; m/z: 402 [M+H]⁺.

To a solution of 1-{[1-(2-{1-[(5-bromo-2-nitropyridin-3-yl)oxy]ethyl}-4-fluorophenyl)-1H-pyrazol-5-yl]methyl}-1H-imidazole-4-carbonitrile (140 mg, 0.27 mmol) in EtOH (6 mL) and H₂O (2 mL) was added ammonium chloride (188 mg, 3.51 mmol) and iron powder (153 mg, 3.51 mmol). The reaction was stirred at 80° C. for 1 h. The mixture was filtered, and the filtrate was concentrated in vacuo. The residue was partitioned between ice water, and EtOAc. The organic layer was separated, washed with brine, dried over anhydrous Na₂SO₄, filtered, and concentrated in vacuo. The residue was purified by flash chromatography (silica gel, 0→20% MeOH in DCM) to give 1-{[1-(2-{1-[(2-amino-5-bromopyridin-3-yl)oxy]ethyl}-4-fluorophenyl)-1H-pyrazol-5-yl]methyl}-1H-imidazole-4-carbonitrile (81 mg, yield: 61%) as a yellow solid. LC/MS (ESI) m/z: 482 [M+H]⁺.

To a solution of 1-{[1-(2-{1-[(2-amino-5-bromopyridin-3-yl)oxy]ethyl}-4-fluorophenyl)-1H-pyrazol-5-yl]methyl}-1H-imidazole-4-carbonitrile (100 mg, 0.21 mmol) in 2-methyl-2-butanol (5 mL) was added potassium acetate (122 mg, 1.24 mmol), Pd(OAc)₂ (19 mg, 0.080 mmol) and cataCXium A (31 mg, 0.080 mmol). The mixture was thrice degassed under N₂, and the reaction was stirred at 120° C. for 16 h. The mixture was diluted with water and extracted with EtOAc. The organic layer was washed with brine, dried over anhydrous Na₂SO₄, filtered, and concentrated in vacuo. The residue was purified by prep-TLC (10% MeOH in DCM) followed by chiral SFC (ChiralPak AS-H 4.6*250 mm, 4→40, MOH+0.05 DEA in CO₂ over 8.5 m) to give the target product (eutomer: $t_R$ 5.25 m=, 5.4 mg; distomer: t 1 5.85 m, 7.6 mg) as a white solid.

LC/MS (ESI) m/z: 402 [M+H]⁺.

The following compounds were prepared in a similar manner:

| Example 59 | 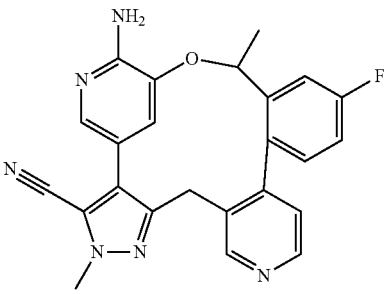 [SMILES: CC1Oc2cc(cnc2N)-c2c(nn(C)c2C#N)Cc2cnccc2-c2ccc(F)cc21] | 23-amino-17-fluoro-4,20-dimethyl-21-oxa-4,5,10,24-tetraazapentacyclo[20.3.1.0$^{2,6}$.0$^{8,13}$.0$^{14,19}$]hexacosa-1(25),2,5,8(13),9,11,14,16,18,22(26),23-undecaene-3-carbonitrile<br>1H NMR (400 MHz, DMSO-d6) δ 8.70 (s, 1H), 8.54 (d, J = 4.9 Hz, 1H), 7.67 (dd, J = 10.2, 2.7 Hz, 1H), 7.55 (d, J = 1.7 Hz, 1H), 7.36-7.17 (m, 3H), 6.14 (s, 2H), 6.06 (s, 1H), 5.11-5.02 (m, 1H), 4.13 (d, J = 15.6 Hz, 1H), 4.07 (s, 3H), 3.3 (d, 1H), 1.80 (d, J = 6.2 Hz, 3H)<br>LCMS Method A; $t_R$: 1.14 min; m/z: 427 [M + H] |
| --- | --- | --- |
| Example 60 | 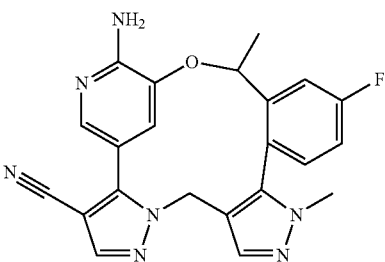 [SMILES: CC1Oc2cc(cnc2N)-c2c(C#N)cnn2Cc2cnn(C)c2-c2ccc(F)cc21] | 22-amino-16-fluoro-11,19-dimethyl-20-oxa-5,6,10,11,23-pentaazapentacyclo[19.3.1.0$^{2,6}$.0$^{8,12}$.0$^{13,18}$]pentacosa-1(24),2,4,8(12),9,13,15,17,21(25),22-decaene-3-carbonitrile<br>1H NMR (400 MHz, DMSO) δ 8.17 (s, 1H), 7.84 (dd, J = 10.3, 2.6 Hz, 1H), 7.64 (d, J = 1.6 Hz, 1H), 7.57 (s, 1H), 7.30 (td, J = 8.3, 2.6 Hz, 1H), 7.22 (dd, J = 8.5, 5.9 Hz, 1H), 6.64 (s, 1H), 6.51 (s, 2H), 5.32 (d, J = 15.9 Hz, 1H), 5.18-5.05 (m, 1H), 4.22 (d, J = 15.8 Hz, 1H), 3.62 (s, 3H), 1.81 (d, J = 6.1 Hz, 3H).<br>LCMS Method C; $t_R$: 1.17 min; m/z: 416 [M + H] |
| Example 61 | 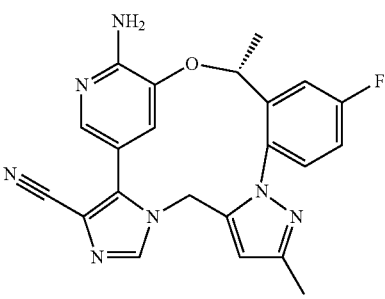 [SMILES: Cc1cc2n(n1)-c1ccc(F)cc1[C@@H](C)Oc1cc(cnc1N)-c1c(C#N)ncn1C2] | (19R)-22-amino-16-fluoro-10,19-dimethyl-20-oxa-4,6,11,12,23-pentaazapentacyclo[19.3.1.0$^{2,6}$.0$^{8,12}$.0$^{13,18}$]pentacosa-1(24),2,4,8,10,13,15,17,21(25),22-decaene-3-carbonitrile<br>1H NMR (400 MHz, DMSO) δ 8.16 (s, 1H), 7.86 (d, J = 10.0 Hz, 1H), 7.47 (d, J = 1.7 Hz, 1H), 7.35 (d, J = 6.8 Hz, 2H), 6.24 (s, 1H), 5.96 (s, 3H), 5.45 (d, J = 14.7 Hz, 1H), 5.00 (s, 1H), 4.62 (d, J = 14.5 Hz, 1H), 2.07 (s, 3H), 1.65 (d, J = 6.4 Hz, 3H).<br>LCMS Method C; $t_R$: 0.91 min; m/z: 416 [M + H] |
| Example 62 | 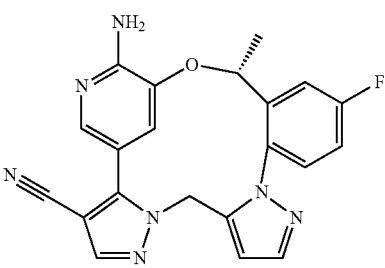 [SMILES: C[C@H]1Oc2cc(cnc2N)-c2c(C#N)cnn2Cc2ccnn2-c2ccc(F)cc21] | (19R)-22-amino-16-fluoro-19-methyl-20-oxa-5,6,11,12,23-pentaazapentacyclo[19.3.1.0$^{2,6}$.0$^{8,12}$.0$^{13,18}$]pentacosa-1(24),2,4,8,10,13,15,17,21(25),22-decaene-3-carbonitrile<br>1H NMR (400 MHz, DMSO) δ 8.22 (s, 1H), 7.86-7.81 (m, 2H), 7.66-7.63 (m, 1H), 7.50-7.44 (m, 1H), 7.36-7.27 (m, 1H), 6.58-6.55 (m, 2H), 6.46-6.44 (m, 1H), 6.08-6.06 (m, 1H), 5.70-5.64 (m, 1H), 5.31-5.14 (m, 1H), 4.55-4.49 (m, 1H), 1.75 (s, 3H).<br>LCMS Method D; $t_R$: 1.26 min; m/z: 402 [M + H] |
| Example 63 | 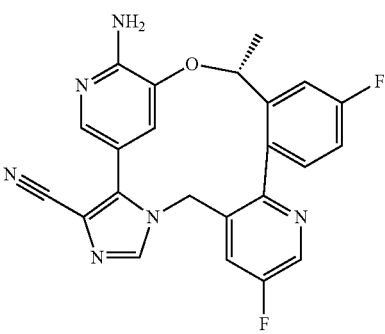 [SMILES: C[C@H]1Oc2cc(cnc2N)-c2c(C#N)ncn2Cc2cc(F)cnc2-c2ccc(F)cc21] | (20R)-23-amino-10,17-difluoro-20-methyl-21-oxa-4,6,12,24-tetraazapentacyclo[20.3.1.0$^{2,6}$.0$^{8,13}$.0$^{14,19}$]hexacosa-1(25),2,4,8,10,12,14(19),15,17,22(26),23-undecaene-3-carbonitrile<br>1H NMR (400 MHz, DMSO) δ 8.79 (d, J = 2.7 Hz, 1H), 8.53 (s, 1H), 7.96 (dd, J = 9.5, 2.6 Hz, 1H), 7.78 (dd, J = 10.3, 2.4 Hz, 1H), 7.65 (d, J = 1.9 Hz, 1H), 7.31-7.22 (m, 2H), 6.50 (s, 2H), 6.21 (d, J = 1.6 Hz, 1H), 5.61 (d, J = 16.4 Hz, 1H), 5.25 (d, J = 6.0 Hz, 1H), 4.37 (d, J = 15.7 Hz, 1H), 1.81 (d, J = 6.2 Hz, 3H).<br>LCMS Method C; $t_R$: 1.20 min; m/z: 431 [M + H] |

| | | -continued |
|---|---|---|
| Example 64 | 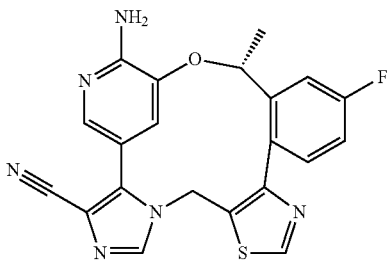 [SMILES: C[C@H]1Oc2cc(cnc2N)-c2c(C#N)ncn2Cc2scnc2-c2ccc(F)cc21] | (19R)-22-amino-16-fluoro-19-methyl-20-oxa-9-thia-4,6,11,23-tetraazapentacyclo[19.3.1.0²,⁶.0⁸,¹².0¹³,¹⁸]pentacosa-1(24),2,4,8(12),10,13(18),14,16,21(25),22-decaene-3-carbonitrile<br>1H NMR (400 MHz, DMSO) δ 9.26 (s, 1H), 8.37 (s, 1H), 7.73 (d, J = 9.8 Hz, 1H), 7.55 (s, 1H), 7.22 (s, 2H), 6.41 (s, 2H), 6.26 (s, 1H), 5.73 (d, J = 16.0 Hz, 1H), 5.14 (s, 1H), 4.49 (d, J = 16.3 Hz, 1H), 1.73 (d, J = 5.4 Hz, 3H).<br>LCMS Method C; $t_R$: 1.06 min; m/z: 419 [M + H] |
| Example 65 | 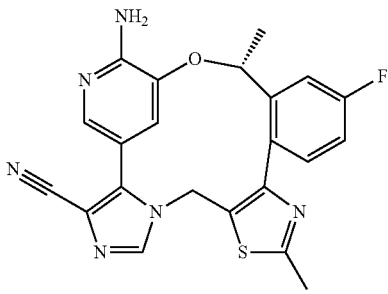 [SMILES: Cc1nc2c(s1)Cn1cnc(C#N)c1-c1cnc(N)c(c1)O[C@H](C)c1cc(F)ccc1-2] | (19R)-22-amino-16-fluoro-10,19-dimethyl-20-oxa-9-thia-4,6,11,23-tetraazapentacyclo[19.3.1.0²,⁶.0⁸,¹².0¹³,¹⁸]pentacosa-1(24),2,4,8(12),10,13(18),14,16,21(25),22-decaene-3-carbonitrile<br>1H NMR (400 MHz, DMSO) δ 8.34 (s, 1H), 7.73 (d, J = 9.6 Hz, 1H), 7.55 (d, J = 1.7 Hz, 1H), 7.20 (d, J = 7.2 Hz, 2H), 6.40 (d, J = 4.6 Hz, 3H), 5.67 (d, J = 16.1 Hz, 1H), 5.23 (d, J = 5.8 Hz, 1H), 4.42 (d, J = 16.1 Hz, 1H), 2.70 (s, 3H), 1.73 (d, J = 6.2 Hz, 3H).<br>LCMS Method C; $t_R$: 0.95 min; m/z: 433 [M + H] |
| Example 66 | 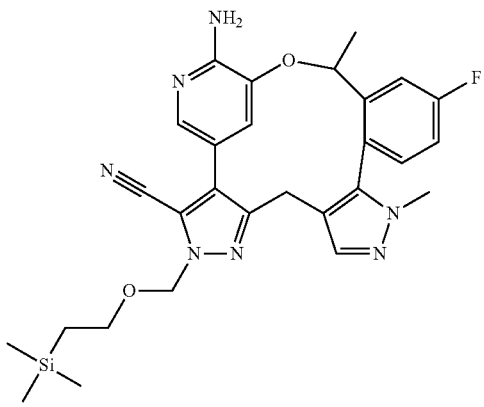 [SMILES: CC1Oc2cc(cnc2N)-c2c(nn(COCC[Si](C)(C)C)c2C#N)Cc2cnn(C)c2-c2ccc(F)cc21] | 22-amino-16-fluoro-11,19-dimethyl-4-{[2-(trimethylsilyl)ethoxy]methyl}-20-oxa-4,5,10,11,23-pentaazapentacyclo[19.3.1.0²,⁶.0⁸,¹².0¹³,¹⁸]pentacosa-1(24),2,5,8(12),9,13,15,17,21(25),22-decaene-3-carbonitrile<br>LCMS Method C; $t_R$: 1.56 min; m/z: 546 [M + H] |
| Example 67 | 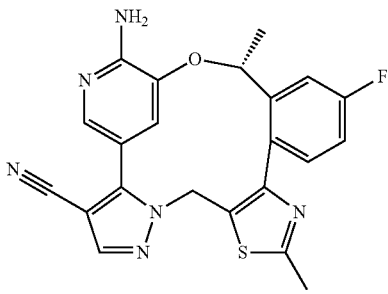 [SMILES: Cc1nc2c(s1)Cn1ncc(C#N)c1-c1cnc(N)c(c1)O[C@H](C)c1cc(F)ccc1-2] | (19R)-22-amino-16-fluoro-10,19-dimethyl-20-oxa-9-thia-5,6,11,23-tetraazapentacyclo[19.3.1.0²,⁶.0⁸,¹².0¹³,¹⁸]pentacosa-1(24),2,4,8(12),10,13,15,17,21(25),22-decaene-3-carbonitrile<br>1H NMR (400 MHz, DMSO-d6) δ 8.12 (s, 1H), 7.66 (dd, J = 10.3, 2.6 Hz, 1H), 7.55 (d, J = 1.9 Hz, 1H), 7.19-7.10 (m, 2H), 6.45-6.39 (m, 3H), 5.57 (d, J = 16.1 Hz, 1H), 5.15 (d, J = 6.4 Hz, 1H), 4.59 (d, J = 16.1 Hz, 1H), 2.62 (s, 3H), 1.67 (d, J = 6.2 Hz, 3H).<br>LCMS Method B; $t_R$: 2.53 min; m/z: 433 [M + H] |
| Example 68 | 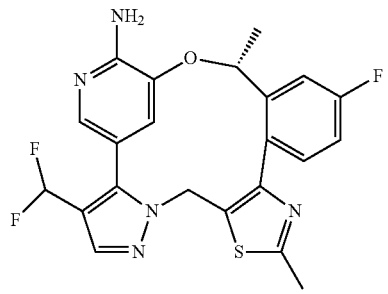 [SMILES: Cc1nc2c(s1)Cn1ncc(C(F)F)c1-c1cnc(N)c(c1)O[C@H](C)c1cc(F)ccc1-2] | (19R)-3-(difluoromethyl)-16-fluoro-10,19-dimethyl-20-oxa-9-thia-5,6,11,23-tetraazapentacyclo[19.3.1.0²,⁶.0⁸,¹².0¹³,¹⁸]pentacosa-1(24),2,4,8 (12),10,13,15,17,21(25),22-decaen-22-amine<br>1H NMR (400 MHz, DMSO) δ 7.86 (s, 1H), 7.78 (dd, J = 10.3, 2.6 Hz, 1H), 7.43 (d, J = 1.7 Hz, 1H), 7.26-7.15 (m, 2H), 6.89 (t, J = 55 Hz, 1H), 6.42 (d, J = 1.7 Hz, 1H), 6.33 (s, 2H), 5.57 (d, J = 16.0 Hz, 1H), 5.30-5.20 (m, 1H), 4.60 (d, J = 16.0 Hz, 1H), 2.68 (s, 3H), 1.73 (d, J = 6.2 Hz, 3H).<br>LCMS Method F; $t_R$: 1.24 min; m/z: 458 [M + H] |

| Example 69 | 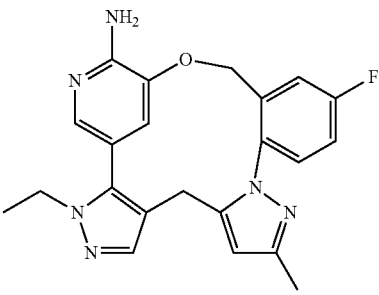 [SMILES: CCn1ncc2c1-c1cnc(N)c(c1)OCc1cc(F)ccc1-n1nc(C)cc1C2] | 3-ethyl-16-fluoro-10-methyl-20-oxa-3,4,11,12,23-pentaazapentacyclo[19.3.1.0$^{2,6}$.0$^{8,12}$.0$^{13,18}$]pentacosa-1(24),2(6),4,8,10,13,15,17,21(25),22-decaen-22-amine<br>1H NMR (400 MHz, DMSO-d6) δ 7.74 (dd, J = 9.4, 2.9 Hz, 1H), 7.64 (s, 1H), 7.50 (d, J = 1.8 Hz, 1H), 7.37-7.26 (m, 2H), 6.18 (s, 2H), 6.10 (d, J = 1.9 Hz, 1H), 6.02 (s, 1H), 5.13 (d, J = 13.5 Hz, 1H), 4.98 (d, J = 13.2 Hz, 1H), 4.07 (qd, J = 7.0, 2.9 Hz, 2H), 3.86 (d, J = 16.2 Hz, 1H), 2.89 (d, J = 16.0 Hz, 1H), 2.19 (s, 3H), 1.31 (t, J = 7.2 Hz, 3H).<br>LCMS Method H; $t_R$: 0.89 min; m/z: 405 [M + H] |
|---|---|---|
| Example 70 | 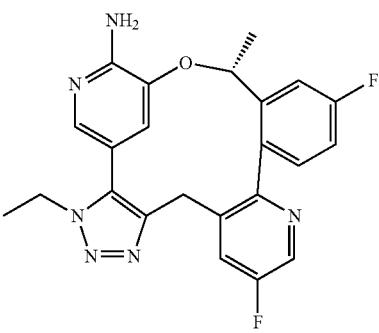 [SMILES: CCn1nnc2c1-c1cnc(N)c(c1)O[C@H](C)c1cc(F)ccc1-c1ncc(F)cc1C2] | (20R)-3-ethyl-10,17-difluoro-20-methyl-21-oxa-3,4,5,12,24-pentaazapentacyclo[20.3.1.0$^{2,6}$.0$^{8,13}$.0$^{14,19}$]hexacosa-1(25),2(6),4,8(13),9,11,14,16,18,22(26),23-undecaen-23-amine<br>1H NMR (400 MHz, DMSO-d6) δ 8.59 (d, J = 2.8 Hz, 1H), 7.67 (ddd, J = 14.7, 9.9, 2.8 Hz, 2H), 7.59 (d, J = 1.9 Hz, 1H), 7.29 (dd, J = 8.6, 5.8 Hz, 1H), 7.22-7.16 (m, 1H), 6.29 (s, 2H), 6.00 (d, J = 1.9 Hz, 1H), 5.13 (d, J = 4.2 Hz, 1H), 4.34 (qd, J = 7.0, 2.9 Hz, 2H), 4.20 (d, J = 15.6 Hz, 1H), 3.25 (s, 1H), 1.72 (d, J = 6.2 Hz, 3H), 1.36 (t, J = 7.3 Hz, 3H).<br>LCMS Method F; $t_R$: 0.90 min; m/z: 435 [M + H] |
| Example 71 | 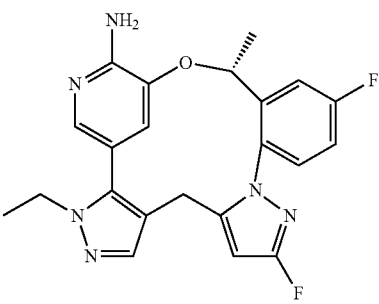 [SMILES: CCn1ncc2c1-c1cnc(N)c(c1)O[C@H](C)c1cc(F)ccc1-n1nc(F)cc1C2] | (19R)-3-ethyl-10,16-difluoro-19-methyl-20-oxa-3,4,11,12,23-pentaazapentacyclo[19.3.1.0$^{2,6}$.0$^{8,12}$.0$^{13,18}$]pentacosa-1(24),2(6),4,8,10,13,15,17,21(25),22-decaen-22-amine<br>1H NMR (400 MHz, DMSO-d6) δ 7.84 (dd, J = 9.8, 2.9 Hz, 1H), 7.65 (s, 1H), 7.50 (d, J = 1.8 Hz, 1H), 7.42 (dd, J = 8.8, 5.2 Hz, 1H), 7.27 (td, J = 8.3, 3.0 Hz, 1H), 6.26-6.16 (m, 3H), 6.03 (d, J = 5.4 Hz, 1H), 5.30 (q, J = 5.9 Hz, 1H), 4.15-4.00 (m, 2H), 3.88 (d, J = 16.2 Hz, 1H), 2.85 (dd, J = 16.2, 1.8 Hz, 1H), 1.70 (d, J = 6.2 Hz, 3H), 1.29 (t, J = 7.2 Hz, 3H).<br>LCMS Method F; $t_R$: 1.09 min; m/z: 423 [M + H] |
| Example 72 | 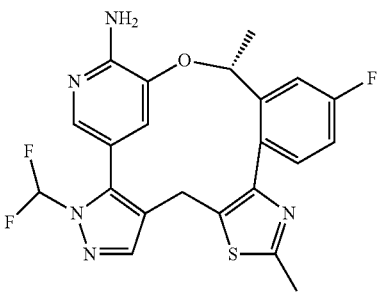 [SMILES: Cc1nc2c(s1)Cc1cnn(C(F)F)c1-c1cnc(N)c(c1)O[C@H](C)c1cc(F)ccc1-2] | (19R)-3-(difluoromethyl)-16-fluoro-10,19-dimethyl-20-oxa-9-thia-3,4,11,23-tetraazapentacyclo[19.3.1.0$^{2,6}$.0$^{8,12}$.0$^{13,18}$]pentacosa-1(24),2(6),4,8(12),10,13,15,17,21(25),22-decaen-22-amine<br>1H NMR (400 MHz, DMSO) δ 7.97 (s, 1H), 7.72 (dd, J = 10.3, 2.6 Hz, 1H), 7.64 (t, J = 56 Hz, 1H), 7.41 (d, J = 1.4 Hz, 1H), 7.23-7.13 (m, 2H), 6.34 (d, J = 1.7 Hz, 1H), 6.32 (s, 2H), 5.23-5.16 (m, 1H), 4.02 (d, J = 15.7 Hz, 1H), 3.18 (d, J = 15.6 Hz, 1H), 2.64 (s, 3H), 1.71 (d, J = 6.2 Hz, 3H).<br>LCMS Method F; $t_R$: 1.19 min; m/z: 458 [M + H] |
| Example 73 | 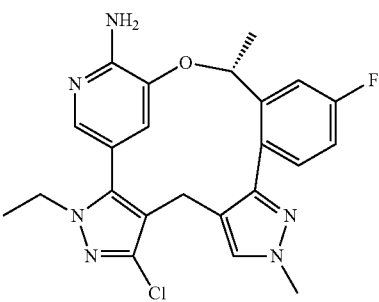 | (19R)-5-chloro-3-ethyl-16-fluoro-10,19-dimethyl-20-oxa-3,4,10,11,23-pentaazapentacyclo[19.3.1.0$^{2,6}$.0$^{8,12}$.0$^{13,18}$]pentacosa-1(24),2(6),4,8,11,13,15,17,21(25),22-decaen-22-amine<br>1H NMR (400 MHz, DMSO) δ 7.71 (dd, J = 10.4, 2.4 Hz, 1H), 7.58 (s, 1H), 7.47 (d, J = 1.8 Hz, 1H), 7.22-7.09 (m, 2H), 6.32-6.15 (m, 3H), 5.36-5.24 (m, 1H), 4.07-3.92 (m, 2H), 3.87 (s, 3H), 3.54 (d, J = 15.9 Hz, 1H), 2.70 (d, J = 15.6 Hz, 1H), 1.71 (d, J = 6.2 Hz, 3H), 1.27 (t, J = 7.2 Hz, 3H).<br>LCMS Method H; $t_R$: 1.06 min; m/z: 453 [M + H] |

| | | |
|---|---|---|
| Example 74 | 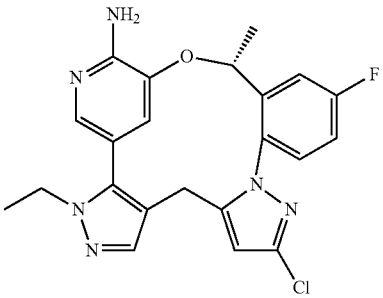 [SMILES: CCn1ncc2c1-c1cnc(N)c(c1)O[C@H](C)c1cc(F)ccc1-n1nc(Cl)cc1C2] | (19R)-10-chloro-3-ethyl-16-fluoro-19-methyl-20-oxa-3,4,11,12,23-pentaazapentacyclo[19.3.1.0$^{2,6}$.0$^{8,12}$.0$^{13,18}$]pentacosa-1(24),2(6),4,8,10,13,15,17,21(25),22-decaen-22-amine<br>1H NMR (400 MHz, DMSO) δ 7.93 (dd, J = 9.8, 2.9 Hz, 1H), 7.72 (s, 1H), 7.56 (d, J = 1.8 Hz, 1H), 7.49 (dd, J = 8.8, 5.2 Hz, 1H), 7.35 (td, J = 8.3, 3.0 Hz, 1H), 6.42 (s, 1H), 6.31 (s, 2H), 6.19 (d, J = 1.7 Hz, 1H), 5.29 (d, J = 4.9 Hz, 1H), 4.12 (tq, J = 14.3, 7.1 Hz, 2H), 3.95 (d, J = 16.5 Hz, 1H), 2.92 (d, J = 16.1 Hz, 1H), 1.77 (d, J = 6.2 Hz, 3H), 1.35 (t, J = 7.2 Hz, 3H).<br>LCMS Method H; $t_R$: 1.14 min; m/z: 439 [M + H] |
| Example 75 | 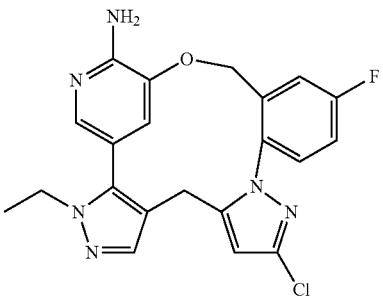 [SMILES: CCn1ncc2c1-c1cnc(N)c(c1)OCc1cc(F)ccc1-n1nc(Cl)cc1C2] | 10-chloro-3-ethyl-16-fluoro-20-oxa-3,4,11,12,23-pentaazapentacyclo[19.3.1.0$^{2,6}$.0$^{8,12}$.0$^{13,18}$]pentacosa-1(24),2(6),4,8,10,13,15,17,21(25),22-decaen-22-amine<br>1H NMR (400 MHz, DMSO) δ 7.80 (dd, J = 9.4, 2.9 Hz, 1H), 7.67 (s, 1H), 7.52 (d, J = 1.7 Hz, 1H), 7.46 (dd, J = 8.8, 5.2 Hz, 1H), 7.34 (td, J = 8.4, 2.9 Hz, 1H), 6.35 (s, 1H), 6.23 (s, 2H), 6.14 (d, J = 1.5 Hz, 1H), 5.08 (dd, J = 80.5, 13.8 Hz, 2H), 4.15-3.99 (m, 2H), 3.92 (d, J = 16.3 Hz, 1H), 2.91 (d, J = 16.1 Hz, 1H), 1.31 (t, J = 7.2 Hz, 3H).<br>LCMS Method F; $t_R$: 1.03 min; m/z: 425 [M + H] |
| Example 76 | 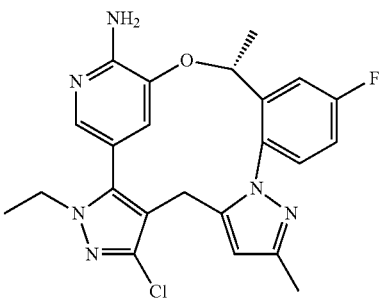 [SMILES: CCn1nc(Cl)c2c1-c1cnc(N)c(c1)O[C@H](C)c1cc(F)ccc1-n1nc(C)cc1C2] | (19R)-5-chloro-3-ethyl-16-fluoro-10,19-dimethyl-20-oxa-3,4,11,12,23-pentaazapentacyclo[19.3.1.0$^{2,6}$.0$^{8,12}$.0$^{13,18}$]pentacosa-1(24),2(6),4,8,10,13,15,17,21(25),22-decaen-22-amine<br>1H NMR (400 MHz, DMSO-d6) δ 7.81 (dd, J = 9.8, 3.0 Hz, 1H), 7.53 (d, J = 1.8 Hz, 1H), 7.39 (dd, J = 8.7, 5.2 Hz, 1H), 7.25 (td, J = 8.3, 3.0 Hz, 1H), 6.31 (s, 2H), 6.10 (d, J = 1.9 Hz, 1H), 6.06 (s, 1H), 5.22 (d, J = 6.6 Hz, 1H), 4.06 (qd, J = 7.0, 3.4 Hz, 2H), 3.81 (d, J = 16.4 Hz, 1H), 2.86 (d, J = 16.3 Hz, 1H), 2.22 (s, 3H), 1.72 (d, J = 6.2 Hz, 3H), 1.30 (t, J = 7.2 Hz, 3H).<br>LCMS Method J; $t_R$: 2.70 min; m/z: 453 [M + H] |
| Example 77 | 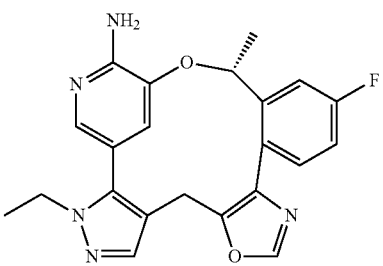 [SMILES: CCn1ncc2c1-c1cnc(N)c(c1)O[C@H](C)c1cc(F)ccc1-c1ncoc1C2] | (19R)-3-ethyl-16-fluoro-19-methyl-9,20-dioxa-3,4,11,23-tetraazapentacyclo[19.3.1.0$^{2,6}$.0$^{8,12}$.0$^{13,18}$]pentacosa-1(24),2(6),4,8(12),10,13,15,17,21(25),22-decaen-22-amine<br>1H NMR (400 MHz, DMSO-d6) δ 8.38 (s, 1H), 7.79 (dd, J = 10.4, 2.7 Hz, 1H), 7.61 (s, 1H), 7.43 (d, J = 1.8 Hz, 1H), 7.20 (dd, J = 8.5, 6.0 Hz, 1H), 7.16 (td, J = 8.4, 2.6 Hz, 1H), 6.27 (d, J = 1.9 Hz, 1H), 6.13 (s, 2H), 5.33 (qd, J = 6.5, 5.8, 1.3 Hz, 1H), 4.06-3.94 (m, 2H), 3.89 (d, J = 15.9 Hz, 1H), 3.17 (d, J = 15.9 Hz, 1H), 1.72 (d, J = 6.2 Hz, 3H), 1.26 (t, J = 7.2 Hz, 3H).<br>LCMS Method G; $t_R$: 2.34 min; m/z: 406 [M + H] |
| Example 78 | 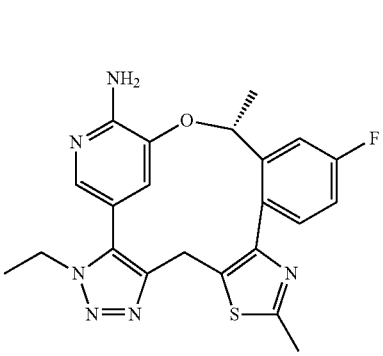 [SMILES: CCn1nnc2c1-c1cnc(N)c(c1)O[C@H](C)c1cc(F)ccc1-c1nc(C)sc1C2] | (19R)-3-ethyl-16-fluoro-10,19-dimethyl-20-oxa-9-thia-3,4,5,11,23-pentaazapentacyclo[19.3.1.0$^{2,6}$.0$^{8,12}$.0$^{13,18}$]pentacosa-1(24),2(6),4,8(12),10,13,15,17,21(25),22-decaen-22-amine<br>1H NMR (400 MHz, DMSO) δ 7.70 (dd, J = 10.3, 2.7 Hz, 1H), 7.57 (d, J = 1.7 Hz, 1H), 7.27 (dd, J = 8.5, 5.9 Hz, 1H), 7.18 (td, J = 8.4, 2.7 Hz, 1H), 6.27 (s, 3H), 5.19-5.11 (m, 1H), 4.37-4.26 (m, 2H), 4.23 (d, J = 15.7 Hz, 1H), 3.40 (t, J = 10.7 Hz, 1H), 2.64 (s, 3H), 1.71 (d, J = 6.2 Hz, 3H), 1.33 (t, J = 7.3 Hz, 3H).<br>LCMS Method F; $t_R$: 0.94 min; m/z: 437 [M + H] |

| Example 79 | 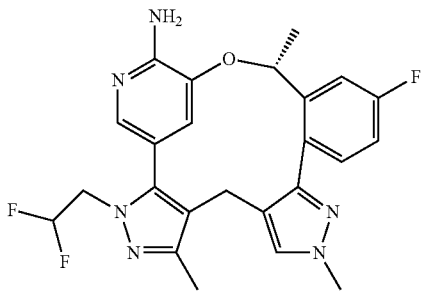 [SMILES: Cc1nn(CC(F)F)c2c1Cc1cn(C)nc1-c1ccc(F)cc1[C@@H](C)Oc1cc-2cnc1N] | (19R)-3-(2,2-difluoroethyl)-16-fluoro-5,10,19-trimethyl-20-oxa-3,4,10,11,23-pentaazapentacyclo[19.3.1.0²,⁶.0⁸,¹².0¹³,¹⁸]pentacosa-1(24),2(6),4,8,11,13,15,17,21(25),22-decaen-22-amine<br>1H NMR (400 MHz, DMSO) δ 7.70 (d, J = 10.4 Hz, 1H), 7.62 (s, 1H), 7.42 (d, J = 1.6 Hz, 1H), 7.15 (d, J = 7.1 Hz, 2H), 6.46 6.32 6.18 (m, 1H), 6.27 (s, 1H), 6.14 (s, 2H), 5.36-5.23 (m, 1H), 4.44-4.24 (m, 2H), 3.86 (s, 3H), 3.51 (d, J = 15.9 Hz, 1H), 2.67 (d, J = 15.7 Hz, 1H), 2.35 (s, 3H), 1.70 (d, J = 6.2 Hz, 3H).<br>LCMS Method F; $t_R$: 0.91 min; m/z: 469 [M + H] |
|---|---|---|
| Example 80 | 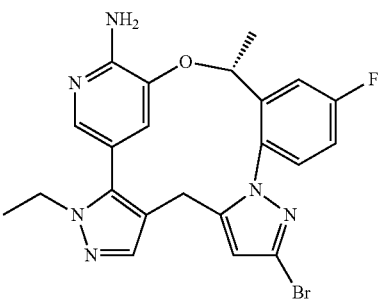 [SMILES: CCn1ncc2c1-c1cnc(N)c(c1)O[C@H](C)c1cc(F)ccc1-n1nc(Br)cc1C2] | (19R)-10-bromo-3-ethyl-16-fluoro-19-methyl-20-oxa-3,4,11,12,23-pentaazapentacyclo[19.3.1.0²,⁶.0⁸,¹².0¹³,¹⁸]pentacosa-1(24),2(6),4,8,10,13,15,17,21(25),22-decaen-22-amine<br>1H NMR (400 MHz, DMSO) δ 7.85 (dd, J = 9.8, 2.9 Hz, 1H), 7.67 (s, 1H), 7.50 (d, J = 1.7 Hz, 1H), 7.40 (dd, J = 8.7, 5.2 Hz, 1H), 7.28 (td, J = 8.4, 3.0 Hz, 1H), 6.40 (s, 1H), 6.22 (s, 2H), 6.11 (d, J = 1.3 Hz, 1H), 5.21 (q, J = 6.4 Hz, 1H), 4.14-3.98 (m, 2H), 3.90 (d, J = 16.4 Hz, 1H), 2.87 (d, J = 16.1 Hz, 1H), 1.72 (d, J = 6.2 Hz, 3H), 1.29 (t, J = 7.2 Hz, 3H).<br>LCMS Method F; $t_R$: 1.11 min; m/z: 483 [M + H] |
| Example 81 | 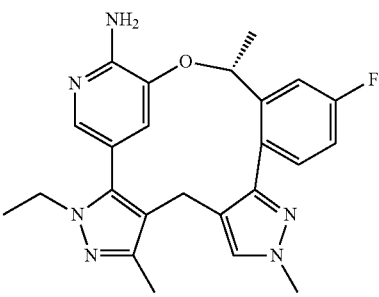 [SMILES: CCn1nc(C)c2c1-c1cnc(N)c(c1)O[C@H](C)c1cc(F)ccc1-c1nn(C)cc1C2] | (19R)-3-ethyl-16-fluoro-5,10,19-trimethyl-20-oxa-3,4,10,11,23-pentaazapentacyclo[19.3.1.0²,⁶.0⁸,¹².0¹³,¹⁸]pentacosa-1(24),2(6),4,8,11,13,15,17,21(25),22-decaen-22-amine<br>1H NMR (400 MHz, DMSO) δ 7.69 (d, J = 10.3 Hz, 1H), 7.59 (s, 1H), 7.39 (d, J = 1.5 Hz, 1H), 7.15 (d, J = 6.1 Hz, 2H), 6.28 (s, 1H), 6.07 (s, 2H), 5.29 (d, J = 4.7 Hz, 1H), 3.97-3.89 (m, 2H), 3.85 (s, 3H), 3.48 (d, J = 15.7 Hz, 1H), 2.65 (d, J = 15.6 Hz, 1H), 2.32 (s, 3H), 1.70 (d, J = 6.2 Hz, 3H), 1.23 (d, J = 7.1 Hz, 3H).<br>LCMS Method H; $t_R$: 0.91 min; m/z: 433 [M + H] |
| Example 82 | 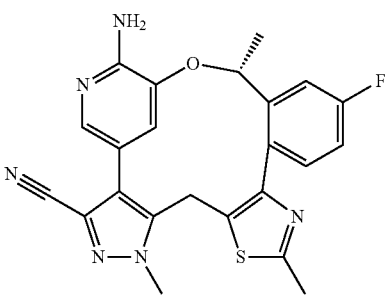 [SMILES: Cc1nc2c(s1)Cc1c(c(C#N)nn1C)-c1cnc(N)c(c1)O[C@H](C)c1cc(F)ccc1-2] | (19R)-22-amino-16-fluoro-5,10,19-trimethyl-20-oxa-9-thia-4,5,11,23-tetraazapentacyclo[19.3.1.0²,⁶.0⁸,¹².0¹³,¹⁸]pentacosa-1(24),2(6),3,8(12),10,13,15,17,21(25),22-decaene-3-carbonitrile<br>1H NMR (400 MHz, DMSO) δ 7.68 (dd, J = 10.2, 1.9 Hz, 1H), 7.52 (d, J = 1.8 Hz, 1H), 7.29-7.19 (m, 2H), 6.30 (d, J = 1.7 Hz, 1H), 6.10 (s, 2H), 5.17-5.04 (m, 1H), 4.44 (d, J = 16.5 Hz, 1H), 4.11 (s, 3H), 3.49 (d, J = 9.2 Hz, 1H), 2.69 (s, 3H), 1.72 (d, J = 6.2 Hz, 3H).<br>LCMS Method F; $t_R$: 0.93 min; m/z: 447 [M + H] |
| Example 83 | 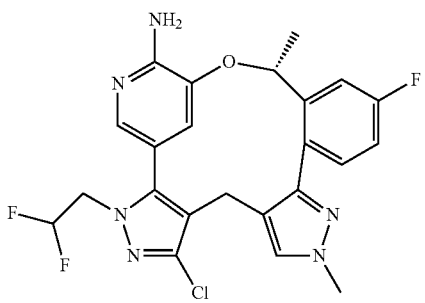 [SMILES: C[C@H]1Oc2cc(cnc2N)-c2c(c(Cl)nn2CC(F)F)Cc2cn(C)nc2-c2ccc(F)cc21] | (19R)-5-chloro-3-(2,2-difluoroethyl)-16-fluoro-10,19-dimethyl-20-oxa-3,4,10,11,23-pentaazapentacyclo[19.3.1.0²,⁶.0⁸,¹².0¹³,¹⁸]pentacosa-1(24),2(6),4,8,11,13,15,17,21(25),22-decaen-22-amine<br>1H NMR (400 MHz, DMSO-d6) δ 7.70 (dd, J = 10.4, 2.6 Hz, 1H), 7.60 (s, 1H), 7.49 (d, J = 1.8 Hz, 1H), 7.20-7.12 (m, 2H), 6.50-6.19 (m, 4H), 5.31 (d, J = 6.4, 2.1 Hz, 1H), 4.52-4.37 (m, 2H), 3.87 (s, 3H), 3.56 (d, J = 15.7 Hz, 1H), 2.71 (d, J = 15.6 Hz, 1H), 1.71 (d, J = 6.2 Hz, 3H).<br>LCMS Method F; $t_R$: 0.99 min; m/z: 489 [M + H] |

| Example | | |
|---|---|---|
| Example 84 | 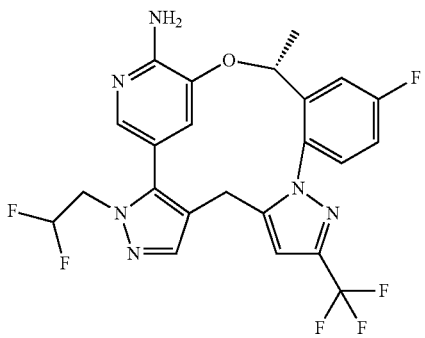 [SMILES: C[C@H]1Oc2cc(cnc2N)-c2c(cnn2CC(F)F)Cc2cc(C(F)(F)F)nn2-c2ccc(F)cc21] | (19R)-3-(2,2-difluoroethyl)-16-fluoro-19-methyl-10-(trifluoromethyl)-20-oxa-3,4,11,12,23-pentaazapentacyclo[19.3.1.0$^2$,$^6$.0$^8$,$^{12}$.0$^{13}$,$^{18}$]pentacosa-1(24),2(6),4,8,10,13,15,17,21(25),22-decaen-22-amine<br>1H NMR (400 MHz, CDCl3) δ 7.73 (s, 1H), 7.62 (d, J = 1.6 Hz, 1H), 7.39 (dd, J = 9.0, 2.8 Hz, 1H), 7.20-7.05 (m, 2H), 6.53 (s, 1H), 6.24 (tt, J = 4, 56 Hz, 1H), 6.19 (d, J = 4 Hz, 1H), 5.23-5.11 (m, 1H), 4.95 (br s, 2H), 4.54-4.38 (m, 2H), 3.83 (d, J = 16.3 Hz, 1H), 3.22 (d, J = 16.2 Hz, 1H), 1.81 (d, J = 6.3 Hz, 3H).<br>LCMS Method F; t$_R$: 1.16 min; m/z: 509 [M + H] |
| Example 85 | 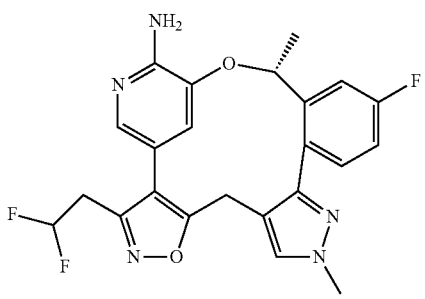 [SMILES: C[C@H]1Oc2cc(cnc2N)-c2c(CC(F)F)noc2Cc2cn(C)nc2-c2ccc(F)cc21] | (19R)-3-(2,2-difluoroethyl)-16-fluoro-10,19-dimethyl-5,20-dioxa-4,10,11,23-tetraazapentacyclo[19.3.1.0$^2$,$^6$.0$^8$,$^{12}$.0$^{13}$,$^{18}$]pentacosa-1(24),2(6),3,8,11,13,15,17,21(25),22-decaen-22-amine<br>1H NMR (400 MHz, MeOD) δ 7.73 (s, 1H), 7.55 (dd, J = 9.9, 2.7 Hz, 1H), 7.41 (d, J = 1.6 Hz, 1H), 7.29 (dd, J = 8.6, 5.7 Hz, 1H), 7.18 (td, J = 8.4, 2.7 Hz, 1H), 6.70 (d, J = 1.6 Hz, 1H), 6.18 (tt, J = 4, 52 Hz, 1H), 5.61-5.52 (m, 1H), 4.16 (d, J = 15.9 Hz, 1H), 3.95 (s, 3H), 3.44 (d, J = 15.9 Hz, 1H), 3.35 (d, J = 4.4 Hz, 1H), 3.26 (d, J = 4.4 Hz, 1H), 1.88 (d, J = 6.3 Hz, 3H).<br>LCMS Method F; t$_R$: 0.96 min; m/z: 456 [M + H] |
| Example 86 | 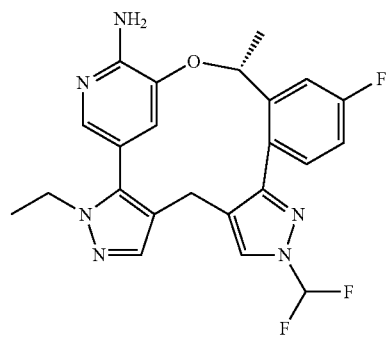 [SMILES: CCn1ncc2c1-c1cnc(N)c(c1)O[C@H](C)c1cc(F)ccc1-c1nn(C(F)F)cc1C2] | (19R)-10-(difluoromethyl)-3-ethyl-16-fluoro-19-methyl-20-oxa-3,4,10,11,23-pentaazapentacyclo[19.3.1.0$^2$,$^6$.0$^8$,$^{12}$.0$^{13}$,$^{18}$]pentacosa-1(24),2(6),4,8,11,13,15,17,21(25),22-decaen-22-amine<br>1H NMR (400 MHz, DMSO) δ 7.97 (t, J = 56 Hz, 1H), 7.88 (s, 2H), 7.72 (d, J = 9.7 Hz, 1H), 7.39 (d, J = 1.8 Hz, 1H), 7.17-7.10 (m, 2H), 6.26 (d, J = 1.6 Hz, 1H), 6.13 (s, 2H), 5.34 (d, J = 4.6 Hz, 1H), 4.14 (d, J = 16.2 Hz, 1H), 4.01 (dt, J = 10.4, 7.0 Hz, 2H), 3.41 (s, 1H), 1.82 (d, J = 6.3 Hz, 3H), 1.23 (t, J = 7.1 Hz, 3H).<br>LCMS Method F; t$_R$: 1.05 min; m/z: 455 [M + H] |
| Example 87 | 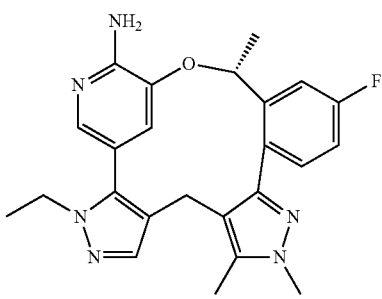 [SMILES: CCn1ncc2c1-c1cnc(N)c(c1)O[C@H](C)c1cc(F)ccc1-c1nn(C)c(C)c1C2] | (19R)-3-ethyl-16-fluoro-9,10,19-trimethyl-20-oxa-3,4,10,11,23-pentaazapentacyclo[19.3.1.0$^2$,$^6$.0$^8$,$^{12}$.0$^{13}$,$^{18}$]pentacosa-1(24),2(6),4,8,11,13,15,17,21(25),22-decaen-22-amine<br>1H NMR (400 MHz, DMSO) δ 7.69-7.62 (m, 2H), 7.37 (t, J = 5.4 Hz, 1H), 7.14-7.02 (m, 2H), 6.39 (d, J = 1.5 Hz, 1H), 6.04 (s, 2H), 5.45 (dd, J = 8.6, 4.0 Hz, 1H), 3.99 (q, J = 7.2 Hz, 2H), 3.74 (s, 3H), 3.62 (d, J = 15.6 Hz, 1H), 2.92 (d, J = 15.5 Hz, 1H), 2.25 (s, 3H), 1.72 (d, J = 6.2 Hz, 3H), 1.26 (t, J = 7.2 Hz, 3H).<br>LCMS Method F; t$_R$: 0.89 min; m/z: 433 [M + H] |
| Example 88 | 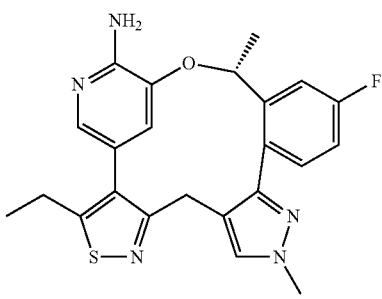 [SMILES: CCc1snc2c1-c1cnc(N)c(c1)O[C@H](C)c1cc(F)ccc1-c1nn(C)cc1C2] | (19R)-3-ethyl-16-fluoro-10,19-dimethyl-20-oxa-4-thia-5,10,11,23-tetraazapentacyclo[19.3.1.0$^2$,$^6$.0$^8$,$^{12}$.0$^{13}$,$^{18}$]pentacosa-1(24),2,5,8,11,13,15,17,21(25),22-decaen-22-amine<br>1H NMR (400 MHz, DMSO) δ 7.79-7.70 (m, 1H), 7.51 (s, 1H), 7.33 (s, 1H), 7.15 (d, J = 6.1 Hz, 2H), 6.25 (s, 1H), 5.97 (s, 2H), 5.36 (d, J = 5.1 Hz, 1H), 3.89-3.81 (m, 4H), 3.00 (d, J = 14.6 Hz, 1H), 2.87 (dd, J = 15.6, 7.6 Hz, 1H), 2.76 (dd, J = 15.6, 7.6 Hz, 1H), 1.71 (d, J = 6.2 Hz, 3H), 1.18 (t, J = 7.5 Hz, 3H).<br>LCMS Method F; t$_R$: 0.78 min; m/z: 436 [M + H] |

| | | |
|---|---|---|
| Example 89 | 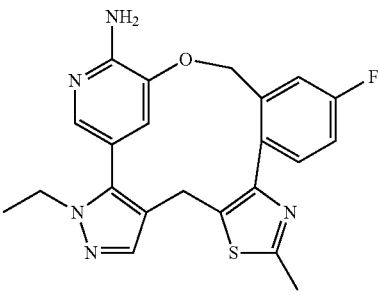 [SMILES: CCn1ncc2c1-c1cnc(N)c(c1)OCc1cc(F)ccc1-c1nc(C)sc1C2] | 3-ethyl-16-fluoro-10-methyl-20-oxa-9-thia-3,4,11,23-tetraazapentacyclo[19.3.1.0$^{2,6}$.0$^{8,12}$.0$^{13,18}$]pentacosa-1(24),2(6),4,8(12),10,13,15,17,21(25),22-decaen-22-amine<br>1H NMR (400 MHz, CDCl3) δ 7.58 (s, 1H), 7.54 (s, 1H), 7.35 (dd, J = 9.3, 2.4 Hz, 1H), 7.15 (dd, J = 8.4, 5.7 Hz, 1H), 7.07-6.98 (m, 1H), 6.56 (s, 1H), 5.21 (d, J = 13.2 Hz, 1H), 5.03 (d, J = 12.8 Hz, 1H), 4.87 (s, 2H), 4.16 (dt, J = 7.3, 5.8 Hz, 2H), 3.88 (d, J = 15.9 Hz, 1H), 3.44 (d, J = 15.8 Hz, 1H), 2.69 (s, 3H), 1.42 (t, J = 7.2 Hz, 3H).<br>LCMS Method F; t$_R$: 0.58 min; m/z: 422 [M + H] |
| Example 90 | 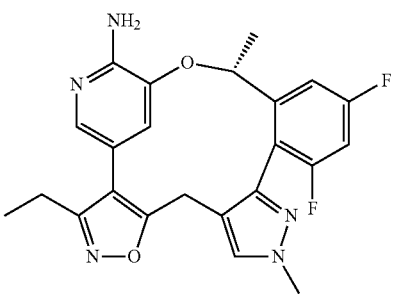 [SMILES: CCc1noc2c1-c1cnc(N)c(c1)O[C@H](C)c1cc(F)cc(F)c1-c1nn(C)cc1C2] | (19R)-3-ethyl-14,16-difluoro-10,19-dimethyl-5,20-dioxa-4,10,11,23-tetraazapentacyclo[19.3.1.0$^{2,6}$.0$^{8,12}$.0$^{13,18}$]pentacosa-1(24),2(6),3,8,11,13,15,17,21(25),22-decaen-22-amine<br>1H NMR (400 MHz, DMSO) δ 7.80 (s, 1H), 7.61 (dd, J = 9.8, 1.6 Hz, 1H), 7.48 (d, J = 1.7 Hz, 1H), 7.29 (td, J = 9.3, 2.5 Hz, 1H), 6.24 (d, J = 1.6 Hz, 1H), 5.99 (s, 2H), 5.25 (q, J = 6.2 Hz, 1H), 3.94 (d, J = 16.0 Hz, 1H), 3.90 (s, 3H), 3.09 (d, J = 14.2 Hz, 1H), 2.80-2.56 (m, 2H), 1.69 (d, J = 6.2 Hz, 3H), 1.12 (t, J = 7.5 Hz, 3H).<br>LCMS Method F; t$_R$: 0.98 min; m/z: 438 [M + H] |
| Example 91 | 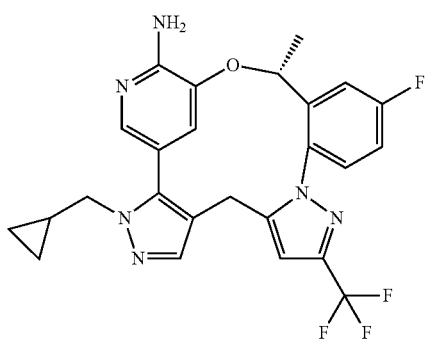 | (19R)-3-(cyclopropylmethyl)-16-fluoro-19-methyl-10-(trifluoromethyl)-20-oxa-3,4,11,12,23-pentaazapentacyclo[19.3.1.0$^{2,6}$.0$^{8,12}$.0$^{13,18}$]pentacosa-1(24),2(6),4,8,10,13,15,17,21(25),22-decaen-22-amine<br>1H NMR (400 MHz, DMSO) δ 7.92 (dd, J = 9.8, 2.9 Hz, 1H), 7.71 (s, 1H), 7.56-7.49 (m, 2H), 7.33 (td, J = 8.3, 2.9 Hz, 1H), 6.76 (s, 1H), 6.27 (s, 2H), 6.04 (d, J = 1.6 Hz, 1H), 5.09 (d, J = 4.7 Hz, 1H), 4.08-3.83 (m, 3H), 2.93 (d, J = 16.2 Hz, 1H), 1.71 (d, J = 6.2 Hz, 3H), 1.18-1.07 (m, 1H), 0.50-0.34 (m, 2H), 0.27 (td, J = 9.0, 4.8 Hz, 1H), 0.17-0.06 (m, 1H).<br>LCMS Method H; t$_R$: 1.47 min; m/z: 499 [M + H] |
| Example 92 | 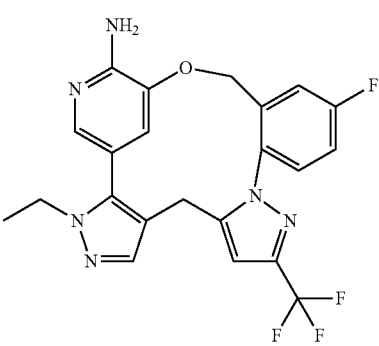 [SMILES: CCn1ncc2c1-c1cnc(N)c(c1)OCc1cc(F)ccc1-n1nc(C(F)(F)F)cc1C2] | 3-ethyl-16-fluoro-10-(trifluoromethyl)-20-oxa-3,4,11,12,23-pentaazapentacyclo[19.3.1.0$^{2,6}$.0$^{8,12}$.0$^{13,18}$]pentacosa-1(24),2(6),4,8,10,13,15,17,21(25),22-decaen-22-amine<br>1H NMR (400 MHz, DMSO) δ 7.84 (dd, J = 9.4, 2.9 Hz, 1H), 7.73 (s, 1H), 7.58-7.50 (m, 2H), 7.38 (td, J = 8.4, 2.9 Hz, 1H), 6.72 (s, 1H), 6.25 (s, 2H), 6.04 (d, J = 1.6 Hz, 1H), 5.22 (d, J = 13.6 Hz, 1H), 4.86 (d, J = 13.6 Hz, 1H), 4.14-4.03 (m, 2H), 3.99 (d, J = 16.3 Hz, 1H), 2.97 (d, J = 16.1 Hz, 1H), 1.32 (t, J = 7.2 Hz, 3H).<br>LCMS Method F; t$_R$: 1.17 min; m/z: 459 [M + H] |
| Example 93 | 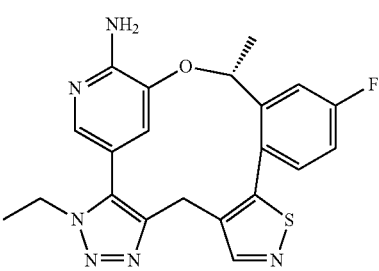 [SMILES: CCn1nnc2c1-c1cnc(N)c(c1)O[C@H](C)c1cc(F)ccc1-c1sncc1C2] | (19R)-3-ethyl-16-fluoro-19-methyl-20-oxa-11-thia-3,4,5,10,23-pentaazapentacyclo[19.3.1.0$^{2,6}$.0$^{8,12}$.0$^{13,18}$]pentacosa-1(24),2(6),4,8(12),9,13,15,17,21(25),22-decaen-22-amine<br>1H NMR (400 MHz, CDCl3) δ 8.67 (s, 1H), 7.60 (s, 1H), 7.36 (dd, J = 9.4, 2.3 Hz, 1H), 7.14 (ddd, J = 14.0, 11.3, 7.4 Hz, 2H), 6.50 (s, 1H), 5.41 (d, J = 6.4 Hz, 1H), 4.89 (s, 2H), 4.39 (dt, J = 13.9, 6.8 Hz, 2H), 4.22 (d, J = 15.5 Hz, 1H), 3.40 (d, J = 15.4 Hz, 1H), 1.79 (d, J = 6.3 Hz, 3H), 1.49 (t, J = 7.3 Hz, 3H).<br>LCMS Method H; t$_R$: 0.89 min; m/z: 423 [M + H] |

| Example 94 | 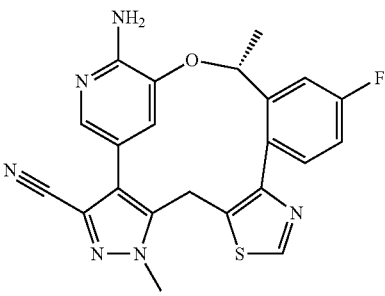 [SMILES: C[C@H]1Oc2cc(cnc2N)-c2c(C#N)nn(C)c2Cc2scnc2-c2ccc(F)cc21] | (19R)-22-amino-16-fluoro-5,19-dimethyl-20-oxa-9-thia-4,5,11,23-tetraazapentacyclo[19.3.1.0²,⁶.0⁸,¹².0¹³,¹⁸]pentacosa-1(24),2(6),3,8(12),10,13,15,17,21(25),22-decaene-3-carbonitrile<br>1H NMR (400 MHz, DMSO) δ 9.25 (s, 1H), 7.71 (dd, J = 10.2, 2.3 Hz, 1H), 7.53 (d, J = 1.8 Hz, 1H), 7.32-7.21 (m, 2H), 6.16 (d, J = 1.8 Hz, 1H), 6.11 (s, 2H), 5.06-4.97 (m, 1H), 4.53 (d, J = 16.6 Hz, 1H), 4.15 (s, 3H), 3.58 (d, J = 16.2 Hz, 1H), 1.73 (d, J = 6.2 Hz, 3H).<br>LCMS Method F; $t_R$: 0.69 min; m/z: 433 [M + H] |
|---|---|---|
| Example 95 | 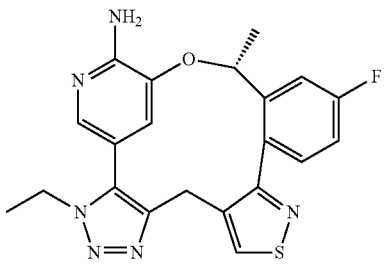 [SMILES: CCn1nnc2c1-c1cnc(N)c(c1)O[C@H](C)c1cc(F)ccc1-c1nscc1C2] | (19R)-3-ethyl-16-fluoro-19-methyl-20-oxa-10-thia-3,4,5,11,23-pentaazapentacyclo[19.3.1.0²,⁶.0⁸,¹².0¹³,¹⁸]pentacosa-1(24),2(6),4,8,11,13,15,17,21(25),22-decaen-22-amine<br>1H NMR (400 MHz, DMSO) δ 8.84 (d, J = 0.9 Hz, 1H), 7.74 (dd, J = 10.3, 2.6 Hz, 1H), 7.57 (d, J = 1.8 Hz, 1H), 7.33 (dd, J = 8.6, 5.8 Hz, 1H), 7.24 (td, J = 8.4, 2.7 Hz, 1H), 6.29 (s, 2H), 5.86 (d, J = 1.6 Hz, 1H), 5.12 (d, J = 4.6 Hz, 1H), 4.37-4.26 (m, 2H), 4.11 (d, J = 16.6 Hz, 1H), 3.18 (d, J = 15.5 Hz, 1H), 1.74 (d, J = 6.2 Hz, 3H), 1.35 (t, J = 7.3 Hz, 3H).<br>LCMS Method A; $t_R$: 1.15 min; m/z: 423 [M + H] |
| Example 96 | 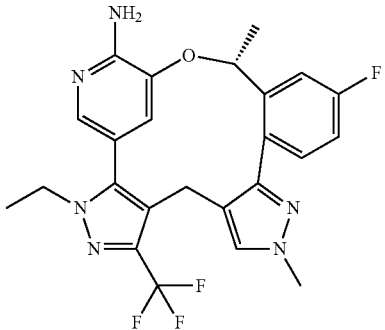 [SMILES: CCn1nc(C(F)(F)F)c2c1-c1cnc(N)c(c1)O[C@H](C)c1cc(F)ccc1-c1nn(C)cc1C2] | (19R)-3-ethyl-16-fluoro-10,19-dimethyl-5-(trifluoromethyl)-20-oxa-3,4,10,11,23-pentaazapentacyclo[19.3.1.0²,⁶.0⁸,¹².0¹³,¹⁸]pentacosa-1(24),2(6),4,8,11,13,15,17,21(25),22-decaen-22-amine<br>1H NMR (400 MHz, DMSO) δ 7.71 (dd, J = 10.4, 2.6 Hz, 1H), 7.51-7.45 (m, 2H), 7.22-7.11 (m, 2H), 6.31-6.20 (m, 3H), 5.36 (d, J = 6.4 Hz, 1H), 4.15-4.09 (m, 2H), 3.87 (s, 3H), 3.68 (s, 1H), 2.79 (d, J = 15.7 Hz, 1H), 1.72 (d, J = 6.2 Hz, 3H), 1.30 (t, J = 7.2 Hz, 3H).<br>LCMS Method F; $t_R$: 1.23 min; m/z: 487 [M + H] |
| Example 97 | 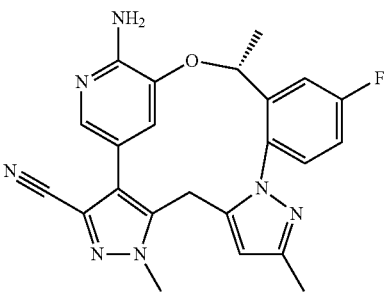 [SMILES: Cc1cc2n(n1)-c1ccc(F)cc1[C@@H](C)Oc1cc(cnc1N)-c1c(C#N)nn(C)c1C2] | (19R)-22-amino-16-fluoro-5,10,19-trimethyl-20-oxa-4,5,11,12,23-pentaazapentacyclo[19.3.1.0²,⁶.0⁸,¹².0¹³,¹⁸]pentacosa-1(24),2(6),3,8,10,13,15,17,21(25),22-decaene-3-carbonitrile<br>1H NMR (400 MHz, MeOD) δ 7.66-7.57 (m, 2H), 7.37 (dd, J = 8.7, 5.1 Hz, 1H), 7.26-7.17 (m, 1H), 6.29-6.21 (m, 2H), 5.30-5.20 (m, 1H), 4.33-4.26 (m, 1H), 4.17 (s, 3H), 3.42 (d, J = 16.9 Hz, 1H), 2.32 (s, 3H), 1.83 (d, J = 6.3 Hz, 3H).<br>LCMS Method F; $t_R$: 0.73 min; m/z: 430 [M + H] |
| Example 98 | 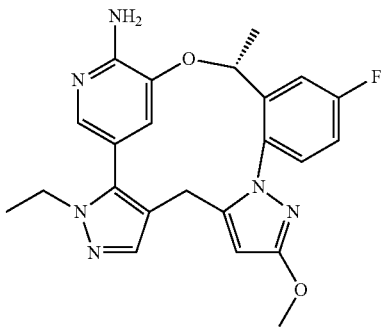 [SMILES: CCn1ncc2c1-c1cnc(N)c(c1)O[C@H](C)c1cc(F)ccc1-n1nc(OC)cc1C2] | (19R)-3-ethyl-16-fluoro-10-methoxy-19-methyl-20-oxa-3,4,11,12,23-pentaazapentacyclo[19.3.1.0²,⁶.0⁸,¹².0¹³,¹⁸]pentacosa-1(24),2(6),4,8,10,13,15,17,21(25),22-decaen-22-amine<br>1H NMR (400 MHz, DMSO) δ 7.80 (dd, J = 9.8, 2.9 Hz, 1H), 7.63 (s, 1H), 7.49 (d, J = 1.7 Hz, 1H), 7.34 (dd, J = 8.7, 5.2 Hz, 1H), 7.23 (td, J = 8.4, 3.0 Hz, 1H), 6.26-6.13 (m, 3H), 5.70 (s, 1H), 5.31 (d, J = 4.8 Hz, 1H), 4.16-3.99 (m, 2H), 3.84 (d, J = 16.4 Hz, 1H), 3.79 (s, 3H), 2.84 (d, J = 16.0 Hz, 1H), 1.72 (d, J = 6.2 Hz, 3H), 1.29 (t, J = 7.2 Hz, 3H).<br>LCMS Method F; $t_R$: 0.71 min; m/z: 435 [M + H] |

| Example 99 | 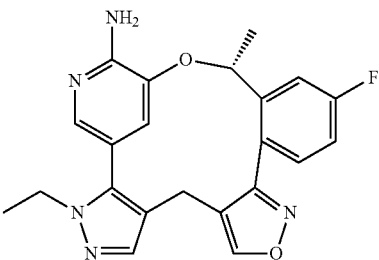 [SMILES: CCn1ncc2c1-c1cnc(N)c(c1)O[C@H](C)c1cc(F)ccc1-c1nocc1C2] | (19R)-3-ethyl-16-fluoro-19-methyl-10,20-dioxa-3,4,11,23-tetraazapentacyclo[19.3.1.0$^{2,6}$.0$^{8,12}$.0$^{13,18}$]pentacosa-1(24),2(6),4,8,11,13,15,17,21(25),22-decaen-22-amine<br>1H NMR (400 MHz, DMSO) δ 8.92 (s, 1H), 7.86-7.81 (m, 1H), 7.63 (s, 1H), 7.45 (d, J = 1.7 Hz, 1H), 7.29 (dd, J = 15.0, 4.2 Hz, 2H), 6.18 (s, 3H), 5.35-5.29 (m, 1H), 4.08-3.97 (m, 2H), 3.68 (d, J = 15.5 Hz, 1H), 2.57 (d, J = 15.8 Hz, 1H), 1.72 (d, J = 6.3 Hz, 3H), 1.27 (d, J = 7.2 Hz, 3H).<br>LCMS Method C; $t_R$: 1.05 min; m/z: 406 [M + H] |
|---|---|---|
| Example 100 | 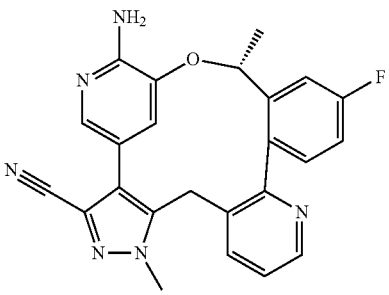 [SMILES: C[C@H]1Oc2cc(cnc2N)-c2c(C#N)nn(C)c2Cc2cccnc2-c2ccc(F)cc21] | (20R)-23-amino-17-fluoro-5,20-dimethyl-21-oxa-4,5,12,24-tetraazapentacyclo[20.3.1.0$^{2,6}$.0$^{8,13}$.0$^{14,19}$]hexacosa-1(25),2(6),3,8(13),9,11,14,16,18,22(26),23-undecaene-3-carbonitrile<br>1H NMR (400 MHz, DMSO-d6) δ 8.64 (d, J = 4.6 Hz, 1H), 7.69 (d, J = 7.9 Hz, 1H), 7.65 (dd, J = 10.3, 2.7 Hz, 1H), 7.56 (d, J = 1.9 Hz, 1H), 7.49 (dd, J = 8.0, 4.7 Hz, 1H), 7.34 (dd, J = 8.5, 5.8 Hz, 1H), 7.23 (td, J = 8.5, 2.7 Hz, 1H), 6.09 (s, 2H), 6.02 (d, J = 2.0 Hz, 1H), 5.01-4.91 (m, 1H), 4.43 (d, J = 16.6 Hz, 1H), 4.20 (s, 3H), 3.39 (d, J = 16.6 Hz, 1H), 1.74 (d, J = 6.2 Hz, 3H).<br>LCMS Method G; $t_R$: 3.05 min; m/z: 427 [M + H] |
| Example 101 | 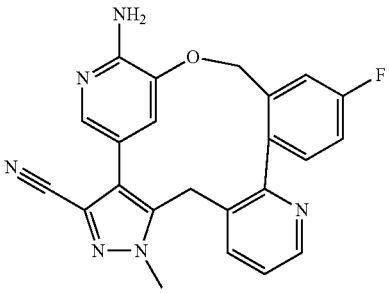 [SMILES: Cn1nc(C#N)c2c1Cc1cccnc1-c1ccc(F)cc1COc1cc-2cnc1N] | 23-amino-17-fluoro-5-methyl-21-oxa-4,5,12,24-tetraazapentacyclo[20.3.1.0$^{2,6}$.0$^{8,13}$.0$^{14,19}$]hexacosa-1(25),2(6),3,8(13),9,11,14,16,18,22(26),23-undecaene-3-carbonitrile<br>1H NMR (400 MHz, DMSO-d6) δ 8.61 (d, J = 4.7 Hz, 1H), 7.68 (d, J = 8.0 Hz, 1H), 7.61 (dd, J = 9.8, 2.6 Hz, 1H), 7.57 (d, J = 1.9 Hz, 1H), 7.48 (dd, J = 8.0, 4.7 Hz, 1H), 7.37 (dd, J = 8.6, 5.7 Hz, 1H), 7.27 (td, J = 8.5, 2.8 Hz, 1H), 6.09 (s, 2H), 6.03 (d, J = 1.5 Hz, 1H), 5.23 (d, J = 13.6 Hz, 1H), 4.71 (d, J = 13.7 Hz, 1H), 4.47 (d, J = 16.6 Hz, 1H), 4.20 (s, 3H), 3.42-3.41 (m, 1H).<br>LCMS Method C; $t_R$: 1.32 min; m/z: 413 [M + H] |
| Example 102 | 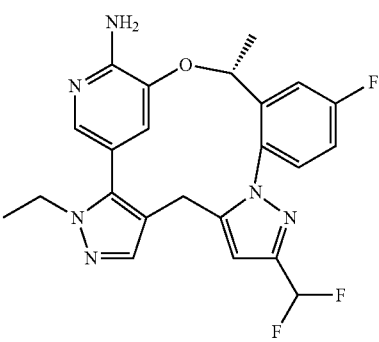 [SMILES: CCn1ncc2c1-c1cnc(N)c(c1)O[C@H](C)c1cc(F)ccc1-n1nc(C(F)F)cc1C2] | (19R)-10-(difluoromethyl)-3-ethyl-16-fluoro-19-methyl-20-oxa-3,4,11,12,23-pentaazapentacyclo[19.3.1.0$^{2,6}$.0$^{8,12}$.0$^{13,18}$]pentacosa-1(24),2(6),4,8,10,13,15,17,21(25),22-decaen-22-amine<br>1H NMR (400 MHz, DMSO) δ 7.89 (dd, J = 9.8, 2.9 Hz, 1H), 7.71 (s, 1H), 7.54-7.43 (m, 2H), 7.35-7.27 (m, 1H), 7.04 (t, J = 52 Hz, 1H), 6.50 (s, 1H), 6.25 (s, 2H), 6.02 (d, J = 1.5 Hz, 1H), 5.11 (q, J = 5.0 Hz, 1H), 4.07 (dt, J = 13.5, 6.8 Hz, 2H), 3.93 (d, J = 16.3 Hz, 1H), 2.91 (d, J = 16.1 Hz, 1H), 1.71 (d, J = 6.2 Hz, 3H), 1.29 (t, J = 7.2 Hz, 3H).<br>LCMS Method H; $t_R$: 1.14 min; m/z: 455 [M + H] |
| Example 103 | 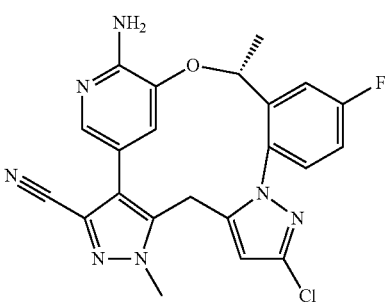 [SMILES: C[C@H]1Oc2cc(cnc2N)-c2c(C#N)nn(C)c2Cc2cc(Cl)nn2-c2ccc(F)cc21] | (19R)-22-amino-10-chloro-16-fluoro-5,19-dimethyl-20-oxa-4,5,11,12,23-pentaazapentacyclo[19.3.1.0$^{2,6}$.0$^{8,12}$.0$^{13,18}$]pentacosa-1(24),2(6),3,8,10,13,15,17,21(25),22-decaene-3-carbonitrile<br>1H NMR (400 MHz, DMSO-d6) δ 7.82 (dd, J = 9.6, 2.9 Hz, 1H), 7.53 (d, J = 1.8 Hz, 1H), 7.47 (dd, J = 8.8, 5.1 Hz, 1H), 7.36 (td, J = 8.3, 3.0 Hz, 1H), 6.70 (s, 1H), 6.18 (s, 2H), 6.06 (d, J = 1.7 Hz, 1H), 5.21-5.13 (m, 1H), 4.43 (d, J = 17.1 Hz, 1H), 4.12 (s, 3H), 3.22 (d, J = 17.0 Hz, 1H), 1.71 (d, J = 6.2 Hz, 3H).<br>LCMS Method F; $t_R$: 1.12 min; m/z: 450 [M + H] |

| Example 104 | 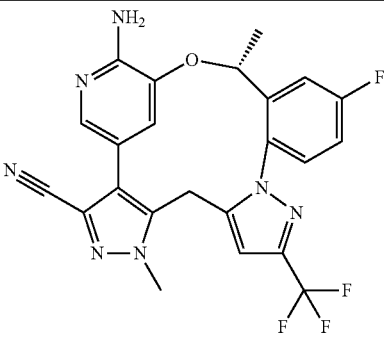 | (19R)-22-amino-16-fluoro-5,19-dimethyl-10-(trifluoromethyl)-20-oxa-4,5,11,12,23-pentaazapentacyclo[19.3.1.0$^{2,6}$.0$^{8,12}$.0$^{13,18}$]pentacosa-1(24),2(6),3,8,10,13,15,17,21(25),22-decaene-3-carbonitrile<br>1H NMR (400 MHz, DMSO) δ 7.87 (dd, J = 9.7, 2.9 Hz, 1H), 7.61-7.50 (m, 2H), 7.41 (td, J = 8.4, 2.9 Hz, 1H), 7.10 (s, 1H), 6.21 (s, 2H), 5.97 (d, J = 1.6 Hz, 1H), 5.08-4.96 (m, 1H), 4.51 (d, J = 17.3 Hz, 1H), 4.16 (s, 3H), 3.30 (d, J = 17.1 Hz, 1H), 1.72 (d, J = 6.2 Hz, 3H).<br>LCMS Method F; $t_R$: 1.24 min; m/z: 484 [M + H] |
|---|---|---|
| Example 105 | 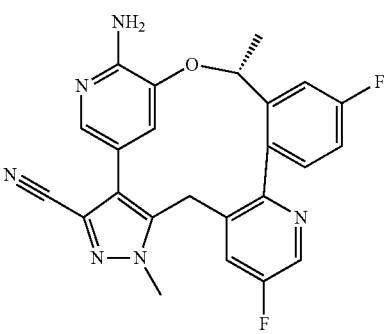 [SMILES: C[C@H]1Oc2cc(cnc2N)-c2c(C#N)nn(C)c2Cc2cc(F)cnc2-c2ccc(F)cc21] | (20R)-23-amino-10,17-difluoro-5,20-dimethyl-21-oxa-4,5,12,24-tetraazapentacyclo[20.3.1.0$^{2,6}$.0$^{8,13}$.0$^{14,19}$]hexacosa-1(25),2(6),3,8(13),9,11,14,16,18,22(26),23-undecaene-3-carbonitrile<br>1H NMR (400 MHz, DMSO) δ 8.67 (d, J = 2.6 Hz, 1H), 7.66 (dd, J = 10.3, 2.7 Hz, 1H), 7.55 (d, J = 1.9 Hz, 2H), 7.32 (dd, J = 8.5, 5.8 Hz, 1H), 7.24 (td, J = 8.4, 2.7 Hz, 1H), 6.11 (s, 2H), 6.01 (d, J = 1.6 Hz, 1H), 5.05-4.92 (m, 1H), 4.47 (d, J = 16.7 Hz, 1H), 4.19 (s, 3H), 3.33 (s, 1H), 1.72 (d, J = 6.2 Hz, 3H).<br>LCMS Method F; $t_R$: 0.78 min; m/z: 445 [M + H] |
| Example 106 | 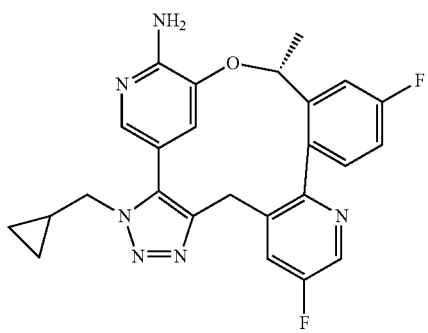 [SMILES: C[C@H]1Oc2cc(cnc2N)-c2c(nnn2CC2CC2)Cc2cc(F)cnc2-c2ccc(F)cc21] | (20R)-3-(cyclopropylmethyl)-10,17-difluoro-20-methyl-21-oxa-3,4,5,12,24-pentaazapentacyclo[20.3.1.0$^{2,6}$.0$^{8,13}$.0$^{14,19}$]hexacosa-1(25),2(6),4,8(13),9,11,14,16,18,22(26),23-undecaen-23-amine<br>1H NMR (400 MHz, DMSO) δ 8.59 (d, J = 2.8 Hz, 1H), 7.73-7.64 (m, 2H), 7.62 (d, J = 1.8 Hz, 1H), 7.29 (dd, J = 8.5, 5.8 Hz, 1H), 7.18 (td, J = 8.4, 2.7 Hz, 1H), 6.29 (s, 2H), 6.00 (d, J = 1.6 Hz, 1H), 5.14 (dd, J = 6.3, 1.7 Hz, 1H), 4.29-4.13 (m, 3H), 3.28 (dd, J = 15.6, 1.5 Hz, 1H), 1.72 (d, J = 6.2 Hz, 3H), 1.16 (tt, J = 10.1, 3.8 Hz, 1H), 0.50-0.39 (m, 2H), 0.36-0.29 (m, 1H), 0.23-0.15 (m, 1H).<br>LCMS Method F; $t_R$: 1.16 min; m/z: 461 [M + H] |
| Example 107 | 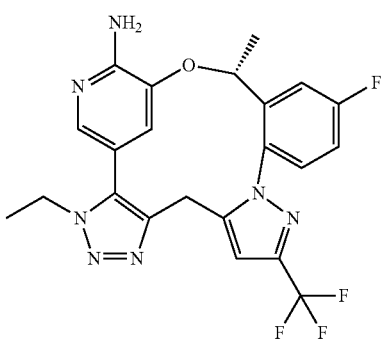 [SMILES: CCn1nnc2c1-c1cnc(N)c(c1)O[C@H](C)c1cc(F)ccc1-n1nc(C(F)(F)F)cc1C2] | (19R)-3-ethyl-16-fluoro-19-methyl-10-(trifluoromethyl)-20-oxa-3,4,5,11,12,23-hexaazapentacyclo[19.3.1.0$^{2,6}$.0$^{8,12}$.0$^{13,18}$]pentacosa-1(24),2(6),4,8,10,13,15,17,21(25),22-decaen-22-amine<br>1H NMR (400 MHz, DMSO) δ 7.89 (dd, J = 9.7, 2.9 Hz, 1H), 7.65-7.58 (m, 2H), 7.37 (td, J = 8.4, 2.9 Hz, 1H), 6.65 (s, 1H), 6.39 (s, 2H), 5.99 (d, J = 1.5 Hz, 1H), 5.10 (d, J = 5.0 Hz, 1H), 4.34 (ddd, J = 26.3, 14.2, 7.1 Hz, 3H), 3.21 (d, J = 16.2 Hz, 1H), 1.72 (d, J = 6.2 Hz, 3H), 1.37 (t, J = 7.3 Hz, 3H).<br>LCMS Method F; $t_R$: 1.32 min; m/z: 474 [M + H] |
| Example 108 | 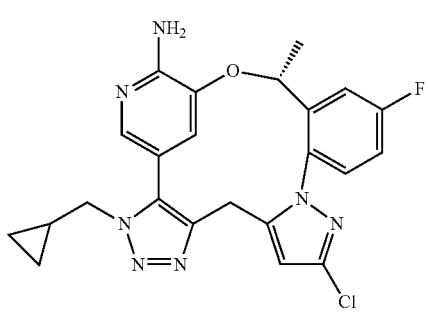 [SMILES: C[C@H]1Oc2cc(cnc2N)-c2c(nnn2CC2CC2)Cc2cc(Cl)nn2-c2ccc(F)cc21] | (19R)-10-chloro-3-(cyclopropylmethyl)-16-fluoro-19-methyl-20-oxa-3,4,5,11,12,23-hexaazapentacyclo[19.3.1.0$^{2,6}$.0$^{8,12}$.0$^{13,18}$]pentacosa-1(24),2(6),4,8,10,13,15,17,21(25),22-decaen-22-amine<br>1H NMR (400 MHz, DMSO) δ 7.84 (dd, J = 9.8, 2.9 Hz, 1H), 7.64 (d, J = 1.8 Hz, 1H), 7.50 (dd, J = 8.8, 5.2 Hz, 1H), 7.32 (td, J = 8.3, 3.0 Hz, 1H), 6.35 (s, 2H), 6.31 (s, 1H), 6.10 (d, J = 1.6 Hz, 1H), 5.25 (q, J = 6.0 Hz, 1H), 4.30-4.15 (m, 3H), 3.14 (d, J = 16.1 Hz, 1H), 1.72 (d, J = 6.2 Hz, 3H), 1.21-1.12 (m, 1H), 0.53-0.40 (m, 2H), 0.32 (dt, J = 7.6, 4.7 Hz, 1H), 0.20 (dq, J = 9.9, 4.8 Hz, 1H).<br>LCMS Method F; $t_R$: 1.26 min; m/z: 466 [M + H] |

| Example 109 | 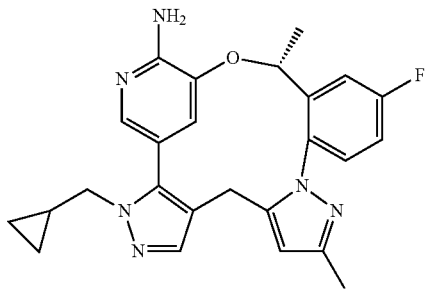 [SMILES: Cc1cc2n(n1)-c1ccc(F)cc1[C@@H](C)Oc1cc(cnc1N)-c1c(cnn1CC1CC1)C2] | (19R)-3-(cyclopropylmethyl)-16-fluoro-10,19-dimethyl-20-oxa-3,4,11,12,23-pentaazapentacyclo[19.3.1.0²,⁶.0⁸,¹².0¹³,¹⁸]pentacosa-1(24),2(6),4,8,10,13,15,17,21(25),22-decaen-22-amine<br>1H NMR (400 MHz, DMSO-d6) δ 7.80 (dd, J = 9.8, 3.0 Hz, 1H), 7.62 (s, 1H), 7.50 (d, J = 1.7 Hz, 1H), 7.30 (dd, J = 8.7. 5.2 Hz, 1H), 7.25 (dd, J = 8.1, 2.8 Hz, 1H), 6.19 (s, 2H), 6.10 (d, J = 1.9 Hz, 1H), 6.04 (s, 1H), 5.21 (d, J = 6.4 Hz, 1H), 4.03-3.98 (m, 1H), 3.88 (d, J = 7.3 Hz, 1H), 3.84 (d, J = 5.8 Hz, 1H), 2.84 (d, J = 16.0 Hz, 1H), 2.19 (s, 3H), 1.70 (d, J = 6.2 Hz, 3H), 1.11 (s, 1H), 0.40 (ddd, J = 16.7, 8.9, 4.7 Hz, 2H), 0.25 (dd, J = 9.2, 4.6 Hz, 1H), 0.09 (dd, J = 9.2, 4.6 Hz, 1H).<br>LCMS Method F; $t_R$: 1.07 min; m/z: 445 [M + H] |
|---|---|---|
| Example 110 | 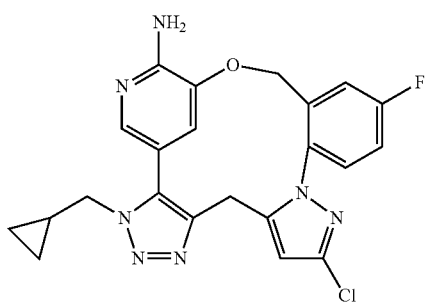 [SMILES: Nc1ncc2cc1OCc1cc(F)ccc1-n1nc(Cl)cc1Cc1nnn(CC3CC3)c1-2] | 10-chloro-3-(cyclopropylmethyl)-16-fluoro-20-oxa-3,4,5,11,12,23-hexaazapentacyclo[19.3.1.0²,⁶.0⁸,¹².0¹³,¹⁸]pentacosa-1(24),2(6),4,8,10,13,15,17,21(25),22-decaen-22-amine<br>1H NMR (400 MHz, DMSO) δ 7.78 (dd, J = 9.4, 3.0 Hz, 1H), 7.67 (d, J = 1.7 Hz, 1H), 7.54 (dd, J = 8.8, 5.1 Hz, 1H), 7.41-7.34 (m, 1H), 6.37 (s, 2H), 6.31 (s, 1H), 6.10 (s, 1H), 5.21 (d, J = 13.6 Hz, 1H), 4.99 (d, J = 13.7 Hz, 1H), 4.30-4.18 (m, 3H), 3.19 (d, J = 16.1 Hz, 1H), 1.19 (m, 1H), 0.54-0.42 (m, 2H), 0.37-0.30 (m, 1H), 0.23 (dd, J = 8.6, 4.0 Hz, 1H).<br>LCMS Method F; $t_R$: 1.19 min; m/z: 452 [M + H] |
| Example 111 | 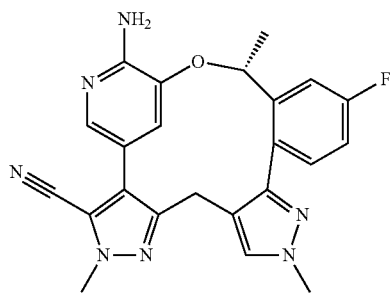 [SMILES: C[C@H]1Oc2cc(cnc2N)-c2c(nn(C)c2C#N)Cc2cn(C)nc2-c2ccc(F)cc21] | (19R)-22-amino-16-fluoro-4,10,19-trimethyl-20-oxa-4,5,10,11,23-pentaazapentacyclo[19.3.1.0²,⁶.0⁸,¹².0¹³,¹⁸]pentacosa-1(24),2,5,8,11,13,15,17,21(25),22-decaene-3-carbonitrile<br>1H NMR (400 MHz, DMSO) δ 7.64 (dd, J = 10.3, 2.6 Hz, 1H), 7.59 (s, 1H), 7.50 (d, J = 1.8 Hz, 1H), 7.26-7.16 (m, 2H), 6.32 (d, J = 1.6 Hz, 1H), 6.08 (s, 2H), 5.32-5.18 (m, 1H), 4.00 (s, 3H), 3.93-3.84 (m, 4H), 2.98 (d, J = 15.3 Hz, 1H), 1.72 (d, J = 6.2 Hz, 3H).<br>LCMS Method F; $t_R$: 0.84 min; m/z: 430 [M + H] |
| Example 112 | 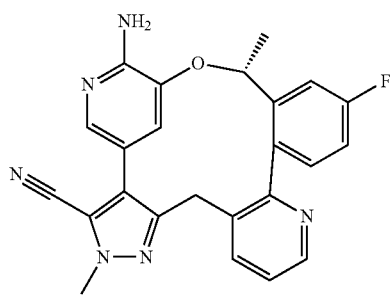 [SMILES: C[C@H]1Oc2cc(cnc2N)-c2c(nn(C)c2C#N)Cc2cccnc2-c2ccc(F)cc21] | (20R)-23-amino-17-fluoro-4,20-dimethyl-21-oxa-4,5,12,24-tetraazapentacyclo[20.3.1.0²,⁶.0⁸,¹³.0¹⁴,¹⁹]hexacosa-1(25),2,5,8(13),9,11,14,16,18,22(26),23-undecaene-3-carbonitrile<br>1H NMR (400 MHz, CDCl3) δ 8.63 (d, J = 4.7 Hz, 1H), 7.95 (d, J = 8.0 Hz, 1H), 7.49 (d, J = 1.6 Hz, 1H), 7.39-7.31 (m, 2H), 7.21-7.17 (m, 1H), 7.14-7.10 (m, 1H), 6.41 (d, J = 1.3 Hz, 1H), 5.24-5.15 (m, 1H), 4.17-4.09 (m, 4H), 3.57 (d, J = 15.5 Hz, 1H), 1.92 (d, J = 6.3 Hz, 3H).<br>LCMS Method H; $t_R$: 0.99 min; m/z: 427 [M + H] |
| Example 113 | 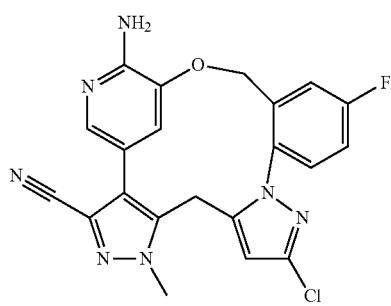 [SMILES: Cn1nc(C#N)c2c1Cc1cc(Cl)nn1-c1ccc(F)cc1COc1cc-2cnc1N] | 22-amino-10-chloro-16-fluoro-5-methyl-20-oxa-4,5,11,12,23-pentaazapentacyclo[19.3.1.0²,⁶.0⁸,¹².0¹³,¹⁸]pentacosa-1(24),2(6),3,8,10,13,15,17,21(25),22-decaene-3-carbonitrile<br>1H NMR (400 MHz, DMSO) δ 7.75 (dd, J = 9.4, 2.9 Hz, 1H), 7.57 (d, J = 1.8 Hz, 1H), 7.51 (dd, J = 8.8, 5.2 Hz, 1H), 7.45-7.37 (m, 1H), 6.69 (s, 1H), 6.17 (s, 2H), 6.07 (d, J = 1.7 Hz, 1H), 5.23 (d, J = 13.8 Hz, 1H), 4.91 (d, J = 14.2 Hz, 1H), 4.47 (d, J = 17.2 Hz, 1H), 4.14 (s, 3H), 3.29-3.26 (m, 1H).<br>LCMS Method H; $t_R$: 1.05 min; m/z: 436 [M + H] |

| Example 114 | 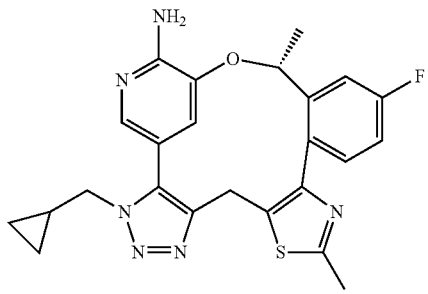 [SMILES: Cc1nc2c(s1)Cc1nnn(CC3CC3)c1-c1cnc(N)c(c1)O[C@H](C)c1cc(F)ccc1-2] | (19R)-3-(cyclopropylmethyl)-16-fluoro-10,19-dimethyl-20-oxa-9-thia-3,4,5,11,23-pentaazapentacyclo[19.3.1.0²,⁶.0⁸,¹².0¹³,¹⁸]pentacosa-1(24),2(6),4,8(12),10,13,15,17,21(25),22-decaen-22-amine<br>1H NMR (400 MHz, DMSO) δ 7.52-7.42 (m, 2H), 7.10 (dd, J = 8.4, 5.9 Hz, 1H), 7.02 (td, J = 8.4, 2.7 Hz, 1H), 6.23 (s, 1H), 5.06 (d, J = 5.0 Hz, 1H), 4.10-3.94 (m, 3H), 3.28 (s, 1H), 2.45 (s, 3H), 1.55 (d, J = 6.2 Hz, 3H), 0.98-0.89 (m, 1H), 0.32-0.21 (m, 2H), 0.12 (dd, J = 9.6, 6.0 Hz, 1H), 0.05--0.05 (m, 1H).<br>LCMS Method F; $t_R$: 1.08 min; m/z: 463 [M + H] |
|---|---|---|
| Example 115 | 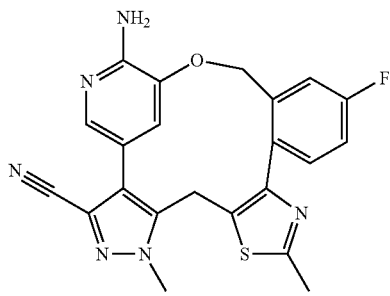 [SMILES: Cc1nc2c(s1)Cc1c(c(C#N)nn1C)-c1cnc(N)c(c1)OCc1cc(F)ccc1-2] | 22-amino-16-fluoro-5,10-dimethyl-20-oxa-9-thia-4,5,11,23-tetraazapentacyclo[19.3.1.0²,⁶.0⁸,¹².0¹³,¹⁸]pentacosa-1(24),2(6),3,8(12),10,13,15,17,21(25),22-decaene-3-carbonitrile<br>1H NMR (400 MHz, DMSO) δ 7.63 (d, J = 9.2 Hz, 1H), 7.54 (d, J = 1.7 Hz, 1H), 7.35-7.25 (m, 2H), 6.33 (d, J = 1.7 Hz, 1H), 6.10 (s, 2H), 5.23 (d, J = 13.2 Hz, 1H), 4.83 (d, J = 12.6 Hz, 1H), 4.47 (d, J = 16.4 Hz, 1H), 4.12 (s, 3H), 3.54 (d, J = 14.7 Hz, 1H), 2.68 (s, 3H).<br>LCMS Method F; $t_R$: 0.94 min; m/z: 433 [M + H] |
| Example 116 | 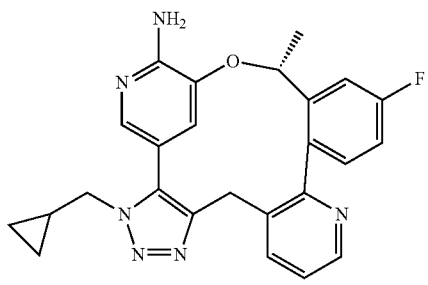 [SMILES: C[C@H]1Oc2cc(cnc2N)-c2c(nnn2CC2CC2)Cc2cccnc2-c2ccc(F)cc21] | (20R)-3-(cyclopropylmethyl)-17-fluoro-20-methyl-21-oxa-3,4,5,12,24-pentaazapentacyclo[20.3.1.0²,⁶.0⁸,¹³.0¹⁴,¹⁹]hexacosa-1(25),2(6),4,8(13),9,11,14,16,18,22(26),23-undecaen-23-amine<br>1H NMR (400 MHz, DMSO) δ 8.57 (dd, J = 4.6, 1.4 Hz, 1H), 7.95 (d, J = 7.2 Hz, 1H), 7.69 (dd, J = 10.4, 2.7 Hz, 1H), 7.63 (d, J = 1.8 Hz, 1H), 7.47 (dd, J = 7.9, 4.7 Hz, 1H), 7.30 (dd, J = 8.5, 5.8 Hz, 1H), 7.18 (td, J = 8.4, 2.7 Hz, 1H), 6.28 (s, 2H), 6.00 (d, J = 1.6 Hz, 1H), 5.17-5.07 (m, 1H), 4.29-4.13 (m, 3H), 3.28 (s, 1H), 1.75 (d, J = 6.2 Hz, 3H), 1.14 (s, 1H), 0.49-0.38 (m, 2H), 0.34-0.27 (m, 1H), 0.18 (dd, J = 8.5, 4.0 Hz, 1H).<br>LCMS Method F; $t_R$: 0.99 min; m/z: 443 [M + H] |
| Example 117 | 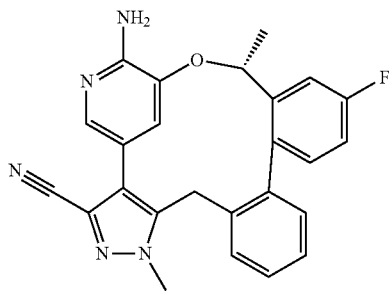 [SMILES: C[C@H]1Oc2cc(cnc2N)-c2c(C#N)nn(C)c2Cc2ccccc2-c2ccc(F)cc21] | (20R)-23-amino-17-fluoro-5,20-dimethyl-21-oxa-4,5,24-triazapentacyclo[20.3.1.0²,⁶.0⁸,¹³.0¹⁴,¹⁹]hexacosa-1(25),2(6),3,8(13),9,11,14,16,18,22(26),23-undecaene-3-carbonitrile<br>1H NMR (400 MHz, DMSO) δ 7.62 (dd, J = 10.3, 2.7 Hz, 1H), 7.57 (s, 1H), 7.50-7.45 (m, 1H), 7.42 (t, J = 7.4 Hz, 1H), 7.33-7.26 (m, 1H), 7.22 (t, J = 7.2 Hz, 2H), 6.13 (d, J = 1.7 Hz, 1H), 6.07 (s, 2H), 4.98 (d, J = 6.7 Hz, 1H), 4.30 (d, J = 16.7 Hz, 1H), 4.18 (s, 3H), 3.36 (s, 1H), 1.77 (d, J = 6.3 Hz, 3H).<br>LCMS Method H; $t_R$: 1.32 min; m/z: 426 [M + H] |
| Example 118 | 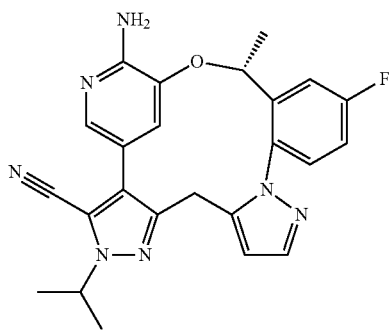 [SMILES: CC(C)n1nc2c(c1C#N)-c1cnc(N)c(c1)O[C@H](C)c1cc(F)ccc1-n1nccc1C2] | (19R)-22-amino-16-fluoro-19-methyl-4-(propan-2-yl)-20-oxa-4,5,11,12,23-pentaazapentacyclo[19.3.1.0²,⁶.0⁸,¹².0¹³,¹⁸]pentacosa-1(24),2,5,8,10,13,15,17,21(25),22-decaene-3-carbonitrile<br>1H NMR (400 MHz, DMSO) δ 7.82-7.69 (m, 2H), 7.56 (d, J = 1.8 Hz, 1H), 7.48 (dd, J = 8.8, 5.2 Hz, 1H), 7.37-7.25 (m, 1H), 6.21 (d, J = 1.1 Hz, 1H), 6.16 (s, 2H), 5.98 (d, J = 1.7 Hz, 1H), 5.20-5.04 (m, 1H), 4.84-4.67 (m, 1H), 4.21 (d, J = 16.1 Hz, 1H), 3.23 (d, J = 15.9 Hz, 1H), 1.73 (d, J = 6.2 Hz, 3H), 1.55 (dd, J = 8.3, 6.7 Hz, 6H).<br>LCMS Method F; $t_R$: 1.18 min; m/z: 444 [M + H] |

| Example 119 | 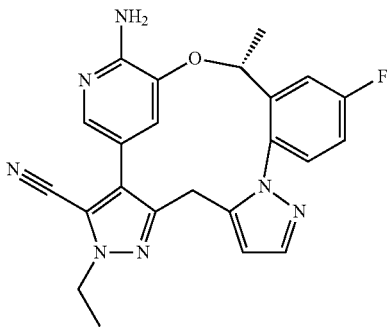 [SMILES: CCn1nc2c(c1C#N)-c1cnc(N)c(c1)O[C@H](C)c1cc(F)ccc1-n1nccc1C2] | (19R)-22-amino-4-ethyl-16-fluoro-19-methyl-20-oxa-4,5,11,12,23-pentaazapentacyclo[19.3.1.0²,⁶.0⁸,¹².0¹³,¹⁸]pentacosa-1(24),2,5,8,10,13,15,17,21(25),22-decaene-3-carbonitrile<br>1H NMR (400 MHz, DMSO) δ 7.77 (dd, J = 9.7, 2.9 Hz, 1H), 7.74 (d, J = 1.8 Hz, 1H), 7.55 (d, J = 1.8 Hz, 1H), 7.49 (dd, J = 8.8, 5.2 Hz, 1H), 7.32 (td, J = 8.3, 3.0 Hz, 1H), 6.24 (d, J = 1.1 Hz, 1H), 6.17 (s, 2H), 5.99 (d, J = 1.6 Hz, 1H), 5.17-5.04 (m, 1H), 4.35 (q, J = 7.2 Hz, 2H), 4.21 (d, J = 16.3 Hz, 1H), 3.23 (d, J = 15.9 Hz, 1H), 1.73 (d, J = 6.2 Hz, 3H), 1.48 (t, J = 7.3 Hz, 3H).<br>LCMS Method F; $t_R$: 1.02 min; m/z: 430 [M + H] |
|---|---|---|
| Example 120 | 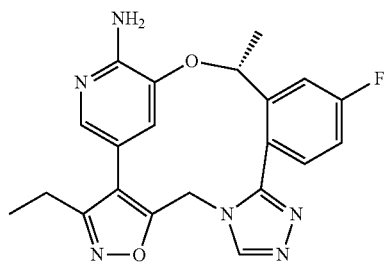 [SMILES: CCc1noc2c1-c1cnc(N)c(c1)O[C@H](C)c1cc(F)ccc1-c1nncn1C2] | (19R)-3-ethyl-16-fluoro-19-methyl-5,20-dioxa-4,8,10,11,23-pentaazapentacyclo[19.3.1.0²,⁶.0⁸,¹².0¹³,¹⁸]pentacosa-1(24),2(6),3,9,11,13,15,17,21(25),22-decaen-22-amine<br>1H NMR (400 MHz, MeOD) δ 8.74 (s, 1H), 7.70 (dd, J = 10.0, 2.7 Hz, 1H), 7.53-7.38 (m, 2H), 7.26 (td, J = 8.2, 2.7 Hz, 1H), 5.86 (d, J = 1.7 Hz, 1H), 5.57-5.50 (m, 1H), 5.47 (d, J = nce15.6 Hz, 1H), 4.79 (d, J = 15.6 Hz, 1H), 2.87-2.61 (m, 2H), 1.88 (d, J = 6.3 Hz, 4H), 1.26-1.14 (m, 4H).<br>LCMS Method F; $t_R$: 0.85 min; m/z: 407 [M + H] |
| Example 121 | 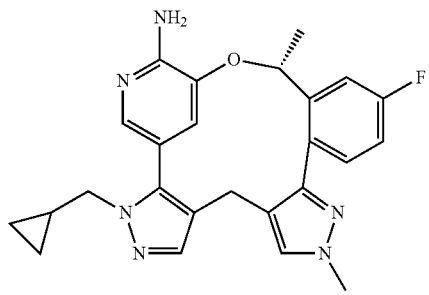 | (19R)-3-(cyclopropylmethyl)-16-fluoro-10,19-dimethyl-20-oxa-3,4,10,11,23-pentaazapentacyclo[19.3.1.0²,⁶.0⁸,¹².0¹³,¹⁸]pentacosa-1(24),2(6),4,8,11,13,15,17,21(25),22-decaen-22-amine<br>1H NMR (400 MHz, DMSO) δ 7.68 (d, J = 9.9 Hz, 1H), 7.58 (d, J = 10.2 Hz, 2H), 7.45 (d, J = 1.7 Hz, 1H), 7.16-7.09 (m, 2H), 6.27 (d, J = 1.4 Hz, 1H), 6.07 (s, 2H), 5.32 (d, J = 4.6 Hz, 1H), 3.95 (dd, J = 14.4, 6.1 Hz, 1H), 3.86-3.77 (m, 4H), 3.58 (d, J = 15.6 Hz, 1H), 2.70 (d, J = 15.4 Hz, 1H), 1.70 (d, J = 6.2 Hz, 3H), 1.13-1.01 (m, 1H), 0.44-0.32 (m, 2H), 0.23 (td, J = 9.1, 4.9 Hz, 1H), 0.06 (td, J = 9.2, 5.0 Hz, 1H).<br>LCMS Method F; $t_R$: 0.79 min; m/z: 445 [M + H] |
| Example 122 | 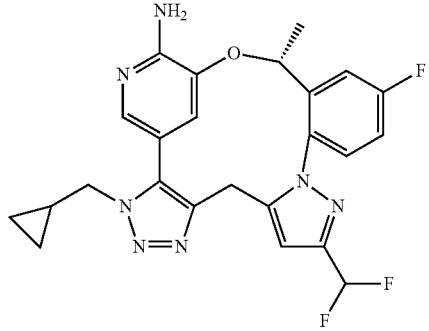 [SMILES: C[C@H]1Oc2cc(cnc2N)-c2c(nnn2CC2CC2)Cc2cc(C(F)F)nn2-c2ccc(F)cc21] | (19R)-3-(cyclopropylmethyl)-10-(difluoromethyl)-16-fluoro-19-methyl-20-oxa-3,4,5,11,12,23-hexaazapentacyclo[19.3.1.0²,⁶.0⁸,¹².0¹³,¹⁸]pentacosa-1(24),2(6),4,8,10,13,15,17,21(25),22-decaen-22-amine<br>1H NMR (400 MHz, DMSO-d6) δ 7.86 (dd, J = 9.9, 2.9 Hz, 1H),7.65 (d, J = 1.8 Hz, 1H), 7.55 (dd, J = 8.8, 5.1 Hz, 1H), 7.37-7.30 (m, 1H), 7.04 (t, J = 54.6 Hz, 1H), 6.45 (s, 1H), 6.36 (s, 2H), 5.98 (s, 1H), 5.13 (d, J = 6.1 Hz, 1H), 4.30 (s, 1H), 4.22 (dd, J = 12.3, 7.0 Hz, 2H), 3.17 (s, 1H), 1.72 (d, J = 6.2 Hz, 3H), 1.17 (s, 1H), 0.50-0.43 (m, 2H), 0.36-0.30 (m, 1H), 0.20 (s, 1H).<br>LCMS Method H; $t_R$: 1.12 min; m/z: 482 [M + H] |
| Example 123 | 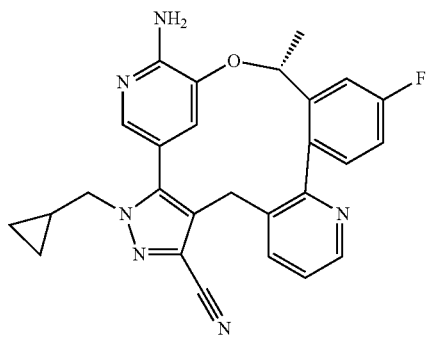 [SMILES: C[C@H]1Oc2cc(cnc2N)-c2c(c(C#N)nn2CC2CC2)Cc2cccnc2-c2ccc(F)cc21] | (20R)-23-amino-3-(cyclopropylmethyl)-17-fluoro-20-methyl-21-oxa-3,4,12,24-tetraazapentacyclo[20.3.1.0²,⁶.0⁸,¹³.0¹⁴,¹⁹]hexacosa-1(25),2(6),4,8(13),9,11,14,16,18,22(26),23-undecaene-5-carbonitrile<br>1H NMR (400 MHz, DMSO) δ 8.63 (dd, J = 4.6, 1.2 Hz, 1H), 7.65 (dd, J = 10.3, 2.7 Hz, 1H), 7.61 (d, J = 7.3 Hz, 1H), 7.57 (d, J = 1.8 Hz, 1H), 7.48 (dd, J = 8.0, 4.7 Hz, 1H), 7.35 (dd, J = 8.5, 5.8 Hz, 1H), 7.24 (td, J = 8.4, 2.7 Hz, 1H), 6.07 (s, 2H), 6.01 (d, J = 1.7 Hz, 1H), 4.97-4.90 (m, 1H), 4.45 (d, J = 16.8 Hz, 1H), 4.40 (d, J = 7.1 Hz, 2H), 3.38 (d, J = 16.7 Hz, 1H), 1.73 (d, J = 6.2 Hz, 3H), 1.43-1.36 (m, 1H), 0.63-0.41 (m, 4H).<br>LCMS Method F; $t_R$: 1.08 min; m/z: 467 [M + H] |

| Example 124 | 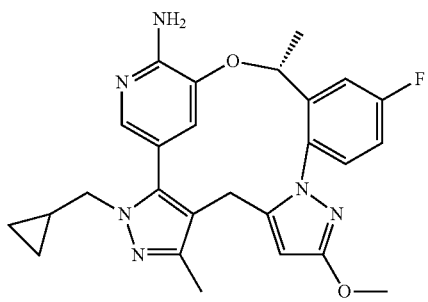 [SMILES: COc1cc2n(n1)-c1ccc(F)cc1[C@@H](C)Oc1cc(cnc1N)-c1c(c(C)nn1CC1CC1)C2] | (19R)-3-(cyclopropylmethyl)-16-fluoro-10-methoxy-5,19-dimethyl-20-oxa-3,4,11,12,23-pentaazapentacyclo[19.3.1.0²,⁶.0⁸,¹².0¹³,¹⁸]pentacosa-1(24),2(6),4,8,10,13,15,17,21(25),22-decaen-22-amine<br>1H NMR (400 MHz, DMSO) δ 7.78 (dd, J = 9.8, 3.0 Hz, 1H), 7.47 (d, J = 1.7 Hz, 1H), 7.35 (dd, J = 8.7, 5.3 Hz, 1H), 7.26-7.17 (m, 1H), 6.22 (d, J = 1.5 Hz, 1H), 6.15 (s, 2H), 5.67 (s, 1H), 5.32-5.22 (m, 1H), 3.95 (dd, J = 14.4, 6.0 Hz, 1H), 3.84-3.69 (m, 5H), 2.30 (s, 3H), 2.78 (d, J = 16.3 Hz, 1H), 1.71 (d, J = 6.2 Hz, 3H), 1.13-1.03 (m, 1H), 0.49-0.29 (m, 2H), 0.28-0.17 (m, 1H), 0.10-0.00 (m, 1H).<br>LCMS Method F; $t_R$: 1.17 min; m/z: 475 [M + H] |
| --- | --- | --- |
| Example 125 | 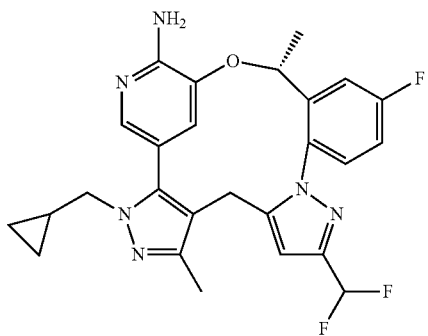 [SMILES: Cc1nn(CC2CC2)c2c1Cc1cc(C(F)F)nn1-c1ccc(F)cc1[C@@H](C)Oc1cc-2cnc1N] | (19R)-3-(cyclopropylmethyl)-10-(difluoromethyl)-16-fluoro-5,19-dimethyl-20-oxa-3,4,11,12,23-pentaazapentacyclo[19.3.1.0²,⁶.0⁸,¹².0¹³,¹⁸]pentacosa-1(24),2(6),4,8,10,13,15,17,21(25),22-decaen-22-amine<br>1H NMR (400 MHz, MeOD) δ 7.67 (dd, J = 9.5, 2.9 Hz, 1H), 7.48 (d, J = 1.8 Hz, 1H), 7.38 (dd, J = 8.7, 5.1 Hz, 1H), 7.24-7.16 (m, 1H), 6.79 (t, J = 56 Hz, 1H), 6.44 (s, 1H), 6.24 (d, J = 1.7 Hz, 1H), 5.23 (d, J = 4.4 Hz, 1H), 4.04 (dd, J = 14.6, 6.1 Hz, 1H), 3.94-3.86 (m, 2H), 3.08 (d, J = 16.6 Hz, 1H), 2.45 (s, 3H), 1.80 (d, J = 6.3 Hz, 3H), 1.12 (s, 1H), 0.46 (dd, J = 19.1, 10.8 Hz, 2H), 0.27 (dd, J = 9.6, 4.7 Hz, 1H), 0.08 (dd, J = 9.8, 4.6 Hz, 1H).<br>LCMS Method H; $t_R$: 1.39 min; m/z: 495 [M + H] |
| Example 126 | 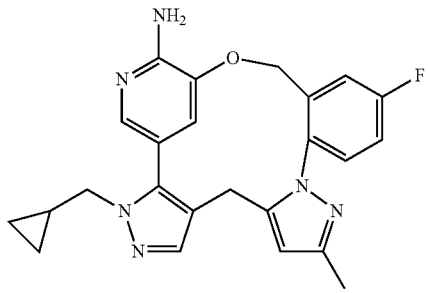 [SMILES: Cc1cc2n(n1)-c1ccc(F)cc1COc1cc(cnc1N)-c1c(cnn1CC1CC1)C2] | 3-(cyclopropylmethyl)-16-fluoro-10-methyl-20-oxa-3,4,11,12,23-pentaazapentacyclo[19.3.1.0²,⁶.0⁸,¹².0¹³,¹⁸]pentacosa-1(24),2(6),4,8,10,13,15,17,21(25),22-decaen-22-amine<br>1H NMR (400 MHz, DMSO) δ 7.75 (dd, J = 9.5, 2.8 Hz, 1H), 7.63 (s, 1H), 7.53 (d, J = 1.8 Hz, 1H), 7.37-7.24 (m, 2H), 6.18 (s, 2H), 6.10 (d, J = 1.6 Hz, 1H), 6.04 (s, 1H), 5.13 (d, J = 13.5 Hz, 1H), 4.98 (d, J = 14.3 Hz, 1H), 4.02 (dd, J = 14.4, 6.1 Hz, 1H), 3.93-3.78 (m, 2H), 2.95-2.83 (m, 1H), 2.20 (s, 3H), 1.18-1.05 (m, 1H), 0.49-0.34 (m, 2H), 0.32-0.21 (m, 1H), 0.18-0.07 (m, 1H).<br>LCMS Method F; $t_R$: 0.68 min; m/z: 431 [M + H] |
| Example 127 | 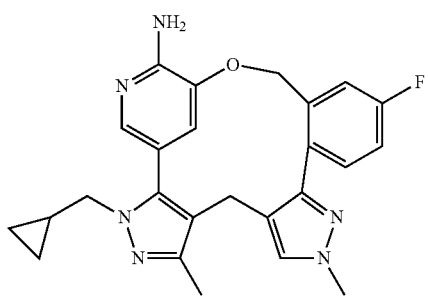 [SMILES: Cc1nn(CC2CC2)c2c1Cc1cn(C)nc1-c1ccc(F)cc1COc1cc-2cnc1N] | 3-(cyclopropylmethyl)-16-fluoro-5,10-dimethyl-20-oxa-3,4,10,11,23-pentaazapentacyclo[19.3.1.0²,⁶.0⁸,¹².0¹³,¹⁸]pentacosa-1(24),2(6),4,8,11,13,15,17,21(25),22-decaen-22-amine<br>1H NMR (400 MHz, MeOD) δ 7.54 (d, J = 7.6 Hz, 2H), 7.42 (s, 1H), 7.26-7.20 (m, 1H), 7.11 (dd, J = 9.7, 7.3 Hz, 1H), 6.48 (s, 1H), 5.17 (s, 2H), 3.99-3.94 (m, 1H), 3.92 (s, 3H), 3.89-3.85 (m, 1H), 3.59 (s, 1H), 2.91 (d, J = 15.8 Hz, 1H), 2.44 (s, 3H), 1.06 (s, 1H), 0.49-0.43 (m, 1H), 0.37 (d, J = 4.7 Hz, 1H), 0.24 (dd, J = 9.8, 4.8 Hz, 1H), 0.06-0.02 (m, 1H).<br>LCMS Method F; $t_R$: 0.93 min; m/z: 445 [M + H] |
| Example 128 | 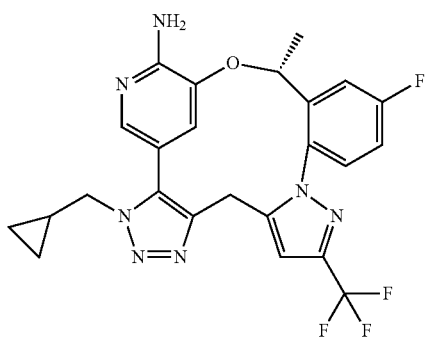 [SMILES: C[C@H]1Oc2cc(cnc2N)-c2c(nnn2CC2CC2)Cc2cc(C(F)(F)F)nn2-c2ccc(F)cc21] | (19R)-3-(cyclopropylmethyl)-16-fluoro-19-methyl-10-(trifluoromethyl)-20-oxa-3,4,5,11,12,23-hexaazapentacyclo[19.3.1.0²,⁶.0⁸,¹².0¹³,¹⁸]pentacosa-1(24),2(6),4,8,10,13,15,17,21(25),22-decaen-22-amine<br>1H NMR (400 MHz, DMSO) δ 7.89 (dd, J = 9.7, 2.9 Hz, 1H), 7.65 (d, J = 1.8 Hz, 1H), 7.60 (dd, J = 8.8, 5.2 Hz, 1H), 7.37 (td, J = 8.3, 2.9 Hz, 1H), 6.67 (s, 1H), 6.38 (s, 2H), 6.01 (d, J = 1.6 Hz, 1H), 5.11 (d, J = 4.8 Hz, 1H), 4.31 (d, J = 15.9 Hz, 1H), 4.22 (ddd, J = 21.9, 14.6, 7.6 Hz, 2H), 3.22 (d, J = 16.2 Hz, 1H), 1.72 (d, J = 6.2 Hz, 3H), 1.18 (m, 1H), 0.56-0.38 (m, 2H), 0.33 (dd, J = 8.7, 4.1 Hz, 1H), 0.21 (dd, J = 8.8, 4.1 Hz, 1H).<br>LCMS Method G; $t_R$: 2.92 min; m/z: 500 [M + H] |

| Example 129 | 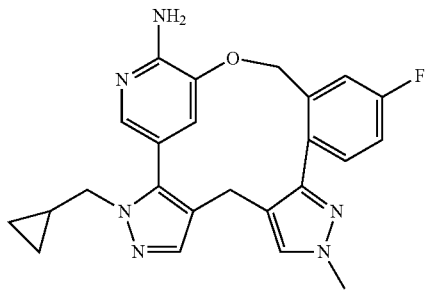 [SMILES: Cn1cc2c(n1)-c1ccc(F)cc1COc1cc(cnc1N)-c1c(cnn1CC1CC1)C2] | 3-(cyclopropylmethyl)-16-fluoro-10-methyl-20-oxa-3,4,10,11,23-pentaazapentacyclo[19.3.1.0$^{2,6}$.0$^{8,12}$.0$^{13,18}$]pentacosa-1(24),2(6),4,8,11,13,15,17,21(25),22-decaen-22-amine<br>1H NMR (400 MHz, DMSO-d6) δ 7.64 (d, J = 9.5 Hz, 1H), 7.58 (d, J = 1.8 Hz, 2H), 7.47 (d, J = 1.7 Hz, 1H), 7.17 (d, J = 6.7 Hz, 2H), 6.28 (d, J = 1.9 Hz, 1H), 6.08 (s, 2H), 5.07 (q, J = 13.1 Hz, 2H), 3.96 (dd, J = 14.4, 6.1 Hz, 1H), 3.84 (s, 3H), 3.79 (d, J = 7.5 Hz, 1H), 3.59 (d, J = 15.4 Hz, 1H), 2.74 (d, J = 15.4 Hz, 1H), 1.07 (d, J = 15.5 Hz, 1H), 0.40 (ddd, J = 15.9, 8.8, 4.9 Hz, 2H), 0.24 (dt, J = 9.0, 4.9 Hz, 1H), 0.09 (dd, J = 8.8, 4.4 Hz, 1H).<br>LCMS Method F; t$_R$: 0.99 min; m/z: 431 [M + H] |
|---|---|---|
| Example 130 | 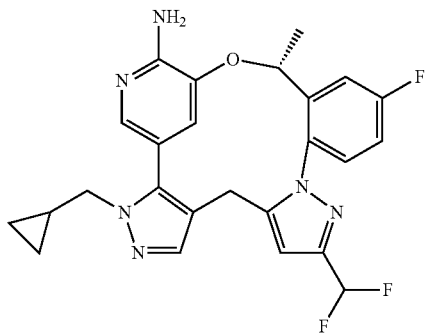 [SMILES: C[C@H]1Oc2cc(cnc2N)-c2c(cnn2CC2CC2)Cc2cc(C(F)F)nn2-c2ccc(F)cc21] | (19R)-3-(cyclopropylmethyl)-10-(difluoromethyl)-16-fluoro-19-methyl-20-oxa-3,4,11,12,23-pentaazapentacyclo[19.3.1.0$^{2,6}$.0$^{8,12}$.0$^{13,18}$]pentacosa-1(24),2(6),4,8,10,13,15,17,21(25),22-decaen-22-amine<br>1H NMR (400 MHz, DMSO) δ 7.88 (dd, J = 9.8, 2.9 Hz, 1H), 7.71 (s, 1H), 7.53 (d, J = 1.7 Hz, 1H), 7.46 (dd, J = 8.7, 5.2 Hz, 1H), 7.31 (td, J = 8.5, 2.9 Hz, 1H), 7.10 (t, J = 54.7 Hz, 1H), 6.52 (s, 1H), 6.24 (s, 2H), 6.03 (s, 1H), 5.11 (d, J = 6.1 Hz, 1H), 3.94 (ddd, J = 39.9, 14.4, 7.8 Hz, 3H), 2.91 (d, J = 16.2 Hz, 1H), 1.72 (d, J = 6.2 Hz, 3H), 1.11 (d, J = 6.0 Hz, 1H), 0.48-0.35 (m, 2H), 0.26 (dd, J = 9.1, 4.2 Hz, 1H), 0.10 (dd, J = 9.2, 4.5 Hz, 1H).<br>LCMS Method F; t$_R$: 1.49 min; m/z: 481 [M + H] |
| Example 131 | 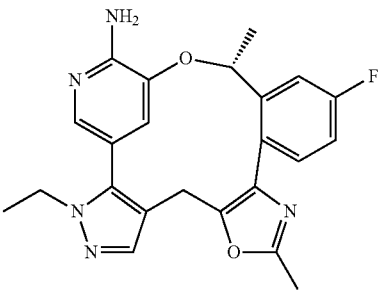 [SMILES: CCn1ncc2c1-c1cnc(N)c(c1)O[C@H](C)c1cc(F)ccc1-c1nc(C)oc1C2] | (19R)-3-ethyl-16-fluoro-10,19-dimethyl-9,20-dioxa-3,4,11,23-tetraazapentacyclo[19.3.1.0$^{2,6}$.0$^{8,12}$.0$^{13,18}$]pentacosa-1(24),2(6),4,8(12),10,13,15,17,21(25),22-decaen-22-amine<br>1H NMR (400 MHz, DMSO) δ 7.87 (s, 1H), 7.69 (s, 1H), 7.68-7.56 (m, 2H), 7.36 (d, J = 1.8 Hz, 1H), 6.91 (td, J = 8.4, 2.8 Hz, 1H), 6.02 (s, 2H), 5.90 (s, 1H), 4.25 (d, J = 16.1 Hz, 1H), 3.98 (dt, J = 13.5, 6.9 Hz, 2H), 3.51 (d, J = 16.5 Hz, 1H), 2.42 (s, 3H), 1.67 (d, J = 6.1 Hz, 3H), 1.25 (t, J = 7.2 Hz, 3H).<br>LCMS Method F; t$_R$: 0.79 min; m/z: 420 [M + H] |
| Example 132 | 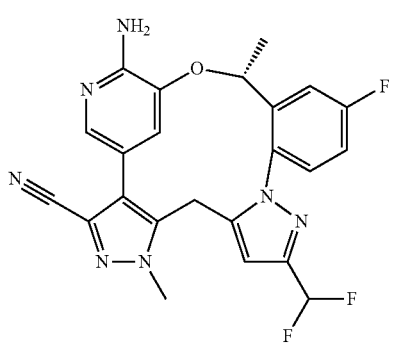 [SMILES: C[C@H]1Oc2cc(cnc2N)-c2c(C#N)nn(C)c2Cc2cc(C(F)F)nn2-c2ccc(F)cc21] | (19R)-22-amino-10-(difluoromethyl)-16-fluoro-5,19-dimethyl-20-oxa-4,5,11,12,23-pentaazapentacyclo[19.3.1.0$^{2,6}$.0$^{8,12}$.0$^{13,18}$]pentacosa-1(24),2(6),3,8,10,13,15,17,21(25),22-decaene-3-carbonitrile<br>1H NMR (400 MHz, DMSO) δ 7.84 (d, J = 6.8 Hz, 1H), 7.55 (d, J = 1.8 Hz, 2H), 7.39 (td, J = 8.3, 3.0 Hz, 1H), 7.07 (t, J = 54.4 Hz, 1H), 6.82 (s, 1H), 6.17 (s, 2H), 5.96 (d, J = 1.7 Hz, 1H), 5.06 (d, J = 5.0 Hz, 1H), 4.49 (d, J = 17.2 Hz, 1H), 4.15 (s, 3H), 3.26 (s, 1H), 1.72 (d, J = 6.2 Hz, 3H).<br>LCMS Method F; t$_R$: 0.95 min; m/z: 466 [M + H] |
| Example 133 | 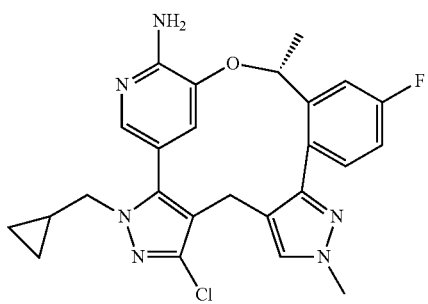 [SMILES: C[C@H]1Oc2cc(cnc2N)-c2c(c(Cl)nn2CC2CC2)Cc2cn(C)nc2-c2ccc(F)cc21] | (19R)-5-chloro-3-(cyclopropylmethyl)-16-fluoro-10,19-dimethyl-20-oxa-3,4,10,11,23-pentaazapentacyclo[19.3.1.0$^{2,6}$.0$^{8,12}$.0$^{13,19}$]pentacosa-1(24),2(6),4,8,11,13,15,17,21(25),22-decaen-22-amine<br>1H NMR (400 MHz, DMSO) δ 7.70 (dd, J = 10.3, 2.5 Hz, 1H), 7.60 (s, 1H), 7.49 (d, J = 1.8 Hz, 1H), 7.22-7.11 (m, 2H), 6.26 (s, 1H), 6.21 (s, 2H), 5.32 (d, J = 6.2 Hz, 1H), 3.95 (dd, J = 14.4, 6.2 Hz, 1H), 3.87 (s, 3H), 3.82-3.75 (m, 1H), 3.54 (d, J = 15.6 Hz, 1H), 2.74-2.67 (m, 1H), 1.71 (d, J = 6.3 Hz, 3H), 1.09 (s, 1H), 0.50-0.34 (m, 2H), 0.25 (dd, J = 9.3, 4.4 Hz, 1H), 0.12-0.04 (m, 1H).<br>LCMS Method F; t$_R$: 1.35 min; m/z: 479 [M + H] |

| | | |
|---|---|---|
| Example 134 | 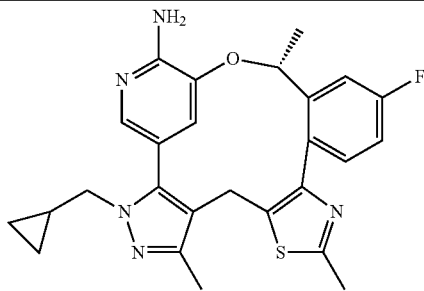 | (19R)-3-(cyclopropylmethyl)-16-fluoro-5,10,19-trimethyl-20-oxa-9-thia-3,4,11,23-tetraazapentacyclo[19.3.1.0$^{2,6}$.0$^{8,12}$.0$^{13,18}$]pentacosa-1(24),2(6),4,8(12),10,13,15,17,21(25),22-decaen-22-amine<br>1H NMR (400 MHz, DMSO) δ 7.65 (dd, J = 10.3, 2.6 Hz, 1H), 7.37 (d, J = 1.7 Hz, 1H), 7.17-7.05 (m, 2H), 6.22 (d, J = 1.6 Hz, 1H), 6.05 (s, 2H), 5.12-5.04 (m, 1H), 3.84 (dd, J = 14.4, 6.0 Hz, 1H), 3.75 (d, J = 15.9 Hz, 1H), 3.68 (dd, J = 14.4, 7.4 Hz, 1H), 3.03 (d, J = 15.9 Hz, 1H), 2.57 (s, 3H), 2.23 (s, 3H), 1.64 (d, J = 6.2 Hz, 3H), 1.06-0.94 (m, 1H), 0.39-0.25 (m, 2H), 0.17-0.10 (m, 1H), −0.01 (dq, J = 9.6, 4.9 Hz, 1H).<br>LCMS Method F; t$_R$: 0.90 min; m/z: 476 [M + H] |
| Example 135 | 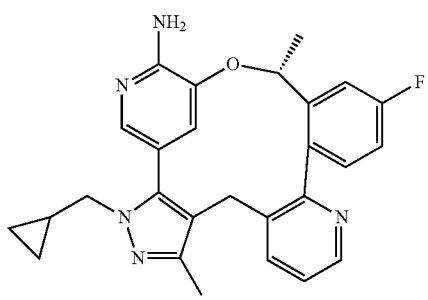 [SMILES: Cc1nn(CC2CC2)c2c1Cc1cccnc1-c1ccc(F)cc1[C@@H](C)Oc1cc-2cnc1N] | (20R)-3-(cyclopropylmethyl)-17-fluoro-5,20-dimethyl-21-oxa-3,4,12,24-tetraazapentacyclo[20.3.1.0$^{2,6}$.0$^{8,13}$.0$^{14,19}$]hexacosa-1(25),2(6),4,8(13),9,11,14,16,18,22(26),23-undecaen-23-amine<br>1H NMR (400 MHz, DMSO) δ 8.60-8.49 (m, 1H), 7.68 (dd, J = 10.3, 2.5 Hz, 2H), 7.48-7.42 (m, 2H), 7.27 (dd, J = 8.5, 5.8 Hz, 1H), 7.15 (td, J = 8.4, 2.7 Hz, 1H), 6.11 (s, 2H), 6.02 (d, J = 1.6 Hz, 1H), 5.04 (d, J = 4.6 Hz, 1H), 3.99 (dd, J = 14.3, 5.9 Hz, 1H), 3.79 (dd, J = 14.6, 7.4 Hz, 2H), 3.02 (d, J = 15.9 Hz, 1H), 2.39 (s, 3H), 1.72 (d, J = 6.2 Hz, 3H), 1.13-1.04 (m, 1H), 0.45-0.31 (m, 2H), 0.22 (td, J = 9.2, 5.0 Hz, 1H), 0.06 (td, J = 9.2, 5.0 Hz, 1H).<br>LCMS Method H; t$_R$: 0.93 min; m/z: 456 [M + H] |
| Example 136 | 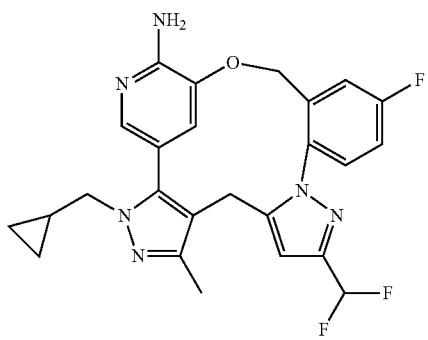 [SMILES: Cc1nn(CC2CC2)c2c1Cc1cc(C(F)F)nn1-c1ccc(F)cc1COc1cc-2cnc1N] | 3-(cyclopropylmethyl)-10-(difluoromethyl)-16-fluoro-5-methyl-20-oxa-3,4,11,12,23-pentaazapentacyclo[19.3.1.0$^{2,6}$.0$^{8,12}$.0$^{13,18}$]pentacosa-1(24),2(6),4,8,10,13,15,17,21(25),22-decaen-22-amine<br>1H NMR (400 MHz, MeOD) δ 7.68 (dd, J = 9.2, 2.9 Hz, 1H), 7.50 (d, J = 1.8 Hz, 1H), 7.41 (dd, J = 8.8, 5.0 Hz, 1H), 7.25 (dd, J = 7.9, 3.0 Hz, 1H), 6.79 (t, J = 54.9 Hz, 1H), 6.44 (s, 1H), 6.20 (d, J = 1.8 Hz, 1H), 5.19 (d, J = 13.8 Hz, 1H), 5.02 (d, J = 15.0 Hz, 1H), 4.03 (d, J = 6.2 Hz, 1H), 3.92 (t, J = 11.4 Hz, 2H), 3.12 (d, J = 16.4 Hz, 1H), 2.45 (s, 3H), 1.12 (s, 1H), 0.47 (d, J = 20.9 Hz, 2H), 0.27 (s, 1H), 0.10 (dt, J = 9.9, 5.0 Hz, 1H).<br>LCMS Method H; t$_R$: 1.07 min; m/z: 481 [M + H] |
| Example 137 | 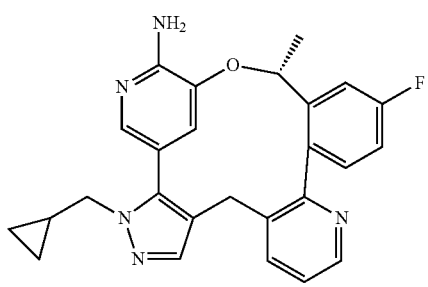 | (20R)-3-(cyclopropylmethyl)-17-fluoro-20-methyl-21-oxa-3,4,12,24-tetraazapentacyclo[20.3.1.0$^{2,6}$.0$^{8,13}$.0$^{14,19}$]hexacosa-1(25),2(6),4,8(13),9,11,14,16,18,22(26),23-undecaen-23-amine<br>1H NMR (400 MHz, DMSO) δ 8.55-8.51 (m, 1H), 7.91 (d, J = 7.2 Hz, 1H), 7.77 (s, 1H), 7.69 (dd, J = 10.4, 2.7 Hz, 1H), 7.49 (d, J = 1.7 Hz, 1H), 7.45 (dd, J = 7.9, 4.7 Hz, 1H), 7.23-7.11 (m, 2H), 6.14 (s, 2H), 6.01 (d, J = 1.5 Hz, 1H), 5.13 (d, J = 6.4 Hz, 1H), 4.02 (dd, J = 14.4, 6.0 Hz, 1H), 3.91-3.78 (m, 2H), 3.09 (d, J = 15.4 Hz, 1H), 1.74 (d, J = 6.2 Hz, 3H), 1.14-1.04 (m, 1H), 0.46-0.31 (m, 2H), 0.23 (dd, J = 9.1, 4.2 Hz, 1H), 0.07 (dt, J = 9.4, 4.7 Hz, 1H).<br>LCMS Method K; t$_R$: 1.05 min; m/z: 442 [M + H] |
| Example 138 | 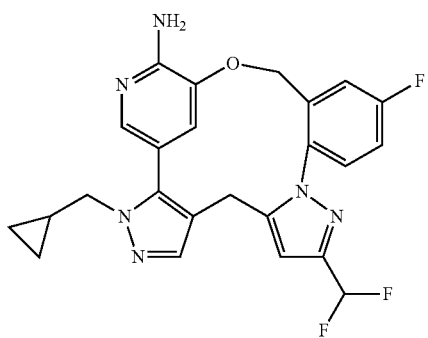 [SMILES: Nc1ncc2cc1OCc1cc(F)ccc1-n1nc(C(F)F)cc1Cc1cnn(CC3CC3)c1-2] | 3-(cyclopropylmethyl)-10-(difluoromethyl)-16-fluoro-20-oxa-3,4,11,12,23-pentaazapentacyclo[19.3.1.0$^{2,6}$.0$^{8,12}$.0$^{13,18}$]pentacosa-1(24),2(6),4,8,10,13,15,17,21(25),22-decaen-22-amine<br>1H NMR (400 MHz, DMSO) δ 7.82 (dd, J = 9.4, 2.9 Hz, 1H), 7.72 (s, 1H), 7.55 (d, J = 1.8 Hz, 1H), 7.49 (dd, J = 8.8, 5.2 Hz, 1H), 7.39-7.31 (m, 1H), 7.03 (t, J = 54.6 Hz, 1H), 6.51 (s, 1H), 6.25 (s, 2H), 6.02 (d, J = 1.7 Hz, 1H), 5.18 (d, J = 13.6 Hz, 1H), 4.89 (d, J = 14.4 Hz, 1H), 4.06-3.84 (m, 3H), 2.95 (d, J = 16.1 Hz, 1H), 1.20-1.07 (m, 1H), 0.51-0.35 (m, 2H), 0.27 (td, J = 9.0, 4.9 Hz, 1H), 0.12 (td, J = 9.2, 5.0 Hz, 1H).<br>LCMS Method H; t$_R$: 0.97 min; m/z: 467 [M + H] |

| Example 139 | 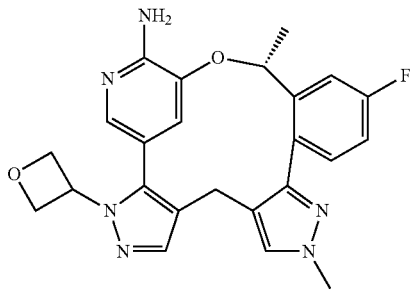 [SMILES: C[C@H]1Oc2cc(cnc2N)-c2c(cnn2C2COC2)Cc2cn(C)nc2-c2ccc(F)cc21] | (19R)-16-fluoro-10,19-dimethyl-3-(oxetan-3-yl)-20-oxa-3,4,10,11,23-pentaazapentacyclo[19.3.1.0$^{2,6}$.0$^{8,12}$.0$^{13,18}$]pentacosa-1(24),2(6),4,8,11,13,15,17,21(25),22-decaen-22-amine<br>1H NMR (400 MHz, DMSO) δ 7.75 (s, 1H), 7.68 (d, J = 10.1 Hz, 1H), 7.58 (s, 1H), 7.24 (d, J = 1.7 Hz, 1H), 7.17-7.12 (m, 2H), 6.27 (s, 1H), 6.15 (s, 2H), 5.47 (t, J = 7.1 Hz, 1H), 5.32 (d, J = 4.7 Hz, 1H), 4.95-4.89 (m, 2H), 4.87 (t, J = 6.4 Hz, 1H), 4.64 (dd, J = 7.6, 6.1 Hz, 1H), 3.85 (d, J = 4.9 Hz, 3H), 3.62 (d, J = 15.7 Hz, 1H), 2.71 (d, J = 15.4 Hz, 1H), 1.70 (d, J = 6.2 Hz, 3H).<br>LCMS Method L; t$_R$: 2.03 min; m/z: 447 [M + H] |
|---|---|---|
| Example 140 | 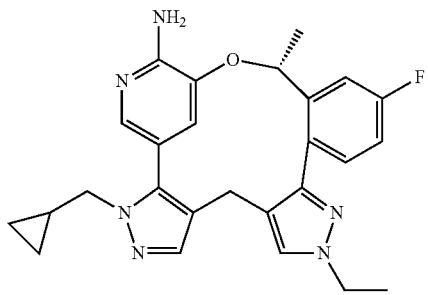 [SMILES: CCn1cc2c(n1)-c1ccc(F)cc1[C@@H](C)Oc1cc(cnc1N)-c1c(cnn1CC1CC1)C2] | (19R)-3-(cyclopropylmethyl)-10-ethyl-16-fluoro-19-methyl-20-oxa-3,4,10,11,23-pentaazapentacyclo[19.3.1.0$^{2,6}$.0$^{8,12}$.0$^{13,18}$]pentacosa-1(24),2(6),4,8,11,13,15,17,21(25),22-decaen-22-amine<br>1H NMR (400 MHz, DMSO) δ 7.69 (dd, J = 10.3, 2.0 Hz, 1H), 7.63 (s, 1H), 7.57 (s, 1H), 7.45 (d, J = 1.7 Hz, 1H), 7.19-7.09 (m, 2H), 6.25 (s, 1H), 6.07 (s, 2H), 5.28 (d, J = 8.2 Hz, 1H), 4.14 (q, J = 7.2 Hz, 2H), 3.96 (dd, J = 14.2, 6.0 Hz, 1H), 3.81 (dd, J = 14.4, 7.3 Hz, 1H), 3.59 (d, J = 15.6 Hz, 1H), 2.72 (d, J = 15.5 Hz, 1H), 1.71 (d, J = 6.2 Hz, 3H), 1.37 (t, J = 7.2 Hz, 3H), 1.08 (t, J = 11.7 Hz, 1H), 0.39 (dd, J = 24.4, 8.6 Hz, 2H), 0.26-0.18 (m, 1H), 0.08 (t, J = 9.1 Hz, 1H).<br>LCMS Method F; t$_R$: 1.10 min; m/z: 459 [M + H] |
| Example 141 | 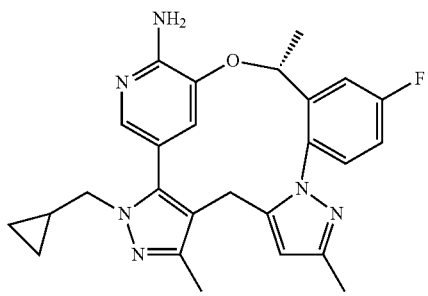 [SMILES: Cc1cc2n(n1)-c1ccc(F)cc1[C@@H](C)Oc1cc(cnc1N)-c1c(c(C)nn1CC1CC1)C2] | (19R)-3-(cyclopropylmethyl)-16-fluoro-5,10,19-trimethyl-20-oxa-3,4,11,12,23-pentaazapentacyclo[19.3.1.0$^{2,6}$.0$^{8,10}$.0$^{13,18}$]pentacosa-1(24),2(6),4,8,10,13,15,17,21(25),22-decaen-22-amine<br>1H NMR (400 MHz, DMSO) δ 7.79 (dd, J = 9.8, 2.9 Hz, 1H), 7.47 (d, J = 1.7 Hz, 1H), 7.32 (dd, J = 8.7, 5.3 Hz, 1H), 7.23 (td, J = 8.3, 2.9 Hz, 1H), 6.15 (s, 2H), 6.11 (d, J = 1.5 Hz, 1H), 6.02 (s, 1H), 5.18 (d, J = 4.7 Hz, 1H), 3.94 (dd, J = 14.4, 6.0 Hz, 1H), 3.83-3.71 (m, 2H), 2.80 (d, J = 16.2 Hz, 1H), 2.32 (s, 3H), 2.20 (s, 3H), 1.70 (d, J = 6.2 Hz, 3H), 1.14-1.03 (m, 1H), 0.45-0.32 (m, 2H), 0.27-0.18 (m, 1H), 0.12-0.03 (m, 1H).<br>LCMS Method H; t$_R$: 1.04 min; m/z: 459 [M + H] |
| Example 142 | 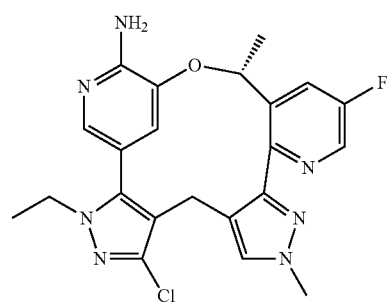 | (19R)-5-chloro-3-ethyl-16-fluoro-10,19-dimethyl-20-oxa-3,4,10,11,14,23-hexaazapentacyclo[19.3.1.0$^{2,6}$.0$^{8,12}$.0$^{13,18}$]pentacosa-1(24),2(6),4,8,11,13,15,17,21(25),22-decaen-22-amine<br>1H NMR (400 MHz, MeOD) δ 8.46 (d, J = 2.8 Hz, 1H), 8.12 (dd, J = 9.3, 2.8 Hz, 1H), 7.60 (s, 1H), 7.45 (s, 1H), 6.48 (d, J = 1.6 Hz, 1H), 5.61-5.44 (m, 1H), 4.19-3.98 (m, 2H), 3.95 (s, 3H), 3.71 (d, J = 16.0 Hz, 1H), 2.87 (d, J = 16.0 Hz, 1H), 1.86 (d, J = 6.3 Hz, 3H), 1.31 (t, J = 7.2 Hz, 3H).<br>LCMS Method H; t$_R$: 1.02 min; m/z: 454 [M + H] |
| Example 143 | 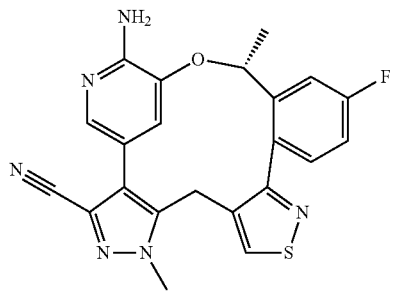 [SMILES: C[C@H]1Oc2cc(cnc2N)-c2c(C#N)nn(C)c2Cc2csnc2-c2ccc(F)cc21] | (19R)-22-amino-16-fluoro-5,19-dimethyl-20-oxa-10-thia-4,5,11,23-tetraazapentacyclo[19.3.1.0$^{2,6}$.0$^{8,12}$.0$^{13,18}$]pentacosa-1(24),2(6),3,8,11,13,15,17,21(25),22-decaene-3-carbonitrile<br>1H NMR (400 MHz, DMSO) δ 9.11 (s, 1H), 7.71 (dd, J = 10.3, 2.5 Hz, 1H), 7.52 (d, J = 1.7 Hz, 1H), 7.38-7.22 (m, 2H), 6.10 (s, 2H), 5.87 (s, 1H), 5.07-4.93 (m, 1H), 4.39-4.24 (d, J = 16.7 Hz, 1H), 4.19 (s, 3H), 3.27 (d, J = 16.7 Hz, 1H), 1.74 (t, J = 6.1 Hz, 3H).<br>LCMS Method K; t$_R$: 1.09 min; m/z: 433 [M + H] |

| Example 144 | 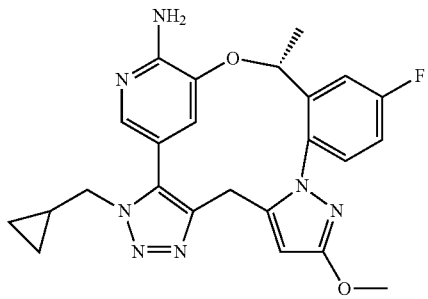 [SMILES: COc1cc2n(n1)-c1ccc(F)cc1[C@@H](C)Oc1cc(cnc1N)-c1c(nnn1CC1CC1)C2] | (19R)-3-(cyclopropylmethyl)-16-fluoro-10-methoxy-19-methyl-20-oxa-3,4,5,11,12,23-hexaazapentacyclo[19.3.1.0²,⁶.0⁸,¹².0¹³,¹⁸]pentacosa-1(24),2(6),4,8,10,13,15,17,21(25),22-decaen-22-amine
1H NMR (400 MHz, DMSO) δ 7.78 (dd, J = 9.7, 2.9 Hz, 1H), 7.63 (d, J = 1.6 Hz, 1H), 7.41 (dd, J = 8.7, 5.2 Hz, 1H), 7.32-7.19 (m, 1H), 6.31 (s, 2H), 6.17 (s, 1H), 5.68 (s, 1H), 5.39-5.28 (m, 1H), 4.32-4.10 (m, 3H), 3.79 (s, 3H), 3.11 (d, J = 16.0 Hz, 1H), 1.73 (d, J = 6.2 Hz, 3H), 1.22-1.07 (m, 1H), 0.52-0.37 (m, 2H), 0.34-0.26 (m, 1H), 0.23-0.12 (m, 1H).
LCMS Method F; $t_R$: 1.07 min; m/z: 462 [M + H] |
| Example 145 | 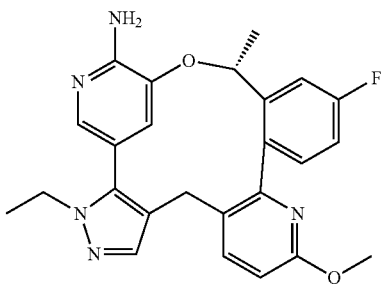 [SMILES: CCn1ncc2c1-c1cnc(N)c(c1)O[C@H](C)c1cc(F)ccc1-c1nc(OC)ccc1C2] | (20R)-3-ethyl-17-fluoro-11-methoxy-20-methyl-21-oxa-3,4,12,24-tetraazapentacyclo[20.3.1.0²,⁶.0⁸,¹³.0¹⁴,¹⁹]hexacosa-1(25),2(6),4,8(13),9,11,14,16,18,22(26),23-undecaen-23-amine
1H NMR (400 MHz, DMSO-d6) δ 7.78 (d, J = 8.7 Hz, 1H), 7.74 (s, 1H), 7.69 (dd, J = 10.4, 2.7 Hz, 1H), 7.45 (d, J = 1.8 Hz, 1H), 7.21 (dd, J = 8.5, 5.9 Hz, 1H), 7.14 (td, J = 8.5, 2.7 Hz, 1H), 6.88 (d, J = 8.6 Hz, 1H), 6.17 (d, J = 1.9 Hz, 1H), 6.12 (s, 2H), 5.27 (d, J = 6.3 Hz, 1H), 4.09-4.00 (m, 2H), 3.82 (s, 3H), 3.73 (d, J = 15.4 Hz, 1H), 3.06 (d, J = 15.3 Hz, 1H), 1.78 (d, J = 6.2 Hz, 3H), 1.26 (t, J = 7.2 Hz, 3H).
LCMS Method H; $t_R$: 1.13 min; m/z: 446 [M + H] |
| Example 146 | 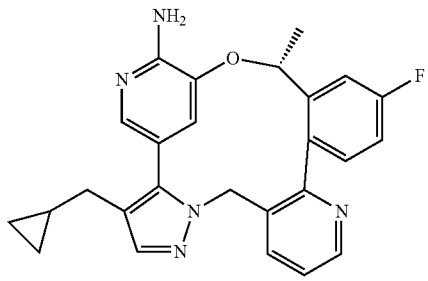 [SMILES: C[C@H]1Oc2cc(cnc2N)-c2c(CC3CC3)cnn2Cc2cccnc2-c2ccc(F)cc21] | (20R)-3-(cyclopropylmethyl)-17-fluoro-20-methyl-21-oxa-5,6,12,24-tetraazapentacyclo[20.3.1.0²,⁶.0⁸,¹³.0¹⁴,¹⁹]hexacosa-1(25),2,4,8(13),9,11,14,16,18,22(26),23-undecaen-23-amine
1H NMR (400 MHz, DMSO) δ 8.64 (dd, J = 4.7, 1.4 Hz, 1H), 8.22 (d, J = 8.1 Hz, 1H), 7.72 (dd, J = 10.4, 2.6 Hz, 1H), 7.58 (s, 1H), 7.51 (dd, J = 8.0, 4.7 Hz, 1H), 7.40 (d, J = 1.8 Hz, 1H), 7.26 (d, J = 8.5, 5.8 Hz, 1H), 7.15 (td, J = 8.4, 2.7 Hz, 1H), 6.14 (s, 2H), 6.05 (d, J = 1.6 Hz, 1H), 5.41 (d, J = 16.0 Hz, 1H), 5.15 (dd, J = 6.3, 1.7 Hz, 1H), 4.45 (d, J = 15.9 Hz, 1H), 2.29 (ddd, J = 39.9, 15.2, 6.7 Hz, 2H), 1.75 (d, J = 6.2 Hz, 3H), 0.92-0.78 (m, 1H), 0.47-0.32 (m, 2H), 0.15--0.03 (m, 2H).
LCMS Method H; $t_R$: 1.23 min; m/z: 442 [M + H] |
| Example 147 | 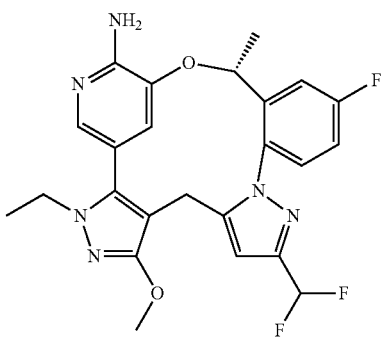 [SMILES: CCn1nc(OC)c2c1-c1cnc(N)c(c1)O[C@H](C)c1cc(F)ccc1-n1nc(C(F)F)cc1C2] | (19R)-10-(difluoromethyl)-3-ethyl-16-fluoro-5-methoxy-19-methyl-20-oxa-3,4,11,12,23-pentaazapentacyclo[19.3.1.0²,⁶.0⁸,¹².0¹³,¹⁸]pentacosa-1(24),2(6),4,8,10,13,15,17,21(25),22-decaen-22-amine
1H NMR (400 MHz, DMSO) δ 7.86 (dd, J = 9.8, 2.9 Hz, 1H), 7.54-7.47 (m, 2H), 7.34-7.27 (m, 1H), 7.04 (t, J = 54.6 Hz, 1H), 6.47 (s, 2H), 6.41 (s, 1H), 6.06 (d, J = 1.4 Hz, 1H), 5.10 (s, 1H), 3.94 (m, 5H), 3.79 (d, J = 16.5 Hz, 1H), 2.77 (d, J = 16.2 Hz, 1H), 1.71 (d, J = 6.2 Hz, 3H), 1.26 (t, J = 7.1 Hz, 3H).
LCMS Method H; $t_R$: 1.42 min; m/z: 485 [M + H] |
| Example 148 | 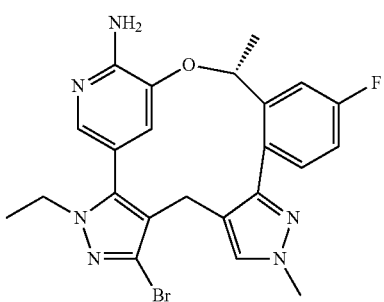 | (19R)-5-bromo-3-ethyl-16-fluoro-10,19-dimethyl-20-oxa-3,4,10,11,23-pentaazapentacyclo[19.3.1.0²,⁶.0⁸,¹².0¹³,¹⁸]pentacosa-1(24),2(6),4,8,11,13,15,17,21(25),22-decaen-22-amine
1H NMR (400 MHz, DMSO) δ 7.70 (d, J = 10.6 Hz, 1H), 7.57 (s, 1H), 7.47 (s, 1H), 7.17 (t, J = 7.4 Hz, 2H), 6.28 (m, 3H), 5.33 (s, 1H), 4.07-3.96 (m, 2H), 3.87 (s, 3H), 3.51 (d, J = 15.8 Hz, 1H), 2.71 (d, J = 15.5 Hz, 1H), 1.71 (d, J = 6.3 Hz, 3H), 1.27 (t, J = 7.2 Hz, 3H).
LCMS Method K; $t_R$: 1.15 min; m/z: 497 [M + H] |

| Example 149 | 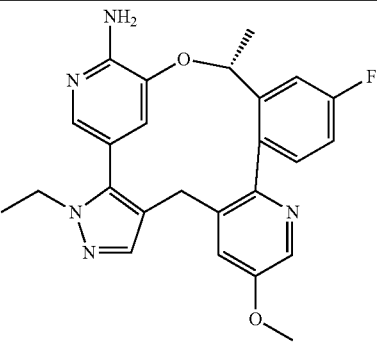 | (20R)-3-ethyl-17-fluoro-10-methoxy-20-methyl-21-oxa-3,4,12,24-tetraazapentacyclo[20.3.1.0²,⁶.0⁸,¹³.0¹⁴,¹⁹]hexacosa-1(25),2(6),4,8(13),9,11,14,16,18,22(26),23-undecaen-23-amine<br>1H NMR (400 MHz, DMSO) δ 8.28 (d, J = 2.8 Hz, 1H), 7.82 (s, 1H), 7.66 (dd, J = 10.4, 2.6 Hz, 1H), 7.46 (d, J = 1.8 Hz, 1H), 7.36 (d, J = 2.6 Hz, 1H), 7.18-7.09 (m, 2H), 6.13 (s, 2H), 6.03 (d, J = 1.6 Hz, 1H), 5.14 (d, J = 4.5 Hz, 1H), 4.06 (q, J = 7.1 Hz, 2H), 3.86 (s, 3H), 3.80 (d, J = 15.6 Hz, 1H), 3.06 (d, J = 15.4 Hz, 1H), 1.73 (d, J = 6.2 Hz, 3H), 1.29 (t, J = 7.2 Hz, 3H).<br>LCMS Method F; $t_R$: 1.32 min; m/z: 446 [M + H] |
|---|---|---|
| Example 150 | 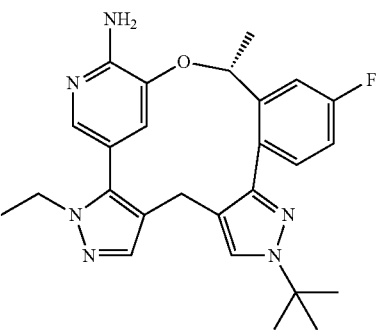 [SMILES: CCn1ncc2c1-c1cnc(N)c(c1)O[C@H](C)c1cc(F)ccc1-c1nn(C(C)(C)C)cc1C2] | (19R)-10-tert-butyl-3-ethyl-16-fluoro-19-methyl-20-oxa-3,4,10,11,23-pentaazapentacyclo[19.3.1.0²,⁶.0⁸,¹².0¹³,¹⁸]pentacosa-1(24),2(6),4,8,11,13,15,17,21(25),22-decaen-22-amine<br>1H NMR (400 MHz, DMSO) δ 7.71 (dd, J = 10.4, 2.6 Hz, 1H), 7.62 (s, 1H), 7.59 (s, 1H), 7.42 (d, J = 1.8 Hz, 1H), 7.16 (ddd, J = 11.0, 8.5, 4.4 Hz, 2H), 6.23 (d, J = 1.6 Hz, 1H), 6.09 (s, 2H), 5.21 (d, J = 4.7 Hz, 1H), 4.00 (q, J = 7.2 Hz, 2H), 3.61 (d, J = 15.7 Hz, 1H), 2.77 (d, J = 15.4 Hz, 1H), 1.71 (d, J = 6.3 Hz, 3H), 1.53 (s, 9H), 1.29 (t, J = 7.2 Hz, 3H).<br>LCMS Method F; $t_R$: 1.02 min; m/z: 461 [M + H] |
| Example 151 | 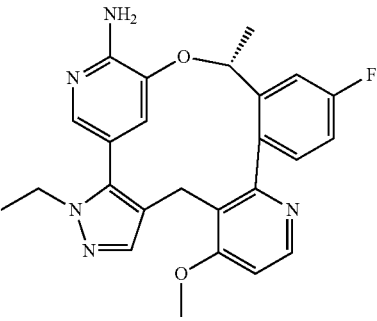 [SMILES: CCn1ncc2c1-c1cnc(N)c(c1)O[C@H](C)c1cc(F)ccc1-c1nccc(OC)c1C2] | (20R)-3-ethyl-17-fluoro-9-methoxy-20-methyl-21-oxa-3,4,12,24-tetraazapentacyclo[20.3.1.0²,⁶.0⁸,¹³.0¹⁴,¹⁹]hexacosa-1(25),2(6),4,8(13),9,11,14,16,18,22(26),23-undecaen-23-amine<br>1H NMR (400 MHz, DMSO) δ 8.41 (s, 1H), 7.68-7.63 (m, 2H), 7.40 (d, J = 1.8 Hz, 1H), 7.05-7.08 (m, 3H), 6.31 (d, J = 1.6 Hz, 1H), 6.08 (s, 2H), 5.47 (d, J = 6.3 Hz, 1H), 3.98 (q, J = 7.2 Hz, 2H), 3.94 (s, 3H), 3.87 (d, J = 15.0 Hz, 1H), 3.19 (d, J = 14.9 Hz, 1H), 1.79 (d, J = 6.2 Hz, 3H), 1.26 (s, 3H).<br>LCMS Method K; $t_R$: 0.60 min; m/z: 446 [M + H] |
| Example 152 | 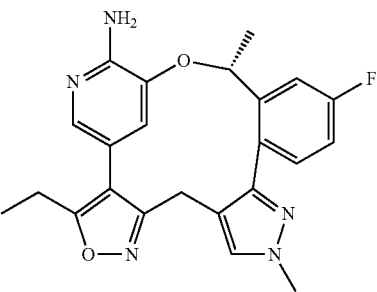 [SMILES: CCc1onc2c1-c1cnc(N)c(c1)O[C@H](C)c1cc(F)ccc1-c1nn(C)cc1C2] | (19R)-3-ethyl-16-fluoro-10,19-dimethyl-4,20-dioxa-5,10,11,23-tetraazapentacyclo[19.3.1.0²,⁶.0⁸,¹².0¹³,¹⁸]pentacosa-1(24),2,5,8,11,13,15,17,21(25),22-decaen-22-amine<br>1H NMR (400 MHz, DMSO) δ 7.72-7.66 (m, 1H), 7.66 (s, 1H), 7.32 (d, J = 1.8 Hz, 1H), 7.26-7.11 (m, 2H), 6.21 (d, J = 1.7 Hz, 1H), 5.98 (s, 2H), 5.33 (dt, J = 6.4, 3.2 Hz, 1H), 3.92 (s, 1H), 3.88 (s, 3H), 2.91 (d, J = 15.0 Hz, 1H), 2.80-2.66 (m, 2H), 1.72 (d, J = 6.3 Hz, 3H), 1.17 (t, J = 7.6 Hz, 3H).<br>LCMS Method F; $t_R$: 0.98 min; m/z: 420 [M + H] |
| Example 153 | 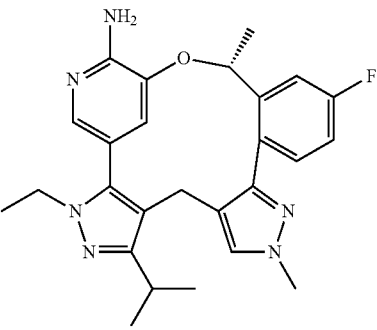 [SMILES: CCn1nc(C(C)C)c2c1-c1cnc(N)c(c1)O[C@H](C)c1cc(F)ccc1-c1nn(C)cc1C2] | (19R)-3-ethyl-16-fluoro-10,19-dimethyl-5-(propan-2-yl)-20-oxa-3,4,10,11,23-pentaazapentacyclo[19.3.1.0²,⁶.0⁸,¹².0¹³,¹⁸]pentacosa-1(24),2(6),4,8,11,13,15,17,21(25),22-decaen-22-amine<br>1H NMR (400 MHz, DMSO) δ 7.67 (dd, J = 10.4, 2.5 Hz, 1H), 7.48 (s, 2H), 7.21 (dd, J = 10.6, 4.4 Hz, 2H), 6.48 (s, 1H), 5.42 (d, J = 5.2 Hz, 1H), 3.98 (dd, J = 14.5, 7.3 Hz, 2H), 3.87 (s, 3H), 3.60 (d, J = 16.1 Hz, 1H), 3.20-3.13 (m, 1H), 2.70 (d, J = 16.0 Hz, 1H), 1.74 (d, J = 6.2 Hz, 3H), 1.44 (d, J = 6.8 Hz, 3H), 1.23 (d, J = 7.3 Hz, 6H).<br>LCMS Method I; $t_R$: 1.32 min; m/z: 461 [M + H] |

| Example 154 | 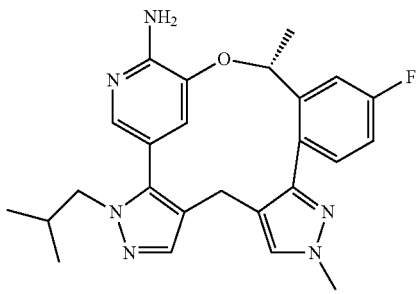 [SMILES: CC(C)Cn1ncc2c1-c1cnc(N)c(c1)O[C@H](C)c1cc(F)ccc1-c1nn(C)cc1C2] | (19R)-16-fluoro-10,19-dimethyl-3-(2-methylpropyl)-20-oxa-3,4,10,11,23-pentaazapentacyclo[19.3.1.0$^{2,6}$.0$^{8,12}$.0$^{13,18}$]pentacosa-1(24),2(6),4,8,11,13,15,17,21(25),22-decaen-22-amine<br>1H NMR (400 MHz, DMSO) δ 7.70 (d, J = 10.3 Hz, 1H), 7.57 (d, J = 2.8 Hz, 2H), 7.42 (d, J = 1.7 Hz, 1H), 7.16-7.10 (m, 2H), 6.25 (d, J = 1.5 Hz, 1H), 6.06 (s, 2H), 5.31 (d, J = 4.7 Hz, 1H), 3.88-3.78 (m, 5H), 3.57 (d, J = 15.6 Hz, 1H), 2.69 (d, J = 15.4 Hz, 1H), 1.99 (d, J = 6.9 Hz, 1H), 1.70 (d, J = 6.3 Hz, 3H), 0.74 (d, J = 6.7 Hz, 3H), 0.61 (d, J = 6.6 Hz, 3H).<br>LCMS Method H; t$_R$: 0.76 min; m/z: 447 [M + H] |
| --- | --- | --- |
| Example 155 | 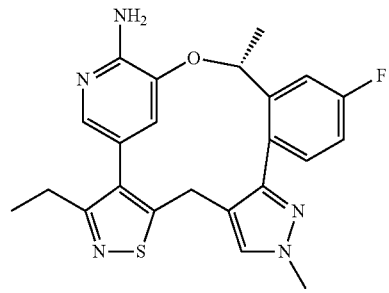 [SMILES: CCc1nsc2c1-c1cnc(N)c(c1)O[C@H](C)c1cc(F)ccc1-c1nn(C)cc1C2] | (19R)-3-ethyl-16-fluoro-10,19-dimethyl-20-oxa-5-thia-4,10,11,23-tetraazapentacyclo[19.3.1.0$^{2,6}$.0$^{8,12}$.0$^{13,18}$]pentacosa-1(24),2(6),3,8,11,13,15,17,21(25),22-decaen-22-amine<br>1H NMR (400 MHz, MeOD) δ 7.52 (dd, J = 6.3, 3.7 Hz, 2H), 7.47 (d, J = 1.8 Hz, 1H), 7.28 (d, J = 5.7 Hz, 1H), 7.13 (s, 1H), 6.69 (d, J = 1.7 Hz, 1H), 5.34-5.28 (m, 1H), 3.93 (s, 3H), 3.85 (d, J = 16.0 Hz, 1H), 3.14 (d, J = 15.9 Hz, 1H), 3.05 (d, J = 7.5 Hz, 2H), 1.82 (d, J = 6.3 Hz, 3H), 1.44 (t, J = 7.5 Hz, 3H).<br>LCMS Method K; t$_R$: 1.25 min; m/z: 436 [M + H] |
| Example 156 | 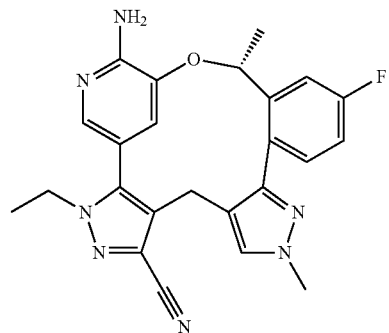 [SMILES: CCn1nc(C#N)c2c1-c1cnc(N)c(c1)O[C@H](C)c1cc(F)ccc1-c1nn(C)cc1C2] | (19R)-22-amino-3-ethyl-16-fluoro-10,19-dimethyl-20-oxa-3,4,10,11,23-pentaazapentacyclo[19.3.1.0$^{2,6}$.0$^{8,12}$.0$^{13,18}$]pentacosa-1(24),2(6),4,8,11,13,15,17,21(25),22-decaene-5-carbonitrile<br>1H NMR (400 MHz, DMSO) δ 7.71 (dd, J = 10.4, 2.6 Hz, 1H), 7.64 (s, 1H), 7.53 (d, J = 1.8 Hz, 1H), 7.27-7.10 (m, 2H), 6.34-6.20 (m, 3H), 5.38-5.27 (m, 1H), 4.20-4.10 (m, 2H), 3.88 (s, 3H), 3.71 (d, J = 15.9 Hz, 1H), 2.83 (d, J = 15.7 Hz, 1H), 1.72 (d, J = 6.2 Hz, 3H), 1.31 (t, J = 7.2 Hz, 3H).<br>LCMS Method F; t$_R$: 1.13 min; m/z: 444 [M + H] |
| Example 157 | 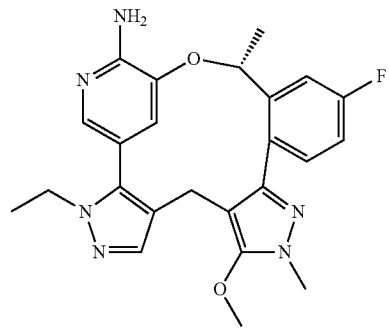 [SMILES: CCn1ncc2c1-c1cnc(N)c(c1)O[C@H](C)c1cc(F)ccc1-c1nn(C)c(OC)c1C2] | (19R)-3-ethyl-16-fluoro-9-methoxy-10,19-dimethyl-20-oxa-3,4,10,11,23-pentaazapentacyclo[19.3.1.0$^{2,6}$.0$^{8,12}$.0$^{13,18}$]pentacosa-1(24),2(6),4,8,11,13,15,17,21(25),22-decaen-22-amine<br>1H NMR (400 MHz, DMSO-d6) δ 7.72-7.65 (m, 1H), 7.56 (s, 1H), 7.40 (d, J = 1.9 Hz, 1H), 7.12 (dd, J = 7.5, 2.4 Hz, 2H), 6.39 (d, J = 1.9 Hz, 1H), 6.06 (s, 2H), 5.55-5.45 (m, 1H), 4.09-3.94 (m, 2H), 3.72 (s, 3H), 3.66 (s, 3H), 3.61 (d, J = 15.7 Hz, 1H), 2.74 (d, J = 15.6 Hz, 1H), 1.71 (d, J = 6.2 Hz, 3H), 1.22 (t, J = 7.2 Hz, 3H).<br>LCMS Method K; t$_R$: 0.79 min; m/z: 449 [M + H] |
| Example 158 | 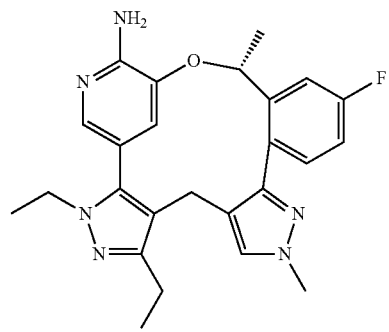 [SMILES: CCc1nn(CC)c2c1Cc1cn(C)nc1-c1ccc(F)cc1[C@@H](C)Oc1cc-2cnc1N] | (19R)-3,5-diethyl-16-fluoro-10,19-dimethyl-20-oxa-3,4,10,11,23-pentaazapentacyclo[19.3.1.0$^{2,6}$.0$^{8,12}$.0$^{13,18}$]pentacosa-1(24),2(6),4,8,11,13,15,17,21(25),22-decaen-22-amine<br>1H NMR (400 MHz, CDCl3) δ 7.50 (d, J = 1.6 Hz, 1H), 7.30 (dd, J = 9.8, 2.6 Hz, 1H), 7.24 (s, 1H), 7.14 (dd, J = 8.5, 5.8 Hz, 1H), 7.00 (td, J = 8.3, 2.7 Hz, 1H), 6.51 (s, 1H), 5.40 (dd, J = 8.5, 4.0 Hz, 1H), 4.81 (s, 2H), 4.09 (tt, J = 13.7, 7.0 Hz, 2H), 3.92 (s, 3H), 3.54 (d, J = 15.9 Hz, 1H), 2.90 (d, J = 15.9 Hz, 1H), 2.82 (q, J = 7.6 Hz, 2H), 1.79 (d, J = 6.3 Hz, 3H), 1.38 (dd, J = 13.2, 7.3 Hz, 6H).<br>LCMS Method K; t$_R$: 1.08 min; m/z: 447 [M + H] |

| Example | | |
|---|---|---|
| Example 159 | 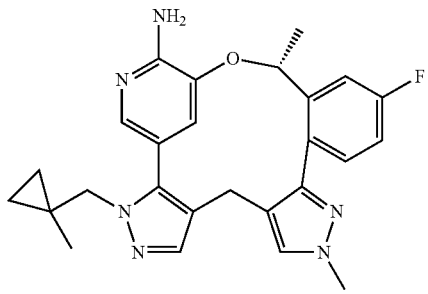 [SMILES: C[C@H]1Oc2cc(cnc2N)-c2c(cnn2CC2(C)CC2)Cc2cn(C)nc2-c2ccc(F)cc21] | (19R)-16-fluoro-10,19-dimethyl-3-[(1-methylcyclopropyl)methyl]-20-oxa-3,4,10,11,23-pentaazapentacyclo[19.3.1.0²,⁶.0⁸,¹².0¹³,¹⁸]pentacosa-1(24),2(6),4,8,11,13,15,17,21(25),22-decaen-22-amine<br>1H NMR (400 MHz, DMSO) δ 7.69 (d, J = 10.2 Hz, 1H), 7.58 (d, J = 7.7 Hz, 2H), 7.42 (d, J = 1.6 Hz, 1H), 7.16-7.08 (m, 2H), 6.26 (d, J = 1.4 Hz, 1H), 6.07 (s, 2H), 5.31 (d, J = 4.6 Hz, 1H), 4.09 (d, J = 14.3 Hz, 1H), 3.85 (s, 3H), 3.82 (d, J = 14.3 Hz, 1H), 3.57 (d, J = 15.6 Hz, 1H), 2.70 (d, J = 15.4 Hz, 1H), 1.70 (d, J = 6.2 Hz, 3H), 0.73 (s, 3H), 0.50 (dt, J = 9.4, 4.7 Hz, 1H), 0.25-0.17 (m, 1H), 0.15-0.03 (m, 2H).<br>LCMS Method F; $t_R$: 0.96 min; m/z: 459 [M + H] |
| Example 160 | 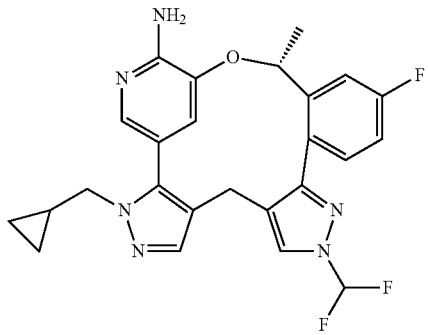 [SMILES: C[C@H]1Oc2cc(cnc2N)-c2c(cnn2CC2CC2)Cc2cn(C(F)F)nc2-c2ccc(F)cc21] | (19R)-3-(cyclopropylmethyl)-10-(difluoromethyl)-16-fluoro-19-methyl-20-oxa-3,4,10,11,23-pentaazapentacyclo[19.3.1.0²,⁶.0⁸,¹².0¹³,¹⁸]pentacosa-1(24),2(6),4,8,11,13,15,17,21(25),22-decaen-22-amine<br>1H NMR (400 MHz, CDCl3) δ 7.78-7.71 (m, 1H), 7.67 (s, 1H), 7.59 (s, 1H), 7.41 (d, J = 9.5 Hz, 1H), 7.13 (dd, J = 13.8, 11.1 Hz, 2H), 6.94 (d, J = 59.4 Hz, 1H), 6.73 (s, 1H), 5.18 (d, J = 6.0 Hz, 1H), 4.96 (s, 2H), 4.13 (dd, J = 14.2, 6.1 Hz, 1H), 3.92 (dd, J = 14.3, 7.0 Hz, 1H), 3.55 (d, J = 15.7 Hz, 1H), 2.90 (d, J = 15.7 Hz, 1H), 1.81-1.73 (m, 3H), 1.78 (m, 1H), 0.53 (d, J = 8.0 Hz, 2H), 0.32 (d, J = 4.2 Hz, 1H), 0.18 (s, 1H).<br>LCMS Method K; $t_R$: 1.22 min; m/z: 481 [M + H] |
| Example 161 | 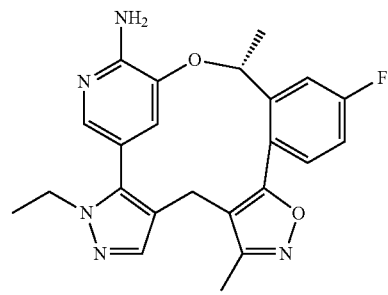 [SMILES: CCn1ncc2c1-c1cnc(N)c(c1)O[C@H](C)c1cc(F)ccc1-c1onc(C)c1C2] | (19R)-3-ethyl-16-fluoro-9,19-dimethyl-11,20-dioxa-3,4,10,23-tetraazapentacyclo[19.3.1.0²,⁶.0⁸,¹².0¹³,¹⁸]pentacosa-1(24),2(6),4,8(12),9,13,15,17,21(25),22-decaen-22-amine<br>1H NMR (400 MHz, DMSO) δ 7.89 (dd, J = 10.2, 2.2 Hz, 1H), 7.68 (s, 1H), 7.42 (d, J = 1.7 Hz, 1H), 7.33-7.19 (m, 2H), 6.49 (d, J = 1.5 Hz, 1H), 6.15 (s, 2H), 5.28-5.12 (m, 1H), 4.09-3.89 (m, 2H), 3.69 (d, J = 15.7 Hz, 1H), 2.94 (d, J = 15.6 Hz, 1H), 2.27 (s, 3H), 1.76 (d, J = 6.2 Hz, 3H), 1.26 (t, J = 7.2 Hz, 3H).<br>LCMS Method F; $t_R$: 1.01 min; m/z: 420 [M + H] |

Example 162 (Method E)

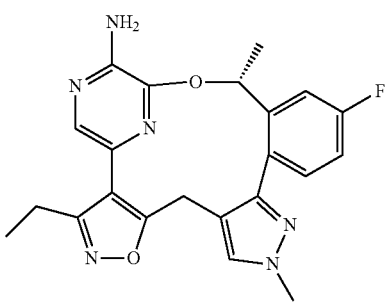 [SMILES: CCc1noc2c1-c1cnc(N)c(n1)O[C@H](C)c1cc(F)ccc1-c1nn(C)cc1C2]

Name: (19R)-3-ethyl-16-fluoro-10,19-dimethyl-5,20-dioxa-4,10,11,23,25-pentaazapentacyclo[19.3.1.0²,⁶,0⁸,¹²,0¹³,¹⁸]pentacosa-1(24),2(6),3,8,11,13,15,17,21(25),22-decaen-22-amine NMR: 1H NMR (400 MHz, DMSO) δ 7.61 (dd, J=10.1, 2.3 Hz, 1H), 7.58 (s, 1H), 7.54 (s, 1H), 7.17 (m, 2H), 6.53 (s, 2H), 5.71-5.60 (m, 1H), 3.82 (s, 3H), 3.77 (d, J=15.5 Hz, 1H), 3.23 (d, J=15.1 Hz, 1H), 2.77 (dq, J=14.9, 7.4 Hz, 1H), 2.63 (dq, J=15.1, 7.5 Hz, 1H), 1.60 (d, J=6.6 Hz, 3H), 1.14 (t, J=7.5 Hz, 3H).

LCMS: Method: F; $t_R$: 1.15 min; m/z: 421 [M+H]

To a solution of (1R)-1-(2-{4-[(3-ethyl-1,2-oxazol-5-yl)methyl]-1-methyl-1H-pyrazol-3-yl}-5-fluorophenyl)ethan-1-ol (0.12 g, 0.36 mmol) in THF (7 mL) was added NaH (70 mg, 1.8 mmol, 60% in mineral oil) at 0° C. After stirring at 0° C. for 1 h, a solution of 5-bromo-3-chloropyrazin-2-amine (75 mg, 0.36 mmol) in THF (1 mL) was added. Stirring was continued at 70° C. for 16 h. The mixture was quenched with sat. aq. NH₄Cl and extracted with EtOAc (20 mL×3). The combined organic layers were washed with brine, dried over anhydrous Na₂SO₄, filtered, and concentrated. The residue was purified by flash chromatography (0→30% EA in PE) to give (R)-5-bromo-3-(1-(2-(4-((3-ethylisoxazol-5-yl)methyl)-1-methyl-1H-pyrazol-3-yl)-5-fluorophenyl)ethoxy)pyrazin-2-amine (120 mg, 62% yield) as a yellow solid. LC-MS (ESI): 501 [M+H]⁺.

A mixture of 5-bromo-3-[(1R)-1-(2-{4-[(3-ethyl-1,2-oxazol-5-yl)methyl]-1-methyl-1H-pyrazol-3-yl}-5-fluorophenyl)ethoxy]pyrazin-2-amine (120 mg, 0.24 mmol), potassium acetate (120 mg, 1.22 mmol), cataCXium A (35 mg, 0.10 mmol) and Pd(OAc)₂ (10 mg, 0.05 mmol) in 2-methyl-2-butanol (12 mL) was stirred at 120° C. for 6 h under N₂. The reaction was filtered, and the filtrate was dissolved in EtOAc (30 mL). This solution was washed with brine (20 mL), dried over anhydrous Na₂SO₄, filtered, and concentrated. The residue was purified by flash chromatography (0-80% EtOAc in PE) followed by prep-HPLC (XBridge C18 OBD 250* 19 mm 5 um, MeCN in H$_2$O+0.1% FA) to afford the target product (24.0 mg, 24% yield) as an off-white solid. LC/MS (ESI) m/z: 421 [M+H]$^+$.

The following compounds were prepared in a similar manner:

| Example | Structure | Name / NMR / LCMS |
|---|---|---|
| Example 163 | 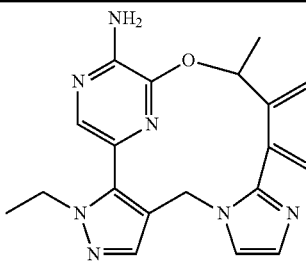 | 3-ethyl-16-fluoro-19-methyl-20-oxa-3,4,8,11,23,25-hexaazapentacyclo[19.3.1.0$^{2,6}$.0$^{8,12}$.0$^{13,18}$]pentacosa-1(24),2(6),4,9,11,13,15,17,21(25),22-decaen-22-amine<br>1H NMR (400 MHz, DMSO) δ 7.89 (s, 1H), 7.66 (dd, J = 10.1, 2.7 Hz, 1H), 7.59 (s, 1H), 7.34 (dd, J = 8.5, 5.8 Hz, 1H), 7.20 (td, J = 8.5, 2.7 Hz, 1H), 7.13 (d, J = 1.2 Hz, 1H), 6.96 (d, J = 1.1 Hz, 1H), 6.76 (s, 2H), 5.69 (dd, J = 6.5, 1.8 Hz, 1H), 4.84 (d, J = 14.2 Hz, 1H), 4.28 (d, J = 14.1 Hz, 1H), 4.10 (q, J = 7.2 Hz, 2H), 1.66 (d, J = 6.6 Hz, 3H), 1.32 (t, J = 7.2 Hz, 3H)<br>LCMS Method C; t$_R$: 0.90 min; m/z: 406 [M + H] |
| Example 164 | 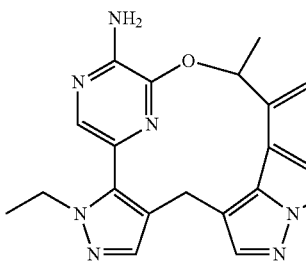 | 3-ethyl-16-fluoro-11,19-dimethyl-20-oxa-3,4,10,11,23,25-hexaazapentacyclo[19.3.1.0$^{2,6}$.0$^{8,12}$.0$^{13,18}$]pentacosa-1(24),2(6),4,8(12),9,13,15,17,21(25),22-decaen-22-amine<br>1H NMR (400 MHz, DMSO-d6) δ 7.80 (dd, J = 10.2, 2.7 Hz, 1H), 7.64 (s, 1H), 7.57 (s, 1H), 7.28 (s, 1H), 7.24 (dd, J = 8.4, 2.8 Hz, 1H), 7.18 (dd, J = 8.5, 5.9 Hz, 1H), 6.71 (s, 2H), 5.69-5.63 (m, 1H), 4.08 (qd, J = 7.0, 3.3 Hz, 2H), 3.50 (s, 3H), 3.35 (s, 1H), 2.75 (d, J = 14.9 Hz, 1H), 1.66 (d, J = 6.6 Hz, 3H), 1.29 (t, J = 7.2 Hz, 3H).<br>LCMS Method C; t$_R$: 1.41 min; m/z: 420 [M + H] |
| Example 165 | 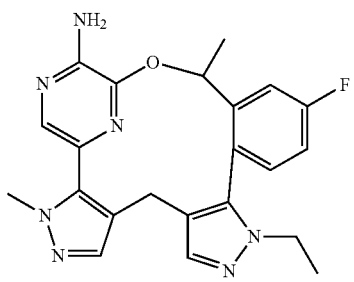 [SMILES: CCn1ncc2c1-c1ccc(F)cc1C(C)Oc1nc(cnc1N)-c1c(cnn1C)C2] | 11-ethyl-16-fluoro-3,19-dimethyl-20-oxa-3,4,10,11,23,25-hexaazapentacyclo[19.3.1.0$^{2,6}$.0$^{8,12}$.0$^{13,18}$]pentacosa-1(24),2(6),4,8(12),9,13,15,17,21(25),22-decaen-22-amine<br>1H NMR (400 MHz, DMSO) δ 7.82-7.74 (m, 1H), 7.67 (s, 1H), 7.59 (s, 1H), 7.28 (s, 1H), 7.28-7.12 (m, 2H), 6.70 (s, 2H), 5.62 (d, J = 4.7 Hz, 1H), 3.85-3.81 (m, 2H), 3.79 (s, 3H), 3.66 (s, 1H), 2.76 (s, 1H), 1.64 (d, J = 6.6 Hz, 3H), 1.22 (t, J = 7.1 Hz, 3H).<br>LCMS Method C; t$_R$: 1.40 min; m/z: 420 [M + H] |

Example 166 (Method G)

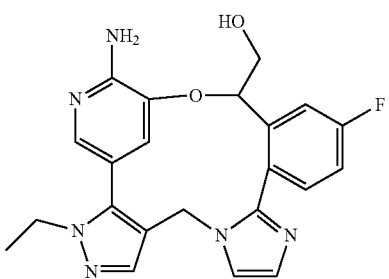 [SMILES: CCn1ncc2c1-c1cnc(N)c(c1)OC(CO)c1cc(F)ccc1-c1nccn1C2]

Name: {22-amino-3-ethyl-16-fluoro-20-oxa-3,4,8,11,23-pentaazapentacyclo[119.3.1.0$^{2,8}$,0$^{8,12}$,0$^{13,18}$]pentacosa-1(24),2(6),4,9,11,13,15,17,21(25),22-decaen-19-yl}methanol NMR: 1H NMR (400 MHz, DMSO) δ 7.88 (s, 1H), 7.67 (dd, J=10.3, 2.7 Hz, 1H), 7.50 (d, J=1.8 Hz, 1H), 7.42 (dd, J=8.6, 5.8 Hz, 1H), 7.29-7.22 (m, 2H), 7.10 (d, J=1.2 Hz, 1H), 6.26 (s, 2H), 5.66 (d, J=1.6 Hz, 1H), 5.35 (d, J=6.5 Hz, 1H), 5.23 (t, J=6.0 Hz, 1H), 5.02 (d, J=14.7 Hz, 1H), 4.18 (d, J=14.6 Hz, 1H), 4.14-4.00 (m, 3H), 3.93-3.82 (m, 1H), 1.28 (t, J=7.2 Hz, 3H).

LCMS Method C; t$_R$: 1.40 min; m/z: 420 [M+H]$^+$.

To a solution of 3-[1-(2-{1-1(5-bromo-1-ethyl-1H-pyrazol-4-yl)methyl]-1H-imidazol-2-yl}-5-fluorophenyl)-2-[(tert-butyldimethylsilyl)oxy]ethoxy]pyridin-2-amine (1.60 g, 2.60 mmol) in CH$_3$CN (20 mL) was added NBS (0.510 g, 2.86 mmol) at −20° C. After the addition, the mixture was stirred at −20° C. for 20 min. The reaction mixture was poured into ice water and extracted with EtOAc. The organic layer was concentrated under reduced pressure and the residue was purified by column chromatography on silica gel (0→100% EtOAc in PE) to give 5-bromo-3-(1-(2-(1-((5-bromo-1-ethyl-1H-pyrazol-4-yl)methyl)-1H-imidazol-2-yl)-5-fluorophenyl)-2-(tert-butyldimethylsilyloxy)ethoxy) pyridin-2-amine (1.00 g, 55% yield) as a pale-yellow oil. LC/MS ESI (m/z): 693 [M+H]$^+$.

To a solution of 5-bromo-3-[1-(2-{1-[(5-bromo-1-ethyl-1H-pyrazol-4-yl)methyl]-1H-imidazol-2-yl}-5-fluorophenyl)-2-[(tert-butyldimethylsilyl)oxy]ethoxy]pyridin-2-amine (760 mg, 1.09 mmol) in DMSO (8.0 mL) and MeOH (0.1 mL) was added CsF (832 mg, 5.41 mmol). The reaction mixture was stirred at r.t. for 1 h and then poured into ice water. The mixture was twice extracted with EtOAc and the combined extracts were concentrated under reduced pressure. The residue was purified by column chromatography (silica gel, 0→3% MeOH in DCM) to give 2-(2-amino-5-bromopyridin-3-yloxy)-2-(2-(1-((5-bromo-1-ethyl-1H-pyrazol-4-yl)methyl)-1H-imidazol-2-yl)-5-fluorophenyl) ethanol (280 mg, 44% yield) as a white solid. LC/MS ESI (m/z): 579 [M+H]$^+$.

To a solution of 5-bromo-3-[1-(2-{1-[(5-bromo-1-ethyl-1H-pyrazol-4-yl)methyl]-1H-imidazol-2-yl}-5-fluorophenyl)-2-[(tert-butyldimethylsilyl)oxy]ethoxy]pyridin-2- amine (200 mg, 0.29 mmol) in MeOH (10.0 mL) was added bis(pinacolato)diboron (306 mg, 1.21 mmol), CsF (367 mg, 2.41 mmol) and H$_2$O (1.0 mL). The mixture was thrice degassed with N$_2$ before a solution of palladium(II) acetate (2 mg, 0.007 mmol) and cataCXium A (5 mg, 0.01 mmol) in toluene (0.5 mL) was added at 70° C. After the addition, the reaction mixture was stirred at 70° C. under N$_2$ for 6 h. After concentration in vacuo, the reaction mixture was directly purified by reversed phase flash chromatography (C18, 2→95% MeCN in H$_2$O) followed by prep-TLC (5% MeOH in DCM) and then prep-HPLC (C18, 0→90% MeCN in H$_2$O+0.1% aq. NH$_3$) to give the target product (6.1 mg, 3.0% yield) as a white solid. LC/MS ESI (m/z): 421 [M+H]$^+$.

Example 167 (Method I)

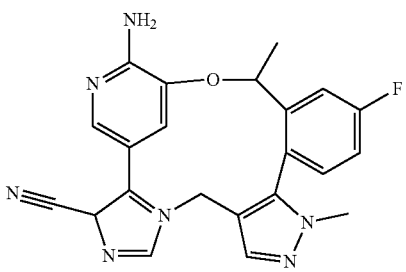

Name: 22-amino-16-fluoro-11,19-dimethyl-20-oxa-4,6,10,11,23-pentaazapentacyclo[19.3.1.0$^{2,6}$,0$^{8,12}$,0$^{13,18}$]pentacosa-1(24),2,4,8(12),9,13,15,17,21(25),22-decaene-3-carbonitrile NMR: 1H NMR (400 MHz, CDCl3) δ 7.90 (d, J=1.8 Hz, 1H), 7.83 (s, 1H), 7.60 (s, 1H), 7.43 (dd, J=9.4, 2.6 Hz, 1H), 7.13 (td, J=8.1, 2.6 Hz, 1H), 7.06 (dd, J=8.5, 5.6 Hz, 1H), 6.75 (d, J=1.6 Hz, 1H), 5.06 (t, J=10.1 Hz, 4H), 4.24 (d, J=16.0 Hz, 1H), 3.72 (s, 3H), 1.86 (d, J=6.3 Hz, 3H).

LCMS: Method B; t$_R$: 1.86 min; m/z: 416 [M+H]

To a solution of 1-((5-(4-fluoro-2-(1-(2-nitropyridin-3-yloxy)ethyl)phenyl)-1-methyl-1H-pyrazol-4-yl)methyl)-1H-imidazole-4-carbonitrile (32 mg, 0.070 mmol) in MeOH (2 mL) was added iron powder (20 mg, 0.36 mmol), and sat. aq. NH$_4$Cl (2 mL). The reaction mixture was stirred at 80° C. for 2 h, and then quenched with water and twice extracted with EtOAc. The combined organic layers were dried over anhydrous Na$_2$SO$_4$, filtered, and concentrated. The residue was purified by flash chromatography (silica gel, 50% EtOAc in PE) to afford 1-((5-(2-(1-(2-aminopyridin-3-yloxy)ethyl)-4-fluorophenyl)-1-methyl-1H-pyrazol-4-yl)methyl)-1H-imidazole-4-carbonitrile (23 mg, 77% yield) as a yellow oil. LC/MS ESI (m/z): 418 [M+H]$^+$.

To a solution of 1-((5-(2-(1-(2-aminopyridin-3-yloxy)ethyl)-4-fluorophenyl)-1-methyl-1H-pyrazol-4-yl)methyl)-1H-imidazole-4-carbonitrile (40 mg, 0.09 mmol) in MeCN (2 mL) was added NBS (19 mg, 0.10 mmol) at 0° C. After stirring at r.t. overnight, the reaction was quenched with water and then extracted with EtOAc twice. The combined organic layers were dried over anhydrous Na$_2$SO$_4$, filtered and concentrated. The residue was purified by preparative TLC (50% EtOAc in PE) to afford 1-((5-(2-(1-(2-amino-5-bromopyridin-3-yloxy)ethyl)-4-fluorophenyl)-1-methyl-1H-pyrazol-4-yl)methyl)-1H-imidazole-4-carbonitrile (32 mg, 67% yield) as a white solid. LC/MS ESI (m/z): 496 [M+H]$^+$.

To a suspension of 1-((5-(2-(1-(2-amino-5-bromopyridin-3-yloxy)ethyl)-4-fluorophenyl)-1-methyl-1H-pyrazol-4-yl)methyl)-1H-imidazole-4-carbonitrile (32 mg, 0.060 mmol) in 2-methyl-2-butanol (2 mL) was added Pd(OAc)$_2$ (3.6 mg, 0.016 mmol), cataCXium A (12 mg, 0.030 mmol) and KOAc (24 mg, 0.24 mmol) at 25° C. The mixture was thrice degassed with N$_2$ and then stirred at 120° C. for 5 h. The reaction was directly concentrated in vacuo, and the residue was purified by preparative TLC (5% MeOH in DCM) followed by prep-HPLC (Gemini 5 um C18 250*21.2 mm, MeCN in H$_2$O+0.1% FA) to give the target product (2.0 mg, 5.9% yield) as a white solid. LC/MS ESI (m/z): 416 [M+H]$^+$.

Example 168 (Method J)

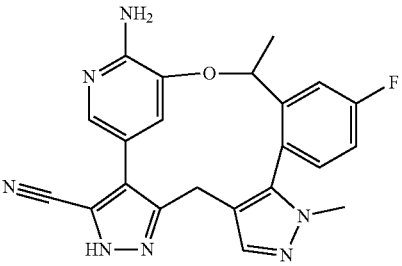 [SMILES: CC1Oc2cc(cnc2N)-c2c(n[nH]c2C#N)Cc2cnn(C)c2-c2ccc(F)cc21]

Name: 22-amino-16-fluoro-11,19-dimethyl-20-oxa-4,5,10,11,23-pentaazapentacyclo[19.3.1.0$^{2,6}$,0$^{8,12}$, 0$^{13,18}$]pentacosa-1(24),2,5,8(12),9,13,15,17,21(25),22-decaene-3-carbonitrile NMR: 1H NMR (400 MHz, DMSO) δ 7.77 (dd, J=10.2, 2.5 Hz, 1H), 7.55 (d, J=1.8 Hz, 1H), 7.44 (s, 1H), 7.34-7.23 (m, 2H), 6.48 (d, J=1.7 Hz, 1H), 6.05 (s, 2H), 5.04-4.93 (m, 1H), 3.90 (d, J=15.8 Hz, 1H), 3.63 (s, 3H), 2.97 (d, J=15.7 Hz, 1H), 1.80 (d, J=6.2 Hz, 3H).

LCMS: Method C; t$_R$: 0.46 min; m/z: 416 [m+H]

To a solution of 22-amino-16-fluoro-11,19-dimethyl-4-{[2-(trimethylsilyl)ethoxy]methyl}-20-oxa-4,5,10,11,23-pentaazapentacyclo[19.3.1.0$^{2,6}$,0$^{8,12}$,0$^{13,18}$]pentacosa-1 (24),2,5,8(12),9,13,15,17,21(25),22-decaene-3-carbonitrile (50 mg, 0.09 mmol) in DCM (8 mL) was added TFA (105 mg, 0.92 mmol). After the addition, the mixture was stirred at r.t. for 12 h. The mixture was concentrated under reduced pressure, and the residue was purified by prep-HPLC (Gemini 5 pm C18 250*21.2 mm; MeCN in H$_2$O+0.1% FA) to give the target product as a white solid (13 mg, yield: 34%). LC-MS (ESI): m/z 416 [M+H]$^+$.

Example 169 (Method K)

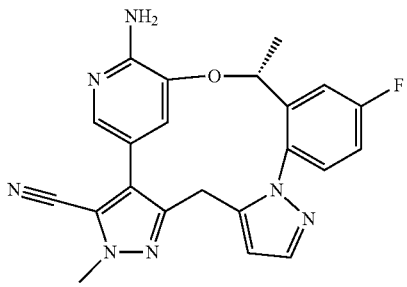 [SMILES: C[C@H]1Oc2cc(cnc2N)-c2c(nn(C)c2C#N)Cc2ccnn2-c2ccc(F)cc21]

Name: (19R)-22-amino-16-fluoro-4,19-dimethyl-20-oxa-4,5,11,12,23-pentaazapentacyclo[19.3.1.0$^{2,6}$,0$^{8,12}$,0$^{13,18}$]pentacosa-1(24),2,5,8,10,13,15,17,21(25),22-decaene-3-carbonitrile NMR: 1H NMR (400 MHz, DMSO-d6) δ 7.79-7.73 (m, 2H), 7.54 (d, J=1.8 Hz, 1H), 7.49 (dd, J=8.8, 5.2 Hz, 1H), 7.32 (td, J=8.3, 2.9 Hz, 1H), 6.25 (d, J=1.3 Hz, 1H), 6.17 (s, 2H), 5.99 (d, J=1.9 Hz, 1H), 5.11 (q, J=6.2, 5.4 Hz, 1H), 4.20 (d, J=16.0 Hz, 1H), 4.03 (s, 3H), 3.23 (d, J=16.1 Hz, 1H), 1.73 (d, J=6.2 Hz, 3H).

LCMS: Method C; t$_R$: 0.83 min; m/z: 416 [m+H]

To a solution of 5-bromo-3-(1-(2-(5-((1-ethyl-1H-pyrazol-4-yl)methyl)-3-fluoro-1H-pyrazol-1-yl)-5-fluorophenyl)ethoxy)-2-nitropyridine (70 mg, 0.13 mmol) in EtOH (2 mL) and H$_2$O (0.5 mL), was added NH$_4$Cl (69 mg, 1.3 mmol) and iron powder (36 mg, 0.64 mmol). The reaction was stirred at 75° C. for 1 h, and then concentrated in vacuo. The residue was purified by prep-TLC (5% MeOH in DCM) to give 3-((1-(2-(1-((2-amino-5-bromopyridin-3-yl)oxy)ethyl)-4-fluorophenyl)-1H-pyrazol-5-yl)(hydroxy)methyl)-1-methyl-1H-pyrazole-5-carbonitrile (64 mg, 97%) as a brown solid. LC/MS ESI (m/z): 512 [M+H]$^+$.

To a solution of 3-((1-(2-(1-((2-amino-5-bromopyridin-3-yl)oxy)ethyl)-4-fluorophenyl)-1H-pyrazol-5-yl)(hydroxy)methyl)-1-methyl-1H-pyrazole-5-carbonitrile (64 mg, 0.12 mmol) in trifluoroacetic acid (3 mL), was added triethylsilane (0.40 mL, 2.5 mmol). The reaction was stirred at 50° C. for 6 h. The mixture was cooled to r.t. and concentrated in vacuo. The residue was diluted with EA (10 mL) and neutralized with sat. aq. NaHCO$_3$. The layers were separated, and the aq. layer was extracted with EA (3×10 mL). The combined organic phases were washed with brine (5 mL), dried over anhydrous Na$_2$SO$_4$, filtered, and concentrated in vacuo. The residue was purified by prep-TLC (5% MeOH in DCM) to give 3-((1-(2-(1-((2-amino-5-bromopyridin-3-yl)oxy)ethyl)-4-fluorophenyl)-1H-pyrazol-5-yl)methyl)-1-methyl-1H-pyrazole-5-carbonitrile (35 mg, 56%) as a white gum. LC/MS ESI (m/z): 496 [M+H]$^+$.

To a mixture of 3-((1-(2-(1-((2-amino-5-bromopyridin-3-yl)oxy)ethyl)-4-fluorophenyl)-1H-pyrazol-5-yl)methyl)-1-methyl-1H-pyrazole-5-carbonitrile (35 mg, 0.071 mmol), Pd(OAc)$_2$ (3 mg, 0.014 mmol) and cataCXium A (8 mg, 0.02 mmol) in 2-methyl-2-butanol (3.5 mL), was added potassium acetate (35 mg, 0.35 mmol). The resulting mixture was thrice degassed with N$_2$, and then stirred at 120° C. overnight. The mixture was cooled to r.t., filtered, and concentrated in vacuo. The residue was purified by prep-TLC (5% MeOH in DCM), followed by prep-HPLC (Gemini 5 um C18 250*21.2 mm, MeCN in H$_2$O+0.1% FA), and finally by chiral SFC (ChiralCel OJ-H 4.6*250 mm, 40% MeOH+0.05% DEA in CO$_2$ over 8.0 min) to obtain the target eutomer (t$_R$4.0 min, 5.0 mg, 17%) as a white solid (LC/MS ESI (m/z): 416 [M+H]$^+$.

Example 170 (Method L)

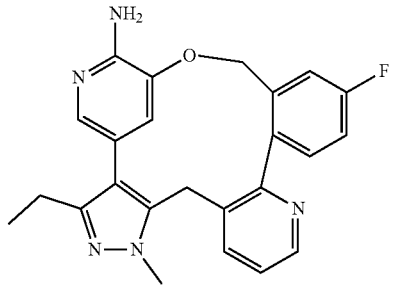 [SMILES: CCc1nn(C)c2c1-c1cnc(N)c(c1)OCc1cc(F)ccc1-c1ncccc1C2]

Name: 3-ethyl-17-fluoro-5-methyl-21-oxa-4,5,12,24-tetraazapentacyclo[20.3.1.0$^{2,6}$,0$^{8,13}$,0$^{14,19}$]hexacosa-1(25),2(6),3,8(13),9,11,14,16,18,22(26),23-undecaen-23-amine NMR: 1H NMR (400 MHz, DMSO) δ 8.58 (d, J=3.4 Hz, 1H), 7.66-7.59 (m, 2H), 7.48 (dd, J=8.0, 4.7 Hz, 1H), 7.37-7.32 (m, 2H), 7.24 (td, J=8.5, 2.7 Hz, 1H), 5.96 (d, J=1.7 Hz, 1H), 5.77 (s, 2H), 5.18 (d, J=13.4 Hz, 1H), 4.71 (d, J=14.7 Hz, 1H), 4.25 (d, J=16.6 Hz, 1H), 4.02 (s, 3H), 3.29 (s, 1H), 2.58 (qd, J=7.5, 1.8 Hz, 2H), 1.11 (t, J=7.5 Hz, 3H).

LCMS: Method C; t$_R$: 2.07 min; m/z: 416 [m+H]

To a solution of 5-bromo-3-((2-(3-((3-ethyl-1-methyl-1H-pyrazol-5-yl)methyl)pyridin-2-yl)-5-fluorobenzyl)oxy)-2-nitropyridine (185 mg, 0.342 mmol) in EtOH (5 mL) and H$_2$O (1 mL), was added iron powder (191 mg, 3.42 mmol), and NH$_4$Cl (366 mg, 6.85 mmol). The mixture was stirred at 80° C. for 3 h, then poured into water (80 mL) and extracted with EtOAc (80 mL×3). The combined organic layers were washed with sat. aq. NaCl (60 mL×2), dried over anhydrous Na$_2$SO$_4$, filtered, and concentrated in vacuo. The residue was purified by column chromatography on silica gel (10→50% EtOAc in PE) to give 5-bromo-3-((2-(3-((3-ethyl-1-methyl-1H-pyrazol-5-yl)methyl)pyridin-2-yl)-5-fluorobenzyl)oxy)pyridin-2-amine (165 mg, 94%) as a white solid. LC/MS (ESI): m/z=496 [M+H]$^+$.

To a solution of 5-bromo-3-((2-(3-((3-ethyl-1-methyl-1H-pyrazol-5-yl)methyl)pyridin-2-yl)-5-fluorobenzyl)oxy)pyridin-2-amine (150 mg, 0.294 mmol) in DMF (5 mL), was added NBS (52 mg, 0.29 mmol). The reaction was stirred at r.t. for 3 h, then poured into water (80 mL) and extracted with EA (80 mL×3). The combined organic layers were washed with sat. NaCl (60 mL×2), dried over anhydrous Na$_2$SO$_4$, filtered, and concentrated in vacuo. The residue was purified by column chromatography on silica gel (10→50% EtOAc in PE) to give 5-bromo-3-((2-(3-((4-bromo-3-ethyl-1-methyl-1H-pyrazol-5-yl)methyl)pyridin-2-yl)-5-fluorobenzyl)oxy)pyridin-2-amine (90 mg, 52%) as a white solid. LC/MS (ESI): m/z=574 [M+H]$^+$.

To a solution of 5-bromo-3-((2-(3-((4-bromo-3-ethyl-1-methyl-1H-pyrazol-5-yl)methyl)pyridin-2-yl)-5-fluorobenzyl)oxy)pyridin-2-amine (80 mg, 0.14 mmol) in MeOH (8 mL) was added 4,4,4',4',5,5,5',5'-octamethyl-2,2'-bi(1,3,2-dioxaborolane) (103 mg, 0.410 mmol), Pd(OAc)$_2$ (7.3 mg, 0.033 mmol), cataCXium A (23 mg, 0.065 mmol), and aq. CsF (2 M, 0.20 mL, 0.40 mmol). The mixture was stirred at 80° C. for 5 h, then poured into water (80 mL) and extracted with EtOAc (80 mL×3). The combined organic layers were washed with sat. NaCl (60 mL×2), dried over anhydrous Na$_2$SO$_4$, filtered, and concentrated in vacuo. The residue was purified by column chromatography on silica gel (50% EtOAc in PE) followed by prep-HPLC (XBridge C18 OBD 250* 19 mm 5 um, MeCN in H$_2$O+0.100 FA) to give the target product (1.9 mg, 3.3%) as a white solid. LC/MS (ESI): m/z=416 [M+H]$^+$.

The following compounds were prepared in a similar manner:

| Example 171 | 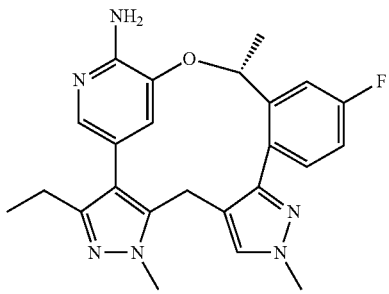 [SMILES: CCc1nn(C)c2c1-c1cnc(N)c(c1)O[C@H](C)c1cc(F)ccc1-c1nn(C)cc1C2] | (19R)-3-ethyl-16-fluoro-5,10,19-trimethyl-20-oxa-4,5,10,11,23-pentaazapentacyclo[19.3.1.0$^{2,6}$.0$^{8,12}$.0$^{13,18}$]pentacosa-1(24),2(6),3,8,11,13,15,17,21(25),22-decaen-22-amine<br>1H NMR (400 MHz, DMSO) δ 7.78 (s, 1H), 7.67 (d, J = 9.9 Hz, 1H), 7.30 (d, J = 1.7 Hz, 1H), 7.19-7.15 (m, 2H), 6.20 (s, 1H), 5.71 (s, 2H), 5.29-5.17 (m, 1H), 3.95 (s, 3H), 3.87 (s, 3H), 3.85-3.80 (m, 1H), 2.93 (d, J = 16.2 Hz, 1H), 2.49-2.46 (m, 2H), 1.69 (d, J = 6.3 Hz, 3H), 1.07 (t, J = 7.5 Hz, 3H).<br>LCMS Method F; t$_R$: 0.82 min; m/z: 433 [M + H] |
| --- | --- | --- |
| Example 172 | 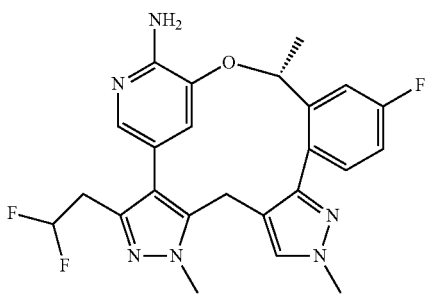 [SMILES: C[C@H]1Oc2cc(cnc2N)-c2c(CC(F)F)nn(C)c2Cc2cn(C)nc2-c2ccc(F)cc21] | (19R)-3-(2,2-difluoroethyl)-16-fluoro-5,10,19-trimethyl-20-oxa-4,5,10,11,23-pentaazapentacyclo[19.3.1.0$^{2,6}$.0$^{8,12}$.0$^{13,18}$]pentacosa-1(24),2(6),3,8,11,13,15,17,21(25),22-decaen-22-amine<br>1H NMR (400 MHz, DMSO-d6) δ 7.80 (s, 1H), 7.68 (d, J = 10.3 Hz, 1H), 7.34 (d, J = 1.7 Hz, 1H), 7.21-7.14 (m, 2H), 6.20 (tt, J = 4, 56 Hz, 1H), 6.20 (s, 1H), 5.78 (s, 2H), 5.33-5.19 (m, 1H), 4.00 (s, 3H), 3.87 (m, 4H), 3.14-3.05 (m, 2H), 2.95 (d, J = 16.2 Hz, 1H), 1.70 (d, J = 6.2 Hz, 3H).<br>LCMS Method H; t$_R$: 0.91 min; m/z: 469 [M + H] |
| Example 173 | 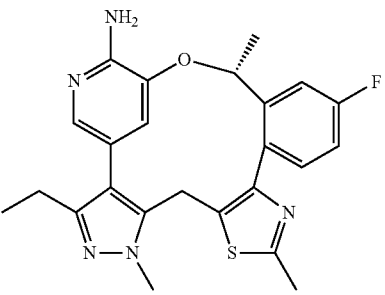 | (19R)-3-ethyl-16-fluoro-5,10,19-trimethyl-20-oxa-9-thia-4,5,11,23-tetraazapentacyclo[19.3.1.0$^{2,6}$.0$^{8,12}$.0$^{13,18}$]pentacosa-1(24),2(6),3,8(12),10,13,15,17,21(25),22-decaen-22-amine<br>1H NMR (400 MHz, Chloroform-d) δ 7.50 (d, J = 1.8 Hz, 1H), 7.33 (dd, J = 9.7, 2.7 Hz, 1H), 7.12 (dd, J = 8.4, 5.6 Hz, 1H), 7.01 (td, J = 8.2, 2.7 Hz, 1H), 6.47 (d, J = 1.8 Hz, 1H), 5.21-5.13 (m, 1H), 4.83 (s, 2H), 4.00 (s, 3H), 3.92 (d, J = 16.3 Hz, 1H), 3.72 (d, J = 16.3 Hz, 1H), 2.72 (s, 3H), 2.65 (p, J = 7.6 Hz, 2H), 1.79 (d, J = 6.3 Hz, 3H), 1.17 (d, J = 7.6 Hz, 3H).<br>LCMS Method H; t$_R$: 0.99 min; m/z: 491 [M + H + MeCN] |
| Example 174 | 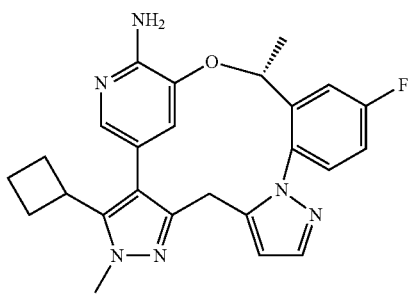 [SMILES: C[C@H]1Oc2cc(cnc2N)-c2c(nn(C)c2C2CCC2)Cc2ccnn2-c2ccc(F)cc21] | (19R)-3-cyclobutyl-16-fluoro-4,19-dimethyl-20-oxa-4,5,11,12,23-pentaazapentacyclo[19.3.1.0$^{2,6}$.0$^{8,12}$.0$^{13,18}$]pentacosa-1(24),2,5,8,10,13,15,17,21(25),22-decaen-22-amine<br>1H NMR (400 MHz, DMSO-d6) δ 7.83 (dd, J = 9.8, 3.0 Hz, 1H), 7.68 (d, J = 1.8 Hz, 1H), 7.40 (dd, J = 8.8, 5.2 Hz, 1H), 7.26 (td, J = 8.3, 3.0 Hz, 1H), 7.20 (d, J = 1.7 Hz, 1H), 6.20 (d, J = 1.9 Hz, 1H), 6.00 (d, J = 1.9 Hz, 1H), 5.89 (br s, 2H), 5.24-5.16 (m, 1H), 3.90 (d, J = 15.7 Hz, 1H), 3.77 (s, 3H), 3.77-3.68 (m, 1H), 3.00 (d, J = 15.6 Hz, 1H), 2.33-2.23 (m, 1H), 2.20-2.09 (m, 2H), 2.00-1.84 (m, 2H), 1.71 (d, J = 6.2 Hz, 3H), 1.71-1.59 (m, 1H).<br>LCMS Method F; t$_R$: 0.90 min; m/z: 445 [M + H] |
| Example 175 | 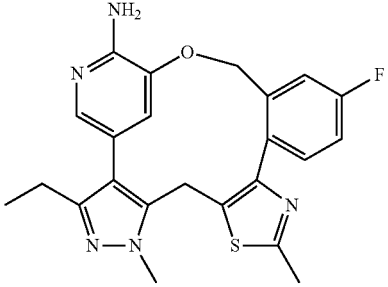 [SMILES: CCc1nn(C)c2c1-c1cnc(N)c(c1)OCc1cc(F)ccc1-c1nc(C)sc1C2] | 3-ethyl-16-fluoro-5,10-dimethyl-20-oxa-9-thia-4,5,11,23-tetraazapentacyclo[19.3.1.0$^{2,6}$.0$^{8,12}$.0$^{13,18}$]pentacosa-1(24),2(6),3,8(12),10,13,15,17,21(25),22-decaen-22-amine<br>1H NMR (400 MHz, DMSO) δ 7.65 (dd, J = 9.8, 2.2 Hz, 1H), 7.34 (d, J = 1.7 Hz, 1H), 7.31-7.17 (m, 2H), 6.25 (d, J = 1.6 Hz, 1H), 5.77 (s, 2H), 5.16 (d, J = 13.2 Hz, 1H), 4.83 (d, J = 14.4 Hz, 1H), 4.25 (d, J = 16.3 Hz, 1H), 3.94 (s, 3H), 3.52-3.39 (m, 1H), 2.66 (s, 3H), 2.57-2.42 (m, 2H), 1.09 (t, J = 7.5 Hz, 3H).<br>LCMS Method K; t$_R$: 0.87 min; m/z: 436 [M + H] |

| Example 176 | 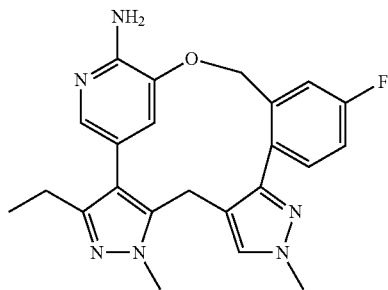 [SMILES: CCc1nn(C)c2c1-c1cnc(N)c(c1)OCc1cc(F)ccc1-c1nn(C)cc1C2] | 3-ethyl-16-fluoro-5,10-dimethyl-20-oxa-4,5,10,11,23-pentaazapentacyclo[19.3.1.0$^{2,6}$.0$^{8,12}$.0$^{13,18}$]pentacosa-1(24),2(6),3,8,11,13,15,17,21(25),22-decaen-22-amine<br>1H NMR (400 MHz, DMSO) δ 7.76 (s, 1H), 7.63 (d, J = 9.4 Hz, 1H), 7.32 (d, J = 1.7 Hz, 1H), 7.24-7.17 (m, 2H), 6.22 (d, J = 1.6 Hz, 1H), 5.72 (s, 2H), 5.10 (d, J = 13.3 Hz, 1H), 4.96 (d, J = 14.1 Hz, 1H), 3.96 (s, 3H), 3.89-3.80 (m, 4H), 2.97 (d, J = 16.1 Hz, 1H), 2.56-2.52 (m, 2H), 1.09 (t, J = 7.5 Hz, 3H).<br>LCMS Method F; t$_R$: 0.28 min; m/z: 419 [M + H] |
|---|---|---|
| Example 177 | 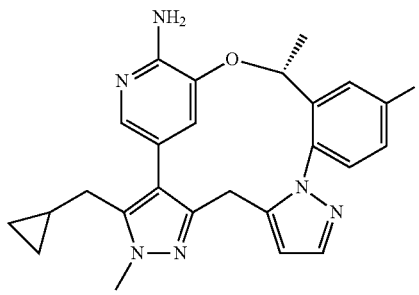 | (19R)-3-(cyclopropylmethyl)-16-fluoro-4,19-dimethyl-20-oxa-4,5,11,12,23-pentaazapentacyclo[19.3.1.0$^{2,6}$.0$^{8,12}$.0$^{13,18}$]pentacosa-1(24),2,5,8,10,13,15,17,21(25),22-decaen-22-amine<br>1H NMR (400 MHz, DMSO) δ 7.81 (dd, J = 9.8, 2.9 Hz, 1H), 7.68 (d, J = 1.8 Hz, 1H), 7.42 (dd, J = 8.7, 5.2 Hz, 1H), 7.33 (d, J = 1.7 Hz, 1H), 7.30-7.23 (m, 1H), 6.23 (d, J = 1.0 Hz, 1H), 5.95 (d, J = 1.4 Hz, 1H), 5.81 (s, 2H), 5.18-5.09 (m, 1H), 3.95 (d, J = 15.9 Hz, 1H), 3.83 (s, 3H), 3.08 (d, J = 15.7 Hz, 1H), 2.62 (d, J = 6.5 Hz, 2H), 1.71 (d, J = 6.2 Hz, 3H), 0.90-0.81 (m, 1H), 0.45-0.32 (m, 2H), 0.16-0.07 (m, 1H), 0.05--0.06 (m, 1H).<br>LCMS Method F; t$_R$: 0.97 min; m/z: 445 [M + H] |
| Example 178 | 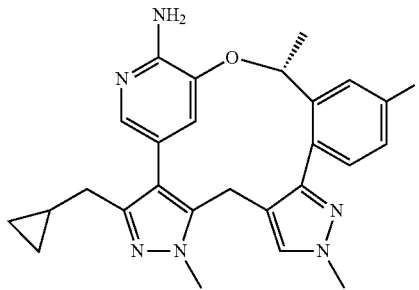 | (19R)-3-(cyclopropylmethyl)-16-fluoro-5,10,19-trimethyl-20-oxa-4,5,10,11,23-pentaazapentacyclo[19.3.1.0$^{2,6}$.0$^{8,12}$.0$^{13,18}$]pentacosa-1(24),2(6),3,8,11,13,15,17,21(25),22-decaen-22-amine<br>1H NMR (400 MHz, DMSO) δ 7.81 (s, 1H), 7.71-7.61 (m, 1H), 7.31 (d, J = 1.7 Hz, 1H), 7.18 (dd, J = 8.0, 1.6 Hz, 2H), 6.24 (d, J = 1.5 Hz, 1H), 5.99 (s, 2H), 5.27 (d, J = 4.6 Hz, 1H), 3.96 (s, 3H), 3.87 (s, 3H), 3.84 (d, J = 16.5 Hz, 1H), 2.94 (d, J = 16.1 Hz, 1H), 2.42 (d, J = 6.5 Hz, 2H), 1.70 (d, J = 6.3 Hz, 3H), 0.97-0.79 (m, 1H), 0.43-0.24 (m, 2H), 0.17-0.02 (m, 1H), 0.01--0.10 (m, 1H).<br>LCMS Method K; t$_R$: 0.56 min; m/z: 459 [M + H] |
| Example 179 | 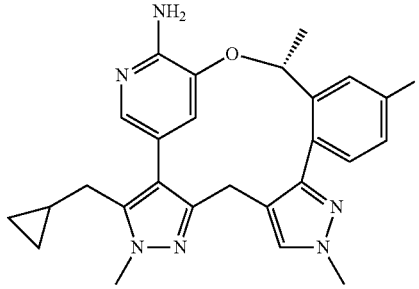 | (19R)-3-(cyclopropylmethyl)-16-fluoro-4,10,19-trimethyl-20-oxa-4,5,10,11,23-pentaazapentacyclo[19.3.1.0$^{2,6}$.0$^{8,12}$.0$^{13,18}$]pentacosa-1(24),2,5,8,11,13,15,17,21(25),22-decaen-22-amine<br>1H NMR (400 MHz, DMSO) δ 7.66 (dd, J = 10.3, 2.1 Hz, 1H), 7.55 (s, 1H), 7.27 (d, J = 1.7 Hz, 1H), 7.18-7.10 (m, 2H), 6.23 (s, 1H), 5.70 (s, 2H), 5.31-5.24 (m, 1H), 3.85 (s, 3H), 3.78 (s, 3H), 3.65 (d, J = 14.9 Hz, 1H), 2.85 (d, J = 15.0 Hz, 1H), 2.58-2.52 (m, 2H), 1.69 (d, J = 6.3 Hz, 3H), 0.87-0.75 (m, 1H), 0.43-0.30 (m, 2H), 0.15-0.06 (m, 1H), 0.03--0.05 (m, 1H).<br>LCMS Method F; t$_R$: 0.74 min; m/z: 459 [M + H] |
| Example 180 | 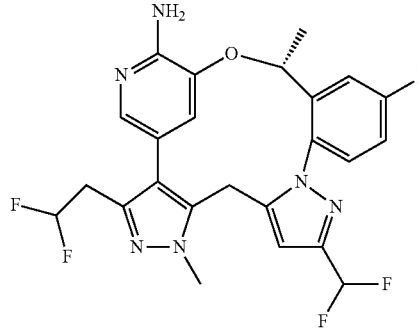 | (19R)-3-(2,2-difluoroethyl)-10-(difluoromethyl)-16-fluoro-5,19-dimethyl-20-oxa-4,5,11,12,23-pentaazapentacyclo[19.3.1.0$^{2,6}$.0$^{8,12}$.0$^{13,18}$]pentacosa-1(24),2(6),3,8,10,13,15,17,21(25),22-decaen-22-amine<br>1H NMR (400 MHz, DMSO) δ 7.87 (dd, J = 9.8, 2.9 Hz, 1H), 7.49 (dd, J = 8.8, 5.2 Hz, 1H), 7.41 (d, J = 1.7 Hz, 1H), 7.35 (td, J = 8.3, 3.0 Hz, 1H), 7.05 (t, J = 54.5 Hz, 1H), 6.65 (s, 1H), 6.16 (dt, J = 56.3, 4.7 Hz, 1H), 5.93 (s, 3H), 5.12-5.00 (m, 1H), 4.32 (d, J = 17.1 Hz, 1H), 4.02 (s, 3H), 3.21-3.14 (m, 2H), 3.10 (dd, J = 16.5, 4.6 Hz, 1H), 1.71 (d, J = 6.2 Hz, 3H).<br>LCMS Method F; t$_R$: 1.05 min; m/z: 505 [M + H] |

Example 181 (Method M)

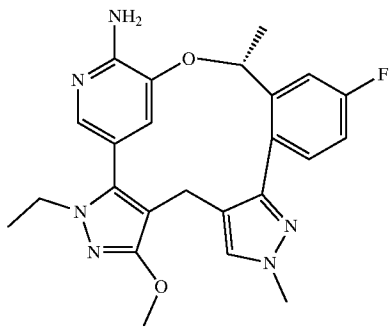 [SMILES: CCn1nc(OC)c2c1-c1cnc(N)c(c1)O[C@H](C)c1cc(F)ccc1-c1nn(C)cc1C2]

Name: (19R)-3-ethyl-16-fluoro-5-methoxy-10,19-dimethyl-20-oxa-3,4,10,11,23-pentaazapentacyclo [19.3.1.0$^{2,6}$,0$^{8,12}$,0$^{13,18}$]pentacosa-1(24),2(6),4,8,11,13,15,17,21(25),22-decaen-22-amine NMR: 1H NMR (400 MHz, DMSO) δ 7.80-7.60 (m, 1H), 7.51 (s, 1H), 7.41 (ci, J=1.8 Hz, 1H), 7.14 (dci, J=7.7, 1.7 Hz, 2H), 6.27 (d,IJ=1.6 Hz, 1H), 6.11 (s, 2H), 5.37-5.21 (m, 1H), 3.92 (s, 3H), 3.91-3.82 (m, 5H), 3.46 (s, 1H), 2.56 (s, 1H), 1.70 (ci, J=6.2 Hz, 3H), 1.23 (t, J=7.1 Hz, 3H).

LCMS: Method F; $t_R$: 0.79 min; m/z: 449 [M+H]$^+$.

A mixture of (19R)-5-(benzyloxy)-3-ethyl-16-fluoro-10,19-dimethyl-20-oxa-3,4,10,11,23-pentaazapentacyclo [19.3.1.0$^{2,6}$,0$^{8,12}$,0$^{13,18[pentacosa-}$1(24),2(6),4,8,11,13,15,17,21(25),22-decaen-22-amine (30 mg, 0.060 mmol) and Pd/C (30 mg, 10% wt.) in anhydrous MeOH (2 mL) was stirred at 25° C. for 1.5 h under a balloon of H$_2$. The reaction was filtered through celite and the filtrate was concentrated in vacuo. The residue was purified by prep-HPLC (Shim-pack GIST C18 250*20 mm; MeCN in H$_2$O+0.1% FA) to give (19R)-22-amino-3-ethyl-16-fluoro-10,19-dimethyl-20-oxa-3,4,10,11,23-pentaazapentacyclo[19.3.1.0$^{2,6}$0$^{8,12}$,0$^{13,18}$]pentacosa-1(24),2(6),8,11,13,15,17,21(25),22-nonaen-5-one (9.8 mg, 39% yield) as a white solid. LC/MS (ESI) m/z: 435.2 [M+H]$^+$.

To a solution of (19R)-22-amino-3-ethyl-16-fluoro-10,19-dimethyl-20-oxa-3,4,10,11,23-pentaazapentacyclo [19.3.1.0$^{2,6}$,0$^{8,12}$,0$^{13,18}$]pentacosa-1(24),2(6),8,11,13,15,17, 21(25),22-nonaen-5-one (64 mg, 0.15 mmol), and K$_2$CO$_3$ (40 mg, 0.29 mmol) in anhydrous DMF (1.5 mL) was added iodomethane (0.010 mL, 0.16 mmol) dropwise at 0° C. The reaction was stirred at 25° C. for 2 h. The reaction mixture was filtered, and the filtrate was partitioned between EtOAc and water. The layers were separated, and the aq. phase was extracted with EA (30 mL). The combined organic layers were washed with brine, dried over anhydrous Na$_2$SO$_4$, filtered, and concentrated in vacuo. The residue was purified by prep-HPLC (Column: YMC-Actus Triart C18 250*21 mm; H$_2$O+0.1% FA) to give the target product (20 mg, 31% yield) as a white solid. LC/MS (ESI) m/z: 449 [M+H]$^+$.

Inhibition Assays

Example 182

Biochemical Kinase Assay

First, 250 nL of compound dissolved in DMSO (100-fold of the desired concentration) was dispensed into a 384-well plate. A 12.5 μL substrate solution containing ATP (2 mM) and fluorogenic phosphorylation substrate AQTO101 (26 μM for ALK and ROS1, AssayQuant) or AQT0104 (26 μM for TRKA, AssayQuant) in buffer (50 mM HEPES pH 7.5, 0.01% Brij-35, 0.5 mM EGTA, 10 mM MgCl$_2$) was added and mixed thoroughly. Then, a 12.5 μL kinase solution containing ALK-wt (1.5 nM, Carna, 08-518), ALK ALK L1196M/G1202R (3 nM, SignalChem, A19-12NG), ROS1-wt (0.6 nM, Carna, 08-163), ROS1-G2032R (0.5 nM, SignalChem, R14-12BG), or TRKA-wt (1 nM, BPS Bio, 40280) kinase domains in buffer (50 nM HEPES pH 7.5, 0.01% Brij-35, 2% glycerol, 0.4 mg/mL BSA, 0.5 mM EGTA, and 10 mM MgCl$_2$) was added and mixed thoroughly. The plate was sealed and read by SpectraMax Paradigm at λ=485 nm every 2 minutes for 120 minutes at 30 LC. Exemplary data is given in Table 3. Initial rates of reaction (v) were calculated from the change in fluorescence intensity over time during the initial, linear portion of the reaction. Finally, apparent inhibitory constants (Ki$^{app}$) were determined from regression of v and I (inhibitor concentration) to Morrison Equation (E=enzyme concentration).

$$v = 1 - \frac{(E + I + K_i^{app}) - \sqrt{(E + I + K_i^{app})^2 - 4EI}}{2E}$$

Exemplary data is given in Table 3 (nd=not determined).

TABLE 3

Biochemical Assay Activity Summary:

| Example | ALK-L1196M-G1202R | ALK-wt | ROS1-G2032R | ROS1-wt | TRKA-wt |
|---|---|---|---|---|---|
| 1 | A | A | A | A | A |
| 2 | B | A | A | A | B |
| 3 | A | A | A | A | A |
| 4 | A | A | A | A | A |
| 5 | A | A | A | A | C |
| 6 | A | A | A | A | B |
| 9 | A | A | A | A | C |
| 10 | A | A | A | A | C |
| 11 | B | A | A | A | C |
| 12 | A | A | A | A | C |
| 13 | A | A | A | A | C |
| 14 | A | A | A | A | B |
| 15 | A | A | A | A | C |
| 16 | A | A | A | A | B |
| 17 | B | A | B | A | B |
| 18 | A | A | A | A | C |
| 19 | A | A | A | A | A |
| 20 | A | A | A | A | B |
| 22 | A | A | A | A | C |
| 24 | A | A | B | A | C |
| 25 | B | A | B | A | C |
| 26 | A | A | A | A | B |
| 27 | A | A | A | A | C |
| 28 | A | A | A | A | A |
| 29 | A | A | A | A | B |
| 30 | A | A | B | A | C |
| 31 | A | A | A | A | A |
| 32 | A | A | A | A | B |
| 33 | A | A | A | A | A |
| 34 | A | A | B | A | C |
| 35 | A | A | A | A | B |
| 36 | A | A | A | A | B |
| 37 | A | A | A | A | B |
| 38 | B | A | A | A | C |
| 39 | B | A | A | A | C |
| 40 | B | A | A | A | C |
| 41 | A | A | A | A | C |
| 42 | A | A | A | A | B |
| 44 | B | A | A | A | B |
| 45 | A | A | A | A | A |
| 46 | A | A | A | nd | A |
| 47 | B | A | A | A | B |

TABLE 3-continued

Biochemical Assay Activity Summary:

| Example | ALK-L1196M-G1202R | ALK-wt | ROS1-G2032R | ROS1-wt | TRKA-wt |
|---|---|---|---|---|---|
| 48 | A | A | A | A | C |
| 49 | B | A | B | A | C |
| 50 | A | A | A | A | A |
| 52 | A | A | A | A | B |
| 53 | A | A | A | A | B |
| 54 | A | A | A | A | C |
| 55 | A | A | A | A | B |
| 58 | A | A | A | A | C |
| 59 | C | A | B | A | B |
| 60 | B | A | B | A | C |
| 61 | C | B | C | B | C |
| 62 | A | A | B | A | C |
| 63 | A | A | A | A | C |
| 64 | A | A | A | A | C |
| 65 | A | A | A | A | C |
| 67 | A | A | A | A | B |
| 68 | A | A | A | A | B |
| 69 | A | A | A | A | B |
| 70 | A | A | A | A | B |
| 71 | A | A | A | A | A |
| 72 | A | A | A | A | B |
| 73 | A | A | A | A | B |
| 74 | A | A | A | A | A |
| 75 | A | A | A | A | B |
| 76 | A | A | A | A | A |
| 77 | A | A | A | A | B |
| 78 | A | A | A | A | B |
| 79 | A | A | A | A | C |
| 80 | A | A | A | A | A |
| 81 | A | A | A | A | B |
| 82 | A | A | A | A | B |
| 83 | A | A | A | A | C |
| 84 | A | A | A | A | C |
| 85 | A | A | A | A | C |
| 86 | B | A | A | A | C |
| 87 | A | A | A | A | A |
| 88 | A | A | A | A | B |
| 89 | A | A | A | A | C |
| 90 | A | A | A | A | B |
| 91 | A | A | A | A | B |
| 92 | A | A | A | A | C |
| 93 | A | A | A | A | B |
| 94 | A | A | A | A | B |
| 98 | A | A | A | A | A |
| 99 | A | A | A | A | B |
| 100 | A | A | A | A | B |
| 102 | A | A | A | A | A |
| 103 | A | A | A | A | B |
| 104 | A | A | A | A | C |
| 105 | A | A | A | A | C |
| 106 | A | A | A | A | B |
| 107 | A | A | A | A | B |
| 108 | A | A | A | A | B |
| 109 | A | A | A | A | A |
| 110 | A | A | A | A | C |
| 111 | A | A | A | A | B |
| 112 | A | A | A | A | B |
| 114 | A | A | A | A | B |
| 116 | A | A | A | A | B |
| 117 | A | A | B | A | C |
| 118 | B | A | C | A | A |
| 119 | A | A | B | A | A |
| 120 | B | A | B | A | B |
| 121 | A | A | A | A | B |
| 122 | A | A | A | A | B |
| 123 | A | A | A | A | C |
| 124 | A | A | A | A | B |
| 126 | A | A | A | A | C |
| 128 | A | A | A | A | B |
| 130 | A | A | A | A | B |
| 132 | A | A | A | A | B |
| 133 | A | A | B | A | C |
| 134 | A | A | A | A | B |
| 135 | A | A | A | A | B |
| 137 | A | A | A | A | B |
| 138 | A | A | A | A | C |
| 139 | A | A | A | A | B |
| 140 | A | A | A | A | B |
| 141 | A | A | A | A | B |
| 143 | A | A | A | A | B |
| 144 | A | A | A | A | B |
| 145 | A | A | A | A | B |
| 146 | A | A | A | A | B |
| 147 | A | A | A | A | A |
| 148 | A | A | B | A | C |
| 149 | A | A | A | A | A |
| 150 | A | A | A | A | B |
| 151 | A | A | A | A | A |
| 152 | A | A | A | A | A |
| 153 | A | A | A | A | A |
| 154 | A | A | A | A | C |
| 155 | A | A | A | A | A |
| 156 | A | A | A | A | B |
| 157 | A | A | A | A | A |
| 158 | A | A | A | A | A |
| 159 | A | A | nd | nd | C |
| 160 | A | A | A | A | C |
| 162 | A | A | A | A | A |
| 163 | A | A | A | A | B |
| 164 | B | A | A | A | C |
| 165 | B | A | B | A | B |
| 166 | B | A | B | A | C |
| 167 | B | A | B | A | C |
| 168 | A | A | A | A | C |
| 169 | A | A | A | A | A |
| 171 | A | A | A | A | A |
| 173 | A | nd | nd | nd | A |
| 174 | A | A | A | A | B |
| 175 | A | A | A | A | B |
| 176 | A | A | B | A | C |
| 177 | A | A | A | A | B |
| 178 | A | A | A | A | B |
| 179 | A | A | A | A | B |
| 180 | A | A | A | A | B |
| 181 | A | A | A | A | B |

Compound potency can be interpreted by binning $K_i^{app}$ values against the targets: bin A for high potency, $K_i^{app}<50$ nM; bin B for medium potency, 50 nM$<K_i^{app}<500$ nM; and bin C for low potency, $K_i^{app}>500$ nM. Compounds are more desirable if they exhibit smaller $K_i^{app}$ values against the on-target kinases (ROS1 or ALK) and larger $K_i^{app}$ values against the off-target kinase (TRKA). Compounds that potently inhibit the on-target kinases (ROS1 or ALK) are also expected to inhibit ROS1 or ALK oncoproteins that are expressed in human cancers, providing support for the potential clinical efficacy of such compounds. Similarly, compounds that do not potently inhibit the off-target kinase (TRKA) are expected to poorly inhibit TRK-family kinases in humans and hence avoid potential clinical toxicity arising from TRKA, TRKB, or TRKC inhibition.

Example 183

Generation of Ba/F3 Stable Cell Lines

Genes encoding CD74-ROS1 wild-type (wt), CD74-ROS1 G2032R, CD74-ROS1 S1986F, CD74-ROS1 L2026M, CD74-ROS1 D2033N, EML4-ALK wt (variant 1), EML4-ALK G1202R (variant 1), EML4-ALK L1196M/G1202R (variant 1), EML4-ALK G1202R/G1269A (variant 1), EML4-ALK G1202R/L1198F (variant 1), and TPM3-TRKA were synthesized at GeneRay, cloned into the retroviral construct pMSCV-puro (Biovector), and packaged into retroviral particles. The virus was used to infect Ba/F3 cells (RIKEN) at multiplicity of infection=1 for 1 day. Infected cells were rescued in media (RPMI-1640 with 10% fetal bovine serum and 1% streptomycin and penicillin) supplemented with mouse IL-3 (10 ng/mL) for 2 days, and stable cell lines were selected by IL-3 withdrawal and puromycin (0.8 μg/mL) for 7 days. Monoclones were selected by single-cell dilution in IL-3-free medium containing puromycin (0.8 μg/mL). Transformation of desired genes was confirmed by Sanger sequencing and western blot using the following antibodies: ROS1 (CST #3287), ALK (CST #3633), and pan-TRK (Abcam #76291).

Cell Proliferation Assay

Stable cells were plated at 1,000 cells/well (40 μL) in a 384-well plate for 1 day. Test compounds (40 nL) were then added in a 3-fold dilution series using the TECAN EVO200 liquid handler and incubated for 72 hours. Plates were equilibrated at room temperature for 15 minutes followed by addition of 40 μL CellTiter-Glo reagent (Promega). Luminescence was measured on a plate reader. Half-maximal inhibitory concentration ($IC_{50}$) was calculated from percent inhibition and inhibitor concentration using four-parameter logistic regression. Compound potency can be interpreted by binning $IC_{50}$ values: bin A for high potency, 0.1 nM≤$IC_{50}$<50 nM; bin B for medium potency, 50 nM≤$IC_{50}$≤500 nM; and bin C for low potency, $IC_{50}$>500 nM. Compounds are more desirable if they exhibit smaller $IC_{50}$ values against the on-target Ba/F3 cells (ROS1- or ALK-fusion) and larger IC50 values against the off-target Ba/F3 cells (TRKA-fusion). Exemplary data is given in Table 4 (nd is not determined).

TABLE 4

Cell Assay Activity Summary:

| Example | CD74-ROS1-G2032R | CD74-ROS1-wt | EML4-ALK-L1196M-G1202R | TPM3-NTRK1-wt | EML4-ALK-wt |
|---|---|---|---|---|---|
| 1 | A | A | A | B | A |
| 2 | A | A | C | B | A |
| 3 | A | nd | A | B | A |
| 4 | A | A | B | B | A |
| 5 | A | A | A | C | A |
| 6 | A | A | B | B | A |
| 7 | B | nd | B | C | nd |
| 8 | A | A | A | B | A |
| 9 | A | A | B | C | A |
| 10 | A | C | B | C | A |
| 11 | A | A | B | C | A |
| 12 | A | A | A | C | A |
| 13 | A | A | A | C | A |
| 14 | A | A | B | C | A |
| 15 | A | A | B | C | A |
| 16 | A | A | B | B | A |
| 17 | A | A | C | B | A |
| 18 | A | A | A | C | A |
| 19 | A | A | A | B | A |
| 20 | A | A | A | B | A |
| 21 | A | A | A | B | A |
| 22 | A | A | A | C | A |
| 23 | A | A | A | B | A |
| 24 | A | A | B | C | A |
| 25 | A | A | B | C | A |
| 26 | A | A | A | B | A |
| 27 | A | A | B | C | A |
| 28 | A | A | A | B | A |
| 29 | A | A | A | C | A |
| 30 | A | A | B | C | A |
| 31 | A | A | A | B | A |
| 32 | A | A | B | B | A |
| 33 | A | A | A | B | A |
| 34 | A | A | B | C | A |
| 35 | A | A | A | B | A |
| 36 | A | A | A | B | A |
| 37 | A | A | A | C | A |
| 38 | A | A | C | C | B |
| 39 | B | A | C | C | A |
| 40 | A | A | B | C | A |
| 41 | A | A | A | B | A |
| 42 | A | A | A | B | A |
| 43 | A | A | A | B | A |
| 44 | A | A | B | C | A |
| 45 | A | A | A | B | A |
| 46 | A | A | A | B | A |
| 47 | A | A | B | B | A |
| 48 | A | A | B | C | A |
| 49 | A | A | A | C | A |
| 50 | A | A | A | B | A |
| 51 | C | C | C | C | C |
| 52 | A | A | A | B | A |
| 53 | A | A | A | B | A |
| 54 | A | A | A | C | A |
| 55 | A | A | A | B | A |
| 56 | C | C | C | C | C |
| 58 | A | A | B | C | A |
| 59 | B | A | C | B | nd |
| 61 | B | A | C | C | B |
| 62 | A | A | B | B | A |
| 63 | A | A | B | C | A |
| 64 | A | A | B | C | A |
| 65 | A | A | B | C | A |
| 67 | A | A | B | B | A |
| 68 | A | A | B | B | A |
| 69 | A | A | A | B | A |
| 70 | A | A | B | B | A |
| 71 | A | A | A | A | A |
| 72 | A | A | A | B | A |
| 73 | A | A | A | B | A |
| 74 | A | A | A | A | A |
| 75 | A | A | A | B | A |
| 76 | A | A | A | B | A |
| 77 | A | A | A | B | A |
| 78 | A | A | A | B | A |
| 79 | A | A | A | C | A |
| 80 | A | A | A | B | A |
| 81 | A | A | A | B | A |
| 82 | A | A | A | B | A |
| 83 | A | A | A | C | A |
| 84 | A | A | B | C | A |
| 85 | A | A | B | C | A |
| 86 | A | A | C | B | A |
| 87 | A | A | A | A | A |
| 88 | A | A | A | B | A |
| 89 | B | A | B | C | A |
| 90 | A | A | A | B | A |
| 91 | A | A | A | B | A |
| 92 | A | A | B | B | A |
| 93 | A | A | B | B | A |
| 94 | A | A | A | B | A |
| 95 | A | A | A | B | A |
| 96 | A | A | B | B | A |
| 97 | A | A | A | B | A |
| 98 | A | A | A | A | A |
| 99 | A | A | A | B | A |
| 100 | A | A | A | B | A |
| 101 | A | A | B | C | A |
| 102 | A | A | A | A | A |
| 103 | A | A | A | B | A |
| 104 | A | A | B | B | A |
| 105 | A | A | B | C | A |
| 106 | A | A | A | B | A |
| 107 | A | A | B | B | A |
| 108 | A | A | A | B | A |
| 109 | A | A | A | B | A |
| 110 | A | A | A | C | A |

TABLE 4-continued

Cell Assay Activity Summary:

| Example | CD74-ROS1-G2032R | CD74-ROS1-wt | EML4-ALK-L1196M-G1202R | TPM3-NTRK1-wt | EML4-ALK-wt |
|---|---|---|---|---|---|
| 111 | A | A | B | B | A |
| 112 | A | A | B | B | A |
| 113 | B | B | C | C | A |
| 114 | A | A | A | C | A |
| 115 | A | A | B | C | A |
| 116 | A | A | A | B | A |
| 117 | A | A | B | C | A |
| 118 | B | A | B | B | A |
| 119 | A | A | B | A | A |
| 120 | B | A | C | C | B |
| 121 | A | A | A | B | A |
| 122 | A | A | A | B | A |
| 123 | B | A | C | C | A |
| 124 | A | A | A | B | A |
| 125 | A | A | A | C | A |
| 126 | A | A | A | C | A |
| 127 | A | A | A | C | A |
| 128 | A | A | A | B | A |
| 129 | A | A | B | C | B |
| 130 | A | A | A | B | A |
| 131 | C | B | C | C | B |
| 132 | A | A | B | B | A |
| 133 | A | A | A | C | A |
| 134 | A | A | A | B | A |
| 135 | A | A | A | B | A |
| 136 | A | A | B | C | B |
| 137 | A | A | A | B | A |
| 138 | A | A | A | C | A |
| 139 | A | A | A | B | A |
| 140 | A | A | A | B | A |
| 141 | A | A | A | B | A |
| 142 | A | nd | A | B | nd |
| 143 | A | A | A | B | A |
| 144 | A | A | A | B | A |
| 145 | A | A | B | B | A |
| 146 | A | A | A | B | A |
| 147 | A | A | B | B | A |
| 148 | nd | nd | nd | C | nd |
| 149 | A | A | B | A | A |
| 150 | A | A | B | B | A |

TABLE 4-continued

Cell Assay Activity Summary:

| Example | CD74-ROS1-G2032R | CD74-ROS1-wt | EML4-ALK-L1196M-G1202R | TPM3-NTRK1-wt | EML4-ALK-wt |
|---|---|---|---|---|---|
| 155 | A | A | C | B | A |
| 156 | nd | nd | A | B | nd |
| 157 | A | A | A | B | A |
| 158 | A | A | A | B | A |
| 159 | A | A | B | C | A |
| 160 | A | A | A | C | A |
| 161 | A | A | A | A | A |
| 162 | A | A | A | B | A |
| 163 | A | A | B | B | A |
| 164 | A | nd | B | C | B |
| 165 | A | A | C | B | B |
| 168 | A | A | B | C | A |
| 169 | A | A | B | B | A |
| 170 | A | A | A | B | A |
| 171 | A | A | A | B | A |
| 172 | A | A | A | B | A |
| 173 | A | A | A | A | A |
| 174 | A | A | B | B | A |
| 175 | A | A | A | B | A |
| 176 | A | A | B | C | A |
| 177 | A | A | A | B | A |
| 178 | A | A | A | B | A |
| 179 | A | A | A | B | A |
| 180 | A | A | B | C | A |
| 181 | A | A | A | B | A |

Potencies of the compounds provided herein were compared to commercially available ALK inhibitors (tested in the same assays) to assess relative potencies across ALK mutations. Exemplary data of one compound of Formula (I) and several ALK inhibitors are given in Table 5.

TABLE 5

Cell Potency Compared to Reference Compounds:

| Cell with ALK fusion | One compound of Formula (I) | Crizotinib | Ceritinib | Alectinib | Brigatinib | Lorlatinib |
|---|---|---|---|---|---|---|
| Wild-type | A | C | B | B | B | A |
| G1202R | A | D | D | D | C | B |
| G1202R/L1196M | A | D | D | D | D | D |
| G1202R/G1269A | A | D | C | D | C | D |
| G1202R/L1198F | A | C | D | D | C | D |

A: ≤10 nM
B: >10 nM and ≤100 nM
C: >100 nM and ≤500 nM
D: >500 nM and <4000 nM

TABLE 4-continued

Cell Assay Activity Summary:

| Example | CD74-ROS1-G2032R | CD74-ROS1-wt | EML4-ALK-L1196M-G1202R | TPM3-NTRK1-wt | EML4-ALK-wt |
|---|---|---|---|---|---|
| 151 | A | A | A | B | A |
| 152 | A | A | A | B | A |
| 153 | nd | nd | nd | C | nd |
| 154 | A | A | B | C | A |

Ba/F3 proliferation is driven by the transduced oncogenes in the same way that cancer cell proliferation in humans is driven by the expression of equivalent oncogenes. Hence, compounds that potently inhibit the proliferation of the on-target Ba/F3 cells (ROS1- or ALK-fusion) are also expected to inhibit human cancers that express equivalent oncogenes, providing support for the potential clinical efficacy of such compounds. Similarly, compounds that do not potently inhibit the off-target Ba/F3 cells (TRKA-fusion) are expected to poorly inhibit TRK-family kinases in humans and hence avoid the clinical toxicity arising from TRKA, TRKB, or TRKC inhibition.

TRKA selectivity was calculated by dividing a compound's TRKA potency by its primary target potency (e.g. TPM3-NTRK1-wt IC$_{50}$/CD74-ROS1-wt IC$_{50}$). Compound selectivity can be interpreted by binning ratio values: bin A for very high selectivity, ratio>30-fold; bin B for high selectivity, ratio>10-fold; bin C for moderate selectivity, ratio>1; and bin D for low selectivity, ratio<1. Compounds are more desirable if they exhibit higher selectivity ratios. Exemplary data are given in Table 6. (nd=not determined).

TABLE 6

Cell Assay Selectivity Summary:

| Example | TPM3-NTRK1-wt/CD74-ROS1-G2032R | TPM3-NTRK1-wt/CD74-ROS1-wt | TPM3-NTRK1-wt/EML4-ALK-L1196M-G1202R | TPM3-NTRK1-wt/EML4-ALK-wt |
|---|---|---|---|---|
| 1 | A | A | A | A |
| 2 | B | A | D | B |
| 3 | A | nd | B | A |
| 4 | B | A | D | C |
| 5 | A | A | A | A |
| 6 | A | A | C | A |
| 7 | A | nd | A | nd |
| 8 | A | A | B | A |
| 9 | B | A | C | A |
| 10 | A | D | C | A |
| 11 | A | A | C | A |
| 12 | A | A | A | A |
| 13 | A | A | A | A |
| 14 | B | A | C | A |
| 15 | A | A | B | A |
| 16 | B | A | C | B |
| 17 | B | A | D | B |
| 18 | A | A | A | A |
| 19 | A | A | C | A |
| 20 | A | A | B | A |
| 21 | A | A | B | A |
| 22 | A | A | A | A |
| 23 | A | A | C | A |
| 24 | A | A | C | A |
| 25 | A | A | B | A |
| 26 | A | A | B | A |
| 27 | A | A | A | A |
| 28 | A | A | C | A |
| 29 | A | A | A | A |
| 30 | A | A | C | A |
| 31 | A | A | C | A |
| 32 | A | A | C | B |
| 33 | A | A | B | A |
| 34 | A | A | B | A |
| 35 | A | A | C | A |
| 36 | A | A | C | A |
| 37 | A | A | A | A |
| 38 | A | A | C | B |
| 39 | A | A | C | A |
| 40 | A | A | A | A |
| 41 | A | A | B | A |
| 42 | A | A | B | A |
| 43 | A | A | C | B |
| 44 | A | A | C | A |
| 45 | A | A | B | A |
| 46 | A | A | C | A |
| 47 | A | A | C | B |
| 48 | A | A | B | A |
| 49 | A | A | B | A |
| 50 | A | A | B | A |
| 51 | C | C | C | D |
| 52 | A | A | C | B |
| 53 | A | A | A | A |
| 54 | A | A | B | A |
| 55 | A | A | C | A |
| 56 | D | D | D | D |
| 58 | A | A | B | A |
| 59 | C | A | D | nd |
| 61 | A | A | B | A |
| 62 | B | A | C | A |
| 63 | A | A | B | A |
| 64 | A | A | B | A |
| 65 | A | A | B | A |
| 67 | A | A | C | A |
| 68 | B | A | C | B |
| 69 | A | A | B | A |

TABLE 6-continued

Cell Assay Selectivity Summary:

| Example | TPM3-NTRK1-wt/CD74-ROS1-G2032R | TPM3-NTRK1-wt/CD74-ROS1-wt | TPM3-NTRK1-wt/EML4-ALK-L1196M-G1202R | TPM3-NTRK1-wt/EML4-ALK-wt |
|---|---|---|---|---|
| 70 | A | A | C | A |
| 71 | A | B | C | B |
| 72 | A | A | C | A |
| 73 | A | A | B | A |
| 74 | A | A | B | A |
| 75 | A | A | C | A |
| 76 | A | A | B | A |
| 77 | A | A | C | A |
| 78 | A | A | B | A |
| 79 | A | A | A | A |
| 80 | A | A | B | A |
| 81 | A | A | B | A |
| 82 | A | A | B | A |
| 83 | A | A | A | A |
| 84 | A | A | C | A |
| 85 | A | A | C | A |
| 86 | B | A | D | C |
| 87 | A | A | C | A |
| 88 | B | A | C | A |
| 89 | A | A | B | A |
| 90 | A | A | C | A |
| 91 | A | A | A | A |
| 92 | A | A | C | C |
| 93 | A | A | C | B |
| 94 | A | A | A | A |
| 95 | A | A | C | A |
| 96 | A | A | C | A |
| 97 | A | A | B | A |
| 98 | A | A | C | B |
| 99 | A | A | C | B |
| 100 | A | A | A | A |
| 101 | A | A | A | A |
| 102 | A | A | C | B |
| 103 | A | A | B | A |
| 104 | A | A | C | A |
| 105 | A | A | B | A |
| 106 | A | A | B | A |
| 107 | A | A | C | C |
| 108 | A | A | B | A |
| 109 | A | A | A | A |
| 110 | A | A | A | A |
| 111 | B | A | C | A |
| 112 | C | A | D | A |
| 113 | A | A | C | A |
| 114 | A | A | A | A |
| 115 | A | A | B | A |
| 116 | A | A | A | A |
| 117 | A | A | B | A |
| 118 | D | A | D | A |
| 119 | D | A | D | A |
| 120 | C | A | D | C |
| 121 | A | A | A | A |
| 122 | A | A | C | B |
| 123 | C | A | C | A |
| 124 | A | A | A | A |
| 125 | A | A | A | A |
| 126 | A | A | A | A |
| 127 | A | A | A | A |
| 128 | A | A | C | B |
| 129 | A | A | A | A |
| 130 | A | A | B | A |
| 131 | B | A | C | B |
| 132 | A | A | C | A |
| 133 | A | A | A | A |
| 134 | A | A | A | A |
| 135 | A | A | A | A |
| 136 | A | A | A | A |
| 137 | A | A | A | A |
| 138 | A | A | A | A |
| 139 | A | A | C | A |
| 140 | A | A | A | A |
| 141 | A | A | A | A |
| 142 | A | nd | B | nd |
| 143 | A | A | B | A |

TABLE 6-continued

Cell Assay Selectivity Summary:

| Example | TPM3-NTRK1-wt/CD74-ROS1-G2032R | TPM3-NTRK1-wt/CD74-ROS1-wt | TPM3-NTRK1-wt/EML4-ALK-L1196M-G1202R | TPM3-NTRK1-wt/EML4-ALK-wt |
|---|---|---|---|---|
| 144 | A | A | B | A |
| 145 | A | A | C | A |
| 146 | A | A | B | A |
| 147 | A | A | C | A |
| 148 | nd | nd | nd | nd |
| 149 | B | A | D | B |
| 150 | A | A | C | B |
| 151 | A | A | C | A |
| 152 | A | A | C | A |
| 153 | nd | nd | nd | nd |
| 154 | A | A | B | A |
| 155 | C | A | D | A |
| 156 | nd | nd | C | nd |
| 157 | A | A | C | A |
| 158 | A | A | C | A |
| 159 | A | A | B | A |
| 160 | A | A | A | A |
| 161 | C | C | D | C |
| 162 | B | A | C | A |
| 163 | A | A | C | A |
| 164 | A | nd | C | B |
| 165 | C | B | D | C |
| 168 | A | A | B | A |
| 169 | C | A | D | A |
| 170 | A | A | B | A |
| 171 | A | A | B | A |
| 172 | A | A | A | A |
| 173 | A | A | B | A |
| 174 | B | A | C | A |
| 175 | A | A | B | A |
| 176 | A | A | B | A |
| 177 | A | A | B | A |
| 178 | A | A | A | A |
| 179 | A | A | A | A |
| 180 | A | A | C | A |
| 181 | A | A | C | A |

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

Equivalents

While specific embodiments of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

What is claimed is:

1. A method of treating a ROS1 or ALK positive cancer, wherein the cancer is lung cancer, glioblastoma, inflammatory myofibroblastic tumor (IMT), bile duct cancer, ovarian cancer, gastric cancer, colorectal cancer, angiosarcoma, melanoma, epithelioid hemangioendothelioma, esophageal cancer, kidney cancer, breast cancer, colon cancer, thyroid cancer, spitzoid tumor, or neuroblastoma, wherein the method comprises administering to a subject in need thereof a therapeutically effective amount of a compound of Formula (I):

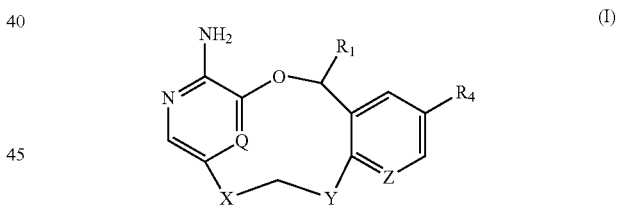

or an enantiomer, a mixture of enantiomers, or a tautomer thereof, or a pharmaceutically acceptable salt thereof, wherein:

Q is CH;

Z is $CR_5$;

X is a 5-membered heteroarylene selected from the group consisting of

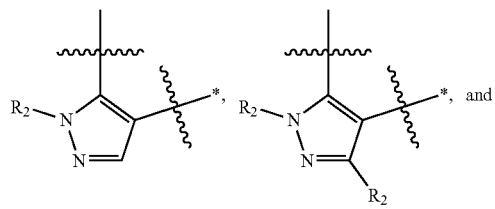

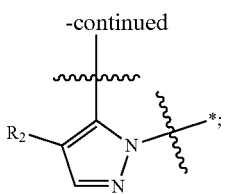

wherein * indicates the point of attachment of X to the methylene group bonded to X and Y;

Y is a 5-membered heteroarylene selected from the group consisting of

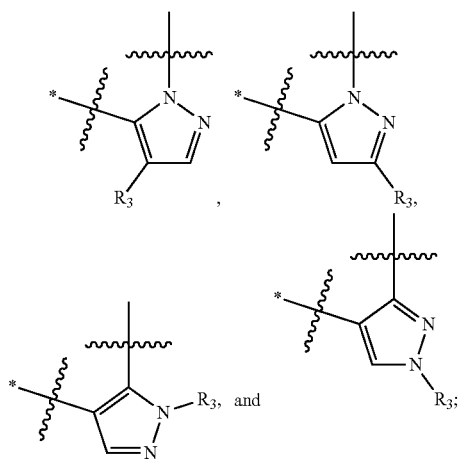

wherein * indicates the point of attachment of Y to the methylene group bonded to X and Y;

$R_1$ is selected from the group consisting of H, methyl, and hydroxymethyl;

each instance of $R_2$ is independently selected from the group consisting of H, CN, halo, $C_{1-4}$ alkoxy, $C_{1-4}$ alkyl, halo-$C_{1-4}$ alkyl, $C_{3-4}$ cycloalkylmethyl, $C_{3-6}$ cycloalkyl, and three- to six-membered heterocyclyl;

each instance of $R_3$ is independently selected from the group consisting of H, halo, CN, $C_{1-4}$ alkoxy, halo-$C_{1-4}$ alkyl, and $C_{1-4}$ alkyl; and each of $R_4$ and $R_5$ is independently H or F.

2. The method of claim 1, wherein the compound is a compound of Formula (I-B):

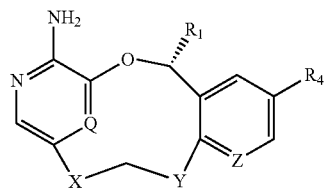

(I-B)

or a pharmaceutically acceptable salt thereof.

3. The method of claim 2, wherein each instance of $R_2$ is independently selected from the group consisting of H, chloro, fluoro, CN, methyl, ethyl, isopropyl, methoxy, trifluoromethyl, 2-fluoroethyl, difluoromethyl, 2,2-difluoroethyl, 2,2,2-trifluoroethyl, cyclopropylmethyl, cyclopropyl, cyclobutyl, and oxetanyl.

4. The method of claim 3, wherein each instance of $R_3$ is independently selected from the group consisting of H, fluoro, chloro, bromo, CN, methoxy, difluoromethyl, trifluoromethyl, methyl, and ethyl.

5. The method of claim 4, wherein $R_4$ is F.

6. The method of claim 5, wherein $R_5$ is H.

7. The method of claim 2, wherein the cancer is lung cancer.

8. The method of claim 7, wherein the lung cancer is non-small cell lung cancer.

9. The method of claim 2, wherein the cancer is a ROS1 positive cancer.

10. The method of claim 9, wherein the ROS1 positive cancer comprises expression of an oncogenic ROS1 gene or oncogenic ROS1 gene-fusion ROS1 protein.

11. The method of claim 2, wherein the cancer is a ALK positive cancer.

12. The method of claim 11, wherein the ALK positive cancer comprises expression of an oncogenic ALK gene or oncogenic ALK gene-fusion.

13. The method of claim 2, wherein the compound is

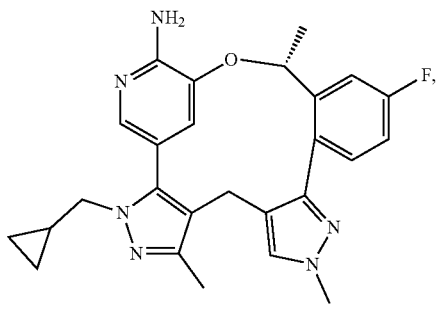 [SMILES: Cc1nn(CC2CC2)c2c1Cc1cn(C)nc1-c1ccc(F)cc1[C@@H](C)Oc1cc-2cnc1N]

or a pharmaceutically acceptable salt thereof.

14. The method of claim 2, wherein the compound is

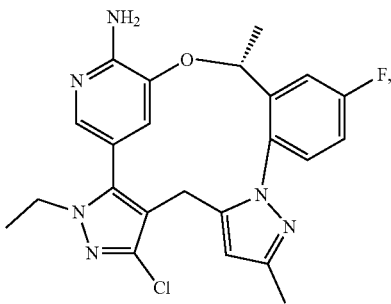 [SMILES: CCn1nc(Cl)c2c1-c1cnc(N)c(c1)O[C@H](C)c1cc(F)ccc1-n1nc(C)cc1C2]

or a pharmaceutically acceptable salt thereof.

15. The method of claim 2, wherein the compound is

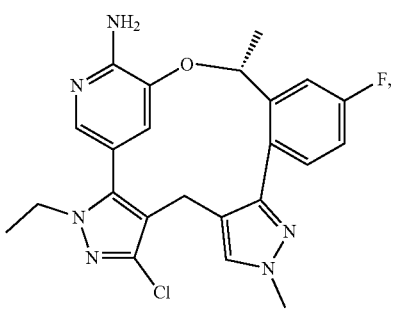 [SMILES: CCn1nc(Cl)c2c1-c1cnc(N)c(c1)O[C@H](C)c1cc(F)ccc1-c1nn(C)cc1C2]

or a pharmaceutically acceptable salt thereof.

16. The method of claim 2, wherein the compound is

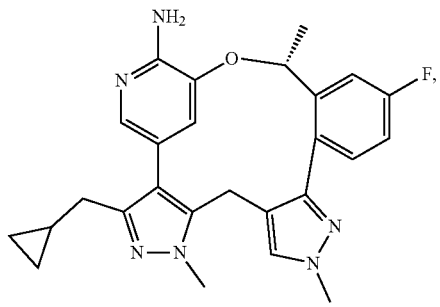 [SMILES: C[C@H]1Oc2cc(cnc2N)-c2c(CC3CC3)nn(C)c2Cc2cn(C)nc2-c2ccc(F)cc21]

or a pharmaceutically acceptable salt thereof.

17. The method of claim 2, wherein the compound is

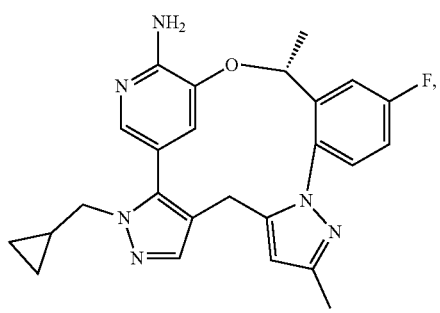 [SMILES: Cc1cc2n(n1)-c1ccc(F)cc1[C@@H](C)Oc1cc(cnc1N)-c1c(cnn1CC1CC1)C2]

or a pharmaceutically acceptable salt thereof.

18. The method of claim 2, wherein the compound is

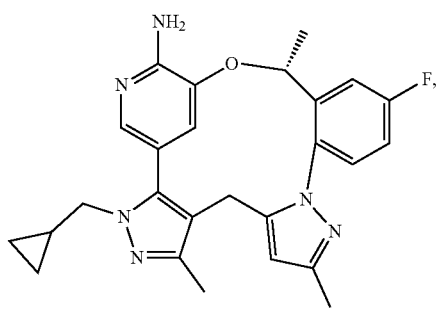 [SMILES: Cc1cc2n(n1)-c1ccc(F)cc1[C@@H](C)Oc1cc(cnc1N)-c1c(c(C)nn1CC1CC1)C2]

or a pharmaceutically acceptable salt thereof.

19. The method of claim 2, wherein the compound is

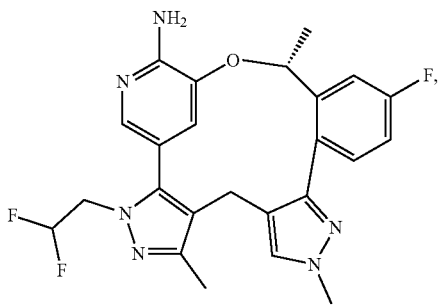 [SMILES: Cc1nn(CC(F)F)c2c1Cc1cn(C)nc1-c1ccc(F)cc1[C@@H](C)Oc1cc-2cnc1N]

or a pharmaceutically acceptable salt thereof.

20. The method of claim 2, wherein the compound is

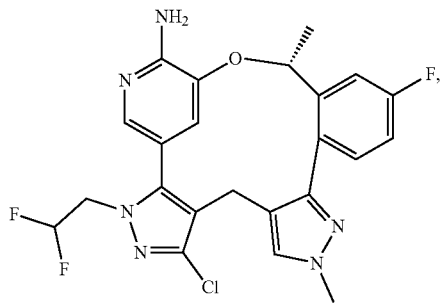

or a pharmaceutically acceptable salt thereof.

21. The method of claim 2, wherein the compound is

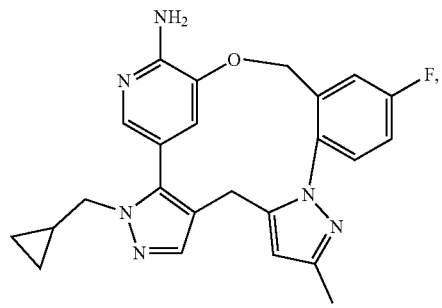 [SMILES: Cc1cc2n(n1)-c1ccc(F)cc1COc1cc(cnc1N)-c1c(cnn1CC1CC1)C2]

or a pharmaceutically acceptable salt thereof.

22. The method of claim 2, wherein the compound is

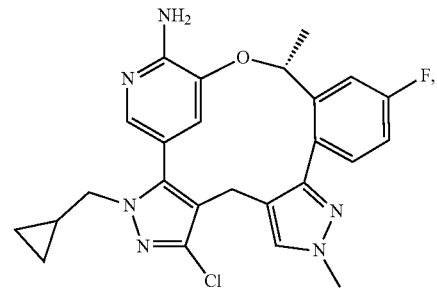 [SMILES: C[C@H]1Oc2cc(cnc2N)-c2c(c(Cl)nn2CC2CC2)Cc2cn(C)nc2-c2ccc(F)cc21]

or a pharmaceutically acceptable salt thereof.

23. The method of claim 2, wherein the compound is

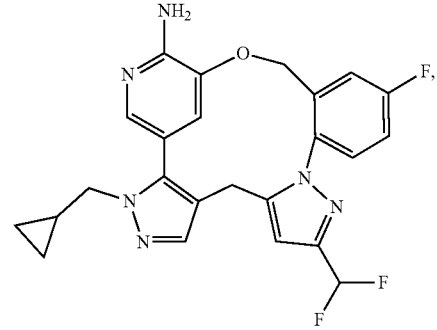 [SMILES: Nc1ncc2cc1OCc1cc(F)ccc1-n1nc(C(F)F)cc1Cc1cnn(CC3CC3)c1-2]

or a pharmaceutically acceptable salt thereof.

24. The method of claim 2, wherein the compound is

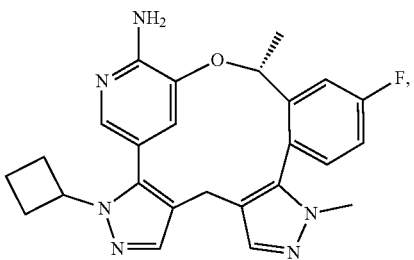 [SMILES: C[C@H]1Oc2cc(cnc2N)-c2c(cnn2C2CCC2)Cc2cnn(C)c2-c2ccc(F)cc21]

or a pharmaceutically acceptable salt thereof.

25. A method of treating a ROS1 or ALK positive cancer, wherein the cancer is lung cancer, glioblastoma, inflammatory myofibroblastic tumor (IMT), bile duct cancer, ovarian cancer, gastric cancer, colorectal cancer, angiosarcoma, melanoma, epithelioid hemangioendothelioma, esophageal cancer, kidney cancer, breast cancer, colon cancer, thyroid cancer, spitzoid tumor, or neuroblastoma, and wherein the method comprises administering to a subject in need thereof a pharmaceutical composition comprising (i) a compound of Formula (I), or an enantiomer, a mixture of enantiomers, or a tautomer thereof, or a pharmaceutically acceptable salt thereof:

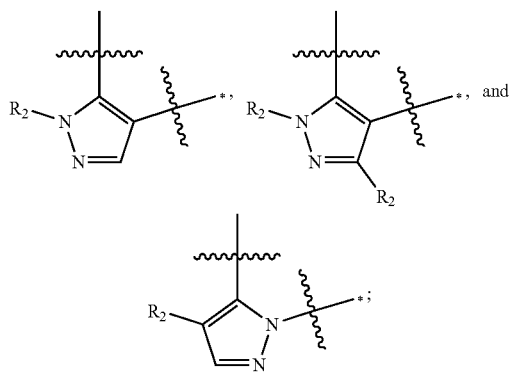

and (ii) a pharmaceutically acceptable carrier or excipient; wherein

Q is CH;

Z is $CR_5$;

X is a 5-membered heteroarylene selected from the group consisting of

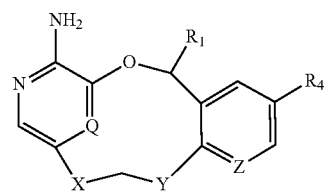

wherein * indicates the point of attachment of X to the methylene group bonded to X and Y;

Y is a 5-membered heteroarylene selected from the group consisting of

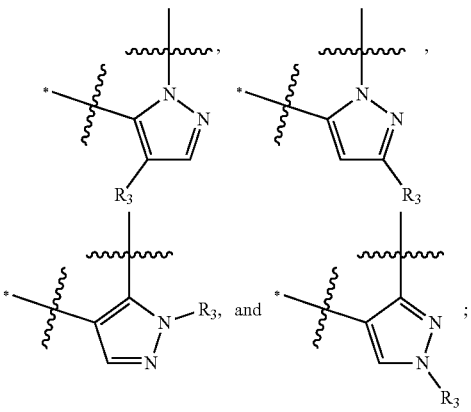

wherein * indicates the point of attachment of Y to the methylene group bonded to X and Y;

$R_1$ is selected from the group consisting of H, methyl, and hydroxymethyl;

each instance of $R_2$ is independently selected from the group consisting of H, CN, halo, $C_{1-4}$ alkoxy, $C_{1-4}$ alkyl, halo-$C_{1-4}$ alkyl, $C_{3-4}$ cycloalkylmethyl, $C_{3-6}$ cycloalkyl, and three- to six-membered heterocyclyl;

each instance of $R_3$ is independently selected from the group consisting of H, halo, CN, $C_{1-4}$ alkoxy, halo-$C_{1-4}$ alkyl, and $C_{1-4}$ alkyl; and each of $R_4$ and $R_5$ is independently H or F.

26. The method of claim 25, wherein the compound is a compound of Formula (I-B):

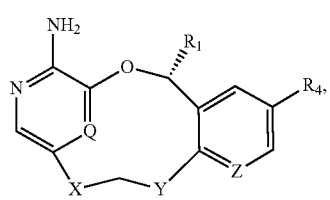

or a pharmaceutically acceptable salt thereof.

27. The method of claim 2, wherein the compound is

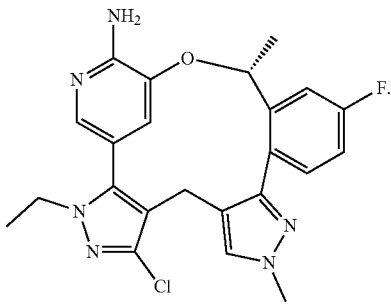 [SMILES: CCn1nc(Cl)c2c1-c1cnc(N)c(c1)O[C@H](C)c1cc(F)ccc1-c1nn(C)cc1C2]

28. The method of claim 10, wherein the oncogenic ROS1 gene or oncogenic ROS1 gene-fusion contains one or more mutations of the human ROS1 gene.

29. The method of claim 28, wherein the one or more mutations in the oncogenic ROS1 gene or oncogenic ROS1 gene-fusion results in expression of a ROS1 protein with a G2032R mutation.

30. The method of claim 12, wherein the oncogenic ALK gene or the oncogenic ALK gene-fusion contains one or more mutations of the human ALK gene.

31. The method of claim 30, wherein the one or more mutations in the oncogenic ALK gene or the oncogenic ALK gene-fusion results in expression of an ALK protein with one or more mutations selected from the group consisting of G1202R and L1196M.

* * * * *

UNITED STATES PATENT AND TRADEMARK OFFICE
CERTIFICATE OF CORRECTION

| | | |
|---|---|---|
| PATENT NO. | : 12,275,742 B2 | Page 1 of 1 |
| APPLICATION NO. | : 17/834127 | |
| DATED | : April 15, 2025 | |
| INVENTOR(S) | : Horan et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 21 days.

Signed and Sealed this
Thirtieth Day of September, 2025

John A. Squires
*Director of the United States Patent and Trademark Office*